US011873291B2

(12) United States Patent
Qiu et al.

(10) Patent No.: US 11,873,291 B2
(45) Date of Patent: Jan. 16, 2024

(54) QUINOLINE CGAS ANTAGONIST COMPOUNDS

(71) Applicants: ImmuneSensor Therapeutics, Inc., Dallas, TX (US); The Board of Regents of the University of Texas System, Austin, TX (US)

(72) Inventors: Jian Qiu, Dallas, TX (US); Qi Wei, Dallas, TX (US); Matt Tschantz, Plano, TX (US); Heping Shi, Coppell, TX (US); Youtong Wu, Dallas, TX (US); Hulling Tan, Dallas, TX (US); Lijun Sun, Dallas, TX (US); Chuo Chen, Dallas, TX (US); Zhijian Chen, Dallas, TX (US)

(73) Assignees: IMMUNESENSOR THERAPEUTICS, INC., Dallas, TX (US); THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 20 days.

(21) Appl. No.: 17/446,951

(22) Filed: Sep. 3, 2021

(65) Prior Publication Data

US 2023/0081291 A1 Mar. 16, 2023

Related U.S. Application Data

(60) Provisional application No. 63/196,146, filed on Jun. 2, 2021, provisional application No. 63/124,713, filed on Dec. 11, 2020, provisional application No. 63/074,446, filed on Sep. 3, 2020.

(51) Int. Cl.

| | |
|---|---|
| ***C07D 215/38*** | (2006.01) |
| ***C07D 401/14*** | (2006.01) |
| ***C07D 215/42*** | (2006.01) |
| ***C07D 215/46*** | (2006.01) |
| ***C07D 401/04*** | (2006.01) |
| ***C07D 403/04*** | (2006.01) |
| ***C07D 405/14*** | (2006.01) |
| ***C07D 409/14*** | (2006.01) |
| ***C07D 413/14*** | (2006.01) |
| ***C07D 417/14*** | (2006.01) |
| ***C07D 471/08*** | (2006.01) |
| ***C07D 491/048*** | (2006.01) |
| ***C07F 9/6503*** | (2006.01) |
| ***C07F 9/6506*** | (2006.01) |

(52) U.S. Cl.

CPC ......... *C07D 401/14* (2013.01); *C07D 215/38* (2013.01); *C07D 215/42* (2013.01); *C07D 215/46* (2013.01); *C07D 401/04* (2013.01); *C07D 403/04* (2013.01); *C07D 405/14* (2013.01); *C07D 409/14* (2013.01); *C07D 413/14* (2013.01); *C07D 417/14* (2013.01); *C07D 471/08* (2013.01); *C07D 491/048* (2013.01); *C07F 9/6506* (2013.01); *C07F 9/65031* (2013.01)

(58) Field of Classification Search

CPC .. C07D 401/14; C07D 401/04; C07D 215/38; C07D 215/42; C07D 215/46; C07D 403/04; C07D 409/14; C07D 413/14; C07D 417/14; C07D 471/08; C07D 491/048; C07F 9/65031; C07F 9/6506

See application file for complete search history.

(56) References Cited

U.S. PATENT DOCUMENTS

| | | | |
|---|---|---|---|
| 3,542,785 | A | 11/1970 | Carney |
| 3,668,207 | A | 6/1972 | Carney |
| 2021/0161898 | A1 | 6/2021 | Leleti et al. |
| 2021/0369747 | A1 | 12/2021 | Li et al. |
| 2022/0073470 | A1 | 3/2022 | Lowery et al. |
| 2023/0103498 | A1 | 4/2023 | Li et al. |
| 2023/0183179 | A1 | 6/2023 | Koyuncu et al. |

FOREIGN PATENT DOCUMENTS

| | | | |
|---|---|---|---|
| CN | 109111426 | * | 1/2019 |
| CN | 109111426 | A | 1/2019 |
| WO | WO-2019051269 | A1 | 3/2019 |
| WO | WO-2019241787 | A1 | 12/2019 |
| WO | WO-2020023846 | A1 | 1/2020 |
| WO | 2020142735 | * | 7/2020 |
| WO | WO-2020142735 | A1 | 7/2020 |
| WO | WO 2021/150645 | A1 | 7/2021 |
| WO | WO 2022/010948 | A1 | 1/2022 |
| WO | WO 2022/051634 | A1 | 3/2022 |

OTHER PUBLICATIONS

Bering, Organic Letters, vol. 17(12), Jun. 2015, 3134-31378. (Year: 2015).*
El-Feky, Journal of Fluorine Chemistry, vol. 161, May 2014, 87-94. (Year: 2014).*
Faldu, International Letters of CHemistry, Physics and Astronomy, vol. 25, Jan. 2014, 28-32. (Year: 2014).*
Kaod, E J MEd Chem, vol. 186, 1-19, Jan. 2020. (Year: 2020).*
Decout, 2021, Nature, vol. 21, 548-569. (Year: 2021).*
Jiang, J Hematology & Oncology, 13:81, 2020, 1-11. (Year: 2020).*
Zhang, E J Med Chem, 2022, vol. 238, 114480, 1-9. (Year: 2022).*
Bering, Luis et al. "Regioselective Metal-Free Cross-Coupling of Quinoline N -Oxides with Boronic Acids" *Org Lett* (2015), 17(12): 3134-3137. XP055862048.

(Continued)

*Primary Examiner* — D Margaret M Seaman
(74) *Attorney, Agent, or Firm* — Hugo Garrido; Carl A. Morales; Fenwick & West LLP

(57) ABSTRACT

The present disclosure provides compounds that are cGAS antagonists, methods of preparation of the compounds, pharmaceutical compositions comprising the compounds, and their use in medical therapy.

52 Claims, No Drawings

(56) References Cited

OTHER PUBLICATIONS

El-Feky, Said A. et al. "Synthesis, molecular modeling and anti-inflammatory screening of novel fluorinated quinoline incorporated benzimidazole derivatives using the Pfitzinger reaction" *J Fluorine Chem* (2014), 161: 87-94. XP055862414.
Faldu, V.J. et al. "Synthesis, Characterization and Biological Evaluation of some Newer 5-[6-Chloro/Fluoro/Nitro-2-(p-Chloro/Fluoro/Methyl Phenyl)-Quinolin-4-yl]-1,3,4-Oxadiazole-2-Thiols" *Int'l Lett Chemistry, Physics and Astronomy* (2014), 25: 26-32. XP055862416.
International Search Report and the Written Opinion of the International Searching Authority dated Nov. 26, 2021 in International Application No. PCT/US2021/049084 (WO/2022/051634 A1).
Lakhani et al. "ChemInform Abstract: Studies on Imidazolines and Benzimidazoles. Preparation and Antimicrobial Activity of 2-(2'-Aryl-6'/7'-substituted-quinolin-4'-yl)-4,5-dihydroimidazoles/benzimidazoles and Their Mannich Bases", *J Indian Chem Soc* (1988), 65(3): 197-199. XP055862106.
Osamia, Lamiaa et al. "Synthesis and molecular modeling of new quinoline derivatives as antitumor agents" *Der Pharma Chemica* (2016 ), 8(14): 100-110. XP55106829.
Pirrung, Michael C. et al. "High-Throughput Catch-and-Release Synthesis of Oxazoline Hydroxamates. Structure-Activity Relationships in Novel Inhibitors of *Escherichia coli* LpxC: In Vitro Enzyme Inhibition and Antibacterial Properties" *J American Chem Soc* (2003), 125(6): 1575-1586. XP055106829.
Rajendran, Suresh et al. "$SnCl_2$ -Catalyzed Selective Atom Economic Imino Diels—Alder Reaction: Synthesis of 2-(1H -Pyrrole [2.3- b ]pyridin-3-yl)quinolines" *J Org Chem* (2012), 77(3): 1468-1476. XP055607680.
Rane, Rajesh A. et al. "Synthesis and evaluation of novel 4-nitropyrrole-based 1,3,4-oxadiazole derivatives as antimicrobial and anti-tubercular agents" *European J Medicinal Chem* (2013), 70: 49-58. XP028794132.
Verbanac, Donatella et al. "Synthesis and evaluation of antibacterial and antioxidant activity of novel 2-phenyl-quinoline analogs derivatized at position 4 with aromatically substituted 4H-1,2,4-triazoles" *J Enzyme Inhibition and Medicinal Chem* (2016), 31(sup2): 104-110. XP055862418.
Yu, X. Y. et al. "A series of quinoline analogues as potent inhibitors of C. albicans prolyl tRNA synthetase" *Bioorg Med Chem Lett* (2001), 11(4): 541-544. XP004230054.
Eiden, F., et al., English abstract "Acetamidacetal-Cyclisierung, 2. Mitt. 2-Aminochinoline und Pyrrolo[2,3-b]chinoline", Archiv Der Pharmazie, Wiley Verlag, Weinheim, vol. 319, No. 4, Jan. 1, 1986, pp. 338-347, XP002483905, ISSN: 0365-6233, DOI: 10.1002/ARDP.19863190409.
International Preliminary Report on Patentability, Chapter I, Patent Cooperation Treaty Application No. PCT/US2021/049084, dated Mar. 16, 2023, 9 pages.
International Search Report and Written Opinion, Patent Cooperation Treaty Application No. PCT/US2023/063623, dated Jun. 5, 2023, 13 pages.
Ishiwaka, T., et al., "Reaction of 2-Aminobenzophenones with Aliphatic Acids in the Presence of Polyphosphoric Acid", Bulletin of the Chemical Society of Japan, vol. 43, Issue 6, Jun. 1970, pp. 1839-1843, XP00905724 7, ISSN: 0009-2673.
Jensen, J.A., et al., "New one-step synthesis of 2,4-bis(dialkylamino)quinolines and 4,6- bis(dialkylamino)thieno[2,3-b]pyridines", Chemica Scripta, Kungliga Vetenskapsakademien, SE, vol. 28, No. 4, Jan. 1, 1988 (Jan. 1, 1988), pp. 435-437, XP009544590, ISSN: 0004-2056.
Kobayashi, K., et al., "A convenient synthesis of quinolines by reactions of o-isocyano-β- methoxystyrenes with nucleophiles", Tetrahedron, vol. 60, No. 50, Dec. 6, 2004 (Dec. 6, 2004), pp. 11639-11645, XP004628626,ISSN: 0040-4020, DOI:10.1016/J.TET.2004.09.069.

* cited by examiner

QUINOLINE CGAS ANTAGONIST COMPOUNDS

1. BACKGROUND

Cyclic GMP-AMP synthase (cGAS) (UniProtKB-Q8N884) is an enzyme that acts as a DNA sensor to elicit an immune response to pathogens via activation of the stimulator of interferon genes (STING) receptor. Aberrant activation of cGAS by self-DNA is shown to underlie debilitating and sometimes fatal autoimmune diseases. Knockout studies in animal models have indicated that inhibiting cGAS is a promising approach for therapeutic intervention. Additionally, recent studies have shown that the cGAS-STING pathway plays a key role in the innate immune response to tumors, and stimulation of the pathway is a promising strategy being tested clinically for cancer immunotherapy.

An ongoing need exists in the art for effective treatments of human autoimmune and auto-inflammatory diseases, such as systemic lupus erythematosus (SLE), scleroderma, psoriasis, Aicardi Goutieres syndrome (AGS), Sjogren's syndrome, rheumatoid arthritis, inflammatory bowel diseases, multiple sclerosis, diabetes, cardiovascular, and neurodegenerative diseases. Accordingly, there remains a need to find potent and selective small molecule inhibitors of cGAS useful for the treatment of these and other debilitating human diseases associated with the aberrant activation of cGAS.

2. SUMMARY

The present disclosure relates to small molecule cGAS antagonist compounds, methods of preparation of the compounds, pharmaceutical compositions comprising the compounds, and their use in medical therapy. In particular, the present disclosure provides quinoline cGAS antagonist compounds, which find utility as inhibitors of cGAS. An advantage of the compounds provided herein is that a broad range of pharmacological activities is possible, consistent with the inhibition of cGAS. In addition, the disclosure provides methods of using the compounds described herein for the treatment of inflammatory, allergic, autoimmune, and infectious diseases. The compounds can also be used for the treatment of senescence- or age-related diseases, such as neurodegenerative diseases, cardiovascular diseases, liver and renal diseases, cancer, and premature aging.

It has now been found that compounds of the disclosure, and pharmaceutically acceptable compositions thereof, are effective for the inhibition of cGAS. Such compounds of the disclosure have the general formula I:

I

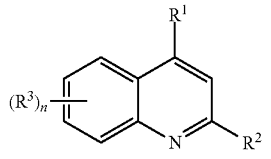

or a pharmaceutically acceptable salt thereof, wherein each variable is as defined and described herein.

Compounds of the present disclosure, and pharmaceutically acceptable compositions thereof, are useful for treating a variety of diseases, disorders, or conditions, associated with aberrant activation of cGAS. Such diseases, disorders, or conditions include those described herein.

Compounds provided by the present disclosure are also useful for the study of cGAS enzymes in biological and pathological phenomena and the comparative evaluation of new cGAS antagonists or other regulators of cGAS, signaling pathways, and cytokine levels in vitro or in vivo.

3. DETAILED DESCRIPTION

In the following disclosure, certain specific details are set forth in order to provide a thorough understanding of various embodiments. However, one skilled in the art will understand that the methods and uses described herein may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

3.1. Definitions

Compounds of the present disclosure include those described generally herein, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ EQ Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1 to 6 aliphatic carbon atoms. In some embodiments, aliphatic groups contain 1 to 5 aliphatic carbon atoms. In other embodiments, aliphatic groups contain 1 to 4 aliphatic carbon atoms. In still other embodiments, aliphatic groups contain 1 to 3 aliphatic carbon atoms, and in yet other embodiments, aliphatic groups contain 1 to 2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7 to 12 ring members and 0 to 4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

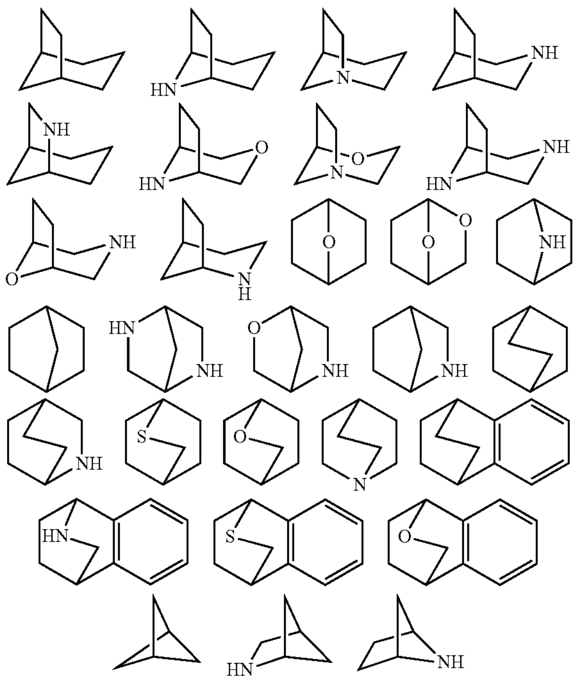

In some embodiments, bicyclo[1.1.1.]pentane is a phenyl isostere.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen; or an oxygen, sulfur, nitrogen, phosphorus, or silicon atom in a heterocyclic ring.

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

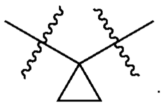 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of 4 to 14 ring members, wherein at least one ring in the system is aromatic and wherein each ring in the system contains 3 to 7 ring members. The term "aryl" may be used interchangeably with the term "aryl ring." In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more nonaromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from 1 to 5 heteroatoms. The term "heteroatom" in the context of "heteroaryl" particularly includes, but is not limited to, nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3b]-1,4-oxazin-3(4H)-one. A heteroaryl group may be monocyclic or bicyclic. A heteroaryl ring may include one or more oxo (=O) or thioxo (=S) substituent. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7- to 10-membered bicyclic heterocyclic moiety that is either saturated or partially unsaturated, and having, in addition to carbon atoms, one or more, preferably 1 to 4, heteroatoms, as defined above. When used in reference to a ring atom of a heterocycle, the term "nitrogen" includes a substituted nitrogen. As an example, in a saturated or partially unsaturated ring may have 0 to 3 heteroatoms selected from oxygen, sulfur or nitrogen.

A heterocyclic ring can be attached to a provided compound at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, bridged bicyclic, or spirocyclic. A heterocyclic ring may include one or more oxo (=O) or thioxo (=S) substituent. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the disclosure may contain "substituted" moieties. In general, the term "substituted" means that one or more hydrogens of the designated moiety are replaced with a suitable substituent. Unless otherwise indicated, an "optionally substituted" group may have a suitable substituent at one or more substitutable position of the group, and when more than one position in any given structure is substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-6}R^\circ$; $—(CH_2)_{0-6}OR^\circ$; $—O(CH_2)_{0-6}R^\circ$; $—O(CH_2)_{0-6}C(O)OR^\circ$; $—(CH_2)_{0-6}CH(OR^\circ)_2$; $—(CH_2)_{0-6}SR^\circ$; $—(CH_2)_{0-6}Ph$, which Ph may be substituted with R°; $—(CH_2)_{0-6}O(CH_2)_{0-1}Ph$ which Ph may be substituted with R°; —CH=CHPh, which Ph may be substituted with R°; $—(CH_2)_{0-6}O(CH_2)_{0-1}$-pyridyl which pyridyl may be substituted with R°; $—NO_2$; —CN; $—N_3$; $—(CH_2)_{0-6}N(R^\circ)_2$; $—(CH_2)_{0-6}N(R^\circ)C(O)R^\circ$; $—N(R^\circ)C(S)R^\circ$; $—(CH_2)_{0-6}N(R^\circ)C(O)NR^\circ_2$; $—N(R^\circ)C(S)NR^\circ_2$; $—(CH_2)_{0-6}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-6}C(O)R^\circ$; $—C(S)R^\circ$; $—(CH_2)_{0-6}C(O)OR^\circ$; $—(CH_2)_{0-6}C(O)SR^\circ$; $—(CH_2)_{0-6}C(O)OSiR^\circ_3$; $—(CH_2)_{0-6}OC(O)R^\circ$; $—OC(O)(CH_2)_{0-6}SR^\circ$, $—(CH_2)_{0-6}SC(O)R^\circ$; $—(CH_2)_{0-6}C(O)NR^\circ_2$; $—C(S)NR^\circ_2$; $—C(S)SR^\circ$; $—SC(S)SR^\circ$, $—(CH_2)_{0-6}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-6}SSR^\circ$; $—(CH_2)_{0-6}S(O)_2R^\circ$; $—(CH_2)_{0-6}S(O)_2OR^\circ$; $—(CH_2)_{0-6}OS(O)_2R^\circ$; $—S(O)_2NR^\circ_2$; $—(CH_2)_{0-6}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—P(O)(OR^\circ)_2$; $—OP(O)(R^\circ)OR^\circ$; $—OP(O)R^\circ_2$; $—OP(O)(OR^\circ)_2$; $SiR^\circ_3$; $—(C_{1-4}$ straight or branched)alkylene)O—$N(R^\circ)_2$; or $—(C_{1-4}$ straight or branched)alkylene)C(O)O—$N(R^\circ)_2$, wherein each R° may be substituted as defined below and is independently hydrogen, $C_{1-6}$ aliphatic, $—CH_2Ph$, $—O(CH_2)_{0-1}Ph$, $—CH_2$-(5- to 6-membered heteroaryl ring), or a 5- to 6-membered saturated, partially unsaturated, or aryl ring having 0 to 4 heteroatoms independently selected from nitrogen, oxygen, or sulfur, or, notwithstanding the definition above, two independent occurrences of R°, taken together with their intervening atom(s), form a 3- to 12-membered saturated, partially unsaturated, or aryl mono- or bicyclic ring having 0 to 4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, $—(CH_2)_{0-2}R^\bullet$, $—(haloR^\bullet)$, $—(CH_2)_{0-2}OH$, $—(CH_2)_{0-2}OR^\bullet$, $—(CH_2)_{0-2}CH(OR^\bullet)_2$, $—O(haloR^\bullet)$, —CN, $—N_3$, $—(CH_2)_{0-2}C(O)R^\bullet$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}NR^\bullet_2$, $—NO_2$, $—SiR^\bullet_3$, $—OSiR^\bullet_3$, $—C(O)SR^\bullet$, $—(C_{1-4}$ straight or branched alkylene)$C(O)OR^\bullet$, or $—SSR^\bullet$ wherein each $R^\bullet$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5- to 6-membered saturated, partially unsaturated, or aryl ring having 0 to 4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following:

=O, =S, $=NNR^*_2$, =NNHC(O)R*, =NNHC(O)OR*, $=NNHS(O)_2R^*$, =NR*, =NOR*, $—O(C(R^*_2))_{2-3}O—$, or $—S(C(R^*_2))_{2-3}S—$, wherein each independent occurrence of R* is selected from hydrogen, $C_{1-6}$ aliphatic which may be substituted as defined below, or an unsubstituted 5- to 6-membered saturated, partially unsaturated, or aryl ring having 0 to 4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of R* is selected from hydrogen, $C_{1-6}$ aliphatic which may be substituted as defined below, or an unsubstituted 5- to 6-membered saturated, partially unsaturated, or aryl ring having 0 to 4 heteroatoms independently selected from nitrogen, oxygen, or sulfur.

Suitable substituents on the aliphatic group of R* include halogen, $—R^{\bullet}$, -(halo$R^{\bullet}$), —OH, $—OR^{\bullet}$, —O(halo$R^{\bullet}$), —CN, —C(O)OH, $—C(O)OR^{\bullet}$, $—NH_2$, $—NHR^{\bullet}$, $—NR^{\bullet}_2$, or $—NO_2$, wherein each $R^{\bullet}$ is unsubstituted or where preceded by "halo" is substituted only with one or more halogens, and is independently $C_{1-4}$ aliphatic, $—CH_2Ph$, $—O(CH_2)_{0-1}Ph$, or a 5- to 6-membered saturated, partially unsaturated, or aryl ring having 0 to 4 heteroatoms independently selected from nitrogen, oxygen, or sulfur.

Suitable substituents on a substitutable nitrogen of an "optionally substituted" group include $—R^{\dagger}$, $—NR^{\dagger}_3$, $—C(O)R^{\dagger}$, $—C(O)OR^{\dagger}$, $—C(O)C(O)R^{\dagger}$, $—C(O)CH_2C(O)R^{\dagger}$, $—S(O)_2R^{\dagger}$, $—S(O)_2NR^{\dagger}_2$, $—C(S)NR^{\dagger}_2$, $—C(NH)NR^{\dagger}_2$, or $—N(R^{\dagger})S(O)_2R^{\dagger}$; wherein each $R^{\dagger}$ is independently hydrogen, $C_{1-6}$ aliphatic which may be substituted as defined below, unsubstituted —OPh, or an unsubstituted 5- to 6-membered saturated, partially unsaturated, or aryl ring having 0 to 4 heteroatoms independently selected from nitrogen, oxygen, or sulfur, or, notwithstanding the definition above, two independent occurrences of $R^{\dagger}$, taken together with their intervening atom(s) form an unsubstituted 3- to 12-membered saturated, partially unsaturated, or aryl monocyclic or bicyclic ring having 0 to 4 heteroatoms independently selected from nitrogen, oxygen, or sulfur.

Suitable substituents on the aliphatic group of $R^{\dagger}$ are independently halogen, $—R^{\bullet}$, -(halo$R^{\bullet}$), —OH, $—OR^{\bullet}$, —O(halo$R^{\bullet}$), —CN, —C(O)OH, $—C(O)OR^{\bullet}$, $—NH_2$, $—NHR^{\bullet}$, $—NR^{\bullet 2}$, or $—NO_2$, wherein each $R^{\bullet}$ is unsubstituted or where preceded by "halo" is substituted only with one or more halogens, and is independently $C_{1-4}$ aliphatic, $CH_2Ph$, $—O(CH_2)_{0-1}Ph$, or a 5- to 6-membered saturated, partially unsaturated, or aryl ring having 0 to 4 heteroatoms independently selected from nitrogen, oxygen, or sulfur.

As used herein, the term "provided compound" refers to any genus, subgenus, and/or species set forth herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, which is incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this disclosure. Such compounds are useful, for example, as analytical tools, as probes in biological assays, or as therapeutic agents in accordance with the present disclosure.

As used herein, the term "antagonist" is defined as a compound that binds to and/or inhibits cGAS with measurable affinity. In certain embodiments, a cGAS antagonist has an $IC_{50}$ and/or binding constant of less than about 30 μM or less than about 2 μM.

3.2. Compounds of the Present Disclosure

Compounds of the present disclosure, and compositions thereof, are useful as cGAS antagonists. In some embodiments, a provided compound inhibits cGAS.

The present disclosure provides a compound of formula I:

I

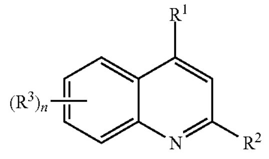

or a pharmaceutically acceptable salt thereof, wherein:

$R^1$ is halogen, —OR, —$NR_2$, —NRC(O)OR, —NRC(O)R, —NRC(O)$NR_2$, —$NRSO_2R$, —SR, —$SO_2R$, —$SO_2NR_2$, —S(O)R, or $R^A$, particularly —$NR_2$ or $R^A$;

each R is independently hydrogen or an optionally substituted group selected from $C_{1-6}$ aliphatic; benzyl; phenyl; a 4- to 10-membered saturated or partially unsaturated monocyclic or bicyclic carbocyclic or heterocyclic ring having 1 to 3 heteroatoms independently selected from nitrogen, oxygen, phosphorus, and sulfur; and a 5- to 6-membered heteroaryl ring having 1 to 4 heteroatoms independently selected from nitrogen, oxygen, phosphorus, and sulfur, or: two R groups on the same nitrogen are optionally taken together with their intervening atoms to form an optionally substituted 4- to 7-membered saturated, partially unsaturated, or heteroaryl ring having 0 to 3 heteroatoms, in addition to the nitrogen, independently selected from nitrogen, oxygen, phosphorus, and sulfur;

$R^2$ is halogen, —OR, —$NR_2$, —$NRNR_2$, —NRC(O)OR, —NRC(O)R, —NRC(O)$NR_2$, —$NRSO_2R$, —SR, —$SO_2R$, —$SO_2NR_2$, —S(O)R, or $R^B$, particularly —$NR_2$ or $R^B$;

each $R^3$ is independently halogen, —OR, —$NR_2$, —SR, or —$R^C$, particularly halogen, such as chloro;

$R^A$, $R^B$, and $R^C$, independently, are an optionally substituted group selected from $C_{1-6}$ aliphatic; phenyl; a 4- to 10-membered saturated or partially unsaturated monocyclic or bicyclic carboxylic or heterocyclic ring having 1 to 3 heteroatoms independently selected from nitrogen, oxygen, phosphorus, and sulfur; and a 5- to 6-membered heteroaryl ring having 1 to 4 heteroatoms independently selected from nitrogen, oxygen, phosphorus, and sulfur; and n is 1, 2, 3, or 4.

In certain embodiments, the present disclosure provides a compound of formula I, wherein:

$R^1$ is $R^A$, wherein $R^A$ is an optionally substituted 5- to 6-membered heteroaryl ring having 1 to 4 heteroatoms independently selected from nitrogen, oxygen, phosphorus, and sulfur (particularly imidazole or pyrazole, including 1-imidazole or 4-pyrazole);

$R^2$ is $R^B$, wherein $R^B$ is a substituted 4- to 7-membered saturated heterocyclic ring having 1 to 3 heteroatoms independently selected from nitrogen, oxygen, phosphorus, and sulfur (particularly pyrrolidine, piperidine, morpholine, and piperazine), e.g., substituted with one or two groups selected from halogen, =O, =$CH_2$, $C_{1-4}$alkyl, $C_{1-4}$haloalkyl, $C_{3-6}$cycloalkyl, —OH, —$(CH_2)_{1-2}$—OH, —$OC_{1-4}$alkyl, —$(CH_2)_{0-2}CO_2H$, —$(CH_2)_{0-2}O(CH_2)_{1-5}CO_2H$, —$(CH_2)_{0-2}O(CH_2)_{1-5}CO_2C_{1-4}$alkyl, —$(CH_2)_{0-2}CO_2C_{1-4}$alkyl, —$NH_2$, —$(CH_2)_{0-2}CONH_2$, —$(CH_2)_{0-2}CONR^a$—$(CH_2)_{1-2}CO_2H$, —$(CH_2)_{0-2}SO_3H$, —$(CH_2)_{0-2}SO_2NH_2$, —$(CH_2)_{0-2}SO_2NHC_{1-4}$alkyl, or —$(CH_2)_{0-2}NR^aSO_2C_{1-4}$alkyl, wherein $R^a$, independently for each occurrence, is H or $C_{1-4}$alkyl; and each $R^3$ is independently halogen, such as chloro, including dichloro, including wherein n is 2 and $R^3$ is chloro at the 7- and 8-positions with respect to the quinoline ring.

In other embodiments, the present disclosure provides a compound of formula I, wherein:

$R^1$ is $R^A$, wherein $R^A$ is an optionally substituted 5- to 6-membered heteroaryl ring having 1 to 4 heteroatoms independently selected from nitrogen, oxygen, phosphorus, and sulfur (particularly imidazole or pyrazole, including 1-imidazole or 4-pyrazole);

$R^2$ is —$NR_2$, wherein one R is H or lower alkyl (particularly methyl), and the other R is substituted $C_{1-6}$ aliphatic, including optionally substituted —$C_{1-5}$alkylene-X; wherein X is selected from —OH, —$OC_{1-4}$alkyl, —$OC_{1-4}$alkylene-$CO_2H$, —O—$C_{1-4}$alkylene-$CO_2C_{1-4}$alkyl, —$CO_2H$, —$CO_2C_{1-4}$alkyl, —$NH_2$, —$CONH_2$, —$CONHC_{1-4}$alkyl, —$CONR^a$—$(CH_2)_{1-2}$—OH, —$CONR^a$—$(CH_2)_{1-2}$—COOH, —$CONR^a$—$(CH_2)_{1-2}$—$CONH_2$, —$SO_3H$, —$SO_2NH_2$, —$SO_2NHC_{1-4}$alkyl, —$NR^aSO_2C_{1-4}$alkyl, —P(O)$(OH)_2$, and —OP(O)(H)(OH), wherein $R^a$, independently for each occurrence, is H or $C_{1-4}$alkyl; and each $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I, wherein:

$R^1$ is —$NR_2$, wherein one R is H or lower alkyl (particularly methyl), and the other R is substituted $C_{1-6}$ aliphatic, including optionally substituted —$C_{1-4}$alkylene-X; wherein X is selected from —OH, —$OC_{1-4}$alkyl, —$CO_2H$, —O—$C_{1-4}$alkylene-$CO_2H$, —O—$C_{1-4}$alkylene-$CO_2C_{1-4}$alkyl, —$CO_2C_{1-4}$alkyl, —$CONH_2$, and —$CONHC_{1-4}$alkyl;

$R^2$ is $R^B$, wherein $R^B$ is an optionally substituted 5- to 6-membered heteroaryl ring having 1 to 4 heteroatoms independently selected from nitrogen, oxygen, phosphorus, and sulfur (particularly imidazole or pyrazole, including 1-imidazole or 4-pyrazole); and each $R^3$ is independently halogen, such as chloro, including dichloro, including wherein n is 2 and $R^3$ is chloro at the 7- and 8-positions with respect to the quinoline ring.

In other embodiments, the present disclosure provides a compound of formula I, wherein:

$R^1$ is $R^A$, wherein $R^A$ is an optionally substituted 5- to 6-membered heteroaryl ring having 1 to 4 heteroatoms independently selected from nitrogen, oxygen, phosphorus, and sulfur (particularly imidazole or pyrazole, including 1-imidazole or 4-pyrazole);

$R^2$ is substituted phenyl (particularly substituted with one or two groups selected from halogen, $C_{1-4}$alkyl, —OH, —$OC_{1-4}$alkyl, —$CO_2H$, —$CO_2C_{1-4}$alkyl, —$(CH_2)_{0-2}O(CH_2)_{1-5}CO_2H$, —$(CH_2)_{0-2}O(CH_2)_{1-5}CO_2C_{1-4}$alkyl, —$NH_2$, and —$CONH_2$); and each $R^3$ is independently halogen, such as chloro, including dichloro, including wherein n is 2 and $R^3$ is chloro at the 7- and 8-positions with respect to the quinoline ring.

In other embodiments, the present disclosure provides a compound of formula I, wherein:

$R^1$ is $R^A$, wherein $R^A$ is an optionally substituted 5- to 6-membered heteroaryl ring having 1 to 4 heteroatoms independently selected from nitrogen, oxygen, phosphorus, and sulfur (particularly imidazole or pyrazole, including 1-imidazole or 4-pyrazole);

$R^2$ is $R^B$, wherein $R^B$ is an optionally substituted $C_{1-6}$ aliphatic, preferably a substituted $C_{1-6}$aliphatic (particularly —$(CR_2)_{1-4}NR(CR_2)_{0-6}CO_2R$); and each $R^3$ is independently halogen, such as chloro, including dichloro, including wherein n is 2 and $R^3$ is chloro at the 7- and 8-positions with respect to the quinoline ring.

In certain embodiments, the disclosure provides a compound, wherein the compound is of formula I*:

I*

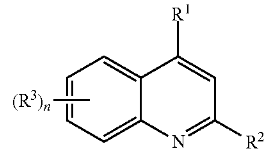

or a pharmaceutically acceptable salt thereof, wherein:

$R^1$ is

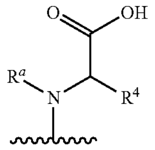

or an optionally substituted 5- to 6-membered heteroaryl ring having 1 to 4 heteroatoms independently selected from nitrogen, oxygen, and sulfur;

$R^2$ is —$NR^aR^5$

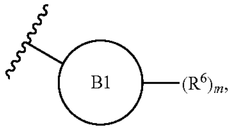

or

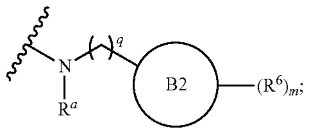

each $R^3$ is independently halogen, —OR, —$NR_2$, —SR, or —$R^C$;

Ring B1 is phenyl, preferably substituted phenyl; a 4- to 10-membered saturated or partially unsaturated monocyclic or bicyclic carboxylic or heterocyclic ring having 1 to 3 heteroatoms independently selected from nitrogen, oxygen, and sulfur; or a 5- to 6-membered heteroaryl ring having 1 to 4 heteroatoms independently selected from nitrogen, oxygen, and sulfur;

Ring B2 is phenyl; a 4- to 7-membered saturated or partially unsaturated carbocyclic or heterocyclic ring having 1 to 3 heteroatoms independently selected from nitrogen, oxygen, and sulfur; or a 5- to 6-membered heteroaryl ring having 1 to 4 heteroatoms independently selected from nitrogen, oxygen, and sulfur;

each R is independently hydrogen or an optionally substituted group selected from $C_{1-6}$ aliphatic; benzyl; phenyl; a 4- to 7-membered saturated or partially unsaturated carbocyclic or heterocyclic ring having 1 to 3 heteroatoms independently selected from nitrogen, oxygen, and sulfur; and a 5- to 6-membered heteroaryl ring having 1 to 4 heteroatoms independently selected from nitrogen, oxygen, and sulfur, $R^4$ is hydrogen or an optionally substituted $C_{1-6}$ aliphatic;

$R^5$ is —$(CR_2)_{0-4}OR$, —$(CR_2)_{0-5}CO_2R$, —$(CR_2)_{0-5}CONR_2$, —$(CR_2)_{0-4}C(O)NR(CR_2)_{0-4}CO_2R$, —$(CR_2)_{0-4}C(O)NR(CR_2)_{0-4}CONR_2$, —$(CR_2)_{0-4}NRC(O)R$, —$(CR_2)_{0-4}SO_3R$, —$(CR_2)_{0-4}SO_2NR_2$, —$(CR_2)_{0-4}OSO_2NR_2$, —$(CR_2)_{0-4}NRSO_2R$, —$(CR_2)_{0-4}NRSO_2OR$, —$(CR_2)_{0-4}OP(OR)_2$, —$(CR_2)_{0-4}OP(O)(OR)_2$, —$(CR_2)_{0-4}P(O)(OR)_2$, —$(CR_2)_{0-4}OP(O)(H)OR$, or $R^B$;

each $R^6$ is independently halogen, —COR, —$(CR_2)_{0-4}CO_2R$, —$(CR_2)_{0-4}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-4}SO_3R$, —$(CR_2)_{0-4}SO_2NR_2$, —$(CR_2)_{0-4}OSO_2NR_2$, —$(CR_2)_{0-4}NRSO_2R$, —$(CR_2)_{0-4}NRSO_2OR$, —$(CR_2)_{0-4}$—$OP(OR)_2$, —$(CR_2)_{0-4}OP(O)(OR)_2$, —$(CR_2)_{0-4}P(O)(OR)_2$, —$(CR_2)_{0-4}OP(O)(H)OR$, —$B(OR)_2$, or $R^B$;

$R^B$ and $R^C$, independently, are an optionally substituted group selected from $C_{1-6}$ aliphatic; phenyl; a 4- to 10-membered saturated or partially unsaturated monocyclic or bicyclic carboxylic or heterocyclic ring having 1 to 3 heteroatoms independently selected from nitrogen, oxygen, and sulfur; and a 5- to 6-membered heteroaryl ring having 1 to 4 heteroatoms independently selected from nitrogen, oxygen, and sulfur;

each $R^a$ is independently H or $C_{1-6}$alkyl;

each m is 0, 1, 2, 3, or 4;

n is 1, 2, 3, or 4;

q is 0, 1, or 2.

In some embodiments, $R^1$ is an optionally substituted 5- to 6-membered heteroaryl ring having 1 to 4 heteroatoms independently selected from nitrogen, oxygen, and sulfur.

In some embodiments, $R^1$ is imidazole. In some embodiments, the imidazole is unsubstituted. In some embodiments, $R^1$ is

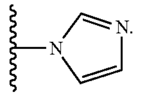 [SMILES: *n1ccnc1]

In some embodiments, $R^1$ is pyrazole. In some embodiments, the pyrazole is unsubstituted. In some embodiments, $R^1$ is

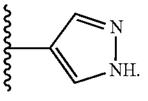 [SMILES: *c1cn[nH]c1]

In some embodiments, $R^1$ is

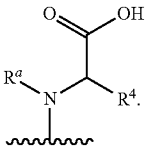

In some embodiments, $R^4$ is $C_{1-6}$ alkyl.

In some embodiments, at least one occurrence of $R^3$ is halogen. In some embodiments, at least one occurrence of $R^3$ is chloro. In some embodiments, n is 2 and both $R^3$ are chloro. In some embodiments, n is 2 and $R^3$ is chloro at the 7- and 8-positions with respect to the quinoline ring.

In some embodiments, $R^2$ is —$NR^aR^5$.

In some embodiments, $R^5$ is —$(CR_2)_{2-4}OR$, —$(CR_2)_{0-5}CO_2R$, —$(CR_2)_{0-5}CONR_2$, —$(CR_2)_{0-4}C(O)NR(CR_2)_{0-4}CO_2R$, —$(CR_2)_{0-4}C(O)NR(CR_2)_{0-4}CONR_2$, —$(CR_2)_{0-4}NRC(O)R$, —$(CR_2)_{0-4}SO_3R$, —$(CR_2)_{0-4}SO_2NR_2$, —$(CR_2)_{0-4}OSO_2NR_2$, —$(CR_2)_{0-4}NRSO_2R$, —$(CR_2)_{0-4}NRSO_2OR$, —$(CR_2)_{0-4}OP(OR)_2$, —$(CR_2)_{0-4}OP(O)(OR)_2$, —$(CR_2)_{0-4}P(O)(OR)_2$, or —$(CR_2)_{0-4}OP(O)(H)OR$.

In some embodiments, $R^5$ is —$(CR_2)_{2-4}OR$, —$(CR_2)_{1-5}CO_2R$, —$(CR_2)_{1-5}CONR_2$, —$(CR_2)_{0-4}C(O)NR(CR_2)_{0-4}CO_2R$, —$(CR_2)_{0-4}C(O)NR(CR_2)_{0-4}CONR_2$, —$(CR_2)_{0-4}NRC(O)R$, —$(CR_2)_{0-4}SO_3R$, —$(CR_2)_{0-4}SO_2NR_2$, —$(CR_2)_{0-4}OSO_2NR_2$, —$(CR_2)_{0-4}NRSO_2R$, —$(CR_2)_{0-4}NRSO_2OR$, —$(CR_2)_{0-4}OP(OR)_2$, —$(CR_2)_{0-4}P(O)(OR)_2$, —$(CR_2)_{0-4}P(O)(OR)_2$, or —$(CR_2)_{0-4}OP(O)(H)OR$.

In some embodiments, $R^5$ is —$(CH_2)_{2-4}OH$, —$(CH_2)_{2-4}O(CH_2)_{1-5}CO_2H$, —$(CH_2)_{2-4}O(CH_2)_{1-5}CO_2C_{1-4}alkyl$, —$(CH_2)_{0-3}CH(CH_2OH)_2$, —$(CH_2)_{2-4}OC_{1-4}alkyl$, —$(CH_2)_{1-5}CO_2H$, —$(CH_2)_{1-5}CO_2C_{1-4}alkyl$, —$(CH_2)_{1-4}CONH_2$, —$(CH_2)_{1-4}CONHC_{1-4}alkyl$, —$(CH_2)_{1-4}CON(C_{1-4}alkyl)_2$, —$(CH_2)_{1-4}C(O)NR^a(CH_2)_{1-4}CO_2H$, —$(CH_2)_{1-4}C(O)NR^a(CH_2)_{1-4}CONH_2$, —$(CH_2)_{1-4}C(O)NR^a(CH_2)_{1-4}CONHC_{1-4}alkyl$, —$(CH_2)_{1-4}C(O)NR^a(CH_2)_{1-4}CON(C_{1-4}alkyl)_2$, —$(CH_2)_{0-4}NR^aC(O)(CH_2)_{1-5}CO_2H$, —$(CH_2)_{0-4}NR^aC(O)(CH_2)_{1-5}CO_2C_{1-4}alkyl$, —$(CH_2)_{2-4}SO_3H$, —$(CH_2)_{2-4}SO_3C_{1-4}alkyl$, —$(CH_2)_{2-4}SO_2NH_2$, —$(CH_2)_{2-4}SO_2NHC_{1-4}alkyl$, —$(CH_2)_{2-4}SO_2N(CH_{1-4}alkyl)_2$, —$(CH_2)_{2-4}OSO_2NH_2$, —$(CH_2)_{2-4}NR^aSO_2C_{1-4}alkyl$, —$(CH_2)_{2-4}NR^aSO_3H$, —$(CH_2)_{1-4}OP(OH)_2$, —$(CH_2)_{1-4}P(O)(OH)_2$, —$(CH_2)_{1-4}P(O)(OH)(OC_{1-4}alkyl)$, or —$(CH_2)_{2-4}OP(O)(H)OH$, wherein $R^a$, independently for each occurrence, is H or $C_{1-6}alkyl$.

In some embodiments, $R^5$ is —$(CH_2)_{2-4}OH$, —$(CH_2)_{2-4}O(CH_2)_{1-5}CO_2H$, —$(CH_2)_{2-4}O(CH_2)_{1-5}CO_2C_{1-4}alkyl$, —$(CH_2)_{0-3}CH(CH_2OH)_2$, —$(CH_2)_{1-5}CO_2H$, —$(CH_2)_{1-5}CONH_2$, —$(CH_2)_{1-4}C(O)NR^a(CH_2)_{1-4}CO_2H$, —$(CH_2)_{1-4}C(O)NR^a(CH_2)_{1-4}CONH_2$, —$(CH_2)_{0-4}NR^aC(O)(CH_2)_{1-5}CO_2H$, —$(CH_2)_{0-4}NR^aC(O)(CH_2)_{1-5}CO_2C_{1-4}alkyl$, —$(CH_2)_{2-4}SO_3H$, —$(CH_2)_{2-4}SO_2NH_2$, —$(CH_2)_{2-4}SO_2NR^aC_{1-4}alkyl$, —$(CH_2)_{2-4}NR^aSO_2C_{1-4}alkyl$, —$(CH_2)_{1-4}P(O)(OH)_2$, or —$(CH_2)_{2-4}OP(O)(H)OH$, wherein $R^a$, independently for each occurrence, is H or $C_{1-4}alkyl$.

In some embodiments, $R^2$ is

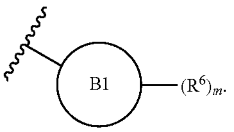

In some embodiments, m is 1, 2, 3, or 4.

In some embodiments, Ring B1 is substituted phenyl. In some embodiments, the phenyl is substituted with one or more carboxyl groups.

In some embodiments, Ring B1 is a 3-carboxyphenyl group that is optionally substituted with one or more $R^6$ groups.

In some embodiments, Ring B1 is a 3,5-dicarboxyphenyl group that is optionally substituted with one or more $R^6$ groups.

In some embodiments, Ring B1 is a 4- to 10-membered saturated or partially unsaturated monocyclic or bicyclic carbocyclic or heterocyclic ring having 1 to 3 heteroatoms independently selected from nitrogen, oxygen, and sulfur.

In some embodiments, Ring B1 is a 5- to 6-membered heteroaryl ring having 1 to 4 heteroatoms independently selected from nitrogen, oxygen, and sulfur.

In some embodiments, $R^2$ is

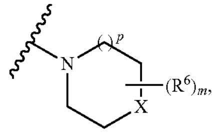

wherein X is absent (i.e., a bond in the ring), —$CR_2$—, —NR—, —O—, —S—, or —$SO_2$—; and p is 0, 1, or 2. In some embodiments, X is —$CR_2$—, —NR—, or —O—. In some embodiments, p is 1. In some embodiments, m is 1, 2, 3, or 4.

In some embodiments, each $R^6$ is independently halogen, —$C_{1-4}alkyl$, —$C_{1-4}haloalkyl$, $C_{3-6}cycloalkyl$, —$(CH_2)_{0-4}CO_2H$, —$(CH_2)_{0-4}CO_2C_{1-4}alkyl$, —$(CH_2)_{0-4}CO_2C_{1-4}haloalkyl$, —$(CH_2)_{0-4}CONH_2$, —$(CH_2)_{0-4}CONHC_{1-4}alkyl$, —$(CH_2)_{0-4}CON(C_{1-4}alkyl)_2$, —$(CH_2)_{0-4}CO(N\text{-proline})$, —$(CH_2)_{0-4}C(O)NR^a(CH_2)_{1-4}CO_2H$, —$(CH_2)_{0-4}C(O)NR^a(CH_2)_{1-4}CONH_2$, —$(CH_2)_{0-4}C(O)NR^a(CH_2)_{1-4}CONH_{1-4}alkyl$, —$(CH_2)_{0-4}C(O)NR^a(CH_2)_{1-4}CON(C_{1-4}alkyl)_2$, —OH, —$(CH_2)_{1-4}OH$, —$(CH_2)_{0-4}OC_{1-4}alkyl$, —$(CH_2)_{0-4}O(CH_2)_{1-5}CO_2H$, —$(CH_2)_{0-4}O(CH_2)_{1-5}CO_2C_{1-4}alkyl$, —$(CH_2)_{0-4}OC(O)C_{1-4}alkyl$, —$NH_2$, —$(CH_2)_{1-4}NH_2$, —$(CH_2)_{0-4}NHC_{1-4}alkyl$, —$(CH_2)_{0-4}N(C_{1-4}alkyl)_2$, —$(CH_2)_{0-4}SO_3H$, —$(CH_2)_{0-4}SO_2NH_2$, —$(CH_2)_{0-4}SO_2NHC_{1-4}alkyl$, —$(CH_2)_{0-4}NR^aSO_2C_{1-4}alkyl$, —$(CH_2)_{0-4}OP(OH)_2$, —$(CH_2)_{0-4}OP(OH)(OC_{1-4}alkyl)$, or —$(CR_2)_{0-4}OP(O)(H)OH$, wherein $R^a$, independently for each occurrence, is H or $C_{1-4}alkyl$.

In some embodiments, each $R^6$ is independently halogen, —$C_{1-4}alkyl$, —$C_{1-4}haloalkyl$, $C_{3-6}cycloalkyl$, —$(CH_2)_{0-4}CO_2H$, —$(CH_2)_{0-4}CO_2C_{1-4}alkyl$, —$(CH_2)_{0-4}CO(N\text{-proline})$, —$(CH_2)_{0-4}C(O)NR^a(CH_2)_{1-4}CO_2H$, —OH, —$(CH_2)_{1-4}OH$, —$(CH_2)_{0-4}OC_{1-4}alkyl$, —$(CH_2)_{0-4}O(CH_2)_{1-5}CO_2H$, —$(CH_2)_{0-4}O(CH_2)_{1-5}CO_2C_{1-4}alkyl$, —$(CH_2)_{0-4}OC(O)C_{1-4}alkyl$, —$(CH_2)_{0-4}SO_3H$, —$(CH_2)_{0-4}SO_2NH_2$, —$(CH_2)_{0-4}NR^aSO_2C_{1-4}alkyl$, —$(CH_2)_{0-4}OP(OH)_2$, or —$(CR_2)_{0-4}OP(O)(H)OH$.

In some embodiments, $R^6$ is independently halogen, —$C_{1-4}alkyl$, —$C_{1-4}haloalkyl$, $C_{3-6}cycloalkyl$, —$(CH_2)_{0-2}CO_2H$, —$(CH_2)_{0-2}CO_2C_{1-4}alkyl$, —$(CH_2)_{1-4}CO(N\text{-proline})$, —$(CH_2)_{0-2}C(O)NR^a(CH_2)_{1-4}CO_2H$, —OH, —$(CH_2)_{1-2}OH$, —$(CH_2)_{0-2}OC_{1-4}alkyl$, —$(CH_2)_{0-4}O(CH_2)_{1-5}CO_2H$, —$(CH_2)_{0-4}O(CH_2)_{1-5}CO_2C_{1-4}alkyl$, —$(CH_2)_{0-2}OC(O)C_{1-4}alkyl$, —$(CH_2)_{0-2}SO_3H$, —$(CH_2)_{0-2}SO_2NH_2$, —$(CH_2)_{0-2}NR^aSO_2C_{0-2}alkyl$, —$(CH_2)_{0-2}OP(OH)_2$, or —$(CR_2)_{0-2}OP(O)(H)OH$, wherein $R^a$, independently for each occurrence, is H or $C_{1-4}alkyl$.

In some embodiments, each $R^6$ is independently halogen, —$C_{1-4}alkyl$, —$C_{1-4}haloalkyl$, $C_{3-6}cycloalkyl$, —$(CH_2)_{1-4}CO_2H$, —$(CH_2)_{1-4}CO(N\text{-proline})$, —$(CH_2)_{1-4}C(O)NR^a(CH_2)_{1-4}CO_2H$, —OH, —$(CH_2)_{1-4}OH$, —$(CH_2)_{0-4}O(CH_2)_{1-5}CO_2H$, —$(CH_2)_{0-4}O(CH_2)_{1-5}CO_2C_{1-4}alkyl$, —$(CH_2)_{1-4}SO_3H$, —$(CH_2)_{1-4}SO_2NH_2$, —$(CH_2)_{1-4}NR^aSO_2C_{1-4}alkyl$, —$(CH_2)_{1-4}OP(OH)_2$, or —$(CR_2)_{1-4}OP(O)(H)OH$.

In some embodiments, each $R^6$ is independently halogen, —$C_{1-4}alkyl$, —$C_{1-4}haloalkyl$, —$CO_2H$, —$CO_2C_{1-4}alkyl$, —CO(N-proline), —$CH_2CO_2H$, —OH, —$OC_{1-4}alkyl$, —$(CH_2)_{0-4}O(CH_2)_{1-5}CO_2H$, —$(CH_2)_{0-4}O(CH_2)_{1-5}CO_2C_{1-4}alkyl$, —$OC(O)C_{1-4}alkyl$, —$SO_3H$, —$SO_2NH_2$, —$NR^aSO_2C_{1-4}alkyl$, —$OP(OH)_2$, or —OP(O)(H)OH.

In some embodiments, $R^2$ is

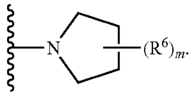

In some embodiments, m is 1, 2, 3, or 4. In some embodiments, m is 1 or 2.

In some embodiments, each $R^6$ is independently halogen, $=CH_2$, $=O$, $—C_{1-4}$alkyl, $—C_{1-4}$haloalkyl, $C_{3-6}$cycloalkyl, $—(CH_2)_{0-4}CO_2H$, $—(CH_2)_{0-4}CO_2C_{1-4}$alkyl, $—(CH_2)_{0-4}CO_2C_{1-4}$haloalkyl, $—(CH_2)_{0-4}CONH_2$, $—(CH_2)_{0-4}CONHC_{1-4}$alkyl, $—(CH_2)_{0-4}CON(C_{1-4}$alkyl$)_2$, $—(CH_2)_{0-4}$CO(N-proline), $—(CH_2)_{0-4}$CO(N-pyrrolidine-3-carboxylic acid), $—(CH_2)_{0-4}C(O)NR^a(CH_2)_{1-4}CO_2H$, $—(CH_2)_{0-4}C(O)NR^a—CH(C_{1-4}$alkyl)-$CO_2H$, $—(CH_2)_{0-4}C(O)NR^a(CH_2)_{1-4}CONH_2$, $—(CH_2)_{0-4}C(O)NR^a(CH_2)_{1-4}CONHC_{1-4}$alkyl, $—(CH_2)_{0-4}C(O)NR^a(CH_2)_{1-4}CON(C_{1-4}$alkyl$)_2$, —OH, $—(CH_2)_{1-4}OH$, $—(CH_2)_{0-4}OC_{1-4}$alkyl, $—(CH_2)_{0-4}O(CH_2)_{1-5}CO_2H$, $—(CH_2)_{0-4}O(CH_2)_{1-5}CO_2C_{1-4}$alkyl, $—(CH_2)_{0-4}OC(O)C_{1-4}$alkyl, $—NH_2$, $—(CH_2)_{1-4}NH_2$, $—(CH_2)_{0-4}NHC_{1-4}$alkyl, $—(CH_2)_{0-4}NR^aC(O)C_{1-4}$alkyl, $—(CH_2)_{0-4}NR^aC(O)Ph$, $—(CH_2)_{0-4}NR^aCO(CH_2)_{1-4}OH$, $—(CH_2)_{0-4}N(C_{1-4}$alkyl$)_2$, $—(CH_2)_{0-4}SO_3H$, $—(CH_2)_{0-4}SO_2NH_2$, $—(CH_2)_{0-4}SO_2NR^aC_{1-4}$alkyl, $—(CH_2)_{0-4}NR^aSO_2C_{1-4}$alkyl, $—(CH_2)_{0-4}NR^aSO_2Ph$, $—(CH_2)_{0-4}NR^aSO_2(CH_2)_{1-4}CO_2H$, $—(CH_2)_{0-4}OP(OH)_2$, $—(CH_2)_{0-4}OP(OH)(OC_{1-4}$alkyl), or $—(CR_2)_{0-4}OP(O)(H)OH$, wherein $R^a$, independently for each occurrence, is H or $C_{1-6}$alkyl.

In some embodiments, each $R^6$ is independently halogen, $=CH_2$, $=O$, $—C_{1-4}$alkyl, $—C_{1-4}$haloalkyl, $C_{3-6}$cycloalkyl, $—(CH_2)_{0-4}CO_2H$, $—(CH_2)_{0-4}CO_2C_{1-4}$alkyl, $—(CH_2)_{0-4}CO_2C_{1-4}$haloalkyl, $—(CH_2)_{0-4}$CO(N-proline), $—(CH_2)_{0-4}$CO(N-pyrrolidine-3-carboxylic acid), $—(CH_2)_{0-4}C(O)NR^a(CH_2)_{1-4}CO_2H$, $—(CH_2)_{0-4}C(O)NR^a—CH(C_{1-4}$alkyl)-$CO_2H$, —OH, $—(CH_2)_{1-4}OH$, $—OC_{1-4}$alkyl, $—(CH_2)_{0-4}O(CH_2)_{1-5}CO_2H$, $—(CH_2)_{0-4}O(CH_2)_{1-5}CO_2C_{1-4}$alkyl, $—(CH_2)_{0-4}NR^aC(O)C_{1-4}$alkyl, $—(CH_2)_{0-4}NR^aC(O)Ph$, $—(CH_2)_{0-4}NR^aCO(CH_2)_{1-4}OH$, $—(CH_2)_{0-4}SO_3H$, $—(CH_2)_{0-4}SO_2NH_2$, $—(CH_2)_{0-4}NR^aSO_2C_{1-4}$alkyl, $—(CH_2)_{0-4}NR^aSO_2Ph$, $—(CH_2)_{0-4}NR^aSO_2(CH_2)_{1-4}CO_2H$, $—(CH_2)_{0-4}OP(OH)_2$, or $—(CR_2)_{0-4}OP(O)(H)OH$, wherein $R^a$, independently for each occurrence, is H or $C_{1-4}$alkyl.

In some embodiments, each $R^6$ is independently halogen, $=CH_2$, $=O$, $—C_{1-4}$alkyl, $—C_{1-4}$haloalkyl, $—CO_2H$, $—CO_2C_{1-4}$alkyl, $—CO_2C_{1-4}$haloalkyl, —CO(N-proline), —CO(N-pyrrolidine-3-carboxylic acid), $—C(O)NR^a(CH_2)_{1-4}CO_2H$, $—C(O)NR^a—CH(C_{1-4}$alkyl)-$CO_2H$, —OH, $—OC_{1-4}$alkyl, $—(CH_2)_{0-4}O(CH_2)_{1-5}CO_2H$, $—(CH_2)_{0-4}O(CH_2)_{1-5}CO_2C_{1-4}$alkyl, $—NR^aC(O)C_{1-4}$alkyl, $—NR^aC(O)Ph$, $—NR^aCO(CH_2)_{1-4}OH$, $—SO_3H$, $—SO_2NH_2$, $—NR^aSO_2C_{1-4}$alkyl, $—NR^aSO_2Ph$, $—NR^aSO_2(CH_2)_{1-4}CO_2H$, $—OP(OH)_2$, or $—OP(O)(H)OH$, wherein $R^a$, independently for each occurrence, is H or $C_{1-4}$alkyl.

In some embodiments, each $R^6$ is independently fluoro, $=O$, $=CH_2$, methyl, cyclohexyl, morpholinyl, phenyl, $—CF_3$, —OMe, —OtBu, $—CO_2H$, $—CO_2C_{1-4}$alkyl, $—CO_2C_{1-4}$haloalkyl, $—(CH_2)_{1-4}O(CH_2)_{1-5}CO_2H$, $—(CH_2)_{1-4}O(CH_2)_{1-5}CO_2C_{1-4}$alkyl, or —OH.

In some embodiments, Ring B1 is a 5- to 6-membered heteroaryl ring having 1 to 4 heteroatoms independently selected from nitrogen, oxygen and sulfur, wherein a carbon atom of the 5- to 6-membered heteroaryl ring is directly bonded to the carbon at the 2-position of the quinolone ring;

In some embodiments, Ring B1 is imidazole or pyrazole. In some embodiments, the imidazole or pyrazole are unsubstituted.

In some embodiments, $R^2$ is

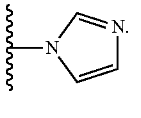

In some embodiments, $R^2$ is

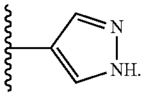

In some embodiments, $R^2$ is

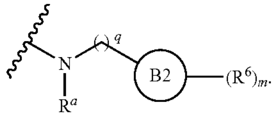

In some embodiments, m is 1, 2, 3, or 4.

In some embodiments, Ring B2 is phenyl.

In some embodiments, Ring B2 is a 4- to 7-membered saturated or partially unsaturated carbocyclic or heterocyclic ring having 1 to 3 heteroatoms independently selected from nitrogen, oxygen, and sulfur.

In some embodiments, Ring B2 is a 5- to 6-membered heteroaryl ring having 1 to 4 heteroatoms independently selected from nitrogen, oxygen, and sulfur.

In some embodiments, $R^2$ is

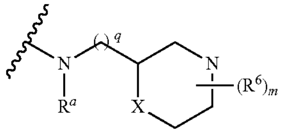

or

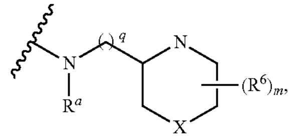

wherein X is absent (i.e., a bond in the ring), $—CR_2—$, —NR—, —O—, —S—, or $—SO_2—$; and m is 1, 2, 3, or 4. In some embodiments, $R^2$ is

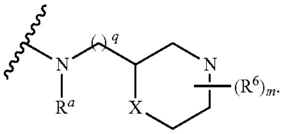

In some embodiments, $R^2$ is

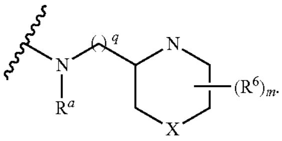

In some embodiments, X is $—CR_2—$, —NR—, or —O—. In some embodiments, q is 1 or 2. In some embodiments, q is 1. In some embodiments, m is 1 or 2.

In some embodiments, each $R^6$ is independently halogen, $—(CH_2)_{0-4}CO_2H$, $—(CH_2)_{0-4}CO_2C_{1-4}$alkyl, $—(CH_2)_{0-4}CONH_2$, $—(CH_2)_{0-4}CONHC_{1-4}$alkyl, —$(CH_2)_{0-4}CON(C_{1-4}alkyl)_2$, —$(CH_2)_{0-4}CO$(N-proline), —$(CH_2)_{0-4}C(C)NR^a(CH_2)_{1-4}CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}$ alkyl$)_2$, —OH, —$(CH_2)_{1-4}OH$, —$(CH_2)_{0-4}OC_{1-4}$alkyl, —$NH_2$, —$(CH_2)_{1-4}NH_2$, —$(CH_2)_{0-4}NHC_{1-4}$alkyl, —$(CH_2)_{0-4}N(C_{1-4}alkyl)_2$, —$(CH_2)_{0-4}SO_3H$, —$(CH_2)_{0-4}SO_2NH_2$, —$(CH_2)_{0-4}SO_2NHC_{1-4}$ alkyl, —$(CH_2)_{0-4}NR^aSO_2C_{1-4}$alkyl, —$(CH_2)_{0-4}OP(OH)_2$, —$(CH_2)_{0-4}OP(OH)(OC_{1-4}$alkyl), or —$(CR_2)_{0-4}OP(O)(H)OH$, wherein $R^a$, independently for each occurrence, is H or $C_{1-4}$alkyl.

In some embodiments, each $R^6$ is independently halogen, —$(CH_2)_{0-4}CO_2H$, —$(CH_2)_{0-4}CO$(N-proline), —$(CH_2)_{0-4}C(O)NR^a(CH_2)_{1-4}CO_2H$, —OH, —$(CH_2)_{1-4}OH$, —$(CH_2)_{0-4}SO_3H$, —$(CH_2)_{0-4}SO_2NH_2$, —$(CH_2)_{0-4}NR^aSO_2C_{1-4}$alkyl, —$(CH_2)_{0-4}OP(OH)_2$, or —$(CR_2)_{0-4}OP(O)(H)OH$, wherein $R^a$, independently for each occurrence, is H or $C_{1-4}$alkyl.

In some embodiments, each $R^6$ is independently halogen, —$CO_2H$, —CO(N-proline), —$C(O)NR^a(CH_2)_{1-4}CO_2H$, —OH, —$SO_3H$, —$SO_2NH_2$, —$NR^aSO_2C_{1-4}$alkyl, —$OP(OH)_2$, or —OP(O)(H)OH, wherein $R^a$, independently for each occurrence, is H or $C_{1-4}$alkyl.

In some embodiments, $R^6$ is not $R^B$.

In some embodiments, m is at least 1, and at least one $R^6$ includes a terminal —$CO_2H$ or —$CO_2C_{1-4}$alkyl group.

In some embodiments, at least one $R^6$ is —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}CO_2H$ or —$(CH_2)_{0-4}CO_2C_{1-4}$alkyl.

In some embodiments, the present disclosure provides a pharmaceutical composition comprising a compound of formula I* or a pharmaceutically acceptable salt thereof.

In some embodiments, the present disclosure provides a method of antagonizing cyclic GMP-AMP synthase (cGAS) in a patient in need thereof, comprising administering an effective amount of a compound of formula I* or a pharmaceutically acceptable salt thereof, or a pharmaceutical composition thereof.

In some embodiments, the present disclosure provides a method of treating an inflammatory, allergic, or autoimmune disease in a patient in need thereof, comprising administering an effective amount of a compound of formula I* or a pharmaceutically acceptable salt thereof, or a pharmaceutical composition thereof.

In some embodiments, the present disclosure provides a compound of formula I or formula I*, wherein $R^1$ is

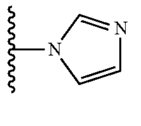

thereby forming a compound of formula I-a-1:

I-a-1

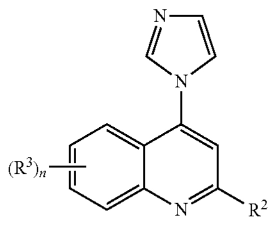

or a pharmaceutically acceptable salt thereof, wherein each of $R^2$, $R^3$, and n is as defined above and described in embodiments herein, both singly and in combination.

In certain embodiments, the present disclosure provides a compound of formula I-a-1, wherein $R^3$ is independently halogen, such as chloro, including dichloro, including wherein n is 2 and $R^3$ is chloro at the 7- and 8-positions with respect to the quinoline ring.

In certain embodiments, the present disclosure provides a compound of formula I-a-1, wherein $R^2$ is $R^B$, wherein $R^B$ is an optionally substituted $C_{1-6}$ aliphatic, preferably a substituted $C_{1-6}$ aliphatic, such as —$(CR_2)_{1-4}NR(CR_2)_{0-6}CO_2R$, —$(CR_2)_{1-4}O(CR_2)_{0-6}CO_2R$, —$(CR_2)_{1-4}CO_2R$, —$(CR_2)_{1-4}OH$, —$(CR_2)_{1-4}NH_2$, —$(CR_2)_{1-4}C(O)NH_2$, —$(CR_2)_{1-4}C(O)NHC_{1-4}$alkyl, or —$(CR_2)_{1-4}C(O)N(C_{1-4}alkyl)_2$, particularly —$(CR_2)_{1-4}NR(CR_2)_{0-6}CO_2R$ or —$(CR_2)_{1-4}CO_2R$. In some embodiments, $R^2$ is —$(CH_2)_{1-4}NR^a(CH_2)_{0-4}CO_2R^a$, such as —$(CH_2)_{1-4}NR^a(CH_2)_{0-4}CO_2H$, wherein $R^a$, independently for each occurrence, is H or $C_{1-4}$alkyl. In other embodiments, $R^2$ is —$(CH_2)_{1-4}N(SO_2C_{1-4}alkyl)(CH_2)_{0-4}CO_2R^a$, such as is —$(CH_2)_{1-4}N(SO_2C_{1-4}alkyl)(CH_2)_{0-4}CO_2H$, wherein $R^a$, independently for each occurrence, is H or $C_{1-4}$alkyl. In other embodiments, $R^2$ is —$(CR_2)_{1-4}CO_2R$, such as —$(CR_2)_{1-4}CO_2H$, including —$(CH_2)_{1-4}CO_2H$. In certain embodiments, $R^2$ includes a terminal —$CO_2H$ group. For example, in certain instances, $R^2$ includes a terminal —$(CH_2)_{0-4}CO_2H$ group.

In some embodiments, the present disclosure provides a compound of formula I or formula I*, wherein $R^1$ is

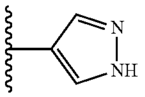 [SMILES: *c1cn[nH]c1]

thereby forming a compound of formula I-a-2:

I-a-2

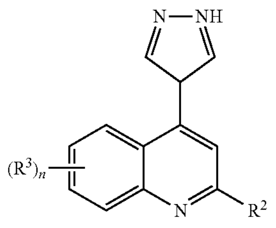

or a pharmaceutically acceptable salt thereof, wherein each of $R^2$, $R^3$, and n is as defined above and described in embodiments herein, both singly and in combination.

In certain embodiments, the present disclosure provides a compound of formula I-a-2, wherein $R^2$ is $R^B$, wherein $R^B$ is an optionally substituted $C_{1-6}$ aliphatic, preferably a substituted $C_{1-6}$ aliphatic, such as —$(CR_2)_{1-4}NR(CR_2)_{0-6}CO_2R$, —$(CR_2)_{1-4}O(CR_2)_{0-6}CO_2R$, —$(CR_2)_{1-4}CO_2R$, —$(CR_2)_{1-4}OH$, —$(CR_2)_{1-4}NH_2$, —$(CR_2)_{1-4}C(O)NH_2$, —$(CR_2)_{1-4}C(O)NHC_{1-4}$alkyl, or —$(CR_2)_{1-4}C(O)N(C_{1-4}alkyl)_2$, particularly —$(CR_2)_{1-4}NR(CR_2)_{0-6}CO_2R$ or —$(CR_2)_{1-4}CO_2R$. In some embodiments, $R^2$ is —$(CH_2)_{1-4}NR^a(CH_2)_{0-4}CO_2R^a$, such as —$(CH_2)_{1-4}NR^a(CH_2)_{0-4}CO_2H$, wherein $R^a$, independently for each occurrence, is H or $C_{1-4}$alkyl. In other embodiments, $R^2$ is —$(CH_2)_{1-4}N(SO_2C_{1-4}alkyl)(CH_2)_{0-4}CO_2R^a$, such as is —$(CH_2)_{1-4}N(SO_2C_{1-4}alkyl)(CH_2)_{0-4}CO_2H$, wherein $R^a$, independently for each occurrence, is H or $C_{1-4}$alkyl. In other embodiments, $R^2$ is —$(CR_2)_{1-4}CO_2R$, such as —$(CR_2)_{1-4}CO_2H$, including —$(CH_2)_{1-4}CO_2H$. In certain embodiments, $R^2$ includes a terminal —$CO_2H$ group. For example, in certain instances, $R^2$ includes a terminal —$(CH_2)_{0-4}CO_2H$ group.

In certain embodiments, the present disclosure provides a compound of formula I-a-2, wherein $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I or formula I*, wherein $R^1$ is —$NR_2$ thereby forming a compound of formula I-a-3:

I-a-3

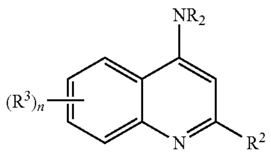

or a pharmaceutically acceptable salt thereof, wherein each of R, $R^2$, $R^3$, and n is as defined above and described in embodiments herein, both singly and in combination.

In certain embodiments, the present disclosure provides a compound of formula I-a-3, wherein $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I or formula I*, wherein $R^1$ is

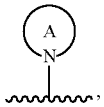

thereby forming a compound of formula I-a-4:

I-a-4

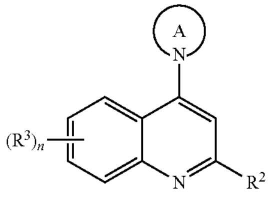

or a pharmaceutically acceptable salt thereof, wherein:

Ring A is an optionally substituted 4- to 7-membered saturated or partially unsaturated heterocyclic ring or heteroaryl ring, having 0 to 3 heteroatoms (in addition to the nitrogen already depicted in Ring A) independently selected from nitrogen, oxygen, phosphorus, and sulfur;

each of $R^2$, $R^3$, and n is as defined above and described in embodiments herein, both singly and in combination.

In certain embodiments, the present disclosure provides a compound of formula I-a-4, wherein $R^2$ is $R^B$, wherein $R^B$ is an optionally substituted $C_{1-6}$ aliphatic, preferably a substituted $C_{1-6}$ aliphatic, such as —$(CR_2)_{1-4}NR(CR_2)_{0-6}CO_2R$, —$(CR_2)_{1-4}O(CR_2)_{0-6}CO_2R$, —$(CR_2)_{1-4}CO_2R$, —$(CR_2)_{1-4}OH$, —$(CR_2)_{1-4}NH_2$, —$(CR_2)_{1-4}C(O)NH_2$, —$(CR_2)_{1-4}C(O)NHC_{1-4}$alkyl, or —$(CR_2)_{1-4}C(O)N(C_{1-4}alkyl)_2$, particularly —$(CR_2)_{1-4}NR(CR_2)_{0-6}CO_2R$ or —$(CR_2)_{1-4}CO_2R$. In some embodiments, $R^2$ is —$(CH_2)_{1-4}NR^a(CH_2)_{0-4}CO_2R^a$, such as —$(CH_2)_{1-4}NR^a(CH_2)_{0-4}CO_2H$, wherein $R^a$, independently for each occurrence, is H or $C_{1-4}$alkyl. In other embodiments, $R^2$ is —$(CH_2)_{1-4}N(SO_2C_{1-4}alkyl)(CH_2)_{0-4}CO_2R^a$, such as is —$(CH_2)_{1-4}N(SO_2C_{1-4}alkyl)(CH_2)_{0-4}CO_2H$, wherein $R^a$, independently for each occurrence, is H or $C_{1-4}$alkyl. In other embodiments, $R^2$ is —$(CR_2)_{1-4}CO_2R$, such as —$(CR_2)_{1-4}CO_2H$, including —$(CH_2)_{1-4}CO_2H$. In certain embodiments, $R^2$ includes a terminal —$CO_2H$ group. For example, in certain instances, $R^2$ includes a terminal —$(CH_2)_{0-4}CO_2H$ group.

In certain embodiments, the present disclosure provides a compound of formula I-a-4, wherein $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I or formula I*, wherein $R^1$ is

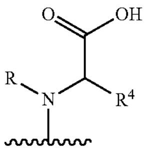

thereby forming a compound of formula I-a-5:

I-a-5

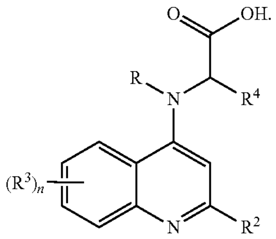

or a pharmaceutically acceptable salt thereof, wherein:

$R^4$ is hydrogen or an optionally substituted $C_{1-6}$ aliphatic; and each of R, $R^2$, $R^3$, and n is as defined above and described in embodiments herein, both singly and in combination.

In some embodiments, the present disclosure provides a compound of formula I-a-5, wherein R and $R^4$ in

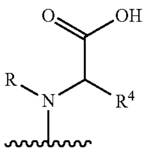

independently are hydrogen or lower alkyl, particularly methyl.

In certain embodiments, the present disclosure provides a compound of formula I-a-5, wherein $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I or formula I*, wherein $R^2$ is —$NR_2$ thereby forming a compound of formula I-b-1:

I-b-1

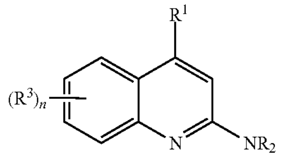

or a pharmaceutically acceptable salt thereof, wherein each of R, $R^1$, $R^3$, and n is as defined above and described in embodiments herein, both singly and in combination.

In certain embodiments, the present disclosure provides a compound of formula I-b-1, wherein $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I or formula I*, wherein $R^2$ is $NRR^5$ thereby forming a compound of formula I-b-2:

I-b-2

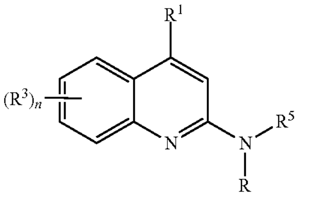

or a pharmaceutically acceptable salt thereof, wherein:

$R^5$ is —$(CR_2)_{2-4}OR$, —$(CR_2)_{0-6}CO_2R$, —$(CR_2)_{0-6}CONR_2$, —$(CR_2)_{0-6}C(O)NR(CR_2)_{0-6}CO_2R$, —$(CR_2)_{0-6}C(O)NR(CR_2)_{0-6}CONR_2$, —$(CR_2)_{0-4}NRC(O)R$, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, or $R^B$; and each of R, $R^1$, $R^3$, $R^B$, and n is as defined above and described in embodiments herein, both singly and in combination.

In certain embodiments, the present disclosure provides a compound of formula I-b-2, wherein $R^5$ is —$(CR_2)_{2-4}OR$, —$(CR_2)_{1-4}CO_2R$, —$(CR_2)_{1-4}CONR_2$, —$(CR_2)_{0-6}C(O)NR(CR_2)_{0-6}CO_2R$, —$(CR_2)_{0-6}C(O)NR(CR_2)_{0-6}CONR_2$, —$(CR_2)_{0-4}NRC(O)R$, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, or $R^B$.

In some embodiments, the present disclosure provides a compound of formula I-b-2, wherein $R^5$ is not $R^B$.

In some embodiments, the present disclosure provides a compound of formula I-b-2, wherein R in —$NRR^5$ is $R^a$, which is H or $C_{1-6}$alkyl.

In certain embodiments, the present disclosure provides a compound of formula I-b-2, wherein $R^3$ is independently halogen, such as chloro, including dichloro, including wherein n is 2 and $R^3$ is chloro at the 7- and 8-positions with respect to the quinoline ring.

In certain embodiments, the present disclosure provides a compound of formula I-b-2, wherein:

$R^1$ is an optionally substituted 5- to 6-membered heteroaryl ring having 1 to 4 heteroatoms independently selected from nitrogen, oxygen, phosphorus, and sulfur (particularly imidazole or pyrazole, including 1-imidazole or 4-pyrazole);

R in —$NRR^5$ is H or lower alkyl, particularly methyl;

$R^5$ is —$(CR_2)_{0-6}OR$, —$(CR_2)_{0-6}CO_2R$, —$(CR_2)_{0-6}CONR_2$, —$(CR_2)_{0-6}C(O)NR(CR_2)_{0-6}CO_2R$, —$(CR_2)_{0-6}C(O)NR(CR_2)_{0-6}CONR_2$, —$(CR_2)_{0-4}NRC(O)R$, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, or —$(CR_2)_{0-6}OP(O)(H)OR$; and each $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-b-2, wherein:

$R^1$ is an optionally substituted imidazole or pyrazole, including 1-imidazole or 4-pyrazole, particularly unsubstituted 1-imidazole or 4-pyrazole;

R in —$NRR^5$ is H or lower alkyl, particularly methyl;

$R^5$ is —$(CH_2)_{2-4}OH$, —$(CH_2)_{2-4}O(CH_2)_{1-5}CO_2H$, —$(CH_2)_{2-4}O(CH_2)_{1-5}CO_2C_{1-4}$alkyl, —$(CH_2)_{0-3}CH(CH_2OH)_2$, —$(CH_2)_{2-4}OC_{1-4}$alkyl, —$(CH_2)_{1-4}CO_2H$, —$(CH_2)_{1-4}CO_2C_{1-4}$alkyl, —$(CH_2)_{1-4}CONH_2$, —$(CH_2)_{1-4}CONHC_{1-4}$alkyl, —$(CH_2)_{1-4}CON(C_{1-4}alkyl)_2$, —$(CH_2)_{1-4}C(O)NR^a(CH_2)_{1-4}CO_2H$, —$(CH_2)_{1-4}C(O)NR^a(CH_2)_{1-4}CONH_2$, —$(CH_2)_{1-4}C(O)NR^a(CH_2)_{1-4}CONHC_{1-4}$alkyl, —$(CH_2)_{1-4}C(O)NR^a(CH_2)_{1-4}CON(C_{1-4}alkyl)_2$, —$(CH_2)_{0-4}NR^aC(O)(CH_2)_{1-5}CO_2H$, —$(CH_2)_{0-4}NR^aC(O)(CH_2)_{1-5}CO_2C_{1-4}$alkyl, —$(CH_2)_{2-4}SO_3H$, —$(CH_2)_{2-4}SO_3C_{1-4}$alkyl, —$(CH_2)_{2-4}SO_2NH_2$, —$(CH_2)_{2-4}SO_2NHC_{1-4}$alkyl, —$(CH_2)_{2-4}SO_2N(C_{1-4}alkyl)_2$, —$(CH_2)_{2-4}OSO_2NH_2$, —$(CH_2)_{2-4}NR^aSO_2C_{1-4}$alkyl, —$(CH_2)_{2-4}NR^aSO_3H$, —$(CH_2)_{1-4}OP(OH)_2$, —$(CH_2)_{1-4}P(O)(OH)_2$, —$(CH_2)_{1-4}P(O)(OH)(OC_{1-4}alkyl)$, or —$(CH_2)_{2-4}OP(O)(H)OH$, wherein $R^a$, independently for each occurrence, is H or $C_{1-4}$alkyl; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-b-2, wherein:

$R^1$ is an optionally substituted imidazole or pyrazole, including 1-imidazole or 4-pyrazole, particularly unsubstituted 1-imidazole or 4-pyrazole;

R in —$NRR^5$ is H or lower alkyl, particularly methyl;

$R^5$ is —$(CH_2)_{2-4}OH$, —$(CH_2)_{2-4}O(CH_2)_{1-5}CO_2H$, —$(CH_2)_{2-4}O(CH_2)_{1-5}CO_2C_{1-4}$alkyl, —$(CH_2)_{0-3}CH(CH_2OH)_2$, —$(CH_2)_{1-4}CO_2H$, —$(CH_2)_{1-4}CONH_2$, —$(CH_2)_{1-4}C(O)NR^a(CH_2)_{1-4}CO_2H$, —$(CH_2)_{1-4}C(O)NR^a(CH_2)_{1-4}CONH_2$, —$(CH_2)_{0-4}NR^aC(O)(CH_2)_{1-5}CO_2H$, —$(CH_2)_{0-4}NR^aC(O)(CH_2)_{1-5}CO_2C_{1-4}$alkyl, —$(CH_2)_{2-4}SO_3H$, —$(CH_2)_{2-4}SO_2NH_2$, —$(CH_2)_{2-4}SO_2NR^aC_{1-4}$alkyl, —$(CH_2)_{2-4}NR^aSO_2C_{1-4}$alkyl, —$(CH_2)_{1-4}P(O)(OH)_2$, or —$(CH_2)_{2-4}OP(O)(H)OH$, wherein $R^a$, independently for each occurrence, is H or $C_{1-4}$alkyl; and each $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-b-2, $R^5$ includes a terminal —$CO_2H$ group. For example, in certain instances, $R^5$ includes a terminal —$(CH_2)_{0-4}CO_2H$ group.

In some embodiments, the present disclosure provides a compound of formula I or formula I*, wherein $R^2$ is

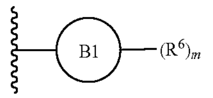

thereby forming a compound of formula I-b-3:

I-b-3

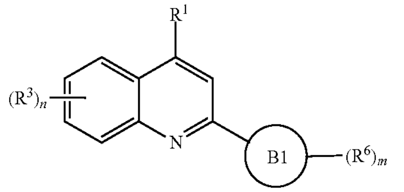

or a pharmaceutically acceptable salt thereof, wherein:

Ring B1 is phenyl, preferably substituted phenyl; a 4- to 10-membered saturated or partially unsaturated monocyclic or bicyclic carboxylic or heterocyclic ring having 1 to 3 heteroatoms independently selected from nitrogen, oxygen, phosphorus, and sulfur; or a 5- to 6-membered heteroaryl ring having 1 to 4 heteroatoms independently selected from nitrogen, oxygen, phosphorus, and sulfur;

each $R^6$ is independently halogen, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

m is 0, 1, 2, 3, or 4, particularly 1, 2, 3, or 4; and each of R, $R^1$, $R^3$, $R^B$, and n is as defined above and described in embodiments herein, both singly and in combination.

In certain embodiments, the present disclosure provides a compound of formula I-b-3, wherein Ring B1 is phenyl, particularly substituted phenyl. In other embodiments, Ring B1 is not phenyl. For example, Ring B1 may be a 4- to 10-membered saturated or partially unsaturated monocyclic or bicyclic carboxylic or heterocyclic ring having 1 to 3 heteroatoms independently selected from nitrogen, oxygen, phosphorus, and sulfur. In some embodiments, Ring B1 is a 5- to 6-membered heteroaryl ring having 1 to 4 heteroatoms independently selected from nitrogen, oxygen, phosphorus, and sulfur.

In some embodiments, the present disclosure provides a compound of formula I-b-3, wherein $R^6$ is not $R^B$.

In certain embodiments, the present disclosure provides a compound of formula I-b-3, wherein $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-b-3, m is 1 or 2, and at least one $R^6$ includes a terminal —$CO_2H$ group. For example, in certain instances, at least one $R^6$ is —$(CH_2)_{0-4}CO_2H$.

In some embodiments, the present disclosure provides a compound of formula I or formula I*, wherein $R^2$ is

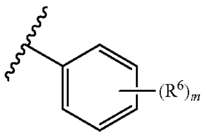

thereby forming a compound of formula I-b-4:

I-b-4

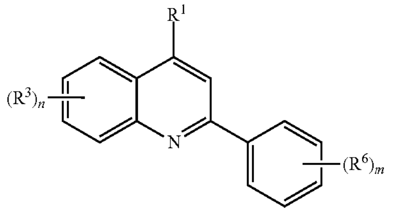

or a pharmaceutically acceptable salt thereof, wherein:

each $R^6$ is independently halogen, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

m is 0, 1, 2, 3, or 4, particularly 1, 2, 3, or 4; and each of R, $R^1$, $R^3$, $R^B$, and n is as defined above and described in embodiments herein, both singly and in combination.

In some embodiments, the present disclosure provides a compound of formula I-b-4, wherein $R^6$ is not $R^B$.

In certain embodiments, the present disclosure provides a compound of formula I-b-4, wherein $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-b-4, m is 1 or 2, and at least one $R^6$ includes a terminal —$CO_2H$ group. For example, in certain instances, at least one $R^6$ is —$(CH_2)_{0-4}CO_2H$.

In some embodiments, the present disclosure provides a compound of formula I or formula I*, wherein $R^2$ is

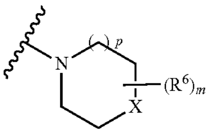

thereby forming a compound of formula I-b-5:

I-b-5

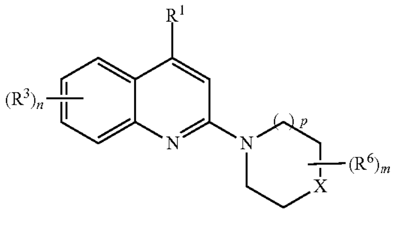

or a pharmaceutically acceptable salt thereof, wherein:

each $R^6$ is independently halogen, $=O$, $-COR$, $-(CR_2)_{0-6}CO_2R$, $-(CR_2)_{0-6}CONR_2$, $-OR$, $-(CR_2)_{1-4}OR$, $-NR_2$, $-(CR_2)_{1-4}NR_2$, $-NRC(O)OR$, $-NRC(O)R$, $-NRC(O)NR_2$, $-SR$, $-SO_2R$, $-S(O)R$, $-(CR_2)_{0-6}SO_3R$, $-(CR_2)_{0-6}SO_2NR_2$, $-(CR_2)_{0-6}OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, $-(CR_2)_{0-6}OP(O)(H)OR$, $-B(OR)_2$, or $R^B$;

X is absent (i.e., a bond in the ring), $-CR_2-$, $-NR-$, $-O-$, $-S-$, or $-SO_2-$; particularly $-CR_2-$, $-NR-$, $-O-$, $-S-$, or $-SO_2-$; more particularly $-CR_2-$, $-NR-$, or $-O-$;

m is 0, 1, 2, 3, or 4, particularly 1, 2, 3, or 4;

p is 0, 1, or 2, particularly 1; and each of R, $R^1$, $R^3$, $R^B$, and n is as defined above and described in embodiments herein, both singly and in combination.

In some embodiments, the present disclosure provides a compound of formula I-b-5, wherein $R^6$ is not $R^B$.

In certain embodiments, the present disclosure provides a compound of formula I-b-5, wherein $R^3$ is independently halogen, such as chloro, including dichloro, including wherein n is 2 and $R^3$ is chloro at the 7- and 8-positions with respect to the quinoline ring.

In certain embodiments, the present disclosure provides a compound of formula I-b-5, wherein:

$R^1$ is an optionally substituted 5- to 6-membered heteroaryl ring having 1 to 4 heteroatoms independently selected from nitrogen, oxygen, phosphorus, and sulfur (particularly imidazole or pyrazole, including 1-imidazole or 4-pyrazole);

each $R^6$ is independently halogen, $-C_{1-4}$alkyl, $-C_{1-4}$haloalkyl, $=CR_2$, $=O$, $-COR$, $-(CR_2)_{0-6}CO_2R$, $-(CR_2)_{0-6}CONR_2$, $-OR$, $-(CR_2)_{1-4}OR$, $-NR_2$, $-(CR_2)_{1-4}NR_2$, $-NRC(O)OR$, $-NRC(O)R$, $-NRC(O)NR_2$, $-SR$, $-SO_2R$, $-S(O)R$, $-(CR_2)_{0-6}SO_3R$, $-(CR_2)_{0-6}SO_2NR_2$, $-(CR_2)_{0-6}OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, $-(CR_2)_{0-6}OP(O)(H)OR$, or $-B(OR)_2$;

m is 1, 2, 3, or 4, particularly 1 or 2;

p is 0 or 1, particularly 1; and each $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-b-5, wherein:

$R^1$ is an optionally substituted imidazole or pyrazole, including 1-imidazole or 4-pyrazole, particularly unsubstituted 1-imidazole or 4-pyrazole;

each $R^6$ is independently halogen, $-C_{1-4}$alkyl, $-C_{1-4}$haloalkyl, $=CH_2$, $=O$, $-(CH_2)_{0-4}CO_2H$, $-(CH_2)_{0-4}CO_2C_{1-4}$alkyl, $-(CH_2)_{0-4}CONH_2$, $-(CH_2)_{0-4}CONHC_{1-4}$alkyl, $-(CH_2)_{0-4}CON(C_{1-4}alkyl)_2$, $-(CH_2)_{0-4}CO$(N-proline), $-(CH_2)_{0-4}C(O)NR^a(CH_2)_{1-4}CO_2H$, $-(CH_2)_{0-4}C(O)NR^a(CH_2)_{1-4}CONH_2$, $-(CH_2)_{0-4}C(O)NR^a(CH_2)_{1-4}CONHC_{1-4}$alkyl, $-(CH_2)_{0-4}C(O)NR^a(CH_2)_{1-4}CON(C_{1-4}alkyl)_2$, $-OH$, $-(CH_2)_{1-4}OH$, $-(CH_2)_{0-4}OC_{1-4}$alkyl, $-(CH_2)_{0-4}O(CH_2)_{1-5}CO_2H$, $-(CH_2)_{0-4}O(CH_2)_{1-5}CO_2C_{1-4}$alkyl, $-NH_2$, $-(CH_2)_{1-4}NH_2$, $-(CH_2)_{0-4}NHC_{1-4}$alkyl, $-(CH_2)_{0-4}N(C_{1-4}alkyl)_2$, $-(CH_2)_{0-4}SO_3H$, $-(CH_2)_{0-4}SO_2NH_2$, $-(CH_2)_{0-4}SO_2NHC_{1-4}$alkyl, $-(CH_2)_{0-4}NR^aSO_2C_{1-4}$alkyl, $-(CH_2)_{0-4}OP(OH)_2$, $-(CH_2)_{0-4}OP(OH)(OC_{1-4}alkyl)$, or $-(CR_2)_{0-4}OP(O)(H)OH$, wherein $R^a$, independently for each occurrence, is H or $C_{1-4}$alkyl;

X is $-CH_2-$, $-NH-$, or $-O-$;

m is 1, 2, 3, or 4, particularly 1 or 2;

p is 1; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula wherein:

$R^1$ is an optionally substituted imidazole or pyrazole, including 1-imidazole or 4-pyrazole, particularly unsubstituted 1-imidazole or 4-pyrazole;

each $R^6$ is independently halogen, $-C_{1-4}$alkyl, $-C_{1-4}$haloalkyl, $=CH_2$, $-(CH_2)_{0-4}CO_2H$, $-(CH_2)_{0-4}CO$(N-proline), $-(CH_2)_{0-4}C(O)NR^a(CH_2)_{1-4}CO_2H$, $-OH$, $-(CH_2)_{1-4}OH$, $-(CH_2)_{0-4}O(CH_2)_{1-5}CO_2H$, $-(CH_2)_{0-4}O(CH_2)_{1-5}CO_2C_{1-4}$alkyl, $-(CH_2)_{0-4}SO_3H$, $-(CH_2)_{0-4}SO_2NH_2$, $-(CH_2)_{0-4}NR^aSO_2C_{1-4}$alkyl, $-(CH_2)_{0-4}OP(OH)_2$, or $-(CR_2)_{0-4}OP(O)(H)OH$;

X is $-CH_2-$, $-NH-$, or $-O-$;

m is 1 or 2;

p is 1; and each $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-b-5, m is 1 or 2, and at least one $R^6$ includes a terminal $-CO_2H$ group. For example, in certain instances, at least one $R^6$ is $-(CH_2)_{0-4}CO_2H$.

In some embodiments, the present disclosure provides a compound of formula I or formula I*, wherein $R^2$ is

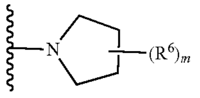

thereby forming a compound of formula I-b-6:

I-b-6

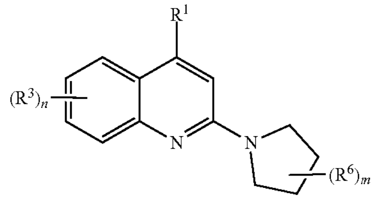

or a pharmaceutically acceptable salt thereof, wherein:

each $R^6$ is independently halogen, $=O$, $=CR_2$, $-COR$, $-(CR_2)_{0-6}CO_2R$, $-(CR_2)_{0-6}CONR_2$, $-OR$, $-(CR_2)_{1-4}OR$, $-NR_2$, $-(CR_2)_{1-4}NR_2$, $-NRC(O)OR$, $-NRC(O)R$, $-NRC(O)NR_2$, $-SR$, $-SO_2R$, $-S(O)R$, $-(CR_2)_{0-6}SO_3R$, $-(CR_2)_{0-6}SO_2NR_2$, $-(CR_2)_{0-6}OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, $-(CR_2)_{0-6}OP(O)(H)OR$, $-B(OR)_2$, or $R^B$;

m is 0, 1, 2, 3, or 4, particularly 1, 2, 3, or 4; and each of R, $R^1$, $R^3$, $R^B$, and n is as defined above and described in embodiments herein, both singly and in combination.

In some embodiments, the present disclosure provides a compound of formula I-b-6, wherein $R^6$ is not $R^B$.

In certain embodiments, the present disclosure provides a compound of formula I-b-6, wherein $R^3$ is independently halogen, such as chloro, including dichloro, including wherein n is 2 and $R^3$ is chloro at the 7- and 8-positions with respect to the quinoline ring.

In certain embodiments, the present disclosure provides a compound of formula I-b-6, wherein:

$R^1$ is an optionally substituted 5- to 6-membered heteroaryl ring having 1 to 4 heteroatoms independently selected from nitrogen, oxygen, phosphorus, and sulfur (particularly imidazole or pyrazole, including 1-imidazole or 4-pyrazole);

each $R^6$ is independently halogen, $—C_{1-4}$alkyl, $—C_{1-4}$haloalkyl, $=CR_2$, $=O$, —COR, $—(CR_2)_{0-6}CO_2R$, $—(CR_2)_{0-6}CONR_2$, —OR, $—(CR_2)_{1-4}OR$, $—NR_2$, $—(CR_2)_{1-4}NR_2$, —NRC(O)OR, —NRC(O)R, —NRC(O)$NR_2$, —SR, $—SO_2R$, —S(O)R, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, or $—B(OR)_2$;

m is 1, 2, 3, or 4, particularly 1 or 2; and each $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-b-6, wherein:

$R^1$ is an optionally substituted imidazole or pyrazole, including 1-imidazole or 4-pyrazole, particularly unsubstituted 1-imidazole or 4-pyrazole;

each $R^6$ is independently halogen, $—C_{1-4}$alkyl, $—C_{1-4}$haloalkyl, $=CH_2$, $=O$, $—(CH_2)_{0-4}CO_2H$, $—(CH_2)_{0-4}CO_2C_{1-4}$alkyl, $—(CH_2)_{0-4}CO_2C_{1-4}$haloalkyl, $—(CH_2)_{0-4}CONH_2$, $—(CH_2)_{0-4}CONHC_{1-4}$alkyl, $—(CH_2)_{0-4}CON(C_{1-4}alkyl)_2$, $—(CH_2)_{0-4}$CO(N-proline), $—(CH_2)_{0-4}$CO(N-pyrrolidine-3-carboxylic acid), $—(CH_2)_{0-4}$(N-pyrazole)-$(CH_2)_{0-4}CO_2H$, $—(CH_2)_{0-4}$CO(N-pyrazole)-$(CH_2)_{0-4}CO_2C_{1-4}$alkyl, $—(CH_2)_{0-4}$(N-pyrrole)-$(CH_2)_{0-4}CO_2H$, $—(CH_2)_{0-4}$CO(N-pyrrole)-$(CH_2)_{0-4}CO_2C_{1-4}$alkyl, $—(CH_2)_{0-4}$—O(phenyl)-$(CH_2)_{0-4}CO_2H$, $—(CH_2)_{0-4}$—O(phenyl)-$(CH_2)_{0-4}CO_2C_{1-4}$alkyl, $—(CH_2)_{0-4}$—O(cycloalkane)-$(CH_2)_{0-4}CO_2H$, $—(CH_2)_{0-4}$—O(cycloalkane)-$(CH_2)_{0-4}CO_2C_{1-4}$alkyl, $—(CH_2)_{0-4}C(O)NR^a(CH_2)_{1-4}CO_2H$, $—(CH_2)_{0-4}C(O)NR^a$—CH($C_{1-4}$alkyl)-$CO_2H$, $—(CH_2)_{0-4}C(O)NR^a(CH_2)_{1-4}CONH_2$, $—(CH_2)_{0-4}C(O)NR^a(CH_2)_{1-4}CONHC_{1-4}$alkyl, $—(CH_2)_{0-4}C(O)NR^a(CH_2)_{1-4}CON(C_{1-4}alkyl)_2$, —OH, $—(CH_2)_{1-4}OH$, $—(CH_2)_{0-4}OC_{1-4}$alkyl, $—(CH_2)_{0-4}O(CH_2)_{1-5}CO_2H$, $—(CH_2)_{0-4}O(CH_2)_{1-5}CO_2C_{1-4}$alkyl, $—(CH_2)_{1-4}O(CH_2)_{1-4}CHFCO_2H$, $—(CH_2)_{1-4}O(CH_2)_{1-4}CHFCO_2C_{1-4}$alkyl, $—(CH_2)_{1-4}OCH(CH_3)(CH_2)_{1-4}CO_2H$, $—(CH_2)_{1-4}OCH(CH_3)(CH_2)_{1-4}CO_2C_{1-4}$alkyl, $—(CH_2)_{1-4}O(CH_2)_{1-4}CH(CH_3)CO_2H$, $—(CH_2)_{1-4}O(CH_2)_{1-4}CH(CH_3)CO_2C_{1-4}$alkyl, $—CHOH(CH_2)_{1-4}O(CH_2)_{1-5}CO_2H$, $—CHOH(CH_2)_{1-4}O(CH_2)_{1-5}CO_2C_{1-4}$alkyl, $—CHCF_3(CH_2)_{1-4}O(CH_2)_{1-5}CO_2H$, $—CHCF_3(CH_2)_{1-4}O—(CH_2)_{1-5}CO_2C_{1-4}$alkyl, $—(CH_2)_{1-4}O(CH_2)_{1-5}CONR^a{}_2$, $—(CH_2)_{1-4}O(CH_2)_{1-5}CONR^aOH$, $—(CH_2)_{1-4}O(CH_2)_{1-5}CONR^aCN$, $—(CH_2)_{1-4}O(CH_2)_{1-5}P(O)OH_2$, $—NH_2$, $—(CH_2)_{0-4}NR^a(CH_2)_{1-4}CO_2H$, $—(CH_2)_{0-4}NR^a(CH_2)_{1-4}CO_2C_{1-4}$alkyl, $—(CH_2)_{1-4}NH_2$, $—(CH_2)_{0-4}NHC_{1-4}$alkyl, $—(CH_2)_{0-4}NR^aC(O)C_{1-4}$alkyl, $—(CH_2)_{0-4}NR^aC(O)Ph$, $—(CH_2)_{0-4}NR^aCO(CH_2)_{1-4}OH$, $—(CH_2)_{0-4}N(C_{1-4}alkyl)_2$, $—(CH_2)_{0-4}SO_3H$, $—(CH_2)_{0-4}SO_2NH_2$, $—(CH_2)_{0-4}SO_2NR^aC_{1-4}$alkyl, $—(CH_2)_{0-4}NR^aSO_2C_{1-4}$alkyl, $—(CH_2)_{0-4}NR^aSO_2Ph$, $—(CH_2)_{0-4}NR^aSO_2(CH_2)_{1-4}CO_2H$, $—(CH_2)_{0-4}OP(OH)_2$, $—(CH_2)_{0-4}OP(OH)(OC_{1-4}alkyl)$, or $—(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-b-6, wherein:

$R^1$ is an optionally substituted imidazole or pyrazole, including 1-imidazole or 4-pyrazole, particularly unsubstituted 1-imidazole or 4-pyrazole;

each $R^6$ is independently halogen, $—C_{1-4}$alkyl, $—C_{1-4}$haloalkyl, $=CH_2$, $—(CH_2)_{0-4}CO_2H$, $—(CH_2)_{0-4}CO_2C_{1-4}$alkyl, $—(CH_2)_{0-4}CO_2C_{1-4}$haloalkyl, $—(CH_2)_{0-4}$CO(N-proline), $—(CH_2)_{0-4}$CO(N-pyrrolidine-3-carboxylic acid), $—(CH_2)_{0-4}C(O)NR^a(CH_2)_{1-4}CO_2H$, $—(CH_2)_{0-4}C(O)NR^a$—CH($C_{1-4}$alkyl)-$CO_2H$, —OH, $—(CH_2)_{1-4}OH$, $—(CH_2)_{0-4}OC_{1-4}$alkyl, $—(CH_2)_{0-4}O(CH_2)_{1-5}CO_2H$, $—(CH_2)_{0-4}O(CH_2)_{1-5}CO_2C_{1-4}$alkyl, $—(CH_2)_{0-4}NR^aC(O)C_{1-4}$alkyl, $—(CH_2)_{0-4}NR^aC(O)Ph$, $—(CH_2)_{0-4}NR^aCO(CH_2)_{1-4}OH$, $—(CH_2)_{0-4}SO_3H$, $—(CH_2)_{0-4}SO_2NH_2$, $—(CH_2)_{0-4}NR^aSO_2C_{1-4}$alkyl, $—(CH_2)_{0-4}NR^aSO_2Ph$, $—(CH_2)_{0-4}NR^aSO_2(CH_2)_{1-4}CO_2H$, $—(CH_2)_{0-4}OP(OH)_2$, or $—(CR_2)_{0-4}OP(O)(H)OH$, wherein $R^a$, independently for each occurrence, is H or $C_{1-4}$alkyl;

m is 1 or 2; and each $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-b-6, m is 1 or 2, and at least one $R^6$ includes a terminal $—CO_2H$ group. For example, in certain instances, at least one $R^6$ is $—(CH_2)_{0-4}CO_2H$.

In some embodiments, the present disclosure provides a compound of formula I or formula I*, wherein $R^2$ is

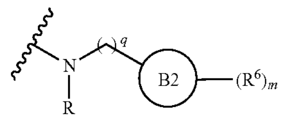

thereby forming a compound of formula I-b-7:

I-b-7

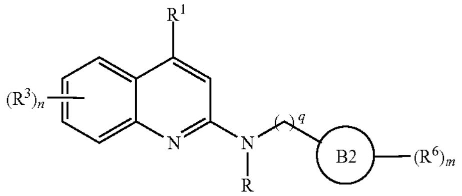

or a pharmaceutically acceptable salt thereof, wherein:

Ring B2 is phenyl; a 4- to 7-membered saturated or partially unsaturated carbocyclic or heterocyclic ring having 1 to 3 heteroatoms independently selected from nitrogen, oxygen, phosphorus, and sulfur; or a 5- to 6-membered heteroaryl ring having 1 to 4 heteroatoms independently selected from nitrogen, oxygen, phosphorus, and sulfur;

each $R^6$ is independently halogen, —COR, $—(CR_2)_{0-6}CO_2R$, $—(CR_2)_{0-6}CONR_2$, —OR, $—(CR_2)_{1-4}OR$, $—NR_2$, $—(CR_2)_{1-4}NR_2$, —NRC(O)OR, —NRC(O)R, —NRC(O)$NR_2$, —SR, $—SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

m is 0, 1, 2, 3, or 4, particularly 1, 2, 3, or 4;

q is 0, 1, or 2; and each of R, $R^3$, $R^B$, and n is as defined above and described in embodiments herein, both singly and in combination.

In certain embodiments, the present disclosure provides a compound of formula I-b-7, wherein Ring B2 is phenyl, particularly substituted phenyl. In other embodiments, Ring B2 is not phenyl. For example, Ring B2 may be a 4- to 10-membered saturated or partially unsaturated monocyclic or bicyclic carboxylic or heterocyclic ring having 1 to 3 heteroatoms independently selected from nitrogen, oxygen, phosphorus, and sulfur. In some embodiments, Ring B2 is a 5- to 6-membered heteroaryl ring having 1 to 4 heteroatoms independently selected from nitrogen, oxygen, phosphorus, and sulfur.

In some embodiments, the present disclosure provides a compound of formula I-b-7, wherein $R^6$ is not $R^B$.

In some embodiments, the present disclosure provides a compound of formula I-b-7, wherein R in

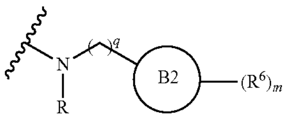

is $R^a$, which is H or $C_{1-6}$alkyl.

In certain embodiments, the present disclosure provides a compound of formula I-b-7, wherein $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-b-7, m is 1 or 2, and at least one $R^6$ includes a terminal —$CO_2H$ group. For example, in certain instances, at least one $R^6$ is —$(CH_2)_{0-4}CO_2H$.

In some embodiments, the present disclosure provides a compound of formula I or formula I*, wherein $R^2$ is

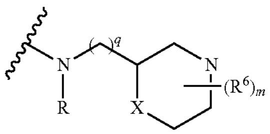 or

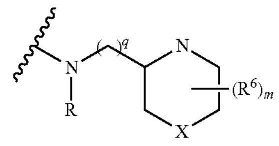

thereby forming a compound of formula I-b-8 or formula I-b-8*, respectively:

I-b-8

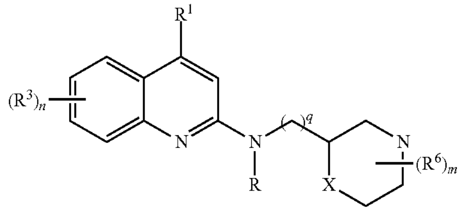

I-b-8*

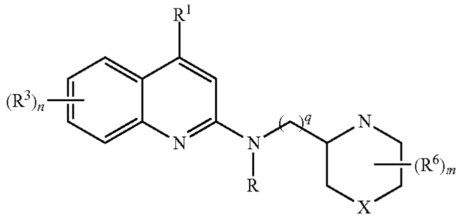

or a pharmaceutically acceptable salt thereof, wherein:

each $R^6$ is independently hydrogen (only on N), halogen (not on N), —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}O(O)(OR)_2$, —$(CR_2)_{0-6}P(O)(OR)_2$, —$(CR_2)_{0-6}OP(O)(H)OR$, —$B(OR)_2$, or $R^B$;

X is absent (i.e., a bond in the ring), —$CR_2$—, —NR—, —O—, —S—, or —$SO_2$—, particularly —$CR_2$—, —NR—, or —O;

m is 1, 2, 3, or 4;

q is 0, 1, or 2; and each of R, $R^1$, $R^3$, $R^B$, and n is as defined above and described in embodiments herein, both singly and in combination.

In some embodiments, the present disclosure provides a compound of formula I-b-8 or formula I-b-8*, wherein $R^6$ is not $R^B$.

In some embodiments, the present disclosure provides a compound of formula I-b-8 or formula I-b-8*, wherein R in

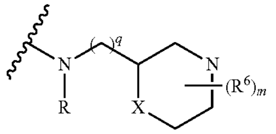

or in

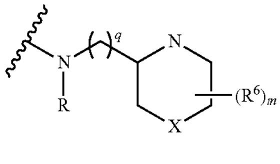

is $R^a$, which is H or $C_{1-6}$alkyl.

In certain embodiments, the present disclosure provides a compound of formula I-b-8 or formula I-b-8*, wherein $R^3$ is independently halogen, such as chloro, including dichloro, including wherein n is 2 and $R^3$ is chloro at the 7- and 8-positions with respect to the quinoline ring.

In certain embodiments, the present disclosure provides a compound of formula I-b-8 or formula I-b-8*, wherein:

$R^1$ is an optionally substituted 5- to 6-membered heteroaryl ring having 1 to 4 heteroatoms independently selected from nitrogen, oxygen, phosphorus, and sulfur (particularly imidazole or pyrazole, including 1-imidazole or 4-pyrazole);

each $R^6$ is independently halogen, $=O$, $-COR$, $-(CR_2)_{0-6}CO_2R$, $-(CR_2)_{0-6}CONR_2$, $-OR$, $-(CR_2)_{1-4}OR$, $-NR_2$, $-(CR_2)_{1-4}NR_2$, $-NRC(O)OR$, $-NRC(O)R$, $-NRC(O)NR_2$, $-SR$, $-SO_2R$, $-S(O)R$, $-(CR_2)_{0-6}SO_3R$, $-(CR_2)_{0-6}SO_2NR_2$, $-(CR_2)_{0-6}OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, $-(CR_2)_{0-6}OP(O)(H)OR$, or $-B(OR)_2$;

m is 1, 2, 3, or 4, particularly 1 or 2;

q is 1 or 2; and each $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-b-8 or formula I-b-8*, wherein:

$R^1$ is an optionally substituted imidazole or pyrazole, including 1-imidazole or 4-pyrazole, particularly unsubstituted 1-imidazole or 4-pyrazole;

each $R^6$ is independently halogen, $=O$, $-(CH_2)_{0-4}CO_2H$, $-(CH_2)_{0-4}CO_2C_{1-4}alkyl$, $-(CH_2)_{0-4}CONH_2$, $-(CH_2)_{0-4}CONHC_{1-4}alkyl$, $-(CH_2)_{0-4}CON(C_{1-4}alkyl)_2$, $-(CH_2)_{0-4}CO$(N-proline), $-(CH_2)_{0-4}C(O)NR^a(CH_2)_{1-4}CO_2H$, $-(CH_2)_{0-4}C(O)NR^a(CH_2)_{1-4}CONH_2$, $-(CH_2)_{0-4}C(O)NR^a(CH_2)_{1-4}CONHC_{1-4}alkyl$, $-(CH_2)_{0-4}C(O)NR^a(CH_2)_{1-4}CON(C_{1-4}alkyl)_2$, $-OH$, $-(CH_2)_{1-4}OH$, $-(CH_2)_{0-4}OC_{1-4}alkyl$, $-NH_2$, $-(CH_2)_{1-4}NH_2$, $-(CH_2)_{0-4}NHC_{1-4}alkyl$, $-(CH_2)_{0-4}N(C_{1-4}alkyl)_2$, $-(CH_2)_{0-4}SO_3H$, $-(CH_2)_{0-4}SO_2NH_2$, $-(CH_2)_{0-4}SO_2NHC_{1-4}alkyl$, $-(CH_2)_{0-4}NR^aSO_2C_{1-4}alkyl$, $-(CH_2)_{0-4}OP(OH)_2$, $-(CH_2)_{0-4}OP(OH)(OC_{1-4}alkyl)$, or $-(CR_2)_{0-4}OP(O)(H)OH$, wherein $R^a$, independently for each occurrence, is H or $C_{1-4}alkyl$;

m is 1, 2, 3, or 4, particularly 1 or 2;

q is 1; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-b-8 or formula I-b-8*, wherein:

$R^1$ is an optionally substituted imidazole or pyrazole, including 1-imidazole or 4-pyrazole, particularly unsubstituted 1-imidazole or 4-pyrazole;

each $R^6$ is independently halogen, $-(CH_2)_{0-4}CO_2H$, $-(CH_2)_{0-4}CO$(N-proline), $-(CH_2)_{0-4}C(O)NR^a(CH_2)_{1-4}CO_2H$, $-OH$, $-(CH_2)_{1-4}OH$, $-(CH_2)_{0-4}SO_3H$, $-(CH_2)_{0-4}SO_2NH_2$, $-(CH_2)_{0-4}NR^aSO_2C_{1-4}alkyl$, $-(CH_2)_{0-4}OP(OH)_2$, or $-(CR_2)_{0-4}OP(O)(H)OH$, wherein $R^a$, independently for each occurrence, is H or $C_{1-4}alkyl$;

m is 1 or 2;

q is 1; and each $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-b-8 or I-b-8*, m is 1 or 2, and at least one $R^6$ includes a terminal $-CO_2H$ group. For example, in certain instances, at least one $R^6$ is $-(CH_2)_{0-4}CO_2H$.

In some embodiments, the present disclosure provides a compound of formula I or formula I*, wherein $R^2$ is

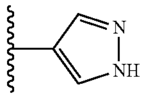 [SMILES: *c1cn[nH]c1]

thereby forming a compound of formula I-b-9:

I-b-9

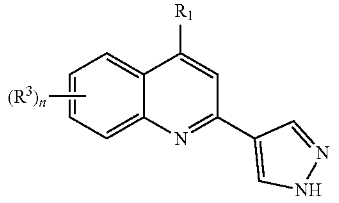

or a pharmaceutically acceptable salt thereof, wherein each of R, $R^1$, $R^3$, and n is as defined above and described in embodiments herein, both singly and in combination.

In certain embodiments, the present disclosure provides a compound of formula I-b-9, wherein $R^3$ is independently halogen, such as chloro, including dichloro, including wherein n is 2 and $R^3$ is chloro at the 7- and 8-positions with respect to the quinoline ring.

In certain embodiments, the present disclosure provides a compound of formula I-b-9, wherein:

$R^1$ is

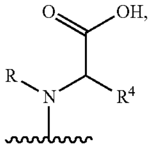

wherein R and $R^4$ independently are hydrogen or an optionally substituted $C_{1-6}$ aliphatic; and each $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-b-9, wherein:

$R^1$ is

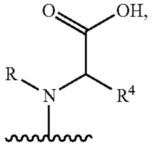

wherein R and $R^4$ independently are hydrogen or lower alkyl, particularly methyl; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-b-9, wherein:

$R^1$ is

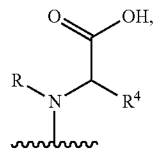

wherein R is hydrogen and $R^4$ is hydrogen or lower alkyl, particularly methyl; and each $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I or formula I*, wherein at least one $R^3$ is halogen, such as chloro at the 8-position, thereby forming a compound of formula I-c-1:

I-c-1

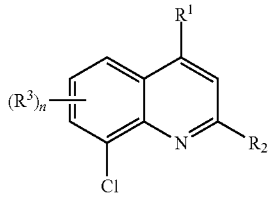

or a pharmaceutically acceptable salt thereof, wherein each of $R^1$, $R^2$, and $R^3$ is as defined above and described in embodiments herein, and n is 0, 1, 2, or 3, both singly and in combination.

In some embodiments, the present disclosure provides a compound of formula I or formula I*, wherein n is 2 and $R^3$ is chloro at the 7- and 8-positions, thereby forming a compound of formula I-c-2:

I-c-2

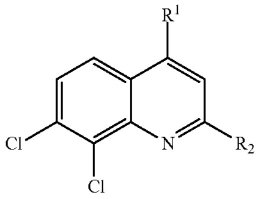

or a pharmaceutically acceptable salt thereof, wherein each of $R^1$ and $R^2$ is as defined above and described in embodiments herein, both singly and in combination.

In some embodiments, the present disclosure provides a compound of formula I or formula I*, wherein $R^1$ is

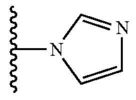 [SMILES: *n1ccnc1]

and $R^2$ is —$NR_2$, thereby forming a compound of formula I-d-1:

I-d-1

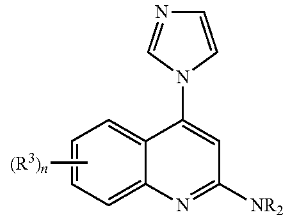

or a pharmaceutically acceptable salt thereof, wherein each of R, $R^3$, and n is as defined above and described in embodiments herein, both singly and in combination.

In certain embodiments, the present disclosure provides a compound of formula I-d-1, wherein $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I or formula I*, wherein $R^1$ is

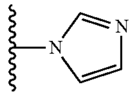 [SMILES: *n1ccnc1]

and $R^2$ is —$NRR^5$, thereby forming a compound of formula I-d-2:

I-d-2

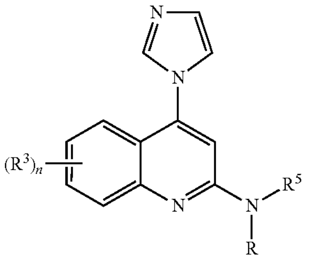

or a pharmaceutically acceptable salt thereof, wherein:

$R^5$ is —$(CR_2)_{2-4}OR$, —$(CR_2)_{0-6}CO_2R$, —$(CR_2)_{0-6}CONR_2$, —$(CR_2)_{0-6}C(O)NR(CR_2)_{0-6}CO_2R$, —$(CR_2)_{0-6}C(O)NR(CR_2)_{0-6}CONR_2$, —$(CR_2)_{0-4}NR^aC(O)R$, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, or $R^B$; and each of R, $R^3$, $R^B$, and n is as defined above and described in embodiments herein, both singly and in combination.

In certain embodiments, the present disclosure provides a compound of formula I-d-2, wherein $R^5$ is —$(CR_2)_{2-4}OR$, —$(CR_2)_{1-4}CO_2R$, —$(CR_2)_{1-4}CONR_2$, —$(CR_2)_{0-6}C(O)NR(CR_2)_{0-6}CO_2R$, —$(CR_2)_{0-6}C(O)NR(CR_2)_{0-6}CONR_2$, —$(CR_2)_{0-4}NR^aC(O)R$, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, or $R^B$.

In some embodiments, the present disclosure provides a compound of formula I-d-2, wherein $R^5$ is not $R^B$.

In some embodiments, the present disclosure provides a compound of formula I-d-2, wherein R in —$NRR^5$ is $R^a$, which is H or $C_{1-6}$alkyl.

In certain embodiments, the present disclosure provides a compound of formula I-d-2, wherein $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-d-2, wherein:

R in —$NRR^5$ is H or lower alkyl, particularly methyl;

$R^5$ is —$(CH_2)_{2-4}OH$, —$(CH_2)_{2-4}O(CH_2)_{1-5}CO_2H$, —$(CH_2)_{2-4}O(CH_2)_{1-5}CO_2C_{1-4}$alkyl, —$(CH_2)_{0-3}CH(CH_2OH)_2$, —$(CH_2)_{2-4}OC_{1-4}$alkyl, —$(CH_2)_{1-4}CO_2H$, —$(CH_2)_{1-4}CO_2C_{1-4}$alkyl, —$(CH_2)_{1-4}CONH_2$, —$(CH_2)_{1-4}CONHC_{1-4}$alkyl, —$(CH_2)_{1-4}CON(C_{1-4}$ alkyl$)_2$, —$(CH_2)_{1-4}C(O)NR^a(CH_2)_{1-4}CO_2H$, —$(CH_2)_{1-4}C(O)NR^a(CH_2)_{1-4}CONH_2$, —$(CH_2)_{1-4}C(O)NR^a(CH_2)_{1-4}CONHC_{1-4}$alkyl, —$(CH_2)_{1-4}C(O)NR^a(CH_2)_{1-4}CON(C_{1-4}alkyl)_2$, —$(CH_2)_{0-4}NR^aC(O)(CH_2)_{1-5}CO_2H$, —$(CH_2)_{0-4}NR^aC(O)(CH_2)_{1-5}CO_2C_{1-4}$alkyl, —$(CH_2)_{2-4}SO_3H$, —$(CH_2)_{2-4}SO_3C_{1-4}$alkyl, —$(CH_2)_{2-4}SO_2NH_2$, —$(CH_2)_{2-4}SO_2NHC_{1-4}$alkyl, —$(CH_2)_{2-4}SO_2N(C_{1-4}alkyl)_2$, —$(CH_2)_{2-4}OSO_2NH_2$, —$(CH_2)_{2-4}NR^aSO_2C_{1-4}$alkyl, —$(CH_2)_{2-4}NR^aSO_3H$, —$(CH_2)_{1-4}OP(OH)_2$, —$(CH_2)_{1-4}P(O)(OH)_2$, —$(CH_2)_{1-4}P(O)(OH)(OC_{1-4}$alkyl), or —$(CH_2)_{2-4}OP(O)(H)OH$, wherein $R^a$, independently for each occurrence, is H or $C_{1-4}$alkyl; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-d-2, wherein:

R in —$NRR^5$ is H or lower alkyl, particularly methyl;

$R^5$ is —$(CH_2)_{2-4}OH$, —$(CH_2)_{2-4}O(CH_2)_{1-5}CO_2H$, —$(CH_2)_{2-4}O(CH_2)_{1-5}CO_2C_{1-4}$alkyl, —$(CH_2)_{0-3}CH(CH_2OH)_2$, —$(CH_2)_{1-4}CO_2H$, —$(CH_2)_{1-4}CONH_2$, —$(CH_2)_{1-4}C(O)NR^a(CH_2)_{1-4}CO_2H$, —$(CH_2)_{1-4}C(O)NR^a(CH_2)_{1-4}CONH_2$, —$(CH_2)_{0-4}NR^aC(O)(CH_2)_{1-5}CO_2H$, —$(CH_2)_{0-4}NR^aC(O)(CH_2)_{1-5}CO_2C_{1-4}$alkyl, —$(CH_2)_{2-4}SO_3H$, —$(CH_2)_{2-4}SO_2NH_2$, —$(CH_2)_{2-4}SO_2NR^aC_{1-4}$alkyl, —$(CH_2)_{2-4}NR^aSO_2C_{1-4}$alkyl, —$(CH_2)_{1-4}P(O)(OH)_2$, or —$(CH_2)_{2-4}OP(O)(H)OH$, wherein $R^a$, independently for each occurrence, is H or $C_{1-4}$alkyl; and each $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-d-2, $R^5$ includes a terminal —$CO_2H$ group. For example, in certain instances, $R^5$ includes a terminal —$(CH_2)_{0-4}CO_2H$ group.

In some embodiments, the present disclosure provides a compound of formula I or formula I*, wherein $R^1$ is

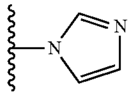 [SMILES: *n1ccnc1]

and $R^2$ is

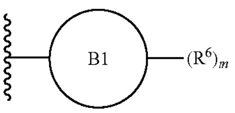

thereby forming a compound of formula I-d-3:

I-d-3

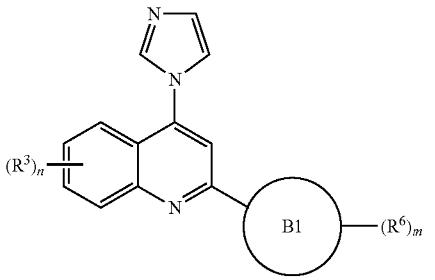

or a pharmaceutically acceptable salt thereof, wherein:

Ring B1 is phenyl, preferably substituted phenyl; a 4- to 10-membered saturated or partially unsaturated monocyclic or bicyclic carboxylic or heterocyclic ring having 1 to 3 heteroatoms independently selected from nitrogen, oxygen, phosphorus, and sulfur; or a 5- to 6-membered heteroaryl ring having 1 to 4 heteroatoms independently selected from nitrogen, oxygen, phosphorus, and sulfur;

each $R^6$ is independently halogen, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —$NRC(O)NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

m is 0, 1, 2, 3, or 4, particularly 1, 2, 3, or 4; and each of R, $R^3$, $R^B$, and n is as defined above and described in embodiments herein, both singly and in combination.

In certain embodiments, the present disclosure provides a compound of formula I-d-3, wherein Ring B1 is phenyl, particularly substituted phenyl. In other embodiments, Ring B1 is not phenyl. For example, Ring B1 may be a 4- to 10-membered saturated or partially unsaturated monocyclic or bicyclic carboxylic or heterocyclic ring having 1 to 3 heteroatoms independently selected from nitrogen, oxygen, phosphorus, and sulfur. In some embodiments, Ring B1 is a 5- to 6-membered heteroaryl ring having 1 to 4 heteroatoms independently selected from nitrogen, oxygen, phosphorus, and sulfur.

In some embodiments, the present disclosure provides a compound of formula I-d-3, wherein $R^6$ is not $R^B$.

In certain embodiments, the present disclosure provides a compound of formula I-d-3, wherein $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-d-3, m is 1 or 2, and at least one $R^6$ includes a terminal —$CO_2H$ group. For example, in certain instances, at least one $R^6$ is —$(CH_2)_{0-4}CO_2H$.

In some embodiments, the present disclosure provides a compound of formula I or formula I*, wherein $R^1$ is

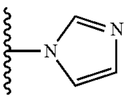

and $R^2$ is

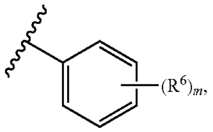

thereby forming a compound of formula I-d-4:

I-d-4

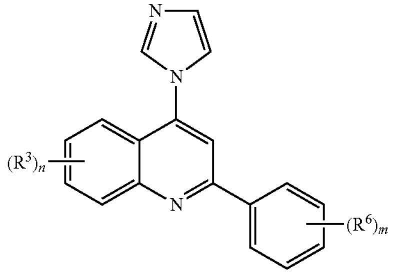

or a pharmaceutically acceptable salt thereof, wherein:

each $R^6$ is independently halogen, —COR, $—(CR_2)_{0-6}CO_2R$, $—(CR_2)_{0-6}CONR_2$, —OR, $—(CR_2)_{1-4}OR$, $—NR_2$, $—(CR_2)_{1-4}NR_2$, —NRC(O)OR, —NRC(O)R, $—NRC(O)NR_2$, —SR, $—SO_2R$, —S(O)R, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, $—B(OR)_2$, or $R^B$;

m is 0, 1, 2, 3, or 4, particularly 1, 2, 3, or 4; and each of R, $R^3$, $R^B$, and n is as defined above and described in embodiments herein, both singly and in combination.

In some embodiments, the present disclosure provides a compound of formula I-d-4, wherein $R^6$ is not $R^B$.

In certain embodiments, the present disclosure provides a compound of formula I-d-4, wherein $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-d-4, m is 1 or 2, and at least one $R^6$ includes a terminal $—CO_2H$ group. For example, in certain instances, at least one $R^6$ is $—(CH_2)_{0-4}CO_2H$.

In some embodiments, the present disclosure provides a compound of formula I or formula I*, wherein $R^1$ is

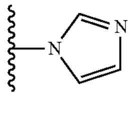 [SMILES: *n1ccnc1]

and $R^2$ is

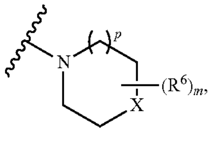

thereby forming a compound of formula I-d-5:

I-d-5

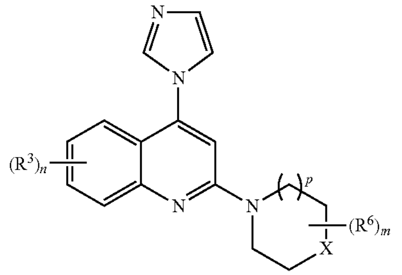

or a pharmaceutically acceptable salt thereof, wherein:

each $R^6$ is independently halogen, =O, —COR, $—(CR_2)_{0-6}CO_2R$, $—(CR_2)_{0-6}CONR_2$, —OR, $—(CR_2)_{1-4}OR$, $—NR_2$, $—(CR_2)_{1-4}NR_2$, —NRC(O)OR, —NRC(O)R, $—NRC(O)NR_2$, —SR, $—SO_2R$, —S(O)R, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, $—B(OR)_2$, or $R^B$;

X is $—CR_2—$, —NR—, —O—, —S—, or $—SO_2—$, particularly $—CR_2—$, —NR—, or —O;

m is 0, 1, 2, 3, or 4, particularly 1, 2, 3, or 4;

p is 0, 1, or 2, particularly 1; and each of R, $R^3$, $R^B$, and n is as defined above and described in embodiments herein, both singly and in combination.

In some embodiments, the present disclosure provides a compound of formula I-d-5, wherein $R^6$ is not $R^B$.

In certain embodiments, the present disclosure provides a compound of formula I-d-5, wherein $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-d-5, wherein:

each $R^6$ is independently halogen, $—C_{1-4}alkyl$, $—C_{1-4}haloalkyl$, $=CH_2$, =O, $—(CH_2)_{0-4}CO_2H$, $—(CH_2)_{0-4}CO_2C_{1-4}alkyl$, $—(CH_2)_{0-4}O(CH_2)_{1-5}CO_2H$, $—(CH_2)_{0-4}O(CH_2)_{1-5}CO_2C_{1-4}alkyl$, $—(CH_2)_{1-4}O(CH_2)_{1-4}CHFCO_2H$, $—(CH_2)_{1-4}O(CH_2)_{1-4}CHFCO_2C_{1-4}alkyl$, $—(CH_2)_{1-4}OCH(CH_3)(CH_2)_{1-4}CO_2H$, $—(CH_2)_{1-4}OCH(CH_3)CO_2C_{1-4}CO_2C_{1-4}alkyl$, $—(CH_2)_{1-4}O(CH_2)_{1-4}CH(CH_3)CO_2H$, $—(CH_2)_{1-4}O(CH_2)_{1-4}CH(CH_3)CO_2C_{1-4}alkyl$, $—CHOH(CH_2)_{1-4}O(CH_2)_{1-5}CO_2H$, $—CHOH(CH_2)_{1-4}O(CH_2)_{1-5}CO_2C_{1-4}alkyl$, $—CHCF_3(CH_2)_{1-4}O(CH_2)_{1-5}CO_2H$, $—CHCF_3(CH_2)_{1-4}O—(CH_2)_{1-5}CO_2C_{1-4}alkyl$, $—(CH_2)_{1-4}O(CH_2)_{1-5}CONR^a{}_2$, $—(CH_2)_{1-4}O(CH_2)_{1-5}CONR^aOH$, $—(CH_2)_{1-4}O(CH_2)_{1-5}CONR^aCN$, $—(CH_2)_{1-4}O(CH_2)_{1-5}P(O)OH_2$, $—(CH_2)_{0-4}CONH_2$, $—(CH_2)_{0-4}CONHC_{1-4}alkyl$, $—(CH_2)_{0-4}CON(C_{1-4}alkyl)_2$, $—(CH_2)_{0-4}CO(N\text{-}proline)$, $—(CH_2)_{0-4}(N\text{-}pyrazole)\text{-}(CH_2)_{0-4}CO_2H$, $—(CH_2)_{0-4}CO(N\text{-}pyrazole)\text{-}(CH_2)_{0-4}CO_2C_{1-4}alkyl$, $—(CH_2)_{0-4}(N\text{-}pyrrole)\text{-}(CH_2)_{0-4}CO_2H$, $—(CH_2)_{0-4}CO(N\text{-}pyrrole)\text{-}(CH_2)_{0-4}CO_2C_{1-4}alkyl$, $—(CH_2)_{0-4}—O(phenyl)\text{-}(CH_2)_{0-4}CO_2H$, $—(CH_2)_{0-4}—O(phenyl)\text{-}(CH_2)_{0-4}CO_2C_{1-4}alkyl$, $—(CH_2)_{0-4}—O(cycloalkane)\text{-}(CH_2)_{0-4}CO_2H$, $—(CH_2)_{0-4}—O(cycloalkane)\text{-}(CH_2)_{0-4}CO_2C_{1-4}alkyl$, $—(CH_2)_{0-4}C(O)NR^a(CH_2)_{1-4}CO_2H$, $—(CH_2)_{0-4}C(O)NR^a(CH_2)_{1-4}CONH_2$, $—(CH_2)_{0-4}C(O)NR^a(CH_2)_{1-4}CONHC_{1-4}alkyl$, $—(CH_2)_{0-4}C(O)NR^a(CH_2)_{1-4}CON(C_{1-4}alkyl)_2$, —OH, $—(CH_2)_{1-4}OH$, $—(CH_2)_{0-4}OC_{1-4}alkyl$, $—NH_2$, $—(CH_2)_{0-4}NR^a(CH_2)_{1-4}CO_2H$, $—(CH_2)_{0-4}NR^a(CH_2)_{1-4}CO_2C_{1-4}$alkyl, $—(CH_2)_{0-4}N[(CH_2)_{1-4}CO_2C_{1-4}$ alkyl$]_2$, $—(CH_2)_{1-4}NH_2—(CH_2)_{0-4}NHC_{1-4}$alkyl, $—(CH_2)_{0-4}N(C_{1-4}$alkyl$)_2$, $—(CH_2)_{0-4}SO_3H$, $—(CH_2)_{0-4}SO_2NH_2$, $—(CH_2)_{0-4}SO_2NHC_{1-4}$alkyl, $—(CH_2)_{0-4}NR^aSO_2C_{1-4}$alkyl, $—(CH_2)_{0-4}OP(OH)_2$, $—(CH_2)_{0-4}OP(OH)(OC_{1-4}$alkyl), or $—(CR_2)_{0-4}OP(O)(H)OH$, wherein $R^a$, independently for each occurrence, is H or $C_{1-4}$alkyl;

X is $—CH_2—$, —NH—, or —O—;

m is 1, 2, 3, or 4, particularly 1 or 2;

p is 1; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-b-5, wherein:

each $R^6$ is independently halogen, $—C_{1-4}$alkyl, $—C_{1-4}$haloalkyl, $=CH_2$, $—(CH_2)_{0-4}CO_2H$, $—(CH_2)_{0-4}CO$(N-proline), $—(CH_2)_{0-4}C(O)NR^a(CH_2)_{1-4}CO_2H$, —OH, $—(CH_2)_{1-4}OH$, $—(CH_2)_{0-4}OC_{1-4}$alkyl, $—(CH_2)_{0-4}O(CH_2)_{1-5}CO_2H$, $—(CH_2)_{1-4}O(CH_2)_{0-5}CO_2C_{1-4}$alkyl, $—(CH_2)_{0-4}SO_3H$, $—(CH_2)_{0-4}SO_2NH_2$, $—(CH_2)_{0-4}NR^aSO_2C_{1-4}$alkyl, $—(CH_2)_{0-4}OP(OH)_2$, or $—(CR_2)_{0-4}OP(O)(H)OH$;

X is $—CH_2—$, —NH—, or —O—;

m is 1 or 2;

p is 1; and each $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-b-5, wherein each $R^6$ is independently fluoro, -methyl, -methoxy, $—(CH_2)_{1-5}CO_2H$, $—(CH_2)_{1-5}CO_2C_{1-4}$alkyl, $—(CH_2)_{1-4}O(CH_2)_{1-5}CO_2H$, $—(CH_2)_{0-4}O(CH_2)_{1-5}CO_2C_{1-4}$alkyl, or —OH; and m is 1, 2, or 3, particularly 1 or 2.

In certain embodiments, for the above disclosed compounds of formula I-d-5, m is 1 or 2, and at least one $R^6$ includes a terminal $—CO_2H$ group. For example, in certain instances, at least one $R^6$ is $—(CH_2)_{0-4}CO_2H$.

In some embodiments, the present disclosure provides a compound of formula I or formula I*, wherein $R^1$ is

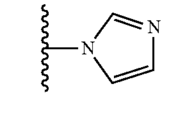

and $R^2$ is

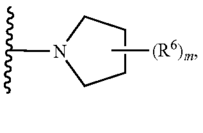

thereby forming a compound of formula I-d-6:

I-d-6

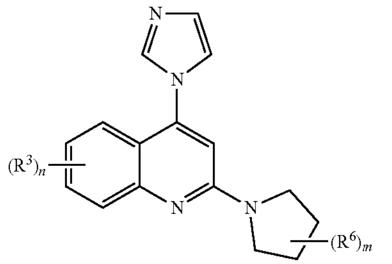

or a pharmaceutically acceptable salt thereof, wherein:

each $R^6$ is independently halogen, =O, —COR, $—(CR_2)_{0-6}CO_2R$, $—(CR_2)_{0-6}CONR_2$, —OR, $—(CR_2)_{1-4}OR$, $—NR_2$, $—(CR_2)_{1-4}NR_2$, —NRC(O)OR, —NRC(O)R, $—NRC(O)NR_2$, —SR, $—SO_2R$, —S(O)R, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, $—B(OR)_2$, or $R^B$;

m is 0, 1, 2, 3, or 4, particularly 1, 2, 3, or 4; and each of R, $R^3$, $R^B$, and n is as defined above and described in embodiments herein, both singly and in combination.

In some embodiments, the present disclosure provides a compound of formula I-d-6, wherein $R^6$ is not $R^B$.

In certain embodiments, the present disclosure provides a compound of formula I-d-6, wherein $R^3$ is independently halogen, such as chloro, including dichloro, including wherein n is 2 and $R^3$ is chloro at the 7- and 8-positions with respect to the quinoline ring.

In certain embodiments, the present disclosure provides a compound of formula I-d-6, wherein:

each $R^6$ is independently halogen, $—C_{1-4}$alkyl, $—C_{1-4}$haloalkyl, $—C_{3-6}$cycloalkyl, $=CR_2$, =O, —COR, $—(CR_2)_{0-6}CO_2R$, $—(CR_2)_{0-6}CONR_2$, —OR, q $—(CR_2)_{1-4}OR$, $—NR_2$, $—(CR_2)_{1-4}NR_2$, —NRC(O)OR, —NRC(O)R, $—NRC(O)NR_2$, —SR, $—SO_2R$, —S(O)R, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, or $—B(OR)_2$;

m is 1, 2, 3, or 4, particularly 1 or 2; and each $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-d-6, wherein:

each $R^6$ is independently halogen, $—C_{1-4}$alkyl, $—C_{1-4}$haloalkyl, $—C_{3-6}$cycloalkyl, $=CH_2$, =O, $—(CH_2)_{0-4}CO_2H$, $—(CH_2)_{0-4}CO_2C_{1-4}$alkyl, $—(CH_2)_{0-4}CO_2C_{1-4}$haloalkyl, $—(CH_2)_{0-4}O(CH_2)_{1-5}CO_2H$, $—(CH_2)_{0-4}O(CH_2)_{1-5}CO_2C_{1-4}$alkyl, $—(CH_2)_{1-4}O(CH_2)_{1-4}CHFCO_2H$, $—(CH_2)_{1-4}O(CH_2)_{1-4}CHFCO_2C_{1-4}$alkyl, $—(CH_2)_{1-4}OCH(CH_3)(CH_2)_{1-4}CO_2H$, $—(CH_2)_{1-4}OCH(CH_3)(CH_2)_{1-4}CO_2C_{1-4}$alkyl, $—(CH_2)_{1-4}O(CH_2)_{1-4}CH(CH_3)CO_2H$, $—(CH_2)_{1-4}O(CH_2)_{1-4}CH(CH_3)CO_2C_{1-4}$alkyl, $—CHOH(CH_2)_{1-4}O(CH_2)_{1-5}CO_2H$, $—CHOH(CH_2)_{1-4}O(CH_2)_{1-5}CO_2C_{1-4}$alkyl, $—CHCF_3(CH_2)_{1-4}O(CH_2)_{1-5}CO_2H$, $—CHCF_3(CH_2)_{1-4}O—(CH_2)_{1-5}CO_2C_{1-4}$alkyl, $—(CH_2)_{1-4}O(CH_2)_{1-5}CONR^a_2$, $—(CH_2)_{1-4}O(CH_2)_{1-5}CONR^aOH$, $—(CH_2)_{1-4}O(CH_2)_{1-5}CONR^aCN$, $—(CH_2)_{1-4}O(CH_2)_{1-5}P(O)OH_2$, $—(CH_2)_{0-4}CONH_2$, $—(CH_2)_{0-4}CONHC_{1-4}$alkyl, $—(CH_2)_{0-4}CON(C_{1-4}alkyl)_2$, $—(CH_2)_{0-4}CO$(N-proline), $—(CH_2)_{0-4}CO$(N-pyrrolidine-3-carboxylic acid), $—(CH_2)_{0-4}$(N-pyrazole)-$(CH_2)_{0-4}CO_{211}$, $—(CH_2)_{0-4}CO$(N-pyrazole)-$(CH_2)_{0-4}CO_2C_{1-4}$alkyl, $—(CH_2)_{0-4}$(N-pyrrole)-$(CH_2)_{0-4}CO_2H$, $—(CH_2)_{0-4}CO$(N-pyrrole)-$(CH_2)_{0-4}CO_2C_{1-4}$alkyl, $—(CH_2)_{0-4}—O$ (phenyl)-$(CH_2)_{0-4}CO_2H$, $—(CH_2)_{0-4}—O$(phenyl)-$(CH_2)_{0-4}CO_2C_{1-4}$alkyl, $—(CH_2)_{0-4}—O$(cycloalkane)-$(CH_2)_{0-4}CO_2H$, $—(CH_2)_{0-4}—O$(cycloalkane)-$(CH_2)_{0-4}CO_2C_{1-4}$alkyl, $—(CH_2)_{0-4}C(O)NR^a(CH_2)_{1-4}CO_2H$, $—(CH_2)_{0-4}C(O)NR^a—CH(C_{1-4}alkyl)-CO_2H$, $—(CH_2)_{0-4}C(O)NR^a(CH_2)_{1-4}CONH_2$, $—(CH_2)_{0-4}C(O)NR^a(CH_2)_{1-4}CONHC_{1-4}$alkyl, $—(CH_2)_{0-4}C(O)NR^a(CH_2)_{1-4}CON(C_{1-4}alkyl)_2$, —OH, $—(CH_2)_{1-4}OH$, $—(CH_2)_{0-4}OC_{1-4}$alkyl, $—(CH_2)_{0-4}OC(O)C_{1-4}$alkyl, $—NH_2$, $—(CH_2)_{0-4}NR^a(CH_2)_{1-4}CO_2H$, $—(CH_2)_{0-4}NR^a(CH_2)_{1-4}CO_2C_{1-4}$alkyl, $—(CH_2)_{1-4}NH_2$, $—(CH_2)_{0-4}NHC_{1-4}$alkyl, $—(CH_2)_{0-4}NR^aC(O)C_{1-4}$alkyl, $—(CH_2)_{0-4}NR^aC(O)Ph$, $—(CH_2)_{0-4}NR^aCO(CH_2)_{1-4}OH$, $—(CH_2)_{0-4}N(C_{1-4}alkyl)_2$, $—(CH_2)_{0-4}SO_3H$, $—(CH_2)_{0-4}SO_2NH_2$, $—(CH_2)_{0-4}SO_2NR^aC_{1-4}$alkyl, $—(CH_2)_{0-4}NR^aSO_2C_{1-4}$alkyl, $—(CH_2)_{0-4}NR^aSO_2Ph$, $—(CH_2)_{0-4}NR^aSO_2(CH_2)_{1-4}CO_2H$, $—(CH_2)_{0-4}OP(OH)_2$, $—(CH_2)_{0-4}OP(OH)(OC_{1-4}alkyl)$, or $—(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-d-6, wherein:

each $R^6$ is independently halogen, $—C_{1-4}$alkyl, $—C_{1-4}$haloalkyl, $—C_{3-6}$cycloalkyl, $=CH_2$, $—(CH_2)_{0-4}CO_2H$, $—(CH_2)_{0-4}O(CH_2)_{1-5}CO_2H$, $—(CH_2)_{0-4}O(CH_2)_{1-5}CO_2C_{1-4}$alkyl, $—(CH_2)_{0-4}CO$(N-proline), $—(CH_2)_{0-4}CO$(N-pyrrolidine-3-carboxylic acid), $—(CH_2)_{0-4}C(O)NR^a(CH_2)_{1-4}CO_2H$, $—(CH_2)_{0-4}C(O)NR^a—CH(C_{1-4}alkyl)-CO_2H$, —OH, $—(CH_2)_{1-4}OH$, $—(CH_2)_{0-4}OC_{1-4}$alkyl, $—(CH_2)_{0-4}OC(O)C_{1-4}$alkyl, $—(CH_2)_{0-4}NR^aC(O)C_{1-4}$alkyl, $—(CH_2)_{0-4}NR^aC(O)Ph$, $—(CH_2)_{0-4}NR^aCO(CH_2)_{1-4}OH$, $—(CH_2)_{0-4}SO_3H$, $—(CH_2)_{0-4}SO_2NH_2$, $—(CH_2)_{0-4}NR^aSO_2C_{1-4}$alkyl, $—(CH_2)_{0-4}NR^aSO_2Ph$, $—(CH_2)_{0-4}NR^aSO_2(CH_2)_{1-4}CO_2H$, $—(CH_2)_{0-4}OP(OH)_2$, or $—(CR_2)_{0-4}OP(O)(H)OH$, wherein $R^a$, independently for each occurrence, is H or $C_{1-4}$alkyl;

m is 1 or 2; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-d-6, wherein each $R^6$ is independently fluoro, -methyl, cyclohexyl, -methoxy, —OtBu, $—CF_3$, $—(CH_2)_{1-5}CO_2H$, $—(CH_2)_{1-5}CO_2C_{1-4}$alkyl, $—(CH_2)_{0-4}O(CH_2)_{1-5}CO_2H$, $—(CH_2)_{0-4}O(CH_2)_{1-5}CO_2C_{1-4}$alkyl, or —OH; and m is 1, 2, or 3, particularly 1 or 2.

In certain embodiments, for the above disclosed compounds of formula I-d-6, m is 1 or 2, and at least one $R^6$ includes a terminal $—CO_2H$ group. For example, in certain instances, at least one $R^6$ is $—(CH_2)_{0-4}CO_2H$.

In some embodiments, the present disclosure provides a compound of formula I or formula I*, wherein $R^1$ is

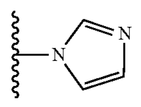 [SMILES: *n1ccnc1]

and $R^2$ is

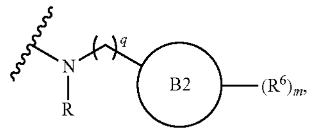

thereby forming a compound of formula I-d-7:

I-d-7

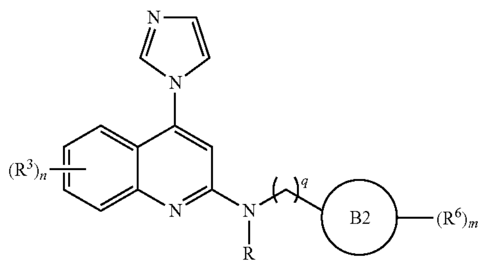

or a pharmaceutically acceptable salt thereof, wherein:

Ring B2 is phenyl; a 4- to 7-membered saturated or partially unsaturated carbocyclic or heterocyclic ring having 1 to 3 heteroatoms independently selected from nitrogen, oxygen, phosphorus, and sulfur; or a 5- to 6-membered heteroaryl ring having 1 to 4 heteroatoms independently selected from nitrogen, oxygen, phosphorus, and sulfur;

each $R^6$ is independently halogen, —COR, $—(CR_2)_{0-6}CO_2R$, $—(CR_2)_{0-6}CONR_2$, —OR, $—(CR_2)_{1-4}OR$, $—NR_2$, $—(CR_2)_{1-4}NR_2$, —NRC(O)OR, —NRC(O)R, $—NRC(O)NR_2$, —SR, $—SO_2R$, —S(O)R, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, $—B(OR)_2$, or $R^B$;

m is 0, 1, 2, 3, or 4, particularly 1, 2, 3, or 4;

q is 0, 1, or 2; and each of R, $R^3$, $R^B$, and n is as defined above and described in embodiments herein, both singly and in combination.

In certain embodiments, the present disclosure provides a compound of formula I-d-7, wherein Ring B2 is phenyl, particularly substituted phenyl. In other embodiments, Ring B2 is not phenyl. For example, Ring B2 may be a 4- to 10-membered saturated or partially unsaturated monocyclic or bicyclic carboxylic or heterocyclic ring having 1 to 3 heteroatoms independently selected from nitrogen, oxygen, phosphorus, and sulfur. In some embodiments, Ring B2 is a 5- to 6-membered heteroaryl ring having 1 to 4 heteroatoms independently selected from nitrogen, oxygen, phosphorus, and sulfur.

In some embodiments, the present disclosure provides a compound of formula I-d-7, wherein $R^6$ is not $R^B$.

In some embodiments, the present disclosure provides a compound of formula I-d-7, wherein R in

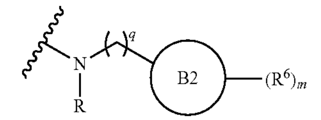

is $R^a$, which is H or $C_{1-6}$alkyl.

In certain embodiments, the present disclosure provides a compound of formula I-d-7, wherein $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-d-7, m is 1 or 2, and at least one $R^6$ includes a terminal —$CO_2H$ group. For example, in certain instances, at least one $R^6$ is —$(CH_2)_{0-4}CO_2H$.

In some embodiments, the present disclosure provides a compound of formula I or formula I*, wherein $R^1$ is

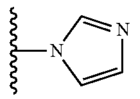

and $R^2$ is

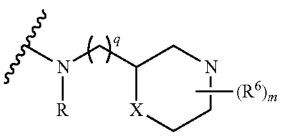

or

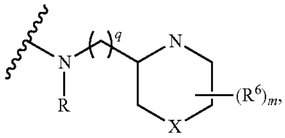

thereby forming a compound of formula I-d-8 or formula I-d-8*, respectively:

I-d-8

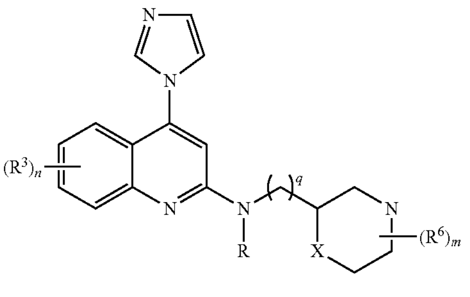

-continued

I-d-8*

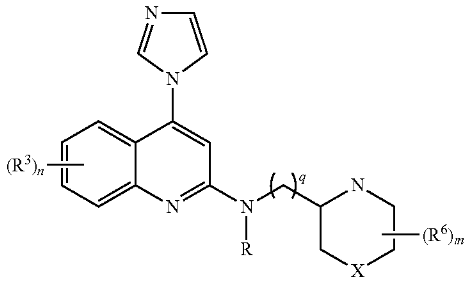

or a pharmaceutically acceptable salt thereof, wherein:

each $R^6$ is independently hydrogen (only on N), halogen (not on N), —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

X is —$CR_2$—, —NR—, —O—, —S—, or —$SO_2$—, particularly —$CR_2$—, —NR—, or —O;

m is 1, 2, 3, or 4;

q is 0, 1, or 2; and each of R, $R^3$, $R^B$, and n is as defined above and described in embodiments herein, both singly and in combination.

In some embodiments, the present disclosure provides a compound of formula I-d-8 or formula I-d-8*, wherein $R^6$ is not $R^B$.

In some embodiments, the present disclosure provides a compound of formula I-d-8 or formula I-d-8*, wherein R in

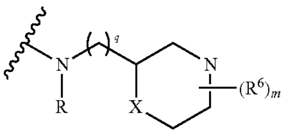

or in

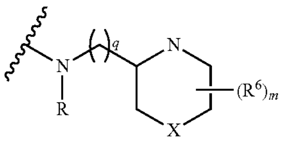

is $R^a$, which is H or $C_{1-6}$alkyl.

In certain embodiments, the present disclosure provides a compound of formula I-d-8 or formula I-d-8*, wherein $R^3$ is independently halogen, such as chloro, including dichloro, including wherein n is 2 and $R^3$ is chloro at the 7- and 8-positions with respect to the quinoline ring.

In certain embodiments, the present disclosure provides a compound of formula I-d-8 or formula I-d-8*, wherein:

each $R^6$ is independently halogen, =O, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, or $—B(OR)_2$;

m is 1, 2, 3, or 4, particularly 1 or 2;

q is 1 or 2; and each $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-d-8 or formula I-d-8*, wherein:

each $R^6$ is independently halogen, =O, $—(CH_2)_{0-4}CO_2H$, $—(CH_2)_{0-4}CO_2C_{1-4}alkyl$, $—(CH_2)_{0-4}CONH_2$, $—(CH_2)_{0-4}CONHC_{1-4}alkyl$, $—(CH_2)_{0-4}CON(C_{1-4}alkyl)_2$, $—(CH_2)_{0-4}CO$(N-proline), $—(CH_2)_{0-4}C(O)NR^a(CH_2)_{1-4}CO_2H$, $—(CH_2)_{0-4}C(O)NR^a(CH_2)_{1-4}CONH_2$, $—(CH_2)_{0-4}C(O)NR^a(CH_2)_{1-4}CONHC_{1-4}alkyl$, $—(CH_2)_{0-4}C(O)NR^a(CH_2)_{1-4}CON(C_{1-4}alkyl)_2$, —OH, $—(CH_2)_{1-4}OH$, $—(CH_2)_{0-4}OC_{1-4}alkyl$, $—NH_2$, $—(CH_2)_{1-4}NH_2$, $—(CH_2)_{0-4}NHC_{1-4}alkyl$, $—(CH_2)_{0-4}N(C_{1-4}alkyl)_2$, $—(CH_2)_{0-4}SO_3H$, $—(CH_2)_{0-4}SO_2NH_2$, $—(CH_2)_{0-4}SO_2NHC_{1-4}alkyl$, $—(CH_2)_{0-4}NR^aSO_2C_{1-4}alkyl$, $—(CH_2)_{0-4}OP(OH)_2$, $—(CH_2)_{0-4}OP(OH)(OC_{1-4}alkyl)$, or $—(CR_2)_{0-4}OP(O)(H)OH$, wherein $R^a$, independently for each occurrence, is H or $C_{1-4}alkyl$;

m is 1, 2, 3, or 4, particularly 1 or 2;

q is 1; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-d-8 or formula I-d-8*, wherein:

each $R^6$ is independently halogen, $—(CH_2)_{0-4}CO_2H$, $—(CH_2)_{0-4}CO$(N-proline), $—(CH_2)_{0-4}C(O)NR^a(CH_2)_{1-4}CO_2H$, —OH, $—(CH_2)_{1-4}OH$, $—(CH_2)_{0-4}SO_3H$, $—(CH_2)_{0-4}SO_2NH_2$, $—(CH_2)_{0-4}NR^aSO_2C_{1-4}alkyl$, $—(CH_2)_{0-4}OP(OH)_2$, or $—(CR_2)_{0-4}OP(O)(H)OH$, wherein $R^a$, independently for each occurrence, is H or $C_{1-4}alkyl$;

m is 1 or 2;

q is 1; and each $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-d-8 or I-d-8*, m is 1 or 2, and at least one $R^6$ includes a terminal $—CO_2H$ group. For example, in certain instances, at least one $R^6$ is $—(CH_2)_{0-4}CO_2H$.

In some embodiments, the present disclosure provides a compound of formula I or formula I*, wherein $R^1$ is

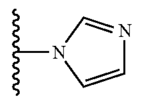 [SMILES: *n1ccnc1]

and $R^2$ is

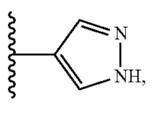 [SMILES: *c1cn[nH]c1]

thereby forming a compound of formula I-d-9:

I-d-9

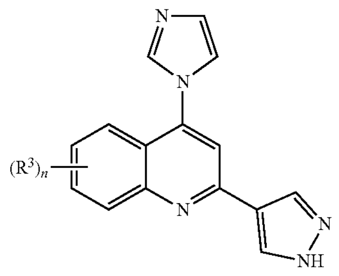

or a pharmaceutically acceptable salt thereof, wherein each of R, $R^1$, $R^3$, and n is as defined above and described in embodiments herein, both singly and in combination.

In certain embodiments, the present disclosure provides a compound of formula I-d-9, wherein $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I or formula I*, wherein $R^1$ is

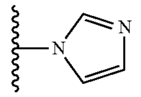 [SMILES: *n1ccnc1]

and $R^2$ is

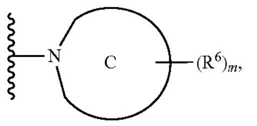

thereby forming a compound of formula I-d-10:

I-d-10

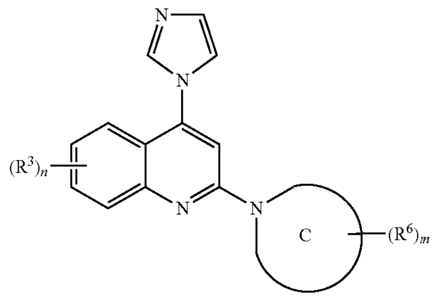

or a pharmaceutically acceptable salt thereof, wherein:

Ring C is pyrrolyl or a 4- to 10-membered saturated or partially unsaturated monocyclic, bicyclic, bridged bicyclic, or spirocyclic heterocyclic ring having 0 to 3 heteroatoms (in addition to the nitrogen already depicted in Ring C) independently selected from nitrogen, oxygen, and sulfur;

each $R^6$ is independently halogen, =O, —COR, $—(CR_2)_{0-6}CO_2R$, $—(CR_2)_{0-6}CONR_2$, —OR, $—(CR_2)_{1-4}OR$, $—NR_2$, $—(CR_2)_{1-4}NR_2$, —NRC(O)OR, —NRC(O)R, $—NRC(O)NR_2$, —SR, $—SO_2R$, —S(O)R, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, $—B(OR)_2$, or $R^B$;

m is 1, 2, 3, or 4; and each of R, $R^B$, $R^3$, and n is as defined above and described in embodiments herein, both singly and in combination.

In some embodiments, the present disclosure provides a compound of formula I-d-10, wherein Ring C is azetidinyl, pyrrolyl, 2,3-dihydro-1H-pyrrolyl, pyrrolidinyl, piperidinyl, morpholinyl, thiazolidinyl, indolinyl, isoindolinyl, octahydroindolyl, azepanyl, an oxazepane, an azabicyclohexane, an azabicycloheptane, an azabicyclooctane, an azabicyclononane, an azaspiroheptane, or an octahydrocyclicpentapyrrole.

In particular embodiments, the present disclosure provides a compound of formula I-d-10, wherein Ring C is pyrrolyl, 2-azabicyclo[3.1.0]hexanyl, 3-azabicyclo[3.1.0]hexane, 5-azaspiro[2.4]heptanyl, or octahydrocyclopenta[b]pyrrolyl.

In particular embodiments, the present disclosure provides a compound of formula I-d-10, wherein Ring C is 3-hydroxyproline, $C_{1-6}$alkyl 3-hydroxyproline ester, or $C_{1-6}$haloalkyl 3-hydroxyproline ester.

In some embodiments, the present disclosure provides a compound of formula I-d-10, wherein:

each $R^6$ is independently fluoro, —CN, methyl, $—C_{3-6}$cycloalkyl, $—CF_3$, $—CO_2H$, $—NH_2$, —OH, $—OC_{1-4}$alkyl, $=CH_2$, =O, tetrazolyl, imidazoyl, thiophenyl, 1,2,4-oxadiazol-3(2H)-onyl, morpholinyl, phenyl, $—(CH_2)_{1-4}OC_{1-4}$alkyl, $—(CH_2)_{1-4}O(CH_2)_{1-5}CO_2H$, $—(CH_2)_{1-4}O(CH_2)_{1-5}CO_2C_{1-4}$alkyl, $—(CH_2)_{1-4}O(CH_2)_{1-4}CHFCO_2H$, $—(CH_2)_{1-4}O(CH_2)_{1-4}CHFCO_2C_{1-4}$alkyl, $—(CH_2)_{1-4}OCH(CH_3)(CH_2)_{1-4}CO_2H$, $—(CH_2)_{1-4}OCH(CH_3)(CH_2)_{1-4}CO_2C_{1-4}$alkyl, $—(CH_2)_{1-4}O(CH_2)_{1-4}CH(CH_3)CO_2H$, $—(CH_2)_{1-4}O(CH_2)_{1-4}CH(CH_3)CO_2C_{1-4}$alkyl, $CHOH(CH_2)_{1-4}O(CH_2)_{1-5}CO_2H$, $—CHOH—(CH_2)_{1-4}O(CH_2)_{1-5}CO_2C_{1-4}$alkyl, $—CHCF_3(CH_2)_{1-4}O(CH_2)_{1-5}CO_2H$, $—CHCF_3(CH_2)_{1-4}O(CH_2)_{1-5}CO_2C_{1-4}$alkyl, $—(CH_2)_{0-4}O(CH_2)_{1-5}CONR^a{}_2$, $—(CH_2)_{1-4}O(CH_2)_{1-5}CONR^aOH$, $—(CH_2)_{1-4}O(CH_2)_{1-5}CONR^aCN$, $—(CH_2)_{1-4}O(CH_2)_{1-5}P(O)OH_2$, $—CH(OH)CF_3$, $—COH(CF_3)_2$, $—(CH_2)_{1-5}CO_2H$, $—(CH_2)_{1-5}CO_2C_{1-4}$alkyl, $—(CH_2)_{0-4}CHCHCO_2H$, $—(CH_2)_{0-4}CHCHCO_2C_{1-4}$alkyl, $—CO_2C_{1-4}$alkyl, $—CO_2C_{1-4}$haloalkyl, $—OCOC_{1-4}$alkyl, $—O(CH_2)_{1-4}CO_2H$, $—O(CH_2)_{1-4}CO_2C_{1-4}$alkyl, $—OCONR^a(CH_2)_{0-4}CO_2H$, $—OCONR^a(CH_2)_{0-4}CO_2C_{1-4}$alkyl, —OCO—(N-morpholine), $—CONH_2$, —CONHOH, $—CONHOC_{1-4}$alkyl, $—(CH_2)_{0-4}C(O)NR^a(CH_2)_{1-4}CO_2H$, $—(CH_2)_{0-4}C(O)NR^a(CH_2)_{1-4}CO_2C_{1-4}$alkyl, $—(CH_2)_{0-4}C(O)NR^a(CH_2)_{1-4}$ (pyrrolid-2-one), $—(CH_2)_{0-4}C(O)NR^a(CH_2)_{1-4}$(piperidin-2-one), $—(CH_2)_{0-4}C(O)NR^a(CH_2)_{1-4}C(OH)(CF_3)_2$, $—(CH_2)_{0-4}C(O)NR^a(CH_2)_{1-4}CONH_2$, $—(CH_2)_{0-4}CONR^aSO_2C_{1-4}$haloalkyl, $—(CH_2)_{0-4}$CO(N-pyrrolidine)-$(CH_2)_{0-4}CO_2H$, $—(CH_2)_{0-4}$CO(N-pyrrolidine)-$(CH_2)_{0-4}CO_2C_{1-4}$alkyl, $—(CH_2)_{0-4}$(N-pyrazole)-$(CH_2)_{0-4}CO_2H$, $—(CH_2)_{0-4}$CO(N-pyrazole)-$(CH_2)_{0-4}CO_2C_{1-4}$alkyl, $—(CH_2)_{0-4}$(N-pyrrole)-$(CH_2)_{0-4}CO_2H$, $—(CH_2)_{0-4}$CO(N-pyrrole)-$(CH_2)_{0-4}CO_2C_{1-4}$alkyl, $—(CH_2)_{0-4}$—O-(phenyl)-$(CH_2)_{0-4}CO_2H$, $—(CH_2)_{0-4}$—O-(phenyl)-$(CH_2)_{0-4}CO_2C_{1-4}$alkyl, $—(CH_2)_{0-4}$—O(cycloalkane)-$(CH_2)_{0-4}CO_2H$, $—(CH_2)_{0-4}$—O(cycloalkane)-$(CH_2)_{0-4}CO_2C_{1-4}$alkyl, $—(CH_2)_{0-4}$CO(N-pyrrolidine)-$(CH_2)_{0-4}SO_2NH_2$, $—(CH_2)_{0-4}$CO(N-pyrrolidine)-(tetrazole), $—(CH_2)_{0-4}$CO(N-piperidine)-$(CH_2)_{0-4}CO_2H$, $—(CH_2)_{0-4}$CO(N-piperidine)-$(CH_2)_{0-4}CO_2C_{1-4}$alkyl, $—(CH_2)_{0-4}$CO(N-morpholine)-$(CH_2)_{0-4}CO_2H$, $—CONR^a$(bicyclo[1.1.1]pentane)-$(CH_2)_{0-4}CO_2H$, $—NH_2$, $—(CH_2)_{0-4}NR^a(CH_2)_{1-4}CO_2H$, $—(CH_2)_{0-4}NR^a(CH_2)_{1-4}CO_2C_{1-4}$alkyl, $—(CH_2)_{0-4}N[(CH_2)_{1-4}CO_2C_{1-4}alkyl]_2$, $—(CH_2)_{0-4}NR^a$CO(isoxazole)-OH, $—(CH_2)_{0-4}NR^aSO_2$(benzene)-$CO_2H$, $—(CH_2)_{0-4}NR^aSO_2(CH_2)_{1-4}CO_2H$, $—(CH_2)_{0-4}NR^aSO_2(CH_2)_{1-4}\ CO_2C_{1-4}$alkyl, $—(CH_2)_{0-4}NR^aSO_2(CH_2)_{1-4}$(imidazolidine-2,4-dione), $—(CH_2)_{0-4}OP(O)(H)OH$, wherein $R^a$, independently for each occurrence, is H or $C_{1-4}$alkyl; and m is 1, 2, 3, or 4.

In particular embodiments, the present disclosure provides a compound of formula I-d-10, wherein each $R^6$ is independently fluoro, -methyl, cyclohexyl, $—CF_3$, $—CO_2H$, $—CO_2C_{1-4}$alkyl, $—CO_2C_{1-4}$haloalkyl, or —OH; and m is 1, 2, or 3, particularly 1 or 2.

In particular embodiments, the present disclosure provides a compound of formula I-d-10, wherein each $R^6$ is independently fluoro, -methyl, cyclohexyl, $—CF_3$, -methoxy, $—(CH_2)_{1-5}CO_2H$, $—(CH_2)_{1-5}CO_2C_{1-4}$alkyl, $—(CH_2)_{0-4}O(CH_2)_{1-5}CO_2H$, $—(CH_2)_{0-4}O(CH_2)_{1-5}CO_2C_{1-4}$alkyl, or —OH; and m is 1, 2, or 3, particularly 1 or 2.

In certain embodiments, the present disclosure provides a compound of formula I-d-10, wherein $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I or formula I*, wherein $R^1$ is

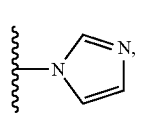

$R^2$ is

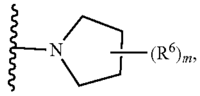

and $R^3$ is chloro at the 7- and 8-positions thereby forming a compound of formula I-d-11:

I-d-11

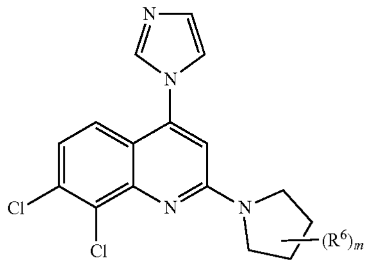

or a pharmaceutically acceptable salt thereof, wherein:

each $R^6$ is independently halogen, =O, —COR, $—(CR_2)_{0-6}CO_2R$, $—(CR_2)_{0-6}CONR_2$, —OR, $—(CR_2)_{1-4}OR$, $—NR_2$, $—(CR_2)_{1-4}NR_2$, —NRC(O)OR, $—NRC(O)R$, $—NRC(O)NR_2$, $—SR$, $—SO_2R$, $—S(O)R$, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, $—B(OR)_2$, or $R^B$;

m is 1, 2, 3, or 4; and each of R and $R^B$ is as defined above and described in embodiments herein, both singly and in combination.

In some embodiments, the present disclosure provides a compound of formula I-d-11, wherein:

each $R^6$ is independently fluoro, —CN, methyl, =O, $=CH_2$, $—C_{3-6}$cycloalkyl, $—CF_3$, $—CO_2H$, $—NH_2$, —OH, tetrazolyl, imidazoyl, thiophenyl, 1,2,4-oxadiazol-3(2H)-onyl, morpholinyl, phenyl, $—(CH_2)_{1-4}OC_{1-4}$alkyl, $—(CH_2)_{0-4}O(CH_2)_{1-5}CO_2H$, $—(CH_2)_{0-4}O(CH_2)_{1-5}CO_2C_{1-4}$alkyl, $—(CH_2)_{1-4}O(CH_2)_{1-4}CHFCO_2H$, $—(CH_2)_{1-4}O(CH_2)_{1-4}CHFCO_2C_{1-4}$alkyl, $—(CH_2)_{1-4}OCH(CH_3)(CH_2)_{1-4}CO_2H$, $—(CH_2)_{1-4}OCH(CH_3)(CH_2)_{1-4}CO_2C_{1-4}$alkyl, $—(CH_2)_{1-4}O(CH_2)_{1-4}CH(CH_3)CO_2H$, $—(CH_2)_{1-4}O(CH_2)_{1-4}CH(CH_3)CO_2C_{1-4}$alkyl, $—CHOH(CH_2)_{1-4}O(CH_2)_{1-5}CO_2H$, $—CHOH(CH_2)_{1-4}O(CH_2)_{1-5}CO_2C_{1-4}$alkyl, $—CHCF_3(CH_2)_{1-4}O(CH_2)_{1-5}CO_2H$, $—CHCF_3(CH_2)_{1-4}O—(CH_2)_{1-5}CO_2C_{1-4}$alkyl, $—(CH_2)_{1-4}O(CH_2)_{1-5}CONR^a_2$, $—(CH_2)_{1-4}O(CH_2)_{1-5}CONR^aOH$, $—(CH_2)_{1-4}O(CH_2)_{1-5}CONR^aCN$, $—(CH_2)_{1-4}O(CH_2)_{1-5}P(O)OH_2$, $—CH(OH)CF_3$, $—COH(CF_3)_2$, $—(CH_2)_{1-5}CO_2H$, $—(CH_2)_{1-5}CO_2C_{1-4}$alkyl, $—(CH_2)_{0-4}CHCHCO_2H$, $—(CH_2)_{0-4}CHCHCO_2C_{1-4}$alkyl, $—CO_2C_{1-4}$alkyl, $—CO_2C_{1-4}$haloalkyl, $—OCOC_{1-4}$alkyl, $—O(CH_2)_{1-4}CO_2H$, $—O(CH_2)_{1-4}CO_2C_{1-4}$alkyl, $—CONR^a(CH_2)_{0-4}CO_2H$, $—OCONR^a(CH_2)_{0-4}CO_2C_{1-4}$alkyl, —OCO—(N-morpholine), $—CONH_2$, —CONHOH, $—CONHOC_{1-4}$alkyl, $—(CH_2)_{0-4}C(O)NR^a(CH_2)_{1-4}CO_2H$, $—(CH_2)_{0-4}C(O)NR^a(CH_2)_{1-4}CO_2C_{1-4}$alkyl, $—(CH_2)_{0-4}C(O)NR^a(CH_2)_{1-4}$(pyrrolid-2-one), $—(CH_2)_{0-4}C(O)NR^a(CH_2)_{1-4}$(piperidin-2-one), $—(CH_2)_{0-4}C(O)NR^a(CH_2)_{1-4}C(OH)(CF_3)_2$, $—(CH_2)_{0-4}C(O)NR^a(CH_2)_{1-4}CONH_2$, $—(CH_2)_{0-4}CONR^aSO_2C_{1-4}$haloalkyl, $—(CH_2)_{0-4}CO$(N-pyrrolidine)-$(CH_2)_{0-4}CO_2H$, $—(CH_2)_{0-4}CO$(N-pyrrolidine)-$(CH_2)_{0-4}CO_2C_{1-4}$alkyl, $—(CH_2)_{0-4}$(N-pyrazole)-$(CH_2)_{0-4}CO_2H$, $—(CH_2)_{0-4}CO$(N-pyrazole)-$(CH_2)_{0-4}CO_2C_{1-4}$alkyl, $—(CH_2)_{0-4}$(N-pyrrole)-$(CH_2)_{0-4}CO_2H$, $—(CH_2)_{0-4}CO$(N-pyrrole)-$(CH_2)_{0-4}CO_2C_{1-4}$alkyl, $—(CH_2)_{0-4}—O$(phenyl)-$(CH_2)_{0-4}CO_2H$, $—(CH_2)_{0-4}—O$(phenyl)-$(CH_2)_{0-4}CO_2C_{1-4}$alkyl, $—(CH_2)_{0-4}—O$(cycloalkane)-$(CH_2)_{0-4}CO_2H$, $—(CH_2)_{0-4}—O$(cycloalkane)-$(CH_2)_{0-4}CO_2C_{1-4}$alkyl, $—(CH_2)_{0-4}CO$(N-pyrrolidine)-$(CH_2)_{0-4}SO_2NH_2$, $—(CH_2)_{0-4}CO$(N-pyrrolidine)-(tetrazole), $—(CH_2)_{0-4}CO$(N-piperidine)-$(CH_2)_{0-4}CO_2H$, $—(CH_2)_{0-4}CO—$(N-piperidine)-$(CH_2)_{0-4}CO_2C_{1-4}$alkyl, $—(CH_2)_{0-4}CO$(N-morpholine)-$(CH_2)_{0-4}CO_2H$, $—CONR^a$(bicyclo[1.1.1]pentane)-$(CH_2)_{0-4}CO_2H$, $—NH_2$, $—(CH_2)_{0-4}NR^a(CH_2)_{1-4}CO_2H$, $—(CH_2)_{0-4}NR^a(CH_2)_{1-4}CO_2C_{1-4}$alkyl, $—(CH_2)_{0-4}N[(CH_2)_{1-4}CO_2C_{1-4}$alkyl$]_2$, $—(CH_2)_{0-4}NR^aCO$(isoxazole)OH, $—(CH_2)_{0-4}NR^aSO_2$(phenyl)-$CO_2H$, $—(CH_2)_{0-4}NR^aSO_2(CH_2)_{1-4}CO_2H$, $—(CH_2)_{0-4}NR^aSO_2(CH_2)_{1-4}CO_2C_{1-4}$alkyl, $—(CH_2)_{0-4}NR^aSO_2(CH_2)_{1-4}$(imidazolidine-2,4-dione), $—(CH_2)_{0-4}OP(O)(H)OH$, wherein $R^a$, independently for each occurrence, is H or $C_{1-4}$alkyl; and m is 1, 2, 3, or 4.

In particular embodiments, the present disclosure provides a compound of formula I-d-11, wherein each $R^6$ is independently fluoro, =O, $=CH_2$, -methyl, cyclohexyl, $—CF_3$, $—CO_2H$, $—CO_2C_{1-4}$alkyl, $—CO_2C_{1-4}$haloalkyl, or —OH; m is 1, 2, or 3, particularly 1 or 2.

In particular embodiments, the present disclosure provides a compound of formula I-d-11, wherein each $R^6$ is independently fluoro, =O, $=CH_2$, -methyl, cyclohexyl, $—CF_3$, -methoxy, —OtBu, $—(CH_2)_{1-5}CO_2H$, $—(CH_2)_{1-5}CO_2C_{1-4}$alkyl, $—(CH_2)_{0-4}O(CH_2)_{1-5}CO_2H$, $—(CH_2)_{0-4}O(CH_2)_{1-5}CO_2C_{1-4}$alkyl, $—(CH_2)_{1-4}O(CH_2)_{1-5}CONR^a_2$, or —OH; and m is 1, 2, or 3, particularly 1 or 2.

In some embodiments, the present disclosure provides a compound of formula I or formula I*, wherein $R^1$ is

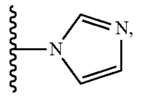

$R^2$ is $—NRR^5$, and $R^3$ is chloro at the 7- and 8-positions thereby forming a compound of formula I-d-12:

I-d-12

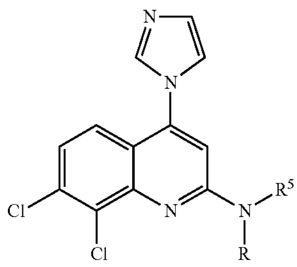

or a pharmaceutically acceptable salt thereof, wherein:

$R^5$ is $—(CR_2)_{2-4}OR$, $—(CR_2)_{0-6}CO_2R$, $—(CR_2)_{0-6}CONR_2$, $—(CR_2)_{0-6}C(O)NR(CR_2)_{0-6}CO_2R$, $—(CR_2)_{0-6}C(O)NR(CR_2)_{0-6}CONR_2$, $—(CR_2)_{0-6}NRCOR$, $—(CR_2)_{0-4}NR^aC(O)R$, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, or $R^B$; and each of R and $R^B$ is as defined above and described in embodiments herein, both singly and in combination.

In some embodiments, the present disclosure provides a compound of formula I-d-12, wherein $R^5$ is not $R^B$.

In particular embodiments, the present disclosure provides a compound of formula I-d-12, wherein $R^5$ is $—(CH_2)_{2-4}OH$, $—(CH_2)_{2-4}O(CH_2)_{1-5}CO_2H$, $—(CH_2)_{2-4}O(CH_2)_{1-5}CO_2C_{1-4}$alkyl, $—(CH_2)_{0-3}CH(CH_2OH)_2$, $—(CH_2)_{2-4}OC_{1-4}$alkyl, $—(CH_2)_{1-4}CO_2H$, $—(CH_2)_{1-4}CO_2C_{1-4}$alkyl, $—(CH_2)_{1-4}CONH_2$, $—(CH_2)_{1-4}CONHC_{1-4}$alkyl, $—(CH_2)_{1-4}CON(C_{1-4}$alkyl$)_2$, $—(CH_2)_{1-4}C(O)NR^a(CH_2)_{1-4}CO_2H$, $—(CH_2)_{1-4}C(O)NR^a(CHMe)CO_2H$, $—(CH_2)_{1-4}C(O)NR^a(CH_2)_{1-4}CONH_2$, $—(CH_2)_{1-4}C(O)NR^a(CH_2)_{1-4}CONHC_{1-4}$alkyl, $—(CH_2)_{1-4}C(O)NR^a(CH_2)_{1-4}CON(C_{1-4}$alkyl$)_2$, $—(CH_2)_{0-4}NR^aC(O)(CH_2)_{1-5}CO_2H$, $—(CH_2)_{0-4}NR^aC(O)(CH_2)_{1-5}CO_2C_{1-4}$alkyl, $—(CH_2)_{2-4}SO_3H$, $—(CH_2)_{2-4}SO_3C_{1-4}$alkyl, $—(CH_2)_{2-4}SO_2NH_2$, $—(CH_2)_{1-4}C(O)NR^a(CH_2)_{2-4}SO_2NH_2$, $—(CH_2)_{1-4}CO$(N-pyrrolidine)-$SO_2NH_2$, $—(CH_2)_{2-4}SO_2NHC_{1-4}$alkyl, $—(CH_2)_{2-4}SO_2N(C_{1-4}$alkyl$)_2$, $—(CH_2)_{2-4}OSO_2NH_2$, $—(CH_2)_{2-4}NR^a(CH_2)_{2-4}CO_2H$, $—(CH_2)_{2-4}NR^aCO(CH_2)_{2-4}CO_2H$, $—(CH_2)_{2-4}NR^aCO$(cyclopentane)-$CO_2H$, $—(CH_2)_{2-4}NR^aCO$(benzene)-OH, $—(CH_2)_{2-4}NR^aCO$(benzene)-$CO_2H$, $—(CH_2)_{2-4}NR^aSO_3H$, $—(CH_2)_{2-4}NR^a$ $SO_2C_{1-4}$alkyl, $-(CH_2)_{2-4}NR^aSO_2(CH_2)_{2-4}OH$, $-(CH_2)_{2-4}NR^aSO_2(CH_2)_{2-4}C_{1-4}$alkyl, $-(CH_2)_{2-4}NR^aSO_2(CH_2)_{2-4}CO_2H$, $-(CH_2)_{2-4}NR^aSO_2$(benzene)-$CO_2H$, $-(CH_2)_{2-4}NR^aSO_2$(benzene)-$CO_2C_{1-4}$alkyl, $-(CH_2)_{2-4}SO_2NR^a(CH_2)_{2-4}OH$, $-(CH_2)_{2-4}$(N-saccharin), $-(CH_2)_{2-4}SO_2NR^a(CH_2)_{2-4}CO_2H$, $-(CH_2)_{2-4}SO_2NR^a$(cyclopentane)-$CO_2H$, $-(CH_2)_{2-4}NR^a$(cyclohexane)-$CO_2C_{1-4}$alkyl, $-(CH_2)_{2-4}SO_2$(N-pyrrolidine)-$CO_2H$, $-(CH_2)_{2-4}SO_2$(N-piperidine)-$CO_2H$, $-(CH_2)_{1-4}OP(OH)_2$, $-(CH_2)_{1-4}P(O)(OH)_2$, $-(CH_2)_{1-4}P(O)(OH)(OC_{1-4}$alkyl), or $-(CH_2)_{2-4}OP(O)(H)OH$, wherein $R^a$, independently for each occurrence, is H, $C_{1-4}$alkyl, or $-SO_2C_{1-4}$alkyl.

In some embodiments, the present disclosure provides a compound of formula I-d-12, wherein R in $-NRR^5$ is $R^a$, which is H or $C_{1-6}$alkyl, particularly methyl.

In some embodiments, the present disclosure provides a compound of formula I or formula I*, wherein $R^1$ is

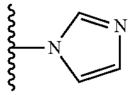 [SMILES: *n1ccnc1]

and $R^2$ is

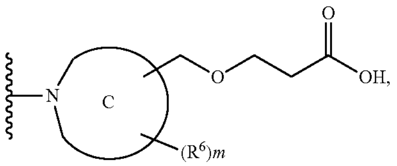

thereby forming a compound of formula I-d-13:

I-d-13

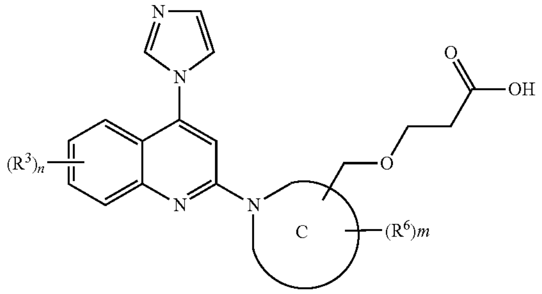

or a pharmaceutically acceptable salt thereof, wherein:

Ring C is pyrrolyl or a 4- to 10-membered saturated or partially unsaturated monocyclic, bicyclic, bridged bicyclic, or spirocyclic heterocyclic ring having 0 to 3 heteroatoms (in addition to the nitrogen already depicted in Ring C) independently selected from nitrogen, oxygen, and sulfur;

each $R^6$ is independently halogen, =O, $-COR$, $-(CR_2)_{0-6}CO_2R$, $-(CR_2)_{0-6}CONR_2$, $-OR$, $-(CR_2)_{1-4}OR$, $-NR_2$, $-(CR_2)_{1-4}NR_2$, $-NRC(O)OR$, $-NRC(O)R$, $-NRC(O)NR_2$, $-SR$, $-SO_2R$, $-S(O)R$, $-(CR_2)_{0-6}SO_3R$, $-(CR_2)_{0-6}SO_2NR_2$, $-(CR_2)_{0-6}OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, $-(CR_2)_{0-6}OP(O)(H)OR$, $-B(OR)_2$, or $R^B$;

m is 0, 1, 2, or 3; and each of R, $R^B$, $R^3$, and n is as defined above and described in embodiments herein, both singly and in combination.

In some embodiments, the present disclosure provides a compound of formula I-d-13, wherein Ring C is azetidinyl, pyrrolyl, 2,3-dihydro-1H-pyrrolyl, pyrrolidinyl, piperidinyl, morpholinyl, thiazolidinyl, indolinyl, isoindolinyl, octahydroindolyl, azepanyl, an oxazepane, an azabicyclohexane, an azabicycloheptane, an azabicyclooctane, an azabicyclononane, an azaspiroheptane, or an octahydrocyclicpentapyrrole.

In particular embodiments, the present disclosure provides a compound of formula I-d-13, wherein each $R^6$ is independently fluoro, -methyl, =O, $=CH_2$, -cyclohexyl, phenyl, morpholinyl, $-OMe$, $-OtBu$, $-CF_3$, $-CO_2H$, $-CO_2C_{1-4}$alkyl, $-CO_2C_{1-4}$haloalkyl, or $-OH$; and m is 0 or 1, or 2, particularly 0 or 1.

In certain embodiments, the present disclosure provides a compound of formula I-d-13, wherein $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I or formula I*, wherein $R^1$ is

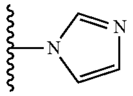

and at least one $R^3$ is halogen, such as chloro at the 8-position, thereby forming a compound of formula I-e-1:

I-e-1

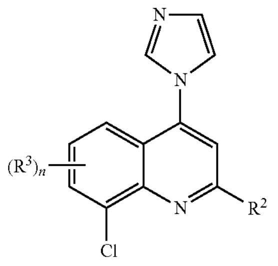

or a pharmaceutically acceptable salt thereof, wherein each of $R^2$ and $R^3$ is as defined above and described in embodiments herein, and n is 0, 1, 2, or 3, both singly and in combination.

In some embodiments, the present disclosure provides a compound of formula I or formula I*, wherein $R^1$ is

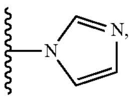

n is 2, and $R^3$ is chloro at the 7- and 8-positions, thereby forming a compound of formula I-e-2:

I-e-2

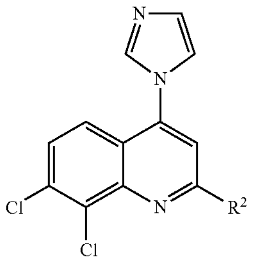

or a pharmaceutically acceptable salt thereof, wherein $R^2$ is defined above and described in embodiments herein.

In some embodiments, the present disclosure provides a compound of formula I or formula I*, wherein $R^1$ is

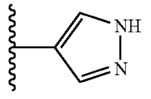 [SMILES: *c1cn[nH]c1]

I-f-1

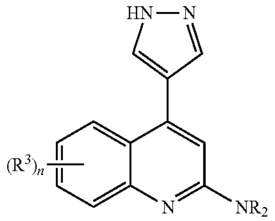

and $R^2$ is $—NR_2$, thereby forming a compound of formula I-f-1:

or a pharmaceutically acceptable salt thereof, wherein each of R, $R^3$, and n is as defined above and described in embodiments herein, both singly and in combination.

In certain embodiments, the present disclosure provides a compound of formula I-f-1, wherein $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I or formula I*, wherein $R^1$ is

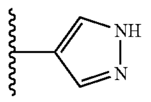

and $R^2$ is $—NRR^5$, thereby forming a compound of formula I-f-2:

I-f-2

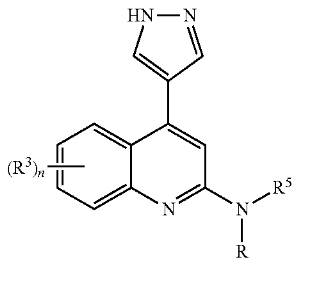

or a pharmaceutically acceptable salt thereof, wherein:

$R^5$ is $—(CR_2)_{2-4}OR$, $—(CR_2)_{0-6}CO_2R$, $—(CR_2)_{0-6}CONR_2$, $—(CR_2)_{0-6}C(O)NR(CR_2)_{0-6}CO_2R$, $—(CR_2)_{0-6}C(O)NR(CR_2)_{0-6}CONR_2$, $—(CR_2)_{0-4}NRC(O)R$, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, or $R^B$; and each of R, $R^3$, $R^B$, and n is as defined above and described in embodiments herein, both singly and in combination.

In certain embodiments, the present disclosure provides a compound of formula I-f-2, wherein $R^5$ is $—(CR_2)_{2-4}OR$, $—(CR_2)_{1-4}CO_2R$, $—(CR_2)_{1-4}CONR_2$, $—(CR_2)_{0-6}C(O)NR(CR_2)_{0-6}CO_2R$, $—(CR_2)_{0-6}C(O)NR(CR_2)_{0-6}CONR_2$, $—(CR_2)_{0-4}NRC(O)R$, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, or $R^B$.

In some embodiments, the present disclosure provides a compound of formula I-f-2, wherein $R^5$ is not $R^B$.

In some embodiments, the present disclosure provides a compound of formula I-f-2, wherein R in $—NRR^5$ is $R^a$, which is H or $C_{1-6}$alkyl.

In certain embodiments, the present disclosure provides a compound of formula I-f-2, wherein $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-f-2, wherein:

R in $—NRR^5$ is H or lower alkyl, particularly methyl;

$R^5$ is $—(CH_2)_{2-4}OH$, $—(CH_2)_{2-4}O(CH_2)_{1-5}CO_2H$, $—(CH_2)_{2-4}O(CH_2)_{1-5}CO_2C_{1-4}$alkyl, $—(CH_2)_{0-3}CH(CH_2OH)_2$, $—(CH_2)_{2-4}OC_{1-4}$alkyl, $—(CH_2)_{1-4}CO_2H$, $—(CH_2)_{1-4}CO_2C_{1-4}$alkyl, $—(CH_2)_{1-4}CONH_2$, $—(CH_2)_{1-4}CONHC_{1-4}$alkyl, $—(CH_2)_{1-4}CON(C_{1-4}$alkyl$)_2$, $—(CH_2)_{1-4}C(O)NR^a(CH_2)_{1-4}CO_2H$, $—(CH_2)_{1-4}C(O)NR^a(CH_2)_{1-4}CONH_2$, $—(CH_2)_{1-4}C(O)NR^a(CH_2)_{1-4}CONHC_{1-4}$alkyl, $—(CH_2)_{1-4}C(O)NR^a(CH_2)_{1-4}CON(C_{1-4}$alkyl$)_2$, $—(CH_2)_{0-4}NR^aC(O)(CH_2)_{1-5}CO_2H$, $—(CH_2)_{0-4}NR^aC(O)(CH_2)_{1-5}CO_2C_{1-4}$alkyl, $—(CH_2)_{2-4}SO_3H$, $—(CH_2)_{2-4}SO_3C_{1-4}$alkyl, $—(CH_2)_{2-4}SO_2NH_2$, $—(CH_2)_{2-4}SO_2NHC_{1-4}$alkyl, $—(CH_2)_{2-4}SO_2N(C_{1-4}$alkyl$)_2$, $—(CH_2)_{2-4}OSO_2NH_2$, $—(CH_2)_{2-4}NR^aSO_2C_{1-4}$alkyl, $—(CH_2)_{2-4}NR^aSO_3H$, $—(CH_2)_{1-4}OP(OH)_2$, $—(CH_2)_{1-4}P(O)(OH)_2$, $—(CH_2)_{1-4}P(O)(OH)(OC_{1-4}$alkyl), or $—(CH_2)_{2-4}OP(O)(H)OH$, wherein $R^a$, independently for each occurrence, is H or $C_{1-4}$alkyl; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-f-2, wherein:

R in $—NRR^5$ is H or lower alkyl, particularly methyl;

$R^5$ is $—(CH_2)_{2-4}OH$, $—(CH_2)_{2-4}O(CH_2)_{1-5}CO_2H$, $—(CH_2)_{2-4}O(CH_2)_{1-5}CO_2C_{1-4}$alkyl, $—(CH_2)_{0-3}CH(CH_2OH)_2$, $—(CH_2)_{1-4}CO_2H$, $—(CH_2)_{1-4}CONH_2$, $—(CH_2)_{1-4}C(O)NR^a(CH_2)_{1-4}CO_2H$, $—(CH_2)_{1-4}C(O)NR^a(CH_2)_{1-4}CONH_2$, $—(CH_2)_{0-4}NR^aC(O)(CH_2)_{1-5}CO_2H$, $—(CH_2)_{0-4}NR^aC(O)(CH_2)_{1-5}CO_2C_{1-4}$alkyl, $—(CH_2)_{2-4}SO_3H$, $—(CH_2)_{2-4}SO_2NH_2$, $—(CH_2)_{2-4}SO_2NR^aC_{1-4}$alkyl, $—(CH_2)_{2-4}NR^aSO_2C_{1-4}$alkyl, $—(CH_2)_{1-4}P(O)(OH)_2$, or $—(CH_2)_{2-4}OP(O)(H)OH$, wherein $R^a$, independently for each occurrence, is H or $C_{1-4}$alkyl; and each $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-f-2, $R^5$ includes a terminal $—CO_2H$ group. For example, in certain instances, $R^5$ includes a terminal $—(CH_2)_{0-4}CO_2H$ group.

In some embodiments, the present disclosure provides a compound of formula I or formula I*, wherein $R^1$ is

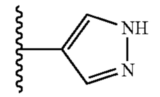 [SMILES: *c1cn[nH]c1]

and $R^2$ is

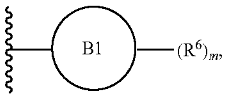

thereby forming a compound of formula I-f-3:

I-f-3

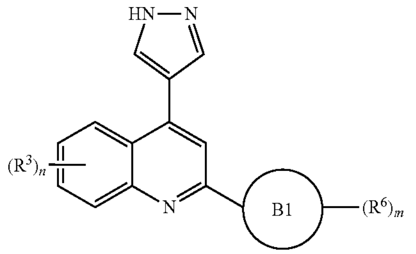

or a pharmaceutically acceptable salt thereof, wherein:

Ring B1 is phenyl; a 4- to 10-membered saturated or partially unsaturated monocyclic or bicyclic carboxylic or heterocyclic ring having 1 to 3 heteroatoms independently selected from nitrogen, oxygen, phosphorus, and sulfur; or a 5- to 6-membered heteroaryl ring having 1 to 4 heteroatoms independently selected from nitrogen, oxygen, phosphorus, and sulfur;

each $R^6$ is independently halogen, —COR, $—(CR_2)_{0-6}CO_2R$, $—(CR_2)_{0-6}CONR_2$, —OR, $—(CR_2)_{1-4}OR$, $—NR_2$, $—(CR_2)_{1-4}NR_2$, —NRC(O)OR, —NRC(O)R, $—NRC(O)NR_2$, —SR, $—SO_2R$, —S(O)R, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, $—B(OR)_2$, or $R^B$;

m is 0, 1, 2, 3, or 4, particularly 1, 2, 3, or 4; and each of R, $R^3$, $R^B$, and n is as defined above and described in embodiments herein, both singly and in combination.

In certain embodiments, the present disclosure provides a compound of formula I-f-3, wherein Ring B1 is phenyl, particularly substituted phenyl. In other embodiments, Ring B1 is not phenyl. For example, Ring B1 may be a 4- to 10-membered saturated or partially unsaturated monocyclic or bicyclic carboxylic or heterocyclic ring having 1 to 3 heteroatoms independently selected from nitrogen, oxygen, phosphorus, and sulfur. In some embodiments, Ring B1 is a 5- to 6-membered heteroaryl ring having 1 to 4 heteroatoms independently selected from nitrogen, oxygen, phosphorus, and sulfur.

In some embodiments, the present disclosure provides a compound of formula I-f-3, wherein $R^6$ is not $R^B$.

In certain embodiments, the present disclosure provides a compound of formula I-f-3, wherein $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-f-3, m is 1 or 2, and at least one $R^6$ includes a terminal $—CO_2H$ group. For example, in certain instances, at least one $R^6$ is $—(CH_2)_{0-4}CO_2H$.

In some embodiments, the present disclosure provides a compound of formula I or formula I*, wherein $R^1$ is

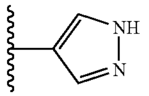 [SMILES: *c1cn[nH]c1]

and $R^2$ is

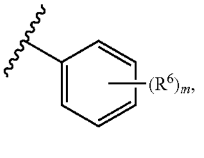

thereby forming a compound of formula I-f-4:

I-f-4

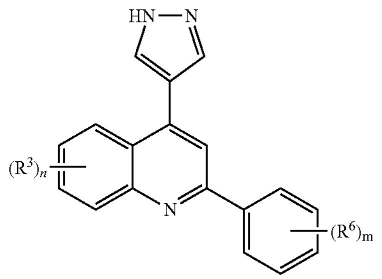

or a pharmaceutically acceptable salt thereof, wherein:

each $R^6$ is independently halogen, —COR, $—(CR_2)_{0-6}CO_2R$, $—(CR_2)_{0-6}CONR_2$, —OR, $—(CR_2)_{1-4}OR$, $—NR_2$, $—(CR_2)_{1-4}NR_2$, —NRC(O)OR, —NRC(O)R, $—NRC(O)NR_2$, —SR, $—SO_2R$, —S(O)R, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, $—B(OR)_2$, or $R^B$;

m is 0, 1, 2, 3, or 4, particularly 1, 2, 3, or 4; and each of R, $R^3$, $R^B$, and n is as defined above and described in embodiments herein, both singly and in combination.

In some embodiments, the present disclosure provides a compound of formula I-f-4, wherein $R^6$ is not $R^B$.

In certain embodiments, the present disclosure provides a compound of formula I-f-4, wherein $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-f-4, m is 1 or 2, and at least one $R^6$ includes a terminal —$CO_2H$ group. For example, in certain instances, at least one $R^6$ is —$(CH_2)_{0\text{-}4}CO_2H$.

In some embodiments, the present disclosure provides a compound of formula I or formula I*, wherein $R^1$ is

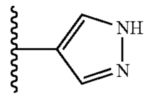 [SMILES: *c1cn[nH]c1]

and $R^2$ is

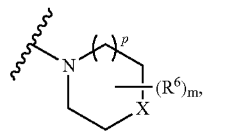

thereby forming a compound of formula I-f-5:

I-f-5

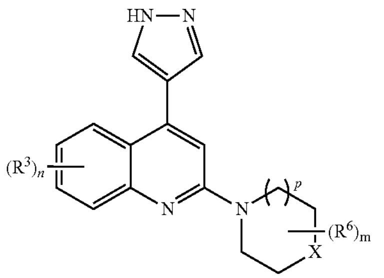

or a pharmaceutically acceptable salt thereof, wherein:

each $R^6$ is independently halogen, =O, —COR, —$(CR_2)_{0\text{-}6}CO_2R$, —$(CR_2)_{0\text{-}6}CONR_2$, —OR, —$(CR_2)_{1\text{-}4}OR$, —$NR_2$, —$(CR_2)_{1\text{-}4}NR_2$, —NRC(O)OR, —NRC(O)R, —NRC(O)$NR_2$, —SR, —$SO_2R$, —S(O)R, —$(CR_2)_{0\text{-}6}SO_3R$, —$(CR_2)_{0\text{-}6}SO_2NR_2$, —$(CR_2)_{0\text{-}6}OSO_2NR_2$, —$(CR_2)_{0\text{-}6}NRSO_2R$, —$(CR_2)_{0\text{-}6}NRSO_2OR$, —$(CR_2)_{0\text{-}6}OP(OR)_2$, —$(CR_2)_{0\text{-}6}OP(O)(OR)_2$, —$(CR_2)_{0\text{-}6}P(O)(OR)_2$, —$(CR_2)_{0\text{-}6}OP(O)(H)OR$, —$B(OR)_2$, or $R^B$;

X is —$CR_2$—, —NR—, —O—, —S—, or —$SO_2$—, particularly —$CR_2$—, —NR—, or —O;

m is 0, 1, 2, 3, or 4, particularly 1, 2, 3, or 4;

p is 0, 1, or 2, particularly 1; and each of R, $R^3$, $R^B$, and n is as defined above and described in embodiments herein, both singly and in combination.

In some embodiments, the present disclosure provides a compound of formula I-f-5, wherein $R^6$ is not $R^B$.

In certain embodiments, the present disclosure provides a compound of formula I-f-5, wherein $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-f-5, wherein:

each $R^6$ is independently halogen, —$C_{1\text{-}4}$alkyl, —$C_{1\text{-}4}$haloalkyl, —$C_{3\text{-}6}$cycloalkyl, =$CH_2$, =O, —$(CH_2)_{0\text{-}4}CO_2H$, —$(CH_2)_{0\text{-}4}CO_2C_{1\text{-}4}$alkyl, —$(CH_2)_{0\text{-}4}O(CH_2)_{1\text{-}5}CO_2H$, —$(CH_2)_{0\text{-}4}O(CH_2)_{1\text{-}5}CO_2C_{1\text{-}4}$alkyl, —$(CH_2)_{0\text{-}4}CONH_2$, —$(CH_2)_{0\text{-}4}CONHC_{1\text{-}4}$alkyl, —$(CH_2)_{0\text{-}4}CON(C_{1\text{-}4}alkyl)_2$, —$(CH_2)_{0\text{-}4}$CO(N-proline), —$(CH_2)_{0\text{-}4}C(O)NR^a(CH_2)_{1\text{-}4}CO_2H$, —$(CH_2)_{0\text{-}4}C(O)NR^a(CH_2)_{1\text{-}4}CONH_2$, —$(CH_2)_{0\text{-}4}C(O)NR^a(CH_2)_{1\text{-}4}CONHC_{1\text{-}4}$alkyl, —$(CH_2)_{0\text{-}4}C(O)NR^a(CH_2)_{1\text{-}4}CON(C_{1\text{-}4}alkyl)_2$, —OH, —$(CH_2)_{1\text{-}4}OH$, —$(CH_2)_{0\text{-}4}OC_{1\text{-}4}$alkyl, —$NH_2$, —$(CH_2)_{1\text{-}4}NH_2$, —$(CH_2)_{0\text{-}4}NHC_{1\text{-}4}$alkyl, —$(CH_2)_{0\text{-}4}N(C_{1\text{-}4}alkyl)_2$, —$(CH_2)_{0\text{-}4}SO_3H$, —$(CH_2)_{0\text{-}4}SO_2NH_2$, —$(CH_2)_{0\text{-}4}SO_2NHC_{1\text{-}4}$alkyl, —$(CH_2)_{0\text{-}4}NR^aSO_2C_{1\text{-}4}$alkyl, —$(CH_2)_{0\text{-}4}OP(OH)_2$, —$(CH_2)_{0\text{-}4}OP(OH)(OC_{1\text{-}4}alkyl)$, or —$(CR_2)_{0\text{-}4}OP(O)(H)OH$, wherein $R^a$, independently for each occurrence, is H or $C_{1\text{-}4}$alkyl;

X is —$CH_2$—, —NH—, or —O—;

m is 1, 2, 3, or 4, particularly 1 or 2;

p is 1; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-f-5, wherein:

each $R^6$ is independently halogen, —$C_{1\text{-}4}$alkyl, —$C_{1\text{-}4}$haloalkyl, —$C_{3\text{-}6}$cycloalkyl, =$CH_2$, —$(CH_2)_{0\text{-}4}CO_2H$, —$(CH_2)_{1\text{-}4}O(CH_2)_{1\text{-}5}CO_2H$, —$(CH_2)_{1\text{-}4}O(CH_2)_{1\text{-}5}CO_2C_{1\text{-}4}$alkyl, —$(CH_2)_{0\text{-}4}$CO(N-proline), —$(CH_2)_{0\text{-}4}C(O)NR^a(CH_2)_{1\text{-}4}CO_2H$, —OH, —$(CH_2)_{1\text{-}4}OH$, —$(CH_2)_{0\text{-}4}SO_3H$, —$(CH_2)_{0\text{-}4}SO_2NH_2$, —$(CH_2)_{0\text{-}4}NR^aSO_2C_{1\text{-}4}$alkyl, —$(CH_2)_{0\text{-}4}OP(OH)_2$, or —$(CR_2)_{0\text{-}4}OP(O)(H)OH$;

X is —$CH_2$—, —NH—, or —O—;

m is 1 or 2;

p is 1; and each $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-f-5, m is 1 or 2, and at least one $R^6$ includes a terminal —$CO_2H$ group. For example, in certain instances, at least one $R^6$ is —$(CH_2)_{0\text{-}4}CO_2H$.

In some embodiments, the present disclosure provides a compound of formula I or formula I*, wherein $R^1$ is

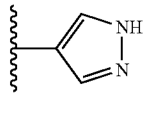

and $R^2$ is

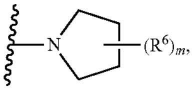

thereby forming a compound of formula I-f-6:

I-f-6

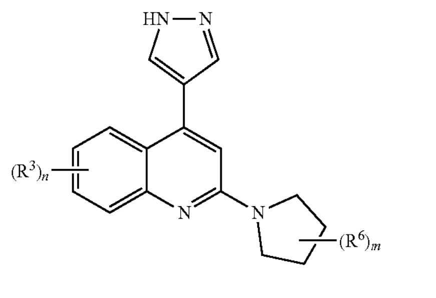

or a pharmaceutically acceptable salt thereof, wherein:

each $R^6$ is independently halogen, $=O$, $-COR$, $-(CR_2)_{0-6}CO_2R$, $-(CR_2)_{0-6}CONR_2$, $-OR$, $-(CR_2)_{1-4}OR$, $-NR_2$, $-(CR_2)_{1-4}NR_2$, $-NRC(O)OR$, $-NRC(O)R$, $-NRC(O)NR_2$, $-SR$, $-SO_2R$, $-S(O)R$, $-(CR_2)_{0-6}SO_3R$, $-(CR_2)_{0-6}SO_2NR_2$, $-(CR_2)_{0-6}OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, $-(CR_2)_{0-6}OP(O)(H)OR$, $-B(OR)_2$, or $R^B$;

m is 0, 1, 2, 3, or 4, particularly 1, 2, 3, or 4; and each of R, $R^3$, $R^B$, and n is as defined above and described in embodiments herein, both singly and in combination.

In some embodiments, the present disclosure provides a compound of formula I-f-6, wherein $R^6$ is not $R^B$.

In certain embodiments, the present disclosure provides a compound of formula I-f-6, wherein $R^3$ is independently halogen, such as chloro, including dichloro, including wherein n is 2 and $R^3$ is chloro at the 7- and 8-positions with respect to the quinoline ring.

In certain embodiments, the present disclosure provides a compound of formula I-f-6, wherein:

each $R^6$ is independently halogen, $-C_{1-4}$alkyl, $-C_{1-4}$haloalkyl, $-C_{3-6}$cycloalkyl, $=CR_2$, $=O$, $-COR$, $-(CR_2)_{0-6}CO_2R$, $-(CR_2)_{0-6}CONR_2$, $-OR$, $-(CR_2)_{1-4}OR$, $-NR_2$, $-(CR_2)_{1-4}NR_2$, $-NRC(O)OR$, $-NRC(O)R$, $-NRC(O)NR_2$, $-SR$, $-SO_2R$, $-S(O)R$, $-(CR_2)_{0-6}SO_3R$, $-(CR_2)_{0-6}SO_2NR_2$, $-(CR_2)_{0-6}OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, $-(CR_2)_{0-6}OP(O)(H)OR$, or $-B(OR)_2$;

m is 1, 2, 3, or 4, particularly 1 or 2; and each $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-f-6, wherein:

each $R^6$ is independently halogen, $-C_{1-4}$alkyl, $-C_{1-4}$haloalkyl, $-C_{3-6}$cycloalkyl, $=CH_2$, $=O$, $-(CH_2)_{0-4}CO_2H$, $-(CH_2)_{0-4}CO_2C_{1-4}$alkyl, $-(CH_2)_{0-4}O(CH_2)_{1-5}CO_2H$, $-(CH_2)_{0-4}O(CH_2)_{1-5}CO_2C_{1-4}$alkyl, $-(CH_2)_{0-4}CONH_2$, $-(CH_2)_{0-4}CONHC_{1-4}$alkyl, $-(CH_2)_{0-4}CON(C_{1-4}alkyl)_2$, $-(CH_2)_{0-4}$CO(N-proline), $-(CH_2)_{0-4}$CO(N-pyrrolidine-3-carboxylic acid), $-(CH_2)_{0-4}C(O)NR^a(CH_2)_{1-4}CO_2H$, $-(CH_2)_{0-4}C(O)NR^a-CH(C_{1-4}alkyl)-CO_2H$, $-(CH_2)_{0-4}C(O)NR^a(CH_2)_{1-4}CONH_2$, $-(CH_2)_{0-4}C(O)NR^a(CH_2)_{1-4}CONHC_{1-4}$alkyl, $-(CH_2)_{0-4}C(O)NR^a(CH_2)_{1-4}CON(C_{1-4}alkyl)_2$, $-OH$, $-(CH_2)_{1-4}OH$, $-(CH_2)_{0-4}OC_{1-4}$alkyl, $-NH_2$, $-(CH_2)_{1-4}NH_2$, $-(CH_2)_{0-4}NHC_{1-4}$alkyl, $-(CH_2)_{0-4}NR^aC(O)C_{1-4}$alkyl, $-(CH_2)_{0-4}NR^aC(O)Ph$, $-(CH_2)_{0-4}NR^aCO(CH_2)_{1-4}OH$, $-(CH_2)_{0-4}N(C_{1-4}alkyl)_2$, $-(CH_2)_{0-4}SO_3H$, $-(CH_2)_{0-4}SO_2NH_2$, $-(CH_2)_{0-4}SO_2NR^aC_{1-4}$alkyl, $-(CH_2)_{0-4}NR^aSO_2C_{1-4}$alkyl, $-(CH_2)_{0-4}NR^aSO_2Ph$, $-(CH_2)_{0-4}NR^aSO_2(CH_2)_{1-4}CO_2H$, $-(CH_2)_{0-4}OP(OH)_2$, $-(CH_2)_{0-4}OP(OH)(OC_{1-4}alkyl)$, or $-(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-f-6, wherein:

each $R^6$ is independently halogen, $-C_{1-4}$alkyl, $-C_{1-4}$haloalkyl, $-C_{3-6}$cycloalkyl, $=CH_2$, $-(CH_2)_{0-4}CO_2H$, $-(CH_2)_{1-4}O(CH_2)_{1-5}CO_2H$, $-(CH_2)_{1-4}O(CH_2)_{1-5}CO_2C_{1-4}$alkyl, $-(CH_2)_{0-4}$CO(N-proline), $-(CH_2)_{0-4}$CO(N-pyrrolidine-3-carboxylic acid), $-(CH_2)_{0-4}C(O)NR^a(CH_2)_{1-4}CO_2H$, $-(CH_2)_{0-4}C(O)NR^a-CH(C_{1-4}alkyl)-CO_2H$, $-OH$, $-(CH_2)_{1-4}OH$, $-(CH_2)_{0-4}OC_{1-4}$alkyl, $-(CH_2)_{0-4}NR^aC(O)C_{1-4}$alkyl, $-(CH_2)_{0-4}NR^aC(O)Ph$, $-(CH_2)_{0-4}NR^aCO(CH_2)_{1-4}OH$, $-(CH_2)_{0-4}SO_3H$, $-(CH_2)_{0-4}SO_2NH_2$, $-(CH_2)_{0-4}NR^aSO_2C_{1-4}$alkyl, $-(CH_2)_{0-4}NR^aSO_2Ph$, $-(CH_2)_{0-4}NR^aSO_2(CH_2)_{1-4}CO_2H$, $-(CH_2)_{0-4}OP(OH)_2$, or $-(CR_2)_{0-4}OP(O)(H)OH$, wherein $R^a$, independently for each occurrence, is H or $C_{1-4}$alkyl;

m is 1 or 2; and each $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-f-6, m is 1 or 2, and at least one $R^6$ includes a terminal $-CO_2H$ group. For example, in certain instances, at least one $R^6$ is $-(CH_2)_{0-4}CO_2H$.

In some embodiments, the present disclosure provides a compound of formula I or formula I*, wherein $R^1$ is

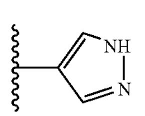 [SMILES: *c1cn[nH]c1]

and $R^2$ is

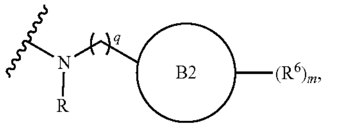

thereby forming a compound of formula I-f-7:

I-f-7

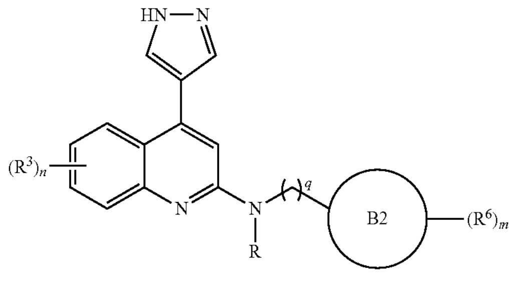

or a pharmaceutically acceptable salt thereof, wherein:

Ring B2 is phenyl; a 4- to 7-membered saturated or partially unsaturated carbocyclic or heterocyclic ring having 1 to 3 heteroatoms independently selected from nitrogen, oxygen, phosphorus, and sulfur; or a 5- to 6-membered heteroaryl ring having 1 to 4 heteroatoms independently selected from nitrogen, oxygen, phosphorus, and sulfur;

each $R^6$ is independently halogen, $-COR$, $-(CR_2)_{0-6}CO_2R$, $-(CR_2)_{0-6}CONR_2$, $-OR$, $-(CR_2)_{1-4}OR$, $-NR_2$, $-(CR_2)_{1-4}NR_2$, $-NRC(O)OR$, —NRC(O)R, —NRC(O)$NR_2$, —SR, —$SO_2$R, —S(O)R, —$(CR_2)_{0-6}SO_3R$, —$(CR_2)_{0-6}SO_2NR_2$, —$(CR_2)_{0-6}$ $OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

m is 0, 1, 2, 3, or 4, particularly 1, 2, 3, or 4;

q is 0, 1, or 2; and each of R, $R^3$, $R^B$, and n is as defined above and described in embodiments herein, both singly and in combination.

In certain embodiments, the present disclosure provides a compound of formula I-f-7, wherein Ring B2 is phenyl, particularly substituted phenyl. In other embodiments, Ring B2 is not phenyl. For example, Ring B2 may be a 4- to 10-membered saturated or partially unsaturated monocyclic or bicyclic carboxylic or heterocyclic ring having 1 to 3 heteroatoms independently selected from nitrogen, oxygen, phosphorus, and sulfur. In some embodiments, Ring B2 is a 5- to 6-membered heteroaryl ring having 1 to 4 heteroatoms independently selected from nitrogen, oxygen, phosphorus, and sulfur.

In some embodiments, the present disclosure provides a compound of formula I-f-7, wherein $R^6$ is not $R^B$.

In some embodiments, the present disclosure provides a compound of formula I-f-7, wherein R in

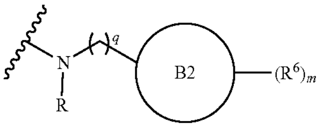

is $R^a$, which is H or $C_{1-6}$alkyl.

In certain embodiments, the present disclosure provides a compound of formula I-f-7, wherein $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-f-7, m is 1 or 2, and at least one $R^6$ includes a terminal —$CO_2H$ group. For example, in certain instances, at least one $R^6$ is —$(CH_2)_{0-4}CO_2H$.

In some embodiments, the present disclosure provides a compound of formula I or formula I*, wherein $R^1$ is

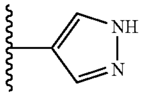 [SMILES: *c1cn[nH]c1]

and $R^2$ is

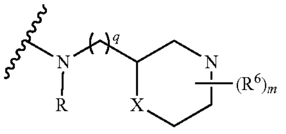

or

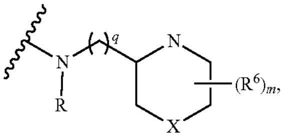

thereby forming a compound of formula I-f-8 or formula I-f-8*, respectively:

I-f-8

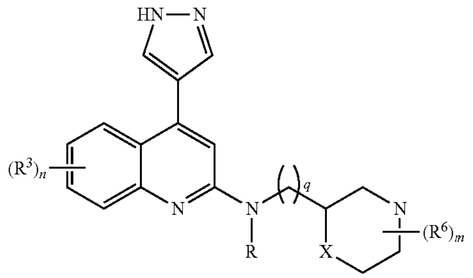

I-f-8*

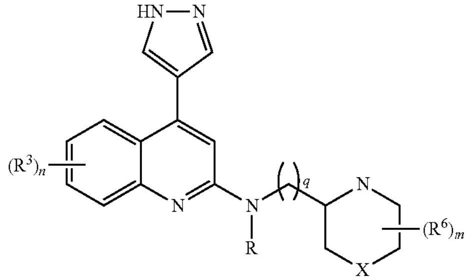

or a pharmaceutically acceptable salt thereof, wherein:

each $R^6$ is independently hydrogen (only on N), halogen (not on N), —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2$R, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

X is —$CR_2$—, —NR—, —O—, —S—, or —$SO_2$—, particularly —$CR_2$—, —NR—, or —O;

m is 1, 2, 3, or 4;

q is 0, 1, or 2; and each of R, $R^3$, $R^B$, and n is as defined above and described in embodiments herein, both singly and in combination.

In some embodiments, the present disclosure provides a compound of formula I-f-8 or formula I-f-8*, wherein $R^6$ is not $R^B$.

In some embodiments, the present disclosure provides a compound of formula I-f-8 or formula I-f-8*, wherein R in

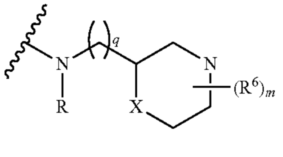

or in

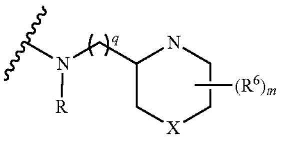

is $R^a$, which is H or $C_{1-6}$alkyl.

In certain embodiments, the present disclosure provides a compound of formula I-f-8 or formula I-f-8*, wherein $R^3$ is independently halogen, such as chloro, including dichloro, including wherein n is 2 and $R^3$ is chloro at the 7- and 8-positions with respect to the quinoline ring.

In certain embodiments, the present disclosure provides a compound of formula I-f-8 or formula I-f-8*, wherein:

each $R^6$ is independently halogen, =O, —COR, $—(CR_2)_{0-6}CO_2R$, $—(CR_2)_{0-6}CONR_2$, —OR, $—(CR_2)_{1-4}OR$, $—NR_2$, $—(CR_2)_{1-4}NR_2$, —NRC(O)OR, —NRC(O)R, $—NRC(O)NR_2$, —SR, $—SO_2R$, —S(O)R, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, or $—B(OR)_2$;

m is 1, 2, 3, or 4, particularly 1 or 2;

q is 1 or 2; and each $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-f-8 or formula I-f-8*, wherein:

each $R^6$ is independently halogen, =O, $—(CH_2)_{0-4}CO_2H$, $—(CH_2)_{0-4}CO_2C_{1-4}$alkyl, $—(CH_2)_{0-4}CONH_2$, $—(CH_2)_{0-4}CONHC_{1-4}$alkyl, $—(CH_2)_{0-4}CON(C_{1-4}alkyl)_2$, $—(CH_2)_{0-4}CO$(N-proline), $—(CH_2)_{0-4}C(O)NR^a(CH_2)_{1-4}CO_2H$, $—(CH_2)_{0-4}C(O)NR^a(CH_2)_{1-4}CONH_2$, $—(CH_2)_{0-4}C(O)NR^a(CH_2)_{1-4}CONHC_{1-4}$alkyl, $—(CH_2)_{0-4}C(O)NR^a(CH_2)_{1-4}CON(C_{1-4}alkyl)_2$, —OH, $—(CH_2)_{1-4}OH$, $—(CH_2)_{0-4}OC_{1-4}$alkyl, $—NH_2$, $—(CH_2)_{1-4}NH_2$, $—(CH_2)_{0-4}NHC_{1-4}$alkyl, $—(CH_2)_{0-4}N(C_{1-4}alkyl)_2$, $—(CH_2)_{0-4}SO_3H$, $—(CH_2)_{0-4}SO_2NH_2$, $—(CH_2)_{0-4}SO_2NHC_{1-4}$alkyl, $—(CH_2)_{0-4}NR^aSO_2C_{1-4}$alkyl, $—(CH_2)_{0-4}OP(OH)_2$, $—(CH_2)_{0-4}OP(OH)(OC_{1-4}$alkyl), or $—(CR_2)_{0-4}OP(O)(H)OH$, wherein $R^a$, independently for each occurrence, is H or $C_{1-4}$alkyl;

m is 1, 2, 3, or 4, particularly 1 or 2;

q is 1; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-f-8 or formula I-f-8*, wherein:

each $R^6$ is independently halogen, $—(CH_2)_{0-4}CO_2H$, $—(CH_2)_{0-4}CO$(N-proline), $—(CH_2)_{0-4}C(O)NR^a(CH_2)_{1-4}CO_2H$, —OH, $—(CH_2)_{1-4}OH$, $—(CH_2)_{0-4}SO_3H$, $—(CH_2)_{0-4}SO_2NH_2$, $—(CH_2)_{0-4}NR^aSO_2C_{1-4}$alkyl, $—(CH_2)_{0-4}OP(OH)_2$, or $—(CR_2)_{0-4}OP(O)(H)OH$, wherein $R^a$, independently for each occurrence, is H or $C_{1-4}$alkyl;

m is 1 or 2;

q is 1; and each $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-f-8 or I-f-8*, m is 1 or 2, and at least one $R^6$ includes a terminal $—CO_2H$ group. For example, in certain instances, at least one $R^6$ is $—(CH_2)_{0-4}CO_2H$.

In some embodiments, the present disclosure provides a compound of formula I or formula I*, wherein $R^1$ is

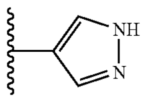 [SMILES: *c1cn[nH]c1]

and $R^2$ is

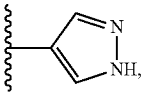 [SMILES: *c1cn[nH]c1]

thereby forming a compound of formula I-f-9:

I-f-9

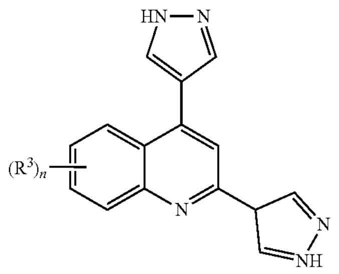

or a pharmaceutically acceptable salt thereof, wherein each of R, $R^1$, $R^3$, and n is as defined above and described in embodiments herein, both singly and in combination.

In certain embodiments, the present disclosure provides a compound of formula I-f-9, wherein $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I or formula I*, wherein $R^1$ is

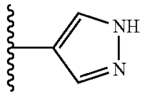 [SMILES: *c1cn[nH]c1]

and at least one $R^3$ is halogen, such as chloro at the 8-position, thereby forming a compound of formula I-g-1:

I-g-1

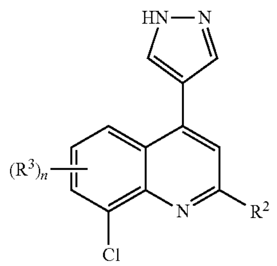

or a pharmaceutically acceptable salt thereof, wherein each of $R^2$ and $R^3$ is as defined above and described in embodiments herein, and n is 0, 1, 2, or 3, both singly and in combination.

In certain embodiments, the present disclosure provides a compound of formula I-g-1, wherein $R^2$ is $R^B$, wherein $R^B$ is an optionally substituted $C_{1-6}$ aliphatic, preferably a substituted $C_{1-6}$ aliphatic, such as $-(CR_2)_{1-4}NR(CR_2)_{0-6}CO_2R$, $-(CR_2)_{1-4}O(CR_2)_{0-4}CO_2R$, $-(CR_2)_{1-4}CO_2R$, $-(CR_2)_{1-4}OH$, $-(CR_2)_{1-4}NH_2$, $-(CR_2)_{1-4}C(O)NH_2$, $-(CR_2)_{1-4}C(C)NHC_{1-4}alkyl$, or $-(CR_2)_{1-4}C(O)N(C_{1-4}alkyl)_2$, particularly $-(CR_2)_{1-4}NR(CR_2)_{0-4}CO_2R$ or $-(CR_2)_{1-4}CO_2R$, In some embodiments, $R^2$ is $-(CH_2)_{1-4}NR^a(CH_2)_{0-4}CO_2R^a$, such as $-(CH_2)_{1-4}NR^a(CH_2)_{0-4}CO_2H$, wherein $R^a$, independently for each occurrence, is H or $C_{1-4}$alkyl. In other embodiments, $R^2$ is $-(CH_2)_{1-4}N(SO_2C_{1-4}alkyl)(CH_2)_{0-4}CO_2R^a$, such as is $-(CH_2)_{1-4}N(SO_2C_{1-4}alkyl)(CH_2)_{0-4}CO_2H$, wherein $R^a$, independently for each occurrence, is H or $C_{1-4}$alkyl. In other embodiments, $R^2$ is $-(CR_2)_{1-4}CO_2R$, such as $-(CR_2)_{1-4}CO_2H$, including $-(CH_2)_{1-4}CO_2H$. In certain embodiments, $R^2$ includes a terminal $-CO_2H$ group. For example, in certain instances, $R^2$ includes a terminal $-(CH_2)_{0-4}CO_2H$ group.

In some embodiments, the present disclosure provides a compound of formula I or formula I*, wherein $R^1$ is

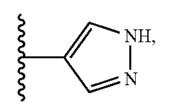

n is 2, and $R^3$ is chloro at the 7- and 8-positions, thereby forming a compound of formula I-g-2:

I-g-2

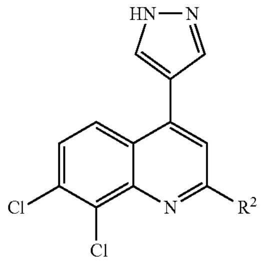

or a pharmaceutically acceptable salt thereof, wherein $R^2$ is defined above and described in embodiments herein.

In certain embodiments, the present disclosure provides a compound of formula I-g-2, wherein $R^2$ is $R^B$, wherein $R^B$ is an optionally substituted $C_{1-6}$ aliphatic, preferably a substituted $C_{1-6}$ aliphatic, such as $-(CR_2)_{1-4}NR(CR_2)_{0-6}CO_2R$, $-(CR_2)_{1-4}O(CR_2)_{0-6}CO_2R$, $-(CR_2)_{1-4}CO_2R$, $-(CR_2)_{1-4}OH$, $-(CR_2)_{1-4}NH_2$, $-(CR_2)_{1-4}C(O)NH_2$, $-(CR_2)_{1-4}C(O)NHC_{1-4}alkyl$, or $-(CR_2)_{1-4}C(O)N(C_{1-4}alkyl)_2$, particularly $-(CR_2)_{1-4}NR(CR_2)_{0-6}CO_2R$ or $-(CR_2)_{1-4}CO_2R$. In some embodiments, $R^2$ is $-(CH_2)_{1-4}NR^a(CH_2)_{0-4}CO_2R^a$, such as $-(CH_2)_{1-4}NR^a(CH_2)_{0-4}CO_2H$, wherein $R^a$, independently for each occurrence, is H or $C_{1-4}$alkyl. In other embodiments, $R^2$ is $-(CH_2)_{1-4}N(SO_2C_{1-4}alkyl)(CH_2)_{0-4}CO_2R^a$, such as is $-(CH_2)_{1-4}N(SO_2C_{1-4}alkyl)(CH_2)_{0-4}CO_2H$, wherein $R^a$, independently for each occurrence, is H or $C_{1-4}$alkyl. In other embodiments, $R^2$ is $-(CR_2)_{1-4}CO_2R$, such as $-(CR_2)_{1-4}CO_2H$, including $-(CH_2)_{1-4}CO_2H$. In certain embodiments, $R^2$ includes a terminal $-CO_2H$ group. For example, in certain instances, $R^2$ includes a terminal $-(CH_2)_{0-4}CO_2H$ group.

In some embodiments, the present disclosure provides a compound of formula I or formula I*, wherein $R^1$ is

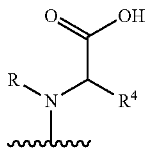

and $R^2$ is $-NR_2$, thereby forming a compound of formula I-h-1:

I-h-1

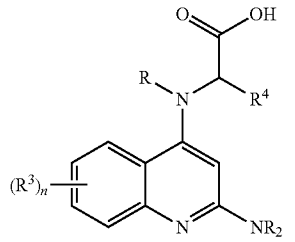

or a pharmaceutically acceptable salt thereof, wherein:

$R^4$ is hydrogen or an optionally substituted $C_{1-6}$ aliphatic; and each of R, $R^3$, and n is as defined above and described in embodiments herein, both singly and in combination.

In some embodiments, the present disclosure provides a compound of formula I-h-1, wherein R and $R^4$ in

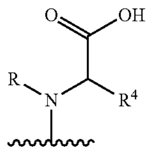

independently are hydrogen or lower alkyl, particularly methyl.

In certain embodiments, the present disclosure provides a compound of formula I-h-1, wherein $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I or formula I*, wherein $R^1$ is

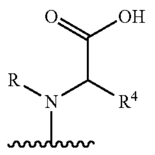

and $R^2$ is $-NRR^5$, thereby forming a compound of formula I-h-2:

I-h-2

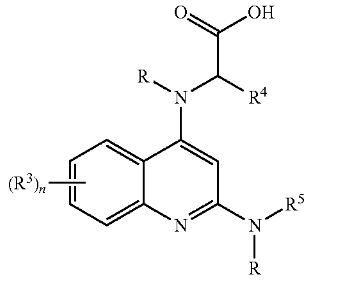

or a pharmaceutically acceptable salt thereof, wherein:

$R^4$ is hydrogen or an optionally substituted $C_{1-6}$ aliphatic;

$R^5$ is $—(CR_2)_{2-4}OR$, $—(CR_2)_{0-6}CO_2R$, $—(CR_2)_{0-6}CONR_2$, $—(CR_2)_{0-6}C(O)NR(CR_2)_{0-6}CO_2R$, $—(CR_2)_{0-6}C(O)NR(CR_2)_{0-6}CONR_2$, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, or $R^B$; and each of R, $R^3$, and n is as defined above and described in embodiments herein, both singly and in combination.

In certain embodiments, the present disclosure provides a compound of formula I-h-2, wherein $R^5$ is $—(CR_2)_{2-4}OR$, $—(CR_2)_{1-4}CO_2R$, $—(CR_2)_{1-4}CONR_2$, $—(CR_2)_{0-6}C(O)NR(CR_2)_{0-6}CO_2R$, $—(CR_2)_{0-6}C(O)NR(CR_2)_{0-6}CONR_2$, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, or $R^B$.

In some embodiments, the present disclosure provides a compound of formula I-h-2, wherein $R^5$ is not $R^B$.

In some embodiments, the present disclosure provides a compound of formula I-h-2, wherein R in $—NRR^5$ is $R^a$, which is H or $C_{1-6}$alkyl.

In some embodiments, the present disclosure provides a compound of formula I-h-2, wherein R and $R^4$ in

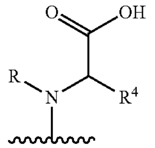

independently are hydrogen or lower alkyl, particularly methyl.

In certain embodiments, the present disclosure provides a compound of formula I-h-2, wherein $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-h-2, wherein:

R in $—NRR^5$ is H or lower alkyl, particularly methyl;

$R^5$ is $—(CH_2)_{2-4}OH$, $—(CH_2)_{0-3}CH(CH_2OH)_2$, $—(CH_2)_{2-4}OC_{1-4}alkyl$, $—(CH_2)_{1-4}CO_2H$, $—(CH_2)_{1-4}CO_2C_{1-4}alkyl$, $—(CH_2)_{1-4}CONH_2$, $—(CF_{12})_{1-4}CONHC_{1-4}alkyl$, $—(CH_2)_{1-4}CON(C_{1-4}alkyl)_2$, $—(CH_2)_{1-4}C(O)NR^a(CH_2)_{1-4}CO_2H$, $—(CH_2)_{1-4}C(O)NR^a(CH_2)_{1-4}CONH_2$, $—(CH_2)_{1-4}C(O)NR^a(CH_2)_{1-4}CONHC_{1-4}alkyl$, $—(CH_2)_{1-4}C(O)NR^a(CH_2)_{1-4}CON(C_{1-4}alkyl)_2$, $—(CH_2)_{2-4}SO_3H$, $—(CH_2)_{2-4}SO_3C_{1-4}alkyl$, $—(CH_2)_{2-4}SO_2NH_2$, $—(CH_2)_{2-4}SO_2NHC_{1-4}alkyl$, $—(CH_2)_{2-4}SO_2N(C_{1-4}alkyl)_2$, $—(CH_2)_{2-4}OSO_2NH_2$, $—(CH_2)_{2-4}NR^aSO_2C_{1-4}alkyl$, $—(CH_2)_{2-4}NR^aSO_3H$, $—(CH_2)_{1-4}OP(OH)_2$, $—(CH_2)_{1-4}P(O)(OH)_2$, $—(CH_2)_{1-4}P(O)(OH)(OC_{1-4}alkyl)$, or $—(CH_2)_{2-4}OP(O)(H)OH$, wherein $R^a$, independently for each occurrence, is H or $C_{1-4}$alkyl; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-h-2, wherein:

R in $—NRR^5$ is H or lower alkyl, particularly methyl;

$R^5$ is $—(CH_2)_{2-4}OH$, $—(CH_2)_{0-3}CH(CH_2OH)_2$, $—(CH_2)_{1-4}CO_2H$, $—(CH_2)_{1-4}CONH_2$, $—(CH_2)_{1-4}C(O)NR^a(CH_2)_{1-4}CO_2H$, $—(CH_2)_{1-4}C(O)NR^a(CH_2)_{1-4}CONH_2$, $—(CH_2)_{2-4}SO_3H$, $—(CH_2)_{2-4}SO_2NH_2$, $—(CH_2)_{2-4}SO_2NR^aC_{1-4}alkyl$, $—(CH_2)_{2-4}NR^aSO_2C_{1-4}alkyl$, $—(CH_2)_{1-4}P(O)(OH)_2$, or $—(CH_2)_{2-4}OP(O)(H)OH$, wherein $R^a$, independently for each occurrence, is H or $C_{1-4}$alkyl; and each $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-h-2, $R^5$ includes a terminal $—CO_2H$ group. For example, in certain instances, $R^5$ includes a terminal $—(CH_2)_{0-4}CO_2H$ group.

In some embodiments, the present disclosure provides a compound of formula I or formula I*, wherein $R^1$ is

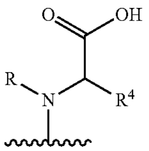

and $R^2$ is

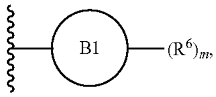

thereby forming a compound of formula I-h-3:

I-h-3

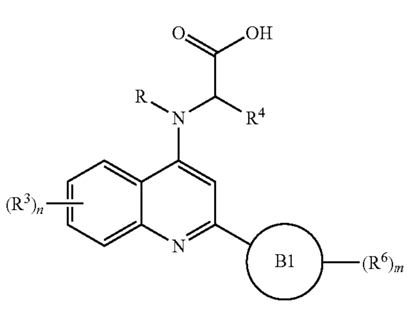

or a pharmaceutically acceptable salt thereof, wherein:

Ring B1 is phenyl; a 4- to 10-membered saturated or partially unsaturated monocyclic or bicyclic carboxylic or heterocyclic ring having 1 to 3 heteroatoms independently selected from nitrogen, oxygen, phosphorus, and sulfur;

or a 5- to 6-membered heteroaryl ring having 1 to 4 heteroatoms independently selected from nitrogen, oxygen, phosphorus, and sulfur;

$R^4$ is hydrogen or an optionally substituted $C_{1-6}$ aliphatic;

each $R^6$ is independently halogen, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

m is 0, 1, 2, 3, or 4, particularly 1, 2, 3, or 4; and each of R, $R^3$, $R^B$, and n is as defined above and described in embodiments herein, both singly and in combination.

In certain embodiments, the present disclosure provides a compound of formula I-h-3, wherein Ring B1 is phenyl, particularly substituted phenyl. In other embodiments, Ring B1 is not phenyl. For example, Ring B1 may be a 4- to 10-membered saturated or partially unsaturated monocyclic or bicyclic carboxylic or heterocyclic ring having 1 to 3 heteroatoms independently selected from nitrogen, oxygen, phosphorus, and sulfur. In some embodiments, Ring B1 is a 5- to 6-membered heteroaryl ring having 1 to 4 heteroatoms independently selected from nitrogen, oxygen, phosphorus, and sulfur.

In some embodiments, the present disclosure provides a compound of formula I-h-3, wherein $R^6$ is not $R^B$.

In some embodiments, the present disclosure provides a compound of formula I-h-3, wherein R and $R^4$ in

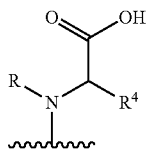

independently are hydrogen or lower alkyl, particularly methyl.

In certain embodiments, the present disclosure provides a compound of formula I-h-3, wherein $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-h-3, m is 1 or 2, and at least one $R^6$ includes a terminal —$CO_2H$ group. For example, in certain instances, at least one $R^6$ is —$(CH_2)_{0-4}CO_2H$.

In some embodiments, the present disclosure provides a compound of formula I or formula I*, wherein $R^1$ is

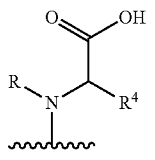

and $R^2$ is

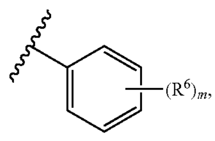

thereby forming a compound of formula I-h-4:

I-h-4

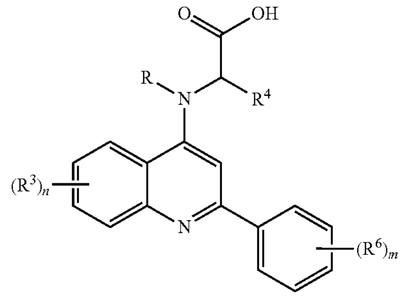

or a pharmaceutically acceptable salt thereof, wherein:

$R^4$ is hydrogen or an optionally substituted $C_{1-6}$ aliphatic;

each $R^6$ is independently halogen, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

m is 0, 1, 2, 3, or 4, particularly 1, 2, 3, or 4; and each of R, $R^3$, $R^B$, and n is as defined above and described in embodiments herein, both singly and in combination.

In some embodiments, the present disclosure provides a compound of formula I-h-4, wherein $R^6$ is not $R^B$.

In some embodiments, the present disclosure provides a compound of formula I-h-4, wherein R and $R^4$ in

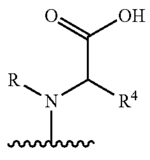

independently are hydrogen or lower alkyl, particularly methyl.

In certain embodiments, the present disclosure provides a compound of formula I-h-4, wherein $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I or formula I*, wherein $R^1$ is

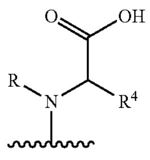

and $R^2$ is

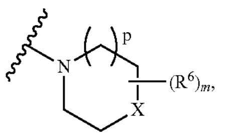

thereby forming a compound of formula I-h-5:

I-h-5

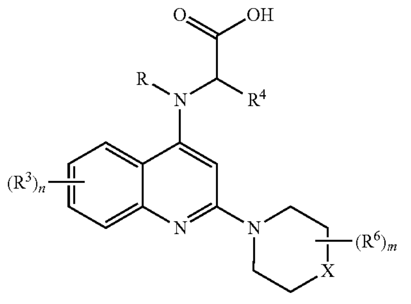

or a pharmaceutically acceptable salt thereof, wherein:

$R^4$ is hydrogen or an optionally substituted $C_{1-6}$ aliphatic;

each $R^6$ is independently halogen, =O, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

X is —$CR_2$—, —NR—, —O—, —S—, or —$SO_2$—, particularly —$CR_2$—, —NR—, or —O;

m is 0, 1, 2, 3, or 4, particularly 1, 2, 3, or 4;

p is 0, 1, or 2, particularly 1; and each of R, $R^3$, $R^B$, and n is as defined above and described in embodiments herein, both singly and in combination.

In some embodiments, the present disclosure provides a compound of formula I-h-5, wherein $R^6$ is not $R^B$.

In some embodiments, the present disclosure provides a compound of formula I-h-5, wherein R and $R^4$ in

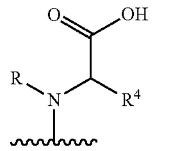

independently are hydrogen or lower alkyl, particularly methyl.

In certain embodiments, the present disclosure provides a compound of formula I-h-5, wherein $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-h-5, wherein:

each $R^6$ is independently halogen, =O, —$(CH_2)_{0-4}CO_2H$, —$(CH_2)_{0-4}CO_2C_{1-4}$alkyl, —$(CH_2)_{0-4}CONH_2$, —$(CH_2)_{0-4}CONHC_{1-4}$alkyl, —$(CH_2)_{0-4}CON(C_{1-4}$ alkyl$)_2$, —$(CH_2)_{0-4}$CO(N-proline), —$(CH_2)_{0-4}C(O)NR^a(CH_2)_{1-4}CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}$alkyl$)_2$, —OH, —$(CH_2)_{1-4}OH$, —$(CH_2)_{0-4}OC_{1-4}$alkyl, —$NH_2$, —$(CH_2)_{1-4}NH_2$, —$(CH_2)_{0-4}NHC_{1-4}$alkyl, —$(CH_2)_{0-4}N(C_{1-4}$alkyl$)_2$, —$(CH_2)_{0-4}SO_3H$, —$(CH_2)_{0-4}SO_2NH_2$, —$(CH_2)_{0-4}SO_2NHC_{1-4}$alkyl, —$(CH_2)_{0-4}NR^aSO_2C_{1-4}$alkyl, —$(CH_2)_{0-4}OP(OH)_2$, —$(CH_2)_{0-4}OP(OH)(OC_{1-4}$alkyl), or —$(CR_2)_{0-4}OP(O)(H)OH$, wherein $R^a$, independently for each occurrence, is H or $C_{1-4}$alkyl;

X is —$CH_2$—, —NH—, or —O—;

m is 1, 2, 3, or 4, particularly 1 or 2;

p is 1; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-h-5, wherein:

each $R^6$ is independently halogen, —$(CH_2)_{0-4}CO_2H$, —$(CH_2)_{0-4}$CO(N-proline), —$(CH_2)_{0-4}C(O)NR^a(CH_2)_{1-4}CO_2H$, —OH, —$(CH_2)_{1-4}OH$, —$(CH_2)_{0-4}SO_3H$, —$(CH_2)_{0-4}SO_2NH_2$, —$(CH_2)_{0-4}NR^aSO_2C_{1-4}$alkyl, —$(CH_2)_{0-4}OP(OH)_2$, or —$(CR_2)_{0-4}OP(O)(H)OH$;

X is —$CH_2$—, —NH—, or —O—;

m is 1 or 2;

p is 1; and each $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-h-5, m is 1 or 2, and at least one $R^6$ includes a terminal —$CO_2H$ group. For example, in certain instances, at least one $R^6$ is —$(CH_2)_{0-4}CO_2H$.

In some embodiments, the present disclosure provides a compound of formula I or formula I*, wherein $R^1$ is

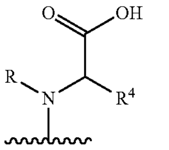

and $R^2$ is

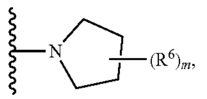

thereby forming a compound of formula I-h-6:

I-h-6

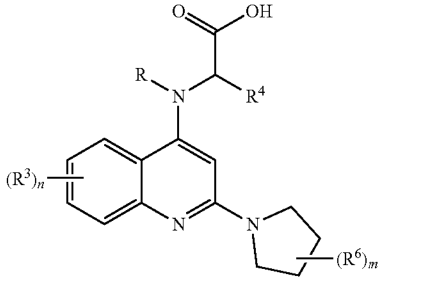

or a pharmaceutically acceptable salt thereof, wherein:

$R^4$ is hydrogen or an optionally substituted $C_{1-6}$ aliphatic;

each $R^6$ is independently halogen, =O, —COR, $—(CR_2)_{0-6}CO_2R$, $—(CR_2)_{0-6}CONR_2$, OR, $—(CR_2)_{1-4}OR$, $—NR_2$, $—(CR_2)_{1-4}NR_2$, —NRC(O)OR, —NRC(O)R, $—NRC(O)NR_2$, —SR, $—SO_2R$, —S(O)R, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, $—B(OR)_2$, or $R^B$;

m is 0, 1, 2, 3, or 4, particularly 1, 2, 3, or 4; and each of R, $R^3$, $R^B$, and n is as defined above and described in embodiments herein, both singly and in combination.

In some embodiments, the present disclosure provides a compound of formula I-h-6, wherein $R^6$ is not $R^B$.

In some embodiments, the present disclosure provides a compound of formula I-h-6, wherein R and $R^4$ in

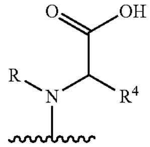

independently are hydrogen or lower alkyl, particularly methyl.

In certain embodiments, the present disclosure provides a compound of formula I-h-6, wherein $R^3$ is independently halogen, such as chloro, including dichloro, including wherein n is 2 and $R^3$ is chloro at the 7- and 8-positions with respect to the quinoline ring.

In certain embodiments, the present disclosure provides a compound of formula I-h-6, wherein:

each $R^6$ is independently halogen, =O, —COR, $—(CR_2)_{0-6}CO_2R$, $—(CR_2)_{0-6}CONR_2$, —OR, $—(CR_2)_{1-4}OR$, $—NR_2$, $—(CR_2)_{1-4}NR_2$, —NRC(O)OR, —NRC(O)R, $—NRC(O)NR_2$, —SR, $—SO_2R$, —S(O)R, $—(CR_2)_{0-6}SO_3R$, $—(CR_2)_{0-6}SO_2NR_2$, $—(CR_2)_{0-6}OSO_2NR_2$, $—(CR_2)_{0-6}NRSO_2R$, $—(CR_2)_{0-6}NRSO_2OR$, $—(CR_2)_{0-6}OP(OR)_2$, $—(CR_2)_{0-6}OP(O)(OR)_2$, $—(CR_2)_{0-6}P(O)(OR)_2$, $—(CR_2)_{0-6}OP(O)(H)OR$, or $—B(OR)_2$;

m is 1, 2, 3, or 4, particularly 1 or 2; and each $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-h-6, wherein:

each $R^6$ is independently halogen, =O, $—(CH_2)_{0-4}CO_2H$, $—(CF_{12})_{0-4}CO_2C_{1-4}$alkyl, $—(CH_2)_{0-4}CONH_2$, $—(CH_2)_{0-4}CONHC_{1-4}$alkyl, $—(CH_2)_{0-4}CON(C_{1-4}$ alkyl$)_2$, $—(CH_2)_{0-4}$CO(N-proline), $—(CH_2)_{0-4}$CO(N-pyrrolidine-3-carboxylic acid), $—(CH_2)_{0-4}C(O)NR^a(CH_2)_{1-4}CO_2H$, $—(CH_2)_{0-4}C(O)NR^a—CH(C_{1-4}$alkyl$)-CO_2H$, $—(CH_2)_{0-4}C(O)NR^a(CH_2)_{1-4}CONH_2$, $—(CH_2)_{0-4}C(O)NR^a(CH_2)_{1-4}CONHC_{1-4}$alkyl, $—(CH_2)_{0-4}C(O)NR^a(CH_2)_{1-4}CON(C_{1-4}$alkyl$)_2$, —OH, $—(CH_2)_{1-4}OH$, $—(CH_2)_{0-4}OC_{1-4}$alkyl, $—NH_2$, $—(CH_2)_{1-4}NH_2$, $—(CH_2)_{0-4}NHC_{1-4}$alkyl, $—(CH_2)_{0-4}NR^aC(O)C_{1-4}$alkyl, $—(CH_2)_{0-4}NR^aC(O)Ph$, $—(CH_2)_{0-4}NR^aCO(CH_2)_{1-4}OH$, $—(CH_2)_{0-4}N(C_{1-4}$ alkyl$)_2$, $—(CH_2)_{0-4}SO_3H$, $—(CH_2)_{0-4}SO_2NH_2$, $—(CH_2)_{0-4}SO_2NR^aC_{1-4}$alkyl, $—(CH_2)_{0-4}NR^aSO_2C_{1-4}$alkyl, $—(CH_2)_{0-4}NR^aSO_2Ph$, $—(CH_2)_{0-4}NR^aSO_2(CH_2)_{1-4}CO_2H$, $—(CH_2)_{0-4}OP(OH)_2$, $—(CH_2)_{0-4}OP(OH)(OC_{1-4}$alkyl), or $—(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-h-6, wherein:

each $R^6$ is independently halogen, $—(CH_2)_{0-4}CO_2H$, $—(CH_2)_{0-4}$CO(N-proline), $—(CH_2)_{0-4}$CO(N-pyrrolidine-3-carboxylic acid), $—(CH_2)_{0-4}C(O)NR^a(CH_2)_{1-4}CO_2H$, $—(CH_2)_{0-4}C(O)NR^a—CH(C_{1-4}$alkyl$)-CO_2H$, —OH, $—(CH_2)_{1-4}OH$, $—(CH_2)_{0-4}NR^aC(O)C_{1-4}$alkyl, $—(CH_2)_{0-4}NR^aC(O)Ph$, $—(CH_2)_{0-4}NR^aCO(CH_2)_{1-4}OH$, $—(CH_2)_{0-4}SO_3H$, $—(CH_2)_{0-4}SO_2NH_2$, $—(CH_2)_{0-4}NR^aSO_2C_{1-4}$alkyl, $—(CH_2)_{0-4}NR^aSO_2Ph$, $—(CH_2)_{0-4}NR^aSO_2(CH_2)_{1-4}CO_2H$, $—(CH_2)_{0-4}OP(OH)_2$, or $—(CR_2)_{0-4}OP(O)(H)OH$, wherein $R^a$, independently for each occurrence, is H or $C_{1-4}$alkyl;

m is 1 or 2; and each $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-h-6, m is 1 or 2, and at least one $R^6$ includes a terminal $—CO_2H$ group. For example, in certain instances, at least one $R^6$ is $—(CH_2)_{0-4}CO_2H$.

In some embodiments, the present disclosure provides a compound of formula I or formula I*, wherein $R^1$ is

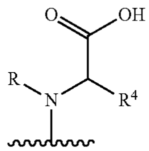

and $R^2$ is

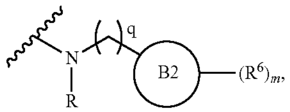

thereby forming a compound of formula I-h-7:

I-h-7

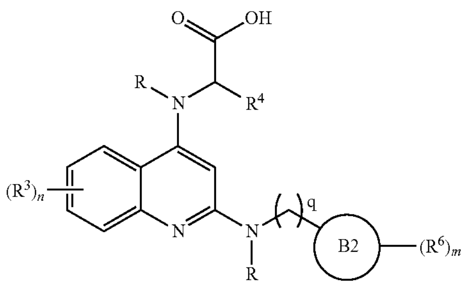

or a pharmaceutically acceptable salt thereof, wherein:

Ring B2 is phenyl; a 4- to 7-membered saturated or partially unsaturated carbocyclic or heterocyclic ring having 1 to 3 heteroatoms independently selected from nitrogen, oxygen, phosphorus, and sulfur; or a 5- to 6-membered heteroaryl ring having 1 to 4 heteroatoms independently selected from nitrogen, oxygen, phosphorus, and sulfur;

$R^4$ is hydrogen or an optionally substituted $C_{1-6}$ aliphatic;

each $R^6$ is independently halogen, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

m is 0, 1, 2, 3, or 4, particularly 1, 2, 3, or 4;

q is 0, 1, or 2; and each of R, $R^3$, $R^B$, and n is as defined above and described in embodiments herein, both singly and in combination.

In certain embodiments, the present disclosure provides a compound of formula I-h-7, wherein Ring B2 is phenyl, particularly substituted phenyl. In other embodiments, Ring B2 is not phenyl. For example, Ring B2 may be a 4- to 10-membered saturated or partially unsaturated monocyclic or bicyclic carboxylic or heterocyclic ring having 1 to 3 heteroatoms independently selected from nitrogen, oxygen, phosphorus, and sulfur. In some embodiments, Ring B2 is a 5- to 6-membered heteroaryl ring having 1 to 4 heteroatoms independently selected from nitrogen, oxygen, phosphorus, and sulfur.

In some embodiments, the present disclosure provides a compound of formula I-h-7, wherein $R^6$ is not $R^B$.

In some embodiments, the present disclosure provides a compound of formula I-h-7, wherein R in

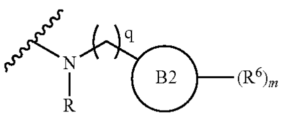

is $R^a$, which is H or $C_{1-6}$alkyl.

In some embodiments, the present disclosure provides a compound of formula I-h-7, wherein R and $R^4$ in

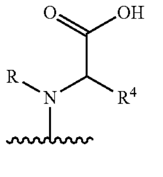

independently are hydrogen or lower alkyl, particularly methyl.

In certain embodiments, the present disclosure provides a compound of formula I-h-7, wherein $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-h-7, m is 1 or 2, and at least one $R^6$ includes a terminal —$CO_2H$ group. For example, in certain instances, at least one $R^6$ is —$(CH_2)_{0-4}CO_2H$.

In some embodiments, the present disclosure provides a compound of formula I or formula I*, wherein $R^1$ is

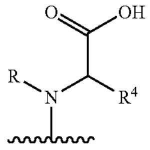

and $R^2$ is

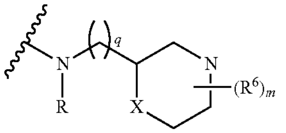

or

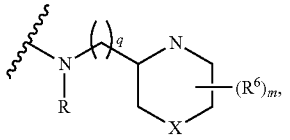

, thereby forming a compound of formula I-h-8 or formula I-h-8*, respectively:

I-h-8

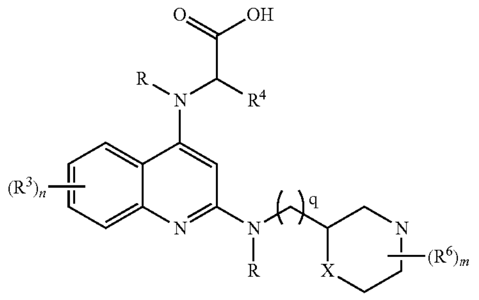

I-h-8*

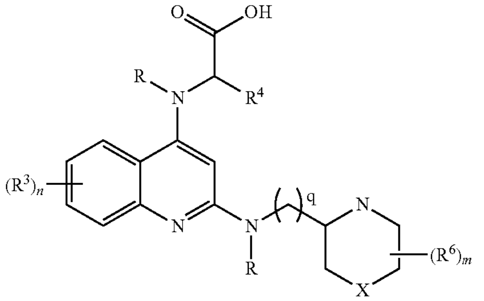

or a pharmaceutically acceptable salt thereof, wherein:

$R^4$ is hydrogen or an optionally substituted $C_{1-6}$ aliphatic;

each $R^6$ is independently hydrogen (only on N), halogen (not on N), —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

X is —$CR_2$—, —NR—, —O—, —S—, or —$SO_2$—, particularly —$CR_2$—, —NR—, or —O;

m is 1, 2, 3, or 4;

q is 0, 1, or 2; and each of R, $R^3$, $R^B$, and n is as defined above and described in embodiments herein, both singly and in combination.

In some embodiments, the present disclosure provides a compound of formula I-h-8 or formula I-h-8*, wherein $R^6$ is not $R^B$.

In some embodiments, the present disclosure provides a compound of formula I-h-8 or formula I-h-8*, wherein R in

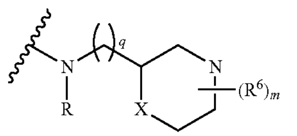

or in

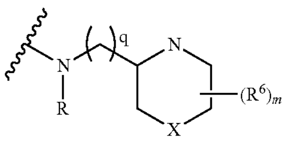

is $R^a$, which is H or $C_{1-6}$alkyl.

In some embodiments, the present disclosure provides a compound of formula I-h-8 or formula I-h-8*, wherein R and $R^4$ in

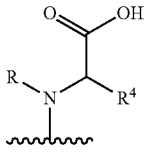

independently are hydrogen or lower alkyl, particularly methyl.

In certain embodiments, the present disclosure provides a compound of formula I-h-8 or formula I-h-8*, wherein $R^3$ is independently halogen, such as chloro, including dichloro, including wherein n is 2 and $R^3$ is chloro at the 7- and 8-positions with respect to the quinoline ring.

In certain embodiments, the present disclosure provides a compound of formula I-h-8 or formula I-h-8*, wherein:

each $R^6$ is independently halogen, =O, —COR, $-(CR_2)_{0-6}CO_2R$, $-(CR_2)_{0-6}CONR_2$, —OR, $-(CR_2)_{1-4}OR$, $-NR_2$, $-(CR_2)_{1-4}NR_2$, —NRC(O)OR, —NRC(O)R, $-NRC(O)NR_2$, —SR, $-SO_2R$, —S(O)R, $-(CR_2)_{0-6}SO_3R$, $-(CR_2)_{0-6}SO_2NR_2$, $-(CR_2)_{0-6}OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, $-(CR_2)_{0-6}OP(O)(H)OR$, or $-B(OR)_2$;

m is 1, 2, 3, or 4, particularly 1 or 2;

q is 1 or 2; and each $R^3$ is independently halogen, such as chloro, including dichloro, including wherein n is 2 and $R^3$ is chloro at the 7- and 8-positions with respect to the quinoline ring.

In particular embodiments, the present disclosure provides a compound of formula I-h-8 or formula I-h-8*, wherein:

each $R^6$ is independently halogen, =O, $-(CH_2)_{0-4}CO_2H$, $-(CF_{12})_{0-4}CO_2C_{1-4}$alkyl, $-(CH_2)_{0-4}CONH_2$, $-(CH_2)_{0-4}CONHC_{1-4}$alkyl, $-(CH_2)_{0-4}CON(C_{1-4}$alkyl$)_2$, $-(CH_2)_{0-4}$CO(N-proline), $-(CH_2)_{0-4}C(O)NR^a(CH_2)_{1-4}CO_2H$, $-(CH_2)_{0-4}C(O)NR^a(CH_2)_{1-4}CONH_2$, $-(CH_2)_{0-4}C(O)NR^a(CH_2)_{1-4}CONHC_{1-4}$alkyl, $-(CH_2)_{0-4}C(O)NR^a(CH_2)_{1-4}CON(C_{1-4}$alkyl$)_2$, —OH, $-(CH_2)_{1-4}OH$, $-(CH_2)_{0-4}OC_{1-4}$alkyl, $-NH_2$, $-(CH_2)_{1-4}NH_2$, $-(CH_2)_{0-4}NHC_{1-4}$alkyl, $-(CH_2)_{0-4}N(C_{1-4}$alkyl$)_2$, $-(CH_2)_{0-4}SO_3H$, $-(CH_2)_{0-4}SO_2NH_2$, $-(CH_2)_{0-4}SO_2NHC_{1-4}$alkyl, $-(CH_2)_{0-4}NR^aSO_2C_{1-4}$alkyl, $-(CH_2)_{0-4}OP(OH)_2$, $-(CH_2)_{0-4}$, —OP(OH)($OC_{1-4}$alkyl), or $-(CR_2)_{0-4}OP(O)(H)OH$, wherein $R^a$, independently for each occurrence, is H or $C_{1-4}$alkyl;

m is 1, 2, 3, or 4, particularly 1 or 2;

q is 1; and each $R^3$ is independently halogen, such as chloro, including dichloro, including wherein n is 2 and $R^3$ is chloro at the 7- and 8-positions with respect to the quinoline ring.

In further particular embodiments, the present disclosure provides a compound of formula I-h-8 or formula I-h-8*, wherein:

each $R^6$ is independently halogen, $-(CH_2)_{0-4}CO_2H$, $-(CH_2)_{0-4}$CO(N-proline), $-(CH_2)_{0-4}C(O)NR^a(CH_2)_{1-4}CO_2H$, —OH, $-(CH_2)_{1-4}OH$, $-(CH_2)_{0-4}SO_3H$, $-(CH_2)_{0-4}SO_2NH_2$, $-(CH_2)_{0-4}NR^aSO_2C_{1-4}$alkyl, $-(CH_2)_{0-4}OP(OH)_2$, or $-(CR_2)_{0-4}OP(O)(H)OH$, wherein $R^a$, independently for each occurrence, is H or $C_{1-4}$alkyl;

m is 1 or 2;

q is 1; and each $R^3$ is independently halogen, such as chloro, including dichloro, including wherein n is 2 and $R^3$ is chloro at the 7- and 8-positions with respect to the quinoline ring.

In certain embodiments, for the above disclosed compounds of formula I-h-8 or I-h-8*, m is 1 or 2, and at least one $R^6$ includes a terminal $-CO_2H$ group. For example, in certain instances, at least one $R^6$ is $-(CH_2)_{0-4}CO_2H$.

In some embodiments, the present disclosure provides a compound of formula I or formula I*, wherein $R^1$ is

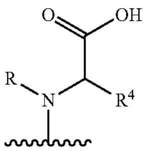

and $R^2$ is

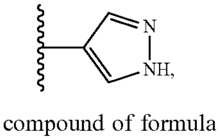

thereby forming a compound of formula I-h-9:

I-H-9

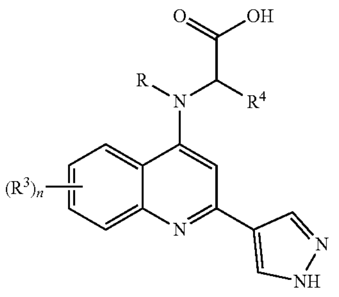

or a pharmaceutically acceptable salt thereof, wherein:

$R^4$ is hydrogen or an optionally substituted $C_{1-6}$ aliphatic; and each of R, $R^3$, and n is as defined above and described in embodiments herein, both singly and in combination.

In some embodiments, the present disclosure provides a compound of formula I-h-9, wherein R and $R^4$ in

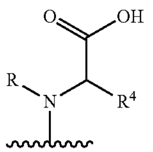

independently are hydrogen or lower alkyl, particularly methyl.

In certain embodiments, the present disclosure provides a compound of formula I-h-9, wherein $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I, wherein $R^1$ is

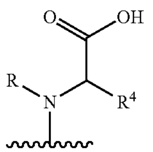

and at least one $R^3$ is halogen, such as chloro at the 8-position, thereby forming a compound of formula I-i-1:

I-i-1

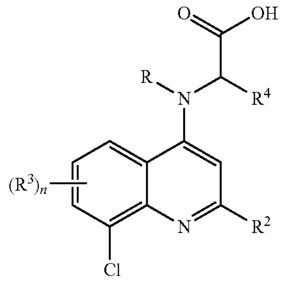

or a pharmaceutically acceptable salt thereof, wherein:

$R^4$ is hydrogen or an optionally substituted $C_{1-6}$ aliphatic; and each of R, $R^2$, and $R^3$ is as defined above and described in embodiments herein, and n is 0, 1, 2, or 3, both singly and in combination.

In some embodiments, the present disclosure provides a compound of formula I-i-1, wherein R and $R^4$ in

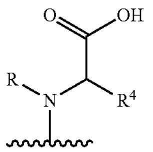

independently are hydrogen or lower alkyl, particularly methyl.

In some embodiments, the present disclosure provides a compound of formula I, wherein $R^1$ is

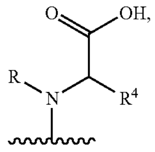

n is 2, and $R^3$ is chloro at the 7- and 8-positions, thereby forming a compound of formula I-i-2:

I-i-2

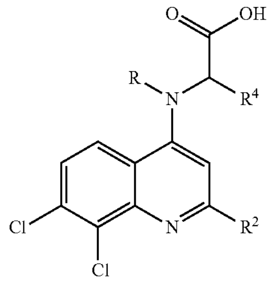

or a pharmaceutically acceptable salt thereof, wherein:

$R^4$ is hydrogen or an optionally substituted $C_{1-6}$ aliphatic; and each of R and $R^2$ is as defined above and described in embodiments herein, both singly and in combination.

In some embodiments, the present disclosure provides a compound of formula I-i-2, wherein R and $R^4$ in

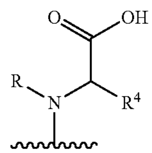

independently are hydrogen or lower alkyl, particularly methyl.

As defined above and described herein, $R^1$ is halogen, —OR, —$NR_2$, —NRC(O)OR, —NRC(O)R, —NRC(O)$NR_2$, —$NRSO_2R$, —SR, —$SO_2R$, —$SO_2NR_2$, —S(O)R, or $R^A$, particularly —$NR_2$ or $R^A$.

In some embodiments, $R^1$ is halogen. In some embodiments, $R^1$ is —OR. In some embodiments, $R^1$ is —$NR_2$. In some embodiments, $R^1$ is —NRC(O)OR. In some embodiments, $R^1$ is —NRC(O)R. In some embodiments, $R^1$ is —NRC(O)$NR_2$. In some embodiments, $R^1$ is —$NRSO_2R$. In some embodiments, $R^1$ is —SR. In some embodiments, $R^1$ is —$SO_2R$. In some embodiments, $R^1$ is —$SO_2NR_2$. In some embodiments, $R^1$ is —S(O)R. In some embodiments, $R^1$ is $R^A$.

In some embodiments, $R^1$ is hydrogen. In some embodiments, $R^1$ is chloro. In some embodiments, $R^1$ is

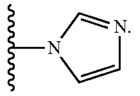 [SMILES: *n1ccnc1]

In some embodiments, $R^1$ is

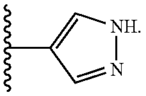 [SMILES: *c1cn[nH]c1]

In some embodiments, $R^1$ is

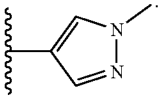 [SMILES: *c1cnn(C)c1]

In some embodiments, $R^1$ is

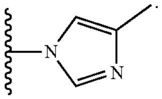 [SMILES: *n1cnc(C)c1]

In some embodiments, $R^1$ is

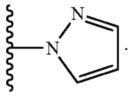

In some embodiments, $R^1$ is

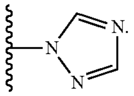

In some embodiments, $R^1$ is

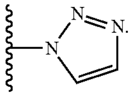

In some embodiments, $R^1$ is

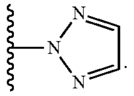

In some embodiments, $R^1$ is

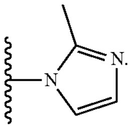

In some embodiments, $R^1$ is

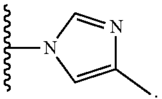 [SMILES: *n1cnc(C)c1]

In some embodiments, $R^1$ is

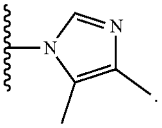 [SMILES: *n1cnc(C)c1C]

In some embodiments, $R^1$ is

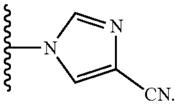 [SMILES: *n1cnc(C#N)c1]

In some embodiments, $R^1$ is

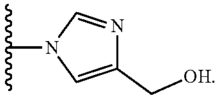

In some embodiments, $R^1$ is

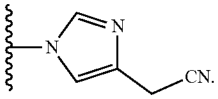 [SMILES: *n1cnc(CC#N)c1]

In some embodiments, $R^1$ is

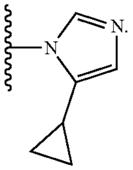

In some embodiments, $R^1$ is

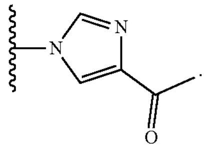

In some embodiments, $R^1$ is

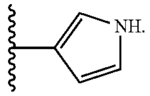 [SMILES: *c1cc[nH]c1]

In some embodiments, $R^1$ is

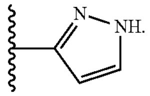 [SMILES: *c1cc[nH]n1]

In some embodiments, $R^1$ is

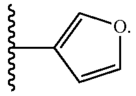 [SMILES: *c1ccoc1]

In some embodiments, $R^1$ is

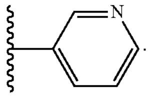 [SMILES: *c1cccnc1]

In some embodiments, $R^1$ is

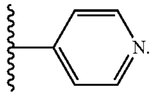 [SMILES: *c1ccncc1]

In some embodiments, $R^1$ is

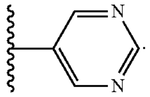

In some embodiments, $R^1$ is

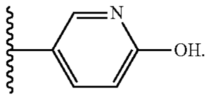

In some embodiments, $R^1$ is

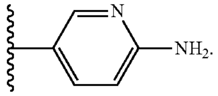 [SMILES: *c1ccc(N)nc1]

In some embodiments, $R^1$ is

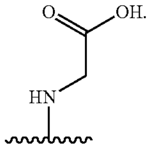 [SMILES: *NCC(=O)O]

In some embodiments, $R^1$ is

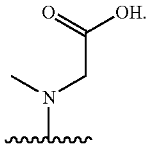 [SMILES: *N(C)CC(=O)O]

In some embodiments, $R^1$ is

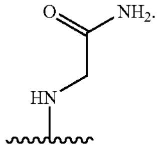 [SMILES: *NCC(N)=O]

In some embodiments, $R^1$ is

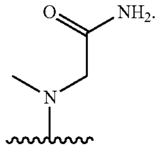 [SMILES: *N(C)CC(N)=O]

In some embodiments, $R^1$ is

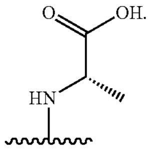 [SMILES: *N[C@@H](C)C(=O)O]

In some embodiments, $R^1$ is

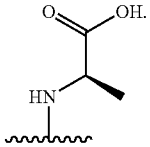 [SMILES: *N[C@H](C)C(=O)O]

In some embodiments, $R^1$ is
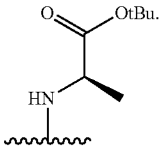 [SMILES: *N[C@H](C)C(=O)OC(C)(C)C]
In some embodiments, $R^1$ is
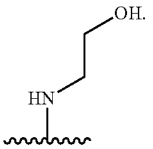
In some embodiments, $R^1$ is
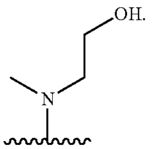 [SMILES: *N(C)CCO]
In some embodiments, $R^1$ is
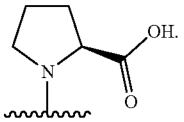 [SMILES: *N1CCC[C@H]1C(=O)O]
In some embodiments, $R^1$ is
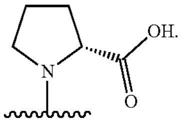 [SMILES: *N1CCC[C@@H]1C(=O)O]
some embodiments, $R^1$ is
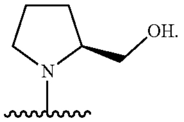 [SMILES: *N1CCC[C@H]1CO]
In some embodiments, $R^1$ is
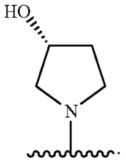
In some embodiments, $R^1$ is
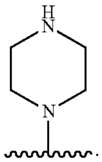 [SMILES: *N1CCNCC1]
In some embodiments, $R^1$ is
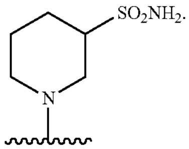 [SMILES: *N1CCCC(S(N)(=O)=O)C1]
In some embodiments, $R^1$ is
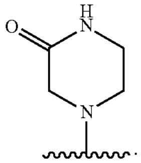
In some embodiments, $R^1$
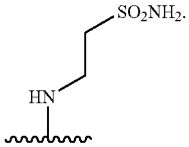 [SMILES: *NCCS(N)(=O)=O]
In some embodiments, $R^1$ is
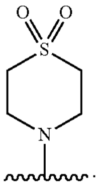
In some embodiments, $R^1$ is
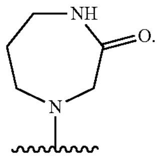 [SMILES: *N1CCCNC(=O)C1]

In some embodiments, $R^1$ is

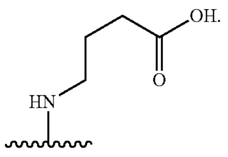 [SMILES: *NCCCC(=O)O]

In some embodiments, $R^1$ is

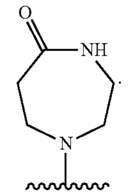

In some embodiments, $R^1$ is

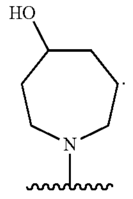 [SMILES: *N1CCCC(O)CC1]

In some embodiments, $R^1$ is

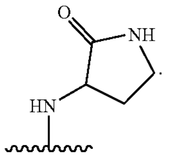 [SMILES: *NC1CCNC1=O]

In some embodiments, $R^1$ is

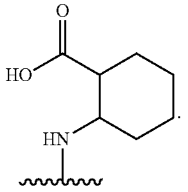 [SMILES: *NC1CCCCC1C(=O)O]

In some embodiments, $R^1$ is selected from those groups depicted in Table 1.

As defined above and described herein, each R is independently hydrogen or an optionally substituted group selected from $C_{1-6}$ aliphatic; benzyl; phenyl; a 4- to 10-membered saturated or partially unsaturated monocyclic or bicyclic carbocyclic or heterocyclic ring having 1 to 3 heteroatoms independently selected from nitrogen, oxygen, phosphorus, and sulfur; and a 5- to 6-membered heteroaryl ring having 1 to 4 heteroatoms independently selected from nitrogen, oxygen, phosphorus, and sulfur, or two R groups on the same nitrogen are optionally taken together with their intervening atoms to form an optionally substituted 4- to 7-membered saturated, partially unsaturated, or heteroaryl ring having 0 to 3 heteroatoms, in addition to the nitrogen, independently selected from nitrogen, oxygen, phosphorus, and sulfur.

In some embodiments, R is hydrogen. In some embodiments, R is an optionally substituted $C_{1-6}$ aliphatic. In some embodiments, R is an optionally substituted benzyl. In some embodiments, R is an optionally substituted phenyl. In some embodiments, R is an optionally substituted 4- to 10-membered saturated or partially unsaturated monocyclic or bicyclic carbocyclic or heterocyclic ring having 1 to 3 heteroatoms independently selected from nitrogen, oxygen, phosphorus, and sulfur. In some embodiments, R is an optionally substituted 5- to 6-membered heteroaryl ring having 1 to 4 heteroatoms independently selected from nitrogen, oxygen, phosphorus, and sulfur. In some embodiments, two R groups on the same nitrogen are optionally taken together with their intervening atoms to form an optionally substituted 4- to 7-membered saturated, partially unsaturated, or heteroaryl ring having 0 to 3 heteroatoms, in addition to the nitrogen, independently selected from nitrogen, oxygen, phosphorus, and sulfur.

In some embodiments, two R groups on the same carbon atom (e.g., $—(CR_2)—$, etc.) are optionally taken together with their intervening atoms to form an optionally substituted 4- to 7-membered saturated or partially unsaturated ring having 0 to 3 heteroatoms independently selected from nitrogen, oxygen, phosphorus, and sulfur.

In some embodiments, two R groups on different atoms (e.g., $—P(O)(OR)_2$, $—B(OR)_2$, etc.) are optionally taken together with their intervening atoms to form an optionally substituted 4- to 7-membered saturated or partially unsaturated ring having 0 to 3 heteroatoms independently selected from nitrogen, oxygen, phosphorus, and sulfur.

In some embodiments, R is hydrogen. In some embodiments, R is methyl. In some embodiments, R is ethyl. In some embodiments, R is isopropyl. In some embodiments, R is phenyl. In some embodiments, R is benzyl. In some embodiments, R is $—(CH_2)_{1-5}CO_2H$. In some embodiments, R is $—(CH_2)_{1-5}CO_2C_{1-4}$alkyl.

In some embodiments, R is selected from those groups depicted in Table 1.

As defined above and described herein, $R^2$ is halogen, —OR, $—NR_2$, —NRC(O)OR, —NRC(O)R, $—NRC(O)NR_2$, $—NRSO_2R$, —SR, $—SO_2R$, $—SO_2NR_2$, —S(O)R, or $R^B$, particularly $—NR_2$ or $R^B$;

In some embodiments, $R^2$ is halogen. In some embodiments, $R^2$ is —OR. In some embodiments, $R^2$ is $—NR_2$. In some embodiments, $R^2$ is —NRC(O)OR. In some embodiments, $R^2$ is —NRC(O)R. In some embodiments, $R^2$ is $—NRC(O)NR_2$. In some embodiments, $R^2$ is $—NRSO_2R$, —SR. In some embodiments, $R^2$ is $—SO_2R$. In some embodiments, $R^2$ is $—SO_2NR_2$. In some embodiments, $R^2$ is —S(O)R. In some embodiments, $R^2$ is $R^B$.

In some embodiments, $R^2$ is hydrogen. In some embodiments, $R^2$ is chloro. In some embodiments, $R^2$ is methyl. In some embodiments, $R^2$ is $—CF_3$. In some embodiments, $R^2$ is phenyl. In some embodiments, $R^2$ is

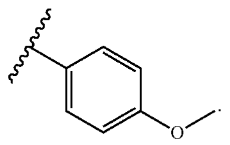 [SMILES: *c1ccc(OC)cc1]

In some embodiments, $R^2$ is
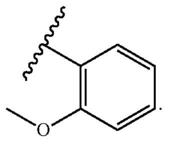 [SMILES: *c1ccccc1OC]
In some embodiments, $R^2$ is
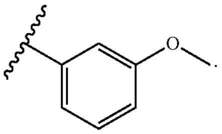 [SMILES: *c1cccc(OC)c1]
In some embodiments, $R^2$ is
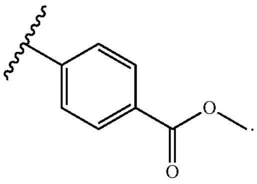 [SMILES: *c1ccc(C(=O)OC)cc1]
In some embodiments, $R^2$ is
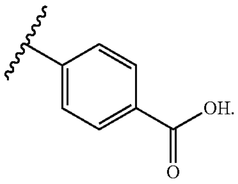 [SMILES: *c1ccc(C(=O)O)cc1]
In some embodiments, $R^2$ is
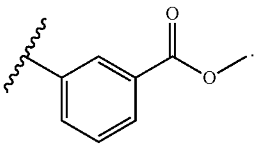 [SMILES: *c1cccc(C(=O)OC)c1]
In some embodiments, $R^2$ is
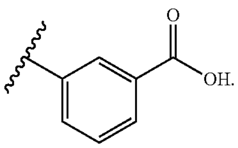 [SMILES: *c1cccc(C(=O)O)c1]
In some embodiments, $R^2$ is
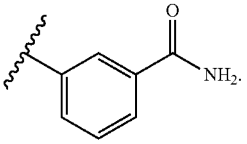 [SMILES: *c1cccc(C(N)=O)c1]
In some embodiments, $R^2$ is
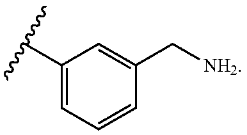 [SMILES: *c1cccc(CN)c1]
In some embodiments, $R^2$ is
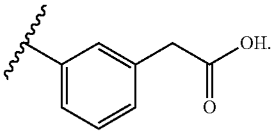 [SMILES: *c1cccc(CC(=O)O)c1]
In some embodiments, $R^2$ is
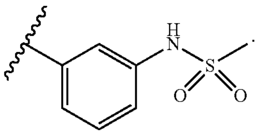 [SMILES: *c1cccc(NS(C)(=O)=O)c1]
In some embodiments, $R^2$ is
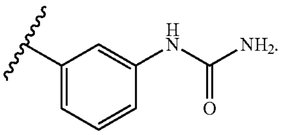 [SMILES: *c1cccc(NC(N)=O)c1]
In some embodiments, $R^2$ is
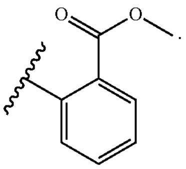 [SMILES: *c1ccccc1C(=O)OC]
In some embodiments, $R^2$ is
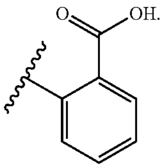 [SMILES: *c1ccccc1C(=O)O]

In some embodiments, $R^2$ is
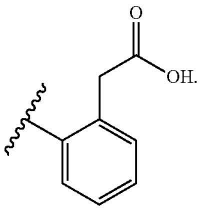 [SMILES: *c1ccccc1CC(=O)O]
In some embodiments, $R^2$ is
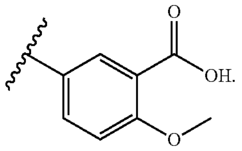 [SMILES: *c1ccc(OC)c(C(=O)O)c1]
In some embodiments, $R^2$ is
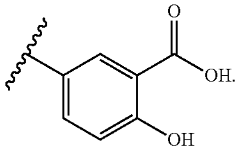 [SMILES: *c1ccc(O)c(C(=O)O)c1]
In some embodiments, $R^2$ is
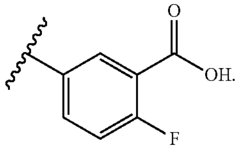 [SMILES: *c1ccc(F)c(C(=O)O)c1]
In some embodiments, $R^2$ is
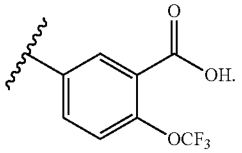 [SMILES: *c1ccc(OC(F)(F)F)c(C(=O)O)c1]
In some embodiments, $R^2$ is
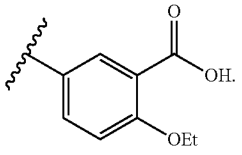 [SMILES: *c1ccc(OCC)c(C(=O)O)c1]
In some embodiments, $R^2$ is
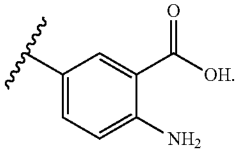 [SMILES: *c1ccc(N)c(C(=O)O)c1]
In some embodiments, $R^2$ is
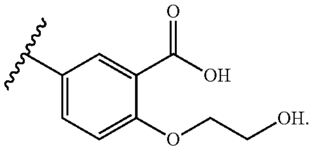 [SMILES: *c1ccc(OCCO)c(C(=O)O)c1]
In some embodiments, $R^2$ is
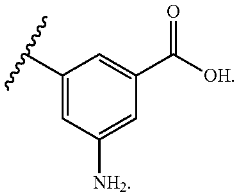 [SMILES: *c1cc(N)cc(C(=O)O)c1]
In some embodiments, $R^2$ is
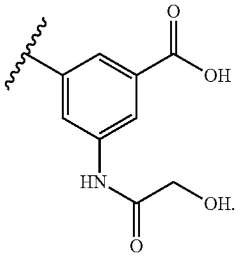 [SMILES: *c1cc(NC(=O)CO)cc(C(=O)O)c1]
In some embodiments, $R^2$ is
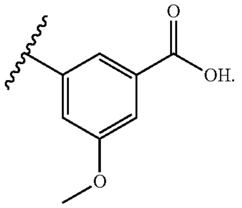 [SMILES: *c1cc(OC)cc(C(=O)O)c1]

In some embodiments, $R^2$ is
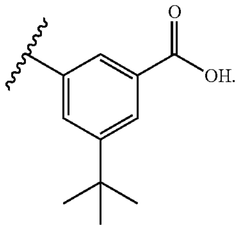 [SMILES: *c1cc(C(=O)O)cc(C(C)(C)C)c1]
In some embodiments, $R^2$ is
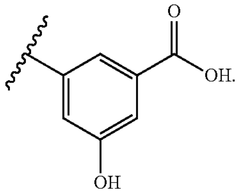 [SMILES: *c1cc(O)cc(C(=O)O)c1]
In some embodiments, $R^2$ is
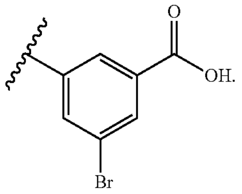 [SMILES: *c1cc(Br)cc(C(=O)O)c1]
In some embodiments, $R^2$ is
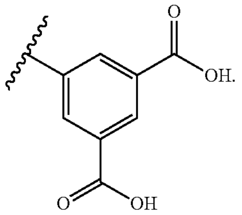 [SMILES: *c1cc(C(=O)O)cc(C(=O)O)c1]
In some embodiments, $R^2$ is
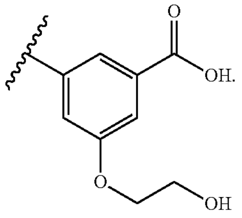 [SMILES: *c1cc(OCCO)cc(C(=O)O)c1]
In some embodiments, $R^2$ is
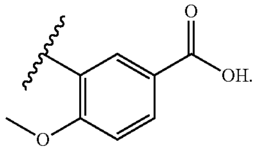 [SMILES: *c1cc(C(=O)O)ccc1OC]
In some embodiments, $R^2$ is
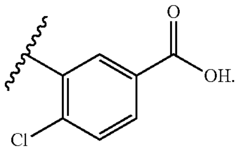 [SMILES: *c1cc(C(=O)O)ccc1Cl]
In some embodiments, $R^2$ is
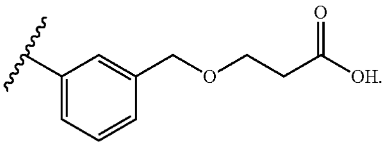 [SMILES: *c1cccc(COCCC(=O)O)c1]
In some embodiments, $R^2$ is
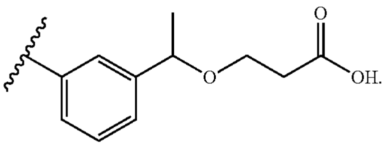 [SMILES: *c1cccc(C(C)OCCC(=O)O)c1]
In some embodiments, $R^2$ is
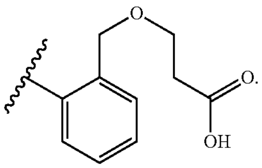 [SMILES: *c1ccccc1COCCC(=O)O]
In some embodiments, $R^2$ is
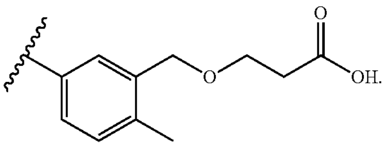 [SMILES: *c1ccc(C)c(COCCC(=O)O)c1]

In some embodiments, $R^2$ is
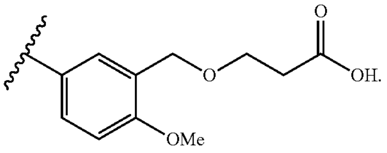 [SMILES: *c1ccc(OC)c(COCCC(=O)O)c1]
In some embodiments, $R^2$ is
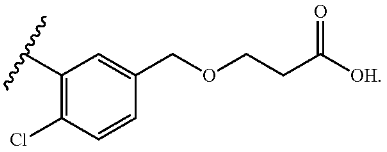 [SMILES: *c1cc(COCCC(=O)O)ccc1Cl]
In some embodiments, $R^2$ is
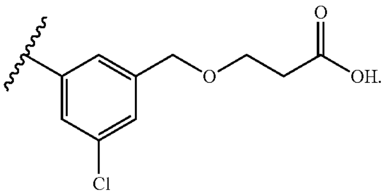 [SMILES: *c1cc(Cl)cc(COCCC(=O)O)c1]
In some embodiments, $R^2$ is
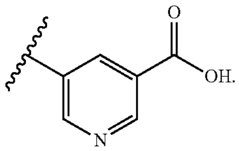 [SMILES: *c1cncc(C(=O)O)c1]
In some embodiments, $R^2$ is
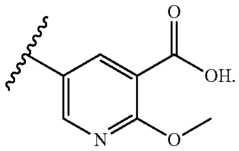 [SMILES: *c1cnc(OC)c(C(=O)O)c1]
In some embodiments, $R^2$ is
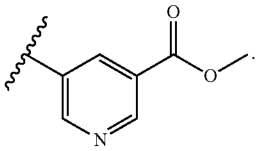 [SMILES: *c1cncc(C(=O)OC)c1]
In some embodiments, $R^2$ is
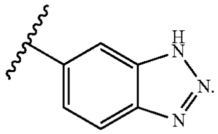 [SMILES: *c1ccc2nn[nH]c2c1]
In some embodiments, $R^2$ is
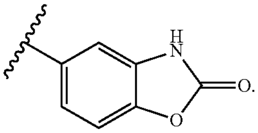 [SMILES: *c1ccc2oc(=O)[nH]c2c1]
In some embodiments, $R^2$ is
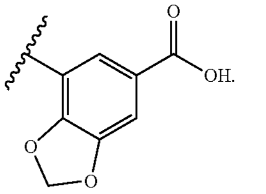 [SMILES: *c1cc(C(=O)O)cc2c1OCO2]
In some embodiments, $R^2$ is
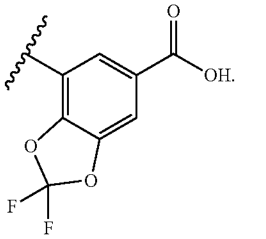 [SMILES: *c1cc(C(=O)O)cc2c1OC(F)(F)O2]
In some embodiments, $R^2$ is
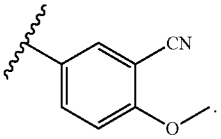 [SMILES: *c1ccc(OC)c(C#N)c1]
In some embodiments, $R^2$ is
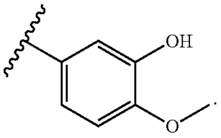 [SMILES: *c1ccc(OC)c(O)c1]

In some embodiments, $R^2$ is
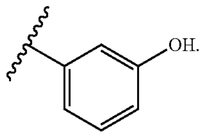 [SMILES: *c1cccc(O)c1]
In some embodiments, $R^2$ is
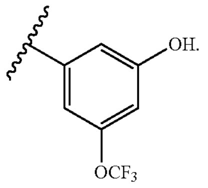 [SMILES: *c1cc(O)cc(OC(F)(F)F)c1]
In some embodiments, $R^2$ is
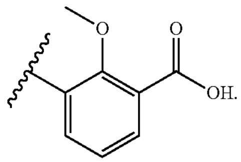 [SMILES: *c1cccc(C(=O)O)c1OC]
In some embodiments, $R^2$ is
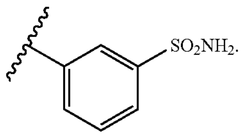 [SMILES: *c1cccc(S(N)(=O)=O)c1]
In some embodiments, $R^2$ is
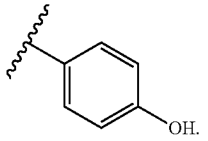 [SMILES: *c1ccc(O)cc1]
In some embodiments, $R^2$ is
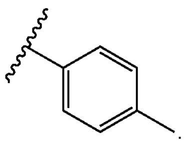 [SMILES: *c1ccc(C)cc1]
In some embodiments, $R^2$ is
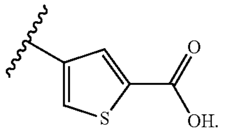 [SMILES: *c1csc(C(=O)O)c1]
In some embodiments, $R^2$ is
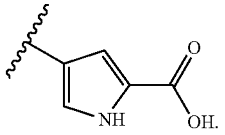 [SMILES: *c1c[nH]c(C(=O)O)c1]
In some embodiments, $R^2$ is
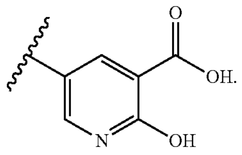 [SMILES: *c1cnc(O)c(C(=O)O)c1]
In some embodiments, $R^2$ is
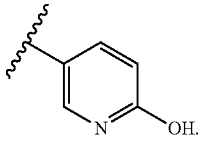 [SMILES: *c1ccc(O)nc1]
In some embodiments, $R^2$ is
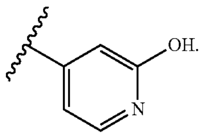 [SMILES: *c1ccnc(O)c1]
In some embodiments, $R^2$ is
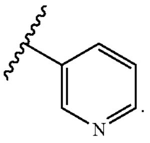
In some embodiments, $R^2$ is
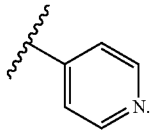 [SMILES: *c1ccncc1]

In some embodiments, $R^2$ is
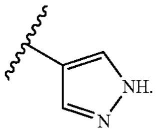 [SMILES: *c1cn[nH]c1]
In some embodiments, $R^2$ is
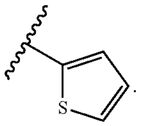 [SMILES: *c1cccs1]
In some embodiments, $R^2$ is
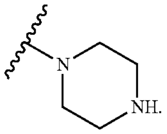 [SMILES: *N1CCNCC1]
In some embodiments, $R^2$ is
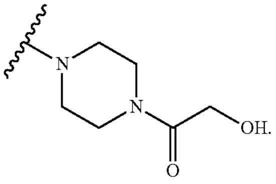 [SMILES: *N1CCN(C(=O)CO)CC1]
In some embodiments, $R^2$ is
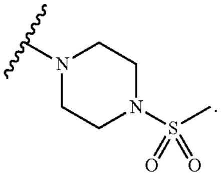 [SMILES: *N1CCN(S(C)(=O)=O)CC1]
In some embodiments, $R^2$ is
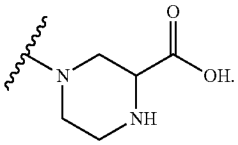 [SMILES: *N1CCNC(C(=O)O)C1]
In some embodiments, $R^2$ is
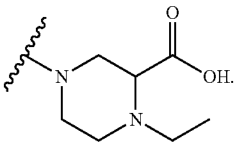 [SMILES: *N1CCN(CC)C(C(=O)O)C1]
In some embodiments, $R^2$ is
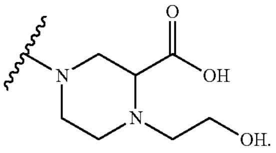 [SMILES: *N1CCN(CCO)C(C(=O)O)C1]
In some embodiments, $R^2$ is
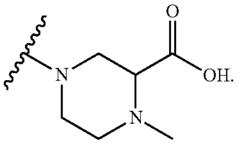 [SMILES: *N1CCN(C)C(C(=O)O)C1]
In some embodiments, $R^2$ is
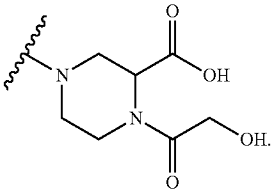 [SMILES: *N1CCN(C(=O)CO)C(C(=O)O)C1]
In some embodiments, $R^2$ is
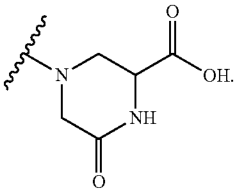 [SMILES: *N1CC(=O)NC(C(=O)O)C1]
In some embodiments, $R^2$ is
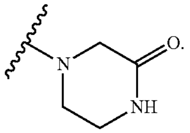 [SMILES: *N1CCNC(=O)C1]

In some embodiments, $R^2$ is
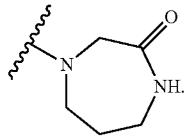 [SMILES: *N1CCCNC(=O)C1]
In some embodiments, $R^2$ is
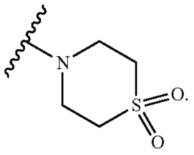 [SMILES: *N1CCS(=O)(=O)CC1]
In some embodiments, $R^2$ is
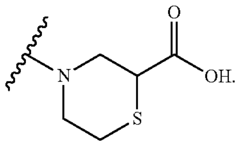 [SMILES: *N1CCSC(C(=O)O)C1]
In some embodiments, $R^2$ is
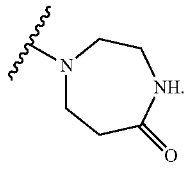 [SMILES: *N1CCNC(=O)CC1]
In some embodiments, $R^2$ is
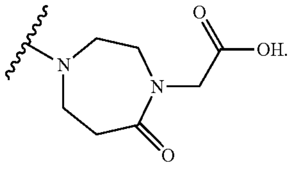 [SMILES: *N1CCC(=O)N(CC(=O)O)CC1]
In some embodiments, $R^2$ is
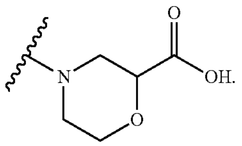 [SMILES: *N1CCOC(C(=O)O)C1]
In some embodiments, $R^2$ is
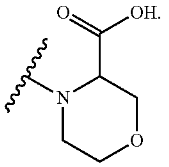 [SMILES: *N1CCOCC1C(=O)O]
In some embodiments, $R^2$ is
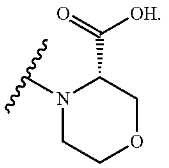
In some embodiments, $R^2$ is
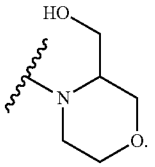 [SMILES: *N1CCOCC1CO]
In some embodiments, $R^2$ is
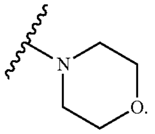 [SMILES: *N1CCOCC1]
In some embodiments, $R^2$ is
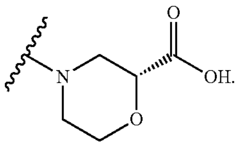 [SMILES: *N1CCO[C@@H](C(=O)O)C1]
In some embodiments, $R^2$ is
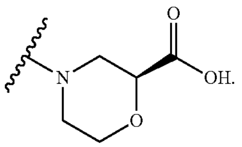 [SMILES: *N1CCO[C@H](C(=O)O)C1]

In some embodiments, $R^2$ is

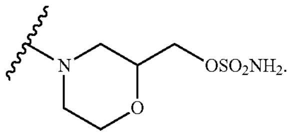

In some embodiments, $R^2$ is

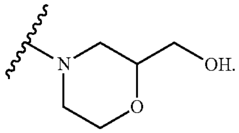 [SMILES: *N1CCOC(CO)C1]

In some embodiments, $R^2$ is

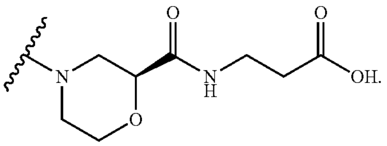 [SMILES: *N1CCO[C@H](C(=O)NCCC(=O)O)C1]

In some embodiments, $R^2$ is

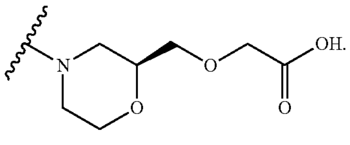 [SMILES: *N1CCO[C@H](COCC(=O)O)C1]

In some embodiments, $R^2$ is

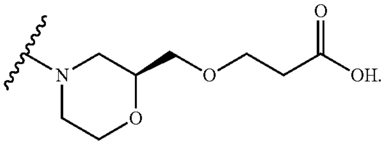

In some embodiments, $R^2$ is

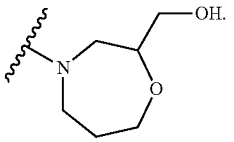 [SMILES: *N1CCCOC(CO)C1]

In some embodiments, $R^2$ is

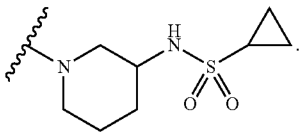 [SMILES: *N1CCCC(NS(=O)(=O)C2CC2)C1]

In some embodiments, $R^2$ is

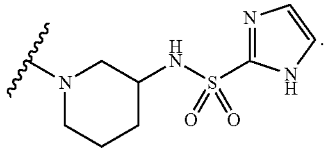 [SMILES: *N1CCCC(NS(=O)(=O)c2ncc[nH]2)C1]

In some embodiments, $R^2$ is

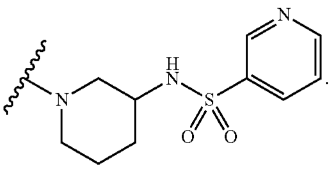 [SMILES: *N1CCCC(NS(=O)(=O)c2cccnc2)C1]

In some embodiments, $R^2$ is

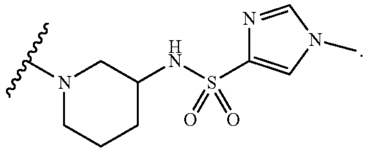 [SMILES: *N1CCCC(NS(=O)(=O)c2cn(C)cn2)C1]

In some embodiments, $R^2$ is

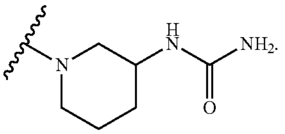 [SMILES: *N1CCCC(NC(N)=O)C1]

In some embodiments, $R^2$ is

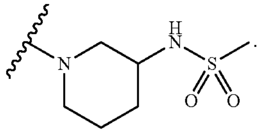 [SMILES: *N1CCCC(NS(C)(=O)=O)C1]

In some embodiments, $R^2$ is

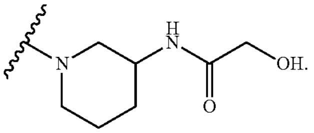 [SMILES: *N1CCCC(NC(=O)CO)C1]

In some embodiments, $R^2$ is

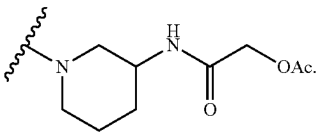 [SMILES: *N1CCCC(NC(=O)COC(C)=O)C1]

In some embodiments, $R^2$ is

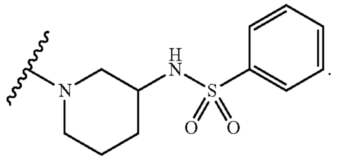 [SMILES: *N1CCCC(NS(=O)(=O)c2ccccc2)C1]

In some embodiments, $R^2$ is

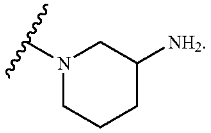 [SMILES: *N1CCCC(N)C1]

In some embodiments, $R^2$ is

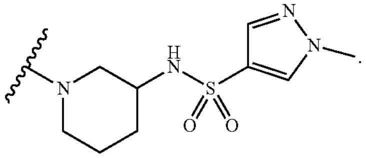 [SMILES: *N1CCCC(NS(=O)(=O)c2cnn(C)c2)C1]

In some embodiments, $R^2$ is

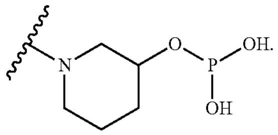 [SMILES: *N1CCCC(OP(O)O)C1]

Some embodiments, $R^2$ is

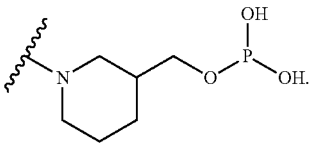 [SMILES: *N1CCCC(COP(O)O)C1]

In some embodiments, $R^2$ is

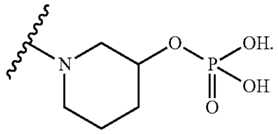 [SMILES: *N1CCCC(OP(=O)(O)O)C1]

In some embodiments, $R^2$ is

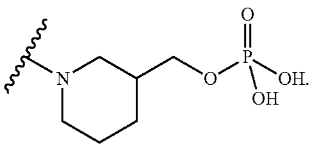 [SMILES: *N1CCCC(COP(=O)(O)O)C1]

In some embodiments, $R^2$ is

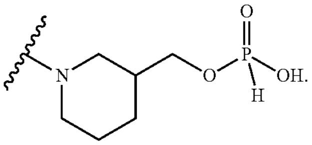 [SMILES: *N1CCCC(CO[PH](=O)O)C1]

In some embodiments, $R^2$ is

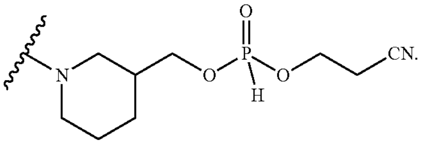 [SMILES: *N1CCCC(CO[PH](=O)OCCC#N)C1]

In some embodiments, $R^2$

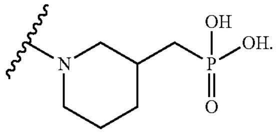 [SMILES: *N1CCCC(CP(=O)(O)O)C1]

In some embodiments, $R^2$ is

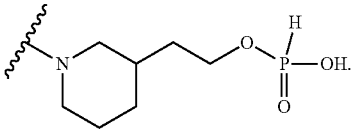 [SMILES: *N1CCCC(CCO[PH](=O)O)C1]

In some embodiments, $R^2$ is

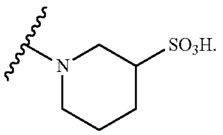 [SMILES: *N1CCCC(S(=O)(=O)O)C1]

In some embodiments, $R^2$ is

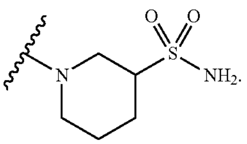 [SMILES: *N1CCCC(S(N)(=O)=O)C1]

In some embodiments, $R^2$ is

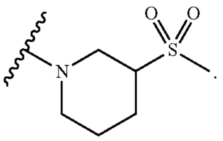 [SMILES: *N1CCCC(S(C)(=O)=O)C1]

In some embodiments, $R^2$ is
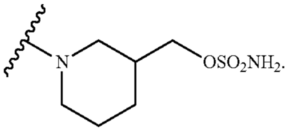
In some embodiments, $R^2$ is
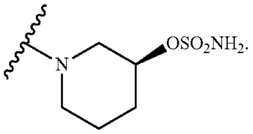
In some embodiments, $R^2$ is
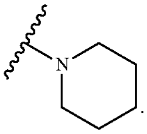
In some embodiments, $R^2$ is
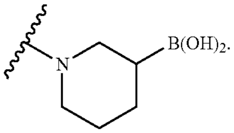 [SMILES: *N1CCCC(B(O)O)C1]
In some embodiments, $R^2$ is
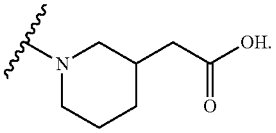 [SMILES: *N1CCCC(CC(=O)O)C1]
In some embodiments, $R^2$ is
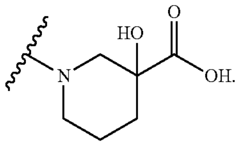 [SMILES: *N1CCCC(O)(C(=O)O)C1]
In some embodiments, $R^2$ is
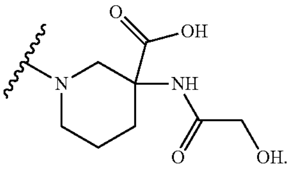 [SMILES: *N1CCCC(NC(=O)CO)(C(=O)O)C1]
In some embodiments, $R^2$ is
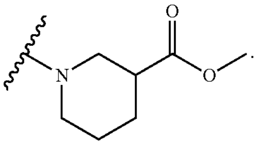 [SMILES: *N1CCCC(C(=O)OC)C1]
In some embodiments, $R^2$ is
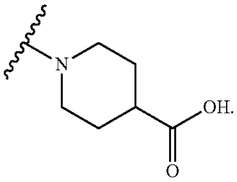 [SMILES: *N1CCC(C(=O)O)CC1]
In some embodiments, $R^2$ is
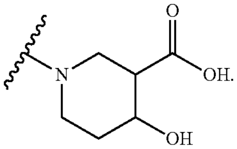 [SMILES: *N1CCC(O)C(C(=O)O)C1]
In some embodiments, $R^2$ is
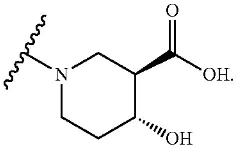 [SMILES: *N1CC[C@@H](O)[C@H](C(=O)O)C1]
In some embodiments, $R^2$ is
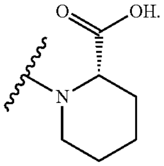 [SMILES: *N1CCCC[C@H]1C(=O)O]
In some embodiments, $R^2$ is
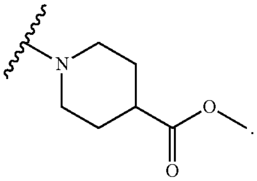 [SMILES: *N1CCC(C(=O)OC)CC1]

In some embodiments, $R^2$ is

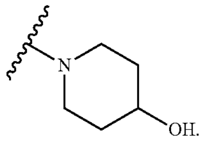 [SMILES: *N1CCC(O)CC1]

In some embodiments, $R^2$ is

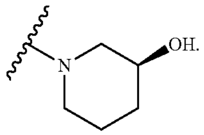 [SMILES: *N1CCC[C@H](O)C1]

In some embodiments, $R^2$ is

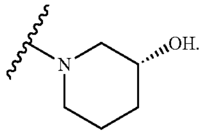 [SMILES: *N1CCC[C@@H](O)C1]

In some embodiments, $R^2$ is

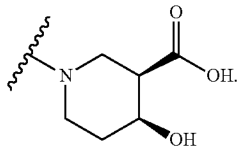 [SMILES: *N1CC[C@H](O)[C@H](C(=O)O)C1]

In some embodiments, $R^2$ is

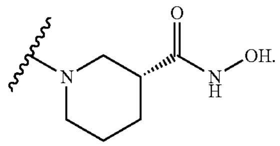 [SMILES: *N1CCC[C@@H](C(=O)NO)C1]

In some embodiments, $R^2$ is

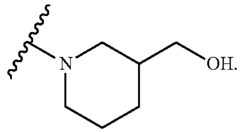 [SMILES: *N1CCCC(CO)C1]

In some embodiments, $R^2$ is

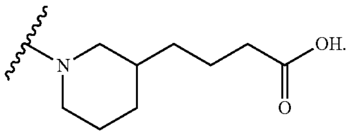 [SMILES: *N1CCCC(CCCC(=O)O)C1]

In some embodiments, $R^2$ is

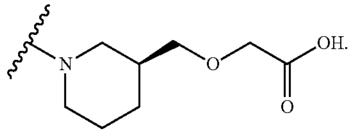 [SMILES: *N1CCC[C@H](COCC(=O)O)C1]

In some embodiments, $R^2$ is

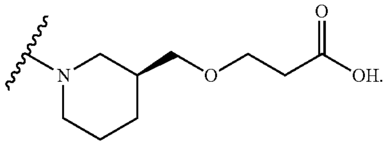 [SMILES: *N1CCC[C@H](COCCC(=O)O)C1]

In some embodiments, $R^2$ is

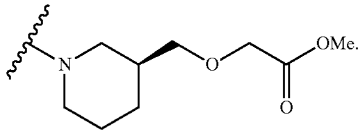 [SMILES: *N1CCC[C@H](COCC(=O)OC)C1]

In some embodiments, $R^2$ is

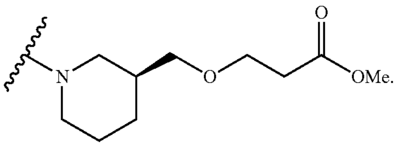 [SMILES: *N1CCC[C@H](COCCC(=O)OC)C1]

In some embodiments, $R^2$ is

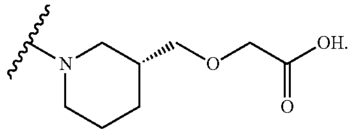 [SMILES: *N1CCC[C@@H](COCC(=O)O)C1]

In some embodiments, $R^2$ is

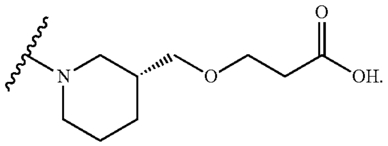 [SMILES: *N1CCC[C@@H](COCCC(=O)O)C1]

In some embodiments, $R^2$ is

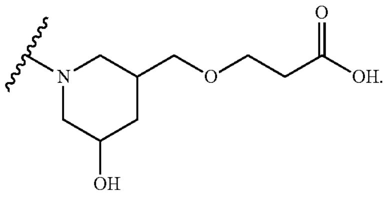 [SMILES: *N1CC(O)CC(COCCC(=O)O)C1]

In some embodiments, $R^2$ is
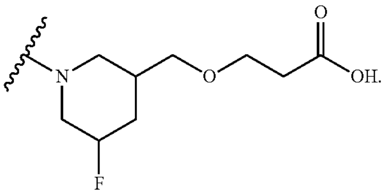 [SMILES: *N1CC(F)CC(COCCC(=O)O)C1]
In some embodiments, $R^2$ is
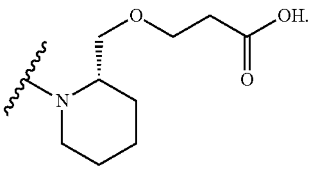 [SMILES: *N1CCCC[C@H]1COCCC(=O)O]
In some embodiments, $R^2$ is
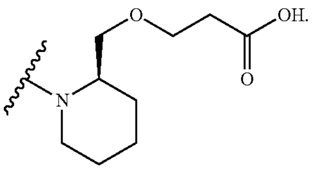 [SMILES: *N1CCCC[C@@H]1COCCC(=O)O]
In some embodiments, $R^2$ is
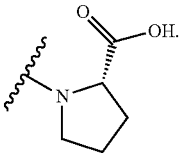 [SMILES: *N1CCC[C@H]1C(=O)O]
In some embodiments, $R^2$ is
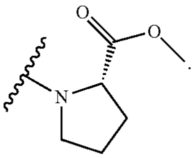 [SMILES: *N1CCC[C@H]1C(=O)OC]
In some embodiments, $R^2$ is
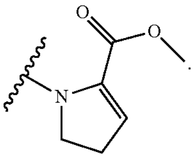 [SMILES: *N1CCC=C1C(=O)OC]
In some embodiments, $R^2$ is
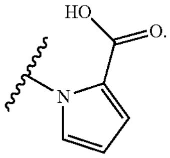 [SMILES: *n1cccc1C(=O)O]
In some embodiments, $R^2$ is is
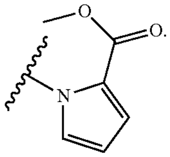 [SMILES: *n1cccc1C(=O)OC]
In some embodiments, $R^2$ is
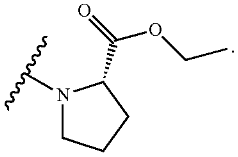 [SMILES: *N1CCC[C@H]1C(=O)OCC]
In some embodiments, $R^2$ is
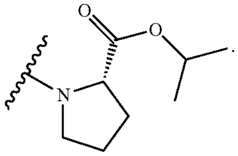 [SMILES: *N1CCC[C@H]1C(=O)OC(C)C]
In some embodiments, $R^2$ is
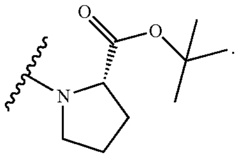 [SMILES: *N1CCC[C@H]1C(=O)OC(C)(C)C]
In some embodiments, $R^2$ is
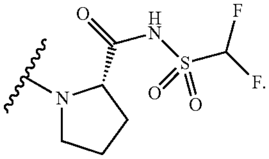 [SMILES: *N1CCC[C@H]1C(=O)NS(=O)(=O)C(F)F]

In some embodiments, $R^2$ is
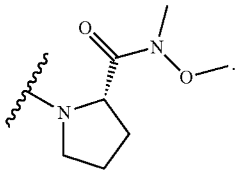 [SMILES: *N1CCC[C@H]1C(=O)N(C)OC]
In some embodiments, $R^2$ is
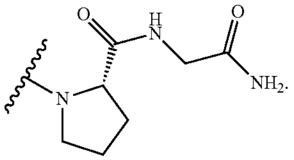 [SMILES: *N1CCC[C@H]1C(=O)NCC(N)=O]
In some embodiments, $R^2$ is
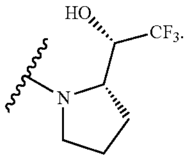 [SMILES: *N1CCC[C@H]1[C@H](O)C(F)(F)F]
In some embodiments, $R^2$ is
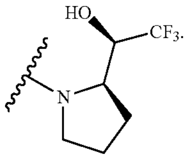 [SMILES: *N1CCC[C@@H]1[C@@H](O)C(F)(F)F]
In some embodiments, $R^2$ is
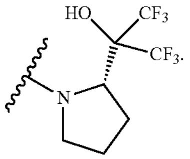 [SMILES: *N1CCC[C@H]1C(O)(C(F)(F)F)C(F)(F)F]
In some embodiments, $R^2$ is
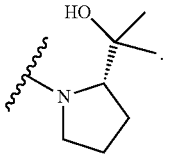 [SMILES: *N1CCC[C@H]1C(C)(C)O]
In some embodiments, $R^2$ is
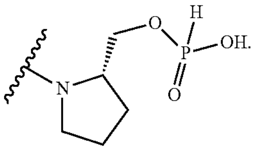 [SMILES: *N1CCC[C@H]1CO[PH](=O)O]
In some embodiments, $R^2$ is
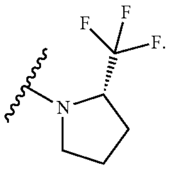 [SMILES: *N1CCC[C@H]1C(F)(F)F]
In some embodiments, $R^2$ is
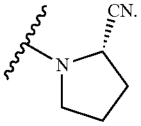 [SMILES: *N1CCC[C@H]1C#N]
In some embodiments, $R^2$ is
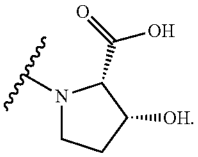 [SMILES: *N1CC[C@@H](O)[C@H]1C(=O)O]
In some embodiments, $R^2$ is
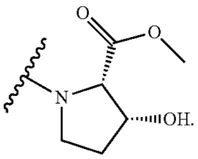 [SMILES: *N1CC[C@@H](O)[C@H]1C(=O)OC]
In some embodiments, $R^2$ is
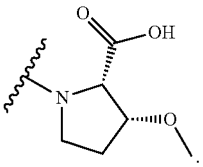 [SMILES: *N1CC[C@@H](OC)[C@H]1C(=O)O]

In some embodiments, $R^2$ is
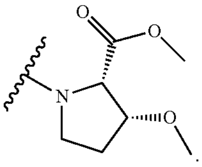 [SMILES: *N1CC[C@@H](OC)[C@H]1C(=O)OC]
In some embodiments, $R^2$ is
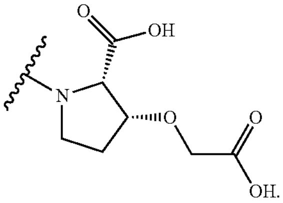 [SMILES: *N1CC[C@@H](OCC(=O)O)[C@H]1C(=O)O]
In some embodiments, $R^2$ is
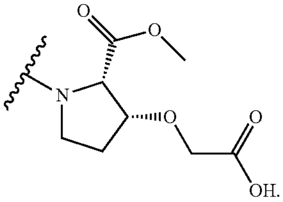 [SMILES: *N1CC[C@@H](OCC(=O)O)[C@H]1C(=O)OC]
In some embodiments, $R^2$ is
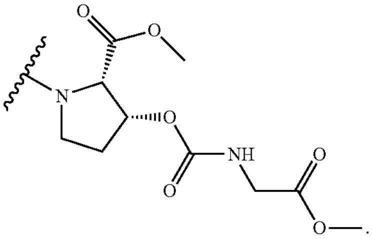 [SMILES: *N1CC[C@@H](OC(=O)NCC(=O)OC)[C@H]1C(=O)OC]
In some embodiments, $R^2$ is
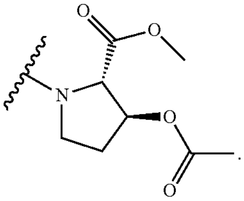 [SMILES: *N1CC[C@H](OC(C)=O)[C@H]1C(=O)OC]
In some embodiments, $R^2$ is
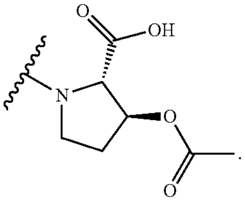 [SMILES: *N1CC[C@H](OC(C)=O)[C@H]1C(=O)O]
In some embodiments, $R^2$ is
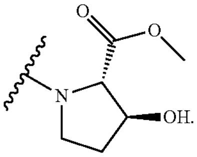 [SMILES: *N1CC[C@H](O)[C@H]1C(=O)OC]
In some embodiments, $R^2$ is
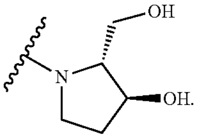 [SMILES: *N1CC[C@H](O)[C@H]1CO]
In some embodiments, $R^2$ is
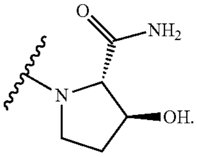 [SMILES: *N1CC[C@H](O)[C@H]1C(N)=O]
In some embodiments, $R^2$ is
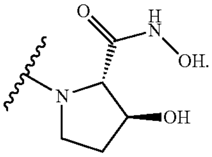 [SMILES: *N1CC[C@H](O)[C@H]1C(=O)NO]
In some embodiments, $R^2$ is
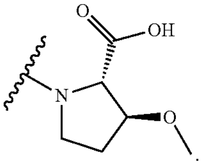 [SMILES: *N1CC[C@H](OC)[C@H]1C(=O)O]

In some embodiments, $R^2$ is
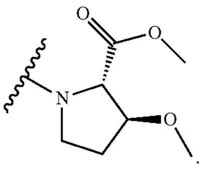 [SMILES: *N1CC[C@H](OC)[C@H]1C(=O)OC]
In some embodiments, $R^2$ is
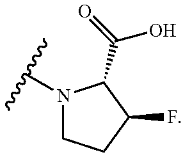 [SMILES: *N1CC[C@H](F)[C@H]1C(=O)O]
In some embodiments, $R^2$ is
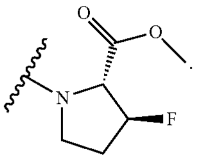 [SMILES: *N1CC[C@H](F)[C@H]1C(=O)OC]
In some embodiments, $R^2$ is
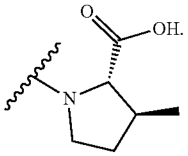 [SMILES: *N1CC[C@H](C)[C@H]1C(=O)O]
In some embodiments, $R^2$ is
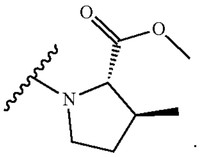 [SMILES: *N1CC[C@H](C)[C@H]1C(=O)OC]
In some embodiments, $R^2$ is
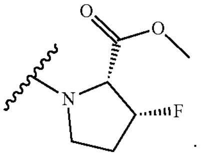 [SMILES: *N1CC[C@@H](F)[C@H]1C(=O)OC]
In some embodiments, $R^2$ is
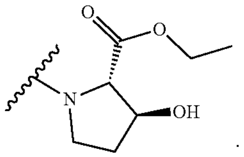 [SMILES: *N1CC[C@H](O)[C@H]1C(=O)OCC]
In some embodiments, $R^2$ is
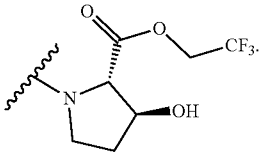 [SMILES: *N1CC[C@H](O)[C@H]1C(=O)OCC(F)(F)F]
In some embodiments, $R^2$ is
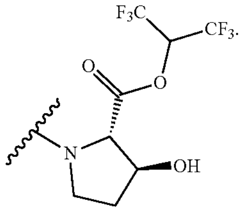 [SMILES: *N1CC[C@H](O)[C@H]1C(=O)OC(C(F)(F)F)C(F)(F)F]
In some embodiments, $R^2$ is
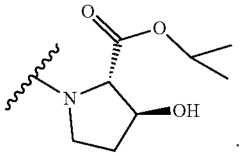 [SMILES: *N1CC[C@H](O)[C@H]1C(=O)OC(C)C]
In some embodiments, $R^2$ is
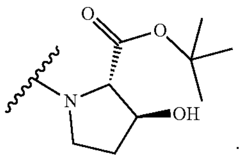 [SMILES: *N1CC[C@H](O)[C@H]1C(=O)OC(C)(C)C]
In some embodiments, $R^2$ is
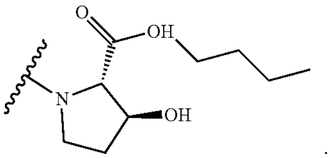 [SMILES: *N1CC[C@H](O)[C@H]1C(=O)OCCCC]

In some embodiments, $R^2$ is
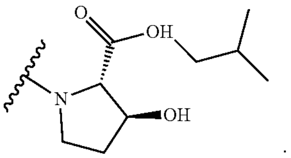 [SMILES: *N1CC[C@H](O)[C@H]1C(=O)OCC(C)C]
In some embodiments, $R^2$ is
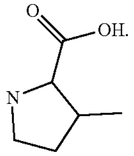
In some embodiments, $R^2$ is
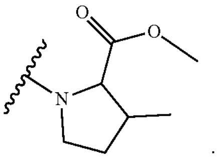 [SMILES: *N1CCC(C)C1C(=O)OC]
In some embodiments, $R^2$ is
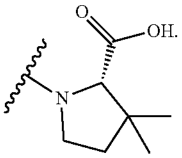 [SMILES: *N1CCC(C)(C)[C@H]1C(=O)O]
In some embodiments, $R^2$ is
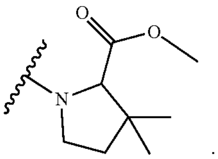 [SMILES: *N1CCC(C)(C)C1C(=O)OC]
In some embodiments, $R^2$ is
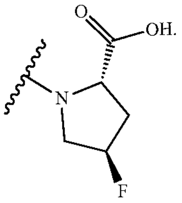 [SMILES: *N1C[C@H](F)C[C@H]1C(=O)O]
In some embodiments, $R^2$ is
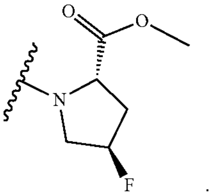 [SMILES: *N1C[C@H](F)C[C@H]1C(=O)OC]
In some embodiments, $R^2$ is
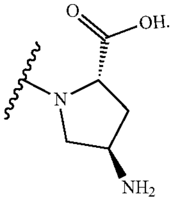 [SMILES: *N1C[C@H](N)C[C@H]1C(=O)O]
In some embodiments, $R^2$ is
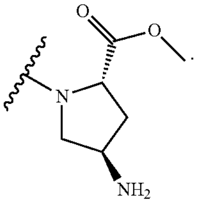 [SMILES: *N1C[C@H](N)C[C@H]1C(=O)OC]
In some embodiments, $R^2$ is
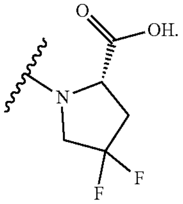 [SMILES: *N1CC(F)(F)C[C@H]1C(=O)O]
In some embodiments, $R^2$ is
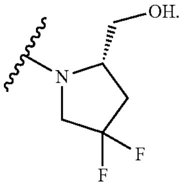 [SMILES: *N1CC(F)(F)C[C@H]1CO]

In some embodiments, $R^2$ is
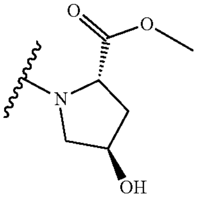
.
In some embodiments, $R^2$ is
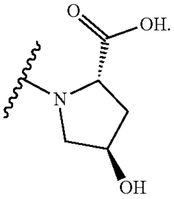 [SMILES: *N1C[C@H](O)C[C@H]1C(=O)O]
In some embodiments, $R^2$ is
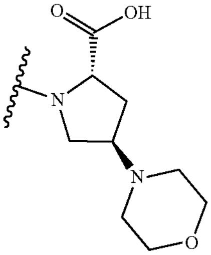
.
In some embodiments, $R^2$ is
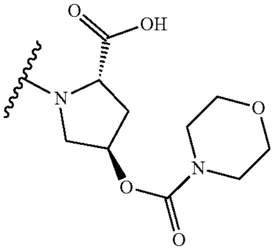
.
In some embodiments, $R^2$ is
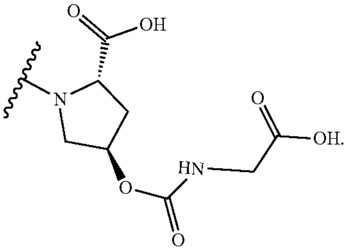 [SMILES: *N1C[C@H](OC(=O)NCC(=O)O)C[C@H]1C(=O)O]
In some embodiments, $R^2$ is
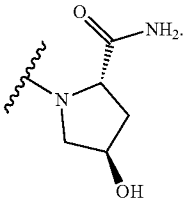 [SMILES: *N1C[C@H](O)C[C@H]1C(N)=O]
In some embodiments, $R^2$ is
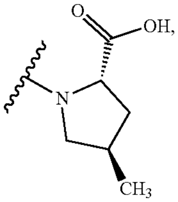 [SMILES: *N1C[C@H](C)C[C@H]1C(=O)O]
In some embodiments, $R^2$ is
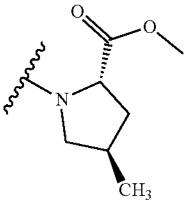
.
In some embodiments, $R^2$ is
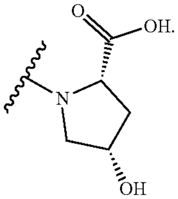 [SMILES: *N1C[C@@H](O)C[C@H]1C(=O)O]
In some embodiments, $R^2$ is
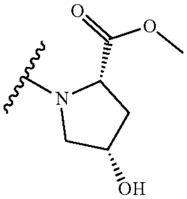
.

In some embodiments, $R^2$ is
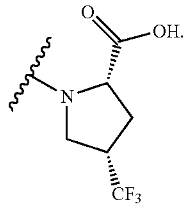 [SMILES: *N1C[C@@H](C(F)(F)F)C[C@H]1C(=O)O]
In some embodiments, $R^2$ is
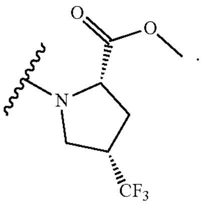 [SMILES: *N1C[C@@H](C(F)(F)F)C[C@H]1C(=O)OC]
In some embodiments, $R^2$ is
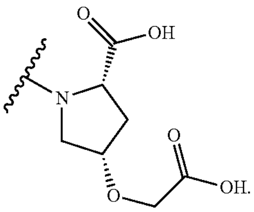 [SMILES: *N1C[C@@H](OCC(=O)O)C[C@H]1C(=O)O]
In some embodiments, $R^2$ is
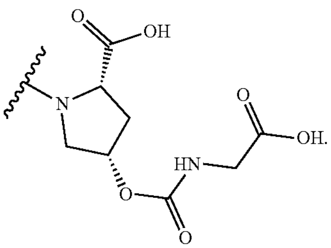 [SMILES: *N1C[C@@H](OC(=O)NCC(=O)O)C[C@H]1C(=O)O]
In some embodiments, $R^2$ is
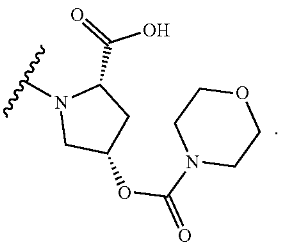 [SMILES: *N1C[C@@H](OC(=O)N2CCOCC2)C[C@H]1C(=O)O]
In some embodiments, $R^2$ is
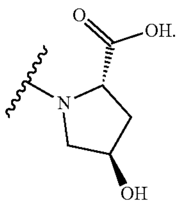 [SMILES: *N1C[C@H](O)C[C@H]1C(=O)O]
In some embodiments, $R^2$ is
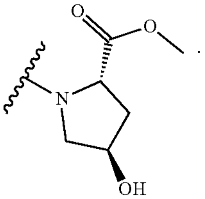 [SMILES: *N1C[C@H](O)C[C@H]1C(=O)OC]
In some embodiments, $R^2$ is
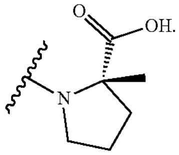 [SMILES: *N1CCC[C@@]1(C)C(=O)O]
In some embodiments, $R^2$ is
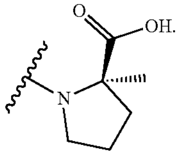 [SMILES: *N1CCC[C@]1(C)C(=O)O]
In some embodiments, $R^2$ is
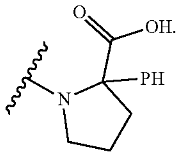
In some embodiments, $R^2$ is
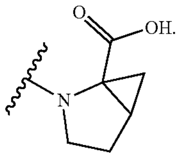 [SMILES: *N1CCC2CC21C(=O)O]

In some embodiments, $R^2$ is
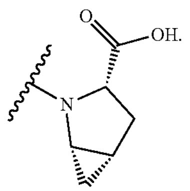 [SMILES: *N1[C@H](C(=O)O)C[C@@H]2C[C@@H]21]
In some embodiments, $R^2$ is
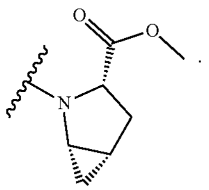 [SMILES: *N1[C@H](C(=O)OC)C[C@@H]2C[C@@H]21]
In some embodiments, $R^2$ is
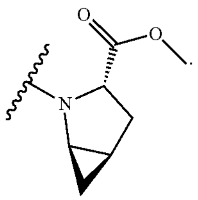 [SMILES: *N1[C@@H]2C[C@@H]2C[C@H]1C(=O)OC]
In some embodiments, $R^2$.
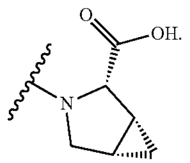 [SMILES: *N1C[C@H]2C[C@H]2[C@H]1C(=O)O]
In some embodiments, $R^2$ is
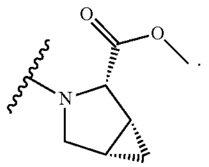 [SMILES: *N1C[C@H]2C[C@H]2[C@H]1C(=O)OC]
In some embodiments, $R^2$ is
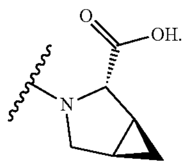 [SMILES: *N1C[C@@H]2C[C@@H]2[C@H]1C(=O)O]
In some embodiments, $R^2$ is
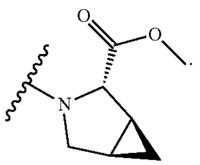 [SMILES: *N1C[C@@H]2C[C@@H]2[C@H]1C(=O)OC]
In some embodiments, $R^2$ is
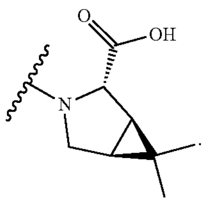 [SMILES: *N1C[C@H]2[C@@H]([C@H]1C(=O)O)C2(C)C]
In some embodiments, $R^2$ is
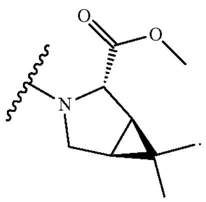 [SMILES: *N1C[C@H]2[C@@H]([C@H]1C(=O)OC)C2(C)C]
In some embodiments, $R^2$ is
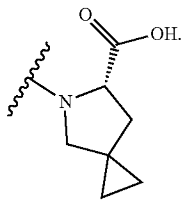 [SMILES: *N1CC2(CC2)C[C@H]1C(=O)O]
In some embodiments, $R^2$ is
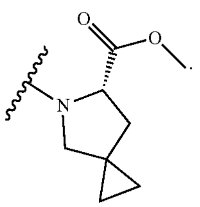 [SMILES: *N1CC2(CC2)C[C@H]1C(=O)OC]

In some embodiments, $R^2$ is
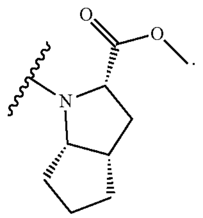 [SMILES: *N1[C@H](C(=O)OC)C[C@@H]2CCC[C@@H]21]
In some embodiments, $R^2$ is
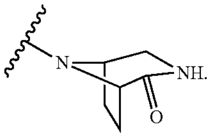 [SMILES: *N1C2CCC1C(=O)NC2]
In some embodiments, $R^2$ is
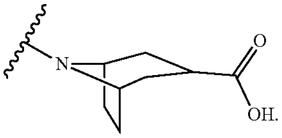 [SMILES: *N1C2CCC1CC(C(=O)O)C2]
In some embodiments, $R^2$ is
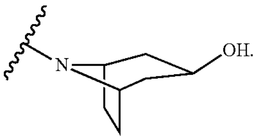 [SMILES: *N1C2CCC1CC(O)C2]
In some embodiments, $R^2$ is
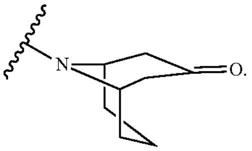 [SMILES: *N1C2CCCC1CC(=O)C2]
In some embodiments, $R^2$ is
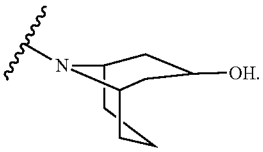 [SMILES: *N1C2CCCC1CC(O)C2]
In some embodiments, $R^2$ is
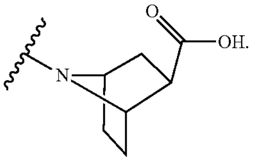 [SMILES: *N1C2CCC1C(C(=O)O)C2]
In some embodiments, $R^2$ is
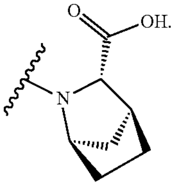 [SMILES: *N1[C@@H]2CC[C@@H](C2)[C@H]1C(=O)O]
In some embodiments, $R^2$ is
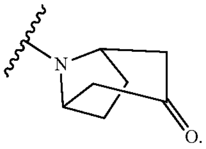 [SMILES: *N1C2CCC1CC(=O)C2]
In some embodiments, $R^2$ is
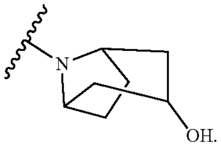 [SMILES: *N1C2CCC1CC(O)C2]
In some embodiments, $R^2$ is
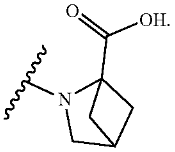 [SMILES: *N1CC2CC1(C(=O)O)C2]
In some embodiments, $R^2$ is
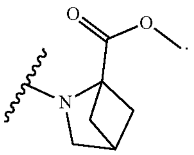 [SMILES: *N1CC2CC1(C(=O)OC)C2]

In some embodiments, $R^2$ is
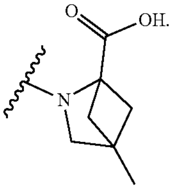 [SMILES: *N1CC2(C)CC1(C(=O)O)C2]
In some embodiments, $R^2$ is
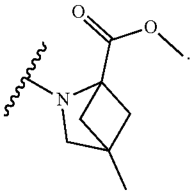 [SMILES: *N1CC2(C)CC1(C(=O)OC)C2]
In some embodiments, $R^2$ is
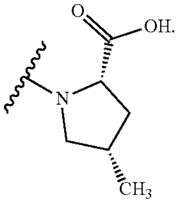 [SMILES: *N1C[C@@H](C)C[C@H]1C(=O)O]
In some embodiments, $R^2$ is
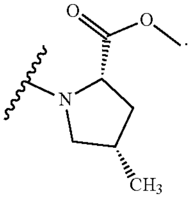
In some embodiments, $R^2$ is
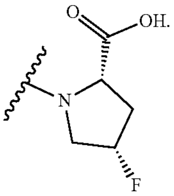 [SMILES: *N1C[C@@H](F)C[C@H]1C(=O)O]
In some embodiments, $R^2$ is
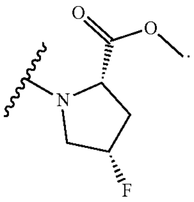 [SMILES: *N1C[C@@H](F)C[C@H]1C(=O)OC]
In some embodiments, $R^2$ is
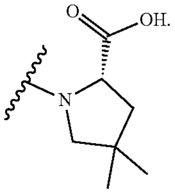 [SMILES: *N1CC(C)(C)C[C@H]1C(=O)O]
In some embodiments, $R^2$ is
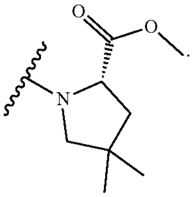 [SMILES: *N1CC(C)(C)C[C@H]1C(=O)OC]
In some embodiments, $R^2$ is
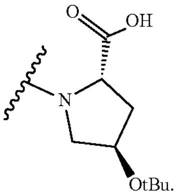 [SMILES: *N1C[C@H](OC(C)(C)C)C[C@H]1C(=O)O]
In some embodiments, $R^2$ is
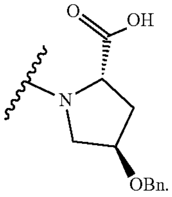 [SMILES: *N1C[C@H](OCc2ccccc2)C[C@H]1C(=O)O]
In some embodiments, $R^2$ is
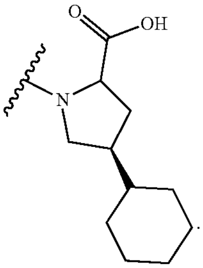 [SMILES: *N1C[C@H](C2CCCCC2)CC1C(=O)O]

In some embodiments, $R^2$
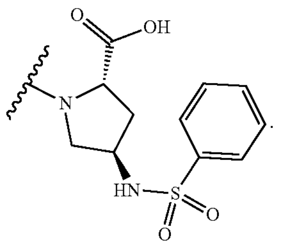 [SMILES: *N1C[C@H](NS(=O)(=O)c2ccccc2)C[C@H]1C(=O)O]
In some embodiments, $R^2$ is
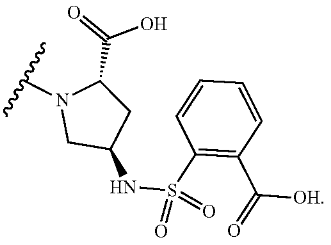 [SMILES: *N1C[C@H](NS(=O)(=O)c2ccccc2C(=O)O)C[C@H]1C(=O)O]
In some embodiments, $R^2$ is
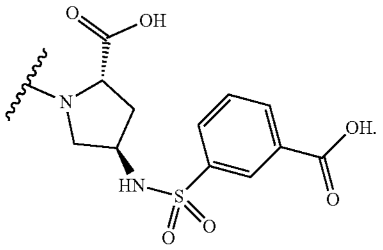 [SMILES: *N1C[C@H](NS(=O)(=O)c2cccc(C(=O)O)c2)C[C@H]1C(=O)O]
In some embodiments, $R^2$ is
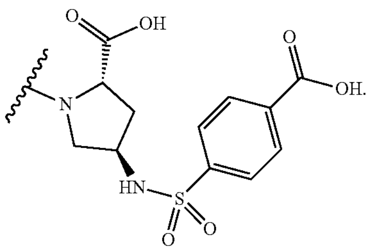 [SMILES: *N1C[C@H](NS(=O)(=O)c2ccc(C(=O)O)cc2)C[C@H]1C(=O)O]
In some embodiments, $R^2$ is
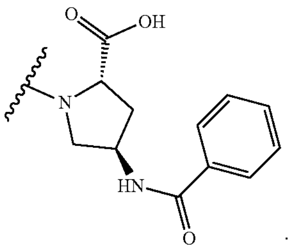 [SMILES: *N1C[C@H](NC(=O)c2ccccc2)C[C@H]1C(=O)O]
In some embodiments, $R^2$ is
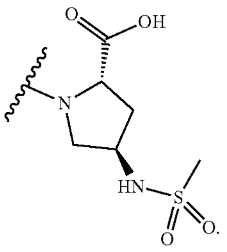 [SMILES: *N1C[C@H](NS(C)(=O)=O)C[C@H]1C(=O)O]
In some embodiments, $R^2$ is
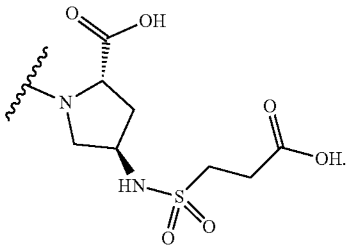 [SMILES: *N1C[C@H](NS(=O)(=O)CCC(=O)O)C[C@H]1C(=O)O]
In some embodiments, $R^2$ is
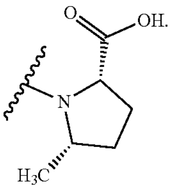 [SMILES: *N1[C@@H](C)CC[C@H]1C(=O)O]
In some embodiments, $R^2$ is
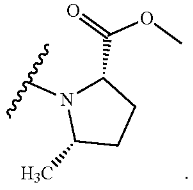 [SMILES: *N1[C@@H](C)CC[C@H]1C(=O)OC]
In some embodiments, $R^2$ is
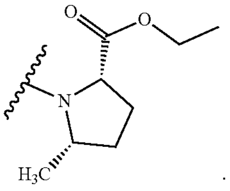 [SMILES: *N1[C@@H](C)CC[C@H]1C(=O)OCC]

In some embodiments, $R^2$ is
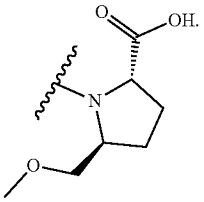 [SMILES: *N1[C@H](COC)CC[C@H]1C(=O)O]
In some embodiments, $R^2$ is
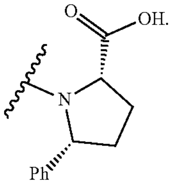 [SMILES: *N1[C@@H](c2ccccc2)CC[C@H]1C(=O)O]
In some embodiments, $R^2$ is
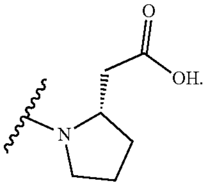 [SMILES: *N1CCC[C@H]1CC(=O)O]
In some embodiments, $R^2$ is
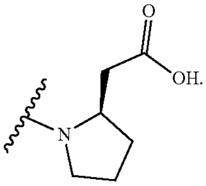 [SMILES: *N1CCC[C@@H]1CC(=O)O]
In some embodiments, $R^2$ is
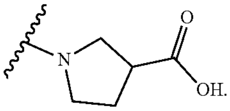 [SMILES: *N1CCC(C(=O)O)C1]
In some embodiments, $R^2$ is
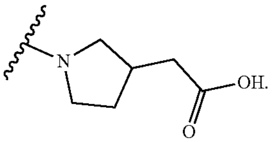 [SMILES: *N1CCC(CC(=O)O)C1]
In some embodiments, $R^2$ is
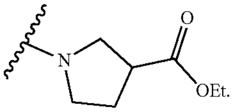 [SMILES: *N1CCC(C(=O)OCC)C1]
In some embodiments, $R^2$ is
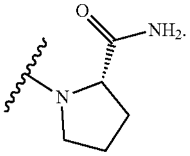 [SMILES: *N1CCC[C@H]1C(N)=O]
In some embodiments, $R^2$ is
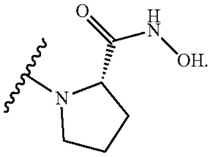 [SMILES: *N1CCC[C@H]1C(=O)NO]
In some embodiments, $R^2$ is
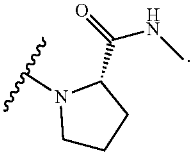 [SMILES: *N1CCC[C@H]1C(=O)NC]
In some embodiments, $R^2$ is
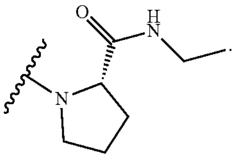 [SMILES: *N1CCC[C@H]1C(=O)NCC]
In some embodiments, $R^2$ is
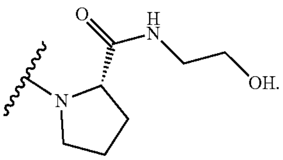 [SMILES: *N1CCC[C@H]1C(=O)NCCO]

In some embodiments, $R^2$ is
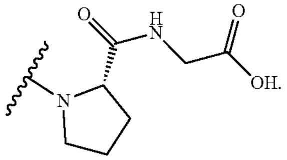 [SMILES: *N1CCC[C@H]1C(=O)NCC(=O)O]
In some embodiments, $R^2$ is
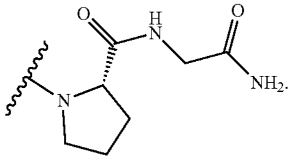 [SMILES: *N1CCC[C@H]1C(=O)NCC(N)=O]
In some embodiments, $R^2$ is
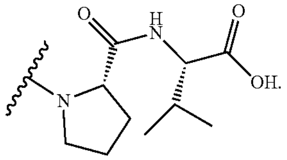 [SMILES: *N1CCC[C@H]1C(=O)N[C@H](C(=O)O)C(C)C]
In some embodiments, $R^2$ is
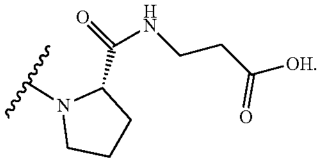 [SMILES: *N1CCC[C@H]1C(=O)NCCC(=O)O]
In some embodiments, $R^2$ is
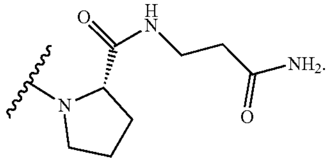 [SMILES: *N1CCC[C@H]1C(=O)NCCC(N)=O]
In some embodiments, $R^2$ is
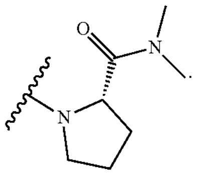 [SMILES: *N1CCC[C@H]1C(=O)N(C)C]
In some embodiments, $R^2$ is
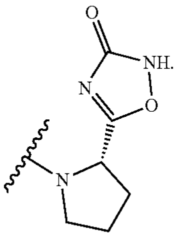 [SMILES: *N1CCC[C@H]1c1nc(=O)[nH]o1]
In some embodiments, $R^2$ is
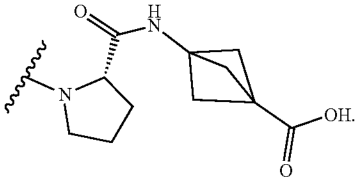 [SMILES: *N1CCC[C@H]1C(=O)NC12CC(C(=O)O)(C1)C2]
In some embodiments, $R^2$ is
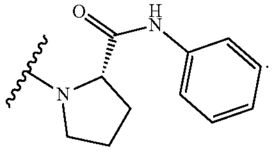 [SMILES: *N1CCC[C@H]1C(=O)Nc1ccccc1]
In some embodiments, $R^2$ is
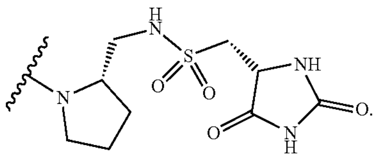
In some embodiments, $R^2$ is
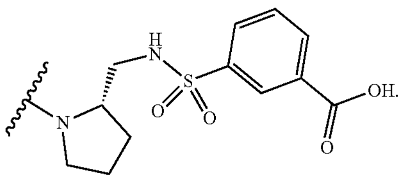 [SMILES: *N1CCC[C@H]1CNS(=O)(=O)c1cccc(C(=O)O)c1]
In some embodiments, $R^2$ is
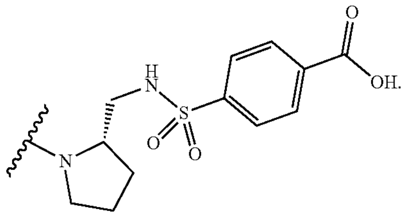 [SMILES: *N1CCC[C@H]1CNS(=O)(=O)c1ccc(C(=O)O)cc1]

In some embodiments, $R^2$ is
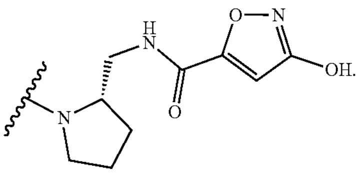 [SMILES: *N1CCC[C@H]1CNC(=O)c1cc(O)no1]
In some embodiments, $R^2$ is
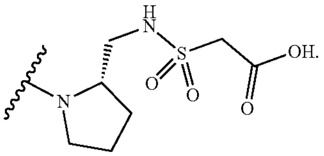 [SMILES: *N1CCC[C@H]1CNS(=O)(=O)CC(=O)O]
In some embodiments, $R^2$ is
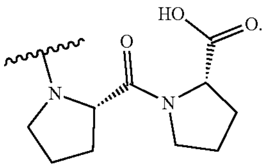 [SMILES: *N1CCC[C@H]1C(=O)N1CCC[C@H]1C(=O)O]
In some embodiments, $R^2$ is
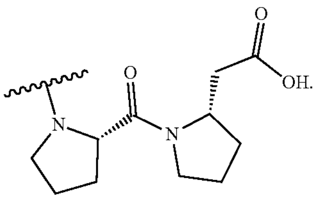 [SMILES: *N1CCC[C@H]1C(=O)N1CCC[C@H]1CC(=O)O]
In some embodiments, $R^2$ is
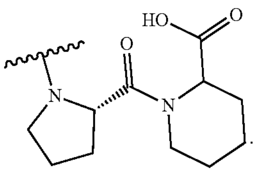 [SMILES: *N1CCC[C@H]1C(=O)N1CCCCC1C(=O)O]
In some embodiments, $R^2$ is
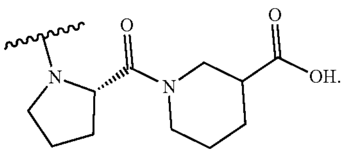 [SMILES: *N1CCC[C@H]1C(=O)N1CCCC(C(=O)O)C1]
In some embodiments, $R^2$ is
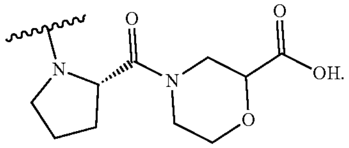 [SMILES: *N1CCC[C@H]1C(=O)N1CCOC(C(=O)O)C1]
In some embodiments, $R^2$ is
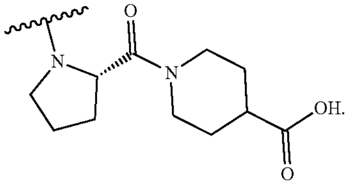 [SMILES: *N1CCC[C@H]1C(=O)N1CCC(C(=O)O)CC1]
In some embodiments, $R^2$ is
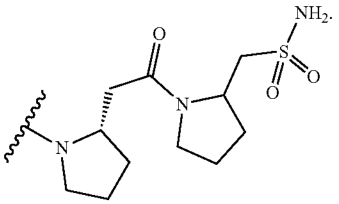 [SMILES: *N1CCC[C@H]1CC(=O)N1CCCC1CS(N)(=O)=O]
In some embodiments, $R^2$ is
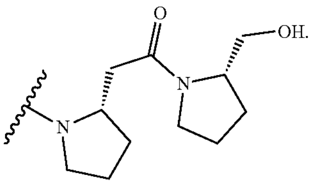 [SMILES: *N1CCC[C@H]1CC(=O)N1CCC[C@H]1CO]
In some embodiments, $R^2$ is
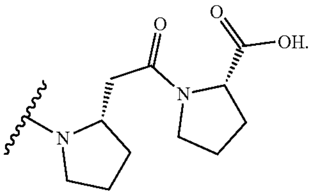 [SMILES: *N1CCC[C@H]1CC(=O)N1CCC[C@H]1C(=O)O]
In some embodiments, $R^2$ is
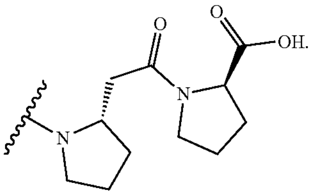 [SMILES: *N1CCC[C@H]1CC(=O)N1CCC[C@@H]1C(=O)O]

In some embodiments, $R^2$ is
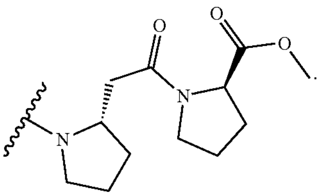 [SMILES: *N1CCC[C@H]1CC(=O)N1CCC[C@@H]1C(=O)OC]
In some embodiments, $R^2$ is
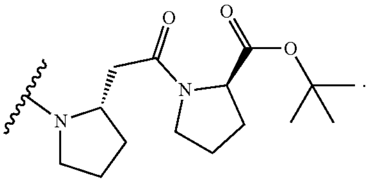 [SMILES: *N1CCC[C@H]1CC(=O)N1CCC[C@@H]1C(=O)OC(C)(C)C]
In some embodiments, $R^2$ is
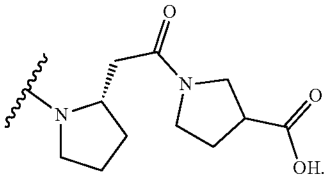 [SMILES: *N1CCC[C@H]1CC(=O)N1CCC(C(=O)O)C1]
In some embodiments, $R^2$ is
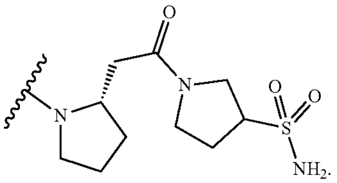 [SMILES: *N1CCC[C@H]1CC(=O)N1CCC(S(N)(=O)=O)C1]
In some embodiments, $R^2$ is
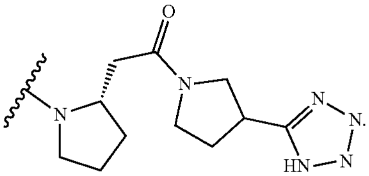
In some embodiments, $R^2$ is
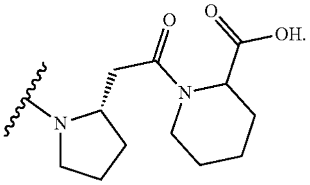 [SMILES: *N1CCC[C@H]1CC(=O)N1CCCCC1C(=O)O]
In some embodiments, $R^2$ is
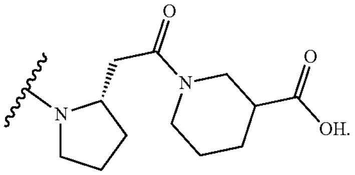 [SMILES: *N1CCC[C@H]1CC(=O)N1CCCC(C(=O)O)C1]
In some embodiments, $R^2$ is
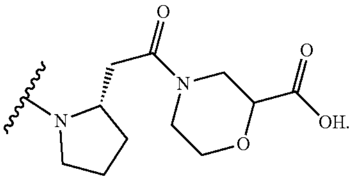 [SMILES: *N1CCC[C@H]1CC(=O)N1CCOC(C(=O)O)C1]
In some embodiments, $R^2$ is
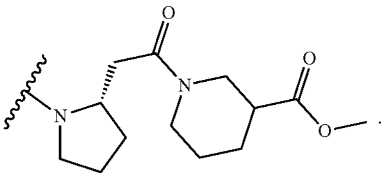 [SMILES: *N1CCC[C@H]1CC(=O)N1CCCC(C(=O)OC)C1]
In some embodiments, $R^2$ is
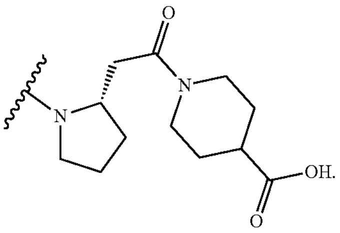 [SMILES: *N1CCC[C@H]1CC(=O)N1CCC(C(=O)O)CC1]
In some embodiments, $R^2$ is
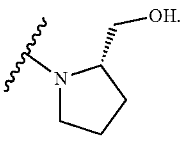 [SMILES: *N1CCC[C@H]1CO]
In some embodiments, $R^2$ is
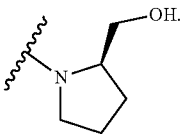 [SMILES: *N1CCC[C@@H]1CO]

In some embodiments, $R^2$ is
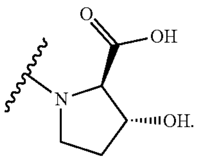 [SMILES: *N1CC[C@@H](O)[C@@H]1C(=O)O]
In some embodiments, $R^2$ is
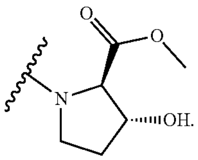 [SMILES: *N1CC[C@@H](O)[C@@H]1C(=O)OC]
In some embodiments, $R^2$ is
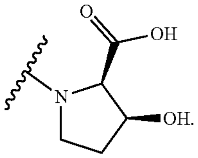 [SMILES: *N1CC[C@H](O)[C@@H]1C(=O)O]
In some embodiments, $R^2$ is
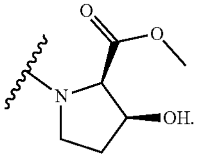 [SMILES: *N1CC[C@H](O)[C@@H]1C(=O)OC]
In some embodiments, $R^2$ is
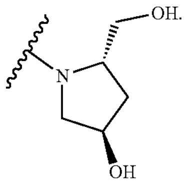 [SMILES: *N1C[C@H](O)C[C@H]1CO]
In some embodiments, $R^2$ is
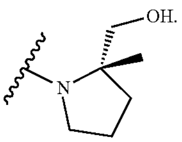 [SMILES: *N1CCC[C@@]1(C)CO]
In some embodiments, $R^2$ is
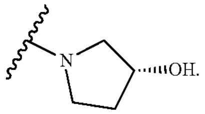 [SMILES: *N1CC[C@@H](O)C1]
In some embodiments, $R^2$ is
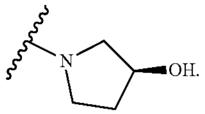 [SMILES: *N1CC[C@H](O)C1]
In some embodiments, $R^2$ is
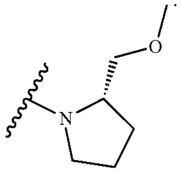 [SMILES: *N1CCC[C@H]1COC]
In some embodiments, $R^2$ is
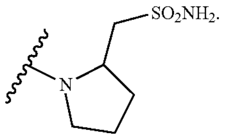 [SMILES: *N1CCCC1CS(N)(=O)=O]
In some embodiments, $R^2$ is
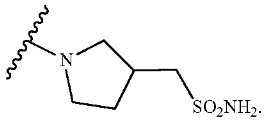 [SMILES: *N1CCC(CS(N)(=O)=O)C1]
In some embodiments, $R^2$ is
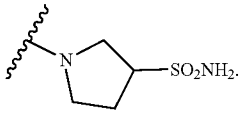 [SMILES: *N1CCC(S(N)(=O)=O)C1]
In some embodiments, $R^2$ is
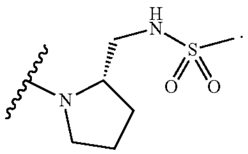 [SMILES: *N1CCC[C@H]1CNS(C)(=O)=O]

In some embodiments, $R^2$ is
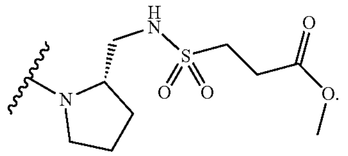 [SMILES: *N1CCC[C@H]1CNS(=O)(=O)CCC(=O)OC]
In some embodiments, $R^2$ is
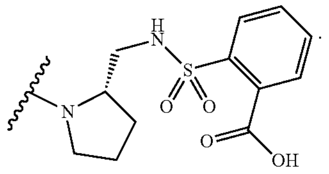 [SMILES: *N1CCC[C@H]1CNS(=O)(=O)c1ccccc1C(=O)O]
In some embodiments, $R^2$ is
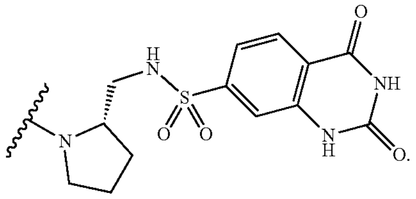 [SMILES: *N1CCC[C@H]1CNS(=O)(=O)c1ccc2c(=O)[nH]c(=O)[nH]c2c1]
In some embodiments, $R^2$ is
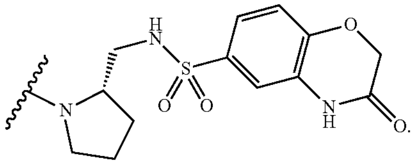 [SMILES: *N1CCC[C@H]1CNS(=O)(=O)c1ccc2c(c1)NC(=O)CO2]
In some embodiments, $R^2$ is
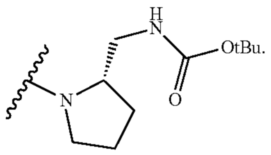 [SMILES: *N1CCC[C@H]1CNC(=O)OC(C)(C)C]
In some embodiments, $R^2$ is
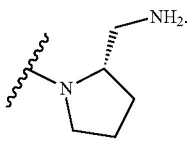 [SMILES: *N1CCC[C@H]1CN]
In some embodiments, $R^2$ is
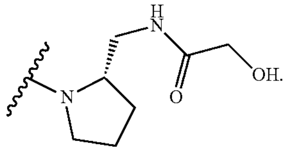 [SMILES: *N1CCC[C@H]1CNC(=O)CO]
In some embodiments, $R^2$ is
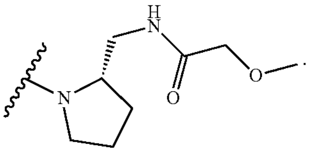 [SMILES: *N1CCC[C@H]1CNC(=O)COC]
In some embodiments, $R^2$ is
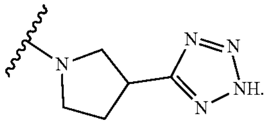 [SMILES: *N1CCC(c2nn[nH]n2)C1]
In some embodiments, $R^2$ is
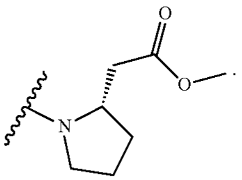 [SMILES: *N1CCC[C@H]1CC(=O)OC]
In some embodiments, $R^2$ is
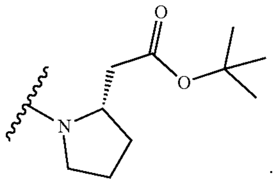 [SMILES: *N1CCC[C@H]1CC(=O)OC(C)(C)C]
In some embodiments, $R^2$ is
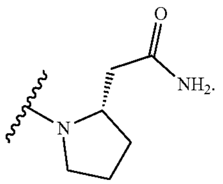 [SMILES: *N1CCC[C@H]1CC(N)=O]

In some embodiments, $R^2$ is
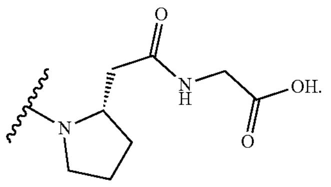 [SMILES: *N1CCC[C@H]1CC(=O)NCC(=O)O]
In some embodiments, $R^2$ is
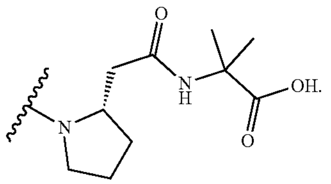 [SMILES: *N1CCC[C@H]1CC(=O)NC(C)(C)C(=O)O]
In some embodiments, $R^2$ is
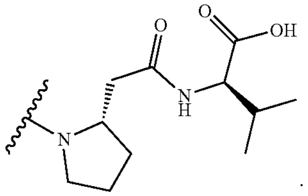 [SMILES: *N1CCC[C@H]1CC(=O)N[C@@H](C(=O)O)C(C)C]
In some embodiments, $R^2$ is
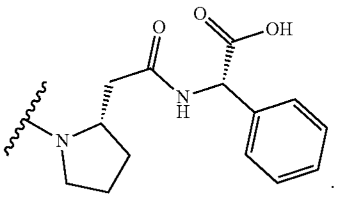 [SMILES: *N1CCC[C@H]1CC(=O)N[C@H](C(=O)O)c1ccccc1]
In some embodiments, $R^2$ is
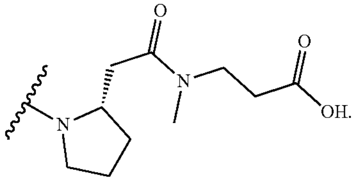 [SMILES: *N1CCC[C@H]1CC(=O)N(C)CCC(=O)O]
In some embodiments, $R^2$ is
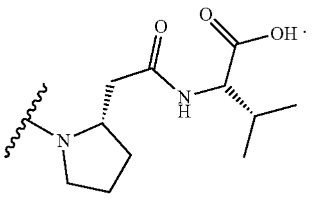
In some embodiments, $R^2$ is
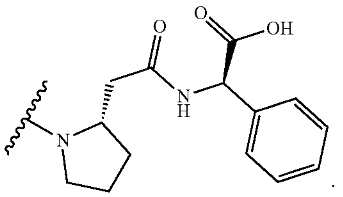 [SMILES: *N1CCC[C@H]1CC(=O)N[C@@H](C(=O)O)c1ccccc1]
In some embodiments, $R^2$ is
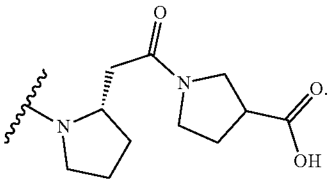 [SMILES: *N1CCC[C@H]1CC(=O)N1CCC(C(=O)O)C1]
In some embodiments, $R^2$ is
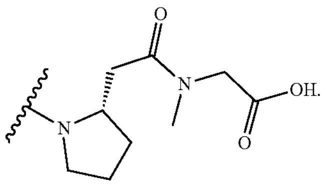 [SMILES: *N1CCC[C@H]1CC(=O)N(C)CC(=O)O]
In some embodiments, $R^2$ is
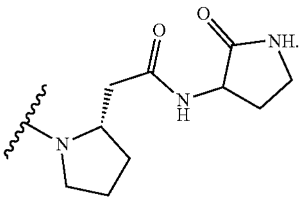 [SMILES: *N1CCC[C@H]1CC(=O)NC1CCNC1=O]
In some embodiments, $R^2$ is
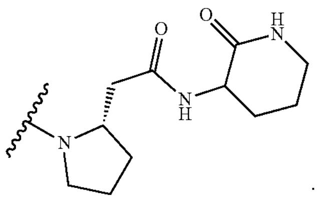 [SMILES: *N1CCC[C@H]1CC(=O)NC1CCCNC1=O]

In some embodiments, $R^2$ is
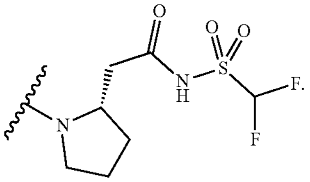 [SMILES: *N1CCC[C@H]1CC(=O)NS(=O)(=O)C(F)F]
In some embodiments, $R^2$ is
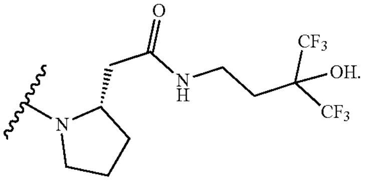 [SMILES: *N1CCC[C@H]1CC(=O)NCCC(O)(C(F)(F)F)C(F)(F)F]
In some embodiments, $R^2$ is
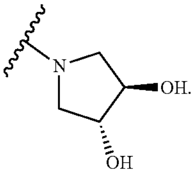 [SMILES: *N1C[C@@H](O)[C@H](O)C1]
In some embodiments, $R^2$ is
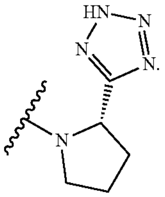 [SMILES: *N1CCC[C@H]1c1nn[nH]n1]
In some embodiments, $R^2$ is
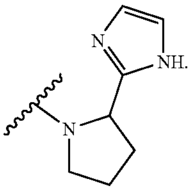 [SMILES: *N1CCCC1c1ncc[nH]1]
In some embodiments, $R^2$ is
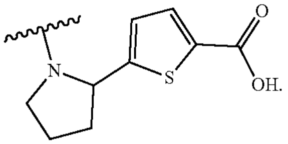 [SMILES: *N1CCCC1c1ccc(C(=O)O)s1]
In some embodiments, $R^2$ is
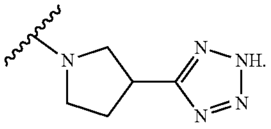 [SMILES: *N1CCC(c2nn[nH]n2)C1]
In some embodiments, $R^2$ is
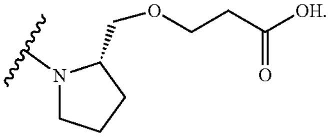 [SMILES: *N1CCC[C@H]1COCCC(=O)O]
In some embodiments, $R^2$ is
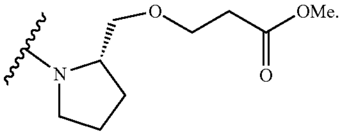 [SMILES: *N1CCC[C@H]1COCCC(=O)OC]
In some embodiments, $R^2$ is
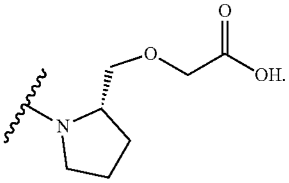 [SMILES: *N1CCC[C@H]1COCC(=O)O]
In some embodiments, $R^2$ is
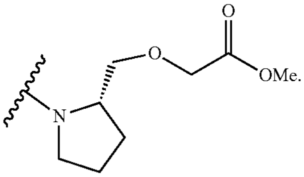 [SMILES: *N1CCC[C@H]1COCC(=O)OC]
In some embodiments, $R^2$ is
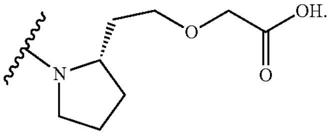 [SMILES: *N1CCC[C@H]1CCOCC(=O)O]

In some embodiments, $R^2$ is
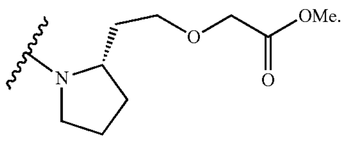 [SMILES: *N1CCC[C@H]1CCOCC(=O)OC]
In some embodiments, $R^2$ is
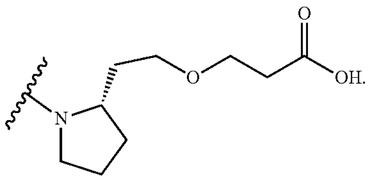 [SMILES: *N1CCC[C@H]1CCOCCC(=O)O]
In some embodiments, $R^2$ is
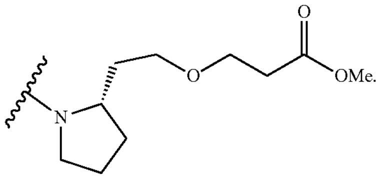 [SMILES: *N1CCC[C@H]1CCOCCC(=O)OC]
In some embodiments, $R^2$ is
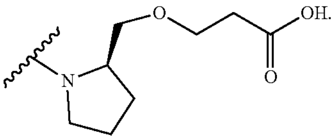 [SMILES: *N1CCC[C@@H]1COCCC(=O)O]
In some embodiments, $R^2$ is
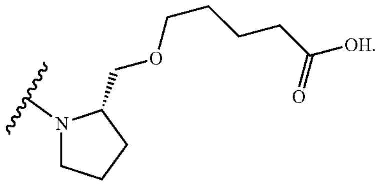 [SMILES: *N1CCC[C@H]1COCCCCC(=O)O]
In some embodiments, $R^2$ is
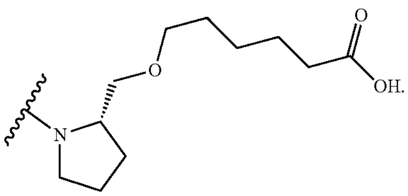 [SMILES: *N1CCC[C@H]1COCCCCCC(=O)O]
In some embodiments, $R^2$ is
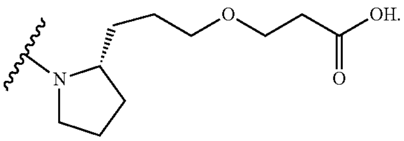 [SMILES: *N1CCC[C@H]1CCCOCCC(=O)O]
In some embodiments, $R^2$ is
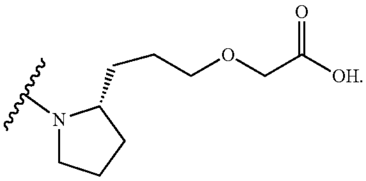 [SMILES: *N1CCC[C@H]1CCCOCC(=O)O]
In some embodiments, $R^2$ is
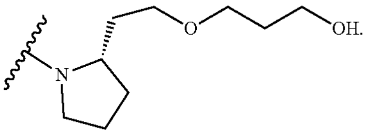 [SMILES: *N1CCC[C@H]1CCOCCCO]
In some embodiments, $R^2$ is
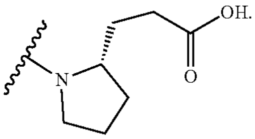 [SMILES: *N1CCC[C@H]1CCC(=O)O]
In some embodiments, $R^2$ is
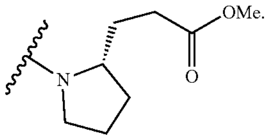 [SMILES: *N1CCC[C@H]1CCC(=O)OC]
In some embodiments, $R^2$ is
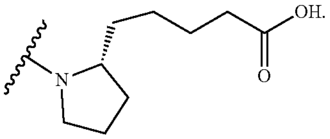 [SMILES: *N1CCC[C@H]1CCCCC(=O)O]
In some embodiments, $R^2$ is
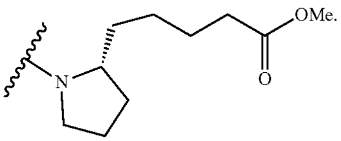 [SMILES: *N1CCC[C@H]1CCCCC(=O)OC]

In some embodiments, $R^2$ is
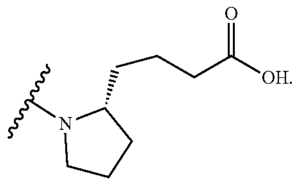 [SMILES: *N1CCC[C@H]1CCCC(=O)O]
In some embodiments, $R^2$ is
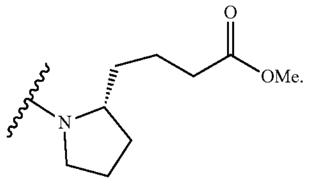 [SMILES: *N1CCC[C@H]1CCCC(=O)OC]
In some embodiments, $R^2$ is
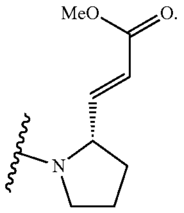 [SMILES: *N1CCC[C@H]1/C=C/C(=O)OC]
In some embodiments, $R^2$ is
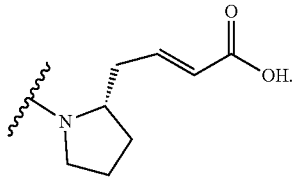 [SMILES: *N1CCC[C@H]1C/C=C/C(=O)O]
In some embodiments, $R^2$ is
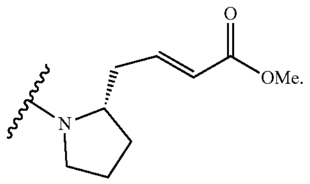 [SMILES: *N1CCC[C@H]1C/C=C/C(=O)OC]
In some embodiments, $R^2$ is
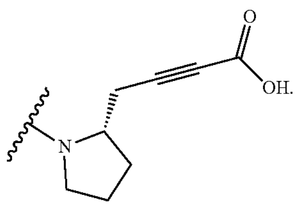 [SMILES: *N1CCC[C@H]1CC#CC(=O)O]
In some embodiments, $R^2$ is
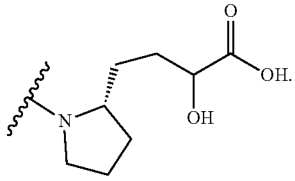 [SMILES: *N1CCC[C@H]1CCC(O)C(=O)O]
In some embodiments, $R^2$ is
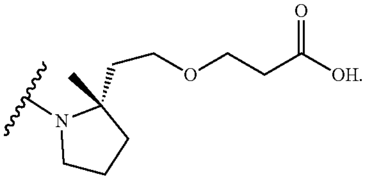 [SMILES: *N1CCC[C@@]1(C)CCOCCC(=O)O]
In some embodiments, $R^2$ is
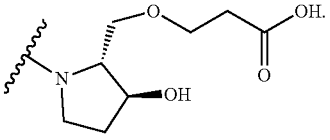 [SMILES: *N1CC[C@H](O)[C@H]1COCCC(=O)O]
In some embodiments, $R^2$ is
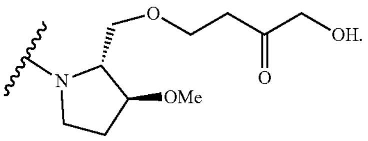 [SMILES: *N1CC[C@H](OC)[C@H]1COCCC(=O)CO]
In some embodiments, $R^2$ is
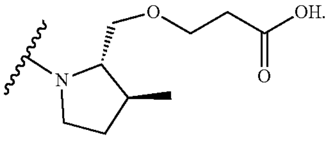 [SMILES: *N1CC[C@H](C)[C@H]1COCCC(=O)O]
In some embodiments, $R^2$ is
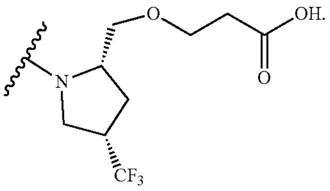 [SMILES: *N1C[C@@H](C(F)(F)F)C[C@H]1COCCC(=O)O]

In some embodiments, $R^2$ is
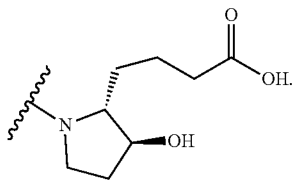 [SMILES: *N1CC[C@H](O)[C@H]1CCCC(=O)O]
In some embodiments, $R^2$ is
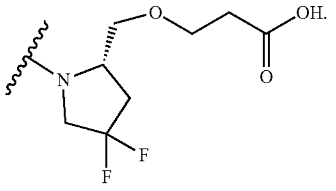 [SMILES: *N1CC(F)(F)C[C@H]1COCCC(=O)O]
In some embodiments, $R^2$ is
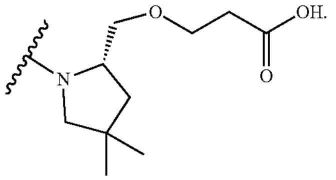 [SMILES: *N1CC(C)(C)C[C@H]1COCCC(=O)O]
In some embodiments, $R^2$ is
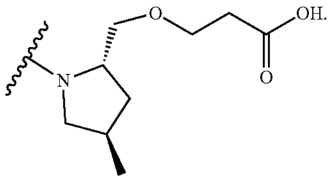 [SMILES: *N1C[C@H](C)C[C@H]1COCCC(=O)O]
In some embodiments, $R^2$ is
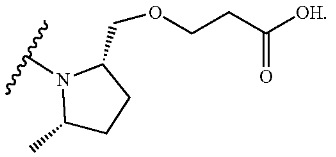 [SMILES: *N1[C@H](COCCC(=O)O)CC[C@@H]1C]
In some embodiments, $R^2$ is
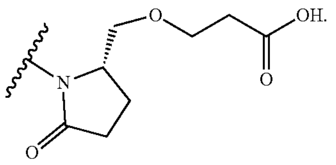 [SMILES: *N1C(=O)CC[C@H]1COCCC(=O)O]
In some embodiments, $R^2$ is
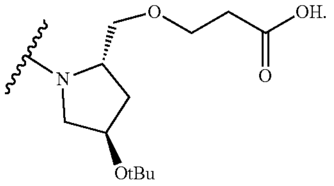 [SMILES: *N1C[C@H](OC(C)(C)C)C[C@H]1COCCC(=O)O]
In some embodiments, $R^2$ is
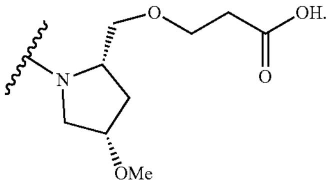 [SMILES: *N1C[C@@H](OC)C[C@H]1COCCC(=O)O]
In some embodiments, $R^2$ is
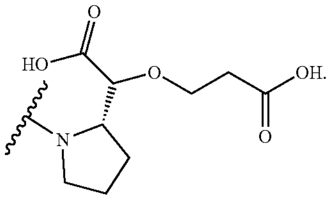 [SMILES: *N1CCC[C@H]1C(OCCC(=O)O)C(=O)O]
In some embodiments, $R^2$ is
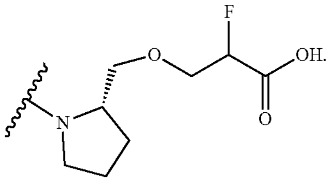 [SMILES: *N1CCC[C@H]1COCC(F)C(=O)O]
In some embodiments, $R^2$ is
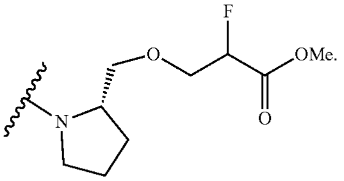 [SMILES: *N1CCC[C@H]1COCC(F)C(=O)OC]
In some embodiments, $R^2$ is
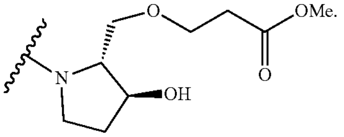 [SMILES: *N1CC[C@H](O)[C@H]1COCCC(=O)OC]

In some embodiments, $R^2$ is
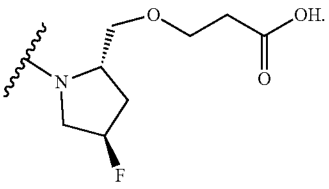 [SMILES: *N1C[C@H](F)C[C@H]1COCCC(=O)O]
In some embodiments, $R^2$ is
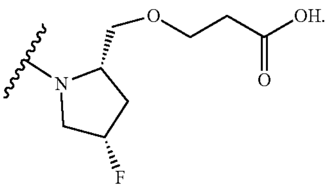 [SMILES: *N1C[C@@H](F)C[C@H]1COCCC(=O)O]
In some embodiments, $R^2$ is
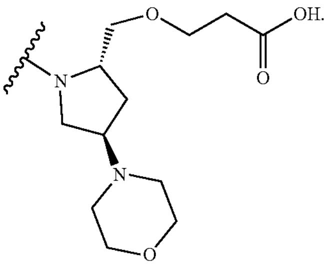 [SMILES: *N1C[C@H](N2CCOCC2)C[C@H]1COCCC(=O)O]
In some embodiments, $R^2$ is
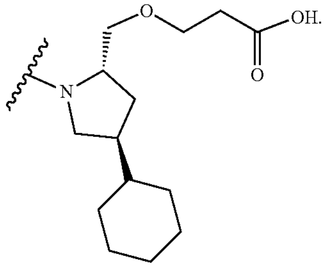 [SMILES: *N1C[C@H](C2CCCCC2)C[C@H]1COCCC(=O)O]
In some embodiments, $R^2$ is
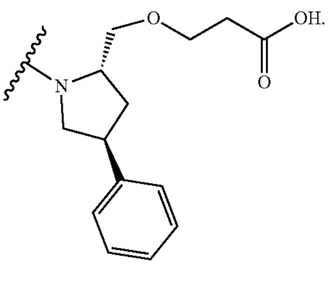 [SMILES: *N1C[C@H](c2ccccc2)C[C@H]1COCCC(=O)O]
In some embodiments, $R^2$ is
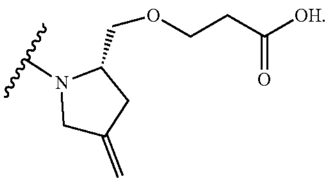 [SMILES: *N1CC(=C)C[C@H]1COCCC(=O)O]
In some embodiments, $R^2$ is
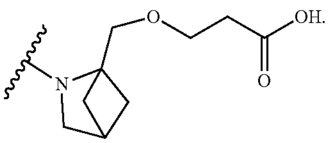 [SMILES: *N1CC2CC1(COCCC(=O)O)C2]
In some embodiments, $R^2$ is
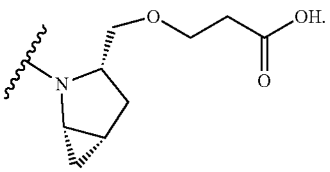 [SMILES: *N1[C@H](COCCC(=O)O)C[C@@H]2C[C@@H]21]
In some embodiments, $R^2$ is
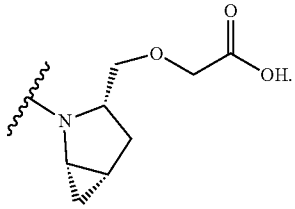 [SMILES: *N1[C@H](COCC(=O)O)C[C@@H]2C[C@@H]21]
In some embodiments, $R^2$ is
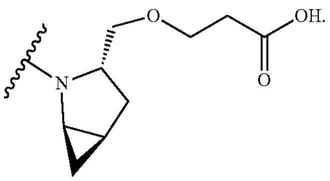 [SMILES: *N1[C@H](COCCC(=O)O)C[C@H]2C[C@H]21]
In some embodiments, $R^2$ is
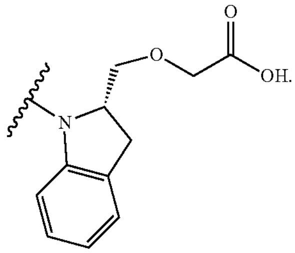 [SMILES: *N1c2ccccc2C[C@H]1COCC(=O)O]

In some embodiments, $R^2$ is
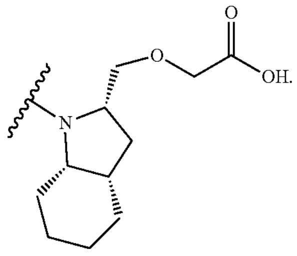 [SMILES: *N1[C@H](COCC(=O)O)C[C@@H]2CCCC[C@@H]21]
In some embodiments, $R^2$ is
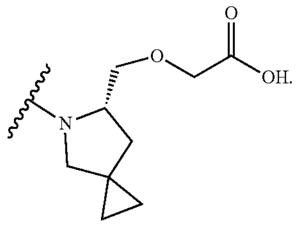 [SMILES: *N1CC2(CC2)C[C@H]1COCC(=O)O]
In some embodiments, $R^2$ is
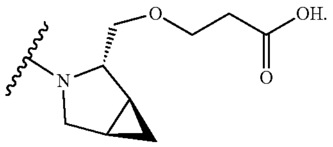 [SMILES: *N1C[C@@H]2C[C@@H]2[C@H]1COCCC(=O)O]
In some embodiments, $R^2$ is
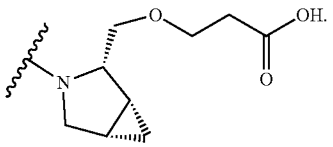 [SMILES: *N1C[C@H]2C[C@H]2[C@H]1COCCC(=O)O]
In some embodiments, $R^2$ is
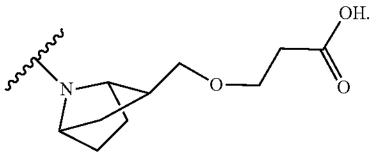 [SMILES: *N1C2CCC1C(COCCC(=O)O)C2]
In some embodiments, $R^2$ is
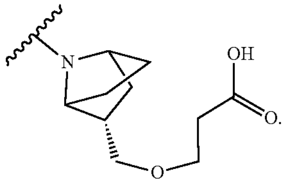 [SMILES: *N1C2CCC1[C@@H](COCCC(=O)O)C2]
In some embodiments, $R^2$ is
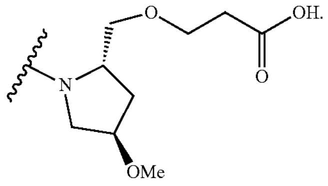 [SMILES: *N1C[C@H](OC)C[C@H]1COCCC(=O)O]
In some embodiments, $R^2$ is
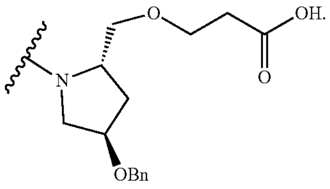 [SMILES: *N1C[C@H](OCc2ccccc2)C[C@H]1COCCC(=O)O]
In some embodiments, $R^2$ is
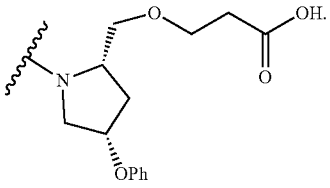 [SMILES: *N1C[C@@H](Oc2ccccc2)C[C@H]1COCCC(=O)O]
In some embodiments, $R^2$ is
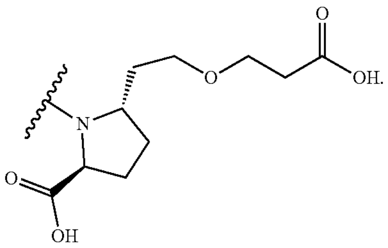 [SMILES: *N1[C@H](CCOCCC(=O)O)CC[C@H]1C(=O)O]
In some embodiments, $R^2$ is
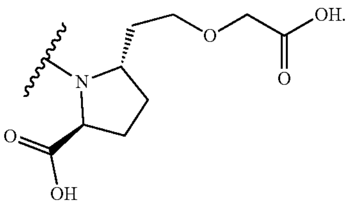 [SMILES: *N1[C@H](CCOCC(=O)O)CC[C@H]1C(=O)O]
In some embodiments, $R^2$ is
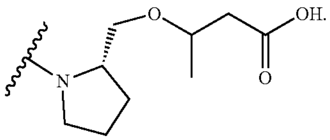 [SMILES: *N1CCC[C@H]1COC(C)CC(=O)O]

In some embodiments, $R^2$ is
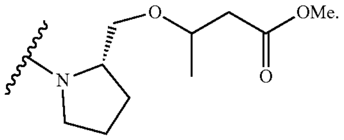 [SMILES: *N1CCC[C@H]1COC(C)CC(=O)OC]
In some embodiments, $R^2$ is
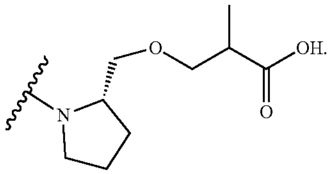 [SMILES: *N1CCC[C@H]1COCC(C)C(=O)O]
In some embodiments, $R^2$ is
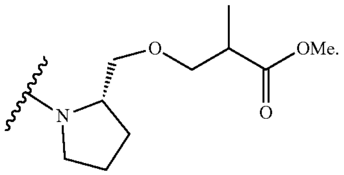 [SMILES: *N1CCC[C@H]1COCC(C)C(=O)OC]
In some embodiments, $R^2$ is
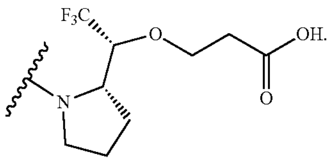 [SMILES: *N1CCC[C@H]1[C@@H](OCCC(=O)O)C(F)(F)F]
In some embodiments, $R^2$ is
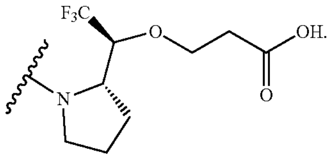 [SMILES: *N1CCC[C@H]1[C@H](OCCC(=O)O)C(F)(F)F]
In some embodiments, $R^2$ is
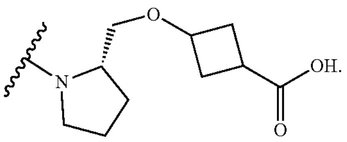 [SMILES: *N1CCC[C@H]1COC1CC(C(=O)O)C1]
In some embodiments, $R^2$ is
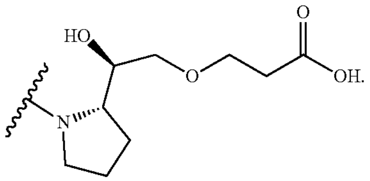 [SMILES: *N1CCC[C@H]1[C@@H](O)COCCC(=O)O]
In some embodiments, $R^2$ is
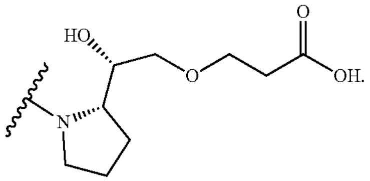 [SMILES: *N1CCC[C@H]1[C@H](O)COCCC(=O)O]
In some embodiments, $R^2$ is
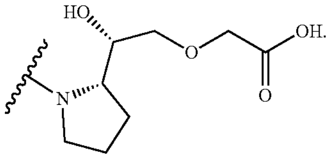 [SMILES: *N1CCC[C@H]1[C@H](O)COCC(=O)O]
In some embodiments, $R^2$ is
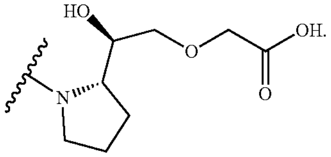 [SMILES: *N1CCC[C@H]1[C@@H](O)COCC(=O)O]
In some embodiments, $R^2$ is
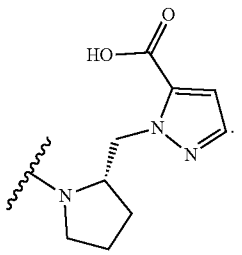 [SMILES: *N1CCC[C@H]1Cn1nccc1C(=O)O]

In some embodiments, $R^2$ is
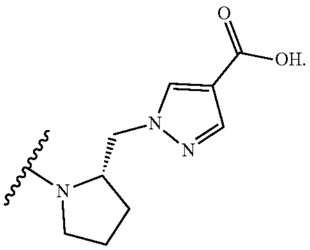 [SMILES: *N1CCC[C@H]1Cn1cc(C(=O)O)cn1]
In some embodiments, $R^2$ is
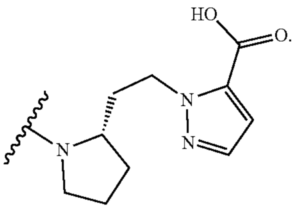 [SMILES: *N1CCC[C@H]1CCn1nccc1C(=O)O]
In some embodiments, $R^2$ is
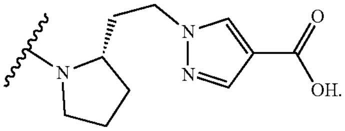 [SMILES: *N1CCC[C@H]1CCn1cc(C(=O)O)cn1]
In some embodiments, $R^2$ is
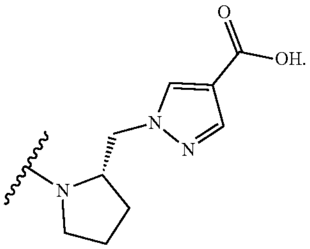 [SMILES: *N1CCC[C@H]1Cn1cc(C(=O)O)cn1]
In some embodiments, $R^2$ is
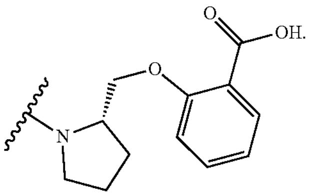 [SMILES: *N1CCC[C@H]1COc1ccccc1C(=O)O]
In some embodiments, $R^2$ is
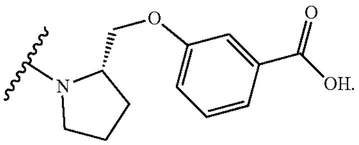 [SMILES: *N1CCC[C@H]1COc1cccc(C(=O)O)c1]
In some embodiments, $R^2$ is
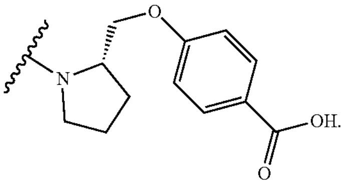 [SMILES: *N1CCC[C@H]1COc1ccc(C(=O)O)cc1]
In some embodiments, $R^2$ is
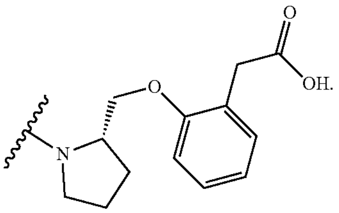 [SMILES: *N1CCC[C@H]1COc1ccccc1CC(=O)O]
In some embodiments, $R^2$ is
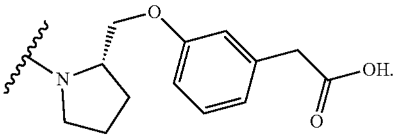 [SMILES: *N1CCC[C@H]1COc1cccc(CC(=O)O)c1]
In some embodiments, $R^2$ is
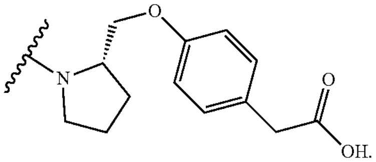 [SMILES: *N1CCC[C@H]1COc1ccc(CC(=O)O)cc1]
In some embodiments, $R^2$ is
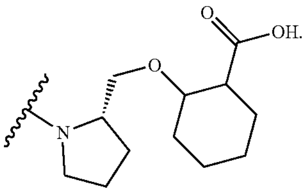 [SMILES: *N1CCC[C@H]1COC1CCCCC1C(=O)O]

In some embodiments, $R^2$ is
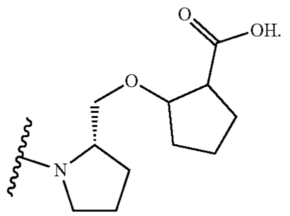 [SMILES: *N1CCC[C@H]1COC1CCCC1C(=O)O]
In some embodiments, $R^2$ is
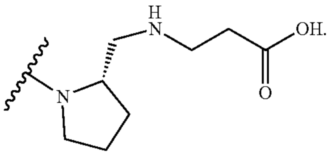
In some embodiments, $R^2$ is
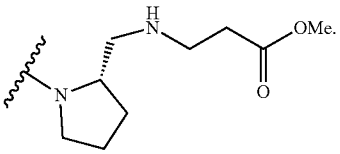 [SMILES: *N1CCC[C@H]1CNCCC(=O)OC]
In some embodiments, $R^2$ is
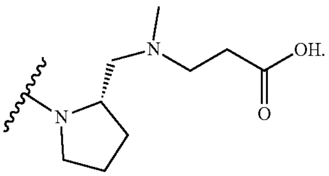 [SMILES: *N1CCC[C@H]1CN(C)CCC(=O)O]
In some embodiments, $R^2$ is
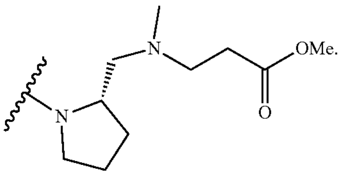 [SMILES: *N1CCC[C@H]1CN(C)CCC(=O)OC]
In some embodiments, $R^2$ is
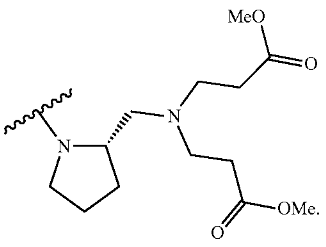 [SMILES: *N1CCC[C@H]1CN(CCC(=O)OC)CCC(=O)OC]
In some embodiments, $R^2$ is
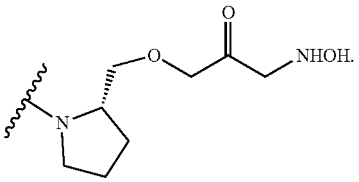
In some embodiments, $R^2$ is
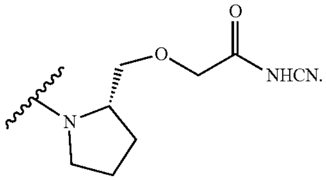
In some embodiments, $R^2$ is
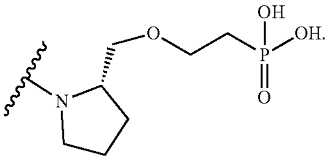 [SMILES: *N1CCC[C@H]1COCCP(=O)(O)O]
In some embodiments, $R^2$ is
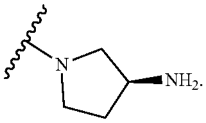 [SMILES: *N1CC[C@H](N)C1]
In some embodiments, $R^2$ is
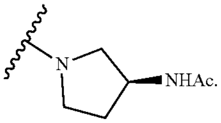 [SMILES: *N1CC[C@H](NC(C)=O)C1]
In some embodiments, $R^2$ is
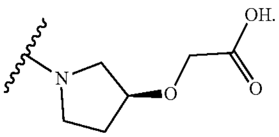 [SMILES: *N1CC[C@H](OCC(=O)O)C1]

In some embodiments, $R^2$ is
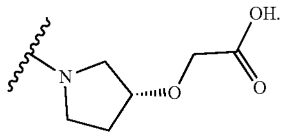 [SMILES: *N1CC[C@@H](OCC(=O)O)C1]
In some embodiments, $R^2$ is
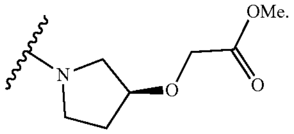 [SMILES: *N1CC[C@H](OCC(=O)OC)C1]
In some embodiments, $R^2$ is
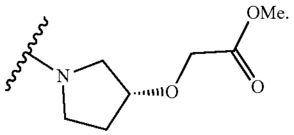 [SMILES: *N1CC[C@@H](OCC(=O)OC)C1]
In some embodiments, $R^2$ is
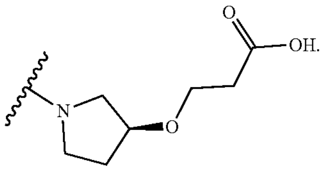 [SMILES: *N1CC[C@H](OCCC(=O)O)C1]
In some embodiments, $R^2$ is
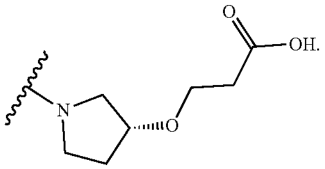 [SMILES: *N1CC[C@@H](OCCC(=O)O)C1]
In some embodiments, $R^2$ is
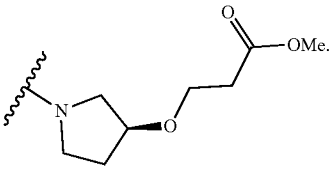 [SMILES: *N1CC[C@H](OCCC(=O)OC)C1]
In some embodiments, $R^2$ is
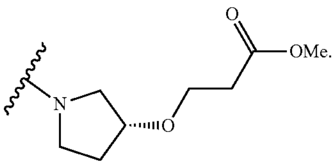 [SMILES: *N1CC[C@@H](OCCC(=O)OC)C1]
In some embodiments, $R^2$ is
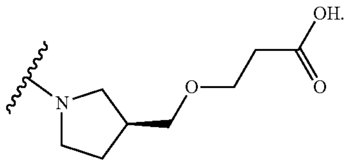 [SMILES: *N1CC[C@H](COCCC(=O)O)C1]
In some embodiments, $R^2$ is
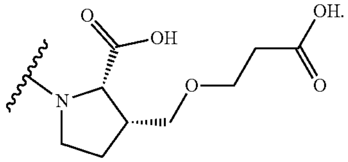 [SMILES: *N1CC[C@@H](COCCC(=O)O)[C@H]1C(=O)O]
In some embodiments, $R^2$ is
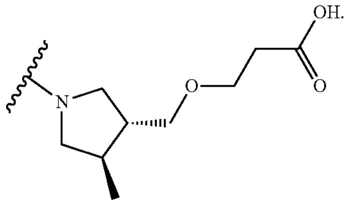 [SMILES: *N1C[C@H](COCCC(=O)O)[C@@H](C)C1]
In some embodiments, $R^2$ is
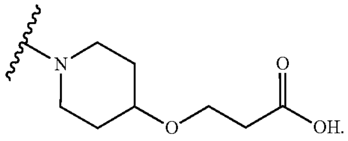 [SMILES: *N1CCC(OCCC(=O)O)CC1]
In some embodiments, $R^2$ is
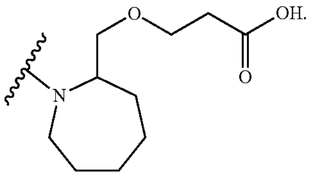 [SMILES: *N1CCCCCC1COCCC(=O)O]
In some embodiments, $R^2$ is
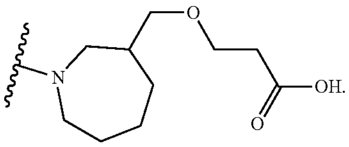 [SMILES: *N1CCCCC(COCCC(=O)O)C1]

In some embodiments, $R^2$ is
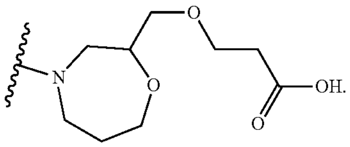 [SMILES: *N1CCCOC(COCCC(=O)O)C1]
In some embodiments, $R^2$ is
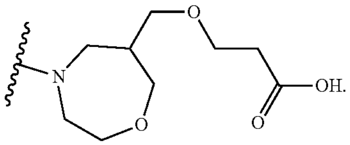 [SMILES: *N1CCOCC(COCCC(=O)O)C1]
In some embodiments, $R^2$ is
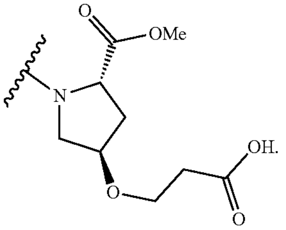 [SMILES: *N1C[C@H](OCCC(=O)O)C[C@H]1C(=O)OC]
In some embodiments, $R^2$ is
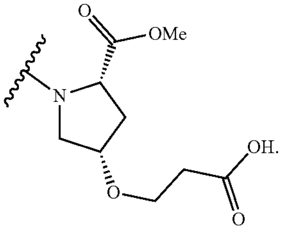 [SMILES: *N1C[C@@H](OCCC(=O)O)C[C@H]1C(=O)OC]
In some embodiments, $R^2$ is
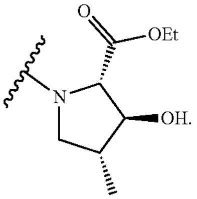 [SMILES: *N1C[C@@H](C)[C@H](O)[C@H]1C(=O)OCC]
In some embodiments, $R^2$ is
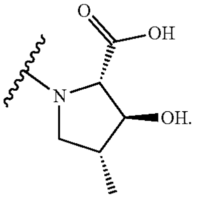 [SMILES: *N1C[C@@H](C)[C@H](O)[C@H]1C(=O)O]
In some embodiments, $R^2$ is
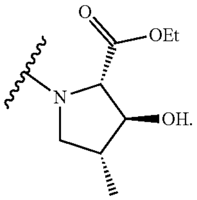 [SMILES: *N1C[C@@H](C)[C@H](O)[C@H]1C(=O)OCC]
In some embodiments, $R^2$ is
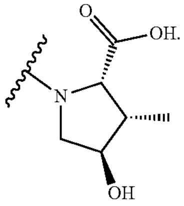 [SMILES: *N1C[C@H](O)[C@@H](C)[C@H]1C(=O)O]
In some embodiments, $R^2$ is
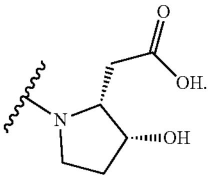 [SMILES: *N1CC[C@@H](O)[C@H]1CC(=O)O]
In some embodiments, $R^2$ is
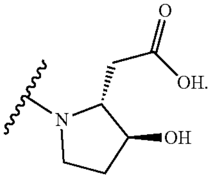 [SMILES: *N1CC[C@H](O)[C@H]1CC(=O)O]
In some embodiments, $R^2$ is
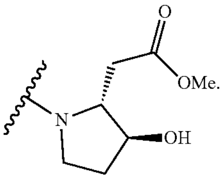 [SMILES: *N1CC[C@H](O)[C@H]1CC(=O)OC]

In some embodiments, $R^2$ is
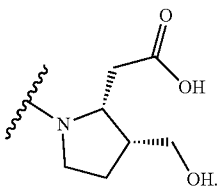 [SMILES: *N1CC[C@@H](CO)[C@H]1CC(=O)O]
In some embodiments, $R^2$ is
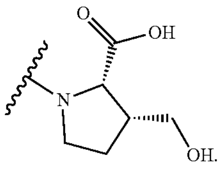 [SMILES: *N1CC[C@@H](CO)[C@H]1C(=O)O]
In some embodiments, $R^2$ is
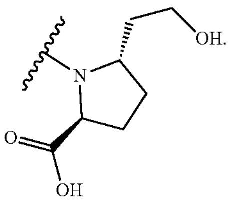 [SMILES: *N1[C@H](CCO)CC[C@H]1C(=O)O]
In some embodiments, $R^2$ is
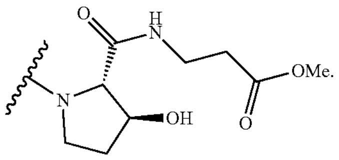 [SMILES: *N1CC[C@H](O)[C@H]1C(=O)NCCC(=O)OC]
In some embodiments, $R^2$ is
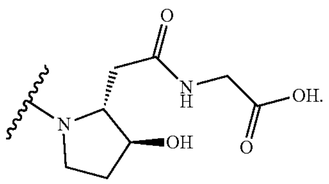 [SMILES: *N1CC[C@H](O)[C@H]1CC(=O)NCC(=O)O]
In some embodiments, $R^2$ is
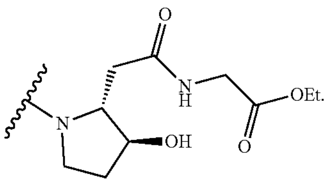 [SMILES: *N1CC[C@H](O)[C@H]1CC(=O)NCC(=O)OCC]
In some embodiments, $R^2$ is
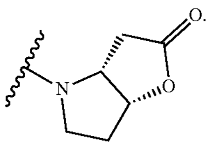 [SMILES: *N1CC[C@H]2OC(=O)C[C@H]21]
In some embodiments, $R^2$ is
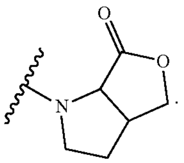 [SMILES: *N1CCC2COC(=O)C21]
In some embodiments, $R^2$ is
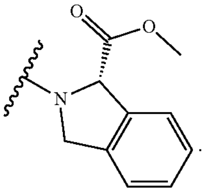 [SMILES: *N1Cc2ccccc2[C@H]1C(=O)OC]
In some embodiments, $R^2$ is
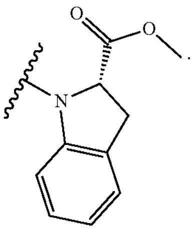 [SMILES: *N1c2ccccc2C[C@H]1C(=O)OC]
In some embodiments, $R^2$ is
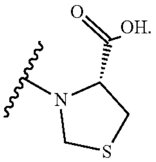 [SMILES: *N1CSC[C@H]1C(=O)O]
In some embodiments, $R^2$ is
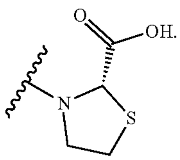 [SMILES: *N1CCS[C@H]1C(=O)O]

In some embodiments, $R^2$ is

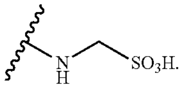

In some embodiments, $R^2$ is

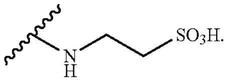 [SMILES: *NCCS(=O)(=O)O]

In some embodiments, $R^2$ is

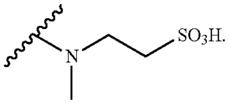 [SMILES: *N(C)CCS(=O)(=O)O]

In some embodiments, $R^2$ is

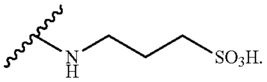 [SMILES: *NCCCS(=O)(=O)O]

In some embodiments, $R^2$ is

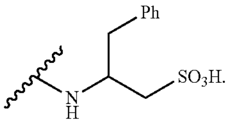 [SMILES: *NC(Cc1ccccc1)CS(=O)(=O)O]

In some embodiments, $R^2$ is

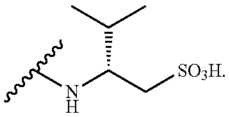 [SMILES: *N[C@@H](CS(=O)(=O)O)C(C)C]

In some embodiments, $R^2$ is

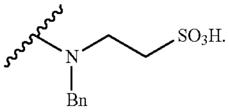 [SMILES: *N(CCS(=O)(=O)O)Cc1ccccc1]

In some embodiments, $R^2$ is

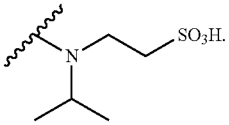 [SMILES: *N(CCS(=O)(=O)O)C(C)C]

In some embodiments, $R^2$ is

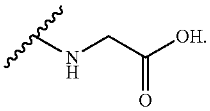 [SMILES: *NCC(=O)O]

In some embodiments, $R^2$ is

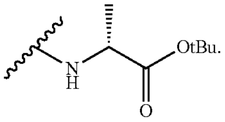 [SMILES: *N[C@H](C)C(=O)OC(C)(C)C]

In some embodiments, $R^2$ is

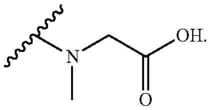 [SMILES: *N(C)CC(=O)O]

In some embodiments, $R^2$ is

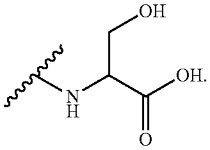 [SMILES: *NC(CO)C(=O)O]

In some embodiments, $R^2$ is

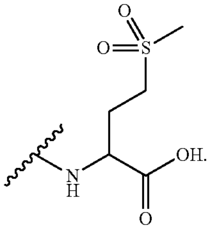 [SMILES: *NC(CCS(C)(=O)=O)C(=O)O]

In some embodiments, $R^2$ is

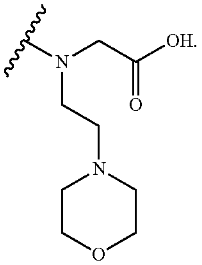 [SMILES: *N(CCN1CCOCC1)CC(=O)O]

In some embodiments, $R^2$ is

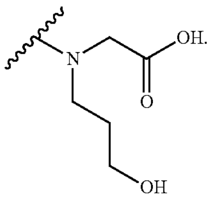 [SMILES: *N(CCCO)CC(=O)O]

In some embodiments, $R^2$ is

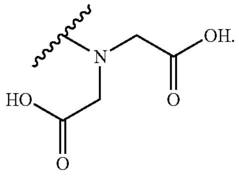 [SMILES: *N(CC(=O)O)CC(=O)O]

In some embodiments, $R^2$ is

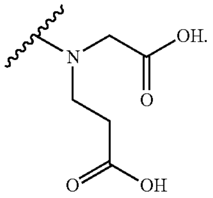 [SMILES: *N(CCC(=O)O)CC(=O)O]

In some embodiments, $R^2$ is

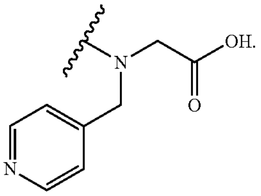 [SMILES: *N(CC(=O)O)Cc1ccncc1]

In some embodiments, $R^2$ is

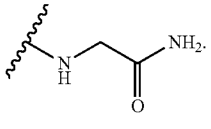 [SMILES: *NCC(N)=O]

In some embodiments, $R^2$ is

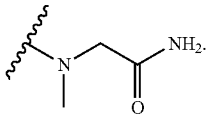 [SMILES: *N(C)CC(N)=O]

In some embodiments, $R^2$ is

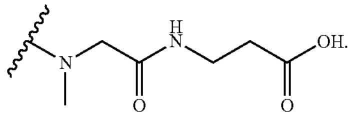 [SMILES: *N(C)CC(=O)NCCC(=O)O]

In some embodiments, $R^2$ is

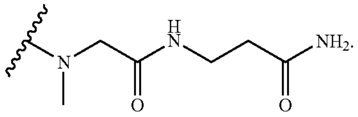 [SMILES: *N(C)CC(=O)NCCC(N)=O]

In some embodiments, $R^2$ is

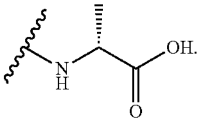 [SMILES: *N[C@H](C)C(=O)O]

In some embodiments, $R^2$ is

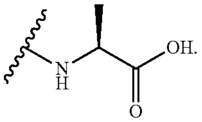 [SMILES: *N[C@@H](C)C(=O)O]

In some embodiments, $R^2$ is

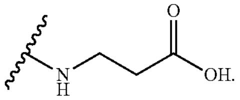 [SMILES: *NCCC(=O)O]

In some embodiments, $R^2$ is

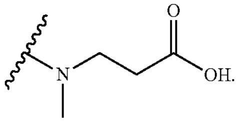 [SMILES: *N(C)CCC(=O)O]

In some embodiments, $R^2$ is

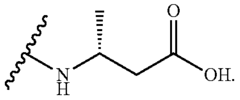 [SMILES: *N[C@H](C)CC(=O)O]

In some embodiments, $R^2$ is

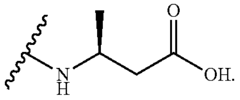 [SMILES: *N[C@@H](C)CC(=O)O]

In some embodiments, $R^2$ is

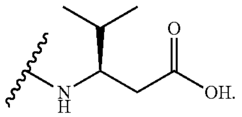 [SMILES: *N[C@H](CC(=O)O)C(C)C]

In some embodiments, $R^2$ is

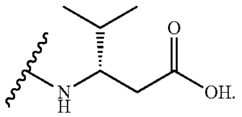 [SMILES: *N[C@@H](CC(=O)O)C(C)C]

In some embodiments, $R^2$ is

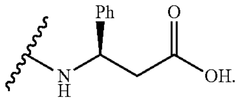 [SMILES: *N[C@H](CC(=O)O)c1ccccc1]

In some embodiments, $R^2$ is

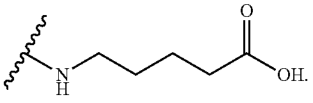 [SMILES: *NCCCCC(=O)O]

In some embodiments, $R^2$ is

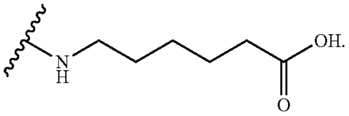 [SMILES: *NCCCCCC(=O)O]

In some embodiments, $R^2$ is

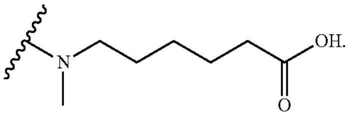 [SMILES: *N(C)CCCCCC(=O)O]

In some embodiments, $R^2$ is

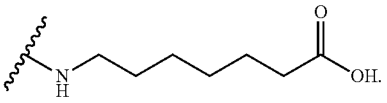 [SMILES: *NCCCCCCC(=O)O]

In some embodiments, $R^2$ is

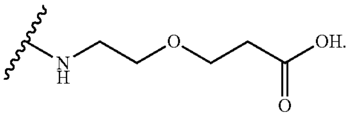 [SMILES: *NCCOCCC(=O)O]

In some embodiments, $R^2$ is

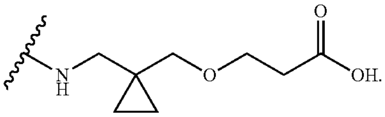 [SMILES: *NCC1(COCCC(=O)O)CC1]

In some embodiments, $R^2$ is

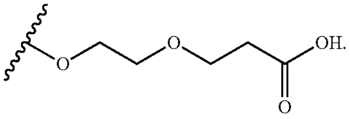 [SMILES: *OCCOCCC(=O)O]

In some embodiments, $R^2$ is

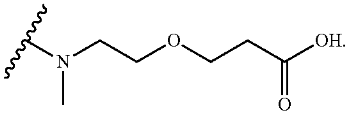 [SMILES: *N(C)CCOCCC(=O)O]

In some embodiments, $R^2$ is

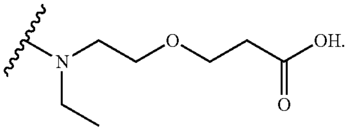 [SMILES: *N(CC)CCOCCC(=O)O]

In some embodiments, $R^2$ is

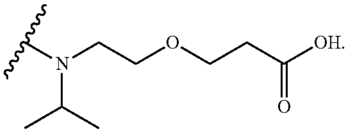 [SMILES: *N(CCOCCC(=O)O)C(C)C]

In some embodiments, $R^2$ is

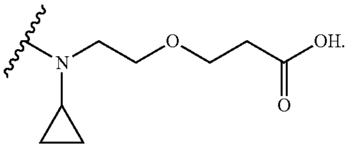 [SMILES: *N(CCOCCC(=O)O)C1CC1]

In some embodiments, $R^2$ is
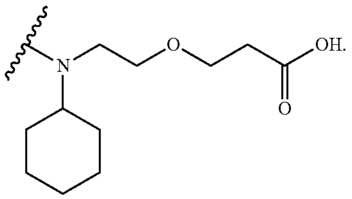 [SMILES: *N(CCOCCC(=O)O)C1CCCCC1]
In some embodiments, $R^2$ is
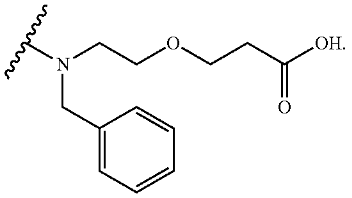 [SMILES: *N(CCOCCC(=O)O)Cc1ccccc1]
In some embodiments, $R^2$ is
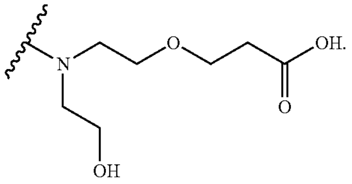 [SMILES: *N(CCO)CCOCCC(=O)O]
In some embodiments, $R^2$ is
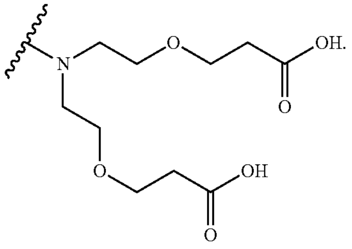 [SMILES: *N(CCOCCC(=O)O)CCOCCC(=O)O]
In some embodiments, $R^2$ is
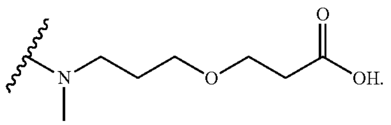 [SMILES: *N(C)CCCOCCC(=O)O]
In some embodiments, $R^2$ is
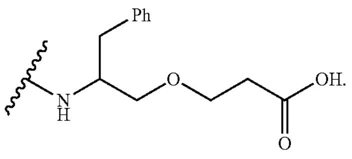 [SMILES: *NC(COCCC(=O)O)Cc1ccccc1]
In some embodiments, $R^2$ is
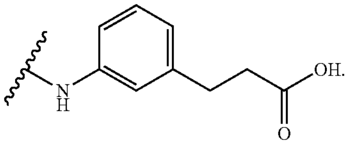 [SMILES: *Nc1cccc(CCC(=O)O)c1]
In some embodiments, $R^2$ is
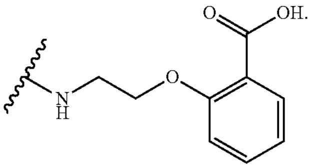 [SMILES: *NCCOc1ccccc1C(=O)O]
In some embodiments, $R^2$ is
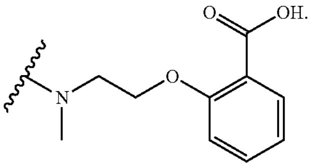 [SMILES: *N(C)CCOc1ccccc1C(=O)O]
In some embodiments, $R^2$ is
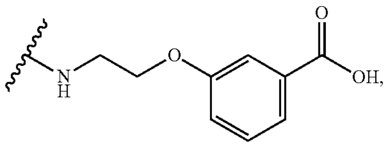 [SMILES: *NCCOc1cccc(C(=O)O)c1]
In some embodiments, $R^2$ is
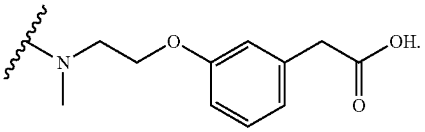 [SMILES: *N(C)CCOc1cccc(CC(=O)O)c1]
In some embodiments, $R^2$ is
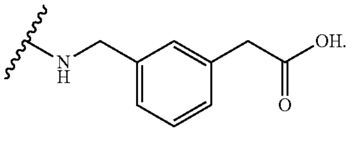 [SMILES: *NCc1cccc(CC(=O)O)c1]

In some embodiments, $R^2$ is
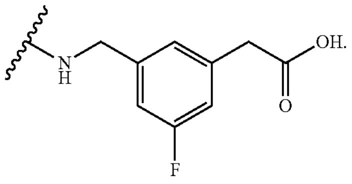 [SMILES: *NCc1cc(F)cc(CC(=O)O)c1]
In some embodiments, $R^2$ is
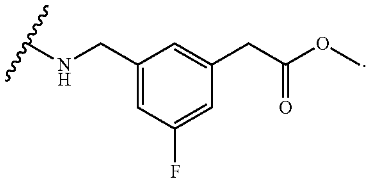 [SMILES: *NCc1cc(F)cc(CC(=O)OC)c1]
In some embodiments, $R^2$ is
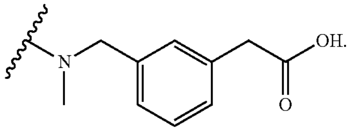 [SMILES: *N(C)Cc1cccc(CC(=O)O)c1]
In some embodiments, $R^2$ is
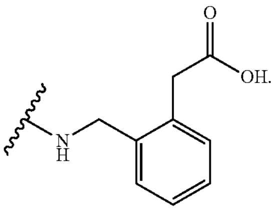 [SMILES: *NCc1ccccc1CC(=O)O]
In some embodiments, $R^2$ is
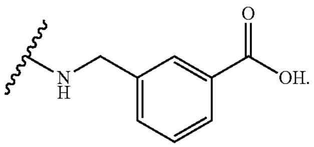 [SMILES: *NCc1cccc(C(=O)O)c1]
In some embodiments, $R^2$ is
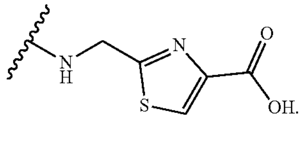 [SMILES: *NCc1nc(C(=O)O)cs1]
In some embodiments, $R^2$ is
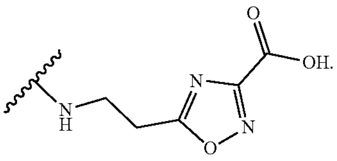 [SMILES: *NCCc1nc(C(=O)O)no1]
In some embodiments, $R^2$ is
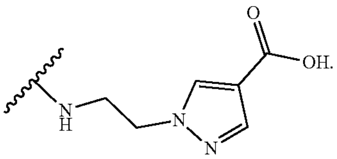 [SMILES: *NCCn1cc(C(=O)O)cn1]
In some embodiments, $R^2$ is
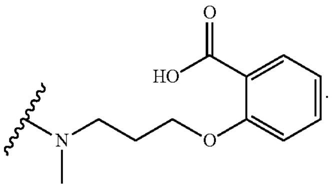 [SMILES: *N(C)CCCOc1ccccc1C(=O)O]
In some embodiments, $R^2$ is
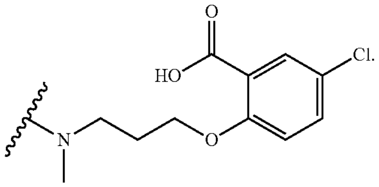 [SMILES: *N(C)CCCOc1ccc(Cl)cc1C(=O)O]
In some embodiments, $R^2$ is
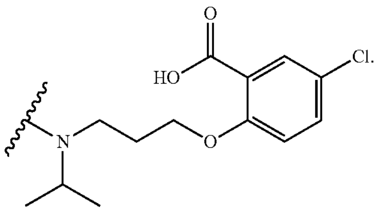 [SMILES: *N(CCCOc1ccc(Cl)cc1C(=O)O)C(C)C]
In some embodiments, $R^2$ is
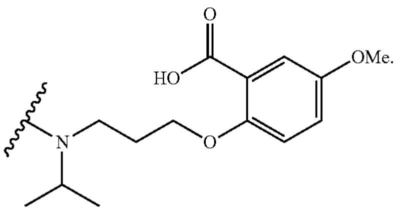 [SMILES: *N(CCCOc1ccc(OC)cc1C(=O)O)C(C)C]

In some embodiments, $R^2$ is
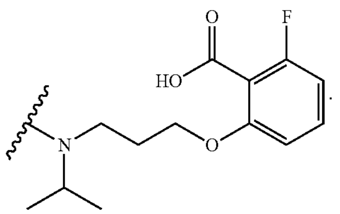 [SMILES: *N(CCCOc1cccc(F)c1C(=O)O)C(C)C]
In some embodiments, $R^2$ is
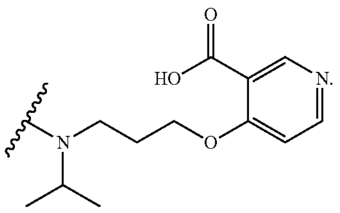 [SMILES: *N(CCCOc1ccncc1C(=O)O)C(C)C]
In some embodiments, $R^2$ is
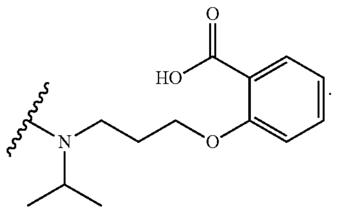 [SMILES: *N(CCCOc1ccccc1C(=O)O)C(C)C]
In some embodiments, $R^2$ is
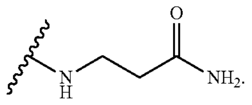 [SMILES: *NCCC(N)=O]
In some embodiments, $R^2$ is
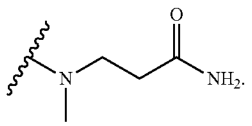 [SMILES: *N(C)CCC(N)=O]
In some embodiments, $R^2$ is
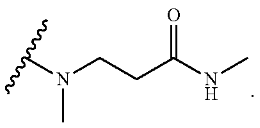 [SMILES: *N(C)CCC(=O)NC]
In some embodiments, $R^2$ is
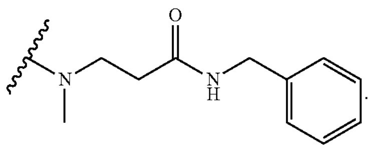 [SMILES: *N(C)CCC(=O)NCc1ccccc1]
In some embodiments, $R^2$ is
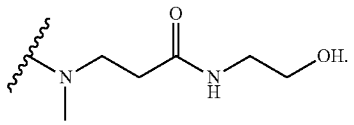 [SMILES: *N(C)CCC(=O)NCCO]
In some embodiments, $R^2$ is
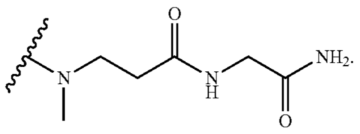 [SMILES: *N(C)CCC(=O)NCC(N)=O]
In some embodiments, $R^2$ is
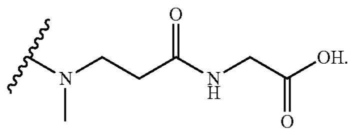 [SMILES: *N(C)CCC(=O)NCC(=O)O]
In some embodiments, $R^2$ is
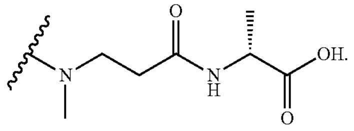 [SMILES: *N(C)CCC(=O)N[C@H](C)C(=O)O]
In some embodiments, $R^2$ is
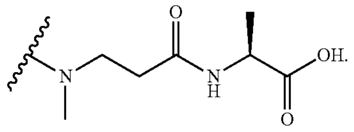 [SMILES: *N(C)CCC(=O)N[C@@H](C)C(=O)O]
In some embodiments, $R^2$ is
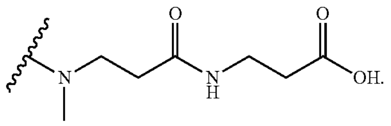 [SMILES: *N(C)CCC(=O)NCCC(=O)O]

In some embodiments, $R^2$ is

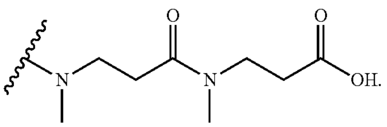 [SMILES: *N(C)CCC(=O)N(C)CCC(=O)O]

In some embodiments, $R^2$ is

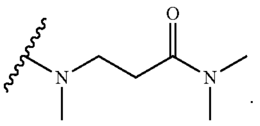 [SMILES: *N(C)CCC(=O)N(C)C]

In some embodiments, $R^2$ is

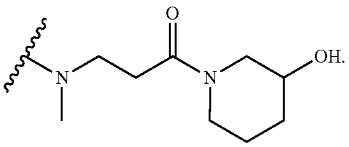 [SMILES: *N(C)CCC(=O)N1CCCC(O)C1]

In some embodiments, $R^2$ is

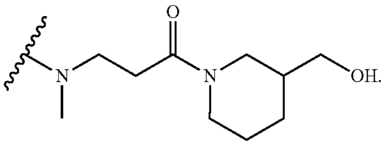 [SMILES: *N(C)CCC(=O)N1CCCC(CO)C1]

In some embodiments, $R^2$ is

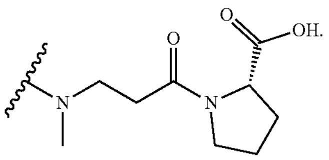 [SMILES: *N(C)CCC(=O)N1CCC[C@H]1C(=O)O]

In some embodiments, $R^2$ is

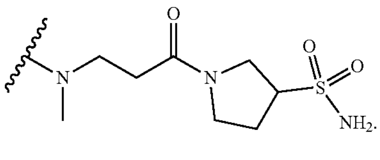 [SMILES: *N(C)CCC(=O)N1CCC(S(N)(=O)=O)C1]

In some embodiments, $R^2$ is

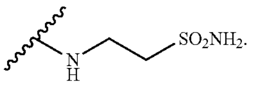 [SMILES: *NCCS(N)(=O)=O]

In some embodiments, $R^2$ is

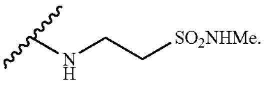

In some embodiments, $R^2$ is

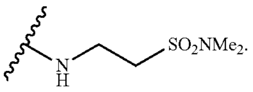

In some embodiments, $R^2$ is

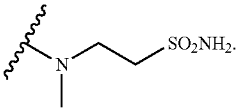 [SMILES: *N(C)CCS(N)(=O)=O]

In some embodiments, $R^2$ is

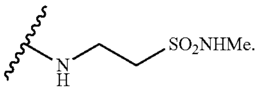

In some embodiments, $R^2$ is

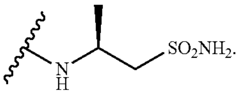 [SMILES: *N[C@@H](C)CS(N)(=O)=O]

In some embodiments, $R^2$ is

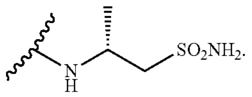 [SMILES: *N[C@H](C)CS(N)(=O)=O]

In some embodiments, $R^2$ is

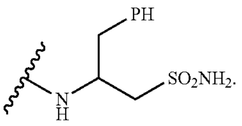

In some embodiments, $R^2$ is

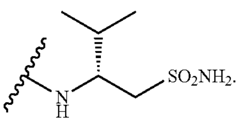 [SMILES: *N[C@@H](CS(N)(=O)=O)C(C)C]

In some embodiments, $R^2$ is

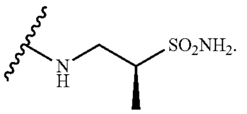 [SMILES: *NC[C@H](C)S(N)(=O)=O]

In some embodiments, $R^2$ is

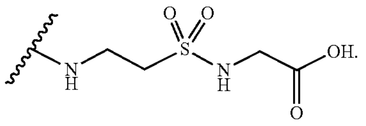 [SMILES: *NCCS(=O)(=O)NCC(=O)O]

In some embodiments, $R^2$ is

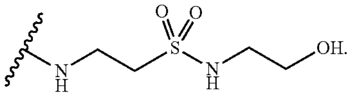 [SMILES: *NCCS(=O)(=O)NCCO]

In some embodiments, $R^2$ is

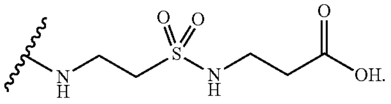 [SMILES: *NCCS(=O)(=O)NCCC(=O)O]

In some embodiments, $R^2$ is

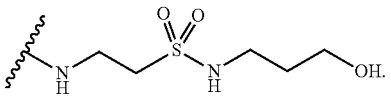 [SMILES: *NCCS(=O)(=O)NCCCO]

In some embodiments, $R^2$ is

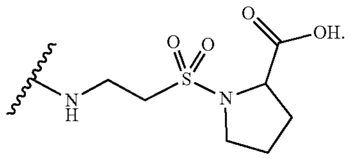 [SMILES: *NCCS(=O)(=O)N1CCCC1C(=O)O]

In some embodiments, $R^2$ is

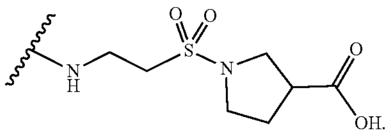 [SMILES: *NCCS(=O)(=O)N1CCC(C(=O)O)C1]

In some embodiments, $R^2$ is

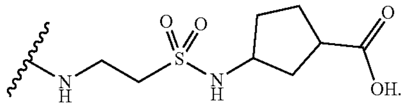 [SMILES: *NCCS(=O)(=O)NC1CCC(C(=O)O)C1]

In some embodiments, $R^2$ is

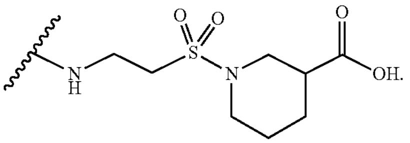 [SMILES: *NCCS(=O)(=O)N1CCCC(C(=O)O)C1]

In some embodiments, $R^2$ is

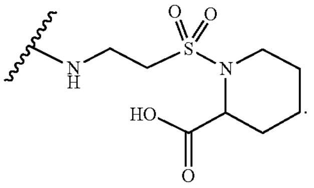 [SMILES: *NCCS(=O)(=O)N1CCCCC1C(=O)O]

In some embodiments, $R^2$ is

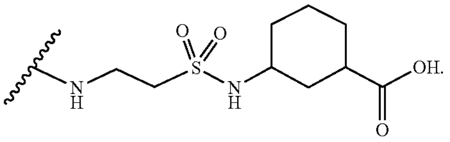 [SMILES: *NCCS(=O)(=O)NC1CCCC(C(=O)O)C1]

In some embodiments, $R^2$ is

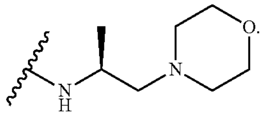 [SMILES: *N[C@@H](C)CN1CCOCC1]

In some embodiments, $R^2$ is

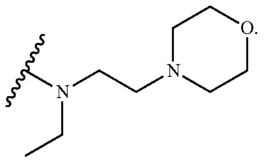 [SMILES: *N(CC)CCN1CCOCC1]

In some embodiments, $R^2$ is

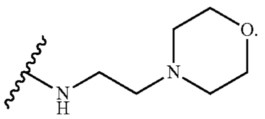 [SMILES: *NCCN1CCOCC1]

In some embodiments, $R^2$ is

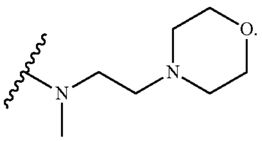 [SMILES: *N(C)CCN1CCOCC1]

In some embodiments, $R^2$ is

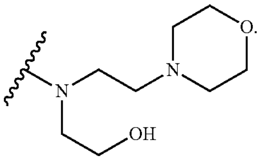 [SMILES: *N(CCO)CCN1CCOCC1]

In some embodiments, $R^2$ is

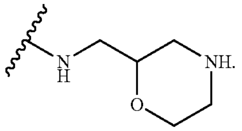 [SMILES: *NCC1CNCCO1]

In some embodiments, $R^2$ is

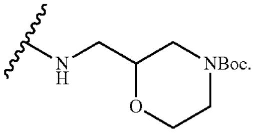 [SMILES: *NCC1CN(C(=O)OC(C)(C)C)CCO1]

In some embodiments, $R^2$ is

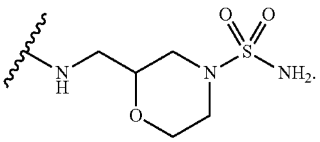 [SMILES: *NCC1CN(S(N)(=O)=O)CCO1]

In some embodiments, $R^2$ is

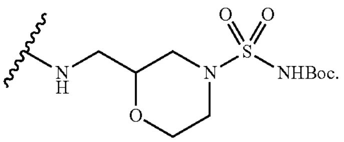 [SMILES: *NCC1CN(S(=O)(=O)NC(=O)OC(C)(C)C)CCO1]

In some embodiments, $R^2$ is

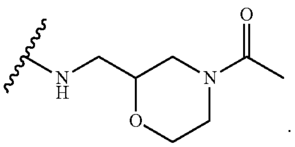 [SMILES: *NCC1CN(C(C)=O)CCO1]

In some embodiments, $R^2$ is

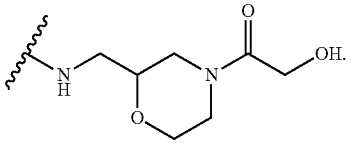 [SMILES: *NCC1CN(C(=O)CO)CCO1]

In some embodiments, $R^2$ is

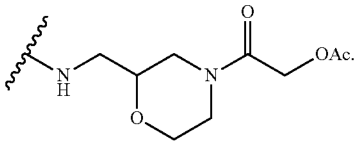 [SMILES: *NCC1CN(C(=O)COC(C)=O)CCO1]

In some embodiments, $R^2$ is

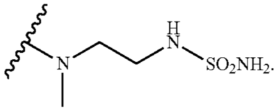 [SMILES: *N(C)CCNS(N)(=O)=O]

In some embodiments, $R^2$ is

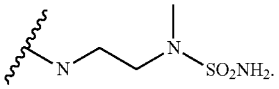

In some embodiments, $R^2$ is

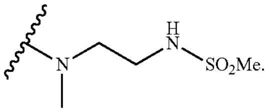 [SMILES: *N(C)CCNS(C)(=O)=O]

In some embodiments, $R^2$ is

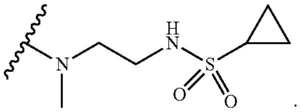 [SMILES: *N(C)CCNS(=O)(=O)C1CC1]

In some embodiments, $R^2$ is

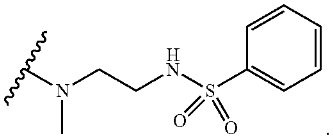 [SMILES: *N(C)CCNS(=O)(=O)c1ccccc1]

In some embodiments, $R^2$ is
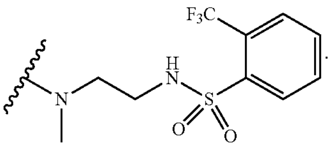 [SMILES: *N(C)CCNS(=O)(=O)c1ccccc1C(F)(F)F]
In some embodiments, $R^2$ is
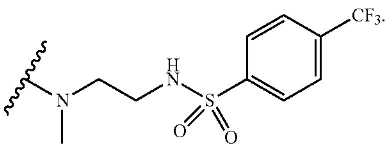 [SMILES: *N(C)CCNS(=O)(=O)c1ccc(C(F)(F)F)cc1]
In some embodiments, $R^2$ is
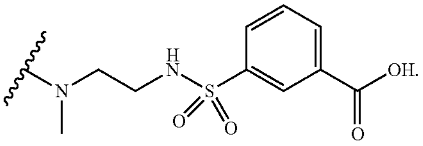 [SMILES: *N(C)CCNS(=O)(=O)c1cccc(C(=O)O)c1]
In some embodiments, $R^2$ is
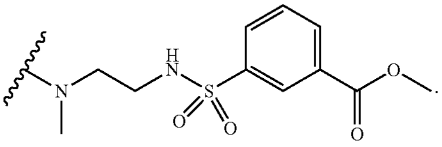 [SMILES: *N(C)CCNS(=O)(=O)c1cccc(C(=O)OC)c1]
In some embodiments, $R^2$ is
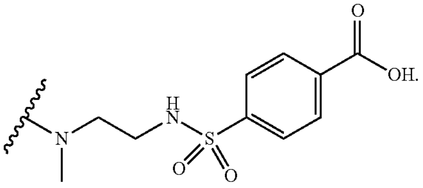 [SMILES: *N(C)CCNS(=O)(=O)c1ccc(C(=O)O)cc1]
In some embodiments, $R^2$ is
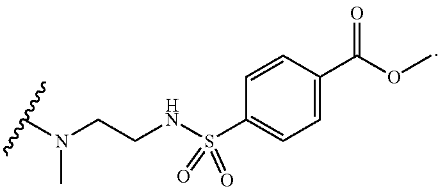 [SMILES: *N(C)CCNS(=O)(=O)c1ccc(C(=O)OC)cc1]
In some embodiments, $R^2$ is
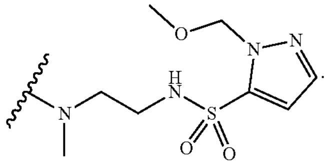 [SMILES: *N(C)CCNS(=O)(=O)c1ccnn1COC]
In some embodiments, $R^2$ is
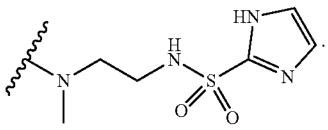 [SMILES: *N(C)CCNS(=O)(=O)c1ncc[nH]1]
In some embodiments, $R^2$ is
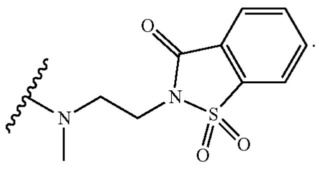 [SMILES: *N(C)CCN1C(=O)c2ccccc2S1(=O)=O]
In some embodiments, $R^2$ is
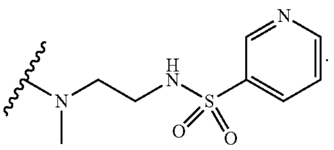 [SMILES: *N(C)CCNS(=O)(=O)c1cccnc1]
In some embodiments, $R^2$ is
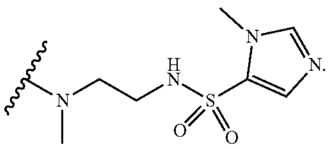 [SMILES: *N(C)CCNS(=O)(=O)c1cncn1C]
In some embodiments, $R^2$ is
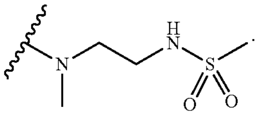 [SMILES: *N(C)CCNS(C)(=O)=O]
In some embodiments, $R^2$ is
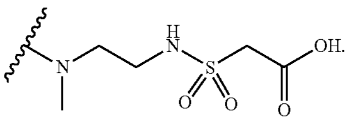 [SMILES: *N(C)CCNS(=O)(=O)CC(=O)O]

In some embodiments, $R^2$ is

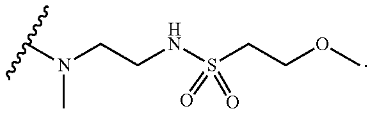 [SMILES: *N(C)CCNS(=O)(=O)CCOC]

In some embodiments, $R^2$ is

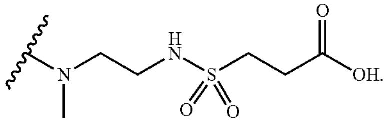 [SMILES: *N(C)CCNS(=O)(=O)CCC(=O)O]

In some embodiments, $R^2$ is

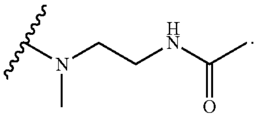 [SMILES: *N(C)CCNC(C)=O]

In some embodiments, $R^2$ is is

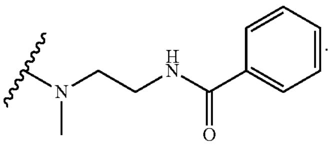 [SMILES: *N(C)CCNC(=O)c1ccccc1]

In some embodiments, $R^2$ is

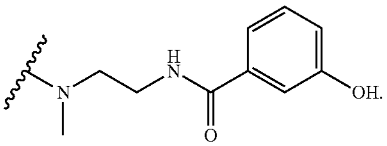 [SMILES: *N(C)CCNC(=O)c1cccc(O)c1]

In some embodiments, $R^2$ is

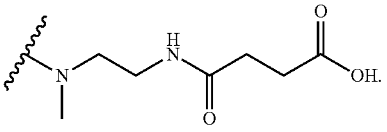 [SMILES: *N(C)CCNC(=O)CCC(=O)O]

In some embodiments, $R^2$ is

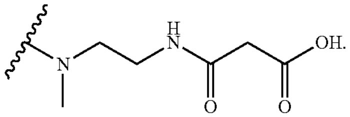 [SMILES: *N(C)CCNC(=O)CC(=O)O]

In some embodiments, $R^2$ is

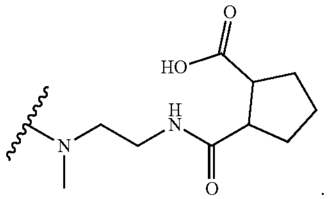 [SMILES: *N(C)CCNC(=O)C1CCCC1C(=O)O]

In some embodiments, $R^2$ is

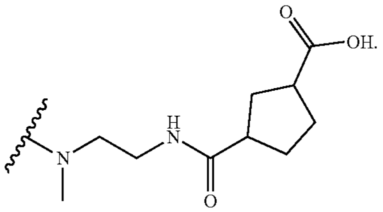 [SMILES: *N(C)CCNC(=O)C1CCC(C(=O)O)C1]

In some embodiments, $R^2$ is

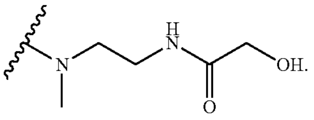 [SMILES: *N(C)CCNC(=O)CO]

In some embodiments, $R^2$ is

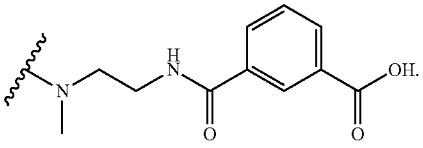 [SMILES: *N(C)CCNC(=O)c1cccc(C(=O)O)c1]

In some embodiments, $R^2$ is

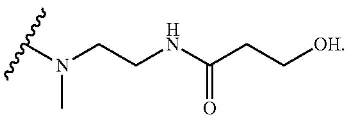 [SMILES: *N(C)CCNC(=O)CCO]

In some embodiments, $R^2$ is

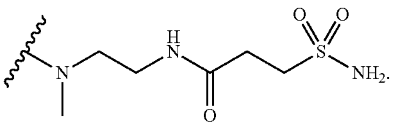 [SMILES: *N(C)CCNC(=O)CCS(N)(=O)=O]

In some embodiments, $R^2$ is

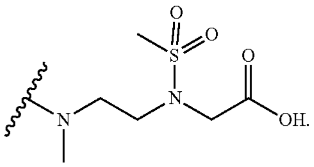 [SMILES: *N(C)CCN(CC(=O)O)S(C)(=O)=O]

In some embodiments, $R^2$ is

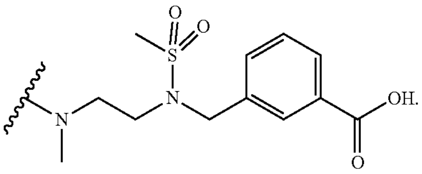 [SMILES: *N(C)CCN(Cc1cccc(C(=O)O)c1)S(C)(=O)=O]

In some embodiments, $R^2$ is

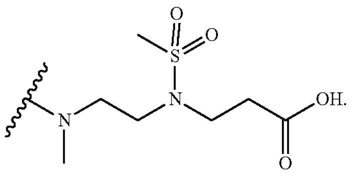 [SMILES: *N(C)CCN(CCC(=O)O)S(C)(=O)=O]

In some embodiments, $R^2$ is

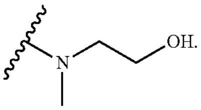 [SMILES: *N(C)CCO]

In some embodiments, $R^2$ is

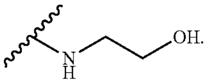 [SMILES: *NCCO]

In some embodiments, $R^2$ is

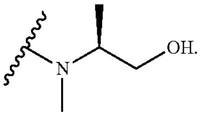 [SMILES: *N(C)[C@@H](C)CO]

In some embodiments, $R^2$ is

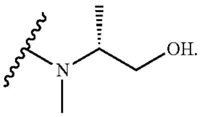 [SMILES: *N(C)[C@H](C)CO]

In some embodiments, $R^2$ is

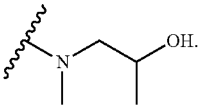 [SMILES: *N(C)CC(C)O]

In some embodiments, $R^2$ is

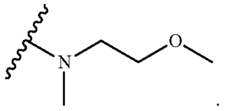 [SMILES: *N(C)CCOC]

In some embodiments, $R^2$ is

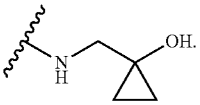 [SMILES: *NCC1(O)CC1]

In some embodiments, $R^2$ is

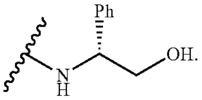

In some embodiments, $R^2$ is

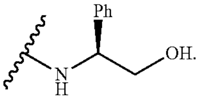 [SMILES: *N[C@H](CO)c1ccccc1]

In some embodiments, $R^2$ is

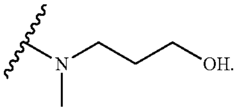 [SMILES: *N(C)CCCO]

In some embodiments, $R^2$ is

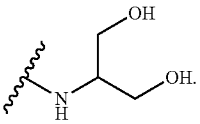 [SMILES: *NC(CO)CO]

In some embodiments, $R^2$ is

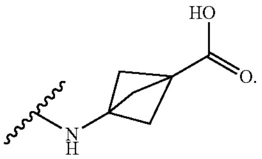 [SMILES: *NC12CC(C(=O)O)(C1)C2]

In some embodiments, $R^2$ is

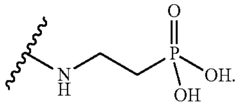 [SMILES: *NCCP(=O)(O)O]

In some embodiments, $R^2$ is

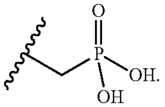 [SMILES: *CP(=O)(O)O]

In some embodiments, $R^2$ is

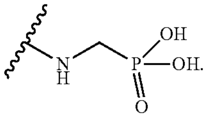 [SMILES: *NCP(=O)(O)O]

In some embodiments, $R^2$ is

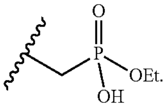 [SMILES: *CP(=O)(O)OCC]

In some embodiments, $R^2$ is

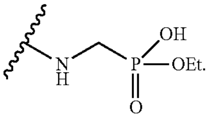 [SMILES: *NCP(=O)(O)OCC]

In some embodiments, $R^2$ is

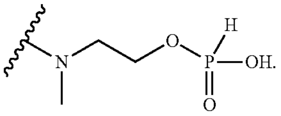 [SMILES: *N(C)CCO[PH](=O)O]

In some embodiments, $R^2$ is

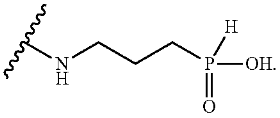 [SMILES: *NCCC[PH](=O)O]

In some embodiments, $R^2$ is

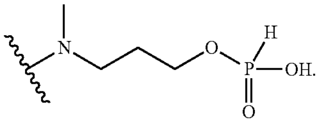 [SMILES: *N(C)CCCO[PH](=O)O]

In some embodiments, $R^2$ is

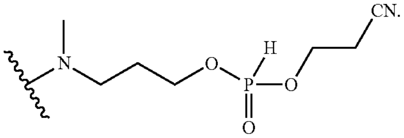 [SMILES: *N(C)CCCO[PH](=O)OCCC#N]

In some embodiments, $R^2$ is

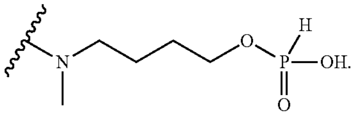 [SMILES: *N(C)CCCCO[PH](=O)O]

In some embodiments, $R^2$ is

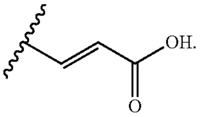 [SMILES: */C=C/C(=O)O]

In some embodiments, $R^2$ is

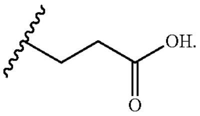 [SMILES: *CCC(=O)O]

In some embodiments, $R^2$ is

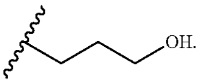 [SMILES: *CCCO]

In some embodiments, $R^2$ is

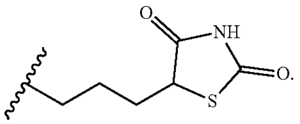 [SMILES: *CCCC1SC(=O)NC1=O]

In some embodiments, $R^2$ is

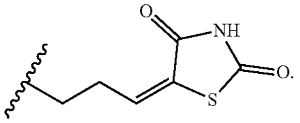 [SMILES: *CC/C=C1/SC(=O)NC1=O]

In some embodiments, $R^2$ is

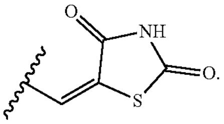 [SMILES: */C=C1/SC(=O)NC1=O]

In some embodiments, $R^2$ is

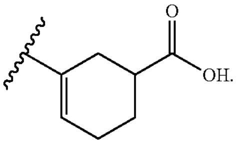 [SMILES: *C1=CCCC(C(=O)O)C1]

In some embodiments, $R^2$ is

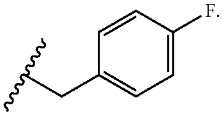 [SMILES: *Cc1ccc(F)cc1]

In some embodiments, $R^2$ is

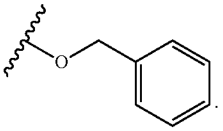 [SMILES: *OCc1ccccc1]

In some embodiments, $R^2$ is

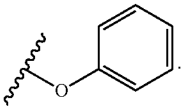

In some embodiments, $R^2$ is

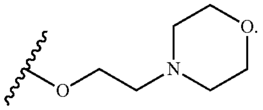 [SMILES: *OCCN1CCOCC1]

In some embodiments, $R^2$ is

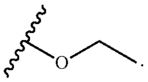

In some embodiments, $R^2$ is

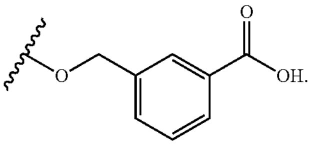 [SMILES: *OCc1cccc(C(=O)O)c1]

In some embodiments, $R^2$ is

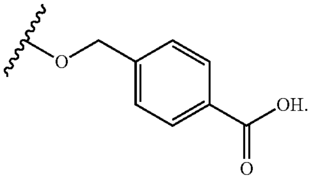 [SMILES: *OCc1ccc(C(=O)O)cc1]

In some embodiments, $R^2$ is

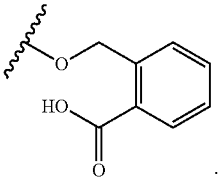 [SMILES: *OCc1ccccc1C(=O)O]

In some embodiments, $R^2$ is

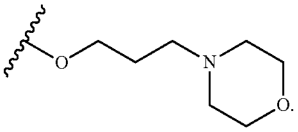 [SMILES: *OCCCN1CCOCC1]

In some embodiments, $R^2$ is

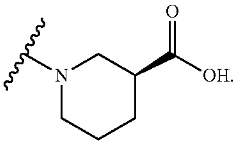 [SMILES: *N1CCC[C@H](C(=O)O)C1]

In some embodiments, $R^2$ is
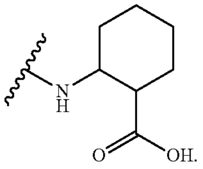 [SMILES: *NC1CCCCC1C(=O)O]
In some embodiments, $R^2$ is
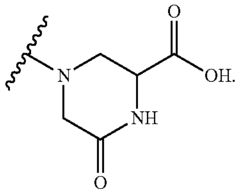 [SMILES: *N1CC(=O)NC(C(=O)O)C1]
In some embodiments, $R^2$ is
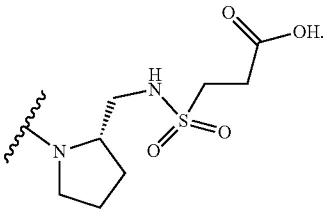 [SMILES: *N1CCC[C@H]1CNS(=O)(=O)CCC(=O)O]
In some embodiments, $R^2$ is
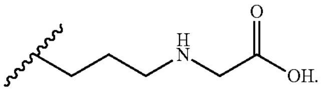 [SMILES: *CCCNCC(=O)O]
In some embodiments, $R^2$ is
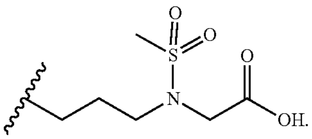 [SMILES: *CCCN(CC(=O)O)S(C)(=O)=O]
In some embodiments, $R^2$ is
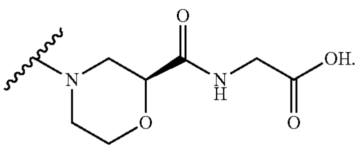 [SMILES: *N1CCO[C@H](C(=O)NCC(=O)O)C1]
In some embodiments, $R^2$ is
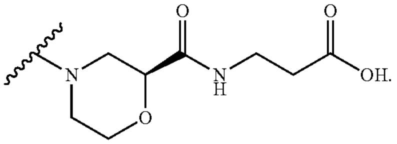 [SMILES: *N1CCO[C@H](C(=O)NCCC(=O)O)C1]
In some embodiments, $R^2$ is
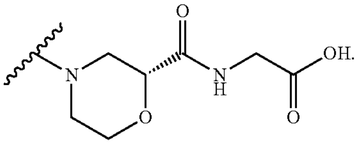 [SMILES: *N1CCO[C@@H](C(=O)NCC(=O)O)C1]
In some embodiments, $R^2$ is
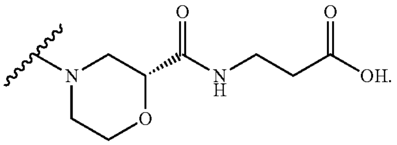 [SMILES: *N1CCO[C@@H](C(=O)NCCC(=O)O)C1]
In some embodiments, $R^2$ is
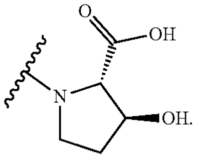 [SMILES: *N1CC[C@H](O)[C@H]1C(=O)O]
In some embodiments, $R^2$ is
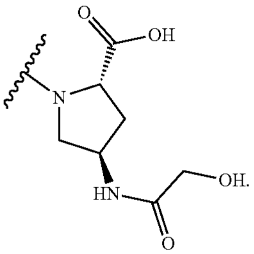 [SMILES: *N1C[C@H](NC(=O)CO)C[C@H]1C(=O)O]
In some embodiments, $R^2$ is
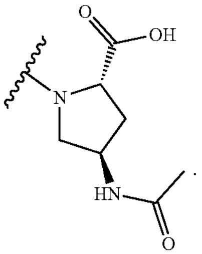 [SMILES: *N1C[C@H](NC(C)=O)C[C@H]1C(=O)O]

In some embodiments, $R^2$ is
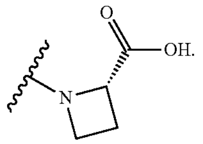 [SMILES: *N1CC[C@H]1C(=O)O]
In some embodiments, $R^2$ is
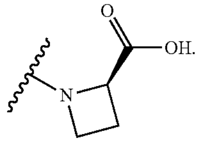 [SMILES: *N1CC[C@@H]1C(=O)O]
In some embodiments, $R^2$ is
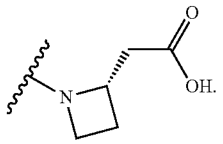 [SMILES: *N1CC[C@H]1CC(=O)O]
In some embodiments, $R^2$ is
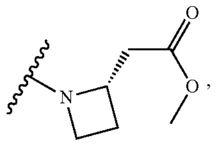 [SMILES: *N1CC[C@H]1CC(=O)OC]
In some embodiments, $R^2$ is
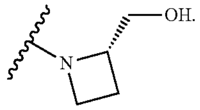 [SMILES: *N1CC[C@H]1CO]
In some embodiments, $R^2$ is
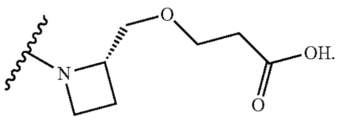 [SMILES: *N1CC[C@H]1COCCC(=O)O]
In some embodiments, $R^2$ is
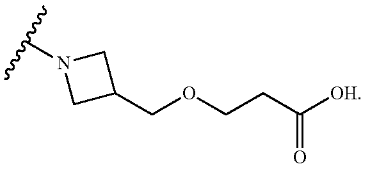 [SMILES: *N1CC(COCCC(=O)O)C1]
In some embodiments, $R^2$ is
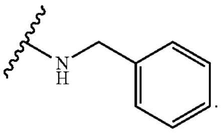 [SMILES: *NCc1ccccc1]
In some embodiments, $R^2$ is
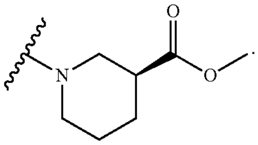 [SMILES: *N1CCC[C@H](C(=O)OC)C1]
In some embodiments, $R^2$ is
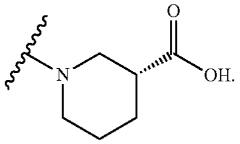 [SMILES: *N1CCC[C@@H](C(=O)O)C1]
In some embodiments, $R^2$ is
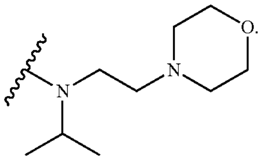 [SMILES: *N(CCN1CCOCC1)C(C)C]
In some embodiments, $R^2$ is
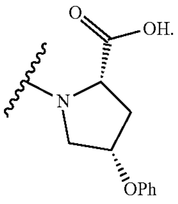 [SMILES: *N1C[C@@H](Oc2ccccc2)C[C@H]1C(=O)O]
In some embodiments, $R^2$ is
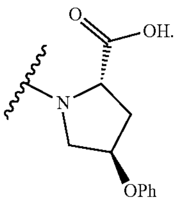 [SMILES: *N1C[C@H](Oc2ccccc2)C[C@H]1C(=O)O]

In some embodiments, $R^2$ is

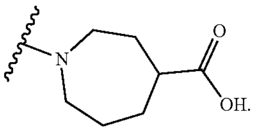 [SMILES: *N1CCCC(C(=O)O)CC1]

In some embodiments, $R^2$ is

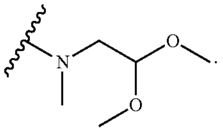 [SMILES: *N(C)CC(OC)OC]

In some embodiments, $R^2$ is

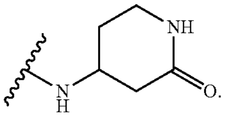 [SMILES: *NC1CCNC(=O)C1]

In some embodiments, $R^2$ is

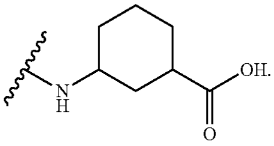 [SMILES: *NC1CCCC(C(=O)O)C1]

In some embodiments, $R^2$ is

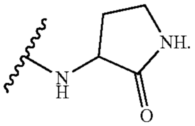 [SMILES: *NC1CCNC1=O]

In some embodiments, $R^2$ is

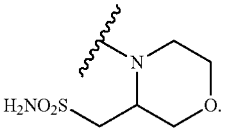

In some embodiments, $R^2$ is

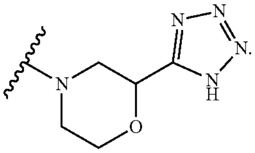 [SMILES: *N1CCOC(c2nnn[nH]2)C1]

In some embodiments, $R^2$ is

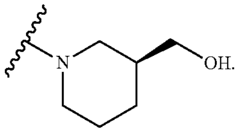 [SMILES: *N1CCC[C@H](CO)C1]

In some embodiments, $R^2$ is

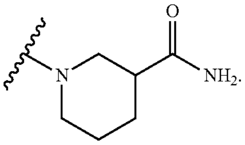 [SMILES: *N1CCCC(C(N)=O)C1]

In some embodiments, $R^2$ is

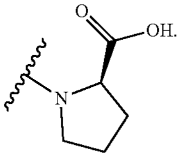 [SMILES: *N1CCC[C@@H]1C(=O)O]

In some embodiments, $R^2$ is

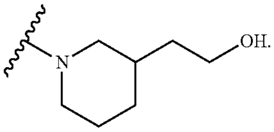 [SMILES: *N1CCCC(CCO)C1]

In some embodiments, $R^2$ is

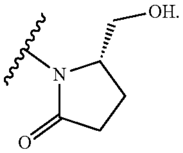 [SMILES: *N1C(=O)CC[C@H]1CO]

In some embodiments, $R^2$ is

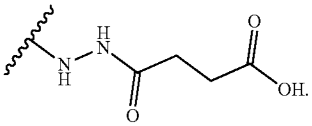 [SMILES: *NNC(=O)CCC(=O)O]

In some embodiments, $R^2$ is

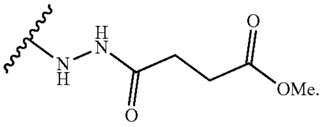 [SMILES: *NNC(=O)CCC(=O)OC]

In some embodiments, $R^2$ is selected from those groups depicted in Table 1.

As defined above and described herein, each $R^3$ is independently halogen, —OR, —$NR_2$, —SR, or $R^C$, particularly halogen, such as chloro.

In some embodiments, $R^3$ is halogen. In some embodiments, $R^3$ is —OR. In some embodiments, $R^3$ is —$NR_2$. In some embodiments, $R^3$ is —SR. In some embodiments, $R^3$ is $R^C$.

In some embodiments, $R^3$ is fluoro. In some embodiments, $R^3$ is chloro. In some embodiments, $R^3$ is bromo. In some embodiments, $R^3$ is —OH. In some embodiments, $R^3$ is —OMe. In some embodiments, $R^3$ is —OEt. In some embodiments, $R^3$ is methyl. In some embodiments, $R^3$ is isopropyl. In some embodiments, $R^3$ is tert-butyl. In some embodiments, $R^3$ is —$CF_3$. In some embodiments, $R^3$ is phenyl. In some embodiments, $R^3$ is

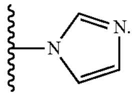

In some embodiments, $R^3$ is selected from those groups depicted in Table 1.

As defined above and described herein, $R^4$ is hydrogen or an optionally substituted $C_{1-6}$ aliphatic.

In some embodiments, $R^4$ is hydrogen. In some embodiments, $R^4$ is an optionally substituted $C_{1-6}$ aliphatic. In some embodiments, $R^4$ is methyl.

In some embodiments, $R^4$ is selected from those groups depicted in Table 1.

As defined above and described herein, $R^5$ is —$(CR_2)_{0-6}OR$, —$(CR_2)_{0-6}CO_2R$, —$(CR_2)_{0-6}CONR_2$, —$(CR_2)_{0-6}C(O)NR(CR_2)_{0-6}CO_2R$, —$(CR_2)_{0-6}C(O)NR(CR_2)_{0-6}CONR_2$, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, or $R^B$ In some embodiments, $R^5$ is —$(CR_2)_{0-6}OR$. In some embodiments, $R^5$ is —$(CR_2)_{0-6}CO_2R$. In some embodiments, $R^5$ is —$(CR_2)_{0-6}CONR_2$. In some embodiments, $R^5$ is —$(CR_2)_{0-6}C(O)NR(CR_2)_{0-6}CO_2R$. In some embodiments, $R^5$ is —$(CR_2)_{0-6}C(O)NR(CR_2)_{0-6}CONR_2$. In some embodiments, $R^5$ is —$(CR_2)_{0-6}SO_3R$. In some embodiments, $R^5$ is —$(CR_2)_{0-6}SO_2NR_2$. In some embodiments, $R^5$ is —$(CR_2)_{0-6}OSO_2NR_2$. In some embodiments, $R^5$ is —$(CR_2)_{0-6}NRSO_2R$. In some embodiments, $R^5$ is —$(CR_2)_{0-6}NRSO_2OR$. In some embodiments, $R^5$ is —$(CR_2)_{0-6}OP(OR)_2$. In some embodiments, $R^5$ is —$(CR_2)_{0-6}OP(O)(OR)_2$. In some embodiments, $R^5$ is —$(CR_2)_{0-6}P(O)(OR)_2$. In some embodiments, $R^5$ is —$(CR_2)_{0-6}OP(O)(H)OR$. In some embodiments, $R^5$ is $R^B$.

In some embodiments, $R^5$ is

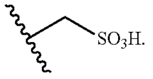

In some embodiments, $R^5$ is

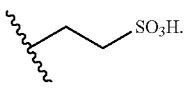

In some embodiments, $R^5$ is

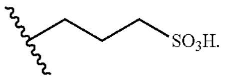 [SMILES: *CCCS(=O)(=O)O]

In some embodiments, $R^5$ is

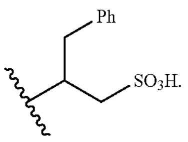 [SMILES: *C(Cc1ccccc1)CS(=O)(=O)O]

In some embodiments, $R^5$ is

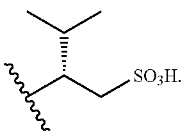 [SMILES: *[C@@H](CS(=O)(=O)O)C(C)C]

In some embodiments, $R^5$ is

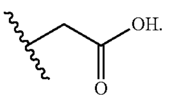

In some embodiments, $R^5$ is

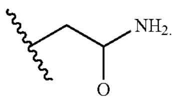 [SMILES: *CC(N)O]

In some embodiments, $R^5$ is

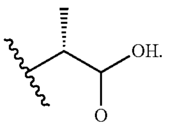 [SMILES: *[C@H](C)C(O)O]

In some embodiments, $R^5$ is

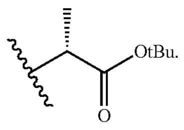 [SMILES: *[C@H](C)C(=O)OC(C)(C)C]

In some embodiments, $R^5$ is

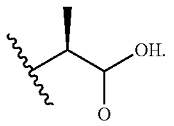 [SMILES: *[C@@H](C)C(O)O]

In some embodiments, $R^5$ is

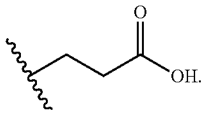 [SMILES: *CCC(=O)O]

In some embodiments, $R^5$ is

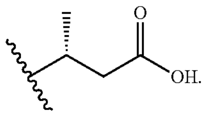 [SMILES: *[C@H](C)CC(=O)O]

In some embodiments, $R^5$ is

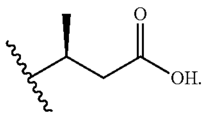 [SMILES: *[C@@H](C)CC(=O)O]

In some embodiments, $R^5$ is

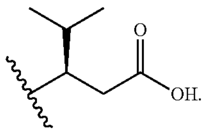 [SMILES: *[C@H](CC(=O)O)C(C)C]

In some embodiments, $R^5$ is

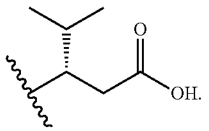 [SMILES: *[C@@H](CC(=O)O)C(C)C]

In some embodiments, $R^5$ is

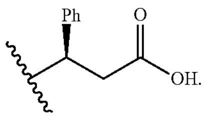 [SMILES: *[C@H](CC(=O)O)c1ccccc1]

In some embodiments, $R^5$ is

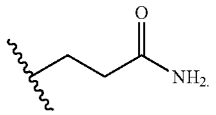 [SMILES: *CCC(N)=O]

In some embodiments, $R^5$ is

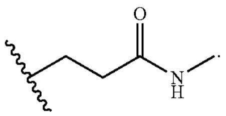 [SMILES: *CCC(=O)NC]

In some embodiments, $R^5$ is

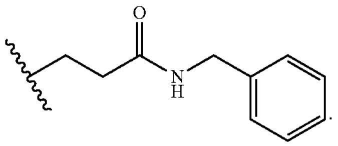 [SMILES: *CCC(=O)NCc1ccccc1]

In some embodiments, $R^5$ is

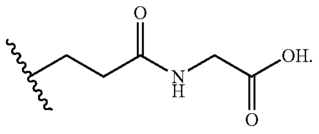 [SMILES: *CCC(=O)NCC(=O)O]

In some embodiments, $R^5$ is

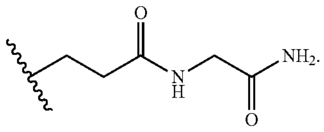 [SMILES: *CCC(=O)NCC(N)=O]

In some embodiments, $R^5$ is

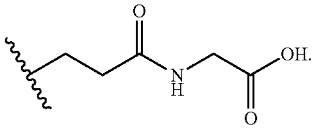 [SMILES: *CCC(=O)NCC(=O)O]

In some embodiments, $R^5$ is

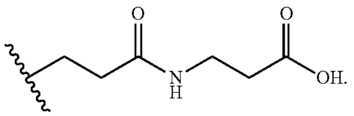 [SMILES: *CCC(=O)NCCC(=O)O]

In some embodiments, $R^5$ is

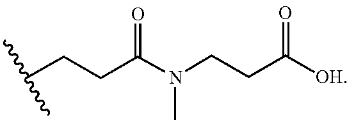 [SMILES: *CCC(=O)N(C)CCC(=O)O]

In some embodiments, $R^5$ is

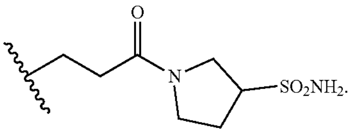 [SMILES: *CCC(=O)N1CCC(S(N)(=O)=O)C1]

In some embodiments, $R^5$ is

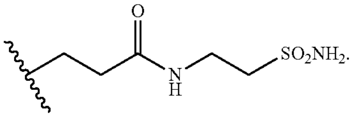 [SMILES: *CCC(=O)NCCS(N)(=O)=O]

In some embodiments, $R^5$ is

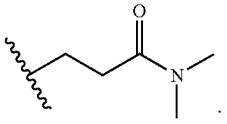 [SMILES: *CCC(=O)N(C)C]

In some embodiments, $R^5$ is

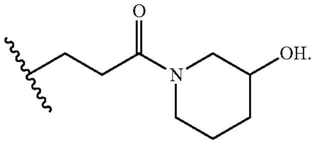 [SMILES: *CCC(=O)N1CCCC(O)C1]

In some embodiments, $R^5$ is

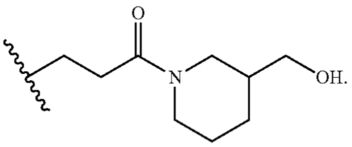 [SMILES: *CCC(=O)N1CCCC(CO)C1]

In some embodiments, $R^5$ is

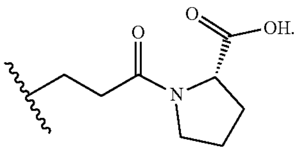 [SMILES: *CCC(=O)N1CCC[C@H]1C(=O)O]

In some embodiments, $R^5$ is

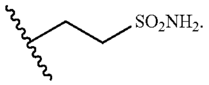 [SMILES: *CCS(N)(=O)=O]

In some embodiments, $R^5$ is

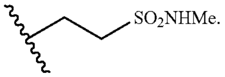

In some embodiments, $R^5$ is

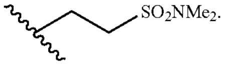

In some embodiments, $R^5$ is

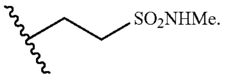

In some embodiments, $R^5$ is

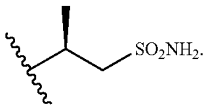 [SMILES: *[C@@H](C)CS(N)(=O)=O]

In some embodiments, $R^5$ is

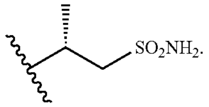 [SMILES: *[C@H](C)CS(N)(=O)=O]

In some embodiments, $R^5$ is

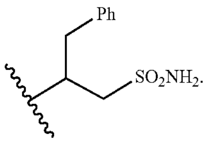 [SMILES: *C(Cc1ccccc1)CS(N)(=O)=O]

In some embodiments, $R^5$ is

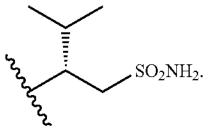 [SMILES: *[C@@H](CS(N)(=O)=O)C(C)C]

In some embodiments, $R^5$ is

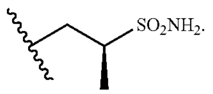 [SMILES: *C[C@H](C)S(N)(=O)=O]

In some embodiments, $R^5$ is

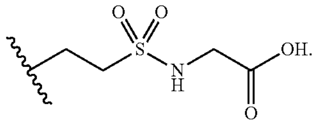 [SMILES: *CCS(=O)(=O)NCC(=O)O]

In some embodiments, $R^5$ is

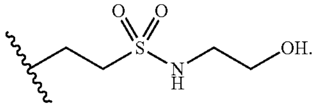 [SMILES: *CCS(=O)(=O)NCCO]

In some embodiments, $R^5$ is

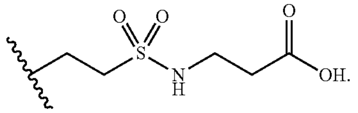 [SMILES: *CCS(=O)(=O)NCCC(=O)O]

In some embodiments, $R^5$ is

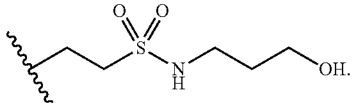 [SMILES: *CCS(=O)(=O)NCCCO]

In some embodiments, $R^5$ is

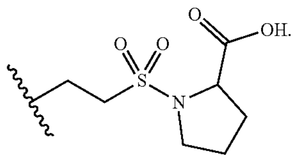 [SMILES: *CCS(=O)(=O)N1CCCC1C(=O)O]

In some embodiments, $R^5$ is

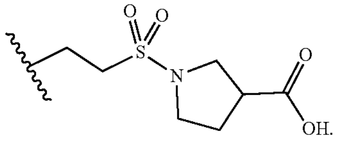 [SMILES: *CCS(=O)(=O)N1CCC(C(=O)O)C1]

In some embodiments, $R^5$ is

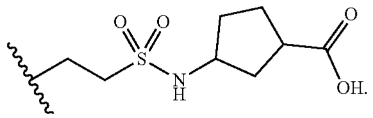 [SMILES: *CCS(=O)(=O)NC1CCC(C(=O)O)C1]

In some embodiments, $R^5$ is

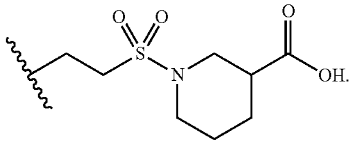 [SMILES: *CCS(=O)(=O)N1CCCC(C(=O)O)C1]

In some embodiments, $R^5$ is

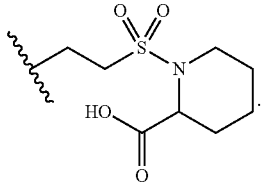 [SMILES: *CCS(=O)(=O)N1CCCCC1C(=O)O]

In some embodiments, $R^5$ is

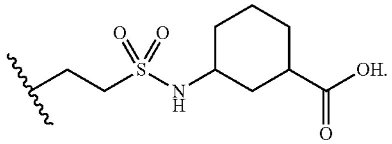 [SMILES: *CCS(=O)(=O)NC1CCCC(C(=O)O)C1]

In some embodiments, $R^5$ is

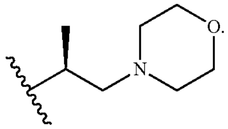 [SMILES: *[C@@H](C)CN1CCOCC1]

In some embodiments, $R^5$ is

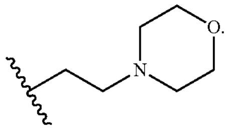 [SMILES: *CCN1CCOCC1]

In some embodiments, $R^5$ is

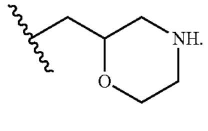 [SMILES: *CC1CNCCO1]

In some embodiments, $R^5$ is
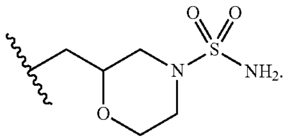 [SMILES: *CC1CN(S(N)(=O)=O)CCO1]
In some embodiments, $R^5$ is
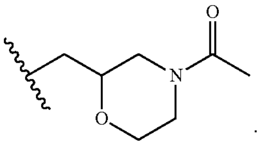 [SMILES: *CC1CN(C(C)=O)CCO1]
In some embodiments, $R^5$ is
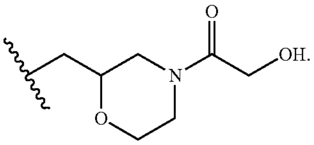 [SMILES: *CC1CN(C(=O)CO)CCO1]
In some embodiments, $R^5$ is
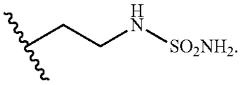 [SMILES: *CCNS(N)(=O)=O]
In some embodiments, $R^5$ is
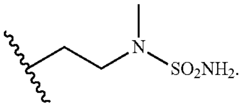 [SMILES: *CCN(C)S(N)(=O)=O]
In some embodiments, $R^5$ is
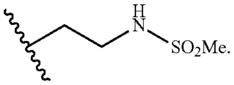 [SMILES: *CCNS(C)(=O)=O]
In some embodiments, $R^5$ is
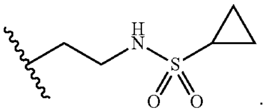 [SMILES: *CCNS(=O)(=O)C1CC1]
In some embodiments, $R^5$ is
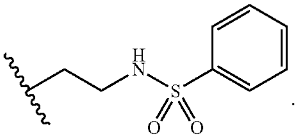 [SMILES: *CCNS(=O)(=O)c1ccccc1]
In some embodiments, $R^5$ is
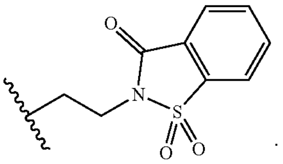 [SMILES: *CCN1C(=O)c2ccccc2S1(=O)=O]
In some embodiments, $R^5$ is
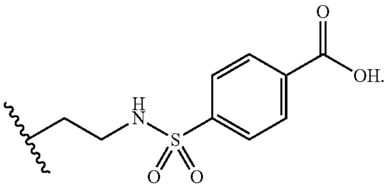 [SMILES: *CCNS(=O)(=O)c1ccc(C(=O)O)cc1]
In some embodiments, $R^5$ is
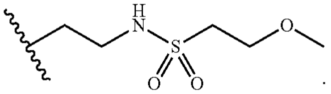 [SMILES: *CCNS(=O)(=O)CCOC]
In some embodiments, $R^5$ is
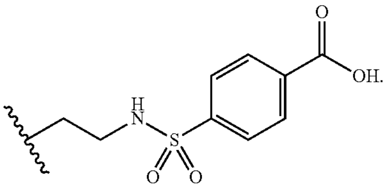 [SMILES: *CCNS(=O)(=O)c1ccc(C(=O)O)cc1]
In some embodiments, $R^5$ is
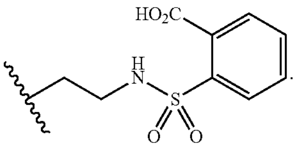 [SMILES: *CCNS(=O)(=O)c1ccccc1C(=O)O]

In some embodiments, $R^5$ is
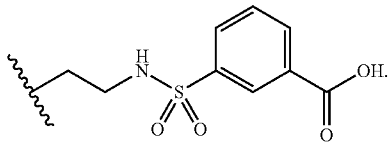 [SMILES: *CCNS(=O)(=O)c1cccc(C(=O)O)c1]
In some embodiments, $R^5$ is
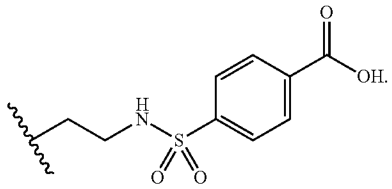 [SMILES: *CCNS(=O)(=O)c1ccc(C(=O)O)cc1]
In some embodiments, $R^5$ is
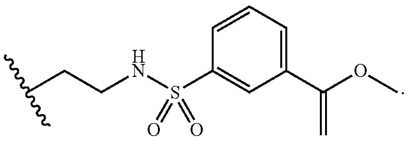 [SMILES: *CCNS(=O)(=O)c1cccc(C(=C)OC)c1]
In some embodiments, $R^5$ is
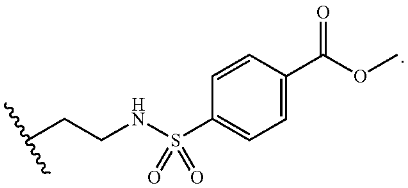 [SMILES: *CCNS(=O)(=O)c1ccc(C(=O)OC)cc1]
In some embodiments, $R^5$ is
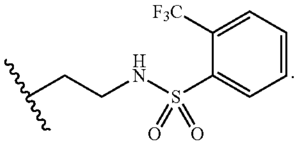 [SMILES: *CCNS(=O)(=O)c1ccccc1C(F)(F)F]
In some embodiments, $R^5$ is
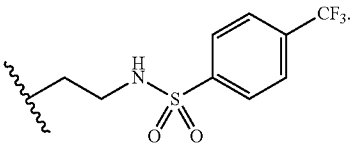 [SMILES: *CCNS(=O)(=O)c1ccc(C(F)(F)F)cc1]
In some embodiments, $R^5$ is
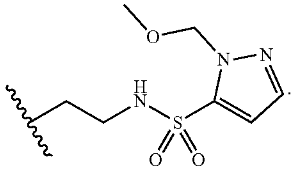 [SMILES: *CCNS(=O)(=O)c1ccnn1COC]
In some embodiments, $R^5$ is
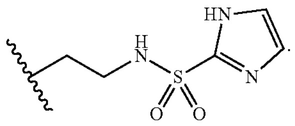 [SMILES: *CCNS(=O)(=O)c1ncc[nH]1]
In some embodiments, $R^5$ is
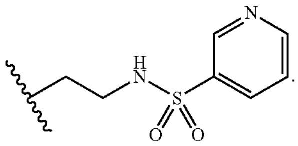 [SMILES: *CCNS(=O)(=O)c1cccnc1]
In some embodiments, $R^5$ is
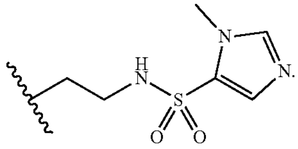 [SMILES: *CCNS(=O)(=O)c1cncn1C]
In some embodiments, $R^5$ is
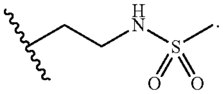 [SMILES: *CCNS(C)(=O)=O]
In some embodiments, $R^5$ is
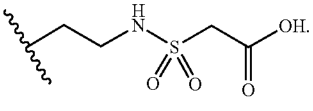 [SMILES: *CCNS(=O)(=O)CC(=O)O]
In some embodiments, $R^5$ is
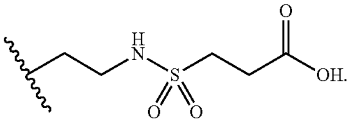 [SMILES: *CCNS(=O)(=O)CCC(=O)O]

In some embodiments, $R^5$ is
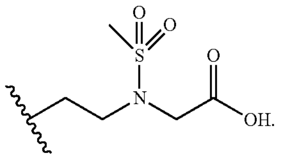 [SMILES: *CCN(CC(=O)O)S(C)(=O)=O]
In some embodiments, $R^5$ is
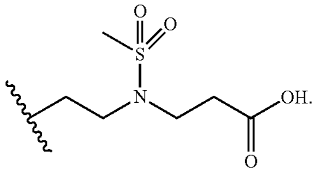 [SMILES: *CCN(CCC(=O)O)S(C)(=O)=O]
In some embodiments, $R^5$ is
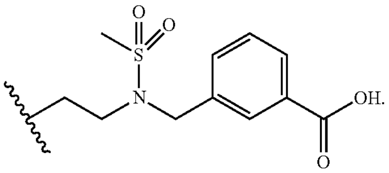 [SMILES: *CCN(Cc1cccc(C(=O)O)c1)S(C)(=O)=O]
In some embodiments, $R^5$ is
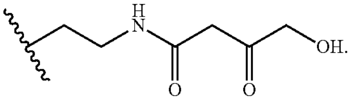 [SMILES: *CCNC(=O)CC(=O)CO]
In some embodiments, $R^5$ is
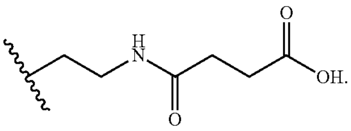 [SMILES: *CCNC(=O)CCC(=O)O]
In some embodiments, $R^5$ is
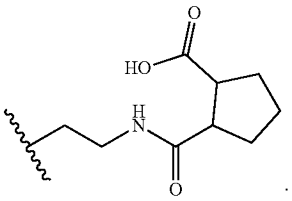 [SMILES: *CCNC(=O)C1CCCC1C(=O)O]
In some embodiments, $R^5$ is
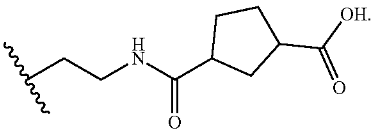 [SMILES: *CCNC(=O)C1CCC(C(=O)O)C1]
In some embodiments, $R^5$ is
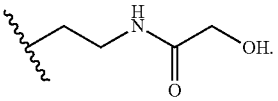 [SMILES: *CCNC(=O)CO]
In some embodiments, $R^5$ is
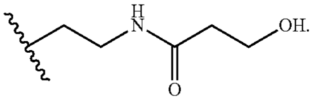 [SMILES: *CCNC(=O)CCO]
In some embodiments, $R^5$ is
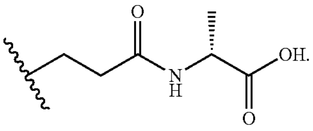 [SMILES: *CCC(=O)N[C@H](C)C(=O)O]
In some embodiments, $R^5$ is
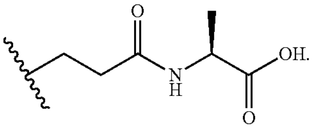 [SMILES: *CCC(=O)N[C@@H](C)C(=O)O]
In some embodiments, $R^5$ is
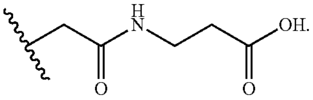 [SMILES: *CC(=O)NCCC(=O)O]
In some embodiments, $R^5$ is
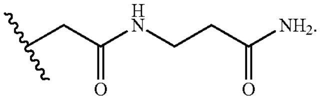 [SMILES: *CC(=O)NCCC(N)=O]

In some embodiments, $R^5$ is

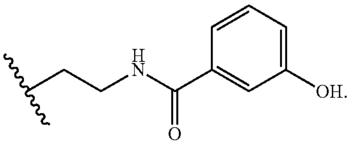 [SMILES: *CCNC(=O)c1cccc(O)c1]

In some embodiments, $R^5$ is

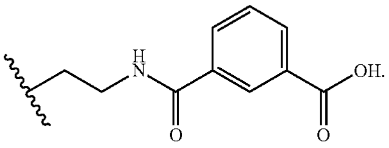 [SMILES: *CCNC(=O)c1cccc(C(=O)O)c1]

In some embodiments, $R^5$ is

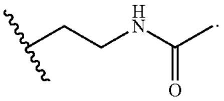 [SMILES: *CCNC(C)=O]

In some embodiments, $R^5$ is

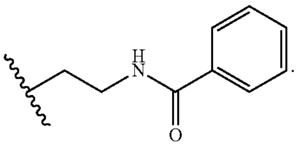 [SMILES: *CCNC(=O)c1ccccc1]

In some embodiments, $R^5$ is

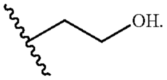 [SMILES: *CCO]

In some embodiments, $R^5$ is

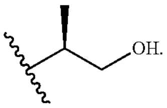 [SMILES: *[C@@H](C)CO]

In some embodiments, $R^5$ is

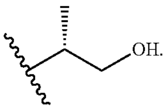 [SMILES: *[C@H](C)CO]

In some embodiments, $R^5$ is

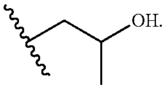 [SMILES: *CC(C)O]

In some embodiments, $R^5$ is

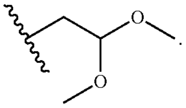 [SMILES: *CC(OC)OC]

In some embodiments, $R^5$ is

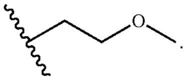 [SMILES: *CCOC]

In some embodiments, $R^5$ is

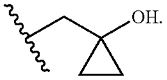 [SMILES: *CC1(O)CC1]

In some embodiments, $R^5$ is

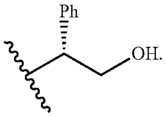

In some embodiments, $R^5$ is

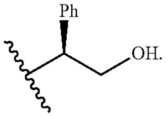 [SMILES: *[C@H](CO)c1ccccc1]

In some embodiments, $R^5$ is

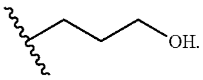

In some embodiments, $R^5$ is

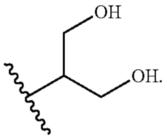 [SMILES: *C(CO)CO]

In some embodiments, $R^5$ is

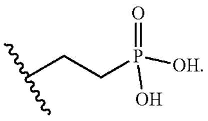 [SMILES: *CCP(=O)(O)O]

In some embodiments, $R^5$ is

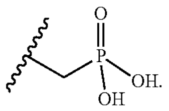

In some embodiments, $R^5$ is

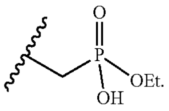 [SMILES: *CP(=O)(O)OCC]

In some embodiments, $R^5$ is

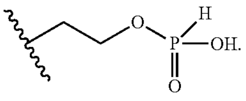 [SMILES: *CCO[PH](=O)O]

In some embodiments, $R^5$ is

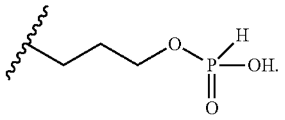 [SMILES: *CCCO[PH](=O)O]

In some embodiments, $R^5$ is

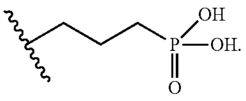 [SMILES: *CCCP(=O)(O)O]

In some embodiments, $R^5$ is

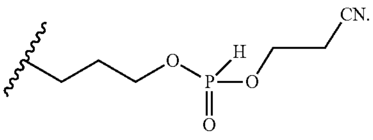 [SMILES: *CCCO[PH](=O)OCCC#N]

In some embodiments, $R^5$ is

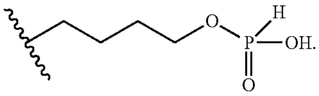 [SMILES: *CCCCO[PH](=O)O]

In some embodiments, $R^5$ is

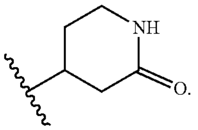 [SMILES: *C1CCNC(=O)C1]

In some embodiments, $R^5$ is

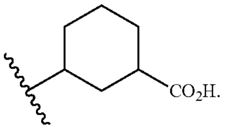 [SMILES: *C1CCCC(C(=O)O)C1]

In some embodiments, $R^5$ is

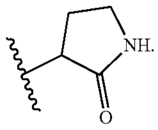 [SMILES: *C1CCNC1=O]

In some embodiments, $R^5$ is

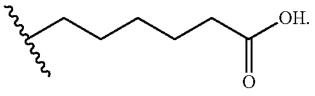 [SMILES: *CCCCCC(=O)O]

In some embodiments, $R^5$ is

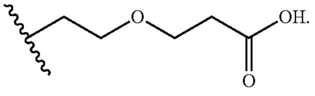 [SMILES: *CCOCCC(=O)O]

In some embodiments, $R^5$ is

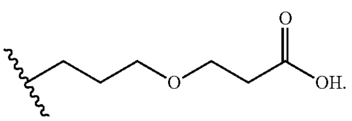 [SMILES: *CCCOCCC(=O)O]

In some embodiments, $R^5$ is

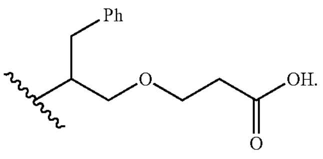 [SMILES: *C(COCCC(=O)O)Cc1ccccc1]

In some embodiments, $R^5$ is

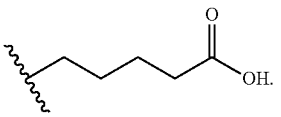 [SMILES: *CCCCC(=O)O]

In some embodiments, $R^5$ is

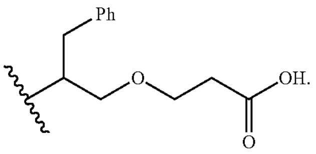 [SMILES: *C(COCCC(=O)O)Cc1ccccc1]

In some embodiments, $R^2$ is

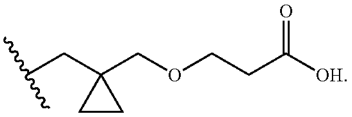 [SMILES: *CC1(COCCC(=O)O)CC1]

In some embodiments, $R^5$ is

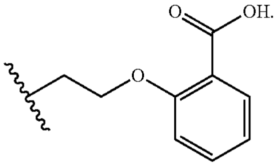 [SMILES: *CCOc1ccccc1C(=O)O]

In some embodiments, $R^5$ is

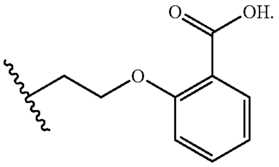 [SMILES: *CCOc1ccccc1C(=O)O]

In some embodiments, $R^5$ is

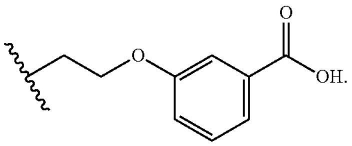 [SMILES: *CCOc1cccc(C(=O)O)c1]

In some embodiments, $R^5$ is

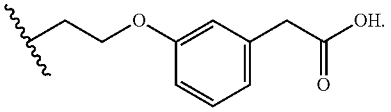 [SMILES: *CCOc1cccc(CC(=O)O)c1]

In some embodiments, $R^5$ is

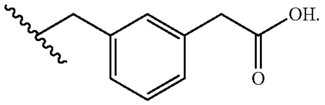 [SMILES: *Cc1cccc(CC(=O)O)c1]

In some embodiments, $R^5$ is

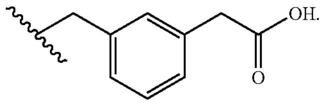 [SMILES: *Cc1cccc(CC(=O)O)c1]

In some embodiments, $R^5$ is

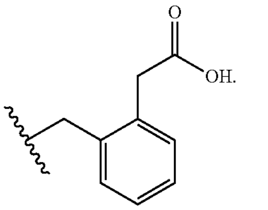 [SMILES: *Cc1ccccc1CC(=O)O]

In some embodiments, $R^5$ is

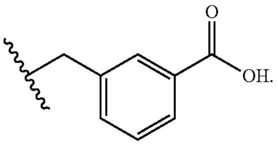 [SMILES: *Cc1cccc(C(=O)O)c1]

In some embodiments, $R^2$ is

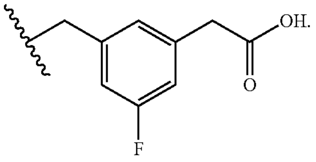 [SMILES: *Cc1cc(F)cc(CC(=O)O)c1]

In some embodiments, $R^2$ is

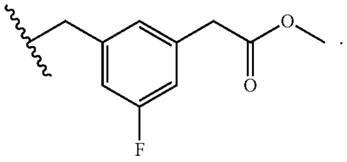 [SMILES: *Cc1cc(F)cc(CC(=O)OC)c1]

In some embodiments, $R^5$ is

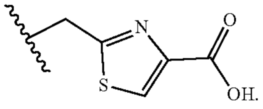 [SMILES: *Cc1nc(C(=O)O)cs1]

In some embodiments, $R^5$ is

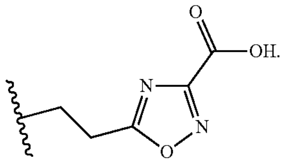 [SMILES: *CCc1nc(C(=O)O)no1]

In some embodiments, $R^5$ is

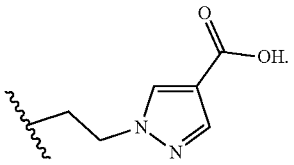 [SMILES: *CCn1cc(C(=O)O)cn1]

In some embodiments, $R^5$ is

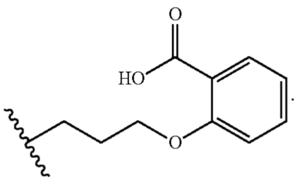

In some embodiments, $R^5$ is

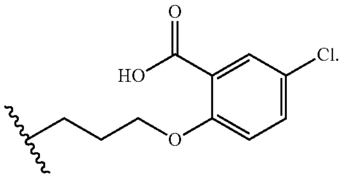 [SMILES: *CCCOc1ccc(Cl)cc1C(=O)O]

In some embodiments, $R^5$ is

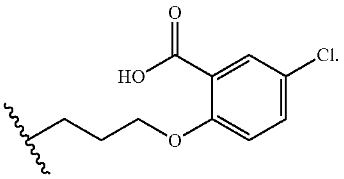 [SMILES: *CCCOc1ccc(Cl)cc1C(=O)O]

In some embodiments, $R^5$ is

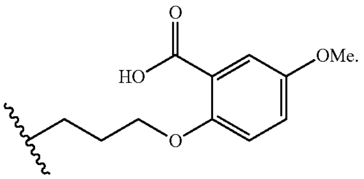 [SMILES: *CCCOc1ccc(OC)cc1C(=O)O]

In some embodiments, $R^5$ is

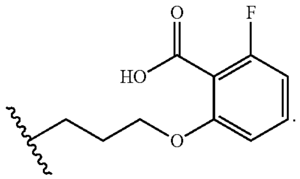 [SMILES: *CCCOc1cccc(F)c1C(=O)O]

In some embodiments, $R^5$ is

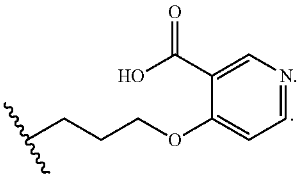 [SMILES: *CCCOc1ccncc1C(=O)O]

In some embodiments, $R^5$ is

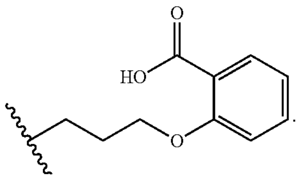 [SMILES: *CCCOc1ccccc1C(=O)O]

In some embodiments, $R^5$ is

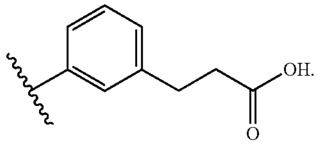 [SMILES: *c1cccc(CCC(=O)O)c1]

In some embodiments, $R^5$ is selected from those groups depicted in Table 1.

As defined above and described herein, each $R^6$ is independently halogen, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$.

In some embodiments, $R^6$ is halogen. In some embodiments, $R^6$ is —COR. In some embodiments, $R^6$ is —$(CR_2)_{0-6}CO_2R$. In some embodiments, $R^6$ is —$(CR_2)_{0-6}CONR_2$. In some embodiments, $R^6$ is —OR. In some embodiments, $R^6$ is —$(CR_2)_{1-4}OR$. In some embodiments, $R^6$ is —$NR_2$. In some embodiments, $R^6$ is —$(CR_2)_{1-4}NR_2$. In some embodiments, $R^6$ is —NRC(O)OR. In some embodiments, $R^6$ is —NRC(O)R. In some embodiments, $R^6$ is —NRC(O)$NR_2$. In some embodiments, $R^6$ is —SR. In some embodiments, $R^6$ is —$SO_2R$. In some embodiments, $R^6$ is —S(O)R. In some embodiments, $R^6$ is —$(CR_2)_{0-6}SO_3R$. In some embodiments, $R^6$ is —$(CR_2)_{0-6}SO_2NR_2$. In some embodiments, $R^6$ is —$(CR_2)_{0-6}OSO_2NR_2$. In some embodiments, $R^6$ is —$(CR_2)_{0-6}NRSO_2R$. In some embodiments, $R^6$ is —$(CR_2)_{0-6}NRSO_2OR$. In some embodiments, $R^6$ is —$(CR_2)_{0-6}OP(OR)_2$. In some embodiments, $R^6$ is —$(CR_2)_{0-6}OP(O)(OR)_2$. In some embodiments, $R^6$ is —$(CR_2)_{0-6}P(O)(OR)_2$. In some embodiments, $R^6$ is —$(CR_2)_{0-6}OP(O)(H)OR$. In some embodiments, $R^6$ is —$B(OR)_2$. In some embodiments, $R^6$ is $R^B$.

In some embodiments, $R^6$ is fluoro. In some embodiments, $R^6$ is chloro. In some embodiments, $R^6$ is bromo. In some embodiments, $R^6$ is —OH. In some embodiments, $R^6$ is —OMe. In some embodiments, $R^6$ is —OEt. In some embodiments, $R^6$ is —OtBu. In some embodiments, $R^6$ is —OBn. In some embodiments, $R^6$ is —$OCH_2CH_2OH$. In some embodiments, $R^6$ is —$OCH_2CO_2H$. In some embodiments, $R^6$ is —$OCONHCH_2CO_2H$. In some embodiments, $R^6$ is —$CF_3$. In some embodiments, $R^6$ is —$OCF_3$. In some embodiments, $R^6$ is —$CH(OH)CF_3$. In some embodiments, $R^6$ is —$C(OH)(CF_3)_2$. In some embodiments, $R^6$ is cyano. In some embodiments, $R^6$ is methyl. In some embodiments, $R^6$ is $=CH_2$. In some embodiments, $R^6$ is ethyl. In some embodiments, $R^6$ is —$CH_2OH$. In some embodiments, $R^6$ is —$CH_2OMe$. In some embodiments, $R^6$ is acetyl. In some embodiments, $R^6$ is —OAc. In some embodiments, $R^6$ is —$NH_2$. In some embodiments, $R^6$ is —NHBoc. In some embodiments, $R^6$ is —$CH_2NH_2$. In some embodiments, $R^6$ is —$CH_2NHBoc$. In some embodiments, $R^6$ is —$CH_2CH_2OH$. In some embodiments, $R^6$ is tert-butyl. In some embodiments, $R^6$ is —$C_{3-6}$cycloalkyl. In some embodiments, $R^6$ is cyclohexyl. In some embodiments, $R^6$ is phenyl. In some embodiments, $R^6$ is N-morpholinyl. In some embodiments, $R^6$ is —$CO_2H$. In some embodiments, $R^6$ is —$CO_2Me$. In some embodiments, $R^6$ is —$CO_2Et$. In some embodiments, $R^6$ is —$CO_2iPr$. In some embodiments, $R^6$ is —$CO_2nBu$. In some embodiments, $R^6$ is —$CO_2isoBu$. In some embodiments, $R^6$ is —$CO_2tBu$. In some embodiments, $R^6$ is —$CO_2CH_2CF_3$. In some embodiments, $R^6$ is —$CO_2CH(CF_3)_2$. In some embodiments, $R^6$ is —$CONH_2$. In some embodiments, $R^6$ is —CONHOH. In some embodiments, $R^6$ is —CONHOMe. In some embodiments, $R^6$ is —CONHMe. In some embodiments, $R^6$ is —CONHEt. In some embodiments, $R^6$ is —$CONMe_2$. In some embodiments, $R^6$ is —$COCH_2OH$. In some embodiments, $R^6$ is —$COCH_2OAc$. In some embodiments, $R^6$ is —$CONHCH_2CH_2OH$. In some embodiments, $R^6$ is —$CONHCH_2CONH_2$. In some embodiments, $R^6$ is —$CONHCH_2CH_2CONH_2$. In some embodiments, $R^6$ is —$CONHCH_2CO_2Me$. In some embodiments, $R^6$ is —$CONHCH_2CH_2CO_2H$. In some embodiments, $R^6$ is —$NH_2$. In some embodiments, $R^6$ is —NHAc. In some embodiments, $R^6$ is —$CH_2CO_2H$. In some embodiments, $R^6$ is —$CH_2CO_2Me$. In some embodiments, $R^6$ is —$CH_2CO_2tBu$. In some embodiments, $R^6$ is —$CH_2CONH_2$. In some embodiments, $R^6$ is —$CH_2NHSO_2Me$. In some embodiments, $R^6$ is —$NHSO_2Me$. In some embodiments, $R^6$ is —$NHSO_2Ph$. In some embodiments, $R^6$ is —$NHCONH_2$. In some embodiments, $R^6$ is —NHCOPh. In some embodiments, $R^6$ is —$NHCOCH_2OH$. In some embodiments, $R^6$ is —$NHCOCH_2OAc$. In some embodiments, $R^6$ is —$NHSO_2CH_2CH_2CO_2H$. In some embodiments, $R^6$ is —$CH_2NHCOCH_2OH$. In some embodiments, $R^6$ is —$CH_2NHCOCH_2CO_2H$. In some embodiments, $R^6$ is —$SO_3H$. In some embodiments, $R^6$ is —$SO_2Me$. In some embodiments, $R^6$ is —$SO_2NH_2$. In some embodiments, $R^6$ is —$SO_2NHBoc$. In some embodiments, $R^6$ is —$CH_2SO_2NH_2$. In some embodiments, $R^6$ is —$OSO_2NH_2$. In some embodiments, $R^6$ is —$OCONHCH_2CO_2Me$. In some embodiments, $R^6$ is —$B(OH)_2$. In some embodiments, $R^6$ is —$CH_2OSO_2NH_2$. In some embodiments, $R^6$ is

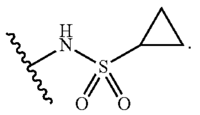 [SMILES: *NS(=O)(=O)C1CC1]

In some embodiments, $R^6$ is

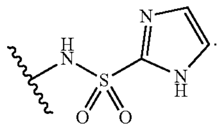 [SMILES: *NS(=O)(=O)c1ncc[nH]1]

In some embodiments, $R^6$ is

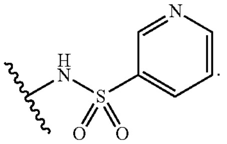 [SMILES: *NS(=O)(=O)c1cccnc1]

In some embodiments, $R^6$ is

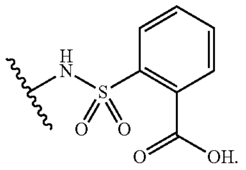 [SMILES: *NS(=O)(=O)c1ccccc1C(=O)O]

In some embodiments, $R^6$ is

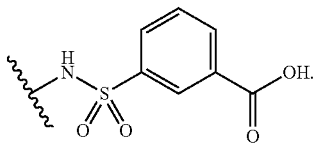 [SMILES: *NS(=O)(=O)c1cccc(C(=O)O)c1]

In some embodiments, $R^6$ is

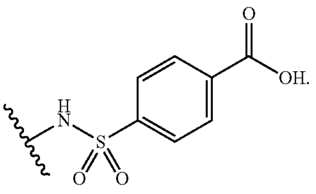 [SMILES: *NS(=O)(=O)c1ccc(C(=O)O)cc1]

In some embodiments, $R^6$ is

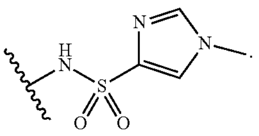 [SMILES: *NS(=O)(=O)c1cn(C)cn1]

In some embodiments, $R^6$ is

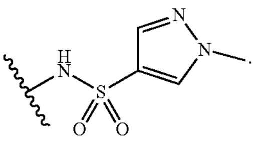 [SMILES: *NS(=O)(=O)c1cnn(C)c1]

In some embodiments, $R^6$ is $-OP(OH)_2$. In some embodiments, $R^6$ is $-CH_2OP(OH)_2$. In some embodiments, $R^6$ is $-CH_2OP(O)(H)OH$. In some embodiments, $R^6$ is $-OP(O)(OH)_2$. In some embodiments, $R^6$ is $-CH_2OP(O)(OH)_2$. In some embodiments, $R^6$ is $-CH_2P(O)(OH)_2$. In some embodiments, $R^6$ is

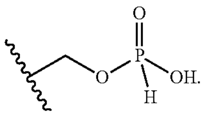 [SMILES: *CO[PH](=O)O]

In some embodiments, $R^6$ is

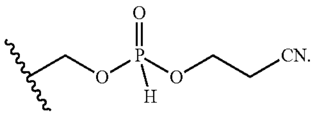 [SMILES: *CO[PH](=O)OCCC#N]

In some embodiments, $R^6$ is

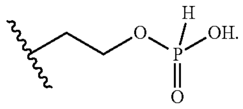 [SMILES: *CCO[PH](=O)O]

In some embodiments, $R^6$ is

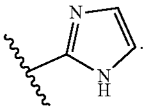

In some embodiments, $R^6$ is

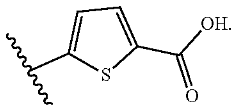 [SMILES: *c1ccc(C(=O)O)s1]

In some embodiments, $R^6$ is

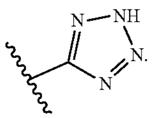 [SMILES: *c1nn[nH]n1]

In some embodiments, $R^6$ is

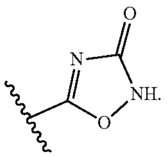 [SMILES: *c1nc(=O)[nH]o1]

In some embodiments, $R^6$ is

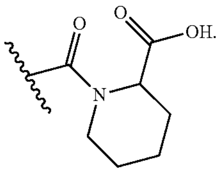 [SMILES: *C(=O)N1CCCCC1C(=O)O]

In some embodiments, $R^6$ is

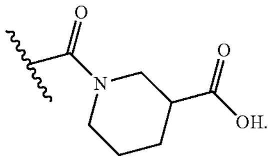 [SMILES: *C(=O)N1CCCC(C(=O)O)C1]

In some embodiments, $R^6$ is

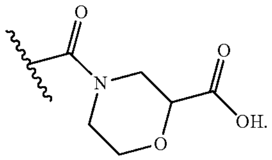 [SMILES: *C(=O)N1CCOC(C(=O)O)C1]

In some embodiments, $R^6$ is

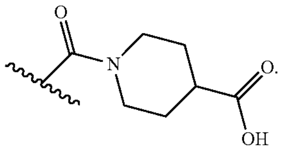 [SMILES: *C(=O)N1CCC(C(=O)O)CC1]

In some embodiments, $R^6$ is

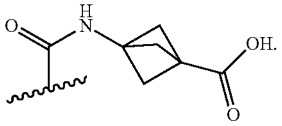 [SMILES: *C(=O)NC12CC(C(=O)O)(C1)C2]

In some embodiments, $R^6$ is
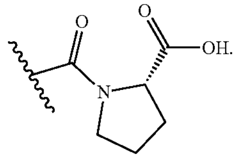 [SMILES: *C(=O)N1CCC[C@H]1C(=O)O]
In some embodiments, $R^6$ is
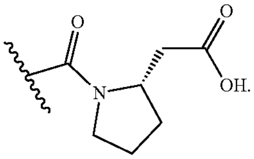 [SMILES: *C(=O)N1CCC[C@H]1CC(=O)O]
In some embodiments, $R^6$ is
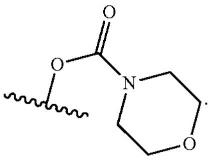 [SMILES: *OC(=O)N1CCOCC1]
In some embodiments, $R^6$ is
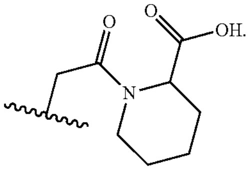 [SMILES: *CC(=O)N1CCCCC1C(=O)O]
In some embodiments, $R^6$ is
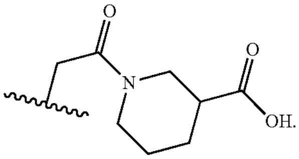 [SMILES: *CC(=O)N1CCCC(C(=O)O)C1]
In some embodiments, $R^6$ is
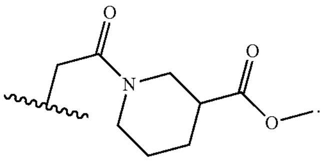 [SMILES: *CC(=O)N1CCCC(C(=O)OC)C1]
In some embodiments, $R^6$ is
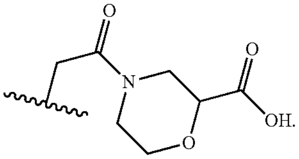 [SMILES: *CC(=O)N1CCOC(C(=O)O)C1]
In some embodiments, $R^6$ is
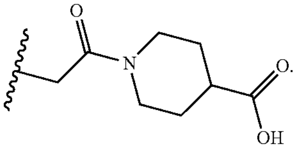 [SMILES: *CC(=O)N1CCC(C(=O)O)CC1]
In some embodiments, $R^6$ is
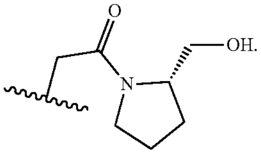 [SMILES: *CC(=O)N1CCC[C@H]1CO]
In some embodiments, $R^6$ is
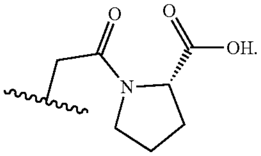 [SMILES: *CC(=O)N1CCC[C@H]1C(=O)O]
In some embodiments, $R^6$ is
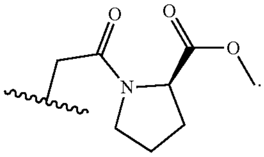 [SMILES: *CC(=O)N1CCC[C@@H]1C(=O)OC]
In some embodiments, $R^6$ is
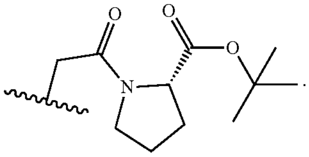 [SMILES: *CC(=O)N1CCC[C@H]1C(=O)OC(C)(C)C]

In some embodiments, $R^6$ is
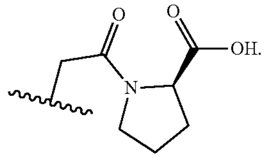 [SMILES: *CC(=O)N1CCC[C@@H]1C(=O)O]
In some embodiments, $R^6$ is
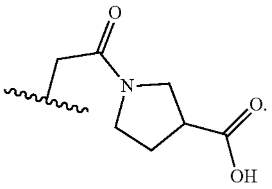 [SMILES: *CC(=O)N1CCC(C(=O)O)C1]
In some embodiments, $R^6$ is
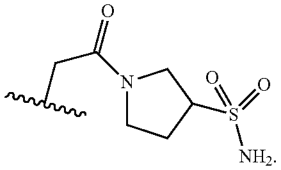 [SMILES: *CC(=O)N1CCC(S(N)(=O)=O)C1]
In some embodiments, $R^6$ is
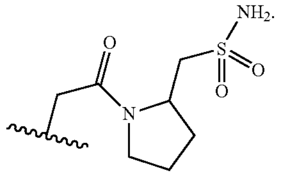 [SMILES: *CC(=O)N1CCCC1CS(N)(=O)=O]
In some embodiments, $R^6$ is
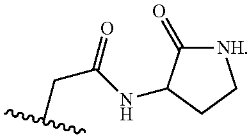 [SMILES: *CC(=O)NC1CCNC1=O]
In some embodiments, $R^6$ is
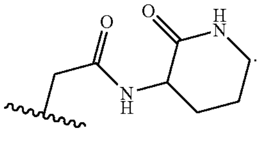 [SMILES: *CC(=O)NC1CCCNC1=O]
In some embodiments, $R^6$ is
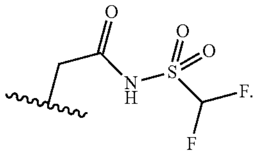 [SMILES: *CC(=O)NS(=O)(=O)C(F)F]
In some embodiments, $R^6$ is
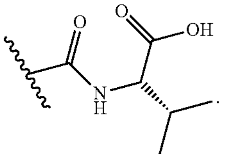
In some embodiments, $R^6$ is
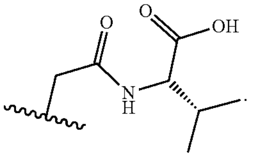
In some embodiments, $R^6$ is
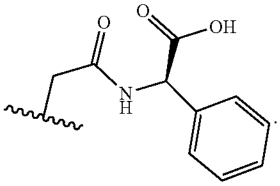 [SMILES: *CC(=O)N[C@@H](C(=O)O)c1ccccc1]
In some embodiments, $R^6$ is
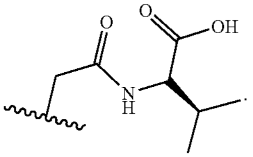
In some embodiments, $R^6$ is
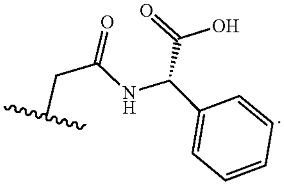 [SMILES: *CC(=O)N[C@H](C(=O)O)c1ccccc1]

In some embodiments, $R^6$ is
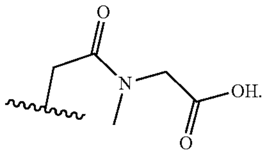 [SMILES: *CC(=O)N(C)CC(=O)O]
In some embodiments, $R^6$ is
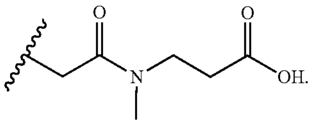 [SMILES: *CC(=O)N(C)CCC(=O)O]
In some embodiments, $R^6$ is
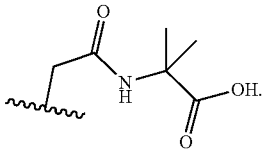 [SMILES: *CC(=O)NC(C)(C)C(=O)O]
In some embodiments, $R^6$ is
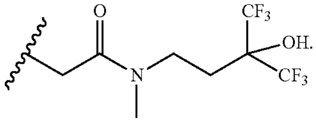 [SMILES: *CC(=O)N(C)CCC(O)(C(F)(F)F)C(F)(F)F]
In some embodiments, $R^6$ is
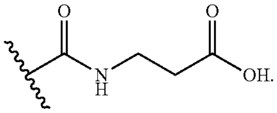 [SMILES: *C(=O)NCCC(=O)O]
In some embodiments, $R^6$ is
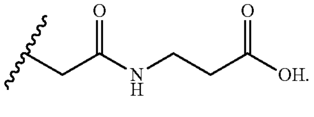 [SMILES: *CC(=O)NCCC(=O)O]
In some embodiments, $R^6$ is
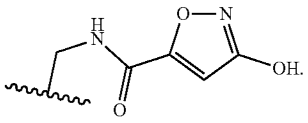 [SMILES: *CNC(=O)c1cc(O)no1]
In some embodiments, $R^6$ is
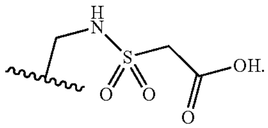 [SMILES: *CNS(=O)(=O)CC(=O)O]
In some embodiments, $R^6$ is
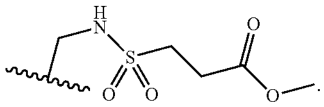 [SMILES: *CNS(=O)(=O)CCC(=O)OC]
In some embodiments, $R^6$ is
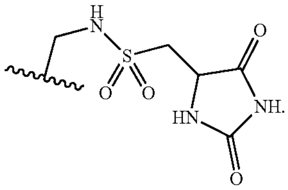 [SMILES: *CNS(=O)(=O)CC1NC(=O)NC1=O]
In some embodiments, $R^6$ is
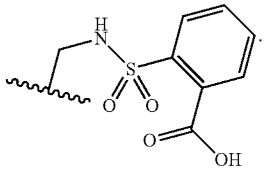 [SMILES: *CNS(=O)(=O)c1ccccc1C(=O)O]
In some embodiments, $R^6$ is
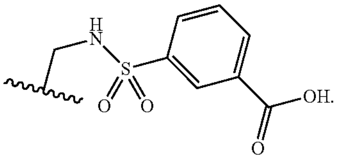 [SMILES: *CNS(=O)(=O)c1cccc(C(=O)O)c1]
In some embodiments, $R^6$ is
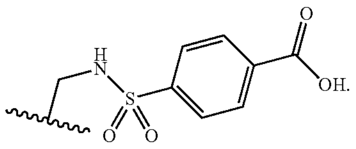 [SMILES: *CNS(=O)(=O)c1ccc(C(=O)O)cc1]

In some embodiments, $R^6$ is

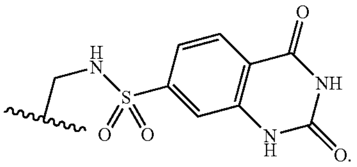 [SMILES: *CNS(=O)(=O)c1ccc2c(=O)[nH]c(=O)[nH]c2c1]

In some embodiments, $R^6$ is

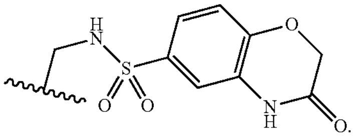 [SMILES: *CNS(=O)(=O)c1ccc2c(c1)NC(=O)CO2]

In some embodiments, $R^6$ is

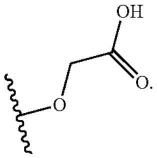 [SMILES: *OCC(=O)O]

In some embodiments, $R^6$ is

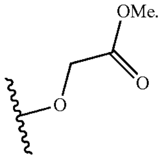 [SMILES: *OCC(=O)OC]

In some embodiments, $R^6$ is

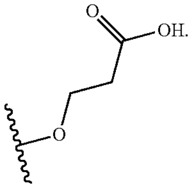 [SMILES: *OCCC(=O)O]

In some embodiments, $R^6$ is

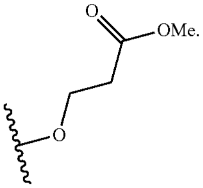 [SMILES: *OCCC(=O)OC]

In some embodiments, $R^6$ is

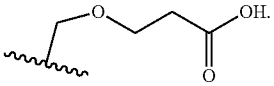 [SMILES: *COCCC(=O)O]

In some embodiments, $R^6$ is

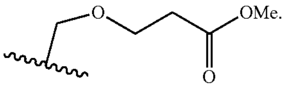 [SMILES: *COCCC(=O)OC]

In some embodiments, $R^6$ is

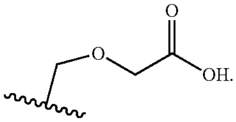 [SMILES: *COCC(=O)O]

In some embodiments, $R^6$ is

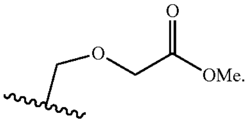 [SMILES: *COCC(=O)OC]

In some embodiments, $R^6$ is

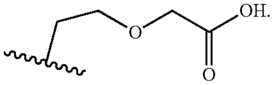

In some embodiments, $R^6$ is

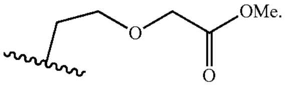

In some embodiments, $R^6$ is

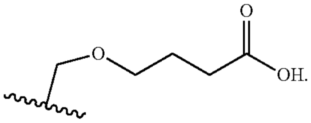 [SMILES: *COCCCC(=O)O]

In some embodiments, $R^6$ is

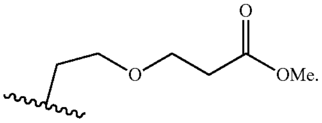 [SMILES: *CCOCCC(=O)OC]

In some embodiments, $R^6$ is

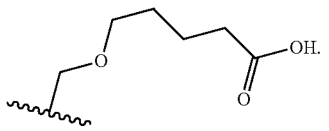 [SMILES: *COCCCCC(=O)O]

In some embodiments, $R^6$ is

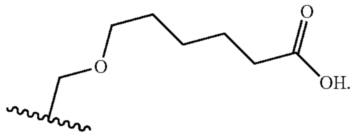 [SMILES: *COCCCCCC(=O)O]

In some embodiments, $R^6$ is

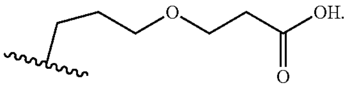 [SMILES: *CCCOCCC(=O)O]

In some embodiments, $R^6$ is

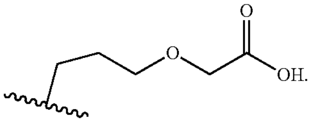 [SMILES: *CCCOCC(=O)O]

In some embodiments, $R^6$ is

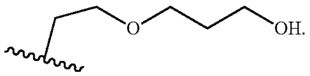 [SMILES: *CCOCCCO]

In some embodiments, $R^6$ is

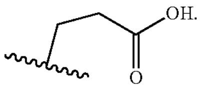 [SMILES: *CCC(=O)O]

In some embodiments, $R^6$ is

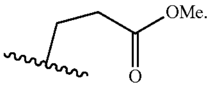 [SMILES: *CCC(=O)OC]

In some embodiments, $R^6$ is

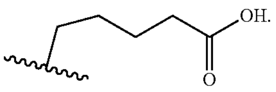 [SMILES: *CCCCC(=O)O]

In some embodiments, $R^6$ is

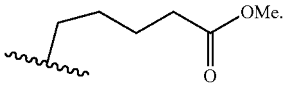

In some embodiments, $R^6$ is

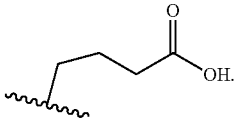 [SMILES: *CCCC(=O)O]

In some embodiments, $R^6$ is

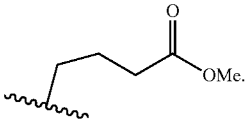 [SMILES: *CCCC(=O)OC]

In some embodiments, $R^6$ is

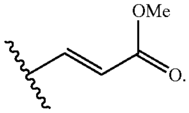 [SMILES: */C=C/C(=O)OC]

In some embodiments, $R^6$ is

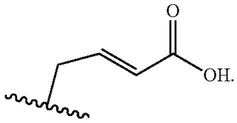 [SMILES: *C/C=C/C(=O)O]

In some embodiments, $R^6$ is

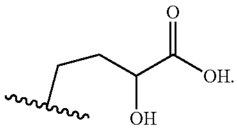 [SMILES: *CCC(O)C(=O)O]

In some embodiments, $R^6$ is

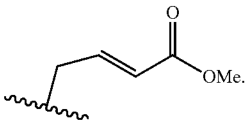 [SMILES: *C/C=C/C(=O)OC]

In some embodiments, $R^6$ is

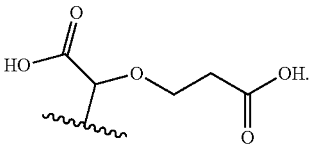 [SMILES: *C(OCCC(=O)O)C(=O)O]

In some embodiments, $R^6$ is

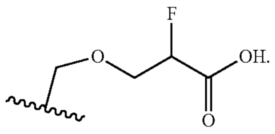 [SMILES: *COCC(F)C(=O)O]

In some embodiments, $R^6$ is

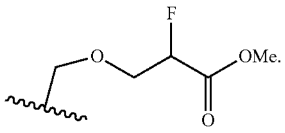 [SMILES: *COCC(F)C(=O)OC]

In some embodiments, $R^6$ is

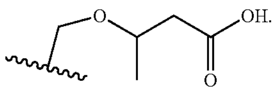 [SMILES: *COC(C)CC(=O)O]

In some embodiments, $R^6$ is

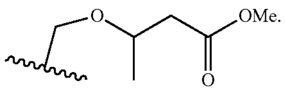 [SMILES: *COC(C)CC(=O)OC]

In some embodiments, $R^6$ is

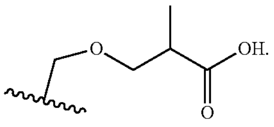 [SMILES: *COCC(C)C(=O)O]

In some embodiments, $R^6$ is

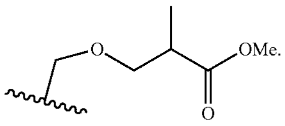 [SMILES: *COCC(C)C(=O)OC]

In some embodiments, $R^6$ is

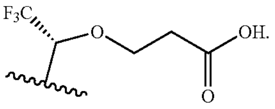 [SMILES: *[C@@H](OCCC(=O)O)C(F)(F)F]

In some embodiments, $R^6$ is

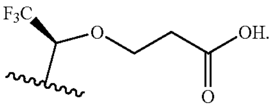 [SMILES: *[C@H](OCCC(=O)O)C(F)(F)F]

In some embodiments, $R^6$ is

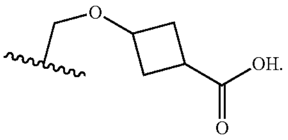 [SMILES: *COC1CC(C(=O)O)C1]

In some embodiments, $R^6$ is

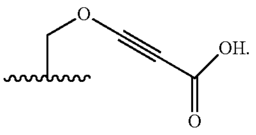 [SMILES: *COC#CC(=O)O]

In some embodiments, $R^6$ is

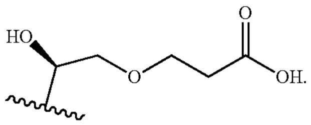 [SMILES: *[C@@H](O)COCCC(=O)O]

In some embodiments, $R^6$ is

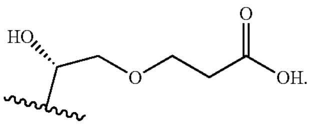 [SMILES: *[C@H](O)COCCC(=O)O]

In some embodiments, $R^6$ is

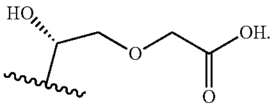 [SMILES: *[C@H](O)COCC(=O)O]

In some embodiments, $R^6$ is
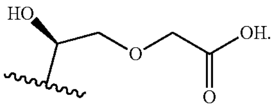 [SMILES: *[C@@H](O)COCC(=O)O]
In some embodiments, $R^6$ is
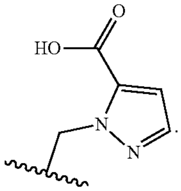 [SMILES: *Cn1nccc1C(=O)O]
In some embodiments, $R^6$ is
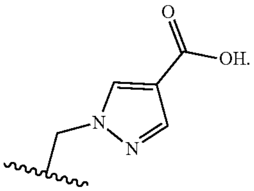 [SMILES: *Cn1cc(C(=O)O)cn1]
In some embodiments, $R^6$ is
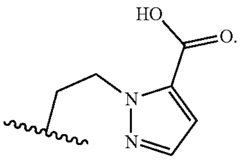 [SMILES: *CCn1nccc1C(=O)O]
In some embodiments, $R^6$ is
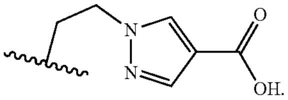 [SMILES: *CCn1cc(C(=O)O)cn1]
In some embodiments, $R^6$ is
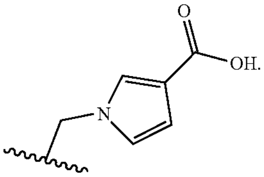 [SMILES: *Cn1ccc(C(=O)O)c1]
In some embodiments, $R^6$ is
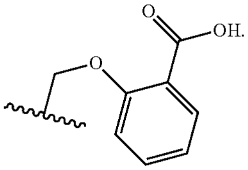 [SMILES: *COc1ccccc1C(=O)O]
In some embodiments, $R^6$ is
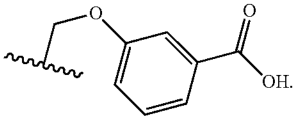 [SMILES: *COc1cccc(C(=O)O)c1]
In some embodiments, $R^6$ is
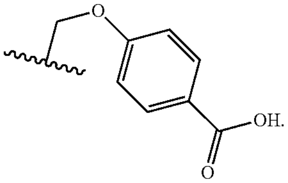 [SMILES: *COc1ccc(C(=O)O)cc1]
In some embodiments, $R^6$ is
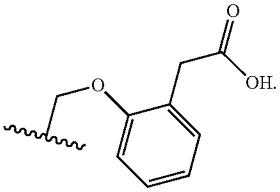 [SMILES: *COc1ccccc1CC(=O)O]
In some embodiments, $R^6$ is
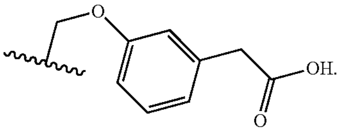 [SMILES: *COc1cccc(CC(=O)O)c1]
In some embodiments, $R^6$ is
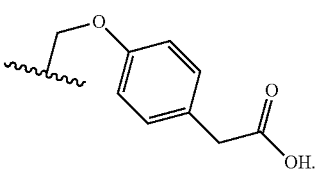 [SMILES: *COc1ccc(CC(=O)O)cc1]

In some embodiments, $R^6$ is

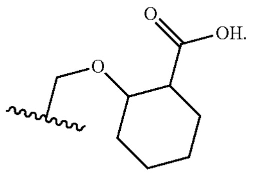 [SMILES: *COC1CCCCC1C(=O)O]

In some embodiments, $R^6$ is

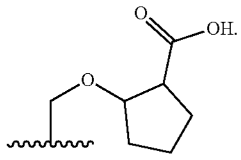 [SMILES: *COC1CCCC1C(=O)O]

In some embodiments, $R^6$ is

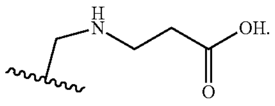 [SMILES: *CNCCC(=O)O]

In some embodiments, $R^6$ is

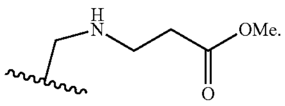 [SMILES: *CNCCC(=O)OC]

In some embodiments, $R^6$ is

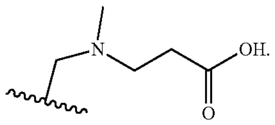 [SMILES: *CN(C)CCC(=O)O]

In some embodiments, $R^6$ is

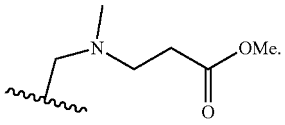 [SMILES: *CN(C)CCC(=O)OC]

In some embodiments, $R^6$ is

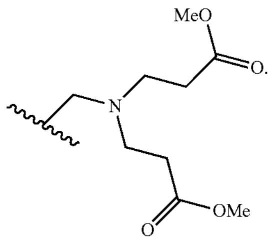 [SMILES: *CN(CCC(=O)OC)CCC(=O)OC]

In some embodiments, $R^6$ is

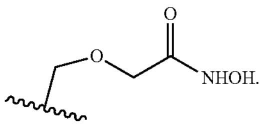

In some embodiments, $R^6$ is

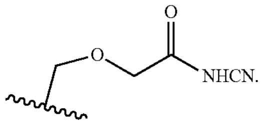

In some embodiments, $R^6$ is

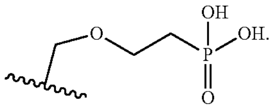 [SMILES: *COCCP(=O)(O)O]

In some embodiments, $R^6$ is

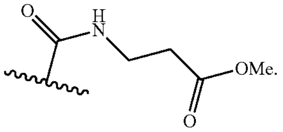 [SMILES: *C(=O)NCCC(=O)OC]

In some embodiments, $R^6$ is

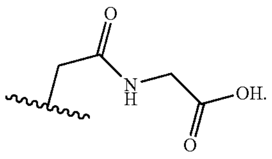 [SMILES: *CC(=O)NCC(=O)O]

In some embodiments, $R^6$ is

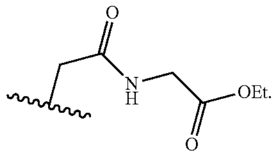 [SMILES: *CC(=O)NCC(=O)OCC]

In some embodiments, $R^6$ is selected from those groups depicted in Table 1.

As defined above and described herein, $R^A$, $R^B$, and $R^C$, independently, are an optionally substituted group selected from $C_{1-6}$ aliphatic; phenyl, including substituted phenyl; a 4- to 10-membered saturated or partially unsaturated monocyclic or bicyclic carboxylic or heterocyclic ring having 1 to 3 heteroatoms independently selected from nitrogen, oxygen, phosphorus, and sulfur; and a 5- to 6-membered heteroaryl ring having 1 to 4 heteroatoms independently selected from nitrogen, oxygen, phosphorus, and sulfur.

In some embodiments, $R^A$, $R^B$, or $R^C$ is an optionally substituted $C_{1-6}$ aliphatic. In some embodiments, $R^A$, $R^B$, or $R^C$ is an optionally substituted phenyl. In some embodiments, $R^A$, $R^B$, or $R^C$ an optionally substituted 4- to 10-membered saturated or partially unsaturated monocyclic or bicyclic carboxylic or heterocyclic ring having 1 to 3 heteroatoms independently selected from nitrogen, oxygen, phosphorus, and sulfur. In some embodiments, $R^A$, $R^B$, or $R^C$ is an optionally substituted 5- to 6-membered heteroaryl ring having 1 to 4 heteroatoms independently selected from nitrogen, oxygen, phosphorus, and sulfur.

In some embodiments, $R^A$, $R^B$, or $R^C$, is selected from those groups depicted in Table 1.

As defined above and described herein, Ring A is an optionally substituted 4- to 7-membered saturated, partially unsaturated, or heteroaryl ring having 0 to 3 heteroatoms, in addition to the nitrogen, independently selected from nitrogen, oxygen, phosphorus, and sulfur.

In some embodiments, Ring A is an optionally substituted 4- to 7-membered saturated, partially unsaturated, or heteroaryl ring having 0 to 3 heteroatoms, in addition to the nitrogen, independently selected from nitrogen, oxygen, phosphorus, and sulfur.

In some embodiments, Ring A is

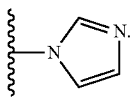

In some embodiments, Ring A is

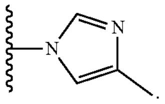 [SMILES: *n1cnc(C)c1]

In some embodiments, Ring A is

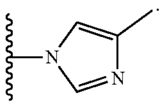 [SMILES: *n1cnc(C)c1]

In some embodiments, Ring A is

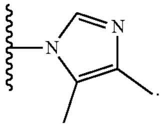 [SMILES: *n1cnc(C)c1C]

In some embodiments, Ring A is

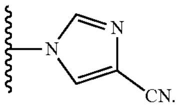 [SMILES: *n1cnc(C#N)c1]

In some embodiments, Ring A is

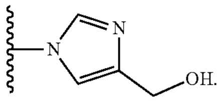

In some embodiments, Ring A is

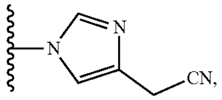 [SMILES: *n1cnc(CC#N)c1]

In some embodiments, Ring A is

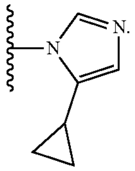 [SMILES: *n1cncc1C1CC1]

In some embodiments, Ring A is

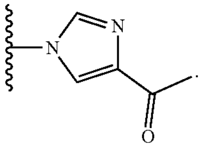 [SMILES: *n1cnc(C(C)=O)c1]

In some embodiments, Ring A is

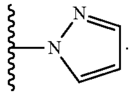

In some embodiments, Ring A is

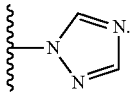 [SMILES: *n1cncn1]

In some embodiments, Ring A is

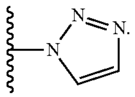 [SMILES: *n1ccnn1]

In some embodiments, Ring A is

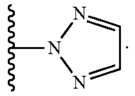

In some embodiments, Ring A is

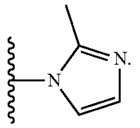 [SMILES: *n1ccnc1C]

In some embodiments, Ring A is

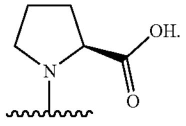 [SMILES: *N1CCC[C@H]1C(=O)O]

In some embodiments, Ring A is

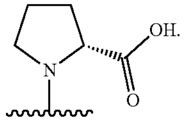 [SMILES: *N1CCC[C@@H]1C(=O)O]

In some embodiments, Ring A is

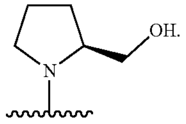 [SMILES: *N1CCC[C@H]1CO]

In some embodiments, Ring A is

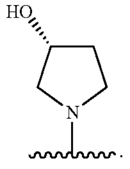

In some embodiments, Ring A is

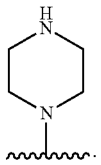

In some embodiments, Ring A is

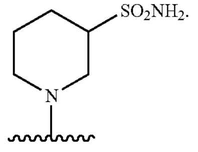 [SMILES: *N1CCCC(S(N)(=O)=O)C1]

In some embodiments, Ring A is

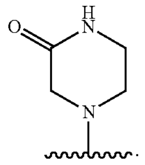 [SMILES: *N1CCNC(=O)C1]

In some embodiments, Ring A is

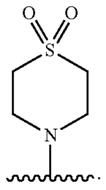 [SMILES: *N1CCS(=O)(=O)CC1]

In some embodiments, Ring A is

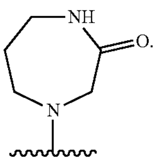 [SMILES: *N1CCCNC(=O)C1]

In some embodiments, Ring A is

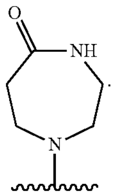 [SMILES: *N1CCNC(=O)CC1]

In some embodiments, Ring A is

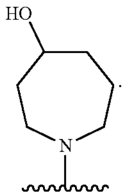

In some embodiments, Ring A is selected from those groups depicted in Table 1.

As defined above and described herein, Ring B1 is phenyl, particularly substituted phenyl; a 4- to 10-membered saturated or partially unsaturated monocyclic or bicyclic carboxylic or heterocyclic ring having 1 to 3 heteroatoms independently selected from nitrogen, oxygen, phosphorus, and sulfur; or a 5- to 6-membered heteroaryl ring having 1 to 4 heteroatoms independently selected from nitrogen, oxygen, phosphorus, and sulfur.

In some embodiments, Ring B1 is phenyl, particularly substituted phenyl. In some embodiments, Ring B1 is a 4- to 10-membered saturated or partially unsaturated monocyclic or bicyclic carboxylic or heterocyclic ring having 1 to 3 heteroatoms independently selected from nitrogen, oxygen, phosphorus, and sulfur. In some embodiments, Ring B1 is a 5- to 6-membered heteroaryl ring having 1 to 4 heteroatoms independently selected from nitrogen, oxygen, phosphorus, and sulfur.

In some embodiments, Ring B1 is

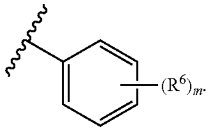

In some embodiments, Ring B1 is

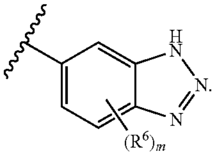

In some embodiments, Ring B1 is

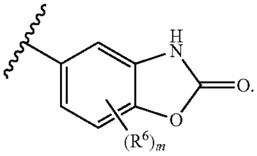

In some embodiments, Ring B1 is

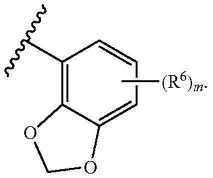

In some embodiments, Ring B1 is

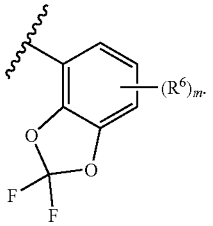

In some embodiments, Ring B1 is

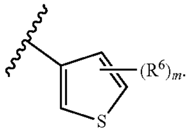

In some embodiments, Ring B1 is

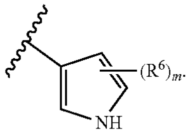

In some embodiments, Ring B1 is

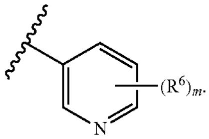

In some embodiments, Ring B1 is

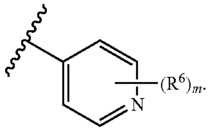

In some embodiments, Ring B1 is

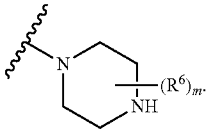

In some embodiments, Ring B1 is

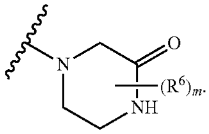

In some embodiments, Ring B1 is

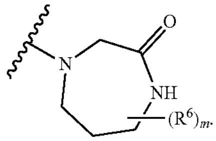

In some embodiments, Ring B1 is

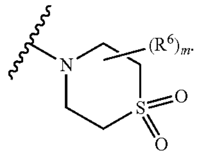

In some embodiments, Ring B1 is

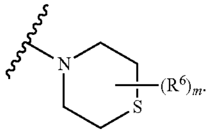

In some embodiments, Ring B1 is

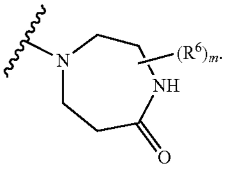

In some embodiments, Ring B1 is

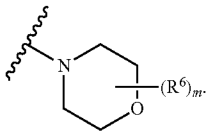

In some embodiments, Ring B1 is

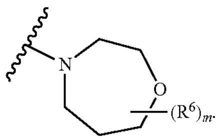

In some embodiments, Ring B1 is

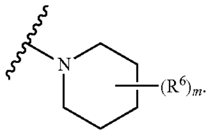

In some embodiments, Ring B1 is

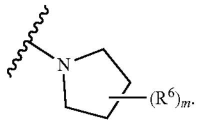

In some embodiments, Ring B1 is

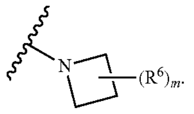

In some embodiments, Ring B1 is selected from those groups depicted in Table 1.

As defined above and described herein, Ring B2 is phenyl, including substituted phenyl; a 4- to 7-membered saturated or partially unsaturated carbocyclic or heterocyclic ring having 1 to 3 heteroatoms independently selected from nitrogen, oxygen, phosphorus, and sulfur; or a 5- to 6-membered heteroaryl ring having 1 to 4 heteroatoms independently selected from nitrogen, oxygen, phosphorus, and sulfur.

In some embodiments, Ring B2 is phenyl. In some embodiments, Ring B2 is a 4- to 7-membered saturated or partially unsaturated carboxylic or heterocyclic ring having 1 to 3 heteroatoms independently selected from nitrogen, oxygen, phosphorus, and sulfur. In some embodiments, Ring B2 is a 5- to 6-membered heteroaryl ring having 1 to 4 heteroatoms independently selected from nitrogen, oxygen, phosphorus, and sulfur.

In some embodiments, Ring B2 is

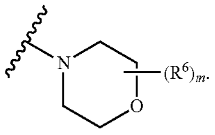

In some embodiments, Ring B2 is

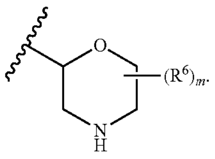

In some embodiments, Ring B2 is

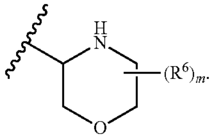

In some embodiments, Ring B2 is selected from those groups depicted in Table 1.

As defined above and described herein, Ring C is pyrrolidinyl or a 4- to 10-membered saturated or partially unsaturated monocyclic, bicyclic, bridged bicyclic, or spirocyclic heterocyclic ring having 0 to 3 heteroatoms (in addition to the nitrogen already depicted in Ring C) independently selected from nitrogen, oxygen, and sulfur.

In some embodiments, Ring C is pyrrolidinyl. In some embodiments, Ring C is a 4- to 10-membered saturated or partially unsaturated monocyclic, bicyclic, bridged bicyclic, or spirocyclic heterocyclic ring having 0 to 3 heteroatoms (in addition to the nitrogen already depicted in Ring C) independently selected from nitrogen, oxygen, and sulfur.

In some embodiments, Ring C is azetidinyl. In some embodiments, Ring C is pyrrolyl. In some embodiments, Ring C is 2,3-dihydro-1H-pyrrolyl. In some embodiments, Ring C is morpholinyl. In some embodiments, Ring C is thiazolidinyl. In some embodiments, Ring C is indolinyl. In some embodiments, Ring C is isoindolinyl. In some embodiments, Ring C is octahydroindolyl. In some embodiments, Ring C is azepanyl. In some embodiments, Ring C is oxazepanyl. In some embodiments, Ring C is an azabicyclohexane. In some embodiments, Ring C is an azabicycloheptane. In some embodiments, Ring C is an azabicyclooctane. In some embodiments, Ring C is an azabicyclononane. In some embodiments, Ring C is an azaspiroheptane. In some embodiments, Ring C is octahydrocyclicpentapyrrole.

In particular embodiments, Ring C is pyrrolidinyl, 2-azabicyclo[3.1.0]hexanyl, 3-azabicyclo[3.1.0]hexane, 5-azaspiro[2.4]heptanyl, or octahydrocyclopenta[b]pyrrolyl.

In some embodiments, Ring C is

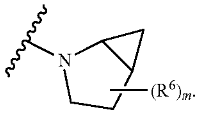

In some embodiments, Ring C is

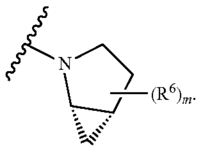

In some embodiments, Ring C is

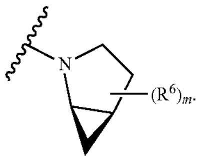

In some embodiments, Ring C is

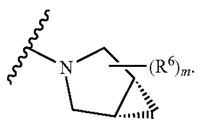

In some embodiments, Ring C is

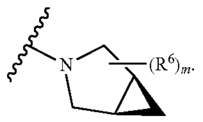

In some embodiments, Ring C is

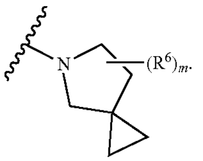

In some embodiments, Ring C is

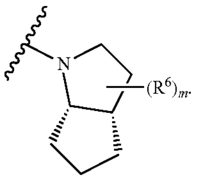

In some embodiments, Ring C is

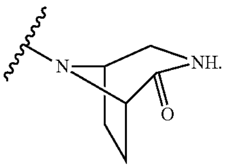 [SMILES: *N1C2CCC1C(=O)NC2]

In some embodiments, Ring C is

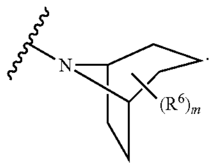

In some embodiments, Ring C is

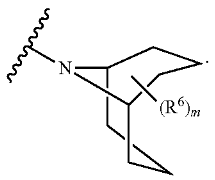

In some embodiments, Ring C is

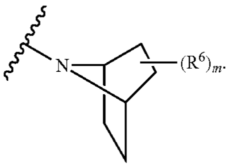

In some embodiments, Ring C is

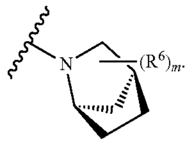

In some embodiments, Ring C is

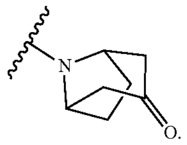 [SMILES: *N1C2CCC1CC(=O)C2]

In some embodiments, Ring C is

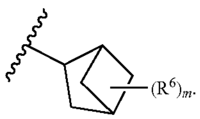

In some embodiments, Ring C is

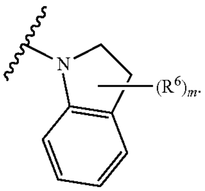

In some embodiments, Ring C is

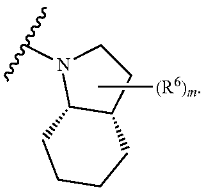

In some embodiments, Ring C is

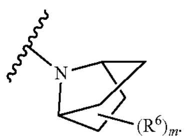

In some embodiments, Ring C is

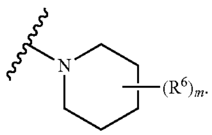

In some embodiments, Ring C is

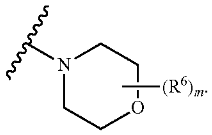

In some embodiments, Ring C is

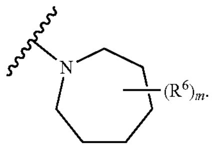

In some embodiments, Ring C is

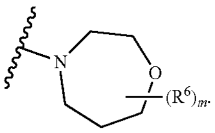

In some embodiments, Ring C is

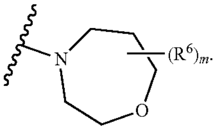

In some embodiments, Ring C is selected from those groups depicted in Table 1.

As defined above and described herein, n is 1, 2, 3, or 4.

In some embodiments, n is 1. In some embodiments, n is 2. In some embodiments, n is 3. In some embodiments, n is 4.

In some embodiments, n is selected from those groups depicted in Table 1.

As defined above and described herein, m is 0, 1, 2, 3, or 4.

In some embodiments, m is 0. In some embodiments, m is 1, 2, 3, or 4. In some embodiments, m is 1. In some embodiments, m is 2. In some embodiments, m is 3. In some embodiments, m is 4.

In some embodiments, m is selected from those groups depicted in Table 1.

As defined above and described herein, p is 0, 1, or 2.

In some embodiments, p is 0. In some embodiments, p is 1. In some embodiments, p is 2.

In some embodiments, p is selected from those groups depicted in Table 1.

As defined above and described herein, q is 0, 1, or 2.

In some embodiments, q is 0. In some embodiments, q is 1. In some embodiments, q is 2.
In some embodiments, q is selected from those groups depicted in Table 1.
Exemplary compounds of the present disclosure are set forth in Table 1, below.
TABLE 1
Exemplary Compounds
| I-# | Structure |
|---|---|
| I-1 | 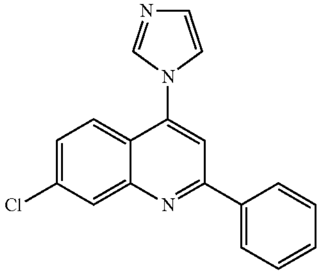 [SMILES: Clc1ccc2c(-n3ccnc3)cc(-c3ccccc3)nc2c1] |
| I-2 | 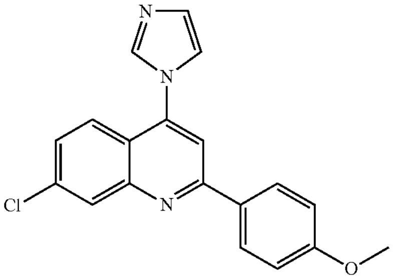 [SMILES: COc1ccc(-c2cc(-n3ccnc3)c3ccc(Cl)cc3n2)cc1] |
| I-3 | 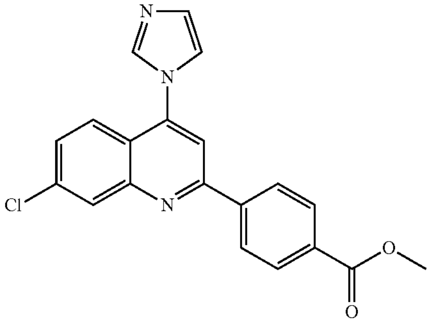 [SMILES: COC(=O)c1ccc(-c2cc(-n3ccnc3)c3ccc(Cl)cc3n2)cc1] |
| I-4 | 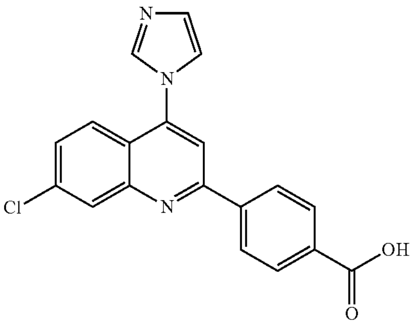 [SMILES: O=C(O)c1ccc(-c2cc(-n3ccnc3)c3ccc(Cl)cc3n2)cc1] |
TABLE 1-continued
Exemplary Compounds
| I-# | Structure |
|---|---|
| I-5 | 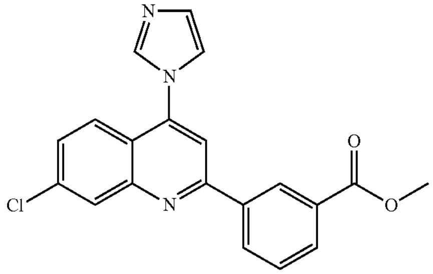 [SMILES: COC(=O)c1cccc(-c2cc(-n3ccnc3)c3ccc(Cl)cc3n2)c1] |
| I-6 | 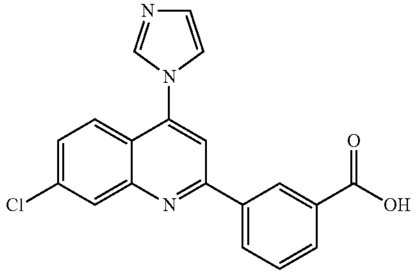 [SMILES: O=C(O)c1cccc(-c2cc(-n3ccnc3)c3ccc(Cl)cc3n2)c1] |
| I-7 | 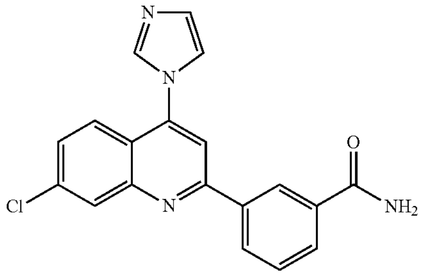 [SMILES: NC(=O)c1cccc(-c2cc(-n3ccnc3)c3ccc(Cl)cc3n2)c1] |
| I-8 | 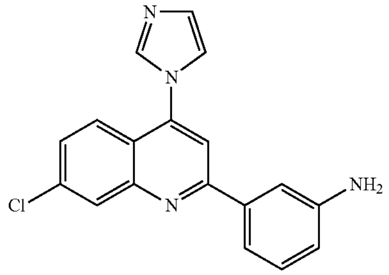 [SMILES: Nc1cccc(-c2cc(-n3ccnc3)c3ccc(Cl)cc3n2)c1] |
| I-9 | 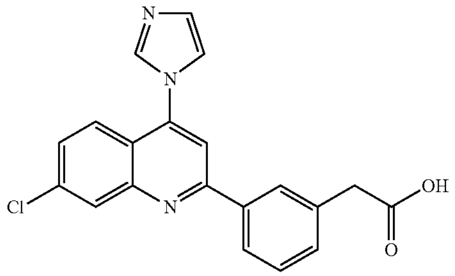 [SMILES: O=C(O)Cc1cccc(-c2cc(-n3ccnc3)c3ccc(Cl)cc3n2)c1] |

TABLE 1-continued
| Exemplary Compounds | |
|---|---|
| I-# | Structure |
| I-10 | 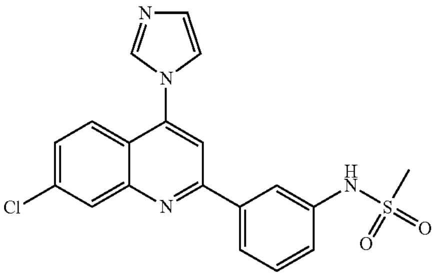 [SMILES: CS(=O)(=O)Nc1cccc(-c2cc(-n3ccnc3)c3ccc(Cl)cc3n2)c1] |
| I-11 | 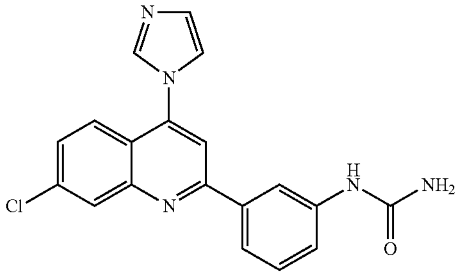 [SMILES: NC(=O)Nc1cccc(-c2cc(-n3ccnc3)c3ccc(Cl)cc3n2)c1] |
| I-12 | 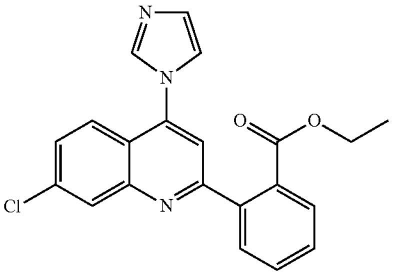 [SMILES: CCOC(=O)c1ccccc1-c1cc(-n2ccnc2)c2ccc(Cl)cc2n1] |
| I-13 | 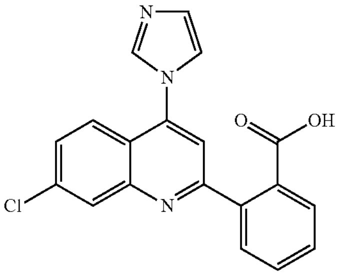 [SMILES: O=C(O)c1ccccc1-c1cc(-n2ccnc2)c2ccc(Cl)cc2n1] |
| I-14 | 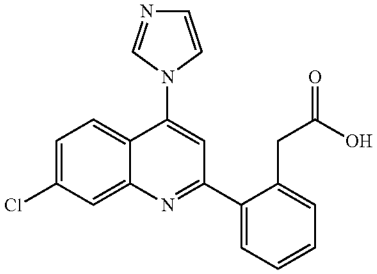 [SMILES: O=C(O)Cc1ccccc1-c1cc(-n2ccnc2)c2ccc(Cl)cc2n1] |
| I-15 | 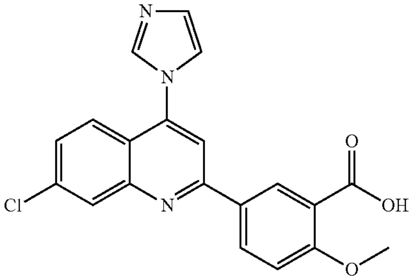 [SMILES: COc1ccc(-c2cc(-n3ccnc3)c3ccc(Cl)cc3n2)cc1C(=O)O] |
| I-16 | 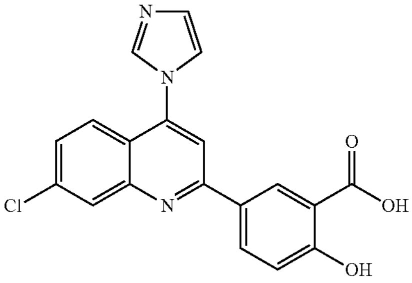 [SMILES: O=C(O)c1cc(-c2cc(-n3ccnc3)c3ccc(Cl)cc3n2)ccc1O] |
| I-17 | 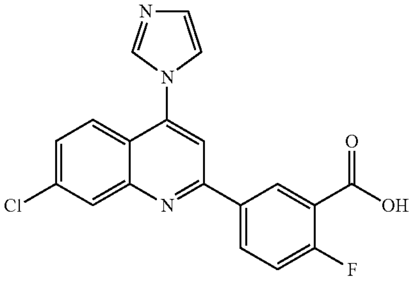 [SMILES: O=C(O)c1cc(-c2cc(-n3ccnc3)c3ccc(Cl)cc3n2)ccc1F] |
| I-18 | 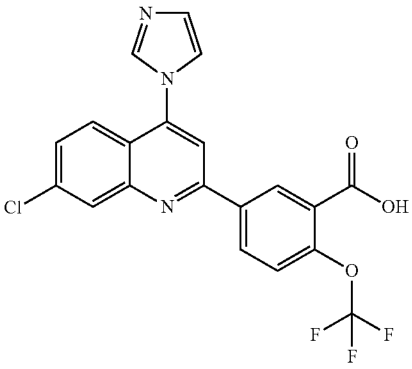 [SMILES: O=C(O)c1cc(-c2cc(-n3ccnc3)c3ccc(Cl)cc3n2)ccc1OC(F)(F)F] |
| I-19 | 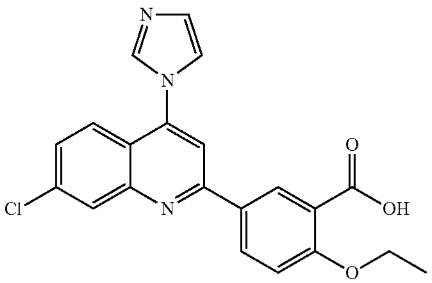 [SMILES: CCOc1ccc(-c2cc(-n3ccnc3)c3ccc(Cl)cc3n2)cc1C(=O)O] |

TABLE 1-continued
| Exemplary Compounds | |
|---|---|
| I-# | Structure |
| I-20 | 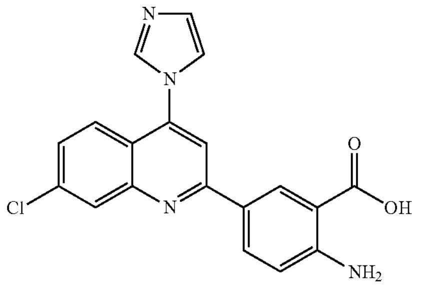 [SMILES: Nc1ccc(-c2cc(-n3ccnc3)c3ccc(Cl)cc3n2)cc1C(=O)O] |
| I-21 | 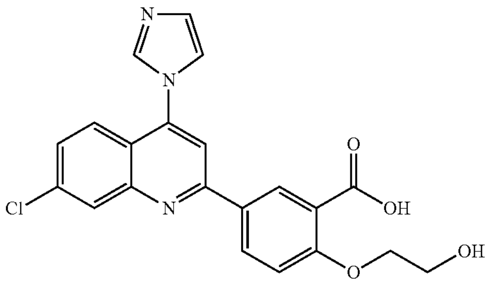 [SMILES: O=C(O)c1cc(-c2cc(-n3ccnc3)c3ccc(Cl)cc3n2)ccc1OCCO] |
| I-22 | 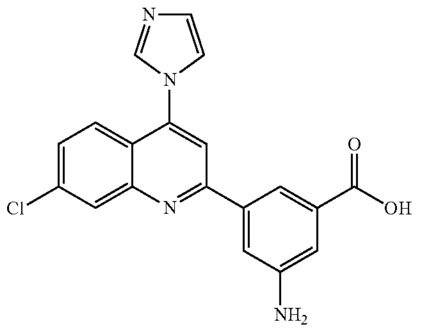 [SMILES: Nc1cc(C(=O)O)cc(-c2cc(-n3ccnc3)c3ccc(Cl)cc3n2)c1] |
| I-23 | 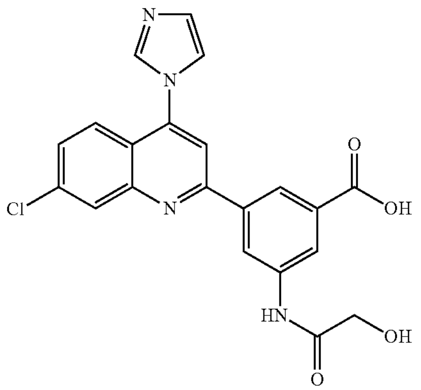 [SMILES: O=C(CO)Nc1cc(C(=O)O)cc(-c2cc(-n3ccnc3)c3ccc(Cl)cc3n2)c1] |
TABLE 1-continued
| Exemplary Compounds | |
|---|---|
| I-# | Structure |
| I-24 | 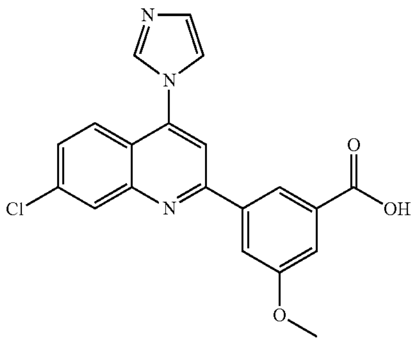 [SMILES: COc1cc(C(=O)O)cc(-c2cc(-n3ccnc3)c3ccc(Cl)cc3n2)c1] |
| I-25 | 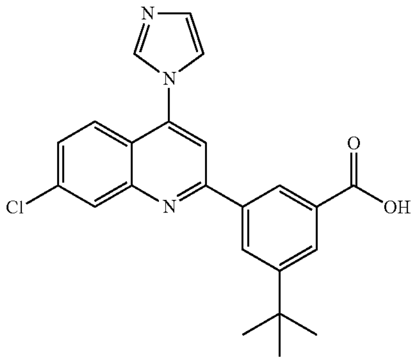 [SMILES: CC(C)(C)c1cc(C(=O)O)cc(-c2cc(-n3ccnc3)c3ccc(Cl)cc3n2)c1] |
| I-26 | 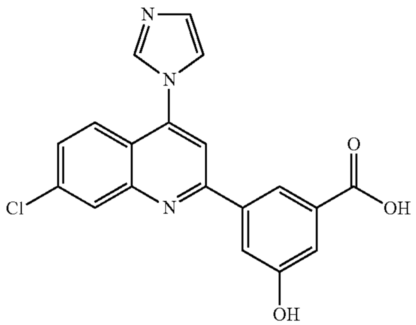 [SMILES: O=C(O)c1cc(O)cc(-c2cc(-n3ccnc3)c3ccc(Cl)cc3n2)c1] |
| I-27 | 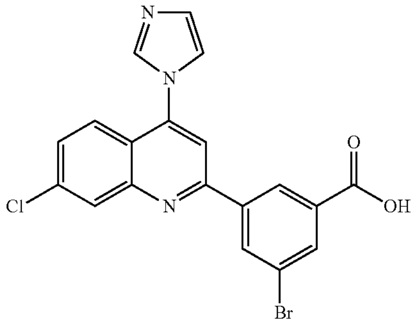 [SMILES: O=C(O)c1cc(Br)cc(-c2cc(-n3ccnc3)c3ccc(Cl)cc3n2)c1] |

TABLE 1-continued
| Exemplary Compounds | |
|---|---|
| I-# | Structure |
| I-28 | 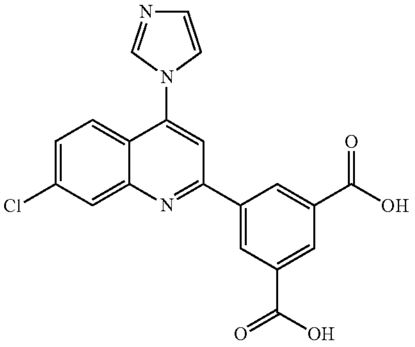 [SMILES: O=C(O)c1cc(C(=O)O)cc(-c2cc(-n3ccnc3)c3ccc(Cl)cc3n2)c1] |
| I-29 | 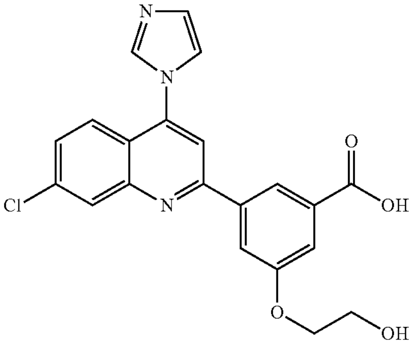 [SMILES: O=C(O)c1cc(OCCO)cc(-c2cc(-n3ccnc3)c3ccc(Cl)cc3n2)c1] |
| I-30 | 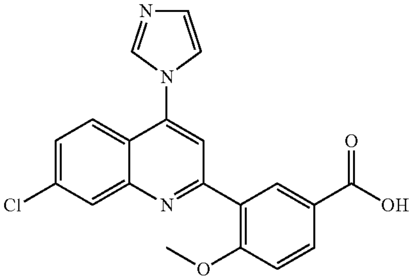 [SMILES: COc1ccc(C(=O)O)cc1-c1cc(-n2ccnc2)c2ccc(Cl)cc2n1] |
| I-31 | 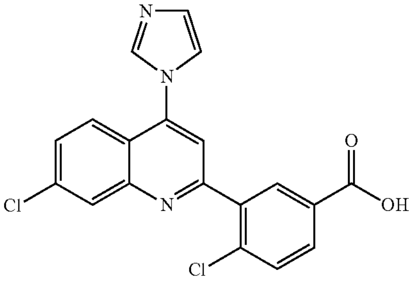 [SMILES: O=C(O)c1ccc(Cl)c(-c2cc(-n3ccnc3)c3ccc(Cl)cc3n2)c1] |
| I-32 | 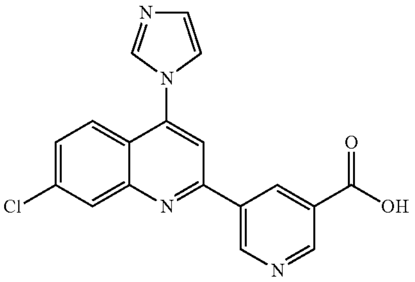 [SMILES: O=C(O)c1cncc(-c2cc(-n3ccnc3)c3ccc(Cl)cc3n2)c1] |
| I-33 | 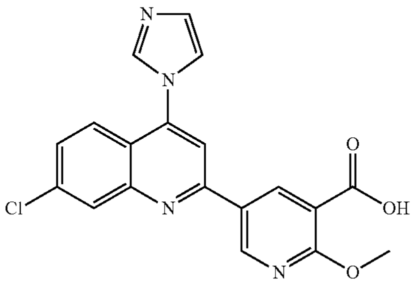 [SMILES: COc1ncc(-c2cc(-n3ccnc3)c3ccc(Cl)cc3n2)cc1C(=O)O] |
| I-34 | 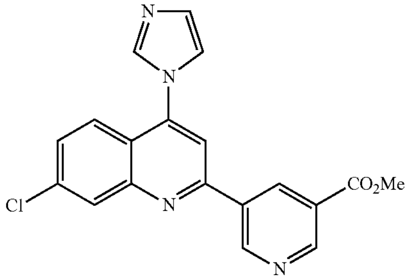 [SMILES: COC(=O)c1cncc(-c2cc(-n3ccnc3)c3ccc(Cl)cc3n2)c1] |
| I-35 | 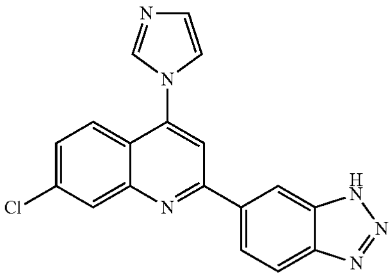 [SMILES: Clc1ccc2c(-n3ccnc3)cc(-c3ccc4nn[nH]c4c3)nc2c1] |
| I-36 | 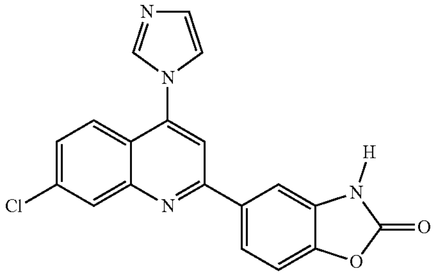 [SMILES: O=c1[nH]c2cc(-c3cc(-n4ccnc4)c4ccc(Cl)cc4n3)ccc2o1] |
| I-37 | 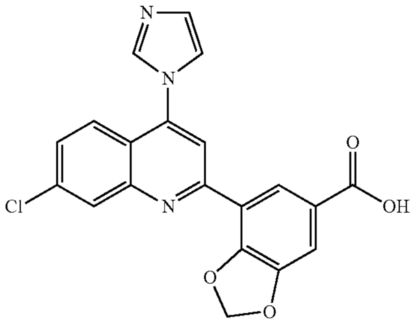 [SMILES: O=C(O)c1cc2c(c(-c3cc(-n4ccnc4)c4ccc(Cl)cc4n3)c1)OCO2] |

TABLE 1-continued
Exemplary Compounds
| I-# | Structure |
|---|---|
| I-38 | 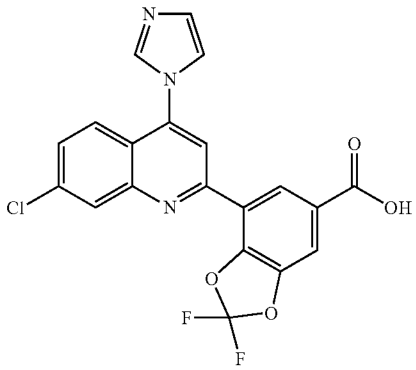 [SMILES: O=C(O)c1cc2c(c(-c3cc(-n4ccnc4)c4ccc(Cl)cc4n3)c1)OC(F)(F)O2] |
| I-39 | 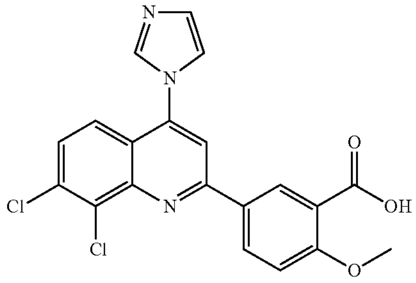 [SMILES: COc1ccc(-c2cc(-n3ccnc3)c3ccc(Cl)c(Cl)c3n2)cc1C(=O)O] |
| I-40 | 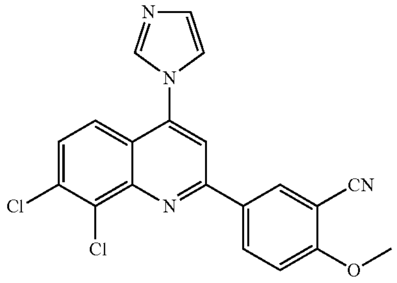 [SMILES: COc1ccc(-c2cc(-n3ccnc3)c3ccc(Cl)c(Cl)c3n2)cc1C#N] |
| I-41 | 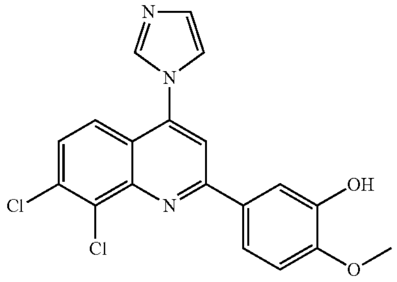 [SMILES: COc1ccc(-c2cc(-n3ccnc3)c3ccc(Cl)c(Cl)c3n2)cc1O] |
| I-42 | 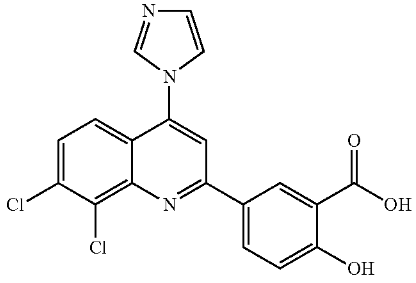 [SMILES: O=C(O)c1cc(-c2cc(-n3ccnc3)c3ccc(Cl)c(Cl)c3n2)ccc1O] |
TABLE 1-continued
Exemplary Compounds
| I-# | Structure |
|---|---|
| I-43 | 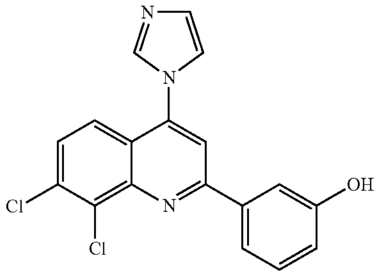 [SMILES: Oc1cccc(-c2cc(-n3ccnc3)c3ccc(Cl)c(Cl)c3n2)c1] |
| I-44 | 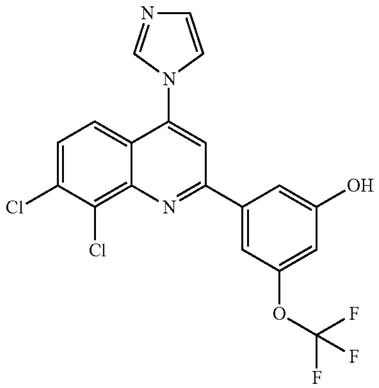 [SMILES: Oc1cc(OC(F)(F)F)cc(-c2cc(-n3ccnc3)c3ccc(Cl)c(Cl)c3n2)c1] |
| I-45 | 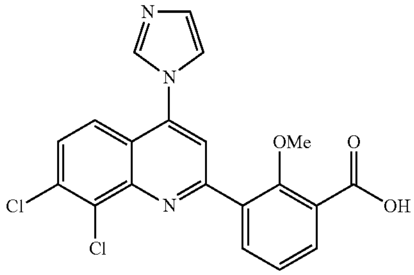 [SMILES: COc1c(C(=O)O)cccc1-c1cc(-n2ccnc2)c2ccc(Cl)c(Cl)c2n1] |
| I-46 | 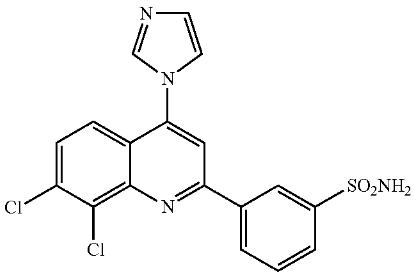 [SMILES: NS(=O)(=O)c1cccc(-c2cc(-n3ccnc3)c3ccc(Cl)c(Cl)c3n2)c1] |
| I-47 | 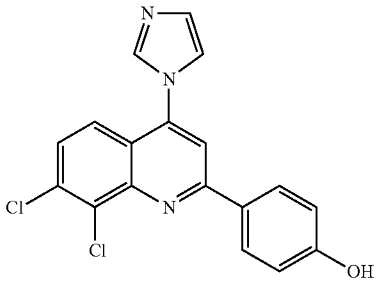 [SMILES: Oc1ccc(-c2cc(-n3ccnc3)c3ccc(Cl)c(Cl)c3n2)cc1] |

TABLE 1-continued
| Exemplary Compounds | |
|---|---|
| I-# | Structure |
| I-48 | 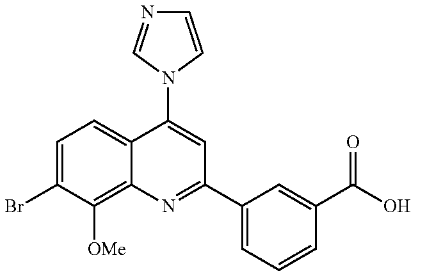 |
| I-49 | 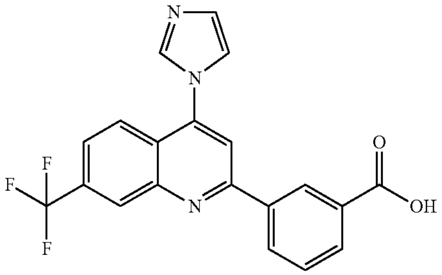 [SMILES: O=C(O)c1cccc(-c2cc(-n3ccnc3)c3ccc(C(F)(F)F)cc3n2)c1] |
| I-50 | 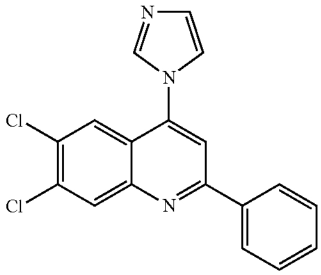 [SMILES: Clc1cc2nc(-c3ccccc3)cc(-n3ccnc3)c2cc1Cl] |
| I-51 | 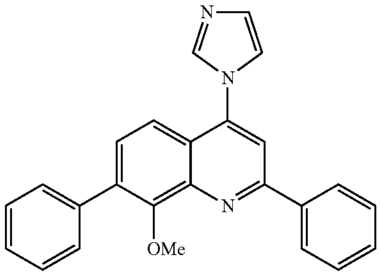 [SMILES: COc1c(-c2ccccc2)ccc2c(-n3ccnc3)cc(-c3ccccc3)nc12] |
| I-52 | 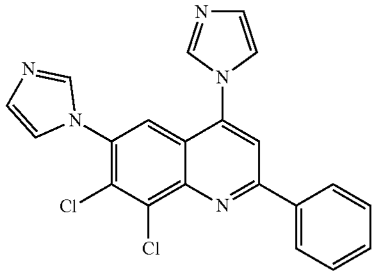 [SMILES: Clc1c(-n2ccnc2)cc2c(-n3ccnc3)cc(-c3ccccc3)nc2c1Cl] |
TABLE 1-continued
| Exemplary Compounds | |
|---|---|
| I-# | Structure |
| I-53 | 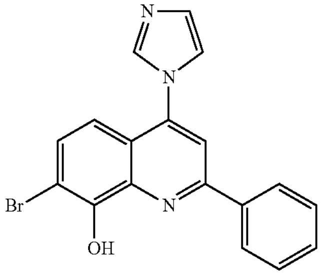 |
| I-54 | 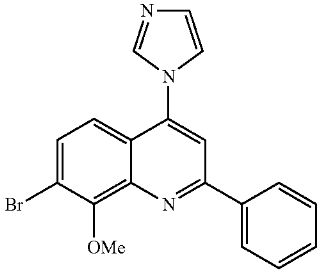 |
| I-55 | 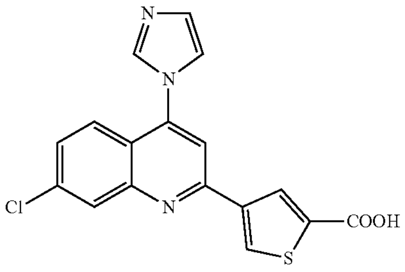 [SMILES: O=C(O)c1cc(-c2cc(-n3ccnc3)c3ccc(Cl)cc3n2)cs1] |
| I-56 | 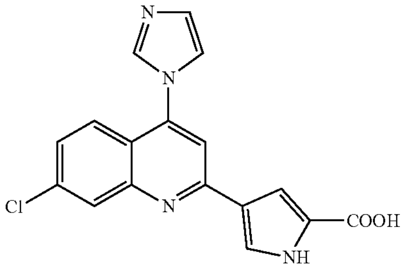 [SMILES: O=C(O)c1cc(-c2cc(-n3ccnc3)c3ccc(Cl)cc3n2)c[nH]1] |
| I-57 | 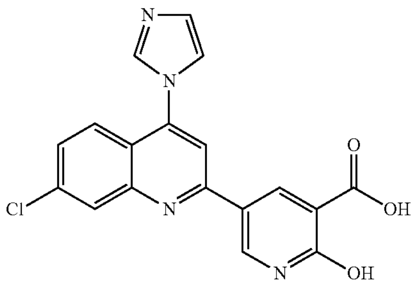 [SMILES: O=C(O)c1cc(-c2cc(-n3ccnc3)c3ccc(Cl)cc3n2)cnc1O] |

TABLE 1-continued
| Exemplary Compounds | |
|---|---|
| I-# | Structure |
| I-58 | 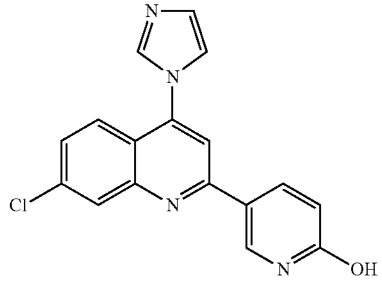 [SMILES: Oc1ccc(-c2cc(-n3ccnc3)c3ccc(Cl)cc3n2)cn1] |
| I-59 | 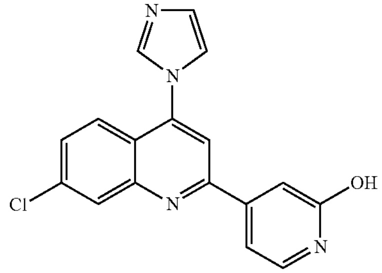 [SMILES: Oc1cc(-c2cc(-n3ccnc3)c3ccc(Cl)cc3n2)ccn1] |
| I-60 | 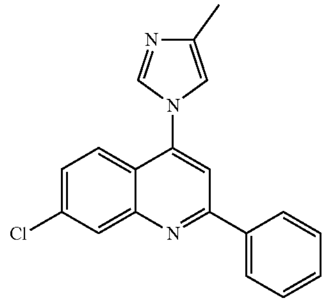 [SMILES: Cc1cn(-c2cc(-c3ccccc3)nc3cc(Cl)ccc23)cn1] |
| I-61 | 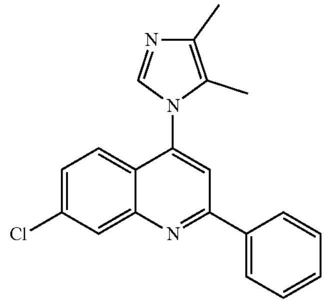 [SMILES: Cc1ncn(-c2cc(-c3ccccc3)nc3cc(Cl)ccc23)c1C] |
| I-62 | 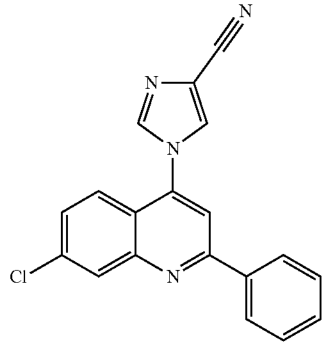 [SMILES: N#Cc1cn(-c2cc(-c3ccccc3)nc3cc(Cl)ccc23)cn1] |
TABLE 1-continued
| Exemplary Compounds | |
|---|---|
| I-# | Structure |
| I-63 | 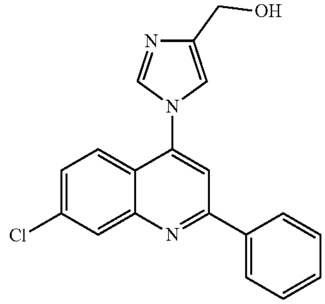 [SMILES: OCc1cn(-c2cc(-c3ccccc3)nc3cc(Cl)ccc23)cn1] |
| I-64 | 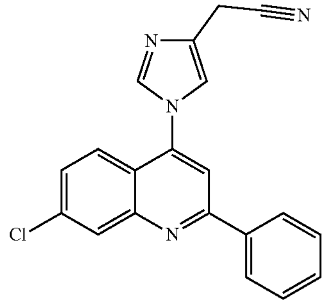 [SMILES: N#CCc1cn(-c2cc(-c3ccccc3)nc3cc(Cl)ccc23)cn1] |
| I-65 | 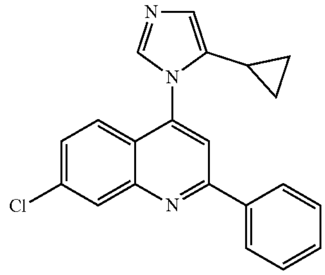 [SMILES: Clc1ccc2c(-n3cncc3C3CC3)cc(-c3ccccc3)nc2c1] |
| I-66 | 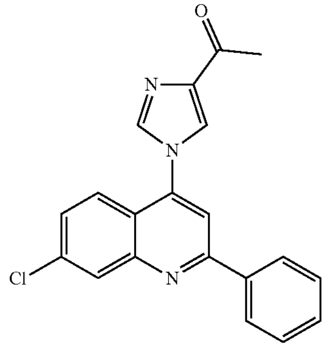 [SMILES: CC(=O)c1cn(-c2cc(-c3ccccc3)nc3cc(Cl)ccc23)cn1] |
| I-67 | 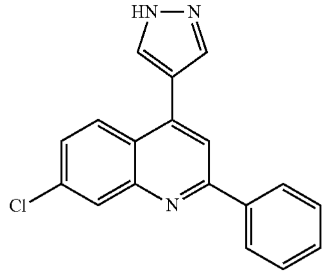 [SMILES: Clc1ccc2c(-c3cn[nH]c3)cc(-c3ccccc3)nc2c1] |

TABLE 1-continued
Exemplary Compounds
| I-# | Structure |
| --- | --- |
| I-68 | 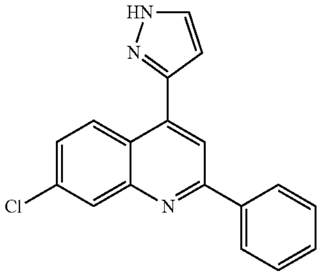 [SMILES: Clc1ccc2c(-c3cc[nH]n3)cc(-c3ccccc3)nc2c1] |
| I-69 | 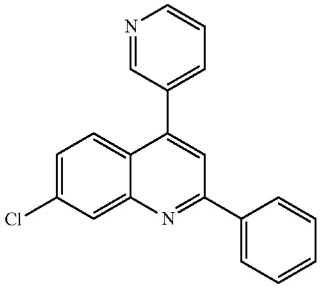 |
| I-70 | 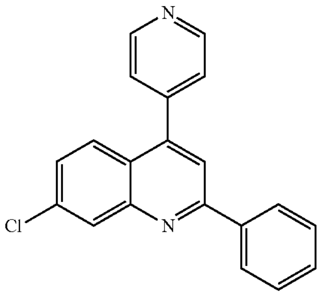 [SMILES: Clc1ccc2c(-c3ccncc3)cc(-c3ccccc3)nc2c1] |
| I-71 | 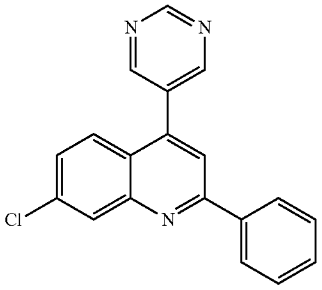 [SMILES: Clc1ccc2c(-c3cncnc3)cc(-c3ccccc3)nc2c1] |
| I-72 | 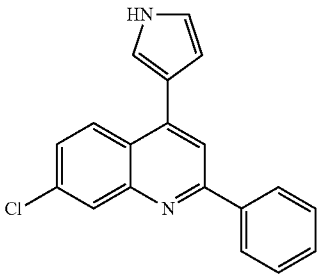 |
TABLE 1-continued
Exemplary Compounds
| I-# | Structure |
| --- | --- |
| I-73 | 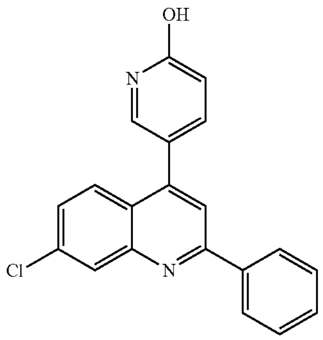 [SMILES: Oc1ccc(-c2cc(-c3ccccc3)nc3cc(Cl)ccc23)cn1] |
| I-74 | 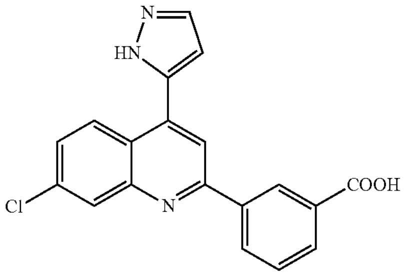 [SMILES: O=C(O)c1cccc(-c2cc(-c3ccn[nH]3)c3ccc(Cl)cc3n2)c1] |
| I-75 | 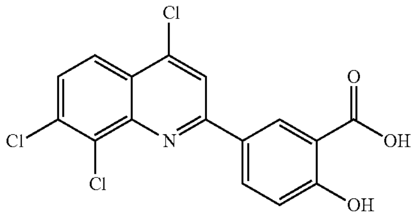 [SMILES: O=C(O)c1cc(-c2cc(Cl)c3ccc(Cl)c(Cl)c3n2)ccc1O] |
| I-76 | 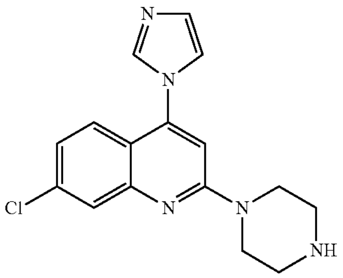 [SMILES: Clc1ccc2c(-n3ccnc3)cc(N3CCNCC3)nc2c1] |
| I-77 | 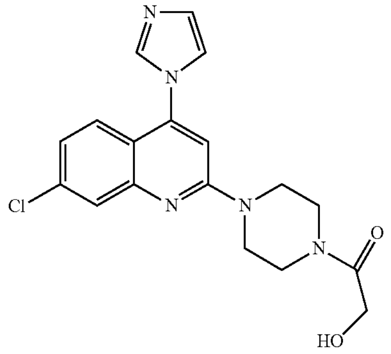 [SMILES: O=C(CO)N1CCN(c2cc(-n3ccnc3)c3ccc(Cl)cc3n2)CC1] |

TABLE 1-continued
Exemplary Compounds
| I-# | Structure |
| --- | --- |
| I-78 | 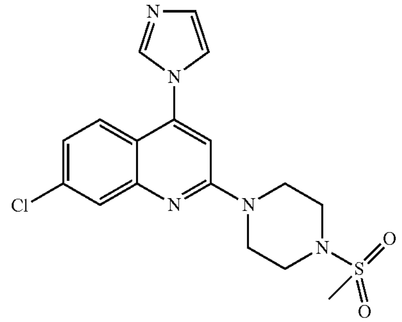 [SMILES: CS(=O)(=O)N1CCN(c2cc(-n3ccnc3)c3ccc(Cl)cc3n2)CC1] |
| I-79 | 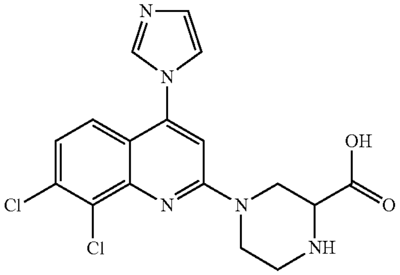 [SMILES: O=C(O)C1CN(c2cc(-n3ccnc3)c3ccc(Cl)c(Cl)c3n2)CCN1] |
| I-80 | 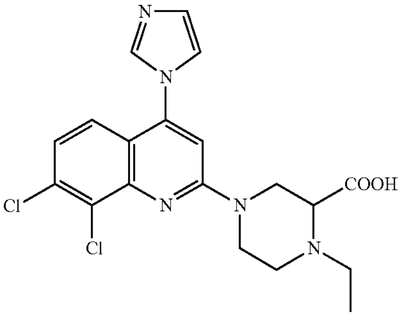 [SMILES: CCN1CCN(c2cc(-n3ccnc3)c3ccc(Cl)c(Cl)c3n2)CC1C(=O)O] |
| I-81 | 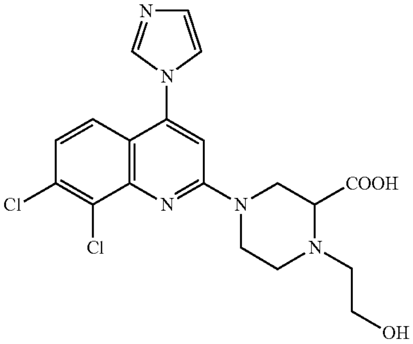 [SMILES: O=C(O)C1CN(c2cc(-n3ccnc3)c3ccc(Cl)c(Cl)c3n2)CCN1CCO] |
| I-82 | 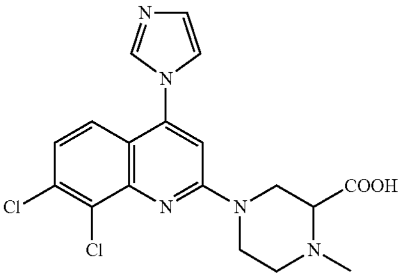 [SMILES: CN1CCN(c2cc(-n3ccnc3)c3ccc(Cl)c(Cl)c3n2)CC1C(=O)O] |
| I-83 | 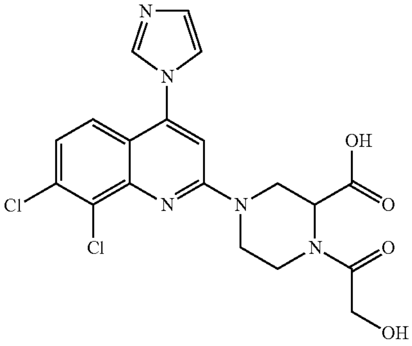 [SMILES: O=C(O)C1CN(c2cc(-n3ccnc3)c3ccc(Cl)c(Cl)c3n2)CCN1C(=O)CO] |
| I-84 | 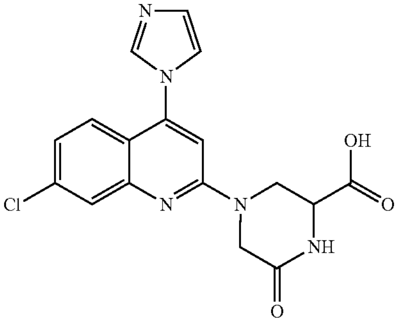 [SMILES: O=C1CN(c2cc(-n3ccnc3)c3ccc(Cl)cc3n2)CC(C(=O)O)N1] |
| I-85 | 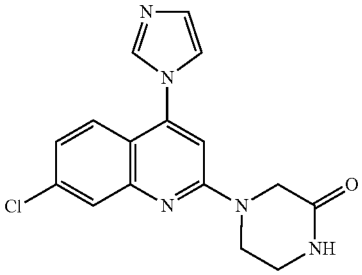 [SMILES: O=C1CN(c2cc(-n3ccnc3)c3ccc(Cl)cc3n2)CCN1] |
| I-86 | 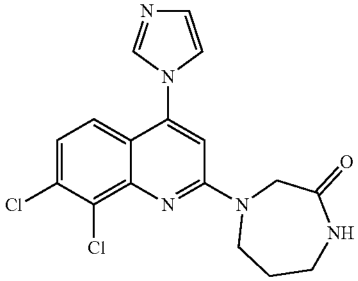 [SMILES: O=C1CN(c2cc(-n3ccnc3)c3ccc(Cl)c(Cl)c3n2)CCCN1] |
| I-87 | 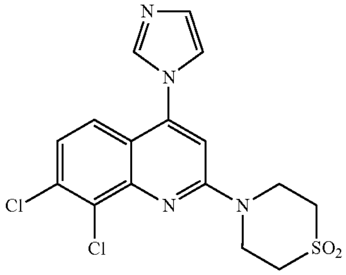 [SMILES: O=S1(=O)CCN(c2cc(-n3ccnc3)c3ccc(Cl)c(Cl)c3n2)CC1] |

TABLE 1-continued
| Exemplary Compounds | |
| --- | --- |
| I-# | Structure |
| I-88 | 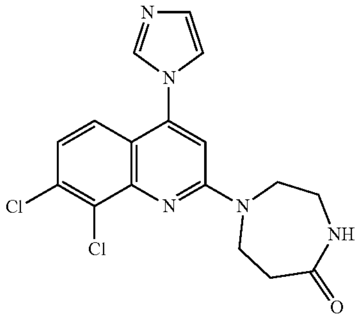 [SMILES: O=C1CCN(c2cc(-n3ccnc3)c3ccc(Cl)c(Cl)c3n2)CCN1] |
| I-89 | 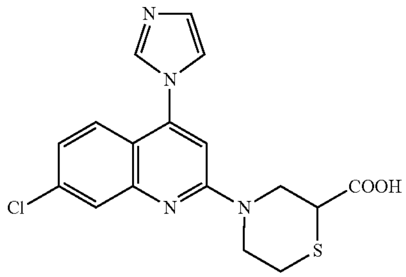 [SMILES: O=C(O)C1CN(c2cc(-n3ccnc3)c3ccc(Cl)cc3n2)CCS1] |
| I-90 | 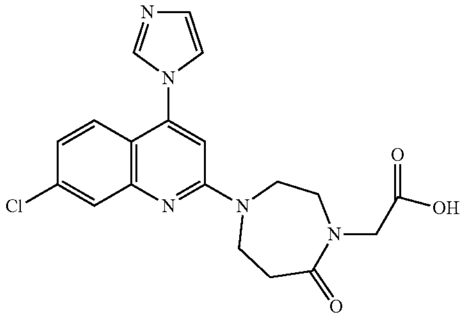 [SMILES: O=C(O)CN1CCN(c2cc(-n3ccnc3)c3ccc(Cl)cc3n2)CCC1=O] |
| I-91 | 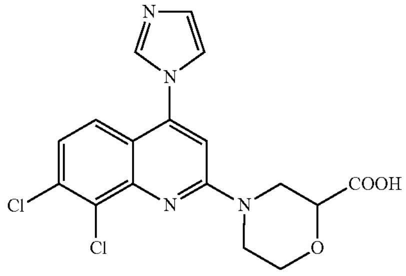 [SMILES: O=C(O)C1CN(c2cc(-n3ccnc3)c3ccc(Cl)c(Cl)c3n2)CCO1] |
| I-92 | 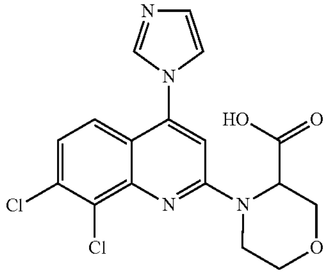 [SMILES: O=C(O)C1COCCN1c1cc(-n2ccnc2)c2ccc(Cl)c(Cl)c2n1] |
TABLE 1-continued
| Exemplary Compounds | |
| --- | --- |
| I-# | Structure |
| I-93 | 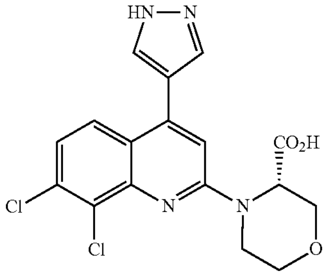 [SMILES: O=C(O)[C@@H]1COCCN1c1cc(-c2cn[nH]c2)c2ccc(Cl)c(Cl)c2n1] |
| 1-94 | 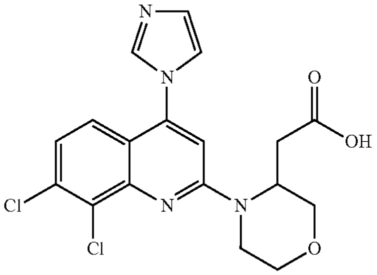 [SMILES: O=C(O)CC1COCCN1c1cc(-n2ccnc2)c2ccc(Cl)c(Cl)c2n1] |
| I-95 | 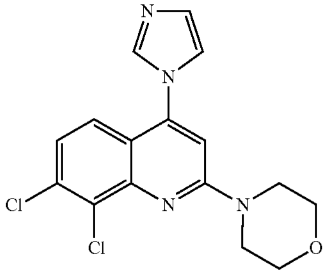 [SMILES: Clc1ccc2c(-n3ccnc3)cc(N3CCOCC3)nc2c1Cl] |
| I-96 | 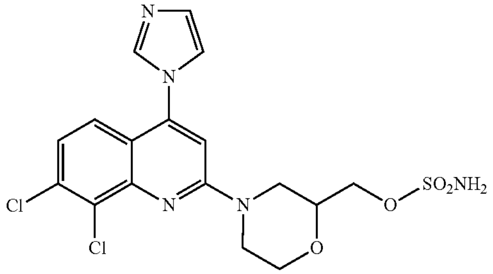 [SMILES: NS(=O)(=O)OCC1CN(c2cc(-n3ccnc3)c3ccc(Cl)c(Cl)c3n2)CCO1] |
| I-97 | 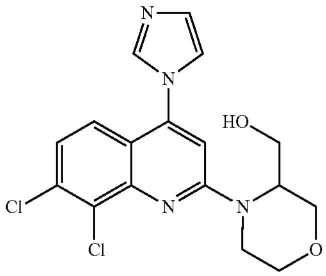 [SMILES: OCC1COCCN1c1cc(-n2ccnc2)c2ccc(Cl)c(Cl)c2n1] |

TABLE 1-continued
| Exemplary Compounds | |
|---|---|
| I-# | Structure |
| I-98 | 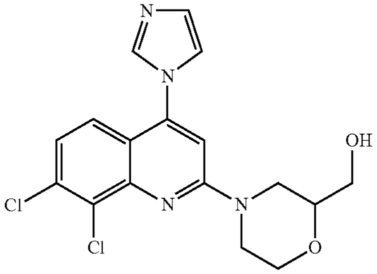 [SMILES: OCC1CN(c2cc(-n3ccnc3)c3ccc(Cl)c(Cl)c3n2)CCO1] |
| I-99 | 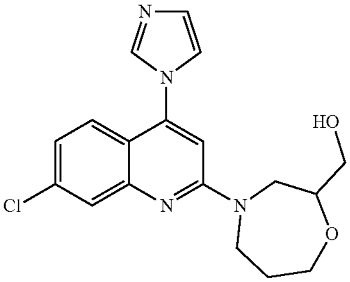 [SMILES: OCC1CN(c2cc(-n3ccnc3)c3ccc(Cl)cc3n2)CCCO1] |
| I-100 | 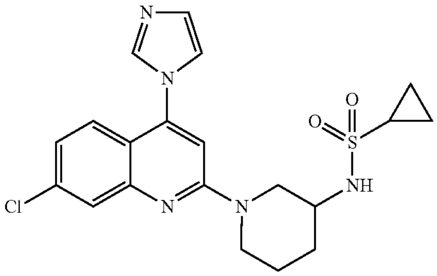 [SMILES: O=S(=O)(NC1CCCN(c2cc(-n3ccnc3)c3ccc(Cl)cc3n2)C1)C1CC1] |
| I-101 | 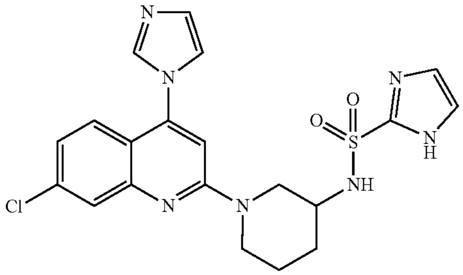 [SMILES: O=S(=O)(NC1CCCN(c2cc(-n3ccnc3)c3ccc(Cl)cc3n2)C1)c1ncc[nH]1] |
| I-102 | 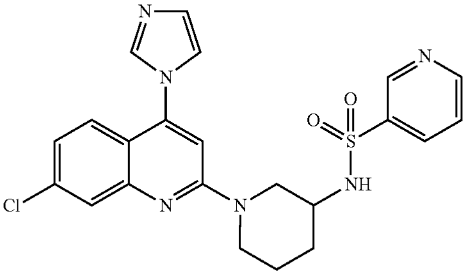 [SMILES: O=S(=O)(NC1CCCN(c2cc(-n3ccnc3)c3ccc(Cl)cc3n2)C1)c1cccnc1] |
TABLE 1-continued
| Exemplary Compounds | |
|---|---|
| I-# | Structure |
| I-103 | 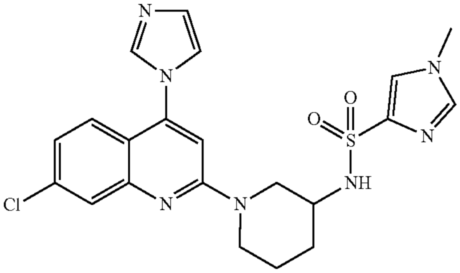 [SMILES: Cn1cnc(S(=O)(=O)NC2CCCN(c3cc(-n4ccnc4)c4ccc(Cl)cc4n3)C2)c1] |
| I-104 | 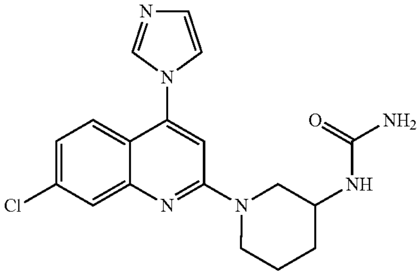 [SMILES: NC(=O)NC1CCCN(c2cc(-n3ccnc3)c3ccc(Cl)cc3n2)C1] |
| I-105 | 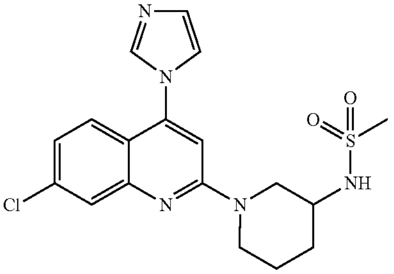 [SMILES: CS(=O)(=O)NC1CCCN(c2cc(-n3ccnc3)c3ccc(Cl)cc3n2)C1] |
| I-106 | 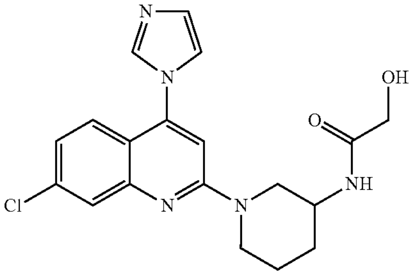 [SMILES: O=C(CO)NC1CCCN(c2cc(-n3ccnc3)c3ccc(Cl)cc3n2)C1] |
| I-107 | 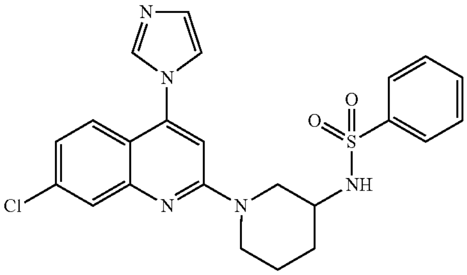 [SMILES: O=S(=O)(NC1CCCN(c2cc(-n3ccnc3)c3ccc(Cl)cc3n2)C1)c1ccccc1] |

TABLE 1-continued
Exemplary Compounds
| I-# | Structure |
|---|---|
| I-108 | 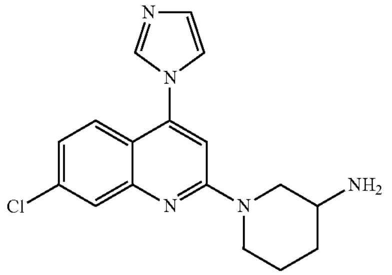 [SMILES: NC1CCCN(c2cc(-n3ccnc3)c3ccc(Cl)cc3n2)C1] |
| I-109 | 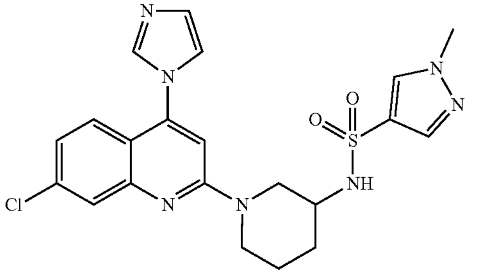 [SMILES: Cn1cc(S(=O)(=O)NC2CCCN(c3cc(-n4ccnc4)c4ccc(Cl)cc4n3)C2)cn1] |
| I-110 | 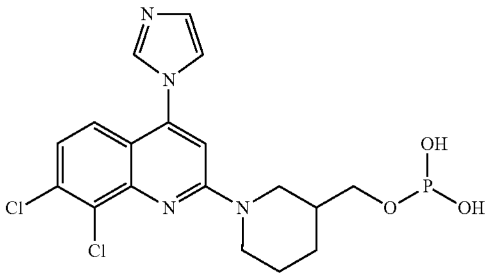 [SMILES: OP(O)OCC1CCCN(c2cc(-n3ccnc3)c3ccc(Cl)c(Cl)c3n2)C1] |
| I-111 | 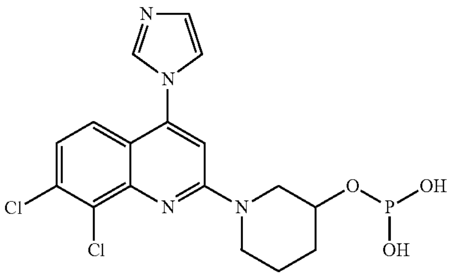 [SMILES: OP(O)OC1CCCN(c2cc(-n3ccnc3)c3ccc(Cl)c(Cl)c3n2)C1] |
| I-112 | 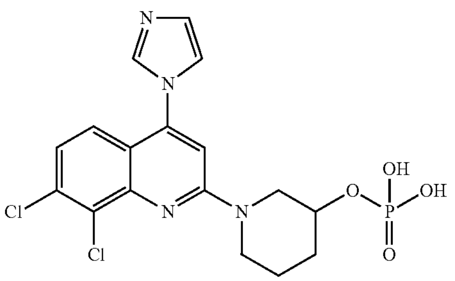 [SMILES: O=P(O)(O)OC1CCCN(c2cc(-n3ccnc3)c3ccc(Cl)c(Cl)c3n2)C1] |
| I-113 | 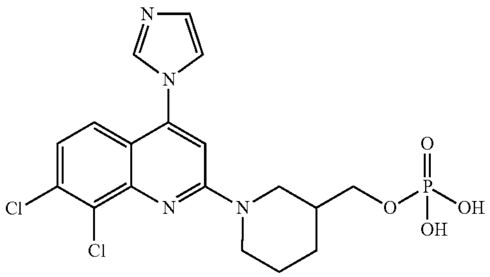 [SMILES: O=P(O)(O)OCC1CCCN(c2cc(-n3ccnc3)c3ccc(Cl)c(Cl)c3n2)C1] |
| I-114 | 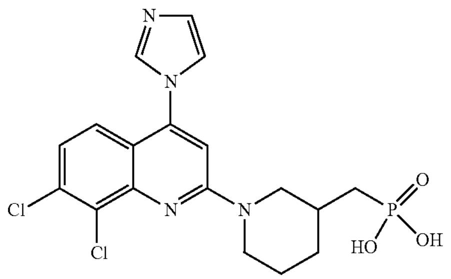 [SMILES: O=P(O)(O)CC1CCCN(c2cc(-n3ccnc3)c3ccc(Cl)c(Cl)c3n2)C1] |
| I-115 | 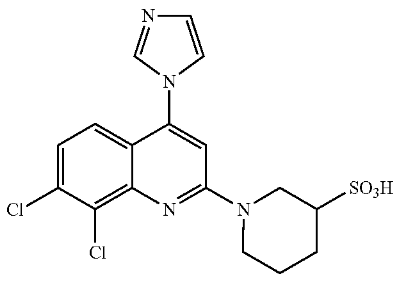 [SMILES: O=S(=O)(O)C1CCCN(c2cc(-n3ccnc3)c3ccc(Cl)c(Cl)c3n2)C1] |
| I-116 | 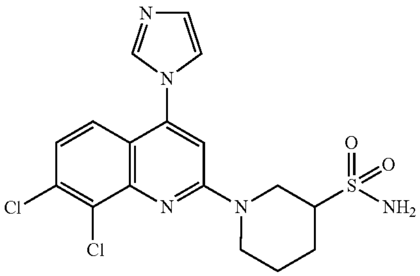 [SMILES: NS(=O)(=O)C1CCCN(c2cc(-n3ccnc3)c3ccc(Cl)c(Cl)c3n2)C1] |
| I-117 | 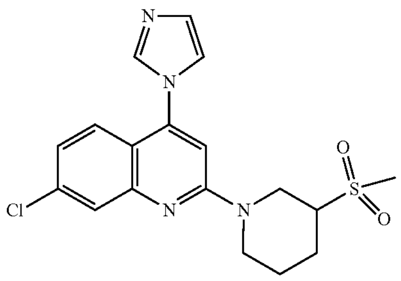 [SMILES: CS(=O)(=O)C1CCCN(c2cc(-n3ccnc3)c3ccc(Cl)cc3n2)C1] |

TABLE 1-continued
| Exemplary Compounds | |
|---|---|
| I-# | Structure |
| I-118 | 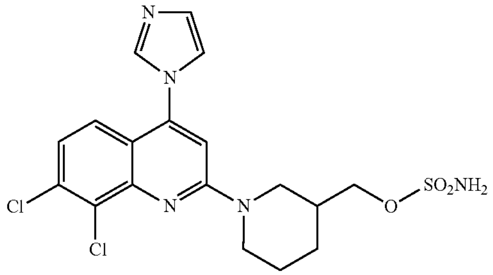 [SMILES: NS(=O)(=O)OCC1CCCN(c2cc(-n3ccnc3)c3ccc(Cl)c(Cl)c3n2)C1] |
| I-119 | 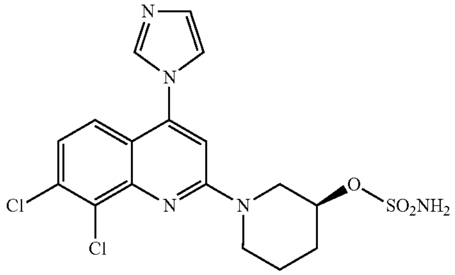 [SMILES: NS(=O)(=O)O[C@H]1CCCN(c2cc(-n3ccnc3)c3ccc(Cl)c(Cl)c3n2)C1] |
| I-120 | 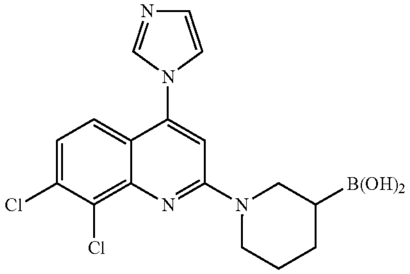 [SMILES: OB(O)C1CCCN(c2cc(-n3ccnc3)c3ccc(Cl)c(Cl)c3n2)C1] |
| I-121 | 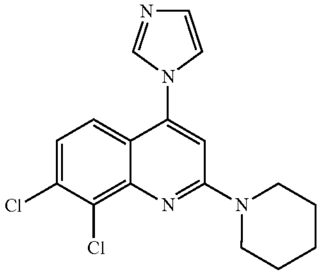 [SMILES: Clc1ccc2c(-n3ccnc3)cc(N3CCCCC3)nc2c1Cl] |
| I-122 | 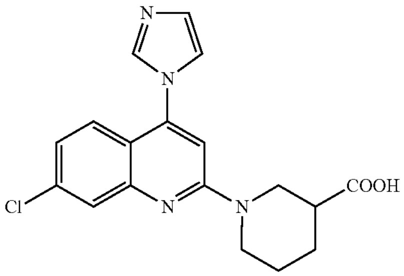 |
TABLE 1-continued
| Exemplary Compounds | |
|---|---|
| I-# | Structure |
| I-123 | 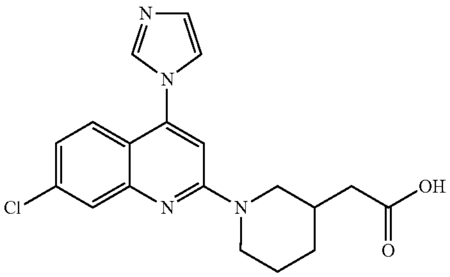 [SMILES: O=C(O)CC1CCCN(c2cc(-n3ccnc3)c3ccc(Cl)cc3n2)C1] |
| I-124 | 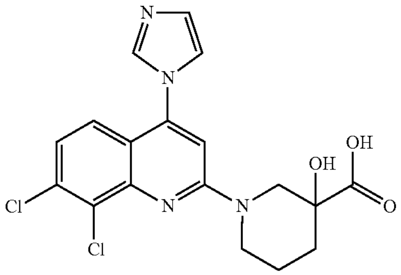 [SMILES: O=C(O)C1(O)CCCN(c2cc(-n3ccnc3)c3ccc(Cl)c(Cl)c3n2)C1] |
| I-125 | 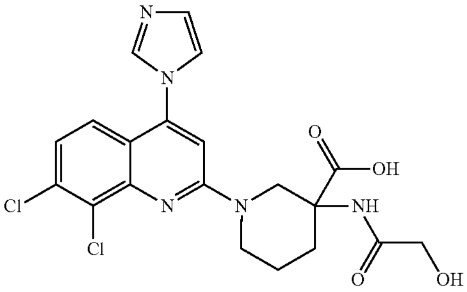 [SMILES: O=C(CO)NC1(C(=O)O)CCCN(c2cc(-n3ccnc3)c3ccc(Cl)c(Cl)c3n2)C1] |
| I-126 | 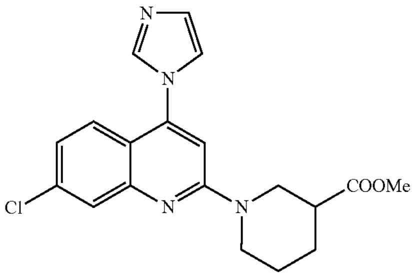 [SMILES: COC(=O)C1CCCN(c2cc(-n3ccnc3)c3ccc(Cl)cc3n2)C1] |
| I-127 | 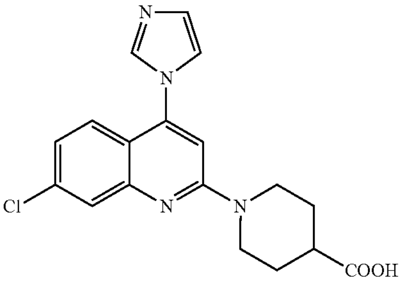 [SMILES: O=C(O)C1CCN(c2cc(-n3ccnc3)c3ccc(Cl)cc3n2)CC1] |

TABLE 1-continued
| Exemplary Compounds | |
|---|---|
| I-# | Structure |
| I-128 | 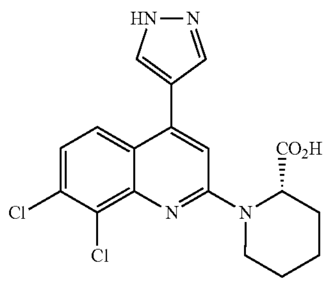 [SMILES: O=C(O)[C@@H]1CCCCN1c1cc(-c2cn[nH]c2)c2ccc(Cl)c(Cl)c2n1] |
| I-130 | 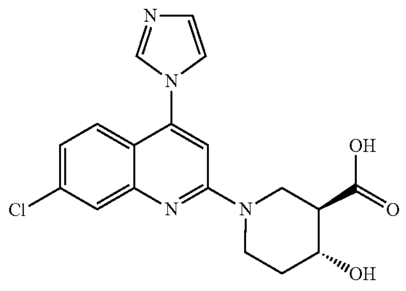 [SMILES: O=C(O)[C@@H]1CN(c2cc(-n3ccnc3)c3ccc(Cl)cc3n2)CC[C@H]1O] |
| I-131 | 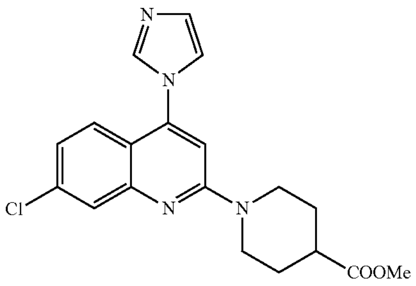 [SMILES: COC(=O)C1CCN(c2cc(-n3ccnc3)c3ccc(Cl)cc3n2)CC1] |
| I-132 | 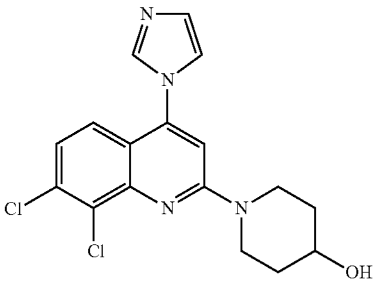 [SMILES: OC1CCN(c2cc(-n3ccnc3)c3ccc(Cl)c(Cl)c3n2)CC1] |
| I-133 | 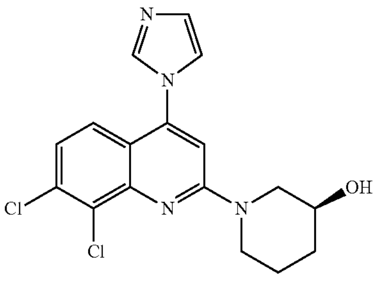 [SMILES: O[C@H]1CCCN(c2cc(-n3ccnc3)c3ccc(Cl)c(Cl)c3n2)C1] |
TABLE 1-continued
| Exemplary Compounds | |
|---|---|
| I-# | Structure |
| I-134 | 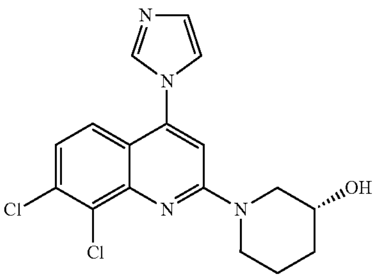 [SMILES: O[C@@H]1CCCN(c2cc(-n3ccnc3)c3ccc(Cl)c(Cl)c3n2)C1] |
| I-135 | 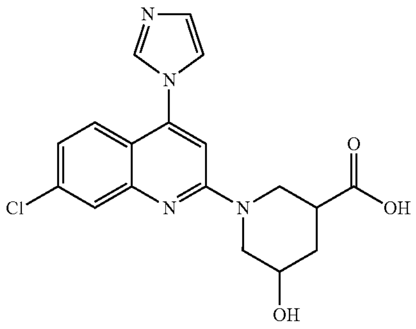 [SMILES: O=C(O)C1CC(O)CN(c2cc(-n3ccnc3)c3ccc(Cl)cc3n2)C1] |
| I-136 | 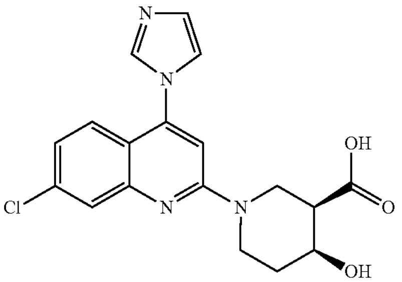 [SMILES: O=C(O)[C@@H]1CN(c2cc(-n3ccnc3)c3ccc(Cl)cc3n2)CC[C@@H]1O] |
| I-137 | 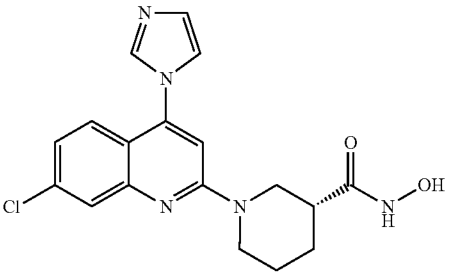 [SMILES: O=C(NO)[C@@H]1CCCN(c2cc(-n3ccnc3)c3ccc(Cl)cc3n2)C1] |
| I-138 | 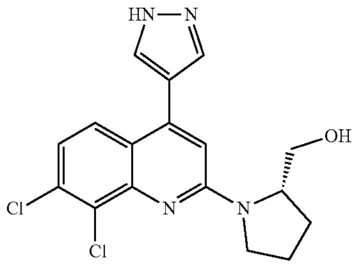 [SMILES: OC[C@@H]1CCCN1c1cc(-c2cn[nH]c2)c2ccc(Cl)c(Cl)c2n1] |

TABLE 1-continued
| Exemplary Compounds | |
|---|---|
| I-# | Structure |
| I-139 | 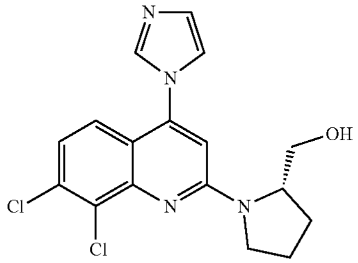 [SMILES: OC[C@@H]1CCCN1c1cc(-n2ccnc2)c2ccc(Cl)c(Cl)c2n1] |
| I-140 | 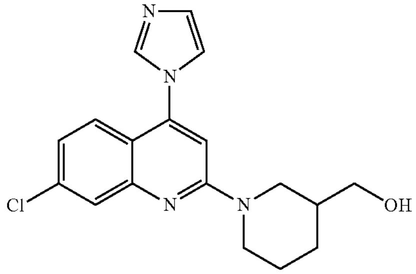 [SMILES: OCC1CCCN(c2cc(-n3ccnc3)c3ccc(Cl)cc3n2)C1] |
| I-141 | 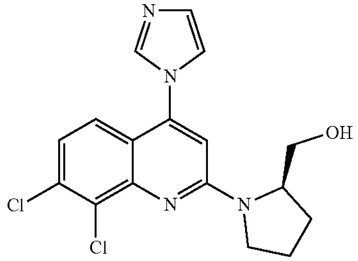 [SMILES: OC[C@H]1CCCN1c1cc(-n2ccnc2)c2ccc(Cl)c(Cl)c2n1] |
| I-142 | 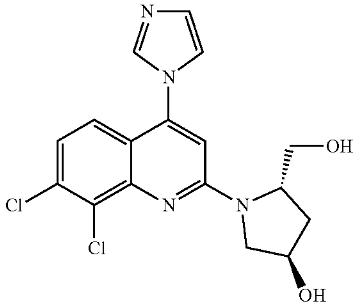 [SMILES: OC[C@@H]1C[C@@H](O)CN1c1cc(-n2ccnc2)c2ccc(Cl)c(Cl)c2n1] |
| I-143 | 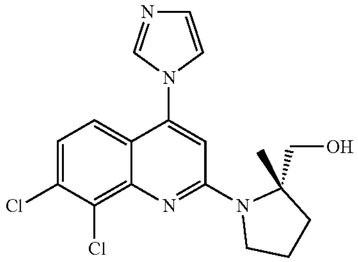 [SMILES: C[C@@]1(CO)CCCN1c1cc(-n2ccnc2)c2ccc(Cl)c(Cl)c2n1] |
TABLE 1-continued
| Exemplary Compounds | |
|---|---|
| I-# | Structure |
| I-144 | 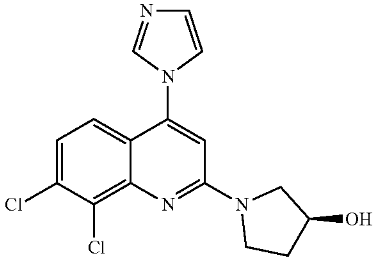 [SMILES: O[C@H]1CCN(c2cc(-n3ccnc3)c3ccc(Cl)c(Cl)c3n2)C1] |
| I-145 | 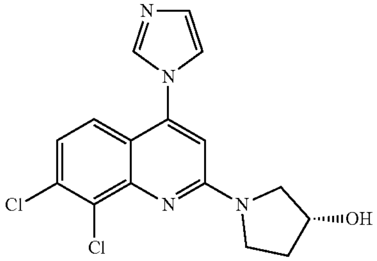 [SMILES: O[C@@H]1CCN(c2cc(-n3ccnc3)c3ccc(Cl)c(Cl)c3n2)C1] |
| I-147 | 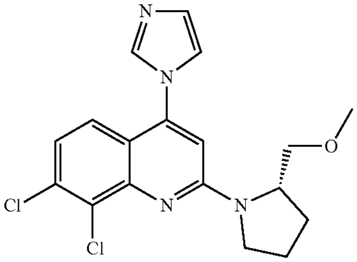 [SMILES: COC[C@@H]1CCCN1c1cc(-n2ccnc2)c2ccc(Cl)c(Cl)c2n1] |
| I-148 | 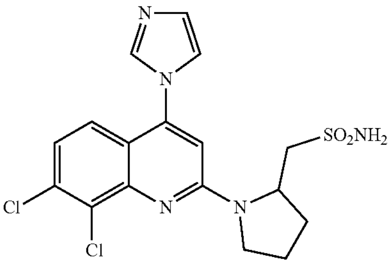 [SMILES: NS(=O)(=O)CC1CCCN1c1cc(-n2ccnc2)c2ccc(Cl)c(Cl)c2n1] |
| I-149 | 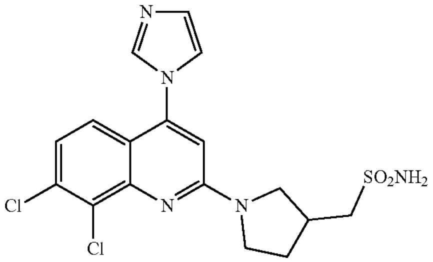 [SMILES: NS(=O)(=O)CC1CCN(c2cc(-n3ccnc3)c3ccc(Cl)c(Cl)c3n2)C1] |

TABLE 1-continued
| Exemplary Compounds | |
|---|---|
| I-# | Structure |
| I-150 | 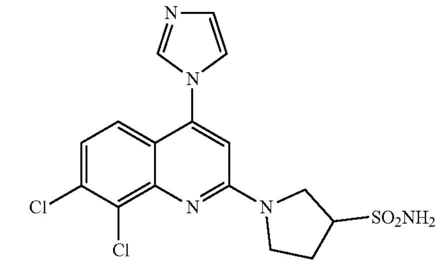 [SMILES: NS(=O)(=O)C1CCN(c2cc(-n3ccnc3)c3ccc(Cl)c(Cl)c3n2)C1] |
| I-151 | 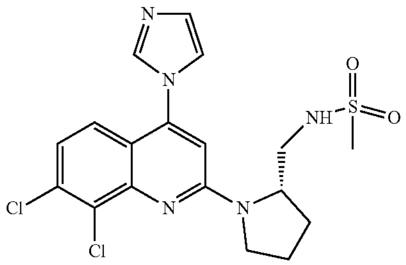 [SMILES: CS(=O)(=O)NC[C@@H]1CCCN1c1cc(-n2ccnc2)c2ccc(Cl)c(Cl)c2n1] |
| I-152 | 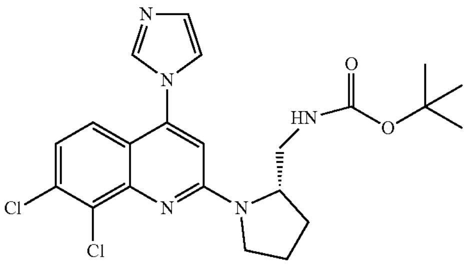 [SMILES: CC(C)(C)OC(=O)NC[C@@H]1CCCN1c1cc(-n2ccnc2)c2ccc(Cl)c(Cl)c2n1] |
| I-153 | 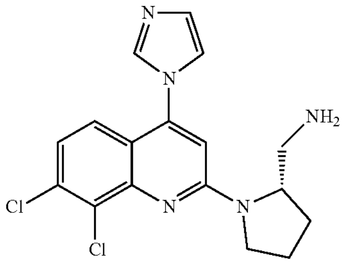 [SMILES: NC[C@@H]1CCCN1c1cc(-n2ccnc2)c2ccc(Cl)c(Cl)c2n1] |
| I-154 | 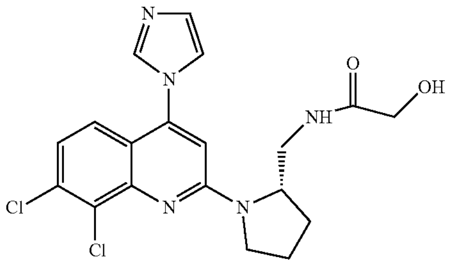 [SMILES: O=C(CO)NC[C@@H]1CCCN1c1cc(-n2ccnc2)c2ccc(Cl)c(Cl)c2n1] |
TABLE 1-continued
| Exemplary Compounds | |
|---|---|
| I-# | Structure |
| I-155 | 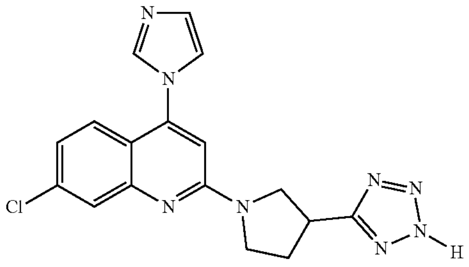 [SMILES: Clc1ccc2c(-n3ccnc3)cc(N3CCC(c4nn[nH]n4)C3)nc2c1] |
| I-156 | 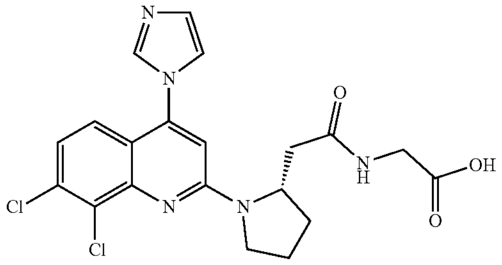 [SMILES: O=C(O)CNC(=O)C[C@@H]1CCCN1c1cc(-n2ccnc2)c2ccc(Cl)c(Cl)c2n1] |
| I-157 | 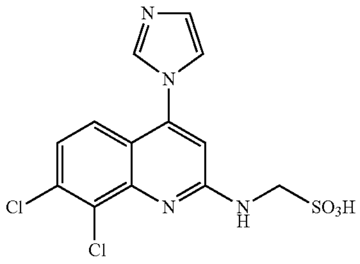 [SMILES: O=S(=O)(O)CNc1cc(-n2ccnc2)c2ccc(Cl)c(Cl)c2n1] |
| I-158 | 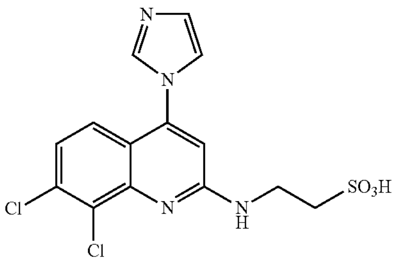 [SMILES: O=S(=O)(O)CCNc1cc(-n2ccnc2)c2ccc(Cl)c(Cl)c2n1] |
| I-159 | 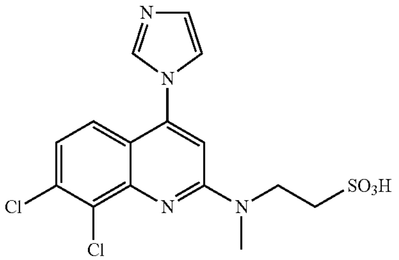 [SMILES: CN(CCS(=O)(=O)O)c1cc(-n2ccnc2)c2ccc(Cl)c(Cl)c2n1] |

TABLE 1-continued
| Exemplary Compounds | |
|---|---|
| I-# | Structure |
| I-160 | 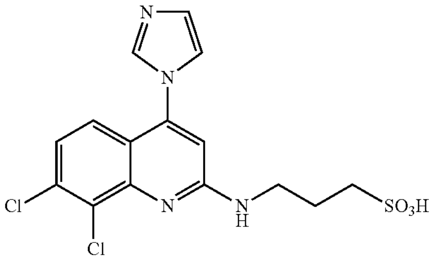 [SMILES: O=S(=O)(O)CCCNc1cc(-n2ccnc2)c2ccc(Cl)c(Cl)c2n1] |
| I-161 | 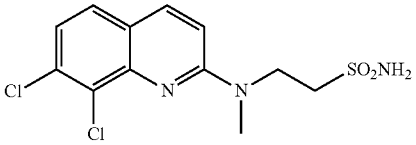 [SMILES: CN(CCS(N)(=O)=O)c1ccc2ccc(Cl)c(Cl)c2n1] |
| I-162 | 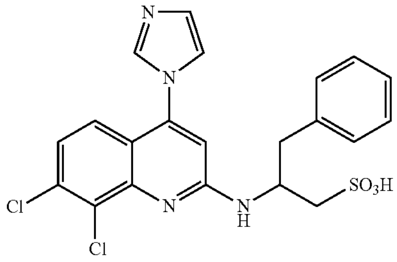 [SMILES: O=S(=O)(O)CC(Cc1ccccc1)Nc1cc(-n2ccnc2)c2ccc(Cl)c(Cl)c2n1] |
| I-163 | 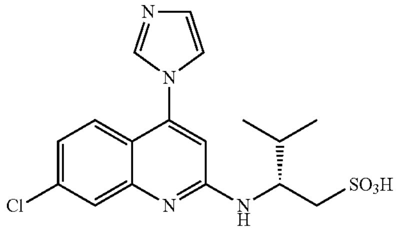 [SMILES: CC(C)[C@H](CS(=O)(=O)O)Nc1cc(-n2ccnc2)c2ccc(Cl)cc2n1] |
| I-164 | 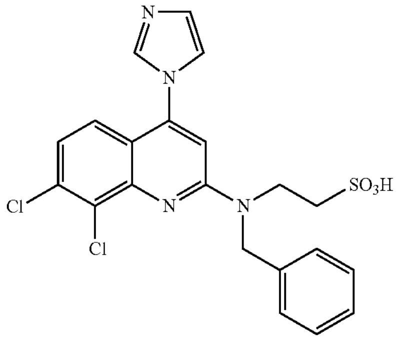 [SMILES: O=S(=O)(O)CCN(Cc1ccccc1)c1cc(-n2ccnc2)c2ccc(Cl)c(Cl)c2n1] |
| I-165 | 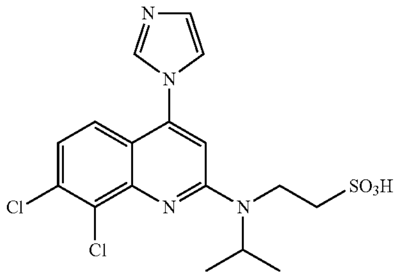 [SMILES: CC(C)N(CCS(=O)(=O)O)c1cc(-n2ccnc2)c2ccc(Cl)c(Cl)c2n1] |
TABLE 1-continued
| Exemplary Compounds | |
|---|---|
| I-# | Structure |
| I-166 | 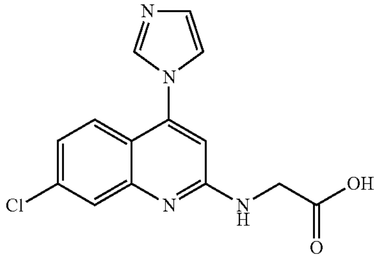 [SMILES: O=C(O)CNc1cc(-n2ccnc2)c2ccc(Cl)cc2n1] |
| I-167 | 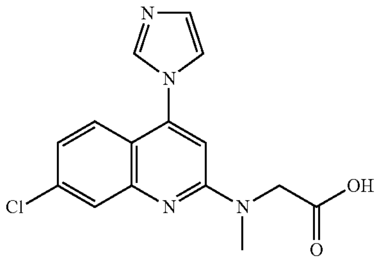 [SMILES: CN(CC(=O)O)c1cc(-n2ccnc2)c2ccc(Cl)cc2n1] |
| I-168 | 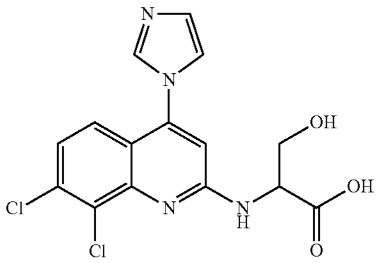 [SMILES: O=C(O)C(CO)Nc1cc(-n2ccnc2)c2ccc(Cl)c(Cl)c2n1] |
| I-169 | 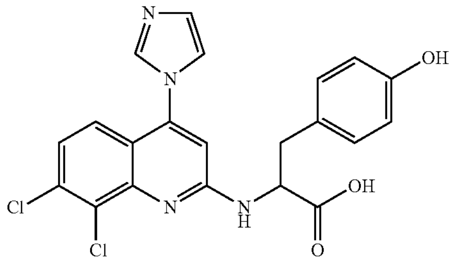 [SMILES: O=C(O)C(Cc1ccc(O)cc1)Nc1cc(-n2ccnc2)c2ccc(Cl)c(Cl)c2n1] |
| I-170 | 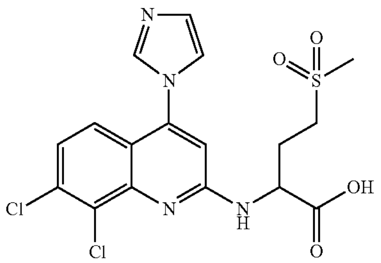 [SMILES: CS(=O)(=O)CCC(Nc1cc(-n2ccnc2)c2ccc(Cl)c(Cl)c2n1)C(=O)O] |
| I-171 | 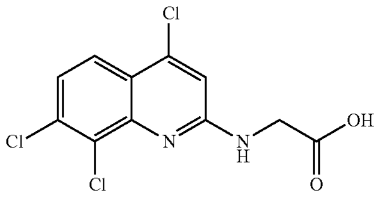 [SMILES: O=C(O)CNc1cc(Cl)c2ccc(Cl)c(Cl)c2n1] |

TABLE 1-continued
| Exemplary Compounds | |
|---|---|
| I-# | Structure |
| I-172 | 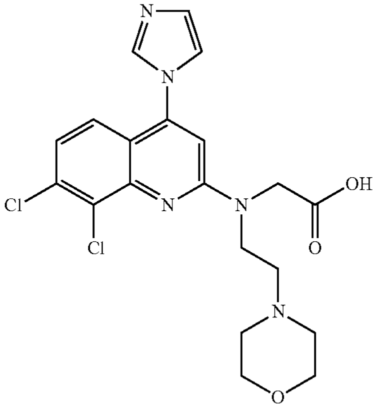 [SMILES: O=C(O)CN(CCN1CCOCC1)c1cc(-n2ccnc2)c2ccc(Cl)c(Cl)c2n1] |
| I-173 | 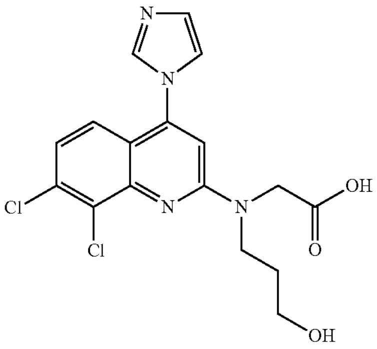 [SMILES: O=C(O)CN(CCCO)c1cc(-n2ccnc2)c2ccc(Cl)c(Cl)c2n1] |
| I-174 | 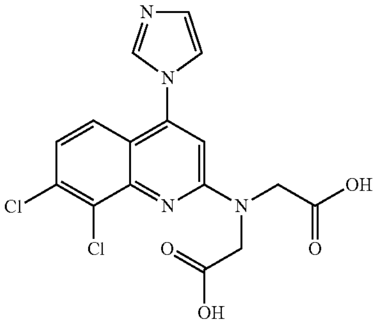 [SMILES: O=C(O)CN(CC(=O)O)c1cc(-n2ccnc2)c2ccc(Cl)c(Cl)c2n1] |
| I-175 | 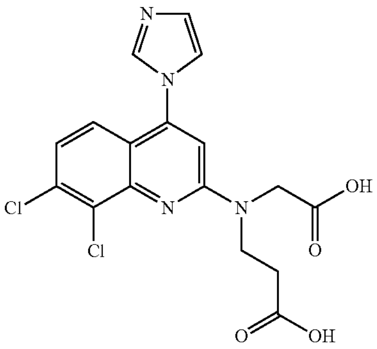 [SMILES: O=C(O)CCN(CC(=O)O)c1cc(-n2ccnc2)c2ccc(Cl)c(Cl)c2n1] |
TABLE 1-continued
| Exemplary Compounds | |
|---|---|
| I-# | Structure |
| I-176 | 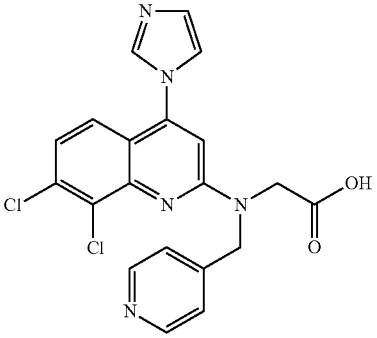 [SMILES: O=C(O)CN(Cc1ccncc1)c1cc(-n2ccnc2)c2ccc(Cl)c(Cl)c2n1] |
| I-177 | 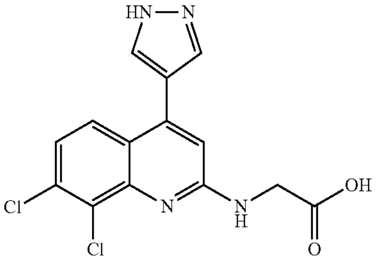 [SMILES: O=C(O)CNc1cc(-c2cn[nH]c2)c2ccc(Cl)c(Cl)c2n1] |
| I-178 | 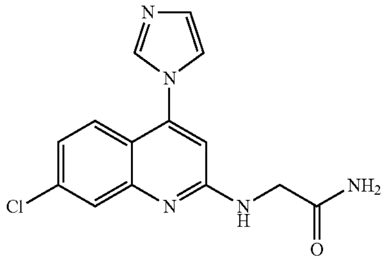 [SMILES: NC(=O)CNc1cc(-n2ccnc2)c2ccc(Cl)cc2n1] |
| I-179 | 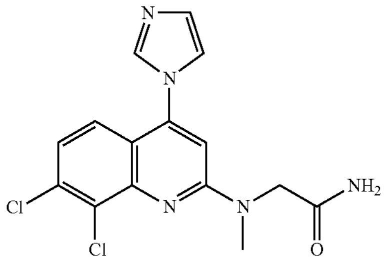 [SMILES: CN(CC(N)=O)c1cc(-n2ccnc2)c2ccc(Cl)c(Cl)c2n1] |
| I-180 | 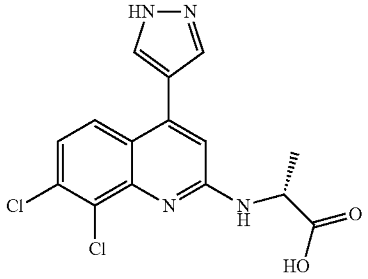 [SMILES: C[C@@H](Nc1cc(-c2cn[nH]c2)c2ccc(Cl)c(Cl)c2n1)C(=O)O] |

TABLE 1-continued
| Exemplary Compounds | |
|---|---|
| I-# | Structure |
| I-181 | 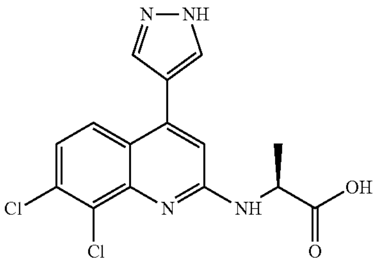 [SMILES: C[C@H](Nc1cc(-c2cn[nH]c2)c2ccc(Cl)c(Cl)c2n1)C(=O)O] |
| I-182 | 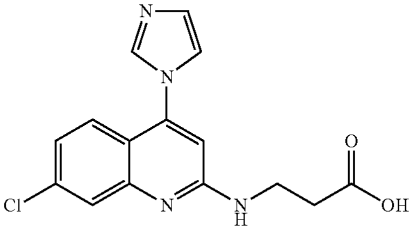 [SMILES: O=C(O)CCNc1cc(-n2ccnc2)c2ccc(Cl)cc2n1] |
| I-183 | 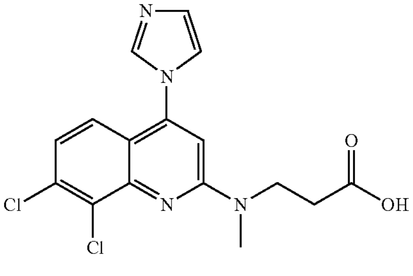 [SMILES: CN(CCC(=O)O)c1cc(-n2ccnc2)c2ccc(Cl)c(Cl)c2n1] |
| I-184 | 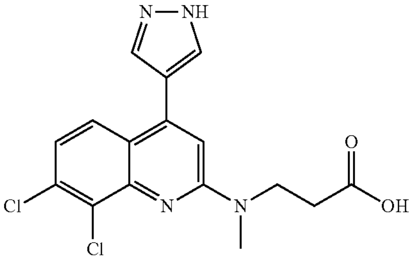 [SMILES: CN(CCC(=O)O)c1cc(-c2cn[nH]c2)c2ccc(Cl)c(Cl)c2n1] |
| I-185 | 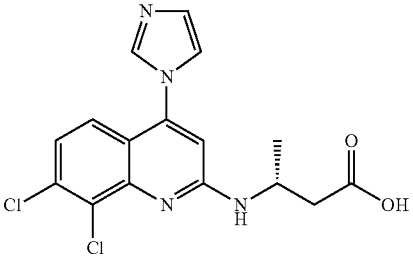 [SMILES: C[C@H](CC(=O)O)Nc1cc(-n2ccnc2)c2ccc(Cl)c(Cl)c2n1] |
TABLE 1-continued
| Exemplary Compounds | |
|---|---|
| I-# | Structure |
| I-186 | 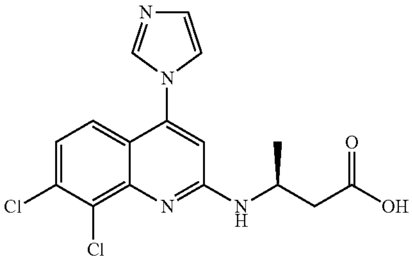 [SMILES: C[C@@H](CC(=O)O)Nc1cc(-n2ccnc2)c2ccc(Cl)c(Cl)c2n1] |
| I-187 | 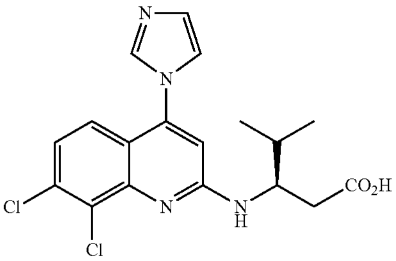 [SMILES: CC(C)[C@@H](CC(=O)O)Nc1cc(-n2ccnc2)c2ccc(Cl)c(Cl)c2n1] |
| I-188 | 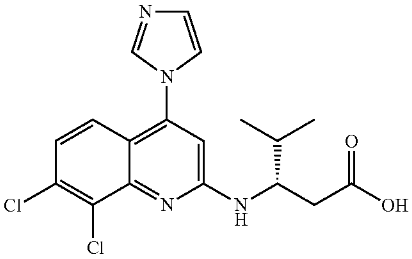 [SMILES: CC(C)[C@H](CC(=O)O)Nc1cc(-n2ccnc2)c2ccc(Cl)c(Cl)c2n1] |
| I-189 | 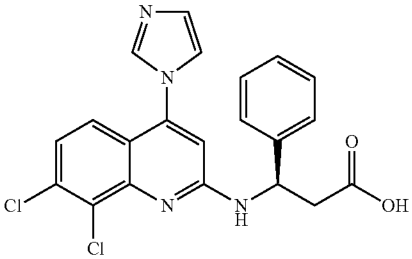 [SMILES: O=C(O)C[C@@H](Nc1cc(-n2ccnc2)c2ccc(Cl)c(Cl)c2n1)c1ccccc1] |
| I-190 | 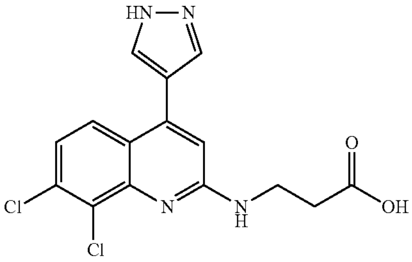 [SMILES: O=C(O)CCNc1cc(-c2cn[nH]c2)c2ccc(Cl)c(Cl)c2n1] |

TABLE 1-continued
| Exemplary Compounds | |
|---|---|
| I-# | Structure |
| I-191 | 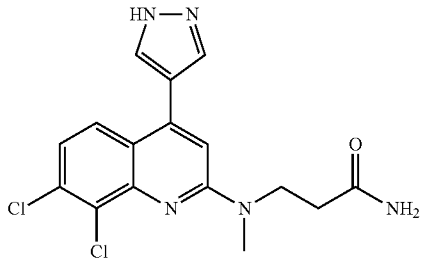 [SMILES: CN(CCC(N)=O)c1cc(-c2cn[nH]c2)c2ccc(Cl)c(Cl)c2n1] |
| I-192 | 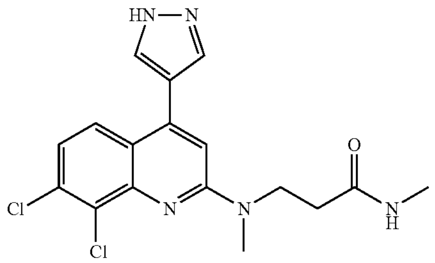 [SMILES: CNC(=O)CCN(C)c1cc(-c2cn[nH]c2)c2ccc(Cl)c(Cl)c2n1] |
| I-193 | 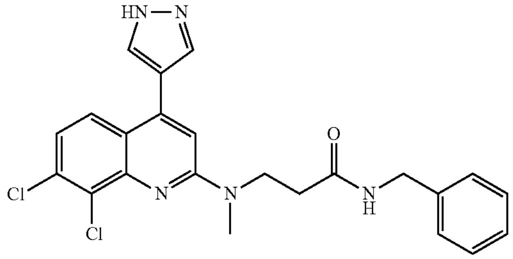 [SMILES: CN(CCC(=O)NCc1ccccc1)c1cc(-c2cn[nH]c2)c2ccc(Cl)c(Cl)c2n1] |
| I-194 | 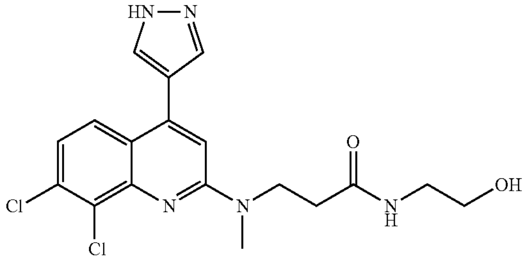 [SMILES: CN(CCC(=O)NCCO)c1cc(-c2cn[nH]c2)c2ccc(Cl)c(Cl)c2n1] |
| I-195 | 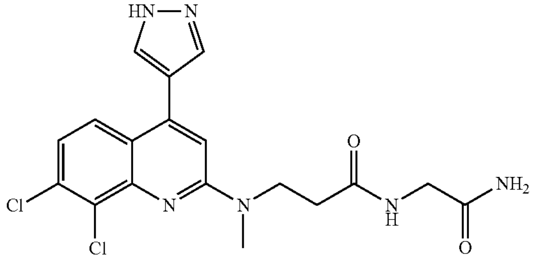 [SMILES: CN(CCC(=O)NCC(N)=O)c1cc(-c2cn[nH]c2)c2ccc(Cl)c(Cl)c2n1] |
TABLE 1-continued
| Exemplary Compounds | |
|---|---|
| I-# | Structure |
| I-196 | 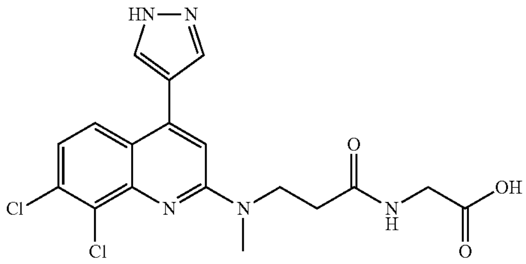 [SMILES: CN(CCC(=O)NCC(=O)O)c1cc(-c2cn[nH]c2)c2ccc(Cl)c(Cl)c2n1] |
| I-197 | 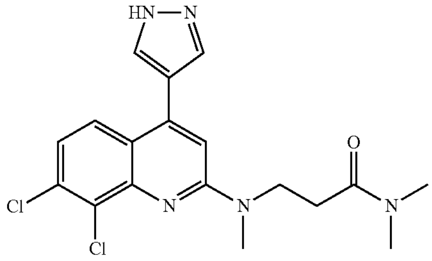 [SMILES: CN(C)C(=O)CCN(C)c1cc(-c2cn[nH]c2)c2ccc(Cl)c(Cl)c2n1] |
| I-198 | 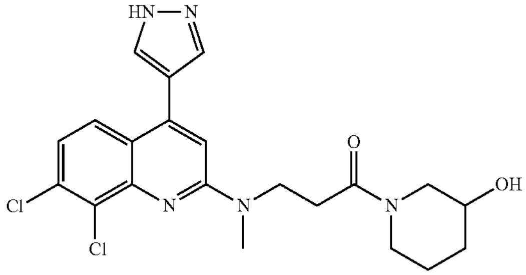 [SMILES: CN(CCC(=O)N1CCCC(O)C1)c1cc(-c2cn[nH]c2)c2ccc(Cl)c(Cl)c2n1] |
| I-199 | 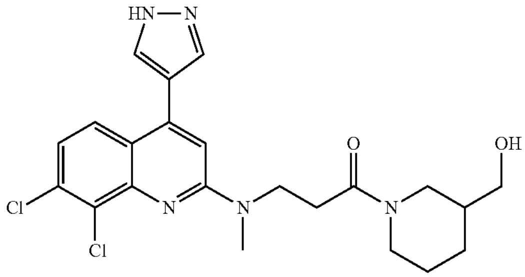 [SMILES: CN(CCC(=O)N1CCCC(CO)C1)c1cc(-c2cn[nH]c2)c2ccc(Cl)c(Cl)c2n1] |
| I-200 | 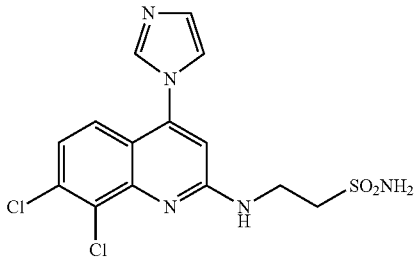 [SMILES: NS(=O)(=O)CCNc1cc(-n2ccnc2)c2ccc(Cl)c(Cl)c2n1] |

TABLE 1-continued
Exemplary Compounds
| I-# | Structure |
|---|---|
| I-201 | 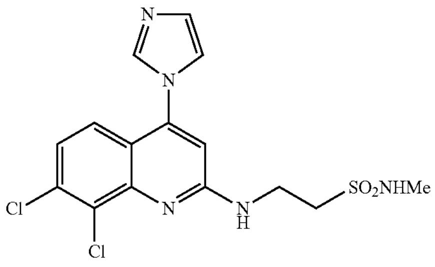 |
| I-202 | 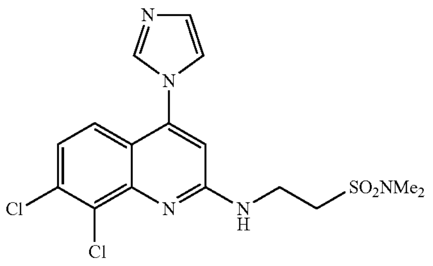 |
| I-203 | 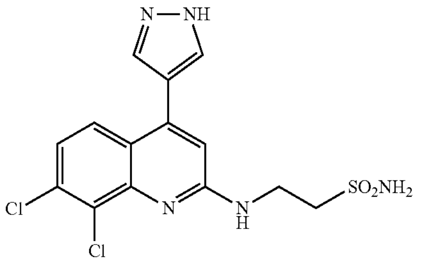 [SMILES: NS(=O)(=O)CCNc1cc(-c2cn[nH]c2)c2ccc(Cl)c(Cl)c2n1] |
| I-204 | 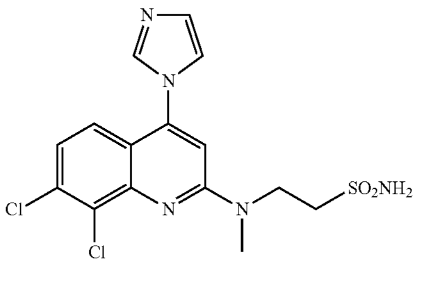 [SMILES: CN(CCS(N)(=O)=O)c1cc(-n2ccnc2)c2ccc(Cl)c(Cl)c2n1] |
| I-205 | 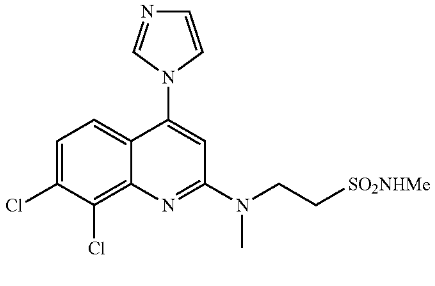 |
| I-206 | 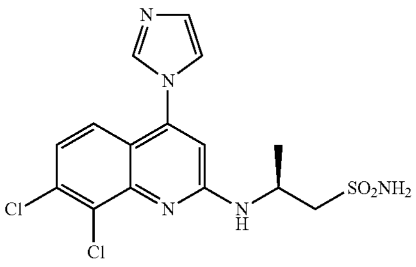 [SMILES: C[C@@H](CS(N)(=O)=O)Nc1cc(-n2ccnc2)c2ccc(Cl)c(Cl)c2n1] |
| I-207 | 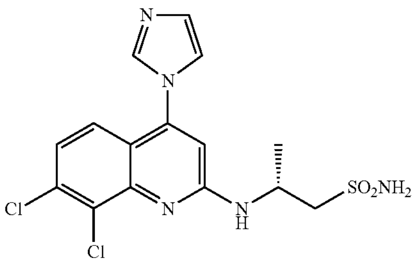 [SMILES: C[C@H](CS(N)(=O)=O)Nc1cc(-n2ccnc2)c2ccc(Cl)c(Cl)c2n1] |
| I-208 | 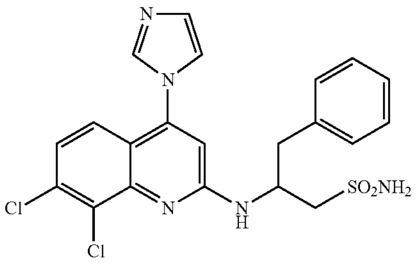 [SMILES: NS(=O)(=O)CC(Cc1ccccc1)Nc1cc(-n2ccnc2)c2ccc(Cl)c(Cl)c2n1] |
| I-209 | 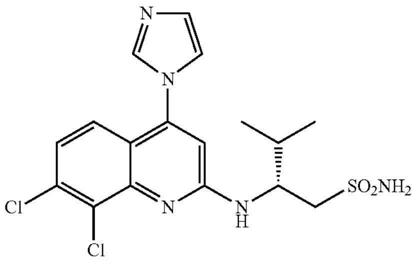 [SMILES: CC(C)[C@H](CS(N)(=O)=O)Nc1cc(-n2ccnc2)c2ccc(Cl)c(Cl)c2n1] |
| I-210 | 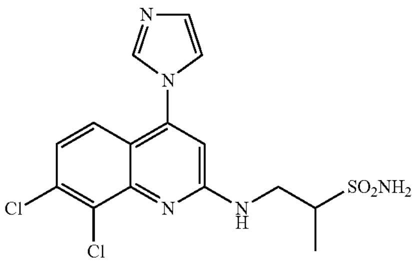 [SMILES: CC(CNc1cc(-n2ccnc2)c2ccc(Cl)c(Cl)c2n1)S(N)(=O)=O] |

TABLE 1-continued
| Exemplary Compounds | |
|---|---|
| I-# | Structure |
| I-211 | 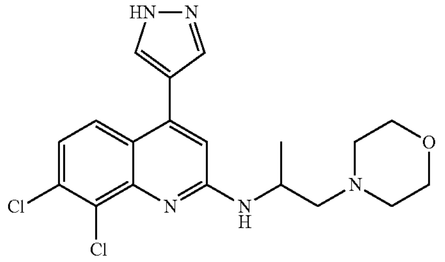 [SMILES: CC(CN1CCOCC1)Nc1cc(-c2cn[nH]c2)c2ccc(Cl)c(Cl)c2n1] |
| I-212 | 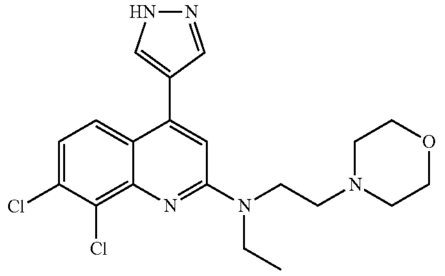 [SMILES: CCN(CCN1CCOCC1)c1cc(-c2cn[nH]c2)c2ccc(Cl)c(Cl)c2n1] |
| I-213 | 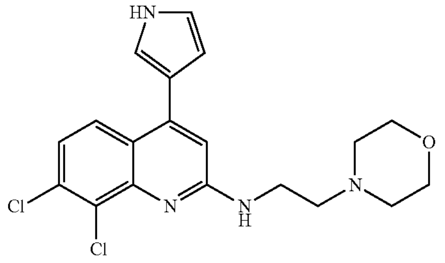 [SMILES: Clc1ccc2c(-c3cc[nH]c3)cc(NCCN3CCOCC3)nc2c1Cl] |
| I-214 | 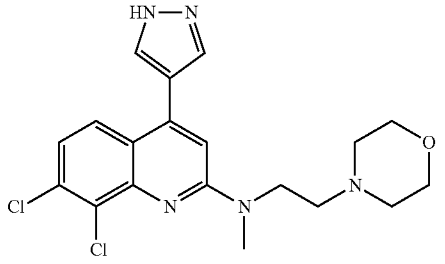 [SMILES: CN(CCN1CCOCC1)c1cc(-c2cn[nH]c2)c2ccc(Cl)c(Cl)c2n1] |
| I-215 | 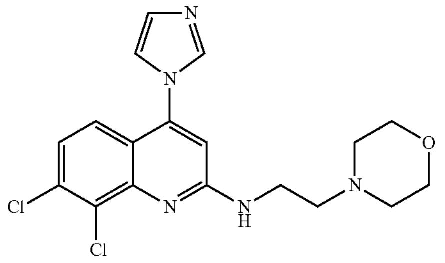 [SMILES: Clc1ccc2c(-n3ccnc3)cc(NCCN3CCOCC3)nc2c1Cl] |
TABLE 1-continued
| Exemplary Compounds | |
|---|---|
| I-# | Structure |
| I-216 | 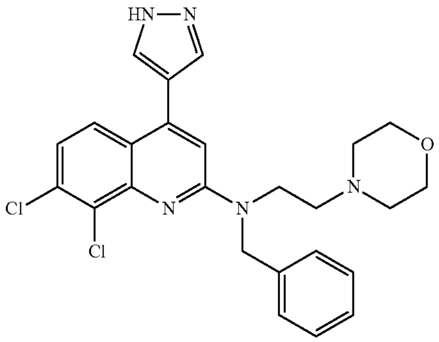 [SMILES: Clc1ccc2c(-c3cn[nH]c3)cc(N(CCN3CCOCC3)Cc3ccccc3)nc2c1Cl] |
| I-217 | 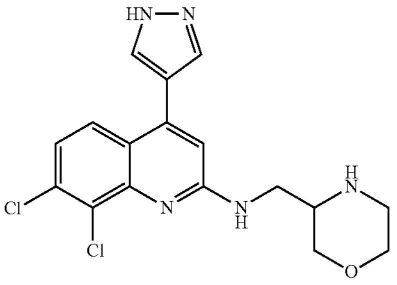 [SMILES: Clc1ccc2c(-c3cn[nH]c3)cc(NCC3COCCN3)nc2c1Cl] |
| I-218 | 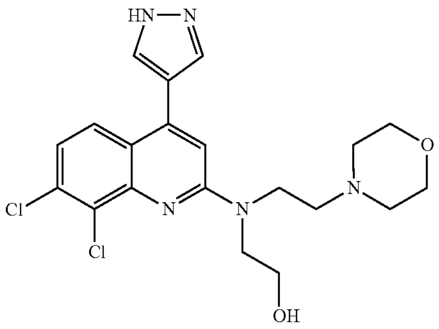 [SMILES: OCCN(CCN1CCOCC1)c1cc(-c2cn[nH]c2)c2ccc(Cl)c(Cl)c2n1] |
| I-219 | 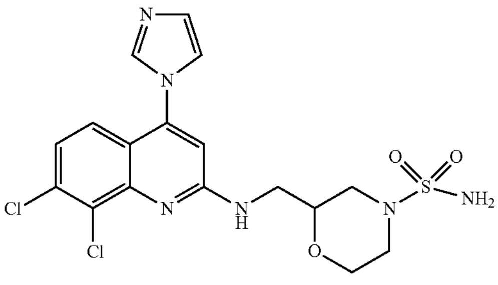 [SMILES: NS(=O)(=O)N1CCOC(CNc2cc(-n3ccnc3)c3ccc(Cl)c(Cl)c3n2)C1] |
| I-220 | 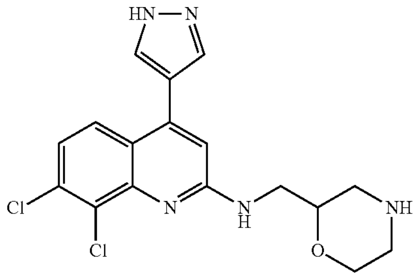 [SMILES: Clc1ccc2c(-c3cn[nH]c3)cc(NCC3CNCCO3)nc2c1Cl] |

TABLE 1-continued
| Exemplary Compounds | |
|---|---|
| I-# | Structure |
| I-221 | 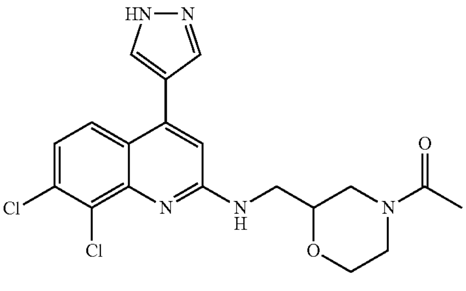 [SMILES: CC(=O)N1CCOC(CNc2cc(-c3cn[nH]c3)c3ccc(Cl)c(Cl)c3n2)C1] |
| I-222 | 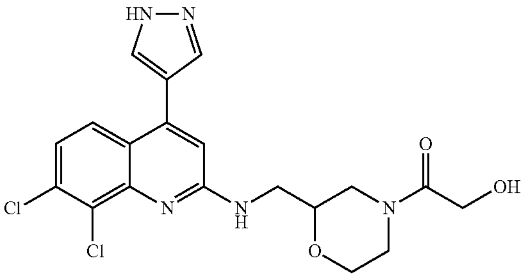 [SMILES: O=C(CO)N1CCOC(CNc2cc(-c3cn[nH]c3)c3ccc(Cl)c(Cl)c3n2)C1] |
| I-223 | 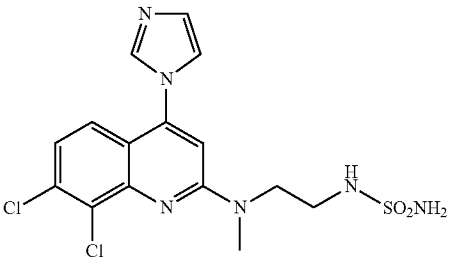 [SMILES: CN(CCNS(N)(=O)=O)c1cc(-n2ccnc2)c2ccc(Cl)c(Cl)c2n1] |
| I-224 | 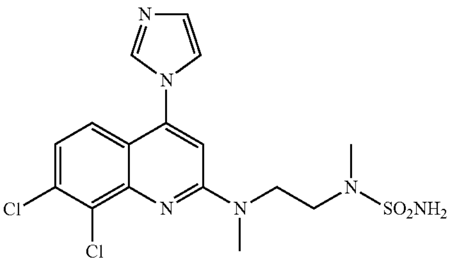 [SMILES: CN(CCN(C)S(N)(=O)=O)c1cc(-n2ccnc2)c2ccc(Cl)c(Cl)c2n1] |
| I-225 | 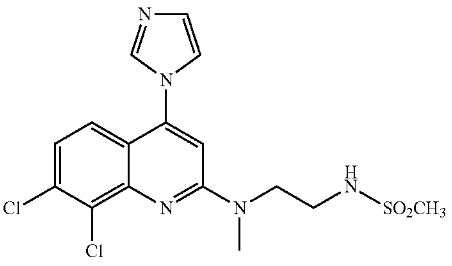 [SMILES: CN(CCNS(C)(=O)=O)c1cc(-n2ccnc2)c2ccc(Cl)c(Cl)c2n1] |
TABLE 1-continued
| Exemplary Compounds | |
|---|---|
| I-# | Structure |
| I-226 | 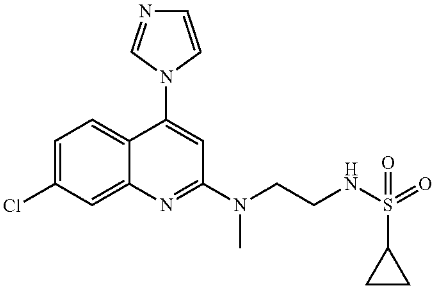 [SMILES: CN(CCNS(=O)(=O)C1CC1)c1cc(-n2ccnc2)c2ccc(Cl)cc2n1] |
| I-227 | 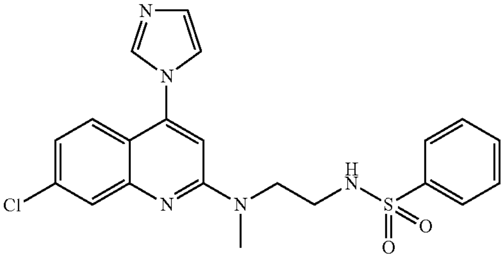 [SMILES: CN(CCNS(=O)(=O)c1ccccc1)c1cc(-n2ccnc2)c2ccc(Cl)cc2n1] |
| I-228 | 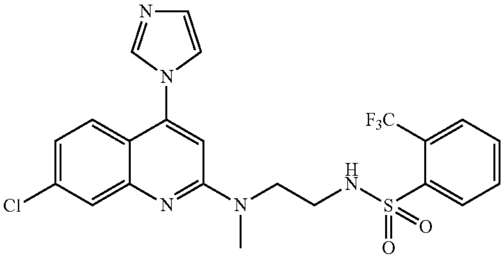 [SMILES: CN(CCNS(=O)(=O)c1ccccc1C(F)(F)F)c1cc(-n2ccnc2)c2ccc(Cl)cc2n1] |
| I-229 | 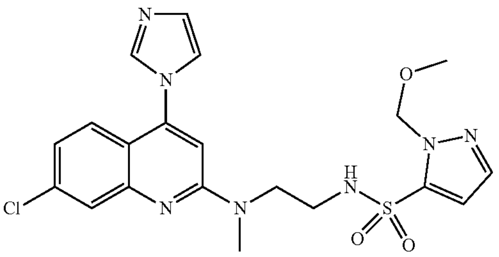 [SMILES: COCn1nccc1S(=O)(=O)NCCN(C)c1cc(-n2ccnc2)c2ccc(Cl)cc2n1] |
| I-230 | 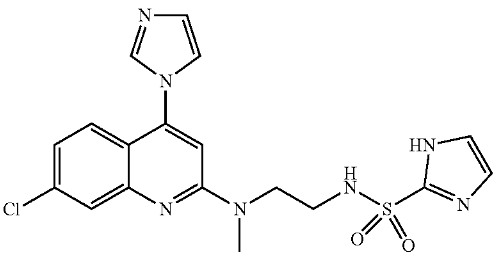 [SMILES: CN(CCNS(=O)(=O)c1ncc[nH]1)c1cc(-n2ccnc2)c2ccc(Cl)cc2n1] |

TABLE 1-continued
| Exemplary Compounds | |
|---|---|
| I-# | Structure |
| I-231 | 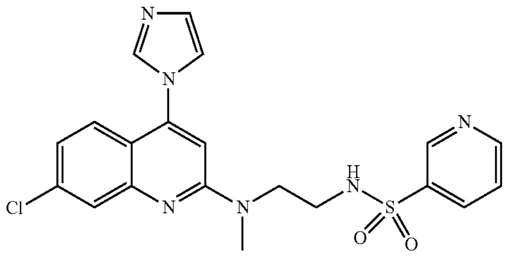 [SMILES: CN(CCNS(=O)(=O)c1cccnc1)c1cc(-n2ccnc2)c2ccc(Cl)cc2n1] |
| I-232 | 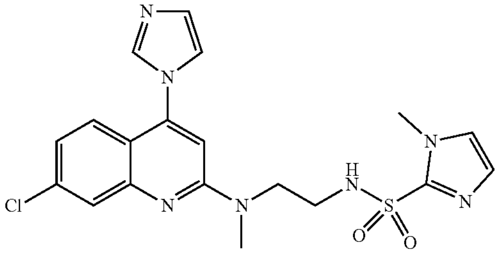 [SMILES: CN(CCNS(=O)(=O)c1nccn1C)c1cc(-n2ccnc2)c2ccc(Cl)cc2n1] |
| I-234 | 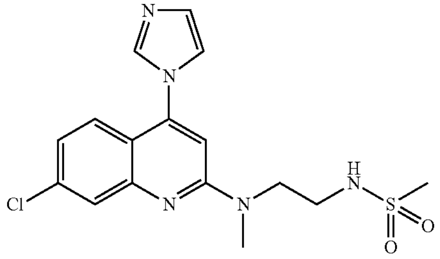 [SMILES: CN(CCNS(C)(=O)=O)c1cc(-n2ccnc2)c2ccc(Cl)cc2n1] |
| I-235 | 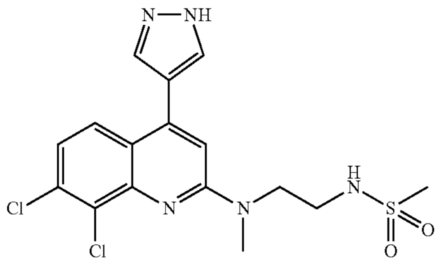 [SMILES: CN(CCNS(C)(=O)=O)c1cc(-c2cn[nH]c2)c2ccc(Cl)c(Cl)c2n1] |
| I-236 | 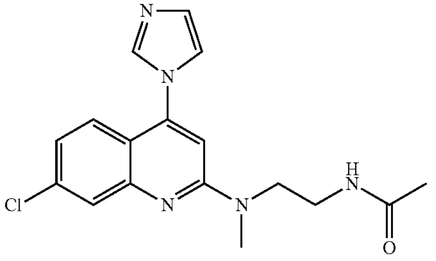 [SMILES: CC(=O)NCCN(C)c1cc(-n2ccnc2)c2ccc(Cl)cc2n1] |
TABLE 1-continued
| Exemplary Compounds | |
|---|---|
| I-# | Structure |
| I-237 | 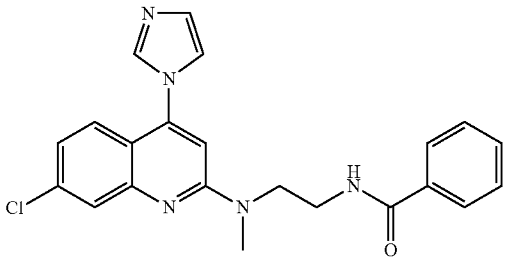 [SMILES: CN(CCNC(=O)c1ccccc1)c1cc(-n2ccnc2)c2ccc(Cl)cc2n1] |
| I-238 | 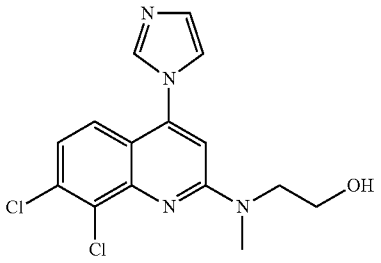 [SMILES: CN(CCO)c1cc(-n2ccnc2)c2ccc(Cl)c(Cl)c2n1] |
| I-239 | 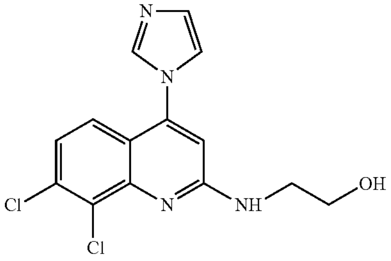 [SMILES: OCCNc1cc(-n2ccnc2)c2ccc(Cl)c(Cl)c2n1] |
| I-240 | 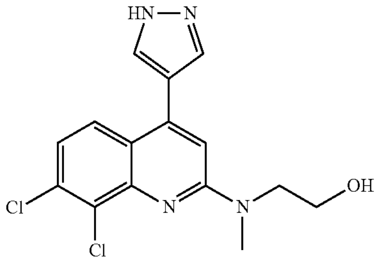 [SMILES: CN(CCO)c1cc(-c2cn[nH]c2)c2ccc(Cl)c(Cl)c2n1] |
| I-241 | 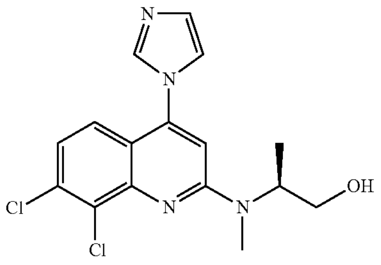 [SMILES: C[C@@H](CO)N(C)c1cc(-n2ccnc2)c2ccc(Cl)c(Cl)c2n1] |

TABLE 1-continued
| Exemplary Compounds | |
|---|---|
| I-# | Structure |
| I-242 | 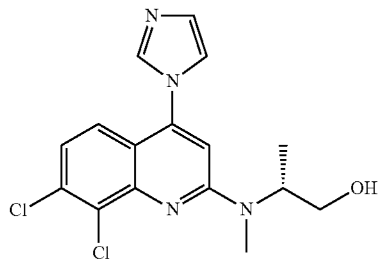 |
| I-243 | 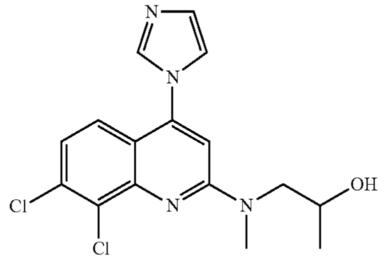 |
| I-244 | 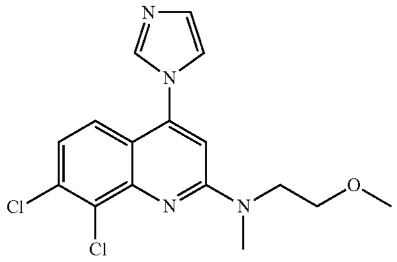 [SMILES: COCCN(C)c1cc(-n2ccnc2)c2ccc(Cl)c(Cl)c2n1] |
| I-245 | 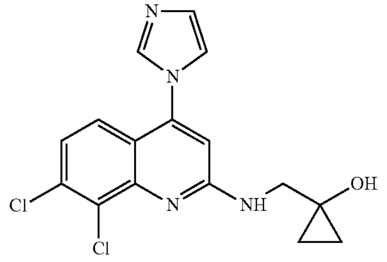 [SMILES: OC1(CNc2cc(-n3ccnc3)c3ccc(Cl)c(Cl)c3n2)CC1] |
| I-246 | 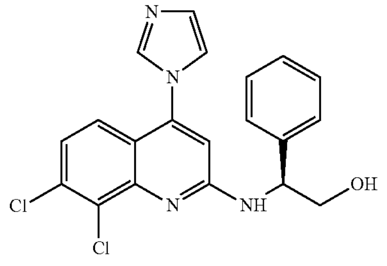 [SMILES: OC[C@@H](Nc1cc(-n2ccnc2)c2ccc(Cl)c(Cl)c2n1)c1ccccc1] |
TABLE 1-continued
| Exemplary Compounds | |
|---|---|
| I-# | Structure |
| I-247 | 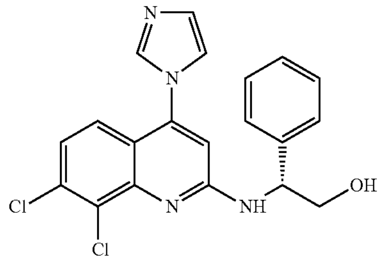 |
| I-248 | 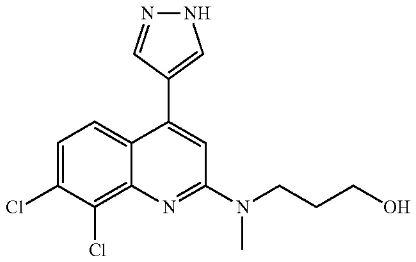 [SMILES: CN(CCCO)c1cc(-c2cn[nH]c2)c2ccc(Cl)c(Cl)c2n1] |
| I-249 | 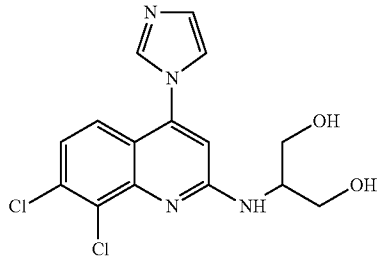 [SMILES: OCC(CO)Nc1cc(-n2ccnc2)c2ccc(Cl)c(Cl)c2n1] |
| I-250 | 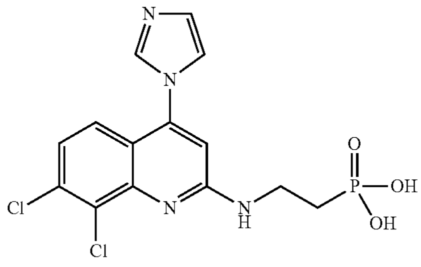 [SMILES: O=P(O)(O)CCNc1cc(-n2ccnc2)c2ccc(Cl)c(Cl)c2n1] |
| I-251 | 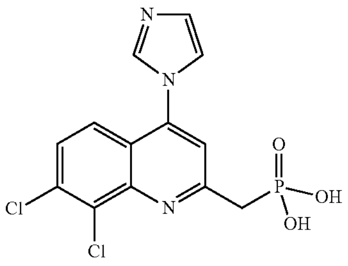 [SMILES: O=P(O)(O)Cc1cc(-n2ccnc2)c2ccc(Cl)c(Cl)c2n1] |

TABLE 1-continued
Exemplary Compounds
| I-# | Structure |
| --- | --- |
| I-252 | 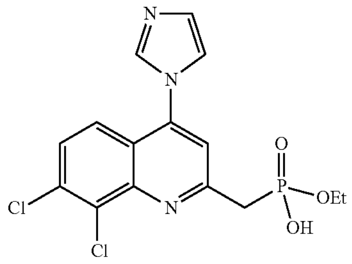 [SMILES: CCOP(=O)(O)Cc1cc(-n2ccnc2)c2ccc(Cl)c(Cl)c2n1] |
| I-253 | 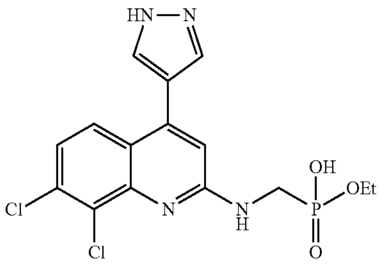 [SMILES: CCOP(=O)(O)CNc1cc(-c2cn[nH]c2)c2ccc(Cl)c(Cl)c2n1] |
| I-254 | 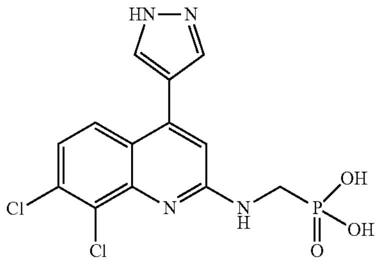 [SMILES: O=P(O)(O)CNc1cc(-c2cn[nH]c2)c2ccc(Cl)c(Cl)c2n1] |
| I-255 | 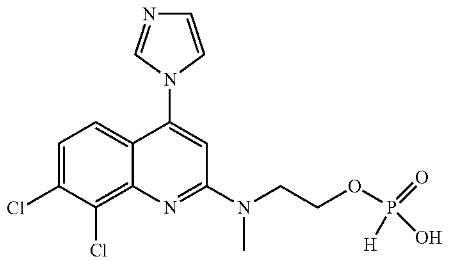 [SMILES: CN(CCO[PH](=O)O)c1cc(-n2ccnc2)c2ccc(Cl)c(Cl)c2n1] |
| I-256 | 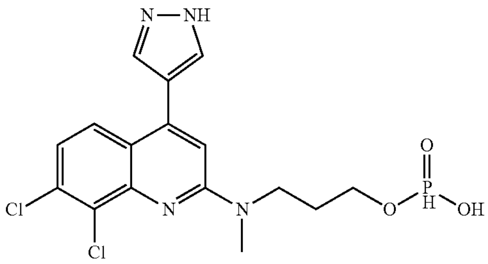 |
| I-257 | 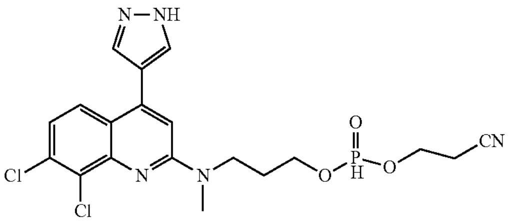 |
TABLE 1-continued
Exemplary Compounds
| I-# | Structure |
| --- | --- |
| I-258 | 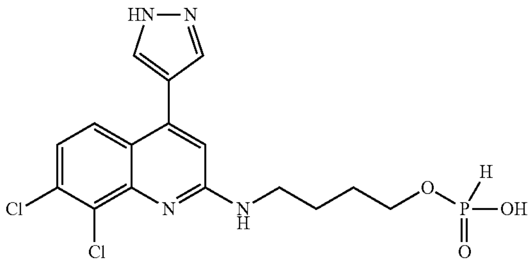 [SMILES: O=[PH](O)OCCCCNc1cc(-c2cn[nH]c2)c2ccc(Cl)c(Cl)c2n1] |
| I-259 | 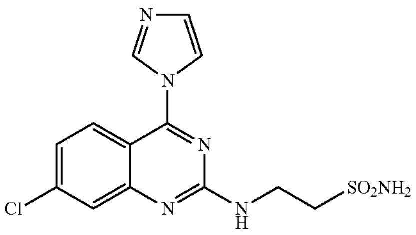 |
| I-260 | 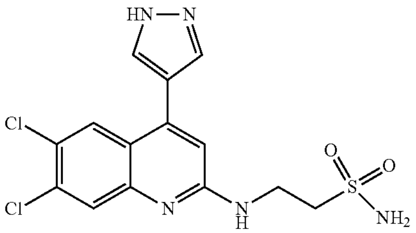 [SMILES: NS(=O)(=O)CCNc1cc(-c2cn[nH]c2)c2cc(Cl)c(Cl)cc2n1] |
| I-261 | 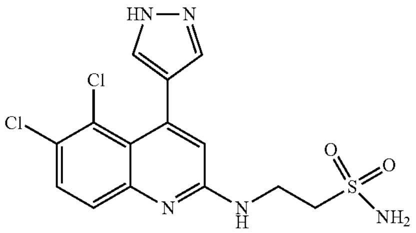 [SMILES: NS(=O)(=O)CCNc1cc(-c2cn[nH]c2)c2c(Cl)c(Cl)ccc2n1] |
| I-262 | 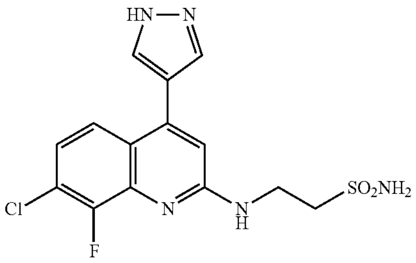 [SMILES: NS(=O)(=O)CCNc1cc(-c2cn[nH]c2)c2ccc(Cl)c(F)c2n1] |
| I-263 | 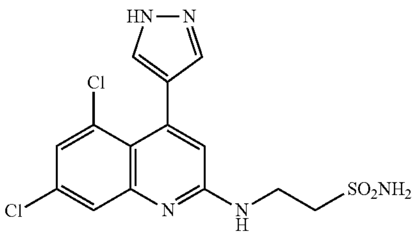 [SMILES: NS(=O)(=O)CCNc1cc(-c2cn[nH]c2)c2c(Cl)cc(Cl)cc2n1] |

TABLE 1-continued
| Exemplary Compounds | |
|---|---|
| I-# | Structure |
| I-264 | 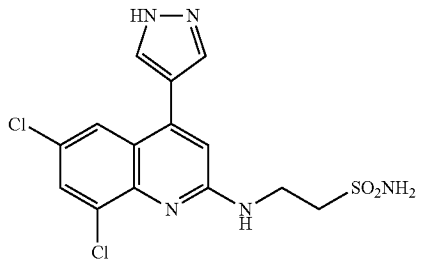 [SMILES: NS(=O)(=O)CCNc1cc(-c2cn[nH]c2)c2cc(Cl)cc(Cl)c2n1] |
| I-265 | 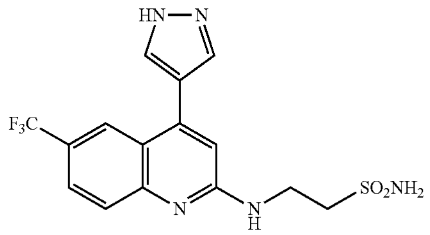 [SMILES: NS(=O)(=O)CCNc1cc(-c2cn[nH]c2)c2cc(C(F)(F)F)ccc2n1] |
| I-266 | 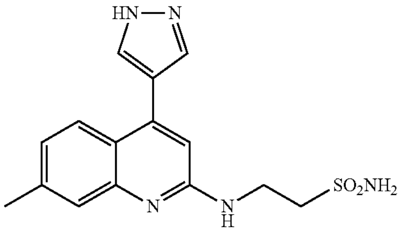 [SMILES: Cc1ccc2c(-c3cn[nH]c3)cc(NCCS(N)(=O)=O)nc2c1] |
| I-267 | 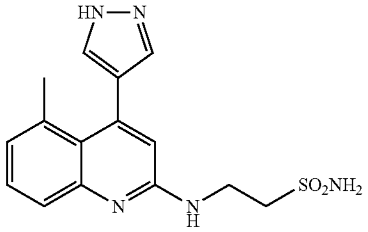 [SMILES: Cc1cccc2nc(NCCS(N)(=O)=O)cc(-c3cn[nH]c3)c12] |
| I-268 | 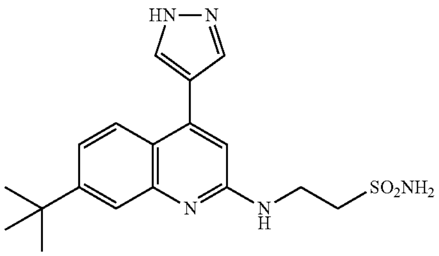 [SMILES: CC(C)(C)c1ccc2c(-c3cn[nH]c3)cc(NCCS(N)(=O)=O)nc2c1] |
| I-269 | 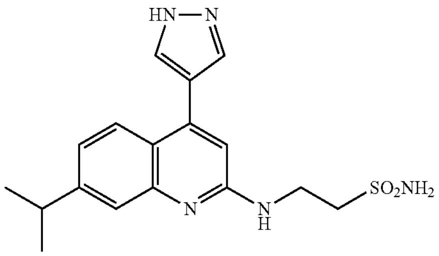 [SMILES: CC(C)c1ccc2c(-c3cn[nH]c3)cc(NCCS(N)(=O)=O)nc2c1] |
| I-270 | 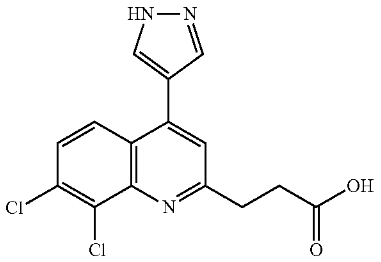 [SMILES: O=C(O)CCc1cc(-c2cn[nH]c2)c2ccc(Cl)c(Cl)c2n1] |
| I-271 | 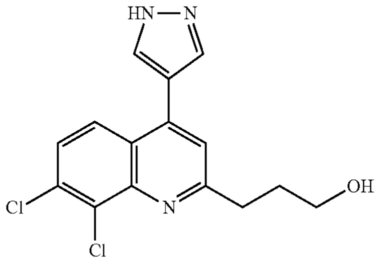 [SMILES: OCCCc1cc(-c2cn[nH]c2)c2ccc(Cl)c(Cl)c2n1] |
| I-272 | 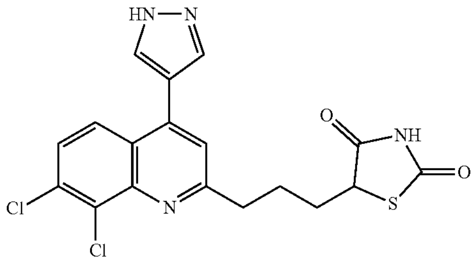 [SMILES: O=C1NC(=O)C(CCCc2cc(-c3cn[nH]c3)c3ccc(Cl)c(Cl)c3n2)S1] |
| I-273 | 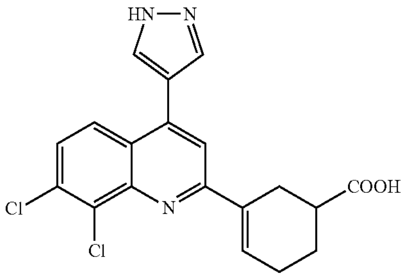 [SMILES: O=C(O)C1CCC=C(c2cc(-c3cn[nH]c3)c3ccc(Cl)c(Cl)c3n2)C1] |
| I-274 | 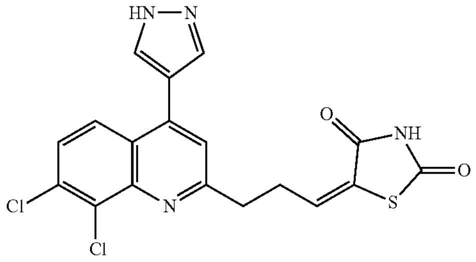 [SMILES: O=C1NC(=O)/C(=C\CCc2cc(-c3cn[nH]c3)c3ccc(Cl)c(Cl)c3n2)S1] |
| I-275 | 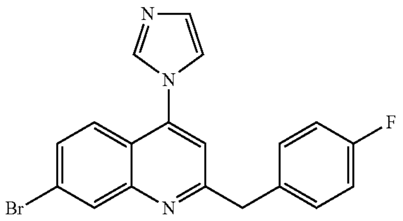 [SMILES: Fc1ccc(Cc2cc(-n3ccnc3)c3ccc(Br)cc3n2)cc1] |

TABLE 1-continued
| Exemplary Compounds | |
|---|---|
| I-# | Structure |
| I-276 | 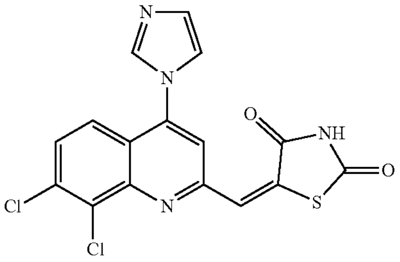 [SMILES: O=C1NC(=O)/C(=C\c2cc(-n3ccnc3)c3ccc(Cl)c(Cl)c3n2)S1] |
| I-277 | 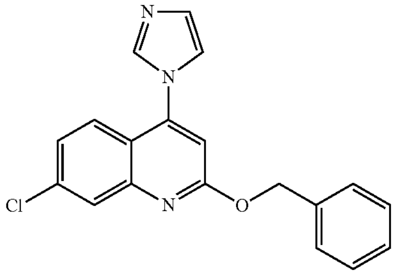 [SMILES: Clc1ccc2c(-n3ccnc3)cc(OCc3ccccc3)nc2c1] |
| I-278 | 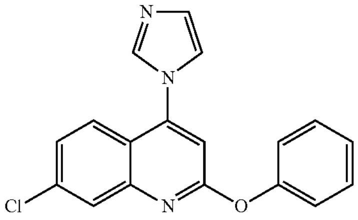 [SMILES: Clc1ccc2c(-n3ccnc3)cc(Oc3ccccc3)nc2c1] |
| I-279 | 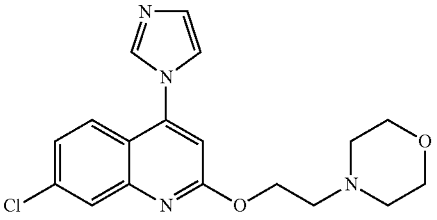 [SMILES: Clc1ccc2c(-n3ccnc3)cc(OCCN3CCOCC3)nc2c1] |
| I-280 | 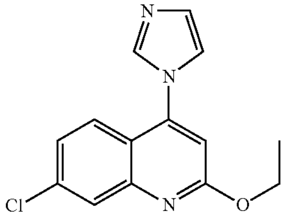 [SMILES: CCOc1cc(-n2ccnc2)c2ccc(Cl)cc2n1] |
| I-281 | 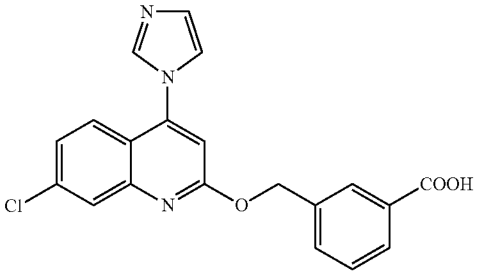 [SMILES: O=C(O)c1cccc(COc2cc(-n3ccnc3)c3ccc(Cl)cc3n2)c1] |
TABLE 1-continued
| Exemplary Compounds | |
|---|---|
| I-# | Structure |
| I-282 | 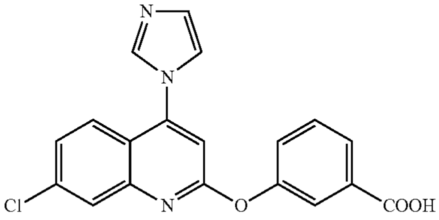 [SMILES: O=C(O)c1cccc(Oc2cc(-n3ccnc3)c3ccc(Cl)cc3n2)c1] |
| I-283 | 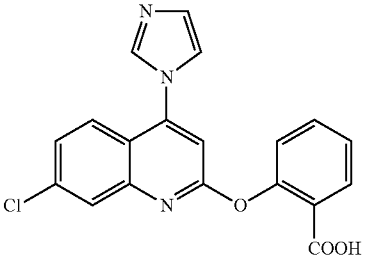 [SMILES: O=C(O)c1ccccc1Oc1cc(-n2ccnc2)c2ccc(Cl)cc2n1] |
| I-284 | 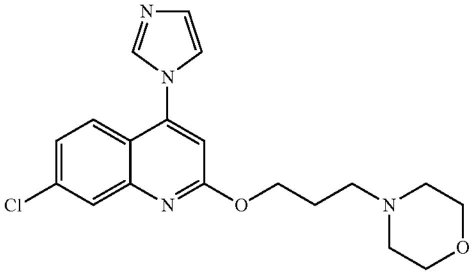 [SMILES: Clc1ccc2c(-n3ccnc3)cc(OCCCN3CCOCC3)nc2c1] |
| I-285 | 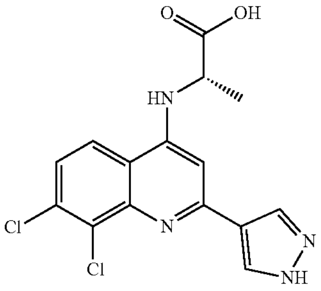 [SMILES: C[C@H](Nc1cc(-c2cn[nH]c2)nc2c(Cl)c(Cl)ccc12)C(=O)O] |
| I-286 | 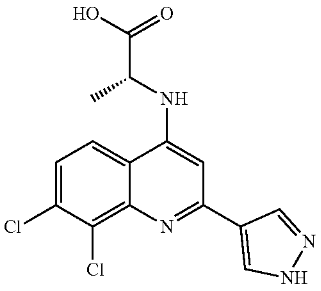 [SMILES: C[C@@H](Nc1cc(-c2cn[nH]c2)nc2c(Cl)c(Cl)ccc12)C(=O)O] |

TABLE 1-continued
Exemplary Compounds
| I-# | Structure |
|---|---|
| I-287 | 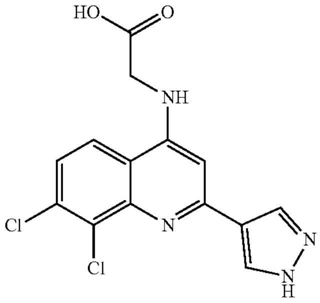 [SMILES: O=C(O)CNc1cc(-c2cn[nH]c2)nc2c(Cl)c(Cl)ccc12] |
| I-288 | 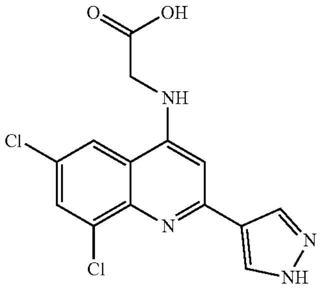 [SMILES: O=C(O)CNc1cc(-c2cn[nH]c2)nc2c(Cl)cc(Cl)cc12] |
| I-289 | 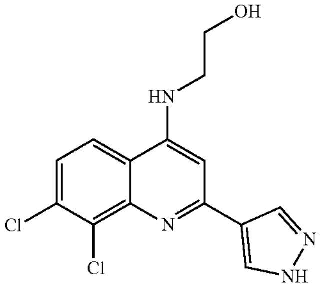 [SMILES: OCCNc1cc(-c2cn[nH]c2)nc2c(Cl)c(Cl)ccc12] |
| I-290 | 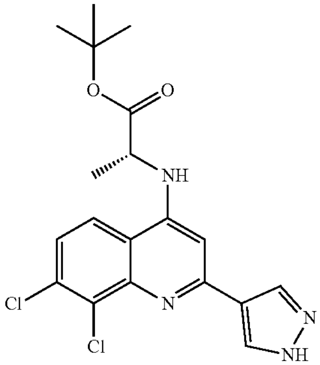 [SMILES: C[C@@H](Nc1cc(-c2cn[nH]c2)nc2c(Cl)c(Cl)ccc12)C(=O)OC(C)(C)C] |
| I-291 | 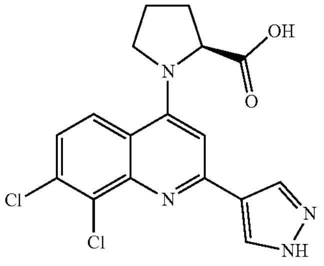 [SMILES: O=C(O)[C@@H]1CCCN1c1cc(-c2cn[nH]c2)nc2c(Cl)c(Cl)ccc12] |
TABLE 1-continued
Exemplary Compounds
| I-# | Structure |
|---|---|
| I-292 | 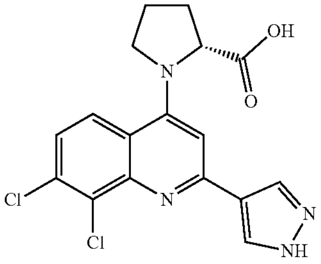 [SMILES: O=C(O)[C@H]1CCCN1c1cc(-c2cn[nH]c2)nc2c(Cl)c(Cl)ccc12] |
| I-293 | 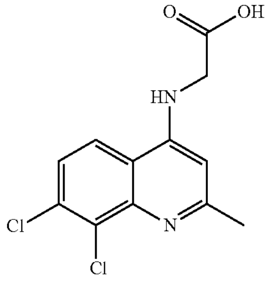 [SMILES: Cc1cc(NCC(=O)O)c2ccc(Cl)c(Cl)c2n1] |
| I-294 | 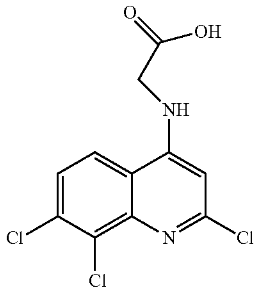 [SMILES: O=C(O)CNc1cc(Cl)nc2c(Cl)c(Cl)ccc12] |
| I-295 | 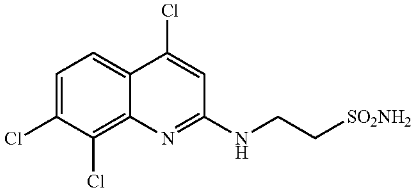 [SMILES: NS(=O)(=O)CCNc1cc(Cl)c2ccc(Cl)c(Cl)c2n1] |
| I-296 | 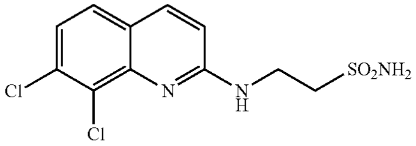 [SMILES: NS(=O)(=O)CCNc1ccc2ccc(Cl)c(Cl)c2n1] |
| I-297 | 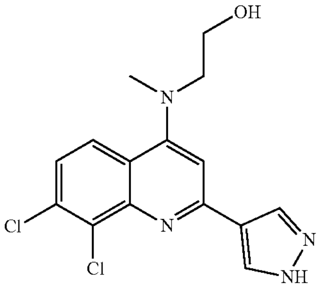 [SMILES: CN(CCO)c1cc(-c2cn[nH]c2)nc2c(Cl)c(Cl)ccc12] |

TABLE 1-continued
| Exemplary Compounds | |
|---|---|
| I-# | Structure |
| I-298 | 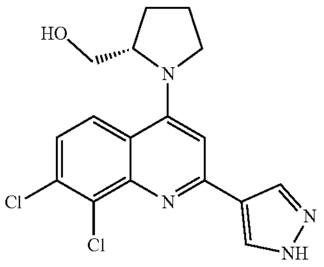 [SMILES: OC[C@@H]1CCCN1c1cc(-c2cn[nH]c2)nc2c(Cl)c(Cl)ccc12] |
| I-299 | 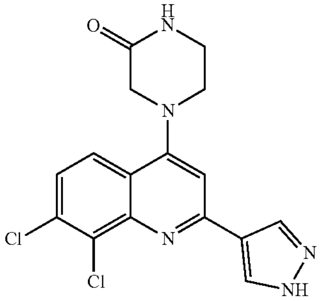 [SMILES: O=C1CN(c2cc(-c3cn[nH]c3)nc3c(Cl)c(Cl)ccc23)CCN1] |
| I-300 | 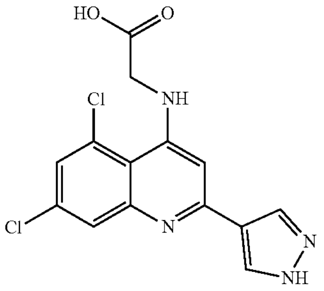 [SMILES: O=C(O)CNc1cc(-c2cn[nH]c2)nc2cc(Cl)cc(Cl)c12] |
| I-301 | 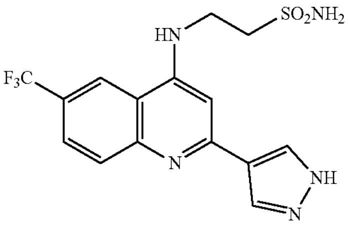 [SMILES: NS(=O)(=O)CCNc1cc(-c2cn[nH]c2)nc2ccc(C(F)(F)F)cc12] |
| I-302 | 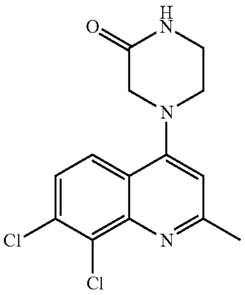 [SMILES: Cc1cc(N2CCNC(=O)C2)c2ccc(Cl)c(Cl)c2n1] |
TABLE 1-continued
| Exemplary Compounds | |
|---|---|
| I-# | Structure |
| I-303 | 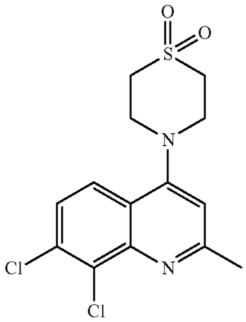 [SMILES: Cc1cc(N2CCS(=O)(=O)CC2)c2ccc(Cl)c(Cl)c2n1] |
| I-304 | 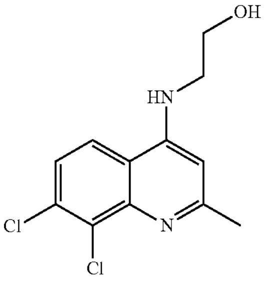 [SMILES: Cc1cc(NCCO)c2ccc(Cl)c(Cl)c2n1] |
| I-305 | 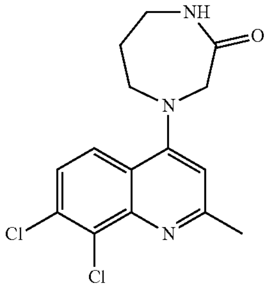 [SMILES: Cc1cc(N2CCCNC(=O)C2)c2ccc(Cl)c(Cl)c2n1] |
| I-306 | 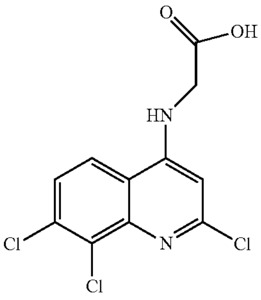 [SMILES: O=C(O)CNc1cc(Cl)nc2c(Cl)c(Cl)ccc12] |
| I-307 | 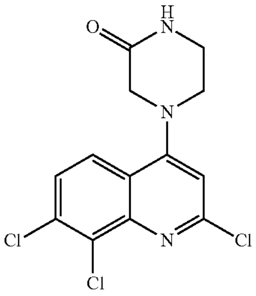 [SMILES: O=C1CN(c2cc(Cl)nc3c(Cl)c(Cl)ccc23)CCN1] |

TABLE 1-continued
| Exemplary Compounds | |
|---|---|
| I-# | Structure |
| I-308 | 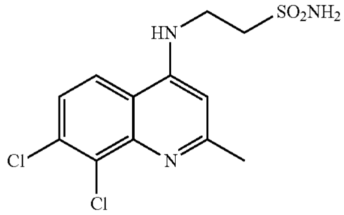 [SMILES: Cc1cc(NCCS(N)(=O)=O)c2ccc(Cl)c(Cl)c2n1] |
| I-309 | 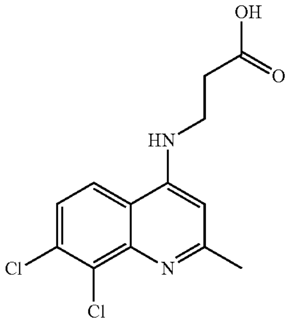 [SMILES: Cc1cc(NCCC(=O)O)c2ccc(Cl)c(Cl)c2n1] |
| I-310 | 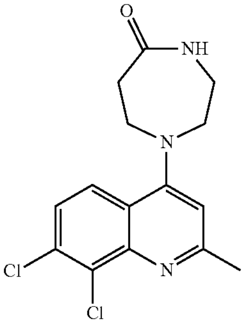 [SMILES: Cc1cc(N2CCNC(=O)CC2)c2ccc(Cl)c(Cl)c2n1] |
| I-311 | 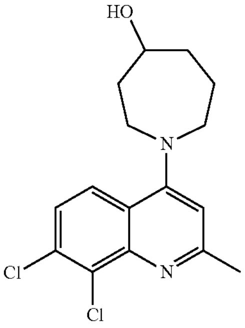 [SMILES: Cc1cc(N2CCCC(O)CC2)c2ccc(Cl)c(Cl)c2n1] |
| I-312 | 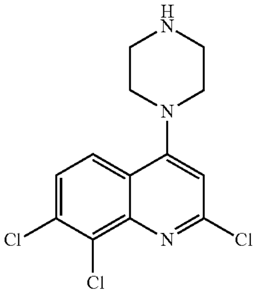 [SMILES: Clc1cc(N2CCNCC2)c2ccc(Cl)c(Cl)c2n1] |
TABLE 1-continued
| Exemplary Compounds | |
|---|---|
| I-# | Structure |
| I-313 | 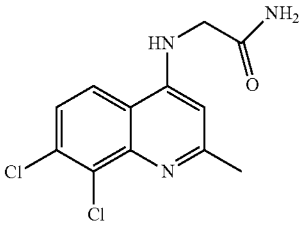 [SMILES: Cc1cc(NCC(N)=O)c2ccc(Cl)c(Cl)c2n1] |
| I-314 | 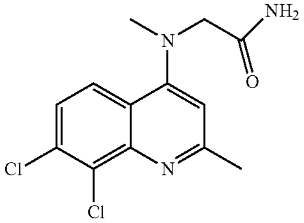 [SMILES: Cc1cc(N(C)CC(N)=O)c2ccc(Cl)c(Cl)c2n1] |
| I-315 | 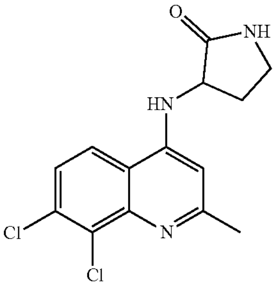 [SMILES: Cc1cc(NC2CCNC2=O)c2ccc(Cl)c(Cl)c2n1] |
| I-316 | 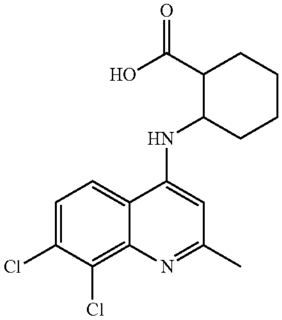 [SMILES: Cc1cc(NC2CCCCC2C(=O)O)c2ccc(Cl)c(Cl)c2n1] |
| I-317 | 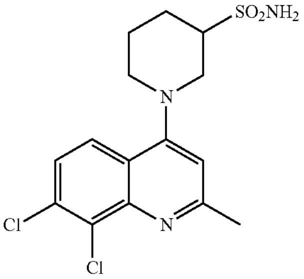 [SMILES: Cc1cc(N2CCCC(S(N)(=O)=O)C2)c2ccc(Cl)c(Cl)c2n1] |

TABLE 1-continued
| Exemplary Compounds | |
|---|---|
| I-# | Structure |
| I-318 | 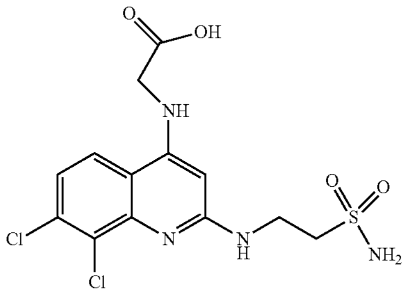 [SMILES: NS(=O)(=O)CCNc1cc(NCC(=O)O)c2ccc(Cl)c(Cl)c2n1] |
| I-319 | 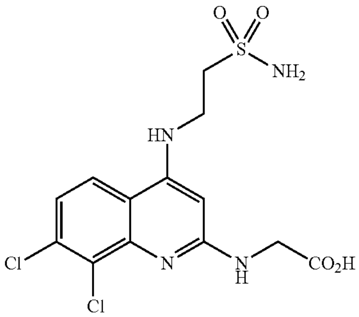 [SMILES: NS(=O)(=O)CCNc1cc(NCC(=O)O)nc2c(Cl)c(Cl)ccc12] |
| I-320 | 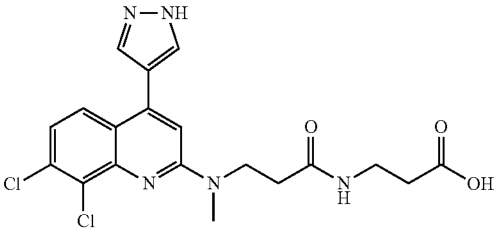 [SMILES: CN(CCC(=O)NCCC(=O)O)c1cc(-c2cn[nH]c2)c2ccc(Cl)c(Cl)c2n1] |
| I-321 | 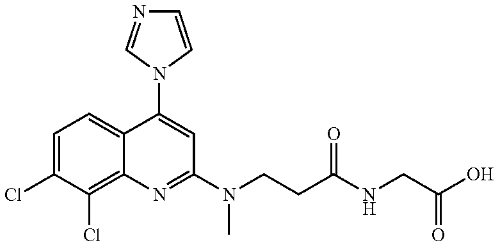 [SMILES: CN(CCC(=O)NCC(=O)O)c1cc(-n2ccnc2)c2ccc(Cl)c(Cl)c2n1] |
| I-322 | 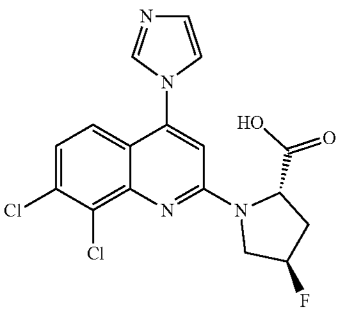 [SMILES: O=C(O)[C@@H]1C[C@@H](F)CN1c1cc(-n2ccnc2)c2ccc(Cl)c(Cl)c2n1] |
TABLE 1-continued
| Exemplary Compounds | |
|---|---|
| I-# | Structure |
| I-323 | 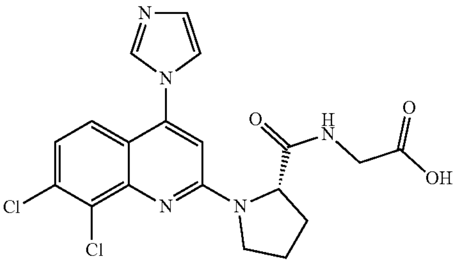 [SMILES: O=C(O)CNC(=O)[C@@H]1CCCN1c1cc(-n2ccnc2)c2ccc(Cl)c(Cl)c2n1] |
| I-324 | 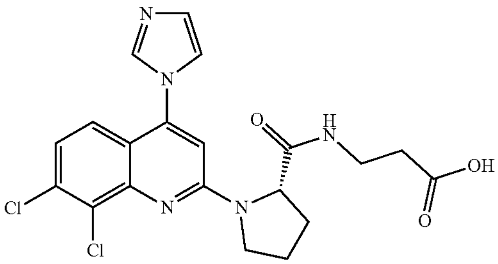 [SMILES: O=C(O)CCNC(=O)[C@@H]1CCCN1c1cc(-n2ccnc2)c2ccc(Cl)c(Cl)c2n1] |
| I-325 | 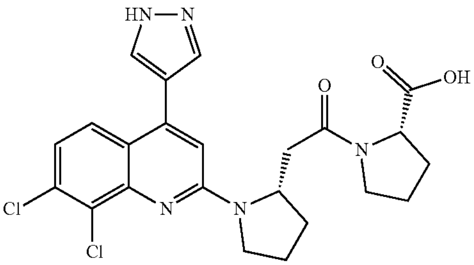 [SMILES: O=C(O)[C@@H]1CCCN1C(=O)C[C@@H]1CCCN1c1cc(-c2cn[nH]c2)c2ccc(Cl)c(Cl)c2n1] |
| I-326 | 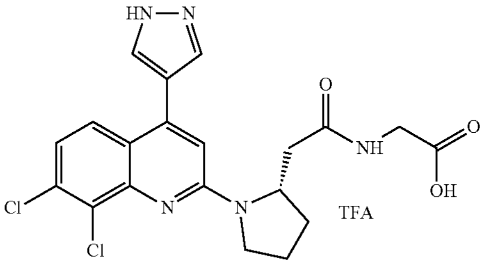 [SMILES: O=C(O)CNC(=O)C[C@@H]1CCCN1c1cc(-c2cn[nH]c2)c2ccc(Cl)c(Cl)c2n1] |
| I-327 | 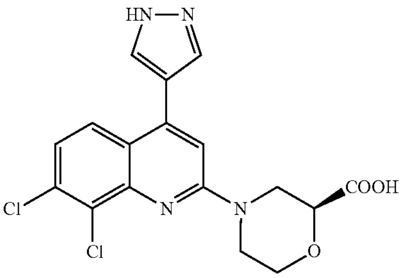 [SMILES: O=C(O)[C@@H]1CN(c2cc(-c3cn[nH]c3)c3ccc(Cl)c(Cl)c3n2)CCO1] |

TABLE 1-continued
| Exemplary Compounds | |
|---|---|
| I-# | Structure |
| I-328 | 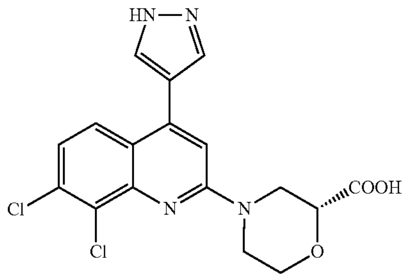 [SMILES: O=C(O)[C@H]1CN(c2cc(-c3cn[nH]c3)c3ccc(Cl)c(Cl)c3n2)CCO1] |
| I-329 | 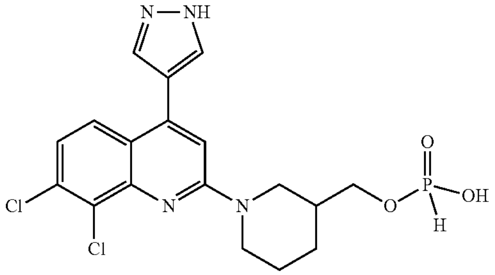 [SMILES: O=[PH](O)OCC1CCCN(c2cc(-c3cn[nH]c3)c3ccc(Cl)c(Cl)c3n2)C1] |
| I-330 | 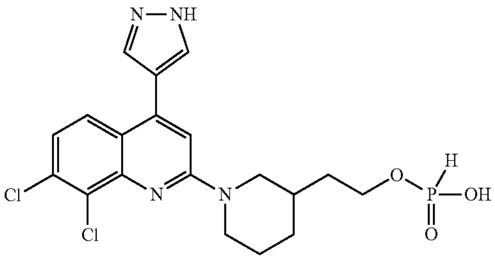 [SMILES: O=[PH](O)OCCC1CCCN(c2cc(-c3cn[nH]c3)c3ccc(Cl)c(Cl)c3n2)C1] |
| I-331 | 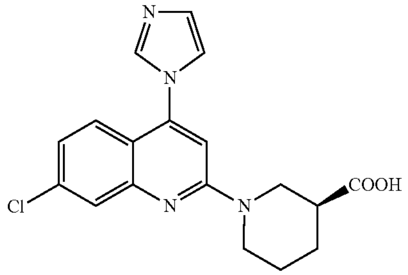 [SMILES: O=C(O)[C@H]1CCCN(c2cc(-n3ccnc3)c3ccc(Cl)cc3n2)C1] |
| I-332 | 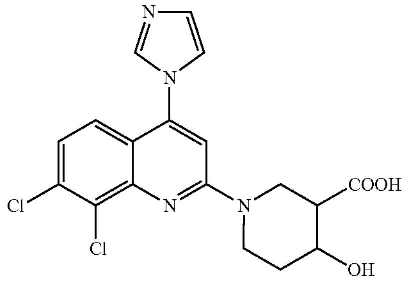 [SMILES: O=C(O)C1CN(c2cc(-n3ccnc3)c3ccc(Cl)c(Cl)c3n2)CCC1O] |
TABLE 1-continued
| Exemplary Compounds | |
|---|---|
| I-# | Structure |
| I-333 | 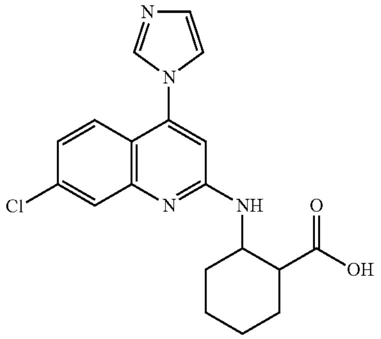 [SMILES: O=C(O)C1CCCCC1Nc1cc(-n2ccnc2)c2ccc(Cl)cc2n1] |
| I-334 | 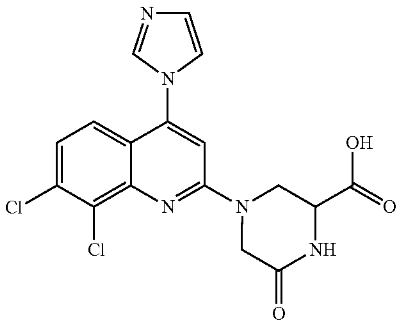 [SMILES: O=C1CN(c2cc(-n3ccnc3)c3ccc(Cl)c(Cl)c3n2)CC(C(=O)O)N1] |
| I-335 | 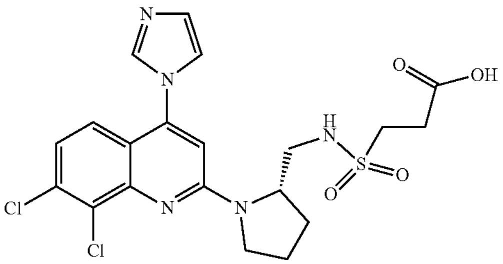 [SMILES: O=C(O)CCS(=O)(=O)NC[C@@H]1CCCN1c1cc(-n2ccnc2)c2ccc(Cl)c(Cl)c2n1] |
| I-336 | 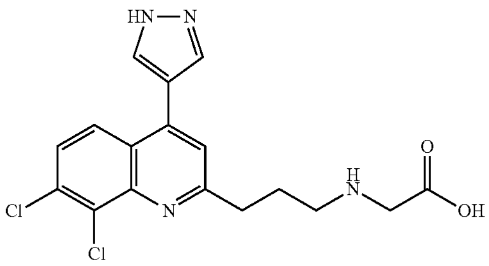 [SMILES: O=C(O)CNCCCc1cc(-c2cn[nH]c2)c2ccc(Cl)c(Cl)c2n1] |
| I-337 | 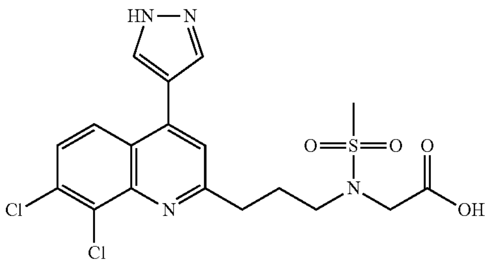 [SMILES: CS(=O)(=O)N(CCCc1cc(-c2cn[nH]c2)c2ccc(Cl)c(Cl)c2n1)CC(=O)O] |

TABLE 1-continued
| Exemplary Compounds | |
|---|---|
| I-# | Structure |
| I-338 | 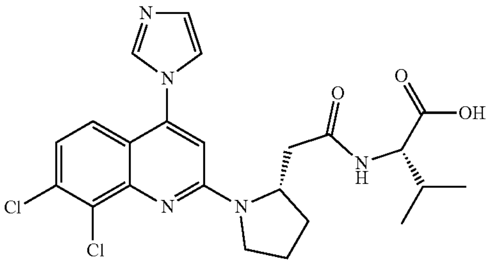 [SMILES: CC(C)[C@H](NC(=O)C[C@@H]1CCCN1c1cc(-n2ccnc2)c2ccc(Cl)c(Cl)c2n1)C(=O)O] |
| I-339 | 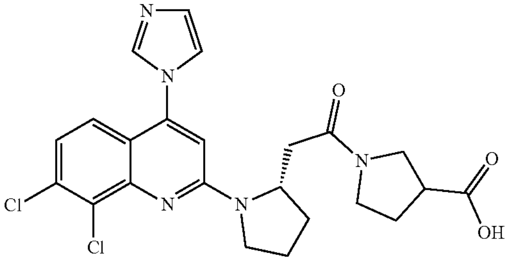 [SMILES: O=C(O)C1CCN(C(=O)C[C@@H]2CCCN2c2cc(-n3ccnc3)c3ccc(Cl)c(Cl)c3n2)C1] |
| I-340 | 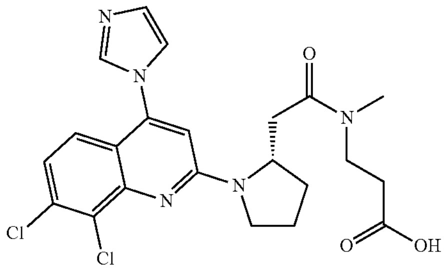 [SMILES: CN(CCC(=O)O)C(=O)C[C@@H]1CCCN1c1cc(-n2ccnc2)c2ccc(Cl)c(Cl)c2n1] |
| I-341 | 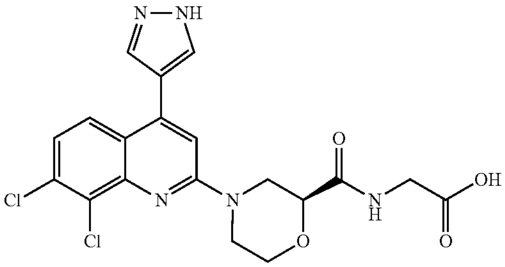 [SMILES: O=C(O)CNC(=O)[C@@H]1CN(c2cc(-c3cn[nH]c3)c3ccc(Cl)c(Cl)c3n2)CCO1] |
| I-342 | 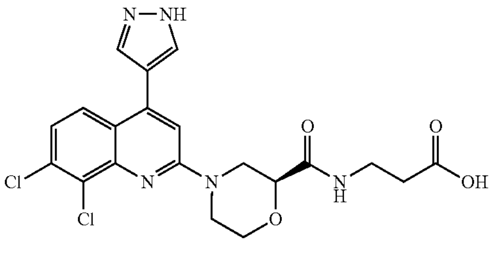 [SMILES: O=C(O)CCNC(=O)[C@@H]1CN(c2cc(-c3cn[nH]c3)c3ccc(Cl)c(Cl)c3n2)CCO1] |
| I-343 | 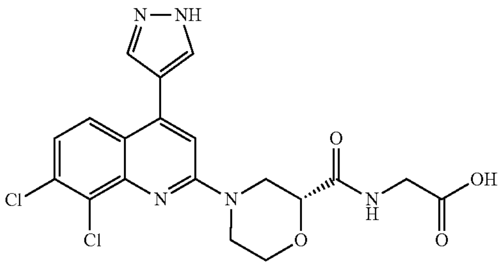 [SMILES: O=C(O)CNC(=O)[C@H]1CN(c2cc(-c3cn[nH]c3)c3ccc(Cl)c(Cl)c3n2)CCO1] |
| I-344 | 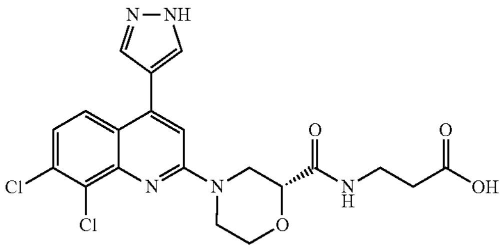 [SMILES: O=C(O)CCNC(=O)[C@H]1CN(c2cc(-c3cn[nH]c3)c3ccc(Cl)c(Cl)c3n2)CCO1] |
| I-345 | 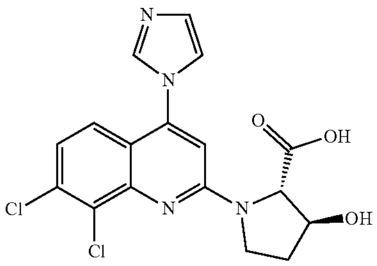 [SMILES: O=C(O)[C@@H]1[C@@H](O)CCN1c1cc(-n2ccnc2)c2ccc(Cl)c(Cl)c2n1] |
| I-346 | 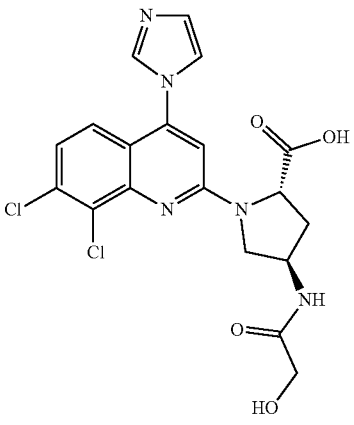 [SMILES: O=C(CO)N[C@@H]1C[C@@H](C(=O)O)N(c2cc(-n3ccnc3)c3ccc(Cl)c(Cl)c3n2)C1] |

TABLE 1-continued
| Exemplary Compounds | |
|---|---|
| I-# | Structure |
| I-347 | 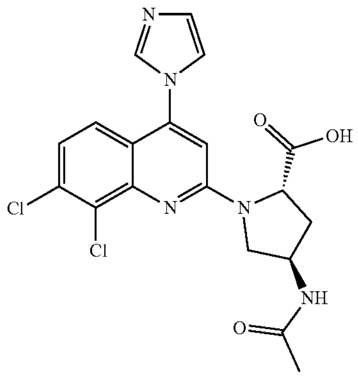 [SMILES: CC(=O)N[C@@H]1C[C@@H](C(=O)O)N(c2cc(-n3ccnc3)c3ccc(Cl)c(Cl)c3n2)C1] |
| I-348 | 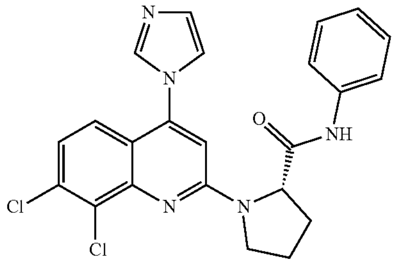 [SMILES: O=C(Nc1ccccc1)[C@@H]1CCCN1c1cc(-n2ccnc2)c2ccc(Cl)c(Cl)c2n1] |
| I-349 | 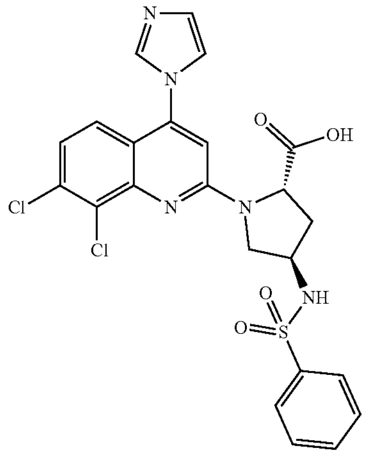 [SMILES: O=C(O)[C@@H]1C[C@@H](NS(=O)(=O)c2ccccc2)CN1c1cc(-n2ccnc2)c2ccc(Cl)c(Cl)c2n1] |
| I-350 | 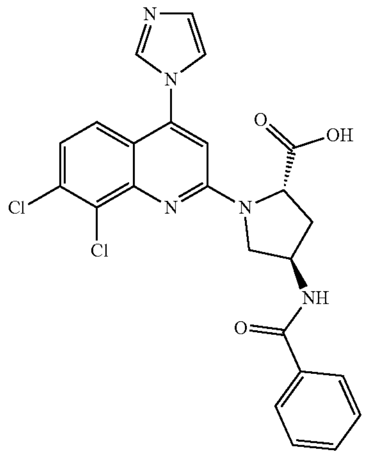 [SMILES: O=C(N[C@@H]1C[C@@H](C(=O)O)N(c2cc(-n3ccnc3)c3ccc(Cl)c(Cl)c3n2)C1)c1ccccc1] |
TABLE 1-continued
| Exemplary Compounds | |
|---|---|
| I-# | Structure |
| I-351 | 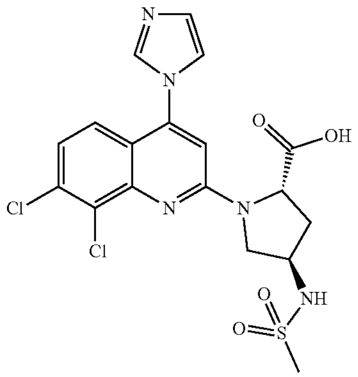 [SMILES: CS(=O)(=O)N[C@@H]1C[C@@H](C(=O)O)N(c2cc(-n3ccnc3)c3ccc(Cl)c(Cl)c3n2)C1] |
| I-352 | 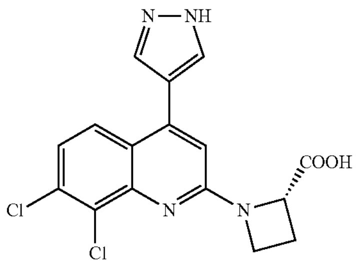 [SMILES: O=C(O)[C@@H]1CCN1c1cc(-c2cn[nH]c2)c2ccc(Cl)c(Cl)c2n1] |
| I-353 | 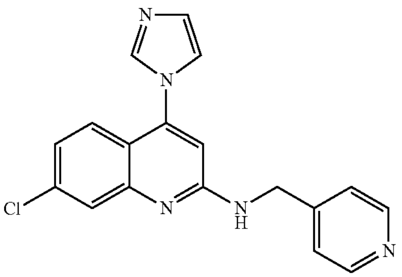 [SMILES: Clc1ccc2c(-n3ccnc3)cc(NCc3ccncc3)nc2c1] |
| I-354 | 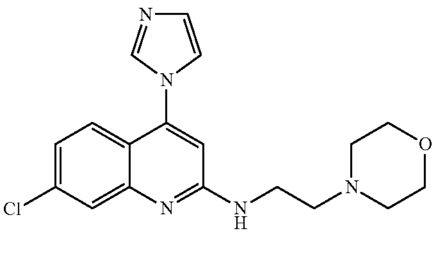 [SMILES: Clc1ccc2c(-n3ccnc3)cc(NCCN3CCOCC3)nc2c1] |
| I-355 | 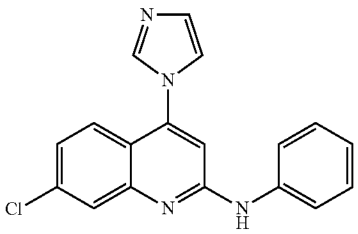 [SMILES: Clc1ccc2c(-n3ccnc3)cc(Nc3ccccc3)nc2c1] |

TABLE 1-continued
| Exemplary Compounds | |
|---|---|
| I-# | Structure |
| I-356 | 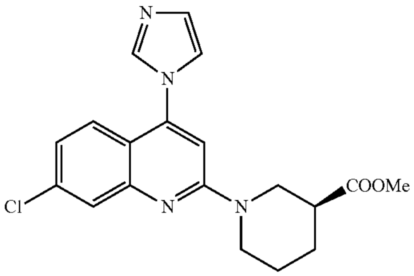 [SMILES: COC(=O)[C@H]1CCCN(c2cc(-n3ccnc3)c3ccc(Cl)cc3n2)C1] |
| I-357 | 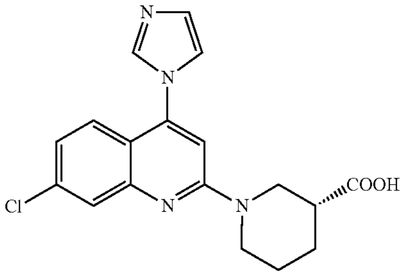 [SMILES: O=C(O)[C@@H]1CCCN(c2cc(-n3ccnc3)c3ccc(Cl)cc3n2)C1] |
| I-358 | 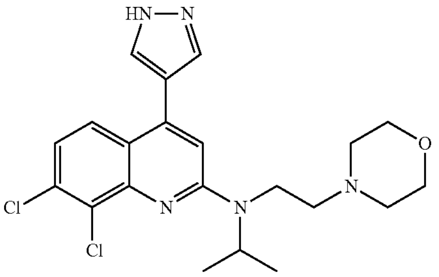 [SMILES: CC(C)N(CCN1CCOCC1)c1cc(-c2cn[nH]c2)c2ccc(Cl)c(Cl)c2n1] |
| I-359 | 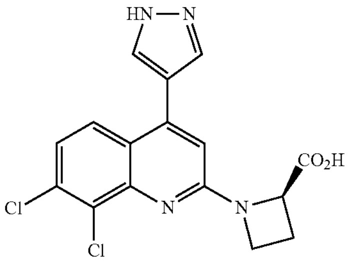 [SMILES: O=C(O)[C@H]1CCN1c1cc(-c2cn[nH]c2)c2ccc(Cl)c(Cl)c2n1] |
| I-360 | 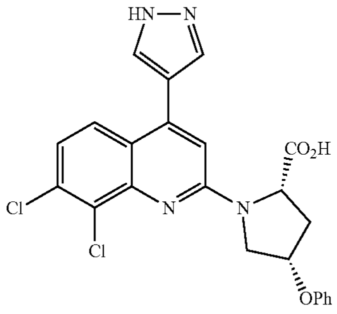 [SMILES: O=C(O)[C@@H]1C[C@H](Oc2ccccc2)CN1c1cc(-c2cn[nH]c2)c2ccc(Cl)c(Cl)c2n1] |
TABLE 1-continued
| Exemplary Compounds | |
|---|---|
| I-# | Structure |
| I-361 | 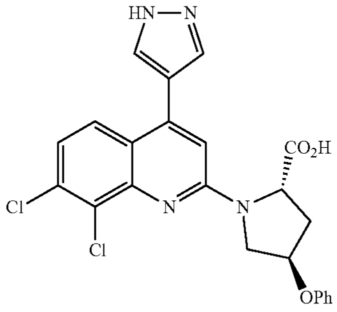 [SMILES: O=C(O)[C@@H]1C[C@@H](Oc2ccccc2)CN1c1cc(-c2cn[nH]c2)c2ccc(Cl)c(Cl)c2n1] |
| I-362 | 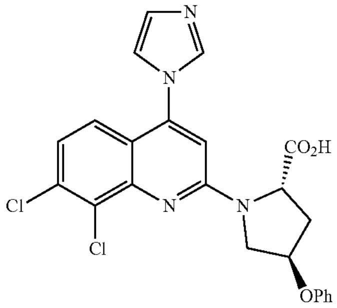 [SMILES: O=C(O)[C@@H]1C[C@@H](Oc2ccccc2)CN1c1cc(-n2ccnc2)c2ccc(Cl)c(Cl)c2n1] |
| I-363 | 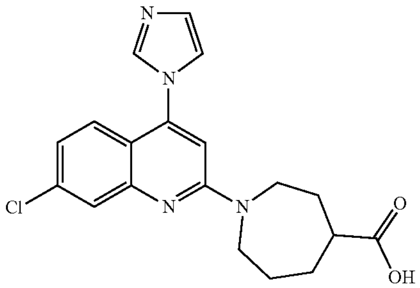 [SMILES: O=C(O)C1CCCN(c2cc(-n3ccnc3)c3ccc(Cl)cc3n2)CC1] |
| I-364 | 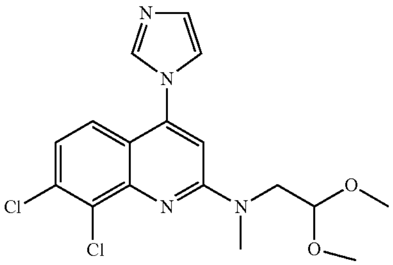 [SMILES: COC(CN(C)c1cc(-n2ccnc2)c2ccc(Cl)c(Cl)c2n1)OC] |
| I-365 | 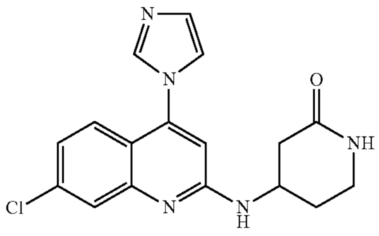 [SMILES: O=C1CC(Nc2cc(-n3ccnc3)c3ccc(Cl)cc3n2)CCN1] |

TABLE 1-continued
| Exemplary Compounds | |
|---|---|
| I-# | Structure |
| I-366 | 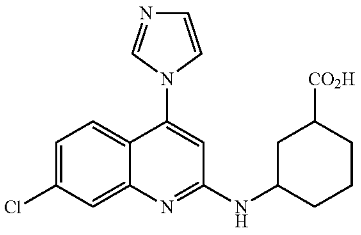 [SMILES: O=C(O)C1CCCC(Nc2cc(-n3ccnc3)c3ccc(Cl)cc3n2)C1] |
| I-367 | 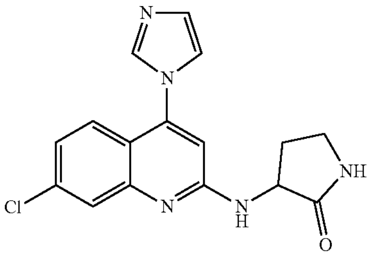 |
| I-368 | 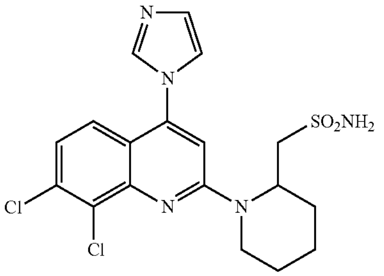 [SMILES: NS(=O)(=O)CC1CCCCN1c1cc(-n2ccnc2)c2ccc(Cl)c(Cl)c2n1] |
| I-369 | 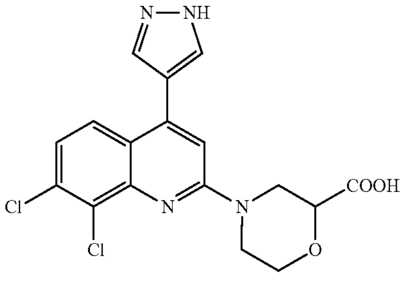 [SMILES: O=C(O)C1CN(c2cc(-c3cn[nH]c3)c3ccc(Cl)c(Cl)c3n2)CCO1] |
| I-370 | 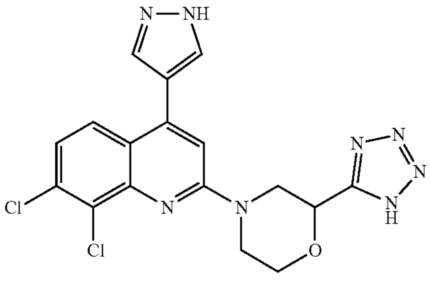 [SMILES: Clc1ccc2c(-c3cn[nH]c3)cc(N3CCOC(c4nnn[nH]4)C3)nc2c1Cl] |
TABLE 1-continued
| Exemplary Compounds | |
|---|---|
| I-# | Structure |
| I-371 | 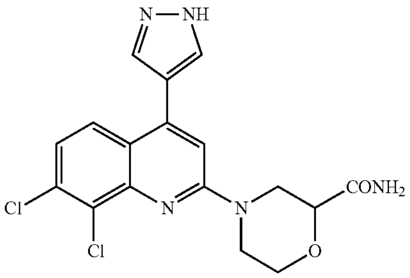 [SMILES: NC(=O)C1CN(c2cc(-c3cn[nH]c3)c3ccc(Cl)c(Cl)c3n2)CCO1] |
| I-372 | 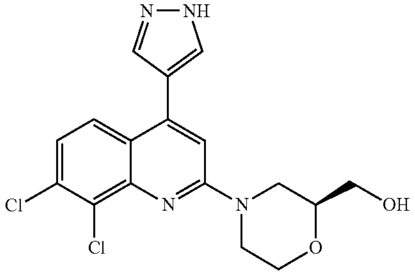 [SMILES: OC[C@@H]1CN(c2cc(-c3cn[nH]c3)c3ccc(Cl)c(Cl)c3n2)CCO1] |
| I-373 | 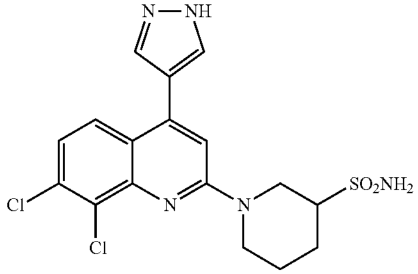 [SMILES: NS(=O)(=O)C1CCCN(c2cc(-c3cn[nH]c3)c3ccc(Cl)c(Cl)c3n2)C1] |
| I-374 | 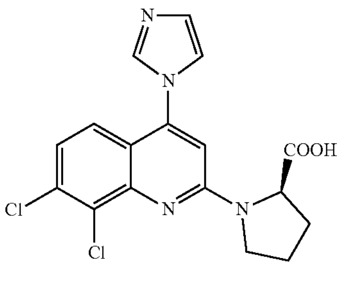 |
| I-375 | 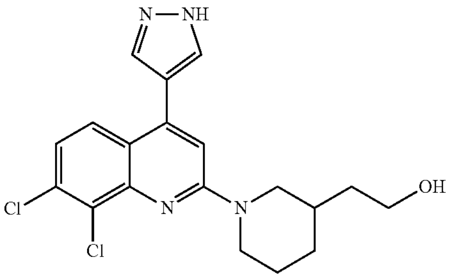 [SMILES: OCCC1CCCN(c2cc(-c3cn[nH]c3)c3ccc(Cl)c(Cl)c3n2)C1] |

TABLE 1-continued
| Exemplary Compounds | |
|---|---|
| I-# | Structure |
| I-376 | 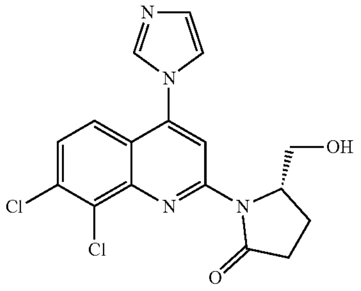 [SMILES: O=C1CC[C@@H](CO)N1c1cc(-n2ccnc2)c2ccc(Cl)c(Cl)c2n1] |
| I-377 | 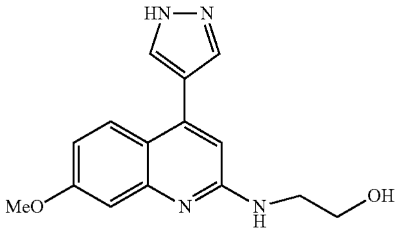 |
| I-378 | 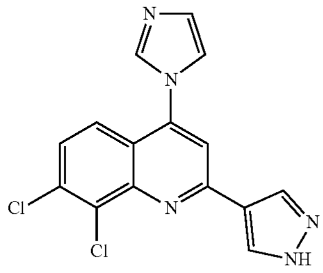 [SMILES: Clc1ccc2c(-n3ccnc3)cc(-c3cn[nH]c3)nc2c1Cl] |
| I-379 | 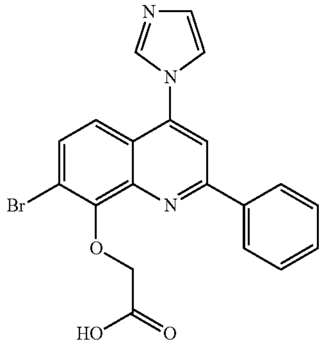 [SMILES: O=C(O)COc1c(Br)ccc2c(-n3ccnc3)cc(-c3ccccc3)nc12] |
| I-380 | 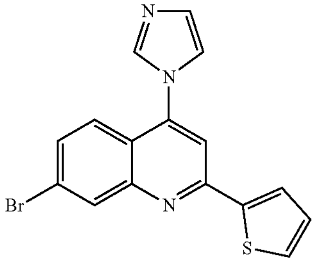 [SMILES: Brc1ccc2c(-n3ccnc3)cc(-c3cccs3)nc2c1] |
TABLE 1-continued
| Exemplary Compounds | |
|---|---|
| I-# | Structure |
| I-381 | 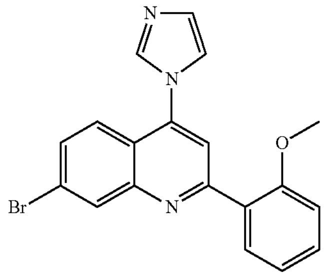 [SMILES: COc1ccccc1-c1cc(-n2ccnc2)c2ccc(Br)cc2n1] |
| I-382 | 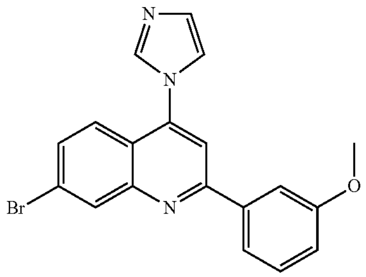 [SMILES: COc1cccc(-c2cc(-n3ccnc3)c3ccc(Br)cc3n2)c1] |
| I-383 | 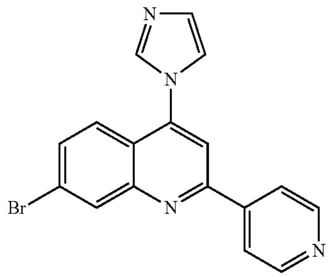 [SMILES: Brc1ccc2c(-n3ccnc3)cc(-c3ccncc3)nc2c1] |
| I-384 | 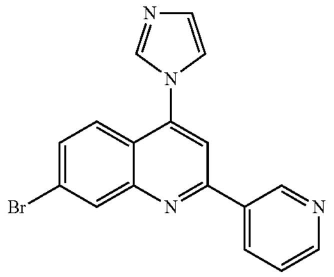 [SMILES: Brc1ccc2c(-n3ccnc3)cc(-c3cccnc3)nc2c1] |
| I-385 | 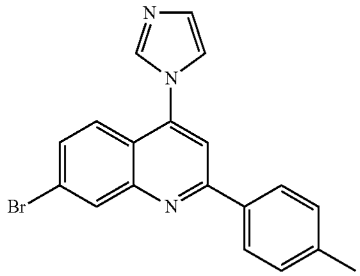 [SMILES: Cc1ccc(-c2cc(-n3ccnc3)c3ccc(Br)cc3n2)cc1] |

TABLE 1-continued
Exemplary Compounds
| I-# | Structure |
|---|---|
| I-386 | 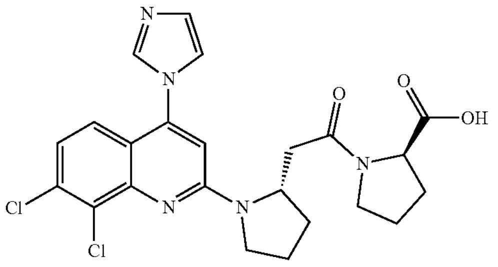 [SMILES: O=C(O)[C@H]1CCCN1C(=O)C[C@@H]1CCCN1c1cc(-n2ccnc2)c2ccc(Cl)c(Cl)c2n1] |
| I-387 | 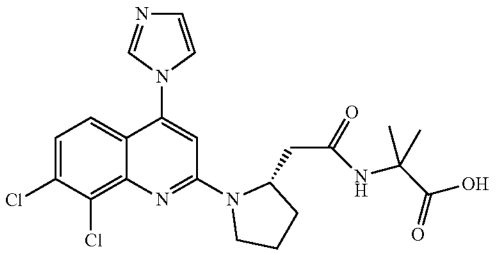 [SMILES: CC(C)(NC(=O)C[C@@H]1CCCN1c1cc(-n2ccnc2)c2ccc(Cl)c(Cl)c2n1)C(=O)O] |
| I-388 | 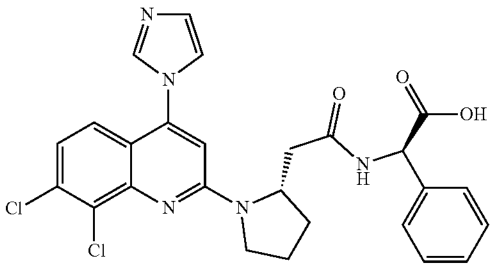 [SMILES: O=C(C[C@@H]1CCCN1c1cc(-n2ccnc2)c2ccc(Cl)c(Cl)c2n1)N[C@@H](C(=O)O)c1ccccc1] |
| I-389 | 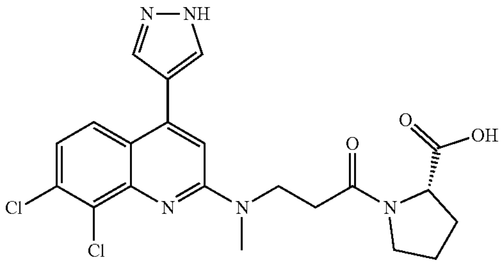 [SMILES: CN(CCC(=O)N1CCC[C@H]1C(=O)O)c1cc(-c2cn[nH]c2)c2ccc(Cl)c(Cl)c2n1] |
| I-390 | 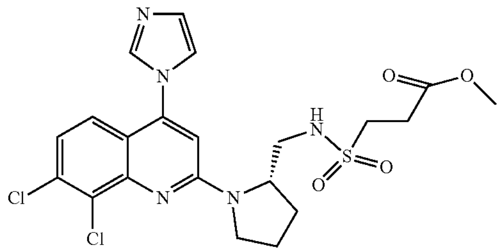 [SMILES: COC(=O)CCS(=O)(=O)NC[C@@H]1CCCN1c1cc(-n2ccnc2)c2ccc(Cl)c(Cl)c2n1] |
TABLE 1-continued
Exemplary Compounds
| I-# | Structure |
|---|---|
| I-391 | 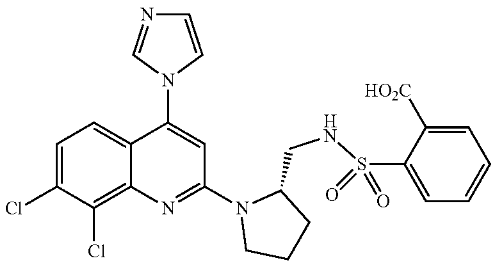 [SMILES: O=C(O)c1ccccc1S(=O)(=O)NC[C@@H]1CCCN1c1cc(-n2ccnc2)c2ccc(Cl)c(Cl)c2n1] |
| I-392 | 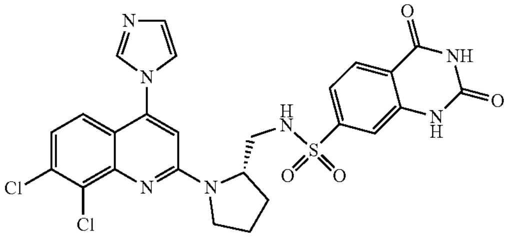 [SMILES: O=c1[nH]c(=O)c2ccc(S(=O)(=O)NC[C@@H]3CCCN3c3cc(-n4ccnc4)c4ccc(Cl)c(Cl)c4n3)cc2[nH]1] |
| I-393 | 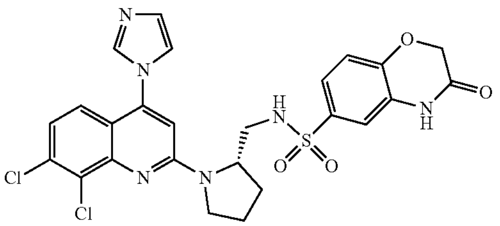 [SMILES: O=C1COc2ccc(S(=O)(=O)NC[C@@H]3CCCN3c3cc(-n4ccnc4)c4ccc(Cl)c(Cl)c4n3)cc2N1] |
| I-394 | 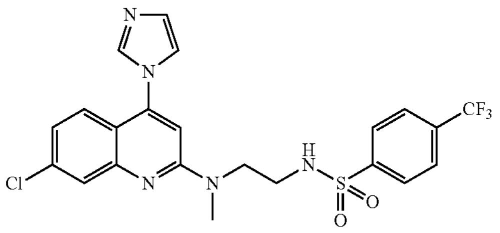 [SMILES: CN(CCNS(=O)(=O)c1ccc(C(F)(F)F)cc1)c1cc(-n2ccnc2)c2ccc(Cl)cc2n1] |
| I-395 | 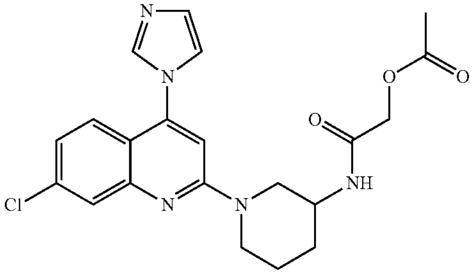 [SMILES: CC(=O)OCC(=O)NC1CCCN(c2cc(-n3ccnc3)c3ccc(Cl)cc3n2)C1] |
| I-396 | 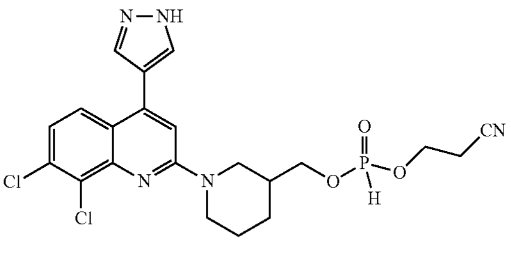 [SMILES: N#CCCO[PH](=O)OCC1CCCN(c2cc(-c3cn[nH]c3)c3ccc(Cl)c(Cl)c3n2)C1] |

TABLE 1-continued
| I-# | Structure |
|---|---|
| I-397 | 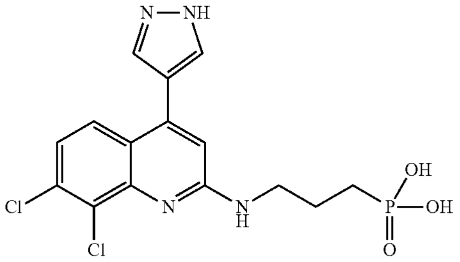 [SMILES: O=P(O)(O)CCCNc1cc(-c2cn[nH]c2)c2ccc(Cl)c(Cl)c2n1] |
| I-398 | 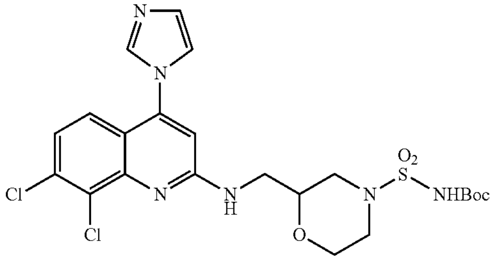 [SMILES: CC(C)(C)OC(=O)NS(=O)(=O)N1CCOC(CNc2cc(-n3ccnc3)c3ccc(Cl)c(Cl)c3n2)C1] |
| I-399 | 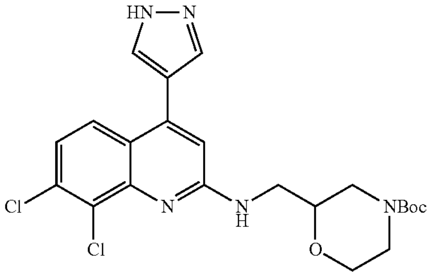 [SMILES: CC(C)(C)OC(=O)N1CCOC(CNc2cc(-c3cn[nH]c3)c3ccc(Cl)c(Cl)c3n2)C1] |
| I-400 | 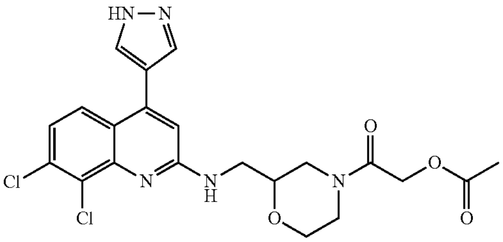 [SMILES: CC(=O)OCC(=O)N1CCOC(CNc2cc(-c3cn[nH]c3)c3ccc(Cl)c(Cl)c3n2)C1] |
| I-401 | 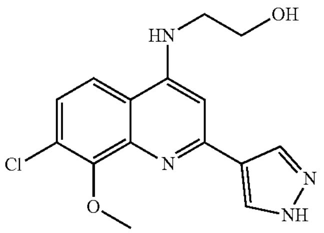 [SMILES: COc1c(Cl)ccc2c(NCCO)cc(-c3cn[nH]c3)nc12] |
| I-402 | 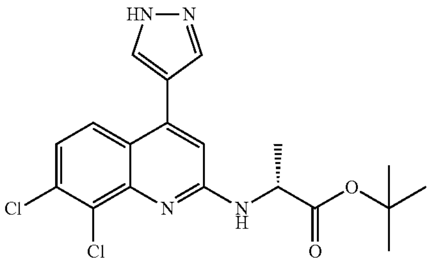 [SMILES: C[C@@H](Nc1cc(-c2cn[nH]c2)c2ccc(Cl)c(Cl)c2n1)C(=O)OC(C)(C)C] |
TABLE 1-continued
| I-# | Structure |
|---|---|
| I-403 | 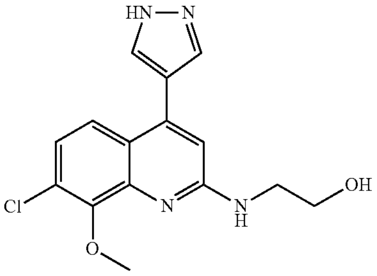 [SMILES: COc1c(Cl)ccc2c(-c3cn[nH]c3)cc(NCCO)nc12] |
| I-404 | 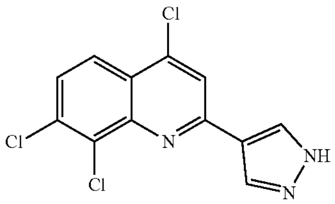 [SMILES: Clc1ccc2c(Cl)cc(-c3cn[nH]c3)nc2c1Cl] |
| I-405 | 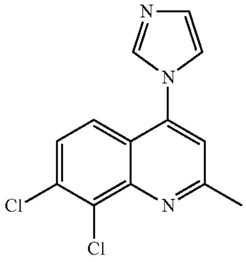 [SMILES: Cc1cc(-n2ccnc2)c2ccc(Cl)c(Cl)c2n1] |
| I-406 | 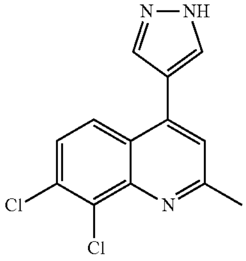 [SMILES: Cc1cc(-c2cn[nH]c2)c2ccc(Cl)c(Cl)c2n1] |
| I-407 | 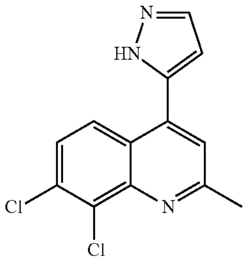 [SMILES: Cc1cc(-c2ccn[nH]2)c2ccc(Cl)c(Cl)c2n1] |

TABLE 1-continued
| Exemplary Compounds | |
|---|---|
| I-# | Structure |
| I-408 | 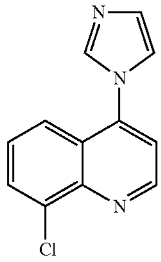 [SMILES: Clc1cccc2c(-n3ccnc3)ccnc12] |
| I-409 | 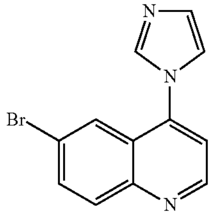 [SMILES: Brc1ccc2nccc(-n3ccnc3)c2c1] |
| I-410 | 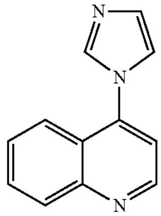 [SMILES: c1ccc2c(-n3ccnc3)ccnc2c1] |
| I-411 | 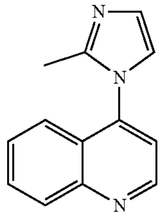 [SMILES: Cc1nccn1-c1ccnc2ccccc12] |
| I-412 | 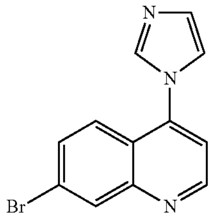 [SMILES: Brc1ccc2c(-n3ccnc3)ccnc2c1] |
| I-413 | 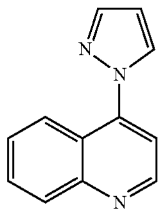 [SMILES: c1ccc2c(-n3cccn3)ccnc2c1] |
TABLE 1-continued
| Exemplary Compounds | |
|---|---|
| I-# | Structure |
| I-414 | 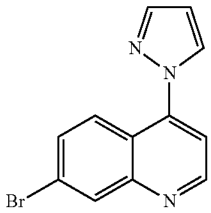 [SMILES: Brc1ccc2c(-n3cccn3)ccnc2c1] |
| I-415 | 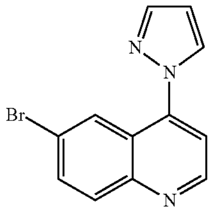 [SMILES: Brc1ccc2nccc(-n3cccn3)c2c1] |
| I-416 | 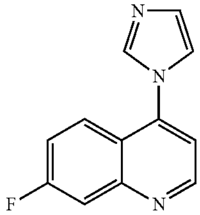 [SMILES: Fc1ccc2c(-n3ccnc3)ccnc2c1] |
| I-417 | 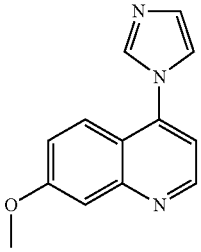 [SMILES: COc1ccc2c(-n3ccnc3)ccnc2c1] |
| I-418 | 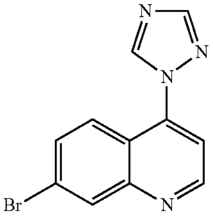 [SMILES: Brc1ccc2c(-n3cncn3)ccnc2c1] |
| I-419 | 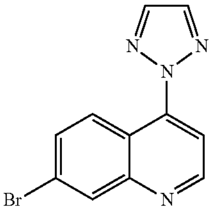 [SMILES: Brc1ccc2c(-n3nccn3)ccnc2c1] |

TABLE 1-continued
| Exemplary Compounds | |
|---|---|
| I-# | Structure |
| I-420 | 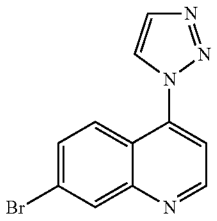 [SMILES: Brc1ccc2c(-n3ccnn3)ccnc2c1] |
| I-421 | 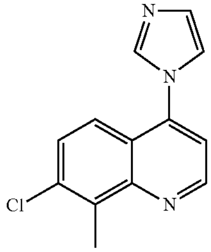 [SMILES: Cc1c(Cl)ccc2c(-n3ccnc3)ccnc12] |
| I-422 | 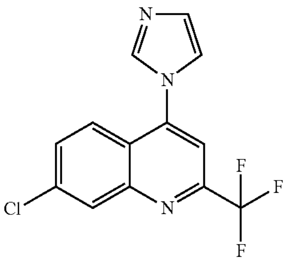 [SMILES: FC(F)(F)c1cc(-n2ccnc2)c2ccc(Cl)cc2n1] |
| I-423 | 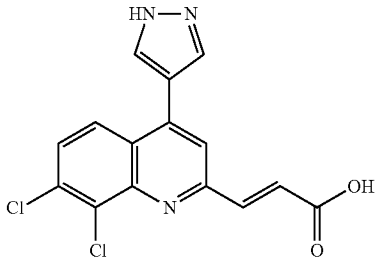 [SMILES: O=C(O)/C=C/c1cc(-c2cn[nH]c2)c2ccc(Cl)c(Cl)c2n1] |
| I-424 | 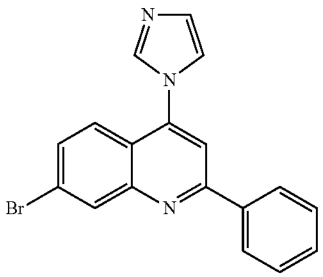 |
| I-425 | 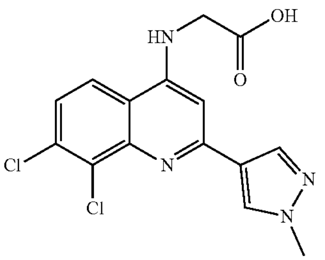 [SMILES: Cn1cc(-c2cc(NCC(=O)O)c3ccc(Cl)c(Cl)c3n2)cn1] |
TABLE 1-continued
| Exemplary Compounds | |
|---|---|
| I-# | Structure |
| I-426 | 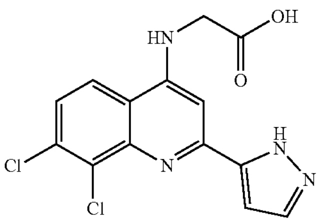 [SMILES: O=C(O)CNc1cc(-c2ccn[nH]2)nc2c(Cl)c(Cl)ccc12] |
| I-427 | 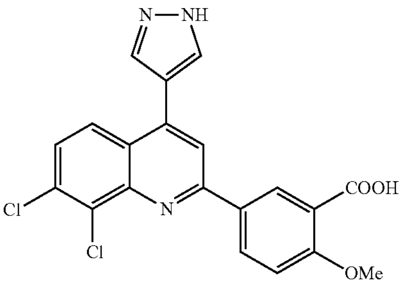 [SMILES: COc1ccc(-c2cc(-c3cn[nH]c3)c3ccc(Cl)c(Cl)c3n2)cc1C(=O)O] |
| I-428 | 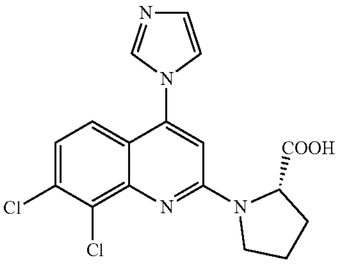 [SMILES: O=C(O)[C@@H]1CCCN1c1cc(-n2ccnc2)c2ccc(Cl)c(Cl)c2n1] |
| I-429 | 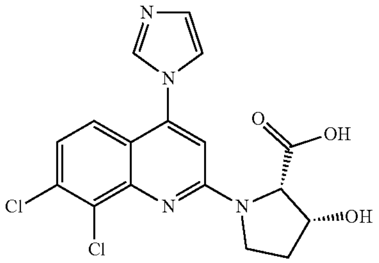 [SMILES: O=C(O)[C@@H]1[C@H](O)CCN1c1cc(-n2ccnc2)c2ccc(Cl)c(Cl)c2n1] |
| I-430 | 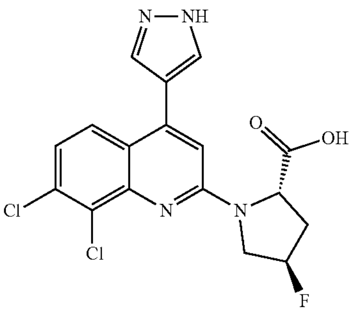 [SMILES: O=C(O)[C@@H]1C[C@@H](F)CN1c1cc(-c2cn[nH]c2)c2ccc(Cl)c(Cl)c2n1] |

TABLE 1-continued
| Exemplary Compounds | |
| --- | --- |
| I-# | Structure |
| I-431 | 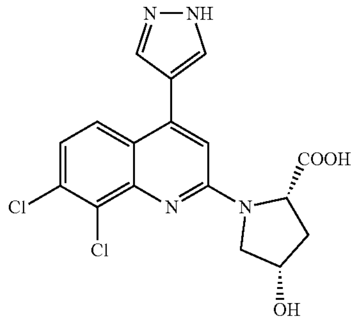 [SMILES: O=C(O)[C@@H]1C[C@H](O)CN1c1cc(-c2cn[nH]c2)c2ccc(Cl)c(Cl)c2n1] |
| I-432 | 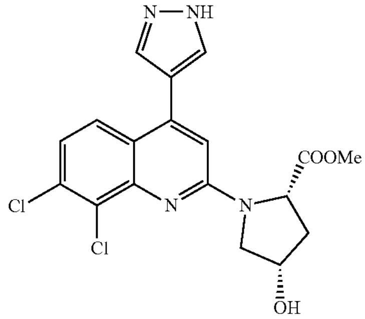 [SMILES: COC(=O)[C@@H]1C[C@H](O)CN1c1cc(-c2cn[nH]c2)c2ccc(Cl)c(Cl)c2n1] |
| I-433 | 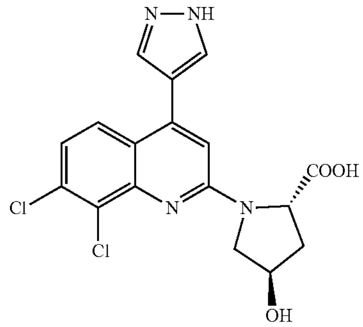 [SMILES: O=C(O)[C@@H]1C[C@@H](O)CN1c1cc(-c2cn[nH]c2)c2ccc(Cl)c(Cl)c2n1] |
| I-434 | 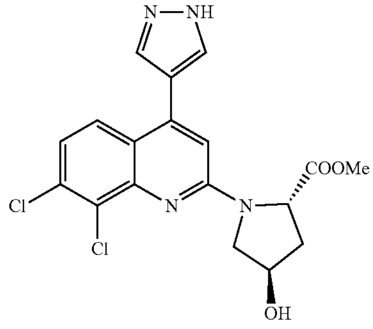 [SMILES: COC(=O)[C@@H]1C[C@@H](O)CN1c1cc(-c2cn[nH]c2)c2ccc(Cl)c(Cl)c2n1] |
TABLE 1-continued
| Exemplary Compounds | |
| --- | --- |
| I-# | Structure |
| I-435 | 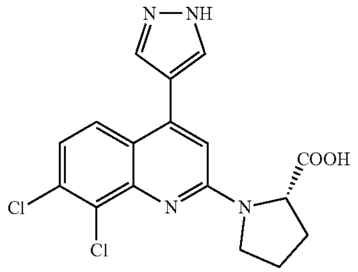 [SMILES: O=C(O)[C@@H]1CCCN1c1cc(-c2cn[nH]c2)c2ccc(Cl)c(Cl)c2n1] |
| I-436 | 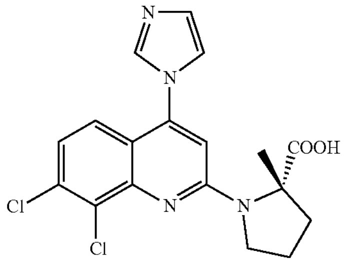 [SMILES: C[C@@]1(C(=O)O)CCCN1c1cc(-n2ccnc2)c2ccc(Cl)c(Cl)c2n1] |
| I-437 | 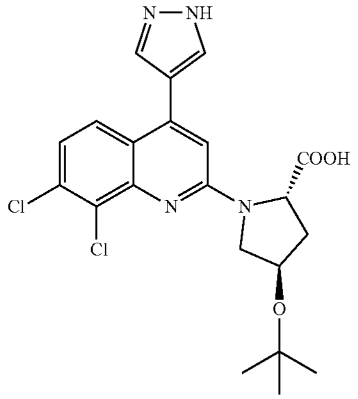 [SMILES: CC(C)(C)O[C@@H]1C[C@@H](C(=O)O)N(c2cc(-c3cn[nH]c3)c3ccc(Cl)c(Cl)c3n2)C1] |
| I-438 | 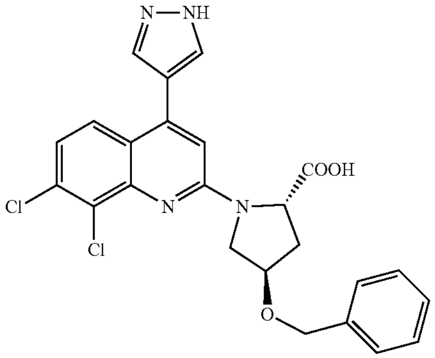 [SMILES: O=C(O)[C@@H]1C[C@@H](OCc2ccccc2)CN1c1cc(-c2cn[nH]c2)c2ccc(Cl)c(Cl)c2n1] |

TABLE 1-continued
| Exemplary Compounds | |
|---|---|
| I-# | Structure |
| I-439 | 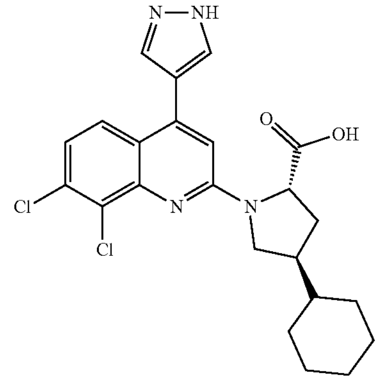 [SMILES: O=C(O)[C@@H]1C[C@@H](C2CCCCC2)CN1c1cc(-c2cn[nH]c2)c2ccc(Cl)c(Cl)c2n1] |
| I-443 | 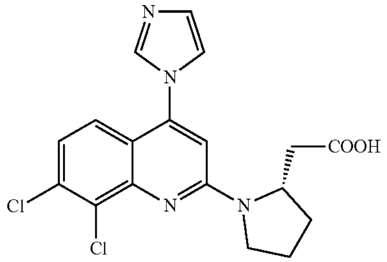 [SMILES: O=C(O)C[C@@H]1CCCN1c1cc(-n2ccnc2)c2ccc(Cl)c(Cl)c2n1] |
| I-444 | 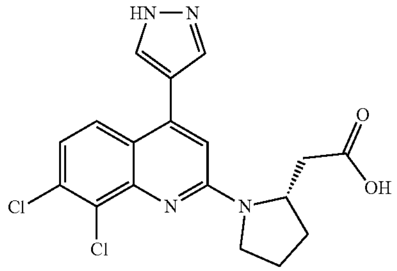 [SMILES: O=C(O)C[C@@H]1CCCN1c1cc(-c2cn[nH]c2)c2ccc(Cl)c(Cl)c2n1] |
| I-445 | 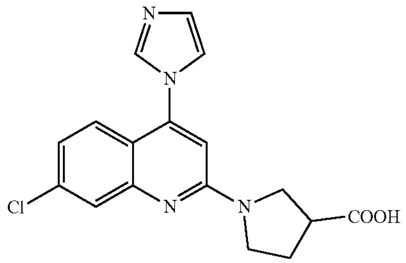 |
| I-446 | 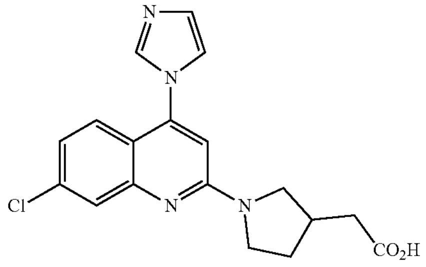 [SMILES: O=C(O)CC1CCN(c2cc(-n3ccnc3)c3ccc(Cl)cc3n2)C1] |
TABLE 1-continued
| Exemplary Compounds | |
|---|---|
| I-# | Structure |
| I-447 | 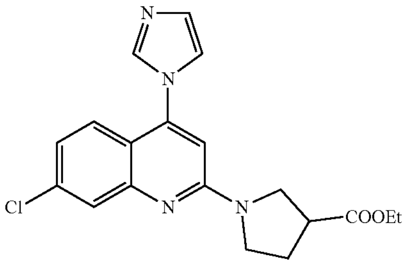 [SMILES: CCOC(=O)C1CCN(c2cc(-n3ccnc3)c3ccc(Cl)cc3n2)C1] |
| I-448 | 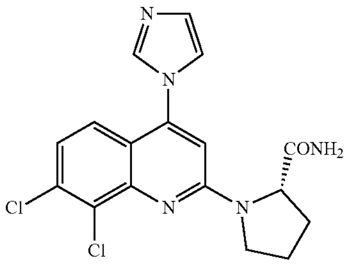 [SMILES: NC(=O)[C@@H]1CCCN1c1cc(-n2ccnc2)c2ccc(Cl)c(Cl)c2n1] |
| I-449 | 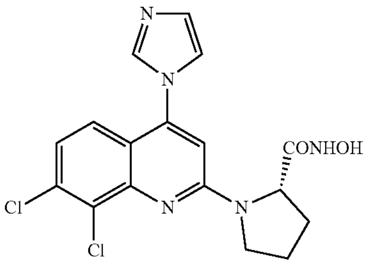 |
| I-450 | 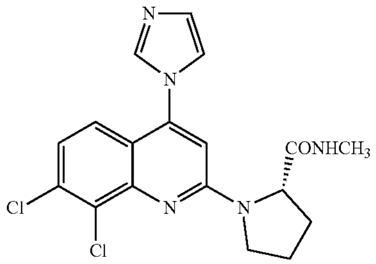 |
| I-451 | 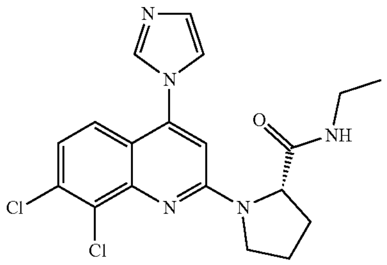 [SMILES: CCNC(=O)[C@@H]1CCCN1c1cc(-n2ccnc2)c2ccc(Cl)c(Cl)c2n1] |

TABLE 1-continued
| Exemplary Compounds | |
|---|---|
| I-# | Structure |
| I-452 | 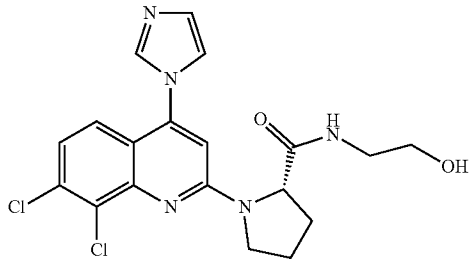 [SMILES: O=C(NCCO)[C@@H]1CCCN1c1cc(-n2ccnc2)c2ccc(Cl)c(Cl)c2n1] |
| I-453 | 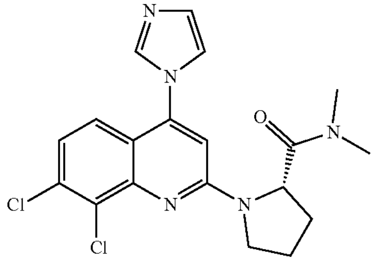 [SMILES: CN(C)C(=O)[C@@H]1CCCN1c1cc(-n2ccnc2)c2ccc(Cl)c(Cl)c2n1] |
| I-454 | 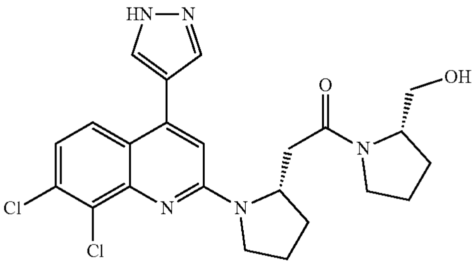 [SMILES: O=C(C[C@@H]1CCCN1c1cc(-c2cn[nH]c2)c2ccc(Cl)c(Cl)c2n1)N1CCC[C@H]1CO] |
| I-455 | 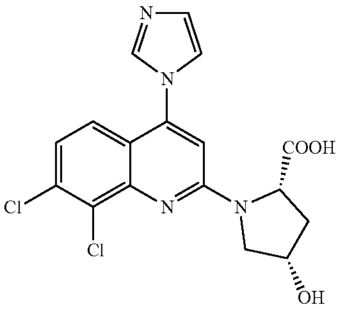 [SMILES: O=C(O)[C@@H]1C[C@H](O)CN1c1cc(-n2ccnc2)c2ccc(Cl)c(Cl)c2n1] |
| I-456 | 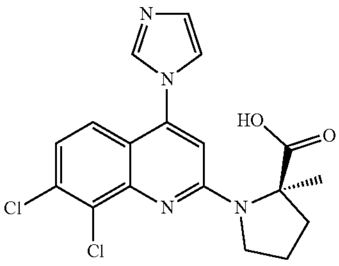 [SMILES: C[C@]1(C(=O)O)CCCN1c1cc(-n2ccnc2)c2ccc(Cl)c(Cl)c2n1] |
TABLE 1-continued
| Exemplary Compounds | |
|---|---|
| I-# | Structure |
| I-457 | 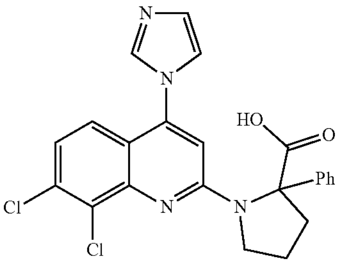 [SMILES: O=C(O)C1(c2ccccc2)CCCN1c1cc(-n2ccnc2)c2ccc(Cl)c(Cl)c2n1] |
| I-458 | 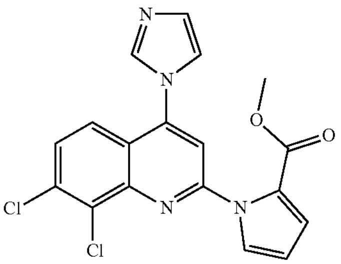 [SMILES: COC(=O)c1cccn1-c1cc(-n2ccnc2)c2ccc(Cl)c(Cl)c2n1] |
| I-459 | 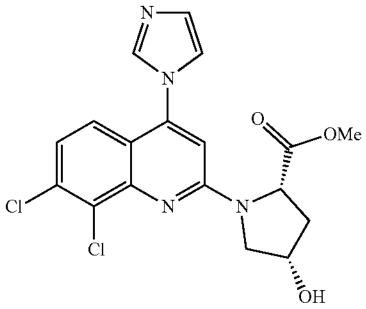 [SMILES: COC(=O)[C@@H]1C[C@H](O)CN1c1cc(-n2ccnc2)c2ccc(Cl)c(Cl)c2n1] |
| I-460 | 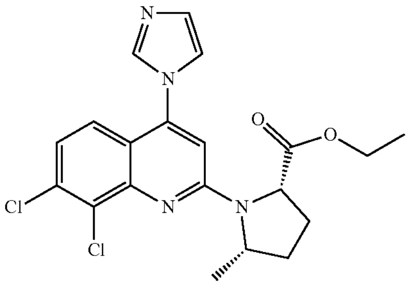 [SMILES: CCOC(=O)[C@@H]1CC[C@H](C)N1c1cc(-n2ccnc2)c2ccc(Cl)c(Cl)c2n1] |
| I-461 | 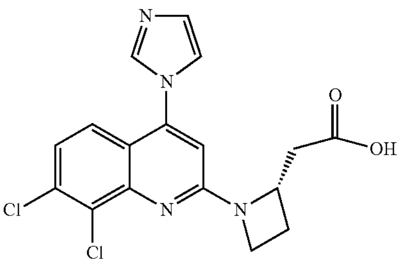 [SMILES: O=C(O)C[C@@H]1CCN1c1cc(-n2ccnc2)c2ccc(Cl)c(Cl)c2n1] |

TABLE 1-continued
| Exemplary Compounds | |
|---|---|
| I-# | Structure |
| I-462 | 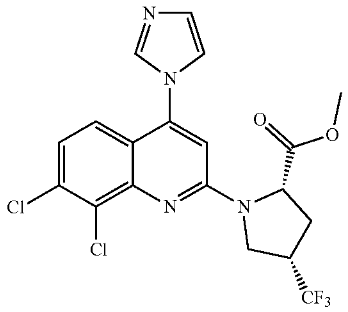 [SMILES: COC(=O)[C@@H]1C[C@H](C(F)(F)F)CN1c1cc(-n2ccnc2)c2ccc(Cl)c(Cl)c2n1] |
| I-463 | 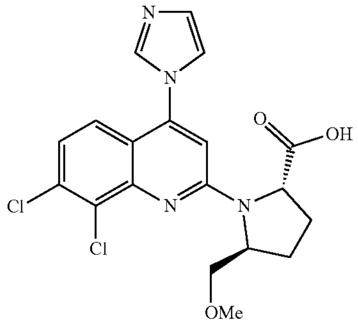 [SMILES: COC[C@@H]1CC[C@@H](C(=O)O)N1c1cc(-n2ccnc2)c2ccc(Cl)c(Cl)c2n1] |
| I-464 | 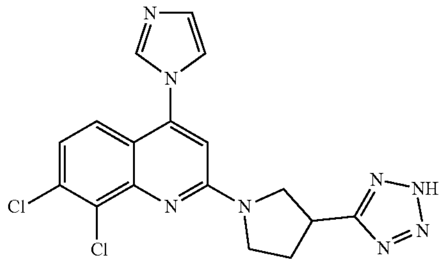 [SMILES: Clc1ccc2c(-n3ccnc3)cc(N3CCC(c4nn[nH]n4)C3)nc2c1Cl] |
| I-465 | 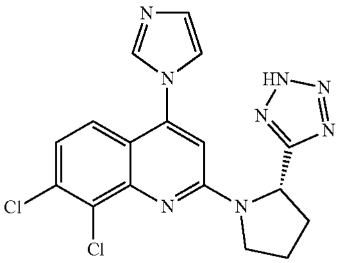 [SMILES: Clc1ccc2c(-n3ccnc3)cc(N3CCC[C@H]3c3nn[nH]n3)nc2c1Cl] |
| I-466 | 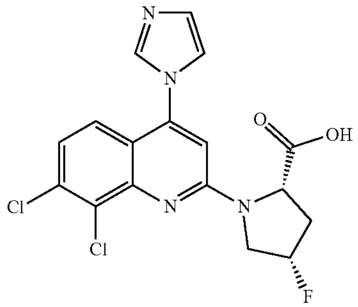 [SMILES: O=C(O)[C@@H]1C[C@H](F)CN1c1cc(-n2ccnc2)c2ccc(Cl)c(Cl)c2n1] |
TABLE 1-continued
| Exemplary Compounds | |
|---|---|
| I-# | Structure |
| I-467 | 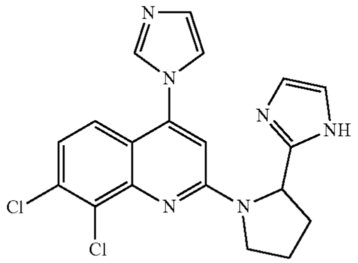 [SMILES: Clc1ccc2c(-n3ccnc3)cc(N3CCCC3c3ncc[nH]3)nc2c1Cl] |
| I-468 | 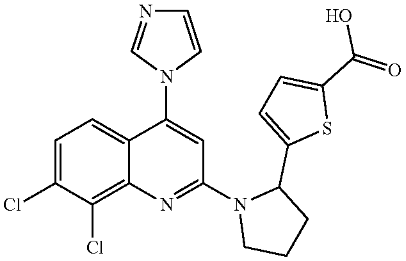 [SMILES: O=C(O)c1ccc(C2CCCN2c2cc(-n3ccnc3)c3ccc(Cl)c(Cl)c3n2)s1] |
| I-469 | 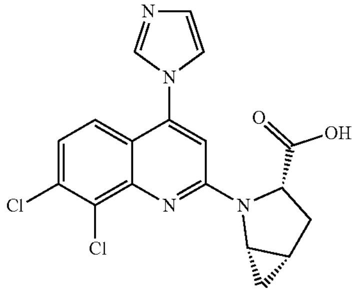 [SMILES: O=C(O)[C@@H]1C[C@@H]2C[C@@H]2N1c1cc(-n2ccnc2)c2ccc(Cl)c(Cl)c2n1] |
| I-470 | 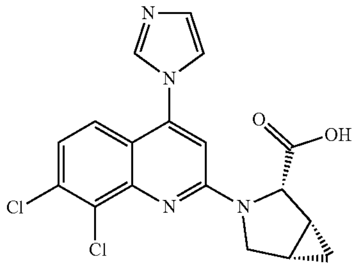 [SMILES: O=C(O)[C@@H]1[C@@H]2C[C@@H]2CN1c1cc(-n2ccnc2)c2ccc(Cl)c(Cl)c2n1] |
| I-471 | 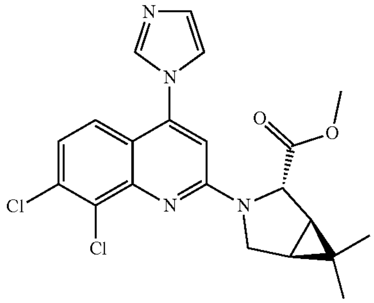 [SMILES: COC(=O)[C@@H]1[C@@H]2[C@H](CN1c1cc(-n3ccnc3)c3ccc(Cl)c(Cl)c3n1)C2(C)C] |

TABLE 1-continued
| Exemplary Compounds | |
|---|---|
| I-# | Structure |
| I-472 | 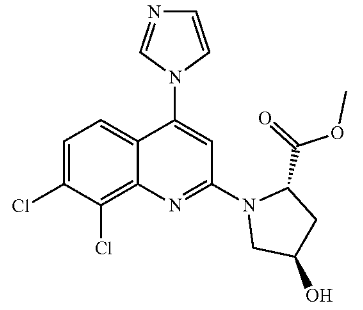 [SMILES: COC(=O)[C@@H]1C[C@@H](O)CN1c1cc(-n2ccnc2)c2ccc(Cl)c(Cl)c2n1] |
| I-473 | 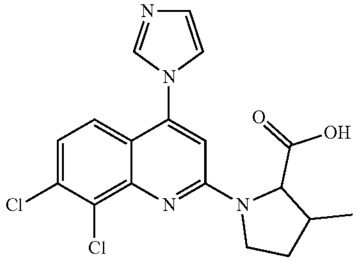 [SMILES: CC1CCN(c2cc(-n3ccnc3)c3ccc(Cl)c(Cl)c3n2)C1C(=O)O] |
| I-474 | 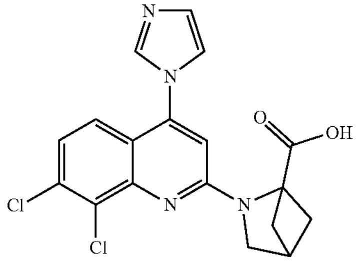 [SMILES: O=C(O)C12CC(CN1c1cc(-n3ccnc3)c3ccc(Cl)c(Cl)c3n1)C2] |
| I-475 | 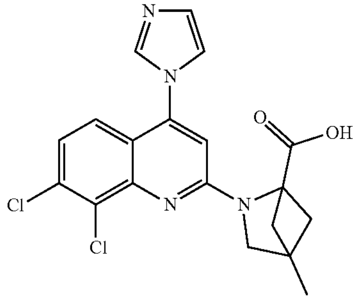 [SMILES: CC12CN(c3cc(-n4ccnc4)c4ccc(Cl)c(Cl)c4n3)C(C(=O)O)(C1)C2] |
| I-476 | 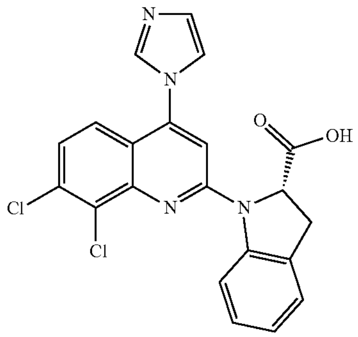 [SMILES: O=C(O)[C@@H]1Cc2ccccc2N1c1cc(-n2ccnc2)c2ccc(Cl)c(Cl)c2n1] |
TABLE 1-continued
| Exemplary Compounds | |
|---|---|
| I-# | Structure |
| I-477 | 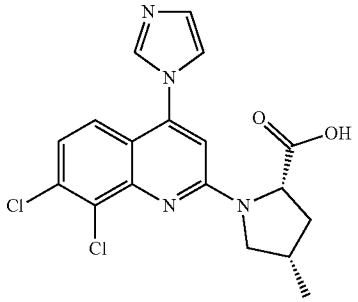 [SMILES: C[C@H]1C[C@@H](C(=O)O)N(c2cc(-n3ccnc3)c3ccc(Cl)c(Cl)c3n2)C1] |
| I-478 | 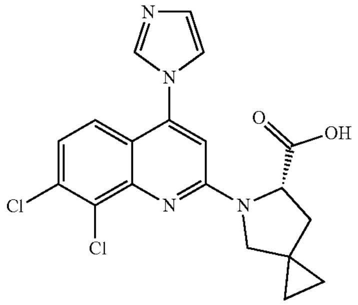 [SMILES: O=C(O)[C@@H]1CC2(CC2)CN1c1cc(-n2ccnc2)c2ccc(Cl)c(Cl)c2n1] |
| I-479 | 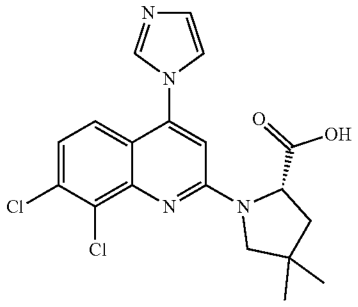 [SMILES: CC1(C)C[C@@H](C(=O)O)N(c2cc(-n3ccnc3)c3ccc(Cl)c(Cl)c3n2)C1] |
| I-480 | 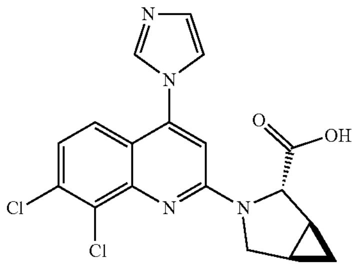 |
| I-481 | 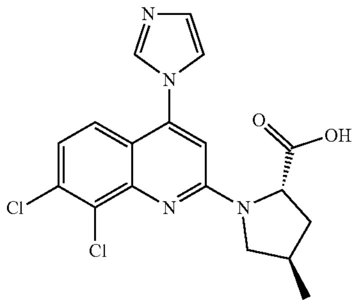 [SMILES: C[C@@H]1C[C@@H](C(=O)O)N(c2cc(-n3ccnc3)c3ccc(Cl)c(Cl)c3n2)C1] |

TABLE 1-continued
| Exemplary Compounds | |
|---|---|
| I-# | Structure |
| I-482 | 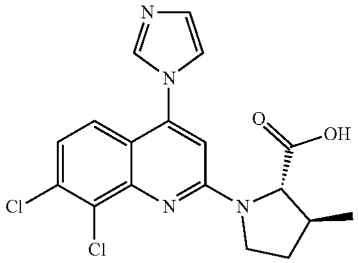 [SMILES: C[C@H]1CCN(c2cc(-n3ccnc3)c3ccc(Cl)c(Cl)c3n2)[C@@H]1C(=O)O] |
| I-483 | 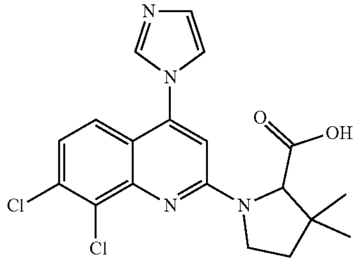 [SMILES: CC1(C)CCN(c2cc(-n3ccnc3)c3ccc(Cl)c(Cl)c3n2)C1C(=O)O] |
| I-484 | 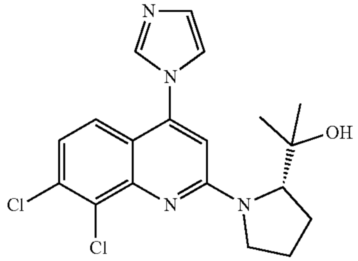 [SMILES: CC(C)(O)[C@@H]1CCCN1c1cc(-n2ccnc2)c2ccc(Cl)c(Cl)c2n1] |
| I-485 | 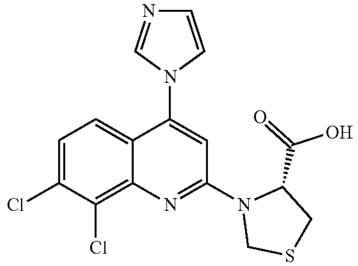 [SMILES: O=C(O)[C@@H]1CSCN1c1cc(-n2ccnc2)c2ccc(Cl)c(Cl)c2n1] |
| I-486 | 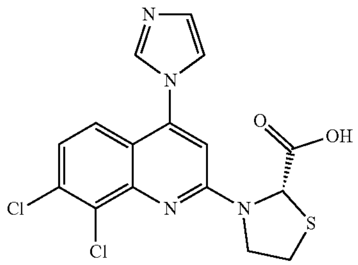 [SMILES: O=C(O)[C@@H]1SCCN1c1cc(-n2ccnc2)c2ccc(Cl)c(Cl)c2n1] |
TABLE 1-continued
| Exemplary Compounds | |
|---|---|
| I-# | Structure |
| I-487 | 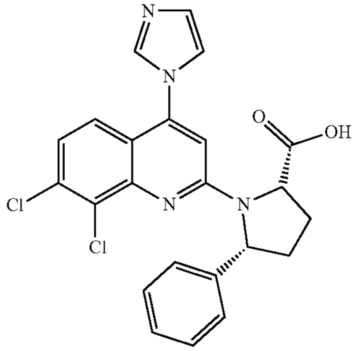 |
| I-488 | 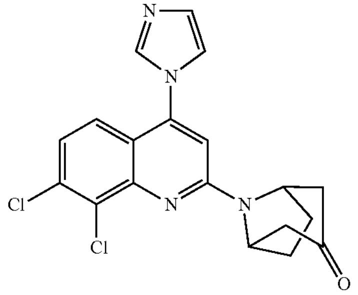 [SMILES: O=C1CC2CCC(C1)N2c1cc(-n2ccnc2)c2ccc(Cl)c(Cl)c2n1] |
| I-489 | 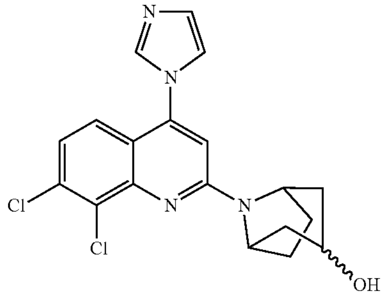 [SMILES: OC1CC2CCC(C1)N2c1cc(-n2ccnc2)c2ccc(Cl)c(Cl)c2n1] |
| I-490 | 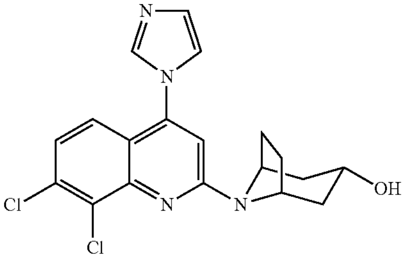 [SMILES: OC1CC2CCC(C1)N2c1cc(-n2ccnc2)c2ccc(Cl)c(Cl)c2n1] |
| I-491 | 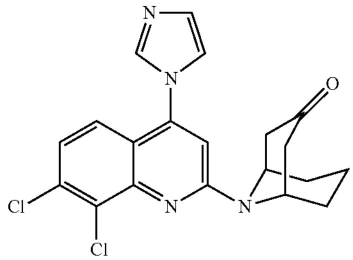 [SMILES: O=C1CC2CCCC(C1)N2c1cc(-n2ccnc2)c2ccc(Cl)c(Cl)c2n1] |

TABLE 1-continued
| Exemplary Compounds | |
|---|---|
| I-# | Structure |
| I-492 | 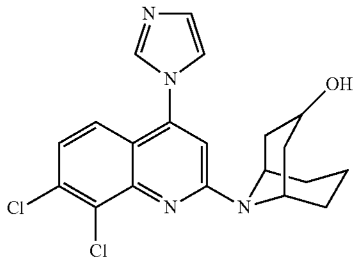 [SMILES: OC1CC2CCCC(C1)N2c1cc(-n2ccnc2)c2ccc(Cl)c(Cl)c2n1] |
| I-493 | 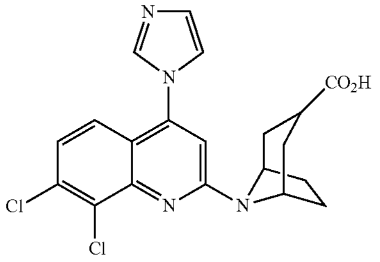 [SMILES: O=C(O)C1CC2CCC(C1)N2c1cc(-n2ccnc2)c2ccc(Cl)c(Cl)c2n1] |
| I-494 | 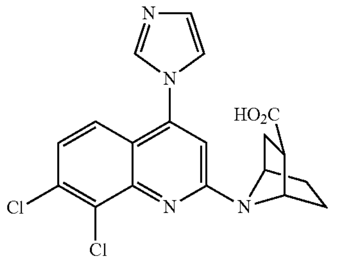 [SMILES: O=C(O)C1CC2CCC1N2c1cc(-n2ccnc2)c2ccc(Cl)c(Cl)c2n1] |
| I-495 | 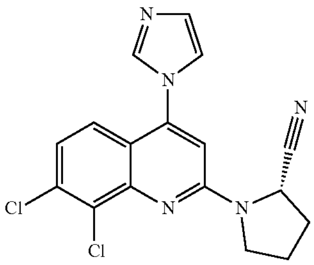 [SMILES: N#C[C@@H]1CCCN1c1cc(-n2ccnc2)c2ccc(Cl)c(Cl)c2n1] |
| I-496 | 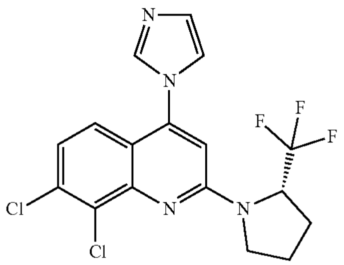 [SMILES: FC(F)(F)[C@@H]1CCCN1c1cc(-n2ccnc2)c2ccc(Cl)c(Cl)c2n1] |
TABLE 1-continued
| Exemplary Compounds | |
|---|---|
| I-# | Structure |
| I-497 | 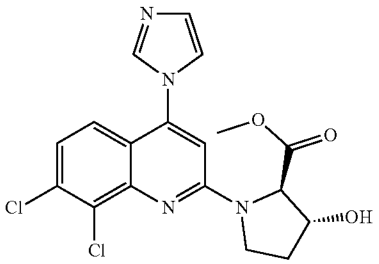 [SMILES: COC(=O)[C@H]1[C@H](O)CCN1c1cc(-n2ccnc2)c2ccc(Cl)c(Cl)c2n1] |
| I-498 | 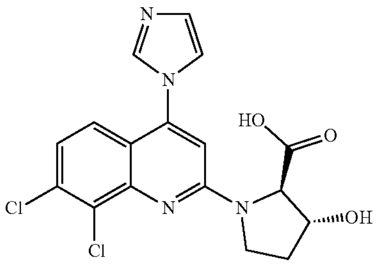 [SMILES: O=C(O)[C@H]1[C@H](O)CCN1c1cc(-n2ccnc2)c2ccc(Cl)c(Cl)c2n1] |
| I-499 | 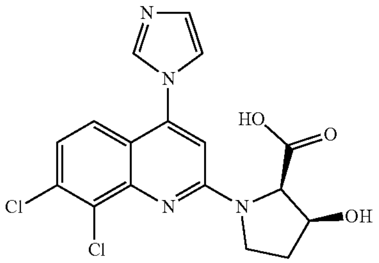 [SMILES: O=C(O)[C@H]1[C@@H](O)CCN1c1cc(-n2ccnc2)c2ccc(Cl)c(Cl)c2n1] |
| I-500 | 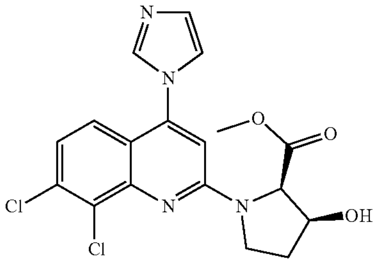 [SMILES: COC(=O)[C@H]1[C@@H](O)CCN1c1cc(-n2ccnc2)c2ccc(Cl)c(Cl)c2n1] |
| I-501 | 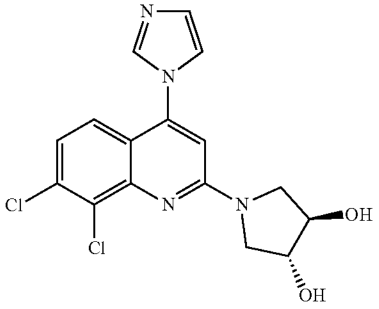 [SMILES: O[C@@H]1CN(c2cc(-n3ccnc3)c3ccc(Cl)c(Cl)c3n2)C[C@H]1O] |

TABLE 1-continued
| Exemplary Compounds | |
|---|---|
| I-# | Structure |
| I-502 | 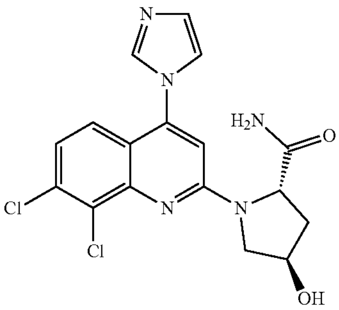 [SMILES: NC(=O)[C@@H]1C[C@@H](O)CN1c1cc(-n2ccnc2)c2ccc(Cl)c(Cl)c2n1] |
| I-503 | 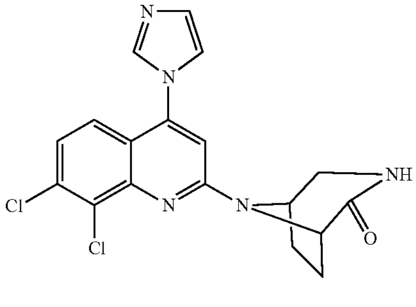 [SMILES: O=C1NCC2CCC1N2c1cc(-n2ccnc2)c2ccc(Cl)c(Cl)c2n1] |
| I-504 | 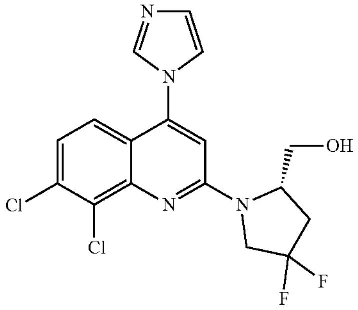 [SMILES: OC[C@@H]1CC(F)(F)CN1c1cc(-n2ccnc2)c2ccc(Cl)c(Cl)c2n1] |
| I-505 | 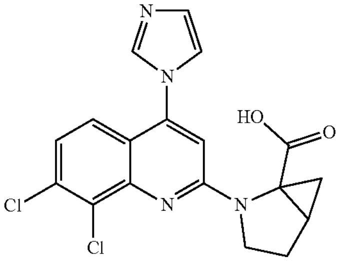 [SMILES: O=C(O)C12CC1CCN2c1cc(-n2ccnc2)c2ccc(Cl)c(Cl)c2n1] |
| I-506 | 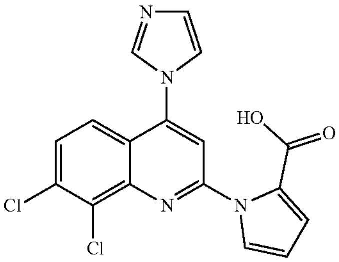 [SMILES: O=C(O)c1cccn1-c1cc(-n2ccnc2)c2ccc(Cl)c(Cl)c2n1] |
TABLE 1-continued
| Exemplary Compounds | |
|---|---|
| I-# | Structure |
| I-507 | 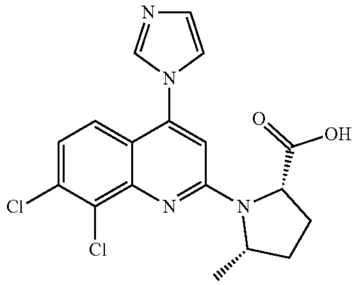 [SMILES: C[C@H]1CC[C@@H](C(=O)O)N1c1cc(-n2ccnc2)c2ccc(Cl)c(Cl)c2n1] |
| I-508 | 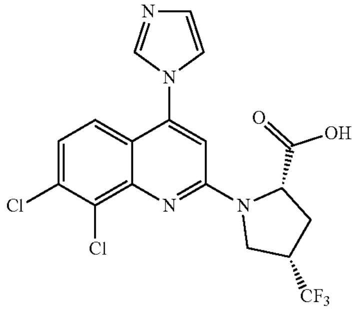 [SMILES: O=C(O)[C@@H]1C[C@H](C(F)(F)F)CN1c1cc(-n2ccnc2)c2ccc(Cl)c(Cl)c2n1] |
| I-509 | 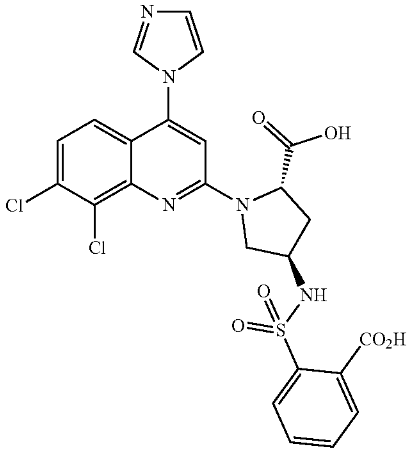 [SMILES: O=C(O)c1ccccc1S(=O)(=O)N[C@@H]1C[C@@H](C(=O)O)N(c2cc(-n3ccnc3)c3ccc(Cl)c(Cl)c3n2)C1] |
| I-510 | 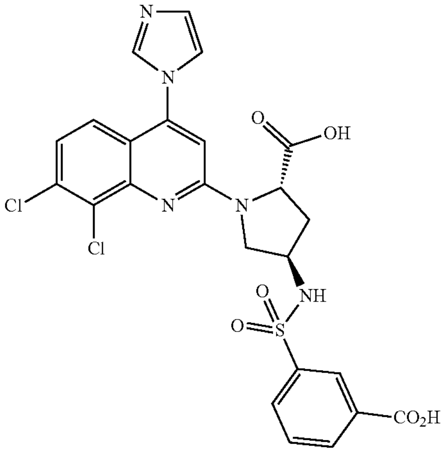 [SMILES: O=C(O)c1cccc(S(=O)(=O)N[C@@H]2C[C@@H](C(=O)O)N(c3cc(-n4ccnc4)c4ccc(Cl)c(Cl)c4n3)C2)c1] |

TABLE 1-continued
| Exemplary Compounds | |
|---|---|
| I-# | Structure |
| I-511 | 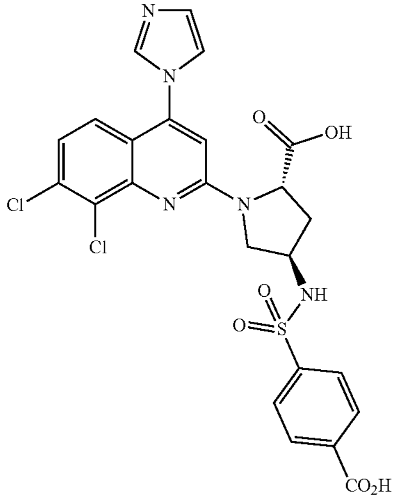 [SMILES: O=C(O)c1ccc(S(=O)(=O)N[C@@H]2C[C@@H](C(=O)O)N(c3cc(-n4ccnc4)c4ccc(Cl)c(Cl)c4n3)C2)cc1] |
| I-512 | 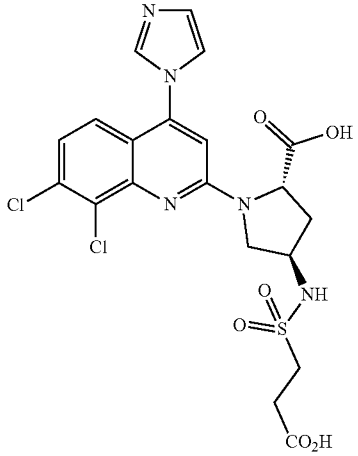 [SMILES: O=C(O)CCS(=O)(=O)N[C@@H]1C[C@@H](C(=O)O)N(c2cc(-n3ccnc3)c3ccc(Cl)c(Cl)c3n2)C1] |
| I-513 | 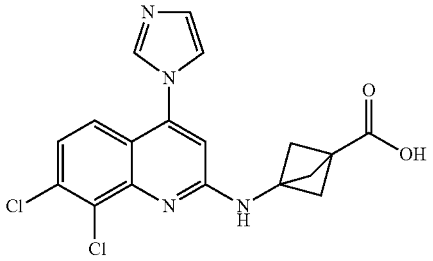 [SMILES: O=C(O)C12CC(Nc3cc(-n4ccnc4)c4ccc(Cl)c(Cl)c4n3)(C1)C2] |
| I-514 | 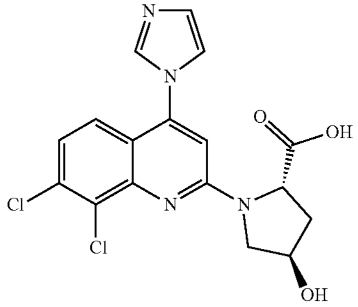 [SMILES: O=C(O)[C@@H]1C[C@@H](O)CN1c1cc(-n2ccnc2)c2ccc(Cl)c(Cl)c2n1] |
TABLE 1-continued
| Exemplary Compounds | |
|---|---|
| I-# | Structure |
| I-515 | 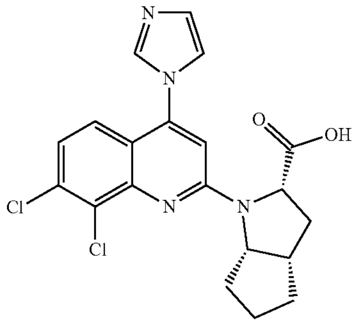 [SMILES: O=C(O)[C@@H]1C[C@@H]2CCC[C@@H]2N1c1cc(-n2ccnc2)c2ccc(Cl)c(Cl)c2n1] |
| I-516 | 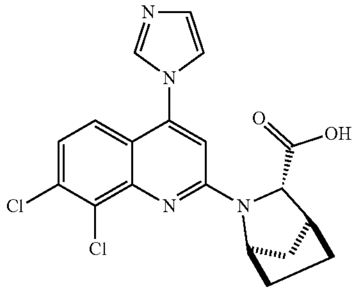 |
| I-517 | 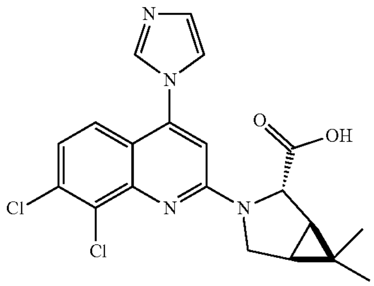 |
| I-518 | 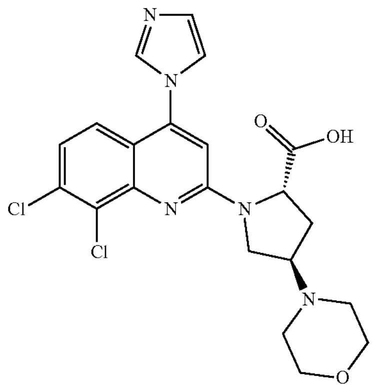 [SMILES: O=C(O)[C@@H]1C[C@@H](N2CCOCC2)CN1c1cc(-n2ccnc2)c2ccc(Cl)c(Cl)c2n1] |

TABLE 1-continued
| Exemplary Compounds | |
|---|---|
| I-# | Structure |
| I-519 | 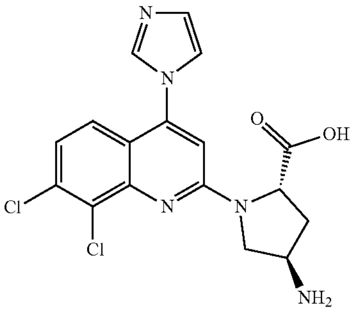 [SMILES: N[C@@H]1C[C@@H](C(=O)O)N(c2cc(-n3ccnc3)c3ccc(Cl)c(Cl)c3n2)C1] |
| I-520 | 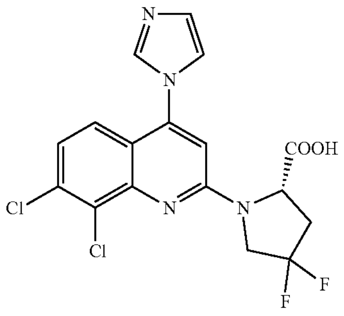 [SMILES: O=C(O)[C@@H]1CC(F)(F)CN1c1cc(-n2ccnc2)c2ccc(Cl)c(Cl)c2n1] |
| I-521 | 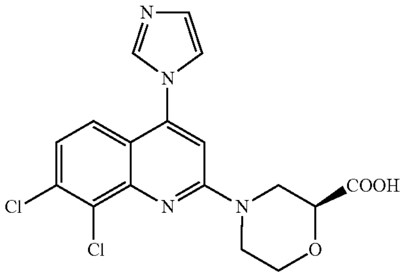 [SMILES: O=C(O)[C@@H]1CN(c2cc(-n3ccnc3)c3ccc(Cl)c(Cl)c3n2)CCO1] |
| I-522 | 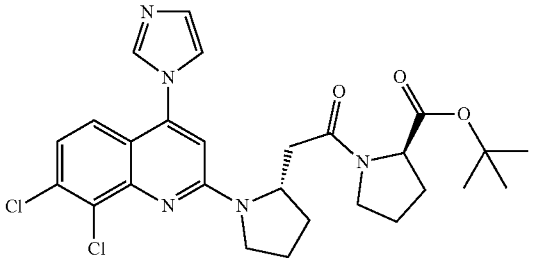 [SMILES: CC(C)(C)OC(=O)[C@H]1CCCN1C(=O)C[C@@H]1CCCN1c1cc(-n2ccnc2)c2ccc(Cl)c(Cl)c2n1] |
| I-524 | 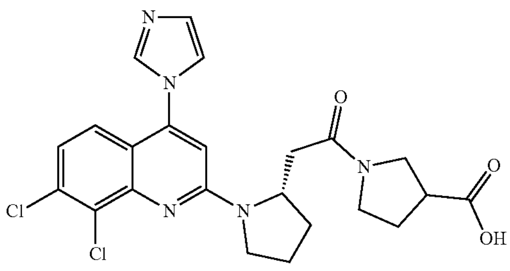 [SMILES: O=C(O)C1CCN(C(=O)C[C@@H]2CCCN2c2cc(-n3ccnc3)c3ccc(Cl)c(Cl)c3n2)C1] |
| I-525 | 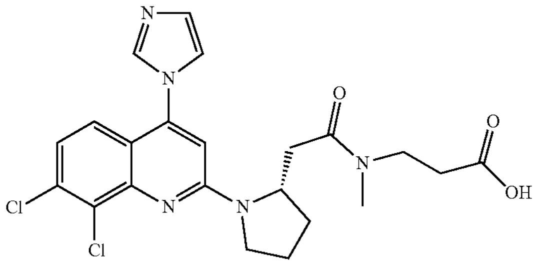 [SMILES: CN(CCC(=O)O)C(=O)C[C@@H]1CCCN1c1cc(-n2ccnc2)c2ccc(Cl)c(Cl)c2n1] |
| I-526 | 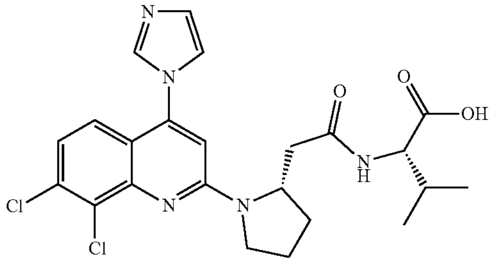 [SMILES: CC(C)[C@H](NC(=O)C[C@@H]1CCCN1c1cc(-n2ccnc2)c2ccc(Cl)c(Cl)c2n1)C(=O)O] |
| I-527 | 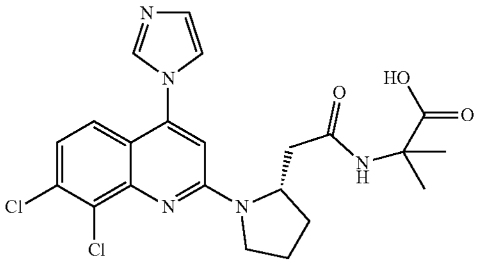 [SMILES: CC(C)(NC(=O)C[C@@H]1CCCN1c1cc(-n2ccnc2)c2ccc(Cl)c(Cl)c2n1)C(=O)O] |
| I-528 | 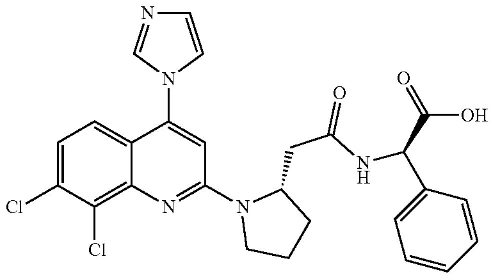 [SMILES: O=C(C[C@@H]1CCCN1c1cc(-n2ccnc2)c2ccc(Cl)c(Cl)c2n1)N[C@@H](C(=O)O)c1ccccc1] |
| I-529 | 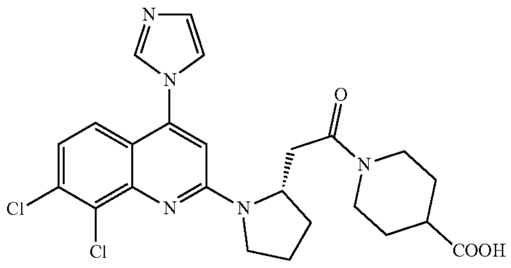 [SMILES: O=C(O)C1CCN(C(=O)C[C@@H]2CCCN2c2cc(-n3ccnc3)c3ccc(Cl)c(Cl)c3n2)CC1] |

TABLE 1-continued
Exemplary Compounds
| I-# | Structure |
| --- | --- |
| I-530 | 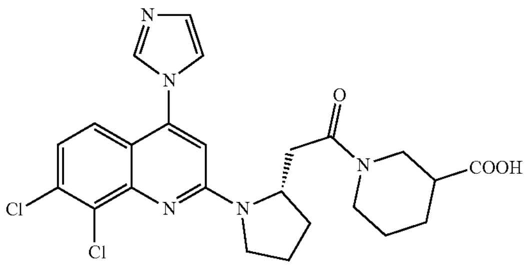 [SMILES: O=C(O)C1CCCN(C(=O)C[C@@H]2CCCN2c2cc(-n3ccnc3)c3ccc(Cl)c(Cl)c3n2)C1] |
| I-531 | 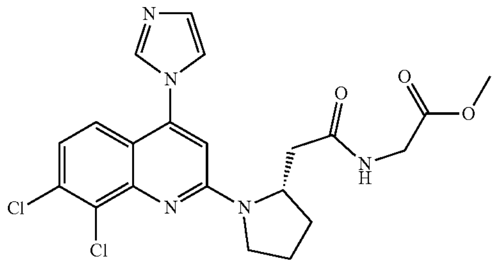 [SMILES: COC(=O)CNC(=O)C[C@@H]1CCCN1c1cc(-n2ccnc2)c2ccc(Cl)c(Cl)c2n1] |
| I-532 | 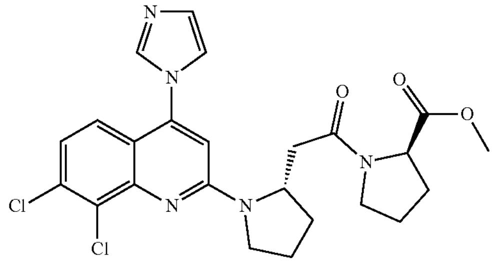 [SMILES: COC(=O)[C@H]1CCCN1C(=O)C[C@@H]1CCCN1c1cc(-n2ccnc2)c2ccc(Cl)c(Cl)c2n1] |
| I-533 | 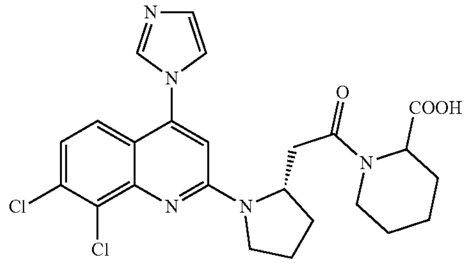 [SMILES: O=C(O)C1CCCCN1C(=O)C[C@@H]1CCCN1c1cc(-n2ccnc2)c2ccc(Cl)c(Cl)c2n1] |
| I-534 | 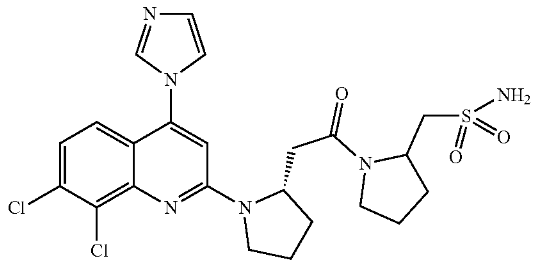 [SMILES: NS(=O)(=O)CC1CCCN1C(=O)C[C@@H]1CCCN1c1cc(-n2ccnc2)c2ccc(Cl)c(Cl)c2n1] |
TABLE 1-continued
Exemplary Compounds
| I-# | Structure |
| --- | --- |
| I-535 | 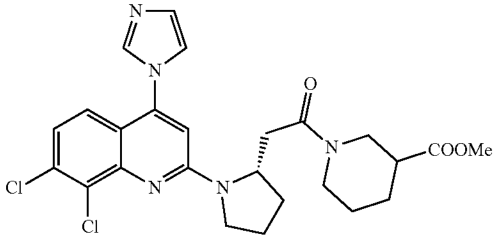 [SMILES: COC(=O)C1CCCN(C(=O)C[C@@H]2CCCN2c2cc(-n3ccnc3)c3ccc(Cl)c(Cl)c3n2)C1] |
| I-536 | 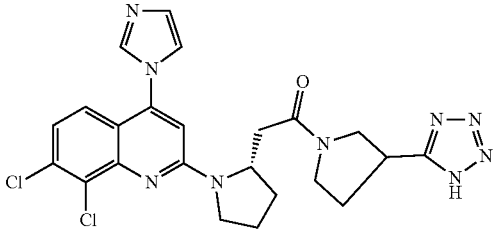 [SMILES: O=C(C[C@@H]1CCCN1c1cc(-n2ccnc2)c2ccc(Cl)c(Cl)c2n1)N1CCC(c2nnn[nH]2)C1] |
| I-537 | 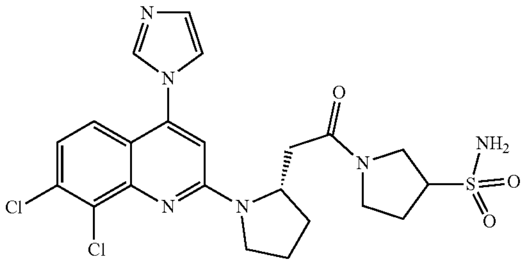 [SMILES: NS(=O)(=O)C1CCN(C(=O)C[C@@H]2CCCN2c2cc(-n3ccnc3)c3ccc(Cl)c(Cl)c3n2)C1] |
| I-538 | 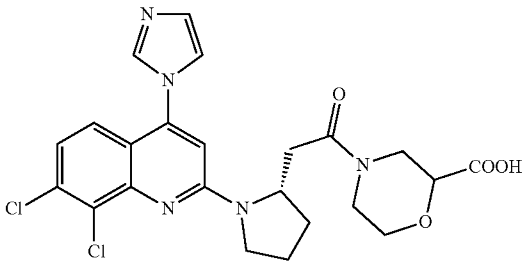 [SMILES: O=C(O)C1CN(C(=O)C[C@@H]2CCCN2c2cc(-n3ccnc3)c3ccc(Cl)c(Cl)c3n2)CCO1] |
| I-539 | 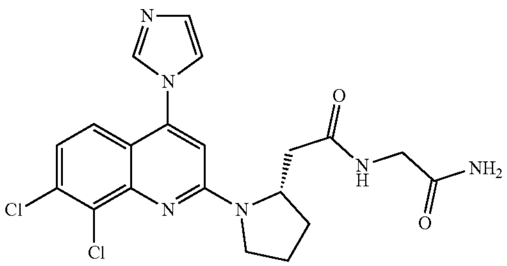 [SMILES: NC(=O)CNC(=O)C[C@@H]1CCCN1c1cc(-n2ccnc2)c2ccc(Cl)c(Cl)c2n1] |
| I-540 | 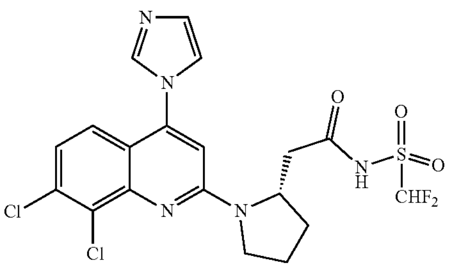 [SMILES: O=C(C[C@@H]1CCCN1c1cc(-n2ccnc2)c2ccc(Cl)c(Cl)c2n1)NS(=O)(=O)C(F)F] |

TABLE 1-continued
| Exemplary Compounds | |
|---|---|
| I-# | Structure |
| I-541 | 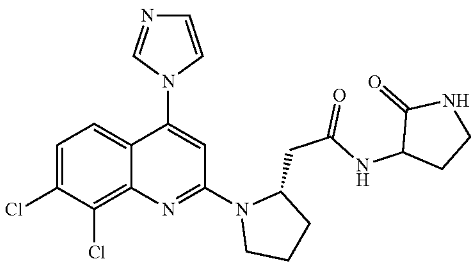 [SMILES: O=C(C[C@@H]1CCCN1c1cc(-n2ccnc2)c2ccc(Cl)c(Cl)c2n1)NC1CCNC1=O] |
| I-542 | 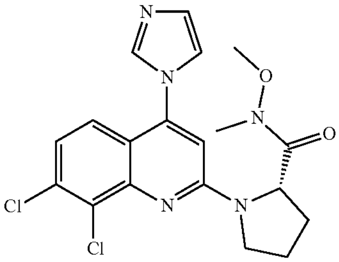 [SMILES: CON(C)C(=O)[C@@H]1CCCN1c1cc(-n2ccnc2)c2ccc(Cl)c(Cl)c2n1] |
| I-543 | 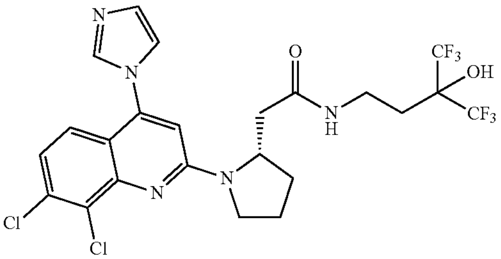 [SMILES: O=C(C[C@@H]1CCCN1c1cc(-n2ccnc2)c2ccc(Cl)c(Cl)c2n1)NCCC(O)(C(F)(F)F)C(F)(F)F] |
| I-544 | 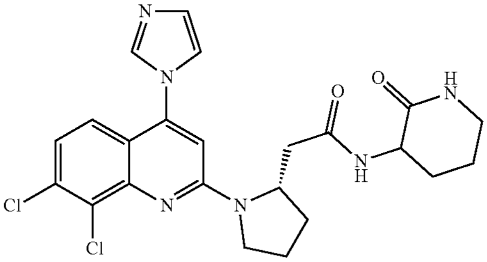 [SMILES: O=C(C[C@@H]1CCCN1c1cc(-n2ccnc2)c2ccc(Cl)c(Cl)c2n1)NC1CCCNC1=O] |
| I-545 | 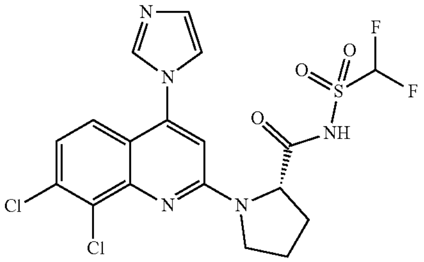 [SMILES: O=C(NS(=O)(=O)C(F)F)[C@@H]1CCCN1c1cc(-n2ccnc2)c2ccc(Cl)c(Cl)c2n1] |
TABLE 1-continued
| Exemplary Compounds | |
|---|---|
| I-# | Structure |
| I-546 | 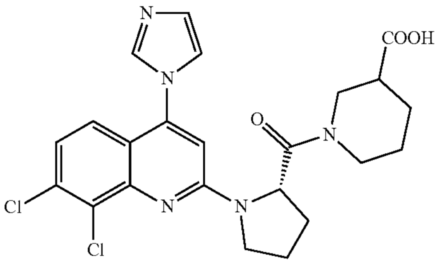 [SMILES: O=C(O)C1CCCN(C(=O)[C@@H]2CCCN2c2cc(-n3ccnc3)c3ccc(Cl)c(Cl)c3n2)C1] |
| I-547 | 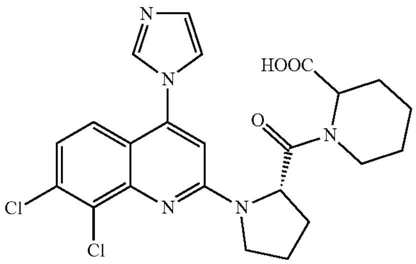 [SMILES: O=C(O)C1CCCCN1C(=O)[C@@H]1CCCN1c1cc(-n2ccnc2)c2ccc(Cl)c(Cl)c2n1] |
| I-548 | 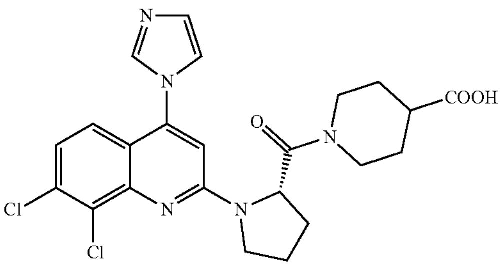 [SMILES: O=C(O)C1CCN(C(=O)[C@@H]2CCCN2c2cc(-n3ccnc3)c3ccc(Cl)c(Cl)c3n2)CC1] |
| I-549 | 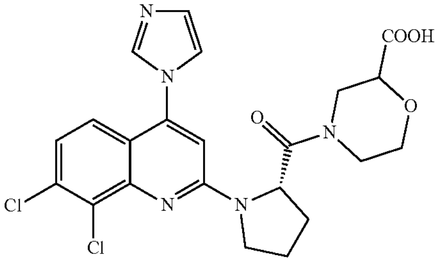 [SMILES: O=C(O)C1CN(C(=O)[C@@H]2CCCN2c2cc(-n3ccnc3)c3ccc(Cl)c(Cl)c3n2)CCO1] |
| I-550 | 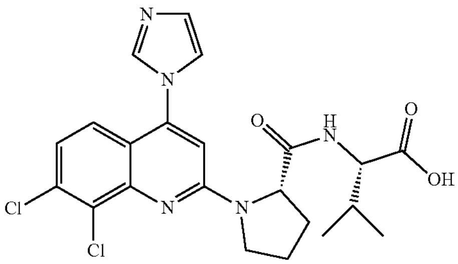 [SMILES: CC(C)[C@H](NC(=O)[C@@H]1CCCN1c1cc(-n2ccnc2)c2ccc(Cl)c(Cl)c2n1)C(=O)O] |

TABLE 1-continued
| Exemplary Compounds | |
|---|---|
| I-# | Structure |
| I-551 | 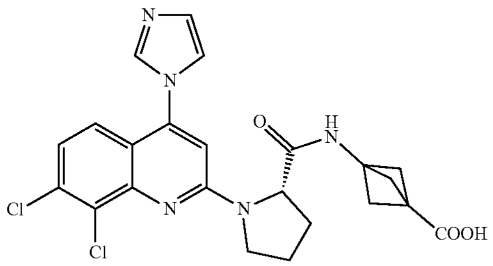 [SMILES: O=C(NC12CC(C(=O)O)(C1)C2)[C@@H]1CCCN1c1cc(-n2ccnc2)c2ccc(Cl)c(Cl)c2n1] |
| I-552 | 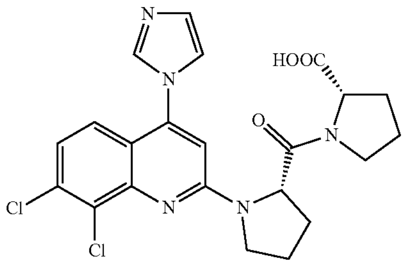 [SMILES: O=C(O)[C@@H]1CCCN1C(=O)[C@@H]1CCCN1c1cc(-n2ccnc2)c2ccc(Cl)c(Cl)c2n1] |
| I-553 | 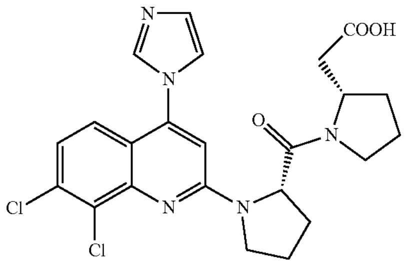 [SMILES: O=C(O)C[C@@H]1CCCN1C(=O)[C@@H]1CCCN1c1cc(-n2ccnc2)c2ccc(Cl)c(Cl)c2n1] |
| I-554 | 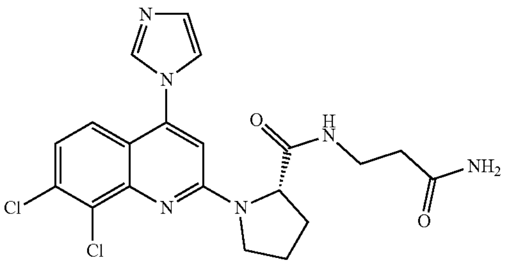 [SMILES: NC(=O)CCNC(=O)[C@@H]1CCCN1c1cc(-n2ccnc2)c2ccc(Cl)c(Cl)c2n1] |
| I-555 | 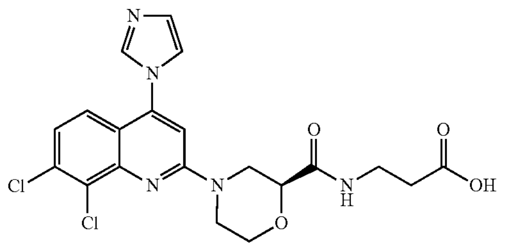 [SMILES: O=C(O)CCNC(=O)[C@@H]1CN(c2cc(-n3ccnc3)c3ccc(Cl)c(Cl)c3n2)CCO1] |
TABLE 1-continued
| Exemplary Compounds | |
|---|---|
| I-# | Structure |
| I-556 | 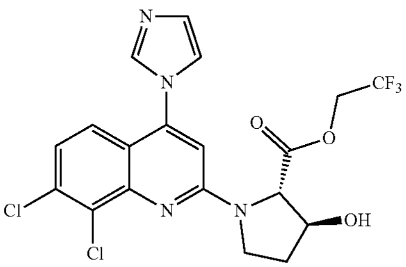 [SMILES: O=C(OCC(F)(F)F)[C@@H]1[C@@H](O)CCN1c1cc(-n2ccnc2)c2ccc(Cl)c(Cl)c2n1] |
| I-557 | 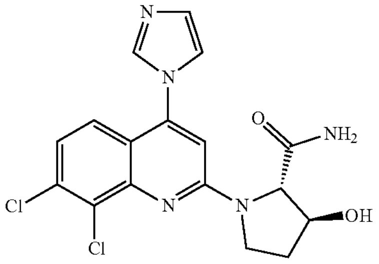 [SMILES: NC(=O)[C@@H]1[C@@H](O)CCN1c1cc(-n2ccnc2)c2ccc(Cl)c(Cl)c2n1] |
| I-558 | 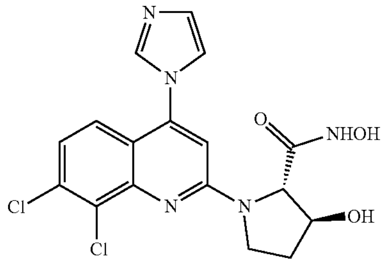 |
| I-559 | 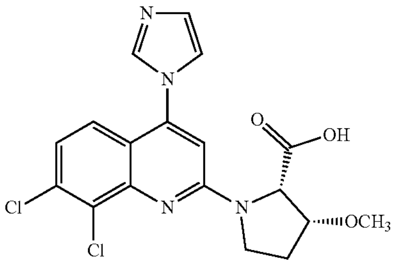 [SMILES: CO[C@@H]1CCN(c2cc(-n3ccnc3)c3ccc(Cl)c(Cl)c3n2)[C@@H]1C(=O)O] |
| I-560 | 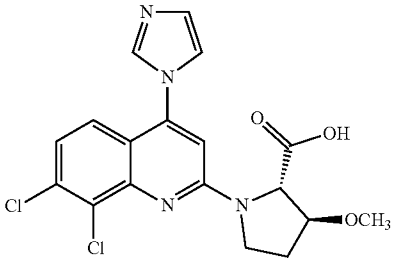 [SMILES: CO[C@H]1CCN(c2cc(-n3ccnc3)c3ccc(Cl)c(Cl)c3n2)[C@@H]1C(=O)O] |

TABLE 1-continued
| Exemplary Compounds | |
|---|---|
| I-# | Structure |
| I-561 | 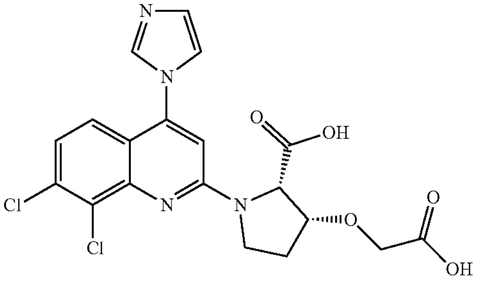 [SMILES: O=C(O)CO[C@@H]1CCN(c2cc(-n3ccnc3)c3ccc(Cl)c(Cl)c3n2)[C@@H]1C(=O)O] |
| I-562 | 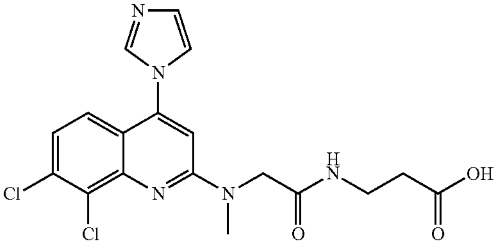 [SMILES: CN(CC(=O)NCCC(=O)O)c1cc(-n2ccnc2)c2ccc(Cl)c(Cl)c2n1] |
| I-563 | 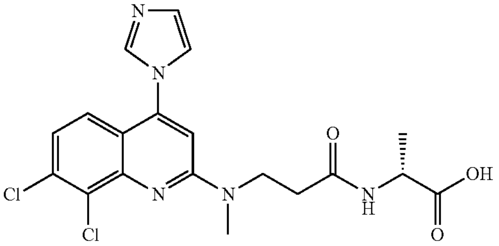 [SMILES: C[C@@H](NC(=O)CCN(C)c1cc(-n2ccnc2)c2ccc(Cl)c(Cl)c2n1)C(=O)O] |
| I-564 | 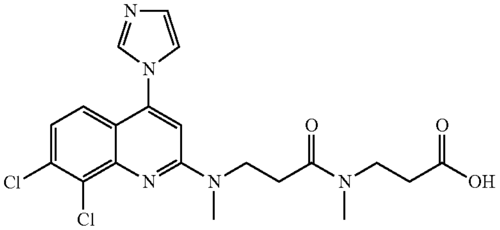 [SMILES: CN(CCC(=O)O)C(=O)CCN(C)c1cc(-n2ccnc2)c2ccc(Cl)c(Cl)c2n1] |
| I-565 | 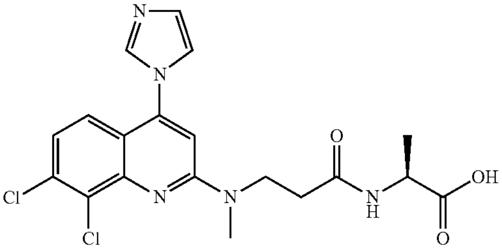 [SMILES: C[C@H](NC(=O)CCN(C)c1cc(-n2ccnc2)c2ccc(Cl)c(Cl)c2n1)C(=O)O] |
| I-566 | 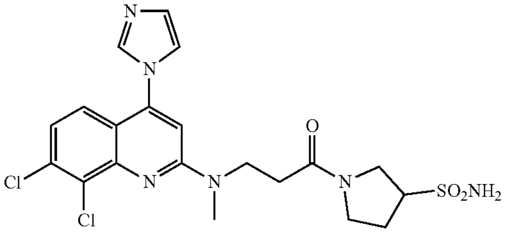 [SMILES: CN(CCC(=O)N1CCC(S(N)(=O)=O)C1)c1cc(-n2ccnc2)c2ccc(Cl)c(Cl)c2n1] |
TABLE 1-continued
| Exemplary Compounds | |
|---|---|
| I-# | Structure |
| I-567 | 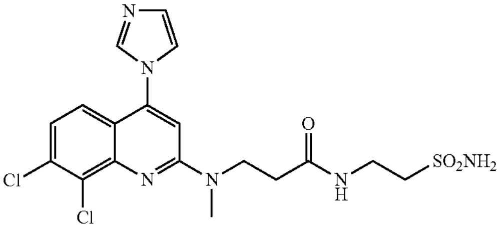 [SMILES: CN(CCC(=O)NCCS(N)(=O)=O)c1cc(-n2ccnc2)c2ccc(Cl)c(Cl)c2n1] |
| I-568 | 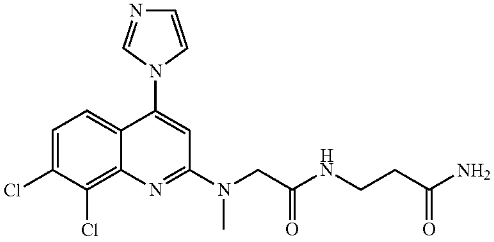 [SMILES: CN(CC(=O)NCCC(N)=O)c1cc(-n2ccnc2)c2ccc(Cl)c(Cl)c2n1] |
| I-569 | 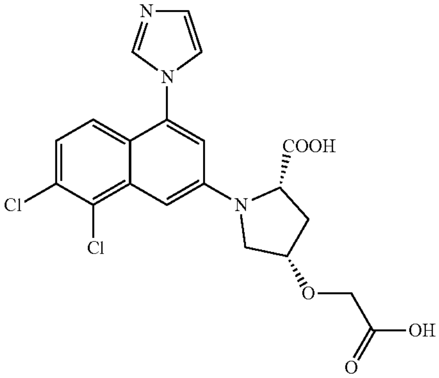 [SMILES: O=C(O)CO[C@H]1C[C@@H](C(=O)O)N(c2cc(-n3ccnc3)c3ccc(Cl)c(Cl)c3c2)C1] |
| I-570 | 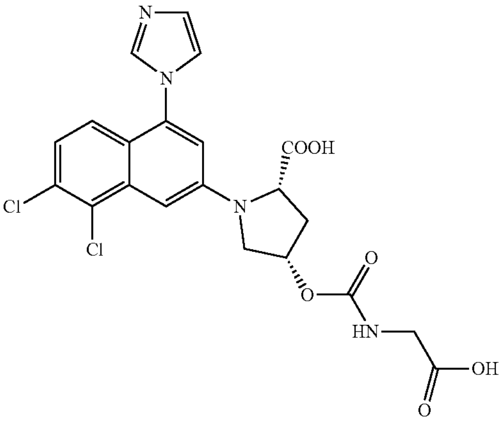 [SMILES: O=C(O)CNC(=O)O[C@H]1C[C@@H](C(=O)O)N(c2cc(-n3ccnc3)c3ccc(Cl)c(Cl)c3c2)C1] |

TABLE 1-continued
Exemplary Compounds
| I-# | Structure |
|---|---|
| I-571 | 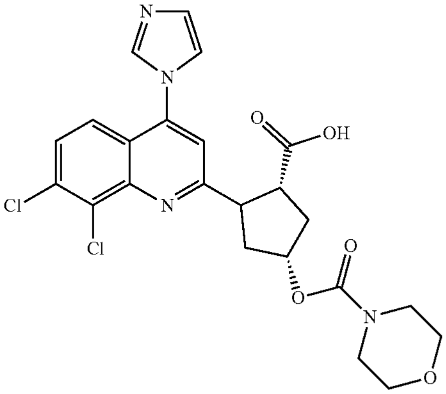 [SMILES: O=C(O)[C@@H]1C[C@H](OC(=O)N2CCOCC2)CC1c1cc(-n2ccnc2)c2ccc(Cl)c(Cl)c2n1] |
| I-572 | 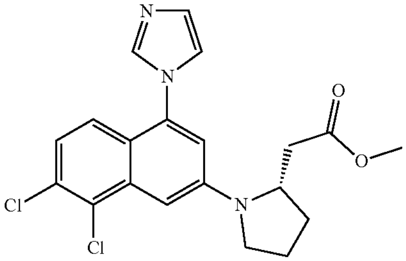 [SMILES: COC(=O)C[C@@H]1CCCN1c1cc(-n2ccnc2)c2ccc(Cl)c(Cl)c2c1] |
| I-573 | 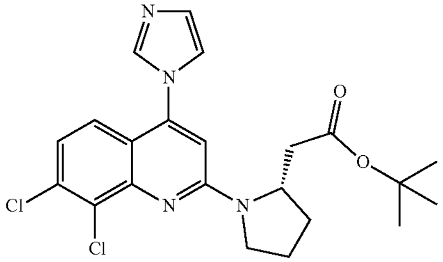 [SMILES: CC(C)(C)OC(=O)C[C@@H]1CCCN1c1cc(-n2ccnc2)c2ccc(Cl)c(Cl)c2n1] |
| I-574 | 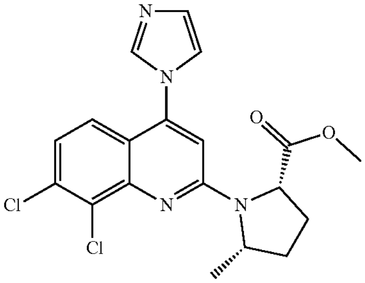 [SMILES: COC(=O)[C@@H]1CC[C@H](C)N1c1cc(-n2ccnc2)c2ccc(Cl)c(Cl)c2n1] |
| I-575 | 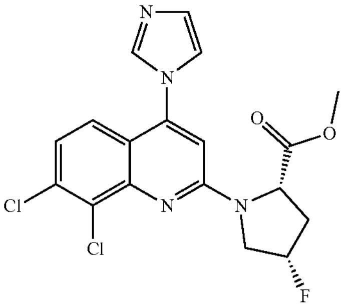 [SMILES: COC(=O)[C@@H]1C[C@H](F)CN1c1cc(-n2ccnc2)c2ccc(Cl)c(Cl)c2n1] |
TABLE 1-continued
Exemplary Compounds
| I-# | Structure |
|---|---|
| I-576 | 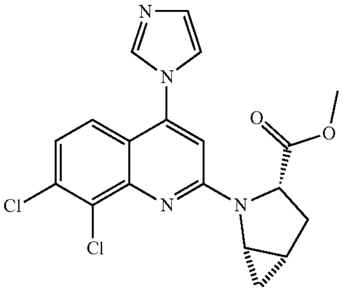 |
| I-577 | 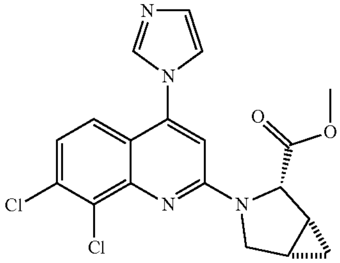 |
| I-578 | 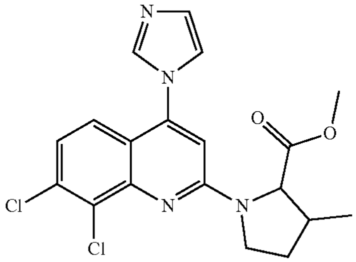 [SMILES: COC(=O)C1C(C)CCN1c1cc(-n2ccnc2)c2ccc(Cl)c(Cl)c2n1] |
| I-579 | 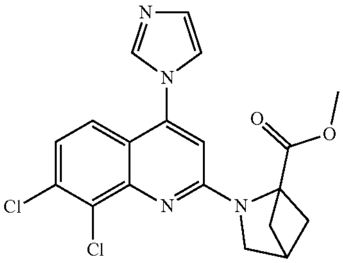 [SMILES: COC(=O)C12CC(CN1c1cc(-n3ccnc3)c3ccc(Cl)c(Cl)c3n1)C2] |
| I-580 | 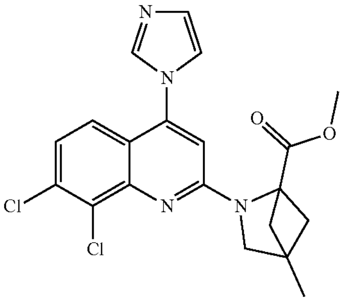 [SMILES: COC(=O)C12CC(C)(CN1c1cc(-n3ccnc3)c3ccc(Cl)c(Cl)c3n1)C2] |

TABLE 1-continued
| Exemplary Compounds | |
|---|---|
| I-# | Structure |
| I-581 | 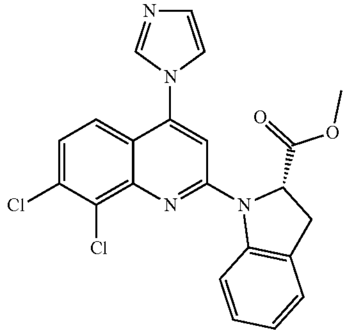 [SMILES: COC(=O)[C@@H]1Cc2ccccc2N1c1cc(-n2ccnc2)c2ccc(Cl)c(Cl)c2n1] |
| I-582 | 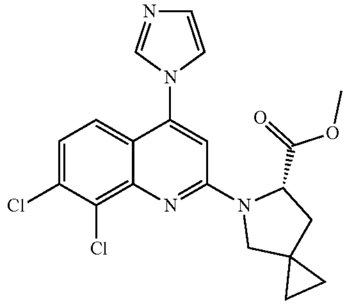 [SMILES: COC(=O)[C@@H]1CC2(CC2)CN1c1cc(-n2ccnc2)c2ccc(Cl)c(Cl)c2n1] |
| I-583 | 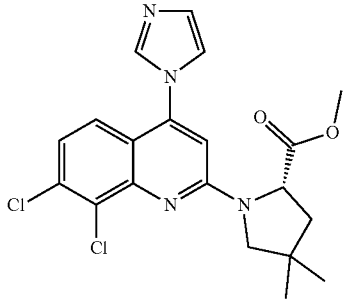 [SMILES: COC(=O)[C@@H]1CC(C)(C)CN1c1cc(-n2ccnc2)c2ccc(Cl)c(Cl)c2n1] |
| I-584 | 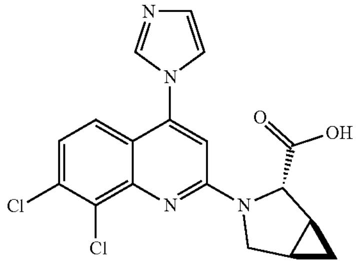 |
| I-585 | 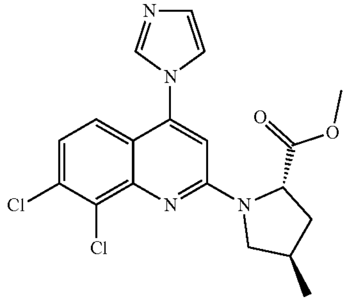 [SMILES: COC(=O)[C@@H]1C[C@@H](C)CN1c1cc(-n2ccnc2)c2ccc(Cl)c(Cl)c2n1] |
TABLE 1-continued
| Exemplary Compounds | |
|---|---|
| I-# | Structure |
| I-586 | 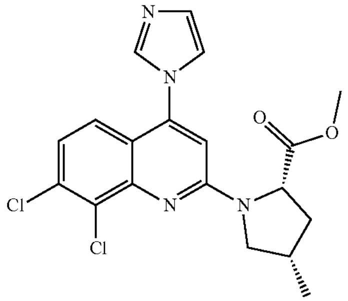 [SMILES: COC(=O)[C@@H]1C[C@H](C)CN1c1cc(-n2ccnc2)c2ccc(Cl)c(Cl)c2n1] |
| I-587 | 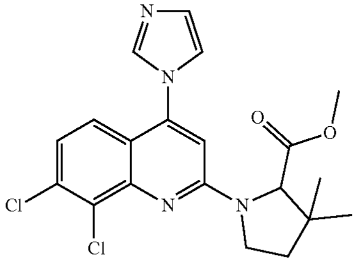 [SMILES: COC(=O)C1N(c2cc(-n3ccnc3)c3ccc(Cl)c(Cl)c3n2)CCC1(C)C] |
| I-588 | 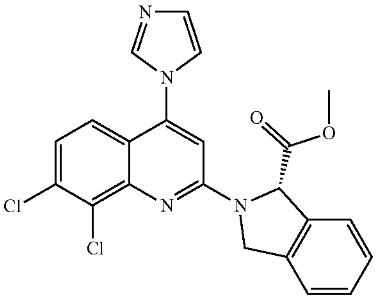 [SMILES: COC(=O)[C@@H]1c2ccccc2CN1c1cc(-n2ccnc2)c2ccc(Cl)c(Cl)c2n1] |
| I-589 | 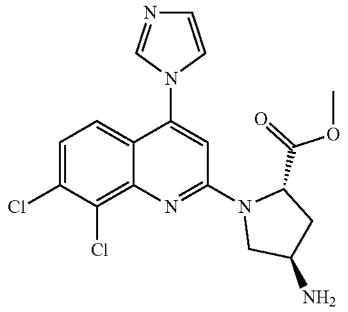 [SMILES: COC(=O)[C@@H]1C[C@@H](N)CN1c1cc(-n2ccnc2)c2ccc(Cl)c(Cl)c2n1] |
| I-590 | 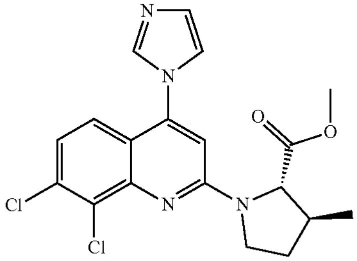 [SMILES: COC(=O)[C@@H]1[C@@H](C)CCN1c1cc(-n2ccnc2)c2ccc(Cl)c(Cl)c2n1] |

TABLE 1-continued
| I-# | Structure |
|---|---|
| I-591 | 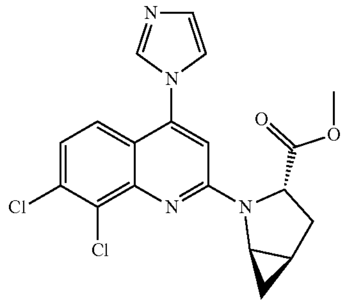 [SMILES: COC(=O)[C@@H]1C[C@H]2C[C@H]2N1c1cc(-n2ccnc2)c2ccc(Cl)c(Cl)c2n1] |
| I-592 | 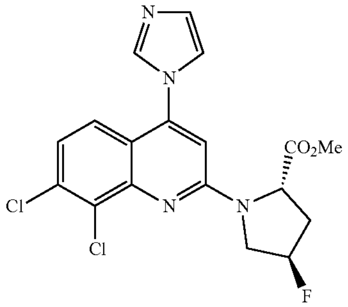 [SMILES: COC(=O)[C@@H]1C[C@@H](F)CN1c1cc(-n2ccnc2)c2ccc(Cl)c(Cl)c2n1] |
| I-593 | 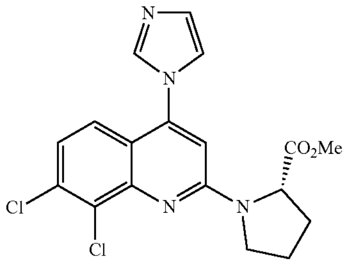 [SMILES: COC(=O)[C@@H]1CCCN1c1cc(-n2ccnc2)c2ccc(Cl)c(Cl)c2n1] |
| I-594 | 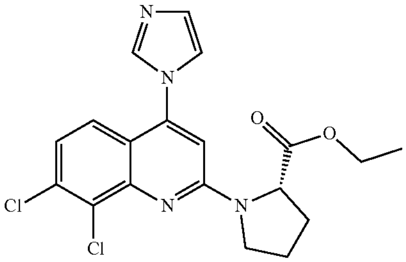 [SMILES: CCOC(=O)[C@@H]1CCCN1c1cc(-n2ccnc2)c2ccc(Cl)c(Cl)c2n1] |
| I-595 | 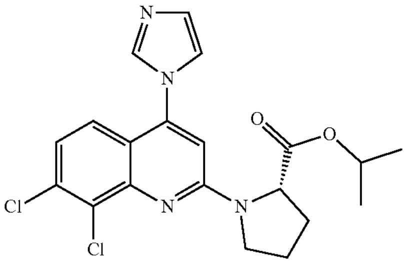 [SMILES: CC(C)OC(=O)[C@@H]1CCCN1c1cc(-n2ccnc2)c2ccc(Cl)c(Cl)c2n1] |
Exemplary Compounds
TABLE 1-continued
| I-# | Structure |
|---|---|
| I-596 | 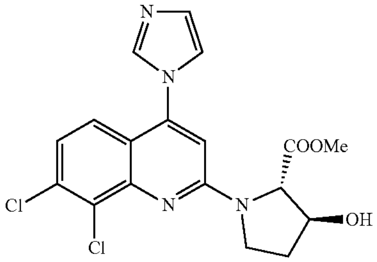 [SMILES: COC(=O)[C@@H]1[C@@H](O)CCN1c1cc(-n2ccnc2)c2ccc(Cl)c(Cl)c2n1] |
| I-597 | 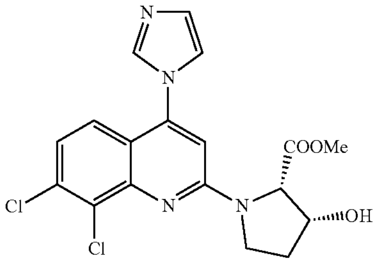 [SMILES: COC(=O)[C@@H]1[C@H](O)CCN1c1cc(-n2ccnc2)c2ccc(Cl)c(Cl)c2n1] |
| I-598 | 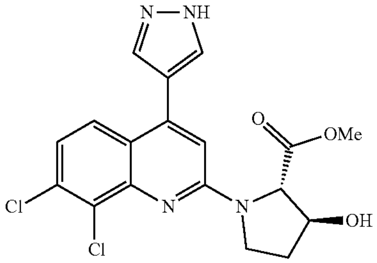 [SMILES: COC(=O)[C@@H]1[C@@H](O)CCN1c1cc(-c2cn[nH]c2)c2ccc(Cl)c(Cl)c2n1] |
| I-599 | 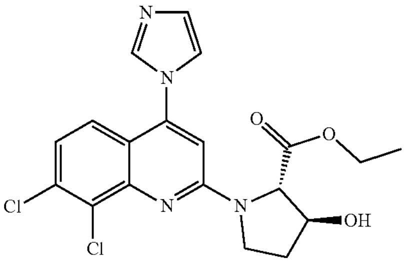 [SMILES: CCOC(=O)[C@@H]1[C@@H](O)CCN1c1cc(-n2ccnc2)c2ccc(Cl)c(Cl)c2n1] |
| I-600 | 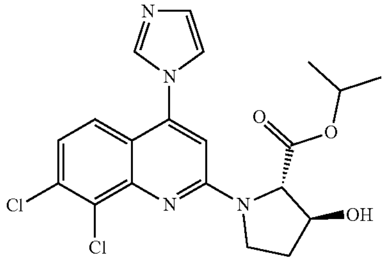 [SMILES: CC(C)OC(=O)[C@@H]1[C@@H](O)CCN1c1cc(-n2ccnc2)c2ccc(Cl)c(Cl)c2n1] |
Exemplary Compounds TABLE 1-continued
| Exemplary Compounds | |
|---|---|
| I-# | Structure |
| I-601 | 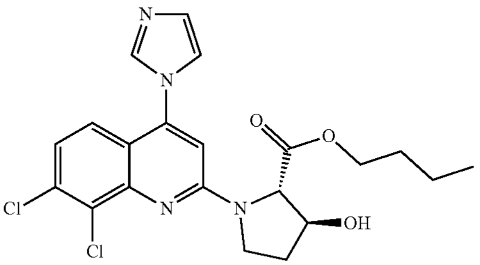 [SMILES: CCCCOC(=O)[C@@H]1[C@@H](O)CCN1c1cc(-n2ccnc2)c2ccc(Cl)c(Cl)c2n1] |
| I-602 | 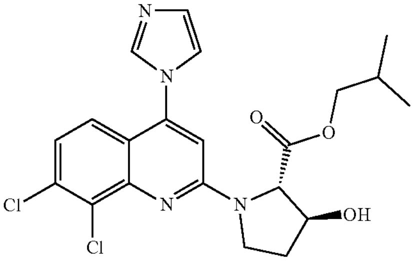 [SMILES: CC(C)COC(=O)[C@@H]1[C@@H](O)CCN1c1cc(-n2ccnc2)c2ccc(Cl)c(Cl)c2n1] |
| I-603 | 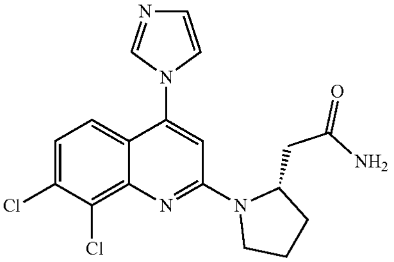 [SMILES: NC(=O)C[C@@H]1CCCN1c1cc(-n2ccnc2)c2ccc(Cl)c(Cl)c2n1] |
| I-604 | 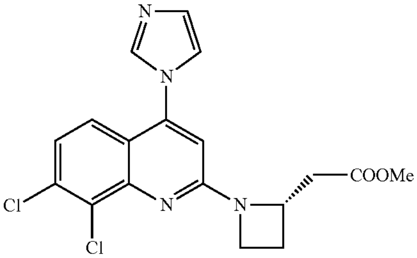 [SMILES: COC(=O)C[C@@H]1CCN1c1cc(-n2ccnc2)c2ccc(Cl)c(Cl)c2n1] |
| I-605 | 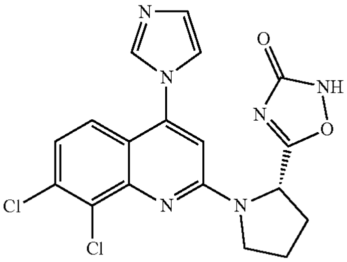 [SMILES: O=c1nc([C@@H]2CCCN2c2cc(-n3ccnc3)c3ccc(Cl)c(Cl)c3n2)o[nH]1] |
TABLE 1-continued
| Exemplary Compounds | |
|---|---|
| I-# | Structure |
| I-606 | 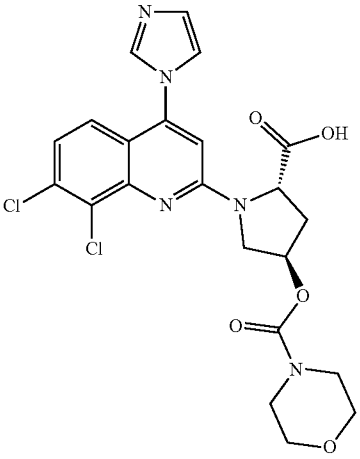 [SMILES: O=C(O)[C@@H]1C[C@@H](OC(=O)N2CCOCC2)CN1c1cc(-n2ccnc2)c2ccc(Cl)c(Cl)c2n1] |
| I-607 | 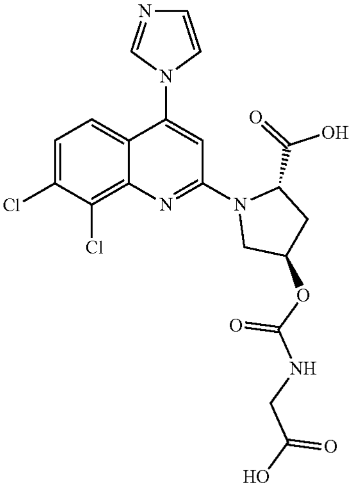 [SMILES: O=C(O)CNC(=O)O[C@@H]1C[C@@H](C(=O)O)N(c2cc(-n3ccnc3)c3ccc(Cl)c(Cl)c3n2)C1] |
| I-608 | 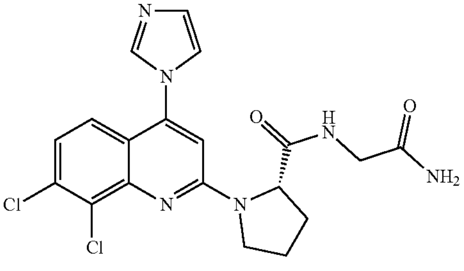 |
| I-609 | 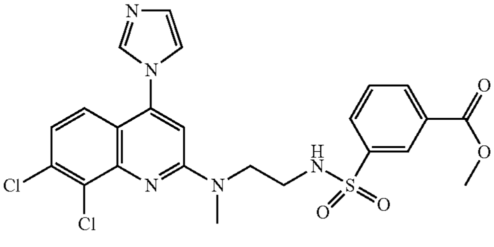 |

TABLE 1-continued
| Exemplary Compounds | |
| --- | --- |
| I-# | Structure |
| I-610 | 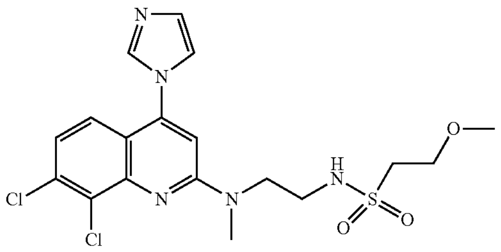 [SMILES: COCCS(=O)(=O)NCCN(C)c1cc(-n2ccnc2)c2ccc(Cl)c(Cl)c2n1] |
| I-611 | 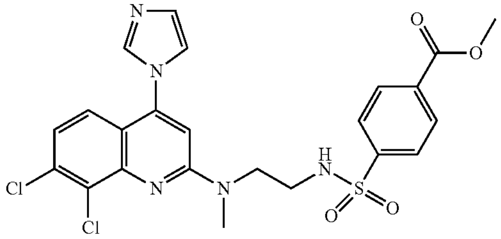 [SMILES: COC(=O)c1ccc(S(=O)(=O)NCCN(C)c2cc(-n3ccnc3)c3ccc(Cl)c(Cl)c3n2)cc1] |
| I-612 | 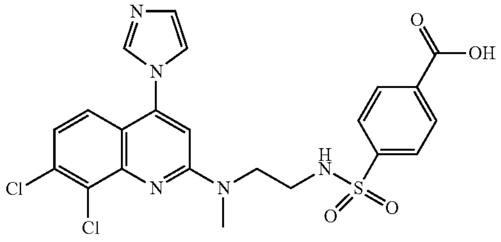 [SMILES: CN(CCNS(=O)(=O)c1ccc(C(=O)O)cc1)c1cc(-n2ccnc2)c2ccc(Cl)c(Cl)c2n1] |
| I-613 | 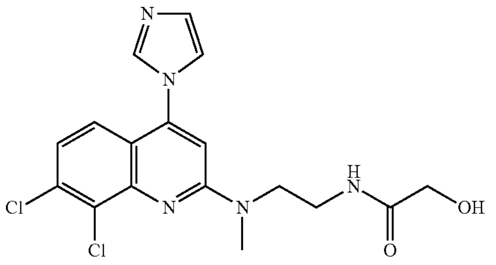 [SMILES: CN(CCNC(=O)CO)c1cc(-n2ccnc2)c2ccc(Cl)c(Cl)c2n1] |
| I-614 | 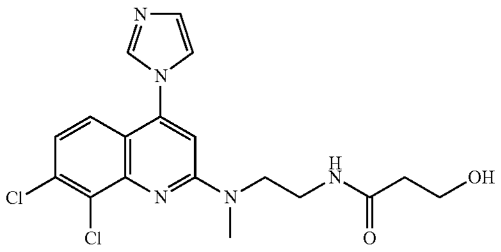 [SMILES: CN(CCNC(=O)CCO)c1cc(-n2ccnc2)c2ccc(Cl)c(Cl)c2n1] |
| I-615 | 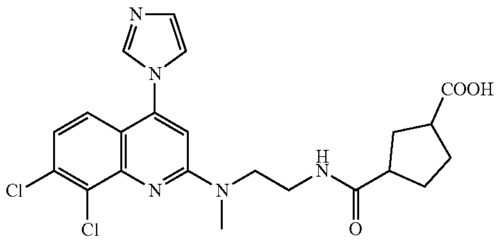 [SMILES: CN(CCNC(=O)C1CCC(C(=O)O)C1)c1cc(-n2ccnc2)c2ccc(Cl)c(Cl)c2n1] |
TABLE 1-continued
| Exemplary Compounds | |
| --- | --- |
| I-# | Structure |
| I-616 | 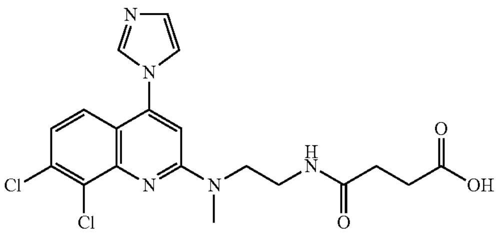 [SMILES: CN(CCNC(=O)CCC(=O)O)c1cc(-n2ccnc2)c2ccc(Cl)c(Cl)c2n1] |
| I-617 | 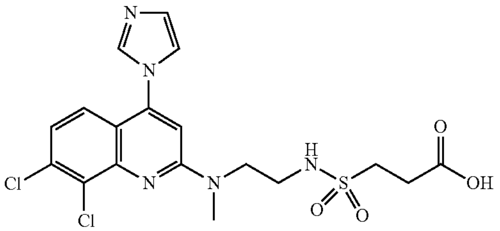 [SMILES: CN(CCNS(=O)(=O)CCC(=O)O)c1cc(-n2ccnc2)c2ccc(Cl)c(Cl)c2n1] |
| I-618 | 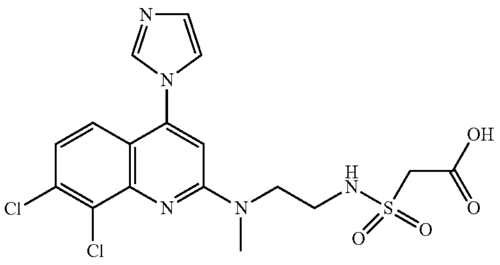 [SMILES: CN(CCNS(=O)(=O)CC(=O)O)c1cc(-n2ccnc2)c2ccc(Cl)c(Cl)c2n1] |
| I-619 | 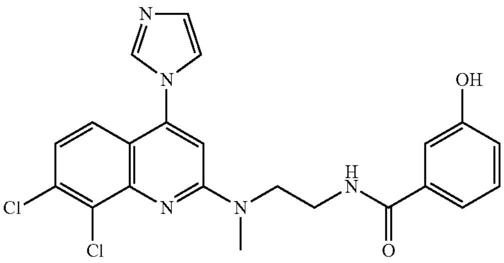 [SMILES: CN(CCNC(=O)c1cccc(O)c1)c1cc(-n2ccnc2)c2ccc(Cl)c(Cl)c2n1] |
| I-620 | 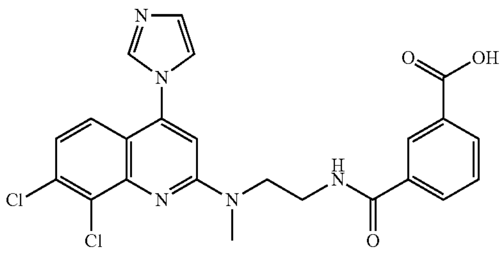 [SMILES: CN(CCNC(=O)c1cccc(C(=O)O)c1)c1cc(-n2ccnc2)c2ccc(Cl)c(Cl)c2n1] |
| I-621 | 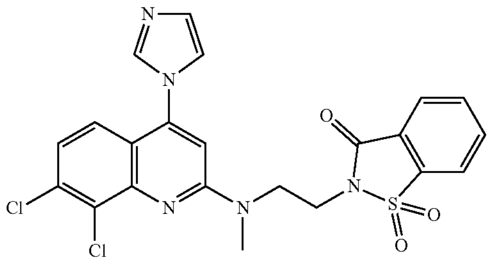 [SMILES: CN(CCN1C(=O)c2ccccc2S1(=O)=O)c1cc(-n2ccnc2)c2ccc(Cl)c(Cl)c2n1] |

TABLE 1-continued
| Exemplary Compounds | |
| --- | --- |
| I-# | Structure |
| I-622 | 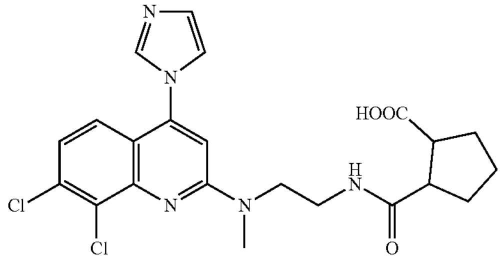 [SMILES: CN(CCNC(=O)C1CCCC1C(=O)O)c1cc(-n2ccnc2)c2ccc(Cl)c(Cl)c2n1] |
| I-623 | 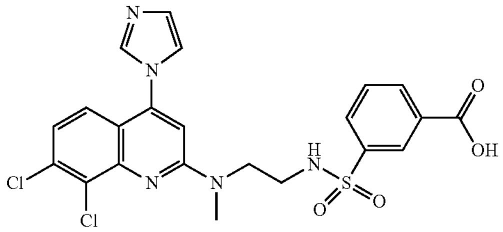 [SMILES: CN(CCNS(=O)(=O)c1cccc(C(=O)O)c1)c1cc(-n2ccnc2)c2ccc(Cl)c(Cl)c2n1] |
| I-624 | 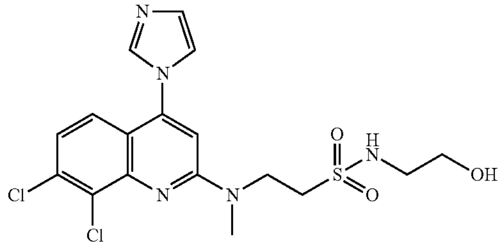 [SMILES: CN(CCS(=O)(=O)NCCO)c1cc(-n2ccnc2)c2ccc(Cl)c(Cl)c2n1] |
| I-625 | 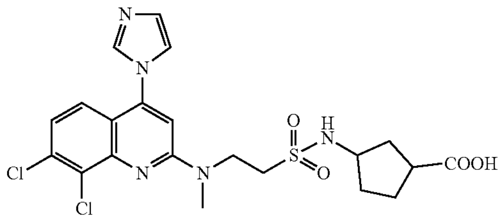 [SMILES: CN(CCS(=O)(=O)NC1CCC(C(=O)O)C1)c1cc(-n2ccnc2)c2ccc(Cl)c(Cl)c2n1] |
| I-626 | 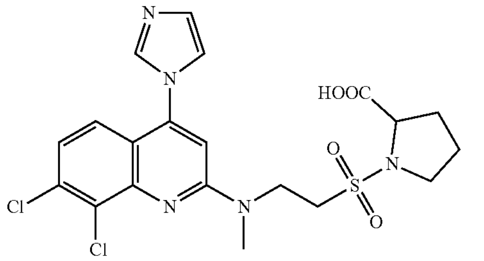 [SMILES: CN(CCS(=O)(=O)N1CCCC1C(=O)O)c1cc(-n2ccnc2)c2ccc(Cl)c(Cl)c2n1] |
| I-627 | 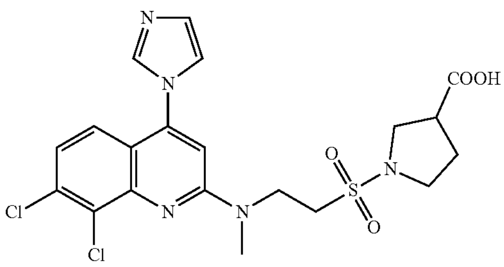 [SMILES: CN(CCS(=O)(=O)N1CCC(C(=O)O)C1)c1cc(-n2ccnc2)c2ccc(Cl)c(Cl)c2n1] |
TABLE 1-continued
| Exemplary Compounds | |
| --- | --- |
| I-# | Structure |
| I-628 | 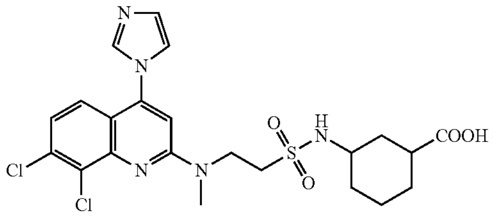 [SMILES: CN(CCS(=O)(=O)NC1CCCC(C(=O)O)C1)c1cc(-n2ccnc2)c2ccc(Cl)c(Cl)c2n1] |
| I-629 | 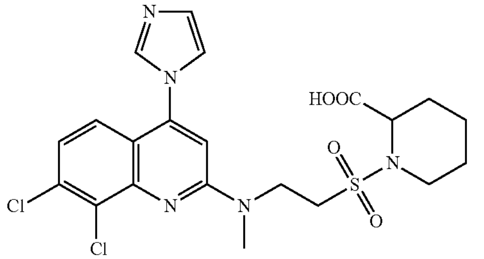 [SMILES: CN(CCS(=O)(=O)N1CCCCC1C(=O)O)c1cc(-n2ccnc2)c2ccc(Cl)c(Cl)c2n1] |
| I-630 | 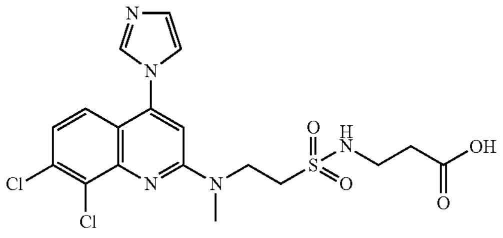 [SMILES: CN(CCS(=O)(=O)NCCC(=O)O)c1cc(-n2ccnc2)c2ccc(Cl)c(Cl)c2n1] |
| I-631 | 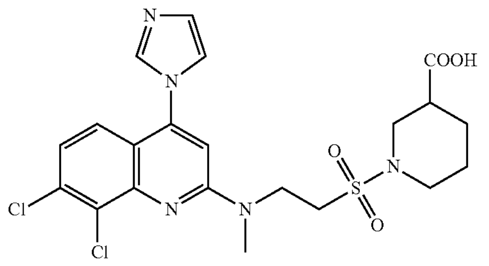 [SMILES: CN(CCS(=O)(=O)N1CCCC(C(=O)O)C1)c1cc(-n2ccnc2)c2ccc(Cl)c(Cl)c2n1] |
| I-632 | 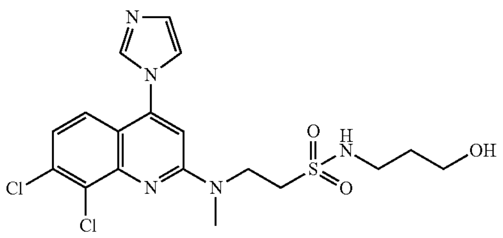 [SMILES: CN(CCS(=O)(=O)NCCCO)c1cc(-n2ccnc2)c2ccc(Cl)c(Cl)c2n1] |
| I-633 | 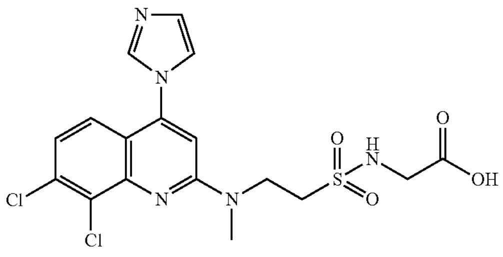 [SMILES: CN(CCS(=O)(=O)NCC(=O)O)c1cc(-n2ccnc2)c2ccc(Cl)c(Cl)c2n1] |

TABLE 1-continued
| I-# | Structure |
|---|---|
| I-634 | 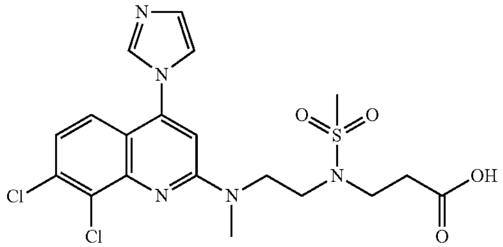 [SMILES: CN(CCN(CCC(=O)O)S(C)(=O)=O)c1cc(-n2ccnc2)c2ccc(Cl)c(Cl)c2n1] |
| I-635 | 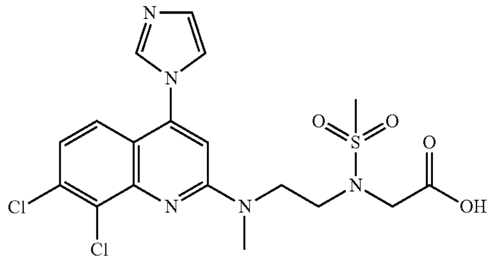 [SMILES: CN(CCN(CC(=O)O)S(C)(=O)=O)c1cc(-n2ccnc2)c2ccc(Cl)c(Cl)c2n1] |
| I-636 | 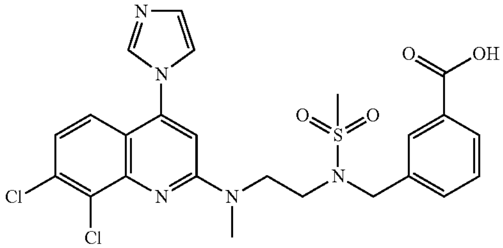 [SMILES: CN(CCN(Cc1cccc(C(=O)O)c1)S(C)(=O)=O)c1cc(-n2ccnc2)c2ccc(Cl)c(Cl)c2n1] |
| I-637 | 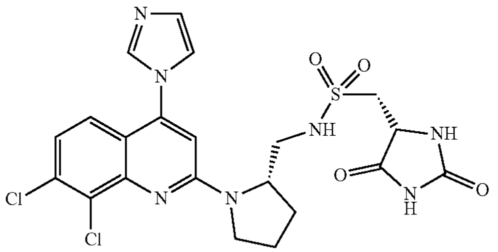 |
| I-638 | 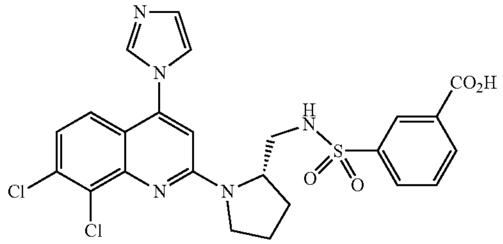 [SMILES: O=C(O)c1cccc(S(=O)(=O)NC[C@@H]2CCCN2c2cc(-n3ccnc3)c3ccc(Cl)c(Cl)c3n2)c1] |
| I-639 | 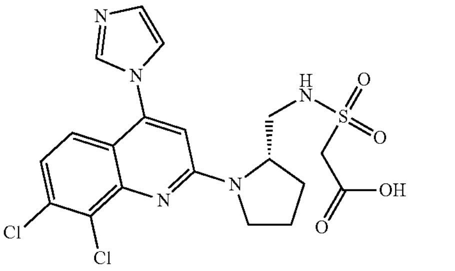 [SMILES: O=C(O)CS(=O)(=O)NC[C@@H]1CCCN1c1cc(-n2ccnc2)c2ccc(Cl)c(Cl)c2n1] |
TABLE 1-continued
| I-# | Structure |
|---|---|
| I-640 | 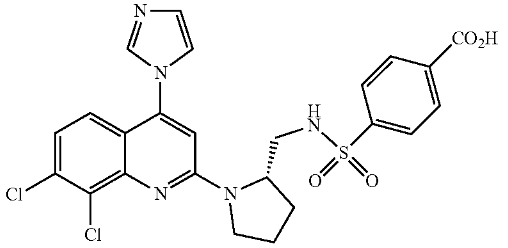 [SMILES: O=C(O)c1ccc(S(=O)(=O)NC[C@@H]2CCCN2c2cc(-n3ccnc3)c3ccc(Cl)c(Cl)c3n2)cc1] |
| I-641 | 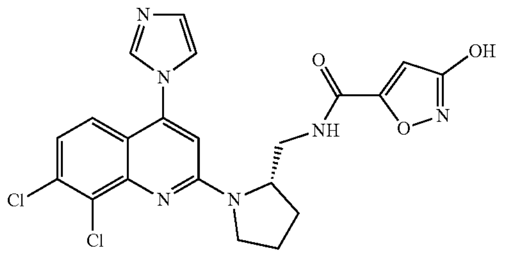 [SMILES: O=C(NC[C@@H]1CCCN1c1cc(-n2ccnc2)c2ccc(Cl)c(Cl)c2n1)c1cc(O)no1] |
| I-642 | 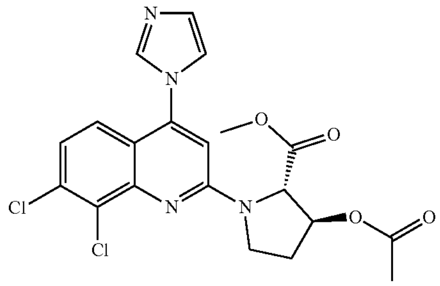 [SMILES: COC(=O)[C@@H]1[C@@H](OC(C)=O)CCN1c1cc(-n2ccnc2)c2ccc(Cl)c(Cl)c2n1] |
| I-643 | 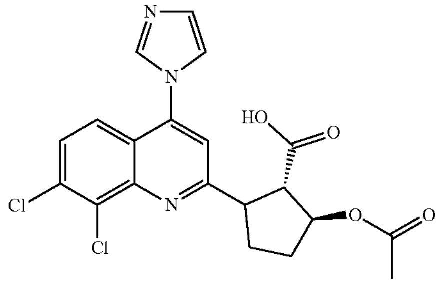 [SMILES: CC(=O)O[C@H]1CCC(c2cc(-n3ccnc3)c3ccc(Cl)c(Cl)c3n2)[C@@H]1C(=O)O] |
| I-644 | 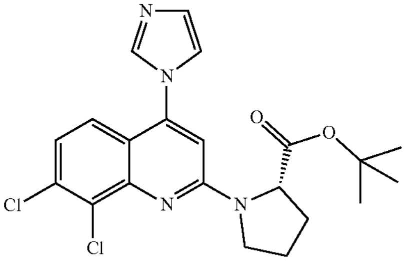 [SMILES: CC(C)(C)OC(=O)[C@@H]1CCCN1c1cc(-n2ccnc2)c2ccc(Cl)c(Cl)c2n1] |

TABLE 1-continued
| Exemplary Compounds | |
|---|---|
| I-# | Structure |
| I-645 | 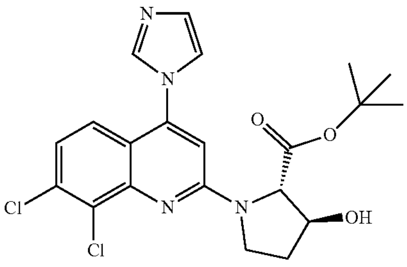 [SMILES: CC(C)(C)OC(=O)[C@@H]1[C@@H](O)CCN1c1cc(-n2ccnc2)c2ccc(Cl)c(Cl)c2n1] |
| I-646 | 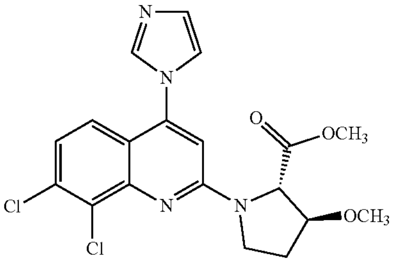 [SMILES: COC(=O)[C@@H]1[C@@H](OC)CCN1c1cc(-n2ccnc2)c2ccc(Cl)c(Cl)c2n1] |
| I-647 | 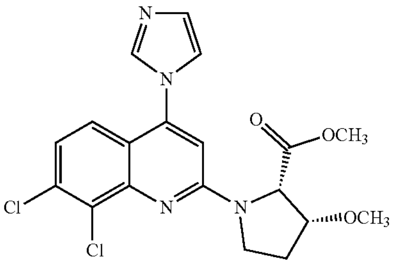 [SMILES: COC(=O)[C@@H]1[C@H](OC)CCN1c1cc(-n2ccnc2)c2ccc(Cl)c(Cl)c2n1] |
| I-648 | 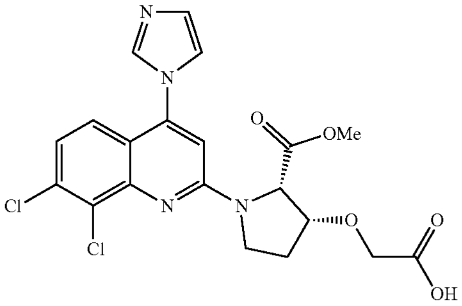 [SMILES: COC(=O)[C@@H]1[C@H](OCC(=O)O)CCN1c1cc(-n2ccnc2)c2ccc(Cl)c(Cl)c2n1] |
| I-649 | 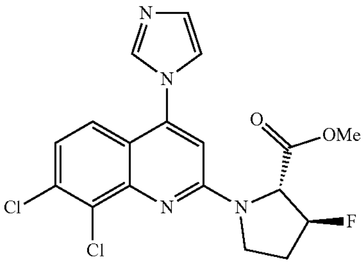 [SMILES: COC(=O)[C@@H]1[C@@H](F)CCN1c1cc(-n2ccnc2)c2ccc(Cl)c(Cl)c2n1] |
TABLE 1-continued
| Exemplary Compounds | |
|---|---|
| I-# | Structure |
| I-650 | 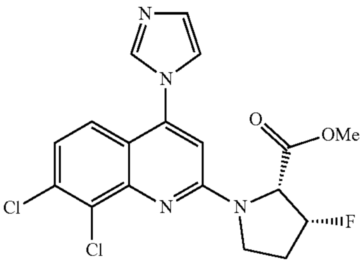 [SMILES: COC(=O)[C@@H]1[C@H](F)CCN1c1cc(-n2ccnc2)c2ccc(Cl)c(Cl)c2n1] |
| I-651 | 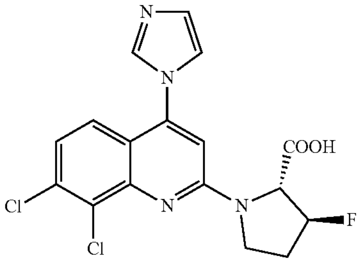 [SMILES: O=C(O)[C@@H]1[C@@H](F)CCN1c1cc(-n2ccnc2)c2ccc(Cl)c(Cl)c2n1] |
| I-652 | 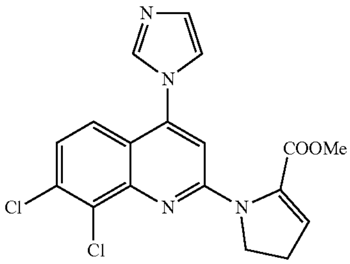 [SMILES: COC(=O)C1=CCCN1c1cc(-n2ccnc2)c2ccc(Cl)c(Cl)c2n1] |
| I-653 | 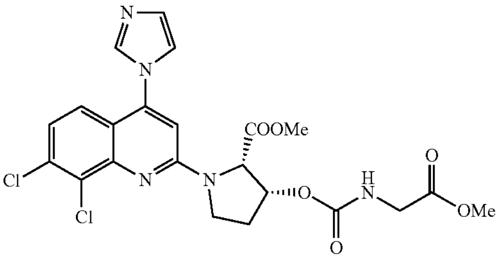 [SMILES: COC(=O)CNC(=O)O[C@@H]1CCN(c2cc(-n3ccnc3)c3ccc(Cl)c(Cl)c3n2)[C@@H]1C(=O)OC] |
| I-654 | 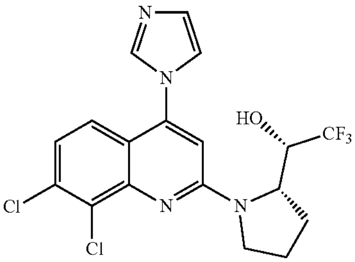 [SMILES: O[C@@H]([C@@H]1CCCN1c1cc(-n2ccnc2)c2ccc(Cl)c(Cl)c2n1)C(F)(F)F] |

TABLE 1-continued
| Exemplary Compounds | |
|---|---|
| I-# | Structure |
| I-655 | 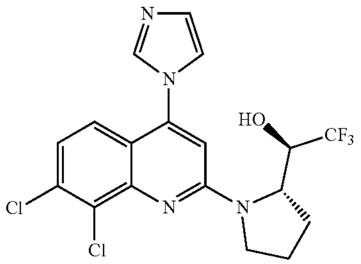 [SMILES: O[C@H]([C@@H]1CCCN1c1cc(-n2ccnc2)c2ccc(Cl)c(Cl)c2n1)C(F)(F)F] |
| I-656 | 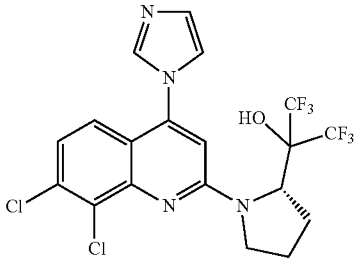 [SMILES: OC([C@@H]1CCCN1c1cc(-n2ccnc2)c2ccc(Cl)c(Cl)c2n1)(C(F)(F)F)C(F)(F)F] |
| I-657 | 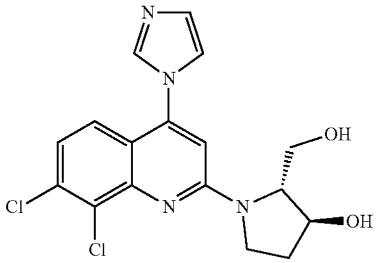 [SMILES: OC[C@@H]1[C@@H](O)CCN1c1cc(-n2ccnc2)c2ccc(Cl)c(Cl)c2n1] |
| I-658 | 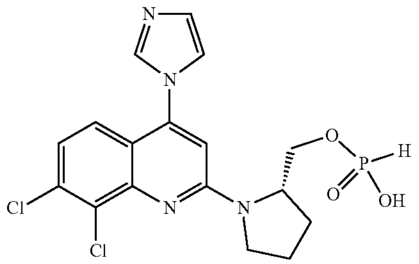 [SMILES: O=[PH](O)OC[C@@H]1CCCN1c1cc(-n2ccnc2)c2ccc(Cl)c(Cl)c2n1] |
| I-659 | 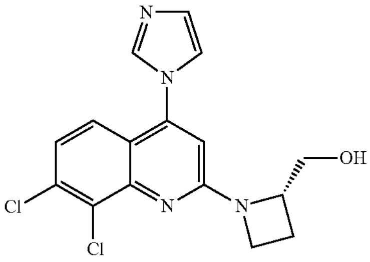 [SMILES: OC[C@@H]1CCN1c1cc(-n2ccnc2)c2ccc(Cl)c(Cl)c2n1] |
TABLE 1-continued
| Exemplary Compounds | |
|---|---|
| I-# | Structure |
| I-660 | 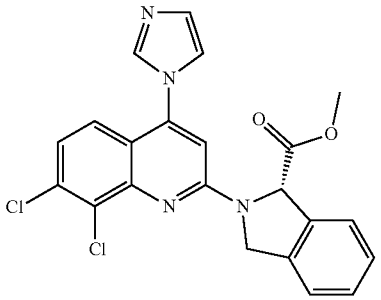 [SMILES: COC(=O)[C@@H]1c2ccccc2CN1c1cc(-n2ccnc2)c2ccc(Cl)c(Cl)c2n1] |
| I-661 | 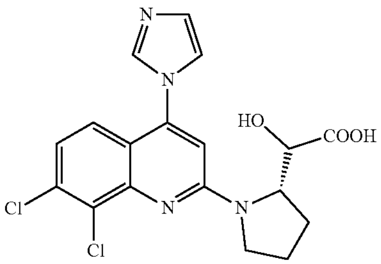 [SMILES: O=C(O)C(O)[C@@H]1CCCN1c1cc(-n2ccnc2)c2ccc(Cl)c(Cl)c2n1] |
| I-662 | 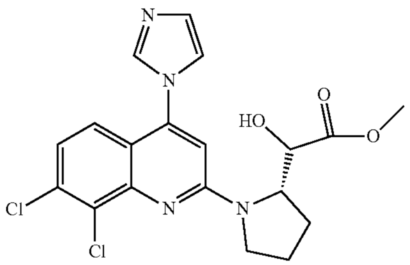 [SMILES: COC(=O)C(O)[C@@H]1CCCN1c1cc(-n2ccnc2)c2ccc(Cl)c(Cl)c2n1] |
| I-663 | 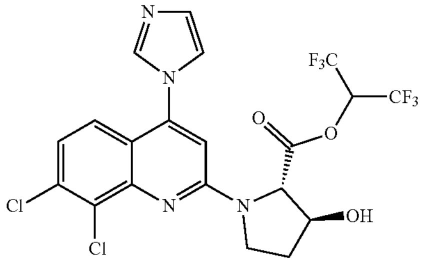 [SMILES: O=C(OC(C(F)(F)F)C(F)(F)F)[C@@H]1[C@@H](O)CCN1c1cc(-n2ccnc2)c2ccc(Cl)c(Cl)c2n1] |
| I-664 | 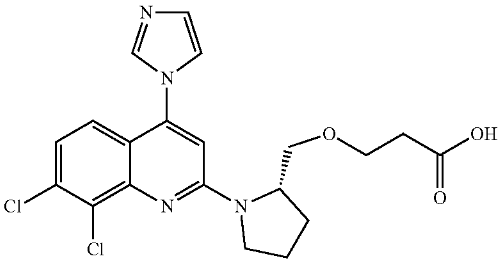 |

TABLE 1-continued
| Exemplary Compounds | |
|---|---|
| I-# | Structure |
| I-665 | 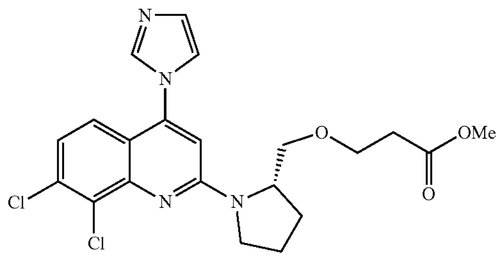 [SMILES: COC(=O)CCOC[C@@H]1CCCN1c1cc(-n2ccnc2)c2ccc(Cl)c(Cl)c2n1] |
| I-666 | 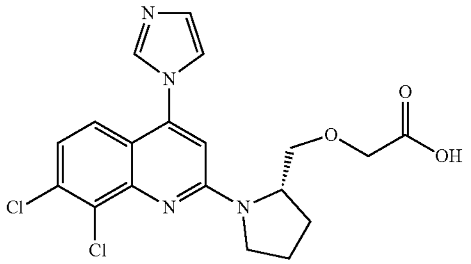 [SMILES: O=C(O)COC[C@@H]1CCCN1c1cc(-n2ccnc2)c2ccc(Cl)c(Cl)c2n1] |
| I-667 | 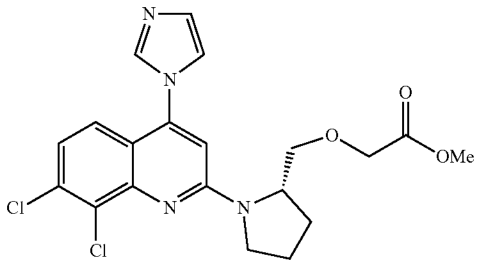 [SMILES: COC(=O)COC[C@@H]1CCCN1c1cc(-n2ccnc2)c2ccc(Cl)c(Cl)c2n1] |
| I-668 | 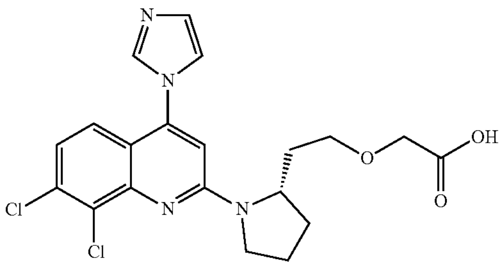 [SMILES: O=C(O)COCC[C@@H]1CCCN1c1cc(-n2ccnc2)c2ccc(Cl)c(Cl)c2n1] |
| I-669 | 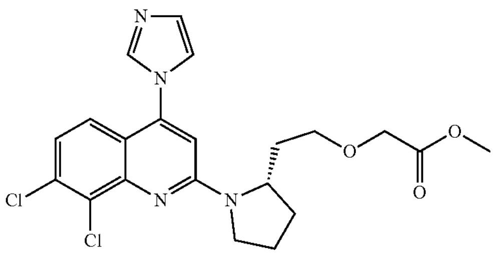 [SMILES: COC(=O)COCC[C@@H]1CCCN1c1cc(-n2ccnc2)c2ccc(Cl)c(Cl)c2n1] |
TABLE 1-continued
| Exemplary Compounds | |
|---|---|
| I-# | Structure |
| I-670 | 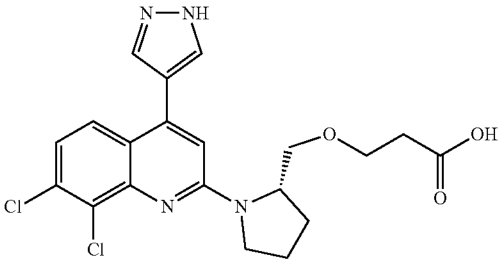 [SMILES: O=C(O)CCOC[C@@H]1CCCN1c1cc(-c2cn[nH]c2)c2ccc(Cl)c(Cl)c2n1] |
| I-671 | 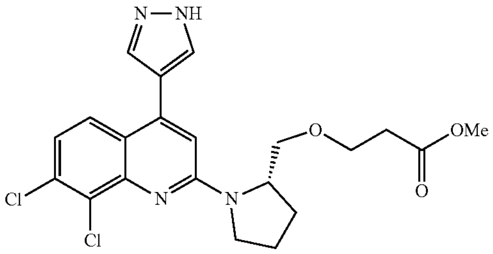 [SMILES: COC(=O)CCOC[C@@H]1CCCN1c1cc(-c2cn[nH]c2)c2ccc(Cl)c(Cl)c2n1] |
| I-672 | 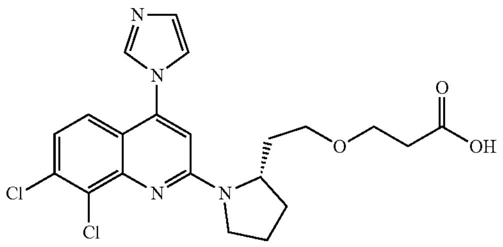 [SMILES: O=C(O)CCOCC[C@@H]1CCCN1c1cc(-n2ccnc2)c2ccc(Cl)c(Cl)c2n1] |
| I-673 | 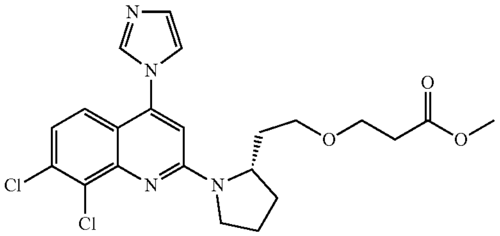 [SMILES: COC(=O)CCOCC[C@@H]1CCCN1c1cc(-n2ccnc2)c2ccc(Cl)c(Cl)c2n1] |
| I-674 | 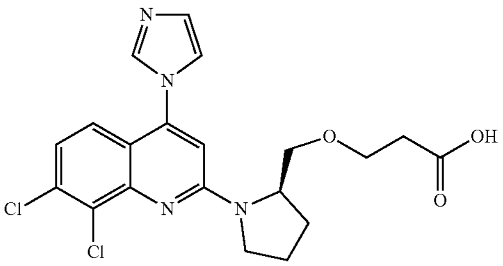 [SMILES: O=C(O)CCOC[C@H]1CCCN1c1cc(-n2ccnc2)c2ccc(Cl)c(Cl)c2n1] |
| I-675 | 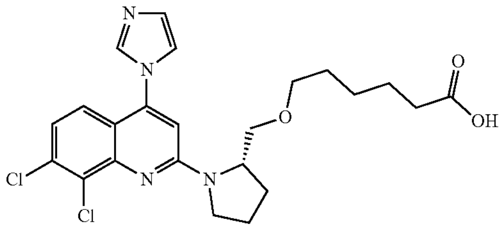 [SMILES: O=C(O)CCCCCOC[C@@H]1CCCN1c1cc(-n2ccnc2)c2ccc(Cl)c(Cl)c2n1] |

TABLE 1-continued
| Exemplary Compounds | |
|---|---|
| I-# | Structure |
| I-676 | 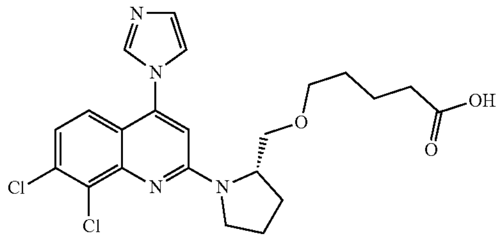 [SMILES: O=C(O)CCCCOC[C@@H]1CCCN1c1cc(-n2ccnc2)c2ccc(Cl)c(Cl)c2n1] |
| I-677 | 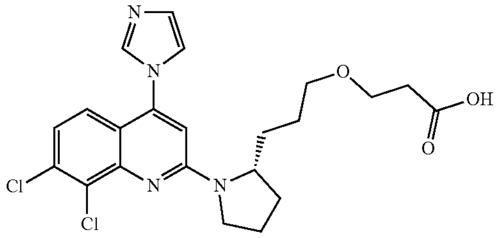 |
| I-678 | 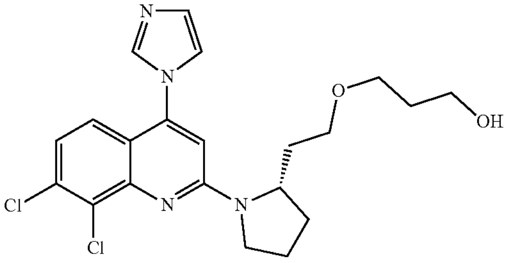 [SMILES: OCCCOCC[C@@H]1CCCN1c1cc(-n2ccnc2)c2ccc(Cl)c(Cl)c2n1] |
| I-679 | 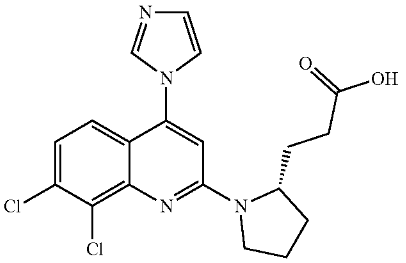 [SMILES: O=C(O)CC[C@@H]1CCCN1c1cc(-n2ccnc2)c2ccc(Cl)c(Cl)c2n1] |
| I-680 | 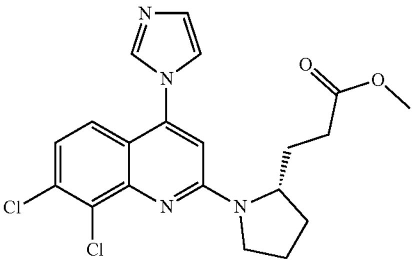 [SMILES: COC(=O)CC[C@@H]1CCCN1c1cc(-n2ccnc2)c2ccc(Cl)c(Cl)c2n1] |
TABLE 1-continued
| Exemplary Compounds | |
|---|---|
| I-# | Structure |
| I-681 | 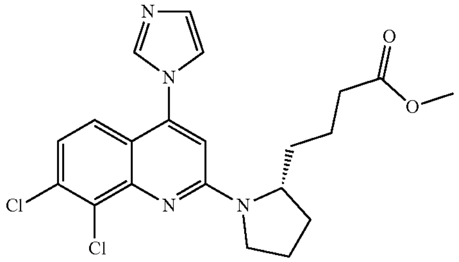 |
| I-682 | 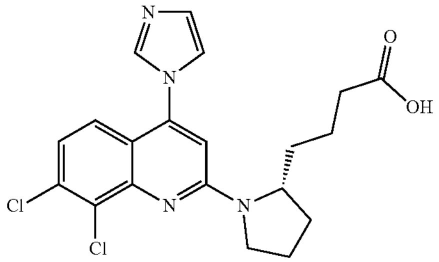 |
| I-683 | 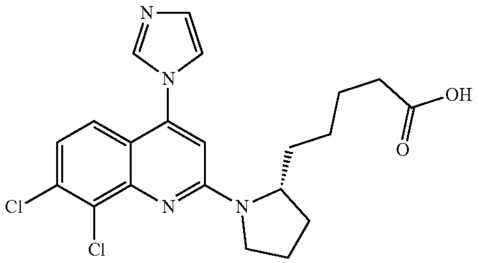 [SMILES: O=C(O)CCCC[C@@H]1CCCN1c1cc(-n2ccnc2)c2ccc(Cl)c(Cl)c2n1] |
| I-684 | 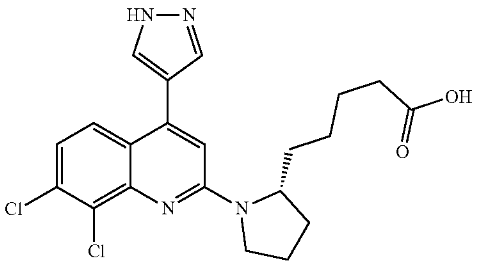 [SMILES: O=C(O)CCCC[C@@H]1CCCN1c1cc(-c2cn[nH]c2)c2ccc(Cl)c(Cl)c2n1] |
| I-685 | 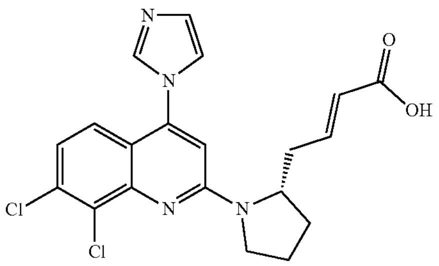 [SMILES: O=C(O)/C=C/C[C@@H]1CCCN1c1cc(-n2ccnc2)c2ccc(Cl)c(Cl)c2n1] |

TABLE 1-continued
| Exemplary Compounds | |
|---|---|
| I-# | Structure |
| I-686 | 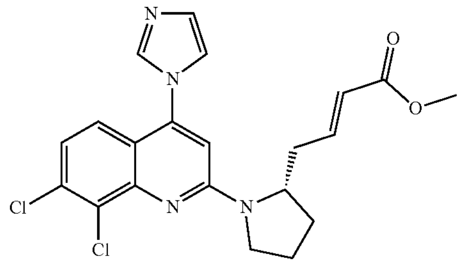 [SMILES: COC(=O)/C=C/C[C@@H]1CCCN1c1cc(-n2ccnc2)c2ccc(Cl)c(Cl)c2n1] |
| I-687 | 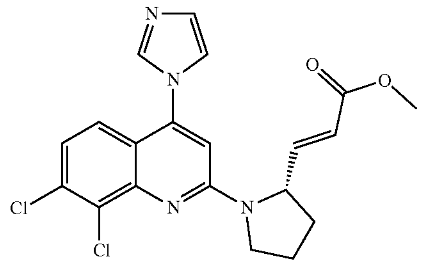 [SMILES: COC(=O)/C=C/[C@@H]1CCCN1c1cc(-n2ccnc2)c2ccc(Cl)c(Cl)c2n1] |
| I-688 | 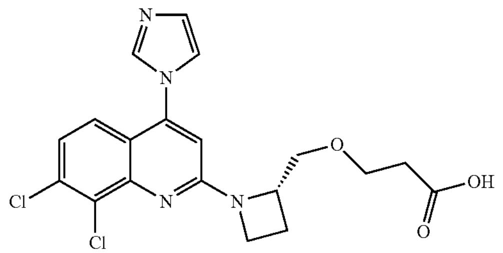 [SMILES: O=C(O)CCOC[C@@H]1CCN1c1cc(-n2ccnc2)c2ccc(Cl)c(Cl)c2n1] |
| I-689 | 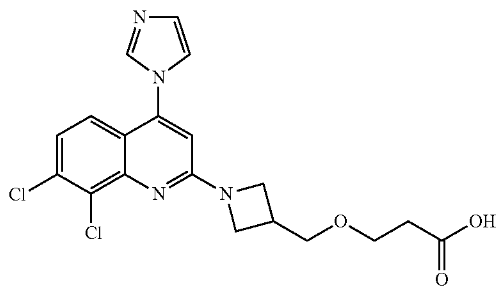 [SMILES: O=C(O)CCOCC1CN(c2cc(-n3ccnc3)c3ccc(Cl)c(Cl)c3n2)C1] |
| I-690 | 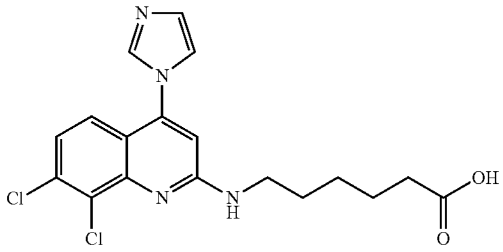 |
TABLE 1-continued
| Exemplary Compounds | |
|---|---|
| I-# | Structure |
| I-691 | 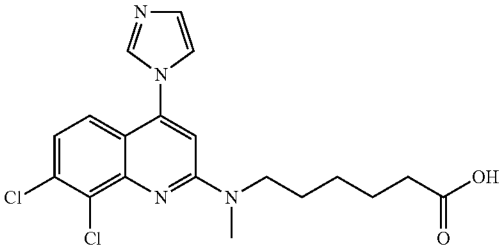 [SMILES: CN(CCCCCC(=O)O)c1cc(-n2ccnc2)c2ccc(Cl)c(Cl)c2n1] |
| I-692 | 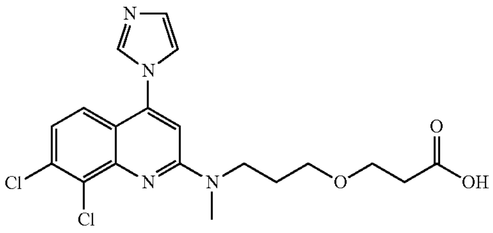 [SMILES: CN(CCCOCCC(=O)O)c1cc(-n2ccnc2)c2ccc(Cl)c(Cl)c2n1] |
| I-693 | 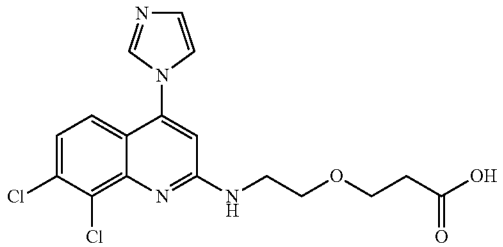 [SMILES: O=C(O)CCOCCNc1cc(-n2ccnc2)c2ccc(Cl)c(Cl)c2n1] |
| I-694 | 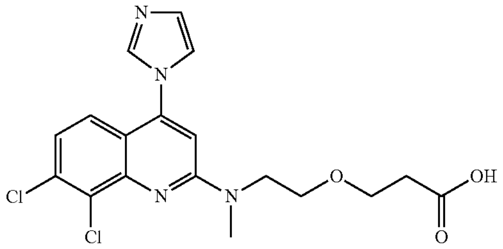 [SMILES: CN(CCOCCC(=O)O)c1cc(-n2ccnc2)c2ccc(Cl)c(Cl)c2n1] |
| I-695 | 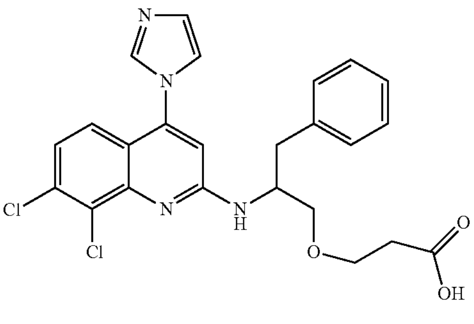 [SMILES: O=C(O)CCOCC(Cc1ccccc1)Nc1cc(-n2ccnc2)c2ccc(Cl)c(Cl)c2n1] |
| I-696 | 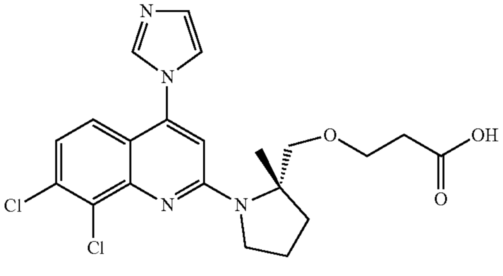 [SMILES: C[C@@]1(COCCC(=O)O)CCCN1c1cc(-n2ccnc2)c2ccc(Cl)c(Cl)c2n1] |

TABLE 1-continued
| Exemplary Compounds | |
|---|---|
| I-# | Structure |
| I-697 | 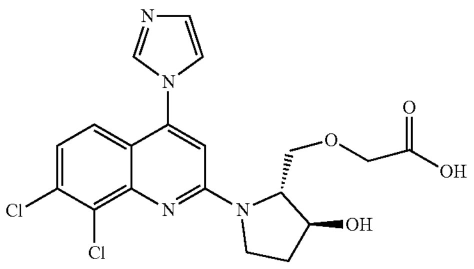 [SMILES: O=C(O)COC[C@@H]1[C@@H](O)CCN1c1cc(-n2ccnc2)c2ccc(Cl)c(Cl)c2n1] |
| I-698 | 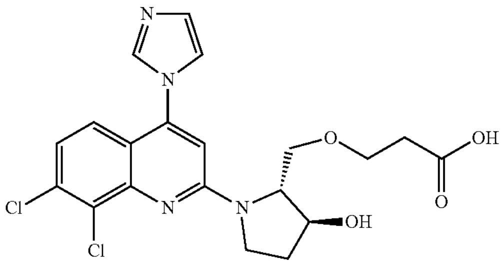 [SMILES: O=C(O)CCOC[C@@H]1[C@@H](O)CCN1c1cc(-n2ccnc2)c2ccc(Cl)c(Cl)c2n1] |
| I-699 | 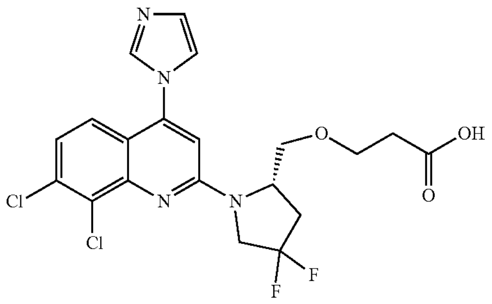 |
| I-700 | 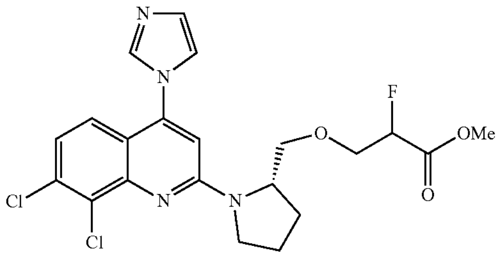 |
| I-701 | 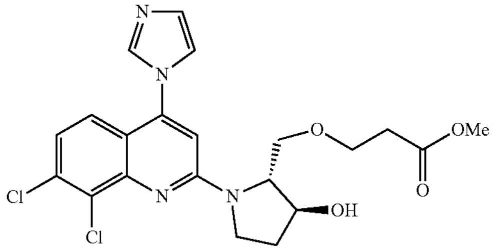 [SMILES: COC(=O)CCOC[C@@H]1[C@@H](O)CCN1c1cc(-n2ccnc2)c2ccc(Cl)c(Cl)c2n1] |
TABLE 1-continued
| Exemplary Compounds | |
|---|---|
| I-# | Structure |
| I-702 | 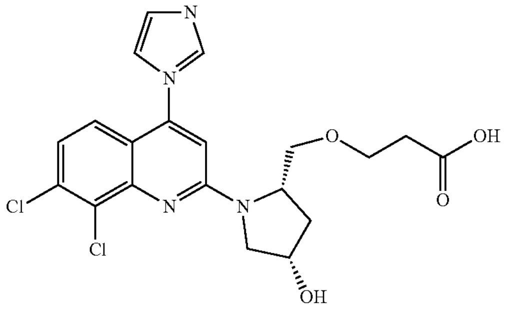 |
| I-703 | 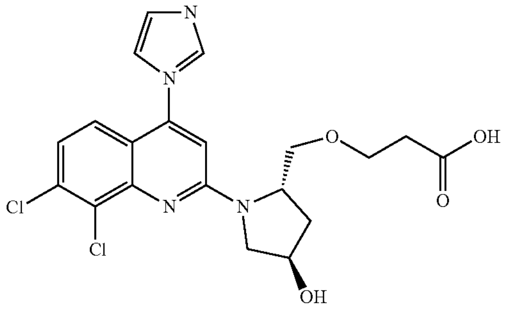 |
| I-704 | 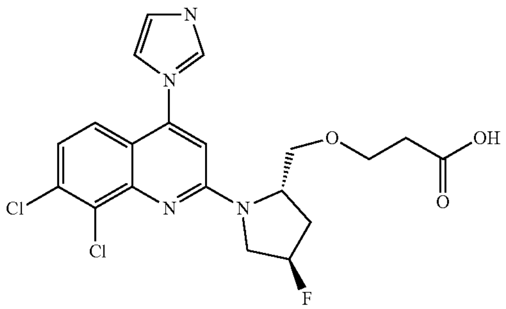 |
| I-705 | 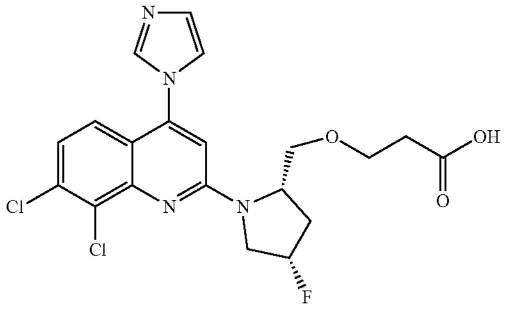 [SMILES: O=C(O)CCOC[C@@H]1C[C@H](F)CN1c1cc(-n2ccnc2)c2ccc(Cl)c(Cl)c2n1] |
| I-706 | 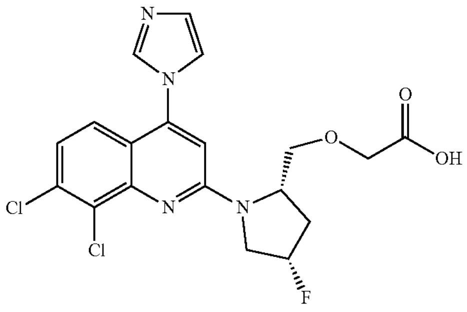 [SMILES: O=C(O)COC[C@@H]1C[C@H](F)CN1c1cc(-n2ccnc2)c2ccc(Cl)c(Cl)c2n1] |

TABLE 1-continued
| Exemplary Compounds | |
|---|---|
| I-# | Structure |
| I-707 | 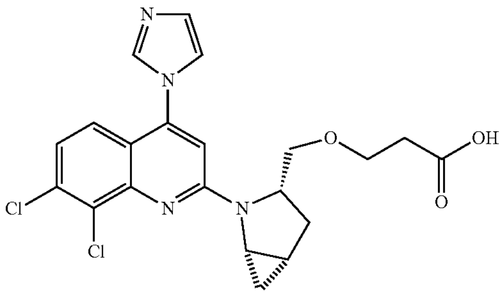 |
| I-708 | 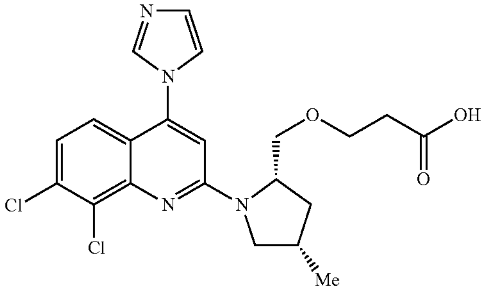 [SMILES: C[C@H]1C[C@@H](COCCC(=O)O)N(c2cc(-n3ccnc3)c3ccc(Cl)c(Cl)c3n2)C1] |
| I-709 | 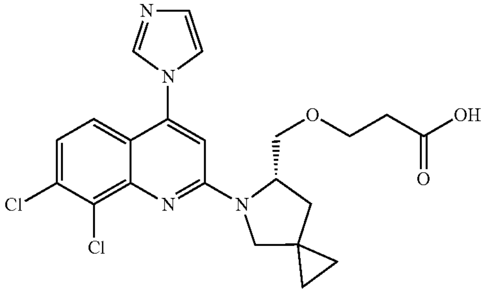 [SMILES: O=C(O)CCOC[C@@H]1CC2(CC2)CN1c1cc(-n2ccnc2)c2ccc(Cl)c(Cl)c2n1] |
| I-710 | 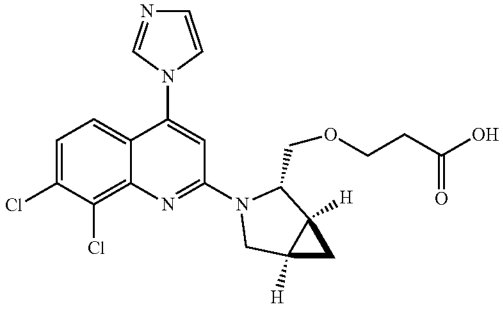 |
| I-711 | 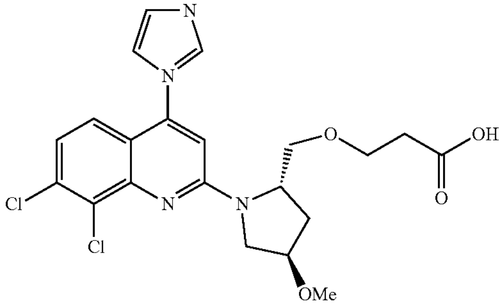 |
TABLE 1-continued
| Exemplary Compounds | |
|---|---|
| I-# | Structure |
| I-712 | 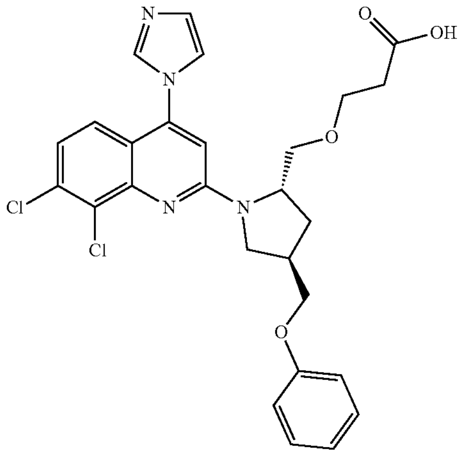 [SMILES: O=C(O)CCOC[C@@H]1C[C@@H](COc2ccccc2)CN1c1cc(-n2ccnc2)c2ccc(Cl)c(Cl)c2n1] |
| I-713 | 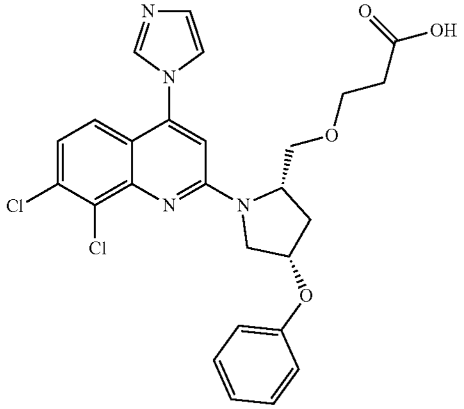 [SMILES: O=C(O)CCOC[C@@H]1C[C@H](Oc2ccccc2)CN1c1cc(-n2ccnc2)c2ccc(Cl)c(Cl)c2n1] |
| I-714 | 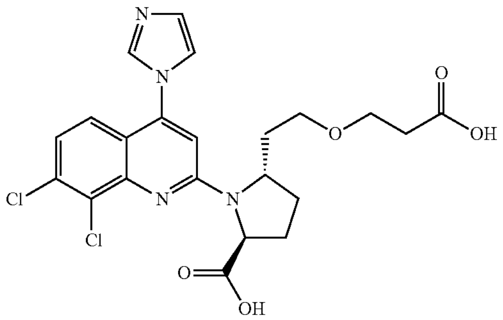 [SMILES: O=C(O)CCOCC[C@@H]1CC[C@@H](C(=O)O)N1c1cc(-n2ccnc2)c2ccc(Cl)c(Cl)c2n1] |
| I-715 | 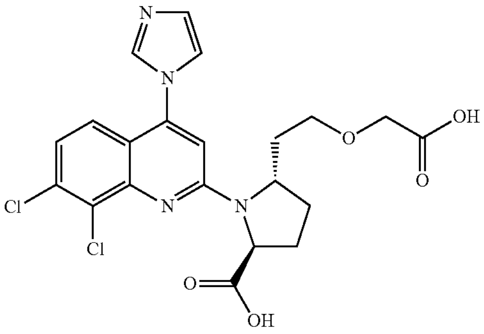 [SMILES: O=C(O)COCC[C@@H]1CC[C@@H](C(=O)O)N1c1cc(-n2ccnc2)c2ccc(Cl)c(Cl)c2n1] |

TABLE 1-continued
| Exemplary Compounds | |
|---|---|
| I-# | Structure |
| I-716 | 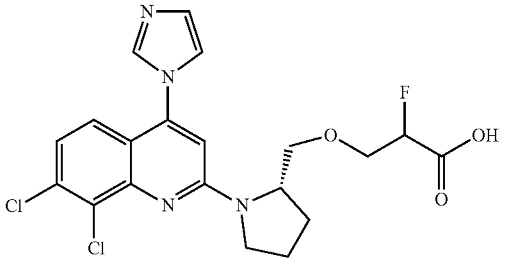 [SMILES: O=C(O)C(F)COC[C@@H]1CCCN1c1cc(-n2ccnc2)c2ccc(Cl)c(Cl)c2n1] |
| I-717 | 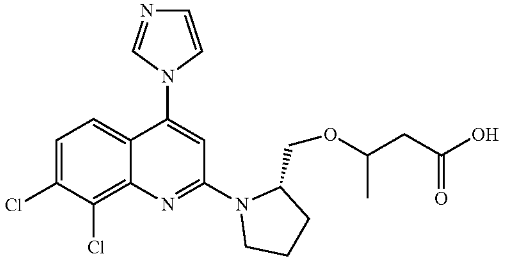 [SMILES: CC(CC(=O)O)OC[C@@H]1CCCN1c1cc(-n2ccnc2)c2ccc(Cl)c(Cl)c2n1] |
| I-718 | 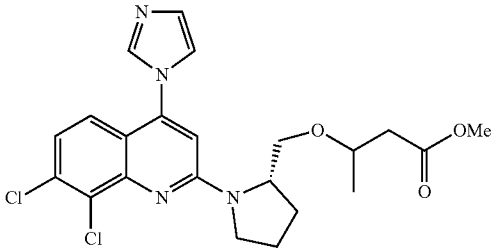 [SMILES: COC(=O)CC(C)OC[C@@H]1CCCN1c1cc(-n2ccnc2)c2ccc(Cl)c(Cl)c2n1] |
| I-719 | 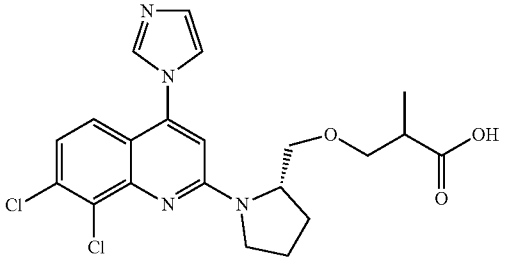 [SMILES: CC(COC[C@@H]1CCCN1c1cc(-n2ccnc2)c2ccc(Cl)c(Cl)c2n1)C(=O)O] |
| I-720 | 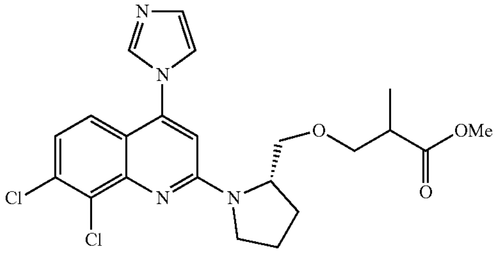 [SMILES: COC(=O)C(C)COC[C@@H]1CCCN1c1cc(-n2ccnc2)c2ccc(Cl)c(Cl)c2n1] |
TABLE 1-continued
| Exemplary Compounds | |
|---|---|
| I-# | Structure |
| I-721 | 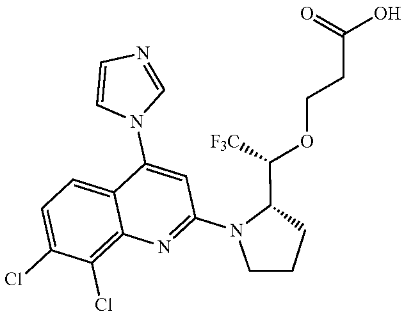 [SMILES: O=C(O)CCO[C@H]([C@@H]1CCCN1c1cc(-n2ccnc2)c2ccc(Cl)c(Cl)c2n1)C(F)(F)F] |
| I-722 | 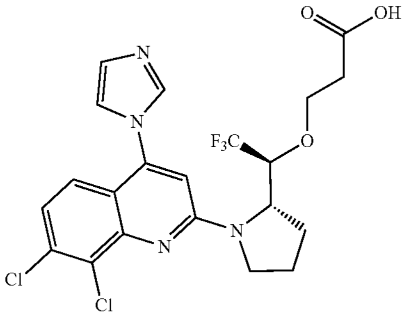 [SMILES: O=C(O)CCO[C@@H]([C@@H]1CCCN1c1cc(-n2ccnc2)c2ccc(Cl)c(Cl)c2n1)C(F)(F)F] |
| I-723 | 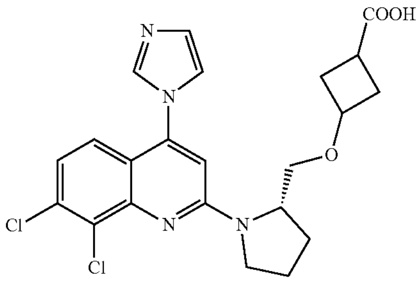 [SMILES: O=C(O)C1CC(OC[C@@H]2CCCN2c2cc(-n3ccnc3)c3ccc(Cl)c(Cl)c3n2)C1] |
| I-724 | 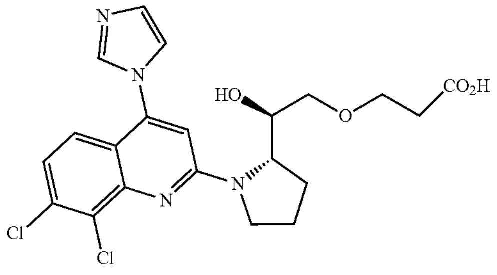 [SMILES: O=C(O)CCOC[C@H](O)[C@@H]1CCCN1c1cc(-n2ccnc2)c2ccc(Cl)c(Cl)c2n1] |
| I-725 | 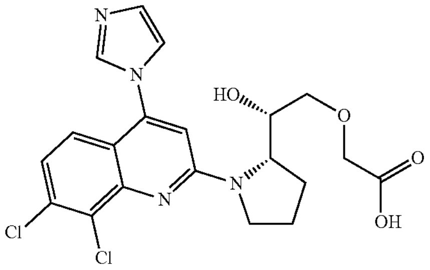 [SMILES: O=C(O)COC[C@@H](O)[C@@H]1CCCN1c1cc(-n2ccnc2)c2ccc(Cl)c(Cl)c2n1] |

TABLE 1-continued
| Exemplary Compounds | |
|---|---|
| I-# | Structure |
| I-726 | 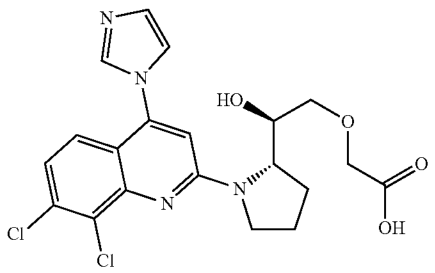 [SMILES: O=C(O)COC[C@H](O)[C@@H]1CCCN1c1cc(-n2ccnc2)c2ccc(Cl)c(Cl)c2n1] |
| I-727 | 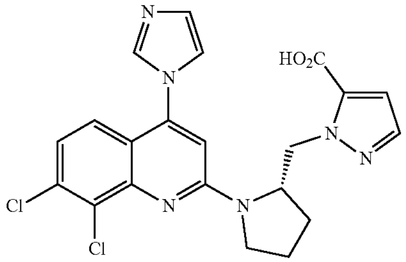 [SMILES: O=C(O)c1ccnn1C[C@@H]1CCCN1c1cc(-n2ccnc2)c2ccc(Cl)c(Cl)c2n1] |
| I-728 | 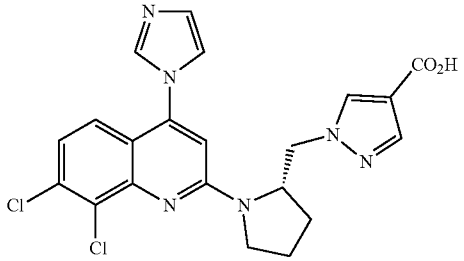 [SMILES: O=C(O)c1cnn(C[C@@H]2CCCN2c2cc(-n3ccnc3)c3ccc(Cl)c(Cl)c3n2)c1] |
| I-729 | 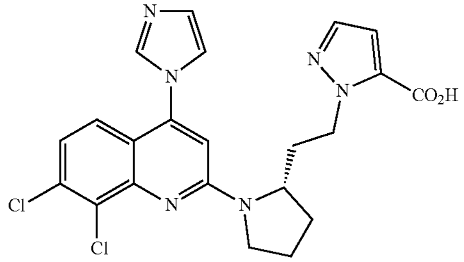 [SMILES: O=C(O)c1ccnn1CC[C@@H]1CCCN1c1cc(-n2ccnc2)c2ccc(Cl)c(Cl)c2n1] |
| I-730 | 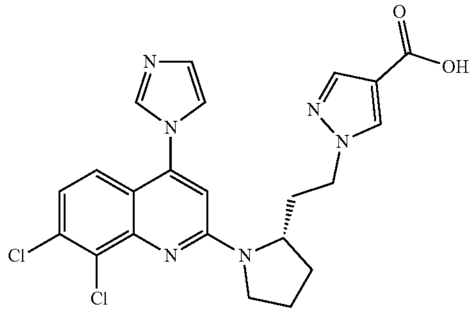 [SMILES: O=C(O)c1cnn(CC[C@@H]2CCCN2c2cc(-n3ccnc3)c3ccc(Cl)c(Cl)c3n2)c1] |
TABLE 1-continued
| Exemplary Compounds | |
|---|---|
| I-# | Structure |
| I-731 | 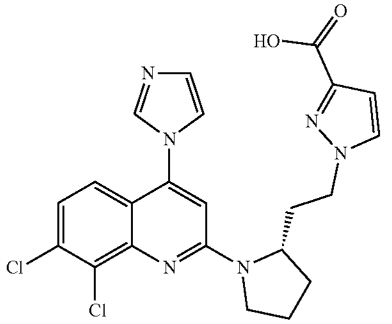 [SMILES: O=C(O)c1ccn(CC[C@@H]2CCCN2c2cc(-n3ccnc3)c3ccc(Cl)c(Cl)c3n2)n1] |
| I-732 | 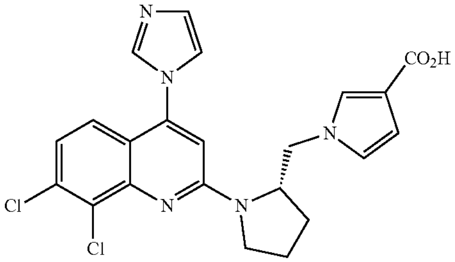 [SMILES: O=C(O)c1ccn(C[C@@H]2CCCN2c2cc(-n3ccnc3)c3ccc(Cl)c(Cl)c3n2)c1] |
| I-733 | 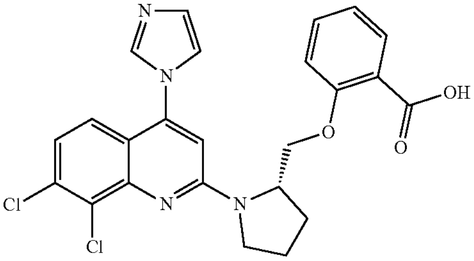 [SMILES: O=C(O)c1ccccc1OC[C@@H]1CCCN1c1cc(-n2ccnc2)c2ccc(Cl)c(Cl)c2n1] |
| I-734 | 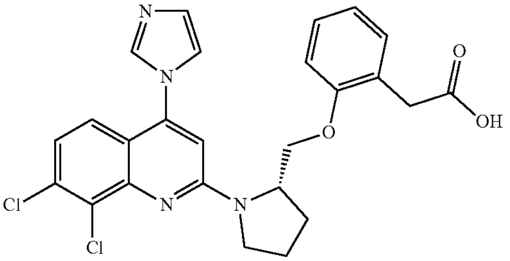 [SMILES: O=C(O)Cc1ccccc1OC[C@@H]1CCCN1c1cc(-n2ccnc2)c2ccc(Cl)c(Cl)c2n1] |
| I-735 | 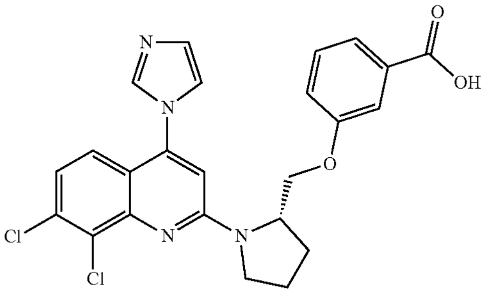 [SMILES: O=C(O)c1cccc(OC[C@@H]2CCCN2c2cc(-n3ccnc3)c3ccc(Cl)c(Cl)c3n2)c1] |

TABLE 1-continued
| Exemplary Compounds | |
|---|---|
| I-# | Structure |
| I-736 | 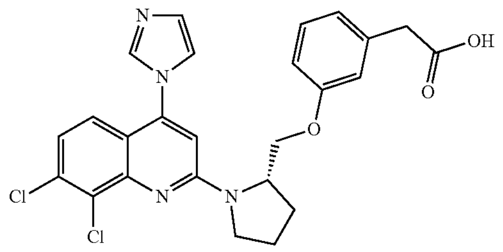 [SMILES: O=C(O)Cc1cccc(OC[C@@H]2CCCN2c2cc(-n3ccnc3)c3ccc(Cl)c(Cl)c3n2)c1] |
| I-737 | 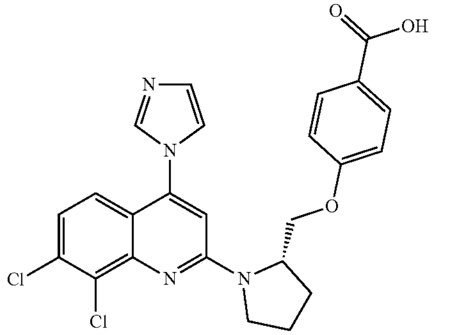 [SMILES: O=C(O)c1ccc(OC[C@@H]2CCCN2c2cc(-n3ccnc3)c3ccc(Cl)c(Cl)c3n2)cc1] |
| I-738 | 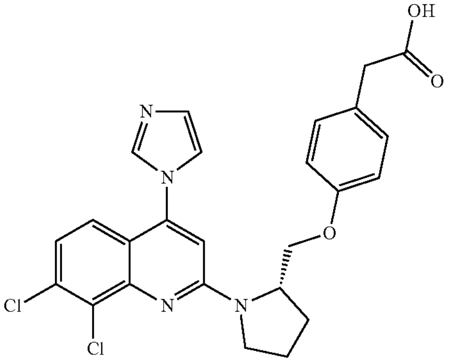 [SMILES: O=C(O)Cc1ccc(OC[C@@H]2CCCN2c2cc(-n3ccnc3)c3ccc(Cl)c(Cl)c3n2)cc1] |
| I-739 | 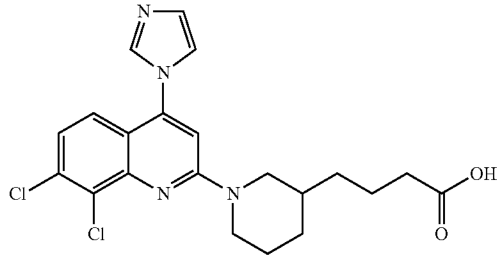 [SMILES: O=C(O)CCCC1CCCN(c2cc(-n3ccnc3)c3ccc(Cl)c(Cl)c3n2)C1] |
| I-740 | 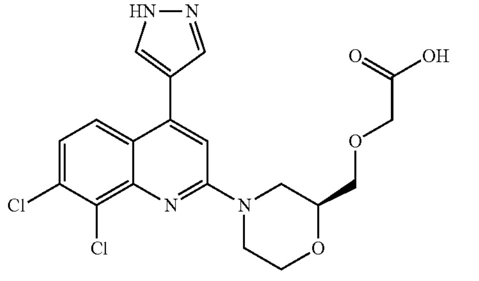 [SMILES: O=C(O)COC[C@@H]1CN(c2cc(-c3cn[nH]c3)c3ccc(Cl)c(Cl)c3n2)CCO1] |
TABLE 1-continued
| Exemplary Compounds | |
|---|---|
| I-# | Structure |
| I-741 | 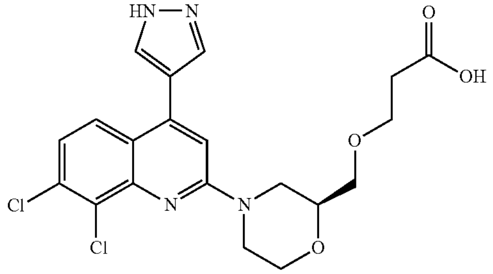 [SMILES: O=C(O)CCOC[C@@H]1CN(c2cc(-c3cn[nH]c3)c3ccc(Cl)c(Cl)c3n2)CCO1] |
| I-742 | 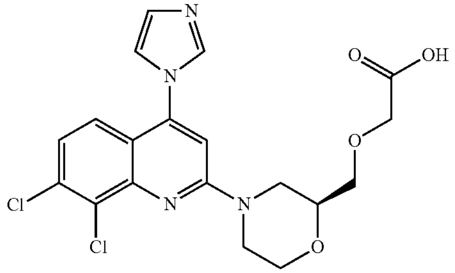 [SMILES: O=C(O)COC[C@@H]1CN(c2cc(-n3ccnc3)c3ccc(Cl)c(Cl)c3n2)CCO1] |
| I-743 | 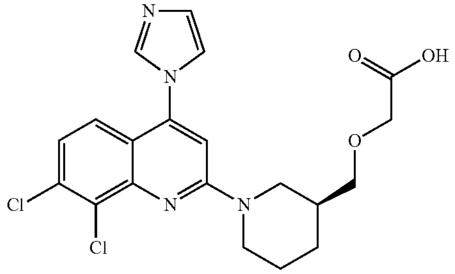 [SMILES: O=C(O)COC[C@H]1CCCN(c2cc(-n3ccnc3)c3ccc(Cl)c(Cl)c3n2)C1] |
| I-744 | 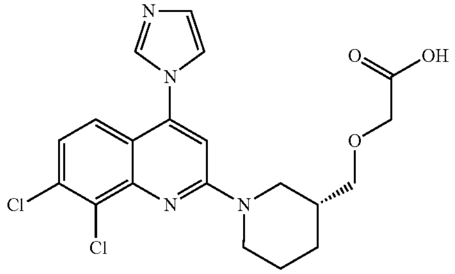 [SMILES: O=C(O)COC[C@@H]1CCCN(c2cc(-n3ccnc3)c3ccc(Cl)c(Cl)c3n2)C1] |
| I-745 | 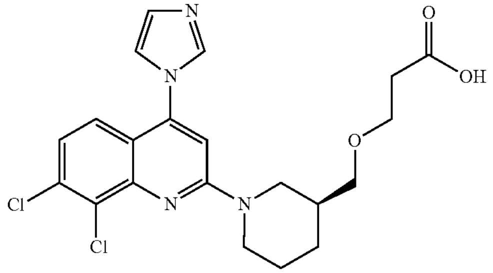 [SMILES: O=C(O)CCOC[C@H]1CCCN(c2cc(-n3ccnc3)c3ccc(Cl)c(Cl)c3n2)C1] |

TABLE 1-continued
| Exemplary Compounds | |
|---|---|
| I-# | Structure |
| I-746 | 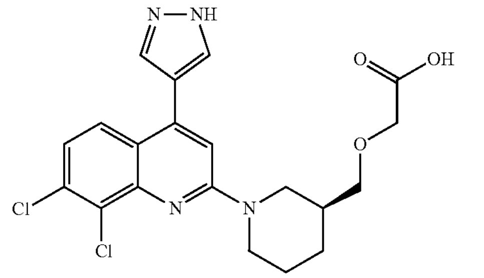 [SMILES: O=C(O)COC[C@H]1CCCN(c2cc(-c3cn[nH]c3)c3ccc(Cl)c(Cl)c3n2)C1] |
| I-747 | 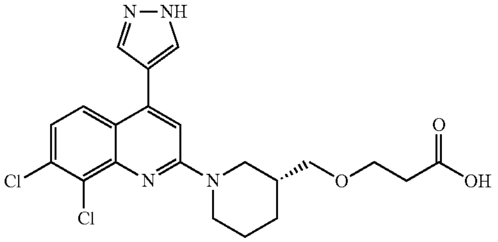 [SMILES: O=C(O)CCOC[C@@H]1CCCN(c2cc(-c3cn[nH]c3)c3ccc(Cl)c(Cl)c3n2)C1] |
| I-748 | 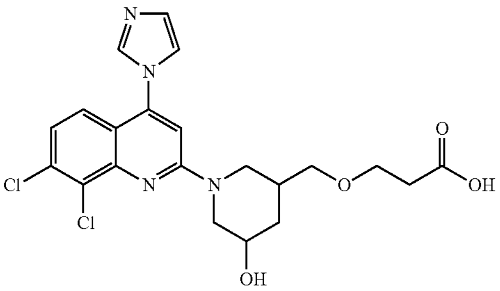 [SMILES: O=C(O)CCOCC1CC(O)CN(c2cc(-n3ccnc3)c3ccc(Cl)c(Cl)c3n2)C1] |
| I-749 | 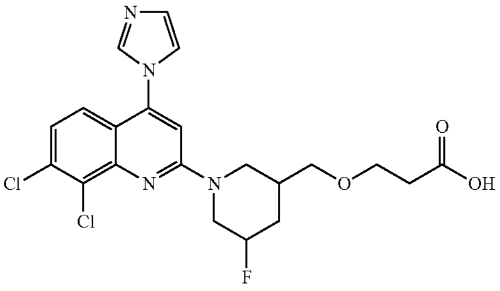 [SMILES: O=C(O)CCOCC1CC(F)CN(c2cc(-n3ccnc3)c3ccc(Cl)c(Cl)c3n2)C1] |
| I-750 | 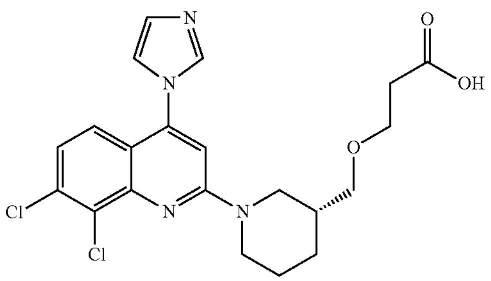 [SMILES: O=C(O)CCOC[C@@H]1CCCN(c2cc(-n3ccnc3)c3ccc(Cl)c(Cl)c3n2)C1] |
TABLE 1-continued
| Exemplary Compounds | |
|---|---|
| I-# | Structure |
| I-751 | 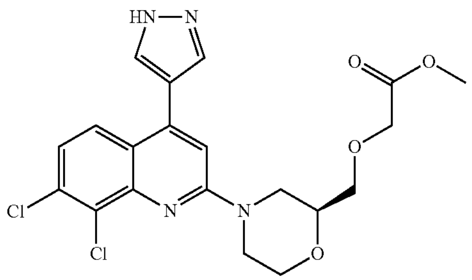 [SMILES: COC(=O)COC[C@@H]1CN(c2cc(-c3cn[nH]c3)c3ccc(Cl)c(Cl)c3n2)CCO1] |
| I-752 | 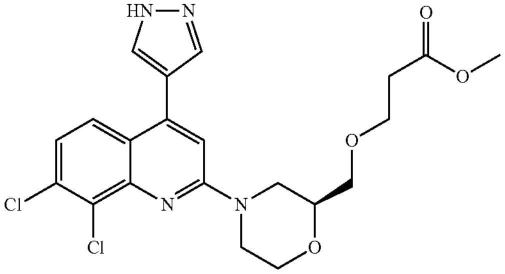 [SMILES: COC(=O)CCOC[C@@H]1CN(c2cc(-c3cn[nH]c3)c3ccc(Cl)c(Cl)c3n2)CCO1] |
| I-753 | 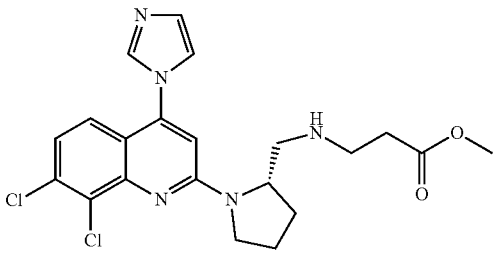 [SMILES: COC(=O)CCNC[C@@H]1CCCN1c1cc(-n2ccnc2)c2ccc(Cl)c(Cl)c2n1] |
| I-754 | 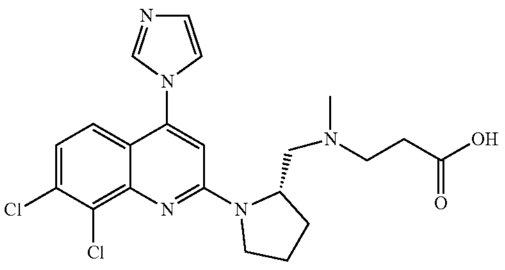 [SMILES: CN(CCC(=O)O)C[C@@H]1CCCN1c1cc(-n2ccnc2)c2ccc(Cl)c(Cl)c2n1] |
| I-755 | 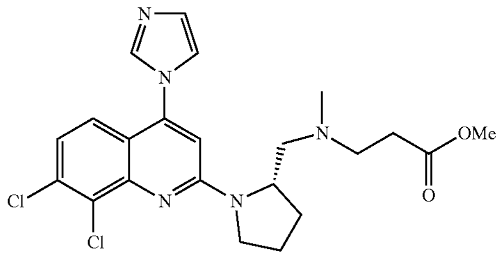 [SMILES: COC(=O)CCN(C)C[C@@H]1CCCN1c1cc(-n2ccnc2)c2ccc(Cl)c(Cl)c2n1] |

TABLE 1-continued
| Exemplary Compounds | |
|---|---|
| I-# | Structure |
| I-756 | 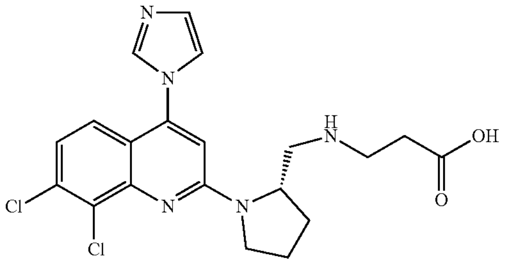 [SMILES: O=C(O)CCNC[C@@H]1CCCN1c1cc(-n2ccnc2)c2ccc(Cl)c(Cl)c2n1] |
| I-757 | 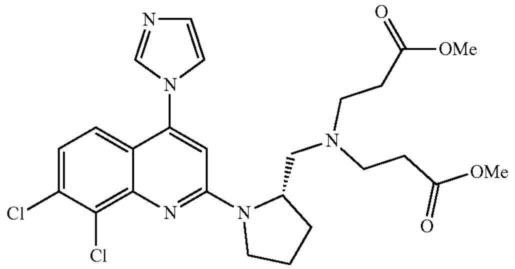 [SMILES: COC(=O)CCN(CCC(=O)OC)C[C@@H]1CCCN1c1cc(-n2ccnc2)c2ccc(Cl)c(Cl)c2n1] |
| I-758 | 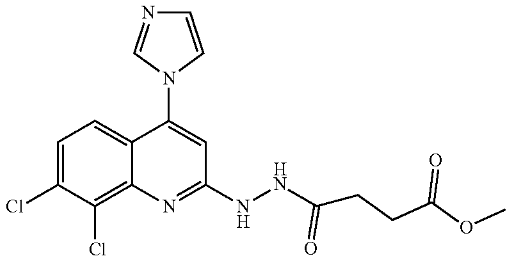 [SMILES: COC(=O)CCC(=O)NNc1cc(-n2ccnc2)c2ccc(Cl)c(Cl)c2n1] |
| I-759 | 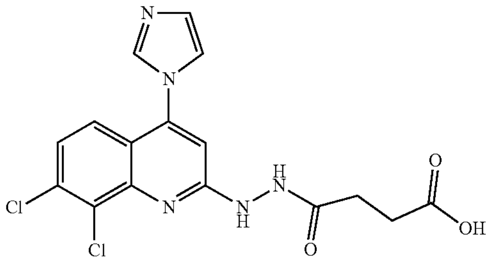 [SMILES: O=C(O)CCC(=O)NNc1cc(-n2ccnc2)c2ccc(Cl)c(Cl)c2n1] |
| I-760 | 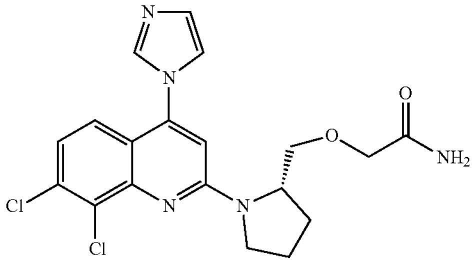 [SMILES: NC(=O)COC[C@@H]1CCCN1c1cc(-n2ccnc2)c2ccc(Cl)c(Cl)c2n1] |
TABLE 1-continued
| Exemplary Compounds | |
|---|---|
| I-# | Structure |
| I-761 | 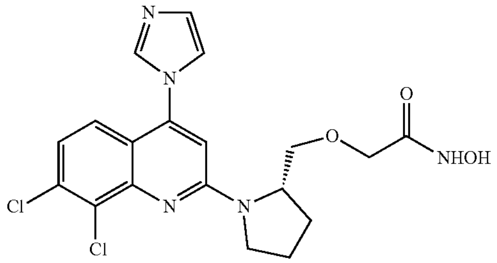 |
| I-762 | 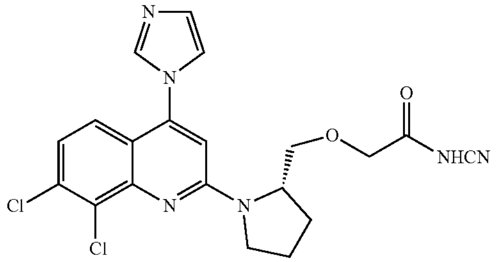 |
| I-763 | 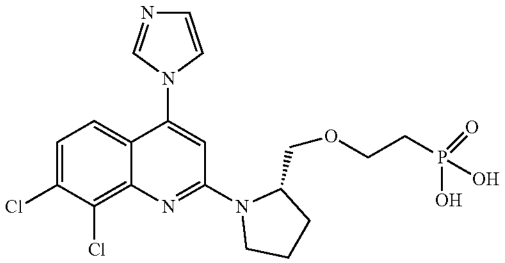 [SMILES: O=P(O)(O)CCOC[C@@H]1CCCN1c1cc(-n2ccnc2)c2ccc(Cl)c(Cl)c2n1] |
| I-764 | 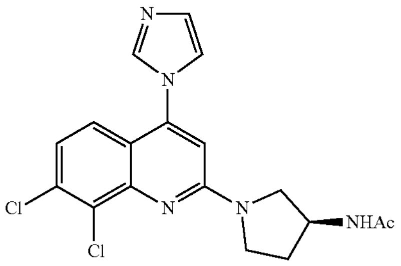 [SMILES: CC(=O)N[C@H]1CCN(c2cc(-n3ccnc3)c3ccc(Cl)c(Cl)c3n2)C1] |
| I-765 | 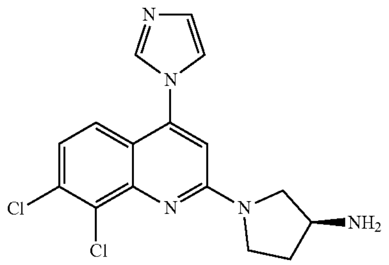 [SMILES: N[C@H]1CCN(c2cc(-n3ccnc3)c3ccc(Cl)c(Cl)c3n2)C1] |

TABLE 1-continued
| Exemplary Compounds | |
|---|---|
| I-# | Structure |
| I-766 | 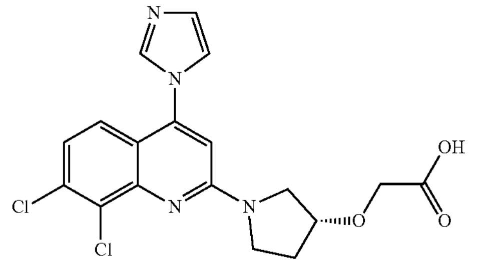 [SMILES: O=C(O)CO[C@@H]1CCN(c2cc(-n3ccnc3)c3ccc(Cl)c(Cl)c3n2)C1] |
| I-767 | 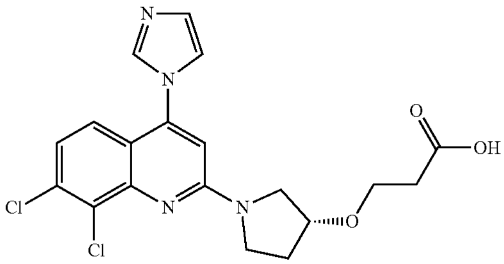 [SMILES: O=C(O)CCO[C@@H]1CCN(c2cc(-n3ccnc3)c3ccc(Cl)c(Cl)c3n2)C1] |
| I-768 | 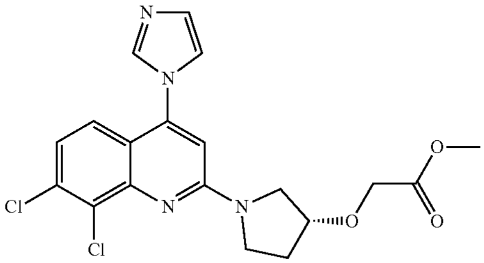 [SMILES: COC(=O)CO[C@@H]1CCN(c2cc(-n3ccnc3)c3ccc(Cl)c(Cl)c3n2)C1] |
| I-769 | 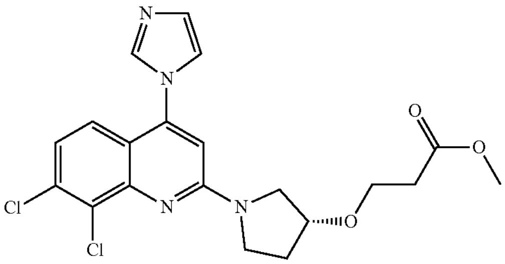 [SMILES: COC(=O)CCO[C@@H]1CCN(c2cc(-n3ccnc3)c3ccc(Cl)c(Cl)c3n2)C1] |
| I-770 | 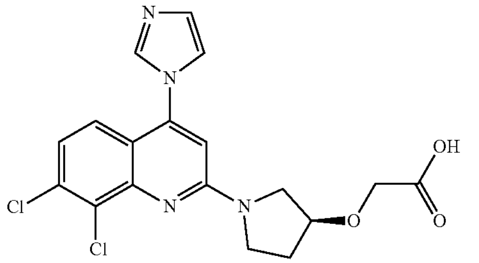 [SMILES: O=C(O)CO[C@H]1CCN(c2cc(-n3ccnc3)c3ccc(Cl)c(Cl)c3n2)C1] |
TABLE 1-continued
| Exemplary Compounds | |
|---|---|
| I-# | Structure |
| I-771 | 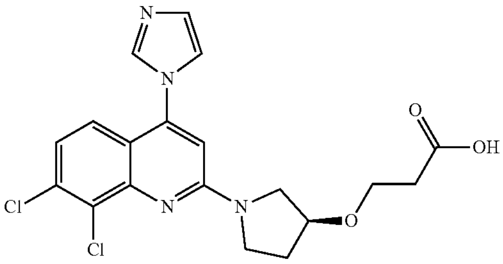 [SMILES: O=C(O)CCO[C@H]1CCN(c2cc(-n3ccnc3)c3ccc(Cl)c(Cl)c3n2)C1] |
| I-772 | 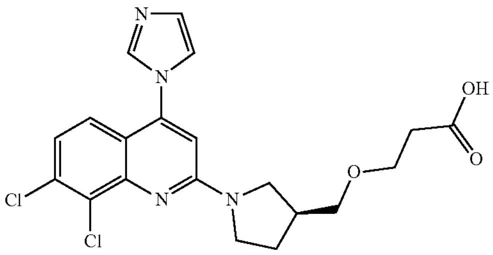 [SMILES: O=C(O)CCOC[C@H]1CCN(c2cc(-n3ccnc3)c3ccc(Cl)c(Cl)c3n2)C1] |
| I-773 | 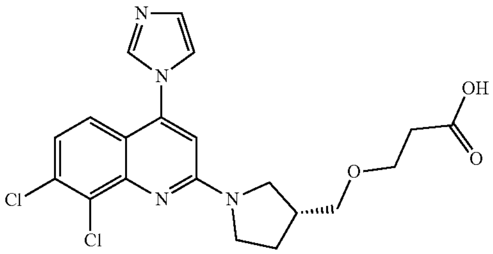 [SMILES: O=C(O)CCOC[C@@H]1CCN(c2cc(-n3ccnc3)c3ccc(Cl)c(Cl)c3n2)C1] |
| I-774 | 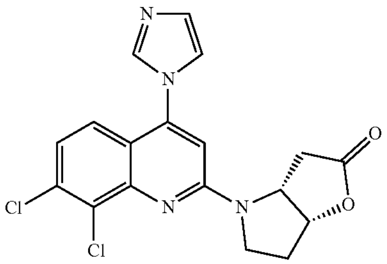 [SMILES: O=C1C[C@@H]2[C@@H](CCN2c2cc(-n3ccnc3)c3ccc(Cl)c(Cl)c3n2)O1] |
| I-775 | 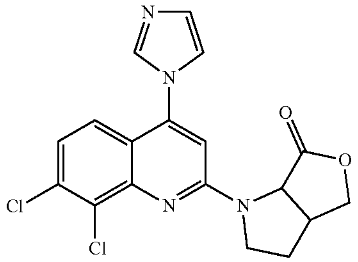 [SMILES: O=C1OCC2CCN(c3cc(-n4ccnc4)c4ccc(Cl)c(Cl)c4n3)C12] |

TABLE 1-continued
| Exemplary Compounds | |
|---|---|
| I-# | Structure |
| I-776 | 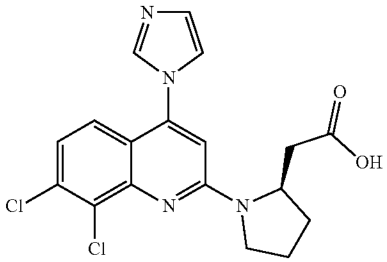 [SMILES: O=C(O)C[C@H]1CCCN1c1cc(-n2ccnc2)c2ccc(Cl)c(Cl)c2n1] |
| I-778 | 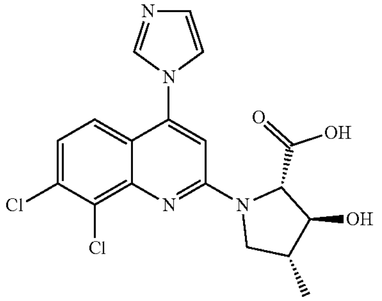 |
| I-779 | 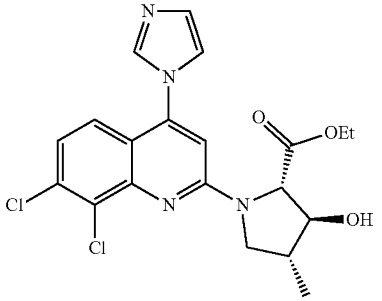 |
| I-780 | 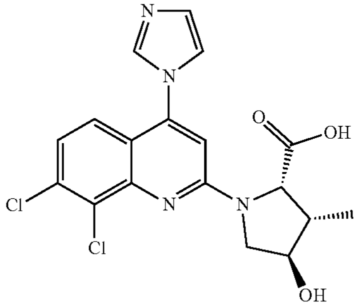 [SMILES: C[C@H]1[C@@H](C(=O)O)N(c2cc(-n3ccnc3)c3ccc(Cl)c(Cl)c3n2)C[C@@H]1O] |
| I-781 | 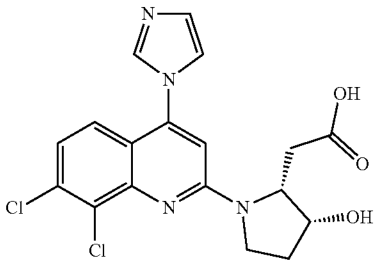 [SMILES: O=C(O)C[C@@H]1[C@H](O)CCN1c1cc(-n2ccnc2)c2ccc(Cl)c(Cl)c2n1] |
TABLE 1-continued
| Exemplary Compounds | |
|---|---|
| I-# | Structure |
| I-782 | 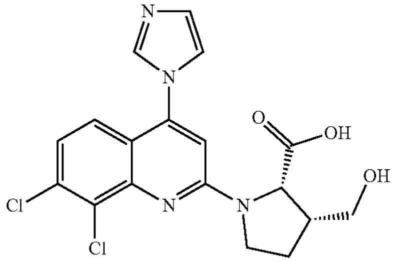 (+/-) |
| I-783 | 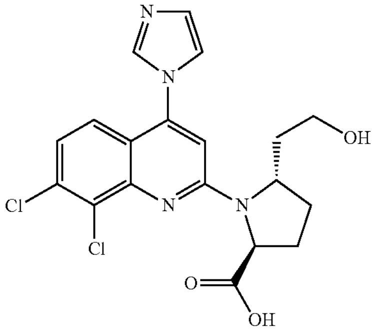 [SMILES: O=C(O)[C@@H]1CC[C@@H](CCO)N1c1cc(-n2ccnc2)c2ccc(Cl)c(Cl)c2n1] |
| I-784 | 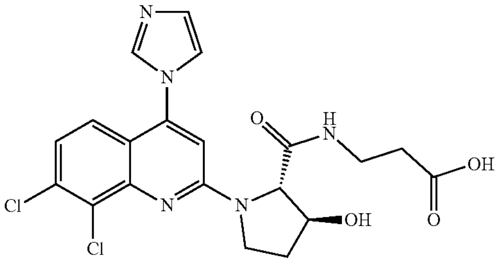 [SMILES: O=C(O)CCNC(=O)[C@@H]1[C@@H](O)CCN1c1cc(-n2ccnc2)c2ccc(Cl)c(Cl)c2n1] |
| I-785 | 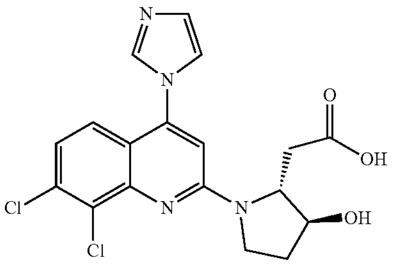 [SMILES: O=C(O)C[C@@H]1[C@@H](O)CCN1c1cc(-n2ccnc2)c2ccc(Cl)c(Cl)c2n1] |
| I-786 | 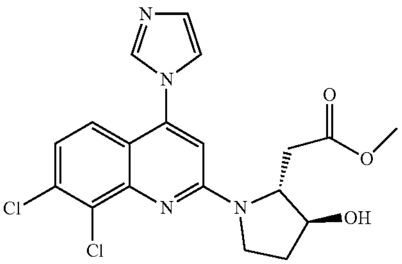 [SMILES: COC(=O)C[C@@H]1[C@@H](O)CCN1c1cc(-n2ccnc2)c2ccc(Cl)c(Cl)c2n1] |

TABLE 1-continued
| Exemplary Compounds | |
|---|---|
| I-# | Structure |
| I-787 | 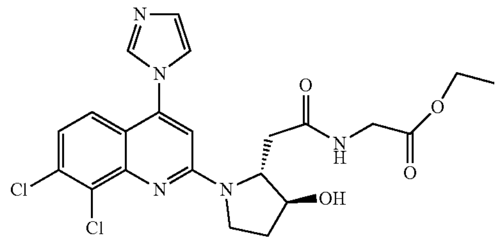 [SMILES: CCOC(=O)CNC(=O)C[C@@H]1[C@@H](O)CCN1c1cc(-n2ccnc2)c2ccc(Cl)c(Cl)c2n1] |
| I-788 | 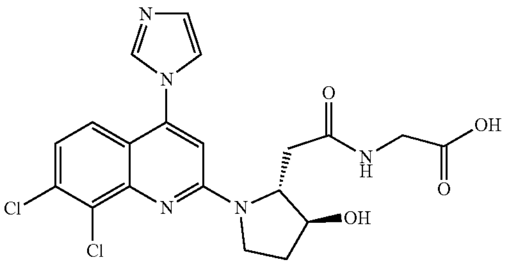 [SMILES: O=C(O)CNC(=O)C[C@@H]1[C@@H](O)CCN1c1cc(-n2ccnc2)c2ccc(Cl)c(Cl)c2n1] |
| I-789 | 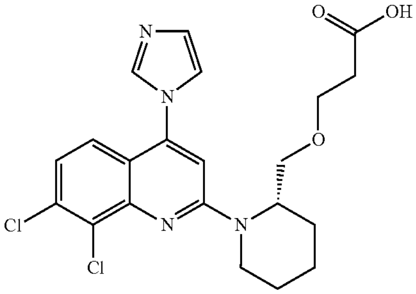 [SMILES: O=C(O)CCOC[C@@H]1CCCCN1c1cc(-n2ccnc2)c2ccc(Cl)c(Cl)c2n1] |
| I-790 | 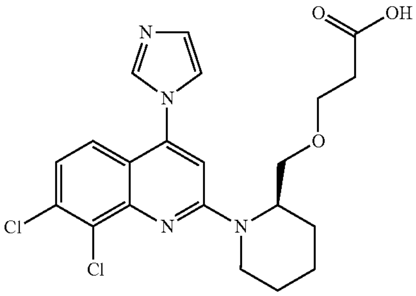 [SMILES: O=C(O)CCOC[C@H]1CCCCN1c1cc(-n2ccnc2)c2ccc(Cl)c(Cl)c2n1] |
| I-791 | 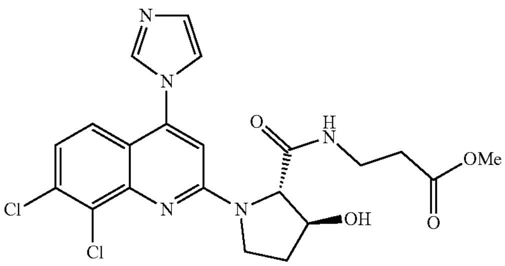 [SMILES: COC(=O)CCNC(=O)[C@@H]1[C@@H](O)CCN1c1cc(-n2ccnc2)c2ccc(Cl)c(Cl)c2n1] |
TABLE 1-continued
| Exemplary Compounds | |
|---|---|
| I-# | Structure |
| I-792 | 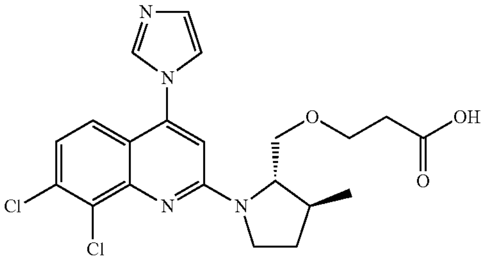 [SMILES: C[C@H]1CCN(c2cc(-n3ccnc3)c3ccc(Cl)c(Cl)c3n2)[C@@H]1COCCC(=O)O] |
| I-793 | 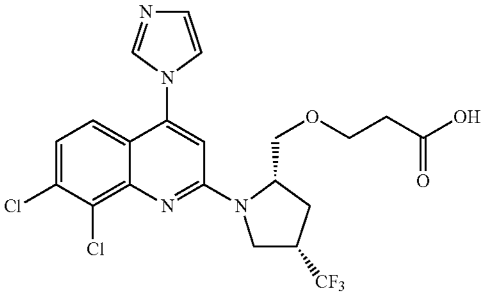 [SMILES: O=C(O)CCOC[C@@H]1C[C@H](C(F)(F)F)CN1c1cc(-n2ccnc2)c2ccc(Cl)c(Cl)c2n1] |
| I-794 | 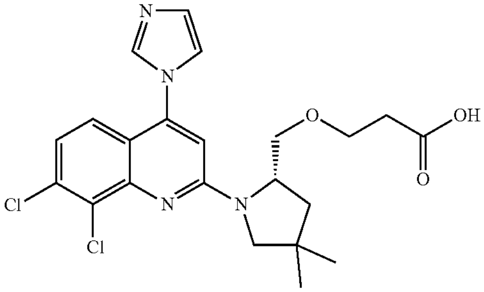 [SMILES: CC1(C)C[C@@H](COCCC(=O)O)N(c2cc(-n3ccnc3)c3ccc(Cl)c(Cl)c3n2)C1] |
| I-795 | 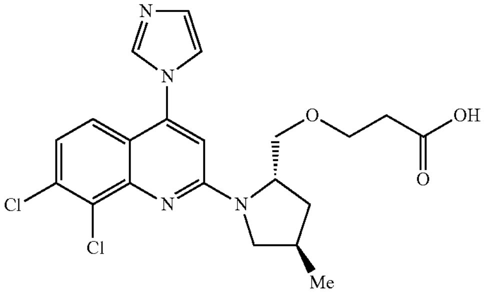 [SMILES: C[C@@H]1C[C@@H](COCCC(=O)O)N(c2cc(-n3ccnc3)c3ccc(Cl)c(Cl)c3n2)C1] |
| I-796 | 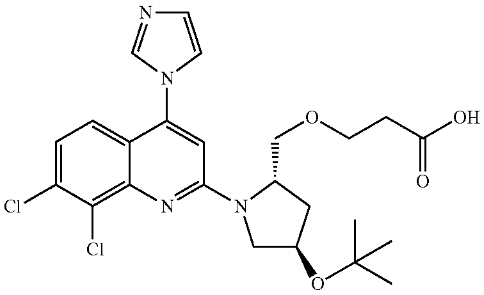 [SMILES: CC(C)(C)O[C@@H]1C[C@@H](COCCC(=O)O)N(c2cc(-n3ccnc3)c3ccc(Cl)c(Cl)c3n2)C1] |

TABLE 1-continued
| Exemplary Compounds | |
|---|---|
| I-# | Structure |
| I-797 | 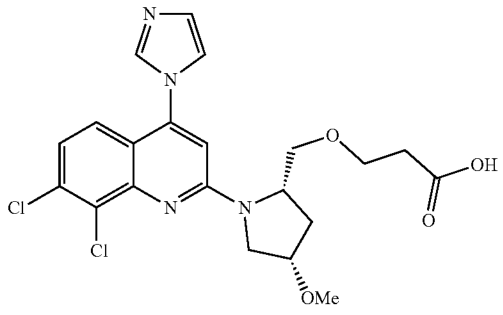 [SMILES: CO[C@H]1C[C@@H](COCCC(=O)O)N(c2cc(-n3ccnc3)c3ccc(Cl)c(Cl)c3n2)C1] |
| I-798 | 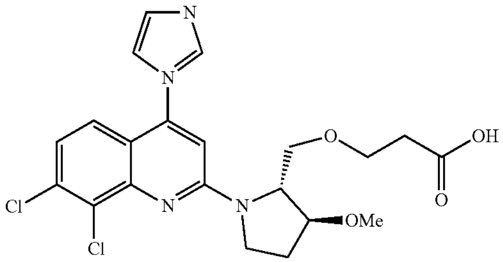 |
| I-799 | 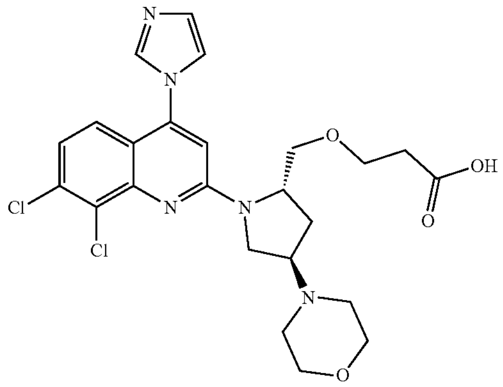 [SMILES: O=C(O)CCOC[C@@H]1C[C@@H](N2CCOCC2)CN1c1cc(-n2ccnc2)c2ccc(Cl)c(Cl)c2n1] |
| I-800 | 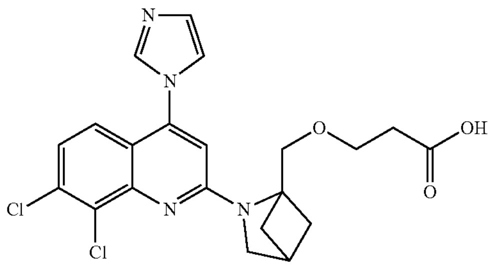 [SMILES: O=C(O)CCOCC12CC(CN1c1cc(-n3ccnc3)c3ccc(Cl)c(Cl)c3n1)C2] |
| I-801 | 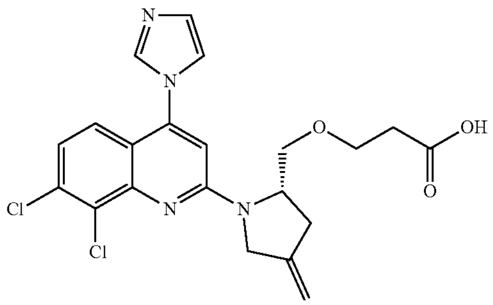 [SMILES: C=C1C[C@@H](COCCC(=O)O)N(c2cc(-n3ccnc3)c3ccc(Cl)c(Cl)c3n2)C1] |
TABLE 1-continued
| Exemplary Compounds | |
|---|---|
| I-# | Structure |
| I-802 | 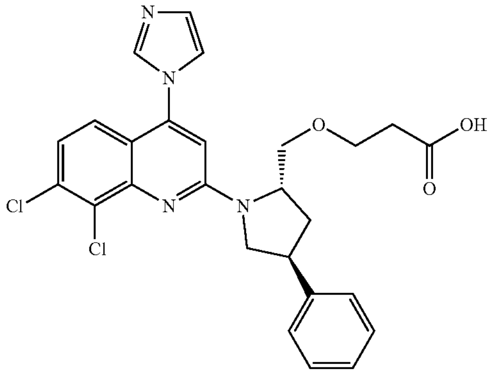 [SMILES: O=C(O)CCOC[C@@H]1C[C@@H](c2ccccc2)CN1c1cc(-n2ccnc2)c2ccc(Cl)c(Cl)c2n1] |
| I-803 | 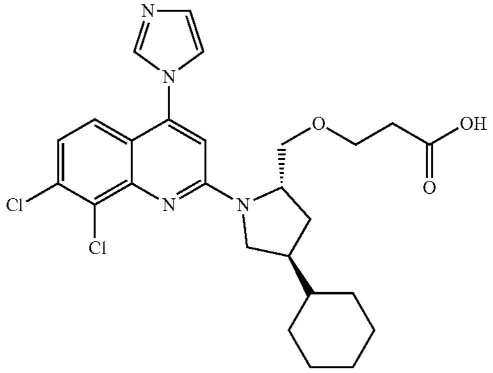 [SMILES: O=C(O)CCOC[C@@H]1C[C@@H](C2CCCCC2)CN1c1cc(-n2ccnc2)c2ccc(Cl)c(Cl)c2n1] |
| I-804 | 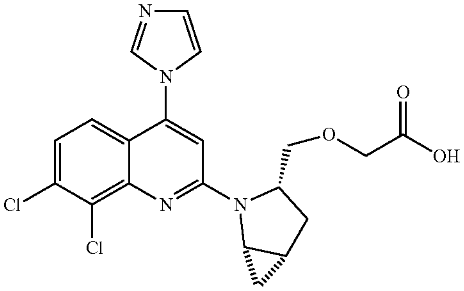 |
| I-805 | 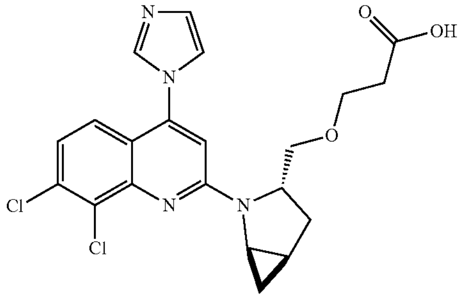 |

TABLE 1-continued
| Exemplary Compounds | |
|---|---|
| I-# | Structure |
| I-806 | 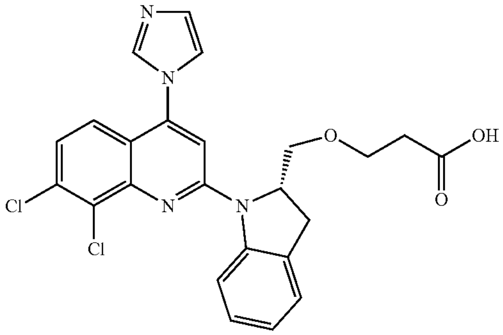 [SMILES: O=C(O)CCOC[C@@H]1Cc2ccccc2N1c1cc(-n2ccnc2)c2ccc(Cl)c(Cl)c2n1] |
| I-807 | 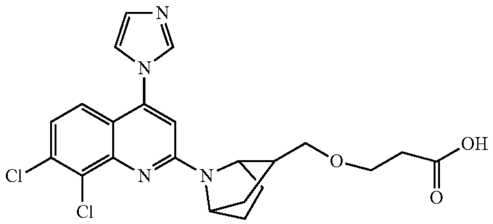 [SMILES: O=C(O)CCOCC1CC2CCC1N2c1cc(-n2ccnc2)c2ccc(Cl)c(Cl)c2n1] |
| I-808 | 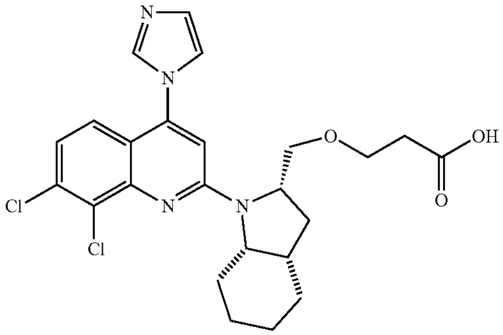 |
| I-809 | 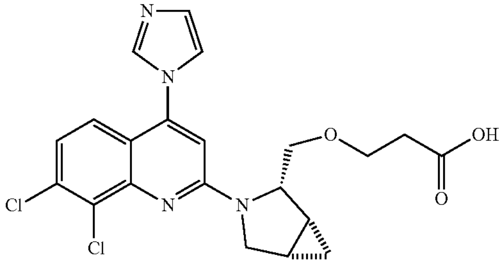 |
| I-810 | 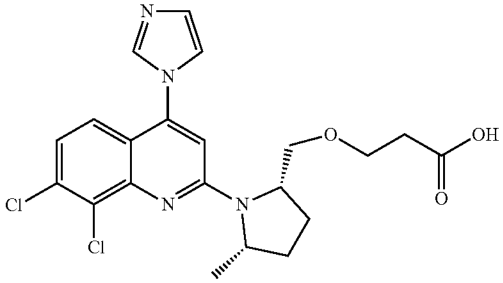 [SMILES: C[C@H]1CC[C@@H](COCCC(=O)O)N1c1cc(-n2ccnc2)c2ccc(Cl)c(Cl)c2n1] |
TABLE 1-continued
| Exemplary Compounds | |
|---|---|
| I-# | Structure |
| I-811 | 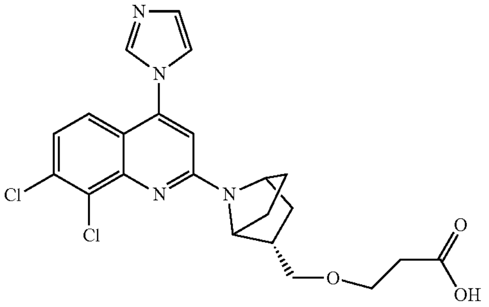 [SMILES: O=C(O)CCOC[C@H]1CC2CCC1N2c1cc(-n2ccnc2)c2ccc(Cl)c(Cl)c2n1] |
| I-812 | 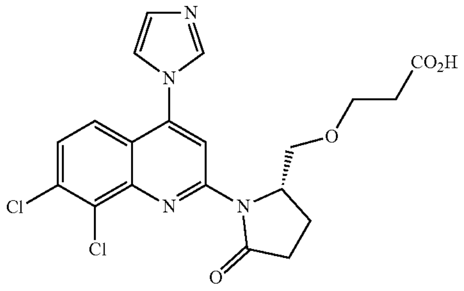 [SMILES: O=C(O)CCOC[C@@H]1CCC(=O)N1c1cc(-n2ccnc2)c2ccc(Cl)c(Cl)c2n1] |
| I-813 | 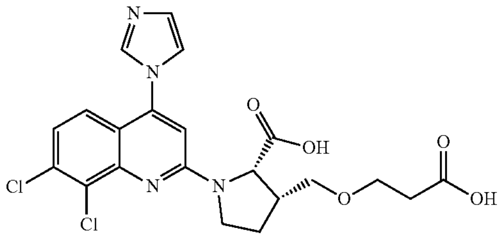 [SMILES: O=C(O)CCOC[C@@H]1CCN(c2cc(-n3ccnc3)c3ccc(Cl)c(Cl)c3n2)[C@@H]1C(=O)O] |
| I-814 | 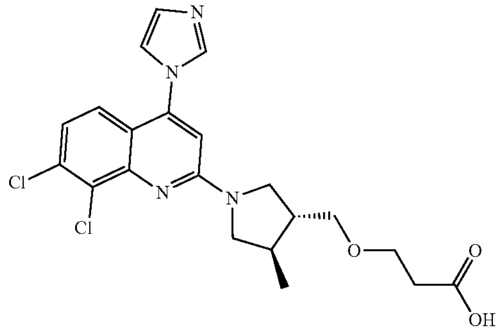 [SMILES: C[C@H]1CN(c2cc(-n3ccnc3)c3ccc(Cl)c(Cl)c3n2)C[C@@H]1COCCC(=O)O] |
| I-815 | 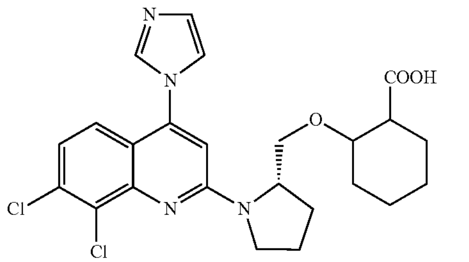 [SMILES: O=C(O)C1CCCCC1OC[C@@H]1CCCN1c1cc(-n2ccnc2)c2ccc(Cl)c(Cl)c2n1] |

| Exemplary Compounds | |
|---|---|
| I-# | Structure |
| I-816 | 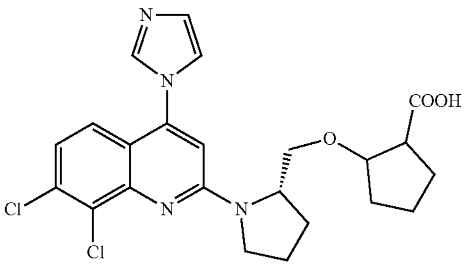 [SMILES: O=C(O)C1CCCC1OC[C@@H]1CCCN1c1cc(-n2ccnc2)c2ccc(Cl)c(Cl)c2n1] |
| I-817 | 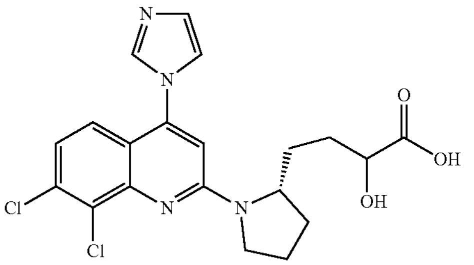 [SMILES: O=C(O)C(O)CC[C@@H]1CCCN1c1cc(-n2ccnc2)c2ccc(Cl)c(Cl)c2n1] |
| I-818 | 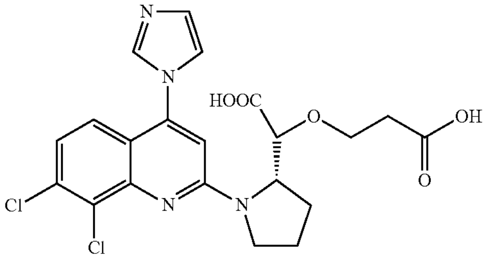 [SMILES: O=C(O)CCOC(C(=O)O)[C@@H]1CCCN1c1cc(-n2ccnc2)c2ccc(Cl)c(Cl)c2n1] |
| I-819 | 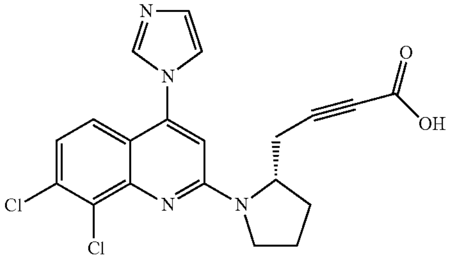 [SMILES: O=C(O)C#CC[C@@H]1CCCN1c1cc(-n2ccnc2)c2ccc(Cl)c(Cl)c2n1] |
| I-820 | 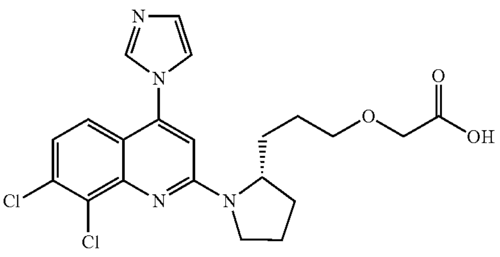 [SMILES: O=C(O)COCCC[C@@H]1CCCN1c1cc(-n2ccnc2)c2ccc(Cl)c(Cl)c2n1] |
| Exemplary Compounds | |
|---|---|
| I-# | Structure |
| I-821 | 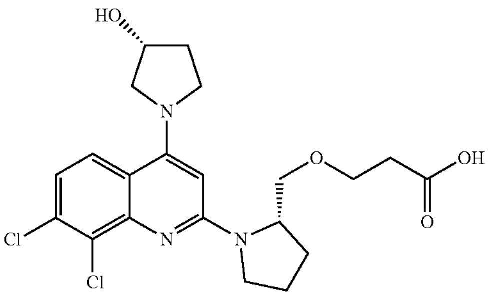 [SMILES: O=C(O)CCOC[C@@H]1CCCN1c1cc(N2CC[C@@H](O)C2)c2ccc(Cl)c(Cl)c2n1] |
| I-822 | 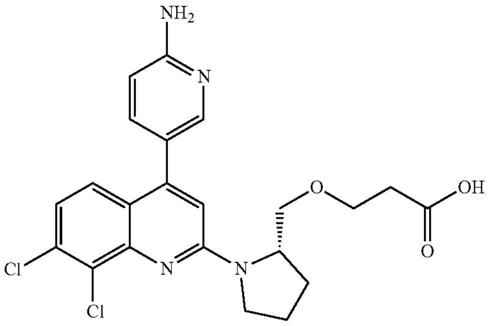 [SMILES: Nc1ccc(-c2cc(N3CCC[C@H]3COCCC(=O)O)nc3c(Cl)c(Cl)ccc23)cn1] |
| I-823 | 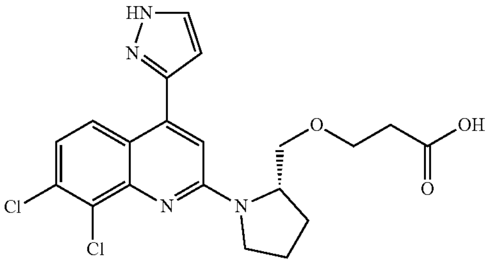 [SMILES: O=C(O)CCOC[C@@H]1CCCN1c1cc(-c2cc[nH]n2)c2ccc(Cl)c(Cl)c2n1] |
| I-824 | 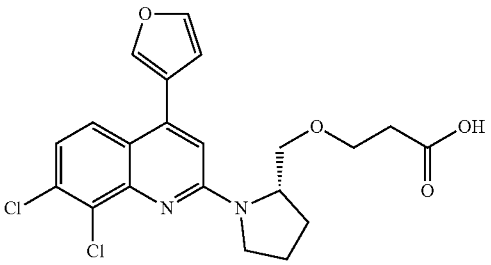 [SMILES: O=C(O)CCOC[C@@H]1CCCN1c1cc(-c2ccoc2)c2ccc(Cl)c(Cl)c2n1] |
| I-825 | 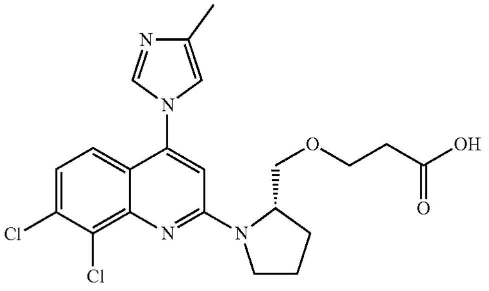 [SMILES: Cc1cn(-c2cc(N3CCC[C@H]3COCCC(=O)O)nc3c(Cl)c(Cl)ccc23)cn1] |

TABLE 1-continued
| Exemplary Compounds | |
|---|---|
| I-# | Structure |
| I-826 | 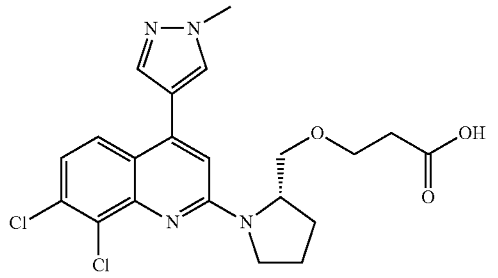 [SMILES: Cn1cc(-c2cc(N3CCC[C@H]3COCCC(=O)O)nc3c(Cl)c(Cl)ccc23)cn1] |
| I-827 | 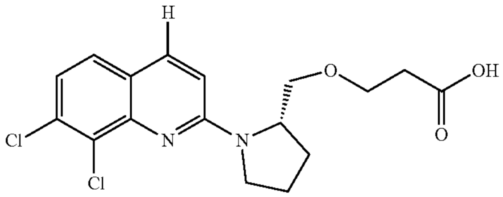 [SMILES: O=C(O)CCOC[C@@H]1CCCN1c1ccc2ccc(Cl)c(Cl)c2n1] |
| I-828 | 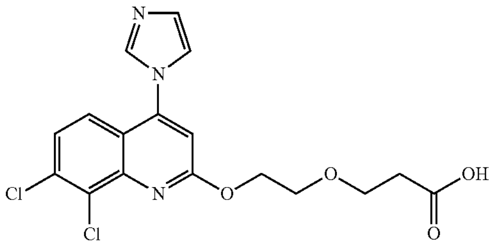 [SMILES: O=C(O)CCOCCOc1cc(-n2ccnc2)c2ccc(Cl)c(Cl)c2n1] |
| I-829 | 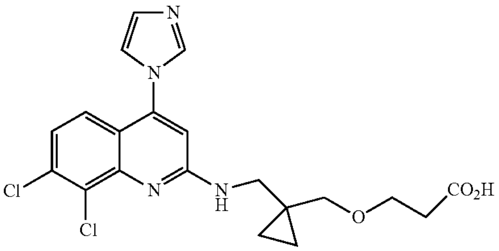 [SMILES: O=C(O)CCOCC1(CNc2cc(-n3ccnc3)c3ccc(Cl)c(Cl)c3n2)CC1] |
| I-830 | 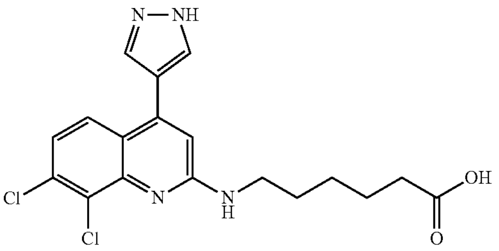 [SMILES: O=C(O)CCCCCNc1cc(-c2cn[nH]c2)c2ccc(Cl)c(Cl)c2n1] |
| I-831 | 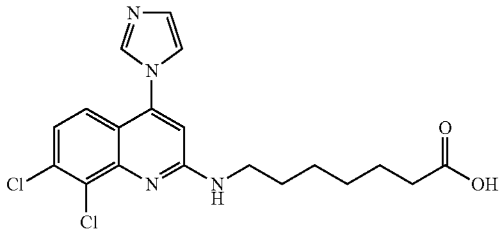 [SMILES: O=C(O)CCCCCCNc1cc(-n2ccnc2)c2ccc(Cl)c(Cl)c2n1] |
TABLE 1-continued
| Exemplary Compounds | |
|---|---|
| I-# | Structure |
| I-832 | 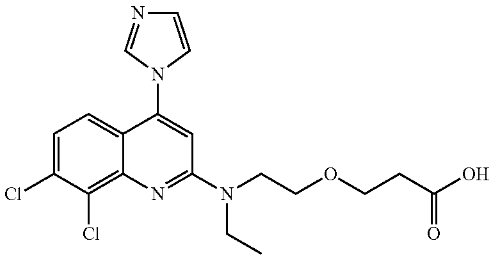 [SMILES: CCN(CCOCCC(=O)O)c1cc(-n2ccnc2)c2ccc(Cl)c(Cl)c2n1] |
| I-833 | 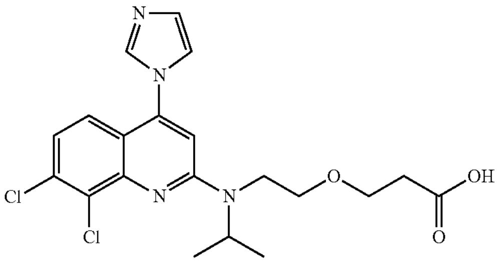 [SMILES: CC(C)N(CCOCCC(=O)O)c1cc(-n2ccnc2)c2ccc(Cl)c(Cl)c2n1] |
| I-834 | 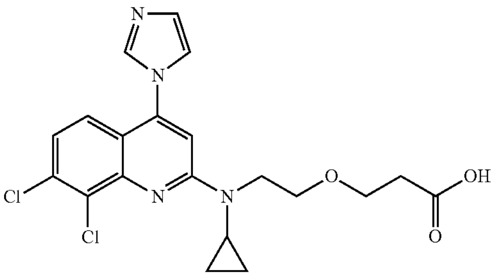 [SMILES: O=C(O)CCOCCN(c1cc(-n2ccnc2)c2ccc(Cl)c(Cl)c2n1)C1CC1] |
| I-835 | 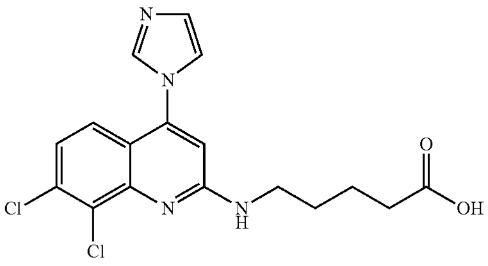 [SMILES: O=C(O)CCCCNc1cc(-n2ccnc2)c2ccc(Cl)c(Cl)c2n1] |
| I-836 | 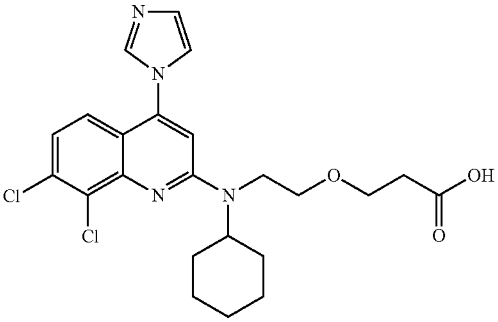 [SMILES: O=C(O)CCOCCN(c1cc(-n2ccnc2)c2ccc(Cl)c(Cl)c2n1)C1CCCCC1] |

TABLE 1-continued
Exemplary Compounds
| I-# | Structure |
|---|---|
| I-837 | 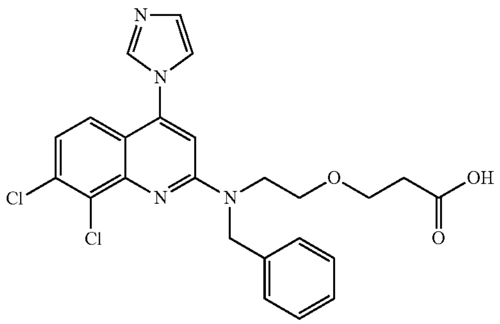 [SMILES: O=C(O)CCOCCN(Cc1ccccc1)c1cc(-n2ccnc2)c2ccc(Cl)c(Cl)c2n1] |
| I-838 | 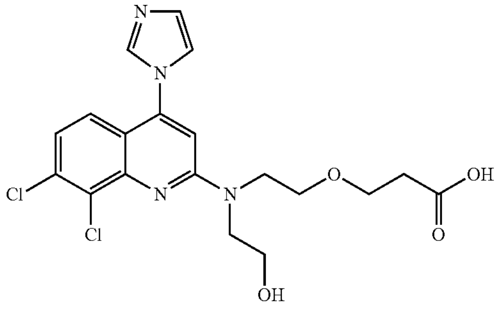 [SMILES: O=C(O)CCOCCN(CCO)c1cc(-n2ccnc2)c2ccc(Cl)c(Cl)c2n1] |
| I-839 | 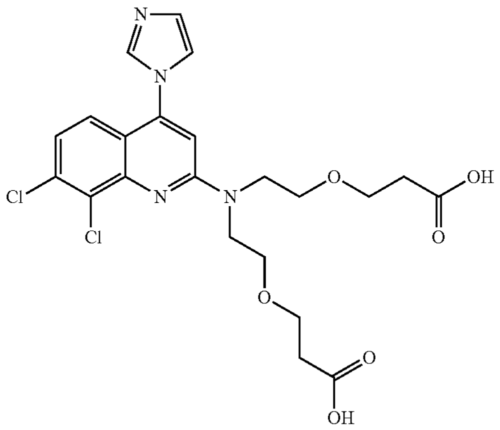 [SMILES: O=C(O)CCOCCN(CCOCCC(=O)O)c1cc(-n2ccnc2)c2ccc(Cl)c(Cl)c2n1] |
| I-840 | 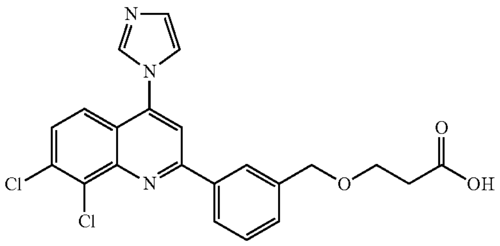 [SMILES: O=C(O)CCOCc1cccc(-c2cc(-n3ccnc3)c3ccc(Cl)c(Cl)c3n2)c1] |
TABLE 1-continued
Exemplary Compounds
| I-# | Structure |
|---|---|
| I-841 | 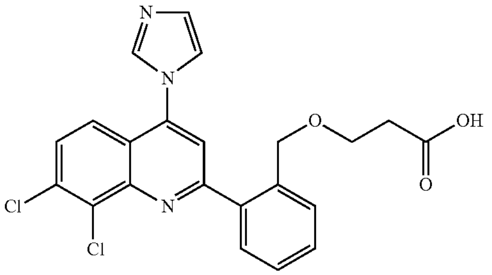 [SMILES: O=C(O)CCOCc1ccccc1-c1cc(-n2ccnc2)c2ccc(Cl)c(Cl)c2n1] |
| I-842 | 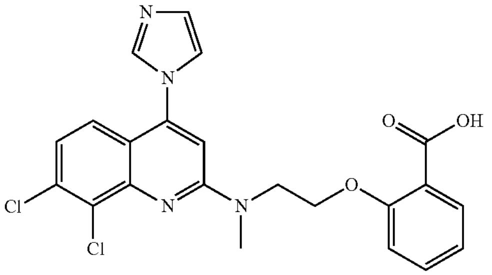 [SMILES: CN(CCOc1ccccc1C(=O)O)c1cc(-n2ccnc2)c2ccc(Cl)c(Cl)c2n1] |
| I-843 | 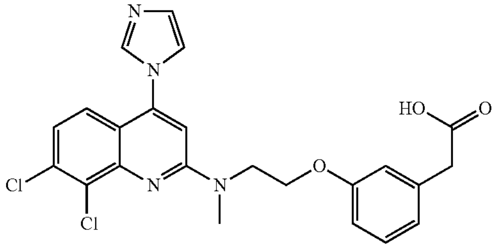 [SMILES: CN(CCOc1cccc(CC(=O)O)c1)c1cc(-n2ccnc2)c2ccc(Cl)c(Cl)c2n1] |
| I-844 | 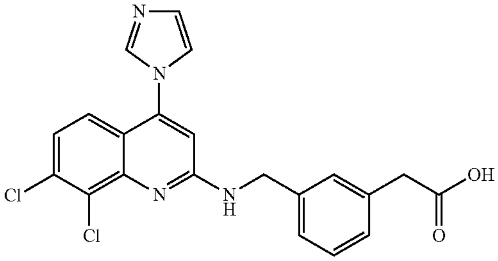 [SMILES: O=C(O)Cc1cccc(CNc2cc(-n3ccnc3)c3ccc(Cl)c(Cl)c3n2)c1] |
| I-845 | 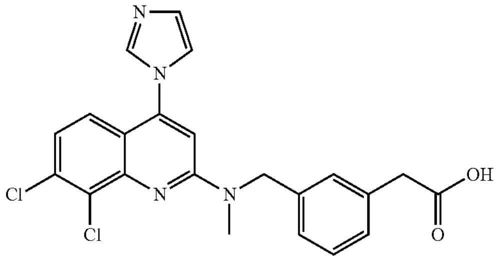 [SMILES: CN(Cc1cccc(CC(=O)O)c1)c1cc(-n2ccnc2)c2ccc(Cl)c(Cl)c2n1] |

TABLE 1-continued
Exemplary Compounds
| I-# | Structure |
| --- | --- |
| I-846 | 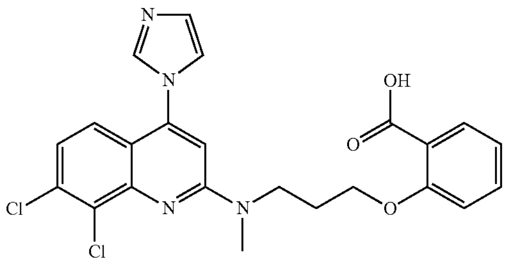 [SMILES: CN(CCCOc1ccccc1C(=O)O)c1cc(-n2ccnc2)c2ccc(Cl)c(Cl)c2n1] |
| I-847 | 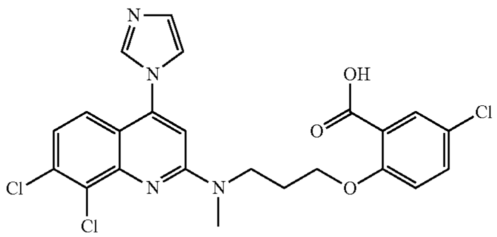 [SMILES: CN(CCCOc1ccc(Cl)cc1C(=O)O)c1cc(-n2ccnc2)c2ccc(Cl)c(Cl)c2n1] |
| I-848 | 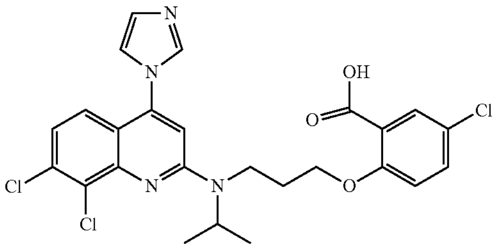 [SMILES: CC(C)N(CCCOc1ccc(Cl)cc1C(=O)O)c1cc(-n2ccnc2)c2ccc(Cl)c(Cl)c2n1] |
| I-849 | 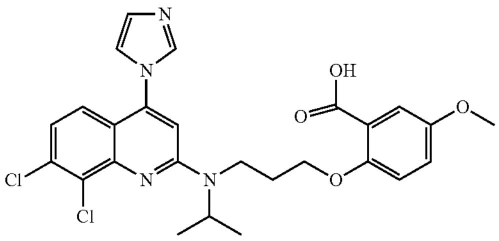 [SMILES: COc1ccc(OCCCN(c2cc(-n3ccnc3)c3ccc(Cl)c(Cl)c3n2)C(C)C)c(C(=O)O)c1] |
| I-850 | 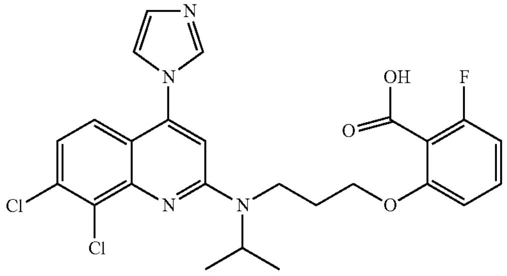 [SMILES: CC(C)N(CCCOc1cccc(F)c1C(=O)O)c1cc(-n2ccnc2)c2ccc(Cl)c(Cl)c2n1] |
| I-851 | 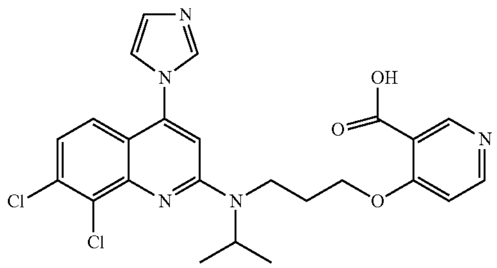 [SMILES: CC(C)N(CCCOc1ccncc1C(=O)O)c1cc(-n2ccnc2)c2ccc(Cl)c(Cl)c2n1] |
TABLE 1-continued
Exemplary Compounds
| I-# | Structure |
| --- | --- |
| I-852 | 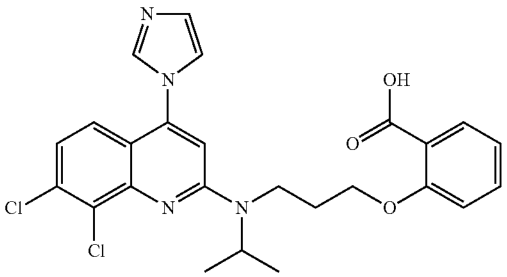 [SMILES: CC(C)N(CCCOc1ccccc1C(=O)O)c1cc(-n2ccnc2)c2ccc(Cl)c(Cl)c2n1] |
| I-853 | 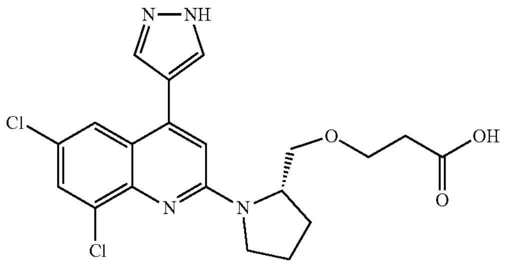 [SMILES: O=C(O)CCOC[C@@H]1CCCN1c1cc(-c2cn[nH]c2)c2cc(Cl)cc(Cl)c2n1] |
| I-854 | 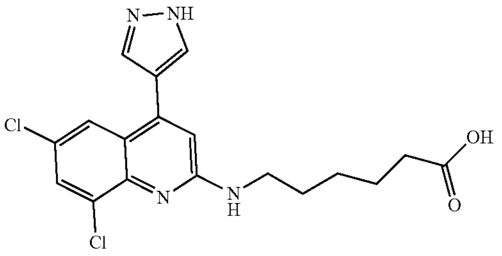 [SMILES: O=C(O)CCCCCNc1cc(-c2cn[nH]c2)c2cc(Cl)cc(Cl)c2n1] |
| I-855 | 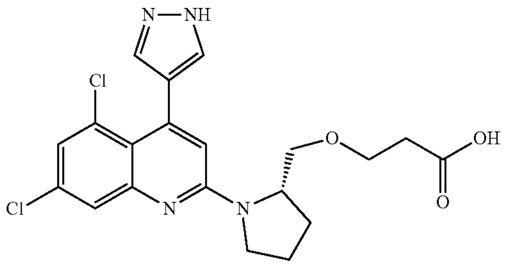 [SMILES: O=C(O)CCOC[C@@H]1CCCN1c1cc(-c2cn[nH]c2)c2c(Cl)cc(Cl)cc2n1] |
| I-856 | 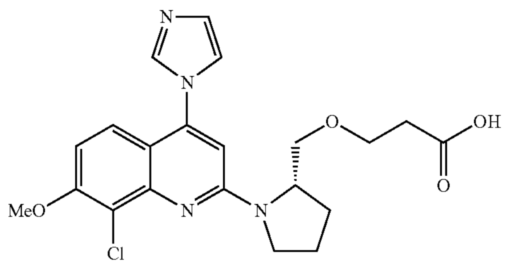 [SMILES: COc1ccc2c(-n3ccnc3)cc(N3CCC[C@H]3COCCC(=O)O)nc2c1Cl] |

TABLE 1-continued
| Exemplary Compounds | |
|---|---|
| I-# | Structure |
| I-857 | 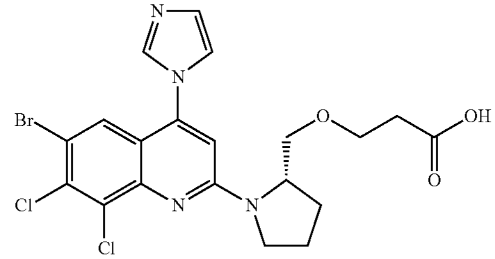 |
| I-858 | 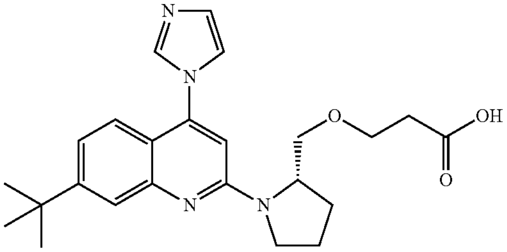 [SMILES: CC(C)(C)c1ccc2c(-n3ccnc3)cc(N3CCC[C@H]3COCCC(=O)O)nc2c1] |
| I-859 | 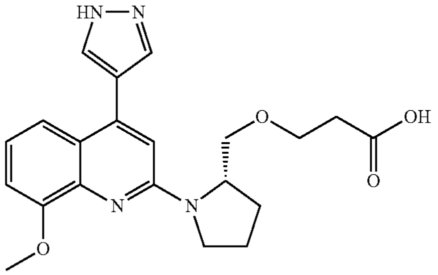 [SMILES: COc1cccc2c(-c3cn[nH]c3)cc(N3CCC[C@H]3COCCC(=O)O)nc12] |
| I-860 | 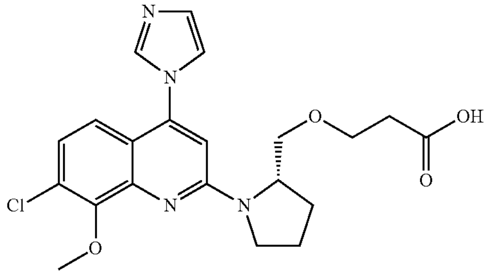 [SMILES: COc1c(Cl)ccc2c(-n3ccnc3)cc(N3CCC[C@H]3COCCC(=O)O)nc12] |
| I-861 | 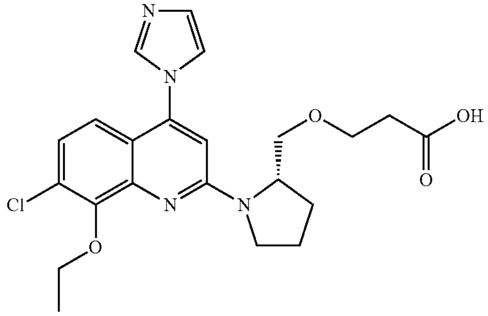 [SMILES: CCOc1c(Cl)ccc2c(-n3ccnc3)cc(N3CCC[C@H]3COCCC(=O)O)nc12] |
TABLE 1-continued
| Exemplary Compounds | |
|---|---|
| I-# | Structure |
| I-862 | 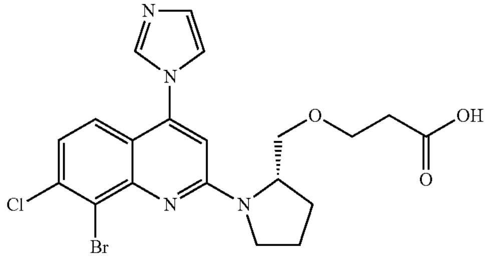 [SMILES: O=C(O)CCOC[C@@H]1CCCN1c1cc(-n2ccnc2)c2ccc(Cl)c(Br)c2n1] |
| I-863 | 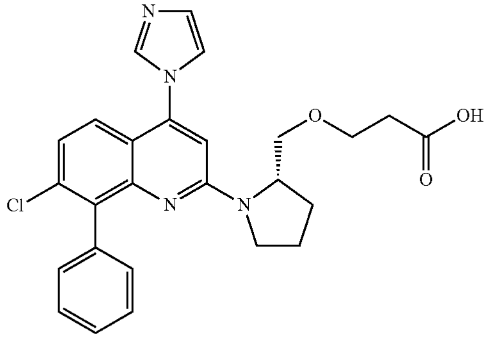 [SMILES: O=C(O)CCOC[C@@H]1CCCN1c1cc(-n2ccnc2)c2ccc(Cl)c(-c3ccccc3)c2n1] |
| I-864 | 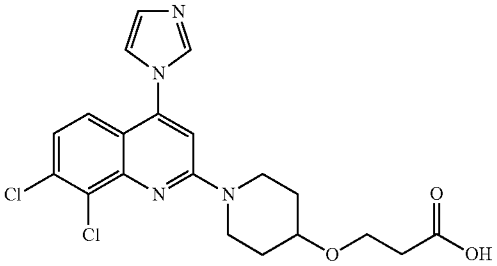 [SMILES: O=C(O)CCOC1CCN(c2cc(-n3ccnc3)c3ccc(Cl)c(Cl)c3n2)CC1] |
| I-865 | 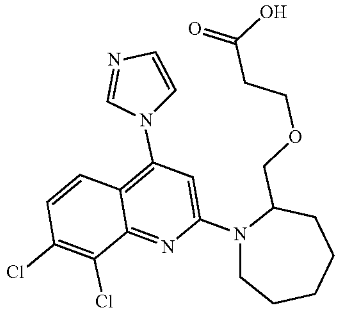 [SMILES: O=C(O)CCOCC1CCCCCN1c1cc(-n2ccnc2)c2ccc(Cl)c(Cl)c2n1] |
| I-866 | 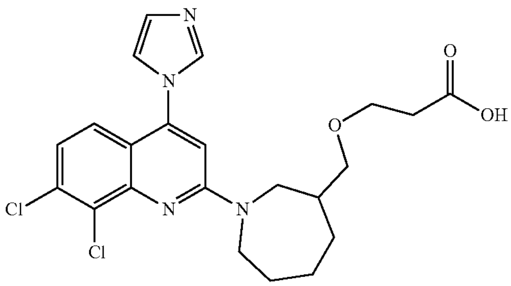 [SMILES: O=C(O)CCOCC1CCCCN(c2cc(-n3ccnc3)c3ccc(Cl)c(Cl)c3n2)C1] |

TABLE 1-continued
| Exemplary Compounds | |
|---|---|
| I-# | Structure |
| I-867 | 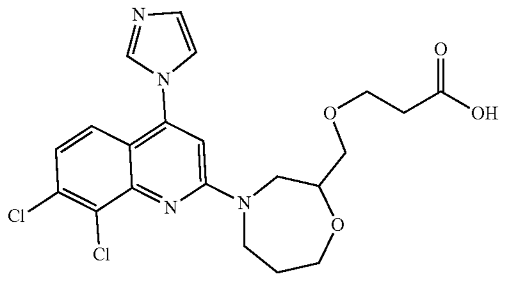 [SMILES: O=C(O)CCOCC1CN(c2cc(-n3ccnc3)c3ccc(Cl)c(Cl)c3n2)CCCO1] |
| I-868 | 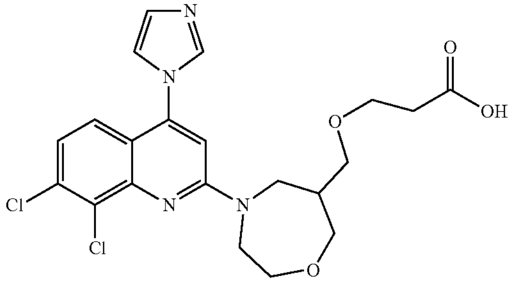 [SMILES: O=C(O)CCOCC1COCCN(c2cc(-n3ccnc3)c3ccc(Cl)c(Cl)c3n2)C1] |
| I-869 | 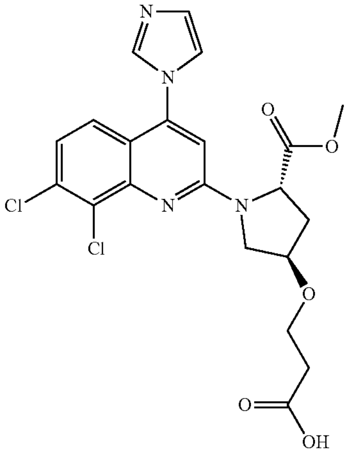 [SMILES: COC(=O)[C@@H]1C[C@@H](OCCC(=O)O)CN1c1cc(-n2ccnc2)c2ccc(Cl)c(Cl)c2n1] |
| I-870 | 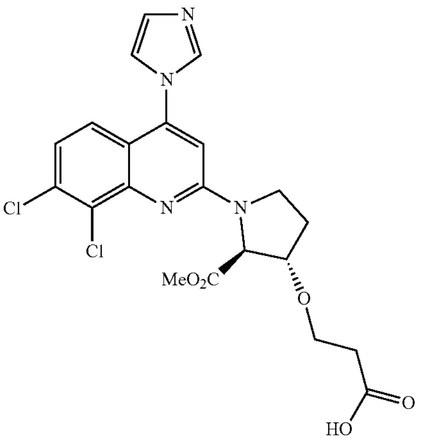 [SMILES: COC(=O)[C@@H]1[C@@H](OCCC(=O)O)CCN1c1cc(-n2ccnc2)c2ccc(Cl)c(Cl)c2n1] |
TABLE 1-continued
| Exemplary Compounds | |
|---|---|
| I-# | Structure |
| I-871 | 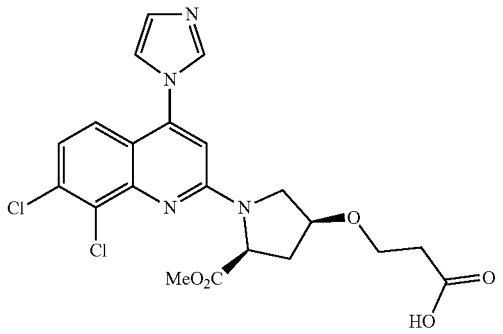 [SMILES: COC(=O)[C@@H]1C[C@H](OCCC(=O)O)CN1c1cc(-n2ccnc2)c2ccc(Cl)c(Cl)c2n1] |
| I-872 | 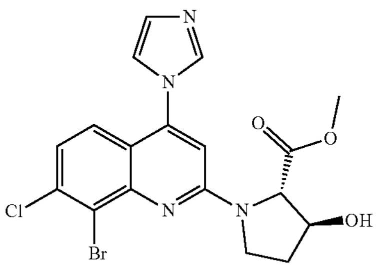 [SMILES: COC(=O)[C@@H]1[C@@H](O)CCN1c1cc(-n2ccnc2)c2ccc(Cl)c(Br)c2n1] |
| I-873 | 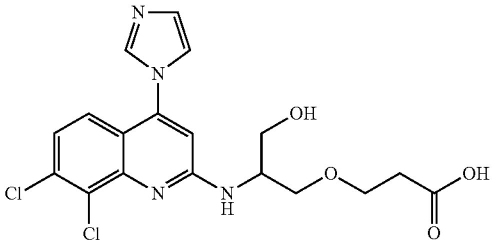 [SMILES: O=C(O)CCOCC(CO)Nc1cc(-n2ccnc2)c2ccc(Cl)c(Cl)c2n1] |
| I-874 | 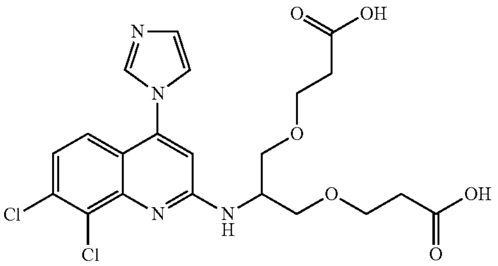 [SMILES: O=C(O)CCOCC(COCCC(=O)O)Nc1cc(-n2ccnc2)c2ccc(Cl)c(Cl)c2n1] |
| I-875 | 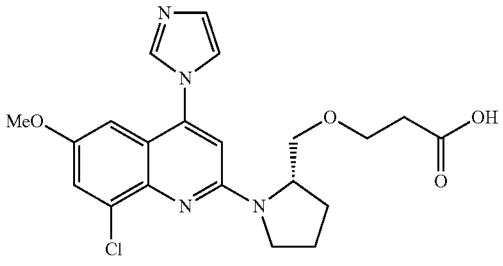 [SMILES: COc1cc(Cl)c2nc(N3CCC[C@H]3COCCC(=O)O)cc(-n3ccnc3)c2c1] |

TABLE 1-continued
| Exemplary Compounds | |
|---|---|
| I-# | Structure |
| I-876 | 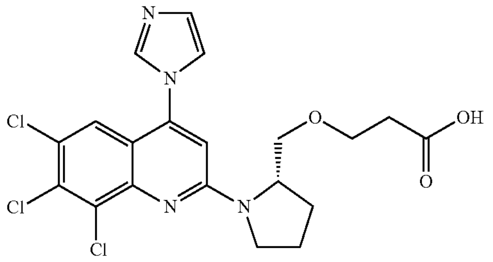 [SMILES: O=C(O)CCOC[C@@H]1CCCN1c1cc(-n2ccnc2)c2cc(Cl)c(Cl)c(Cl)c2n1] |
| I-877 | 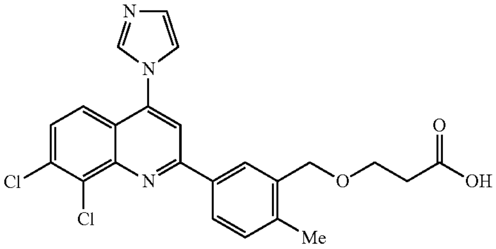 [SMILES: Cc1ccc(-c2cc(-n3ccnc3)c3ccc(Cl)c(Cl)c3n2)cc1COCCC(=O)O] |
| I-878 | 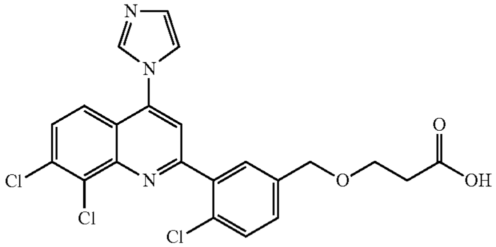 [SMILES: O=C(O)CCOCc1ccc(Cl)c(-c2cc(-n3ccnc3)c3ccc(Cl)c(Cl)c3n2)c1] |
| I-879 | 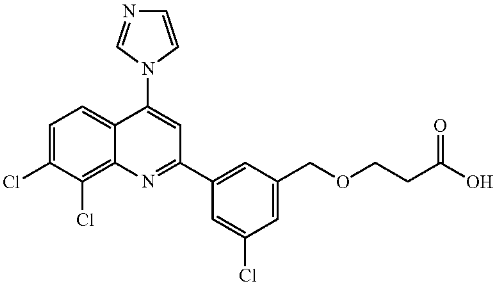 [SMILES: O=C(O)CCOCc1cc(Cl)cc(-c2cc(-n3ccnc3)c3ccc(Cl)c(Cl)c3n2)c1] |
| I-880 | 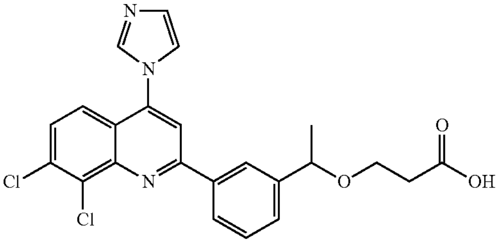 [SMILES: CC(OCCC(=O)O)c1cccc(-c2cc(-n3ccnc3)c3ccc(Cl)c(Cl)c3n2)c1] |
TABLE 1-continued
| Exemplary Compounds | |
|---|---|
| I-# | Structure |
| I-881 | 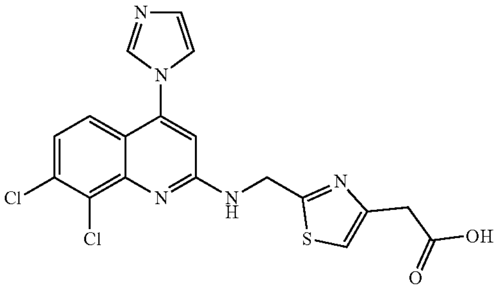 [SMILES: O=C(O)Cc1csc(CNc2cc(-n3ccnc3)c3ccc(Cl)c(Cl)c3n2)n1] |
| I-882 | 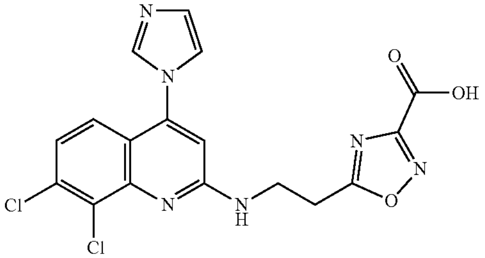 [SMILES: O=C(O)c1noc(CCNc2cc(-n3ccnc3)c3ccc(Cl)c(Cl)c3n2)n1] |
| I-883 | 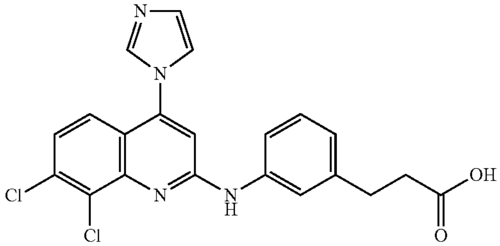 [SMILES: O=C(O)CCc1cccc(Nc2cc(-n3ccnc3)c3ccc(Cl)c(Cl)c3n2)c1] |
| I-884 | 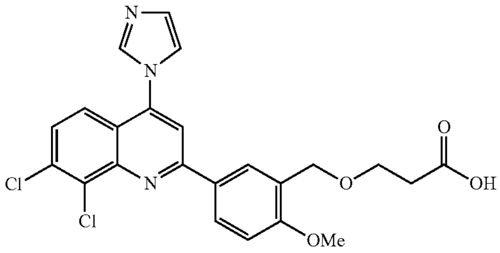 [SMILES: COc1ccc(-c2cc(-n3ccnc3)c3ccc(Cl)c(Cl)c3n2)cc1COCCC(=O)O] |
| I-885 | 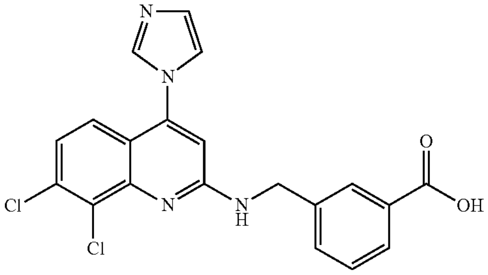 [SMILES: O=C(O)c1cccc(CNc2cc(-n3ccnc3)c3ccc(Cl)c(Cl)c3n2)c1] |

TABLE 1-continued

| Exemplary Compounds | |
|---|---|
| I-# | Structure |
| I-886 | 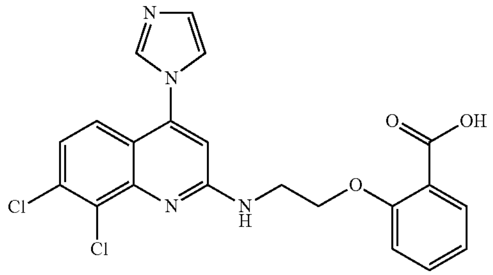 [SMILES: O=C(O)c1ccccc1OCCNc1cc(-n2ccnc2)c2ccc(Cl)c(Cl)c2n1] |
| I-887 | 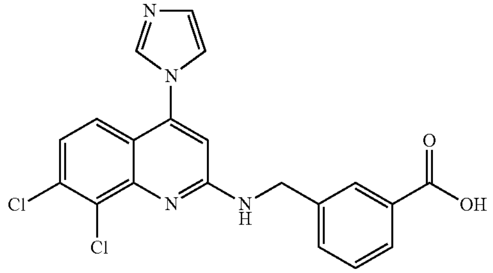 [SMILES: O=C(O)c1cccc(CNc2cc(-n3ccnc3)c3ccc(Cl)c(Cl)c3n2)c1] |
| I-888 | 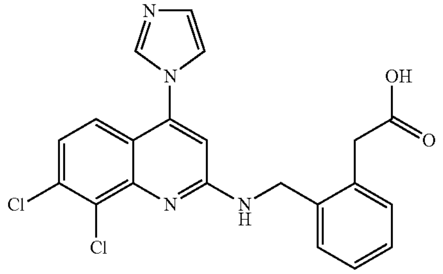 [SMILES: O=C(O)Cc1ccccc1CNc1cc(-n2ccnc2)c2ccc(Cl)c(Cl)c2n1] |
| I-889 | 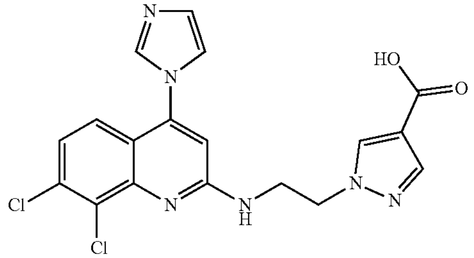 [SMILES: O=C(O)c1cnn(CCNc2cc(-n3ccnc3)c3ccc(Cl)c(Cl)c3n2)c1] |
| I-890 | 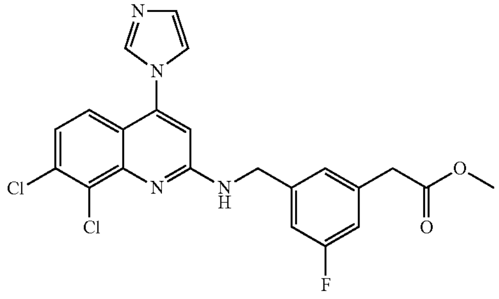 [SMILES: COC(=O)Cc1cc(F)cc(CNc2cc(-n3ccnc3)c3ccc(Cl)c(Cl)c3n2)c1] |

TABLE 1-continued

| Exemplary Compounds | |
|---|---|
| I-# | Structure |
| I-891 | 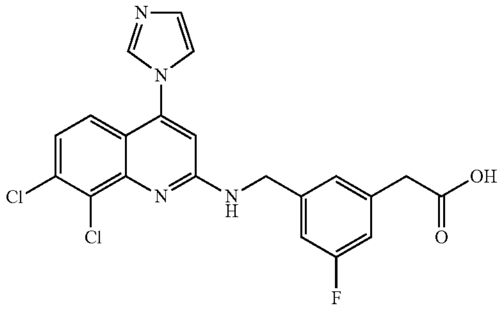 [SMILES: O=C(O)Cc1cc(F)cc(CNc2cc(-n3ccnc3)c3ccc(Cl)c(Cl)c3n2)c1] |

In some embodiments, the present disclosure provides a compound set forth in Table 1, above, or a pharmaceutically acceptable salt thereof.

3.3. Pharmaceutical Compositions of the Present Compounds

While it is possible that, for use in therapy, a provided compound may be administered as the raw chemical, it is possible to present the provided compound as the active ingredient in a pharmaceutical composition. Such compositions can be prepared in a manner well known in the pharmaceutical art and comprise at least one active compound. Accordingly in one embodiment, the disclosure further provides pharmaceutical compositions comprising a provided compound or a pharmaceutically acceptable salt thereof and one or more pharmaceutically acceptable excipients. The excipient(s) must be acceptable in the sense of being compatible with the other ingredients of the composition and not deleterious to the recipient thereof. In accordance with another aspect of the disclosure there is also provided a process for the preparation of a pharmaceutical composition including a provided compound or pharmaceutically acceptable salt thereof, with one or more pharmaceutically acceptable excipients. The pharmaceutical composition can be for use in the treatment and/or prophylaxis of any of the conditions described herein.

Generally, a provided compound is administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like. Pharmaceutical compositions may be presented in unit dose forms containing a predetermined amount of active ingredient per unit dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions.

Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert excipient such as ethanol, glycerol, water and the like. Powders are prepared by reducing the compound to a suitable fine size and mixing with a similarly prepared pharmaceutical excipient such as an edible carbohydrate, as, for example, starch or mannitol. Flavoring, preservative, dispersing and coloring agent can also be present.

Capsules are made by preparing a powder mixture, as described above, and filling formed gelatin sheaths. Excipients including glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, excipients including suitable binders, glidants, lubricants, sweetening agents, flavors, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing a provided compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. A provided compound can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, suspensions, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like.

The compounds of the disclosure may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspension drops, gels or dry powders.

Compositions for intranasal administration include aqueous compositions administered to the nose by drops or by pressurized pump. Suitable compositions contain water as the diluent or carrier for this purpose. Compositions for administration to the lung or nose may contain one or more excipients, for example one or more suspending agents, one or more preservatives, one or more surfactants, one or more tonicity adjusting agents, one or more co-solvents, and may include components to control the pH of the composition, for example a buffer system. Further, the compositions may contain other excipients such as antioxidants, for example sodium metabisulphite, and taste-masking agents. Compositions may also be administered to the nose or other regions of the respiratory tract by nebulization. Intranasal compositions may permit a provided compound or pharmaceutically acceptable salt thereof to be delivered to all areas of the nasal cavities (the target tissue) and further, may permit the provided compound or pharmaceutically acceptable salt thereof to remain in contact with the target tissue for longer periods of time. A suitable dosing regimen for intranasal compositions would be for the patient to inhale slowly through the nose subsequent to the nasal cavity being cleared. During inhalation, the composition would be administered to one nostril while the other is manually compressed. This procedure would then be repeated for the other nostril. Typically, one or two sprays per nostril would be administered by the above procedure one, two, or three times each day, ideally once daily. Of particular interest are intranasal compositions suitable for once-daily administration.

The suspending agent(s), if included, will typically be present in an amount of from 0.1 to 5% (w/w), such as from 1.5% to 2.4% (w/w), based on the total weight of the composition. Examples of pharmaceutically acceptable suspending agents include, but are not limited to, Avicef (microcrystalline cellulose and carboxymethylcellulose sodium), carboxymethylcellulose sodium, veegum, tragacanth, bentonite, methylcellulose, xanthan gum, carbopol and polyethylene glycols.

Compositions for administration to the lung or nose may contain one or more excipients may be protected from microbial or fungal contamination and growth by inclusion of one or more preservatives. Examples of pharmaceutically acceptable antimicrobial agents or preservatives include, but are not limited to, quaternary ammonium compounds (for example benzalkonium chloride, benzethonium chloride, cetrimide, cetylpyridinium chloride, lauralkonium chloride and myristyl picolinium chloride), mercurial agents (for example phenylmercuric nitrate, phenylmercuric acetate and thimerosal), alcoholic agents (for example chlorobutanol, phenylethyl alcohol and benzyl alcohol), antibacterial esters (for example esters of p-hydroxybenzoic acid), chelating agents such as disodium edetate (EDTA) and other antimicrobial agents such as chlorhexidine, chlorocresol, sorbic acid and its salts (such as potassium sorbate) and polymyxin. Examples of pharmaceutically acceptable antifungal agents or preservatives include, but are not limited to, sodium benzoate, sorbic acid, sodium propionate, methylparaben, ethylparaben, propylparaben, and butylparaben. The preservative(s), if included, may be present in an amount of from 0.001 to 1% (w/w), such as from 0.015% to 0.5% (w/w) based on the total weight of the composition. Compositions (for example wherein at least one compound is in suspension) may include one or more surfactants which functions to facilitate dissolution of the medicament particles in the aqueous phase of the composition. For example, the amount of surfactant used is an amount which will not cause foaming during mixing. Examples of pharmaceutically acceptable surfactants include fatty alcohols, esters, and ethers, such as polyoxyethylene (20) sorbitan monooleate (Polysorbate 80), macrogol ethers, and poloxamers. The surfactant may be present in an amount of between about 0.01 to 10% (w/w), such as from 0.01 to 0.75% (w/w), for example about 0.5% (w/w), based on the total weight of the composition.

One or more tonicity-adjusting agent(s) may be included to achieve tonicity with body fluids (e.g., fluids of the nasal cavity) resulting in reduced levels of irritancy. Examples of pharmaceutically acceptable tonicity-adjusting agents include, but are not limited to, sodium chloride, dextrose, xylitol, calcium chloride, glucose, glycerine, and sorbitol. A tonicity-adjusting agent, if present, may be included in an amount of from 0.1 to 10% (w/w), such as from 4.5 to 5.5% (w/w), for example about 5.0% (w/w), based on the total weight of the composition.

The compositions of the disclosure may be buffered by the addition of suitable buffering agents such as sodium citrate, citric acid, trometamol, phosphates such as disodium phosphate (e.g., dodecahydrate, heptahydrate, dihydrate and anhydrous forms), or sodium phosphate and mixtures thereof.

A buffering agent, if present, may be included in an amount of from 0.1 to 5% (w/w), for example 1 to 3% (w/w) based on the total weight of the composition.

Examples of taste-masking agents include sucralose, sucrose, saccharin or a salt thereof, fructose, dextrose, glycerol, corn syrup, aspartame, acesulfame-K, xylitol, sorbitol, erythritol, ammonium glycyrrhizinate, thaumatin, neotame, mannitol, menthol, eucalyptus oil, camphor, a natural flavoring agent, an artificial flavoring agent, and combinations thereof.

One or more co-solvent may be included to aid solubility of the medicament compound(s) and/or other excipients. Examples of pharmaceutically acceptable co-solvents include, but are not limited to, propylene glycol, dipropylene glycol, ethylene glycol, glycerol, ethanol, polyethylene glycols (for example PEG300 or PEG400), and methanol. In one embodiment, the co-solvent is propylene glycol.

Co-solvent(s), if present, may be included in an amount of from 0.05 to 30% (w/w), such as from 1 to 25% (w/w), for example from 1 to 10% (w/w) based on the total weight of the composition.

Compositions for inhaled administration include aqueous, organic or aqueous/organic mixtures, dry powder or crystalline compositions administered to the respiratory tract by pressurized pump or inhaler, for example, reservoir dry powder inhalers, unit-dose dry powder inhalers, pre-metered multi-dose dry powder inhalers, nasal inhalers or pressurized aerosol inhalers, nebulizers or insufflators. Suitable compositions contain water as the diluent or carrier for this purpose and may be provided with conventional excipients such as buffering agents, tonicity modifying agents and the like. Aqueous compositions may also be administered to the nose and other regions of the respiratory tract by nebulization. Such compositions may be aqueous solutions or suspensions or aerosols delivered from pressurized packs, such as a metered dose inhaler, with the use of a suitable liquefied propellant.

Compositions for administration topically to the nose (for example, for the treatment of rhinitis) or to the lung, include pressurized aerosol compositions and aqueous compositions delivered to the nasal cavities by pressurized pump. Compositions which are non-pressurized and are suitable for administration topically to the nasal cavity are of particular interest. Suitable compositions contain water as the diluent or carrier for this purpose. Aqueous compositions for administration to the lung or nose may be provided with conventional excipients such as buffering agents, tonicity-modifying agents and the like. Aqueous compositions may also be administered to the nose by nebulization.

A fluid dispenser may typically be used to deliver a fluid composition to the nasal cavities. The fluid composition may be aqueous or non-aqueous, but typically aqueous. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity.

Dry powder compositions for topical delivery to the lung by inhalation may, for example, be presented in capsules and cartridges of for example gelatin, or blisters of for example laminated aluminum foil, for use in an inhaler or insufflator. Powder blend compositions generally contain a powder mix for inhalation of a provided compound or pharmaceutically acceptable salt thereof and a suitable powder base (carrier/diluent/excipient substance) such as mono-, di-, or polysaccharides (e.g., lactose or starch). Dry powder compositions may also include, in addition to the drug and carrier, a further excipient (e.g., a ternary agent such as a sugar ester for example cellobiose octaacetate, calcium stearate, or magnesium stearate.

Pharmaceutical compositions adapted for parental administration include aqueous and nonaqueous sterile injection solutions which may contain antioxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (e.g., lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the compositions may include other agents conventional in the art having regard to the type of formulation in question, for example, those suitable for oral administration may include flavoring agents.

3.4. Uses of the Present Pharmaceutical Compositions and Compounds in Therapy A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or more usually in a number (e.g., two, three, four, five, or six) of sub-doses per day such that the total daily dose is the same.

Suitably, the amount of the compound of the present disclosure administered may be an amount selected from 0.01 mg to 10 g per day (calculated as the free or unsalted compound).

In some embodiments, a provided compound or a pharmaceutically acceptable salt thereof may be employed alone or in combination with other therapeutic agents. A provided compound or a pharmaceutically acceptable salt thereof and the other pharmaceutically active agent(s) may be administered together or separately and, when administered separately, administration may occur simultaneously or sequentially, in any order, by any convenient route in separate or combined pharmaceutical compositions. The amounts of a provided compound or a pharmaceutically acceptable salt thereof and the other pharmaceutically active agent(s) and the relative timings of administration will be selected in order to achieve the desired combined therapeutic effect. A provided compound or a pharmaceutically acceptable salt thereof and further therapeutic agent(s) may be employed in combination by administration simultaneously in a unitary pharmaceutical composition including both compounds. Alternatively, the combination may be administered separately in separate pharmaceutical compositions, each including one of the compounds in a sequential manner wherein, for example, the compound of the present disclosure is administered first and the other second and vice versa. Such sequential administration may be close in time (e.g. simultaneously) or remote in time. Furthermore, it does not matter if the compounds are administered in the same dosage form, e.g., one compound may be administered topically and the other compound may be administered orally. Suitably, both compounds are administered orally.

The combinations may be presented as a combination kit. By the term "combination kit" "or kit of parts" as used herein is meant the pharmaceutical composition or compositions that are used to administer the combination according to the present disclosure. When both compounds are administered simultaneously, the combination kit can contain both compounds in a single pharmaceutical composition, such as a tablet, or in separate pharmaceutical compositions. When the compounds are not administered simultaneously, the combination kit will contain each compound in separate pharmaceutical compositions either in a single package or in separate pharmaceutical compositions in separate packages. The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited. For example, one agent may be administered once a day, and the other agent may be administered 2 or 3 times a day, or one agent may be administered once a week, and the other agent may be administered once a day and the like. It will be clear to a person skilled in the art that, where appropriate, the other therapeutic ingredients(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

When combined in the same composition it will be appreciated that the two compounds must be stable and compatible with each other and the other components of the composition and may be formulated for administration. When formulated separately they may be provided in any convenient composition, conveniently, in such a manner as known for such compounds in the art.

When a provided compound or a pharmaceutically acceptable salt thereof is used in combination with a second therapeutic agent active against the same disease, condition, or disorder, the dose of each compound may differ from that when the compound is used alone. Appropriate doses will be readily appreciated by those skilled in the art.

In one embodiment, the mammal in the methods and uses of the present disclosure is a human. The provided compounds or pharmaceutically acceptable salts thereof are useful in the treatment of diseases and conditions in which modulation of cGAS is beneficial. As modulators of the immune response, a provided compound or a pharmaceutically acceptable salts thereof may also be useful, as stand-alone, in combination or as adjuvants, in the treatment of diseases and conditions in which modulation of cGAS is beneficial.

In one embodiment, the disease or condition is an inflammatory, allergic, or autoimmune diseases such as systemic lupus erythematosus, psoriasis, insulin-dependent diabetes mellitus (IDDM), scleroderma, Aicardi Goutieres syndrome, dermatomyositis, inflammatory bowel diseases, multiple sclerosis, rheumatoid arthritis, and Sjogren's syndrome (SS).

In another embodiment, the disease or condition is an infectious disease such as bacterial, viral or parasitic disease in which modulation of cGAS activity is beneficial.

In another embodiment, the disease or condition is a senescence- or age-related disease, including a neurodegenerative disease such as Alzheimer's or Parkinson disease, cardiovascular diseases such as atherosclerosis or myocardial infarction, liver or renal diseases, cancer, or premature aging.

Inflammation represents a group of vascular, cellular, and neurological responses to trauma. Inflammation can be characterized as the movement of inflammatory cells such as monocytes, neutrophils, and granulocytes into the tissues. This is usually associated with reduced endothelial barrier function and edema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (e.g., in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self-tissues. The aim of anti-inflammatory therapy is therefore to reduce this inflammation, to inhibit autoimmunity when present and to allow for the physiological process or healing and tissue repair to progress.

In some embodiments, a provided compound or a pharmaceutically acceptable salt thereof may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knew, ankle, and foot, and conditions affecting tissues connecting muscles to bones such as tendons. Examples of musculoskeletal inflammation which may be treated with compounds of the present disclosure include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic). Ocular inflammation refers to inflammation of any structure of the eye, including the eye lids. Examples of ocular inflammation which may be treated with the compounds of the present disclosure include blepharitis, blepharochalasis, conjunctivitis, dacryoadenitis, keratitis, keratoconjunctivitis sicca (dry eye), scleritis, trichiasis, and uveitis. Examples of inflammation of the nervous system which may be treated with the compounds of the present disclosure include encephalitis, Guillain-Barre syndrome, meningitis, neuromyotonia, narcolepsy, multiple sclerosis, myelitis, and schizophrenia.

Examples of inflammation of the vasculature or lymphatic system which may be treated with a provided compound or a pharmaceutically acceptable salt thereof include arthrosclerosis, arthritis, phlebitis, vasculitis, and lymphangitis.

Examples of inflammatory conditions of the digestive system which may be treated with a provided compound or a pharmaceutically acceptable salt thereof include cholangitis, cholecystitis, enteritis, enterocolitis, gastritis, gastroenteritis, inflammatory bowel disease (such as Crohn's disease and ulcerative colitis), ileitis, and proctitis.

Examples of inflammatory conditions of the reproductive system which may be treated with a provided compound or a pharmaceutically acceptable salt thereof include cervicitis, chorioamnionitis, endometritis, epididymitis, omphalitis, oophoritis, orchitis, salpingitis, tubo-ovarian abscess, urethritis, vaginitis, vulvitis, and vulvodynia.

The agents may be used to treat autoimmune conditions having an inflammatory component. Such conditions include systemic lupus erythematosus, acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome. Grave's disease, Guillain-Barre syndrome, Hashimoto's disease, Henoch-Schonlein purpura, Kawasaki's disease, microscopic colitis, microscopic polyarteritis, mixed connective tissue disease, multiple sclerosis, myasthenia gravis, opsoclonus myoclonus syndrome, optic neuritis, ord's thyroiditis, pemphigus, polyarteritis nodosa, polymyalgia, rheumatoid arthritis, Reiter's syndrome, Sjogren's syndrome, Aicardi Goutières syndrome, temporal arteritis, Wegener's granulomatosis, warm autoimmune haemolytic anemia, interstitial cystitis, lyme disease, morphea, psoriasis, sarcoidosis, scleroderma, ulcerative colitis, and vitiligo.

In some embodiments, a provided compound or a pharmaceutically acceptable salt thereof may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celliac disease).

Other inflammatory conditions which may be treated with a provided compound or a pharmaceutically acceptable salt thereof include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xenografts, serum sickness, and graft vs host disease), acute pancreatitis, chronic pancreatitis, acute respiratory distress syndrome. Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukemia and lymphomas in adults, acute leukemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis. Type 1 diabetes, asthma, inflammatory bowel disease, systemic lupus erythematosis, psoriasis, chronic pulmonary disease, and inflammation accompanying infectious conditions (e.g., sepsis).

In some embodiments, the disclosure provides a provided compound or a pharmaceutically acceptable salt thereof for use in the treatment of an inflammatory, allergic, or autoimmune disease.

In some embodiments, the disclosure provides a method of treating an inflammatory, allergic, or autoimmune disease comprising: administering to a patient in need thereof a therapeutically effective amount of a provided compound or a pharmaceutically acceptable salt thereof.

In some embodiments, the disclosure provides the use of a provided compound or a pharmaceutically acceptable salt thereof in the manufacture of a medicament for the treatment of an inflammatory, allergic, or autoimmune disease.

In some embodiments, a provided compound or a pharmaceutically acceptable salts thereof may be used in combination with one or more other agents in the prevention or treatment of an allergic inflammatory autoimmune disease, wherein such other agents can include: antigen immunotherapy agents; antihistamines; steroids, NSAIDs; bronchodilators (e.g. beta 2 agonists, adrenergic agonists, anticholinergic agents, theophylline); methotrexate; leukotriene modulators; monoclonal antibody agents such as anti-lgE, anti-TNF, anti-IL-5, anti-IL-6, anti-IL-12, anti-IL-1 and similar agents; receptor therapies agents such as entanercept; and antigen non-specific immunotherapeutic agents such interferon or other cytokines/chemokines, cytokine/chemokine receptor modulators, cytokine agonists or antagonists, and TLR antagonist.

In some embodiments, the present disclosure provides a pharmaceutical composition comprising a provided compound or a pharmaceutically acceptable salt thereof, and at least one further therapeutic agent useful in the treatment of an allergic, inflammatory, or autoimmune disease.

In some embodiments, the present disclosure provides a pharmaceutical composition comprising a provided compound or a pharmaceutically acceptable salt thereof, and at least one further therapeutic agent useful in the treatment of an allergic, inflammatory, or autoimmune disease for use in therapy.

In some embodiments, the present disclosure provides a pharmaceutical composition comprising a provided compound or pharmaceutically acceptable salt thereof, and at least one further therapeutic agent useful in the treatment of an allergic inflammatory or autoimmune disease, for use in the treatment of allergic, inflammatory, or autoimmune disease.

In some embodiments, the present disclosure provides the use of a pharmaceutical composition comprising a provided compound or a pharmaceutically acceptable salt thereof, and at least one further therapeutic agent useful in the treatment of an allergic, inflammatory, or autoimmune disease in the manufacture of a medicament for the treatment of an allergic, inflammatory or autoimmune disease.

In some embodiments, the present disclosure provides a method of treating an allergic, inflammatory or autoimmune disease comprising: administering to a patient in need thereof a therapeutically effective amount of a pharmaceutical composition comprising a provided compound or a pharmaceutically acceptable salt thereof, and at least one further therapeutic agent useful in the treatment of an allergic, inflammatory, or autoimmune disease.

In some embodiments, the present disclosure provides a pharmaceutical composition comprising a provided compound or a pharmaceutically acceptable salt thereof, at least one further therapeutic agent useful in the treatment of an allergic, inflammatory, or autoimmune disease, and one or more of pharmaceutically acceptable excipients.

In some embodiments, the present disclosure provides a provided compound or a pharmaceutically acceptable salt thereof, for use in the treatment of an infectious disease.

In some embodiments, the present disclosure provides a method of treating an infectious disease comprising administering to a patient in need thereof a therapeutically effective amount of a provided compound or a pharmaceutically acceptable salt thereof.

In some embodiments, the present disclosure provides the use of a provided compound or a pharmaceutically acceptable salt thereof, in the manufacture of a medicament for the treatment of an infectious disease. In one embodiment, a compound of the present disclosure may be employed with other therapeutic methods of treating infectious disease. In particular, bacterial and parasite infections, such as *Mycobacterium tuberculosis* and malaria, respectively, which exploit the type-I interferon pathway for their advantage, may be treated with a cGAS inhibitor.

In some embodiments, a provided compound or a pharmaceutically acceptable salts thereof may be used in combination with one or more agents useful in the prevention or treatment of bacterial and viral infections. Examples of such agents include: polymerase inhibitors; replication inhibitors such as acyclovir, famciclovir, ganciclovir, cidofovir and lamivudine; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034; nucleoside and nucleotide reverse transcriptase inhibitors such as zidovudine, didanosine, lamivudine, zalcitabine, abacavir, stavidine, adefovir, adefovir dipivoxil, fozivudine, todoxil, emtricitabine, alovudine, amdoxovir, and elvucitabine; non-nucleoside reverse transcriptase inhibitors (including an agent having antioxidation activity such as immunocal or oltipraz) such as nevirapine, delavirdine, efavirenz, loviride, immunocal, oltipraz, capravirine, TMC-278, TMC-125, and etravirine; entry inhibitors such as enfuvirtide (T-20), T-1249, PRO-542, PRO-140, TNX-355, BMS-806, 5-Helix and similar agents; integrase inhibitors such as L-870 and 180; budding inhibitors such as PA-344 and PA-457; chemokine receptor inhibitors such as vicriviroc (Sch-C), Sch-D, TAK779, maraviroc (UK-427, 857), and TAK449; neuraminidase inhibitors such as CS-8958, zanamivir, oseltamivir, and peramivir; ion channel blockers such as amantadine or rimantadine; interfering RNA and antisense oligonucleotides and such as ISIS-14803; and antiviral agents of undetermined mechanism of action, such as ribavirin.

In some embodiments, a provided compound or a pharmaceutically acceptable salts thereof may also be used in combination with one or more other agents which may be useful in the prevention or treatment of viral infections such as immune therapies (e.g. interferon or other cytokines/chemokines, cytokine/chemokine receptor modulators, cytokine agonists or antagonists and similar agents); therapeutic vaccines; antifibrotic agents; and antiinflammatory agents such as corticosteroids or NSAIDs (non-steroidal antiinflammatory agents).

In some embodiments, the present disclosure provides a pharmaceutical composition comprising a provided compound or a pharmaceutically acceptable salt thereof, and at least one further therapeutic agent useful in the treatment of an infectious disease.

In some embodiments, the present disclosure provides a pharmaceutical composition comprising a provided compound or a pharmaceutically acceptable salt thereof, and at least one further therapeutic agent useful in the treatment of an infectious disease for use in therapy.

In some embodiments, the present disclosure provides a pharmaceutical composition comprising a provided compound or pharmaceutically acceptable salt thereof, and at least one further therapeutic agent useful in the treatment of an infectious disease, for use in the treatment of an infectious disease.

In some embodiments, the present disclosure provides the use of a pharmaceutical composition comprising a provided compound or a pharmaceutically acceptable salt thereof, and at least one further therapeutic agent useful in the treatment of an infectious disease in the manufacture of a medicament for the treatment of an infectious disease.

In some embodiments, the present disclosure provides a method of treating an infectious disease comprising administering to a patient in need thereof, a therapeutically effective amount of a pharmaceutical composition comprising a provided compound or a pharmaceutically acceptable salt thereof, and at least one further therapeutic agent useful in the treatment of an infectious disease.

In some embodiments, the present disclosure provides a pharmaceutical composition comprising a provided compound or a pharmaceutically acceptable salt thereof, at least one further therapeutic agent useful in the treatment of infectious disease, and one or more of pharmaceutically acceptable excipients.

In some embodiments, the disclosure provides a provided compound or a pharmaceutically acceptable salt thereof for use in the treatment of a senescence- or age-related disease.

In some embodiments, the disclosure provides a method of treating a senescence- or age-related disease comprising: administering to a patient in need thereof a therapeutically effective amount of a provided compound or a pharmaceutically acceptable salt thereof.

In some embodiments, the disclosure provides the use of a provided compound or a pharmaceutically acceptable salt thereof in the manufacture of a medicament for the treatment of a senescence- or age-related disease.

In some embodiments, the present disclosure provides a pharmaceutical composition comprising a provided compound or a pharmaceutically acceptable salt thereof, and at least one further therapeutic agent useful in the treatment of a senescence- or age-related disease.

In some embodiments, the present disclosure provides a pharmaceutical composition comprising a provided compound or a pharmaceutically acceptable salt thereof, and at least one further therapeutic agent useful in the treatment of a senescence- or age-related disease for use in therapy.

In some embodiments, the present disclosure provides a pharmaceutical composition comprising a provided compound or pharmaceutically acceptable salt thereof, and at least one further therapeutic agent useful in the treatment of a senescence- or age-related disease, for use in the treatment of a senescence- or age-related disease.

In some embodiments, the present disclosure provides the use of a pharmaceutical composition comprising a provided compound or a pharmaceutically acceptable salt thereof, and at least one further therapeutic agent useful in the treatment of a senescence- or age-related disease in the manufacture of a medicament for the treatment of a senescence- or age-related disease.

In some embodiments, the present disclosure provides a method of treating a senescence- or age-related disease comprising administering to a patient in need thereof, a therapeutically effective amount of a pharmaceutical composition comprising a provided compound or a pharmaceutically acceptable salt thereof, and at least one further therapeutic agent useful in the treatment of a senescence- or age-related disease.

In some embodiments, the present disclosure provides a pharmaceutical composition comprising a provided compound or a pharmaceutically acceptable salt thereof, at least one further therapeutic agent useful in the treatment of a senescence- or age-related disease, and one or more of pharmaceutically acceptable excipients.

The provided compounds may be prepared by methods known in the art of organic synthesis as set forth in the schemes below and/or the specific Examples described below. In all of the methods, it is well understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3' edition, John Wiley & Sons). These groups are removed at a convenient stage of the compound synthesis using methods that are readily apparent to those skilled in the art. The selection of processes as well as the reaction conditions and order of their execution shall be consistent with the preparation of the provided compounds.

The following list provides definitions of certain abbreviations as used herein. It will be appreciated that the list is not exhaustive, but the meaning of those abbreviations not herein below defined will be readily apparent to those skilled in the art: AIBN is 2,2'-azobisisobutyronitrile; ATP is adenosine 5'-triphosphate; BPO is benzoyl peroxide; n-BuLi is n-butyllithium; BzCl is benzoyl chloride; CDI is 1,1'-carbonyldiimidazole; cGAS is cyclic GMP-AMP synthase; CO is carbon monooxide; $Cu(OAc)_2$ is copper(II) acetate; CuCN is copper(I) cyanide; CuI is copper(I) iodide; DAST is (diethylamino)sulfur trifluoride; DBU is 1,8-diazabicyclo[5.4.0]undec-7-ene; DCE is dichloroethane; DCM is dichloromethane; DDQ is 2,3-dichloro-5,6-dicyano-p-benzoquinone; DHP is 3,4-dihydro-2H-pyran; DIAD is diisopropyl azodicarboxylate; DIBAL-H is diisobutylaluminum hydride; DIPA is diisopropylamine; DIPEA is N,N-diisopropylethylamine; DMAP is 4-(dimethylamino)pyridine; DMB is 2,4-dimethoxybenzyl; DMF is N,N-dimethylformamide; DMP is Dess-Martin periodinane; DMSO is dimethyl sulfoxide; EA is ethyl acetate; EtMgBr is ethylmagnesium bromide; $Et_2O$ is diethyl ether; EtOH is ethanol; GTP is guanosine triphosphate; HCl is hydrochloric acid; HMTA is hexamethylenetetramine; HOAc is acetic acid; HPLC is high performance liquid chromatography; LAH is lithium aluminum hydride; mCPBA is 3-chloroperbenzoic acid; MeCN is acetonitrile; MeI is iodomethane; MeOH is methanol; MeMgBr is methylmagnesium bromide; MOMCl is chloromethyl methyl ether; MOM is methoxymethoxy; MS is mass spectrometer or mass spectrum; MSCl is methanesulfonyl chloride; MTBE is methyl tert-butyl ether; NaH is sodium hydride; NaOH is sodium hydroxide; NBS is N-bromosuccinimide; NMM is N-methylmorpholine; NMR is nuclear magnetic resonance; $Pd(dba)_2$ is bis(dibenzylideneacetone)palladium(O); $Pd(dppf)Cl_2$ is [1,1'-bis(diphenylphosphino)ferrocene]dichloropalladium(II); $Pd(OAc)_2$ is palladium(II) acetate; $Pd(PPh_3)_2Cl_2$ is bis(triphenylphosphine)palladium(II) dichloride; $Pd(PPh_3)_4$ is tetrakis(triphenylphosphine) palladium(O); Pd/C is palladium on carbon; PDC is pyridinium dichromate; PE is petroleum ether; PMB is 4-methoxybenzyl; $PPh_3$ is triphenylphosphine; prep-HPLC is preparative high performance liquid chromatography; prep-TLC is preparative thin-layer chromatography; Py is pyridine; TBAF is tetra-n-butylammonium fluoride; TBSCl is tert-butyldimethylsilyl chloride; TEA is triethylamine; TFA is trifluoroacetic acid; THF is tetrahydrofuran; THP is tetrahydropyranyl; TLC is thin-layer chromatography; TSA is p-toluenesulfonic acid monohydrate, and TsCl is p-toluenesulfonyl chloride.

4. EXAMPLES

The following Examples provide syntheses of the provided compounds and their in vitro activity.

Intermediates

Preparation of 2,7,8-trichloro-4-(1H-imidazol-1-yl)quinoline (Intermediate 1)

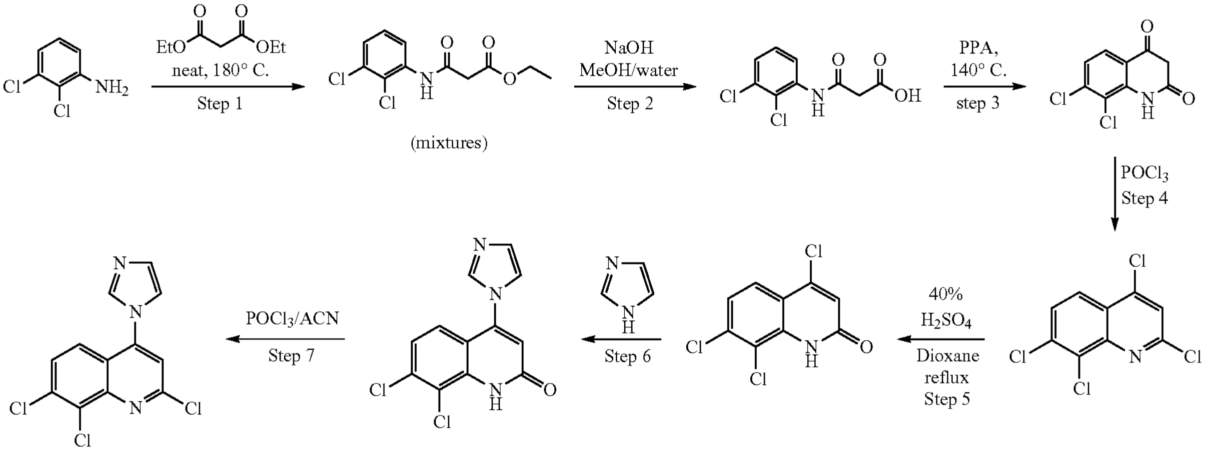

Intermediate 1

Step 1: Preparation of ethyl 3-((2,3-dichlorophenyl)amino)-3-oxopropanoate. 2,3-dichloroaniline (10.33 g, 64 mmol, 1.0 eq) was mixed with diethyl malonate 1-2 (24 mL, 24.3 g, 158 mmol) and heated at 180° C. for 16 hours until product formation ceased (confirmed by LC-MS). The resulting oil mixture was used in the next step. MS (ES): $[M+1]^+$ 276.

Step 2: Preparation of 3-((2,3-dichlorophenyl)amino)-3-oxopropanoic acid. The mixture of the first step was diluted with MeOH (80 mL) and water (80 mL) and chilled with an ice-water bath. To the above solution was added a solution of NaOH (12 g, ~2 eq to the amount of diethyl malonate) in 50 mL water slowly. After stirring 30 to 60 min, solids precipitated. Water was added to help stirring. After stirring for 3 to 4 hours at room temperature, starting material was consumed (confirmed by LC-MS), the reaction mixture was acidified with conc. HCl to pH 1 to form a precipitate. After filtration, rinsing with water, and drying under vacuum, the titled compound (10.57 g) was used in the next step without further purification. MS (ES): $[M+1]^+$ 248.

Step 3: Preparation of 7,8-dichloroquinoline-2,4(1H,3H)-dione. The product of step 2 (10.57 g) was suspended and stirred with PPA (55 g) at 140° C. for 3 hours until all solids were dissolved. After starting material was consumed (confirmed by LC-MS), the reaction mixture was quenched with ice. The formed solids were collected by filtration and rinsed with water. After drying under vacuum, the titled compound (17 g) was used in the next step without further purification. MS (ES): $[M+1]^+$ 230

Step 4: Preparation of 2,4,7,8-tetrachloroquinoline (1.6). The product of step 3 was suspended in $POCl_3$ (45 g) and heated at 130° C. until all solids were dissolved. After starting material was consumed (confirmed by LC-MS), excess $POCl_3$ was removed by under vacuum. The residue was treated with ice-water (exothermic) to afford solids and the suspended solids were stirred for 4 hours. Filtration, rinsing with water, and drying under vacuum afforded the crude product as a brown solid (9.25 g) that was suspended in hexane (400 mL) and heated at reflux. After hot filtration to remove residual solids and cooling slowly to room temperature, 5.73 g of the titled compound was obtained as a light brown solid. The solids concentrated from the filtrate and undissolved solids from the above recrystallization were purified by a flash silica column to afford additional product (1.7 g). MS (ES): $[M+1]^+$ 266.0. $^1H$ NMR (400 Hz, $CDCl_3$): δ 8.074-8.046 (dd, J=9.2 and 2.4 Hz, 1H), 7.705-7.677 (dd, J=9.2 and 2.4 Hz, 1H), 7.571 (s, 1H) ppm.

Step 5: Preparation of 4,7,8-trichloroquinolin-2(1H)-one. The product of step 4 (4.93 g) was suspended in dioxane (80 mL), conc. $H_2SO_4$ (16 mL), water (24 mL), and heated to reflux for 12 to 16 hours. A clear solution was initially formed followed by the precipitation of solids. After starting material was consumed (confirmed by LC-MS) and the reaction mixture was cooled, 100 mL of ACN was added to form a precipitate. Filtration, rinsing with CAN, and drying under vacuum afforded the titled compound (4.12 g) as colorless powder. MS (ES): $[M+1]^+$ 248.0.

Step 6: Preparation of 7,8-dichloro-4-(1H-imidazol-1-yl) quinolin-2(1H)-one (I-8). The product of step 5 (4.12 g) was suspended in DMF (20 mL) with imidazole (4 g) and heated to 130° C. until starting material was consumed (confirmed by LC-MS). Additional imidazole can be added to push the reaction to the completion. After cooling, ACN (150 mL) was added to form a precipitate which was collected by filtration and rinsing with CAN afforded the titled compound (1.8, 3.90 g). MS (ES): $[M+1]^+$ 280.0. $^1H$ NMR (400 Hz, DMSO-d6): δ 8.089 (s, 1H), 7.650 (s, 1H), 7.494-7.516 (d, J=8.8 Hz, 1H), 7.316-7.338 (d, J=8.8 Hz, 1H), 7.225 (s. 1H), 6.795 (s, 1H) ppm.

Step 7: 2,7,8-trichloro-4-(1H-imidazol-1-yl) quinoline (Intermediate 1). The product of step 6 (3.90 g) was suspended in ACN (100 mL) and $POCl_3$ (8 mL) and heated to reflux until all solids were dissolved and starting material was consumed (confirmed by LC-MS). After concentrating under vacuum, the residue was cooled in an ice bath and carefully neutralized by 5% NaOH to pH 7 to precipitate Intermediate 1. Filtration, rinsing with water, and drying under vacuum afforded Intermediate 1 (3.8 g) as light tan solid. MS (ES): $[M+1]^+$ 298. $^1H$ NMR (400 Hz, DMSO-d6): δ 8.200 (s, 1H), 8.005 (s, 1H), 7.925-7.948 (d, J=9.2 Hz, 1H), 7.785-7.808 (d, J=9.2 Hz, 1H), 7.772 (s. 1H), 7.286 (s, 1H) ppm.

Preparation of 2,7,8-trichloro-4-(1H-pyrazol-4-yl)quinoline (Intermediate 2)

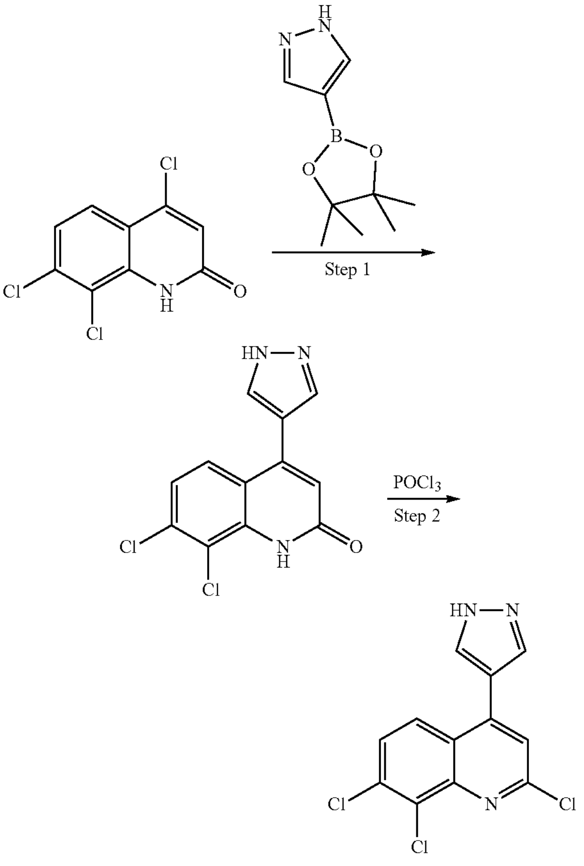

Intermediate 2

Step 1: Preparation of 7,8-dichloro-4-(1H-pyrazol-4-yl) quinolin-2(1H)-one. 4,7,8-trichloroquinolin-2(1H)-one (300 mg, 1.21 mmol), $Na_2CO_3$ (321 mg, 3.03 mmol), and $Pd(PPh_3)_4$ (140 mg, 0.121 mmol) were added to a round-bottom flask and diluted with dioxane (10 mL) and water (5 mL). The mixture was cooled in an ice-bath, and vacuumed and purged with $N_2$ three times. A solution of boron ester 2.1 (703 mg, 3.62 mmol) in dioxane (3 mL) was prepared and degassed. Under $N_2$, a portion of the boron ester 2.1 (1 mL, 1.0 eq) in dioxane was added to the reaction mixture via a syringe. The reaction mixture was heated at 110° C. for 2 h while LC-MS showed that around 50% of 1.7 was consumed. The rest of the boron ester 2.1 in dioxane was added under $N_2$. After heating and stirring for an additional 3 h, compound 1.7 was consumed (confirmed by LC-MS). After cooling to room temperature, the reaction mixture was further diluted with water (20 mL). The precipitated solids were collected by centrifuge or filtration and washed with DCM (5 mL×3). After drying under the vacuum, the titled compound was afforded (2.2, 315 mg). MS: $[M+1]^+$ 280.

Step 2: Preparation of 2,7,8-trichloro-4-(1H-pyrazol-4-yl) quinoline (Intermediate 2). The product of step 1 (208 mg, 0.743 mmol) was suspended in ACN (2.5 mL) and $POCl_3$ (0.42 mL). The resultant mixture was heated at 80° C. for 3 h or until less than 10% of compound 2.2 remained (confirmed by LC-MS). After the concentrating under vacuum, the residue was cooled in an ice bath and carefully neutralized by 5% NaOH to pH 7 to precipitate Intermediate 2 as a yellow solid. The solids were collected by centrifuge or filtration and washed with water (15 mL×3). After drying in vacuo, Intermediate 2 was afforded (180 mg). MS: [M+1]$^+$ 298. $^1$HNMR (400 MHz, DMSO-D6) δ: 8.8.25-8.30 (m, 3H), 7.84 (d, J=9.2 Hz, 1H) and 7.72 (s, 1H) ppm.

Preparation of 2,7-dichloro-4-(1H-imidazol-1-yl) quinoline (Intermediate 3)

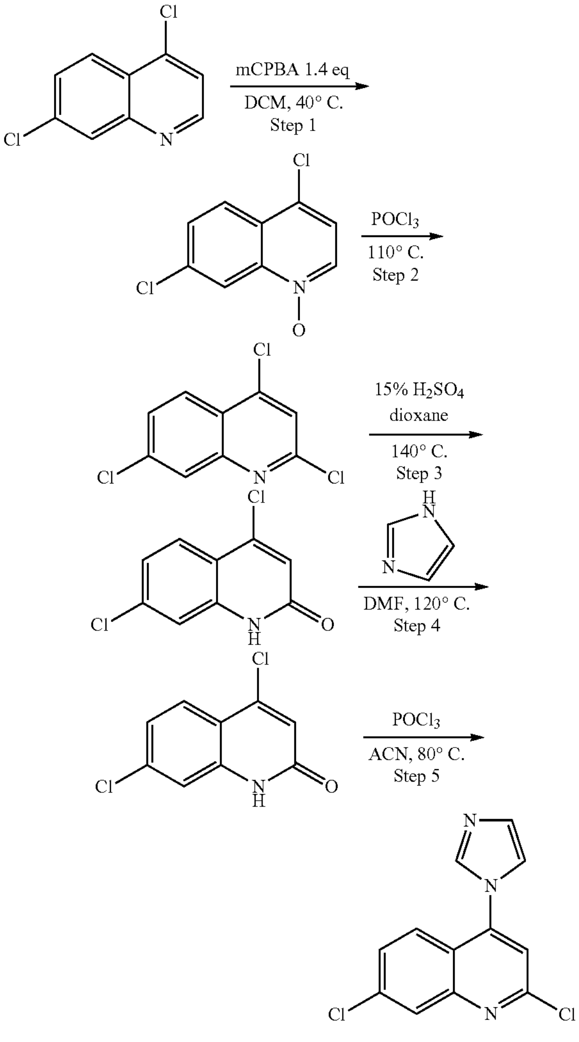

Intermediate 3

Step 1: Preparation of 4,7-dichloroquinoline 1-oxide. To a solution of 4,7-dichloroquinoline (20.0 g, 101.5 mmol) in DCM (400 mL) at room temperature was added 3-chloroperoxybenzoic acid (mCPBA) (28.8 g, 85% purity, 142.1 mmol) in portions and the resulting solution was stirred at 40° C. for 2 hrs. The solution was then washed with aqueous $NaHCO_3$ (2×50 mL), aqueous $Na_2S_2O_3$ (100 mL×2), dried over anhydrous $Mg_2SO_4$, filtered, concentrated under reduced pressure, and dried under high vacuum to yield the titled product (21 g) as a white solid. MS: [M+1]$^+$ 214.1.

Step 2: Preparation of 2,4,7-trichloroquinoline. The product of step 1 (20.0 g, 1.0 eq) was dissolved in $POCl_3$(74 mL) at rt and the resulting solution was stirred at 110° C. for 2 hrs. The mixture was concentrated under reduced pressure and adjusted to pH 9 with a 10% NaOH solution. The precipitate was collected, washed with water, and dried to afford the titled compound (18 g, yield 83%) as an off-white solid. MS: [M+1]$^+$ 234.0. NMR (400 Hz, $CDCl_3$): δ 8.148-8.126 (d, J=8.8 Hz, 1H), 8.033 (s, 1H), 7.622-7.596 (dd, J=1.4 Hz, 1H), 7.510 (s, 1H) ppm.

Step 3: Preparation of 4,7-dichloroquinolin-2(1H)-one. To a solution of the product of step 2 (5.0 g, 1.0 eq) in 1,4-diaoxane (125 mL) was added 15% $H_2SO_4$ (250 mL) at 25° C. The resulting mixture was stirred at 140° C. for 12 hrs. The precipitated solids were collected by filtration, washed with water, and dried to afford the titled compound (3.9 g) as a gray solid. MS: [M+1]$^+$ 214.1. $^1$H NMR (400 Hz, $CDCl_3$): δ 12.122 (s, 1H), 7.880-7.859 (d, J=8.4 Hz, 1H), 7.406 (s, 1H), 7.368-7.343 (dd, J=1.4 Hz, 1H), 6.865 (s, 1H) ppm.

Step 4: Preparation of 7-chloro-4-(1H-imidazol-1-yl)quinolin-2(1H)-one. To a solution of 4,7-dichloroquinolin-2 (1H)-one (9.0 g, 1.0 eq) in DMF (18 mL) was added imidazole (48.8 g, 17 eq). After stirring at 120° C. for 21 hrs, the reaction mixture was diluted with ACN (100 mL) and stirred for 0.5 hrs. The precipitated solid was collected, washed with ACN, and dried in vacuo to afford the crude titled compound (6.7 g) as a gray solid. MS: [M+1]$^+$ 246.1. $^1$H NMR (400 MHz, DMSO): δ 12.19 (s, 1H), 8.09 (s, 1H), 7.65 (s, 1H), 7.46 (d, J=2.0 Hz, 1H), 7.39 (d, J=8.8 Hz, 1H), 7.29 (dd, J=8.8, 2.0 Hz, 1H), 7.21 (s, 1H), 6.66 (s, 1H) ppm.

Step 5: Preparation of 2,7-dichloro-4-(1H-imidazol-1-yl) quinolone (Intermediate 3). To a solution of compound 3.5 (5.0 g, 1.0 eq) in ACN (50 mL) was added $POCl_3$ (10 mL) and the resulting mixture was stirred at 80° C. for 0.5 hrs. The mixture was concentrated in vacuo and the residue was carefully quenched with 5-10% NaOH solution to pH 7 in an ice-bath. The precipitated solid was collected, washed with water, and dried in vacuo to yield Intermediate 3 (4.1 g) as a white solid. MS (ES): [M+1]$^+$ 264. $^1$H NMR (400 Hz, $CDCl_3$): δ 8.164 (s, 1H), 7.970 (s, 1H), 7.786-7.763 (d, J=9.2 Hz, 1H), 7.631-7.608 (d, J=9.2 Hz, 1H), 7.422 (s, 1H), 7.357 (s, 1H) ppm.

Preparation of 2,4-dichloro-7-(trifluoromethyl)quinoline (Intermediate 4A) and 2,4-dichloro-5-(trifluoromethyl)quinoline (Intermediate 4B)

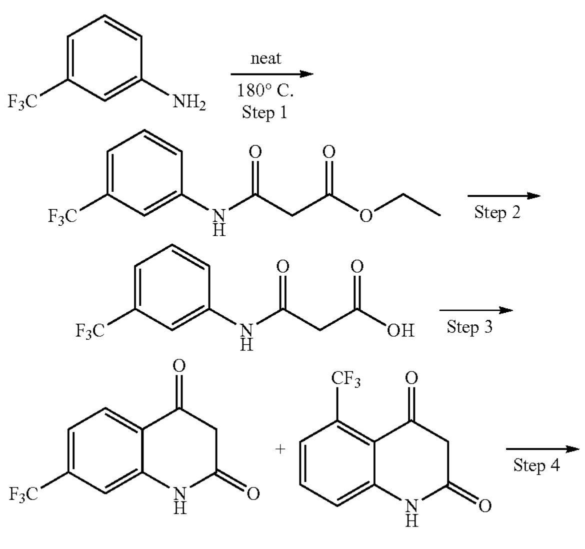

-continued

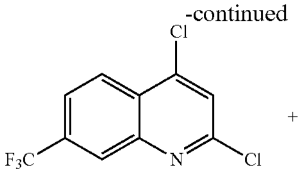

+

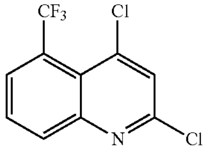

Intermediate 4A Intermediate 4B

Step 1: 3-Oxo-3-((3-(trifluoromethyl) phenyl) amino) propanoic acid. A mixture of 3-(trifluoromethyl) aniline (5.74 g) and diethyl malonate (14.9 g) was stirred and heated at 180° C. over 4 hours. The resultant mixture was dissolved in MeOH (30 mL) and water (10 mL). The solution was cooled in an ice-bath and treated with NaOH (7.1 g). After stirring at room temperature over 2 hours and removal of MeOH under vacuum, the resultant mixture was further diluted with water (60 mL) and acidified to pH 1 to 2 with conc. HCl. After extraction with EtOAc (30 mL×4), the combined organic layers were washed by brine and dried over $Na_2SO_4$. Evaporation of EtOAc under reduced pressure afforded 4.3 (8.76 g) as oil. MS: $[M+1]^+$ 276.

Step 2: 7-(Trifluoromethyl) quinoline-2,4(1H,3H)-dione 4-4 and 5-(trifluoromethyl) quinoline-2,4 (1H,3H)-dione. Neat 4.3 (8.76 g) was suspended in PPA (42 g) and heated at 130° C. over 4 hours. The resultant mixture was further diluted with water (120 mL) and the aqueous layer was extracted with EtOAc (40 mL×3). The combined organic layers were washed with brine and dried over $Na_2SO_4$. Evaporation under reduced pressure afforded a mixture of two titled regioisomers (5.99 g) as sticky solids. MS: $[M+1]^+$ 230.

Step 3: 2,4-Dichloro-7-(trifluoromethyl)quinoline (Intermediate 4A) and 2,4-dichloro-5-(trifluoromethyl)quinoline (Intermediate 4B). The mixture of 4.4 and 4.5 (5.99 g) from the previous step were suspended in $POCl_3$, stirred, and heated at reflux over 3 h. $POCl_3$ was removed under reduced pressure and the resultant mixtures were carefully quenched with ice. The aqueous layer was extracted with EtOAc (30 mL×3) and the combined organic layers were washed with brine and dried over $Na_2SO_4$. Column chromatography, eluting with a gradient of DCM/Hexane from 0 to 50%, afforded Intermediate 4A (3.1 g) and Intermediate 4B (0.59 g). 4A: MS $[M+1]^+$ : 266.1. $^1$HNMR (400 MHz, CD3Cl) δ: 8.38 (s, 1H), 8.37 (d, J=8 Hz, 1H), 7.86 (dd, J=8 and 4 Hz) and 7.66 (s, 1H) ppm. 4B: MS $[M+1]^+$ : 266.1. $^1$HNMR (400 MHz, CD3Cl) δ: 8.29 (d, J=8 Hz, 1H), 8.18 (d, J=8 Hz, 1H), 7.85 (t, J=8 Hz) and 7.72 (s, 1H) ppm.

Following the above procedures to prepare Intermediates 1 and 4, the following intermediates were prepared.

| Starting Material | Intermediate # | Structure | MS: $[M + 1]^+$ | Intermediate # | Structure | MS: $[M + 1]^+$ |
|---|---|---|---|---|---|---|
| 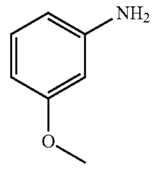 | 5A | 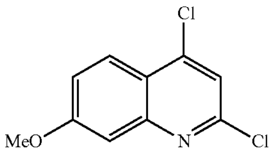 [SMILES: COc1ccc2c(Cl)cc(Cl)nc2c1] | 228 | 5B | 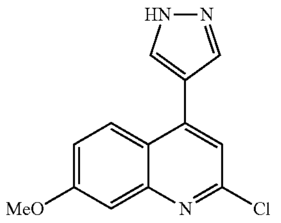 [SMILES: COc1ccc2c(-c3cn[nH]c3)cc(Cl)nc2c1] | 260 |
| 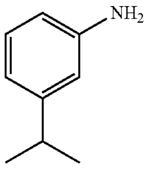 | 6A | 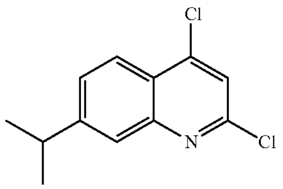 | 240 | 6B | 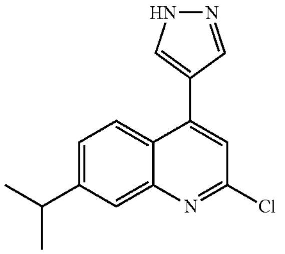 [SMILES: CC(C)c1ccc2c(-c3cn[nH]c3)cc(Cl)nc2c1] | 272 |
| 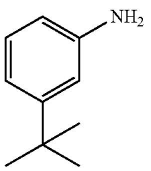 | 7A | 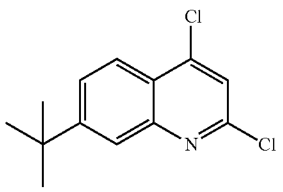 [SMILES: CC(C)(C)c1ccc2c(Cl)cc(Cl)nc2c1] | 254 | 7B | 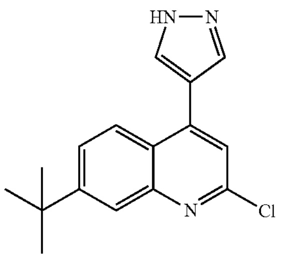 [SMILES: CC(C)(C)c1ccc2c(-c3cn[nH]c3)cc(Cl)nc2c1] | 286 |

-continued
| Starting Material | Inter-mediate # | Structure | MS: [M + 1]+ | Inter-mediate # | Structure | MS: [M + 1]+ |
|---|---|---|---|---|---|---|
| 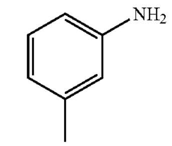 | 8A | 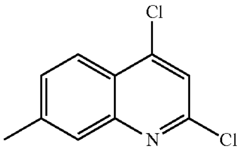 | 212 | 8B | 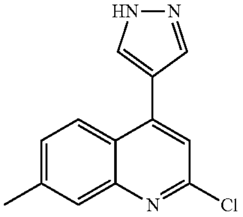 [SMILES: Cc1ccc2c(-c3cn[nH]c3)cc(Cl)nc2c1] | 244 |
| 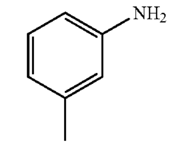 | 9A | 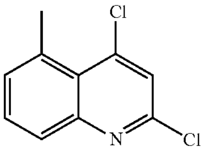 | 212 | 9B | 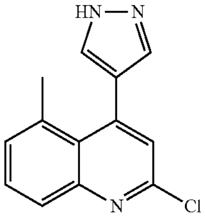 [SMILES: Cc1cccc2nc(Cl)cc(-c3cn[nH]c3)c12] | 244 |
| 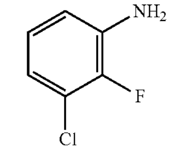 | 10A | 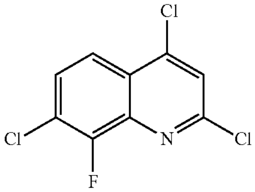 [SMILES: Fc1c(Cl)ccc2c(Cl)cc(Cl)nc12] | 250 | 10B | 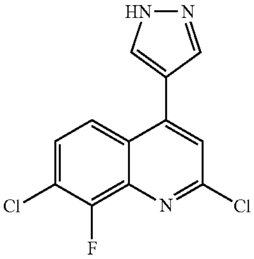 [SMILES: Fc1c(Cl)ccc2c(-c3cn[nH]c3)cc(Cl)nc12] | 282 |
| 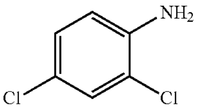 | 11A | 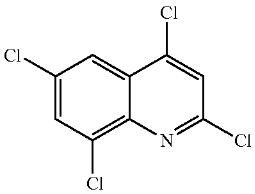 [SMILES: Clc1cc(Cl)c2nc(Cl)cc(Cl)c2c1] | 266 | 11B | 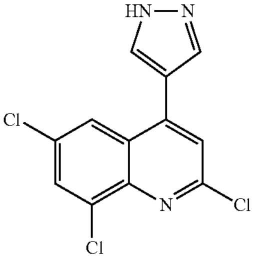 [SMILES: Clc1cc(Cl)c2nc(Cl)cc(-c3cn[nH]c3)c2c1] | 298 |
| 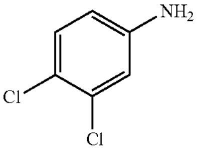 | 12A | 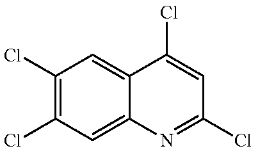 [SMILES: Clc1cc(Cl)c2cc(Cl)c(Cl)cc2n1] | 266 | 12B | 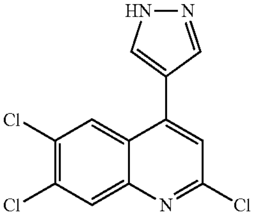 [SMILES: Clc1cc(-c2cn[nH]c2)c2cc(Cl)c(Cl)cc2n1] | 298 |
| 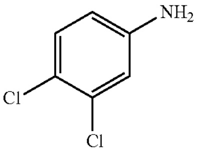 | 13A | 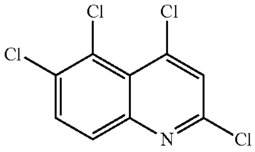 [SMILES: Clc1cc(Cl)c2c(Cl)c(Cl)ccc2n1] | 266 | 13B | 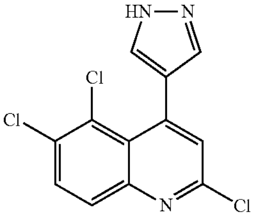 [SMILES: Clc1cc(-c2cn[nH]c2)c2c(Cl)c(Cl)ccc2n1] | 298 |

-continued
| Starting Material | Inter-mediate # | Structure | MS: [M + 1]$^+$ | Inter-mediate # | Structure | MS: [M + 1]$^+$ |
|---|---|---|---|---|---|---|
| 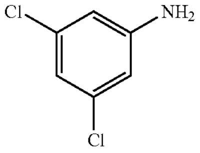 | 14A | 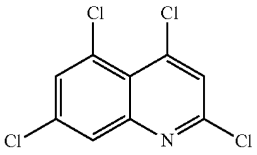 [SMILES: Clc1cc(Cl)c2c(Cl)cc(Cl)nc2c1] | 266 | 14B | 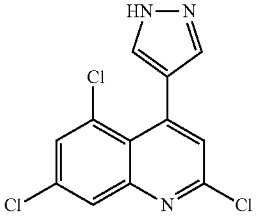 [SMILES: Clc1cc(Cl)c2c(-c3cn[nH]c3)cc(Cl)nc2c1] | 298 |
| 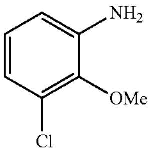 | 15A | 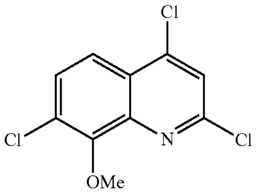 [SMILES: COc1c(Cl)ccc2c(Cl)cc(Cl)nc12] | 262 | 15B | 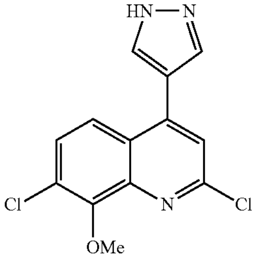 [SMILES: COc1c(Cl)ccc2c(-c3cn[nH]c3)cc(Cl)nc12] | 294 |
| 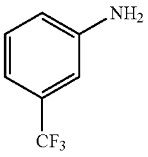 | — | — | — | 16 | 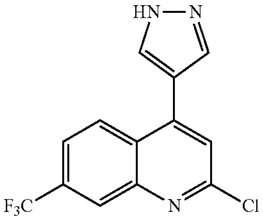 [SMILES: FC(F)(F)c1ccc2c(-c3cn[nH]c3)cc(Cl)nc2c1] | 298 |
| 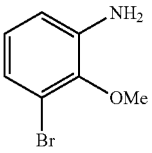 | 17 | 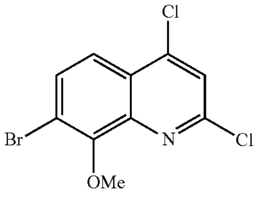 | 306 | — | — | — |
| 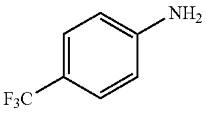 | 18 | 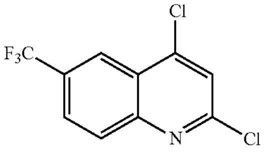 [SMILES: FC(F)(F)c1ccc2nc(Cl)cc(Cl)c2c1] | 266 | — | — | — |
Example 1: Synthesis of 7-chloro-4-(1H-imidazol-1-yl)-N-(pyridin-4-ylmethyl)quinolin-2-amine (I-353)
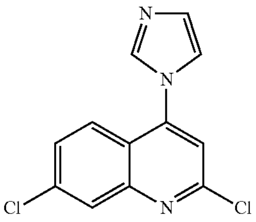
+
-continued
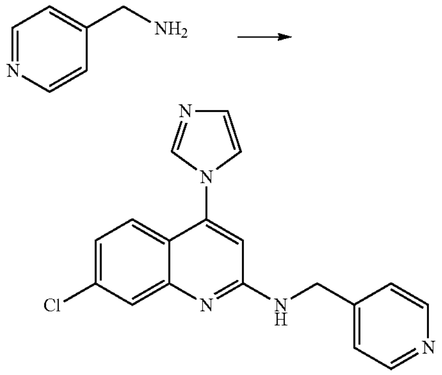
I-353

To a solution of 2,7-dichloro-4-(1H-imidazol-1-yl) quinoline (132 mg, 0.5 mmol) in DMF (2 mL) was added pyridin-4-ylmethanamine (0.15 mL, 1.5 mmol). The solution was vigorously stirred at 120° C. for 3 h. After cooling down to room temperature, the solvent was removed by evaporation to give a crude. The crude was purified directly by column chromatography on silica gel to give the title product as a solid (115 mg, 68% yield). MS: $[M+1]^+$ 336.1.

The following compounds are prepared essentially by the same method described above to prepare I-353.

| I-# | Starting Material | Structure | MS [M + 1]+ |
|---|---|---|---|
| I-354 | 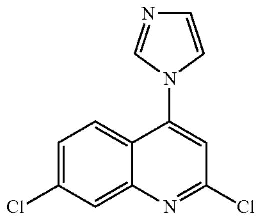 [SMILES: Clc1ccc2c(-n3ccnc3)cc(Cl)nc2c1] 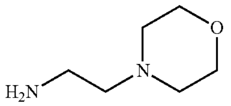 | 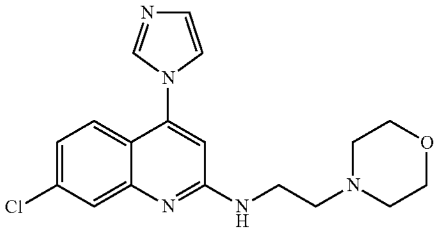 [SMILES: Clc1ccc2c(-n3ccnc3)cc(NCCN3CCOCC3)nc2c1] | 358 |
| I-126 | 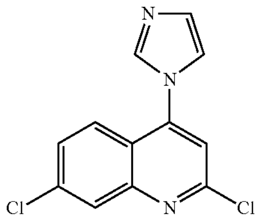 [SMILES: Clc1ccc2c(-n3ccnc3)cc(Cl)nc2c1] 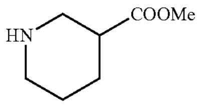 | 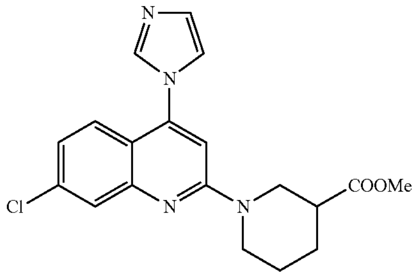 [SMILES: COC(=O)C1CCCN(c2cc(-n3ccnc3)c3ccc(Cl)cc3n2)C1] | 371 |
| I-131 | 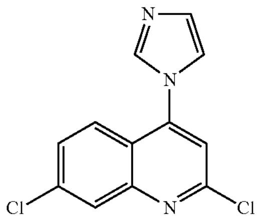 [SMILES: Clc1ccc2c(-n3ccnc3)cc(Cl)nc2c1] 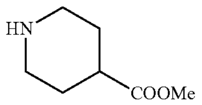 | 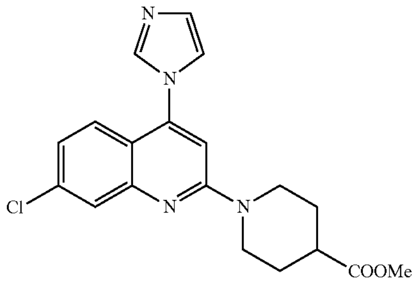 [SMILES: COC(=O)C1CCN(c2cc(-n3ccnc3)c3ccc(Cl)cc3n2)CC1] | 371 |
| I-355 | 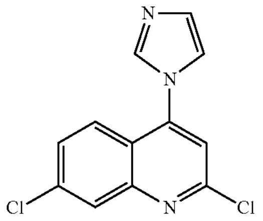 [SMILES: Clc1ccc2c(-n3ccnc3)cc(Cl)nc2c1] 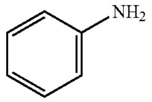 | 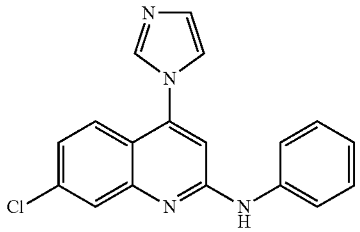 [SMILES: Clc1ccc2c(-n3ccnc3)cc(Nc3ccccc3)nc2c1] | 321 |
| I-447 | 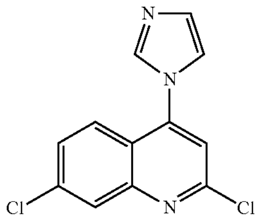 [SMILES: Clc1ccc2c(-n3ccnc3)cc(Cl)nc2c1] 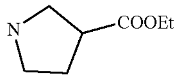 | 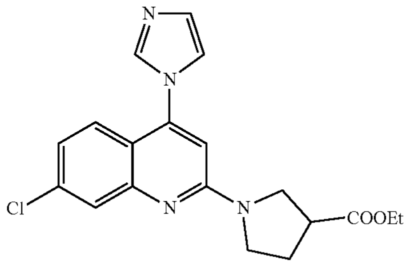 [SMILES: CCOC(=O)C1CCN(c2cc(-n3ccnc3)c3ccc(Cl)cc3n2)C1] | 371 |

-continued
| I-# | Starting Material | | Structure | MS [M + 1]+ |
|---|---|---|---|---|
| I-356 | 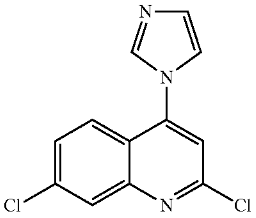 [SMILES: Clc1ccc2c(-n3ccnc3)cc(Cl)nc2c1] | 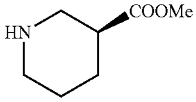 | 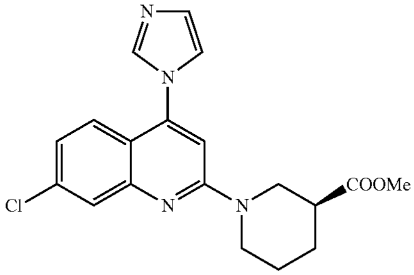 [SMILES: COC(=O)[C@H]1CCCN(c2cc(-n3ccnc3)c3ccc(Cl)cc3n2)C1] | 371 |
| I-357 | 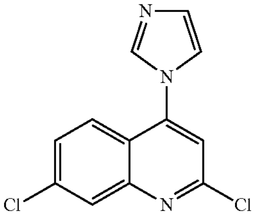 [SMILES: Clc1ccc2c(-n3ccnc3)cc(Cl)nc2c1] | 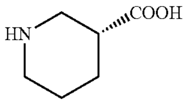 | 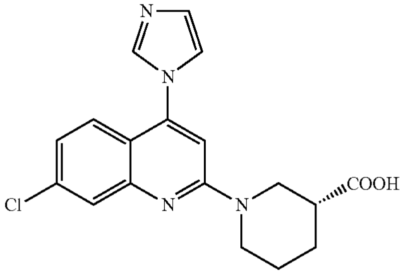 [SMILES: O=C(O)[C@@H]1CCCN(c2cc(-n3ccnc3)c3ccc(Cl)cc3n2)C1] | 357 |
| I-115 | 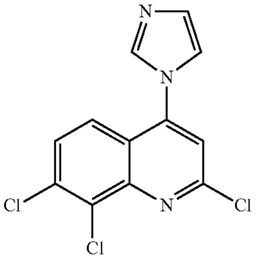 [SMILES: Clc1cc(-n2ccnc2)c2ccc(Cl)c(Cl)c2n1] | 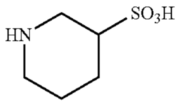 | 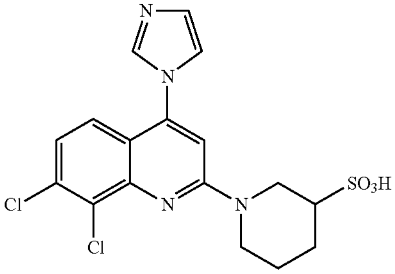 [SMILES: O=S(=O)(O)C1CCCN(c2cc(-n3ccnc3)c3ccc(Cl)c(Cl)c3n2)C1] | 427 |
| I-121 | 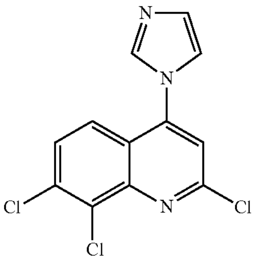 [SMILES: Clc1cc(-n2ccnc2)c2ccc(Cl)c(Cl)c2n1] | 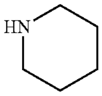 | 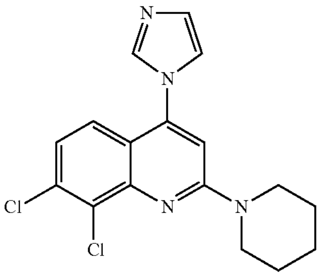 [SMILES: Clc1ccc2c(-n3ccnc3)cc(N3CCCCC3)nc2c1Cl] | 347 |
| I-95 | 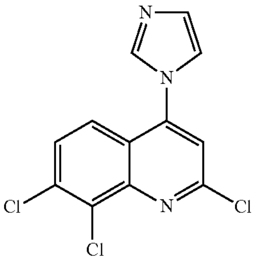 [SMILES: Clc1cc(-n2ccnc2)c2ccc(Cl)c(Cl)c2n1] | 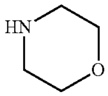 | 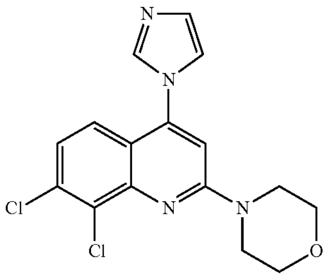 [SMILES: Clc1ccc2c(-n3ccnc3)cc(N3CCOCC3)nc2c1Cl] | 349 |

-continued
| I-# | Starting Material | Structure | MS [M + 1]+ |
|---|---|---|---|
| I-87 | 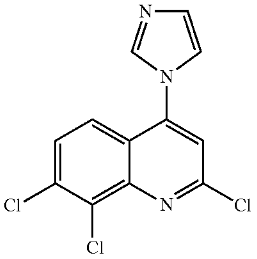 [SMILES: Clc1cc(-n2ccnc2)c2ccc(Cl)c(Cl)c2n1] 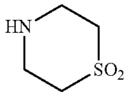 | 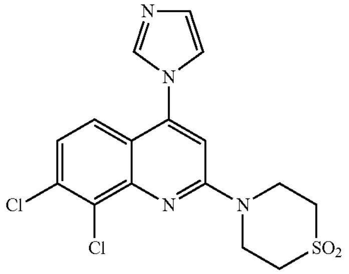 [SMILES: O=S1(=O)CCN(c2cc(-n3ccnc3)c3ccc(Cl)c(Cl)c3n2)CC1] | 397 |
| I-91 | 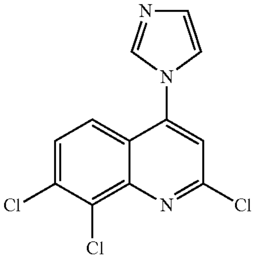 [SMILES: Clc1cc(-n2ccnc2)c2ccc(Cl)c(Cl)c2n1] 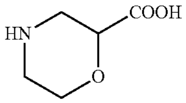 | 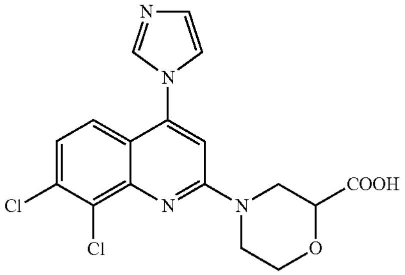 [SMILES: O=C(O)C1CN(c2cc(-n3ccnc3)c3ccc(Cl)c(Cl)c3n2)CCO1] | 393 |
| I-211 | 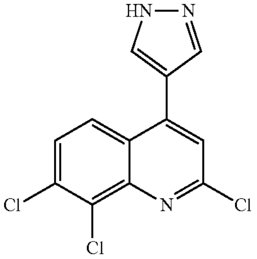 [SMILES: Clc1cc(-c2cn[nH]c2)c2ccc(Cl)c(Cl)c2n1] 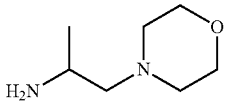 | 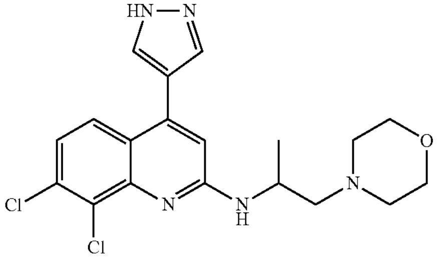 [SMILES: CC(CN1CCOCC1)Nc1cc(-c2cn[nH]c2)c2ccc(Cl)c(Cl)c2n1] | 406 |
| I-212 | 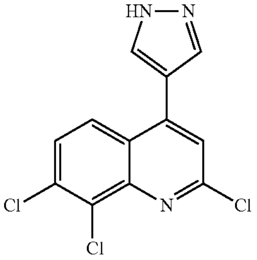 [SMILES: Clc1cc(-c2cn[nH]c2)c2ccc(Cl)c(Cl)c2n1] 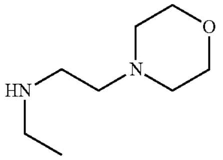 | 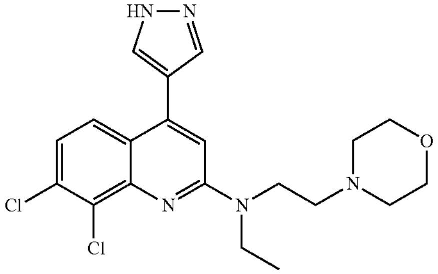 [SMILES: CCN(CCN1CCOCC1)c1cc(-c2cn[nH]c2)c2ccc(Cl)c(Cl)c2n1] | 420 |
| I-213 | 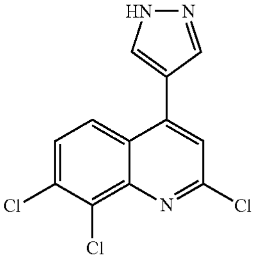 [SMILES: Clc1cc(-c2cn[nH]c2)c2ccc(Cl)c(Cl)c2n1] 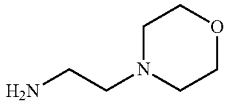 | 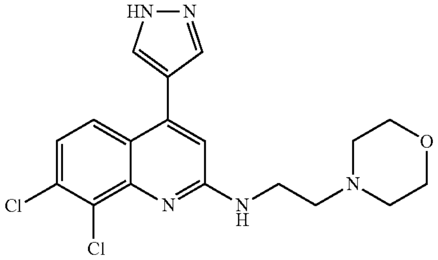 [SMILES: Clc1ccc2c(-c3cn[nH]c3)cc(NCCN3CCOCC3)nc2c1Cl] | 392 |

-continued
| I-# | Starting Material | | Structure | MS [M + 1]+ |
|---|---|---|---|---|
| I-214 | 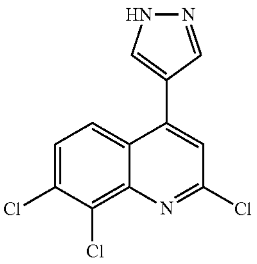 [SMILES: Clc1cc(-c2cn[nH]c2)c2ccc(Cl)c(Cl)c2n1] | 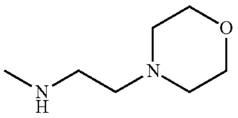 | 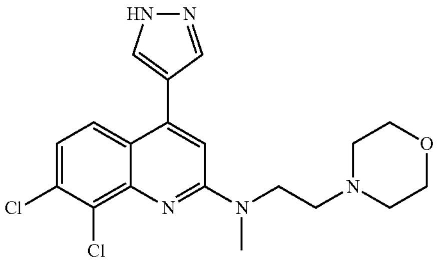 [SMILES: CN(CCN1CCOCC1)c1cc(-c2cn[nH]c2)c2ccc(Cl)c(Cl)c2n1] | 406 |
| I-215 | 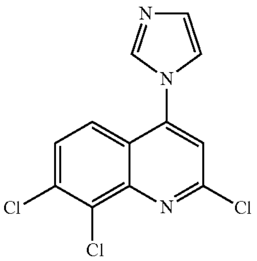 [SMILES: Clc1cc(-n2ccnc2)c2ccc(Cl)c(Cl)c2n1] | 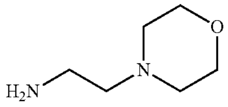 | 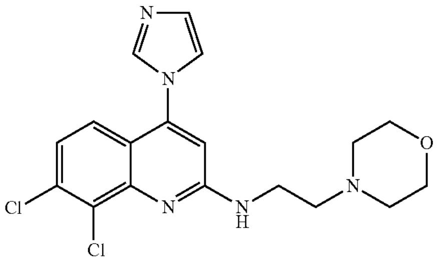 [SMILES: Clc1ccc2c(-n3ccnc3)cc(NCCN3CCOCC3)nc2c1Cl] | 392 |
| I-216 | 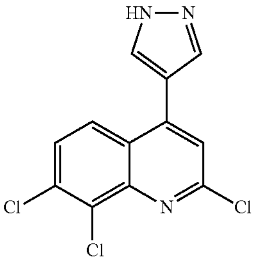 [SMILES: Clc1cc(-c2cn[nH]c2)c2ccc(Cl)c(Cl)c2n1] | 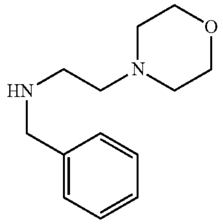 [SMILES: c1ccc(CNCCN2CCOCC2)cc1] | 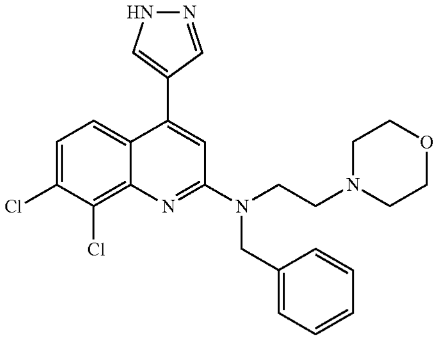 [SMILES: Clc1ccc2c(-c3cn[nH]c3)cc(N(CCN3CCOCC3)Cc3ccccc3)nc2c1Cl] | 482 |
| I-358 | 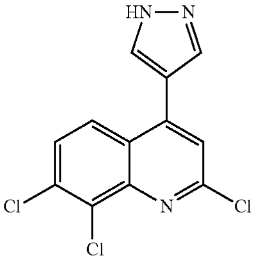 [SMILES: Clc1cc(-c2cn[nH]c2)c2ccc(Cl)c(Cl)c2n1] | 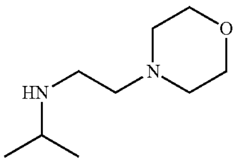 | 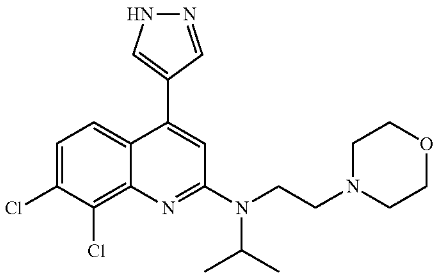 [SMILES: CC(C)N(CCN1CCOCC1)c1cc(-c2cn[nH]c2)c2ccc(Cl)c(Cl)c2n1] | 434 |
| I-218 | 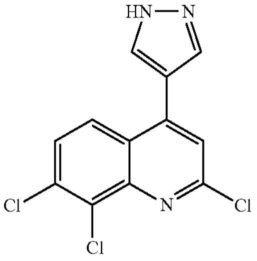 [SMILES: Clc1cc(-c2cn[nH]c2)c2ccc(Cl)c(Cl)c2n1] | 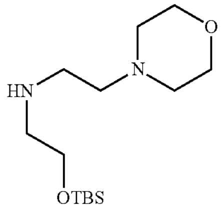 [SMILES: CC(C)(C)[Si](C)(C)OCCNCCN1CCOCC1] | 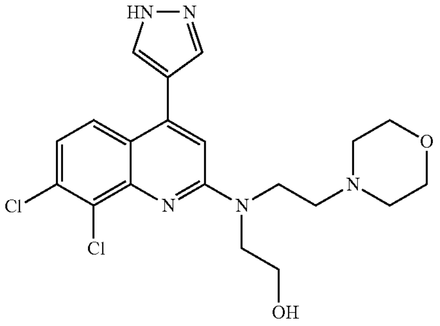 [SMILES: OCCN(CCN1CCOCC1)c1cc(-c2cn[nH]c2)c2ccc(Cl)c(Cl)c2n1] | 436 |

-continued
| I-# | Starting Material | | Structure | MS [M + 1]+ |
|---|---|---|---|---|
| I-434 | 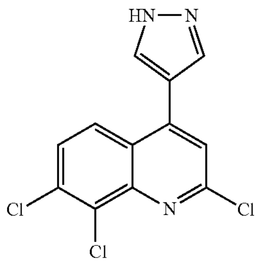 [SMILES: Clc1cc(-c2cn[nH]c2)c2ccc(Cl)c(Cl)c2n1] | 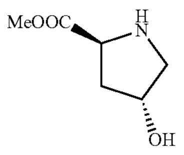 | 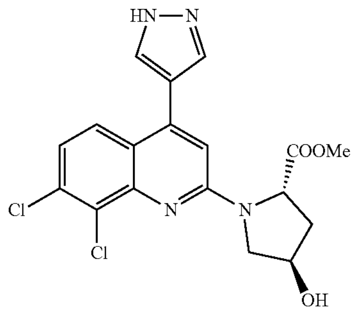 [SMILES: COC(=O)[C@@H]1C[C@@H](O)CN1c1cc(-c2cn[nH]c2)c2ccc(Cl)c(Cl)c2n1] | 407 |
| I-433 | 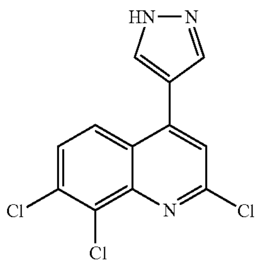 [SMILES: Clc1cc(-c2cn[nH]c2)c2ccc(Cl)c(Cl)c2n1] | 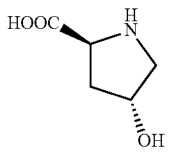 | 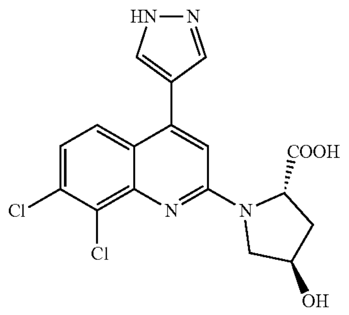 [SMILES: O=C(O)[C@@H]1C[C@@H](O)CN1c1cc(-c2cn[nH]c2)c2ccc(Cl)c(Cl)c2n1] | 393 |
| I-437 | 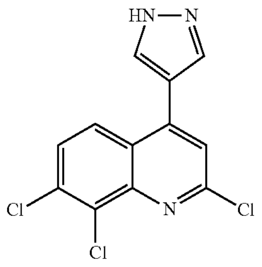 [SMILES: Clc1cc(-c2cn[nH]c2)c2ccc(Cl)c(Cl)c2n1] | 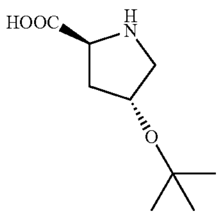 | 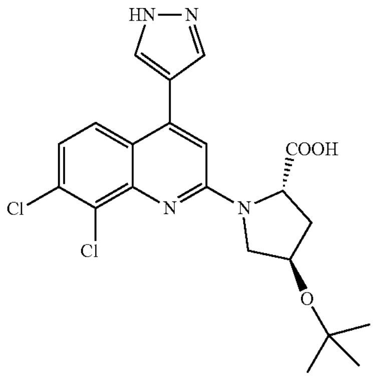 [SMILES: CC(C)(C)O[C@@H]1C[C@@H](C(=O)O)N(c2cc(-c3cn[nH]c3)c3ccc(Cl)c(Cl)c3n2)C1] | 449 |
| I-438 | 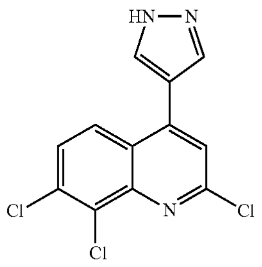 [SMILES: Clc1cc(-c2cn[nH]c2)c2ccc(Cl)c(Cl)c2n1] | 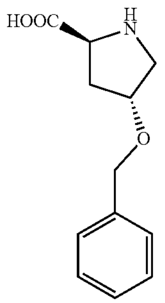 [SMILES: O=C(O)[C@@H]1C[C@@H](OCc2ccccc2)CN1] | 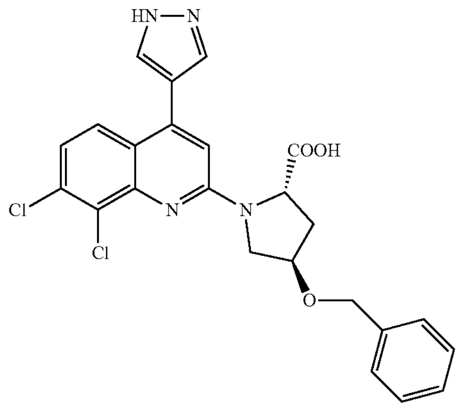 [SMILES: O=C(O)[C@@H]1C[C@@H](OCc2ccccc2)CN1c1cc(-c2cn[nH]c2)c2ccc(Cl)c(Cl)c2n1] | 483 |

-continued
| I-# | Starting Material | Structure | MS [M + 1]+ |
| --- | --- | --- | --- |
| I-352 | 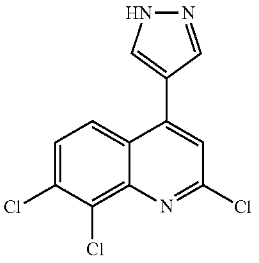 [SMILES: Clc1cc(-c2cn[nH]c2)c2ccc(Cl)c(Cl)c2n1] 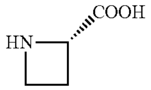 | 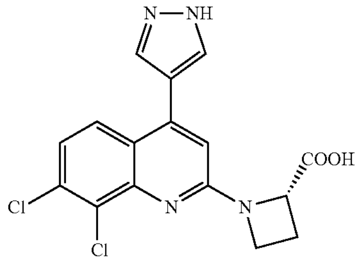 [SMILES: O=C(O)[C@@H]1CCN1c1cc(-c2cn[nH]c2)c2ccc(Cl)c(Cl)c2n1] | 363 |
| I-432 | 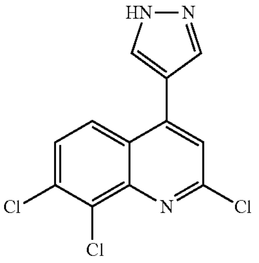 [SMILES: Clc1cc(-c2cn[nH]c2)c2ccc(Cl)c(Cl)c2n1] 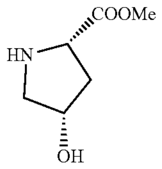 | 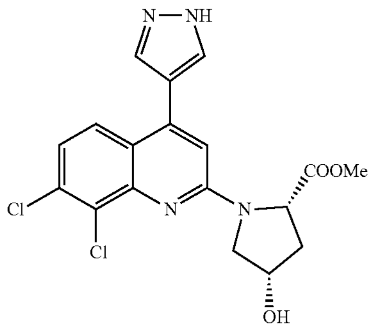 [SMILES: COC(=O)[C@@H]1C[C@H](O)CN1c1cc(-c2cn[nH]c2)c2ccc(Cl)c(Cl)c2n1] | 407 |
| I-359 | 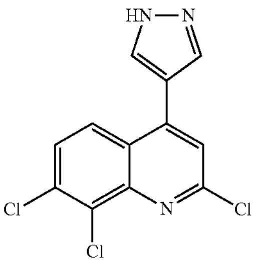 [SMILES: Clc1cc(-c2cn[nH]c2)c2ccc(Cl)c(Cl)c2n1] 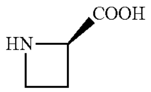 | 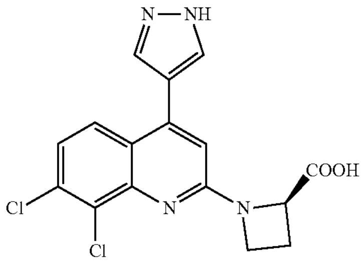 [SMILES: O=C(O)[C@H]1CCN1c1cc(-c2cn[nH]c2)c2ccc(Cl)c(Cl)c2n1] | 363 |
| I-431 | 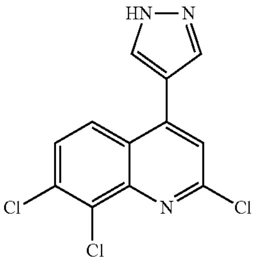 [SMILES: Clc1cc(-c2cn[nH]c2)c2ccc(Cl)c(Cl)c2n1] 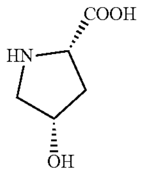 | 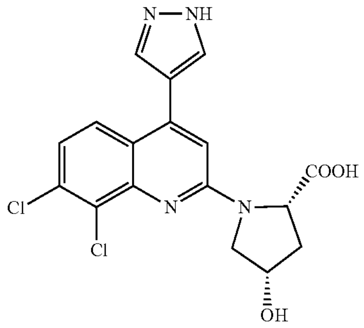 [SMILES: O=C(O)[C@@H]1C[C@H](O)CN1c1cc(-c2cn[nH]c2)c2ccc(Cl)c(Cl)c2n1] | 393 |
| I-360 | 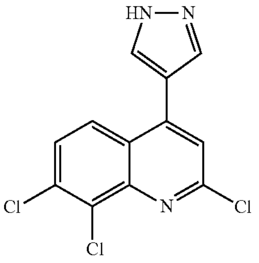 [SMILES: Clc1cc(-c2cn[nH]c2)c2ccc(Cl)c(Cl)c2n1] 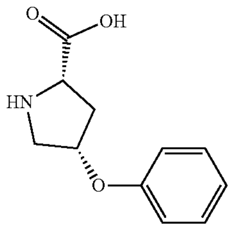 [SMILES: O=C(O)[C@@H]1C[C@H](Oc2ccccc2)CN1] | 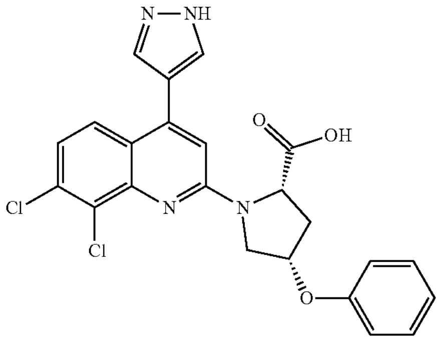 [SMILES: O=C(O)[C@@H]1C[C@H](Oc2ccccc2)CN1c1cc(-c2cn[nH]c2)c2ccc(Cl)c(Cl)c2n1] | 469 |

-continued
| I-# | Starting Material | | Structure | MS [M + 1]+ |
|---|---|---|---|---|
| I-361 | 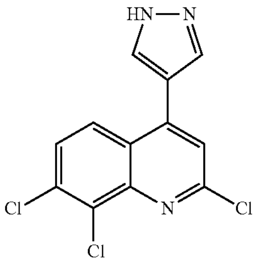 [SMILES: Clc1cc(-c2cn[nH]c2)c2ccc(Cl)c(Cl)c2n1] | 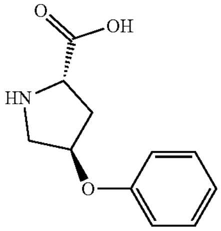 [SMILES: O=C(O)[C@@H]1C[C@@H](Oc2ccccc2)CN1] | 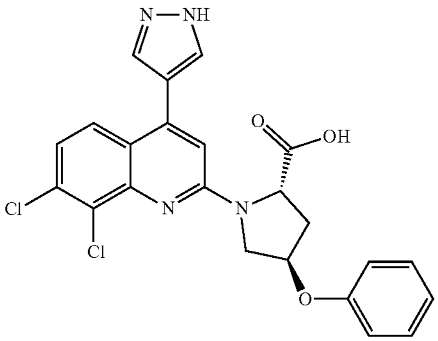 [SMILES: O=C(O)[C@@H]1C[C@@H](Oc2ccccc2)CN1c1cc(-c2cn[nH]c2)c2ccc(Cl)c(Cl)c2n1] | 469 |
| I-362 | 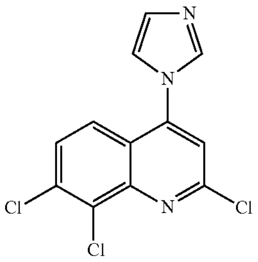 [SMILES: Clc1cc(-n2ccnc2)c2ccc(Cl)c(Cl)c2n1] | 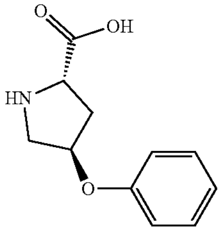 [SMILES: O=C(O)[C@@H]1C[C@@H](Oc2ccccc2)CN1] | 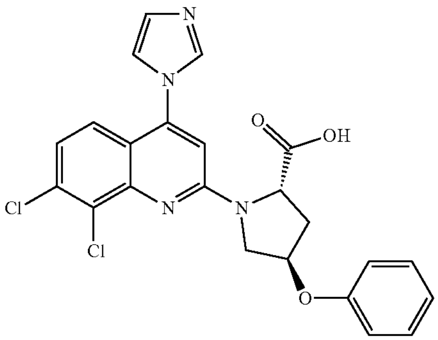 [SMILES: O=C(O)[C@@H]1C[C@@H](Oc2ccccc2)CN1c1cc(-n2ccnc2)c2ccc(Cl)c(Cl)c2n1] | 469 |
| I-444 | 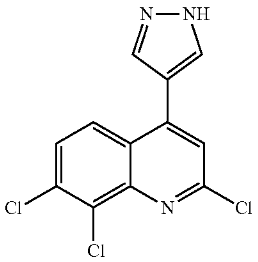 [SMILES: Clc1cc(-c2cn[nH]c2)c2ccc(Cl)c(Cl)c2n1] | 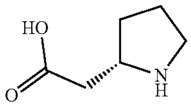 | 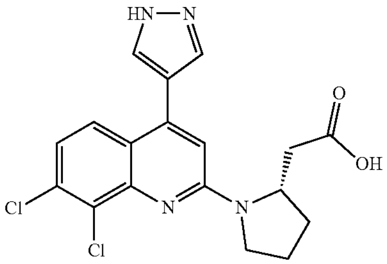 [SMILES: O=C(O)C[C@@H]1CCCN1c1cc(-c2cn[nH]c2)c2ccc(Cl)c(Cl)c2n1] | 391 |
| I-244 | 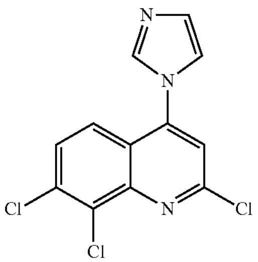 [SMILES: Clc1cc(-n2ccnc2)c2ccc(Cl)c(Cl)c2n1] | 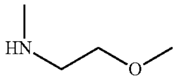 | 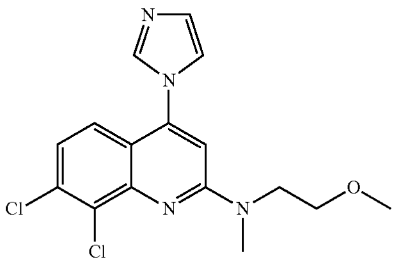 [SMILES: COCCN(C)c1cc(-n2ccnc2)c2ccc(Cl)c(Cl)c2n1] | 351 |
| I-92 | 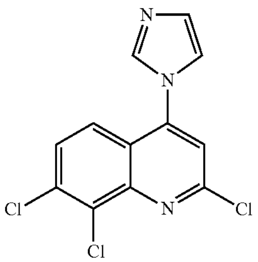 [SMILES: Clc1cc(-n2ccnc2)c2ccc(Cl)c(Cl)c2n1] | 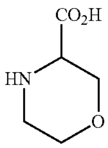 | 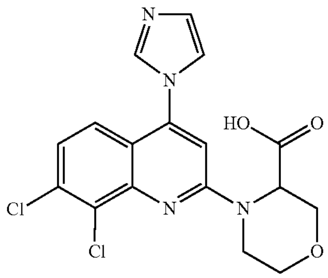 [SMILES: O=C(O)C1COCCN1c1cc(-n2ccnc2)c2ccc(Cl)c(Cl)c2n1] | 393 |

-continued
| I-# | Starting Material | | Structure | MS [M + 1]+ |
|---|---|---|---|---|
| I-241 | 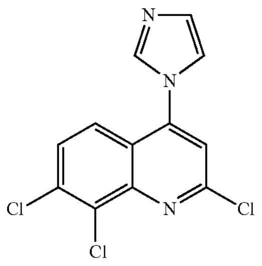 [SMILES: Clc1cc(-n2ccnc2)c2ccc(Cl)c(Cl)c2n1] | 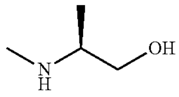 | 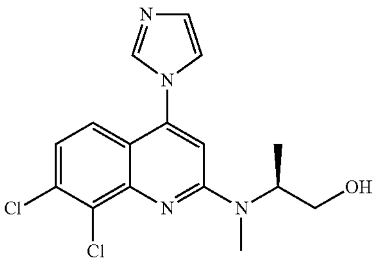 [SMILES: C[C@@H](CO)N(C)c1cc(-n2ccnc2)c2ccc(Cl)c(Cl)c2n1] | 351 |
| I-242 | 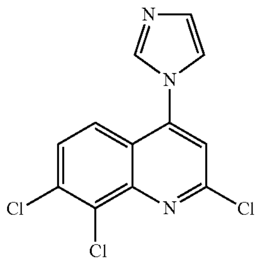 [SMILES: Clc1cc(-n2ccnc2)c2ccc(Cl)c(Cl)c2n1] | 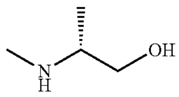 | 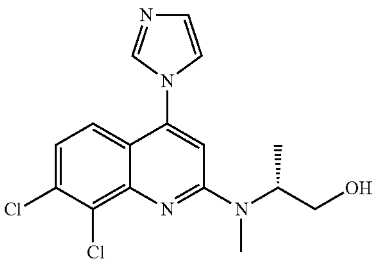 [SMILES: C[C@H](CO)N(C)c1cc(-n2ccnc2)c2ccc(Cl)c(Cl)c2n1] | 351 |
| I-93 | 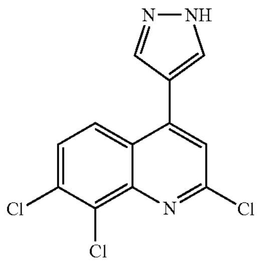 [SMILES: Clc1cc(-c2cn[nH]c2)c2ccc(Cl)c(Cl)c2n1] | 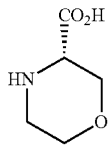 | 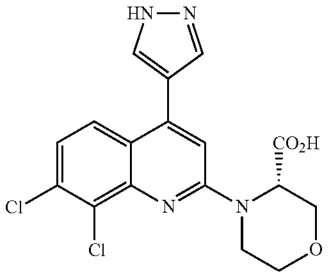 [SMILES: O=C(O)[C@@H]1COCCN1c1cc(-c2cn[nH]c2)c2ccc(Cl)c(Cl)c2n1] | 393 |
| I-94 | 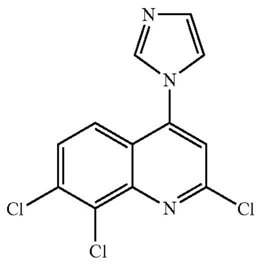 [SMILES: Clc1cc(-n2ccnc2)c2ccc(Cl)c(Cl)c2n1] | 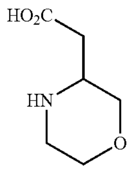 | 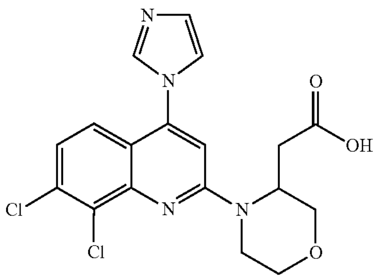 [SMILES: O=C(O)CC1COCCN1c1cc(-n2ccnc2)c2ccc(Cl)c(Cl)c2n1] | 407 |
| I-85 | 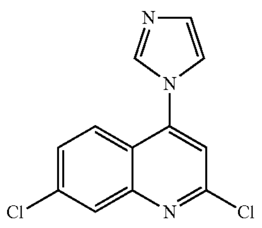 [SMILES: Clc1ccc2c(-n3ccnc3)cc(Cl)nc2c1] | 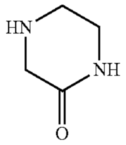 | 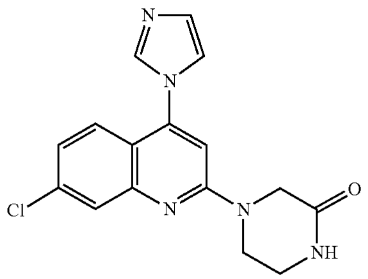 [SMILES: O=C1CN(c2cc(-n3ccnc3)c3ccc(Cl)cc3n2)CCN1] | 328 |

-continued
| I-# | Starting Material | | Structure | MS [M + 1]+ |
| --- | --- | --- | --- | --- |
| I-138 | 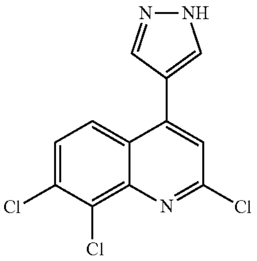 [SMILES: Clc1cc(-c2cn[nH]c2)c2ccc(Cl)c(Cl)c2n1] | 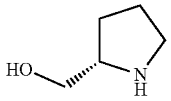 | 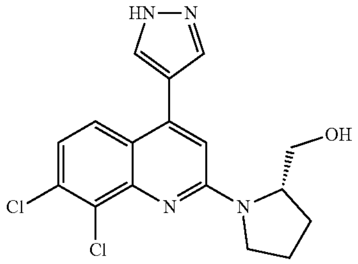 [SMILES: OC[C@@H]1CCCN1c1cc(-c2cn[nH]c2)c2ccc(Cl)c(Cl)c2n1] | 363 |
| I-139 | 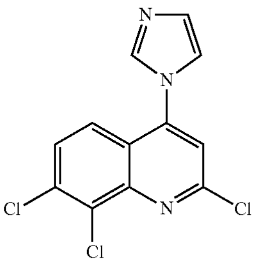 [SMILES: Clc1cc(-n2ccnc2)c2ccc(Cl)c(Cl)c2n1] | 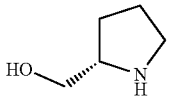 | 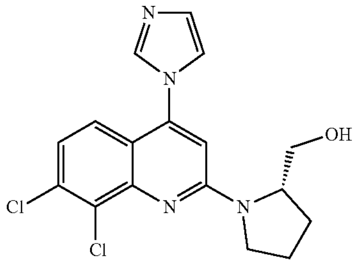 [SMILES: OC[C@@H]1CCCN1c1cc(-n2ccnc2)c2ccc(Cl)c(Cl)c2n1] | 363 |
| I-240 | 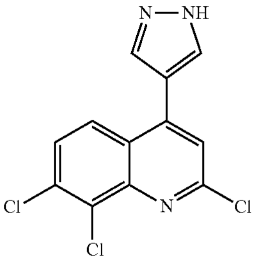 [SMILES: Clc1cc(-c2cn[nH]c2)c2ccc(Cl)c(Cl)c2n1] | 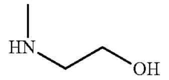 | 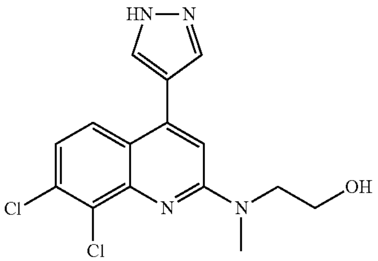 [SMILES: CN(CCO)c1cc(-c2cn[nH]c2)c2ccc(Cl)c(Cl)c2n1] | 337 |
| I-239 | 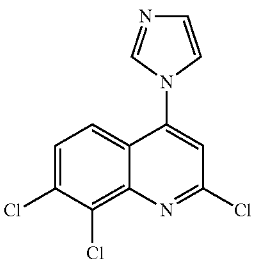 [SMILES: Clc1cc(-n2ccnc2)c2ccc(Cl)c(Cl)c2n1] | 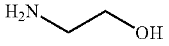 | 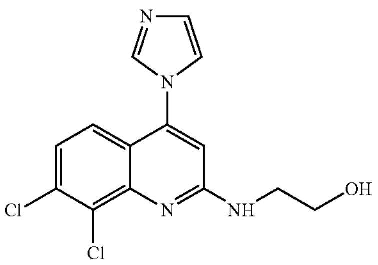 [SMILES: OCCNc1cc(-n2ccnc2)c2ccc(Cl)c(Cl)c2n1] | 323 |
| I-249 | 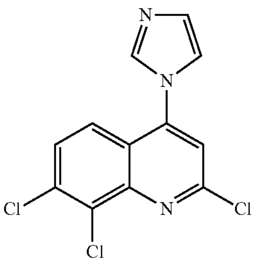 [SMILES: Clc1cc(-n2ccnc2)c2ccc(Cl)c(Cl)c2n1] | 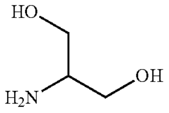 | 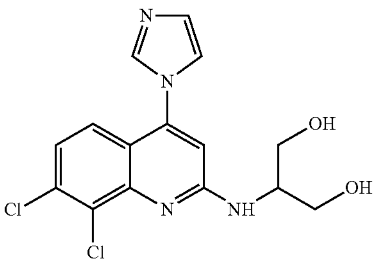 [SMILES: OCC(CO)Nc1cc(-n2ccnc2)c2ccc(Cl)c(Cl)c2n1] | 353 |

-continued
| I-# | Starting Material | | Structure | MS [M + 1]+ |
|---|---|---|---|---|
| I-245 | 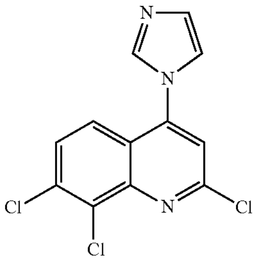 [SMILES: Clc1cc(-n2ccnc2)c2ccc(Cl)c(Cl)c2n1] | 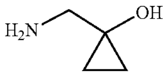 | 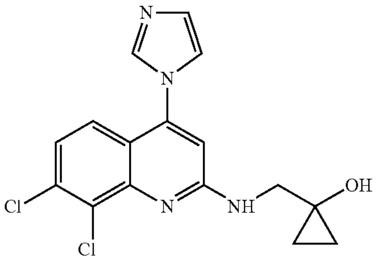 [SMILES: OC1(CNc2cc(-n3ccnc3)c3ccc(Cl)c(Cl)c3n2)CC1] | 349 |
| I-141 | 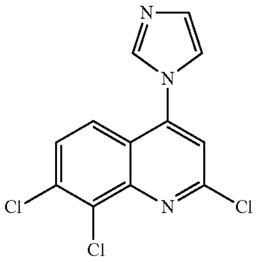 [SMILES: Clc1cc(-n2ccnc2)c2ccc(Cl)c(Cl)c2n1] | 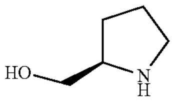 | 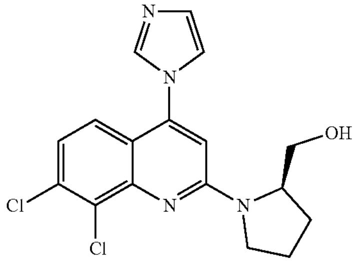 [SMILES: OC[C@H]1CCCN1c1cc(-n2ccnc2)c2ccc(Cl)c(Cl)c2n1] | 363 |
| I-243 | 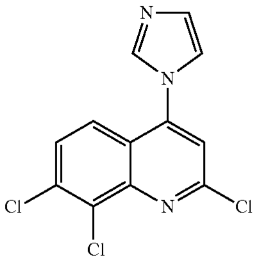 [SMILES: Clc1cc(-n2ccnc2)c2ccc(Cl)c(Cl)c2n1] | 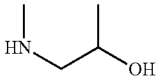 | 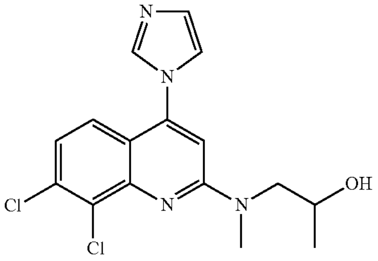 [SMILES: CC(O)CN(C)c1cc(-n2ccnc2)c2ccc(Cl)c(Cl)c2n1] | 351 |
| I-86 | 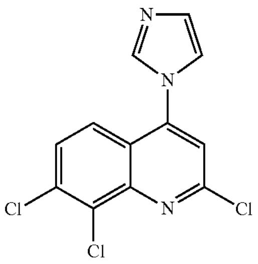 [SMILES: Clc1cc(-n2ccnc2)c2ccc(Cl)c(Cl)c2n1] | 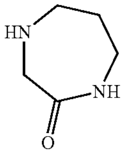 | 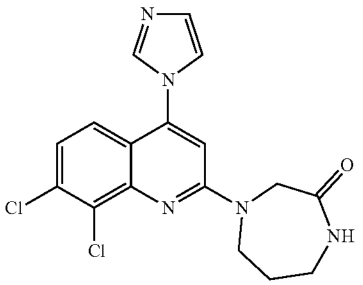 [SMILES: O=C1CN(c2cc(-n3ccnc3)c3ccc(Cl)c(Cl)c3n2)CCCN1] | 376 |
| I-246 | 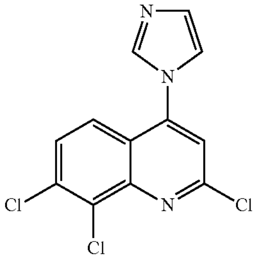 [SMILES: Clc1cc(-n2ccnc2)c2ccc(Cl)c(Cl)c2n1] | 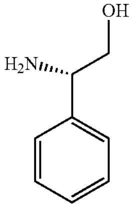 | 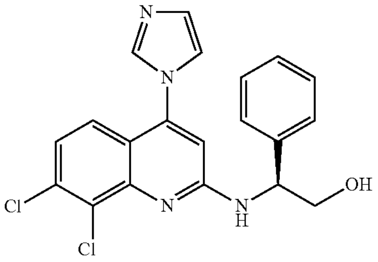 [SMILES: OC[C@@H](Nc1cc(-n2ccnc2)c2ccc(Cl)c(Cl)c2n1)c1ccccc1] | 399 |

-continued
| I-# | Starting Material | Structure | MS [M + 1]+ |
| --- | --- | --- | --- |
| I-247 | 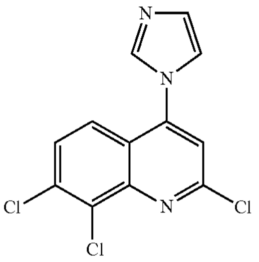 [SMILES: Clc1cc(-n2ccnc2)c2ccc(Cl)c(Cl)c2n1] 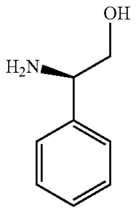 | 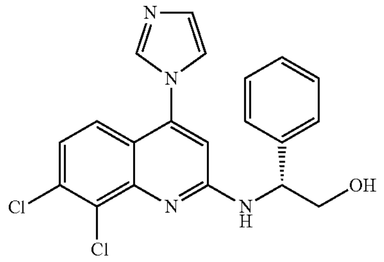 [SMILES: OC[C@H](Nc1cc(-n2ccnc2)c2ccc(Cl)c(Cl)c2n1)c1ccccc1] | 399 |
| I-155 | 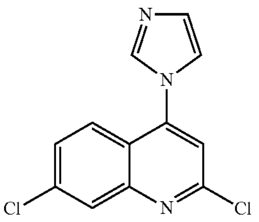 [SMILES: Clc1ccc2c(-n3ccnc3)cc(Cl)nc2c1] 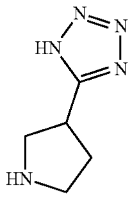 | 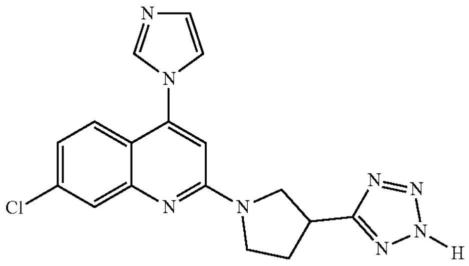 [SMILES: Clc1ccc2c(-n3ccnc3)cc(N3CCC(c4nn[nH]n4)C3)nc2c1] | 367 |
| I-128 | 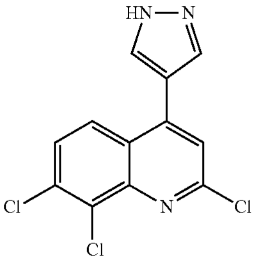 [SMILES: Clc1cc(-c2cn[nH]c2)c2ccc(Cl)c(Cl)c2n1] 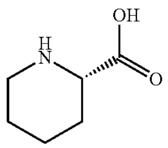 | 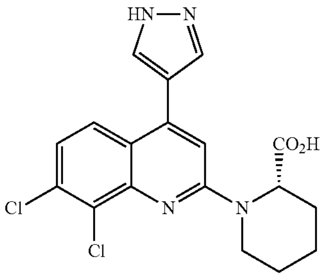 [SMILES: O=C(O)[C@@H]1CCCCN1c1cc(-c2cn[nH]c2)c2ccc(Cl)c(Cl)c2n1] | 391 |
| I-152 | 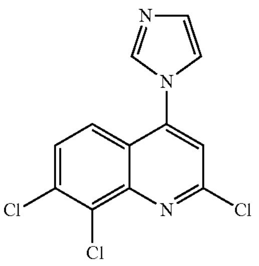 [SMILES: Clc1cc(-n2ccnc2)c2ccc(Cl)c(Cl)c2n1] 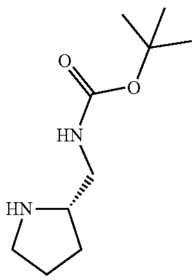 | 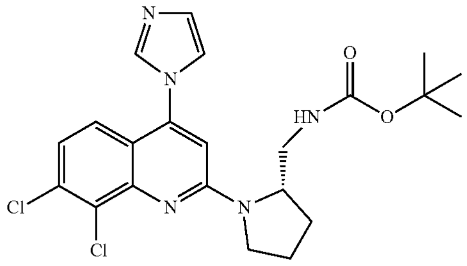 [SMILES: CC(C)(C)OC(=O)NC[C@@H]1CCCN1c1cc(-n2ccnc2)c2ccc(Cl)c(Cl)c2n1] | 462 |
| I-363 | 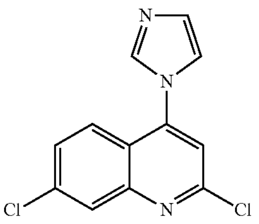 [SMILES: Clc1ccc2c(-n3ccnc3)cc(Cl)nc2c1] 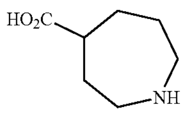 | 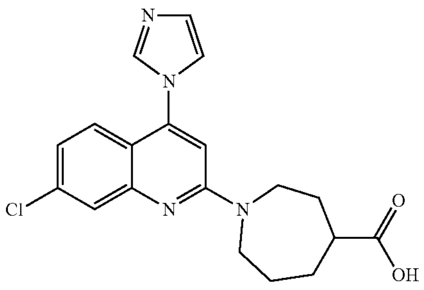 [SMILES: O=C(O)C1CCCN(c2cc(-n3ccnc3)c3ccc(Cl)cc3n2)CC1] | 371 |

-continued
| I-# | Starting Material | | Structure | MS [M + 1]+ |
|---|---|---|---|---|
| I-140 | 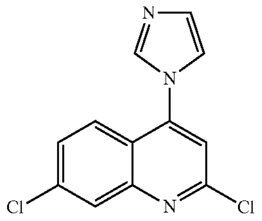 [SMILES: Clc1ccc2c(-n3ccnc3)cc(Cl)nc2c1] | 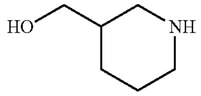 | 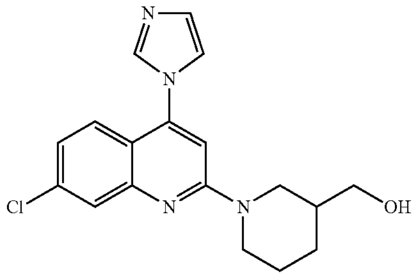 [SMILES: OCC1CCCN(c2cc(-n3ccnc3)c3ccc(Cl)cc3n2)C1] | 343 |
| I-99 | 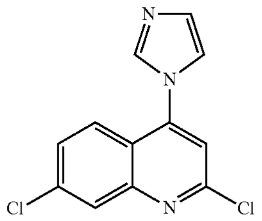 [SMILES: Clc1ccc2c(-n3ccnc3)cc(Cl)nc2c1] | 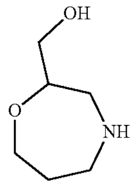 | 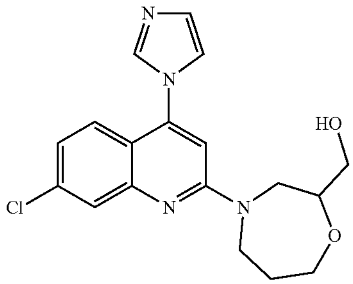 [SMILES: OCC1CN(c2cc(-n3ccnc3)c3ccc(Cl)cc3n2)CCCO1] | 359 |
| I-97 | 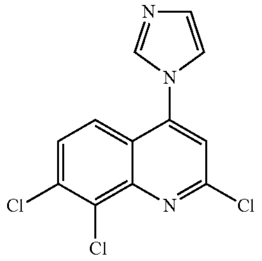 [SMILES: Clc1cc(-n2ccnc2)c2ccc(Cl)c(Cl)c2n1] | 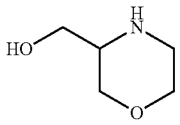 | 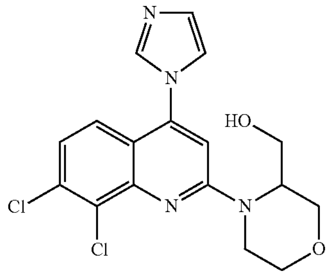 [SMILES: OCC1COCCN1c1cc(-n2ccnc2)c2ccc(Cl)c(Cl)c2n1] | 379 |
| I-88 | 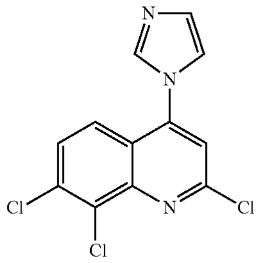 [SMILES: Clc1cc(-n2ccnc2)c2ccc(Cl)c(Cl)c2n1] | 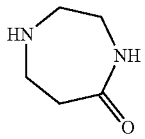 | 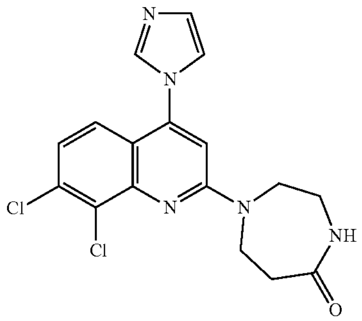 [SMILES: O=C1CCN(c2cc(-n3ccnc3)c3ccc(Cl)c(Cl)c3n2)CCN1] | 342 |
| I-446 | 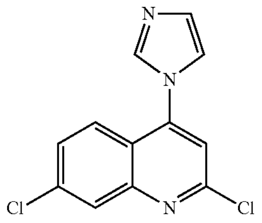 [SMILES: Clc1ccc2c(-n3ccnc3)cc(Cl)nc2c1] | 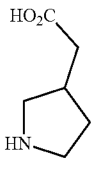 | 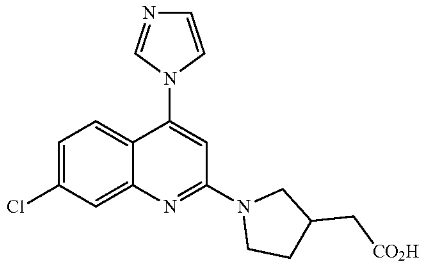 | 357 |

-continued
| I-# | Starting Material | Structure | MS [M + 1]+ |
| --- | --- | --- | --- |
| I-364 | 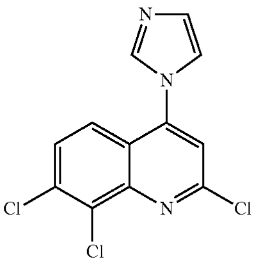 [SMILES: Clc1cc(-n2ccnc2)c2ccc(Cl)c(Cl)c2n1] 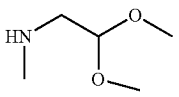 | 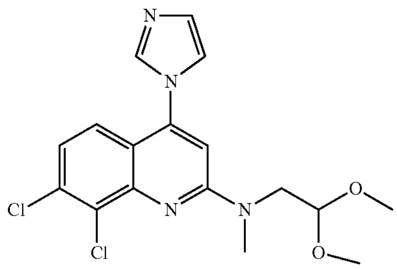 [SMILES: COC(CN(C)c1cc(-n2ccnc2)c2ccc(Cl)c(Cl)c2n1)OC] | 381 |
| I-117 | 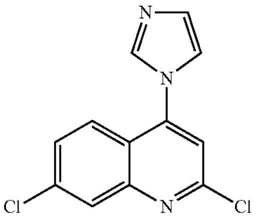 [SMILES: Clc1ccc2c(-n3ccnc3)cc(Cl)nc2c1] 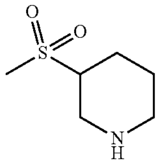 | 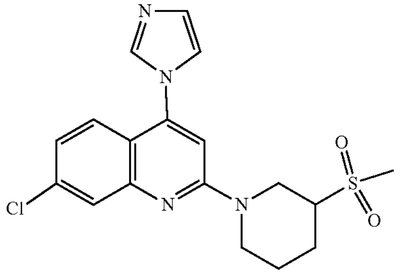 [SMILES: CS(=O)(=O)C1CCCN(c2cc(-n3ccnc3)c3ccc(Cl)cc3n2)C1] | 391 |
| I-365 | 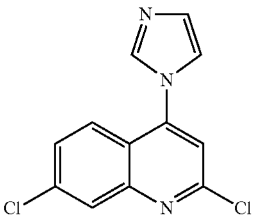 [SMILES: Clc1ccc2c(-n3ccnc3)cc(Cl)nc2c1] 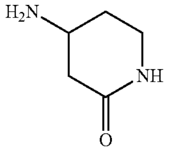 | 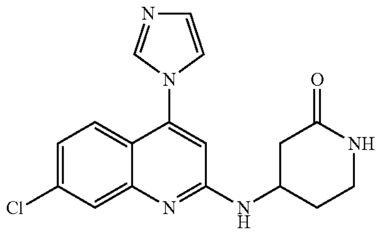 [SMILES: O=C1CC(Nc2cc(-n3ccnc3)c3ccc(Cl)cc3n2)CCN1] | 342 |
| I-366 | 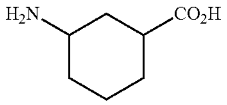 | 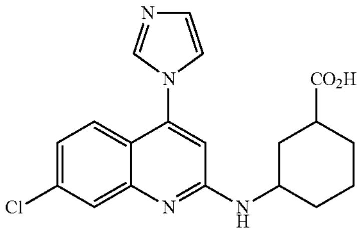 [SMILES: O=C(O)C1CCCC(Nc2cc(-n3ccnc3)c3ccc(Cl)cc3n2)C1] | 371 |
| I-367 | 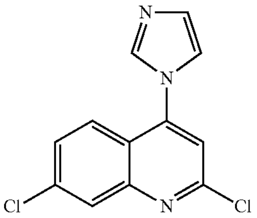 [SMILES: Clc1ccc2c(-n3ccnc3)cc(Cl)nc2c1] 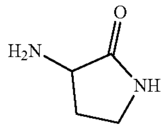 | 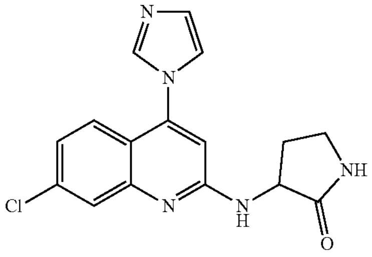 [SMILES: O=C1NCCC1Nc1cc(-n2ccnc2)c2ccc(Cl)cc2n1] | 328 |
| I-116 | 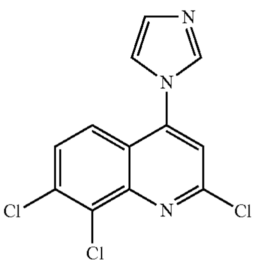 [SMILES: Clc1cc(-n2ccnc2)c2ccc(Cl)c(Cl)c2n1] 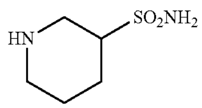 | 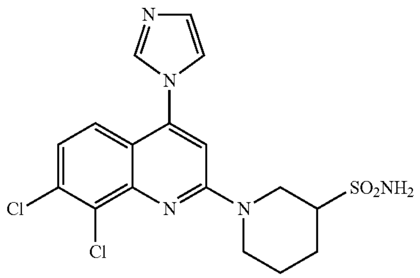 [SMILES: NS(=O)(=O)C1CCCN(c2cc(-n3ccnc3)c3ccc(Cl)c(Cl)c3n2)C1] | 426 |

-continued
| I-# | Starting Material | | Structure | MS [M + 1]+ |
|---|---|---|---|---|
| I-89 | 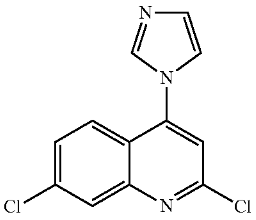 [SMILES: Clc1ccc2c(-n3ccnc3)cc(Cl)nc2c1] | 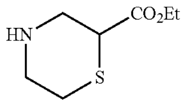 [SMILES: CCOC(=O)C1CNCCS1] | 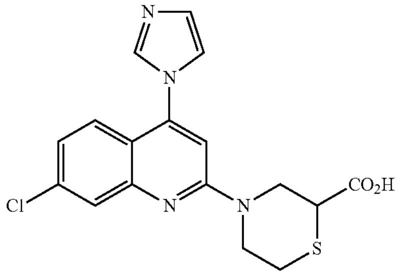 [SMILES: O=C(O)C1CN(c2cc(-n3ccnc3)c3ccc(Cl)cc3n2)CCS1] | 375 |
| I-158 | 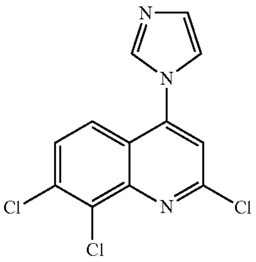 [SMILES: Clc1cc(-n2ccnc2)c2ccc(Cl)c(Cl)c2n1] | 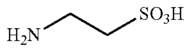 | 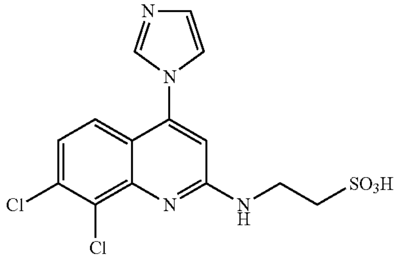 [SMILES: O=S(=O)(O)CCNc1cc(-n2ccnc2)c2ccc(Cl)c(Cl)c2n1] | 387 |
| I-160 | 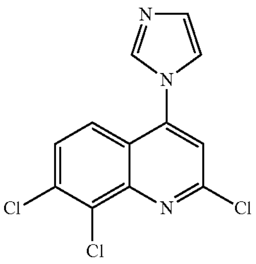 [SMILES: Clc1cc(-n2ccnc2)c2ccc(Cl)c(Cl)c2n1] | 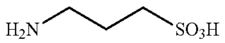 | 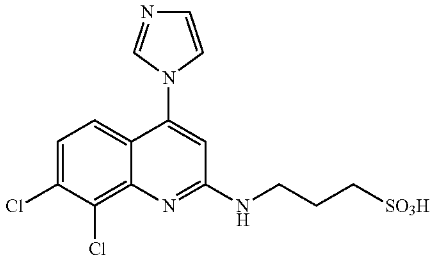 [SMILES: O=S(=O)(O)CCCNc1cc(-n2ccnc2)c2ccc(Cl)c(Cl)c2n1] | 401 |
| I-200 | 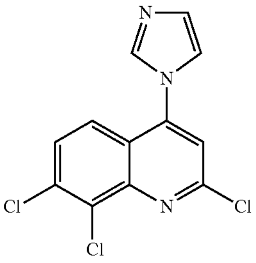 [SMILES: Clc1cc(-n2ccnc2)c2ccc(Cl)c(Cl)c2n1] | 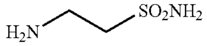 | 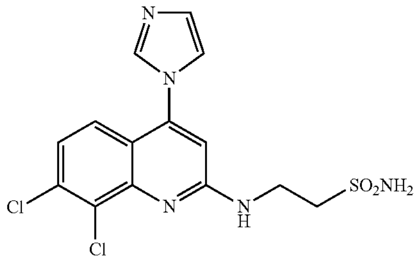 [SMILES: NS(=O)(=O)CCNc1cc(-n2ccnc2)c2ccc(Cl)c(Cl)c2n1] | 386 |
| I-201 | 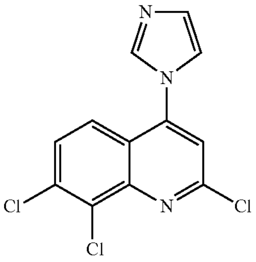 [SMILES: Clc1cc(-n2ccnc2)c2ccc(Cl)c(Cl)c2n1] | 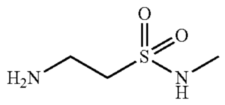 | 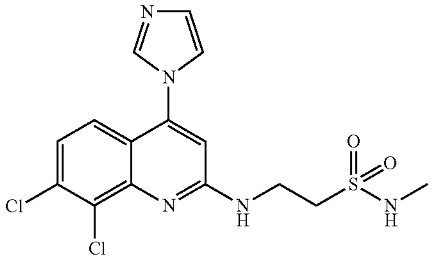 | 400 |

-continued
| I-# | Starting Material | | Structure | MS [M + 1]+ |
|---|---|---|---|---|
| I-202 | 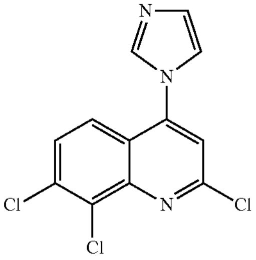 [SMILES: Clc1cc(-n2ccnc2)c2ccc(Cl)c(Cl)c2n1] | 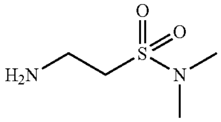 | 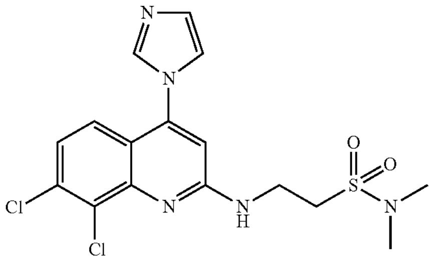 [SMILES: CN(C)S(=O)(=O)CCNc1cc(-n2ccnc2)c2ccc(Cl)c(Cl)c2n1] | 414 |
| I-178 | 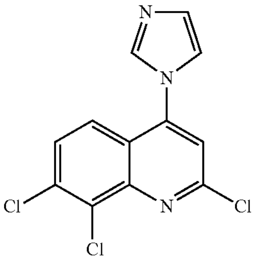 [SMILES: Clc1cc(-n2ccnc2)c2ccc(Cl)c(Cl)c2n1] | 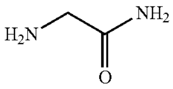 | 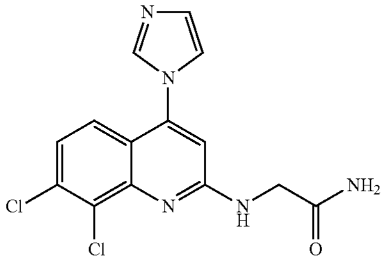 [SMILES: NC(=O)CNc1cc(-n2ccnc2)c2ccc(Cl)c(Cl)c2n1] | 336 |
| I-179 | 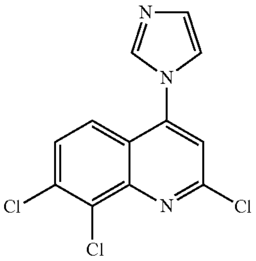 [SMILES: Clc1cc(-n2ccnc2)c2ccc(Cl)c(Cl)c2n1] | 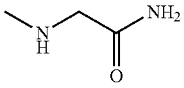 | 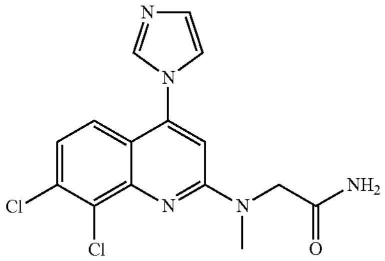 [SMILES: CN(CC(N)=O)c1cc(-n2ccnc2)c2ccc(Cl)c(Cl)c2n1] | 350 |
| I-204 | 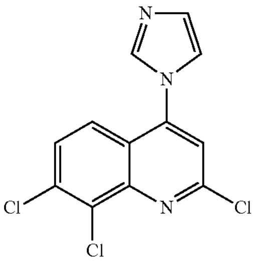 [SMILES: Clc1cc(-n2ccnc2)c2ccc(Cl)c(Cl)c2n1] | 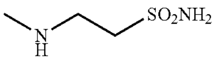 | 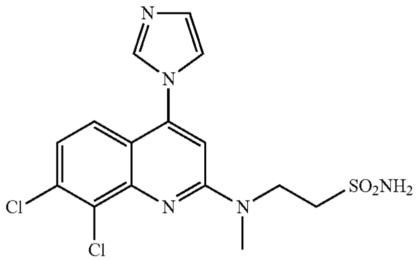 [SMILES: CN(CCS(N)(=O)=O)c1cc(-n2ccnc2)c2ccc(Cl)c(Cl)c2n1] | 400 |
| I-159 | 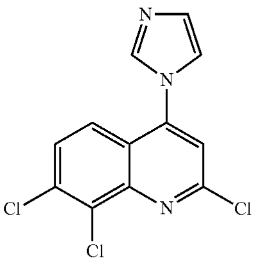 [SMILES: Clc1cc(-n2ccnc2)c2ccc(Cl)c(Cl)c2n1] | 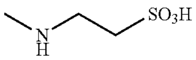 | 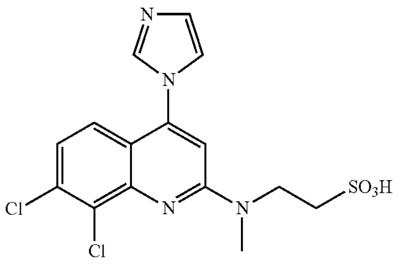 [SMILES: CN(CCS(=O)(=O)O)c1cc(-n2ccnc2)c2ccc(Cl)c(Cl)c2n1] | 401 |

-continued
| I-# | Starting Material | | Structure | MS [M + 1]+ |
|---|---|---|---|---|
| I-205 | 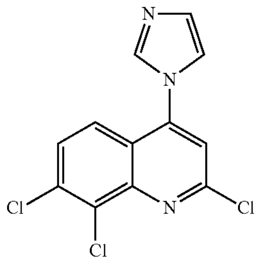 [SMILES: Clc1cc(-n2ccnc2)c2ccc(Cl)c(Cl)c2n1] | 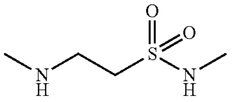 | 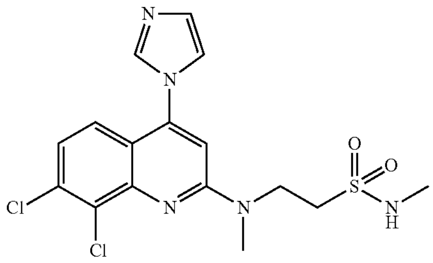 [SMILES: CNS(=O)(=O)CCN(C)c1cc(-n2ccnc2)c2ccc(Cl)c(Cl)c2n1] | 414 |
| I-148 | 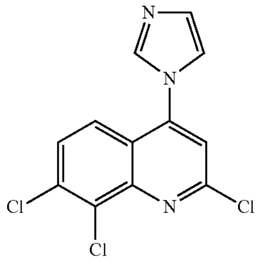 [SMILES: Clc1cc(-n2ccnc2)c2ccc(Cl)c(Cl)c2n1] | 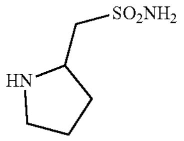 | 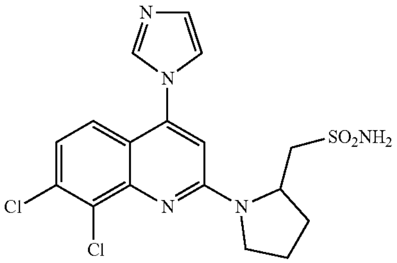 [SMILES: NS(=O)(=O)CC1CCCN1c1cc(-n2ccnc2)c2ccc(Cl)c(Cl)c2n1] | 426 |
| I-149 | 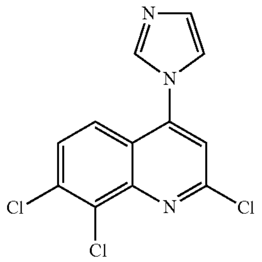 [SMILES: Clc1cc(-n2ccnc2)c2ccc(Cl)c(Cl)c2n1] | 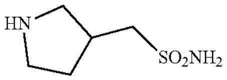 | 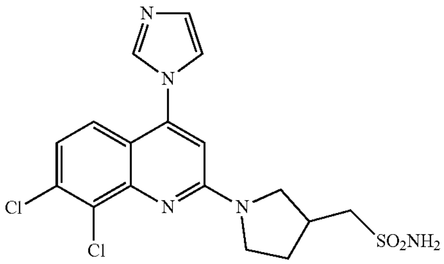 [SMILES: NS(=O)(=O)CC1CCN(c2cc(-n3ccnc3)c3ccc(Cl)c(Cl)c3n2)C1] | 426 |
| I-150 | 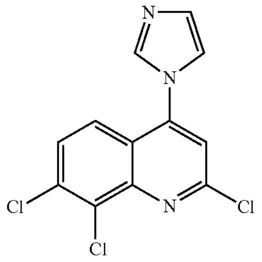 [SMILES: Clc1cc(-n2ccnc2)c2ccc(Cl)c(Cl)c2n1] | 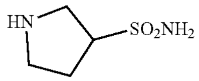 | 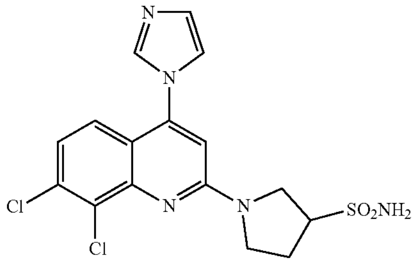 [SMILES: NS(=O)(=O)C1CCN(c2cc(-n3ccnc3)c3ccc(Cl)c(Cl)c3n2)C1] | 412 |
| I-368 | 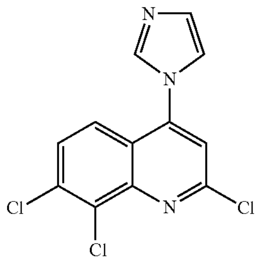 [SMILES: Clc1cc(-n2ccnc2)c2ccc(Cl)c(Cl)c2n1] | 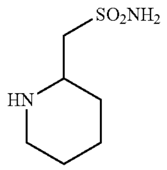 [SMILES: NS(=O)(=O)CC1CCCCN1] | 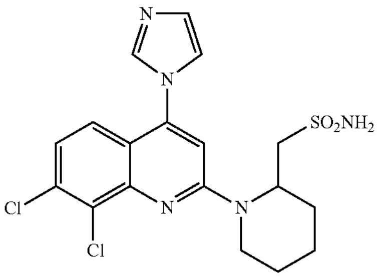 [SMILES: NS(=O)(=O)CC1CCCCN1c1cc(-n2ccnc2)c2ccc(Cl)c(Cl)c2n1] | 440 |

-continued
| I-# | Starting Material | Structure | MS [M + 1]+ |
| --- | --- | --- | --- |
| I-206 | 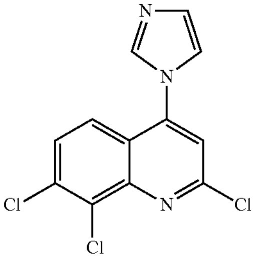 [SMILES: Clc1cc(-n2ccnc2)c2ccc(Cl)c(Cl)c2n1] 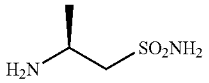 | 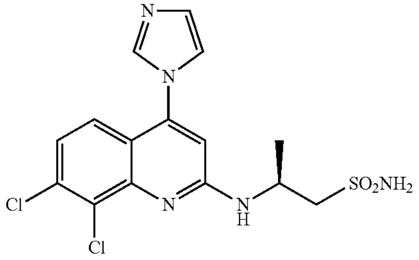 [SMILES: C[C@@H](CS(N)(=O)=O)Nc1cc(-n2ccnc2)c2ccc(Cl)c(Cl)c2n1] | 400 |
| I-207 | 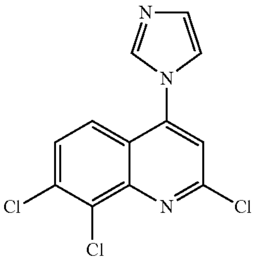 [SMILES: Clc1cc(-n2ccnc2)c2ccc(Cl)c(Cl)c2n1] 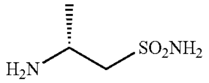 | 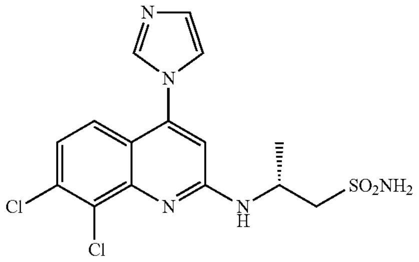 [SMILES: C[C@H](CS(N)(=O)=O)Nc1cc(-n2ccnc2)c2ccc(Cl)c(Cl)c2n1] | 400 |
| I-210 | 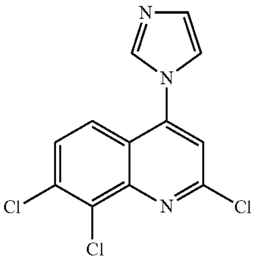 [SMILES: Clc1cc(-n2ccnc2)c2ccc(Cl)c(Cl)c2n1] 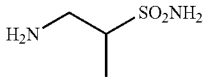 | 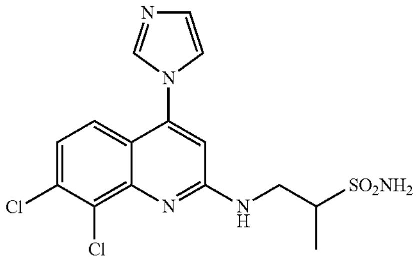 [SMILES: CC(CNc1cc(-n2ccnc2)c2ccc(Cl)c(Cl)c2n1)S(N)(=O)=O] | 400 |
| I-190 | 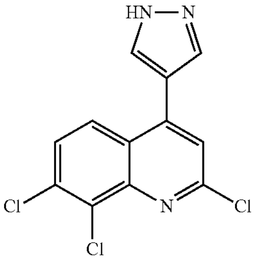 [SMILES: Clc1cc(-c2cn[nH]c2)c2ccc(Cl)c(Cl)c2n1] 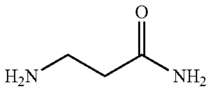 | 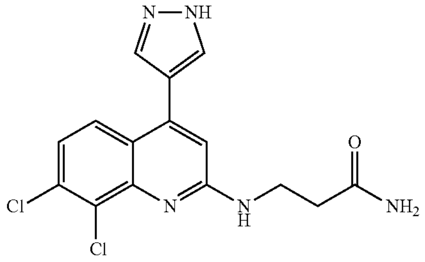 [SMILES: NC(=O)CCNc1cc(-c2cn[nH]c2)c2ccc(Cl)c(Cl)c2n1] | 350 |
| I-191 | 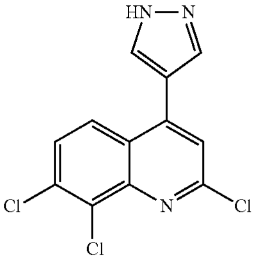 [SMILES: Clc1cc(-c2cn[nH]c2)c2ccc(Cl)c(Cl)c2n1] 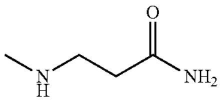 | 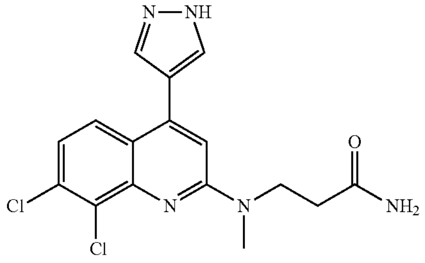 [SMILES: CN(CCC(N)=O)c1cc(-c2cn[nH]c2)c2ccc(Cl)c(Cl)c2n1] | 364 |

-continued
| I-# | Starting Material | Structure | MS [M + 1]+ |
|---|---|---|---|
| I-192 | 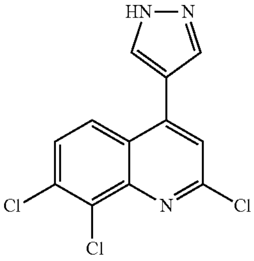 [SMILES: Clc1cc(-c2cn[nH]c2)c2ccc(Cl)c(Cl)c2n1] 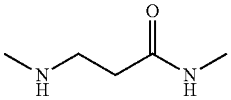 | 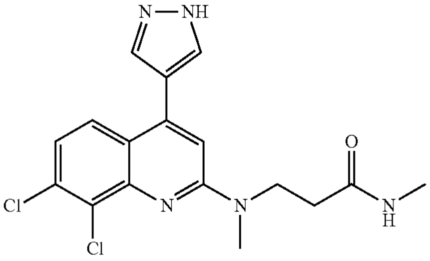 [SMILES: CNC(=O)CCN(C)c1cc(-c2cn[nH]c2)c2ccc(Cl)c(Cl)c2n1] | 378 |
| I-428 | 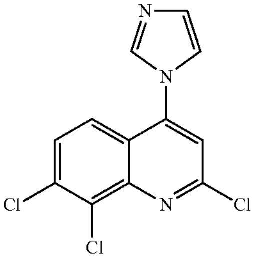 [SMILES: Clc1cc(-n2ccnc2)c2ccc(Cl)c(Cl)c2n1] 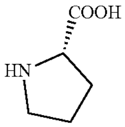 | 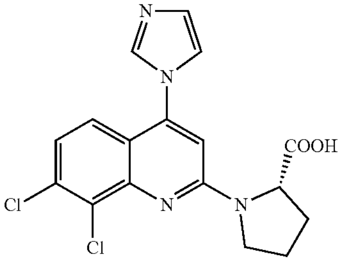 [SMILES: O=C(O)[C@@H]1CCCN1c1cc(-n2ccnc2)c2ccc(Cl)c(Cl)c2n1] | 377 |
| I-327 | 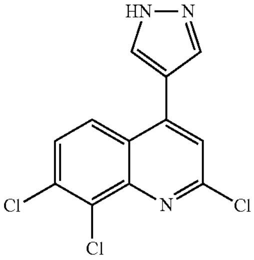 [SMILES: Clc1cc(-c2cn[nH]c2)c2ccc(Cl)c(Cl)c2n1] 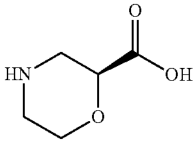 | 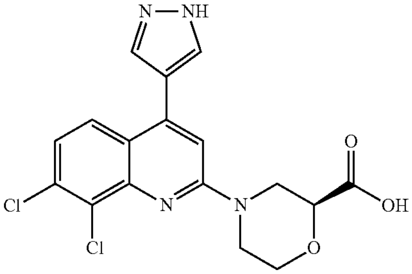 [SMILES: O=C(O)[C@@H]1CN(c2cc(-c3cn[nH]c3)c3ccc(Cl)c(Cl)c3n2)CCO1] | 393 |
| I-369 | 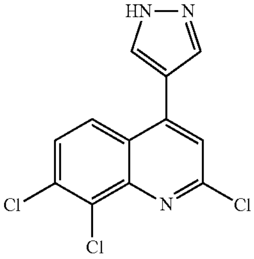 [SMILES: Clc1cc(-c2cn[nH]c2)c2ccc(Cl)c(Cl)c2n1] 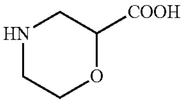 | 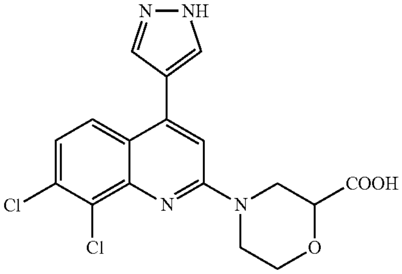 [SMILES: O=C(O)C1CN(c2cc(-c3cn[nH]c3)c3ccc(Cl)c(Cl)c3n2)CCO1] | 393 |
| I-370 | 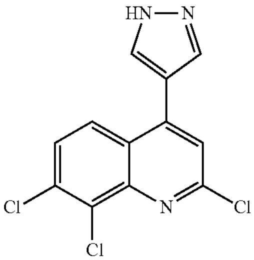 [SMILES: Clc1cc(-c2cn[nH]c2)c2ccc(Cl)c(Cl)c2n1] 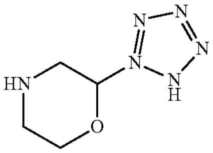 | 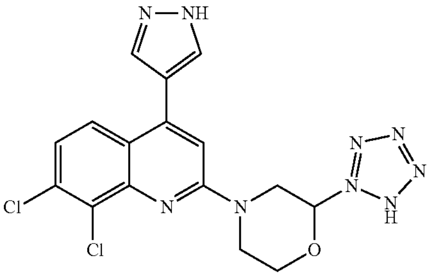 | 417 |

-continued
| I-# | Starting Material | | Structure | MS [M + 1]+ |
|---|---|---|---|---|
| I-328 | 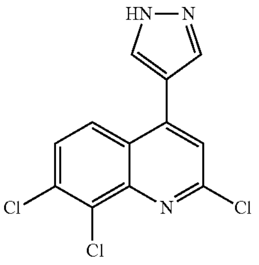 [SMILES: Clc1cc(-c2cn[nH]c2)c2ccc(Cl)c(Cl)c2n1] | 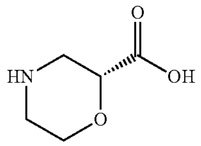 | 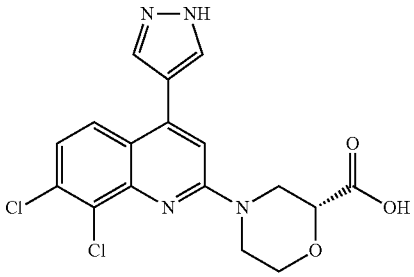 [SMILES: O=C(O)[C@H]1CN(c2cc(-c3cn[nH]c3)c3ccc(Cl)c(Cl)c3n2)CCO1] | 393 |
| I-238 | 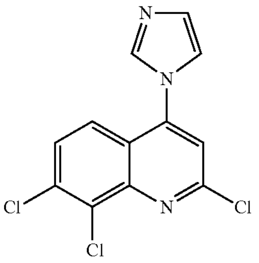 [SMILES: Clc1cc(-n2ccnc2)c2ccc(Cl)c(Cl)c2n1] | 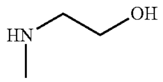 | 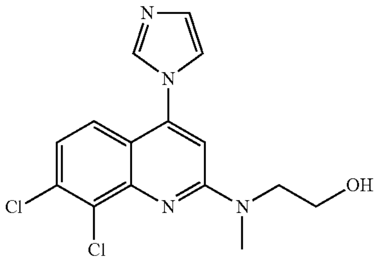 [SMILES: CN(CCO)c1cc(-n2ccnc2)c2ccc(Cl)c(Cl)c2n1] | 337 |
| I-145 | 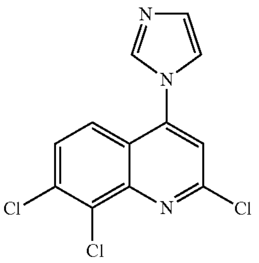 [SMILES: Clc1cc(-n2ccnc2)c2ccc(Cl)c(Cl)c2n1] | 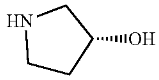 | 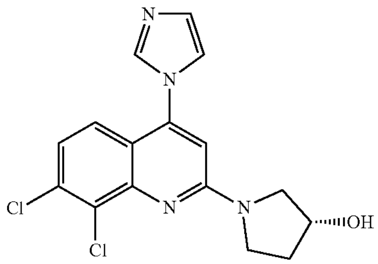 [SMILES: O[C@@H]1CCN(c2cc(-n3ccnc3)c3ccc(Cl)c(Cl)c3n2)C1] | 349 |
| I-203 | 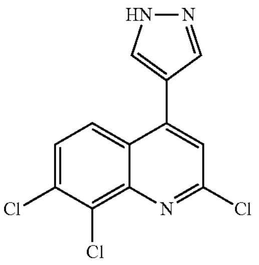 [SMILES: Clc1cc(-c2cn[nH]c2)c2ccc(Cl)c(Cl)c2n1] | 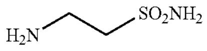 | 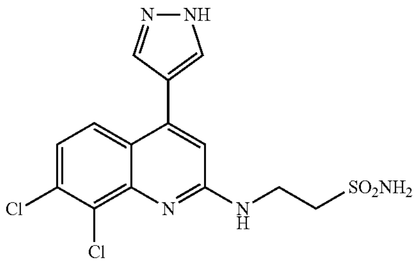 [SMILES: NS(=O)(=O)CCNc1cc(-c2cn[nH]c2)c2ccc(Cl)c(Cl)c2n1] | 386 |
| I-144 | 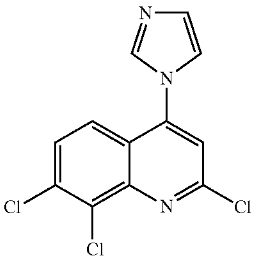 [SMILES: Clc1cc(-n2ccnc2)c2ccc(Cl)c(Cl)c2n1] | 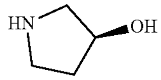 | 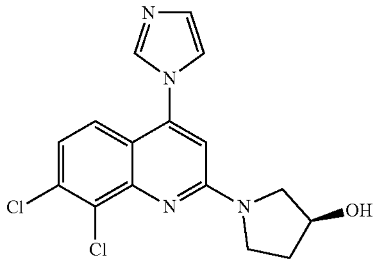 [SMILES: O[C@H]1CCN(c2cc(-n3ccnc3)c3ccc(Cl)c(Cl)c3n2)C1] | 349 |

-continued
| I-# | Starting Material | Structure | MS [M + 1]+ |
| --- | --- | --- | --- |
| I-371 | 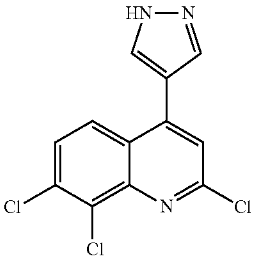 [SMILES: Clc1cc(-c2cn[nH]c2)c2ccc(Cl)c(Cl)c2n1] 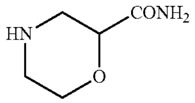 | 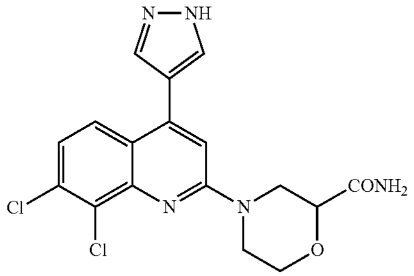 [SMILES: NC(=O)C1CN(c2cc(-c3cn[nH]c3)c3ccc(Cl)c(Cl)c3n2)CCO1] | 392 |
| I-372 | 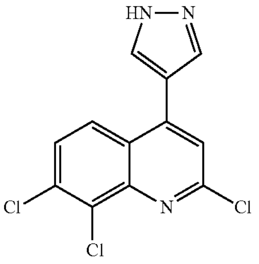 [SMILES: Clc1cc(-c2cn[nH]c2)c2ccc(Cl)c(Cl)c2n1] 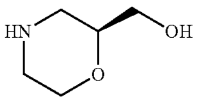 | 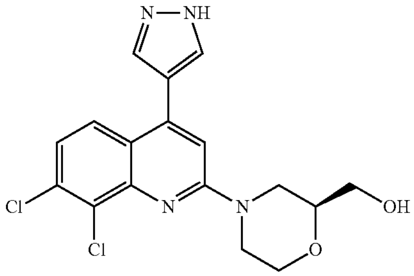 [SMILES: OC[C@@H]1CN(c2cc(-c3cn[nH]c3)c3ccc(Cl)c(Cl)c3n2)CCO1] | 379 |
| I-373 | 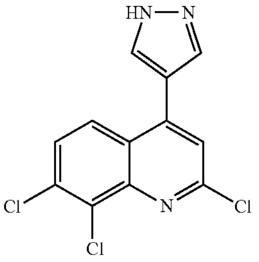 [SMILES: Clc1cc(-c2cn[nH]c2)c2ccc(Cl)c(Cl)c2n1] 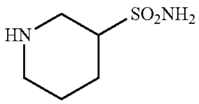 | 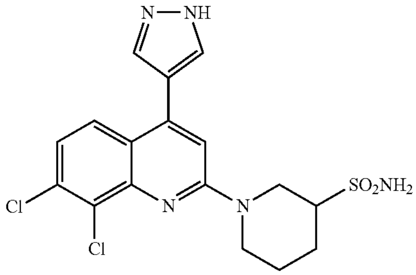 [SMILES: NS(=O)(=O)C1CCCN(c2cc(-c3cn[nH]c3)c3ccc(Cl)c(Cl)c3n2)C1] | 426 |
| I-250 | 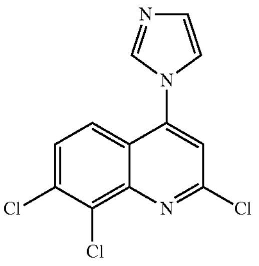 [SMILES: Clc1cc(-n2ccnc2)c2ccc(Cl)c(Cl)c2n1] 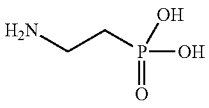 | 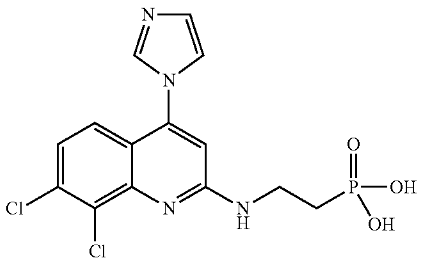 [SMILES: O=P(O)(O)CCNc1cc(-n2ccnc2)c2ccc(Cl)c(Cl)c2n1] | 387 |
| I-248 | 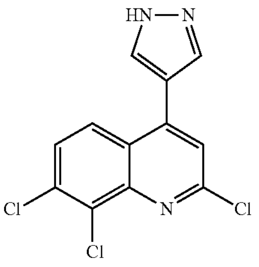 [SMILES: Clc1cc(-c2cn[nH]c2)c2ccc(Cl)c(Cl)c2n1] 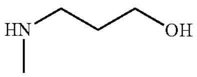 | 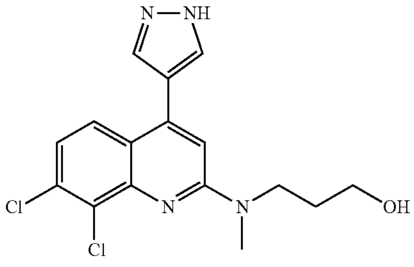 [SMILES: CN(CCCO)c1cc(-c2cn[nH]c2)c2ccc(Cl)c(Cl)c2n1] | 351 |

-continued
| I-# | Starting Material | Structure | MS [M + 1]+ |
|---|---|---|---|
| I-374 | 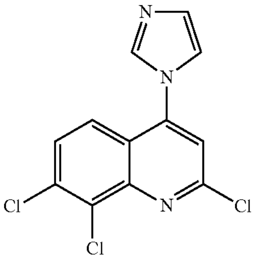 [SMILES: Clc1cc(-n2ccnc2)c2ccc(Cl)c(Cl)c2n1] 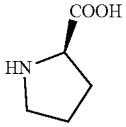 | 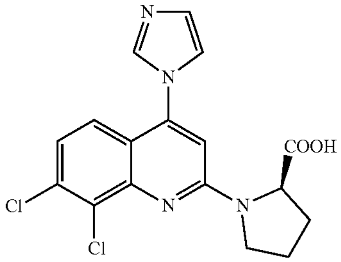 [SMILES: O=C(O)[C@H]1CCCN1c1cc(-n2ccnc2)c2ccc(Cl)c(Cl)c2n1] | 377 |
| I-375 | 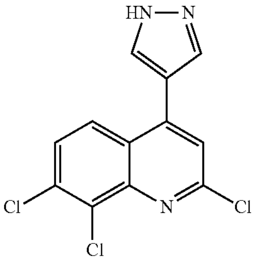 [SMILES: Clc1cc(-c2cn[nH]c2)c2ccc(Cl)c(Cl)c2n1] 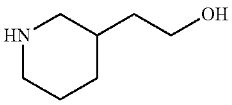 | 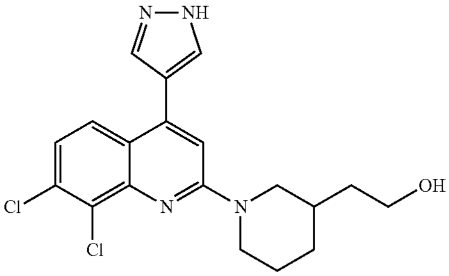 [SMILES: OCCC1CCCN(c2cc(-c3cn[nH]c3)c3ccc(Cl)c(Cl)c3n2)C1] | 391 |
| I-157 | 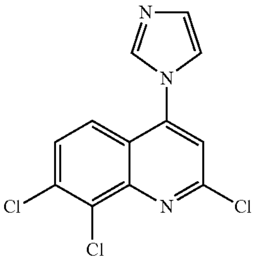 [SMILES: Clc1cc(-n2ccnc2)c2ccc(Cl)c(Cl)c2n1] 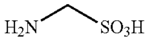 | 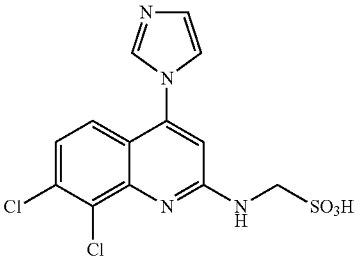 [SMILES: O=S(=O)(O)CNc1cc(-n2ccnc2)c2ccc(Cl)c(Cl)c2n1] | 373 |
| I-98 | 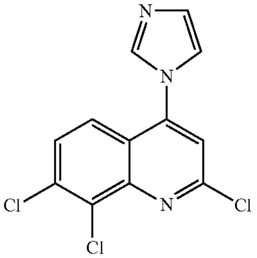 [SMILES: Clc1cc(-n2ccnc2)c2ccc(Cl)c(Cl)c2n1] 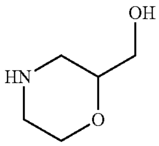 | 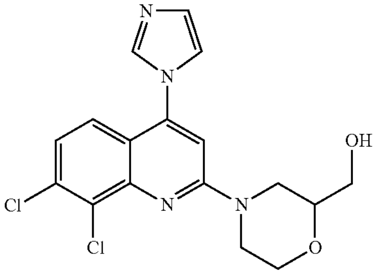 [SMILES: OCC1CN(c2cc(-n3ccnc3)c3ccc(Cl)c(Cl)c3n2)CCO1] | 379 |
| I-443 | 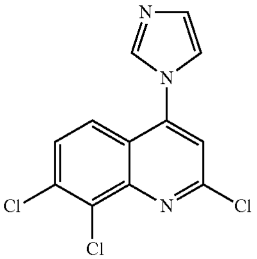 [SMILES: Clc1cc(-n2ccnc2)c2ccc(Cl)c(Cl)c2n1] 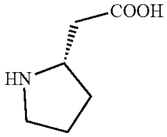 | 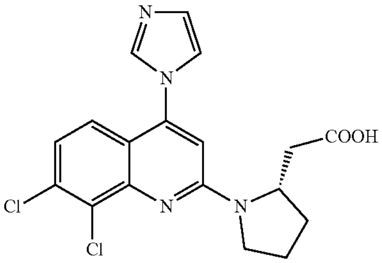 [SMILES: O=C(O)C[C@@H]1CCCN1c1cc(-n2ccnc2)c2ccc(Cl)c(Cl)c2n1] | 391 |

-continued
| I-# | Starting Material | | Structure | MS [M + 1]+ |
|---|---|---|---|---|
| I-142 | 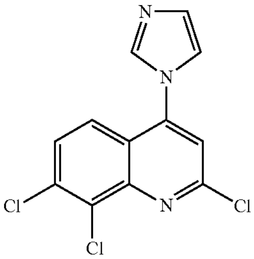 [SMILES: Clc1cc(-n2ccnc2)c2ccc(Cl)c(Cl)c2n1] | 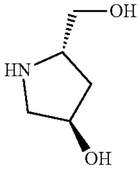 | 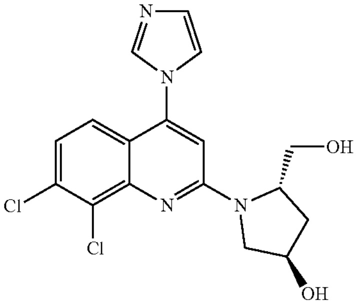 [SMILES: OC[C@@H]1C[C@@H](O)CN1c1cc(-n2ccnc2)c2ccc(Cl)c(Cl)c2n1] | 379 |
| I-435 | 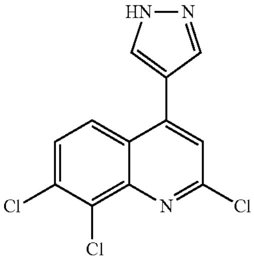 [SMILES: Clc1cc(-c2cn[nH]c2)c2ccc(Cl)c(Cl)c2n1] | 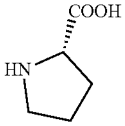 | 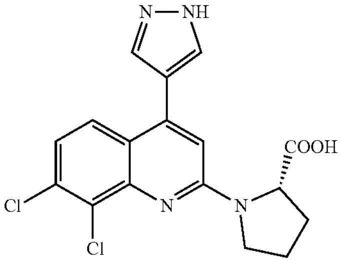 [SMILES: O=C(O)[C@@H]1CCCN1c1cc(-c2cn[nH]c2)c2ccc(Cl)c(Cl)c2n1] | 377 |
| I-143 | 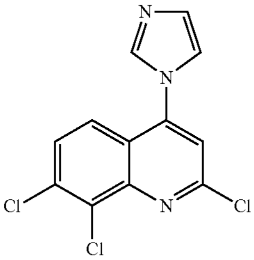 [SMILES: Clc1cc(-n2ccnc2)c2ccc(Cl)c(Cl)c2n1] | 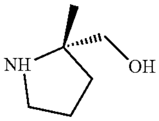 | 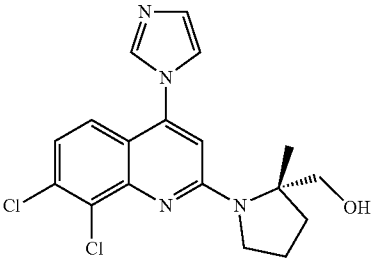 [SMILES: C[C@@]1(CO)CCCN1c1cc(-n2ccnc2)c2ccc(Cl)c(Cl)c2n1] | 377 |
| I-436 | 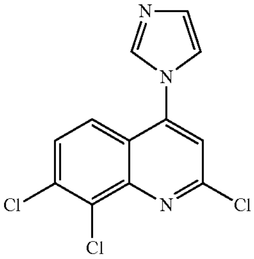 [SMILES: Clc1cc(-n2ccnc2)c2ccc(Cl)c(Cl)c2n1] | 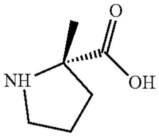 | 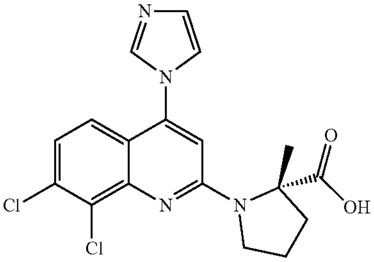 [SMILES: C[C@@]1(C(=O)O)CCCN1c1cc(-n2ccnc2)c2ccc(Cl)c(Cl)c2n1] | 391 |
| I-448 | 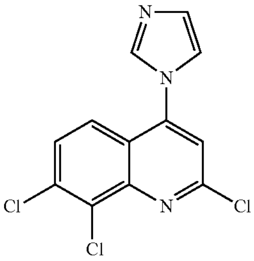 [SMILES: Clc1cc(-n2ccnc2)c2ccc(Cl)c(Cl)c2n1] | 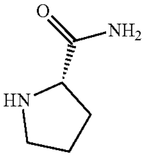 | 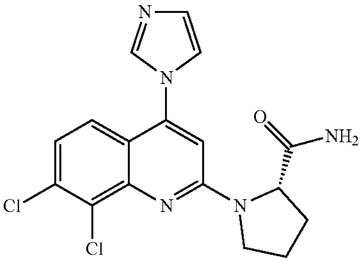 [SMILES: NC(=O)[C@@H]1CCCN1c1cc(-n2ccnc2)c2ccc(Cl)c(Cl)c2n1] | 376 |

-continued
| I-# | Starting Material | Structure | MS [M + 1]+ |
|---|---|---|---|
| I-451 | 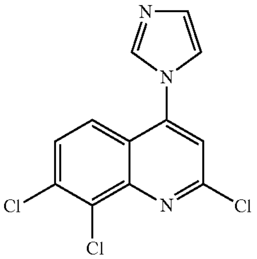 [SMILES: Clc1cc(-n2ccnc2)c2ccc(Cl)c(Cl)c2n1] 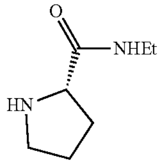 | 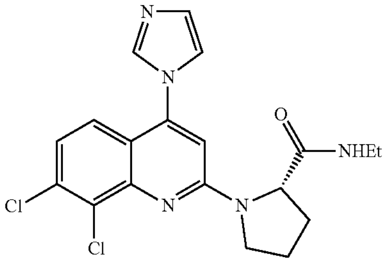 | 404 |
| I-348 | 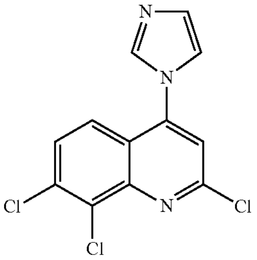 [SMILES: Clc1cc(-n2ccnc2)c2ccc(Cl)c(Cl)c2n1] 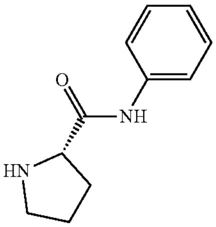 [SMILES: O=C(Nc1ccccc1)[C@@H]1CCCN1] | 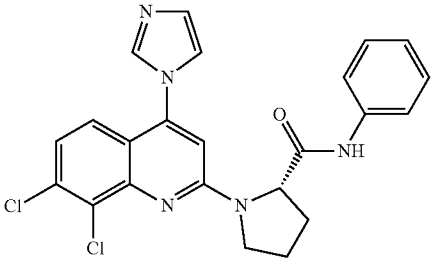 [SMILES: O=C(Nc1ccccc1)[C@@H]1CCCN1c1cc(-n2ccnc2)c2ccc(Cl)c(Cl)c2n1] | 452 |
| I-429 | 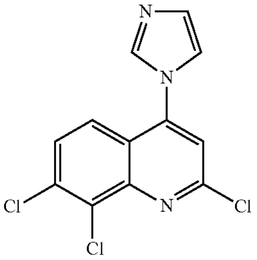 [SMILES: Clc1cc(-n2ccnc2)c2ccc(Cl)c(Cl)c2n1] 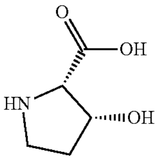 | 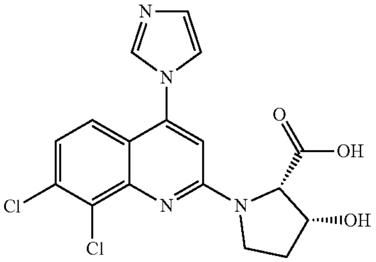 [SMILES: O=C(O)[C@@H]1[C@H](O)CCN1c1cc(-n2ccnc2)c2ccc(Cl)c(Cl)c2n1] | 393 |
| I-453 | 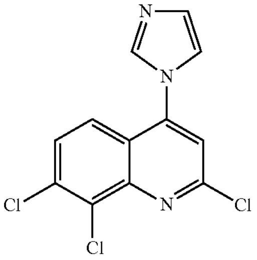 [SMILES: Clc1cc(-n2ccnc2)c2ccc(Cl)c(Cl)c2n1] 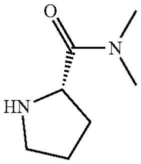 | 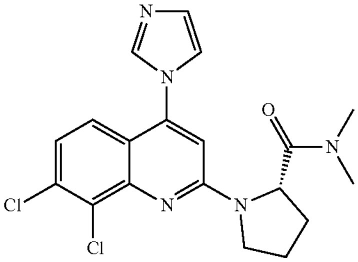 [SMILES: CN(C)C(=O)[C@@H]1CCCN1c1cc(-n2ccnc2)c2ccc(Cl)c(Cl)c2n1] | 404 |
| I-449 | 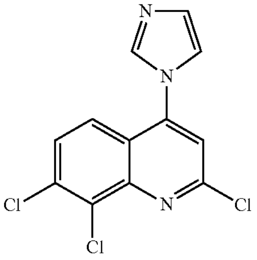 [SMILES: Clc1cc(-n2ccnc2)c2ccc(Cl)c(Cl)c2n1] 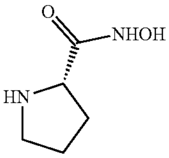 | 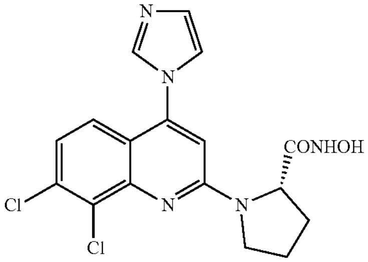 | 392 |

-continued
| I-# | Starting Material | Structure | MS [M + 1]+ |
|---|---|---|---|
| I-450 | 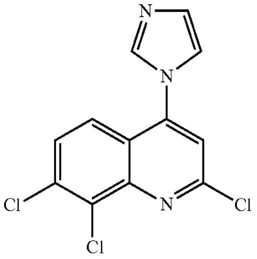 [SMILES: Clc1cc(-n2ccnc2)c2ccc(Cl)c(Cl)c2n1] 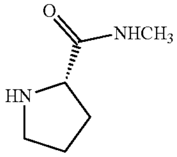 | 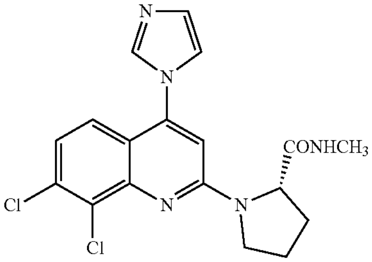 | 390 |
| I-147 | 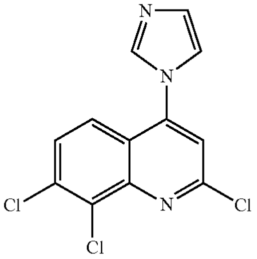 [SMILES: Clc1cc(-n2ccnc2)c2ccc(Cl)c(Cl)c2n1] 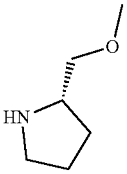 | 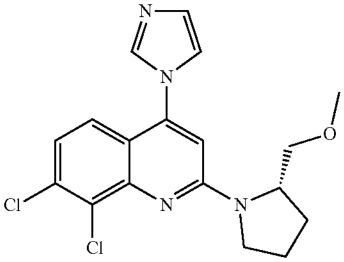 [SMILES: COC[C@@H]1CCCN1c1cc(-n2ccnc2)c2ccc(Cl)c(Cl)c2n1] | 377 |
| I-345 | 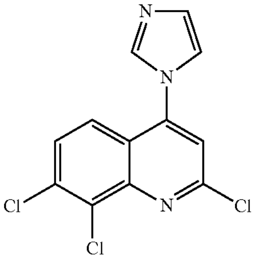 [SMILES: Clc1cc(-n2ccnc2)c2ccc(Cl)c(Cl)c2n1] 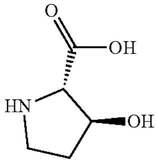 | 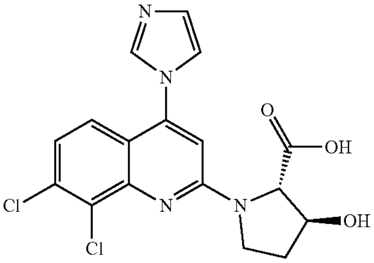 [SMILES: O=C(O)[C@@H]1[C@@H](O)CCN1c1cc(-n2ccnc2)c2ccc(Cl)c(Cl)c2n1] | 393 |
| I-376 | 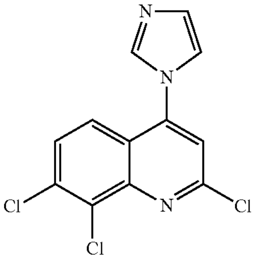 [SMILES: Clc1cc(-n2ccnc2)c2ccc(Cl)c(Cl)c2n1] 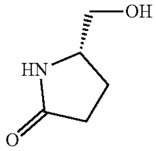 | 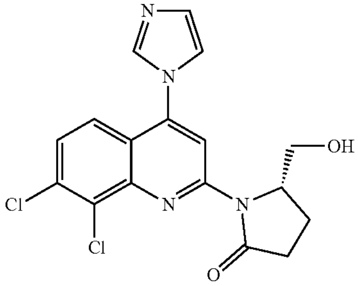 [SMILES: O=C1CC[C@@H](CO)N1c1cc(-n2ccnc2)c2ccc(Cl)c(Cl)c2n1] | 377 |
| I-430 | 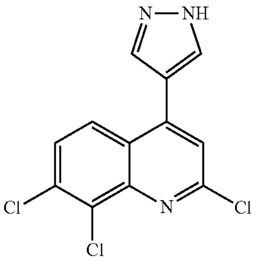 [SMILES: Clc1cc(-c2cn[nH]c2)c2ccc(Cl)c(Cl)c2n1] 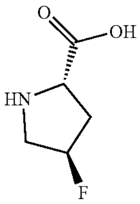 | 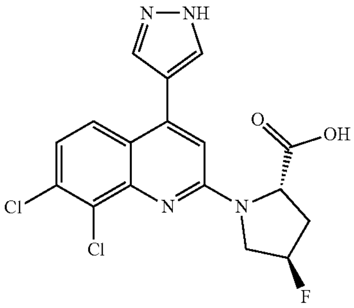 [SMILES: O=C(O)[C@@H]1C[C@@H](F)CN1c1cc(-c2cn[nH]c2)c2ccc(Cl)c(Cl)c2n1] | 395 |

-continued
| I-# | Starting Material | Structure | MS [M + 1]+ |
| --- | --- | --- | --- |
| I-439 | 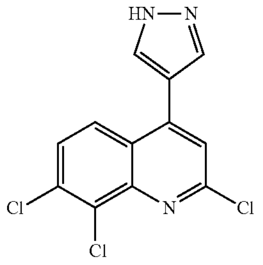 [SMILES: Clc1cc(-c2cn[nH]c2)c2ccc(Cl)c(Cl)c2n1] 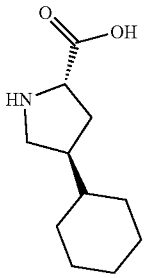 | 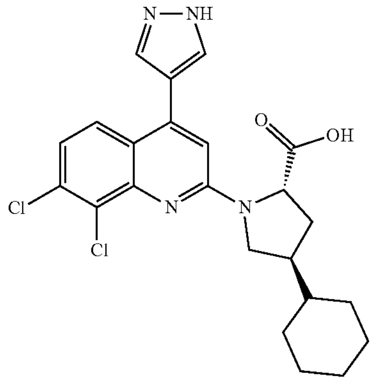 [SMILES: O=C(O)[C@@H]1C[C@@H](C2CCCCC2)CN1c1cc(-c2cn[nH]c2)c2ccc(Cl)c(Cl)c2n1] | 459 |
| I-322 | 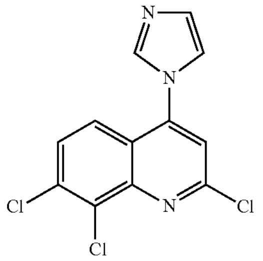 [SMILES: Clc1cc(-n2ccnc2)c2ccc(Cl)c(Cl)c2n1] 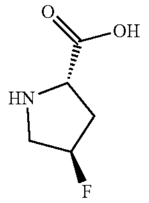 | 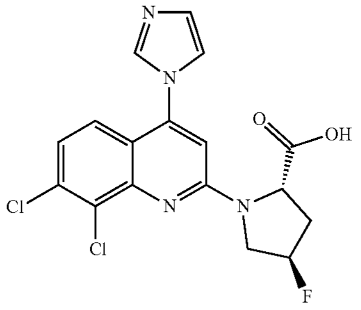 [SMILES: O=C(O)[C@@H]1C[C@@H](F)CN1c1cc(-n2ccnc2)c2ccc(Cl)c(Cl)c2n1] | 395 |
| I-377 | 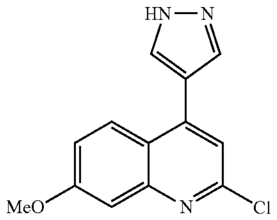 [SMILES: COc1ccc2c(-c3cn[nH]c3)cc(Cl)nc2c1] 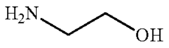 | 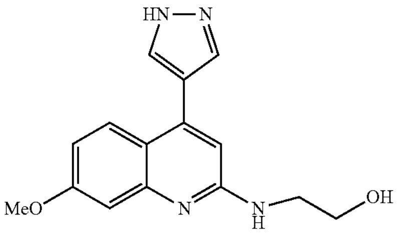 [SMILES: COc1ccc2c(-c3cn[nH]c3)cc(NCCO)nc2c1] | 285 |
| I-269 | 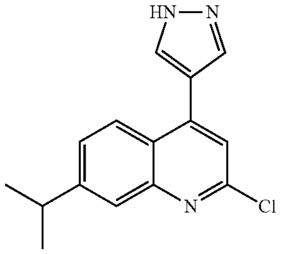 [SMILES: CC(C)c1ccc2c(-c3cn[nH]c3)cc(Cl)nc2c1] 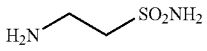 | 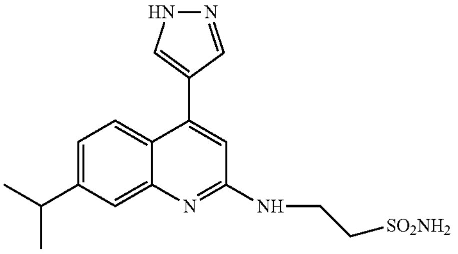 [SMILES: CC(C)c1ccc2c(-c3cn[nH]c3)cc(NCCS(N)(=O)=O)nc2c1] | 360 |
| I-268 | 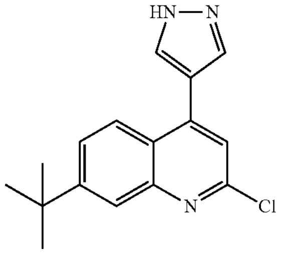 [SMILES: CC(C)(C)c1ccc2c(-c3cn[nH]c3)cc(Cl)nc2c1] 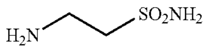 | 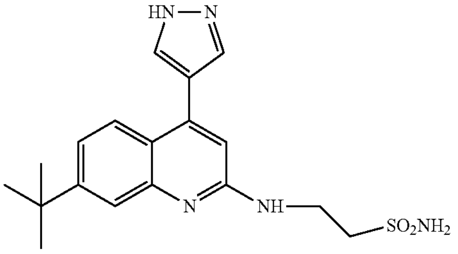 [SMILES: CC(C)(C)c1ccc2c(-c3cn[nH]c3)cc(NCCS(N)(=O)=O)nc2c1] | 374 |

-continued
| I-# | Starting Material | Structure | MS [M + 1]+ |
|---|---|---|---|
| I-267 | 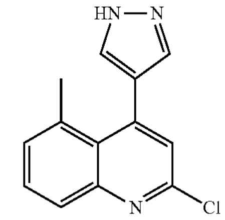 [SMILES: Cc1cccc2nc(Cl)cc(-c3cn[nH]c3)c12] 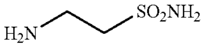 | 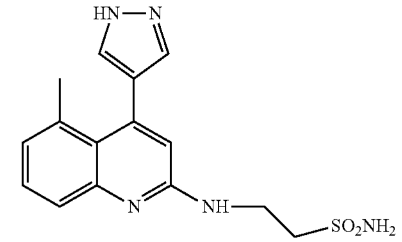 [SMILES: Cc1cccc2nc(NCCS(N)(=O)=O)cc(-c3cn[nH]c3)c12] | 332 |
| I-266 | 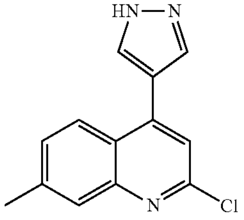 [SMILES: Cc1ccc2c(-c3cn[nH]c3)cc(Cl)nc2c1] 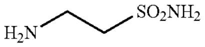 | 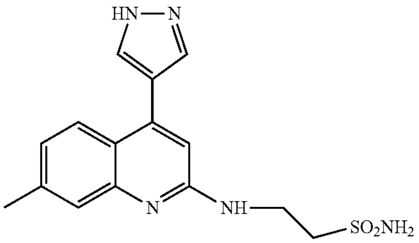 [SMILES: Cc1ccc2c(-c3cn[nH]c3)cc(NCCS(N)(=O)=O)nc2c1] | 332 |
| I-264 | 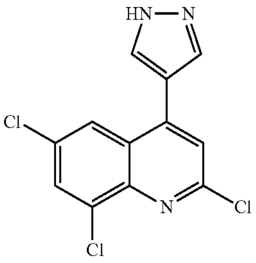 [SMILES: Clc1cc(Cl)c2nc(Cl)cc(-c3cn[nH]c3)c2c1] 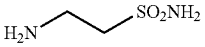 | 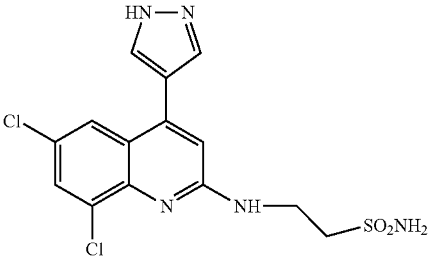 [SMILES: NS(=O)(=O)CCNc1cc(-c2cn[nH]c2)c2cc(Cl)cc(Cl)c2n1] | 386 |
| I-263 | 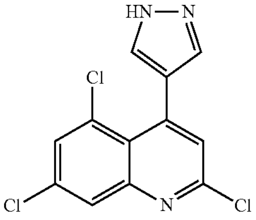 [SMILES: Clc1cc(Cl)c2c(-c3cn[nH]c3)cc(Cl)nc2c1] 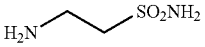 | 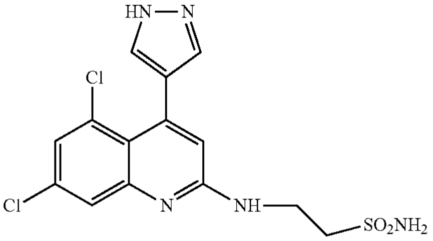 [SMILES: NS(=O)(=O)CCNc1cc(-c2cn[nH]c2)c2c(Cl)cc(Cl)cc2n1] | 386 |
| I-262 | 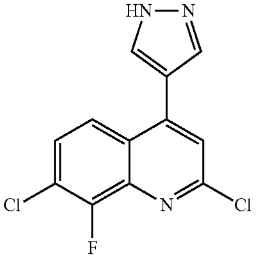 [SMILES: Fc1c(Cl)ccc2c(-c3cn[nH]c3)cc(Cl)nc12] 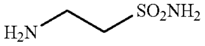 | 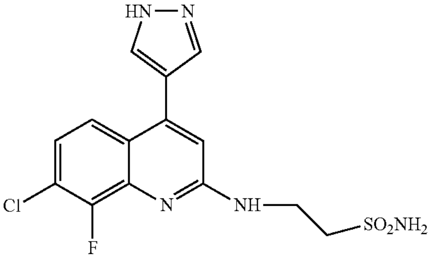 [SMILES: NS(=O)(=O)CCNc1cc(-c2cn[nH]c2)c2ccc(Cl)c(F)c2n1] | 370 |
| I-261 | 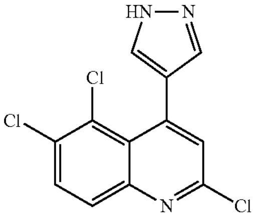 [SMILES: Clc1cc(-c2cn[nH]c2)c2c(Cl)c(Cl)ccc2n1] 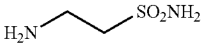 | 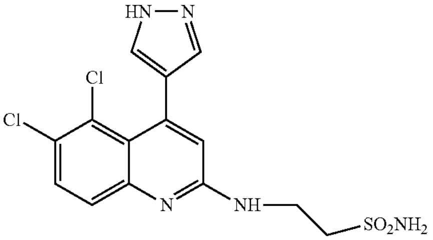 [SMILES: NS(=O)(=O)CCNc1cc(-c2cn[nH]c2)c2c(Cl)c(Cl)ccc2n1] | 386 |

-continued
| I-# | Starting Material | Structure | MS [M + 1]+ |
|---|---|---|---|
| I-260 | 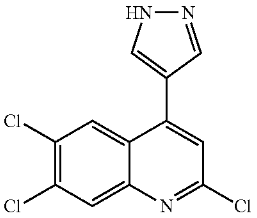 [SMILES: Clc1cc(-c2cn[nH]c2)c2cc(Cl)c(Cl)cc2n1] 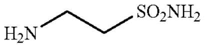 | 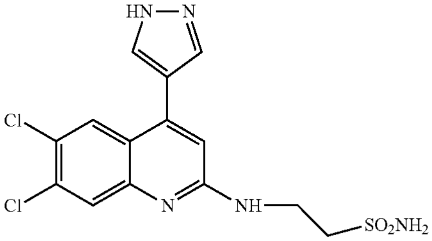 [SMILES: NS(=O)(=O)CCNc1cc(-c2cn[nH]c2)c2cc(Cl)c(Cl)cc2n1] | 386 |
| I-259 | 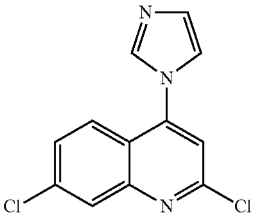 [SMILES: Clc1ccc2c(-n3ccnc3)cc(Cl)nc2c1] 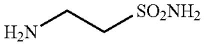 | 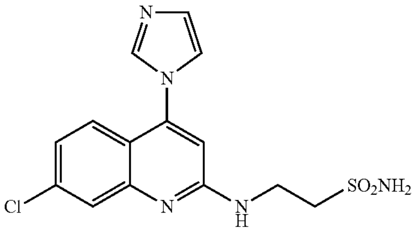 [SMILES: NS(=O)(=O)CCNc1cc(-n2ccnc2)c2ccc(Cl)cc2n1] | 353 |
| I-132 | 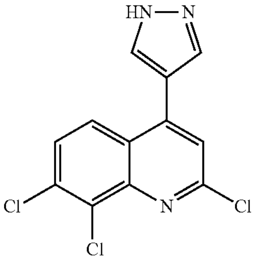 [SMILES: Clc1cc(-c2cn[nH]c2)c2ccc(Cl)c(Cl)c2n1] 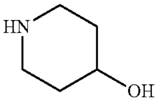 | 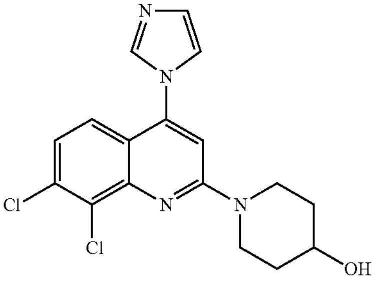 [SMILES: OC1CCN(c2cc(-n3ccnc3)c3ccc(Cl)c(Cl)c3n2)CC1] | 363 |
| I-133 | 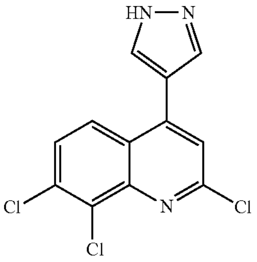 [SMILES: Clc1cc(-c2cn[nH]c2)c2ccc(Cl)c(Cl)c2n1] 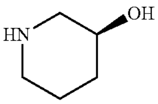 | 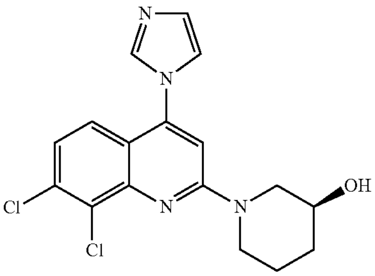 [SMILES: O[C@H]1CCCN(c2cc(-n3ccnc3)c3ccc(Cl)c(Cl)c3n2)C1] | 363 |
| I-134 | 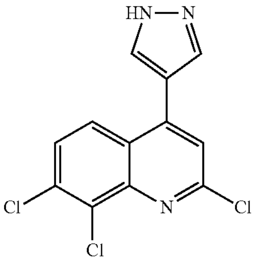 [SMILES: Clc1cc(-c2cn[nH]c2)c2ccc(Cl)c(Cl)c2n1] 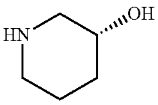 | 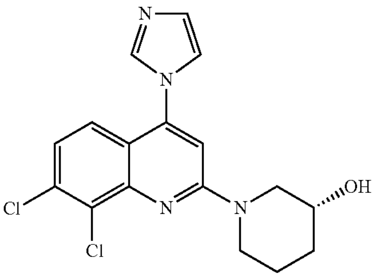 [SMILES: O[C@@H]1CCCN(c2cc(-n3ccnc3)c3ccc(Cl)c(Cl)c3n2)C1] | 363 |

-continued
| I-# | Starting Material | Structure | MS [M + 1]+ |
| --- | --- | --- | --- |
| I-455 | 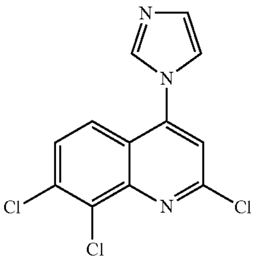 [SMILES: Clc1cc(-n2ccnc2)c2ccc(Cl)c(Cl)c2n1] 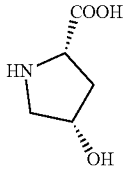 | 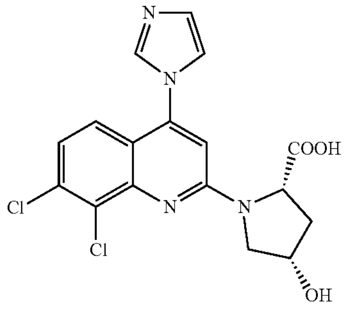 [SMILES: O=C(O)[C@@H]1C[C@H](O)CN1c1cc(-n2ccnc2)c2ccc(Cl)c(Cl)c2n1] | 393 |
| I-456 | 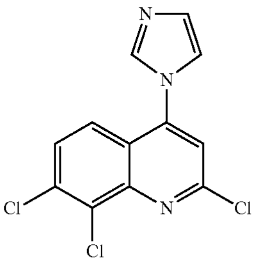 [SMILES: Clc1cc(-n2ccnc2)c2ccc(Cl)c(Cl)c2n1] 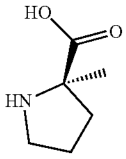 | 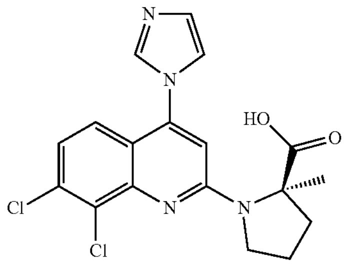 [SMILES: C[C@]1(C(=O)O)CCCN1c1cc(-n2ccnc2)c2ccc(Cl)c(Cl)c2n1] | 391 |
| I-457 | 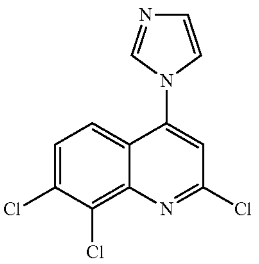 [SMILES: Clc1cc(-n2ccnc2)c2ccc(Cl)c(Cl)c2n1] 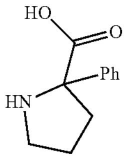 | 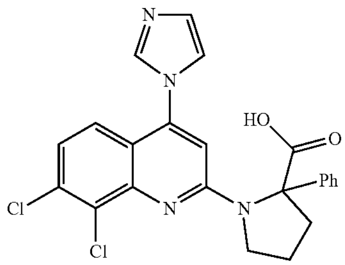 [SMILES: O=C(O)C1(c2ccccc2)CCCN1c1cc(-n2ccnc2)c2ccc(Cl)c(Cl)c2n1] | 453 |
| I-458 | 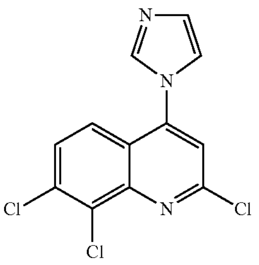 [SMILES: Clc1cc(-n2ccnc2)c2ccc(Cl)c(Cl)c2n1] 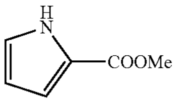 | 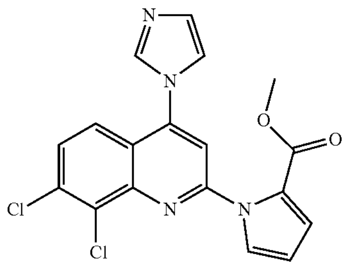 [SMILES: COC(=O)c1cccn1-c1cc(-n2ccnc2)c2ccc(Cl)c(Cl)c2n1] | 387 |
| I-459 | 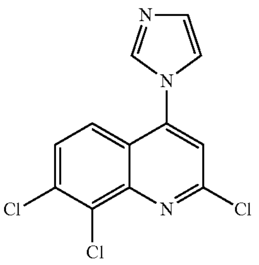 [SMILES: Clc1cc(-n2ccnc2)c2ccc(Cl)c(Cl)c2n1] 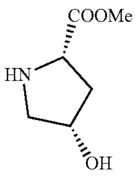 | 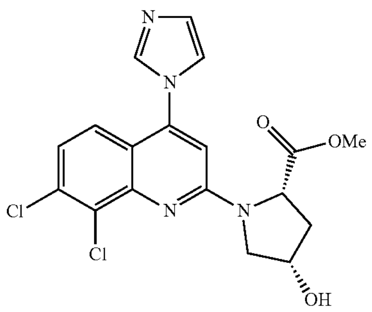 [SMILES: COC(=O)[C@@H]1C[C@H](O)CN1c1cc(-n2ccnc2)c2ccc(Cl)c(Cl)c2n1] | 407 |

-continued
| I-# | Starting Material | Structure | MS [M + 1]+ |
|---|---|---|---|
| I-460 | 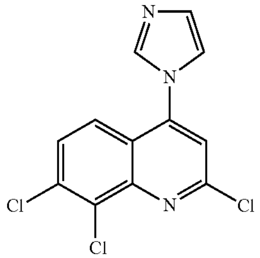 [SMILES: Clc1cc(-n2ccnc2)c2ccc(Cl)c(Cl)c2n1] 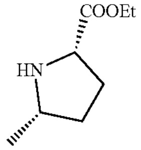 | 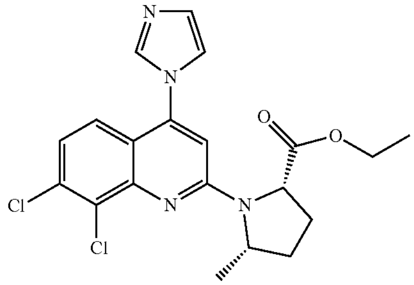 [SMILES: CCOC(=O)[C@@H]1CC[C@H](C)N1c1cc(-n2ccnc2)c2ccc(Cl)c(Cl)c2n1] | 419 |
| I-461 | 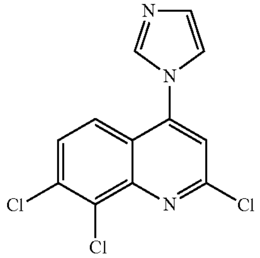 [SMILES: Clc1cc(-n2ccnc2)c2ccc(Cl)c(Cl)c2n1] 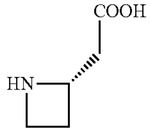 | 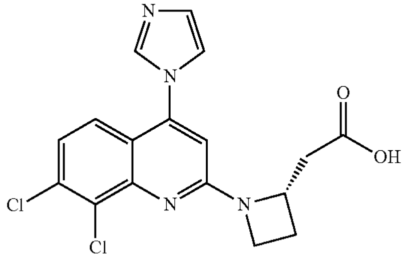 [SMILES: O=C(O)C[C@@H]1CCN1c1cc(-n2ccnc2)c2ccc(Cl)c(Cl)c2n1] | 377 |
| I-462 | 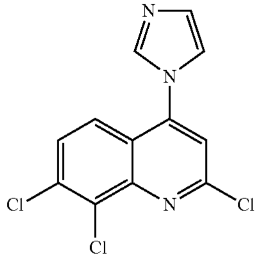 [SMILES: Clc1cc(-n2ccnc2)c2ccc(Cl)c(Cl)c2n1] 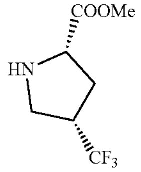 | 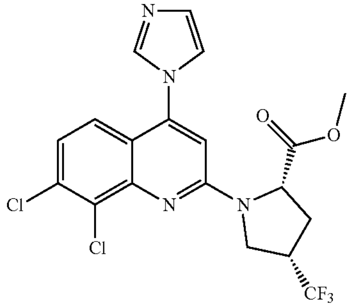 [SMILES: COC(=O)[C@@H]1C[C@H](C(F)(F)F)CN1c1cc(-n2ccnc2)c2ccc(Cl)c(Cl)c2n1] | 459 |
| I-463 | 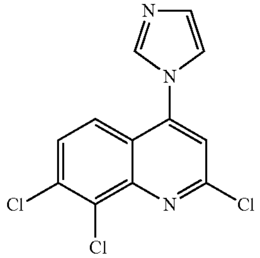 [SMILES: Clc1cc(-n2ccnc2)c2ccc(Cl)c(Cl)c2n1] 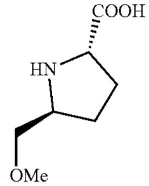 [SMILES: COC[C@@H]1CC[C@@H](C(=O)O)N1] | 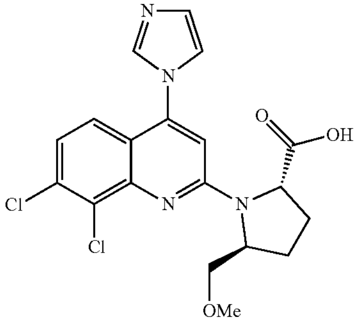 [SMILES: COC[C@@H]1CC[C@@H](C(=O)O)N1c1cc(-n2ccnc2)c2ccc(Cl)c(Cl)c2n1] | 421 |
| I-464 | 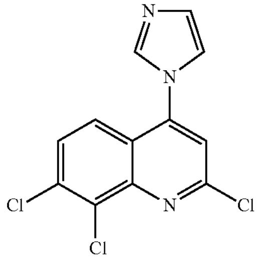 [SMILES: Clc1cc(-n2ccnc2)c2ccc(Cl)c(Cl)c2n1] 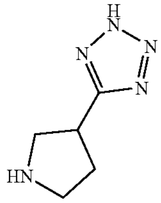 | 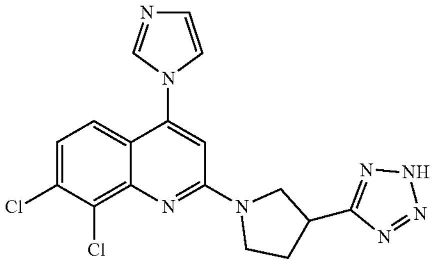 [SMILES: Clc1ccc2c(-n3ccnc3)cc(N3CCC(c4nn[nH]n4)C3)nc2c1Cl] | 401 |

-continued
| I-# | Starting Material | Structure | MS [M + 1]+ |
|---|---|---|---|
| I-465 | 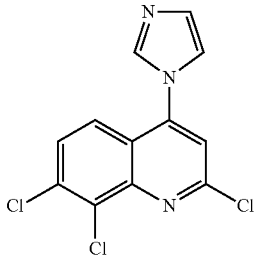 [SMILES: Clc1cc(-n2ccnc2)c2ccc(Cl)c(Cl)c2n1] 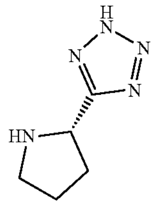 | 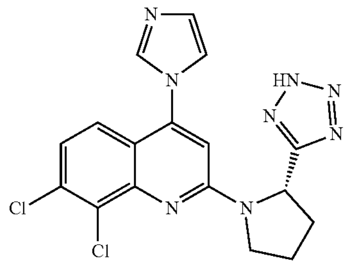 [SMILES: Clc1ccc2c(-n3ccnc3)cc(N3CCC[C@H]3c3nn[nH]n3)nc2c1Cl] | 401 |
| I-466 | 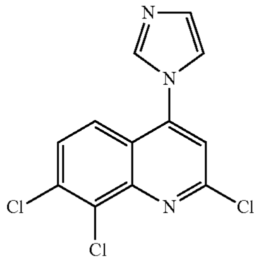 [SMILES: Clc1cc(-n2ccnc2)c2ccc(Cl)c(Cl)c2n1] 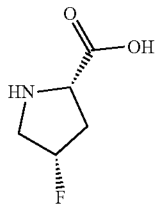 | 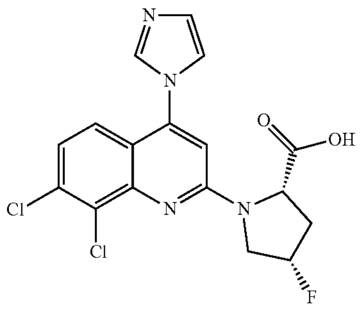 [SMILES: O=C(O)[C@@H]1C[C@H](F)CN1c1cc(-n2ccnc2)c2ccc(Cl)c(Cl)c2n1] | 395 |
| I-467 | 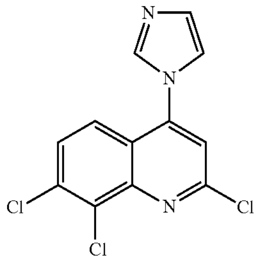 [SMILES: Clc1cc(-n2ccnc2)c2ccc(Cl)c(Cl)c2n1] 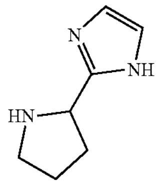 | 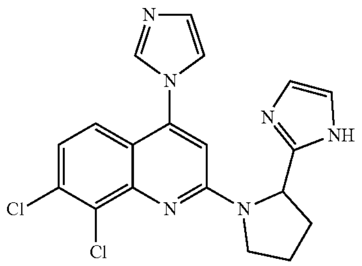 [SMILES: Clc1ccc2c(-n3ccnc3)cc(N3CCCC3c3ncc[nH]3)nc2c1Cl] | 399 |
| I-468 | 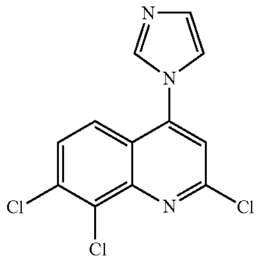 [SMILES: Clc1cc(-n2ccnc2)c2ccc(Cl)c(Cl)c2n1] 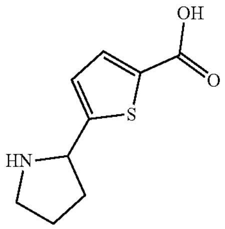 [SMILES: O=C(O)c1ccc(C2CCCN2)s1] | 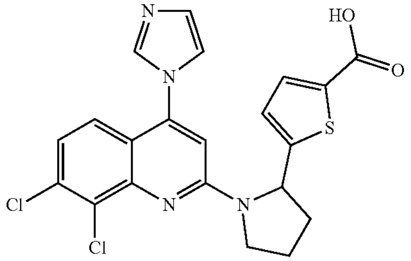 [SMILES: O=C(O)c1ccc(C2CCCN2c2cc(-n3ccnc3)c3ccc(Cl)c(Cl)c3n2)s1] | 459 |
| I-469 | 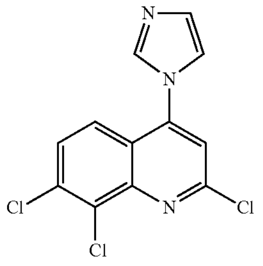 [SMILES: Clc1cc(-n2ccnc2)c2ccc(Cl)c(Cl)c2n1] 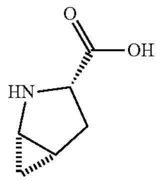 | 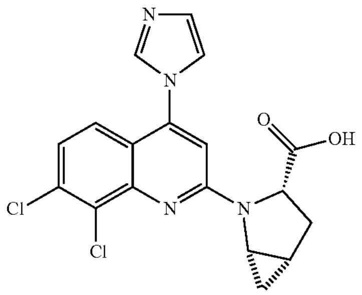 | 389 |

-continued
| I-# | Starting Material | Structure | MS [M + 1]+ |
|---|---|---|---|
| I-470 | 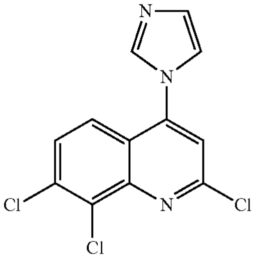 [SMILES: Clc1cc(-n2ccnc2)c2ccc(Cl)c(Cl)c2n1] 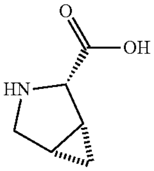 | 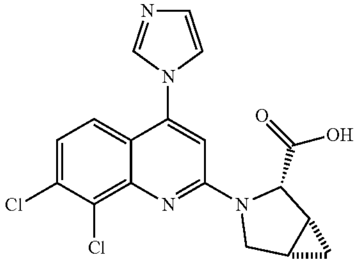 | 389 |
| I-471 | 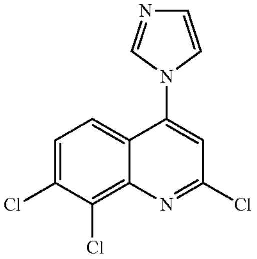 [SMILES: Clc1cc(-n2ccnc2)c2ccc(Cl)c(Cl)c2n1] 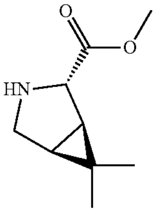 | 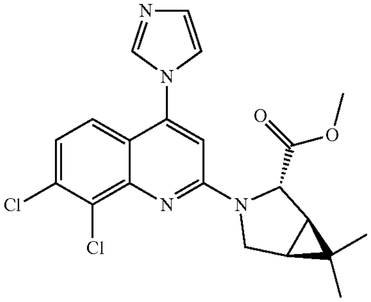 [SMILES: COC(=O)[C@@H]1[C@@H]2[C@H](CN1c1cc(-n3ccnc3)c3ccc(Cl)c(Cl)c3n1)C2(C)C] | 431 |
| I-472 | 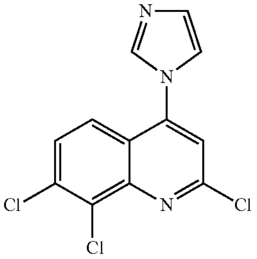 [SMILES: Clc1cc(-n2ccnc2)c2ccc(Cl)c(Cl)c2n1] 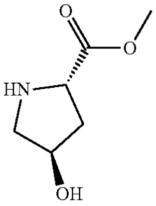 | 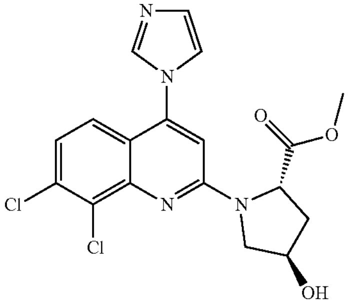 [SMILES: COC(=O)[C@@H]1C[C@@H](O)CN1c1cc(-n2ccnc2)c2ccc(Cl)c(Cl)c2n1] | 407 |
| I-473 | 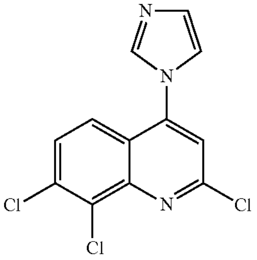 [SMILES: Clc1cc(-n2ccnc2)c2ccc(Cl)c(Cl)c2n1] 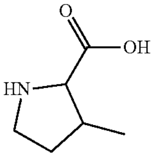 | 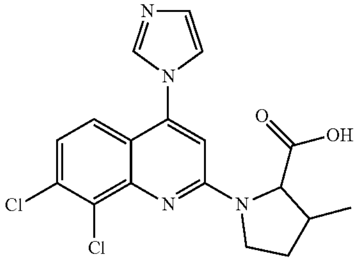 [SMILES: CC1CCN(c2cc(-n3ccnc3)c3ccc(Cl)c(Cl)c3n2)C1C(=O)O] | 391 |
| I-474 | 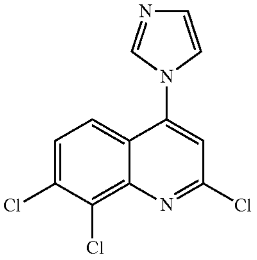 [SMILES: Clc1cc(-n2ccnc2)c2ccc(Cl)c(Cl)c2n1] 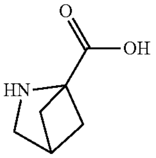 | 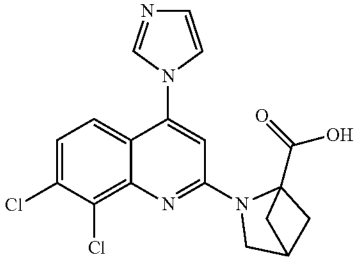 [SMILES: O=C(O)C12CC(CN1c1cc(-n3ccnc3)c3ccc(Cl)c(Cl)c3n1)C2] | 389 |

-continued
| I-# | Starting Material | Structure | MS [M + 1]+ |
| --- | --- | --- | --- |
| I-475 | 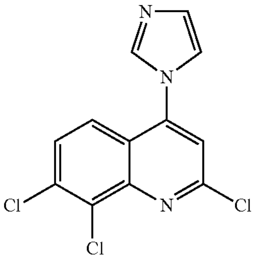 [SMILES: Clc1cc(-n2ccnc2)c2ccc(Cl)c(Cl)c2n1] 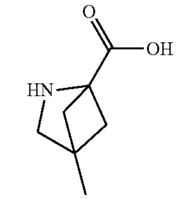 | 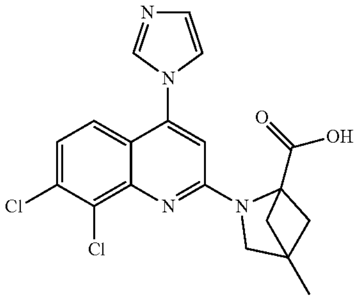 [SMILES: CC12CN(c3cc(-n4ccnc4)c4ccc(Cl)c(Cl)c4n3)C(C(=O)O)(C1)C2] | 403 |
| I-476 | 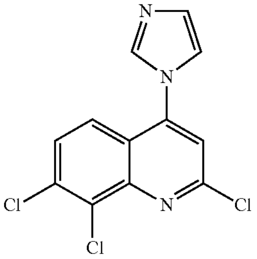 [SMILES: Clc1cc(-n2ccnc2)c2ccc(Cl)c(Cl)c2n1] 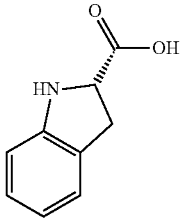 | 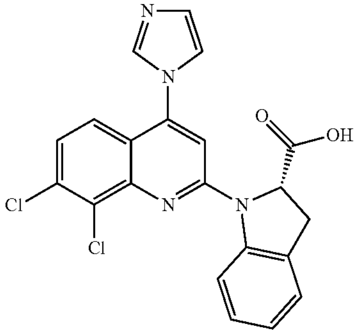 [SMILES: O=C(O)[C@@H]1Cc2ccccc2N1c1cc(-n2ccnc2)c2ccc(Cl)c(Cl)c2n1] | 425 |
| I-477 | 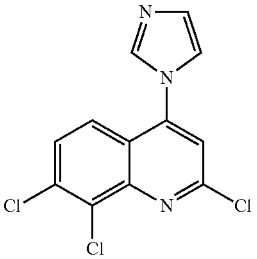 [SMILES: Clc1cc(-n2ccnc2)c2ccc(Cl)c(Cl)c2n1] 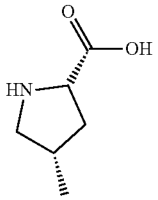 | 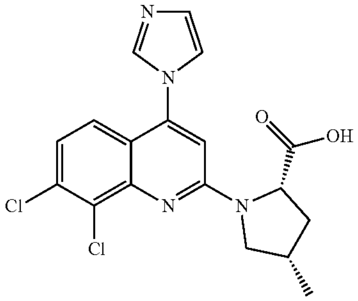 [SMILES: C[C@H]1C[C@@H](C(=O)O)N(c2cc(-n3ccnc3)c3ccc(Cl)c(Cl)c3n2)C1] | 391 |
| I-478 | 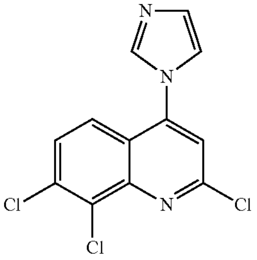 [SMILES: Clc1cc(-n2ccnc2)c2ccc(Cl)c(Cl)c2n1] 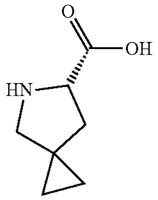 | 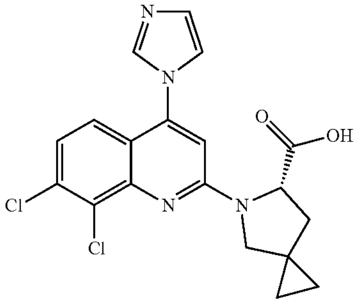 [SMILES: O=C(O)[C@@H]1CC2(CC2)CN1c1cc(-n2ccnc2)c2ccc(Cl)c(Cl)c2n1] | 403 |
| I-479 | 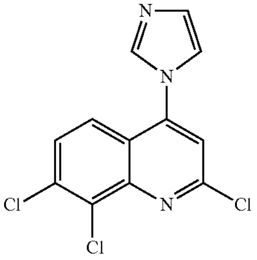 [SMILES: Clc1cc(-n2ccnc2)c2ccc(Cl)c(Cl)c2n1] 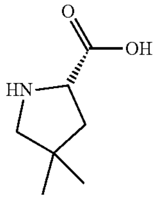 | 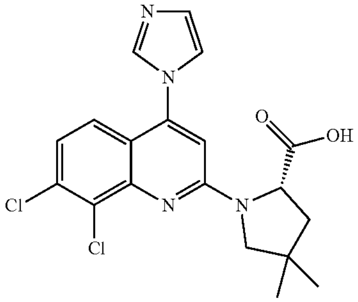 [SMILES: CC1(C)C[C@@H](C(=O)O)N(c2cc(-n3ccnc3)c3ccc(Cl)c(Cl)c3n2)C1] | 405 |

-continued
| I-# | Starting Material | Structure | MS [M + 1]+ |
|---|---|---|---|
| I-480 | 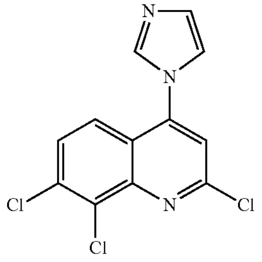 [SMILES: Clc1cc(-n2ccnc2)c2ccc(Cl)c(Cl)c2n1] 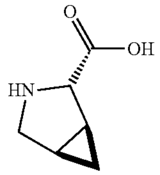 | 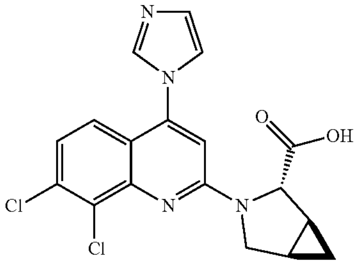 | 389 |
| I-481 | 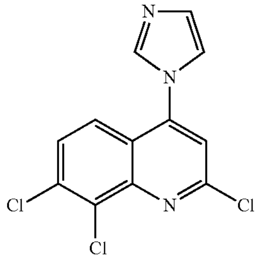 [SMILES: Clc1cc(-n2ccnc2)c2ccc(Cl)c(Cl)c2n1] 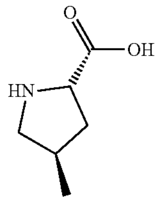 | 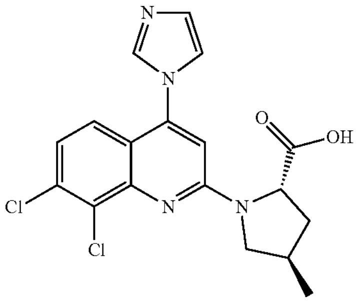 [SMILES: C[C@@H]1C[C@@H](C(=O)O)N(c2cc(-n3ccnc3)c3ccc(Cl)c(Cl)c3n2)C1] | 391 |
| I-482 | 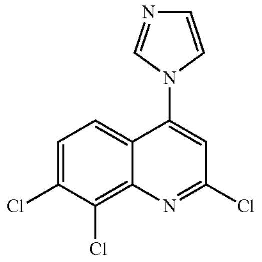 [SMILES: Clc1cc(-n2ccnc2)c2ccc(Cl)c(Cl)c2n1] 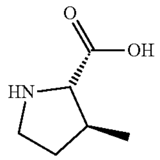 | 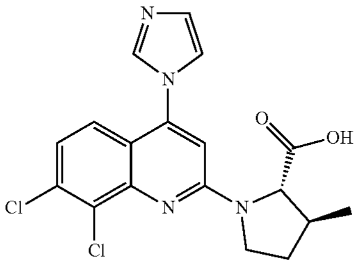 [SMILES: C[C@H]1CCN(c2cc(-n3ccnc3)c3ccc(Cl)c(Cl)c3n2)[C@@H]1C(=O)O] | 391 |
| I-483 | 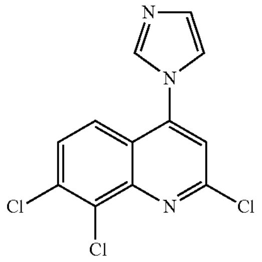 [SMILES: Clc1cc(-n2ccnc2)c2ccc(Cl)c(Cl)c2n1] 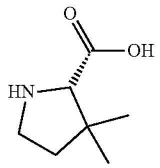 | 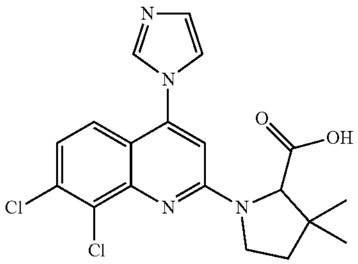 [SMILES: CC1(C)CCN(c2cc(-n3ccnc3)c3ccc(Cl)c(Cl)c3n2)C1C(=O)O] | 405 |
| I-484 | 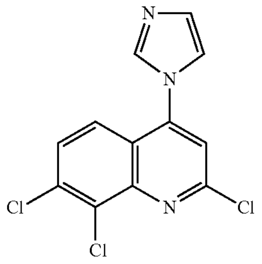 [SMILES: Clc1cc(-n2ccnc2)c2ccc(Cl)c(Cl)c2n1] 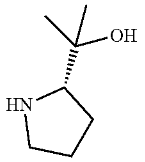 | 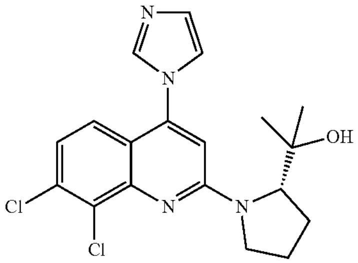 [SMILES: CC(C)(O)[C@@H]1CCCN1c1cc(-n2ccnc2)c2ccc(Cl)c(Cl)c2n1] | 391 |

-continued
| I-# | Starting Material | | Structure | MS [M + 1]+ |
|---|---|---|---|---|
| I-485 | 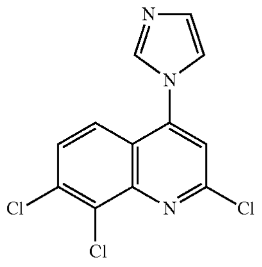 [SMILES: Clc1cc(-n2ccnc2)c2ccc(Cl)c(Cl)c2n1] | 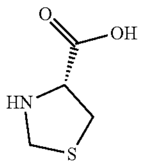 | 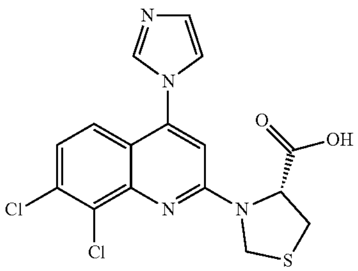 [SMILES: O=C(O)[C@@H]1CSCN1c1cc(-n2ccnc2)c2ccc(Cl)c(Cl)c2n1] | 395 |
| I-486 | 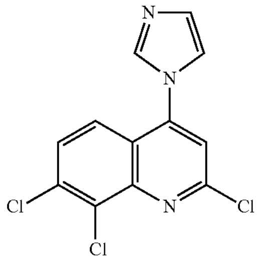 [SMILES: Clc1cc(-n2ccnc2)c2ccc(Cl)c(Cl)c2n1] | 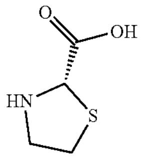 | 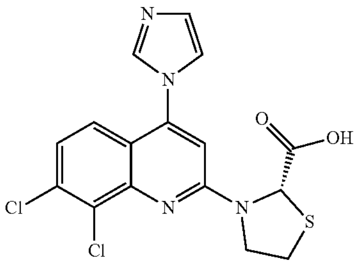 [SMILES: O=C(O)[C@@H]1SCCN1c1cc(-n2ccnc2)c2ccc(Cl)c(Cl)c2n1] | 395 |
| I-487 | 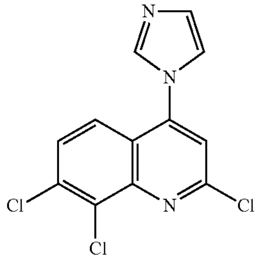 [SMILES: Clc1cc(-n2ccnc2)c2ccc(Cl)c(Cl)c2n1] | 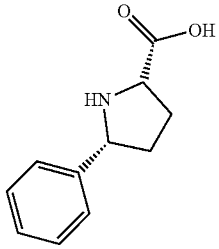 | 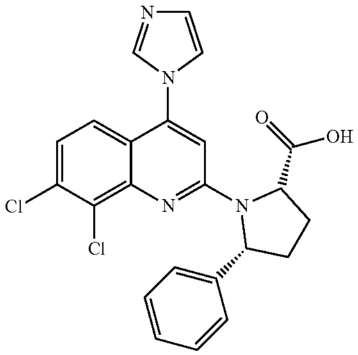 | 453 |
| I-488 | 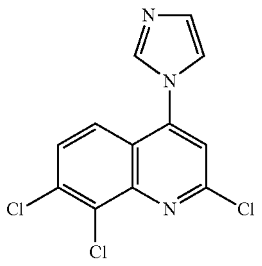 [SMILES: Clc1cc(-n2ccnc2)c2ccc(Cl)c(Cl)c2n1] | 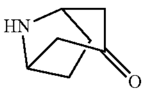 | 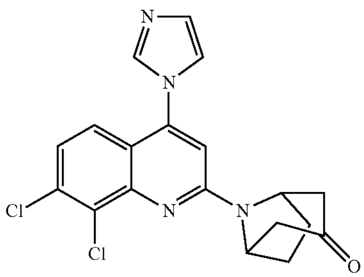 [SMILES: O=C1CC2CCC(C1)N2c1cc(-n2ccnc2)c2ccc(Cl)c(Cl)c2n1] | 387 |
| I-489 | 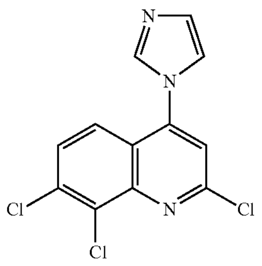 [SMILES: Clc1cc(-n2ccnc2)c2ccc(Cl)c(Cl)c2n1] | 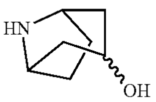 | 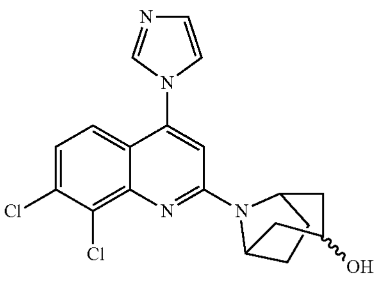 [SMILES: OC1CC2CCC(C1)N2c1cc(-n2ccnc2)c2ccc(Cl)c(Cl)c2n1] | 389 |

-continued
| I-# | Starting Material | Structure | MS [M + 1]+ |
| --- | --- | --- | --- |
| I-490 | 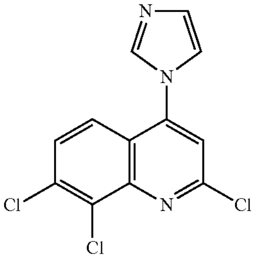 [SMILES: Clc1cc(-n2ccnc2)c2ccc(Cl)c(Cl)c2n1] 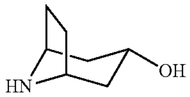 | 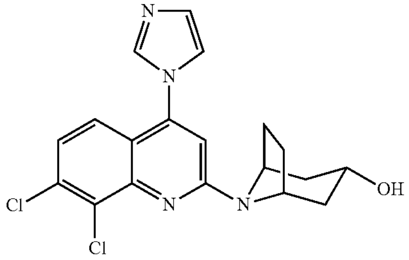 [SMILES: OC1CC2CCC(C1)N2c1cc(-n2ccnc2)c2ccc(Cl)c(Cl)c2n1] | 389 |
| I-491 | 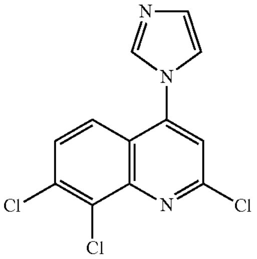 [SMILES: Clc1cc(-n2ccnc2)c2ccc(Cl)c(Cl)c2n1] 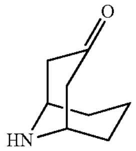 | 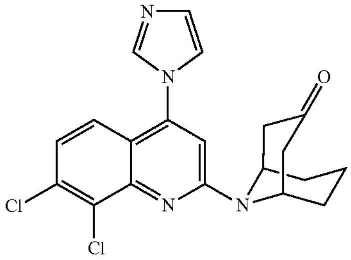 [SMILES: O=C1CC2CCCC(C1)N2c1cc(-n2ccnc2)c2ccc(Cl)c(Cl)c2n1] | 401 |
| I-492 | 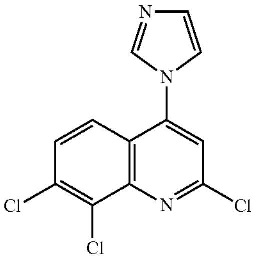 [SMILES: Clc1cc(-n2ccnc2)c2ccc(Cl)c(Cl)c2n1] 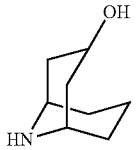 | 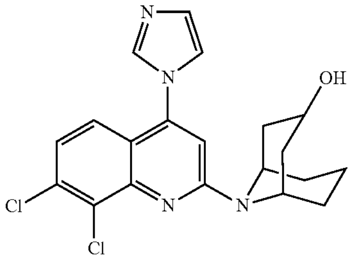 [SMILES: OC1CC2CCCC(C1)N2c1cc(-n2ccnc2)c2ccc(Cl)c(Cl)c2n1] | 403 |
| I-493 | 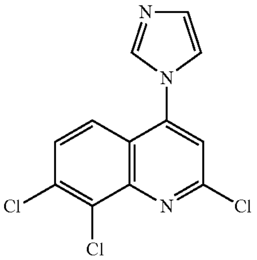 [SMILES: Clc1cc(-n2ccnc2)c2ccc(Cl)c(Cl)c2n1] 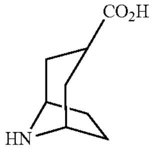 [SMILES: O=C(O)C1CC2CCC(C1)N2] | 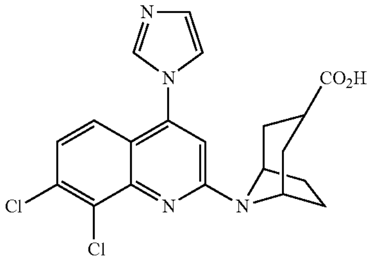 [SMILES: O=C(O)C1CC2CCC(C1)N2c1cc(-n2ccnc2)c2ccc(Cl)c(Cl)c2n1] | 417 |
| I-494 | 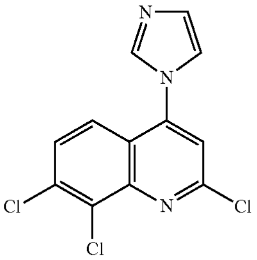 [SMILES: Clc1cc(-n2ccnc2)c2ccc(Cl)c(Cl)c2n1] 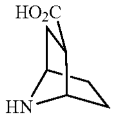 | 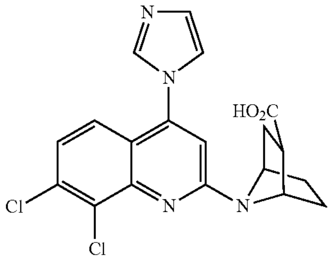 [SMILES: O=C(O)C1CC2CCC1N2c1cc(-n2ccnc2)c2ccc(Cl)c(Cl)c2n1] | 403 |

-continued
| I-# | Starting Material | Structure | MS [M + 1]+ |
|---|---|---|---|
| I-495 | 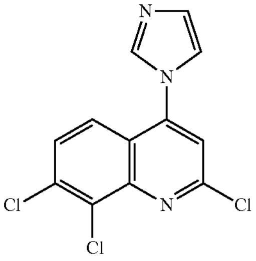 [SMILES: Clc1cc(-n2ccnc2)c2ccc(Cl)c(Cl)c2n1] 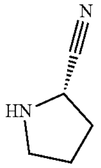 | 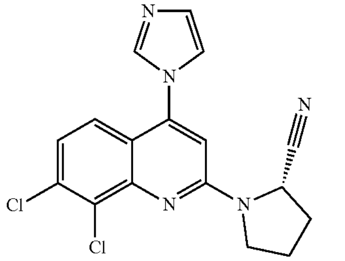 [SMILES: N#C[C@@H]1CCCN1c1cc(-n2ccnc2)c2ccc(Cl)c(Cl)c2n1] | 358 |
| I-496 | 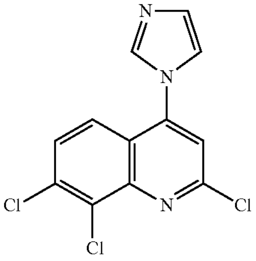 [SMILES: Clc1cc(-n2ccnc2)c2ccc(Cl)c(Cl)c2n1] 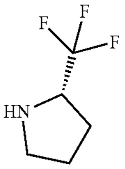 | 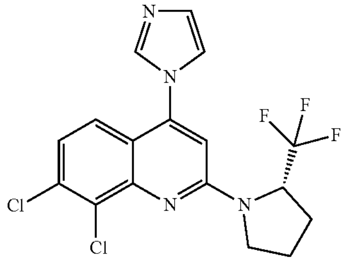 [SMILES: FC(F)(F)[C@@H]1CCCN1c1cc(-n2ccnc2)c2ccc(Cl)c(Cl)c2n1] | 401 |
| I-497 | 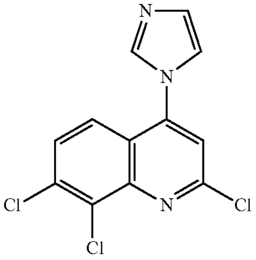 [SMILES: Clc1cc(-n2ccnc2)c2ccc(Cl)c(Cl)c2n1] 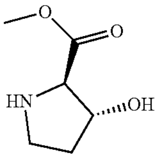 | 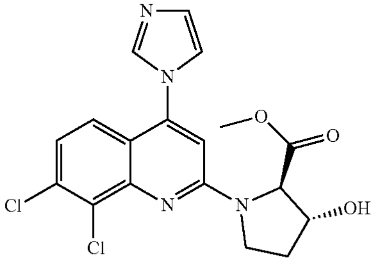 [SMILES: COC(=O)[C@H]1[C@H](O)CCN1c1cc(-n2ccnc2)c2ccc(Cl)c(Cl)c2n1] | 407 |
| I-498 | 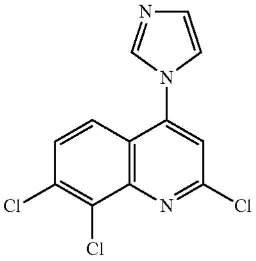 [SMILES: Clc1cc(-n2ccnc2)c2ccc(Cl)c(Cl)c2n1] 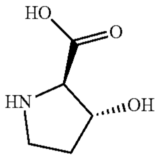 | 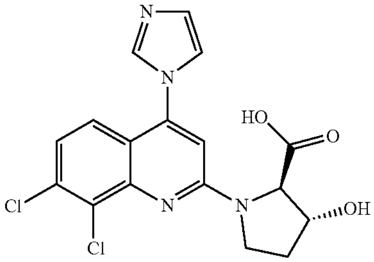 [SMILES: O=C(O)[C@H]1[C@H](O)CCN1c1cc(-n2ccnc2)c2ccc(Cl)c(Cl)c2n1] | 393 |
| I-499 | 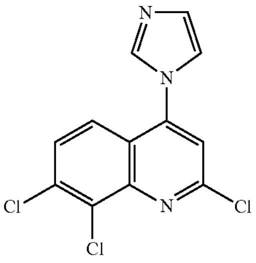 [SMILES: Clc1cc(-n2ccnc2)c2ccc(Cl)c(Cl)c2n1] 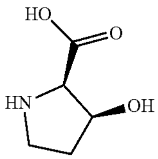 | 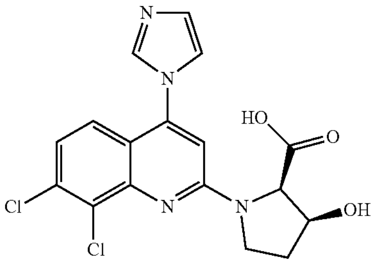 [SMILES: O=C(O)[C@H]1[C@@H](O)CCN1c1cc(-n2ccnc2)c2ccc(Cl)c(Cl)c2n1] | 393 |

-continued
| I-# | Starting Material | Structure | MS [M + 1]+ |
|---|---|---|---|
| I-500 | 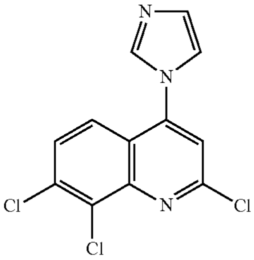 [SMILES: Clc1cc(-n2ccnc2)c2ccc(Cl)c(Cl)c2n1] 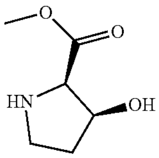 | 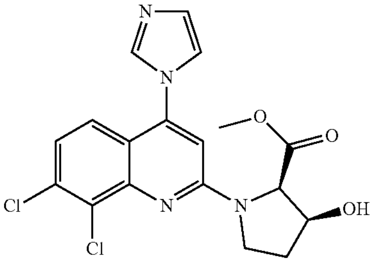 [SMILES: COC(=O)[C@H]1[C@@H](O)CCN1c1cc(-n2ccnc2)c2ccc(Cl)c(Cl)c2n1] | 407 |
| I-501 | 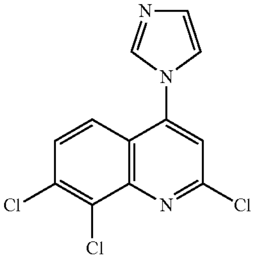 [SMILES: Clc1cc(-n2ccnc2)c2ccc(Cl)c(Cl)c2n1] 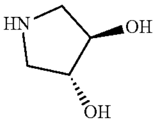 | 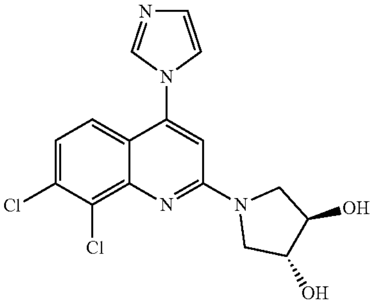 [SMILES: O[C@@H]1CN(c2cc(-n3ccnc3)c3ccc(Cl)c(Cl)c3n2)C[C@H]1O] | 365 |
| I-502 | 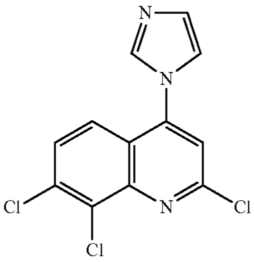 [SMILES: Clc1cc(-n2ccnc2)c2ccc(Cl)c(Cl)c2n1] 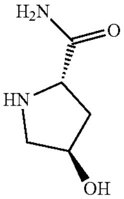 | 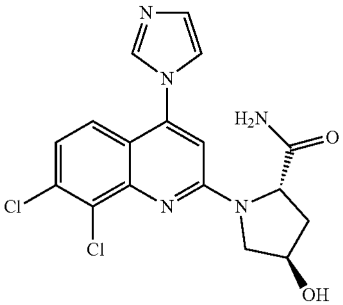 [SMILES: NC(=O)[C@@H]1C[C@@H](O)CN1c1cc(-n2ccnc2)c2ccc(Cl)c(Cl)c2n1] | 392 |
| I-503 | 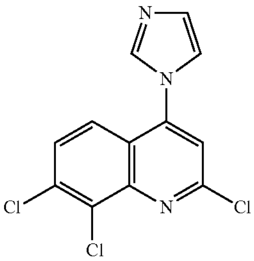 [SMILES: Clc1cc(-n2ccnc2)c2ccc(Cl)c(Cl)c2n1] 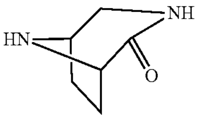 | 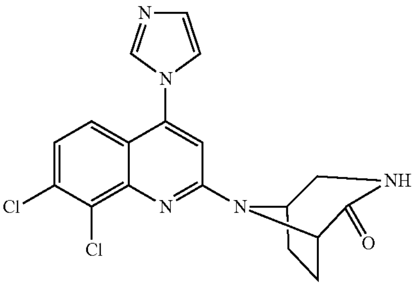 [SMILES: O=C1NCC2CCC1N2c1cc(-n2ccnc2)c2ccc(Cl)c(Cl)c2n1] | 388 |
| I-504 | 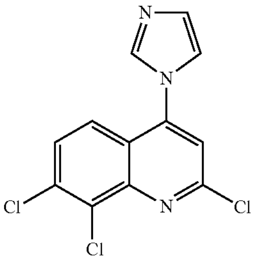 [SMILES: Clc1cc(-n2ccnc2)c2ccc(Cl)c(Cl)c2n1] 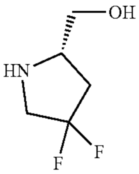 | 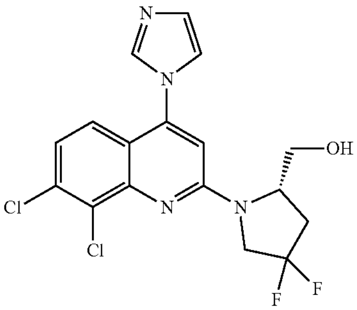 [SMILES: OC[C@@H]1CC(F)(F)CN1c1cc(-n2ccnc2)c2ccc(Cl)c(Cl)c2n1] | 399 |

-continued
| I-# | Starting Material | | Structure | MS [M + 1]+ |
|---|---|---|---|---|
| I-659 | 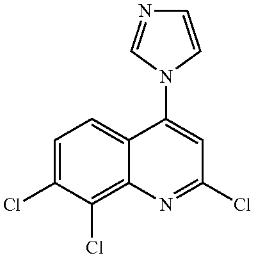 [SMILES: Clc1cc(-n2ccnc2)c2ccc(Cl)c(Cl)c2n1] | 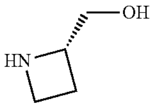 | 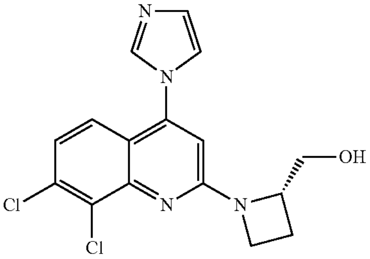 [SMILES: OC[C@@H]1CCN1c1cc(-n2ccnc2)c2ccc(Cl)c(Cl)c2n1] | 349 |
| I-644 | 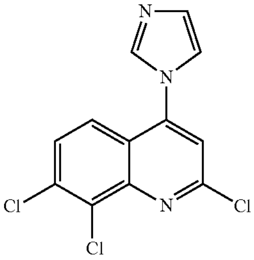 [SMILES: Clc1cc(-n2ccnc2)c2ccc(Cl)c(Cl)c2n1] | 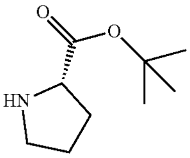 | 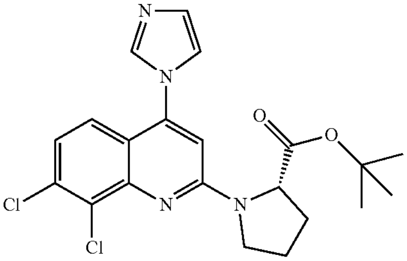 [SMILES: CC(C)(C)OC(=O)[C@@H]1CCCN1c1cc(-n2ccnc2)c2ccc(Cl)c(Cl)c2n1] | 433 |
| I-660 | 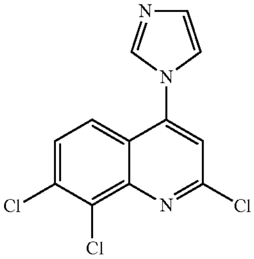 [SMILES: Clc1cc(-n2ccnc2)c2ccc(Cl)c(Cl)c2n1] | 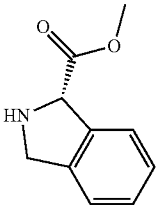 | 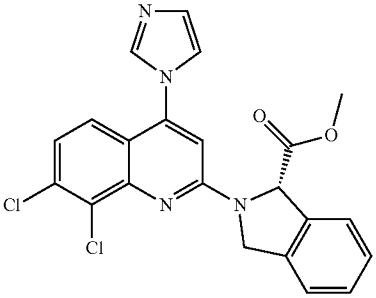 [SMILES: COC(=O)[C@@H]1c2ccccc2CN1c1cc(-n2ccnc2)c2ccc(Cl)c(Cl)c2n1] | 439 |
| I-835 | 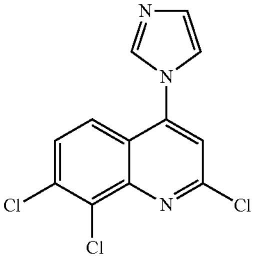 [SMILES: Clc1cc(-n2ccnc2)c2ccc(Cl)c(Cl)c2n1] | 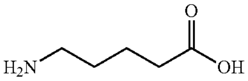 | 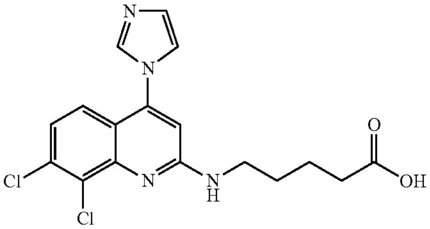 [SMILES: O=C(O)CCCCNc1cc(-n2ccnc2)c2ccc(Cl)c(Cl)c2n1] | 379 |
| I-888 | 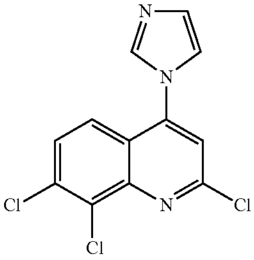 [SMILES: Clc1cc(-n2ccnc2)c2ccc(Cl)c(Cl)c2n1] | 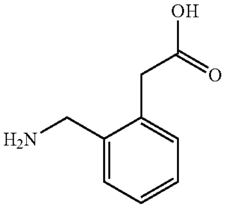 [SMILES: NCc1ccccc1CC(=O)O] | 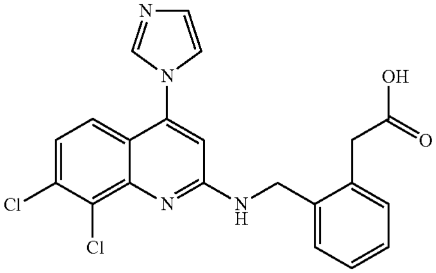 [SMILES: O=C(O)Cc1ccccc1CNc1cc(-n2ccnc2)c2ccc(Cl)c(Cl)c2n1] | 427 |

-continued

| I-# | Starting Material | | Structure | MS [M + 1]+ |
|---|---|---|---|---|
| I-881 | 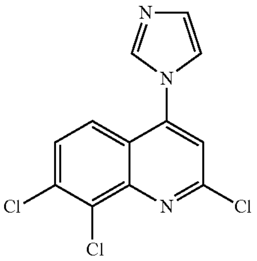 [SMILES: Clc1cc(-n2ccnc2)c2ccc(Cl)c(Cl)c2n1] | 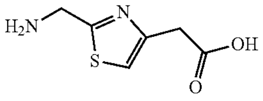 [SMILES: NCc1nc(CC(=O)O)cs1] | 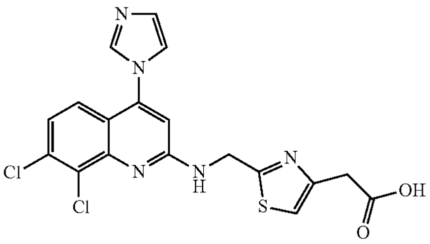 [SMILES: O=C(O)Cc1csc(CNc2cc(-n3ccnc3)c3ccc(Cl)c(Cl)c3n2)n1] | 434 |
| I-883 | 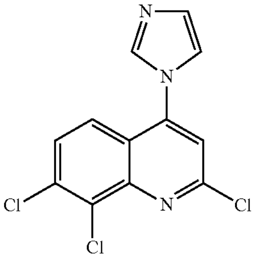 [SMILES: Clc1cc(-n2ccnc2)c2ccc(Cl)c(Cl)c2n1] | 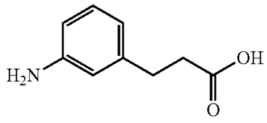 [SMILES: Nc1cccc(CCC(=O)O)c1] | 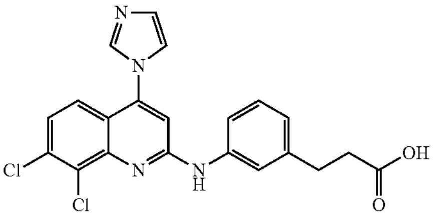 [SMILES: O=C(O)CCc1cccc(Nc2cc(-n3ccnc3)c3ccc(Cl)c(Cl)c3n2)c1] | 427 |
| I-872 | 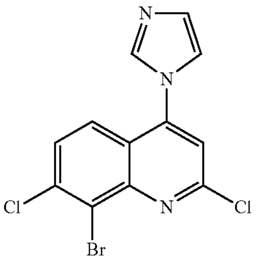 | 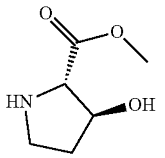 | 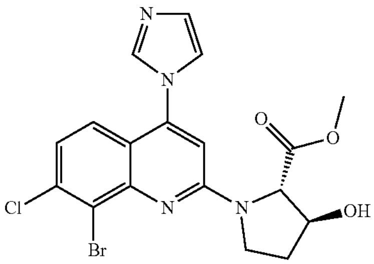 [SMILES: COC(=O)[C@@H]1[C@@H](O)CCN1c1cc(-n2ccnc2)c2ccc(Cl)c(Br)c2n1] | 451 |

Example 2: Synthesis of 2-(1-(7-chloro-4-(1H-imidazol-1-yl)quinolin-2-yl)piperidin-3-yl)acetic acid (I-123)

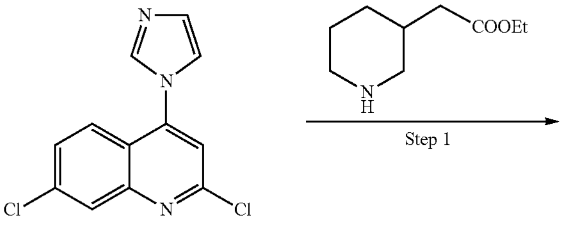

-continued

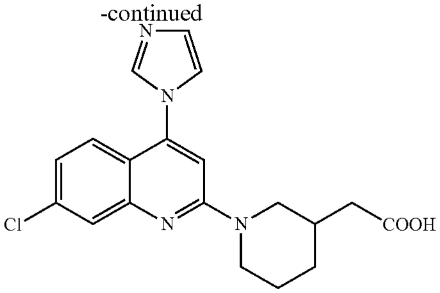

I-123

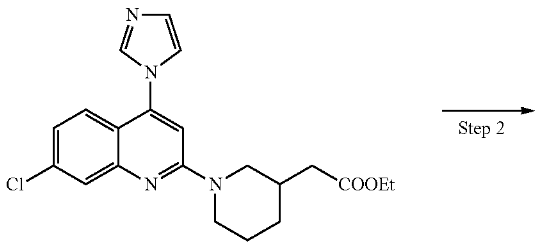

Step 1: Ethyl 2-(1-(7-chloro-4-(1H-imidazol-1-yl)quinolin-2-yl)piperidin-3-yl)acetate. To a solution of 2,7-dichloro-4-(1H-imidazol-1-yl)quinoline (38 mg, 0.144 mmol) in DMF (1 mL) was added ethyl 2-(piperidin-3-yl)acetate (50 mg, 0.3 mmol). The solution was vigorously stirred at 140° C. for 3 h. After cooling down to room temperature, the solvent was removed by evaporation and the residue was purified by column chromatography on silica gel to give the titled product as an oil (MS: $[M+1]^+$ 399.1).

Step 2: 2-(1-(7-Chloro-4-(1H-imidazol-1-yl)quinolin-2-yl)piperidin-3-yl)acetic acid. To a solution of ethyl 2-(1-(7-chloro-4-(1H-imidazol-1-yl)quinolin-2-yl)piperidin-3-yl) acetate (20 mg, 0.05 mmol) in MeOH (2 mL) was added 10% NaOH (aq., 0.5 mL). The mixture was stirred at 50° C. for 1 h. After cooling to room temperature, the crude was acidified by 1 N HCl (2.5 mL). The titled compound was collected as a solid by filtration (MS: $[M+1]^+$ 371.1).
The following compounds were prepared essentially by the same method as described above for I-123.
| I-# | Starting Material | Structure | MS $[M + 1]^+$ |
|---|---|---|---|
| I-84 | 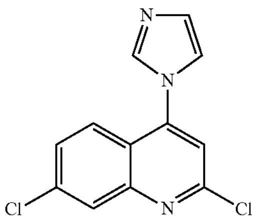 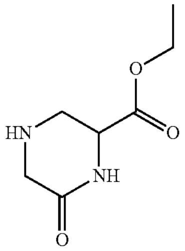 | 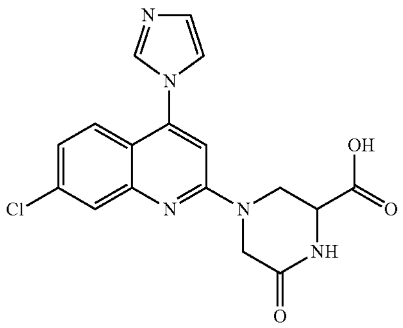 [SMILES: O=C1CN(c2cc(-n3ccnc3)c3ccc(Cl)cc3n2)CC(C(=O)O)N1] | 372 |
| I-122 | 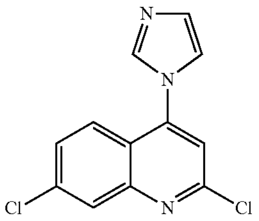 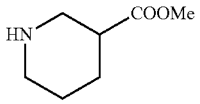 | 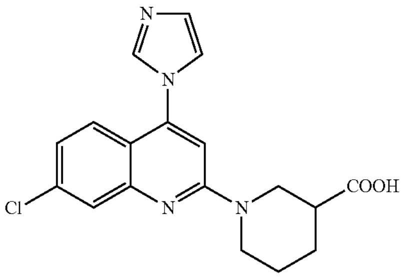 [SMILES: O=C(O)C1CCCN(c2cc(-n3ccnc3)c3ccc(Cl)cc3n2)C1] | 357.1 |
| I-127 | 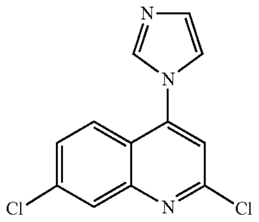 [SMILES: Clc1ccc2c(-n3ccnc3)cc(Cl)nc2c1] 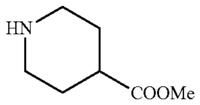 | 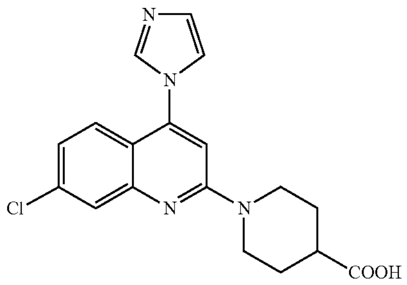 [SMILES: O=C(O)C1CCN(c2cc(-n3ccnc3)c3ccc(Cl)cc3n2)CC1] | 357.1 |
| I-445 | 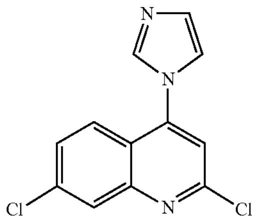 [SMILES: Clc1ccc2c(-n3ccnc3)cc(Cl)nc2c1] 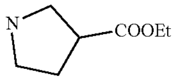 | 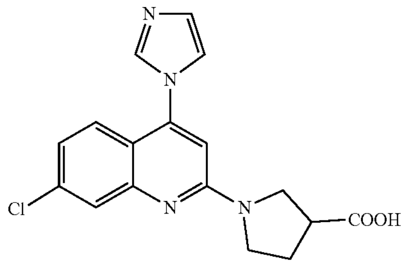 [SMILES: O=C(O)C1CCN(c2cc(-n3ccnc3)c3ccc(Cl)cc3n2)C1] | 343.0 |
| I-331 | 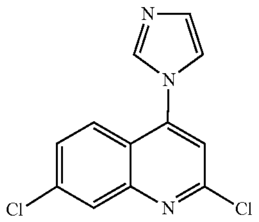 [SMILES: Clc1ccc2c(-n3ccnc3)cc(Cl)nc2c1] 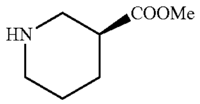 | 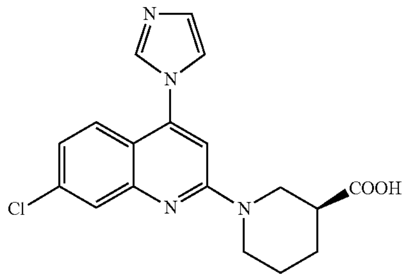 [SMILES: O=C(O)[C@H]1CCCN(c2cc(-n3ccnc3)c3ccc(Cl)cc3n2)C1] | 357.1 |

-continued
| I-# | Starting Material | Structure | MS [M + 1]+ |
|---|---|---|---|
| I-135 | 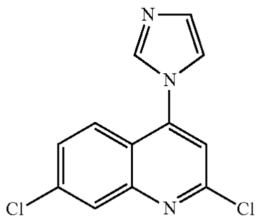 [SMILES: Clc1ccc2c(-n3ccnc3)cc(Cl)nc2c1] 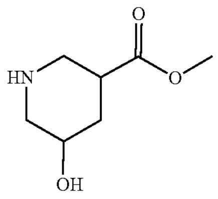 | 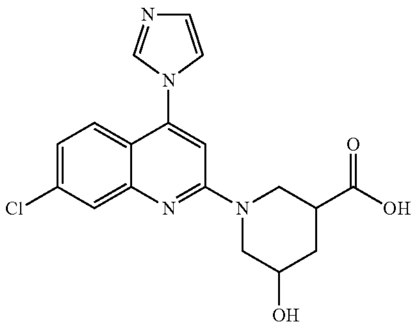 [SMILES: O=C(O)C1CC(O)CN(c2cc(-n3ccnc3)c3ccc(Cl)cc3n2)C1] | 373.1 |
| I-332 | 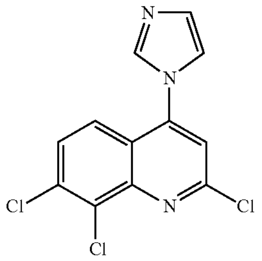 [SMILES: Clc1cc(-n2ccnc2)c2ccc(Cl)c(Cl)c2n1] 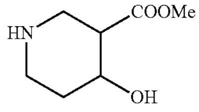 [SMILES: COC(=O)C1CNCCC1O] | 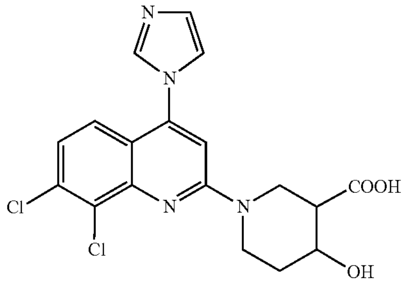 [SMILES: O=C(O)C1CN(c2cc(-n3ccnc3)c3ccc(Cl)c(Cl)c3n2)CCC1O] | 373 |
| I-334 | 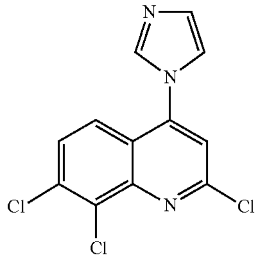 [SMILES: Clc1cc(-n2ccnc2)c2ccc(Cl)c(Cl)c2n1] 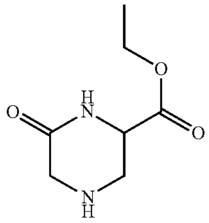 | 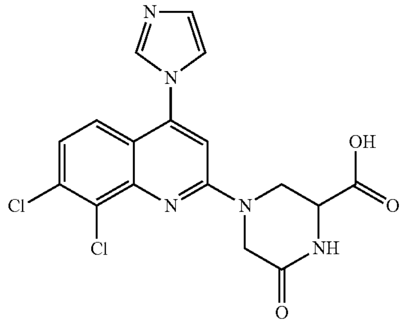 [SMILES: O=C1CN(c2cc(-n3ccnc3)c3ccc(Cl)c(Cl)c3n2)CC(C(=O)O)N1] | 406 |
| I-130 | 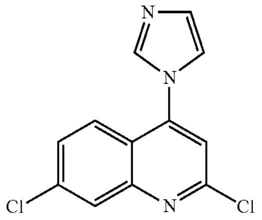 [SMILES: Clc1ccc2c(-n3ccnc3)cc(Cl)nc2c1] 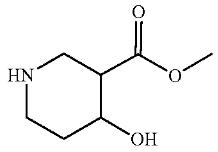 | 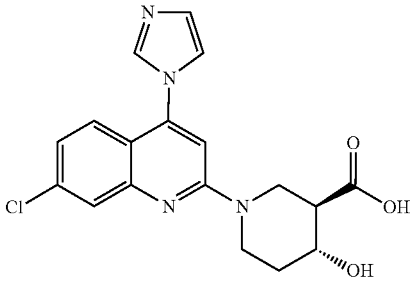 [SMILES: O=C(O)[C@@H]1CN(c2cc(-n3ccnc3)c3ccc(Cl)cc3n2)CC[C@H]1O] | 373.1 |
| I-136 | | 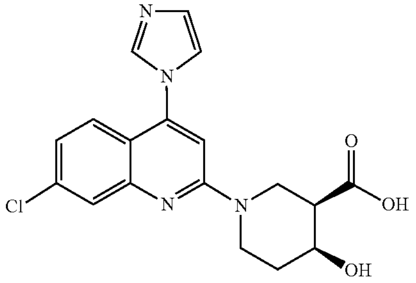 [SMILES: O=C(O)[C@@H]1CN(c2cc(-n3ccnc3)c3ccc(Cl)cc3n2)CC[C@@H]1O] | 373.1 |

-continued
| I-# | Starting Material | | Structure | MS [M + 1]+ |
|---|---|---|---|---|
| I-124 | 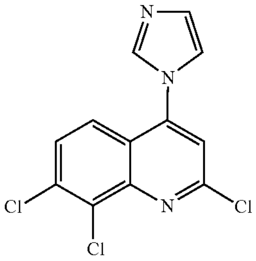 [SMILES: Clc1cc(-n2ccnc2)c2ccc(Cl)c(Cl)c2n1] | 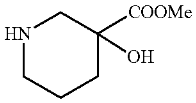 [SMILES: COC(=O)C1(O)CCCNC1] | 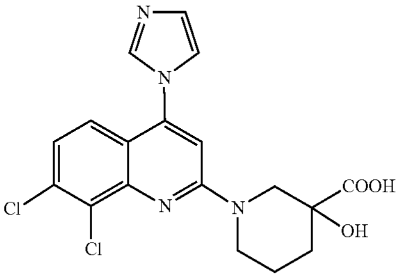 [SMILES: O=C(O)C1(O)CCCN(c2cc(-n3ccnc3)c3ccc(Cl)c(Cl)c3n2)C1] | 407 |
| I-333 | 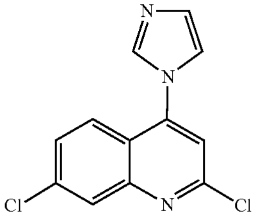 [SMILES: Clc1ccc2c(-n3ccnc3)cc(Cl)nc2c1] | 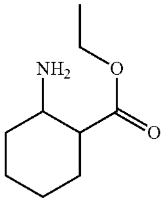 | 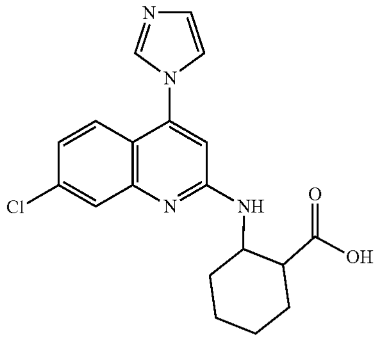 [SMILES: O=C(O)C1CCCCC1Nc1cc(-n2ccnc2)c2ccc(Cl)cc2n1] | 371 |
| I-505 | 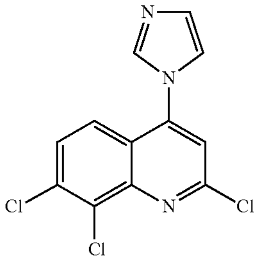 [SMILES: Clc1cc(-n2ccnc2)c2ccc(Cl)c(Cl)c2n1] | 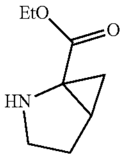 | 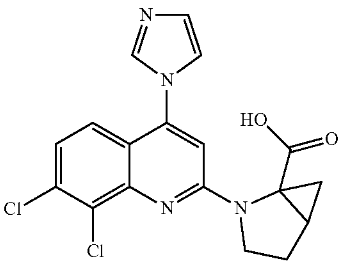 [SMILES: O=C(O)C12CC1CCN2c1cc(-n2ccnc2)c2ccc(Cl)c(Cl)c2n1] | 389 |
| I-506 | 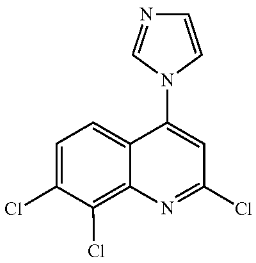 [SMILES: Clc1cc(-n2ccnc2)c2ccc(Cl)c(Cl)c2n1] | 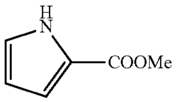 | 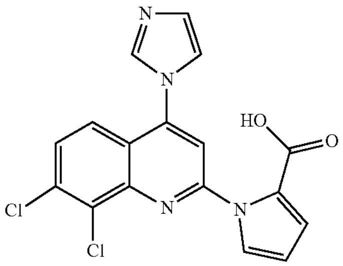 [SMILES: O=C(O)c1cccn1-c1cc(-n2ccnc2)c2ccc(Cl)c(Cl)c2n1] | 373 |
| I-507 | 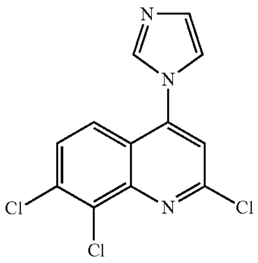 [SMILES: Clc1cc(-n2ccnc2)c2ccc(Cl)c(Cl)c2n1] | 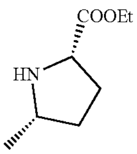 | 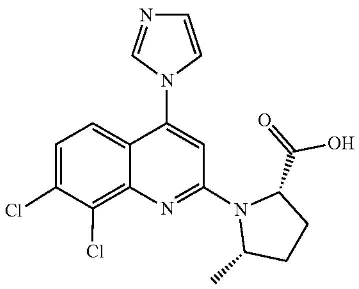 [SMILES: C[C@H]1CC[C@@H](C(=O)O)N1c1cc(-n2ccnc2)c2ccc(Cl)c(Cl)c2n1] | 391 |

-continued
| I-# | Starting Material | Structure | MS [M + 1]+ |
| --- | --- | --- | --- |
| I-508 | 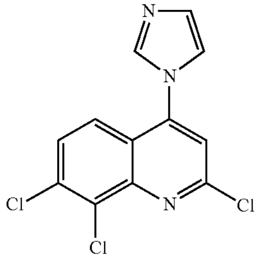 [SMILES: Clc1cc(-n2ccnc2)c2ccc(Cl)c(Cl)c2n1] 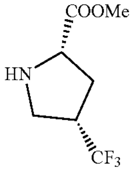 | 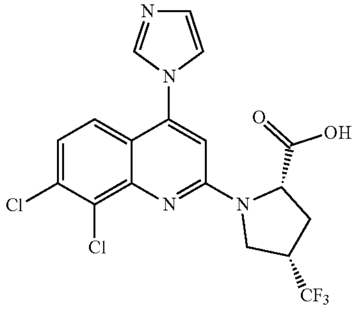 [SMILES: O=C(O)[C@@H]1C[C@H](C(F)(F)F)CN1c1cc(-n2ccnc2)c2ccc(Cl)c(Cl)c2n1] | 445 |
| I-509 | 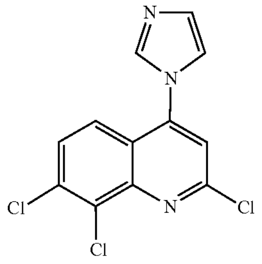 [SMILES: Clc1cc(-n2ccnc2)c2ccc(Cl)c(Cl)c2n1] 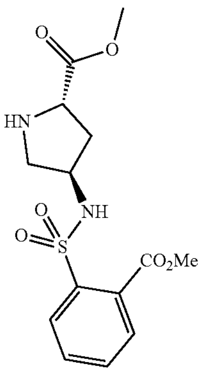 [SMILES: COC(=O)c1ccccc1S(=O)(=O)N[C@H]1CN[C@H](C(=O)OC)C1] | 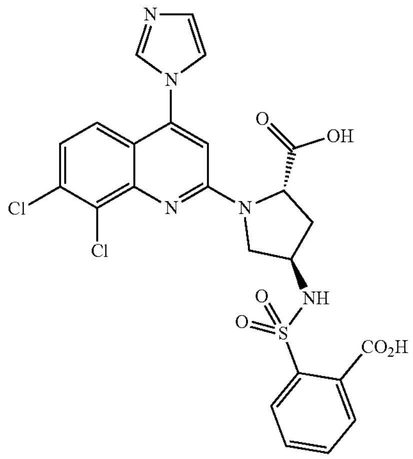 [SMILES: O=C(O)c1ccccc1S(=O)(=O)N[C@@H]1C[C@@H](C(=O)O)N(c2cc(-n3ccnc3)c3ccc(Cl)c(Cl)c3n2)C1] | 576 |
| I-510 | 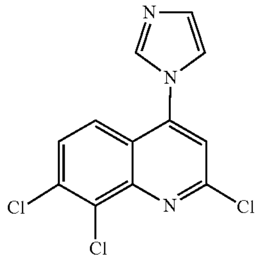 [SMILES: Clc1cc(-n2ccnc2)c2ccc(Cl)c(Cl)c2n1] 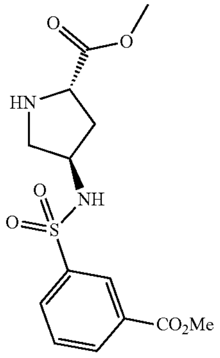 [SMILES: COC(=O)c1cccc(S(=O)(=O)N[C@H]2CN[C@H](C(=O)OC)C2)c1] | 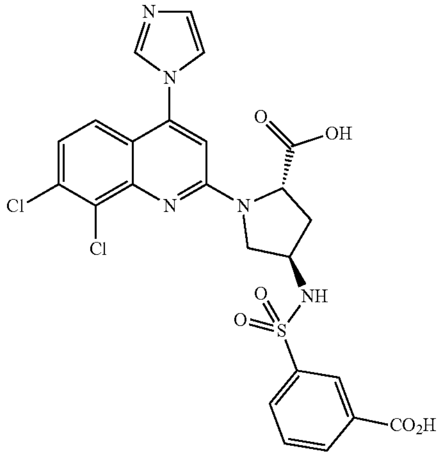 [SMILES: O=C(O)c1cccc(S(=O)(=O)N[C@@H]2C[C@@H](C(=O)O)N(c3cc(-n4ccnc4)c4ccc(Cl)c(Cl)c4n3)C2)c1] | 576 |

-continued
| I-# | Starting Material | | Structure | MS [M + 1]⁺ |
|---|---|---|---|---|
| I-511 | 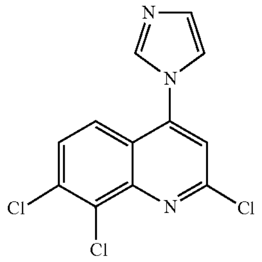 [SMILES: Clc1cc(-n2ccnc2)c2ccc(Cl)c(Cl)c2n1] | 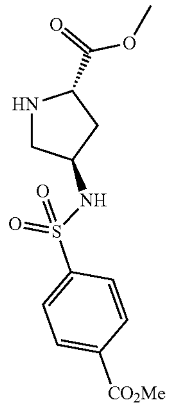 [SMILES: COC(=O)c1ccc(S(=O)(=O)N[C@H]2CN[C@H](C(=O)OC)C2)cc1] | 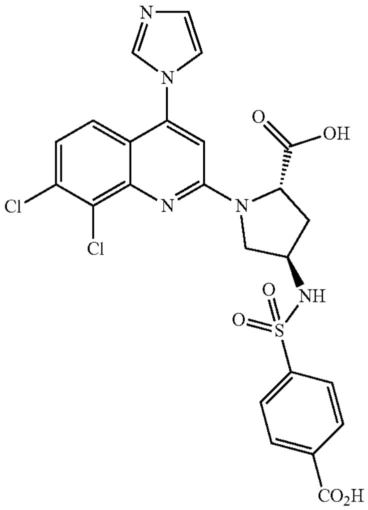 [SMILES: O=C(O)c1ccc(S(=O)(=O)N[C@@H]2C[C@@H](C(=O)O)N(c3cc(-n4ccnc4)c4ccc(Cl)c(Cl)c4n3)C2)cc1] | 576 |
| I-512 | 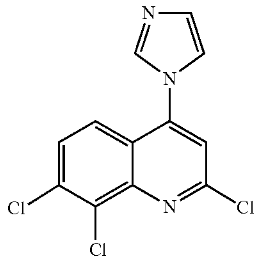 [SMILES: Clc1cc(-n2ccnc2)c2ccc(Cl)c(Cl)c2n1] | 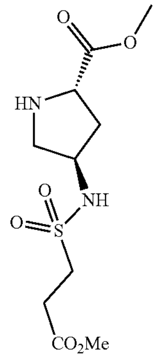 [SMILES: COC(=O)CCS(=O)(=O)N[C@H]1CN[C@H](C(=O)OC)C1] | 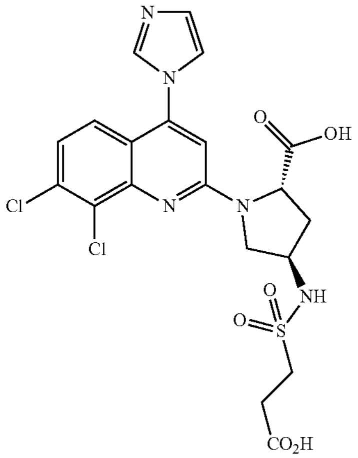 [SMILES: O=C(O)CCS(=O)(=O)N[C@@H]1C[C@@H](C(=O)O)N(c2cc(-n3ccnc3)c3ccc(Cl)c(Cl)c3n2)C1] | 528 |
| I-513 | 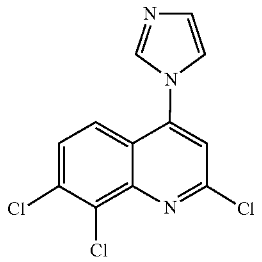 [SMILES: Clc1cc(-n2ccnc2)c2ccc(Cl)c(Cl)c2n1] | 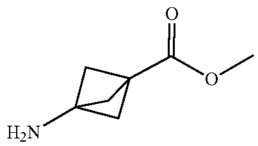 | 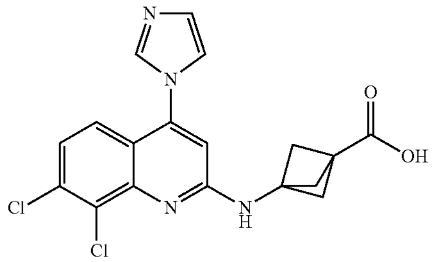 [SMILES: O=C(O)C12CC(Nc3cc(-n4ccnc4)c4ccc(Cl)c(Cl)c4n3)(C1)C2] | 389 |
| I-514 | 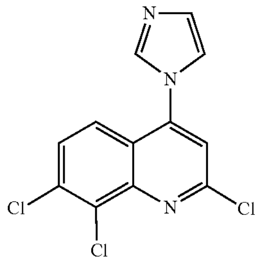 [SMILES: Clc1cc(-n2ccnc2)c2ccc(Cl)c(Cl)c2n1] | 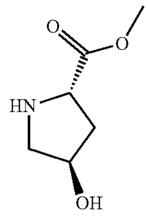 | 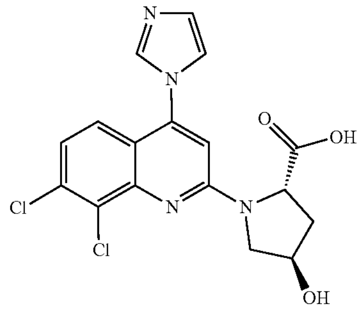 [SMILES: O=C(O)[C@@H]1C[C@@H](O)CN1c1cc(-n2ccnc2)c2ccc(Cl)c(Cl)c2n1] | 393 |

-continued
| I-# | Starting Material | Structure | MS [M + 1]+ |
| --- | --- | --- | --- |
| I-515 | 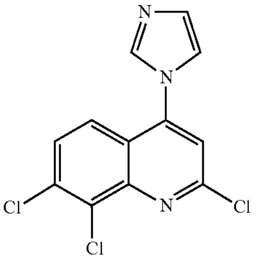 [SMILES: Clc1cc(-n2ccnc2)c2ccc(Cl)c(Cl)c2n1] 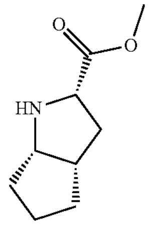 | 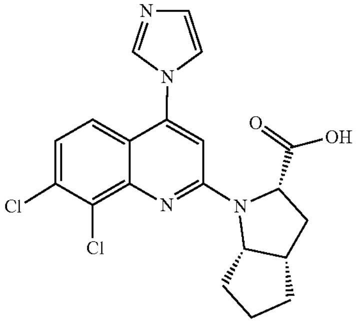 [SMILES: O=C(O)[C@@H]1C[C@@H]2CCC[C@@H]2N1c1cc(-n2ccnc2)c2ccc(Cl)c(Cl)c2n1] | 417 |
| I-516 | 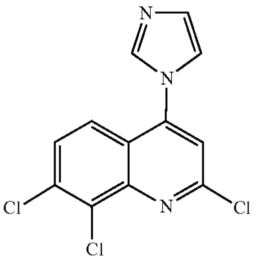 [SMILES: Clc1cc(-n2ccnc2)c2ccc(Cl)c(Cl)c2n1] 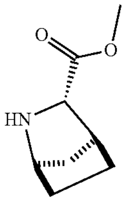 | 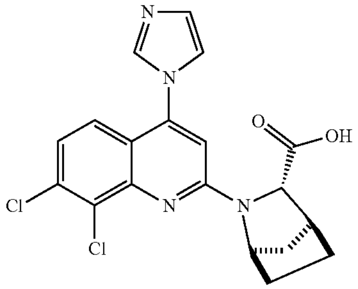 [SMILES: O=C(O)[C@@H]1[C@H]2CC[C@H](C2)N1c1cc(-n2ccnc2)c2ccc(Cl)c(Cl)c2n1] | 403 |
| I-517 | 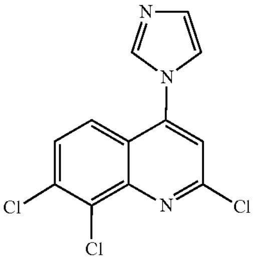 [SMILES: Clc1cc(-n2ccnc2)c2ccc(Cl)c(Cl)c2n1] 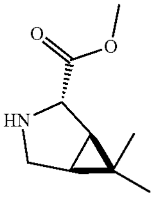 | 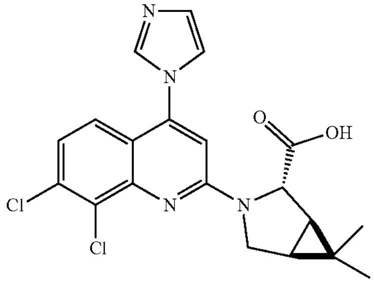 | 417 |
| I-518 | 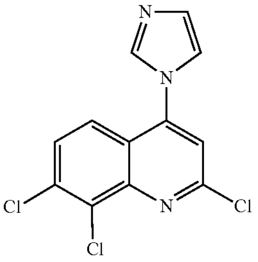 [SMILES: Clc1cc(-n2ccnc2)c2ccc(Cl)c(Cl)c2n1] 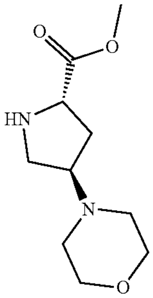 | 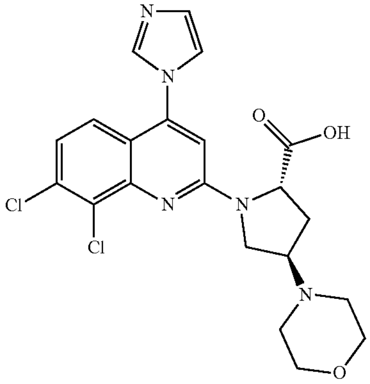 [SMILES: O=C(O)[C@@H]1C[C@@H](N2CCOCC2)CN1c1cc(-n2ccnc2)c2ccc(Cl)c(Cl)c2n1] | 462 |

-continued
| I-# | Starting Material | Structure | MS [M + 1]+ |
| --- | --- | --- | --- |
| I-519 | 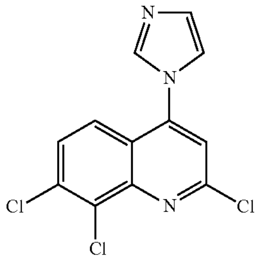 [SMILES: Clc1cc(-n2ccnc2)c2ccc(Cl)c(Cl)c2n1] 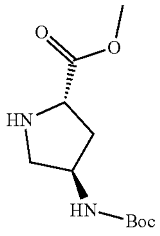 | 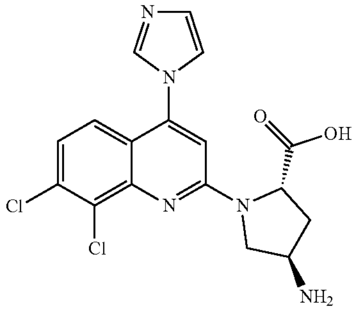 [SMILES: N[C@@H]1C[C@@H](C(=O)O)N(c2cc(-n3ccnc3)c3ccc(Cl)c(Cl)c3n2)C1] | 392 |
| I-520 | 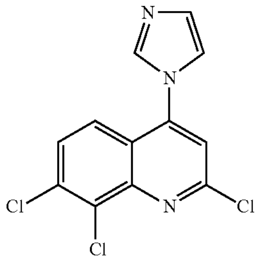 [SMILES: Clc1cc(-n2ccnc2)c2ccc(Cl)c(Cl)c2n1] 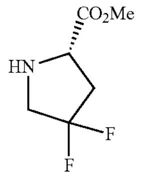 [SMILES: COC(=O)[C@@H]1CC(F)(F)CN1] | 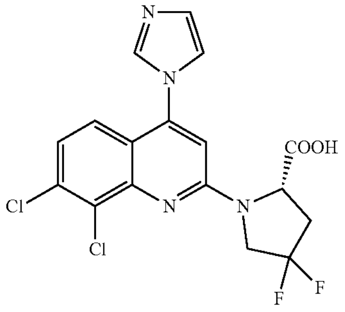 [SMILES: O=C(O)[C@@H]1CC(F)(F)CN1c1cc(-n2ccnc2)c2ccc(Cl)c(Cl)c2n1] | 413 |
| I-521 | 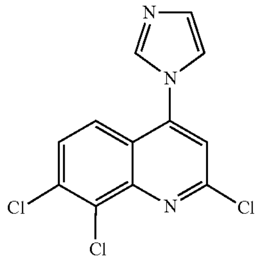 [SMILES: Clc1cc(-n2ccnc2)c2ccc(Cl)c(Cl)c2n1] 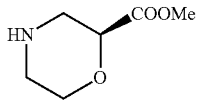 | 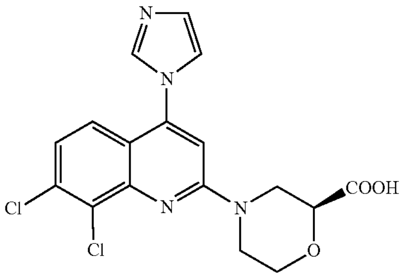 [SMILES: O=C(O)[C@@H]1CN(c2cc(-n3ccnc3)c3ccc(Cl)c(Cl)c3n2)CCO1] | 393 |
| I-844 | 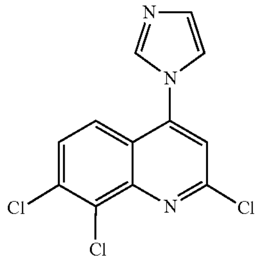 [SMILES: Clc1cc(-n2ccnc2)c2ccc(Cl)c(Cl)c2n1] 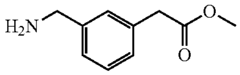 | 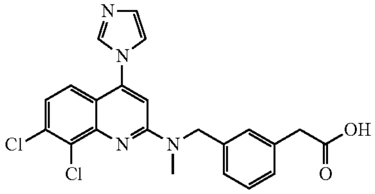 [SMILES: CN(Cc1cccc(CC(=O)O)c1)c1cc(-n2ccnc2)c2ccc(Cl)c(Cl)c2n1] | 427 |
| I-845 | 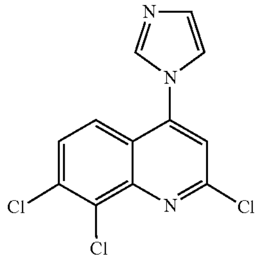 [SMILES: Clc1cc(-n2ccnc2)c2ccc(Cl)c(Cl)c2n1] 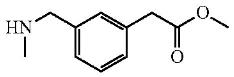 | 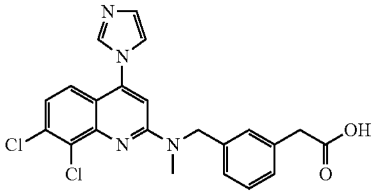 [SMILES: CN(Cc1cccc(CC(=O)O)c1)c1cc(-n2ccnc2)c2ccc(Cl)c(Cl)c2n1] | 441 |

-continued
| I-# | Starting Material | | Structure | MS [M + 1]⁺ |
|---|---|---|---|---|
| I-831 | 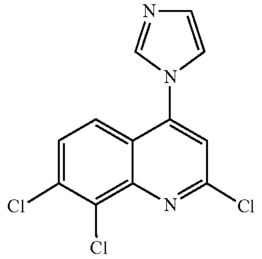 [SMILES: Clc1cc(-n2ccnc2)c2ccc(Cl)c(Cl)c2n1] | 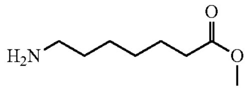 | 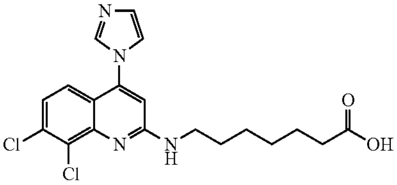 [SMILES: O=C(O)CCCCCCNc1cc(-n2ccnc2)c2ccc(Cl)c(Cl)c2n1] | 407 |
| I-887 | 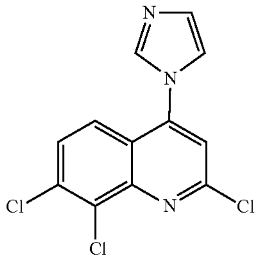 [SMILES: Clc1cc(-n2ccnc2)c2ccc(Cl)c(Cl)c2n1] | 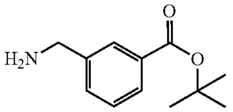 | 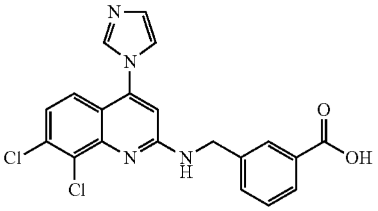 [SMILES: O=C(O)c1cccc(CNc2cc(-n3ccnc3)c3ccc(Cl)c(Cl)c3n2)c1] | 413 |
| I-854 | 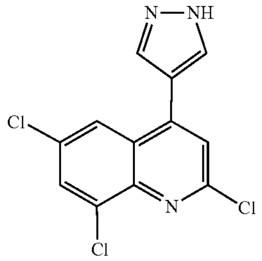 [SMILES: Clc1cc(Cl)c2nc(Cl)cc(-c3cn[nH]c3)c2c1] | 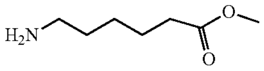 | 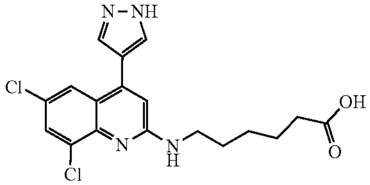 [SMILES: O=C(O)CCCCCNc1cc(-c2cn[nH]c2)c2cc(Cl)cc(Cl)c2n1] | 393 |
| I-830 | 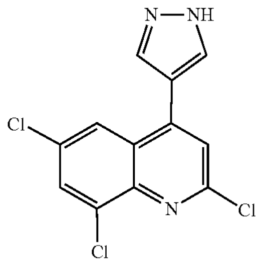 [SMILES: Clc1cc(Cl)c2nc(Cl)cc(-c3cn[nH]c3)c2c1] | 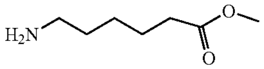 | 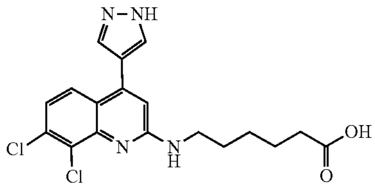 [SMILES: O=C(O)CCCCCNc1cc(-c2cn[nH]c2)c2ccc(Cl)c(Cl)c2n1] | 393 |
| I-882 | 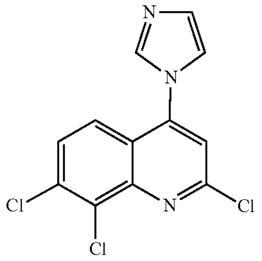 [SMILES: Clc1cc(-n2ccnc2)c2ccc(Cl)c(Cl)c2n1] | 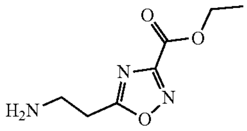 | 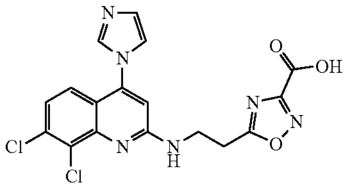 [SMILES: O=C(O)c1noc(CCNc2cc(-n3ccnc3)c3ccc(Cl)c(Cl)c3n2)n1] | 419 |

Example 3: Synthesis of (7-chloro-4-(1H-imidazol-1-yl)quinolin-2-yl)glycine (I-166)

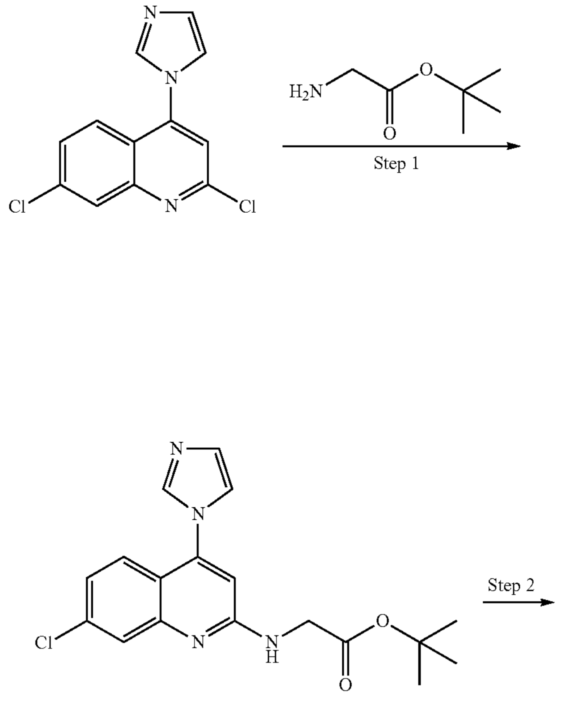

-continued

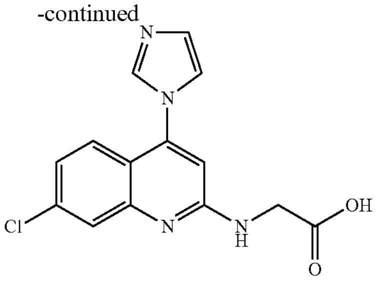

I-66

Step 1: tert-Butyl (7-chloro-4-(1H-imidazol-1-yl)quinolin-2-yl)glycinate. A mixture of 2,7-dichloro-4-(1H-imidazol-1-yl)quinoline (30 mg, 0.114 mmol), tert-butyl glycinate (38 mg, 0.228 mmol), triethylamine (0.2 mL) and dioxane (2 mL) was heated at 100° C. for 16 h. After cooling to room temperature, the crude was diluted with water (5 mL) and extracted by EtOAc (2×5 mL). The combined organics were dried and concentrated. The residue was purified by column chromatography on silica gel (25-100% EtOAc/Hexanes) to give tert-butyl (7-chloro-4-(1H-imidazol-1-yl)quinolin-2-yl) glycinate as a solid (MS: $[M+1]^+$ 359.1).

Step 2: (7-Chloro-4-(1H-imidazol-1-yl)quinolin-2-yl)glycine. Tert-butyl (7-chloro-4-(1H-imidazol-1-yl)quinolin-2-yl)glycinate (20 mg, 0.056 mmol) was placed in a vial with dichloromethane (3 mL). Hydrochloric acid (2.0 M in diethyl ether) was added and the reaction was stirred at r.t. for 16 h. The volatiles were concentrated off and the resulting solid was triturated with dichloromethane, then dried in vacuo to afford (7-chloro-4-(1H-imidazol-1-yl)quinolin-2-yl)glycine as a solid (MS: $[M+1]^+$ 303.1).

The following compounds were prepared essentially by the same method as described above to prepare I-166:

| I-# | Starting Material | Structure | MS $[M + 1]^+$ |
| --- | --- | --- | --- |
| I-182 | 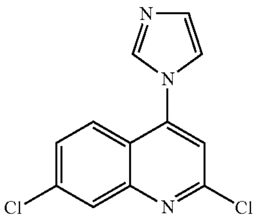 [SMILES: Clc1ccc2c(-n3ccnc3)cc(Cl)nc2c1] 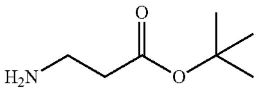 | 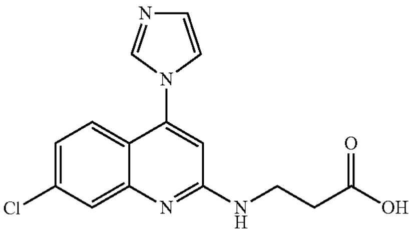 [SMILES: O=C(O)CCNc1cc(-n2ccnc2)c2ccc(Cl)cc2n1] | 317.1 |
| I-167 | 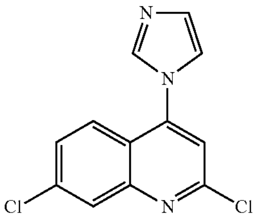 [SMILES: Clc1ccc2c(-n3ccnc3)cc(Cl)nc2c1] 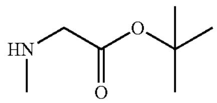 | 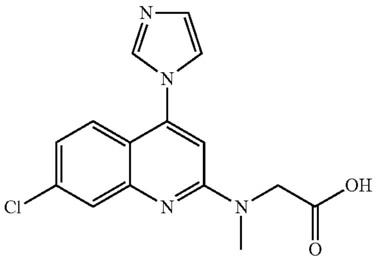 [SMILES: CN(CC(=O)O)c1cc(-n2ccnc2)c2ccc(Cl)cc2n1] | 317.1 |

Example 4: Synthesis of 5-(7-chloro-4-(1H-imidazol-1-yl)quinolin-2-yl)-2-hydroxynicotinic acid (I-57)

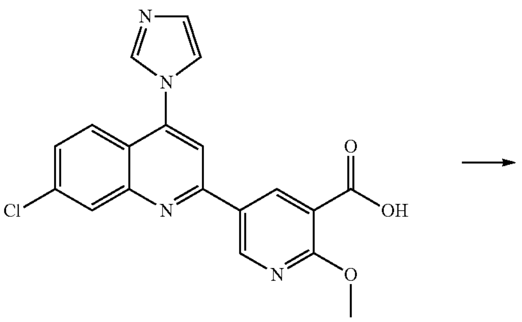

I-33

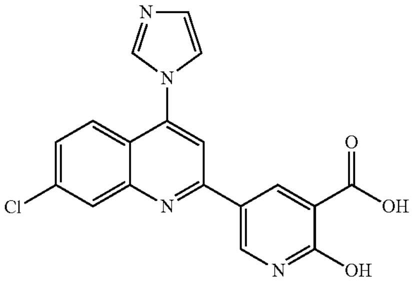

I-57

5-(7-chloro-4-(1H-imidazol-1-yl)quinolin-2-yl)-2-methoxynicotinic acid (I-33, 15 mg, 0.04 mmol) was placed in a vial with acetic acid (1 mL). Hydrobromic acid (33% in acetic acid, 0.2 mL) was added and the reaction was stirred at r.t. for 16 h. The volatiles were concentrated off and the resulting residue was purified on a silica prep plate to afford the title compound (MS: $[M+1]^+$ 367.0).

Example 5: Synthesis of (7,8-Dichloro-4-(1H-imidazol-1-yl)quinolin-2-yl)serine (I-168)

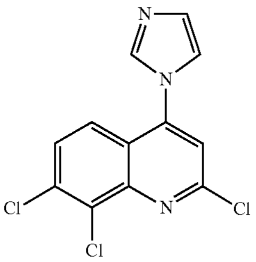

+

-continued

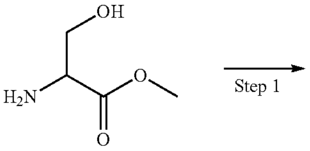

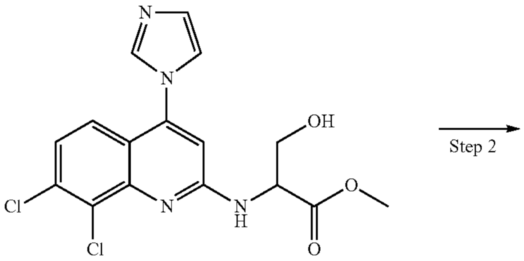

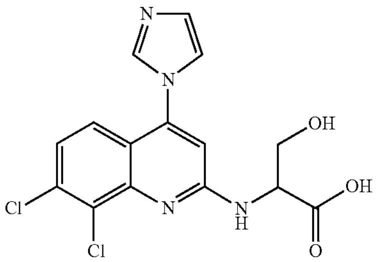

I-168

Step 1: Methyl (7,8-dichloro-4-(1H-imidazol-1-yl)quinolin-2-yl)serinate. To a solution of 2,7,8-trichloro-4-(1H-imidazol-1-yl)quinoline (30 mg, 0.1 mmol) in DMSO (0.2 mL) was added DL-Serine methyl ester HCl (39 mg, 0.25 mmol) and N,N-diisopropylethylamine (0.1 mL) and the solution was stirred at 95° C. for 16 h. After cooling to room temperature, water (5 mL) was added and the organics were extracted into 10% methanol in dichloromethane (2×5 mL). The combined organics were dried ($Na_2SO_4$) and concentrated. The resulting residue was purified by silica chromatography using 0-15% MeOH/dichloromethane to afford methyl (7,8-dichloro-4-(1H-imidazol-1-yl)quinolin-2-yl) serinate (MS: $[M+1]^+$ 381.0).

Step 2: (7,8-Dichloro-4-(1H-imidazol-1-yl)quinolin-2-yl) serine. Methyl (7,8-dichloro-4-(1H-imidazol-1-yl)quinolin-2-yl)serinate (12 mg, 0.031 mmol) was placed in a vial with THF (0.6 mL), methanol (0.2 mL), and water (0.2 mL). Lithium hydroxide monohydrate (4 mg, 0.09 mmol) was added and the reaction was allowed to stir at r.t. for 16 h. The volatiles were concentrated off and the resulting residue neutralized by the addition of 1 N hydrochloric acid. The resulting solution was lyophilized to afford the titled compound (MS: $[M+1]^+$ 367.0).

The following compounds were prepared essentially by the same method described above to prepare I-168:

| I-# | Starting Material | | Structure | MS [M + 1]$^+$ |
|---|---|---|---|---|
| I-169 | 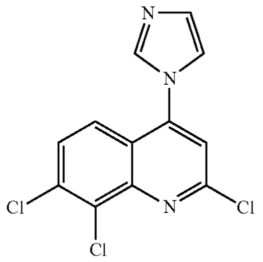 [SMILES: Clc1cc(-n2ccnc2)c2ccc(Cl)c(Cl)c2n1] | 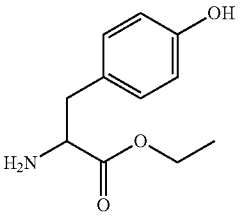 | 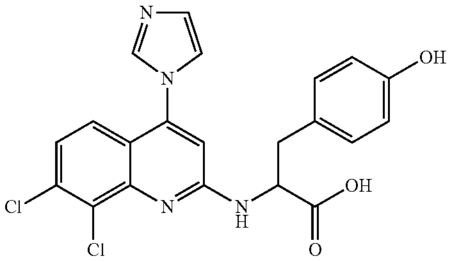 [SMILES: O=C(O)C(Cc1ccc(O)cc1)Nc1cc(-n2ccnc2)c2ccc(Cl)c(Cl)c2n1] | 443.0 |
| I-185 | 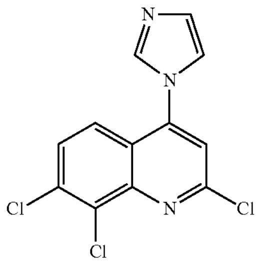 [SMILES: Clc1cc(-n2ccnc2)c2ccc(Cl)c(Cl)c2n1] | 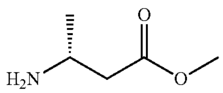 | 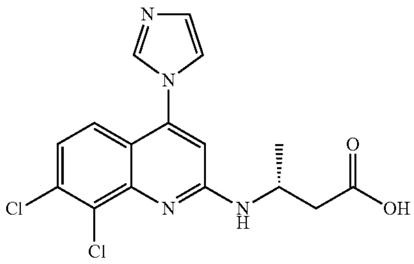 [SMILES: C[C@H](CC(=O)O)Nc1cc(-n2ccnc2)c2ccc(Cl)c(Cl)c2n1] | 365.0 |
| I-186 | 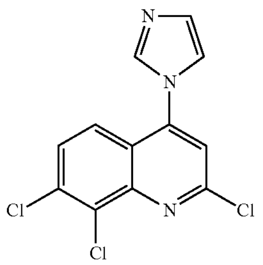 [SMILES: Clc1cc(-n2ccnc2)c2ccc(Cl)c(Cl)c2n1] | 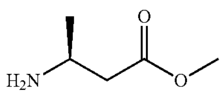 | 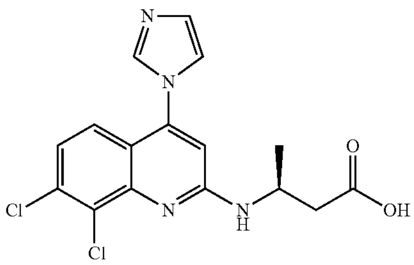 [SMILES: C[C@@H](CC(=O)O)Nc1cc(-n2ccnc2)c2ccc(Cl)c(Cl)c2n1] | 365.0 |
| I-189 | 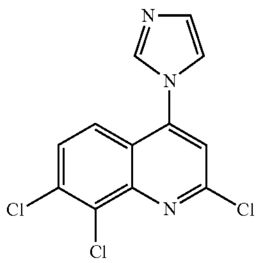 [SMILES: Clc1cc(-n2ccnc2)c2ccc(Cl)c(Cl)c2n1] | 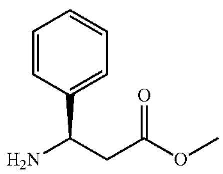 | 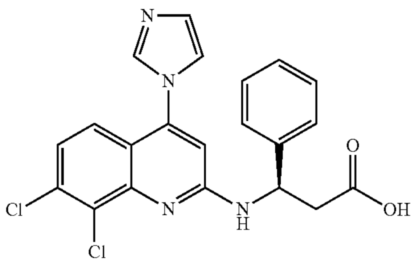 [SMILES: O=C(O)C[C@@H](Nc1cc(-n2ccnc2)c2ccc(Cl)c(Cl)c2n1)c1ccccc1] | 427.0 |
| I-187 | 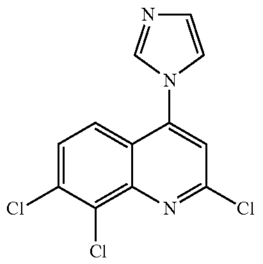 [SMILES: Clc1cc(-n2ccnc2)c2ccc(Cl)c(Cl)c2n1] | 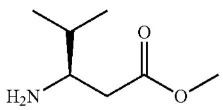 | 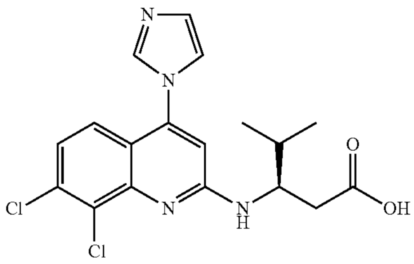 [SMILES: CC(C)[C@@H](CC(=O)O)Nc1cc(-n2ccnc2)c2ccc(Cl)c(Cl)c2n1] | 393.0 |
| I-184 | 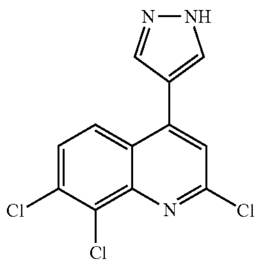 [SMILES: Clc1cc(-c2cn[nH]c2)c2ccc(Cl)c(Cl)c2n1] | 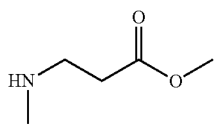 | 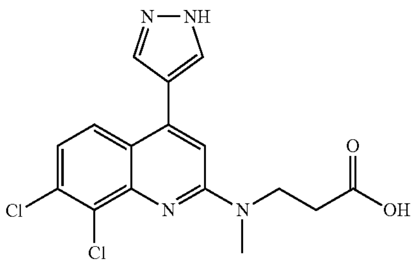 [SMILES: CN(CCC(=O)O)c1cc(-c2cn[nH]c2)c2ccc(Cl)c(Cl)c2n1] | 365.0 |

-continued

| I-# | Starting Material | Structure | MS [M + 1]+ |
|---|---|---|---|
| I-183 | 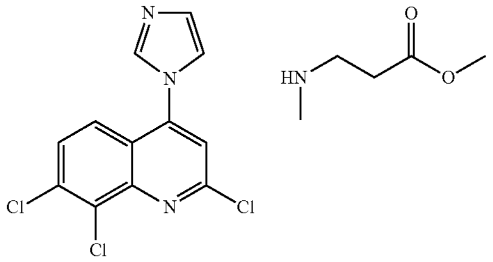 | 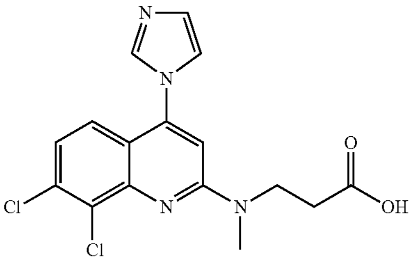 [SMILES: CN(CCC(=O)O)c1cc(-n2ccnc2)c2ccc(Cl)c(Cl)c2n1] | 365.1 |
| I-188 | 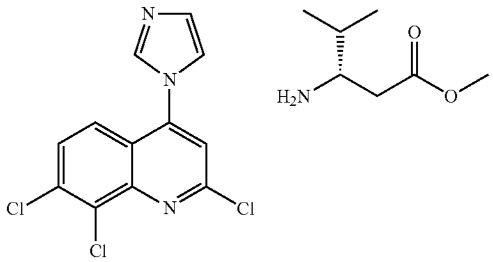 | 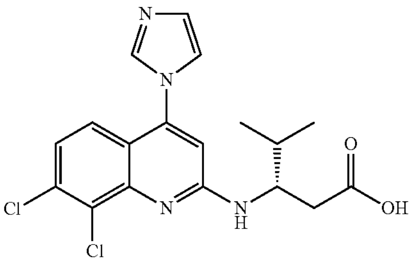 [SMILES: CC(C)[C@H](CC(=O)O)Nc1cc(-n2ccnc2)c2ccc(Cl)c(Cl)c2n1] | 393.0 |

Example 6: Synthesis of N-(7,8-dichloro-4-(1H-imidazol-1-yl)quinoline-2-yl)-N-(2-morpholinoethyl)glycine (I-172)

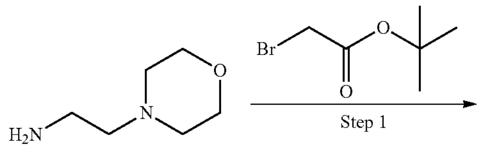

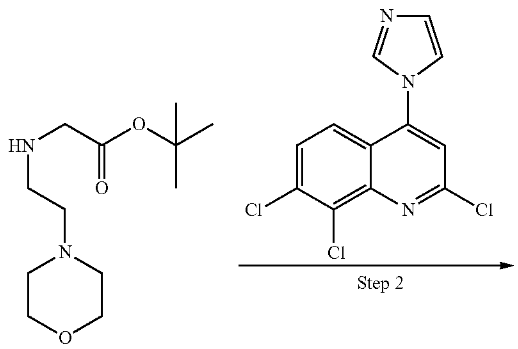

-continued

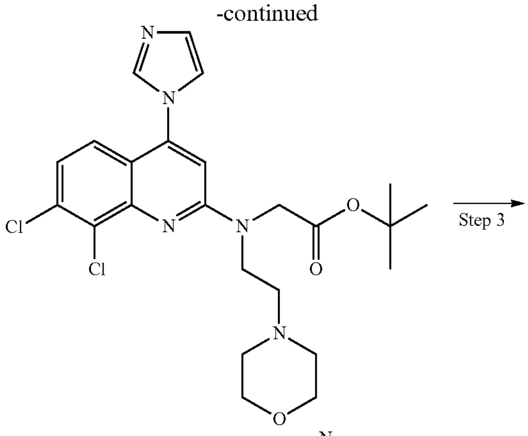

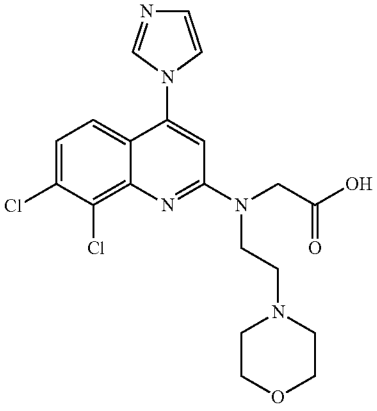

I-172

Step 1: tert-Butyl (2-morpholinoethyl)glycinate. To a solution of 2-morpholinoethan-1-amine (260 mg, 2.0 mmol) in acetonitrile (5 mL) was added $K_2CO_3$ (1.38 g, 10 mmol). The reaction was cooled to 0° C. and tert-butyl 2-bromoacetate (390 mg, 2.0 mmol) in acetonitrile (5 mL) was added dropwise. The reaction was stirred at 0° C. for 1 h then filtered through Celite and concentrated. The residue was purified by column chromatography to afford tert-butyl (2-morpholinoethyl)glycinate as an oil (200 mg) (MS: $[M+1]^+$ 245.2).

Step 2: tert-Butyl N-(7,8-dichloro-4-(1H-imidazol-1-yl) quinolin-2-yl)-N-(2-morpholinoethyl)glycinate. To a solution of 2,7,8-trichloro-4-(1H-imidazol-1-yl)quinoline (30 mg, 0.1 mmol) in DMSO (0.2 mL) was added tert-butyl (2-morpholinoethyl)glycinate (200 mg) and N,N-diisopropylethylamine (0.1 mL). The solution was stirred at 95° C. for 16 h. After cooling down to room temperature, water (5 mL) was added and the organics were extracted into 10% methanol in dichloromethane (2×5 mL). The combined organics were dried ($Na_2SO_4$) and concentrated. The resulting residue was purified by silica chromatography using 0-15% MeOH/dichloromethane to afford tert-butyl N-(7,8-dichloro-4-(1H-imidazol-1-yl)294uinoline-2-yl)-N-(2-morpholinoethypglycinate (10 mg) (MS: $[M+1]^+$ 506.1).

Step 3: N-(7,8-dichloro-4-(1H-imidazol-1-yl)quinoline-2-yl)-N-(2-morpholinoethyl)glycine. tert-Butyl N-(7,8-dichloro-4-(1H-imidazol-1-yl)quinolin-2-yl)-N-(2-morpholinoethyl)glycinate (10 mg, 0.02 mmol) was placed in a vial with dichloromethane (1 mL). Trifluoroacetic acid (0.1 mL) was added and the reaction stirred at r.t. for 16 h. The volatiles were removed by rotary evaporation and the residue was dried under vacuum to afford N-(7,8-dichloro-4-(1H-imidazol-1-yl)quinolin-2-yl)-N-(2-morpholinoethyl) glycine (MS: $[M+1]^+$ 450.1).

The following compounds were prepared essentially by the same methods described above to prepare I-172:

| I-# | Starting Material | Structure | MS $[M + 1]^+$ |
|---|---|---|---|
| I-173 | 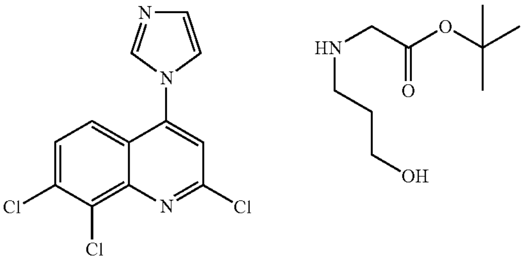 | 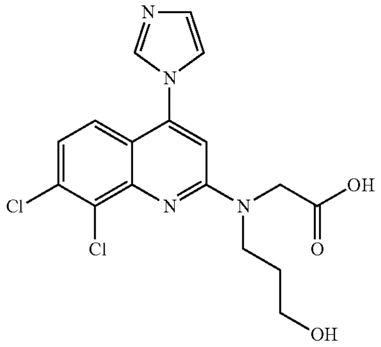 [SMILES: O=C(O)CN(CCCO)c1cc(-n2ccnc2)c2ccc(Cl)c(Cl)c2n1] | 395.0 |
| I-174 | 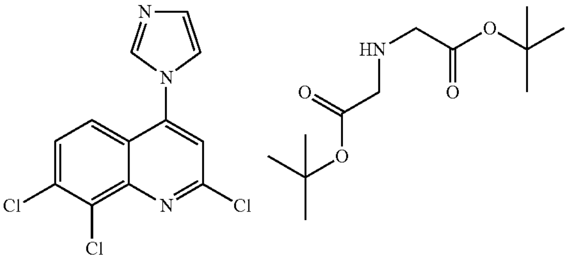 | 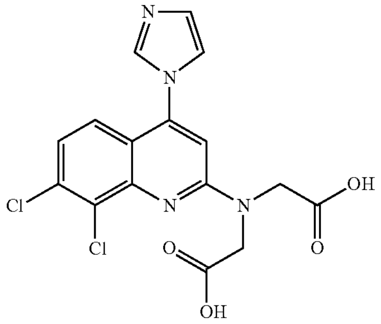 [SMILES: O=C(O)CN(CC(=O)O)c1cc(-n2ccnc2)c2ccc(Cl)c(Cl)c2n1] | 395.1 |
| I-175 | 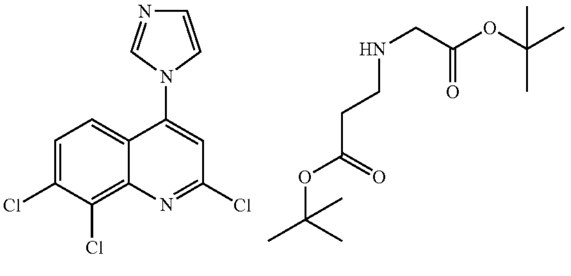 | 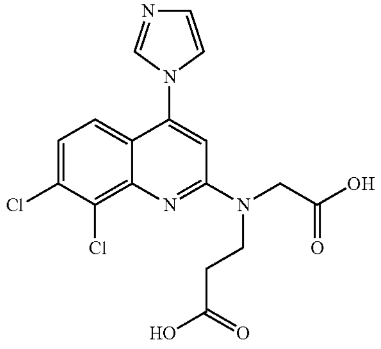 [SMILES: O=C(O)CCN(CC(=O)O)c1cc(-n2ccnc2)c2ccc(Cl)c(Cl)c2n1] | 409.1 |

-continued

| I-# | Starting Material | Structure | MS [M + 1]$^+$ |
|---|---|---|---|
| I-176 | 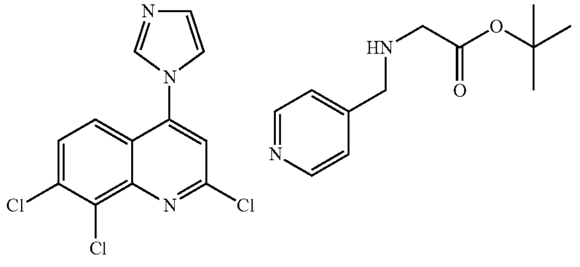 | 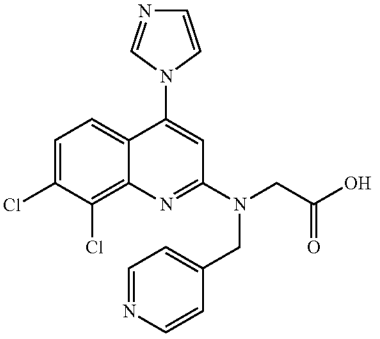 [SMILES: O=C(O)CN(Cc1ccncc1)c1cc(-n2ccnc2)c2ccc(Cl)c(Cl)c2n1] | 428.0 |

Example 7: Synthesis of 2-((7,8-Dichloro-4-(1H-imidazol-1-yl)quinolin-2-yl)amino)-4-(methylsulfonyl)butanoic acid (I-170)

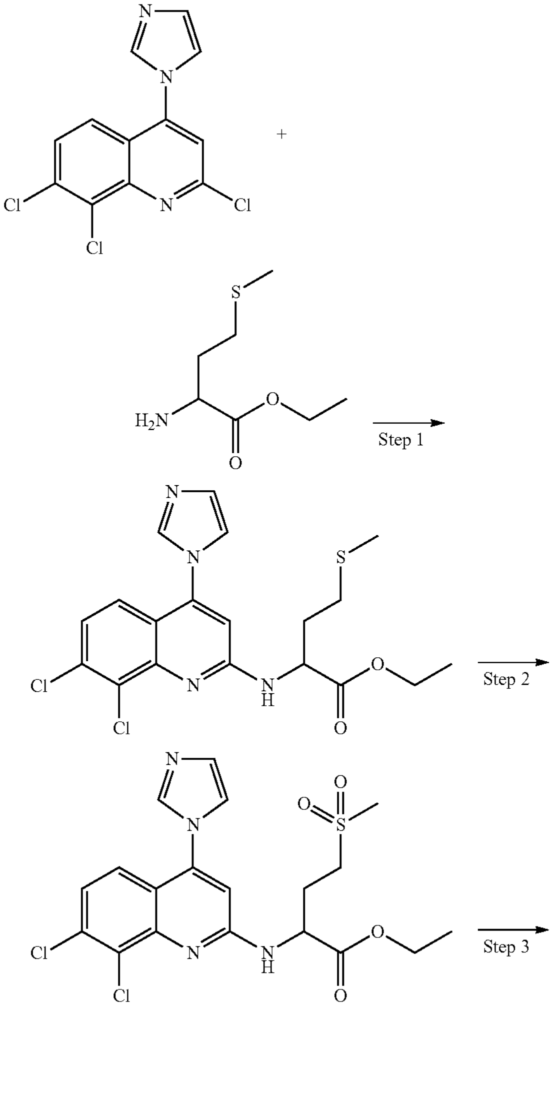

-continued

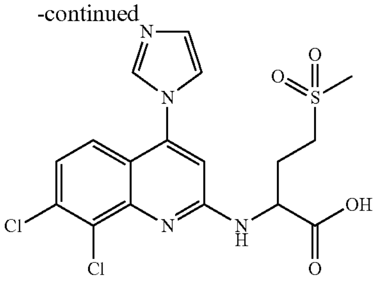

I-170

Step 1: Ethyl (7,8-dichloro-4-(1H-imidazol-1-yl)quinolin-2-yl)methioninate. To a solution of 2,7,8-trichloro-4-(1H-imidazol-1-yl)quinoline (30 mg, 0.1 mmol) in DMSO (0.2 mL) was added ethyl methioninate (47 mg, 0.2 mmol) and N,N-diisopropylethylamine (0.1 mL). The solution was stirred at 95° C. for 16 h. After cooling down to room temperature, water (5 mL) was added and the organics were extracted into 10% methanol in dichloromethane (2×5 mL). The combined organics were dried ($Na_2SO_4$) and concentrated. The resulting residue was purified by silica chromatography using 0-100% EtOAc/hexanes to afford ethyl (7,8-dichloro-4-(1H-imidazol-1-yl)quinolin-2-yl)methioninate (20 mg) (MS: $[M+1]^+$ 439.0).

Step 2: Ethyl 2-((7,8-dichloro-4-(1H-imidazol-1-yl)quinolin-2-yl)amino)-4-(methylsulfonyl)butanoate. Ethyl (7,8-dichloro-4-(1H-imidazol-1-yl)quinolin-2-yl)methioninate (20 mg, 0.045 mmol) was placed in a vial with dichloromethane (2 mL). m-CPBA (20 mg, 0.09 mmol) was added and the reaction was allowed to stir at r.t. for 16 h. Sodium sulfite (2 mL, 10% aq.) was added and the organics were dried ($Na_2SO_4$) and purified by silica chromatography using 0-10% $MeOH/CH_2Cl_2$ to afford ethyl 2-((7,8-dichloro-4-(1H-imidazol-1-yl)quinolin-2-yl)amino)-4-(methylsulfonyl)butanoate (10 mg) (MS: $[M+1]^+$ 471.1).

Step 3: 2-((7,8-Dichloro-4-(1H-imidazol-1-yl)quinolin-2-yl)amino)-4-(methylsulfonyl)butanoic acid. Ethyl 2-((7,8-dichloro-4-(1H-imidazol-1-yl)quinolin-2-yl)amino)-4-(methylsulfonyl)butanoate (20 mg, 0.042 mmol) was placed in a vial with THF (1 mL) and water (0.25 mL). Lithium hydroxide monohydrate (5 mg, 0.13 mmol) was added and the reaction mixture was stirred at r.t. for 3 h. The volatiles were removed by rotary evaporation and the residue was neutralized by the addition of 1N HCl (aq.). The resulting solution was lyophilized to afford 2-((7,8-dichloro-4-(1H-imidazol-1-yl)quinolin-2-yl)amino)-4-(methylsulfonyl)butanoic acid (12 mg) (MS: $[M+1]^+$ 443.0).

Example 8: Synthesis of 7-chloro-4-(1H-imidazol-1-yl)-2-(4-methoxyphenyl)quinoline (I-2)

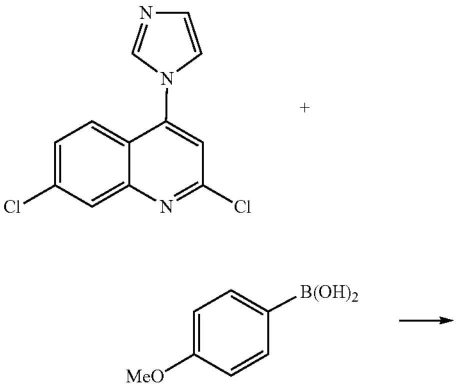

-continued

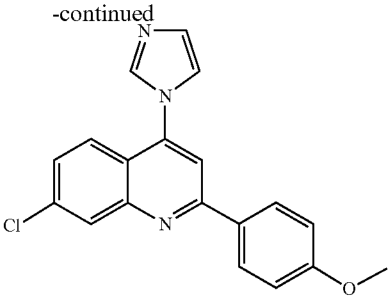

I-2

A mixture of 2,7-dichloro-4-(1H-imidazol-1-yl)quinoline (132 mg, 0.5 mmol), (4-methoxyphenyl)boronic acid (114 mg, 0.75 mmol), $Na_2CO_3$ (265 mg, 2.5 mmol), 1,4-dioxane (4 mL) and $H_2O$ (1 mL) was purged by $N_2$ for 30 min. Tetrakis(triphenylphosphine)palladium (55 mg, 0.05 mmol) was added to the mixture above under $N_2$. The mixture was vigorously stirred at 100° C. for 3 h. After cooling down to room temperature, the crude was diluted by EtOAc (20 mL) and washed by water (5 mL×2) and brine (5 mL×2). The organic phase was concentrated and purified by column chromatography on silica gel to give the titled product I-2 as a solid (MS: $[M+1]^+$ 336.1).

The following compounds were prepared essentially by the same methods described above to prepare I-2.

| I-# | Starting Material | | Structure | MS $[M + 1]^+$ |
|---|---|---|---|---|
| I-5 | 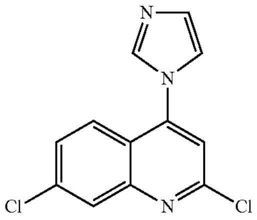 | 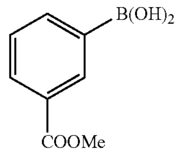 [SMILES: COC(=O)c1cccc(B(O)O)c1] | 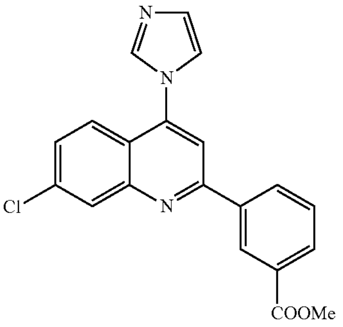 [SMILES: COC(=O)c1cccc(-c2cc(-n3ccnc3)c3ccc(Cl)cc3n2)c1] | 364.1 |
| I-12 | 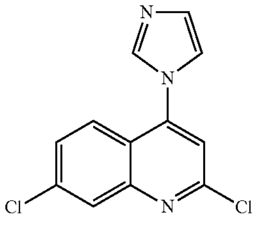 [SMILES: Clc1ccc2c(-n3ccnc3)cc(Cl)nc2c1] | 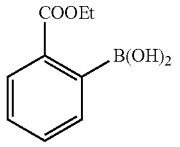 [SMILES: CCOC(=O)c1ccccc1B(O)O] | 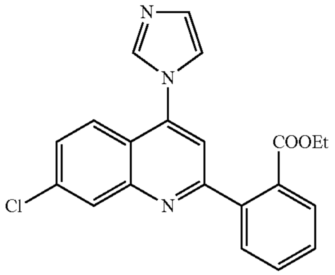 [SMILES: CCOC(=O)c1ccccc1-c1cc(-n2ccnc2)c2ccc(Cl)cc2n1] | 378.1 |
| I-3 | 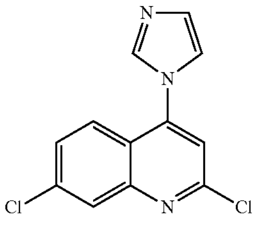 | 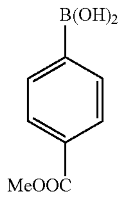 [SMILES: COC(=O)c1ccc(B(O)O)cc1] | 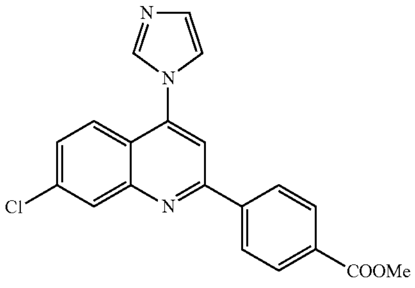 [SMILES: COC(=O)c1ccc(-c2cc(-n3ccnc3)c3ccc(Cl)cc3n2)cc1] | 364.1 |

-continued
| I-# | Starting Material | Structure | MS [M + 1]$^+$ |
| --- | --- | --- | --- |
| I-35 | 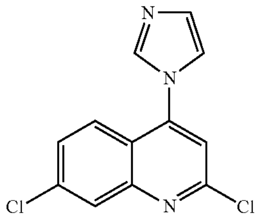 [SMILES: Clc1ccc2c(-n3ccnc3)cc(Cl)nc2c1] 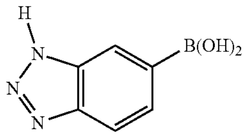 [SMILES: OB(O)c1ccc2nn[nH]c2c1] | 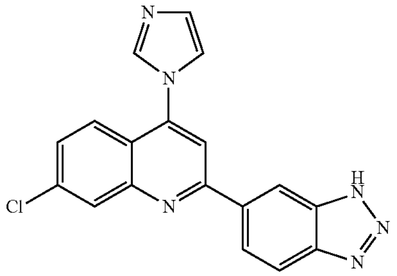 [SMILES: Clc1ccc2c(-n3ccnc3)cc(-c3ccc4nn[nH]c4c3)nc2c1] | 347 |
| I-36 | 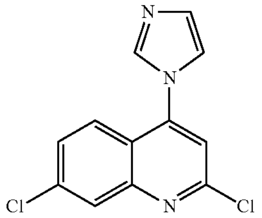 [SMILES: Clc1ccc2c(-n3ccnc3)cc(Cl)nc2c1] 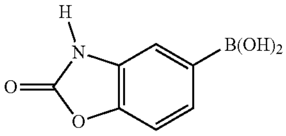 [SMILES: O=c1[nH]c2cc(B(O)O)ccc2o1] | 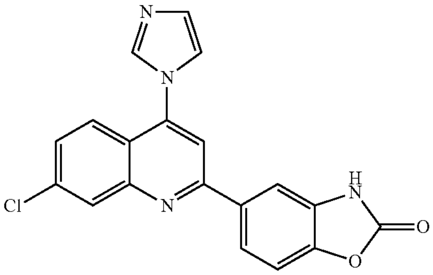 [SMILES: O=c1[nH]c2cc(-c3cc(-n4ccnc4)c4ccc(Cl)cc4n3)ccc2o1] | 363 |
| I-25 | 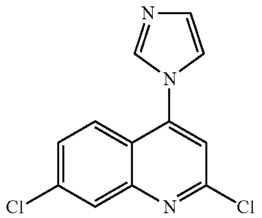 [SMILES: Clc1ccc2c(-n3ccnc3)cc(Cl)nc2c1] 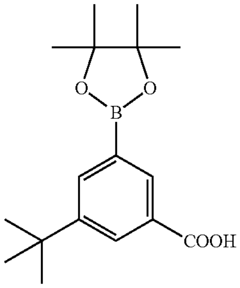 [SMILES: CC(C)(C)c1cc(B2OC(C)(C)C(C)(C)O2)cc(C(=O)O)c1] | 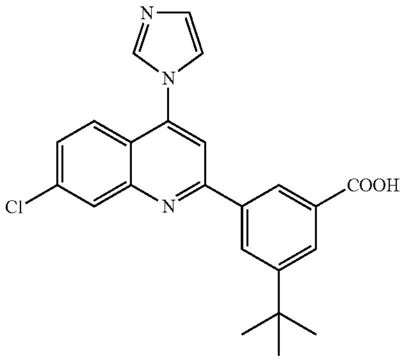 [SMILES: CC(C)(C)c1cc(C(=O)O)cc(-c2cc(-n3ccnc3)c3ccc(Cl)cc3n2)c1] | 406.1 |
| I-31 | 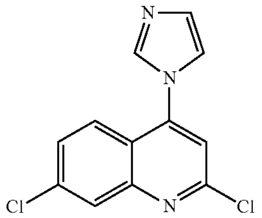 [SMILES: Clc1ccc2c(-n3ccnc3)cc(Cl)nc2c1] 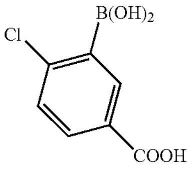 [SMILES: O=C(O)c1ccc(Cl)c(B(O)O)c1] | 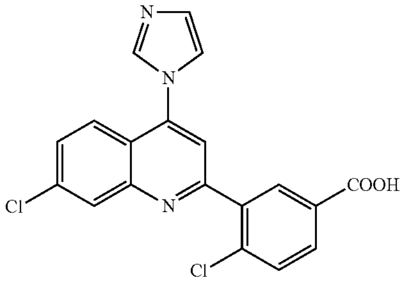 [SMILES: O=C(O)c1ccc(Cl)c(-c2cc(-n3ccnc3)c3ccc(Cl)cc3n2)c1] | 384.0 |
| I-18 | 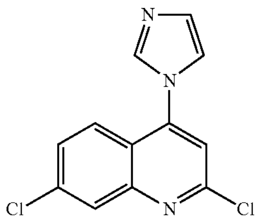 [SMILES: Clc1ccc2c(-n3ccnc3)cc(Cl)nc2c1] 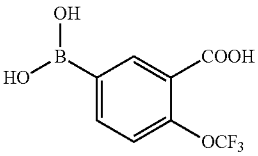 | 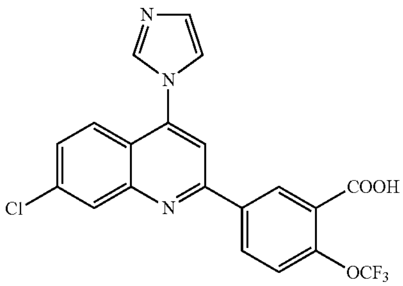 [SMILES: O=C(O)c1cc(-c2cc(-n3ccnc3)c3ccc(Cl)cc3n2)ccc1OC(F)(F)F] | 434 |

-continued
| I-# | Starting Material | | Structure | MS $[M + 1]^+$ |
|---|---|---|---|---|
| I-45 | 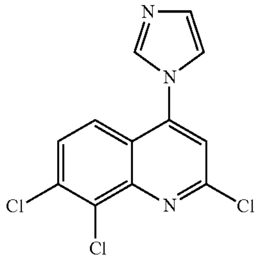 [SMILES: Clc1cc(-n2ccnc2)c2ccc(Cl)c(Cl)c2n1] | 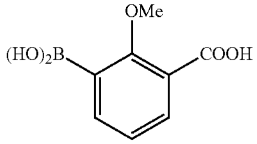 [SMILES: COc1c(B(O)O)cccc1C(=O)O] | 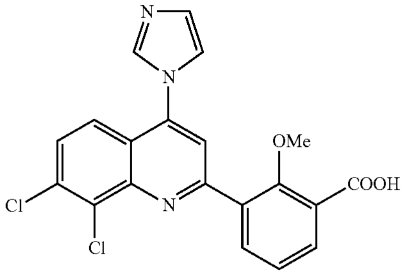 [SMILES: COc1c(C(=O)O)cccc1-c1cc(-n2ccnc2)c2ccc(Cl)c(Cl)c2n1] | 414 |
| I-40 | 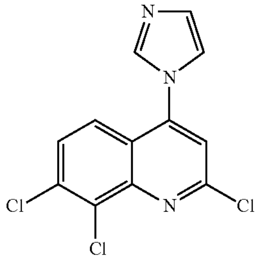 [SMILES: Clc1cc(-n2ccnc2)c2ccc(Cl)c(Cl)c2n1] | 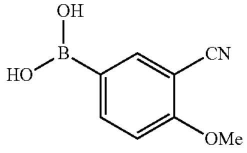 [SMILES: COc1ccc(B(O)O)cc1C#N] | 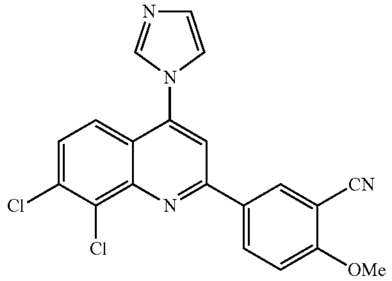 [SMILES: COc1ccc(-c2cc(-n3ccnc3)c3ccc(Cl)c(Cl)c3n2)cc1C#N] | 395 |
| I-46 | 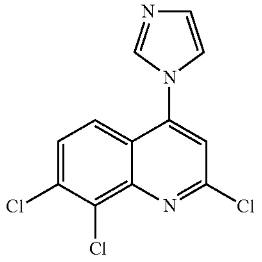 [SMILES: Clc1cc(-n2ccnc2)c2ccc(Cl)c(Cl)c2n1] | 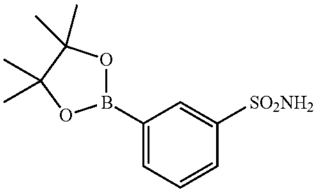 [SMILES: CC1(C)OB(c2cccc(S(N)(=O)=O)c2)OC1(C)C] | 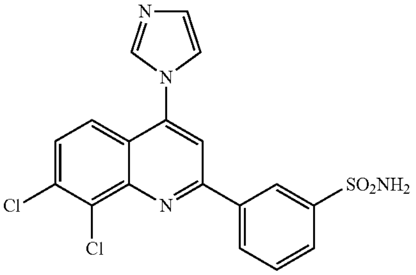 [SMILES: NS(=O)(=O)c1cccc(-c2cc(-n3ccnc3)c3ccc(Cl)c(Cl)c3n2)c1] | 419 |
| I-41 | 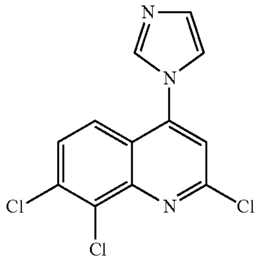 [SMILES: Clc1cc(-n2ccnc2)c2ccc(Cl)c(Cl)c2n1] | 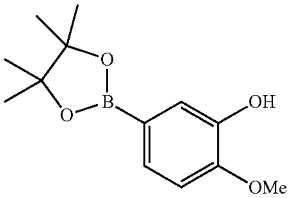 [SMILES: COc1ccc(B2OC(C)(C)C(C)(C)O2)cc1O] | 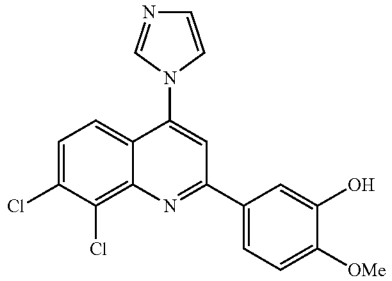 [SMILES: COc1ccc(-c2cc(-n3ccnc3)c3ccc(Cl)c(Cl)c3n2)cc1O] | 386 |
| I-43 | 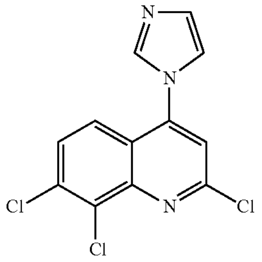 [SMILES: Clc1cc(-n2ccnc2)c2ccc(Cl)c(Cl)c2n1] | 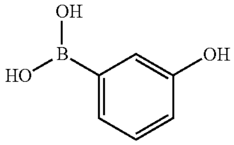 | 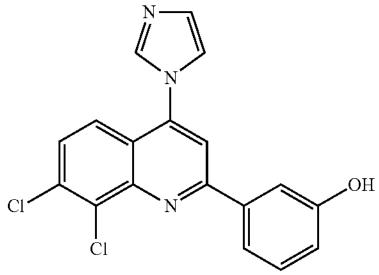 [SMILES: Oc1cccc(-c2cc(-n3ccnc3)c3ccc(Cl)c(Cl)c3n2)c1] | 356 |

-continued
| I-# | Starting Material | | Structure | MS [M + 1]+ |
|---|---|---|---|---|
| I-44 | 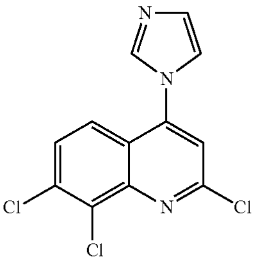 [SMILES: Clc1cc(-n2ccnc2)c2ccc(Cl)c(Cl)c2n1] | 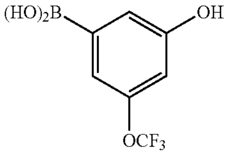 [SMILES: OB(O)c1cc(O)cc(OC(F)(F)F)c1] | 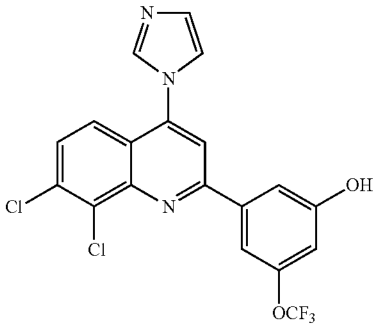 [SMILES: Oc1cc(OC(F)(F)F)cc(-c2cc(-n3ccnc3)c3ccc(Cl)c(Cl)c3n2)c1] | 440 |
| I-47 | 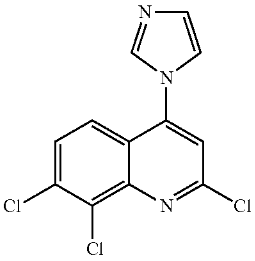 [SMILES: Clc1cc(-n2ccnc2)c2ccc(Cl)c(Cl)c2n1] | 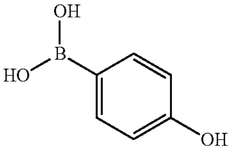 | 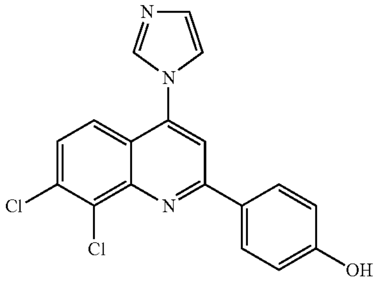 [SMILES: Oc1ccc(-c2cc(-n3ccnc3)c3ccc(Cl)c(Cl)c3n2)cc1] | 356 |
| I-20 | 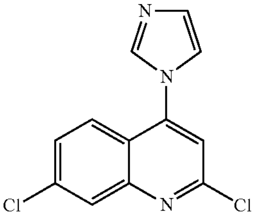 [SMILES: Clc1ccc2c(-n3ccnc3)cc(Cl)nc2c1] | 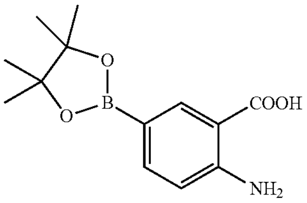 [SMILES: CC1(C)OB(c2ccc(N)c(C(=O)O)c2)OC1(C)C] | 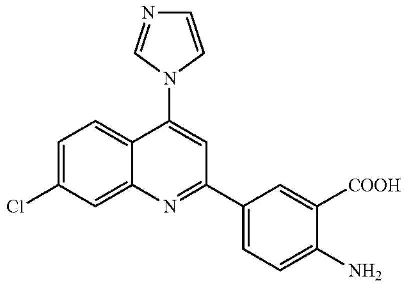 [SMILES: Nc1ccc(-c2cc(-n3ccnc3)c3ccc(Cl)cc3n2)cc1C(=O)O] | 365 |
| I-28 | 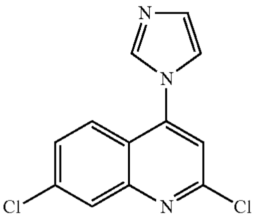 [SMILES: Clc1ccc2c(-n3ccnc3)cc(Cl)nc2c1] | 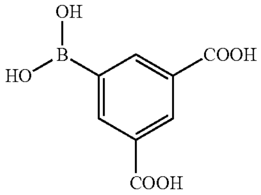 [SMILES: O=C(O)c1cc(B(O)O)cc(C(=O)O)c1] | 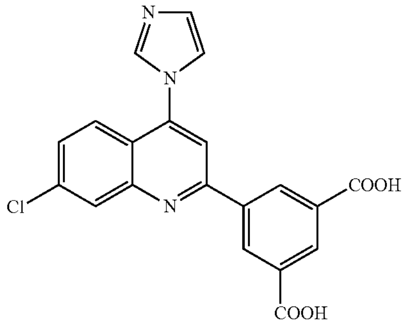 [SMILES: O=C(O)c1cc(C(=O)O)cc(-c2cc(-n3ccnc3)c3ccc(Cl)cc3n2)c1] | 394 |
| I-378 | 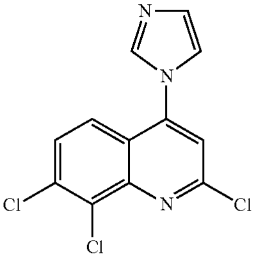 [SMILES: Clc1cc(-n2ccnc2)c2ccc(Cl)c(Cl)c2n1] | 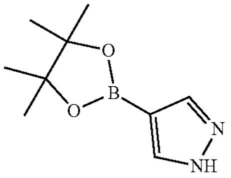 | 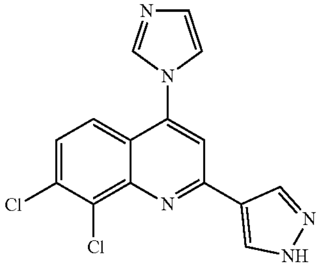 [SMILES: Clc1ccc2c(-n3ccnc3)cc(-c3cn[nH]c3)nc2c1Cl] | 330.0 |

Example 9: Synthesis of 7-chloro-4-(1H-imidazol-1-yl)-2-(4-methoxyphenyl)quinoline (I-6)

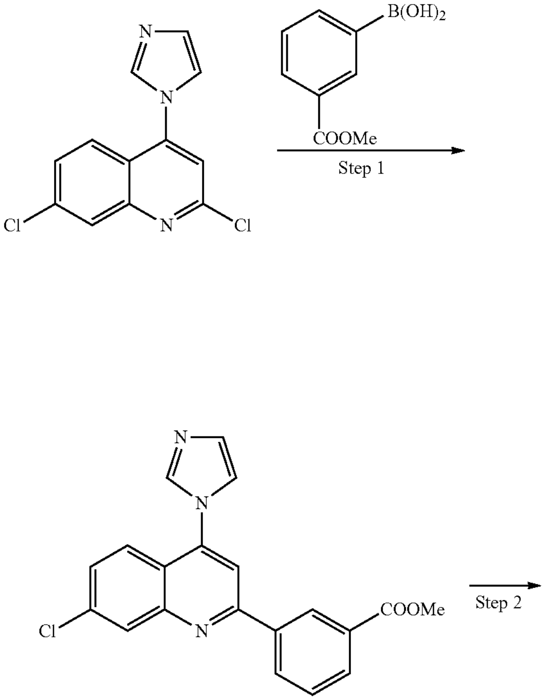

-continued

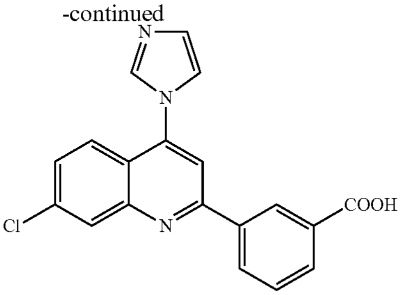

I-6

Step 1: Methyl 3-(7-chloro-4-(1H-imidazol-1-yl)quinolin-2-yl)benzoate. A mixture of 2,7-dichloro-4-(1H-imidazol-1-yl)quinoline (132 mg, 0.5 mmol), (3-(methoxycarbonyl)phenyl)boronic acid (136 mg, 0.75 mmol), $Na_2CO_3$ (265 mg, 2.5 mmol), 1,4-dioxane (4 mL) and $H_2O$ (1 mL) was purged by $N_2$ for 30 min. Tetrakis(triphenylphosphine) palladium (55 mg, 0.05 mmol) was added to the mixture above under $N_2$. The mixture was vigorously stirred at 100° C. for 2 h. After cooling down to room temperature, the crude was diluted by EtOAc (20 mL) and washed by water (5 mL×2) and brine (5 mL×2). The organic phase was concentrated and purified by column chromatography on silica gel to give the titled product as a solid (MS: $[M+1]^+$ 364.1).

Step 2: 3-(7-Chloro-4-(1H-imidazol-1-yl)quinolin-2-yl) benzoic acid. To a solution of methyl 3-(7-chloro-4-(1H-imidazol-1-yl)quinolin-2-yl)benzoate (80 mg, 0.22 mmol) in MeOH (4 mL) was added 10% NaOH (aq., 1 mL). The mixture was stirred at 50° C. for 1 h. After cooling down to room temperature, the crude was acidified by 1 N HCl (5 mL). The titled compound was collected as a solid by filtration (MS: $[M+1]^+$ 350.1).

The following compounds are prepared essentially by the same method described above to prepare I-6:

| I-# | Starting Material | Structure | MS $[M + 1]^+$ |
|---|---|---|---|
| I-13 | 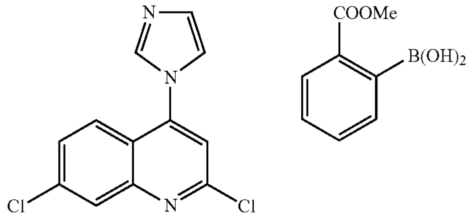 | 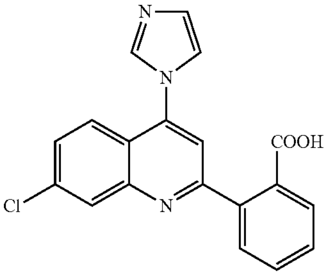 [SMILES: O=C(O)c1ccccc1-c1cc(-n2ccnc2)c2ccc(Cl)cc2n1] | 350.1 |
| I-4 | 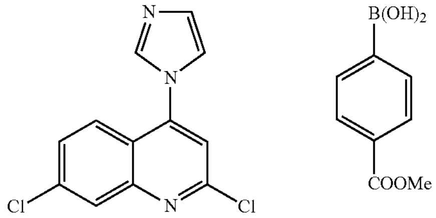 | 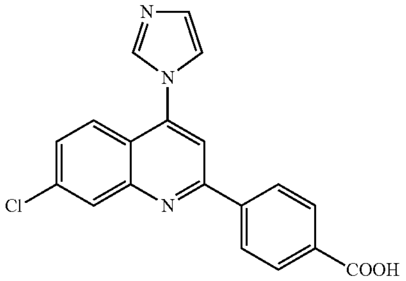 [SMILES: O=C(O)c1ccc(-c2cc(-n3ccnc3)c3ccc(Cl)cc3n2)cc1] | 350.1 |

-continued
| I-# | Starting Material | Structure | MS [M + 1]$^+$ |
| --- | --- | --- | --- |
| I-15 | 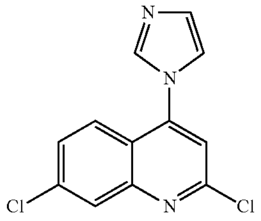 [SMILES: Clc1ccc2c(-n3ccnc3)cc(Cl)nc2c1] 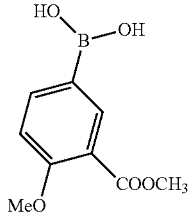 [SMILES: COC(=O)c1cc(B(O)O)ccc1OC] | 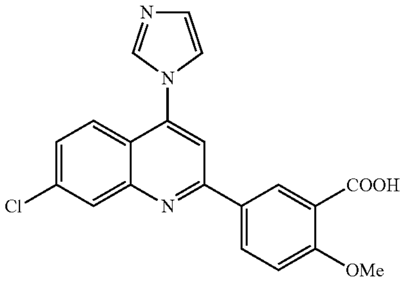 [SMILES: COc1ccc(-c2cc(-n3ccnc3)c3ccc(Cl)cc3n2)cc1C(=O)O] | 380 |
| I-30 | 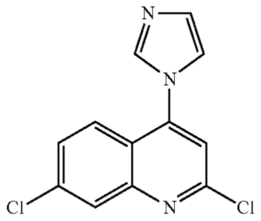 [SMILES: Clc1ccc2c(-n3ccnc3)cc(Cl)nc2c1] 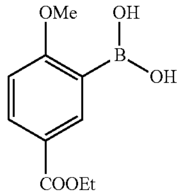 [SMILES: CCOC(=O)c1ccc(OC)c(B(O)O)c1] | 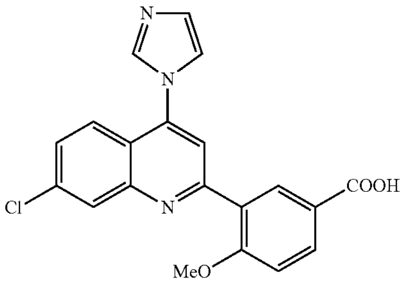 [SMILES: COc1ccc(C(=O)O)cc1-c1cc(-n2ccnc2)c2ccc(Cl)cc2n1] | 380 |
| I-55 | 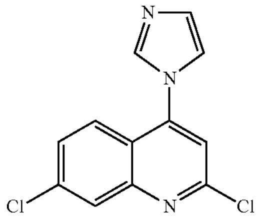 [SMILES: Clc1ccc2c(-n3ccnc3)cc(Cl)nc2c1] 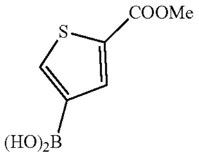 [SMILES: COC(=O)c1cc(B(O)O)cs1] | 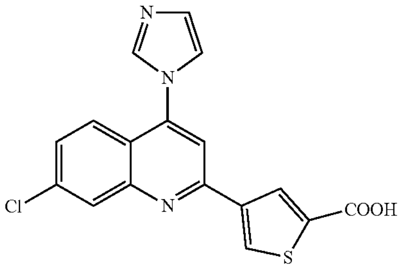 [SMILES: O=C(O)c1cc(-c2cc(-n3ccnc3)c3ccc(Cl)cc3n2)cs1] | 356 |
| I-37 | 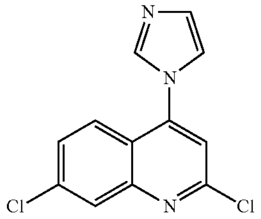 [SMILES: Clc1ccc2c(-n3ccnc3)cc(Cl)nc2c1] 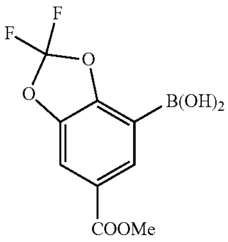 [SMILES: COC(=O)c1cc2c(c(B(O)O)c1)OC(F)(F)O2] | 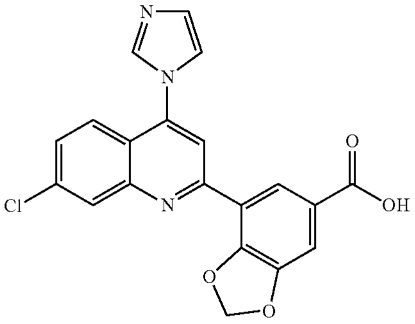 byproduct | 394.0 |
| I-38 | | 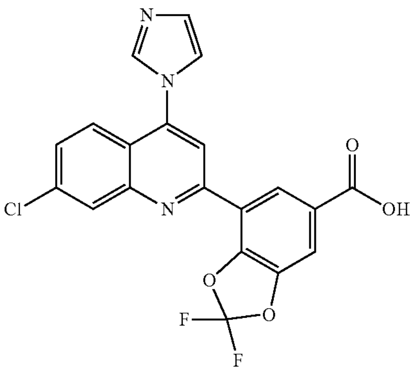 [SMILES: O=C(O)c1cc2c(c(-c3cc(-n4ccnc4)c4ccc(Cl)cc4n3)c1)OC(F)(F)O2] | 430.0 |

-continued
| I-# | Starting Material | Structure | MS [M + 1]$^+$ |
|---|---|---|---|
| I-27 | 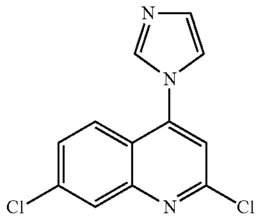 [SMILES: Clc1ccc2c(-n3ccnc3)cc(Cl)nc2c1] 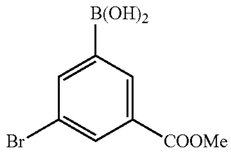 [SMILES: COC(=O)c1cc(Br)cc(B(O)O)c1] | 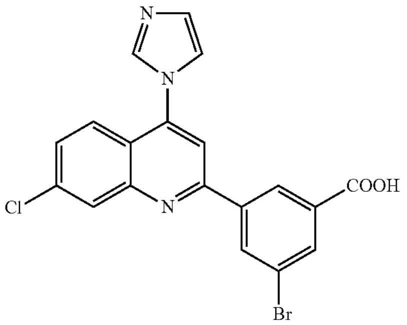 [SMILES: O=C(O)c1cc(Br)cc(-c2cc(-n3ccnc3)c3ccc(Cl)cc3n2)c1] | 428.0 |
| I-17 | 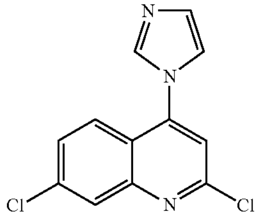 [SMILES: Clc1ccc2c(-n3ccnc3)cc(Cl)nc2c1] 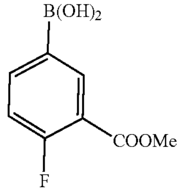 [SMILES: COC(=O)c1cc(B(O)O)ccc1F] | 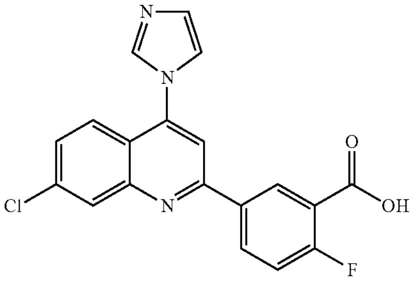 [SMILES: O=C(O)c1cc(-c2cc(-n3ccnc3)c3ccc(Cl)cc3n2)ccc1F] | 368.0 |
| I-14 | 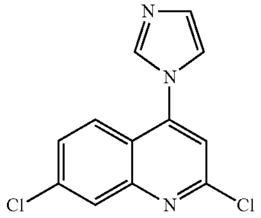 [SMILES: Clc1ccc2c(-n3ccnc3)cc(Cl)nc2c1] 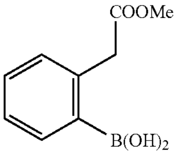 [SMILES: COC(=O)Cc1ccccc1B(O)O] | 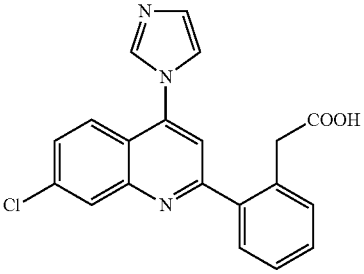 [SMILES: O=C(O)Cc1ccccc1-c1cc(-n2ccnc2)c2ccc(Cl)cc2n1] | 364.1 |
| I-9 | 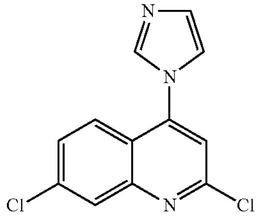 [SMILES: Clc1ccc2c(-n3ccnc3)cc(Cl)nc2c1] 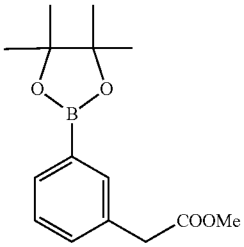 [SMILES: COC(=O)Cc1cccc(B2OC(C)(C)C(C)(C)O2)c1] | 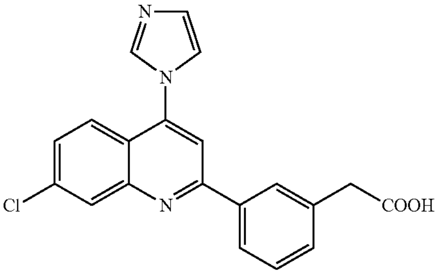 [SMILES: O=C(O)Cc1cccc(-c2cc(-n3ccnc3)c3ccc(Cl)cc3n2)c1] | 364.1 |
| I-32 | 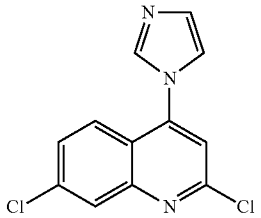 [SMILES: Clc1ccc2c(-n3ccnc3)cc(Cl)nc2c1] 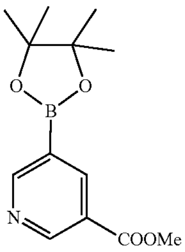 [SMILES: COC(=O)c1cncc(B2OC(C)(C)C(C)(C)O2)c1] | 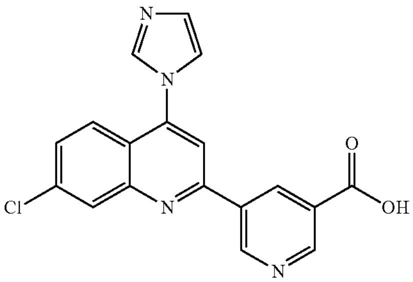 [SMILES: O=C(O)c1cncc(-c2cc(-n3ccnc3)c3ccc(Cl)cc3n2)c1] | 351.0 |

-continued

| I-# | Starting Material | | Structure | MS [M + 1]$^+$ |
|---|---|---|---|---|
| I-33 | 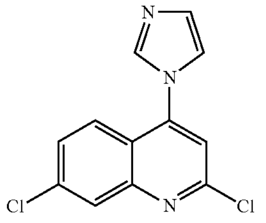 [SMILES: Clc1ccc2c(-n3ccnc3)cc(Cl)nc2c1] | 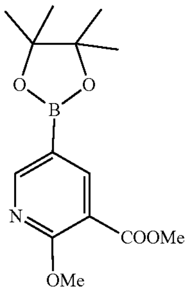 [SMILES: COC(=O)c1cc(B2OC(C)(C)C(C)(C)O2)cnc1OC] | 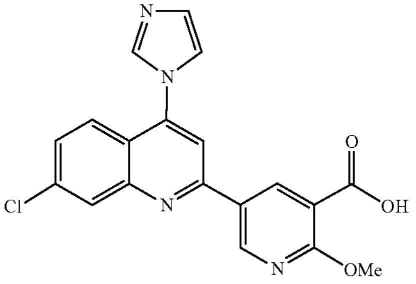 [SMILES: COc1ncc(-c2cc(-n3ccnc3)c3ccc(Cl)cc3n2)cc1C(=O)O] | 381.1 |

Example 10: Synthesis of 3-(7-chloro-4-(1H-imidazol-1-yl)quinolin-2-yl)benzamide (I-7)

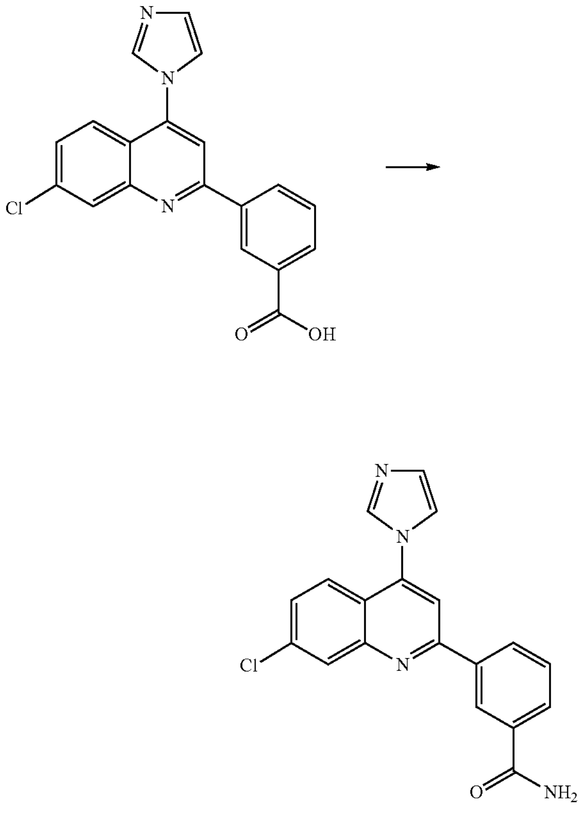

I-7

To a solution of 3-(7-chloro-4-(1H-imidazol-1-yl)quinolin-2-yl)benzoic acid (25 mg, 0.07 mmol) in THF (1 mL) was added $SOCl_2$ (0.015 mL, 0.2 mmol). After 1 h, $NH_4OH$ (aq., 0.5 mL) was added. After 3 h, the solvent was removed by evaporation to give a crude. The crude was purified directly by column chromatography on silica gel to give the titled product as a solid (MS: [M+1]$^+$ 349.1).

Example 11: Synthesis of 3-(7-chloro-4-(1H-imidazol-1-yl)quinolin-2-yl)-5-methoxybenzoic acid (I-24) and 3-(7-chloro-4-(1H-imidazol-1-yl)quinolin-2-yl)-5-hydroxybenzoic acid (I-26)

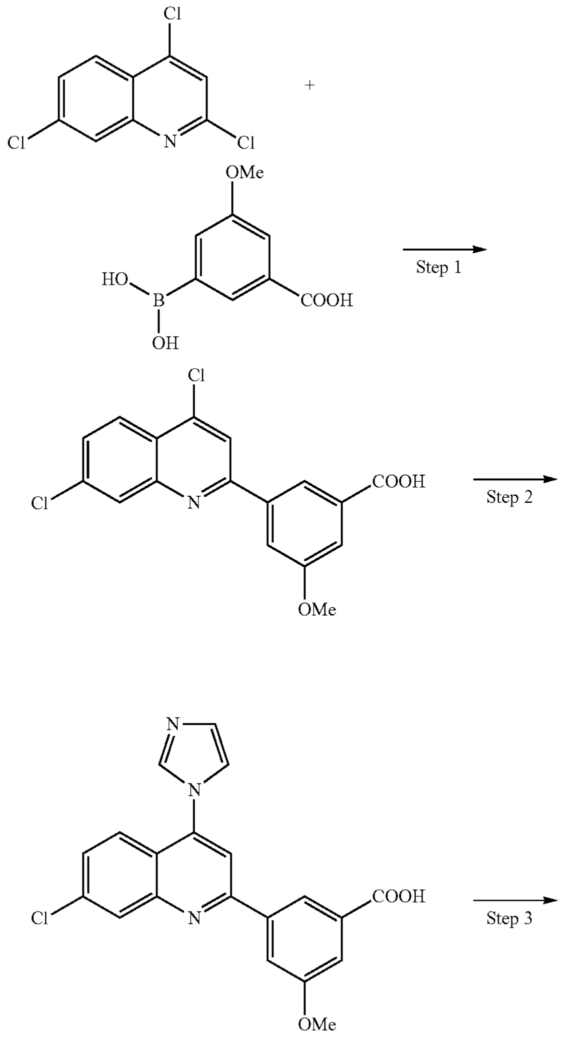

I-24

-continued

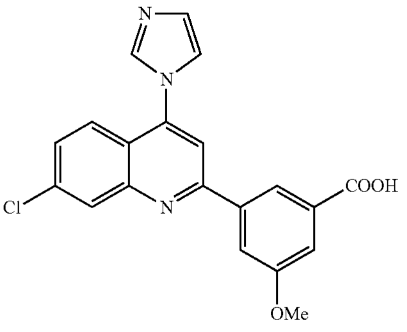

I-26

Step 1: 3-(4,7-dichloroquinolin-2-yl)-5-methoxybenzoic acid was prepared essentially by the same methods described above to prepare I-2.

Step 2: 3-(7-chloro-4-(1H-imidazol-1-yl)quinolin-2-yl)-5-methoxybenzoic acid. To a vial were added 3-(4,7-dichloroquinolin-2-yl)-5-methoxybenzoic acid (50 mg, 0.144 mmol), imidazole (49 mg, 0.718 mmol), $Cs_2CO_3$ (70 mg, 0.216 mmol) and DMF (1.0 mL). The resulting reaction mixture was stirred at 110° C. overnight. At room temperature the reaction mixture was diluted by $H_2O$ (4 mL) and acidified by HCl (1 N) to pH about 3. A lot of white solid precipitated, centrifuged and washed by $H_2O$ (2×4 mL). The residue was dried in vacuo to afford the titled compound as white solid (30 mg). MS: $[M+1]^+$ 380.

Step 3: 3-(7-chloro-4-(1H-imidazol-1-yl)quinolin-2-yl)-5-hydroxybenzoic acid. To a vial were added 3-(7-chloro-4-(1H-imidazol-1-yl)quinolin-2-yl)-5-methoxybenzoic acid (7.9 mg, 0.0208 mmol), NaI (20 mg, 0.133 mmol) and HBr in HOAc (33%, 1.0 mL). The resulting mixture was stirred at 50° C. overnight. The mixture was cooled to room temperature and diluted by $H_2O$ (10 mL), centrifuged, and washed with $H_2O$ (4 mL). The residue was dried under high vacuum to afford the title product as off-white solid (18 mg) (MS: $[M+1]^+$ 366).

Example 12: Synthesis of 5-(7-chloro-4-(1H-imidazol-1-yl)quinolin-2-yl)-2-hydroxybenzoic acid (I-16) and 5-(7-chloro-4-(1H-imidazol-1-yl)quinolin-2-yl)-2-ethoxybenzoic acid (I-19)

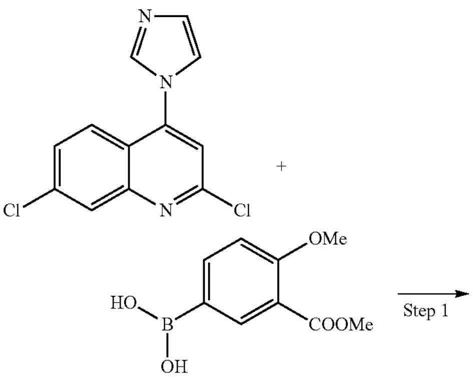

-continued

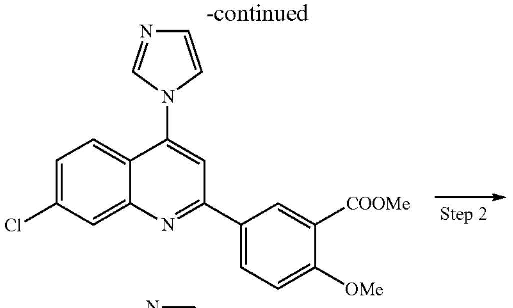

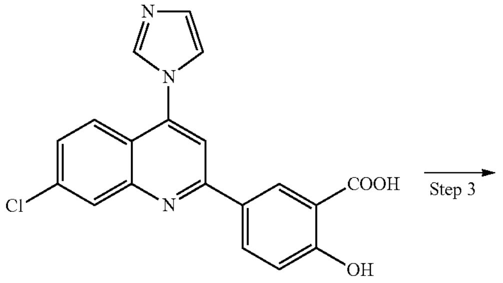

I-16

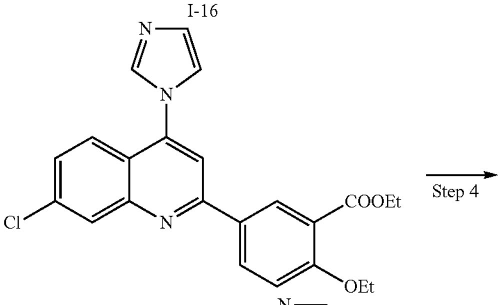

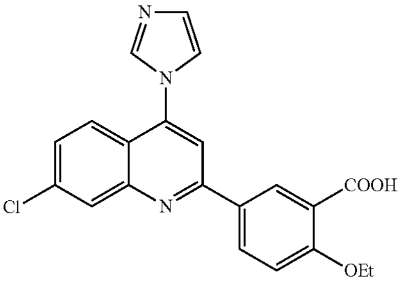

I-19

Step 1: Methyl 5-(7-chloro-4-(1H-imidazol-1-yl)quinolin-2-yl)-2-methoxybenzoate was prepared according to the procedure above to prepare compound I-2.

Step 2: 5-(7-Chloro-4-(1H-imidazol-1-yl)quinolin-2-yl)-2-hydroxybenzoic acid (I-16) was prepared according to the procedure above to prepare compound I-26. (MS: $[M+1]^+$ 366).

Step 3: Ethyl 5-(7-chloro-4-(1H-imidazol-1-yl)quinolin-2-yl)-2-ethoxybenzoate. To a vial were added 5-(7-chloro-4-(1H-imidazol-1-yl)quinolin-2-yl)-2-hydroxybenzoic acid (14 mg, 0.0383 mmol), ethyl iodide (22 µl, 0.274 mmol), $Cs_2CO_3$ (62 mg, 0.191 mmol) and DMF (1.0 mL). The resulting reaction mixture was stirred at room temperature overnight. The mixture was diluted with ethyl acetate (40 mL), washed by $H_2O$ (4×20 mL) and brine (15 mL). After concentration, the crude was used in next step.

Step 4: 5-(7-Chloro-4-(1H-imidazol-1-yl)quinolin-2-yl)-2-ethoxybenzoic acid. To the crude product above were added MeOH (0.6 mL), THF (0.4 mL) and a solution of NaOH in $H_2O$ (7.66 mg/0.2 mL). The resulting reaction mixture was stirred at room temperature overnight. Then the mixture was diluted by $H_2O$ (3 mL) and acidified by HOAc to pH 4. The cloudy mixture was centrifuged and the residue was washed by $H_2O$ (2×1.5 mL), dried over high vacuum to afford the title product as off-white solid (6 mg) (MS: $[M+1]^+$ 394).

Example 13: Synthesis of 3-amino-5-(7-chloro-4-(1H-imidazol-1-yl)quinolin-2-yl)benzoic acid (I-22)

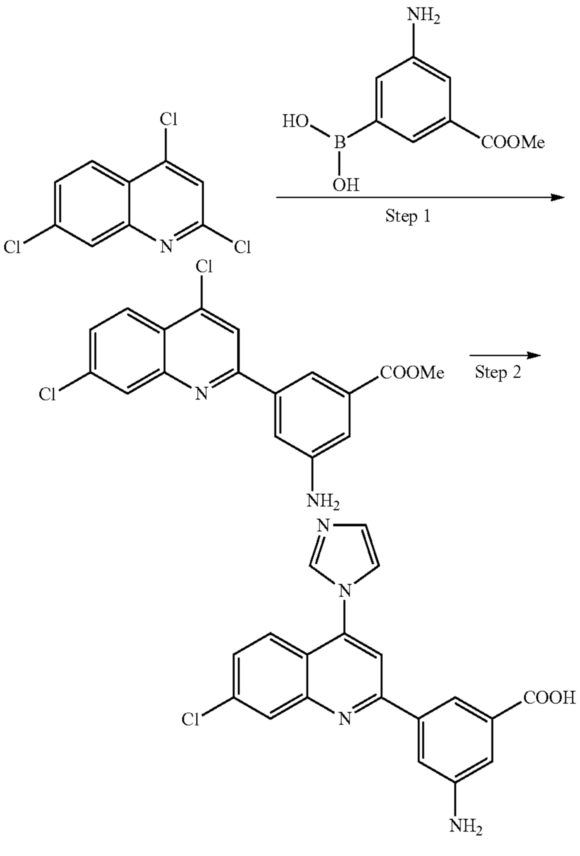

I-22

Step 1: methyl 3-amino-5-(4,7-dichloroquinolin-2-yl) benzoate was prepared according to the procedure above to prepare compound I-2.

Step 2: 3-amino-5-(7-chloro-4-(1H-imidazol-1-yl)quinolin-2-yl)benzoic acid was prepared according to the procedure above to prepare compound I-24 (MS: $[M+1]^+$ 365).

Example 14: Synthesis of 4-(7-chloro-4-(1H-imidazol-1-yl)quinolin-2-yl)-1H-pyrrole-2-carboxylic acid (I-56)

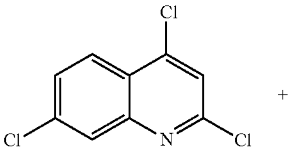

-continued

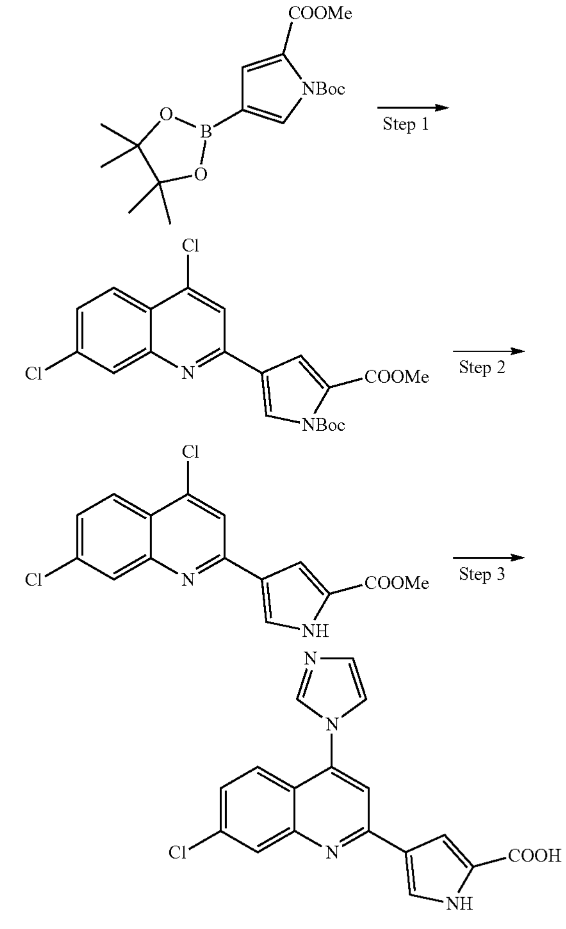

I-56

Step 1: 1-(tert-Butyl) 2-methyl 4-(4,7-dichloroquinolin-2-yl)-1H-pyrrole-1,2-dicarboxylate was prepared according to the procedure described above to prepare compound I-2.

Step 2: Methyl 4-(4,7-dichloroquinolin-2-yl)-1H-pyrrole-2-carboxylate was prepared according to the procedure described above to prepare compound I-172 (step 3).

Step 3: 4-(7-chloro-4-(1H-imidazol-1-yl)quinolin-2-yl)-1H-pyrrole-2-carboxylic acid was prepared according to the procedure described above to prepare compound I-24 (step 2). (MS: $[M+1]^+$339).

Example 15: Synthesis of 3-(7-Chloro-4-(1H-pyrazol-5-yl)quinolin-2-yl)benzoic acid (I-74)

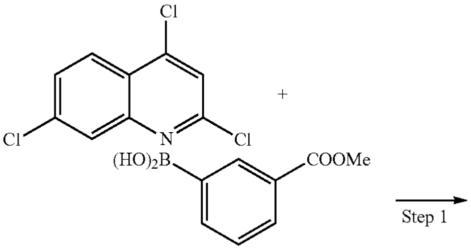

-continued

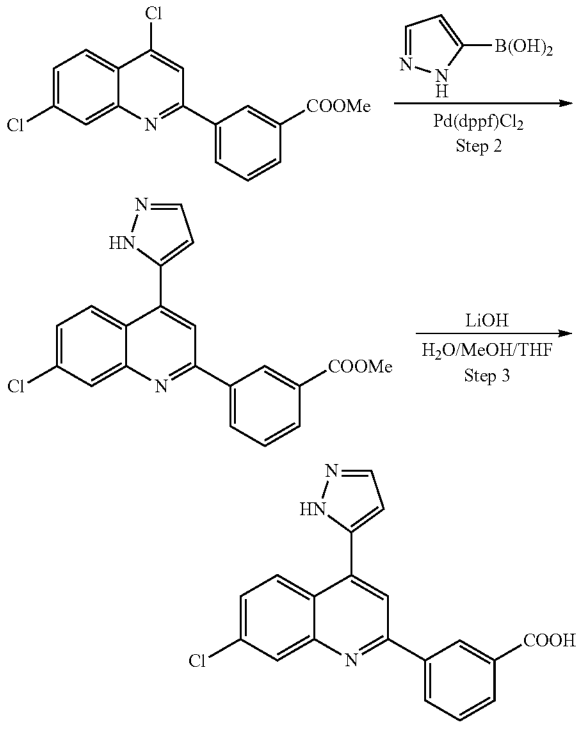

I-74

Step 1: Methyl 3-(4,7-dichloroquinolin-2-yl)benzoate was prepared according to the procedure described above to prepare compound I-2.

Step 2: Methyl 3-(7-chloro-4-(1H-pyrazol-5-yl)quinolin-2-yl)benzoate was prepared according to the procedure described above to prepare compound I-2.

Step 3: 3-(7-Chloro-4-(1H-pyrazol-5-yl)quinolin-2-yl) benzoic acid was prepared according to the procedure described above to prepare compound I-24 (step 2). (MS: $[M+1]^+$ 350).

Example 16: Synthesis of 3-(7-chloro-4-(1H-imidazol-1-yl)quinolin-2-yl)-5-(2-hydroxyacetamido)benzoic acid (I-23)

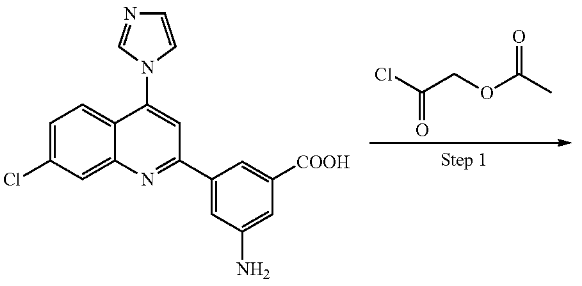

I-22

-continued

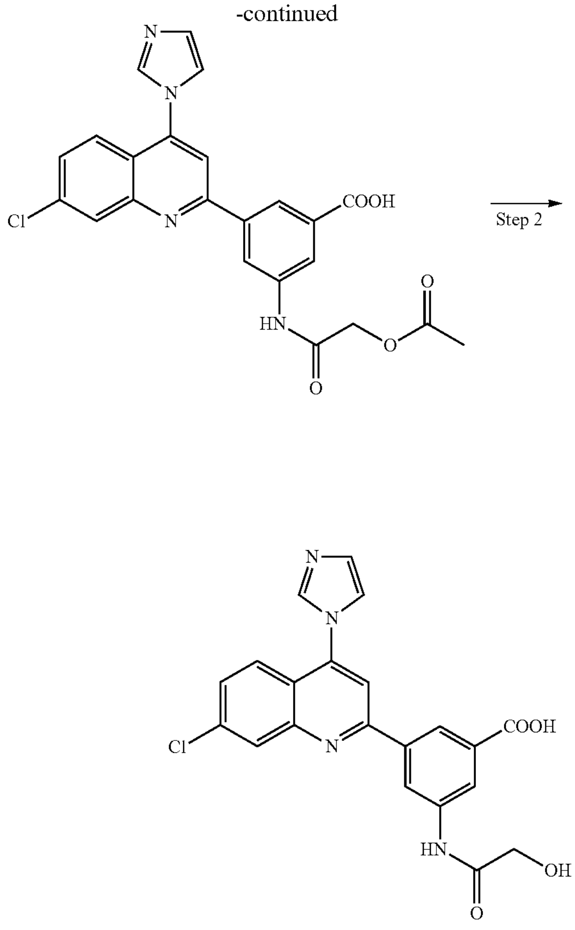

I-23

Step 1: 3-(2-Acetoxyacetamido)-5-(7-chloro-4-(1H-imidazol-1-yl)quinolin-2-yl)benzoic acid. To a vial were added 3-amino-5-(7-chloro-4-(1H-imidazol-1-yl)quinolin-2-yl) benzoic acid (9.3 mg, 0.0255 mmol), DCM (0.5 mL) and TEA (8.9 µl, 0.0637 mmol). A solution of 2-chloro-2-oxoethyl acetate in DCM (4.18 mg/0.1 mL, 0.0306 mmol) was added and the resulting reaction mixture was stirred at room temperature for 1 h. $H_2O$ (0.5 mL) was added to quench the reaction. Most of DCM was removed under reduced pressure and the crude was used in next step.

Step 2: 3-(7-Chloro-4-(1H-imidazol-1-yl)quinolin-2-yl)-5-(2-hydroxyacetamido)benzoic acid. To the crude product above (3-(2-acetoxyacetamido)-5-(7-chloro-4-(1H-imidazol-1-yl)quinolin-2-yl)benzoic acid) were added MeOH (0.5 mL), THF (1.0 mL) and a solution of LiOH—$H_2O$ in $H_2O$ (5.36 mg/0.2 mL, 0.127 mmol). The resulting reaction mixture was stirred at room temperature for 16 h. All volatiles were removed and the mixture was diluted by $H_2O$ (2.5 mL). After centrifugation, the residue was washed by $H_2O$ (2×3 mL), dried under high vacuum to afford the title product as white solid (MS: $[M+1]^+$ 423).

Example 17: Synthesis of 5-(7-chloro-4-(1H-imidazol-1-yl)quinolin-2-yl)-2-(2-hydroxyethoxy)benzoic acid (I-21)

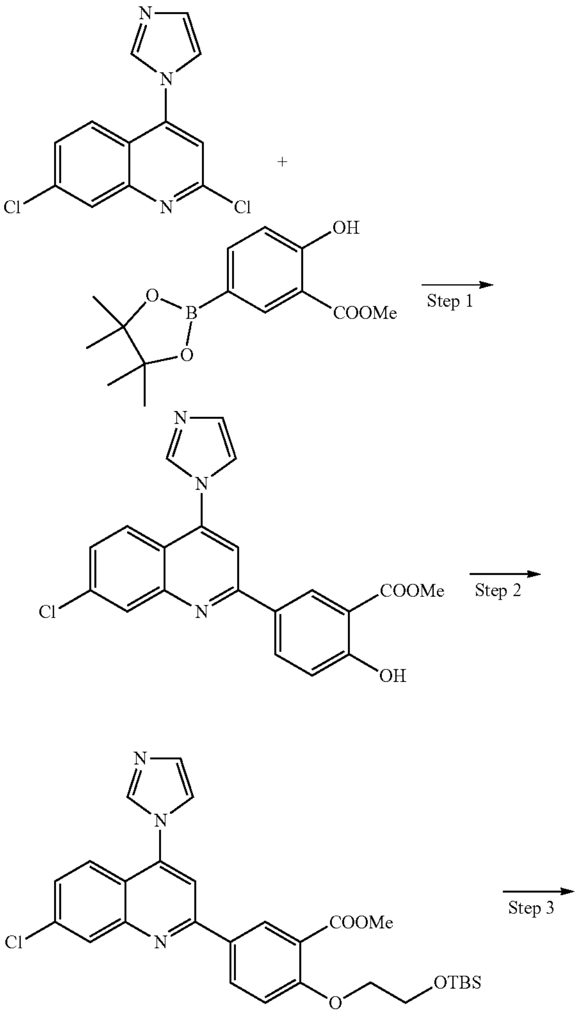

-continued

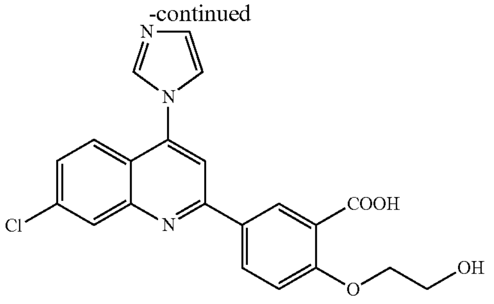

I-21

Step 1: Methyl 5-(7-chloro-4-(1H-imidazol-1-yl)quinolin-2-yl)-2-hydroxybenzoate was prepared according to the procedure described above to prepare compound I-2.

Step 2: Methyl 2-(2-((tert-butyldimethylsilyl)oxy)ethoxy)-5-(7-chloro-4-(1H-imidazol-1-yl)quinolin-2-yl)benzoate. To a vial were added methyl 5-(7-chloro-4-(1H-imidazol-1-yl)quinolin-2-yl)-2-hydroxybenzoate (10 mg, 0.0263 mmol), $Cs_2CO_3$ (10.3 mg, 0.0316 mmol) and a solution of (2-bromoethoxy)(tert-butyl)dimethylsilane in DMF (6.8 μl/0.5 mL, 0.0316 mmol). The resulting reaction mixture was stirred at room temperature for 1 h. Then the mixture was diluted by ethyl acetate (30 mL), washed by $H_2O$ (4×10 mL) and brine (10 mL), dried over $Na_2SO_4$. After concentration, the crude was used in next step.

Step 3: 5-(7-Chloro-4-(1H-imidazol-1-yl)quinolin-2-yl)-2-(2-hydroxyethoxy)benzoic acid. To the crude step 2 were added MeOH (0.5 mL), THF (1.0 mL) and a solution of LiOH—$H_2O$ in $H_2O$ (5.5 mg/0.5 mL, 0.132 mmol). The resulting reaction mixture was stirred at room temperature for 48 h. The mixture was acidized by acetic acid to pH 5. Most of volatiles were removed and the residue was diluted with $H_2O$ (1.5 mL), centrifuged, washed by $H_2O$ (2×1.5 mL), dried under high vacuum to afford the title product as off-white solid (MS: $[M+1]^+$ 410).

The following compounds are prepared essentially by the same method described above to prepare I-21.

| I-# | Starting Material | Structure | MS $[M + 1]^+$ |
|---|---|---|---|
| I-29 | 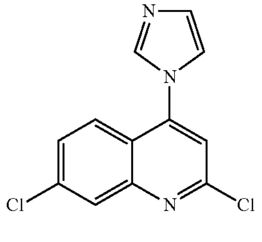 [SMILES: Clc1ccc2c(-n3ccnc3)cc(Cl)nc2c1] 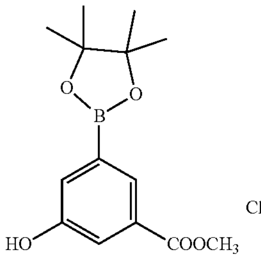 | 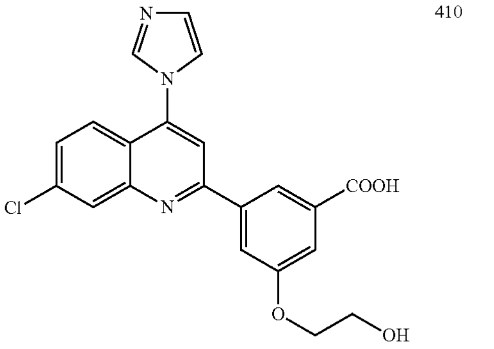 | 410 |

Example 18: Synthesis of 5-(7,8-dichloro-4-(1H-imidazol-1-yl)quinolin-2-yl)-2-hydroxybenzoic acid (I-42)

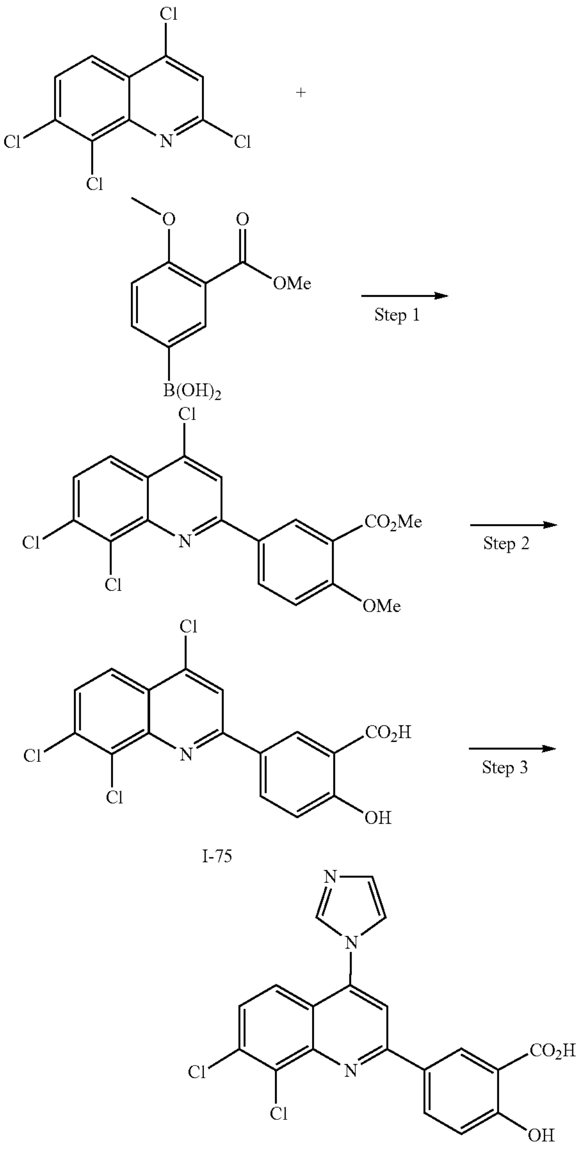

I-75

I-42

Step 1: Methyl 2-methoxy-5-(4,7,8-trichloroquinolin-2-yl)benzoate. To a suspension of 2,4,7,8-tetrachloroquinoline (200 mg, 0.75 mmol) with (4-methoxy-3-(methoxycarbonyl)phenyl) boronic acid (205.3 mg, 0.98 mmol) and $Na_2CO_3$ (178 mg, 1.68 mmol) in dioxane (8.0 mL) and water (2.0 mL) was added $Pd(PPh_3)_4$ (79.2 mg). The resultant mixture was vacuumed and purged with $N_2$ for three cycles, then stirred and heated at 80° C. over two hours. After cooling to room temperature, the reaction mixture was dissolved in DCM (50 mL) and washed with water and brine. The resultant organic layer was separated and dried over anhydrous $Na_2SO_4$. A silica gel flash column chromatography eluting with DCM/Hexane afforded the desired colorless product (MS: $[M+1]^+$ 396).

Step 2: 2-Hydroxy-5-(4,7,8-trichloroquinolin-2-yl)benzoic acid (I-75). Methyl 2-methoxy-5-(4,7,8-trichloroquinolin-2-yl) benzoate (17 mg) in DCM (1.5 mL) was treated with 1M $BBr_3$ in DCM (0.1 mL) at room temperature over 8 hours. The resulting mixture was diluted with EtOAc (25 mL), washed with water (10 mL) and dried over $Na_2SO_4$. Concentration under vacuum afforded the desired light brown solid (11 mg), 2-hydroxy-5-(4,7,8-trichloroquinolin-2-yl) benzoic acid (MS: $[M+1]^+$ 368).

Step 3: 5-(7,8-dichloro-4-(1H-imidazol-1-yl)quinolin-2-yl)-2-hydroxybenzoic acid. To a solution of 2-hydroxy-5-(4,7,8-trichloroquinolin-2-yl) benzoic acid (11 mg) in DMF (0.5 mL) was added imidazole (55 mg) and $K_2CO_3$ (50 mg). The resultant solution was stirred and heated at 120° C. over 5 hours until the starting material was completely consumed. The reaction mixture was diluted with water (3 mL) and treated with Dowex resin until the pH to 3. The resultant colorless solid was isolated by filtration and washed with water (3 mL). After drying under vacuum, the desired product was obtained (MS: $[M+1]^+$ 400).

Example 19: Synthesis of 3-(4-(1H-imidazol-1-yl)-7-(trifluoromethyl)quinolin-2-yl)benzoic acid (I-49)

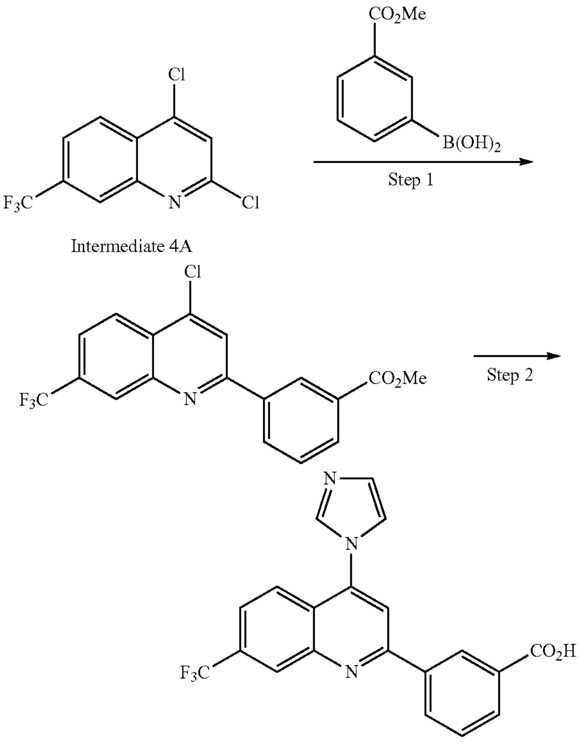

Intermediate 4A

I-49

Step 1: Methyl 3-(4-chloro-7-(trifluoromethyl)quinolin-2-yl)benzoate. To a mixture of 2,4-dichloro-7-(trifluoromethyl)quinoline (217 mg, 0.82 mmol) with (3-(methoxycarbonyl)phenyl)boronic acid (190.9 mg, 1.06 mmol) in dioxane (7 mL) and water (3 mL) were added $Na_2CO_3$ (191 mg, 1.804 mmol) and $Pd(PPh_3)_4$ (95 mg, 0.082 mmol). The resultant mixture was placed under vacuum and purged with nitrogen repeatedly three times, then was stirred and heated at 90° C. over 3 hours. The reaction mixture was diluted with water (25 mL) and extracted with EtOAc (20 mL). After isolation of the organic layer and a column chromatography eluting with a gradient of DCM/Hexane from 0 to 60%), the desired product (254 mg) methyl 3-(4-chloro-7-(trifluoromethyl)quinolin-2-yl)benzoate (MS: $[M+1]^+366$).

Step 2: 3-(4-(1H-Imidazol-1-yl)-7-(trifluoromethyl)quinolin-2-yl)benzoic acid. A mixture of methyl 3-(4-chloro-7-(trifluoromethyl)quinolin-2-yl)benzoate (42 mg, 0.12 mmol), imidazole (40 mg) and $Cs_2CO_3$ was added DMF (0.6 mL). The suspended solution was stirred and heated at 100° C. over 6 hours. The reaction mixture was diluted with water (2 mL) and acidified with HOAc to pH 3 to precipitate the product. The product was isolated by centrifuge and rinsed with water and 50% acetonitrile/water. The wet solid was dried in vacuo to afford the title compound (30 mg) ($[M+1]^+$ : 384).

Example 20: Synthesis of 3-(7-Bromo-4-(1H-imidazol-1-yl)-8-methoxyquinolin-2-yl)benzoic acid (I-48)

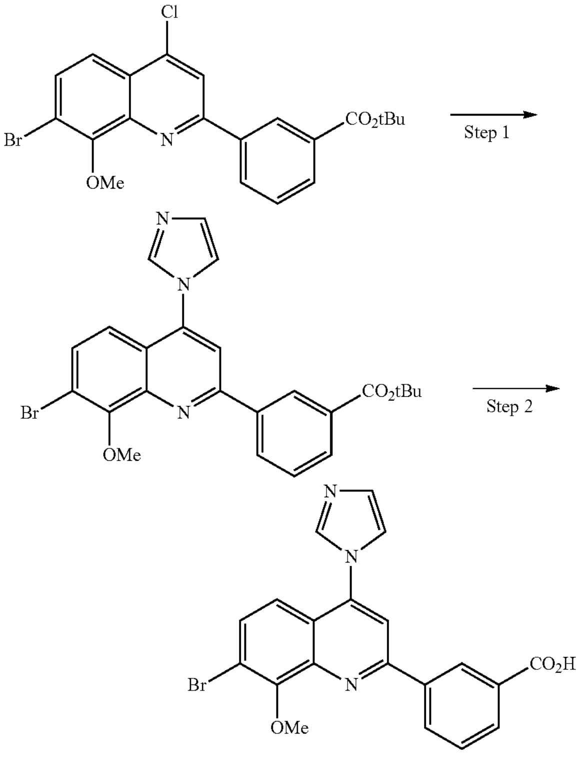

I-48

Following step 1 in the preparation of I-49, tert-butyl 3-(7-bromo-4-chloro-8-methoxyquinolin-2-yl) benzoate was prepared from Intermediate 17.

Step 1: tert-Butyl 3-(7-bromo-4-(1H-imidazol-1-yl)-8-methoxyquinolin-2-yl)benzoate. To a mixture of tert-butyl 3-(7-bromo-4-chloro-8-methoxyquinolin-2-yl) benzoate (125 mg) and $Cs_2CO_3$ (136.8 mg) in DMF (2 mL) was added imidazole (96 mg). The suspended solution was stirred and heated at 130° C. over 2 h. Aqueous work-up with EtOAc and a column chromatography eluting with EtOAc/Hexane afforded the desired product tert-butyl 3-(7-bromo-4-(1H-imidazol-1-yl)-8-methoxyquinolin-2-yl) benzoate (120 mg) (MS: $[M+1]^+$ 480).

Step 2: 3-(7-Bromo-4-(1H-imidazol-1-yl)-8-methoxyquinolin-2-yl)benzoic acid. To a solution of tert-butyl 3-(7-bromo-4-(1H-imidazol-1-yl)-8-methoxyquinolin-2-yl)benzoate (65 mg) in DCM (0.2 mL) and MeOH (0.2 mL) was added TFA (0.4 mL). The resultant solution was stirred over 5 h and concentrated to dryness. The resultant oily residue was suspended in water (0.5 mL) and lyophilized to afford the title compound 3-(7-bromo-4-(1H-imidazol-1-yl)-8-methoxyquinolin-2-yl) benzoic acid (60 mg) as light brown powder (MS: $[M+1]^+$ 424).

Example 21: Synthesis of 7-bromo-4-(1H-imidazol-1-yl)-8-methoxy-2-phenylquinoline (I-54)

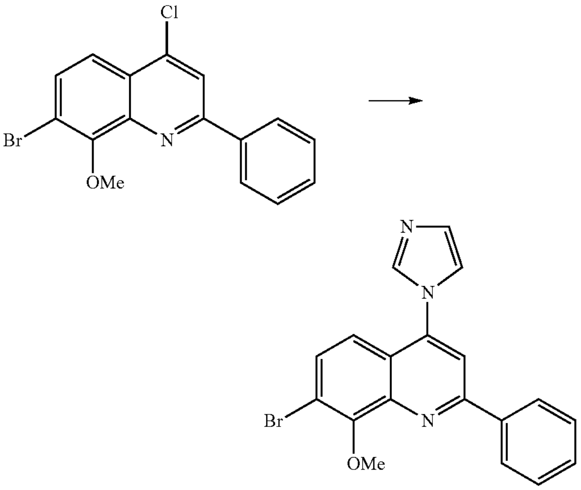

I-54

7-Bromo-4-chloro-8-methoxy-2-phenylquinoline was prepared following step 1 in the preparation procedure of methyl 3-(4-chloro-7-(trifluoromethyl)quinolin-2-yl)benzoate.

To a solution of 7-bromo-4-chloro-8-methoxy-2-phenylquinoline (63 mg) in DMF (2.0 mL) were added imidazole (129 mg) and $Cs_2CO_3$ (62 mg). The resultant mixture was heated at 80° C. overnight. The reaction mixture was diluted with water (4 mL) to precipitate the desired product. Isolation of the product and rinsing with water (2 mL) afforded the title compound (55 mg) 7-bromo-4-(1H-imidazol-1-yl)-8-methoxy-2-phenylquinoline (MS: $[M+1]^+$ 380).

Example 22: Synthesis of 7-bromo-4-(1H-imidazol-1-yl)-2-phenylquinolin-8-ol (I-53)

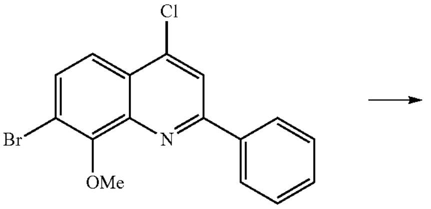

-continued

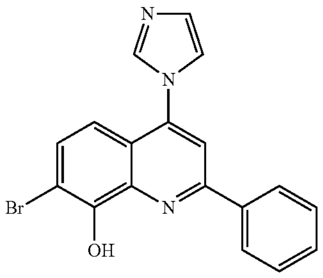

I-53

To a solution of 7-bromo-4-chloro-8-methoxy-2-phenylquinoline (20 mg) in DMF (0.5 mL) were added imidazole (50 mg) and $Cs_2CO_3$ (50 mg). The resultant mixture was stirred at 120° C. overnight. The reaction mixture was diluted with water (3 mL) to precipitate the desired product. Isolation of the product and rinsing with water (1 mL) afforded the title compound (MS: $[M+1]^+$ 366).

Example 23: Synthesis of 2-((7-bromo-4-(1H-imidazol-1-yl)-2-phenylquinolin-8-yl)oxy)acetic acid (I-379)

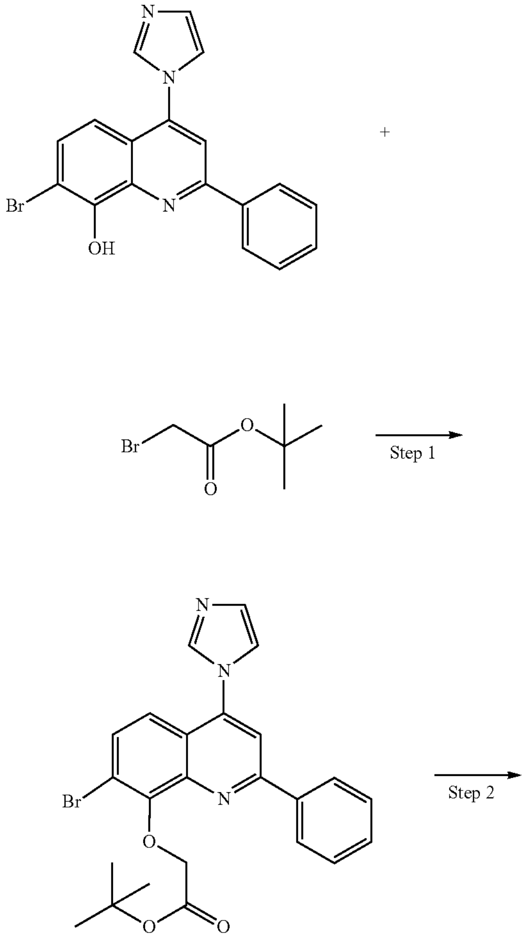

-continued

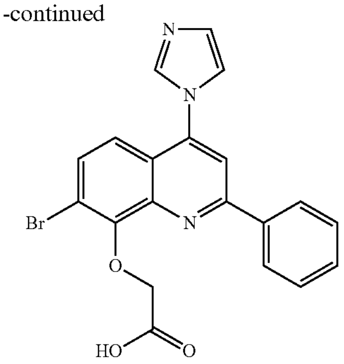

I-379

Step 1: tert-Butyl 2-((7-bromo-4-(1H-imidazol-1-yl)-2-phenylquinolin-8-yl)oxy)acetate. To a solution of 7-bromo-4-(1H-imidazol-1-yl)-2-phenylquinolin-8-ol (10 mg) in DMSO (2 mL) were added tert-butyl 2-bromoacetate (40 mg) and $K_2CO_3$ (40 mg). The resultant solution was stirred at room temperature for 3 hrs and diluted with water/EtOAc (20 mL). The organic layer was separated, washed with brine, and dried over $Na_2SO_4$, then a column chromatography eluting with hexane/EtOAc afforded the desired product (9 mg). MS: $[M+1]^+$ 480.

Step 2: 2-((7-Bromo-4-(1H-imidazol-1-yl)-2-phenylquinolin-8-yl)oxy)acetic acid. To a solution of tert-butyl 2-((7-bromo-4-(1H-imidazol-1-yl)-2-phenylquinolin-8-yl)oxy)acetate (9 mg) in DCM (0.8 mL) was added TFA (0.2 mL). The resultant solution was stirred overnight and concentrated to dryness. Lyophilization afforded the desired product (6.6 mg) (MS: $[M+1]^+$ 424).

Example 24: Synthesis of 3-(7-chloro-4-(1H-imidazol-1-yl)quinolin-2-yl)aniline (I-8)

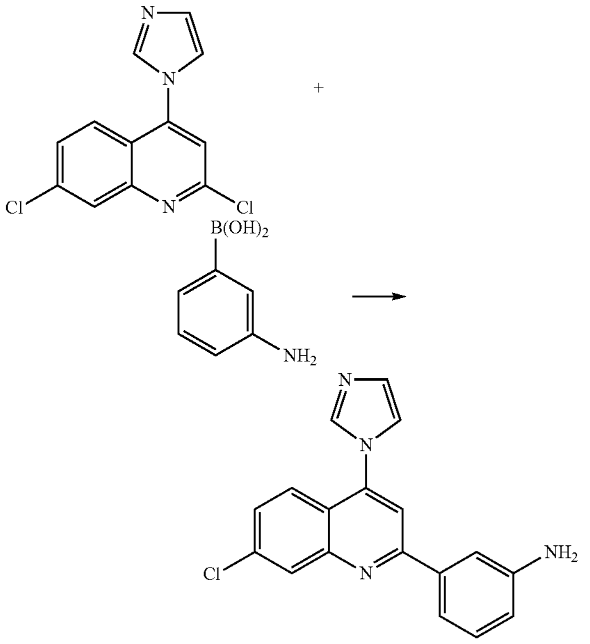

I-8

2,7-Dichloro-4-(1H-imidazol-1-yl)quinoline (26 mg, 0.10 mmol) was placed in a vial with dioxane 2.3 mL) and water (0.5 mL) under $N_2$. (3-Aminophenyl)boronic acid (21 mg, 0.15 mmol) and potassium carbonate (70 mg, 0.50 mmol) were added followed by tetrakis(triphenylphosphine)palladium(0) (6 mg, 0.005 mmol). The mixture was stirred at 100° C. for 16 h. Water (5 mL) was added and the organics were extracted into 10% methanol in dichloromethane (2×5 mL). The combined organics were dried ($Na_2SO_4$) and concentrated. Purification by silica chromatography afforded 3-(7-chloro-4-(1H-imidazol-1-yl)quinolin-2-yl)aniline (MS: $[M+1]^+$ 321.1).

The following compounds are prepared essentially by the same method described above to prepare I-8.

| I-# | Starting Material | Structure | MS $[M+1]^+$ |
|---|---|---|---|
| I-34 | 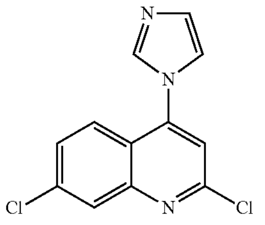 [SMILES: Clc1ccc2c(-n3ccnc3)cc(Cl)nc2c1] 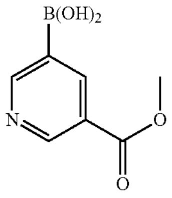 | 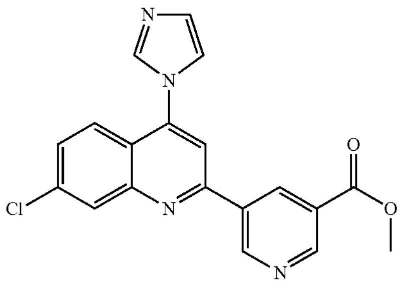 [SMILES: COC(=O)c1cncc(-c2cc(-n3ccnc3)c3ccc(Cl)cc3n2)c1] | 365.0 |
| I-58 | 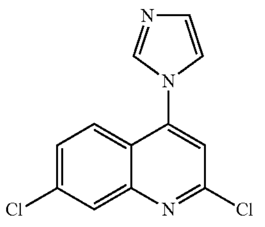 [SMILES: Clc1ccc2c(-n3ccnc3)cc(Cl)nc2c1] 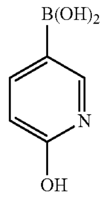 | 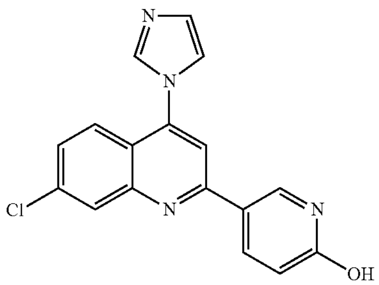 [SMILES: Oc1ccc(-c2cc(-n3ccnc3)c3ccc(Cl)cc3n2)cn1] | 323.1 |
| I-59 | 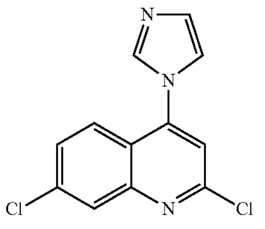 [SMILES: Clc1ccc2c(-n3ccnc3)cc(Cl)nc2c1] 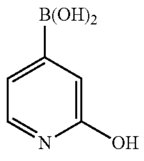 | 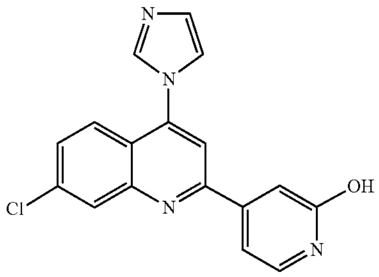 [SMILES: Oc1cc(-c2cc(-n3ccnc3)c3ccc(Cl)cc3n2)ccn1] | 323.0 |

Example 25: Synthesis of N-(3-(7-chloro-4-(1H-imidazol-1-yl)quinolin-2-yl)phenyl)methanesulfonamide (I-10)

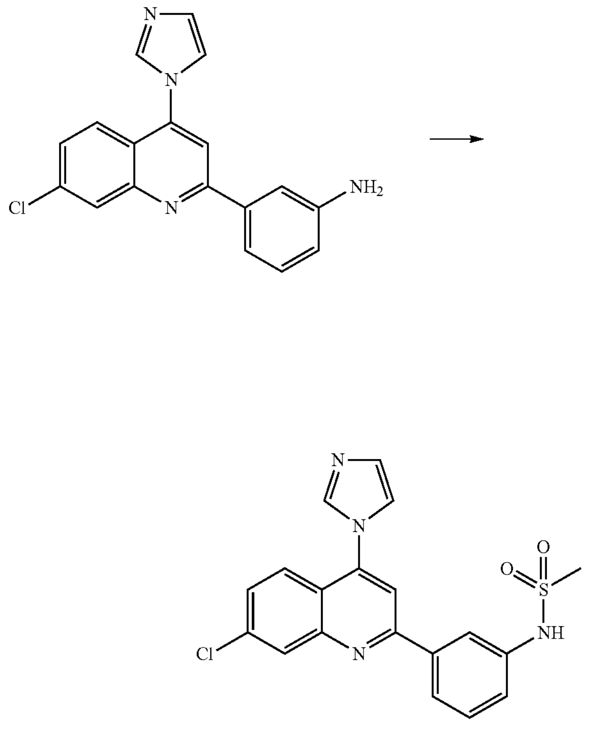

I-10

3-(7-Chloro-4-(1H-imidazol-1-yl)quinolin-2-yl)aniline (12 mg, 0.04 mmol) was placed in a vial with dichloromethane (2 mL) and TEA (0.1 mL) and cooled to 0° C. Methanesulfonyl chloride (6 mg, 0.06 mmol) was added and the solution was stirred at rt for 16 h. Water (3 mL) was added and the aqueous extracted with ethyl acetate (2×5 mL). The combined organics were dried and concentrated and the residue purified by silica chromatography to afford N-(3-(7-chloro-4-(1H-imidazol-1-yl)quinolin-2-yl)phenyl)methanesulfonamide (MS: $[M+1]^+$ 399.0).

Example 26: Synthesis of 1-(3-(7-chloro-4-(1H-imidazol-1-yl)quinolin-2-yl)phenyl)urea (I-11)

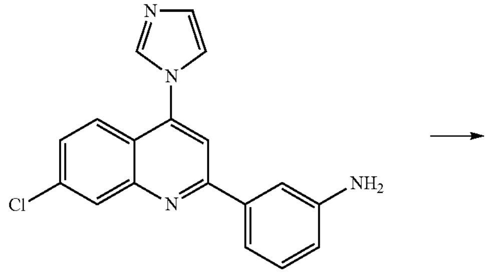

-continued

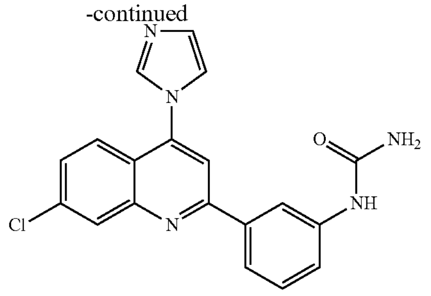

I-11

3-(7-Chloro-4-(1H-imidazol-1-yl)quinolin-2-yl)aniline (10 mg, 0.03 mmol) was placed in a vial with acetic acid (0.2 mL). Potassium cyanate (25 mg, 0.31 mmol) in water was then added dropwise to the vial and the solution was stirred at rt for 1.5 h. Water (3 mL) was added and the aqueous extracted with 10% methanol/dichloromethane (2×5 mL). The combined organics were dried and concentrated and the residue was purified by silica chromatography to afford 1-(3-(7-chloro-4-(1H-imidazol-1-yl)quinolin-2-yl)phenyl)urea (MS: $[M+1]^+$ 364.1).

Example 27: Synthesis of 7-bromo-4-(1H-imidazol-1-yl)-2-(thiophen-2-yl)quinoline (I-380)

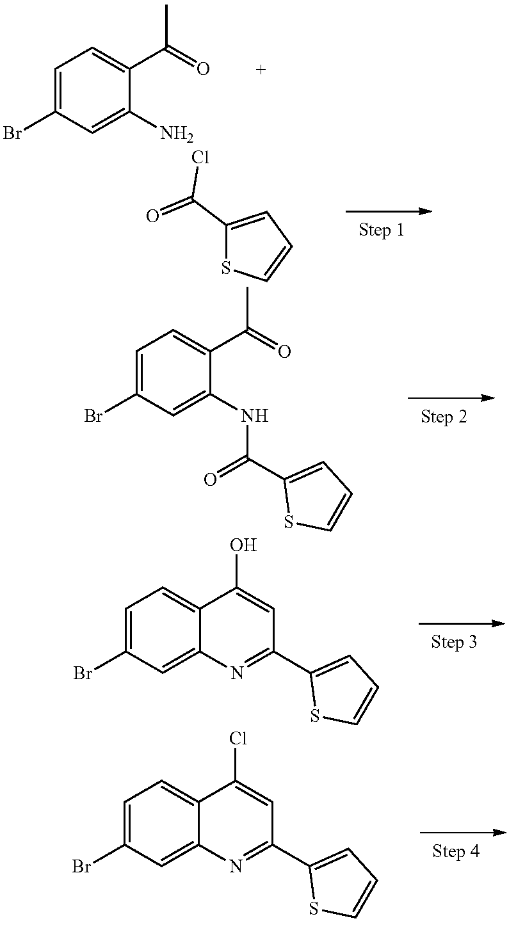

-continued

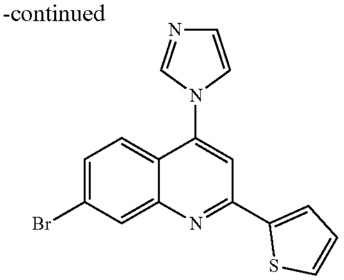

I-380

Step 1: N-(2-Acetyl-5-bromophenyl)thiophene-2-carboxamide. 1-(2-Amino-4-bromophenyl)ethan-1-one (214 mg, 1.00 mmol) was placed in a flask with dichloromethane (5 mL) and triethylamine (0.15 mL, 1.10 mmol) then cooled to 0° C. Thiophene-2-carbonyl chloride (147 mg, 1.10 mmol) was added dropwise. The reaction was warmed to r.t. and stirred for 16 h. The volatiles were removed and the resulting solids were triturated with dichloromethane, filtered and vacuum dried to afford N-(2-acetyl-5-bromophenyl)thiophene-2-carboxamide as a solid (MS: $[M+1]^+$ 323.9).

Step 2: 7-Bromo-2-(thiophen-2-yl)quinolin-4-ol. N-(2-acetyl-5-bromophenyl)thiophene-2-carboxamide (250 mg, 0.77 mmol) was placed in a flask with dioxane (10 mL). Sodium hydroxide (108 mg, 2.7 mmol) was added and the mixture heated to 110° C. for 2 h. Ethanol (2 mL) was added and the resulting solids filtered off. The filtrate was concentrated to dryness. Water (4 mL) and hexanes (1 mL) were added and the mixture was stirred for 5 minutes. The solution was acidified with HCl (1.0 N aq.) and the resulting solids filtered and vacuum dried to afford 7-bromo-2-(thiophen-2-yl)quinolin-4-ol as a solid (MS: $[M+1]^+$ 306.0).

Step 3: 7-Bromo-4-chloro-2-(thiophen-2-yl)quinoline. 7-Bromo-2-(thiophen-2-yl)quinolin-4-ol (180 mg, 0.59 mmol) was placed in a flask with phosphorus oxychloride (3 mL). The reaction was heated to 110° C. for 3 h. After cooling to r.t., ice was added. The aqueous portion was extracted with ethyl acetate (2×5 mL) and the combined organics dried ($Na_2SO_4$) then concentrated to afford 7-bromo-4-chloro-2-(thiophen-2-yl)quinoline (MS: $[M+1]^+$ 323.9).

Step 4: 7-bromo-4-(1H-imidazol-1-yl)-2-(thiophen-2-yl)quinoline. 7-Bromo-4-chloro-2-(thiophen-2-yl)quinoline (65 mg, 0.2 mmol) was placed in a flask with imidazole (34 mg, 0.50 mmol), potassium t-butoxide (34 mg, 0.30 mmol), Bis(triphenylphosphine)palladium(II) dichloride (7 mg, 0.01 mmol) and DMA (3 mL) under $N_2$. The mixture was heated at 110° C. for 2 h. After cooling down to room temperature, the crude was diluted by EtOAc (20 mL) and washed by water (5 mL×2) and brine (5 mL×2). The organic phase was concentrated and purified by column chromatography on silica gel to give 7-bromo-4-(1H-imidazol-1-yl)-2-(thiophen-2-yl)quinoline as a solid (MS: $[M+1]^+$ 356.0).

The following compounds are prepared essentially by the same method described above to prepare I-380.

| I-# | Starting Material | Structure | MS $[M + 1]^+$ |
|---|---|---|---|
| I-381 | 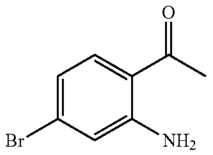 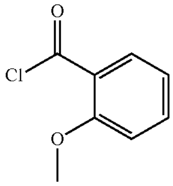 | 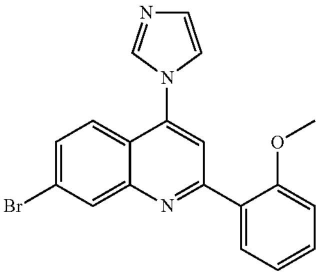 [SMILES: COc1ccccc1-c1cc(-n2ccnc2)c2ccc(Br)cc2n1] | 380.0 |
| I-382 | 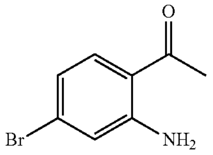 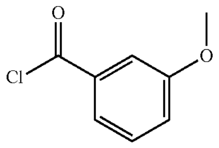 | 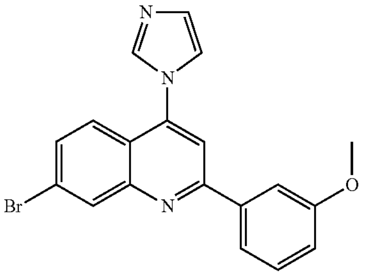 [SMILES: COc1cccc(-c2cc(-n3ccnc3)c3ccc(Br)cc3n2)c1] | 380.0 |
| I-1 | 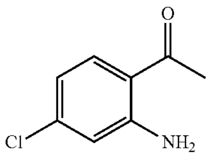 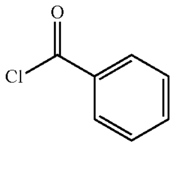 | 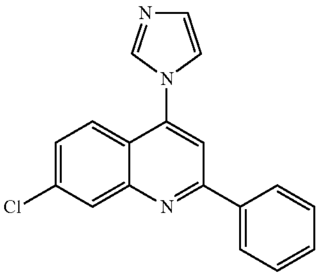 [SMILES: Clc1ccc2c(-n3ccnc3)cc(-c3ccccc3)nc2c1] | 306.1 |

-continued
| I-# | Starting Material | Structure | MS [M + 1]$^+$ |
|---|---|---|---|
| I-275 | 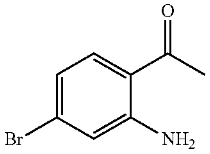 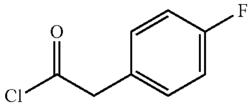 [SMILES: O=C(Cl)Cc1ccc(F)cc1] | 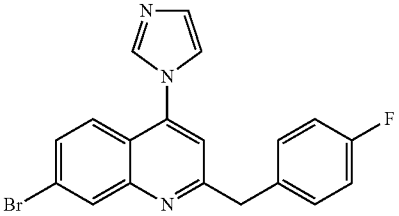 [SMILES: Fc1ccc(Cc2cc(-n3ccnc3)c3ccc(Br)cc3n2)cc1] | 382.1 |
| I-383 | 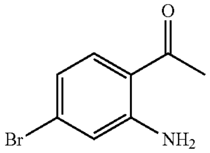 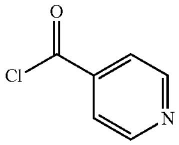 | 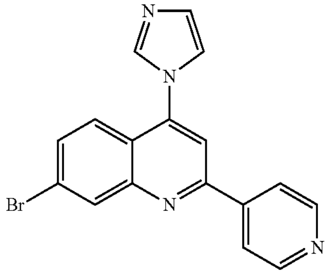 [SMILES: Brc1ccc2c(-n3ccnc3)cc(-c3ccncc3)nc2c1] | 351.0 |
| I-384 | 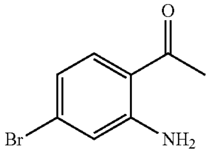 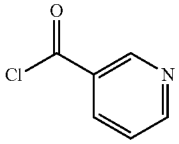 | 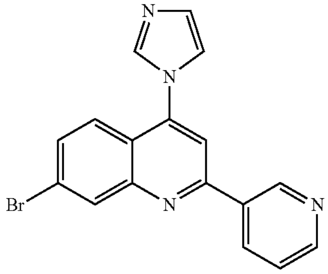 [SMILES: Brc1ccc2c(-n3ccnc3)cc(-c3cccnc3)nc2c1] | 351.0 |
| I-385 | 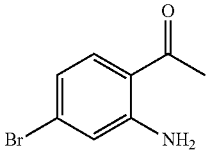 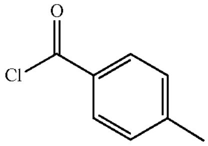 | 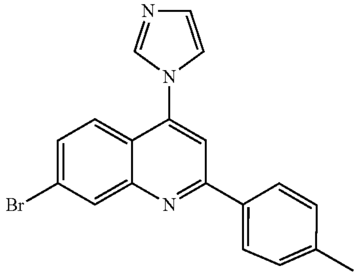 [SMILES: Cc1ccc(-c2cc(-n3ccnc3)c3ccc(Br)cc3n2)cc1] | 364.0 |
| I-50 | 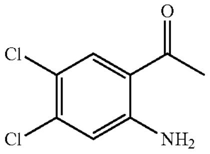 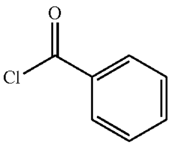 | 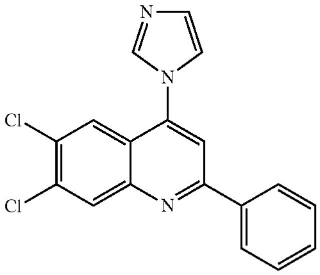 [SMILES: Clc1cc2nc(-c3ccccc3)cc(-n3ccnc3)c2cc1Cl] | 340.0 |

Example 28: Synthesis of (S)-(2-(1-(7,8-dichloro-4-(1H-imidazol-1-yl)quinolin-2-yl)pyrrolidin-2-yl) acetyl)glycine (I-156)

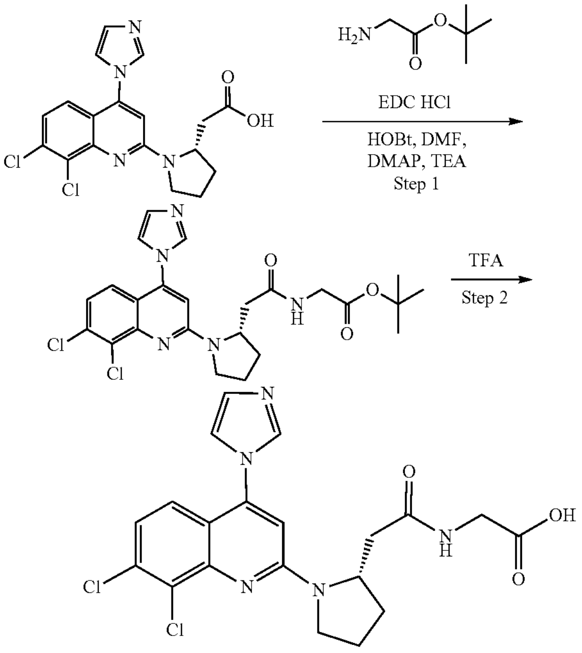

I-156

Step 1: tert-Butyl (S)-(2-(1-(7,8-dichloro-4-(1H-imidazol-1-yl)quinolin-2-yl)pyrrolidin-2-yl)acetyl)glycinate. To a mixture of (S)-2-(1-(7,8-dichloro-4-(1H-imidazol-1-yl)quinolin-2-yl)pyrrolidin-2-yl)acetic acid (9.4 mg), tert-butyl glycinate (8.05 mg), EDC HCl (9.2 mg), HOBt (6.5 mg) and DMAP (8.7 mg) was added DMF (0.2 mL) and TEA (0.05 mL). The resulting mixture was stirred overnight at room temperature and diluted with EtOAc (20 mL). The organic solution was washed with water, brine and dried over anhy. $Na_2SO_4$. A column chromatography eluting with a gradient of hexanes and EtOAc afforded the desired product (9.0 mg) as yellow solids (MS: $[M+1]^+$ 544.2).

Step 2: (S)-(2-(1-(7,8-Dichloro-4-(1H-imidazol-1-yl)quinolin-2-yl)pyrrolidin-2-yl)acetyl)glycine. To a solution of tert-butyl (S)-(2-(1-(7,8-dichloro-4-(1H-imidazol-1-yl)quinolin-2-yl)pyrrolidin-2-yl)acetyl)glycinate (9.0 mg) in DCM (0.4 mL) was added TFA (0.1 mL). After stirring over 4 hours, the reaction mixture was concentrated to dryness under reduced pressure and diluted with water for lyophilization. A total of 9.2 mg of the title compound, (S)-(2-(1-(7,8-dichloro-4-(1H-imidazol-1-yl)quinolin-2-yl)pyrrolidin-2-yl)acetyl)glycine, was afforded (MS $[M+1]^+$ 448).

The following compounds are prepared essentially by the same method described above to prepare I-156.

| I-# | Starting Materials | | Structure | MS $[M + 1]^+$ |
|---|---|---|---|---|
| I-325 | 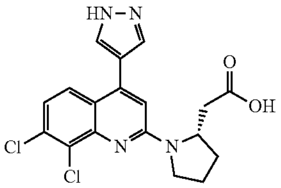 [SMILES: O=C(O)C[C@@H]1CCCN1c1cc(-c2cn[nH]c2)c2ccc(Cl)c(Cl)c2n1] | 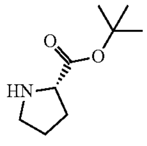 | 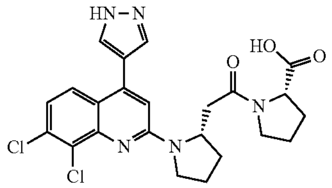 [SMILES: O=C(O)[C@@H]1CCCN1C(=O)C[C@@H]1CCCN1c1cc(-c2cn[nH]c2)c2ccc(Cl)c(Cl)c2n1] | 488 |
| I-326 | 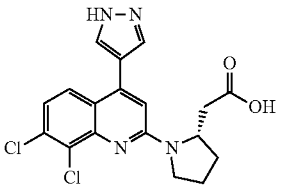 [SMILES: O=C(O)C[C@@H]1CCCN1c1cc(-c2cn[nH]c2)c2ccc(Cl)c(Cl)c2n1] | 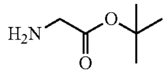 | 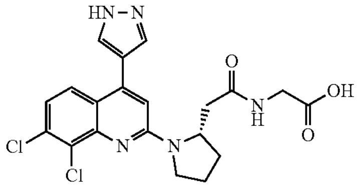 [SMILES: O=C(O)CNC(=O)C[C@@H]1CCCN1c1cc(-c2cn[nH]c2)c2ccc(Cl)c(Cl)c2n1] | 448 |
| I-454 | 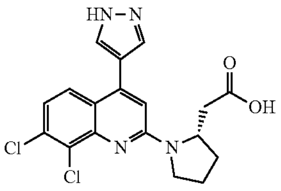 [SMILES: O=C(O)C[C@@H]1CCCN1c1cc(-c2cn[nH]c2)c2ccc(Cl)c(Cl)c2n1] | 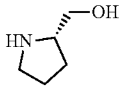 | 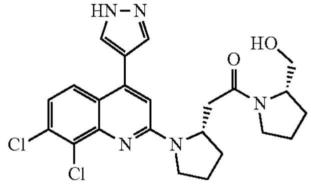 [SMILES: O=C(C[C@@H]1CCCN1c1cc(-c2cn[nH]c2)c2ccc(Cl)c(Cl)c2n1)N1CCC[C@H]1CO] | 474 |

-continued
| I-# | Starting Materials | | Structure | MS [M + 1]+ |
|---|---|---|---|---|
| I-386 | 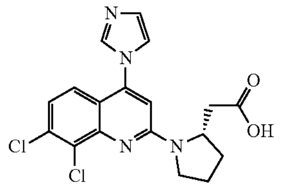 2242 | 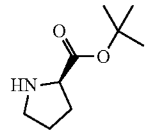 | 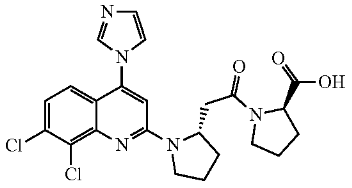 [SMILES: O=C(O)[C@H]1CCCN1C(=O)C[C@@H]1CCCN1c1cc(-n2ccnc2)c2ccc(Cl)c(Cl)c2n1] | 488 |
| I-339 | 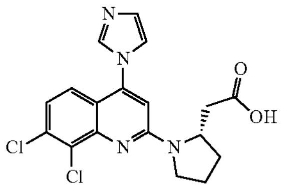 | 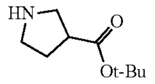 [SMILES: CC(C)(C)OC(=O)C1CCNC1] | 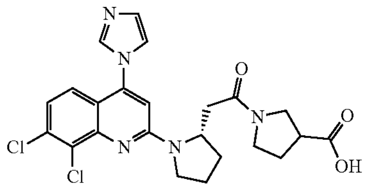 [SMILES: O=C(O)C1CCN(C(=O)C[C@@H]2CCCN2c2cc(-n3ccnc3)c3ccc(Cl)c(Cl)c3n2)C1] | 488 |
| I-340 | 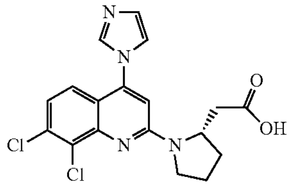 [SMILES: O=C(O)C[C@@H]1CCCN1c1cc(-n2ccnc2)c2ccc(Cl)c(Cl)c2n1] | 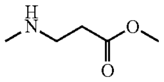 | 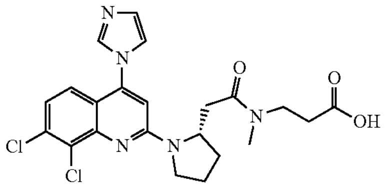 [SMILES: CN(CCC(=O)O)C(=O)C[C@@H]1CCCN1c1cc(-n2ccnc2)c2ccc(Cl)c(Cl)c2n1] | 476 |
| I-338 | 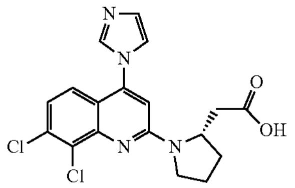 [SMILES: O=C(O)C[C@@H]1CCCN1c1cc(-n2ccnc2)c2ccc(Cl)c(Cl)c2n1] | 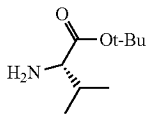 | 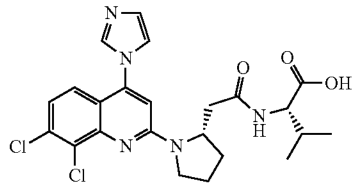 [SMILES: CC(C)[C@H](NC(=O)C[C@@H]1CCCN1c1cc(-n2ccnc2)c2ccc(Cl)c(Cl)c2n1)C(=O)O] | 490 |
| I-387 | 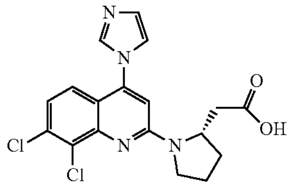 [SMILES: O=C(O)C[C@@H]1CCCN1c1cc(-n2ccnc2)c2ccc(Cl)c(Cl)c2n1] | 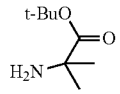 | 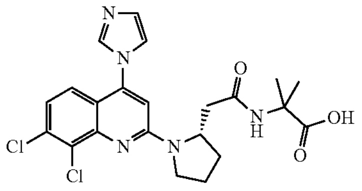 [SMILES: CC(C)(NC(=O)C[C@@H]1CCCN1c1cc(-n2ccnc2)c2ccc(Cl)c(Cl)c2n1)C(=O)O] | 476 |
| I-388 | 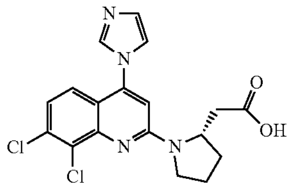 [SMILES: O=C(O)C[C@@H]1CCCN1c1cc(-n2ccnc2)c2ccc(Cl)c(Cl)c2n1] | 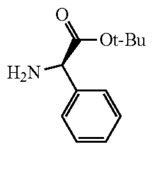 | 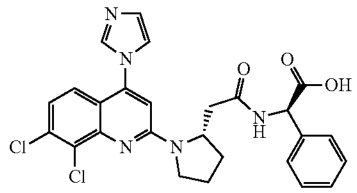 [SMILES: O=C(C[C@@H]1CCCN1c1cc(-n2ccnc2)c2ccc(Cl)c(Cl)c2n1)N[C@@H](C(=O)O)c1ccccc1] | 524.1 |
| I-196 | 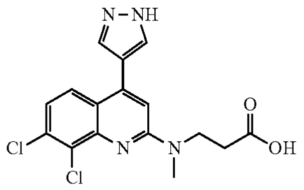 [SMILES: CN(CCC(=O)O)c1cc(-c2cn[nH]c2)c2ccc(Cl)c(Cl)c2n1] | 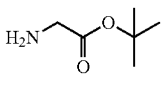 | 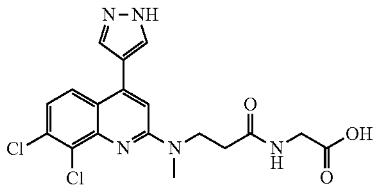 [SMILES: CN(CCC(=O)NCC(=O)O)c1cc(-c2cn[nH]c2)c2ccc(Cl)c(Cl)c2n1] | 422 |

-continued
| I-# | Starting Materials | | Structure | MS [M + 1]+ |
|---|---|---|---|---|
| I-389 | 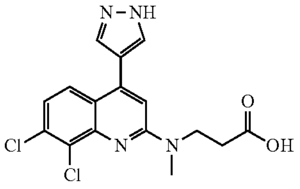 [SMILES: CN(CCC(=O)O)c1cc(-c2cn[nH]c2)c2ccc(Cl)c(Cl)c2n1] | 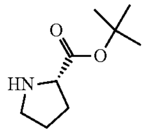 | 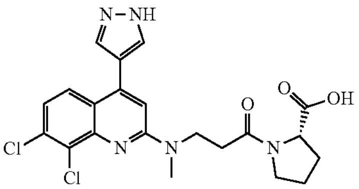 [SMILES: CN(CCC(=O)N1CCC[C@H]1C(=O)O)c1cc(-c2cn[nH]c2)c2ccc(Cl)c(Cl)c2n1] | 462 |
| I-321 | 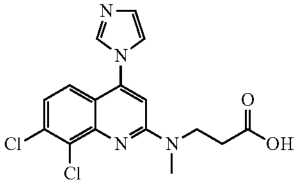 [SMILES: CN(CCC(=O)O)c1cc(-n2ccnc2)c2ccc(Cl)c(Cl)c2n1] | 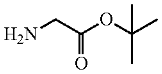 | 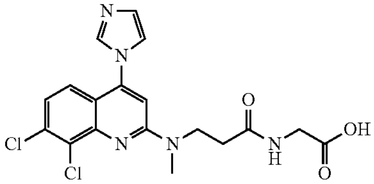 [SMILES: CN(CCC(=O)NCC(=O)O)c1cc(-n2ccnc2)c2ccc(Cl)c(Cl)c2n1] | 422 |
| I-320 | 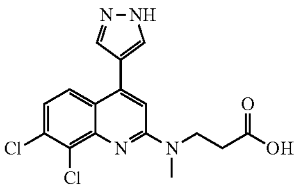 [SMILES: CN(CCC(=O)O)c1cc(-c2cn[nH]c2)c2ccc(Cl)c(Cl)c2n1] | 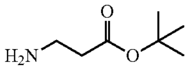 | 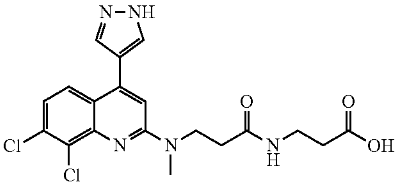 [SMILES: CN(CCC(=O)NCCC(=O)O)c1cc(-c2cn[nH]c2)c2ccc(Cl)c(Cl)c2n1] | 436 |
| I-323 | 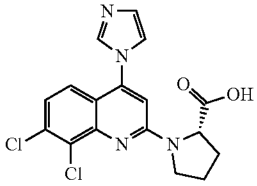 [SMILES: O=C(O)[C@@H]1CCCN1c1cc(-n2ccnc2)c2ccc(Cl)c(Cl)c2n1] | 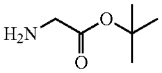 | 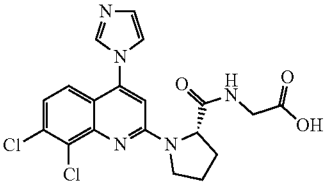 [SMILES: O=C(O)CNC(=O)[C@@H]1CCCN1c1cc(-n2ccnc2)c2ccc(Cl)c(Cl)c2n1] | 434 |
| I-324 | 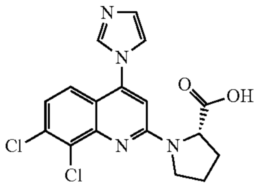 [SMILES: O=C(O)[C@@H]1CCCN1c1cc(-n2ccnc2)c2ccc(Cl)c(Cl)c2n1] | 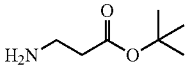 | 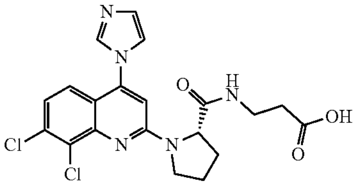 [SMILES: O=C(O)CCNC(=O)[C@@H]1CCCN1c1cc(-n2ccnc2)c2ccc(Cl)c(Cl)c2n1] | 448 |
| I-341 | 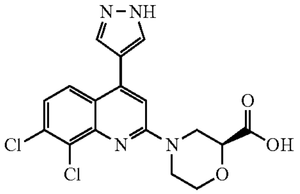 [SMILES: O=C(O)[C@@H]1CN(c2cc(-c3cn[nH]c3)c3ccc(Cl)c(Cl)c3n2)CCO1] | 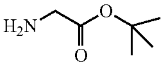 | 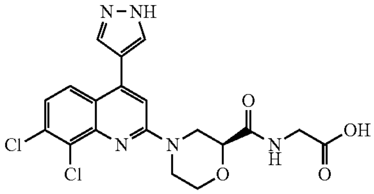 [SMILES: O=C(O)CNC(=O)[C@@H]1CN(c2cc(-c3cn[nH]c3)c3ccc(Cl)c(Cl)c3n2)CCO1] | 450 |
| I-342 | 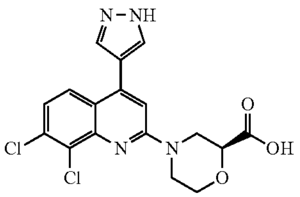 [SMILES: O=C(O)[C@@H]1CN(c2cc(-c3cn[nH]c3)c3ccc(Cl)c(Cl)c3n2)CCO1] | 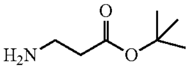 | 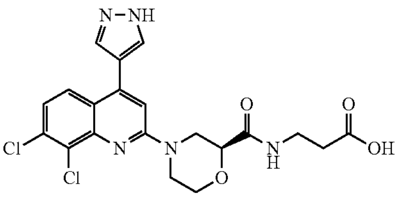 [SMILES: O=C(O)CCNC(=O)[C@@H]1CN(c2cc(-c3cn[nH]c3)c3ccc(Cl)c(Cl)c3n2)CCO1] | 464 |

-continued
| I-# | Starting Materials | | Structure | MS $[M + 1]^+$ |
|---|---|---|---|---|
| I-343 | 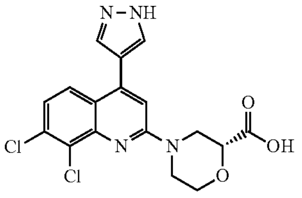 [SMILES: O=C(O)[C@H]1CN(c2cc(-c3cn[nH]c3)c3ccc(Cl)c(Cl)c3n2)CCO1] | 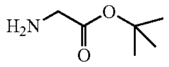 | 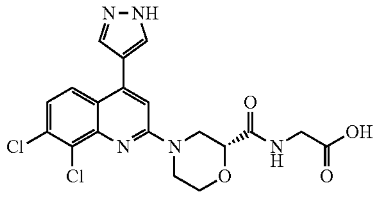 [SMILES: O=C(O)CNC(=O)[C@H]1CN(c2cc(-c3cn[nH]c3)c3ccc(Cl)c(Cl)c3n2)CCO1] | 450 |
| I-344 | 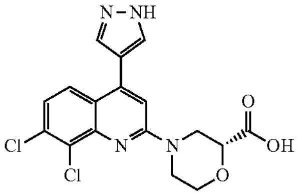 [SMILES: O=C(O)[C@H]1CN(c2cc(-c3cn[nH]c3)c3ccc(Cl)c(Cl)c3n2)CCO1] | 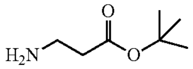 | 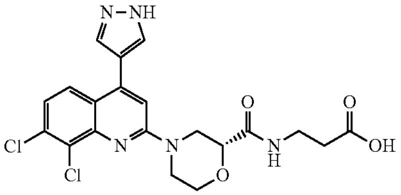 [SMILES: O=C(O)CCNC(=O)[C@H]1CN(c2cc(-c3cn[nH]c3)c3ccc(Cl)c(Cl)c3n2)CCO1] | 464 |
| I-522 | 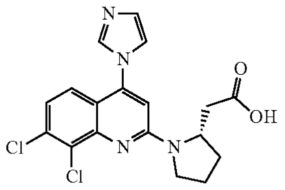 | 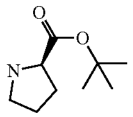 | 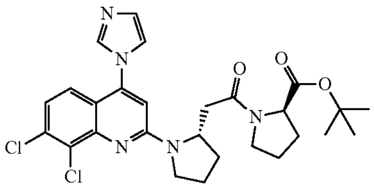 [SMILES: CC(C)(C)OC(=O)[C@H]1CCCN1C(=O)C[C@@H]1CCCN1c1cc(-n2ccnc2)c2ccc(Cl)c(Cl)c2n1] | 544 |
| I-524 | 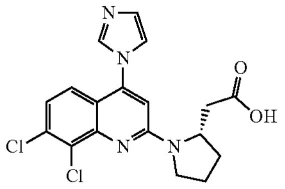 | 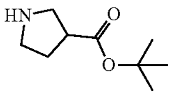 | 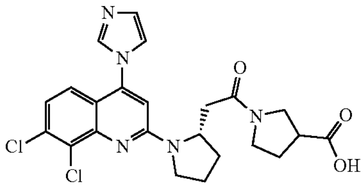 [SMILES: O=C(O)C1CCN(C(=O)C[C@@H]2CCCN2c2cc(-n3ccnc3)c3ccc(Cl)c(Cl)c3n2)C1] | 488 |
| I-525 | 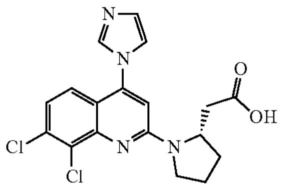 | 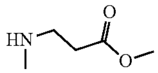 | 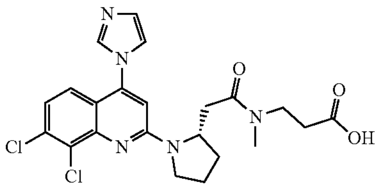 [SMILES: CN(CCC(=O)O)C(=O)C[C@@H]1CCCN1c1cc(-n2ccnc2)c2ccc(Cl)c(Cl)c2n1] | 476 |
| I-526 | 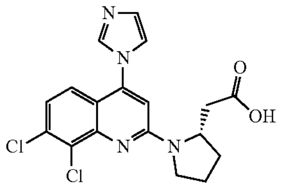 [SMILES: O=C(O)C[C@@H]1CCCN1c1cc(-n2ccnc2)c2ccc(Cl)c(Cl)c2n1] | 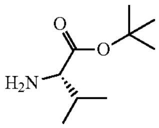 | 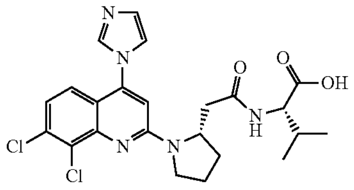 [SMILES: CC(C)[C@H](NC(=O)C[C@@H]1CCCN1c1cc(-n2ccnc2)c2ccc(Cl)c(Cl)c2n1)C(=O)O] | 490 |
| I-527 | 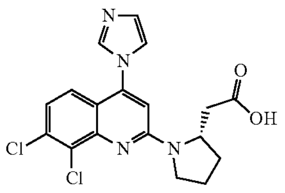 | 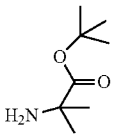 | 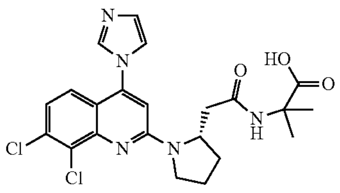 [SMILES: CC(C)(NC(=O)C[C@@H]1CCCN1c1cc(-n2ccnc2)c2ccc(Cl)c(Cl)c2n1)C(=O)O] | 476 |

-continued
| I-# | Starting Materials | | Structure | MS $[M + 1]^+$ |
|---|---|---|---|---|
| I-528 | 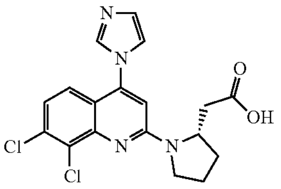 [SMILES: O=C(O)C[C@@H]1CCCN1c1cc(-n2ccnc2)c2ccc(Cl)c(Cl)c2n1] | 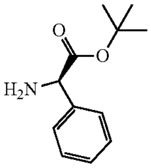 | 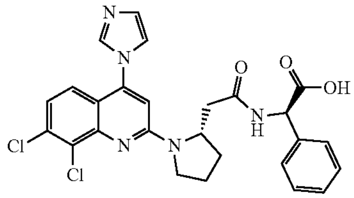 [SMILES: O=C(C[C@@H]1CCCN1c1cc(-n2ccnc2)c2ccc(Cl)c(Cl)c2n1)N[C@@H](C(=O)O)c1ccccc1] | 524 |
| I-529 | 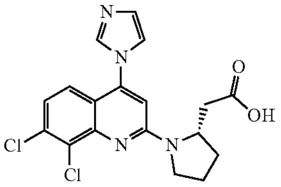 | 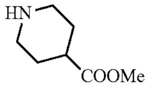 | 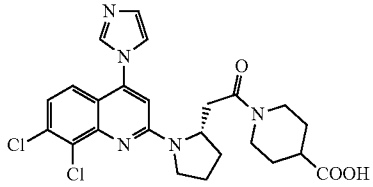 [SMILES: O=C(O)C1CCN(C(=O)C[C@@H]2CCCN2c2cc(-n3ccnc3)c3ccc(Cl)c(Cl)c3n2)CC1] | 502 |
| I-530 | 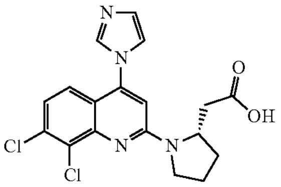 | 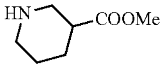 | 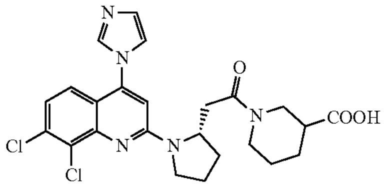 [SMILES: O=C(O)C1CCCN(C(=O)C[C@@H]2CCCN2c2cc(-n3ccnc3)c3ccc(Cl)c(Cl)c3n2)C1] | 502 |
| I-531 | 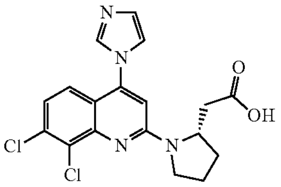 | 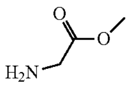 | 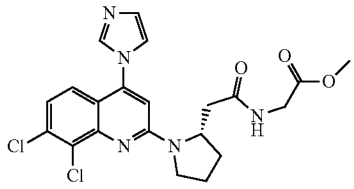 [SMILES: COC(=O)CNC(=O)C[C@@H]1CCCN1c1cc(-n2ccnc2)c2ccc(Cl)c(Cl)c2n1] | 462 |
| I-532 | 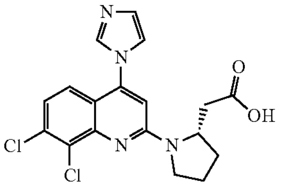 | 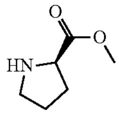 | 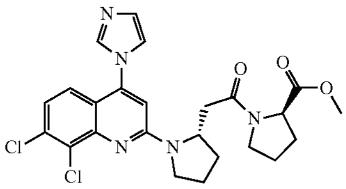 [SMILES: COC(=O)[C@H]1CCCN1C(=O)C[C@@H]1CCCN1c1cc(-n2ccnc2)c2ccc(Cl)c(Cl)c2n1] | 502 |
| I-533 | 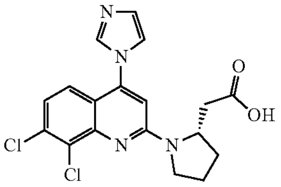 | 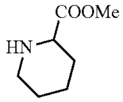 | 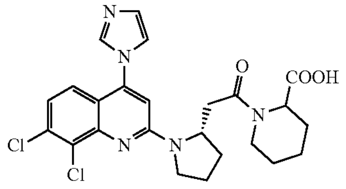 [SMILES: O=C(O)C1CCCCN1C(=O)C[C@@H]1CCCN1c1cc(-n2ccnc2)c2ccc(Cl)c(Cl)c2n1] | 502 |
| I-534 | 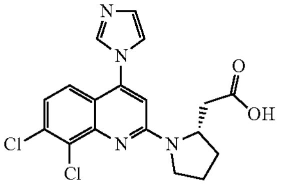 | 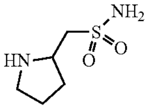 | 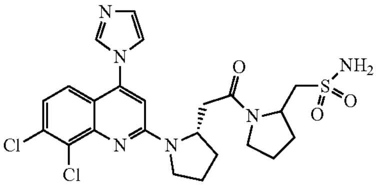 [SMILES: NS(=O)(=O)CC1CCCN1C(=O)C[C@@H]1CCCN1c1cc(-n2ccnc2)c2ccc(Cl)c(Cl)c2n1] | 537 |
| I-535 | 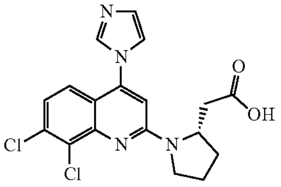 | 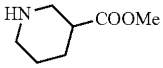 | 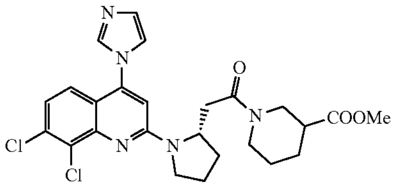 [SMILES: COC(=O)C1CCCN(C(=O)C[C@@H]2CCCN2c2cc(-n3ccnc3)c3ccc(Cl)c(Cl)c3n2)C1] | 516 |

-continued
| I-# | Starting Materials | | Structure | MS $[M + 1]^+$ |
|---|---|---|---|---|
| I-536 | 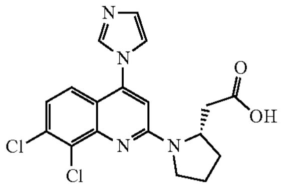 | 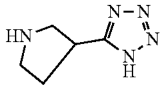 | 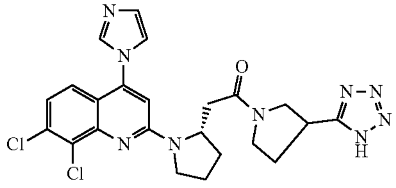 [SMILES: O=C(C[C@@H]1CCCN1c1cc(-n2ccnc2)c2ccc(Cl)c(Cl)c2n1)N1CCC(c2nnn[nH]2)C1] | 512 |
| I-537 | 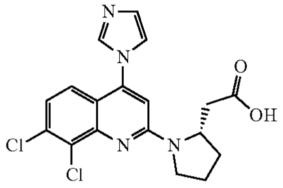 | 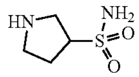 | 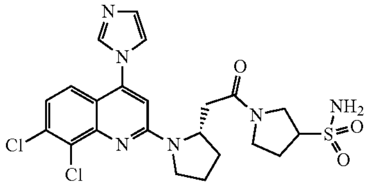 [SMILES: NS(=O)(=O)C1CCN(C(=O)C[C@@H]2CCCN2c2cc(-n3ccnc3)c3ccc(Cl)c(Cl)c3n2)C1] | 523 |
| I-538 | 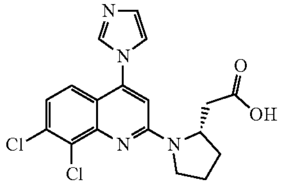 | 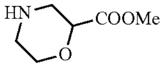 | 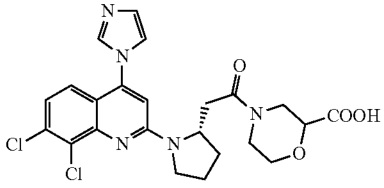 [SMILES: O=C(O)C1CN(C(=O)C[C@@H]2CCCN2c2cc(-n3ccnc3)c3ccc(Cl)c(Cl)c3n2)CCO1] | 504 |
| I-539 | 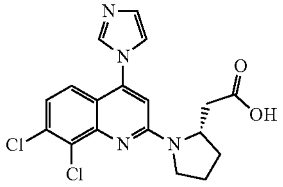 | 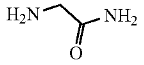 | 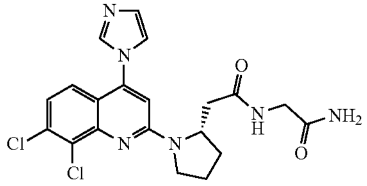 [SMILES: NC(=O)CNC(=O)C[C@@H]1CCCN1c1cc(-n2ccnc2)c2ccc(Cl)c(Cl)c2n1] | 477 |
| I-540 | 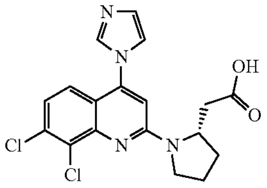 [SMILES: O=C(O)C[C@@H]1CCCN1c1cc(-n2ccnc2)c2ccc(Cl)c(Cl)c2n1] | 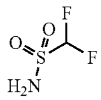 | 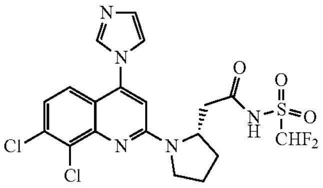 [SMILES: O=C(C[C@@H]1CCCN1c1cc(-n2ccnc2)c2ccc(Cl)c(Cl)c2n1)NS(=O)(=O)C(F)F] | 504 |
| I-541 | 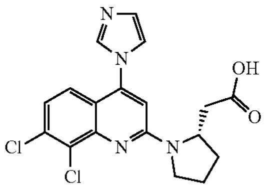 [SMILES: O=C(O)C[C@@H]1CCCN1c1cc(-n2ccnc2)c2ccc(Cl)c(Cl)c2n1] | 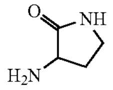 | 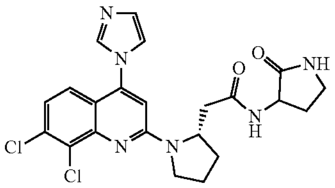 [SMILES: O=C(C[C@@H]1CCCN1c1cc(-n2ccnc2)c2ccc(Cl)c(Cl)c2n1)NC1CCNC1=O] | 473 |
| I-542 | 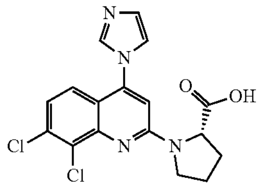 [SMILES: O=C(O)[C@@H]1CCCN1c1cc(-n2ccnc2)c2ccc(Cl)c(Cl)c2n1] | 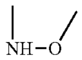 | 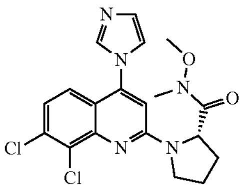 [SMILES: CON(C)C(=O)[C@@H]1CCCN1c1cc(-n2ccnc2)c2ccc(Cl)c(Cl)c2n1] | 420 |
| I-543 | 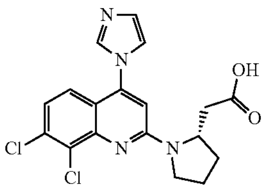 [SMILES: O=C(O)C[C@@H]1CCCN1c1cc(-n2ccnc2)c2ccc(Cl)c(Cl)c2n1] | 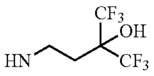 | 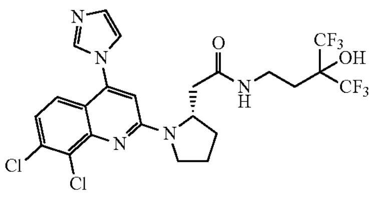 [SMILES: O=C(C[C@@H]1CCCN1c1cc(-n2ccnc2)c2ccc(Cl)c(Cl)c2n1)NCCC(O)(C(F)(F)F)C(F)(F)F] | 584 |

-continued
| I-# | Starting Materials | Structure | MS [M + 1]$^+$ |
| --- | --- | --- | --- |
| I-544 | 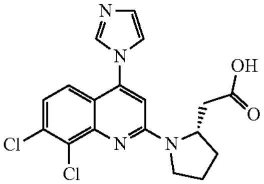 [SMILES: O=C(O)C[C@@H]1CCCN1c1cc(-n2ccnc2)c2ccc(Cl)c(Cl)c2n1] 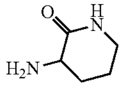 | 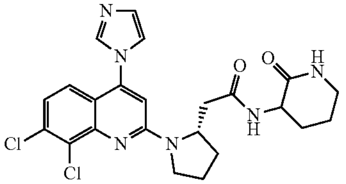 [SMILES: O=C(C[C@@H]1CCCN1c1cc(-n2ccnc2)c2ccc(Cl)c(Cl)c2n1)NC1CCCNC1=O] | 487 |
| I-452 | 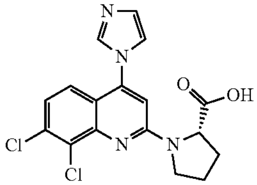 [SMILES: O=C(O)[C@@H]1CCCN1c1cc(-n2ccnc2)c2ccc(Cl)c(Cl)c2n1] 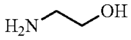 | 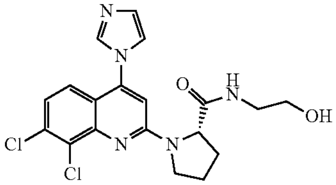 [SMILES: O=C(NCCO)[C@@H]1CCCN1c1cc(-n2ccnc2)c2ccc(Cl)c(Cl)c2n1] | 420 |
| I-545 | 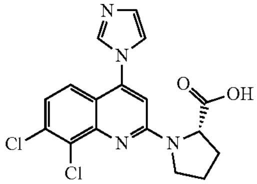 [SMILES: O=C(O)[C@@H]1CCCN1c1cc(-n2ccnc2)c2ccc(Cl)c(Cl)c2n1] 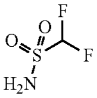 | 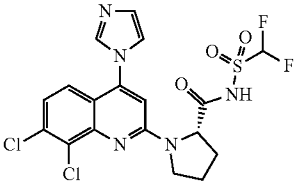 [SMILES: O=C(NS(=O)(=O)C(F)F)[C@@H]1CCCN1c1cc(-n2ccnc2)c2ccc(Cl)c(Cl)c2n1] | 490 |
| I-546 | 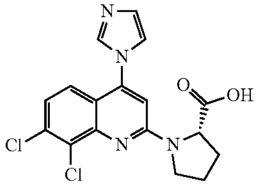 [SMILES: O=C(O)[C@@H]1CCCN1c1cc(-n2ccnc2)c2ccc(Cl)c(Cl)c2n1] 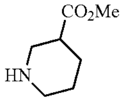 | 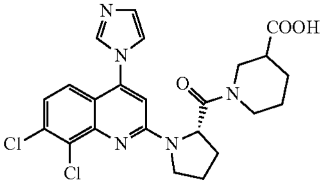 [SMILES: O=C(O)C1CCCN(C(=O)[C@@H]2CCCN2c2cc(-n3ccnc3)c3ccc(Cl)c(Cl)c3n2)C1] | 488 |
| I-547 | 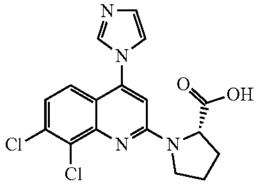 [SMILES: O=C(O)[C@@H]1CCCN1c1cc(-n2ccnc2)c2ccc(Cl)c(Cl)c2n1] 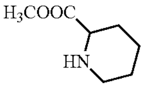 | 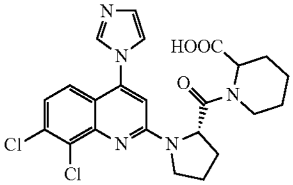 [SMILES: O=C(O)C1CCCCN1C(=O)[C@@H]1CCCN1c1cc(-n2ccnc2)c2ccc(Cl)c(Cl)c2n1] | 488 |
| I-548 | 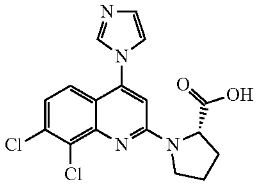 [SMILES: O=C(O)[C@@H]1CCCN1c1cc(-n2ccnc2)c2ccc(Cl)c(Cl)c2n1] 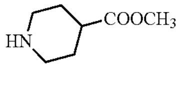 | 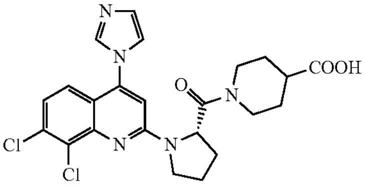 [SMILES: O=C(O)C1CCN(C(=O)[C@@H]2CCCN2c2cc(-n3ccnc3)c3ccc(Cl)c(Cl)c3n2)CC1] | 488 |
| I-549 | 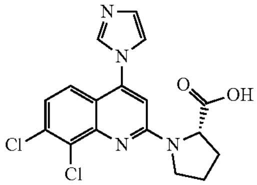 [SMILES: O=C(O)[C@@H]1CCCN1c1cc(-n2ccnc2)c2ccc(Cl)c(Cl)c2n1] 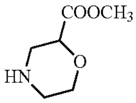 | 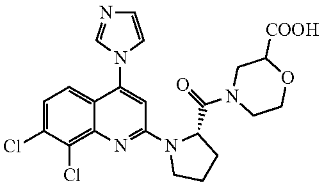 | 490 |
| I-550 | 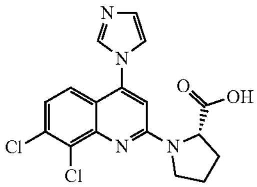 [SMILES: O=C(O)[C@@H]1CCCN1c1cc(-n2ccnc2)c2ccc(Cl)c(Cl)c2n1] 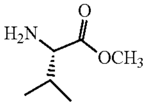 | 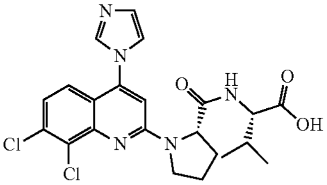 [SMILES: CC(C)[C@H](NC(=O)[C@@H]1CCCN1c1cc(-n2ccnc2)c2ccc(Cl)c(Cl)c2n1)C(=O)O] | 476 |

-continued
| I-# | Starting Materials | | Structure | MS [M + 1]+ |
|---|---|---|---|---|
| I-551 | 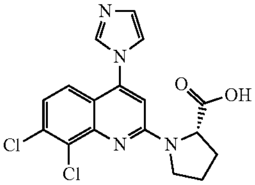 [SMILES: O=C(O)[C@@H]1CCCN1c1cc(-n2ccnc2)c2ccc(Cl)c(Cl)c2n1] | 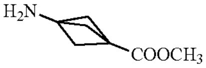 | 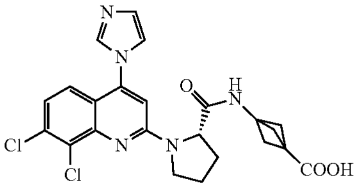 [SMILES: O=C(NC12CC(C(=O)O)(C1)C2)[C@@H]1CCCN1c1cc(-n2ccnc2)c2ccc(Cl)c(Cl)c2n1] | 486 |
| I-552 | 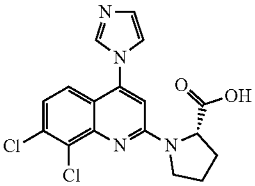 [SMILES: O=C(O)[C@@H]1CCCN1c1cc(-n2ccnc2)c2ccc(Cl)c(Cl)c2n1] | 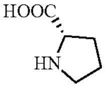 | 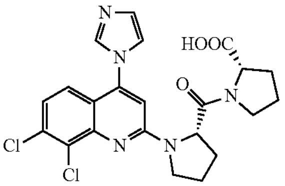 [SMILES: O=C(O)[C@@H]1CCCN1C(=O)[C@@H]1CCCN1c1cc(-n2ccnc2)c2ccc(Cl)c(Cl)c2n1] | 474 |
| I-553 | 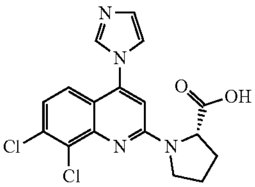 [SMILES: O=C(O)[C@@H]1CCCN1c1cc(-n2ccnc2)c2ccc(Cl)c(Cl)c2n1] | 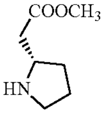 | 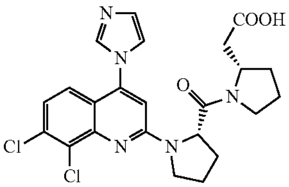 [SMILES: O=C(O)C[C@@H]1CCCN1C(=O)[C@@H]1CCCN1c1cc(-n2ccnc2)c2ccc(Cl)c(Cl)c2n1] | 488 |
| I-554 | 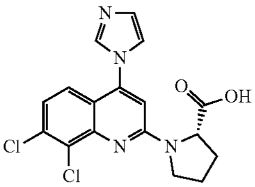 [SMILES: O=C(O)[C@@H]1CCCN1c1cc(-n2ccnc2)c2ccc(Cl)c(Cl)c2n1] | 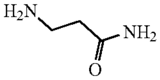 | 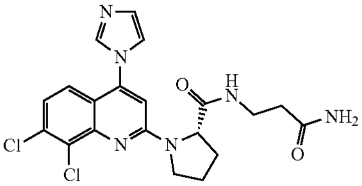 [SMILES: NC(=O)CCNC(=O)[C@@H]1CCCN1c1cc(-n2ccnc2)c2ccc(Cl)c(Cl)c2n1] | 448 |
| I-555 | 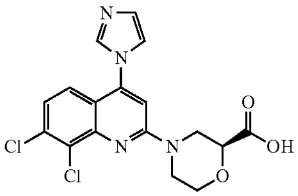 [SMILES: O=C(O)[C@@H]1CN(c2cc(-n3ccnc3)c3ccc(Cl)c(Cl)c3n2)CCO1] | 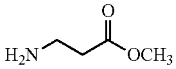 | 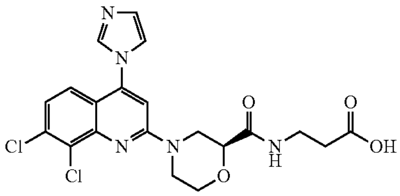 [SMILES: O=C(O)CCNC(=O)[C@@H]1CN(c2cc(-n3ccnc3)c3ccc(Cl)c(Cl)c3n2)CCO1] | 464 |
| I-608 | 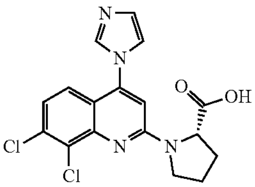 [SMILES: O=C(O)[C@@H]1CCCN1c1cc(-n2ccnc2)c2ccc(Cl)c(Cl)c2n1] | 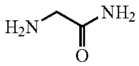 | 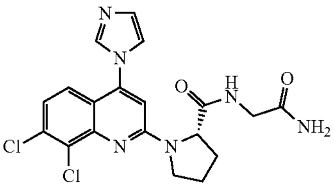 [SMILES: NC(=O)CNC(=O)[C@@H]1CCCN1c1cc(-n2ccnc2)c2ccc(Cl)c(Cl)c2n1] | 433 |
| I-562 | 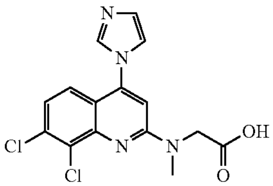 [SMILES: CN(CC(=O)O)c1cc(-n2ccnc2)c2ccc(Cl)c(Cl)c2n1] | 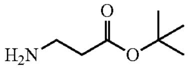 | 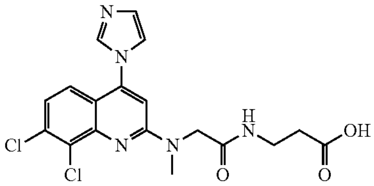 [SMILES: CN(CC(=O)NCCC(=O)O)c1cc(-n2ccnc2)c2ccc(Cl)c(Cl)c2n1] | 422 |

-continued
| I-# | Starting Materials | | Structure | MS [M + 1]+ |
|---|---|---|---|---|
| I-563 | 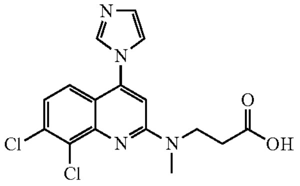 [SMILES: CN(CCC(=O)O)c1cc(-n2ccnc2)c2ccc(Cl)c(Cl)c2n1] | 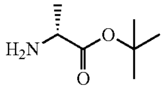 | 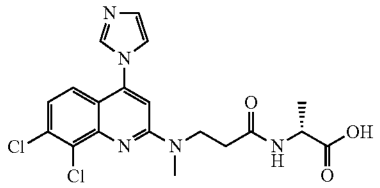 [SMILES: C[C@@H](NC(=O)CCN(C)c1cc(-n2ccnc2)c2ccc(Cl)c(Cl)c2n1)C(=O)O] | 436 |
| I-564 | 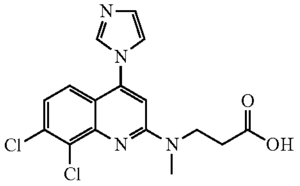 [SMILES: CN(CCC(=O)O)c1cc(-n2ccnc2)c2ccc(Cl)c(Cl)c2n1] | 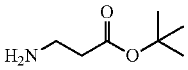 | 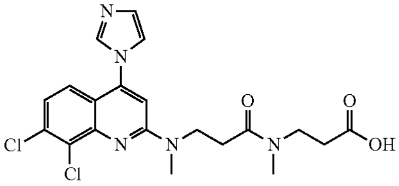 [SMILES: CN(CCC(=O)O)C(=O)CCN(C)c1cc(-n2ccnc2)c2ccc(Cl)c(Cl)c2n1] | 450 |
| I-565 | 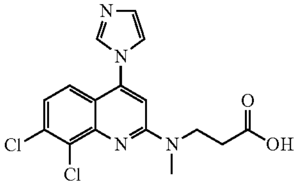 [SMILES: CN(CCC(=O)O)c1cc(-n2ccnc2)c2ccc(Cl)c(Cl)c2n1] | 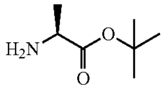 | 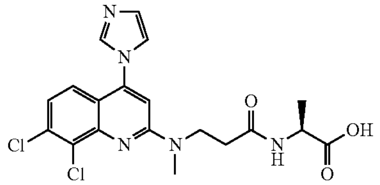 [SMILES: C[C@H](NC(=O)CCN(C)c1cc(-n2ccnc2)c2ccc(Cl)c(Cl)c2n1)C(=O)O] | 436 |
| I-566 | 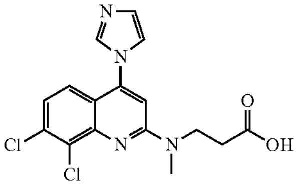 [SMILES: CN(CCC(=O)O)c1cc(-n2ccnc2)c2ccc(Cl)c(Cl)c2n1] | 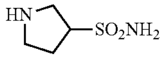 | 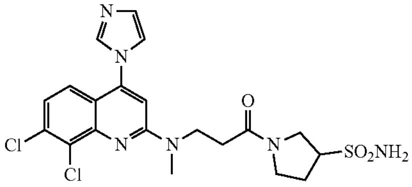 [SMILES: CN(CCC(=O)N1CCC(S(N)(=O)=O)C1)c1cc(-n2ccnc2)c2ccc(Cl)c(Cl)c2n1] | 497 |
| I-567 | 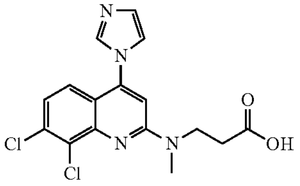 [SMILES: CN(CCC(=O)O)c1cc(-n2ccnc2)c2ccc(Cl)c(Cl)c2n1] | 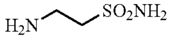 | 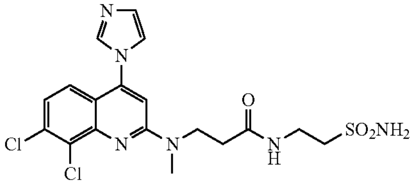 [SMILES: CN(CCC(=O)NCCS(N)(=O)=O)c1cc(-n2ccnc2)c2ccc(Cl)c(Cl)c2n1] | 471 |
| I-568 | 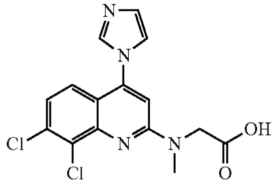 [SMILES: CN(CC(=O)O)c1cc(-n2ccnc2)c2ccc(Cl)c(Cl)c2n1] | 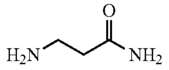 | 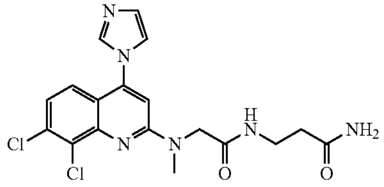 [SMILES: CN(CC(=O)NCCC(N)=O)c1cc(-n2ccnc2)c2ccc(Cl)c(Cl)c2n1] | 421 |
The following compounds were prepared essentially by the same method as step 1 described above for I-156.
| I-# | Starting Material | | Structure | MS [M + 1]+ |
|---|---|---|---|---|
| I-556 | 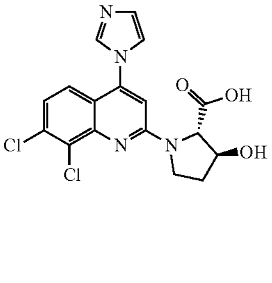 [SMILES: O=C(O)[C@@H]1[C@@H](O)CCN1c1cc(-n2ccnc2)c2ccc(Cl)c(Cl)c2n1] | 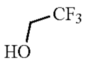 | 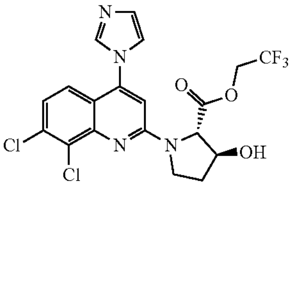 [SMILES: O=C(OCC(F)(F)F)[C@@H]1[C@@H](O)CCN1c1cc(-n2ccnc2)c2ccc(Cl)c(Cl)c2n1] | 475 |

-continued
| I-# | Starting Material | | Structure | MS $[M + 1]^+$ |
|---|---|---|---|---|
| I-557 | 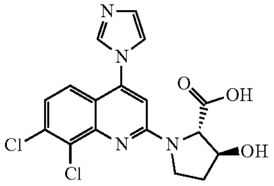 [SMILES: O=C(O)[C@@H]1[C@@H](O)CCN1c1cc(-n2ccnc2)c2ccc(Cl)c(Cl)c2n1] | $NH_4Cl$ | 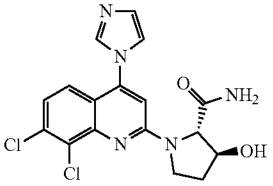 [SMILES: NC(=O)[C@@H]1[C@@H](O)CCN1c1cc(-n2ccnc2)c2ccc(Cl)c(Cl)c2n1] | 392 |
| I-558 | 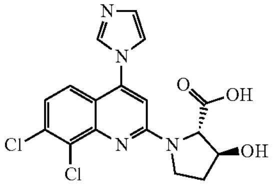 [SMILES: O=C(O)[C@@H]1[C@@H](O)CCN1c1cc(-n2ccnc2)c2ccc(Cl)c(Cl)c2n1] | $NH_2OH$ | 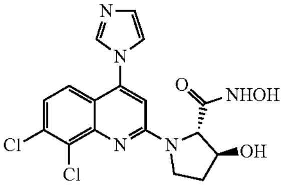 | 408 |
| I-603 | 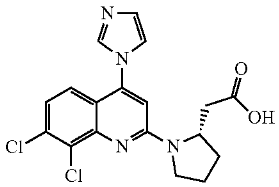 [SMILES: O=C(O)C[C@@H]1CCCN1c1cc(-n2ccnc2)c2ccc(Cl)c(Cl)c2n1] | $NH_3$ | 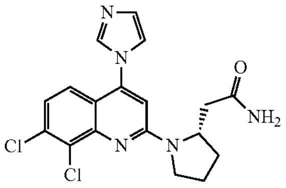 [SMILES: NC(=O)C[C@@H]1CCCN1c1cc(-n2ccnc2)c2ccc(Cl)c(Cl)c2n1] | 390 |
The following compounds were prepared essentially by the same method as step 2 described above for I-156.
| I-# | Starting Material | | Structure | MS $[M + 1]^+$ |
|---|---|---|---|---|
| I-559 | 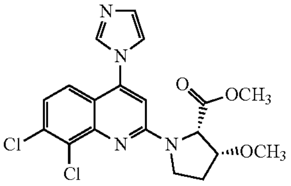 [SMILES: COC(=O)[C@@H]1[C@H](OC)CCN1c1cc(-n2ccnc2)c2ccc(Cl)c(Cl)c2n1] | LiOH | 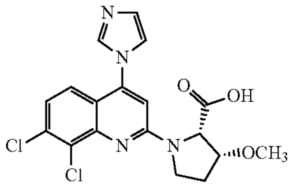 [SMILES: CO[C@@H]1CCN(c2cc(-n3ccnc3)c3ccc(Cl)c(Cl)c3n2)[C@@H]1C(=O)O] | 407 |
| I-560 | 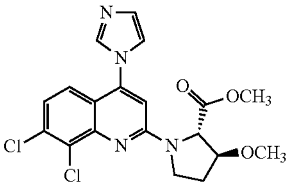 [SMILES: COC(=O)[C@@H]1[C@@H](OC)CCN1c1cc(-n2ccnc2)c2ccc(Cl)c(Cl)c2n1] | LiOH | 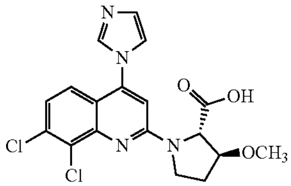 [SMILES: CO[C@H]1CCN(c2cc(-n3ccnc3)c3ccc(Cl)c(Cl)c3n2)[C@@H]1C(=O)O] | 407 |
| I-561 | 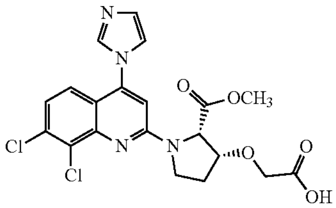 [SMILES: COC(=O)[C@@H]1[C@H](OCC(=O)O)CCN1c1cc(-n2ccnc2)c2ccc(Cl)c(Cl)c2n1] | LiOH | 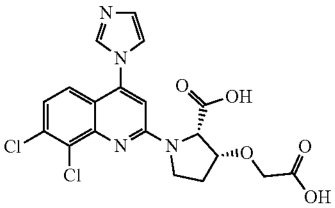 [SMILES: O=C(O)CO[C@@H]1CCN(c2cc(-n3ccnc3)c3ccc(Cl)c(Cl)c3n2)[C@@H]1C(=O)O] | 451 |

Example 29: Synthesis of N-benzyl-3-((7,8-dichloro-4-(1H-pyrazol-4-yl)quinolin-2-yl)(methyl)amino)propenamide (I-193)

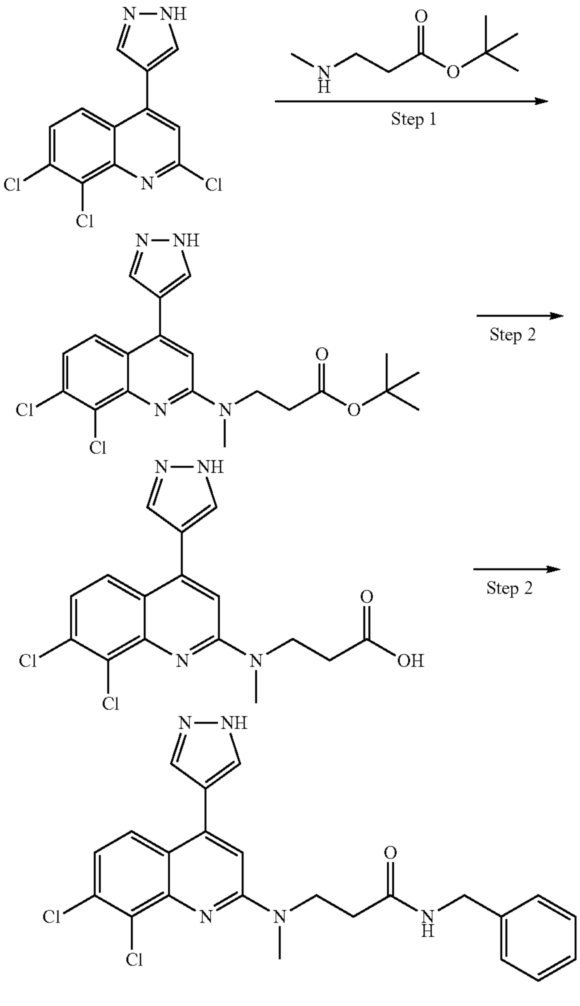

I-193

Step 1: tert-Butyl 3-((7,8-dichloro-4-(1H-pyrazol-4-yl)quinolin-2-yl)(methyl)amino)propanoate. To a solution of 2,7,8-trichloro-4-(1H-pyrazol-4-yl)quinoline (125 mg, 0.42 mmol) in DMSO (0.5 mL) was added tert-butyl 3-(methylamino)propanoate (133 mg, 0.84 mmol) and N,N-diisopropylethylamine (0.22 mL, 1.26 mmol). The solution is stirred at 95° C. for 16 h. After cooling down to room temperature, water (5 mL) was added and the organics were extracted into 10% methanol in dichloromethane (2×5 mL). The combined organics are dried ($Na_2SO_4$) and concentrated. The resulting residue was purified by silica chromatography using 20-80% EtOAc/hexanes to afford tert-butyl 3-((7,8-dichloro-4-(1H-pyrazol-4-yl)quinolin-2-yl)(methyl)amino)propanoate (120 mg) (MS: $[M+1]^+$ 421).

Step 2: 3-((7,8-Dichloro-4-(1H-pyrazol-4-yl)quinolin-2-yl)(methyl)amino)propanoic acid. To a solution of tert-butyl 3-((7,8-dichloro-4-(1H-pyrazol-4-yl)quinolin-2-yl)(methyl)amino)propanoate (100 mg, 0.24 mmol) in dichloromethane (3 mL) was added hydrochloric acid (0.5 mL, 4.0 M in dioxane). The reaction is stirred at rt for 16 h. The volatiles are removed by rotary evaporation and the resulting solids were used without further purification (MS: $[M+1]^+$ 365).

Step 3: N-Benzyl-3-((7,8-dichloro-4-(1H-pyrazol-4-yl)quinolin-2-yl)(methyl)amino)propenamide. To a solution of 3-((7,8-dichloro-4-(1H-pyrazol-4-yl)quinolin-2-yl)(methyl)amino)propanoic acid (20 mg, 0.055 mmol) in dimethylformamide (0.3 mL) was added HATU (31 mg, 0.082 mmol), N,N-diisopropylethylamine (0.1 mL, 0.57 mmol) and benzylamine (9 mg, 0.082 mmol). The reaction is stirred at rt for 16 hrs. Water (5 mL) was added and the organics were extracted into 10% methanol in dichloromethane (2×5 mL). The combined organics were dried ($Na_2SO_4$) and concentrated. The resulting residue was purified by silica chromatography using 0-15% MeOH/$CH_2Cl_2$ to afford the titled compound (MS: $[M+1]^+$ 454).

The following compounds are prepared essentially by the same method described above to prepare I-193.

| I-# | Starting Material | Structure | MS [M + 1]+ |
|---|---|---|---|
| I-194 | 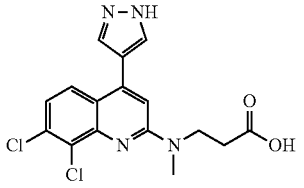 [SMILES: CN(CCC(=O)O)c1cc(-c2cn[nH]c2)c2ccc(Cl)c(Cl)c2n1] 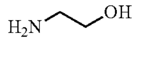 | 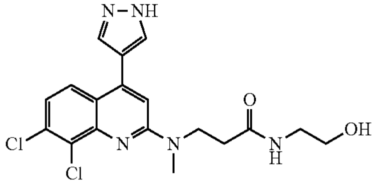 [SMILES: CN(CCC(=O)NCCO)c1cc(-c2cn[nH]c2)c2ccc(Cl)c(Cl)c2n1] | 408 |
| I-195 | 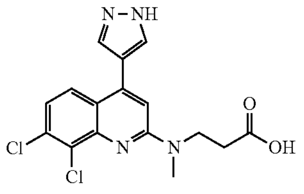 [SMILES: CN(CCC(=O)O)c1cc(-c2cn[nH]c2)c2ccc(Cl)c(Cl)c2n1] 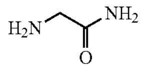 | 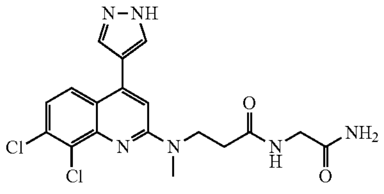 [SMILES: CN(CCC(=O)NCC(N)=O)c1cc(-c2cn[nH]c2)c2ccc(Cl)c(Cl)c2n1] | 421 |

-continued

| I-# | Starting Material | | Structure | MS [M + 1]+ |
|---|---|---|---|---|
| I-197 | 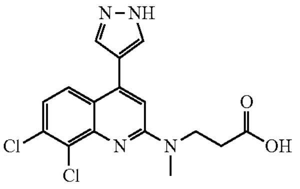 [SMILES: CN(CCC(=O)O)c1cc(-c2cn[nH]c2)c2ccc(Cl)c(Cl)c2n1] | 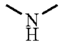 | 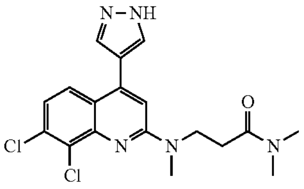 [SMILES: CN(C)C(=O)CCN(C)c1cc(-c2cn[nH]c2)c2ccc(Cl)c(Cl)c2n1] | 392 |
| I-198 | 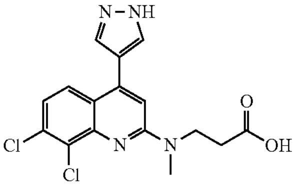 [SMILES: CN(CCC(=O)O)c1cc(-c2cn[nH]c2)c2ccc(Cl)c(Cl)c2n1] | 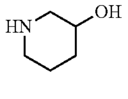 | 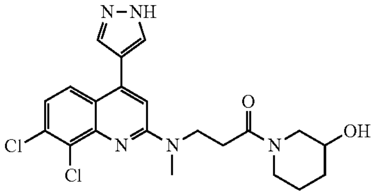 [SMILES: CN(CCC(=O)N1CCCC(O)C1)c1cc(-c2cn[nH]c2)c2ccc(Cl)c(Cl)c2n1] | 448 |
| I-199 | 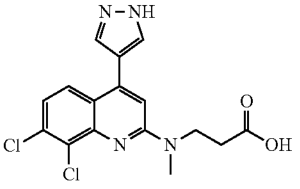 [SMILES: CN(CCC(=O)O)c1cc(-c2cn[nH]c2)c2ccc(Cl)c(Cl)c2n1] | 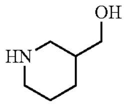 | 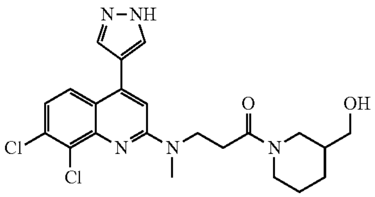 [SMILES: CN(CCC(=O)N1CCCC(CO)C1)c1cc(-c2cn[nH]c2)c2ccc(Cl)c(Cl)c2n1] | 462 |

Example 30: Synthesis of (S)-((1-(7,8-dichloro-4-(1H-imidazol-1-yl)quinolin-2-yl)pyrrolidin-2-yl) methyl)carbamate (I-153)

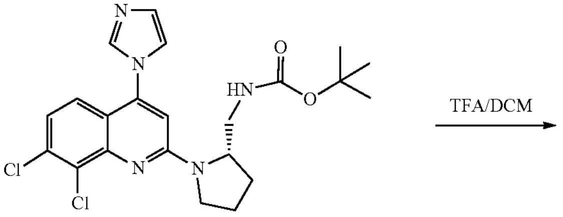

I-152

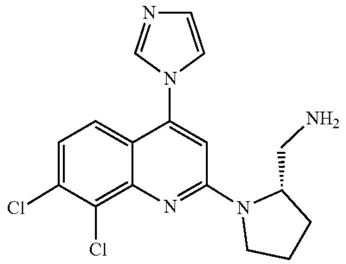

I-153

To a solution of tert-butyl (S)-((1-(7,8-dichloro-4-(1H-imidazol-1-yl)quinolin-2-yl)pyrrolidin-2-yl)methyl)carbamate (174 mg) in DCM (2 mL) was added TFA (0.4 mL). After the resultant solution was stirred over 6 hours, evaporation under reduced pressure and lyophilization afforded the title compound (200 mg) as brown powder-tert-butyl (S)-((1-(7,8-dichloro-4-(1H-imidazol-1-yl)quinolin-2-yl) pyrrolidin-2-yl)methyl)carbamate (MS: $[M+1]^+$ 362).

Example 31: Synthesis of (S)—N-((1-(7,8-dichloro-4-(1H-imidazol-1-yl)quinolin-2-yl)pyrrolidin-2-yl) methyl)-2-hydroxyacetamide (I-154)

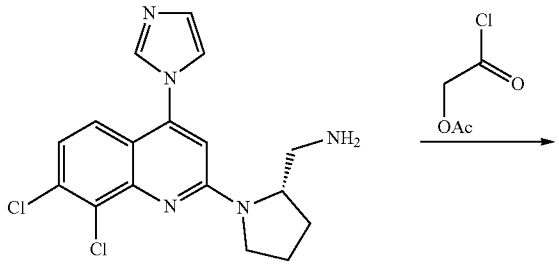

I-153

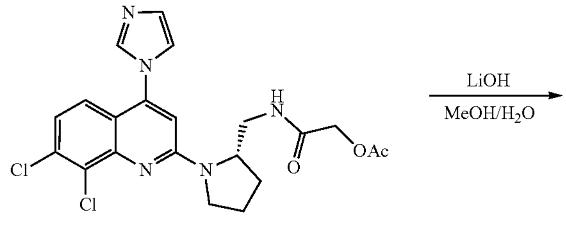

-continued

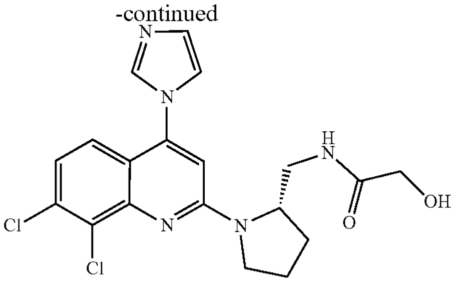

I-154

To a solution of (S)-(1-(7,8-dichloro-4-(1H-imidazol-1-yl)quinolin-2-yl)pyrrolidin-2-yl)methanamine TFA salt (50 mg) in DCM (0.4 mL) and TEA (0.05 mL) was added 2-chloro-2-oxoethyl acetate (17 mg). After stirred over 4 hours, the reaction mixture was diluted with EtOAc (20 mL) and the organic layer was washed with $NaHCO_3$ and brine. A column chromatography with a gradient of hexane and 5% MeOH in EtOAc afforded the desired intermediate 13.4 mg (MS: $[M+1]^+$ 462.). The intermediate (13.4 mg) was dissolved in MeOH (0.4 mL) and water (0.1 mL) and treated with LiOH $H_2O$ (4 mg) over 2 hours. The reaction mixture was diluted with water (1 mL) and acidified with HOAc (0.02 mL) to precipitate out the product which was further lyophilized to the final product 2260 (7.8 mg) as a powder (MS: $[M+1]^+$ 420).

The following compounds are prepared essentially by the same method described above to prepare I-154.

| I-# | Starting Materials | Structure | MS $[M + 1]^+$ |
|---|---|---|---|
| I-151 | 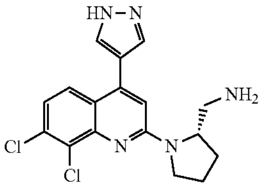 [SMILES: NC[C@@H]1CCCN1c1cc(-c2cn[nH]c2)c2ccc(Cl)c(Cl)c2n1] 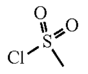 | 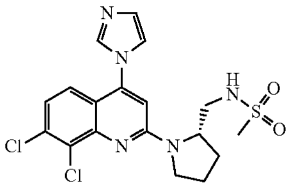 [SMILES: CS(=O)(=O)NC[C@@H]1CCCN1c1cc(-n2ccnc2)c2ccc(Cl)c(Cl)c2n1] | 440 |
| I-390 | 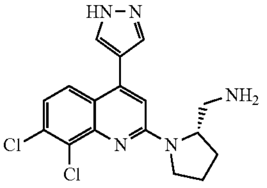 [SMILES: NC[C@@H]1CCCN1c1cc(-c2cn[nH]c2)c2ccc(Cl)c(Cl)c2n1] 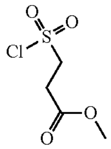 | 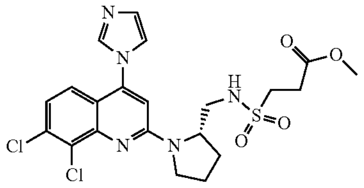 [SMILES: COC(=O)CCS(=O)(=O)NC[C@@H]1CCCN1c1cc(-n2ccnc2)c2ccc(Cl)c(Cl)c2n1] | 512 |
| I-335 | 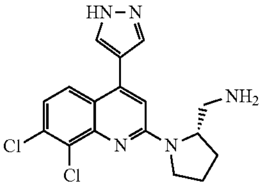 [SMILES: NC[C@@H]1CCCN1c1cc(-c2cn[nH]c2)c2ccc(Cl)c(Cl)c2n1] 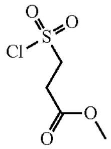 | 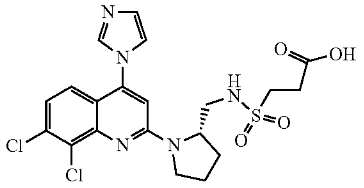 [SMILES: O=C(O)CCS(=O)(=O)NC[C@@H]1CCCN1c1cc(-n2ccnc2)c2ccc(Cl)c(Cl)c2n1] | 498 |
| I-391 | 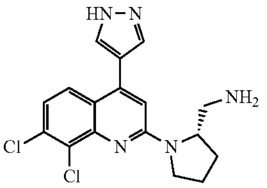 [SMILES: NC[C@@H]1CCCN1c1cc(-c2cn[nH]c2)c2ccc(Cl)c(Cl)c2n1] 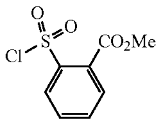 | 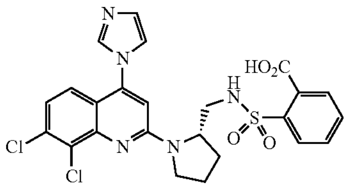 [SMILES: O=C(O)c1ccccc1S(=O)(=O)NC[C@@H]1CCCN1c1cc(-n2ccnc2)c2ccc(Cl)c(Cl)c2n1] | 546 |
| I-392 | 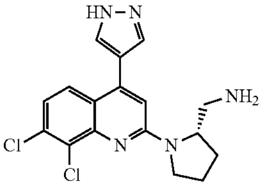 [SMILES: NC[C@@H]1CCCN1c1cc(-c2cn[nH]c2)c2ccc(Cl)c(Cl)c2n1] 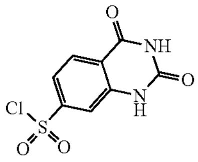 [SMILES: O=c1[nH]c(=O)c2ccc(S(=O)(=O)Cl)cc2[nH]1] | 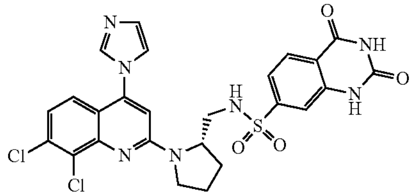 [SMILES: O=c1[nH]c(=O)c2ccc(S(=O)(=O)NC[C@@H]3CCCN3c3cc(-n4ccnc4)c4ccc(Cl)c(Cl)c4n3)cc2[nH]1] | 586 |
| I-393 | 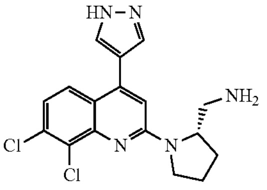 [SMILES: NC[C@@H]1CCCN1c1cc(-c2cn[nH]c2)c2ccc(Cl)c(Cl)c2n1] 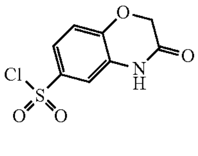 [SMILES: O=C1COc2ccc(S(=O)(=O)Cl)cc2N1] | 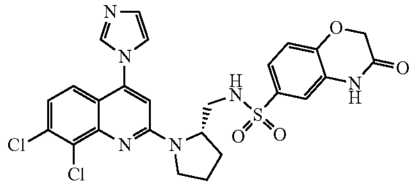 [SMILES: O=C1COc2ccc(S(=O)(=O)NC[C@@H]3CCCN3c3cc(-n4ccnc4)c4ccc(Cl)c(Cl)c4n3)cc2N1] | 573 |

-continued
| I-# | Starting Materials | | Structure | MS [M + 1]+ |
|---|---|---|---|---|
| I-637 | 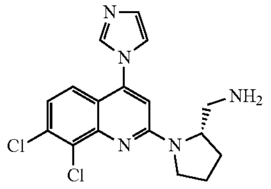 [SMILES: NC[C@@H]1CCCN1c1cc(-n2ccnc2)c2ccc(Cl)c(Cl)c2n1] | 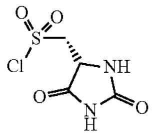 | 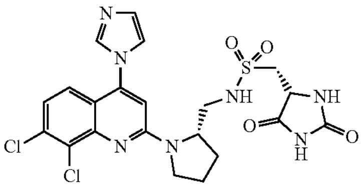 | 538 |
| I-638 | 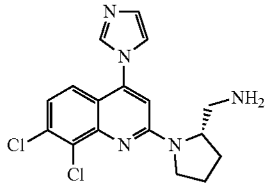 [SMILES: NC[C@@H]1CCCN1c1cc(-n2ccnc2)c2ccc(Cl)c(Cl)c2n1] | 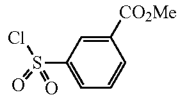 [SMILES: COC(=O)c1cccc(S(=O)(=O)Cl)c1] | 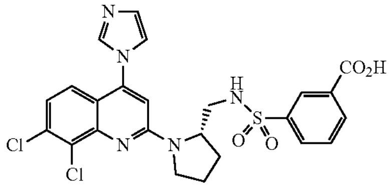 [SMILES: O=C(O)c1cccc(S(=O)(=O)NC[C@@H]2CCCN2c2cc(-n3ccnc3)c3ccc(Cl)c(Cl)c3n2)c1] | 546 |
| I-639 | 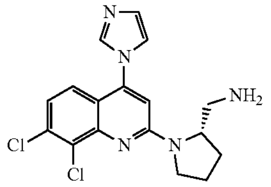 [SMILES: NC[C@@H]1CCCN1c1cc(-n2ccnc2)c2ccc(Cl)c(Cl)c2n1] | 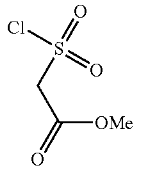 | 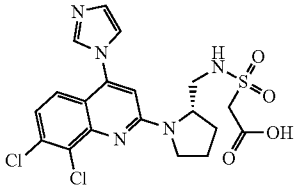 [SMILES: O=C(O)CS(=O)(=O)NC[C@@H]1CCCN1c1cc(-n2ccnc2)c2ccc(Cl)c(Cl)c2n1] | 484 |
| I-640 | 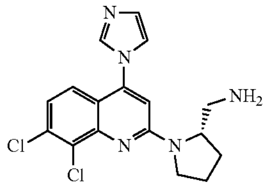 [SMILES: NC[C@@H]1CCCN1c1cc(-n2ccnc2)c2ccc(Cl)c(Cl)c2n1] | 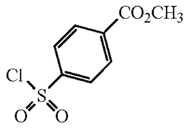 [SMILES: COC(=O)c1ccc(S(=O)(=O)Cl)cc1] | 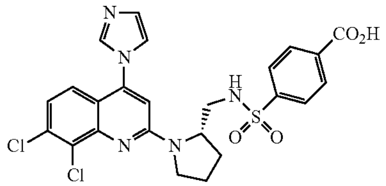 [SMILES: O=C(O)c1ccc(S(=O)(=O)NC[C@@H]2CCCN2c2cc(-n3ccnc3)c3ccc(Cl)c(Cl)c3n2)cc1] | 546 |
| I-641 | 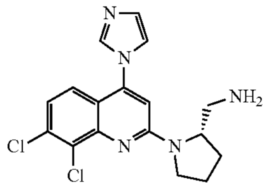 [SMILES: NC[C@@H]1CCCN1c1cc(-n2ccnc2)c2ccc(Cl)c(Cl)c2n1] | 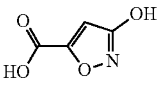 | 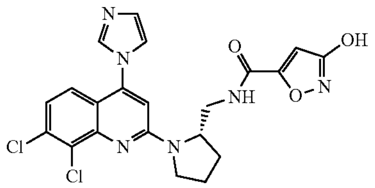 [SMILES: O=C(NC[C@@H]1CCCN1c1cc(-n2ccnc2)c2ccc(Cl)c(Cl)c2n1)c1cc(O)no1] | 473 |
Example 32: Synthesis of N-(2-((7,8-dichloro-4-(1H-imidazol-1-yl)quinolin-2-yl)(methyl)amino)ethyl)aminosulfonamide (I-223)
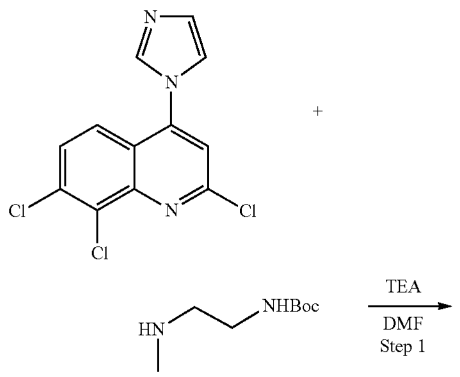
-continued
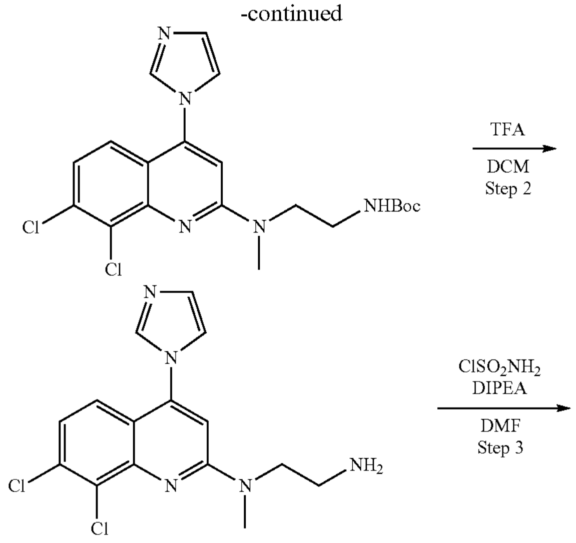

-continued

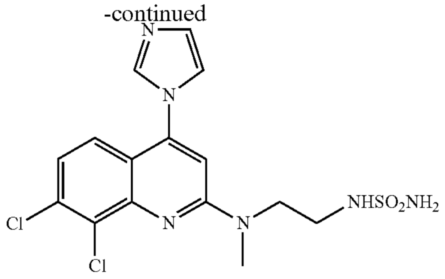

I-223

Step 1: tert-Butyl 2-((7,8-dichloro-4-(1H-imidazol-1-yl)quinolin-2-yl)(methyl)amino)ethylcarbamate. To a vial were added 2,7,8-trichloro-4-(1H-imidazol-1-yl)quinoline (100 mg, 0.335 mmol), tert-butyl 2-(methylamino)ethylcarbamate (175 mg, 1.01 mmol), DMF (2.0 mL), and TEA (187 µl, 1.34 mmol). The resulting reaction mixture was stirred at 70° C. for 3 h and cooled to room temperature, followed by adding $H_2O$ (20 mL). The cloud mixture was centrifuged and the residue was extracted by DCM (2×10 mL). The organic phase was washed by $H_2O$ (10 mL), brine (10 mL), dried over $Na_2SO_4$, concentrated to afford an off-white solid (132 mg) (MS: $[M+1]^+$ 436).

Step 2: N-(2-aminoethyl)-7,8-dichloro-4-(1H-imidazol-1-yl)-N-methylquinolin-2-amine. To a vial were added tert-butyl 2-((7,8-dichloro-4-(1H-imidazol-1-yl)quinolin-2-yl)(methyl)amino)ethylcarbamate (131 mg, 0.300 mmol), DCM (1.5 mL) and TFA (1.5 mL). The resulting mixture was stirred at room temperature for 2 hrs. Then all volatile solvents were removed under reduced pressure and the residue was dried under high vacuum to afford the title product. The crude was used in next step.

Step 3: N-(2-((7,8-dichloro-4-(1H-imidazol-1-yl)quinolin-2-yl)(methyl)amino)ethyl)aminosulfonamide. To a vial were added N-(2-aminoethyl)-7,8-dichloro-4-(1H-imidazol-1-yl)-N-methylquinolin-2-amine (12.5 mg, 0.0373 mmol), DMF (0.5 mL), sulfamoyl chloride (26 mg, 0.224 mmol) and DIPEA (52 µl, 0.296 mmol). The resulting reaction mixture was stirred at 50° C. overnight. The reaction mixture was diluted by ethyl acetate (15 mL). The organic phase was washed by $H_2O$ (3×5 mL), brine (5 mL), dried over $Na_2SO_4$. After concentration, 30% of the crude was purified by PTLC to afford the title product as an off-white solid (1.3 mg) (MS: $[M+1]^+$ 415).

The following compounds are prepared essentially by the same method described above to prepare I-223.

| I-# | Starting Material | Structure | MS [M + 1]+ |
|---|---|---|---|
| I-224 | 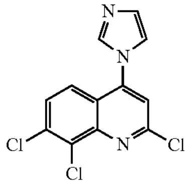 [SMILES: Clc1cc(-n2ccnc2)c2ccc(Cl)c(Cl)c2n1] 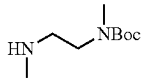 | 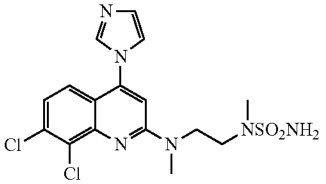 | 429 |
| I-346 | 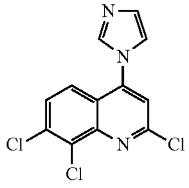 [SMILES: Clc1cc(-n2ccnc2)c2ccc(Cl)c(Cl)c2n1] 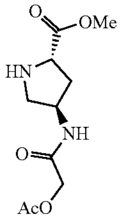 | 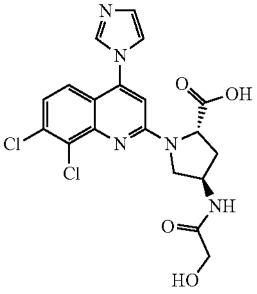 [SMILES: O=C(CO)N[C@@H]1C[C@@H](C(=O)O)N(c2cc(-n3ccnc3)c3ccc(Cl)c(Cl)c3n2)C1] | 450 |
| I-347 | 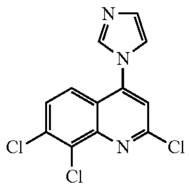 [SMILES: Clc1cc(-n2ccnc2)c2ccc(Cl)c(Cl)c2n1] 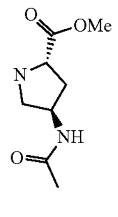 | 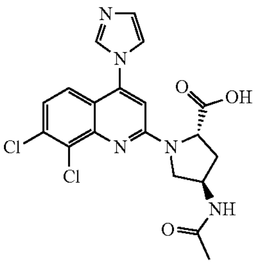 | 434 |

-continued
| I-# | Starting Material | | Structure | MS [M + 1]+ |
|---|---|---|---|---|
| I-349 | 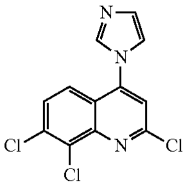 [SMILES: Clc1cc(-n2ccnc2)c2ccc(Cl)c(Cl)c2n1] | 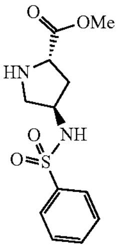 | 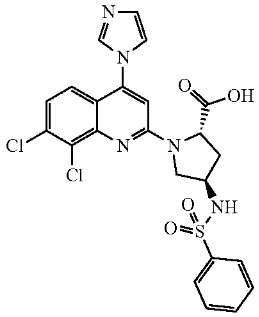 [SMILES: O=C(O)[C@@H]1C[C@@H](NS(=O)(=O)c2ccccc2)CN1c1cc(-n2ccnc2)c2ccc(Cl)c(Cl)c2n1] | 532 |
| I-350 | 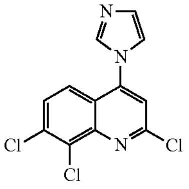 [SMILES: Clc1cc(-n2ccnc2)c2ccc(Cl)c(Cl)c2n1] | 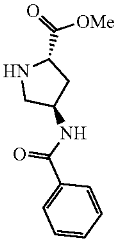 | 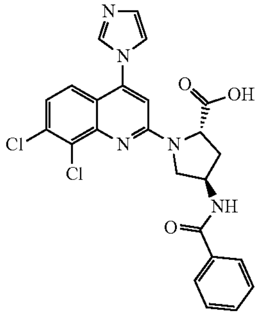 [SMILES: O=C(N[C@@H]1C[C@@H](C(=O)O)N(c2cc(-n3ccnc3)c3ccc(Cl)c(Cl)c3n2)C1)c1ccccc1] | 496 |
| I-351 | 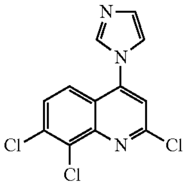 [SMILES: Clc1cc(-n2ccnc2)c2ccc(Cl)c(Cl)c2n1] | 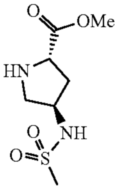 | 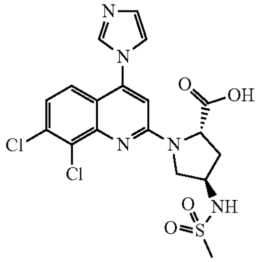 [SMILES: CS(=O)(=O)N[C@@H]1C[C@@H](C(=O)O)N(c2cc(-n3ccnc3)c3ccc(Cl)c(Cl)c3n2)C1] | 470 |
The following compounds were prepared essentially by the same method to prepare I-223. Some analogues were prepared from a general amide formation and a following hydrolysis of an ester to form the corresponding acid.
| I-# | Starting Material | | Structure | MS [M + 1]+ |
|---|---|---|---|---|
| I-609 | 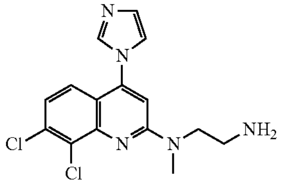 [SMILES: CN(CCN)c1cc(-n2ccnc2)c2ccc(Cl)c(Cl)c2n1] | 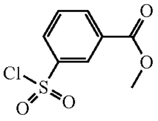 | 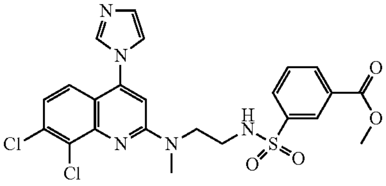 [SMILES: COC(=O)c1cccc(S(=O)(=O)NCCN(C)c2cc(-n3ccnc3)c3ccc(Cl)c(Cl)c3n2)c1] | 534 |
| I-610 | 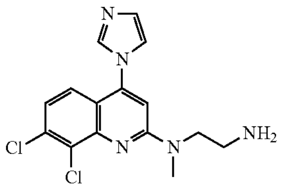 [SMILES: CN(CCN)c1cc(-n2ccnc2)c2ccc(Cl)c(Cl)c2n1] | 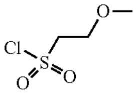 | 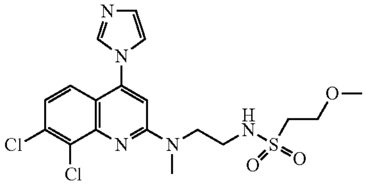 [SMILES: COCCS(=O)(=O)NCCN(C)c1cc(-n2ccnc2)c2ccc(Cl)c(Cl)c2n1] | 458 |

-continued
| I-# | Starting Material | | Structure | MS [M + 1]+ |
|---|---|---|---|---|
| I-611 | 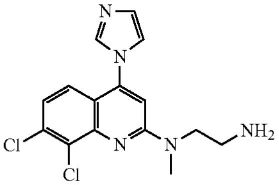 [SMILES: CN(CCN)c1cc(-n2ccnc2)c2ccc(Cl)c(Cl)c2n1] | 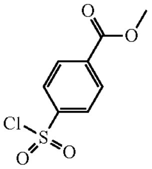 | 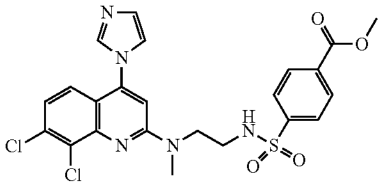 [SMILES: COC(=O)c1ccc(S(=O)(=O)NCCN(C)c2cc(-n3ccnc3)c3ccc(Cl)c(Cl)c3n2)cc1] | 534 |
| I-612 | 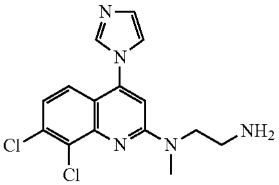 [SMILES: CN(CCN)c1cc(-n2ccnc2)c2ccc(Cl)c(Cl)c2n1] | 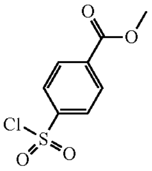 | 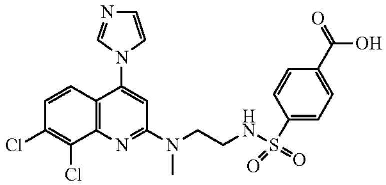 [SMILES: CN(CCNS(=O)(=O)c1ccc(C(=O)O)cc1)c1cc(-n2ccnc2)c2ccc(Cl)c(Cl)c2n1] | 520 |
| I-613 | 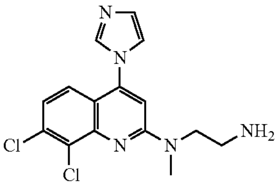 [SMILES: CN(CCN)c1cc(-n2ccnc2)c2ccc(Cl)c(Cl)c2n1] | 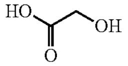 | 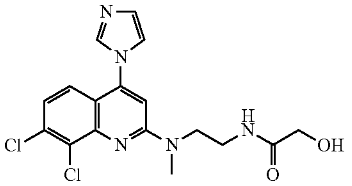 [SMILES: CN(CCNC(=O)CO)c1cc(-n2ccnc2)c2ccc(Cl)c(Cl)c2n1] | 394 |
| I-614 | 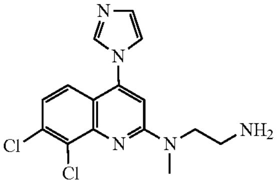 [SMILES: CN(CCN)c1cc(-n2ccnc2)c2ccc(Cl)c(Cl)c2n1] | 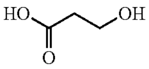 | 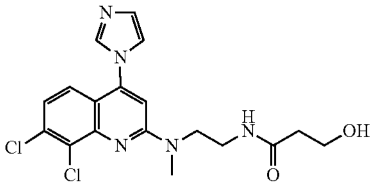 [SMILES: CN(CCNC(=O)CCO)c1cc(-n2ccnc2)c2ccc(Cl)c(Cl)c2n1] | 408 |
| I-615 | 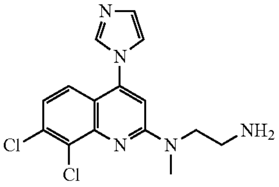 [SMILES: CN(CCN)c1cc(-n2ccnc2)c2ccc(Cl)c(Cl)c2n1] | 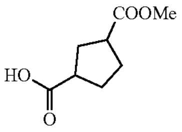 [SMILES: COC(=O)C1CCC(C(=O)O)C1] | 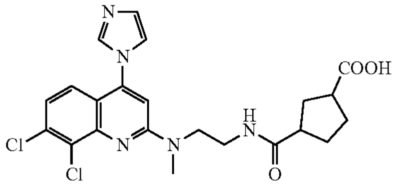 [SMILES: CN(CCNC(=O)C1CCC(C(=O)O)C1)c1cc(-n2ccnc2)c2ccc(Cl)c(Cl)c2n1] | 476 |
| I-616 | 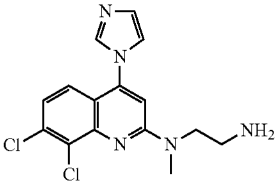 [SMILES: CN(CCN)c1cc(-n2ccnc2)c2ccc(Cl)c(Cl)c2n1] | 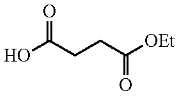 | 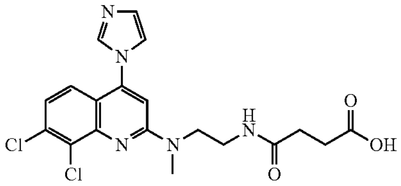 [SMILES: CN(CCNC(=O)CCC(=O)O)c1cc(-n2ccnc2)c2ccc(Cl)c(Cl)c2n1] | 436 |
| I-617 | 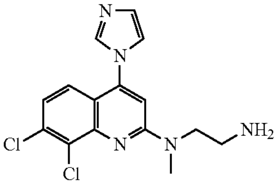 [SMILES: CN(CCN)c1cc(-n2ccnc2)c2ccc(Cl)c(Cl)c2n1] | 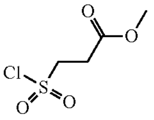 | 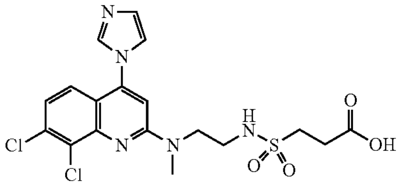 [SMILES: CN(CCNS(=O)(=O)CCC(=O)O)c1cc(-n2ccnc2)c2ccc(Cl)c(Cl)c2n1] | 472 |
| I-618 | 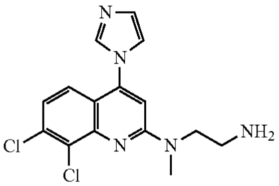 [SMILES: CN(CCN)c1cc(-n2ccnc2)c2ccc(Cl)c(Cl)c2n1] | 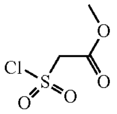 | 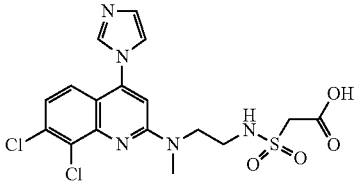 [SMILES: CN(CCNS(=O)(=O)CC(=O)O)c1cc(-n2ccnc2)c2ccc(Cl)c(Cl)c2n1] | 458 |

-continued
| I-# | Starting Material | Structure | MS [M + 1]+ |
|---|---|---|---|
| I-619 | 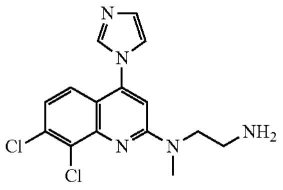 [SMILES: CN(CCN)c1cc(-n2ccnc2)c2ccc(Cl)c(Cl)c2n1] 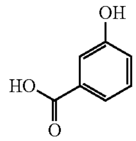 | 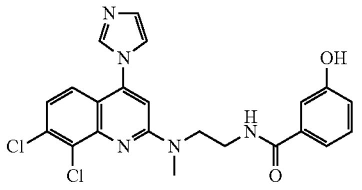 [SMILES: CN(CCNC(=O)c1cccc(O)c1)c1cc(-n2ccnc2)c2ccc(Cl)c(Cl)c2n1] | 456 |
| I-620 | 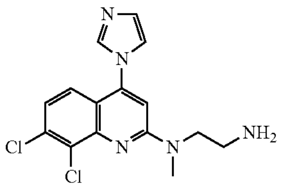 [SMILES: CN(CCN)c1cc(-n2ccnc2)c2ccc(Cl)c(Cl)c2n1] 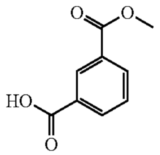 | 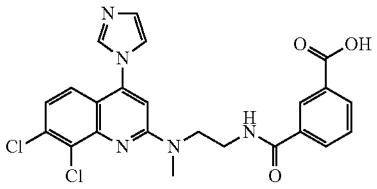 [SMILES: CN(CCNC(=O)c1cccc(C(=O)O)c1)c1cc(-n2ccnc2)c2ccc(Cl)c(Cl)c2n1] | 484 |
| I-621 | 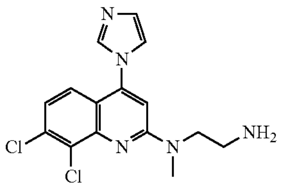 [SMILES: CN(CCN)c1cc(-n2ccnc2)c2ccc(Cl)c(Cl)c2n1] 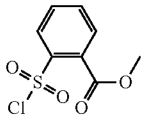 | 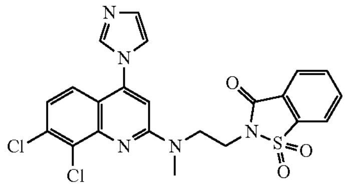 [SMILES: CN(CCN1C(=O)c2ccccc2S1(=O)=O)c1cc(-n2ccnc2)c2ccc(Cl)c(Cl)c2n1] | 502 |
| I-622 | 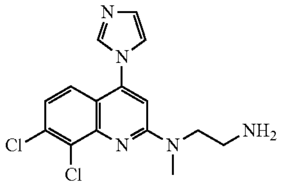 [SMILES: CN(CCN)c1cc(-n2ccnc2)c2ccc(Cl)c(Cl)c2n1] 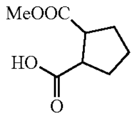 | 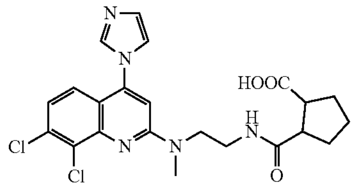 [SMILES: CN(CCNC(=O)C1CCCC1C(=O)O)c1cc(-n2ccnc2)c2ccc(Cl)c(Cl)c2n1] | 476 |
| I-623 | 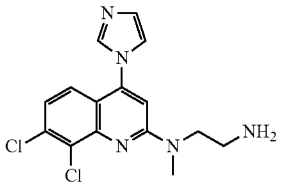 [SMILES: CN(CCN)c1cc(-n2ccnc2)c2ccc(Cl)c(Cl)c2n1] 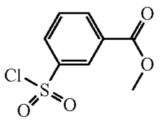 | 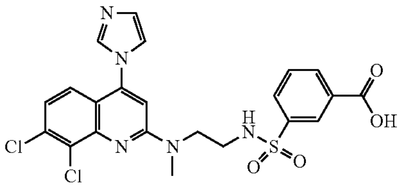 [SMILES: CN(CCNS(=O)(=O)c1cccc(C(=O)O)c1)c1cc(-n2ccnc2)c2ccc(Cl)c(Cl)c2n1] | 520 |
Example 33: Synthesis of (S)-1-(7,8-dichloro-4-(1H-imidazol-1-yl)quinolin-2-yl)piperidin-3-ol (I-119)
-continued
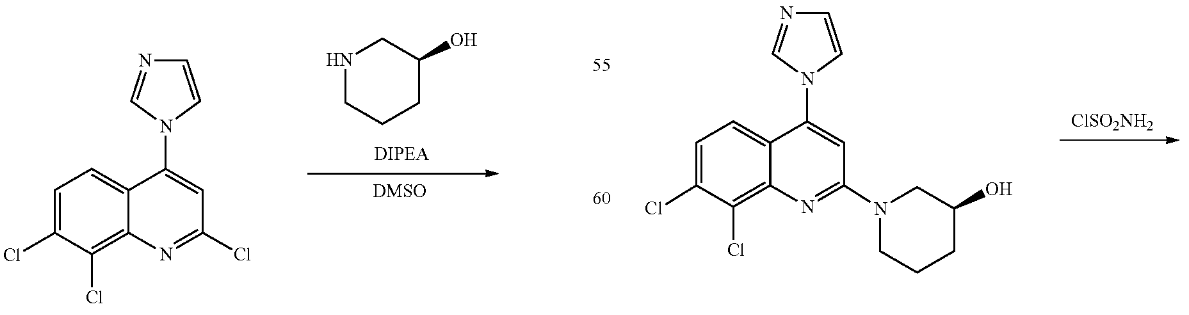

-continued

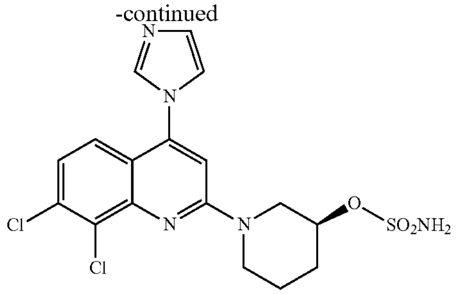

I-119

Step 1: 1-(7,8-Dichloro-4-(1H-imidazol-1-yl)quinolin-2-yl)piperidin-3-ol was the same as that for compound I-353 (MS: $[M+1]^+$ 263).

Step 2: (S)-1-(7,8-dichloro-4-(1H-imidazol-1-yl)quinolin-2-yl)piperidin-3-yl sulfamate. To a vial were added 1-(7,8-dichloro-4-(1H-imidazol-1-yl)quinolin-2-yl)piperidin-3-ol (20 mg, 0.0551 mmol), DMF (0.3 mL) and TEA (50 μl, 0.364 mmol). A stock solution of sulfamoyl chloride in DMF (38 mg/100 μl, 0.33 mmol) was added. The resulting reaction mixture was stirred at 100° C. for 6 hrs and cooled to room temperature followed by adding 4 mL of water. The mixture was centrifuged and the residue was purified by PTLC (30% MeOH/DCM) to afford the desired product as white solid (1 mg) (MS: $[M+1]^+$ 442).

The following compounds are prepared essentially by the same methods as for I-223.

-continued

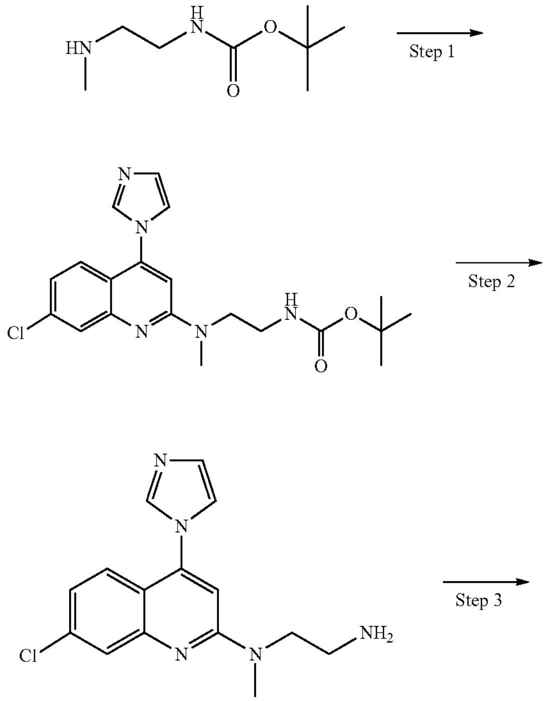

| I-# | Starting Material | | Structure | MS [M + 1]+ |
|---|---|---|---|---|
| I-118 | 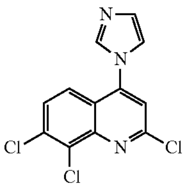 [SMILES: Clc1cc(-n2ccnc2)c2ccc(Cl)c(Cl)c2n1] | 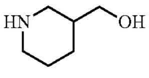 | 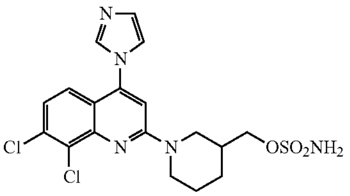 | 456 |
| I-96 | 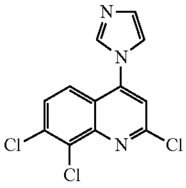 [SMILES: Clc1cc(-n2ccnc2)c2ccc(Cl)c(Cl)c2n1] | 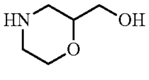 | 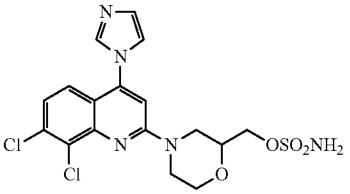 | 458 |

Example 34: Synthesis of N-(2-((7-chloro-4-(1H-imidazol-1-yl)quinolin-2-yl)(methyl)amino)ethyl)cyclopropanesulfonamide (I-226)

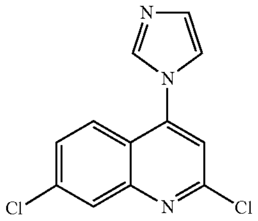

+

-continued

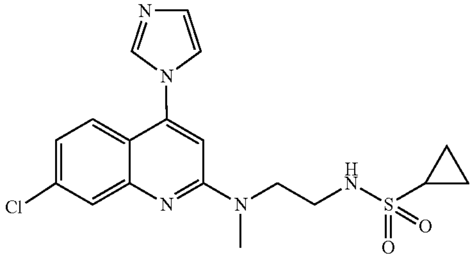

I-226

Step 1: tert-Butyl (2-((7-chloro-4-(1H-imidazol-1-yl)quinolin-2-yl)(methyl)amino)ethyl)carbamate. To a solution of 2,7-dichloro-4-(1H-imidazol-1-yl)quinoline (528 mg, 2.0 mmol) in DMF (2 mL) was added tert-butyl (2-(methylamino)ethyl)carbamate (871 mg, mmol) and Hunig's base (0.5 mL). The solution was stirred at 95° C. for 16 h. After cooling down to room temperature, water (10 mL) was added and the organics were extracted into 10% Methanol/dichloromethane (2×5 mL). The combined organics were dried ($Na_2SO_4$) and concentrated. The resulting residue was purified by silica column chromatography using 50-100% EtOAc/Hex to afford tert-butyl (2-((7-chloro-4-(1H-imidazol-1-yl)quinolin-2-yl)(methyl)amino)ethyl)carbamate as a solid (MS: $[M+1]^+$-Boc 302).

Step 2: N1-(7-Chloro-4-(1H-imidazol-1-yl)quinolin-2-yl)-N1-methylethane-1,2-diamine. To a vial was added tert-butyl (2-((7-chloro-4-(1H-imidazol-1-yl)quinolin-2-yl)(methyl)amino)ethyl)carbamate (120 mg, 0.30 mmol). Hydrochloric acid (4.0M in dioxane (1.0 mL) was added and the reaction allowed to stir at rt for 16 h. The resulting solids were filtered off and dried to afford N1-(7-chloro-4-(1H-imidazol-1-yl)quinolin-2-yl)-N1-methylethane-1,2-diamine hydrochloride as a solid (MS: $[M+1]^+$ 302).

Step 3: N-(2-((7-Chloro-4-(1H-imidazol-1-yl) quinolin-2-yl) (methyl) amino)ethyl) cyclopropanesulfonamide. To a vial was added N1-(7-chloro-4-(1H-imidazol-1-yl)quinolin-2-yl)-N1-methylethane-1,2-diamine hydrochloride (20 mg, 0.06 mmol) in DMF (0.5 mL) and Hunig's base (0.1 mL). Cyclopropanesulfonyl chloride (17 mg, 0.12 mmol) was added and the reaction allowed to stir at rt for 16h. Water (5 mL) was added and the aqueous extracted with ethyl acetate (2×5 mL). The combined organics were dried ($Na_2SO_4$) then purified by silica chromatography using 0-10% MeOH/$CH_2Cl_2$ to afford 12 mg N-(2-((7-chloro-4-(1H-imidazol-1-yl)quinolin-2-yl)(methyl)amino)ethyl)cyclopropanesulfonamide (MS: $[M+1]^+$ 406).

The following compounds are prepared essentially by the same method described above to prepare I-226.

| I-# | Starting Material | Structure | MS $[M + 1]^+$ |
|---|---|---|---|
| I-227 | 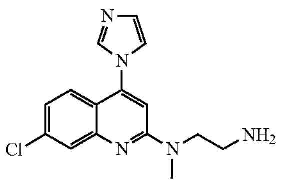 [SMILES: CN(CCN)c1cc(-n2ccnc2)c2ccc(Cl)cc2n1] 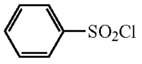 | 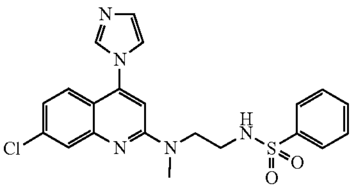 [SMILES: CN(CCNS(=O)(=O)c1ccccc1)c1cc(-n2ccnc2)c2ccc(Cl)cc2n1] | 442 |
| I-228 | 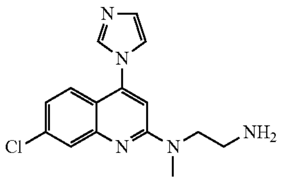 [SMILES: CN(CCN)c1cc(-n2ccnc2)c2ccc(Cl)cc2n1] 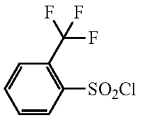 | 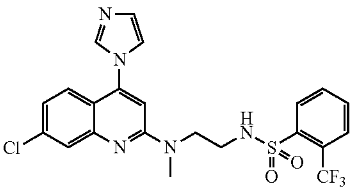 [SMILES: CN(CCNS(=O)(=O)c1ccccc1C(F)(F)F)c1cc(-n2ccnc2)c2ccc(Cl)cc2n1] | 510 |
| I-394 | 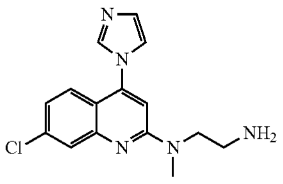 [SMILES: CN(CCN)c1cc(-n2ccnc2)c2ccc(Cl)cc2n1] 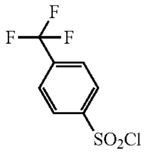 | 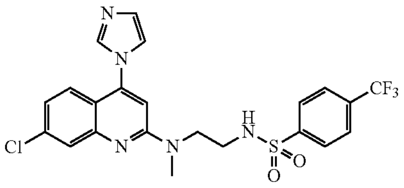 [SMILES: CN(CCNS(=O)(=O)c1ccc(C(F)(F)F)cc1)c1cc(-n2ccnc2)c2ccc(Cl)cc2n1] | 510 |
| I-232 | 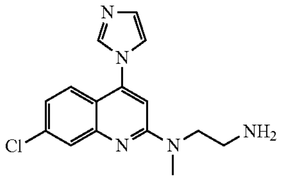 [SMILES: CN(CCN)c1cc(-n2ccnc2)c2ccc(Cl)cc2n1] 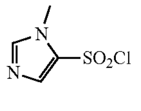 | 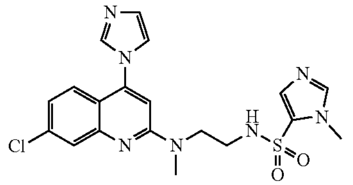 [SMILES: CN(CCNS(=O)(=O)c1cncn1C)c1cc(-n2ccnc2)c2ccc(Cl)cc2n1] | 446 |
| I-229 | 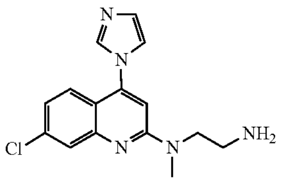 [SMILES: CN(CCN)c1cc(-n2ccnc2)c2ccc(Cl)cc2n1] 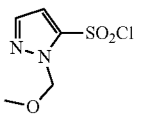 | 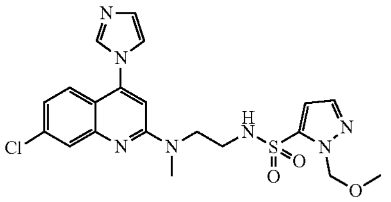 [SMILES: COCn1nccc1S(=O)(=O)NCCN(C)c1cc(-n2ccnc2)c2ccc(Cl)cc2n1] | 476 |

-continued
| I-# | Starting Material | Structure | MS [M + 1]$^+$ |
| --- | --- | --- | --- |
| I-230 | 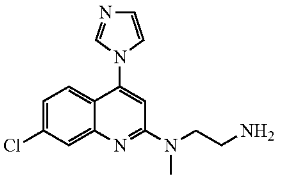 [SMILES: CN(CCN)c1cc(-n2ccnc2)c2ccc(Cl)cc2n1] 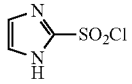 | 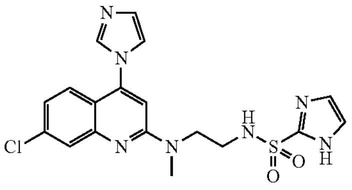 [SMILES: CN(CCNS(=O)(=O)c1ncc[nH]1)c1cc(-n2ccnc2)c2ccc(Cl)cc2n1] | 432 |
| I-231 | 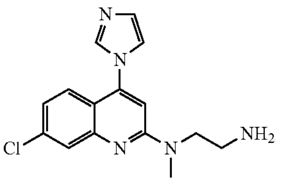 [SMILES: CN(CCN)c1cc(-n2ccnc2)c2ccc(Cl)cc2n1] 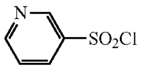 | 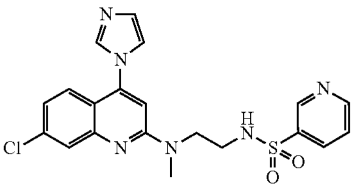 [SMILES: CN(CCNS(=O)(=O)c1cccnc1)c1cc(-n2ccnc2)c2ccc(Cl)cc2n1] | 443 |
| I-236 | 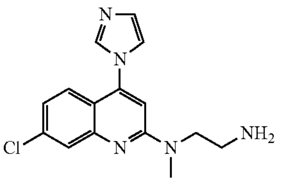 [SMILES: CN(CCN)c1cc(-n2ccnc2)c2ccc(Cl)cc2n1] 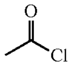 | 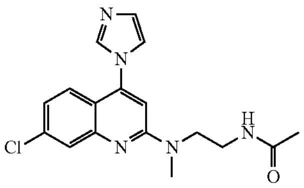 [SMILES: CC(=O)NCCN(C)c1cc(-n2ccnc2)c2ccc(Cl)cc2n1] | 344 |
| I-237 | 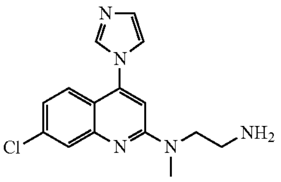 [SMILES: CN(CCN)c1cc(-n2ccnc2)c2ccc(Cl)cc2n1] 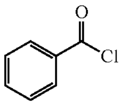 | 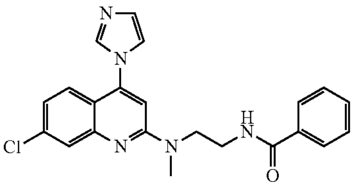 [SMILES: CN(CCNC(=O)c1ccccc1)c1cc(-n2ccnc2)c2ccc(Cl)cc2n1] | 406 |
| I-234 | 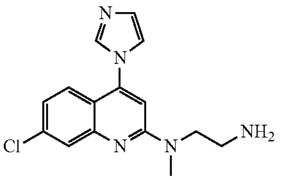 [SMILES: CN(CCN)c1cc(-n2ccnc2)c2ccc(Cl)cc2n1] 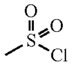 | 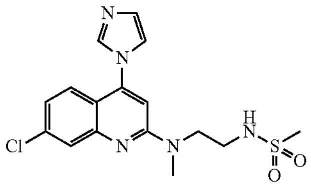 [SMILES: CN(CCNS(C)(=O)=O)c1cc(-n2ccnc2)c2ccc(Cl)cc2n1] | 380 |
| I-235 | 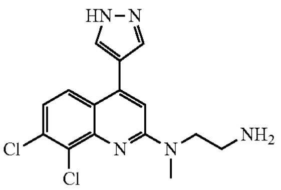 [SMILES: CN(CCN)c1cc(-c2cn[nH]c2)c2ccc(Cl)c(Cl)c2n1] 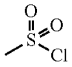 | 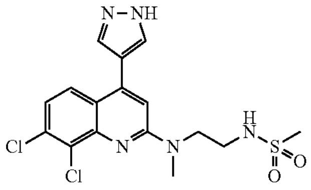 [SMILES: CN(CCNS(C)(=O)=O)c1cc(-c2cn[nH]c2)c2ccc(Cl)c(Cl)c2n1] | 414 |
| I-225 | 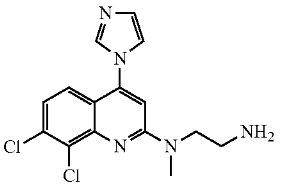 [SMILES: CN(CCN)c1cc(-n2ccnc2)c2ccc(Cl)c(Cl)c2n1] 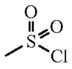 | 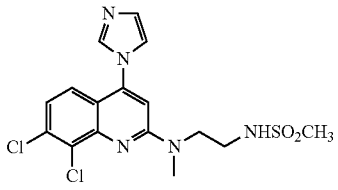 | 414 |

Example 35: Synthesis of (1-(7-chloro-4-(1H-imidazol-1-yl)quinolin-2-yl)piperidin-3-amine) (I-108)

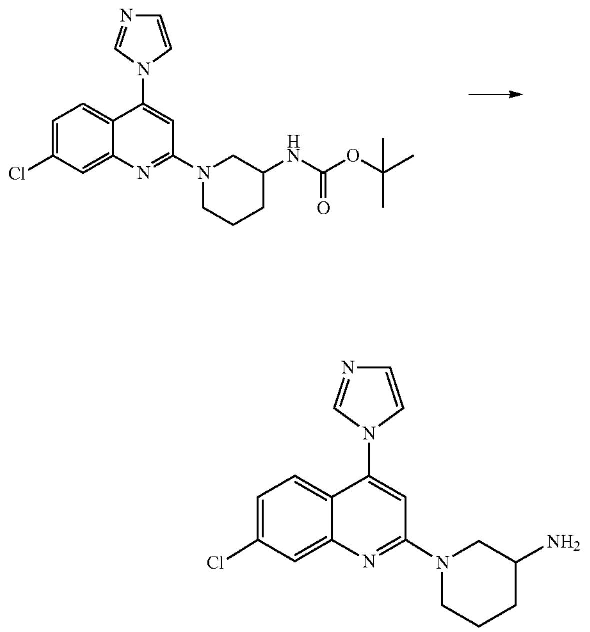

I-108

To a vial was added tert-butyl (1-(7-chloro-4-(1H-imidazol-1-yl)quinolin-2-yl)piperidin-3-yl)carbamate (90 mg, 0.21 mmol) with dichloromethane (5 mL). Trifluoromethanesulfonic acid (0.5 mL) was added and the reaction was stirred at rt for 16 h. The volatiles were removed by rotary evaporation and the crude product (1-(7-chloro-4-(1H-imidazol-1-yl)quinolin-2-yl)piperidin-3-amine) (di-TFA salt) was used directly in the next step (MS: $[M+1]^+$ 328).

Example 36: Synthesis of N-(1-(7-chloro-4-(1H-imidazol-1-yl)quinolin-2-yl)piperidin-3-yl)methanesulfonamide (I-105)

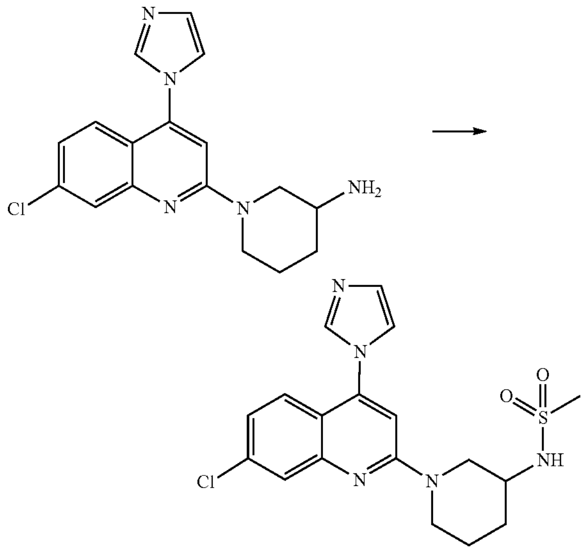

I-105

To a solution of 1-(7-chloro-4-(1H-imidazol-1-yl)quinolin-2-yl)piperidin-3-amine (di TFA salt) (55 mg, 0.10 mmol) in dichloromethane (3 mL) and DMF (0.3 mL) was added triethylamine (0.3 mL) followed by methanesulfonyl chloride (23 mg, 0.20 mmol). The mixture is stirred at rt for 3 h. Water (5 mL) was added and the organics were extracted into 10% methanol in dichloromethane (2×5 mL). The combined organics were dried ($Na_2SO_4$) and concentrated. Purification by silica chromatography afforded N-(1-(7-chloro-4-(1H-imidazol-1-yl)quinolin-2-yl)piperidin-3-yl) methanesulfonamide (33 mg) (MS: $[M+1]^+$ 406).

The following compounds are prepared essentially by the same method described above to prepare I-105.

| I-# | Starting Material | Structure | MS [M + 1]+ |
|---|---|---|---|
| I-395 | 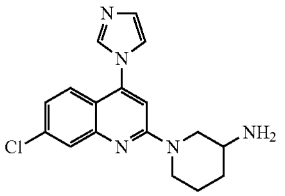 [SMILES: NC1CCCN(c2cc(-n3ccnc3)c3ccc(Cl)cc3n2)C1] 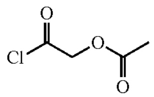 | 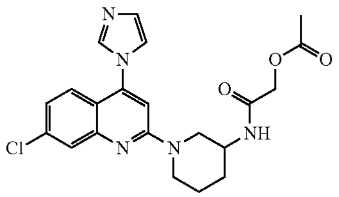 [SMILES: CC(=O)OCC(=O)NC1CCCN(c2cc(-n3ccnc3)c3ccc(Cl)cc3n2)C1] | 428 |
| I-100 | 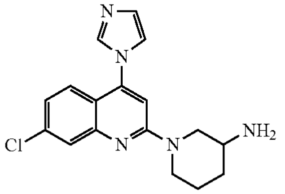 [SMILES: NC1CCCN(c2cc(-n3ccnc3)c3ccc(Cl)cc3n2)C1] 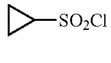 | 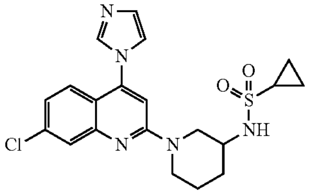 [SMILES: O=S(=O)(NC1CCCN(c2cc(-n3ccnc3)c3ccc(Cl)cc3n2)C1)C1CC1] | 432 |

-continued
| I-# | Starting Material | Structure | MS [M + 1]+ |
|---|---|---|---|
| I-103 | 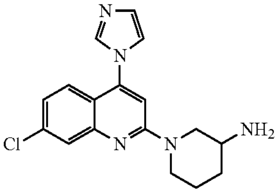 [SMILES: NC1CCCN(c2cc(-n3ccnc3)c3ccc(Cl)cc3n2)C1] 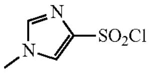 | 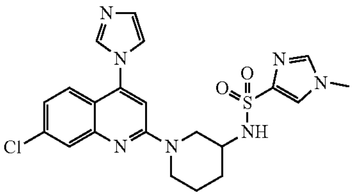 [SMILES: Cn1cnc(S(=O)(=O)NC2CCCN(c3cc(-n4ccnc4)c4ccc(Cl)cc4n3)C2)c1] | 472 |
| I-107 | 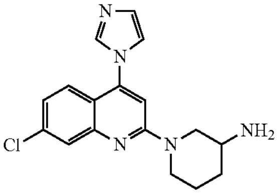 [SMILES: NC1CCCN(c2cc(-n3ccnc3)c3ccc(Cl)cc3n2)C1] 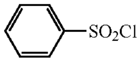 | 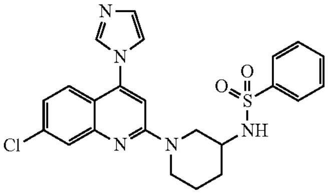 [SMILES: O=S(=O)(NC1CCCN(c2cc(-n3ccnc3)c3ccc(Cl)cc3n2)C1)c1ccccc1] | 468 |
| I-102 | 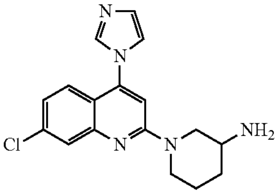 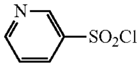 | 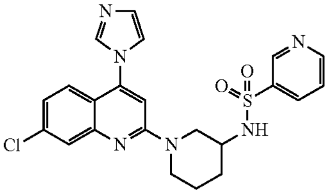 [SMILES: O=S(=O)(NC1CCCN(c2cc(-n3ccnc3)c3ccc(Cl)cc3n2)C1)c1cccnc1] | 469 |
| I-109 | 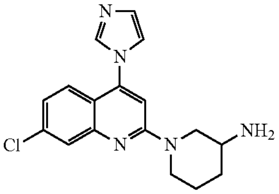 [SMILES: NC1CCCN(c2cc(-n3ccnc3)c3ccc(Cl)cc3n2)C1] 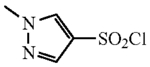 | 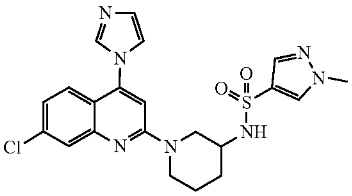 [SMILES: Cn1cc(S(=O)(=O)NC2CCCN(c3cc(-n4ccnc4)c4ccc(Cl)cc4n3)C2)cn1] | 472 |
| I-101 | 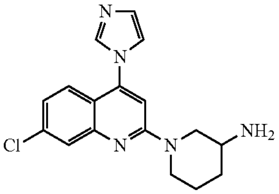 [SMILES: NC1CCCN(c2cc(-n3ccnc3)c3ccc(Cl)cc3n2)C1] 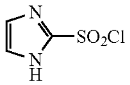 | 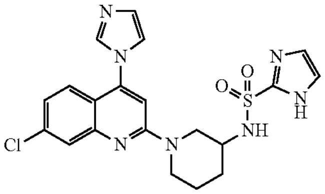 [SMILES: O=S(=O)(NC1CCCN(c2cc(-n3ccnc3)c3ccc(Cl)cc3n2)C1)c1ncc[nH]1] | 458 |
Example 37: Synthesis of 1-(7,8-dichloro-4-(1H-imidazol-1-yl)quinolin-2-yl)piperidin-3-yl hydrogen phosphonate (I-111)
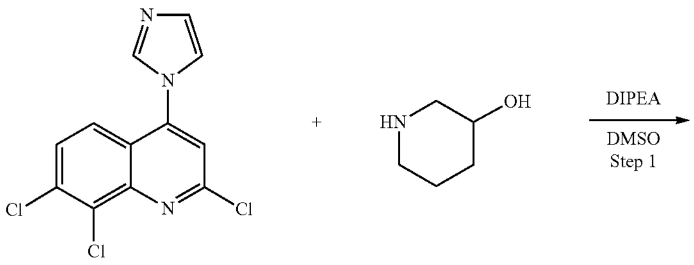

-continued

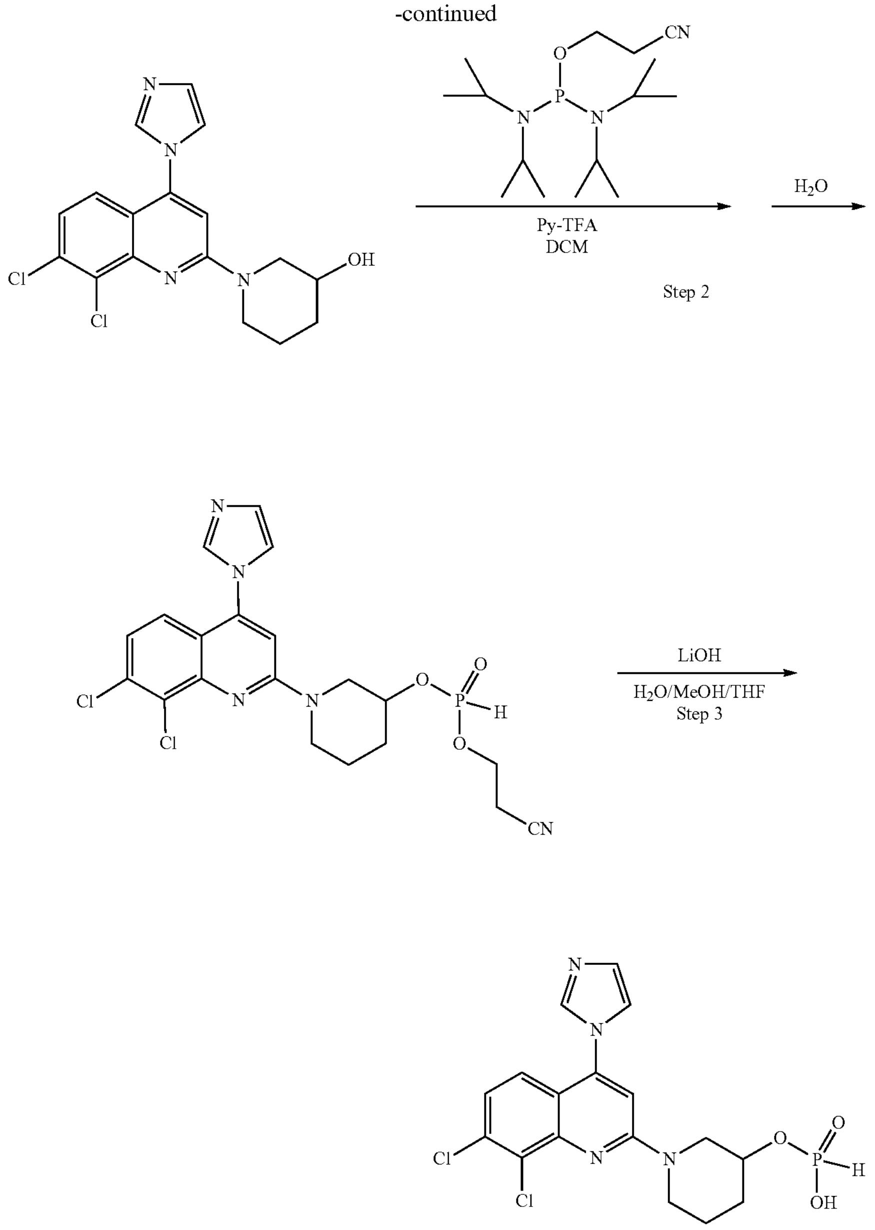

I-111

Step 1: 1-(7,8-Dichloro-4-(1H-imidazol-1-yl)quinolin-2-yl)piperidin-3-ol was prepared according to the procedure described above to prepare compound I-353.

Step 2: 2-Cyanoethyl 1-(7,8-dichloro-4-(1H-imidazol-1-yl)quinolin-2-yl)piperidin-3-yl phosphonate. To a vial were added 1-(7,8-dichloro-4-(1H-imidazol-1-yl)quinolin-2-yl) piperidin-3-ol (20 mg, 0.0551 mmol), DCM (1.0 mL), pyridinium trifluoroacetate (10.6 mg, 0.0551 mmol). Then 3-(bis(diisopropylamino)phosphinooxy) propanenitrile (26 0.0826 mmol) was added. The resulting reaction mixture was stirred at room temperature overnight. The reaction was monitored by LC-MS. $H_2O$ (0.1 mL) was added and the reaction mixture was stirred for 1 hr. All volatiles were removed under reduced pressure. The crude was used in next step.

Step 3: 1-(7,8-Dichloro-4-(1H-imidazol-1-yl)quinolin-2-yl)piperidin-3-yl hydrogen phosphonate. To a vial containing crude product 2-cyanoethyl 1-(7,8-dichloro-4-(1H-imidazol-1-yl)345uinoline-2-yl)piperidin-3-yl phosphonate in step 2 were added MeOH (0.5 mL), THF (1.0 mL) and a solution of LiOH $H_2O$ in $H_2O$ (4.63 mg/0.5 mL, 0.110 mmol). The resulting reaction mixture was stirred overnight, acidified to pH 5, and concentrated. The crude was purified by HPLC to afford the title product as a white solid (8 mg) (MS: $[M+1]^+$ 427).

The following compounds are prepared essentially by the same method described above to prepare I-111.

| I-# | Starting Material | Structure | MS [M + 1]+ |
|---|---|---|---|
| I-110 | 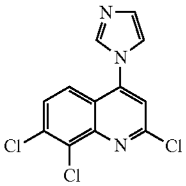 [SMILES: Clc1cc(-n2ccnc2)c2ccc(Cl)c(Cl)c2n1] 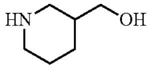 | 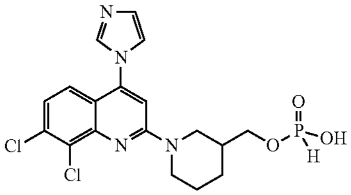 [SMILES: O=[PH](O)OCC1CCCN(c2cc(-n3ccnc3)c3ccc(Cl)c(Cl)c3n2)C1] | 441 |
| I-255 | 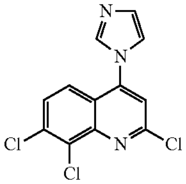 [SMILES: Clc1cc(-n2ccnc2)c2ccc(Cl)c(Cl)c2n1] 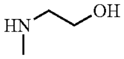 | 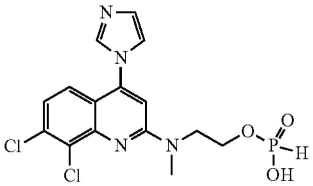 [SMILES: CN(CCO[PH](=O)O)c1cc(-n2ccnc2)c2ccc(Cl)c(Cl)c2n1] | 401 |
| I-396 | 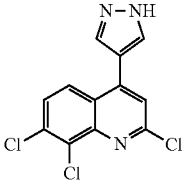 [SMILES: Clc1cc(-c2cn[nH]c2)c2ccc(Cl)c(Cl)c2n1] 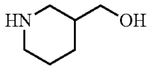 | 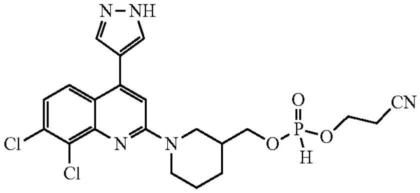 [SMILES: N#CCCO[PH](=O)OCC1CCCN(c2cc(-c3cn[nH]c3)c3ccc(Cl)c(Cl)c3n2)C1] | 494 |
| I-329 | 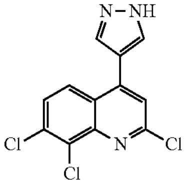 [SMILES: Clc1cc(-c2cn[nH]c2)c2ccc(Cl)c(Cl)c2n1] 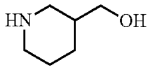 | 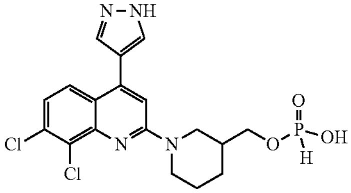 [SMILES: O=[PH](O)OCC1CCCN(c2cc(-c3cn[nH]c3)c3ccc(Cl)c(Cl)c3n2)C1] | 441 |
| I-257 | 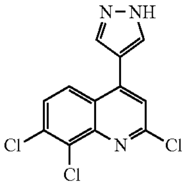 [SMILES: Clc1cc(-c2cn[nH]c2)c2ccc(Cl)c(Cl)c2n1] 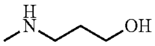 | 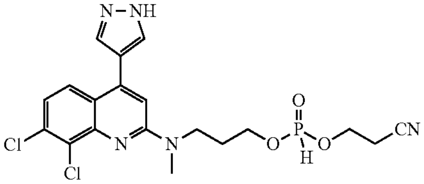 [SMILES: CN(CCCO[PH](=O)OCCC#N)c1cc(-c2cn[nH]c2)c2ccc(Cl)c(Cl)c2n1] | 468 |
| I-256 | 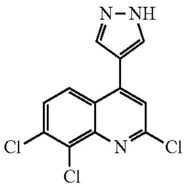 [SMILES: Clc1cc(-c2cn[nH]c2)c2ccc(Cl)c(Cl)c2n1] 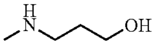 | 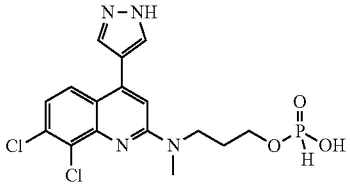 [SMILES: CN(CCCO[PH](=O)O)c1cc(-c2cn[nH]c2)c2ccc(Cl)c(Cl)c2n1] | 415 |
| I-330 | 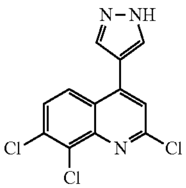 [SMILES: Clc1cc(-c2cn[nH]c2)c2ccc(Cl)c(Cl)c2n1] 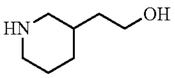 | 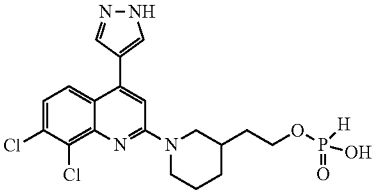 [SMILES: O=[PH](O)OCCC1CCCN(c2cc(-c3cn[nH]c3)c3ccc(Cl)c(Cl)c3n2)C1] | 455 |
| I-258 | 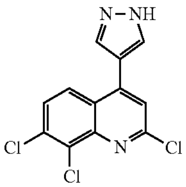 [SMILES: Clc1cc(-c2cn[nH]c2)c2ccc(Cl)c(Cl)c2n1] 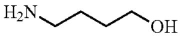 | 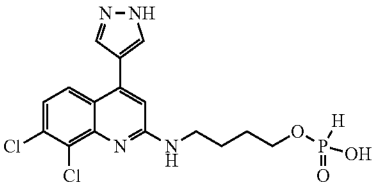 [SMILES: O=[PH](O)OCCCCNc1cc(-c2cn[nH]c2)c2ccc(Cl)c(Cl)c2n1] | 415 |

Example 38: Synthesis of 1-(7,8-dichloro-4-(1H-imidazol-1-yl)quinolin-2-yl)piperidin-3-yl dihydrogen phosphate (I-112)

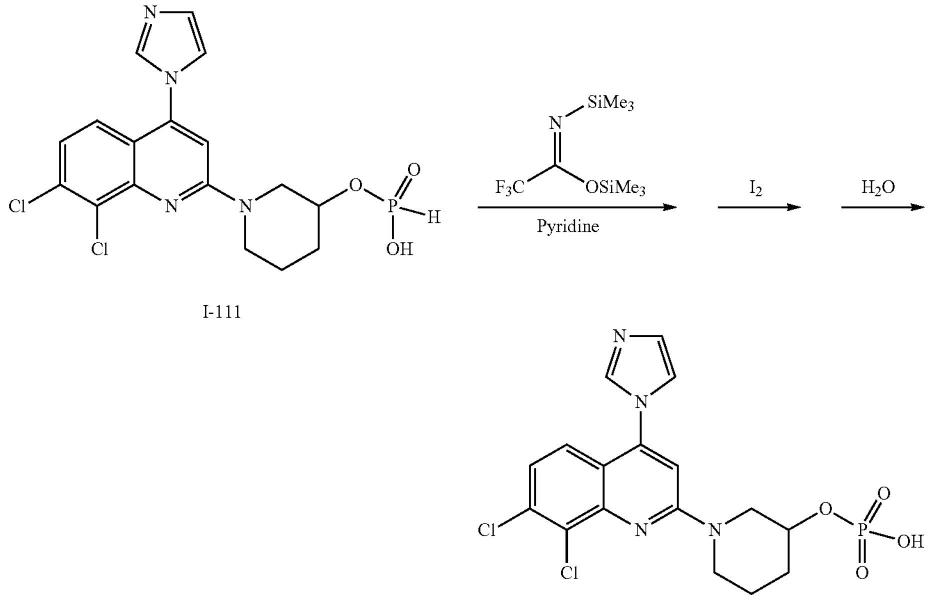

I-111

I-112

To a vial were added product I-111 (6.2 mg, 0.0145 mmol) and pyridine (0.3 mL). Trimethylsilyl 2,2,2-trifluoro-N-(trimethylsilyl)acetimidate (0.019 mL, 0.0726 mmol) was then added. The resulting reaction mixture was stirred for 5 min. A solution of $I_2$ in pyridine (4.4 mg/0.1 mL) was then added dropwise and the reaction mixture was stirred for 5 min. The volatiles were removed under reduced pressure. The crude was purified by prep HPLC to afford the title product as a white solid (2.6 mg) (MS: $[M+1]^+$ 443).

Example 39: Synthesis of (1-(7,8-dichloro-4-(1H-imidazol-1-yl)quinolin-2-yl)piperidin-3-yl)methyl dihydrogen phosphate (I-113)

I-113

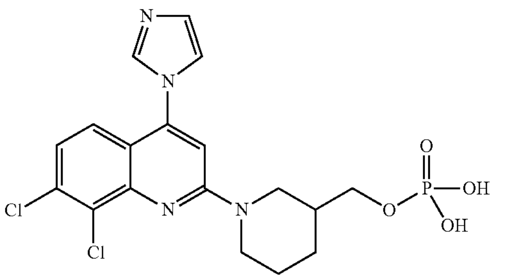

(1-(7,8-Dichloro-4-(1H-imidazol-1-yl)quinolin-2-yl)piperidin-3-yl)methyl dihydrogen phosphate was prepared according to the procedure described above to prepare compound I-112 (MS: $[M+1]^+$ 457).

Example 40: Synthesis of Ethyl hydrogen (7,8-dichloro-4-(1H-pyrazol-4-yl)quinolin-2-ylamino)methylphosphonate (I-253) and (7,8-dichloro-4-(1H-pyrazol-4-yl)quinolin-2-ylamino)methylphosphonic acid (I-254)

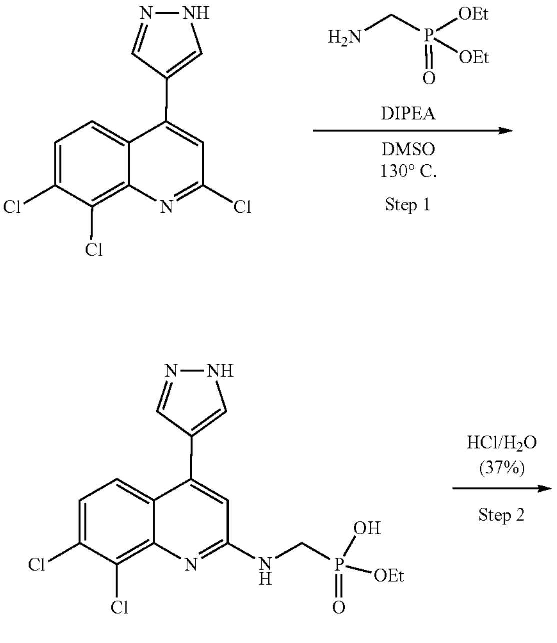

I-253

-continued

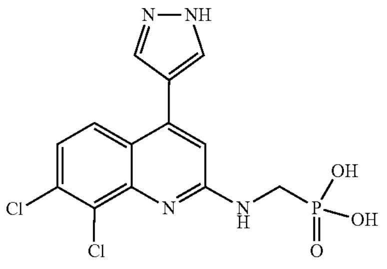

I-254

Step 1: Ethyl hydrogen (7,8-dichloro-4-(1H-pyrazol-4-yl) quinolin-2-ylamino)methylphosphonate. To a vial were added 2,7,8-trichloro-4-(1H-pyrazol-4-yl)quinoline (30 mg, 0.10 mmol), DMSO (0.3 mL), diethyl aminomethylphosphonate (50 mg, 0.3 mmol), and DIPEA (52 µl, 0.3 mmol). The resulting reaction mixture was stirred at 130° C. for 20 hrs. The crude was purified by prep HPLC to afford product 2157 as a white solid (5.2 mg) (MS: $[M+1]^+$ 401).

Step 2: (7,8-dichloro-4-(1H-pyrazol-4-yl)quinolin-2-ylamino)methylphosphonic acid. To a vial were added ethyl hydrogen (7,8-dichloro-4-(1H-pyrazol-4-yl)quinolin-2-ylamino)methylphosphonate (3.7 mg, 0.0092 mmol) and hydrochloric acid (37%, 0.5 mL). The resulting reaction mixture was stirred at 70° C. overnight. All starting material was converted to desired product. After concentration, the title product was obtained as a white solid (3.5 mg) (MS: $[M+1]^+$ 373).

Example 41: Synthesis of (3-((7,8-dichloro-4-(1H-pyrazol-4-yl)quinolin-2-yl)amino)propyl)phosphonic acid (I-397)

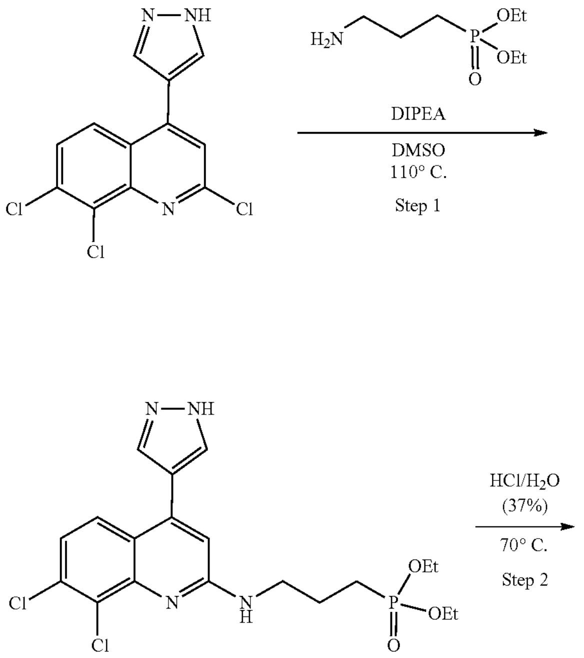

-continued

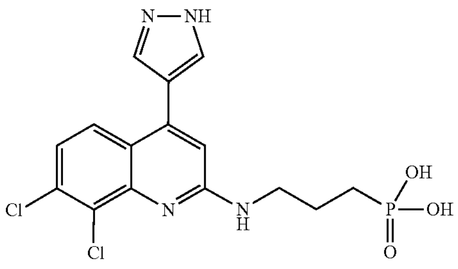

I-397

Step 1: Diethyl 3-(7,8-dichloro-4-(1H-pyrazol-4-yl)quinolin-2-ylamino)propylphosphonate. To a vial were added 2,7,8-trichloro-4-(1H-pyrazol-4-yl)quinoline (30 mg, 0.10 mmol), DMSO (0.3 mL), diethyl 3-aminopropylphosphonate (58.6 mg, 0.30 mmol) and DIPEA (52 µl, 0.30 mmol). The resulting reaction mixture was stirred at 110° C. for 5 hrs followed by addition of $H_2O$ (4 mL). The precipitated white solid was collected by a centrifuge, and the crude was purified by silica gel chromatography (eluted by 5% MeOH/DCM) to afford the desired product as a white solid (9 mg) (MS: $[M+1]^+$ 457).

Step 2: 3-(7,8-Dichloro-4-(1H-pyrazol-4-yl)quinolin-2-ylamino)propylphosphonic acid. To a vial were added diethyl 3-(7,8-dichloro-4-(1H-pyrazol-4-yl)quinolin-2-ylamino)propylphosphonate (4.5 mg, 0.0098 mmol) and hydrochloric acid (37%, 0.5 mL). The resulting reaction mixture was stirred at 70° C. overnight. All starting material was converted to desired product. After concentration, the title product was obtained as a white solid (4.0 mg) (MS: $[M+1]^+$ 401).

Example 42: Synthesis of diethyl (1-(7,8-dichloro-4-(1H-imidazol-1-yl)quinolin-2-yl)piperidin-3-yl) methylphosphonate (I-114)

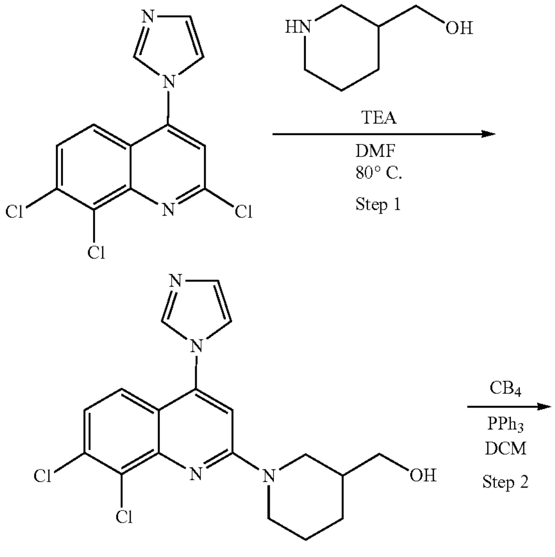

-continued

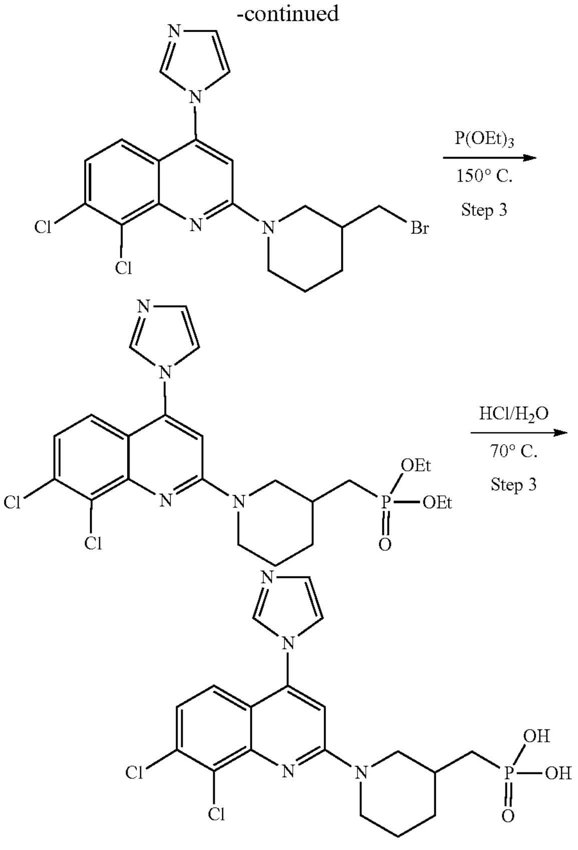

I-114

Step 1: (1-(7,8-Dichloro-4-(1H-imidazol-1-yl)quinolin-2-yl)piperidin-3-yl)methanol was prepared according to the procedure described above to prepare compound I-353. (MS: $[M+1]^+$ 377).

Step 2: 2-(3-(Bromomethyl)piperidin-1-yl)-7,8-dichloro-4-(1H-imidazol-1-yl)quinoline. To a vial were added (1-(7,8-dichloro-4-(1H-imidazol-1-yl)quinolin-2-yl)piperidin-3-yl)methanol (100 mg, 0.265 mmol), $CBr_4$ (176 mg, 0.53 mmol), and DCM (5 mL). The mixture was cooled in ice-water bath for 20 min followed by addition of a solution of $Ph_3P$ in DCM (105 mg/1 mL, 0.398 mmol). The resulting mixture was stirred at 0° C. for 1 hr. The mixture was concentrated, purified by silica gel chromatography eluting by 50% to 60% of ethyl acetate in hexanes to afford desired product as an off-white solid (85 mg) (MS: $[M+1]^+$ 439).

Step 3: Diethyl (1-(7,8-dichloro-4-(1H-imidazol-1-yl)quinolin-2-yl)piperidin-3-yl)methylphosphonate. To a vial were added 2-(3-(bromomethyl)piperidin-1-yl)-7,8-dichloro-4-(1H-imidazol-1-yl)quinoline (20 mg, 0.0455 mmol) and triethyl phosphate (0.5 mL). The resulting mixture was stirred at 150° C. for 10 hrs. The reaction mixture (30%) was purified by PTLC to afford the desired product as a white solid (2.0 mg) (MS: $[M+1]^+$ 497).

Step 4: (1-(7,8-Dichloro-4-(1H-imidazol-1-yl)quinolin-2-yl)piperidin-3-yl)methylphosphonic acid was prepared according to the procedure described above to prepare compound I-397 (step 2) (MS: $[M+1]^+$ 441).

Example 43: Synthesis of Ethyl hydrogen (7,8-dichloro-4-(1H-imidazol-1-yl)quinolin-2-yl)methylphosphonate (I-252)

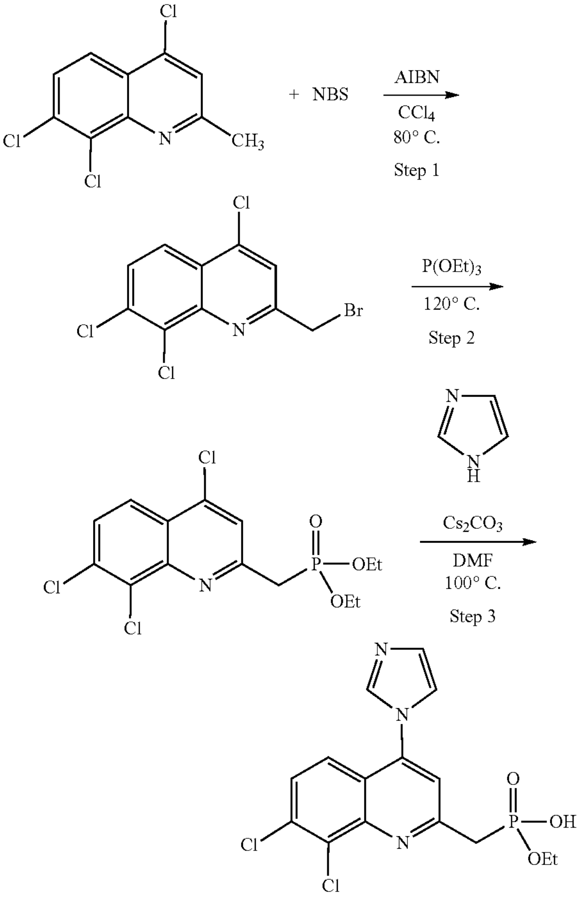

I-252

Step 1: 2-(Bromomethyl)-4,7,8-trichloroquinoline. To a flask were added 4,7,8-trichloro-2-methylquinoline (493 mg, 2.0 mmol), NBS (356 mg, 2.0 mmol), AIBN (66 mg, 0.40 mmol) and $CCl_4$ (6 mL). The reaction mixture was degassed by bubbling $N_2$ flow for 20 min and stirred at 65° C. for 16 hrs. under $N_2$. After being cooled to room temperature, the mixture was diluted by ethyl acetate (50 mL), washed by $H_2O$ (20 mL) and brine (20 mL), dried over $Na_2SO_4$. After concentration, the crude was used in next step.

Step 2: Diethyl (4,7,8-trichloroquinolin-2-yl)methylphosphonate was prepared according to the procedure described above to prepare compound 2060 step 3 (MS: $[M+1]^+$ 382).

Step 3: Ethyl hydrogen (7,8-dichloro-4-(1H-imidazol-1-yl)quinolin-2-yl)methylphosphonate was prepared according to the procedure described above to prepare compound I-56 (step 3) (MS: $[M+1]^+$386).

Example 44: Synthesis of ((7,8-dichloro-4-(1H-imidazol-1-yl)quinolin-2-yl)methyl)phosphonic acid (I-251)

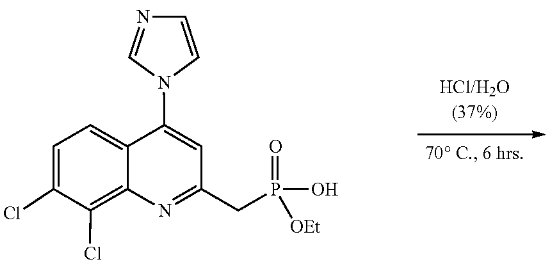

I-252

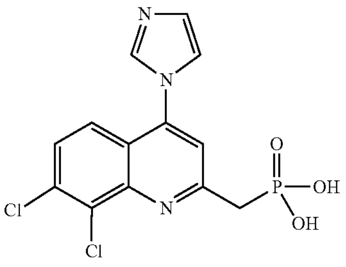

I-251

((7,8-Dichloro-4-(1H-imidazol-1-yl)quinolin-2-yl)methyl)phosphonic acid was prepared according to the procedure described above to prepare compound I-397 (step 2) (MS: $[M+1]^+$ 358).

Example 45: Synthesis of 2-(benzyloxy)-7-chloro-4-(1H-imidazol-1-yl)quinoline (I-277)

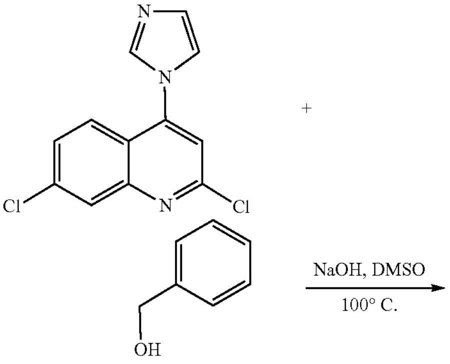

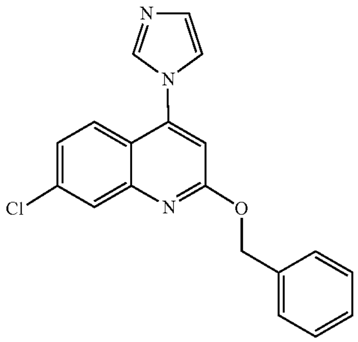

I-277

To a vial were added 2,7-dichloro-4-(1H-imidazol-1-yl)quinoline (132 mg, 0.5 mmol), DMSO (1 mL), benzyl alcohol (62 μl, 0.6 mmol) and NaOH (24 mg, 0.6 mmol). The mixture was stirred at 100° C. overnight. The 10% of the reaction mixture was purified by PTLC, eluted by 7.5% MeOH/DCM to afford the title product as white solid (4.5 mg, 27% yield) (MS: $[M+1]^+$ 336.1).

The following compounds are prepared essentially by the same method described above to prepare I-277.

| I-# | Starting Material | | Structure | MS [M + 1]+ |
|---|---|---|---|---|
| I-278 | 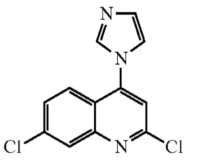 [SMILES: Clc1ccc2c(-n3ccnc3)cc(Cl)nc2c1] | 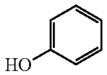 | 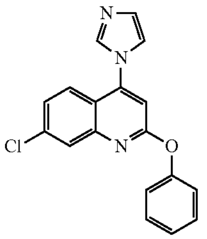 [SMILES: Clc1ccc2c(-n3ccnc3)cc(Oc3ccccc3)nc2c1] | 322 |

-continued
| I-# | Starting Material | Structure | MS [M + 1]+ |
|---|---|---|---|
| I-282 | 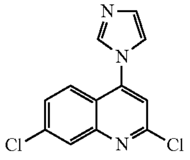 [SMILES: Clc1ccc2c(-n3ccnc3)cc(Cl)nc2c1] 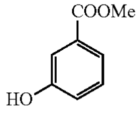 [SMILES: COC(=O)c1cccc(O)c1] | 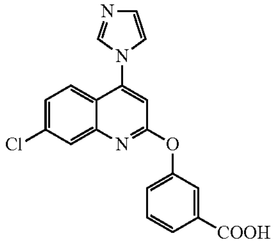 [SMILES: O=C(O)c1cccc(Oc2cc(-n3ccnc3)c3ccc(Cl)cc3n2)c1] | 366 |
| I-281 | 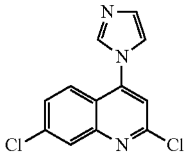 [SMILES: Clc1ccc2c(-n3ccnc3)cc(Cl)nc2c1] 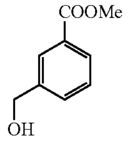 [SMILES: COC(=O)c1cccc(CO)c1] | 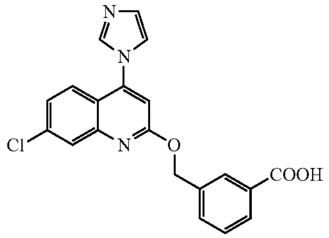 [SMILES: O=C(O)c1cccc(COc2cc(-n3ccnc3)c3ccc(Cl)cc3n2)c1] | 380 |
| I-284 | 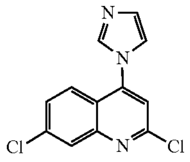 [SMILES: Clc1ccc2c(-n3ccnc3)cc(Cl)nc2c1] 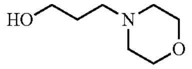 | 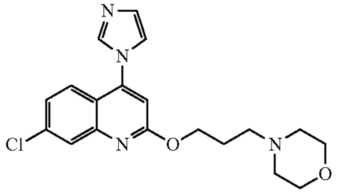 [SMILES: Clc1ccc2c(-n3ccnc3)cc(OCCCN3CCOCC3)nc2c1] | 373 |
| I-283 | 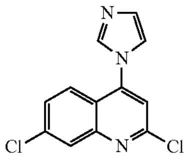 [SMILES: Clc1ccc2c(-n3ccnc3)cc(Cl)nc2c1] 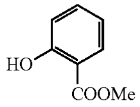 [SMILES: COC(=O)c1ccccc1O] | 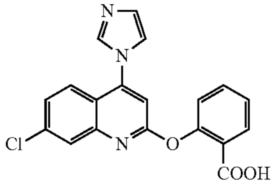 [SMILES: O=C(O)c1ccccc1Oc1cc(-n2ccnc2)c2ccc(Cl)cc2n1] | 366 |
| I-280 | 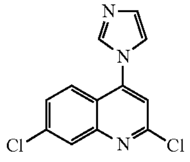 [SMILES: Clc1ccc2c(-n3ccnc3)cc(Cl)nc2c1] 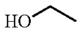 | 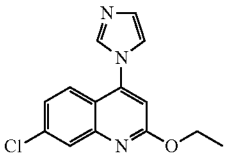 [SMILES: CCOc1cc(-n2ccnc2)c2ccc(Cl)cc2n1] | 274 |
| I-279 | 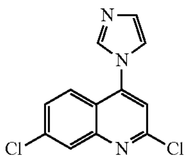 [SMILES: Clc1ccc2c(-n3ccnc3)cc(Cl)nc2c1] 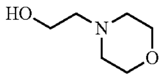 | 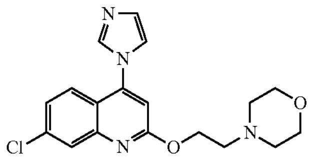 [SMILES: Clc1ccc2c(-n3ccnc3)cc(OCCN3CCOCC3)nc2c1] | 359 |

Example 46: Synthesis of (7,8-Dichloro-2-(1H-pyrazol-3-yl)quinolin-4-yl)glycine (I-287)

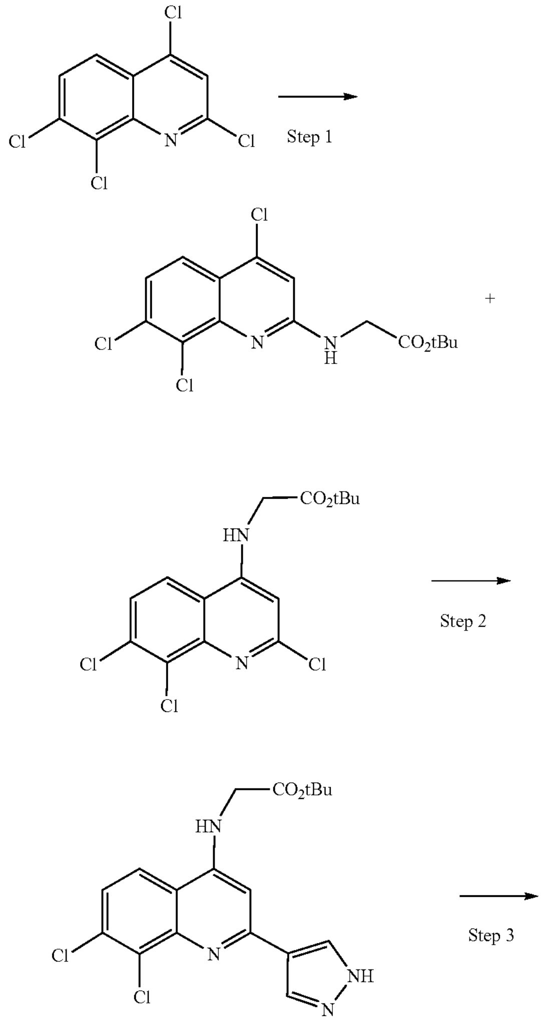

-continued

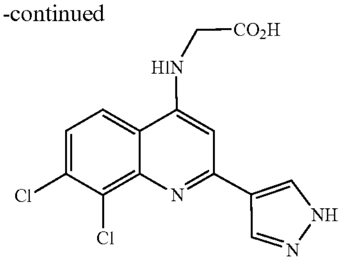

I-287

Step 1: tert-Butyl (4,7,8-trichloroquinolin-2-yl)glycinate and tert-butyl (2,7,8-trichloroquinolin-4-yl)glycinate. To a solution of 2,4,7,8-tetrachloroquinoline (270 mg) and tert-butyl glycinate HCl (270 mg) in DMSO (0.8 mL) was added $K_2CO_3$ (276 mg). The resultant reaction mixture was heated at 85° C. over 4 h. Aqueous work up with EtOAc (30 mL) and a column chromatography eluting with a gradient of DCM/Hexane from 0 to 50% afforded two colorless compounds. The earlier eluted fraction is 4-substituted product (120 mg) (MS: $[M+1]^+$ 361) and the later fraction with 2-substituted product (62 mg) (MS: $[M+1]^+$ 361).

Step 2: tert-Butyl (7,8-dichloro-2-(1H-pyrazol-4-yl)quinolin-4-yl)glycinate. To a mixture of tert-butyl (2,7,8-trichloroquinolin-4-yl)glycinate (52 mg), 4-(4,4,5,5-tetramethyl-1,3,2-dioxaborolan-2-yl)-1H-pyrazole (50 mg), $K_2CO_3$ (48 mg) and $Pd(PPh_3)_4$ (16 mg) were added dioxane (2 mL) and water (0.5 mL). The resultant suspended solution was vacuumed and purged with nitrogen repeatedly three time, then stirred and heated at 85° C. under nitrogen over 4 hours. An aqueous work-up with EtOAc and a column chromatography gave the desired colorless product (27 mg) (MS: $[M+1]^+$ 393).

Step 3: (7,8-Dichloro-2-(1H-pyrazol-3-yl)quinolin-4-yl) glycine. To a solution of tert-butyl (7,8-dichloro-2-(1H-pyrazol-3-yl) quinolin-4-yl) glycinate (27 mg) in DCM (0.5 mL) was added TFA (0.2 mL). The resultant solution was stirred overnight. After removal of DCM and TFA under reduced pressure, the resultant was mixed with 0.4 mL water and lyophilized to afford the title product (MS: $[M+1]^+$ 337).

The following compounds are prepared essentially by the same method described above to prepare I-287 and some analogues are prepared from intermediates by additional deprotection.

| I-# | Starting Material | Structure | MS $[M+1]^+$ |
| --- | --- | --- | --- |
| I-285 | 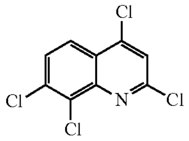 [SMILES: Clc1cc(Cl)c2ccc(Cl)c(Cl)c2n1] 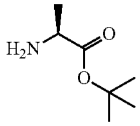 | 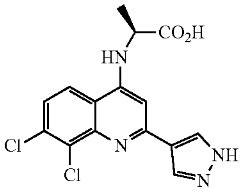 [SMILES: C[C@H](Nc1cc(-c2cn[nH]c2)nc2c(Cl)c(Cl)ccc12)C(=O)O] | 351 |
| I-290 | 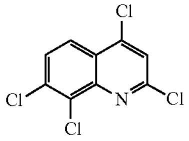 [SMILES: Clc1cc(Cl)c2ccc(Cl)c(Cl)c2n1] 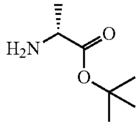 | 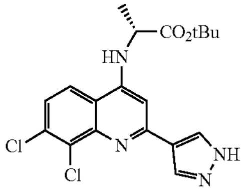 | 407 |

-continued
| I-# | Starting Material | Structure | MS $[M + 1]^+$ |
|---|---|---|---|
| I-286 | 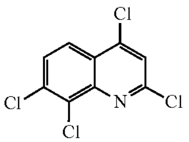 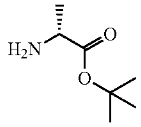 | 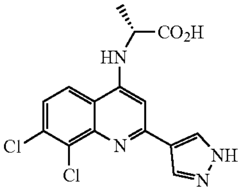 [SMILES: C[C@@H](Nc1cc(-c2cn[nH]c2)nc2c(Cl)c(Cl)ccc12)C(=O)O] | 351 |
| I-300 | 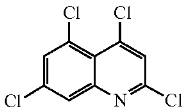 [SMILES: Clc1cc(Cl)c2c(Cl)cc(Cl)nc2c1] 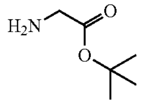 | 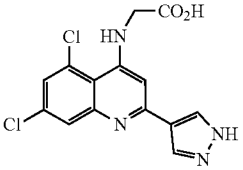 [SMILES: O=C(O)CNc1cc(-c2cn[nH]c2)nc2cc(Cl)cc(Cl)c12] | 337 |
| I-288 | 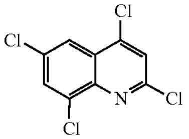 [SMILES: Clc1cc(Cl)c2nc(Cl)cc(Cl)c2c1] 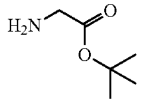 | 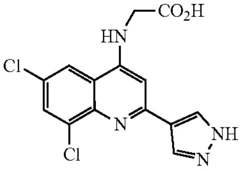 [SMILES: O=C(O)CNc1cc(-c2cn[nH]c2)nc2c(Cl)cc(Cl)cc12] | 337 |
| I-301 | 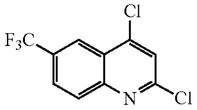 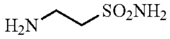 | 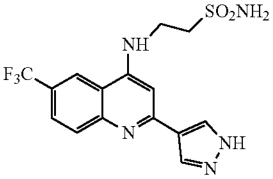 [SMILES: NS(=O)(=O)CCNc1cc(-c2cn[nH]c2)nc2ccc(C(F)(F)F)cc12] | 386 |
| I-401 | 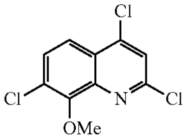 [SMILES: COc1c(Cl)ccc2c(Cl)cc(Cl)nc12] 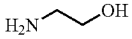 | 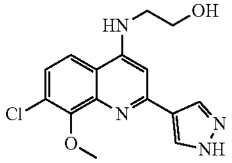 [SMILES: COc1c(Cl)ccc2c(NCCO)cc(-c3cn[nH]c3)nc12] | 319 |
| I-295 | 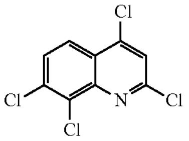 [SMILES: Clc1cc(Cl)c2ccc(Cl)c(Cl)c2n1] 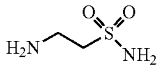 | 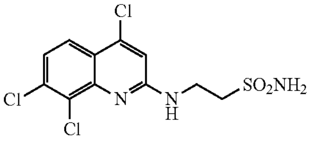 [SMILES: NS(=O)(=O)CCNc1cc(Cl)c2ccc(Cl)c(Cl)c2n1] | 354 |
| I-296 | 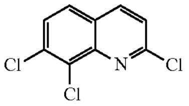 [SMILES: Clc1ccc2ccc(Cl)c(Cl)c2n1] 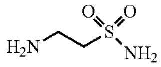 | 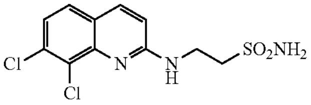 [SMILES: NS(=O)(=O)CCNc1ccc2ccc(Cl)c(Cl)c2n1] | 320 |
| I-161 | 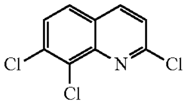 [SMILES: Clc1ccc2ccc(Cl)c(Cl)c2n1] 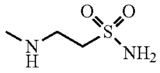 | 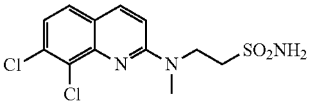 [SMILES: CN(CCS(N)(=O)=O)c1ccc2ccc(Cl)c(Cl)c2n1] | 334 |
| I-306 | 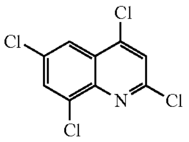 [SMILES: Clc1cc(Cl)c2nc(Cl)cc(Cl)c2c1] 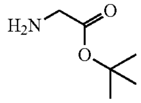 | 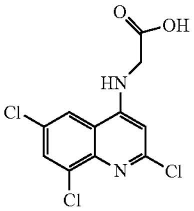 [SMILES: O=C(O)CNc1cc(Cl)nc2c(Cl)cc(Cl)cc12] | 305 |

-continued

| I-# | Starting Material | | Structure | MS [M + 1]$^+$ |
|---|---|---|---|---|
| I-294 | 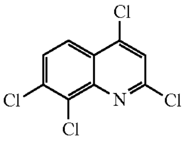 [SMILES: Clc1cc(Cl)c2ccc(Cl)c(Cl)c2n1] | 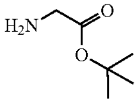 | 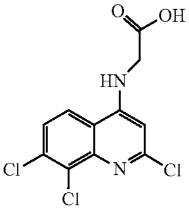 [SMILES: O=C(O)CNc1cc(Cl)nc2c(Cl)c(Cl)ccc12] | 305 |
| I-171 | 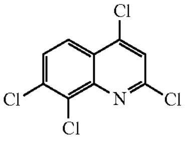 [SMILES: Clc1cc(Cl)c2ccc(Cl)c(Cl)c2n1] | 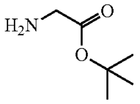 | 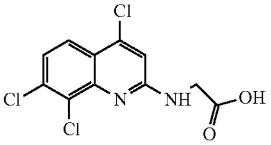 [SMILES: O=C(O)CNc1cc(Cl)c2ccc(Cl)c(Cl)c2n1] | 305 |
| I-307 | 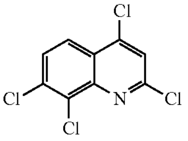 [SMILES: Clc1cc(Cl)c2ccc(Cl)c(Cl)c2n1] | 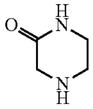 | 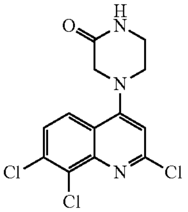 [SMILES: O=C1CN(c2cc(Cl)nc3c(Cl)c(Cl)ccc23)CCN1] | 330 |
| I-312 | 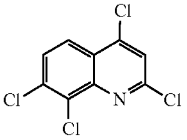 [SMILES: Clc1cc(Cl)c2ccc(Cl)c(Cl)c2n1] | 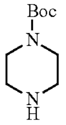 | 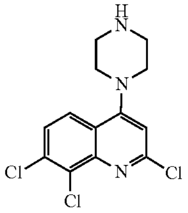 [SMILES: Clc1cc(N2CCNCC2)c2ccc(Cl)c(Cl)c2n1] | 316 |

Example 47: Synthesis of (7,8-dichloro-4-((2-sulfamoylethyl)amino)quinolin-2-yl)glycine (I-319)

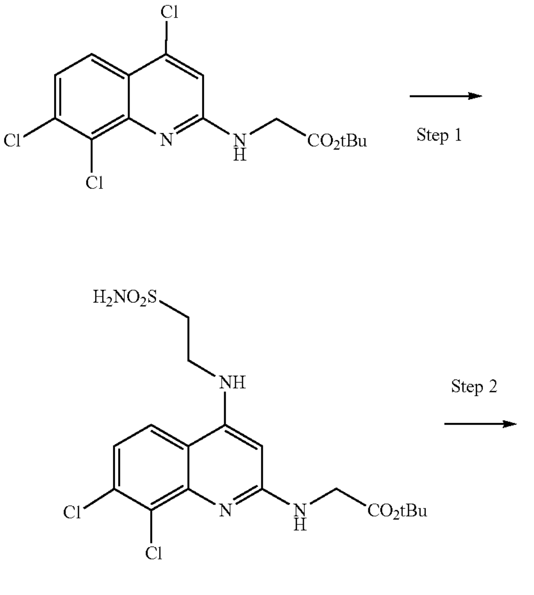

-continued

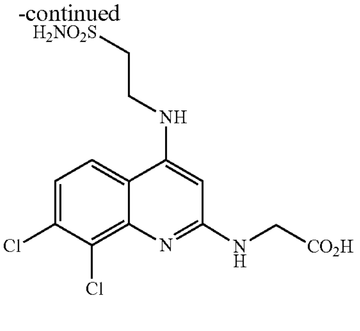

I-319

Step 1: tert-Butyl (7,8-dichloro-4-((2-sulfamoylethyl) amino)quinolin-2-yl)glycinate. To a mixture of tert-butyl (4,7,8-trichloroquinolin-2-yl) glycinate (28 mg), 2-aminoethane-1-sulfonamide (20 mg) and $K_2CO_3$ (22 mg) was added DMSO (0.4 mL). After stirring at 130° C. overnight, the reaction mixture was diluted with water and extracted with EtOAc (15 mL). A column chromatography afforded the desired product (6 mg) (MS: [M+1]$^+$ 449).

Step 2: (7,8-Dichloro-4-((2-sulfamoylethyl)amino)quinolin-2-yl)glycine. The acidic deprotection of tert-butyl (7,8-dichloro-4-((2-sulfamoylethyl) amino) quinolin-2-yl) glycinate (6 mg) in DCM (0.4 mL) with TFA (0.1 mL) afforded the desired product (5 mg) (MS: [M+1]$^+$ 393).

Example 48: Synthesis of (7,8-dichloro-2-((2-sulfamoylethyl)amino)quinolin-4-yl)glycine (I-318)

I-318

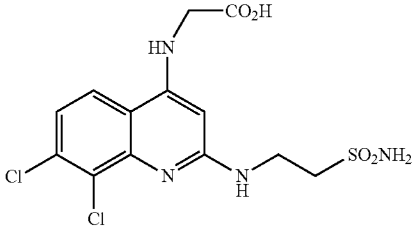

Following the similar preparation procedure of I-319, tert-butyl (4,7,8-trichloroquinolin-2-yl)glycinate (27.8 mg) was treated with 2-aminoethane-1-sulfonamide (18.5 mg) in DMSO and the following deprotection afforded the desired product (5.9 mg) (MS: $[M+1]^+$ 393).

Example 49: Synthesis of (7,8-dichloro-4-(1H-pyrazol-4-yl)quinolin-2-yl)glycine (I-177)

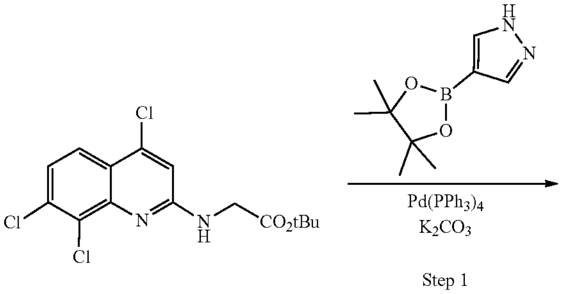

-continued

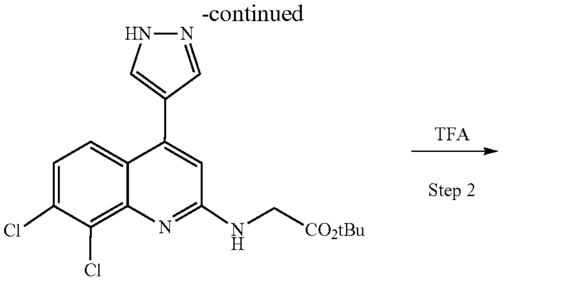

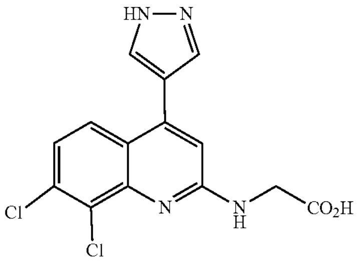

I-177

(7,8-Dichloro-4-(1H-pyrazol-4-yl)quinolin-2-yl)glycine was prepared essentially by the same method described above to prepare I-287.

The following compounds are prepared essentially by the same method described above to prepare I-177.

| I-# | Starting Material | Structure | MS $[M + 1]^+$ |
|---|---|---|---|
| I-402 | 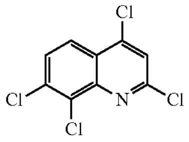 [SMILES: Clc1cc(Cl)c2ccc(Cl)c(Cl)c2n1] 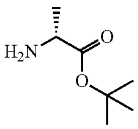 | 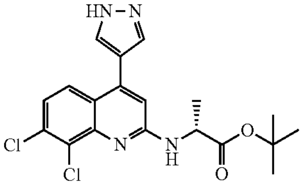 [SMILES: C[C@@H](Nc1cc(-c2cn[nH]c2)c2ccc(Cl)c(Cl)c2n1)C(=O)OC(C)(C)C] | 407 |
| I-180 | 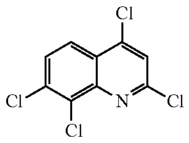 [SMILES: Clc1cc(Cl)c2ccc(Cl)c(Cl)c2n1] 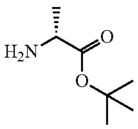 | 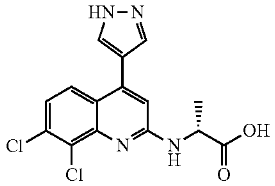 [SMILES: C[C@@H](Nc1cc(-c2cn[nH]c2)c2ccc(Cl)c(Cl)c2n1)C(=O)O] | 351 |
| I-181 | 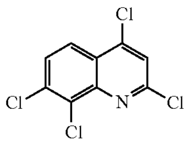 [SMILES: Clc1cc(Cl)c2ccc(Cl)c(Cl)c2n1] 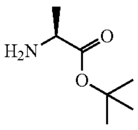 | 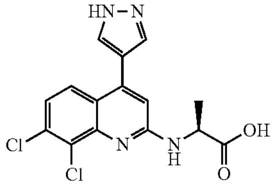 [SMILES: C[C@H](Nc1cc(-c2cn[nH]c2)c2ccc(Cl)c(Cl)c2n1)C(=O)O] | 351 |

-continued

| I-# | Starting Material | | Structure | MS [M + 1]$^+$ |
|---|---|---|---|---|
| I-265 | 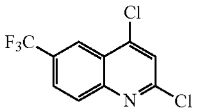 [SMILES: FC(F)(F)c1ccc2nc(Cl)cc(Cl)c2c1] | 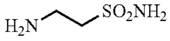 | 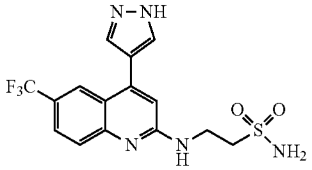 [SMILES: NS(=O)(=O)CCNc1cc(-c2cn[nH]c2)c2cc(C(F)(F)F)ccc2n1] | 386 |
| I-403 | 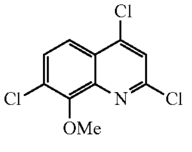 [SMILES: COc1c(Cl)ccc2c(Cl)cc(Cl)nc12] | 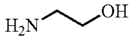 | 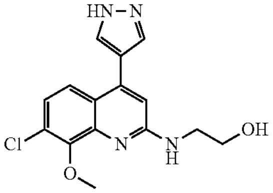 [SMILES: COc1c(Cl)ccc2c(-c3cn[nH]c3)cc(NCCO)nc12] | 319 |

Example 50: Synthesis of 4,7,8-trichloro-2-(1H-pyrazol-4-yl)quinoline (I-404) and 2-((7,8-dichloro-2-(1H-pyrazol-4-yl)quinolin-4-yl)amino)ethan-1-ol (I-289)

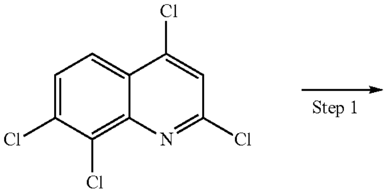

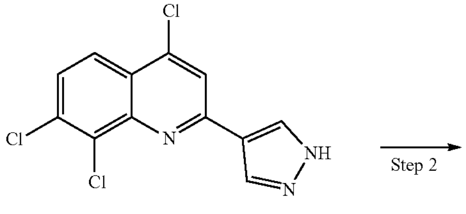

I-404

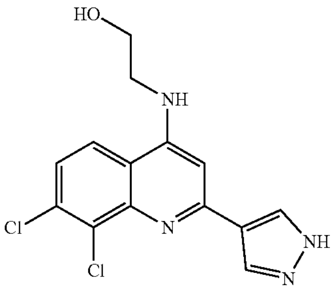

I-289

Step 1: 4,7,8-Trichloro-2-(1H-pyrazol-4-yl)quinoline. To a mixture of 2,4,7,8-tetrachloroquinoline (430 mg), 4-(4,4,5,5-tetramethyl-1,3,2-dioxaborolan-2-yl)-1H-pyrazole (345 mg), $Na_2CO_3$ (513 mg) and $Pd(PPh_3)_4$ (186 mg) were added dioxane (6 mL) and water (3 mL). The resultant mixture was vacuumed and purged with $N_2$ repeatedly three time, then stirred and heated at 90° C. over 2 hours. A solution of 4-(4,4,5,5-tetramethyl-1,3,2-dioxaborolan-2-yl)-1H-pyrazole (300 mg) in dioxane (2 mL) was added to the reaction mixture. After 1.5 h, the second portion of 4-(4,4,5,5-tetramethyl-1,3,2-dioxaborolan-2-yl)-1H-pyrazole (300 mg) in dioxane (2 mL) was added. After 1.5 hour, the starting material-2,4,7,8-tetrachloroquinoline was completely consumed and only one major product was observed by LC-MS. The reaction mixture was diluted with water (4 mL) to precipitate out the desired product. After isolation by a filtration, the isolated solid was washed with water (4 mL) and EtOAc/Hexane (1:1, 6 mL) to afford the desired product I-404 (350 mg) (MS: [M+1]$^+$ 298).

Step 2: 2-((7,8-Dichloro-2-(1H-pyrazol-4-yl)quinolin-4-yl)amino)ethan-1-ol. To a mixture of 4,7,8-trichloro-2-(1H-pyrazol-4-yl) quinoline (45 mg) and 2-aminoethan-1-ol (46 mg) were added $Na_2CO_3$ (32 mg) and DMSO (0.4 mL). The resultant suspension was stirred at 110° C. overnight until the starting material was consumed. Dilution with water (3 mL) precipitated the desired product. Isolation by centrifuge, rinsing with water and drying under vacuum afforded the title product (27.2 mg) (MS: [M+1]$^+$ 323).

The following compounds are prepared essentially by the same method described above to prepare I-289.

| I-# | Starting Materials | | Structure | MS [M + 1]+ |
|---|---|---|---|---|
| I-297 | 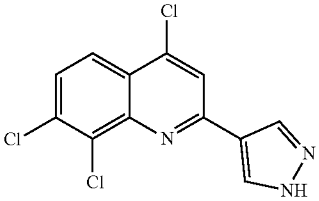 [SMILES: Clc1ccc2c(Cl)cc(-c3cn[nH]c3)nc2c1Cl] | 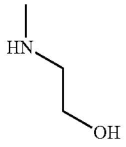 | 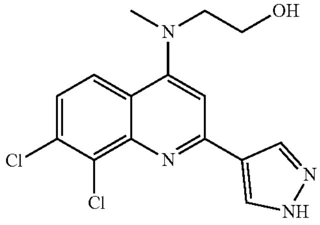 [SMILES: CN(CCO)c1cc(-c2cn[nH]c2)nc2c(Cl)c(Cl)ccc12] | 337 |
| I-292 | 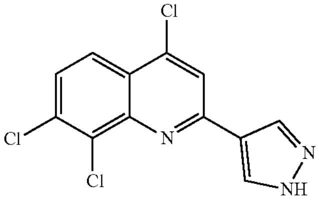 [SMILES: Clc1ccc2c(Cl)cc(-c3cn[nH]c3)nc2c1Cl] | 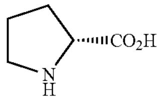 | 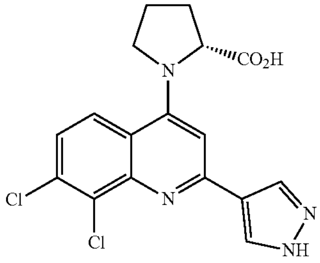 [SMILES: O=C(O)[C@H]1CCCN1c1cc(-c2cn[nH]c2)nc2c(Cl)c(Cl)ccc12] | 377 |
| I-291 | 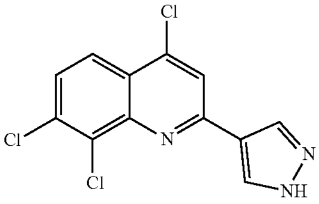 [SMILES: Clc1ccc2c(Cl)cc(-c3cn[nH]c3)nc2c1Cl] | 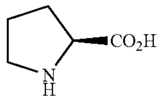 | 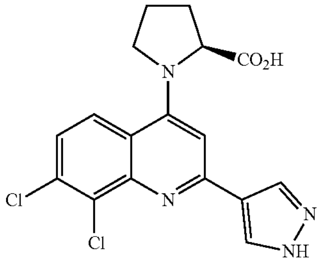 [SMILES: O=C(O)[C@@H]1CCCN1c1cc(-c2cn[nH]c2)nc2c(Cl)c(Cl)ccc12] | 377 |
| I-298 | 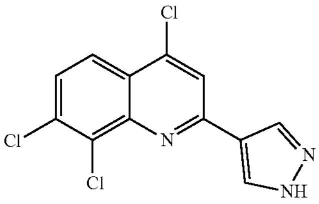 [SMILES: Clc1ccc2c(Cl)cc(-c3cn[nH]c3)nc2c1Cl] | 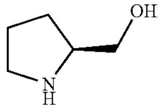 | 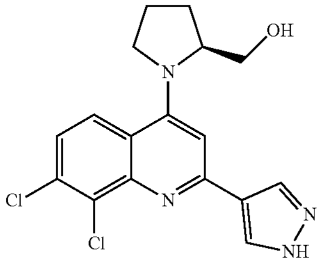 [SMILES: OC[C@@H]1CCCN1c1cc(-c2cn[nH]c2)nc2c(Cl)c(Cl)ccc12] | 363 |
| I-299 | 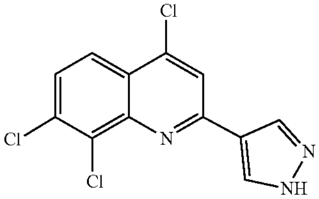 [SMILES: Clc1ccc2c(Cl)cc(-c3cn[nH]c3)nc2c1Cl] | 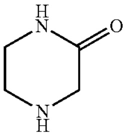 | 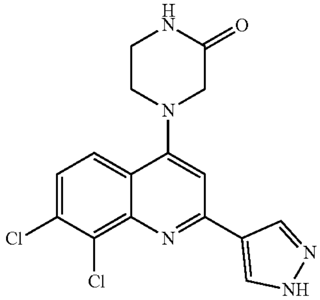 [SMILES: O=C1CN(c2cc(-c3cn[nH]c3)nc3c(Cl)c(Cl)ccc23)CCN1] | 362 |
The following compounds are prepared essentially by the same method described above to prepare I-289 (Suzuki coupling, nucleophilic substitution, and deprotection).

| Example | Starting Materials | | | Structure | MS [M + 1]+ |
|---|---|---|---|---|---|
| I-425 | 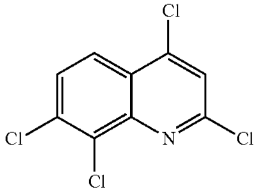 [SMILES: Clc1cc(Cl)c2ccc(Cl)c(Cl)c2n1] | 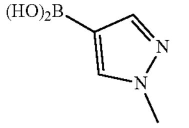 | 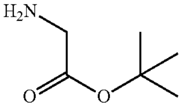 | 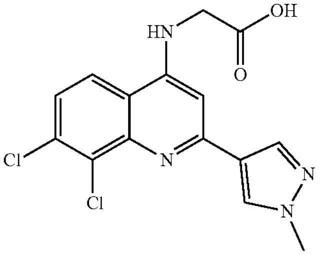 [SMILES: Cn1cc(-c2cc(NCC(=O)O)c3ccc(Cl)c(Cl)c3n2)cn1] | 351 |
| I-426 | 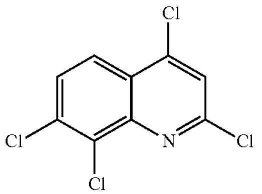 [SMILES: Clc1cc(Cl)c2ccc(Cl)c(Cl)c2n1] | 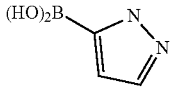 | 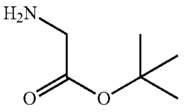 | 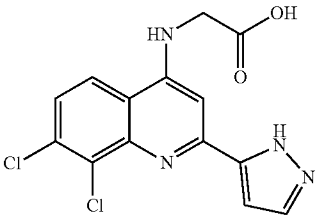 [SMILES: O=C(O)CNc1cc(-c2ccn[nH]2)nc2c(Cl)c(Cl)ccc12] | 337 |

Example 51: Synthesis of 2-(benzyloxy)-7-chloro-4-(1H-imidazol-1-yl)quinoline (I-405)

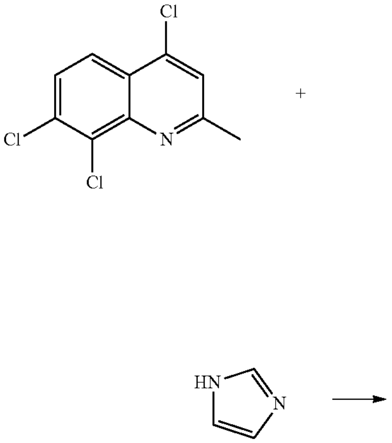

-continued

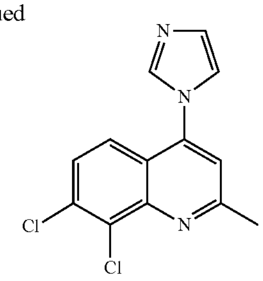

I-405

To a solution of 4,7,8-trichloro-2-methylquinoline (0.5 g) in DMF (4 mL) were added $K_2CO_3$ (0.2 g) and imidizaole (0.54 g). The resultant suspension was heated at 120° C. over 2 h. The reaction mixture was diluted with water (8 mL) to precipitate out the title compound. Filtration and rinsing with water afforded the title compound (0.55 g)-7,8-dichloro-4-(1H-imidazol-1-yl)-2-methylquinoline (MS: $[M+1]^+$ 278).

The following compounds are prepared essentially by the same method described above to prepare I-405. Some analogues were isolated in pure form by precipitation from water and others were purified by column chromatography.

| I-# | Starting Materials | | Structure | MS $[M + 1]^+$ |
|---|---|---|---|---|
| I-316 | 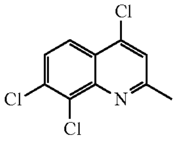 | 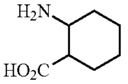 | 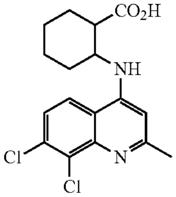 [SMILES: Cc1cc(NC2CCCCC2C(=O)O)c2ccc(Cl)c(Cl)c2n1] | 353 |

-continued
| I-# | Starting Materials | | Structure | MS [M + 1]$^+$ |
|---|---|---|---|---|
| I-315 | 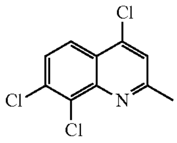 | 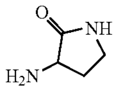 | 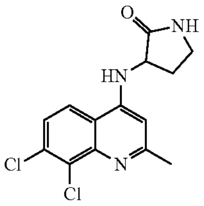 [SMILES: Cc1cc(NC2CCNC2=O)c2ccc(Cl)c(Cl)c2n1] | 310 |
| I-313 | 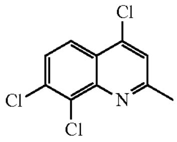 | 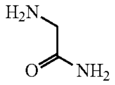 | 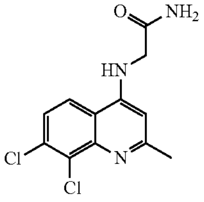 [SMILES: Cc1cc(NCC(N)=O)c2ccc(Cl)c(Cl)c2n1] | 284 |
| I-314 | 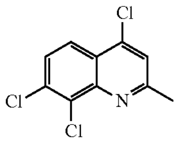 | 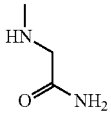 | 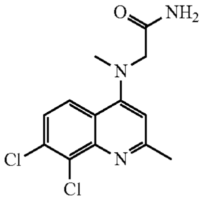 [SMILES: Cc1cc(N(C)CC(N)=O)c2ccc(Cl)c(Cl)c2n1] | 298 |
| I-305 | 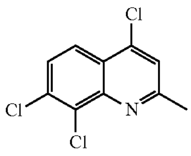 | 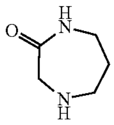 | 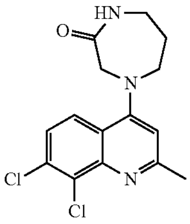 [SMILES: Cc1cc(N2CCCNC(=O)C2)c2ccc(Cl)c(Cl)c2n1] | 324 |
| I-310 | 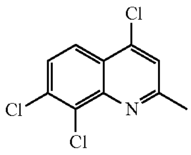 | 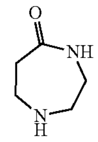 | 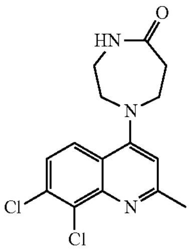 [SMILES: Cc1cc(N2CCNC(=O)CC2)c2ccc(Cl)c(Cl)c2n1] | 324 |
| I-302 | 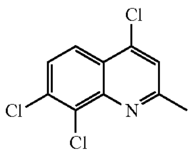 | 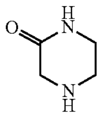 | 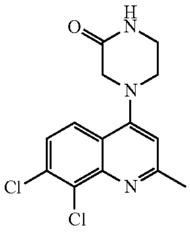 [SMILES: Cc1cc(N2CCNC(=O)C2)c2ccc(Cl)c(Cl)c2n1] | 310 |

-continued
| I-# | Starting Materials | | Structure | MS $[M + 1]^+$ |
|---|---|---|---|---|
| I-311 | 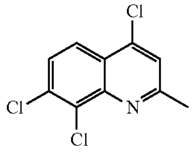 | 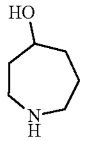 | 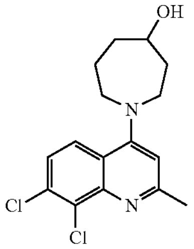 [SMILES: Cc1cc(N2CCCC(O)CC2)c2ccc(Cl)c(Cl)c2n1] | 325 |
| I-317 | 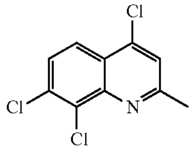 | 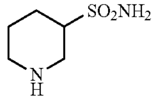 | 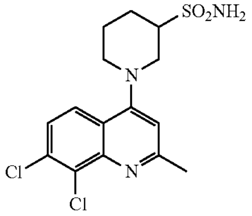 [SMILES: Cc1cc(N2CCCC(S(N)(=O)=O)C2)c2ccc(Cl)c(Cl)c2n1] | 374.0 |
| I-308 | 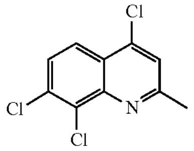 | 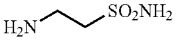 | 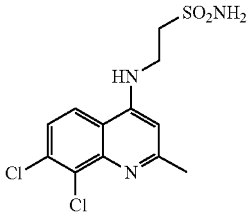 [SMILES: Cc1cc(NCCS(N)(=O)=O)c2ccc(Cl)c(Cl)c2n1] | 334.0 |
| I-303 | 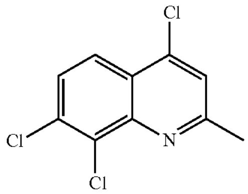 | 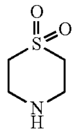 | 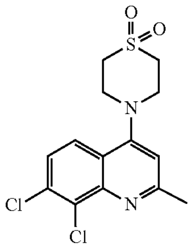 [SMILES: Cc1cc(N2CCS(=O)(=O)CC2)c2ccc(Cl)c(Cl)c2n1] | 345.0 |
| I-293 | 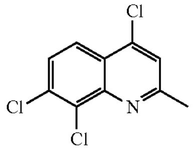 | 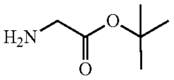 | 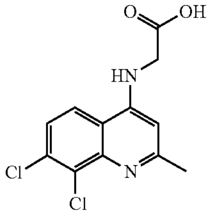 [SMILES: Cc1cc(NCC(=O)O)c2ccc(Cl)c(Cl)c2n1] | 285.0 |
| I-304 | 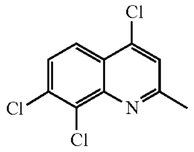 | 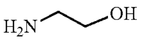 | 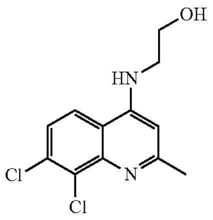 [SMILES: Cc1cc(NCCO)c2ccc(Cl)c(Cl)c2n1] | 271.0 |

-continued
| I-# | Starting Materials | | Structure | MS [M + 1]$^+$ |
|---|---|---|---|---|
| I-309 | 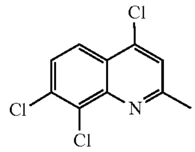 | 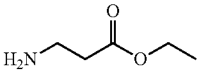 | 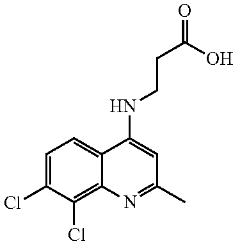 [SMILES: Cc1cc(NCCC(=O)O)c2ccc(Cl)c(Cl)c2n1] | 299.0 |
| I-66 | 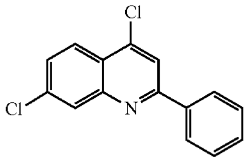 [SMILES: Clc1ccc2c(Cl)cc(-c3ccccc3)nc2c1] | 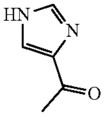 | 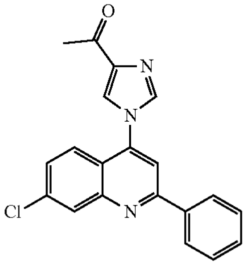 [SMILES: CC(=O)c1cn(-c2cc(-c3ccccc3)nc3cc(Cl)ccc23)cn1] | 348 |
| I-65 | 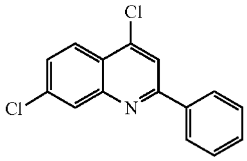 [SMILES: Clc1ccc2c(Cl)cc(-c3ccccc3)nc2c1] | 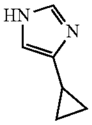 | 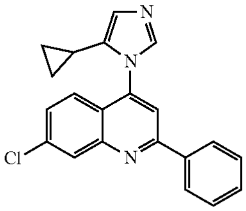 [SMILES: Clc1ccc2c(-n3cncc3C3CC3)cc(-c3ccccc3)nc2c1] | 346 |
| I-64 | 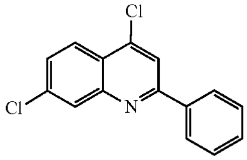 [SMILES: Clc1ccc2c(Cl)cc(-c3ccccc3)nc2c1] | 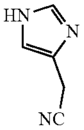 | 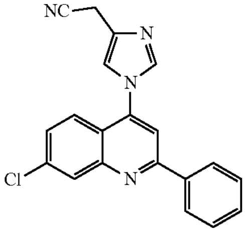 [SMILES: N#CCc1cn(-c2cc(-c3ccccc3)nc3cc(Cl)ccc23)cn1] | 345 |
| I-62 | 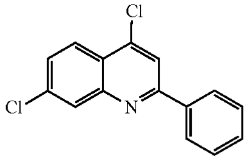 [SMILES: Clc1ccc2c(Cl)cc(-c3ccccc3)nc2c1] | 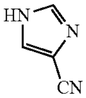 | 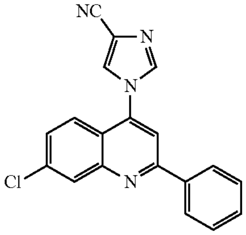 [SMILES: N#Cc1cn(-c2cc(-c3ccccc3)nc3cc(Cl)ccc23)cn1] | 331 |
| I-61 | 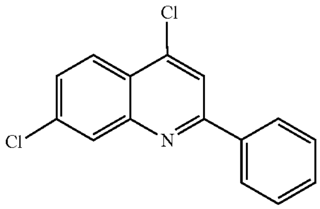 [SMILES: Clc1ccc2c(Cl)cc(-c3ccccc3)nc2c1] | 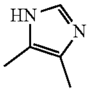 | 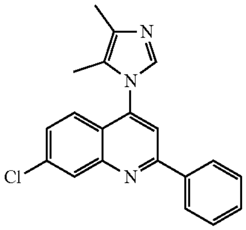 [SMILES: Cc1ncn(-c2cc(-c3ccccc3)nc3cc(Cl)ccc23)c1C] | 334 |

-continued

| I-# | Starting Materials | | Structure | MS [M + 1]$^+$ |
|---|---|---|---|---|
| I-63 | 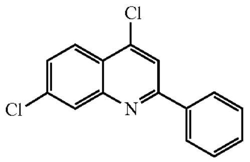 [SMILES: Clc1ccc2c(Cl)cc(-c3ccccc3)nc2c1] | 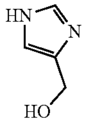 | 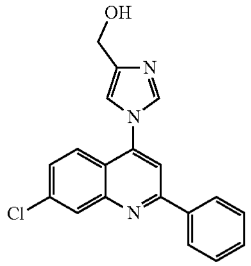 [SMILES: OCc1cn(-c2cc(-c3ccccc3)nc3cc(Cl)ccc23)cn1] | 336 |
| I-60 | 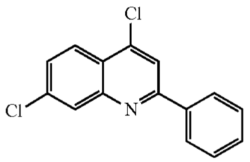 [SMILES: Clc1ccc2c(Cl)cc(-c3ccccc3)nc2c1] | 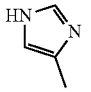 | 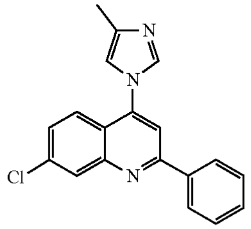 [SMILES: Cc1cn(-c2cc(-c3ccccc3)nc3cc(Cl)ccc23)cn1] | 320 |
| I-52 | 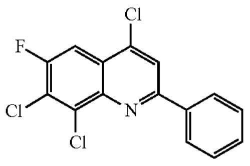 [SMILES: Fc1cc2c(Cl)cc(-c3ccccc3)nc2c(Cl)c1Cl] | 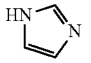 | 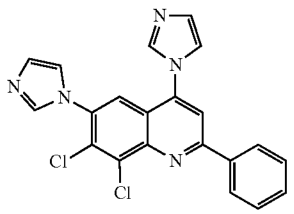 [SMILES: Clc1c(-n2ccnc2)cc2c(-n3ccnc3)cc(-c3ccccc3)nc2c1Cl] | 406 |
| I-39 | 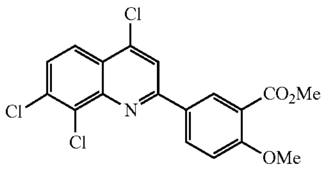 [SMILES: COC(=O)c1cc(-c2cc(Cl)c3ccc(Cl)c(Cl)c3n2)ccc1OC] | 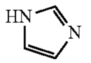 | 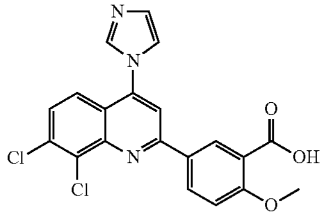 [SMILES: COc1ccc(-c2cc(-n3ccnc3)c3ccc(Cl)c(Cl)c3n2)cc1C(=O)O] | 414 |

Example 52: Synthesis of 7,8-dichloro-2-methyl-4-(1H-pyrazol-4-yl)quinoline (I-406)

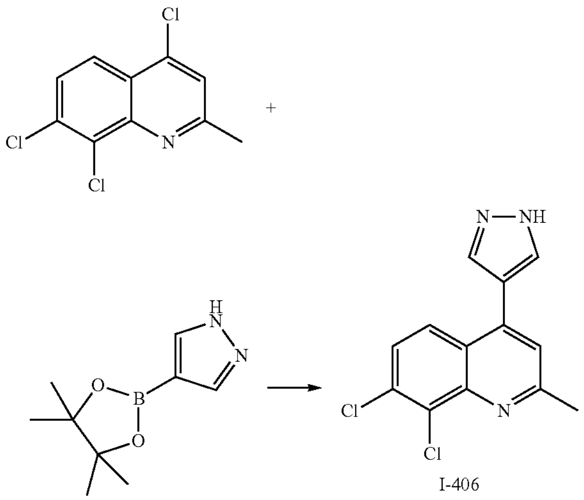 [SMILES: Cc1cc(Cl)c2ccc(Cl)c(Cl)c2n1 ; CC1(C)OB(c2cn[nH]c2)OC1(C)C ; Cc1cc(-c2cn[nH]c2)c2ccc(Cl)c(Cl)c2n1]

I-406

To a mixture of 4,7,8-trichloro-2-methylquinoline (0.2 g), 4-(4,4,5,5-tetramethyl-1,3,2-dioxaborolan-2-yl)-1H-pyrazole (281 mg), $K_2CO_3$ (278 mg) and $Pd(PPh_3)_4$ (85 mg) were added dioxane (4 mL) and water (2 mL). The resultant mixture was vacuumed and purged with $N_2$ repeatedly three time, then stirred and heated at 90° C. over 2 hours. A solution of 4-(4,4,5,5-tetramethyl-1,3,2-dioxaborolan-2-yl)-1H-pyrazole (150 mg) in dioxane (2 mL) was degassed and added to the reaction mixture. After 2 hours, the second portion of 4-(4,4,5,5-tetramethyl-1,3,2-dioxaborolan-2-yl)-1H-pyrazole (150 mg) in dioxane (2 mL) was added. After stirring overnight, 2,4,7,8-tetrachloroquinoline was completely consumed. Aqueous work-up and column purification eluting with hexane/EtOAc afforded the title compound (108 mg)-7,8-dichloro-2-methyl-4-(1H-pyrazol-4-yl) quinoline-MS: [M+1]$^+$ 278.

The following compounds are prepared essentially by the same method described above to prepare I-406 and the Suzuki coupling in I-42.

| I-# | Starting Materials | Structure | MS [M + 1]$^+$ |
|---|---|---|---|
| I-407 | 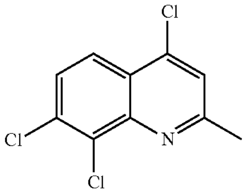 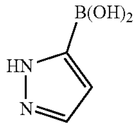 | 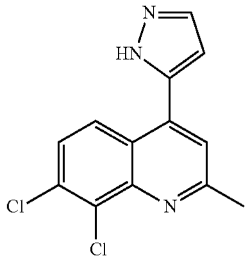 [SMILES: Cc1cc(-c2ccn[nH]2)c2ccc(Cl)c(Cl)c2n1] | 278 |
| I-67 | 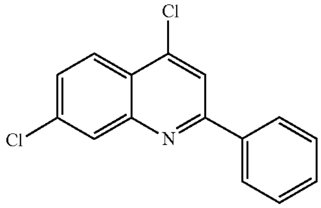 [SMILES: Clc1ccc2c(Cl)cc(-c3ccccc3)nc2c1] 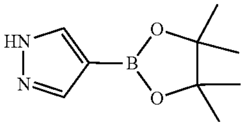 | 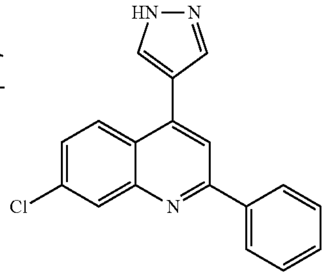 | 306 |
| I-68 | 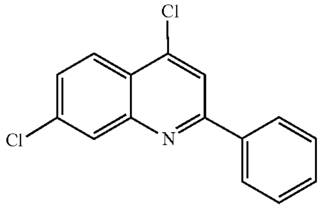 [SMILES: Clc1ccc2c(Cl)cc(-c3ccccc3)nc2c1] 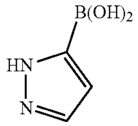 | 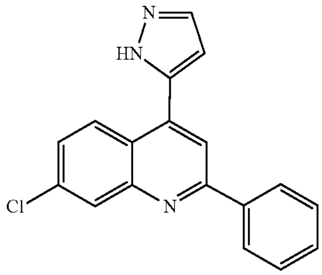 [SMILES: Clc1ccc2c(-c3ccn[nH]3)cc(-c3ccccc3)nc2c1] | 306 |
| I-73 | 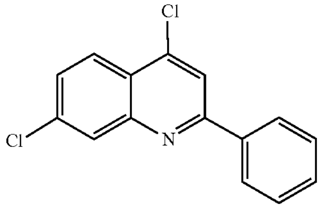 [SMILES: Clc1ccc2c(Cl)cc(-c3ccccc3)nc2c1] 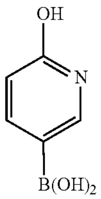 | 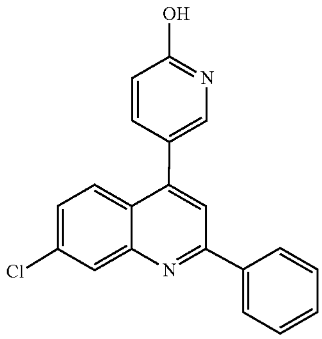 [SMILES: Oc1ccc(-c2cc(-c3ccccc3)nc3cc(Cl)ccc23)cn1] | 333 |
| I-72 | 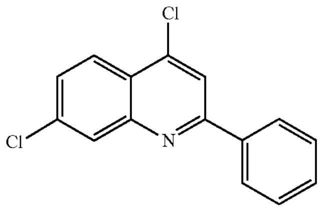 [SMILES: Clc1ccc2c(Cl)cc(-c3ccccc3)nc2c1] 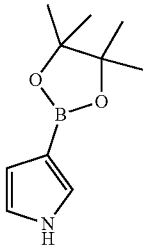 | 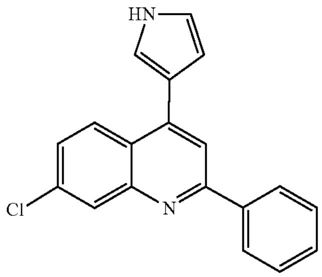 [SMILES: Clc1ccc2c(-c3cc[nH]c3)cc(-c3ccccc3)nc2c1] | 305 |

-continued

| I-# | Starting Materials | Structure | MS [M + 1]+ |
|---|---|---|---|
| I-70 | 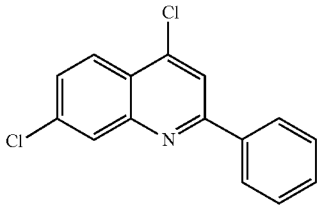 [SMILES: Clc1ccc2c(Cl)cc(-c3ccccc3)nc2c1] 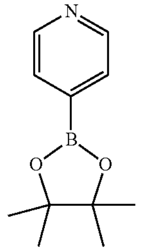 | 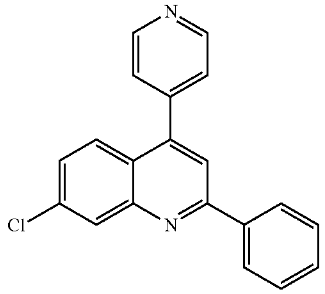 [SMILES: Clc1ccc2c(-c3ccncc3)cc(-c3ccccc3)nc2c1] | 317 |
| I-69 | 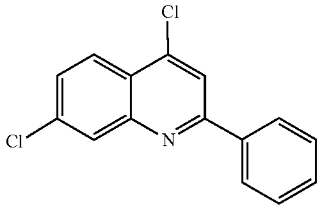 [SMILES: Clc1ccc2c(Cl)cc(-c3ccccc3)nc2c1] 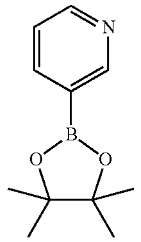 | 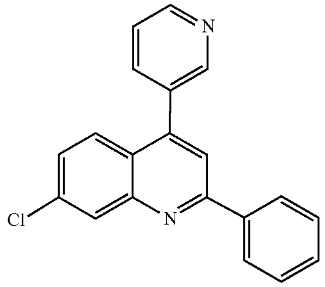 [SMILES: Clc1ccc2c(-c3cccnc3)cc(-c3ccccc3)nc2c1] | 317 |
| I-71 | 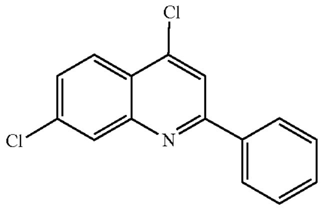 [SMILES: Clc1ccc2c(Cl)cc(-c3ccccc3)nc2c1] 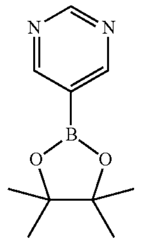 | 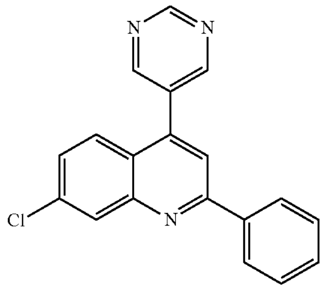 [SMILES: Clc1ccc2c(-c3cncnc3)cc(-c3ccccc3)nc2c1] | 318 |

Example 53: Synthesis of 8-chloro-4-(1H-imidazol-1-yl)quinoline (I-408)

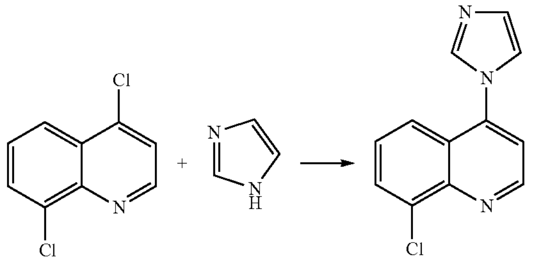

I-408

4,8-Dichloroquinoline (50 mg, 0.25 mmol) was placed in a vial with dioxane (2 mL). Imidazole (68 mg, 1.0 mmol) was added and the reaction was heated to 130° C. for 16 h. Water (10 mL) was added to the reaction and then the organics were extracted into ethyl acetate (2×5 mL). The organic phase was dried ($Na_2SO_4$) and concentrated. The residue was purified by silica chromatography using 30-100% (EtOAc/Hexanes) to afford 8-chloro-4-(1H-imidazol-1-yl)quinoline as a solid (MS: $[M+1]^+$ 230).

The following compounds are prepared essentially by the same method described above to prepare I-408.

| I-# | Starting Material | Structure | MS [M + 1]+ |
|---|---|---|---|
| I-409 | 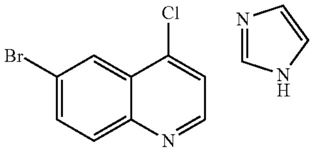 | 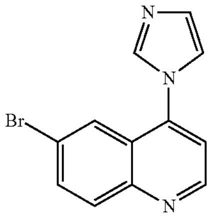 [SMILES: Brc1ccc2nccc(-n3ccnc3)c2c1] | 274 |
| I-410 | 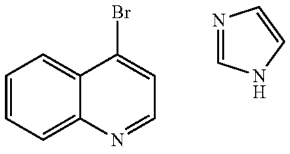 | 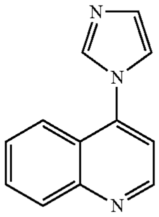 [SMILES: c1ccc2c(-n3ccnc3)ccnc2c1] | 196 |
| I-411 | 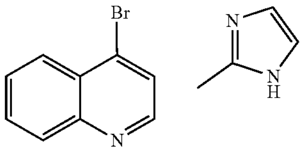 | 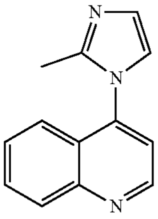 [SMILES: Cc1nccn1-c1ccnc2ccccc12] | 210 |
| I-412 | 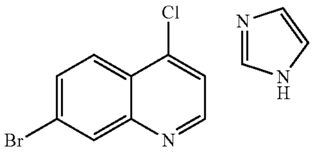 | 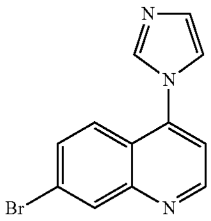 [SMILES: Brc1ccc2c(-n3ccnc3)ccnc2c1] | 274 |
| I-413 | 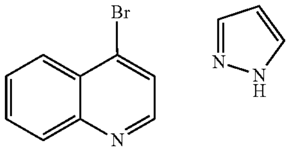 | 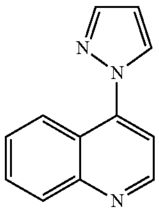 [SMILES: c1ccc2c(-n3cccn3)ccnc2c1] | 196 |
| I-414 | 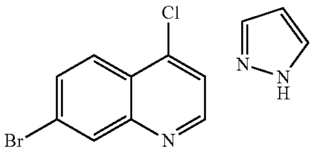 | 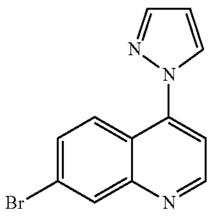 [SMILES: Brc1ccc2c(-n3cccn3)ccnc2c1] | 274 |
| I-415 | 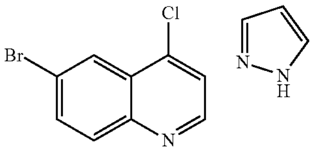 | 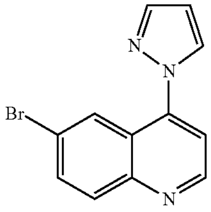 [SMILES: Brc1ccc2nccc(-n3cccn3)c2c1] | 274 |

-continued
| I-# | Starting Material | Structure | MS [M + 1]+ |
|---|---|---|---|
| I-416 | 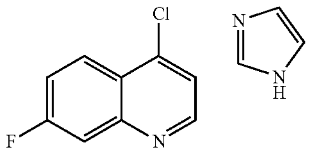 | 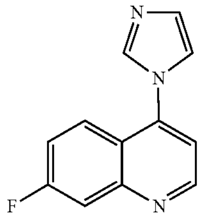 | 214 |
| I-417 | 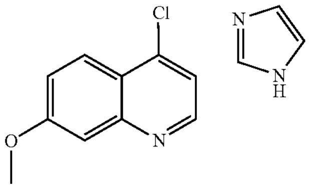 | 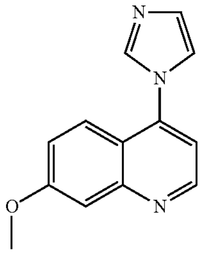 [SMILES: COc1ccc2c(-n3ccnc3)ccnc2c1] | 226.1 |
| I-418 | 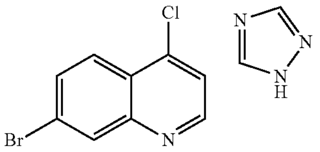 | 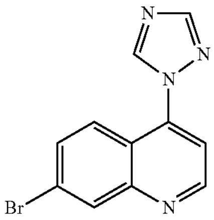 [SMILES: Brc1ccc2c(-n3cncn3)ccnc2c1] | 275.0 |
| I-419 | 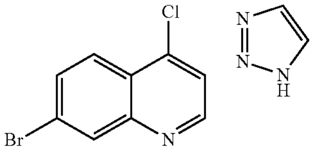 | 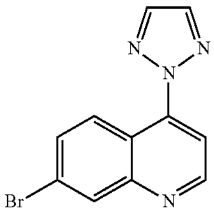 [SMILES: Brc1ccc2c(-n3nccn3)ccnc2c1] | 2 |
| I-420 | 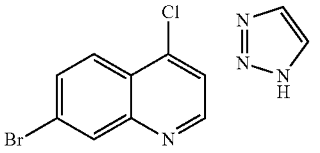 | 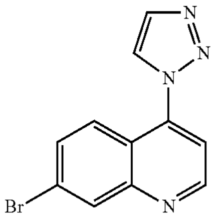 [SMILES: Brc1ccc2c(-n3ccnn3)ccnc2c1] | 74.9 |
Example 54: Synthesis of 7-chloro-4-(1H-imidazol-1-yl)-8-methylquinoline (I-421)
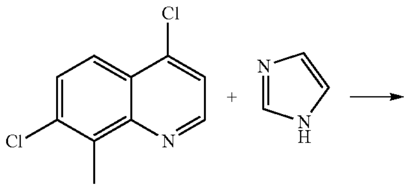
-continued
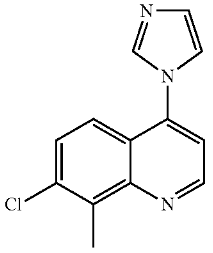
I-421
4,7-Dichloro-8-methylquinoline (53 mg, 0.25 mmol), imidazole (43 mg, 0.63 mmol), potassium t-butoxide (42 mg, 0.38 mmol), Bis(triphenylphosphine)palladium(II) dichloride (9 mg, 0.013 mmol) and DMF (3 mL) were placed in a vial under $N_2$. The mixture was heated at 110° C. for 2 h. After cooling down to room temperature, the crude is diluted by EtOAc (20 mL) and washed by water (5 mL×2) and brine (5 mL×2). The organic phase is concentrated and purified by column chromatography on silica gel to give 7-chloro-4-(1H-imidazol-1-yl)-8-methylquinoline as a solid. (MS: $[M+1]^+$ 244.0)

The following compounds are prepared essentially by the same method described above to prepare I-421.

-continued

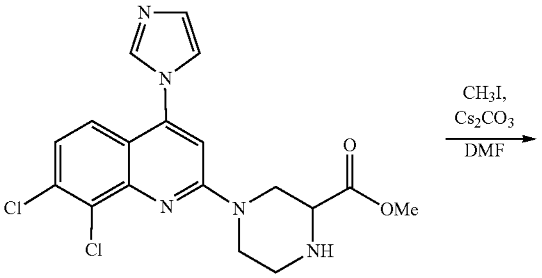

| I-# | Starting Material | Structure | MS $[M + 1]^+$ |
|---|---|---|---|
| I-422 | 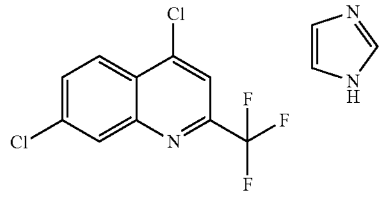 | 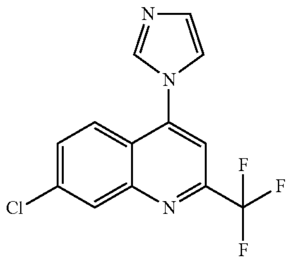 [SMILES: FC(F)(F)c1cc(-n2ccnc2)c2ccc(Cl)cc2n1] | 298 |

Example 55: Synthesis of 7-chloro-4-(1H-imidazol-1-yl)-8-methylquinoline (I-82)

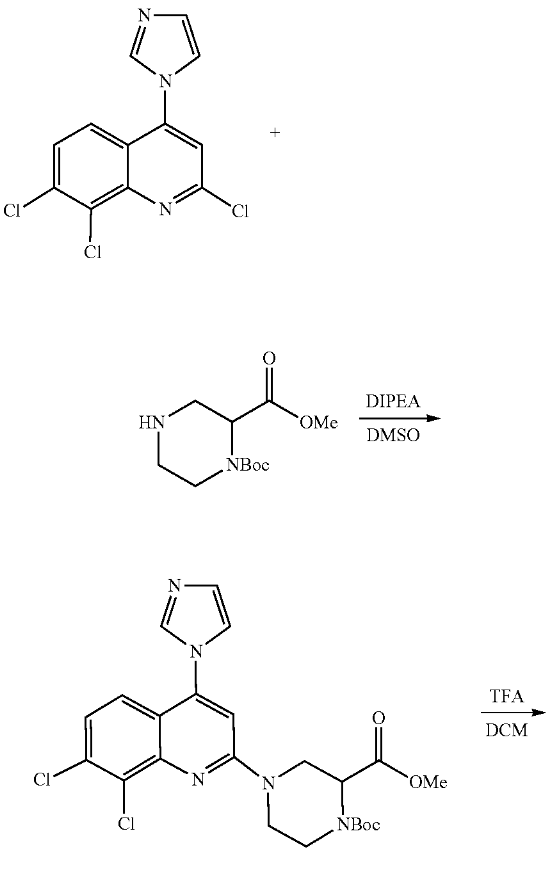

-continued

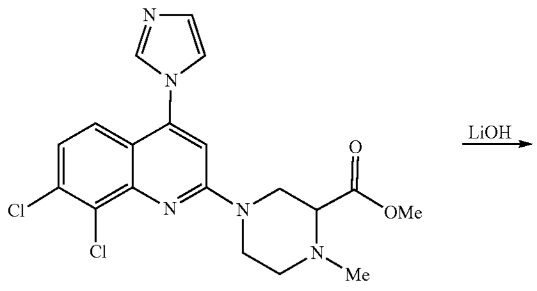

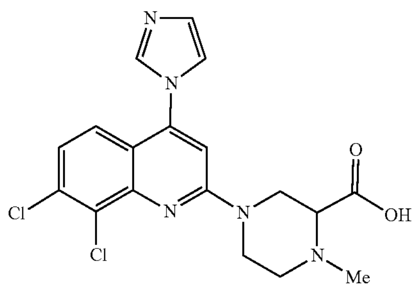

I-82

Step 1: 1-tert-Butyl 2-methyl 4-(7,8-dichloro-4-(1H-imidazol-1-yl)quinolin-2-yl)piperazine-1,2-dicarboxylate was prepared essentially by the same method described above to prepare I-79.

Step 2: Methyl 4-(7,8-dichloro-4-(1H-imidazol-1-yl)quinolin-2-yl)piperazine-2-carboxylate. To a vial were added 1-tert-butyl 2-methyl 4-(7,8-dichloro-4-(1H-imidazol-1-yl)quinolin-2-yl)piperazine-1,2-dicarboxylate (276 mg), DCM (1.0 mL) and TFA (1.0 mL). The resulting reaction mixture was stirred at room temperature for 2 hrs. All solvents were removed under reduced pressure. The residue was dried under high vacuum and the crude was used in next step (MS: $[M+1]^+$ 506).

Step 3: Methyl 4-(7,8-dichloro-4-(1H-imidazol-1-yl)quinolin-2-yl)-1-methylpiperazine-2-carboxylate. To a vial were added methyl 4-(7,8-dichloro-4-(1H-imidazol-1-yl)quinolin-2-yl)piperazine-2-carboxylate (0.025 mmol), DMF (0.5 mL), $Cs_2CO_3$ (16 mg, 0.05 mmol), a solution of $CH_3I$ in DMF (1.87 μl/0.5 mL, 0.03 mmol). The resulting reaction mixture was stirred at room temperature for 3 hrs. The reaction mixture was diluted with ethyl acetate (20 mL), washed by water (5 mL×2) and brine (5 mL), and dried over $Na_2SO_4$. The crude was purified by silica gel chromatography to afford 4 mg of the title compound (MS: $[M+1]^+$ 420).

Step 4: 4-(7,8-Dichloro-4-(1H-imidazol-1-yl)quinolin-2-yl)-1-methylpiperazine-2-carboxylic acid. To a vial were added methyl 4-(7,8-dichloro-4-(1H-imidazol-1-yl)quinolin-2-yl)-1-methylpiperazine-2-carboxylate (4.4 mg, 0.0105 mmol), MeOH (0.25 mL), THF (0.5 mL), a solution of LiOH—$H_2O$ in $H_2O$ (2.2 mg/0.25 mL, 0.0523 mmol). The resulting reaction mixture was stirred at room temperature overnight, acidified to pH 4. The cloudy mixture was centrifuged and the residue was dried under high vacuum to afford 4 mg the titled product as a white solid (MS: $[M+1]^+$ 406).

The following compounds were prepared essentially by the same method described above to prepare I-82.

Example 56: Synthesis of 4-(7,8-Dichloro-4-(1H-imidazol-1-yl)quinolin-2-yl)piperazine-2-carboxylic acid (I-79)

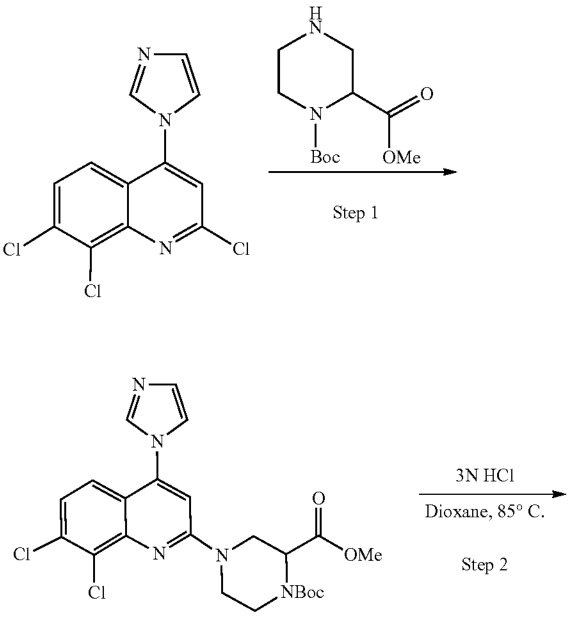

| I-# | Starting Material | Structure | MS [M + 1]+ |
| --- | --- | --- | --- |
| I-80 | 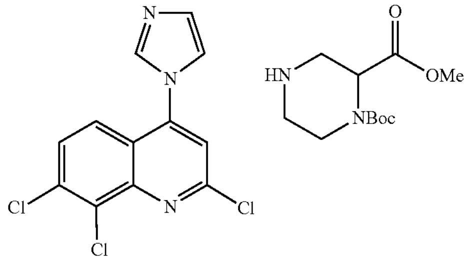 | 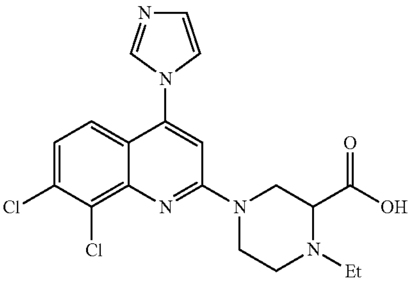 [SMILES: CCN1CCN(c2cc(-n3ccnc3)c3ccc(Cl)c(Cl)c3n2)CC1C(=O)O] | 420 |
| I-81 | 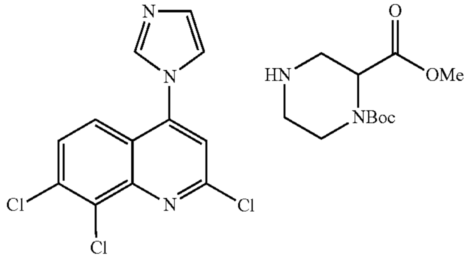 | 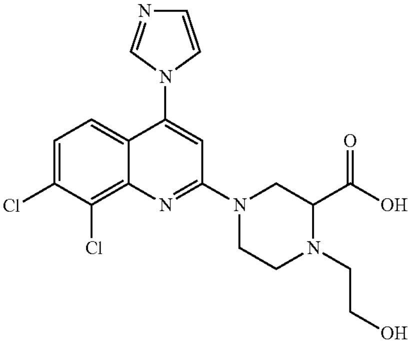 [SMILES: O=C(O)C1CN(c2cc(-n3ccnc3)c3ccc(Cl)c(Cl)c3n2)CCN1CCO] | 436 |

-continued

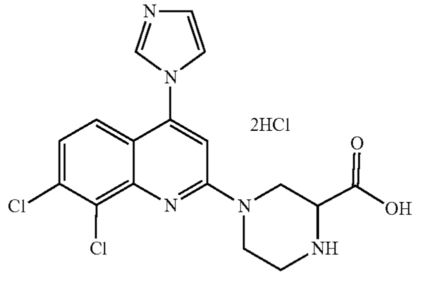

I-79

Step 1: 1-(tert-Butyl) 2-methyl 4-(7,8-dichloro-4-(1H-imidazol-1-yl)quinolin-2-yl)piperazine-1,2-dicarboxylate. A solution of 2,7,8-trichloro-4-(1H-imidazol-1-yl) quinoline (120 mg), 1-(tert-butyl) 2-methyl piperazine-1,2-dicarboxylate (230 mg), and DIPEA (0.1 mL) in DMF (0.6 mL) was heated at 90° C. overnight until the starting material was consumed. Aqueous work-up with EtOAc (25 mL)/water (10 mL) and a column chromatography eluting with a gradient of hexanes and EtOAc afforded the title compound (85 mg) (MS: $[M+1]^+$ 506).

Step 2: 4-(7,8-Dichloro-4-(1H-imidazol-1-yl)quinolin-2-yl)piperazine-2-carboxylic acid. To a solution of 1-(tert-butyl) 2-methyl 4-(7,8-dichloro-4-(1H-imidazol-1-yl)quinolin-2-yl)piperazine-1,2-dicarboxylate (85 mg) in dioxane (2 mL) was added 2 N HCl (2 mL). The resultant mixture was heated at 80° C. over 4 hours until the Boc protecting group and the methyl ester were removed. Evaporation under reduced pressure and lyophilization afforded the title compound (80 mg) as a di-HCl salt (MS: $[M+1]^+$392).

Example 57: Synthesis of 4-(7,8-dichloro-4-(1H-imidazol-1-yl)quinolin-2-yl)-1-(2-hydroxyacetyl) piperazine-2-carboxylic acid (I-83)

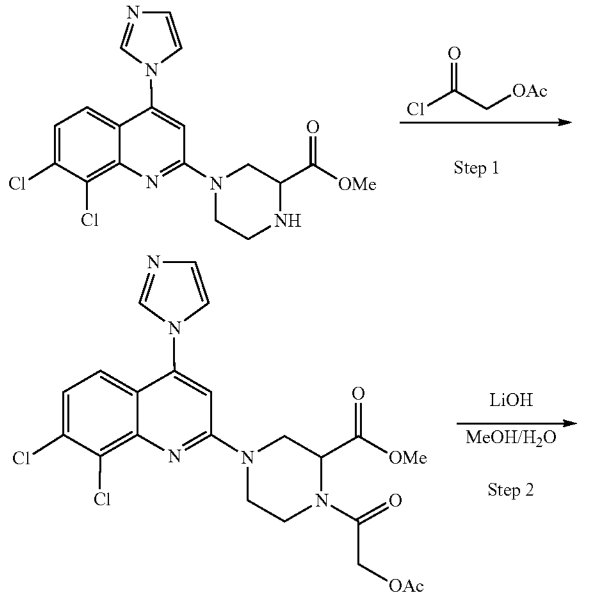

-continued

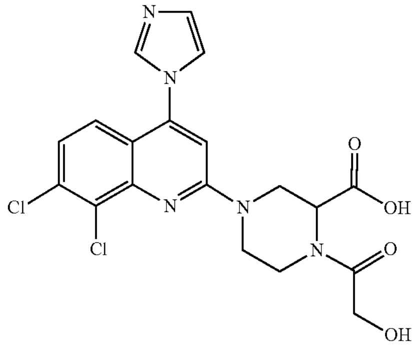

I-83

Step 1: Methyl 1-(2-acetoxyacetyl)-4-(7,8-dichloro-4-(1H-imidazol-1-yl)quinolin-2-yl)piperazine-2-carboxylate. Methyl 4-(7,8-dichloro-4-(1H-imidazol-1-yl)quinolin-2-yl) piperazine-2-carboxylate TFA salt (20 mg) in DMF (0.5 mL) and TEA (0.1 mL) was treated with 2-chloro-2-oxoethyl acetate (20 mg) over 4 hours. Aqueous work up with EtOAc/water/sat $NaHCO_3$/brine and purification by column chromatography afforded methyl 1-(2-acetoxyacetyl)-4-(7,8-dichloro-4-(1H-imidazol-1-yl)quinolin-2-yl)piperazine-2-carboxylate (12 mg) (MS: $[M+1]^+$ 506).

Step 2: 4-(7,8-Dichloro-4-(1H-imidazol-1-yl)quinolin-2-yl)-1-(2-hydroxyacetyl)piperazine-2-carboxylic acid. The intermediate was dissolved in MeOH (0.8 mL) and water (0.2 mL) and treated with LiOH—$H_2O$ (20 mg) overnight. The reaction mixture was diluted with water (2 mL) and acidified with HOAc (0.02 mL) to precipitate 4-(7,8-dichloro-4-(1H-imidazol-1-yl)quinolin-2-yl)-1-(2-hydroxyacetyl)piperazine-2-carboxylic acid (7 mg) (MS: $[M+1]^+$ 450).

Example 58: Synthesis of 1-(7,8-dichloro-4-(1H-imidazol-1-yl) quinolin-2-yl)-3-(2-hydroxyacetamido) piperidine-3-carboxylic acid (I-125)

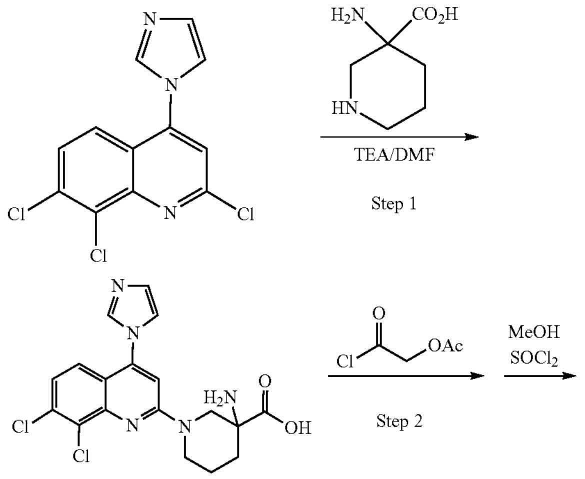

-continued

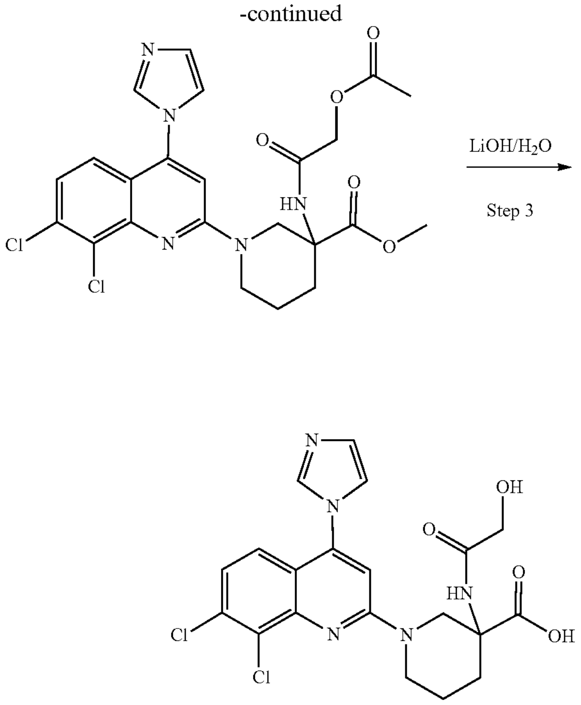

I-125

Step 1: 3-Amino-1-(7,8-dichloro-4-(1H-imidazol-1-yl) quinolin-2-yl)piperidine-3-carboxylic acid. A solution of 2,7,8-trichloro-4-(1H-imidazol-1-yl) quinoline (30 mg) with 3-aminopiperidine-3-carboxylic acid (65 mg) and triethylamine (0.2 mL) in DMF (0.5 mL) was heated at 90° C. over 5 hours until the starting material was consumed. The resultant mixture was diluted with water (2 mL), frozen and lyophilized to afford a mixture containing the title compound, which was used in the next step directly (MS: $[M+1]^+$ 406).

Step 2: Methyl 1-(7,8-dichloro-4-(1H-imidazol-1-yl)quinolin-2-yl)-3-(2-hydroxyacetamido)piperidine-3-carboxylate. The mixture from the above step was suspended in anhydrous DCM (2 mL) and mixed with 2-chloro-2-oxoethyl acetate (0.06 mL) and TEA (0.1 mL). The resultant mixture was stirred at room temperature over 3 hours until the starting was completely consumed. The reaction mixture was concentrated to dryness under reduced pressure. The resultant mixture was dissolved in anhydrous MeOH (5 mL) and treated with a couple of drops of $SOCl_2$. After stirring overnight, the acid was converted to the methyl ester. After solvent evaporation under reduced pressure and aqueous work up with EtOAc, column chromatography afforded the desired methyl ester (12 mg). (MS: $[M+1]^+$ 478)

Step 3: 1-(7,8-dichloro-4-(1H-imidazol-1-yl) quinolin-2-yl)-3-(2-hydroxyacetamido) piperidine-3-carboxylic acid. Methyl 1-(7,8-dichloro-4-(1H-imidazol-1-yl)quinolin-2-yl)-3-(2-hydroxyacetamido)piperidine-3-carboxylate (12 mg) was treated with LiOH—$H_2O$ (8 mg) in MeOH (2 mL) and water (0.5 mL) over 4 hours. After evaporation of the organic solvents under reduced pressure, the resultant solid mixtures were carefully suspended in water (1 mL) and neutralized with HOAc (0.020 mL). The solid was isolated by centrifuge and rinsed with water (1 mL). The resultant wet cake was lyophilized to afford the title compound (7 mg) as a colorless powder (MS: $[M+1]^+$ 464).

Example 59: Synthesis of 7-chloro-4-(1H-imidazol-1-yl)-2-(piperazin-1-yl)quinoline (I-76)

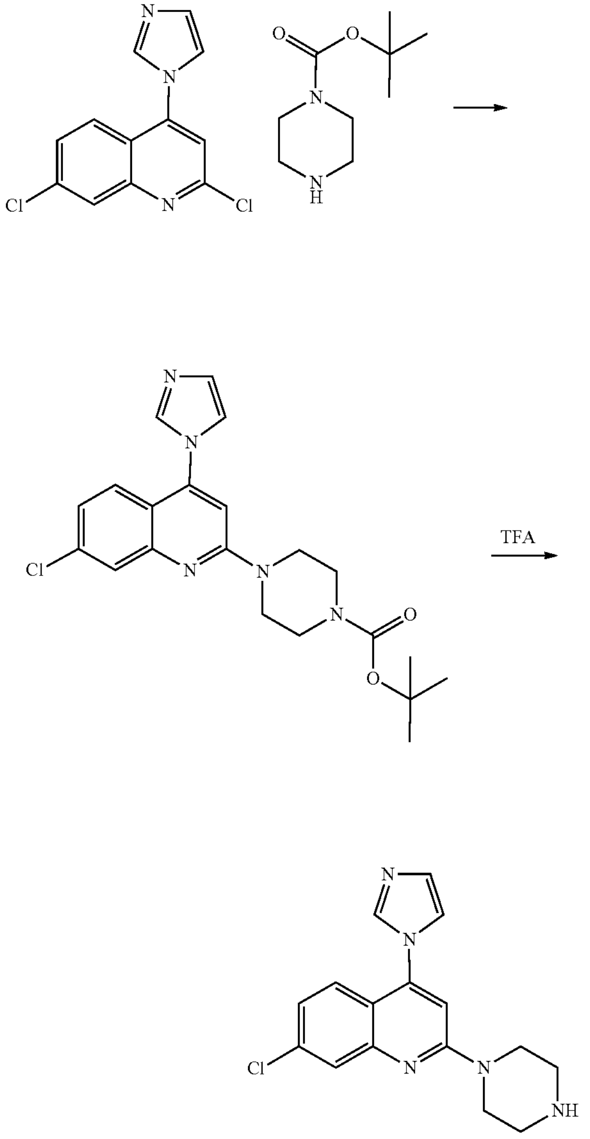

I-76

A solution of 2,7-dichloro-4-(1H-imidazol-1-yl)quinoline (46 mg) in EtOH (5 mL) was treated with tert-butyl piperazine-1-carboxylate (60 mg) in the presence of $K_2CO_3$ (48 mg) overnight at 80° C. Aqueous work-up with EtOAc and water removed inorganic bases. The separation of the organic layer and evaporation of organic solvents afforded the desired tert-butyl 4-(7-chloro-4-(1H-imidazol-1-yl)quinolin-2-yl)piperazine-1-carboxylate intermediate. Deprotection with DCM (3 mL) and TFA (1 mL) in 4 hours at room temperature gave the TFA salt of the desired product. The TFA salt were dissolved in DMF (1 mL) and precipitated out as neutral product (40 mg) after adding an aqueous solution of $NaHCO_3$ to afford the title compound (30 mg) (MS: $[M+1]^+$ 314).

Example 60: Synthesis of 1-(4-(7-chloro-4-(1H-imidazol-1-yl)quinolin-2-yl)piperazin-1-yl)-2-hydroxyethan-1-one (I-77)

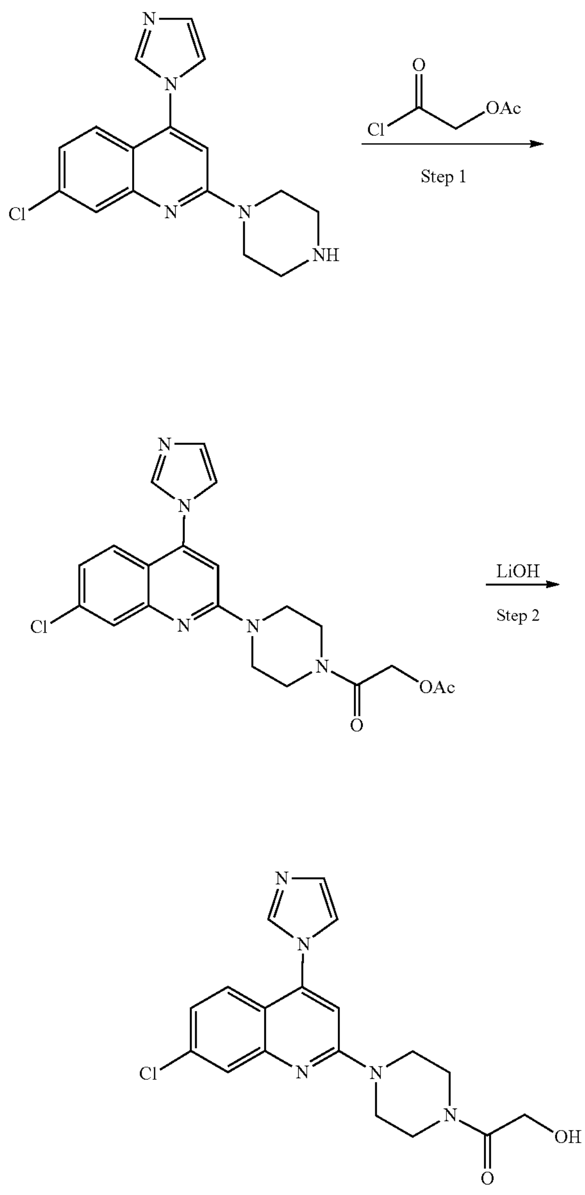

I-77

A solution of 7-chloro-4-(1H-imidazol-1-yl)-2-(piperazin-1-yl)quinoline (10 mg, 1981) in DMF (1 mL) was added to a mixture of 2-chloro-2-oxoethyl acetate (56 mg) and TEA (0.1 mL). After stirring over 2 hours, aqueous work-up with EtOAc (10 mL) and evaporation under reduced pressure afforded a residue with the desired intermediate 2-(4-(7-chloro-4-(1H-imidazol-1-yl)quinolin-2-yl) piperazin-1-yl)-2-oxoethyl acetate (20 mg). (MS: $[M+1]^+$ 414). This residue was treated with LiOH (60 mg) in MeOH (4 mL) and water (1 mL) over 4 hours. Aqueous work-up with EtOAc and a column chromatography afforded the desired product (7 mg) (MS: $[M+1]^+$ 372).

Example 61: Synthesis of 7-chloro-4-(1H-imidazol-1-yl)-2-(4-(methylsulfonyl) piperazin-1-yl) quinoline (I-78)

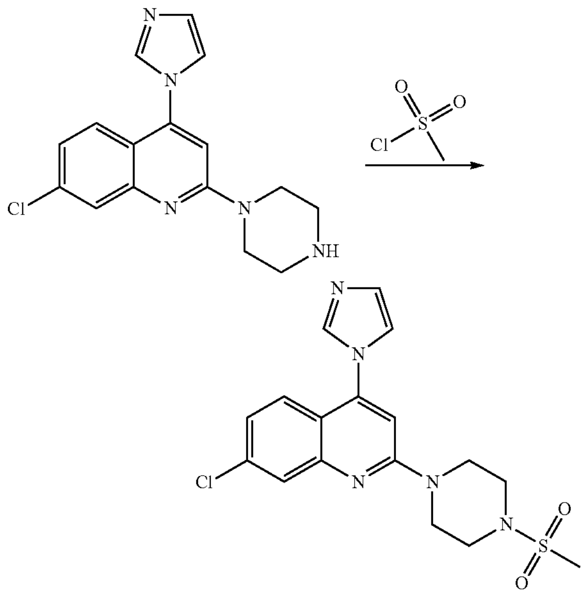

I-78

To a solution of 7-chloro-4-(1H-imidazol-1-yl)-2-(piperazin-1-yl) quinoline (10 mg) in DMF (1 mL) were added methanesulfonyl chloride (30 mg) and TEA (0.1 mL). After stirring overnight, aqueous work-up with EtOAc/water and a column chromatography afforded the titled product (8 mg) (MS: $[M+1]^+$ 392).

Example 62: Synthesis of 2-(4-(7-chloro-4-(1H-imidazol-1-yl)quinolin-2-yl)-2-oxo-1,4-diazepan-1-yl)acetic acid (I-90)

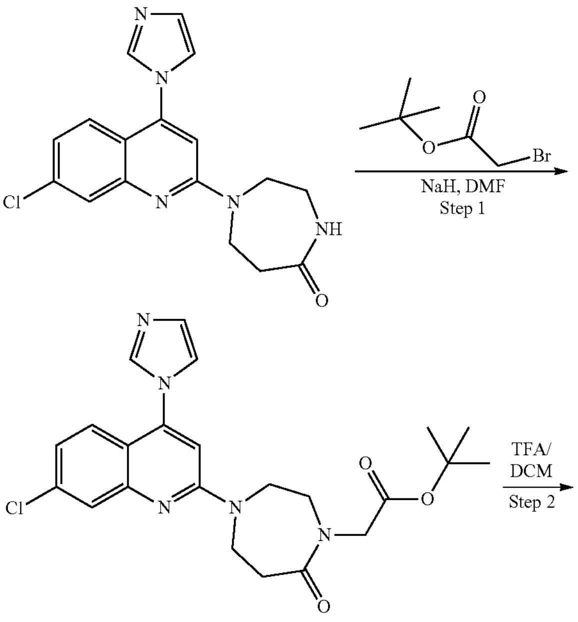

-continued

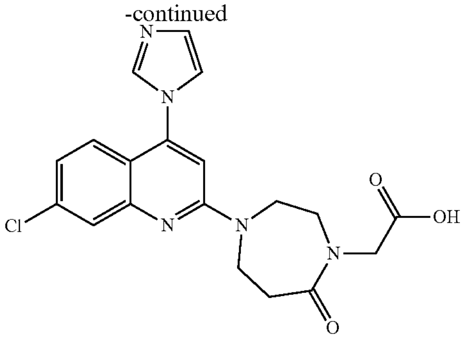

I-90

Step 1: tert-butyl 2-(4-(7-chloro-4-(1H-imidazol-1-yl)quinolin-2-yl)-2-oxo-1,4-diazepan-1-yl)acetate. To a solution of 4-(7-chloro-4-(1H-imidazol-1-yl)quinolin-2-yl)-1,4-diazepan-2-one (20 mg) and tert-butyl 2-bromoacetate (30 mg) in anhydrous DMF was added NaH (10 mg, 65% in mineral oil). After stirring 3 hours, the reaction mixture was diluted with EtOAc (10 mL) and carefully quenched with water (5 mL). Isolation of the organic layer and a column chromatography eluting with a gradient of hexanes and EtOAc afforded the desired intermediate tert-butyl 2-(4-(7-chloro-4-(1H-imidazol-1-yl)quinolin-2-yl)-2-oxo-1,4-diazepan-1-yl)acetate (20 mg) (MS: $[M+1]^+$ 456).

Step 2: 2-(4-(7-chloro-4-(1H-imidazol-1-yl)quinolin-2-yl)-2-oxo-1,4-diazepan-1-yl)acetic acid. tert-butyl 2-(4-(7-chloro-4-(1H-imidazol-1-yl)quinolin-2-yl)-2-oxo-1,4-diazepan-1-yl)acetate was further treated with TFA (0.4 mL) in DCM (0.8 mL). Removal of DCM and TFA under reduced pressure and lyophilization afforded the desired product (10 mg)-2-(4-(7-chloro-4-(1H-imidazol-1-yl)quinolin-2-yl)-2-oxo-1,4-diazepan-1-yl)acetic acid (MS: $[M+1]^+$ 400).

Example 63: Synthesis of (R)-1-(7-chloro-4-(1H-imidazol-1-yl)quinolin-2-yl)-N-hydroxypiperidine-3-carboxamide (I-137)

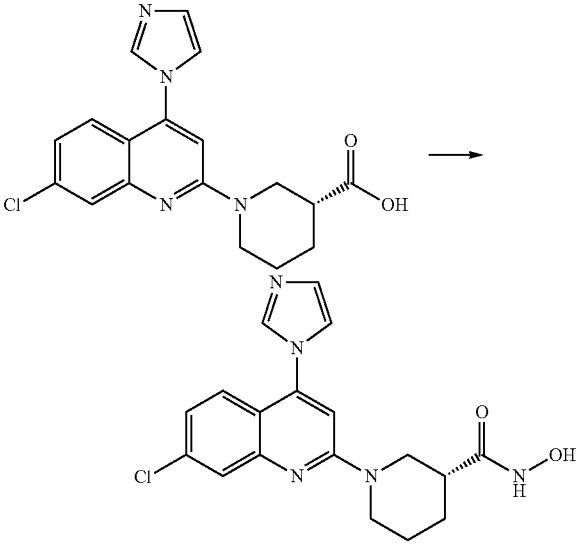

I-137

To a solution of (R)-1-(7-chloro-4-(1H-imidazol-1-yl)quinolin-2-yl)piperidine-3-carboxylic acid (25 mg, 0.05 mmol, TEA salt) in DMF (2 mL) was added $(COCl)_2$ (0.017 mL, 0.2 mmol) at 0° C. The solution was stirred at rt for 1 h. The mixture was evaporated to give a crude as white solid.

Hydroxylamine hydrochloride (35 mg, 0.5 mmol) and TEA (0.1 mL) was dissolved in THF (0.5 mL) and water (0.1 mL) at 0° C. A solution of the crude from the first step in DCM (1 mL) was added. The mixture was stirred at rt overnight. The crude was purified directly by column chromatography on silica gel to give (R)-1-(7-chloro-4-(1H-imidazol-1-yl)quinolin-2-yl)-N-hydroxypiperidine-3-carboxamide as a solid. (11 mg, 59% yield) (MS: $[M+1]^+$ 372).

Example 64: Synthesis of (1-(7,8-Dichloro-4-(1H-imidazol-1-yl)quinolin-2-yl)piperidin-3-yl)boronic acid (I-120)

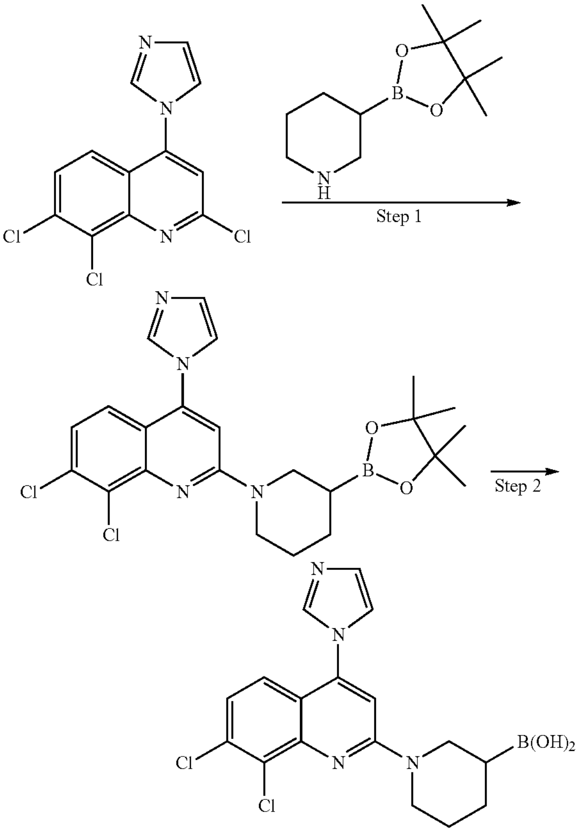

I-120

Step 1: 7,8-Dichloro-4-(1H-imidazol-1-yl)-2-(3-(4,4,5,5-tetramethyl-1,3,2-dioxaborolan-2-yl)piperidin-1-yl)quinoline. To a solution of 2,7,8-trichloro-4-(1H-imidazol-1-yl)quinoline (30 mg, 0.1 mmol) and 3-(4,4,5,5-tetramethyl-1,3,2-dioxaborolan-2-yl)piperidine (38 mg, 0.15 mmol) in DMF (1 mL) was added $NaHCO_3$ (42 mg, 0.5 mmol). The solution was vigorously stirred at 100° C. for 2 h. After cooling down to room temperature, water (2 mL) was added. The crude was collected by filtration (50 mg) which is used for next step without purification (MS: $[M+1]^+$ 472).

Step 2: (1-(7,8-Dichloro-4-(1H-imidazol-1-yl)quinolin-2-yl)piperidin-3-yl)boronic acid. To a mixture of 7,8-dichloro-4-(1H-imidazol-1-yl)-2-(3-(4,4,5,5-tetramethyl-1,3,2-dioxaborolan-2-yl)piperidin-1-yl)quinoline (50 mg, 0.1 mmol), $NaIO_4$ (43 mg, 0.2 mmol) and $NH_4OAc$ (15 mg, 0.2 mmol) was added water (1 mL) and acetone (1 mL). The mixture was stirred at rt overnight. After evaporation, the crude was purified directly by column chromatography on silica gel to give the titled product as a solid (35 mg) (MS: $[M+1]^+$ 391).

Example 65: Synthesis of tert-butyl ((2-(((7,8-dichloro-4-(1H-imidazol-1-yl)quinolin-2-yl)amino)methyl)morpholino)sulfonyl)carbamate (I-398) and 2-(((7,8-dichloro-4-(1H-imidazol-1-yl)quinolin-2-yl)amino)methyl)morpholine-4-sulfonamide (I-219)

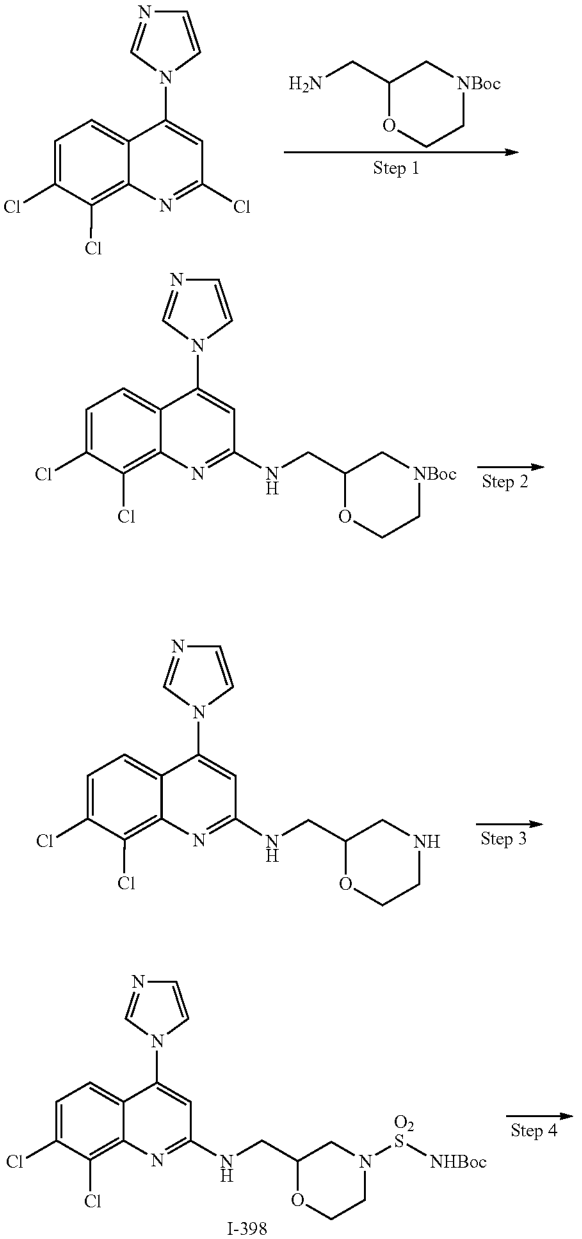

I-398

-continued

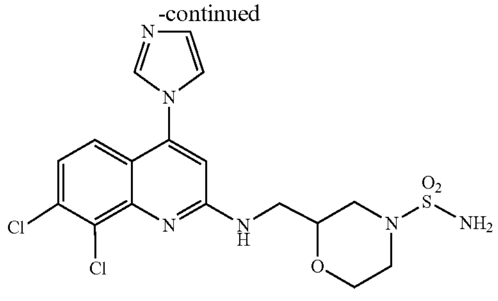

I-219

Step 1: tert-Butyl 2-(((7,8-dichloro-4-(1H-imidazol-1-yl)quinolin-2-yl)amino)methyl)morpholine-4-carboxylate. To a solution of 2,7,8-trichloro-4-(1H-imidazol-1-yl)quinoline (300 mg, 1 mmol) in DMF (2 mL) was added tert-butyl 2-(aminomethyl)morpholine-4-carboxylate (320 mg, 1.5 mmol) and $NaHCO_3$ (336 mg, 4 mmol). The mixture was vigorously stirred at 120° C. for 2 h. After cooling down to rt, DMF was removed by evaporation. The residue was dissolved in DCM (20 mL) and washed by $H_2O$ (10 mL) and brine (10 mL×2). The organic phase was collected and concentrated to give white solid (500 mg) which was used directly without purification (MS: $[M+1]^+$478).

Step 2: 7,8-Dichloro-4-(1H-imidazol-1-yl)-N-(morpholin-2-ylmethyl)quinolin-2-amine. A solution of tert-butyl 2-(((7,8-dichloro-4-(1H-imidazol-1-yl)quinolin-2-yl)amino)methyl)morpholine-4-carboxylate (500 mg crude from step 1) in 50% TFA in DCM (5 mL) was stirred at rt for 1 h. After evaporation, the crude was purified directly by column chromatography on silica gel to give the titled product as a solid. (110 mg) (MS: $[M+1]^+$ 378).

Step 3: tert-Butyl ((2-(((7,8-dichloro-4-(1H-imidazol-1-yl)quinolin-2-yl)amino)methyl)morpholino)sulfonyl)carbamate. To a solution of chlorosulfonyl isocyanate (0.1 mL, 1.15 mmol) in DCM (1 mL) was added t-BuOH (0.085 mL, 1.15 mmol) at 0° C. for 30 min. To a solution of 7,8-dichloro-4-(1H-imidazol-1-yl)-N-(morpholin-2-ylmethyl)quinolin-2-amine (48 mg, 0.1 mmol) and triethylamine (0.04 mL, 0.3 mmol) in DCM (1 mL) was added the N-chlorosulfonyl carbamate solution above (0.1 mL, 0.115 mmol) at 0° C. After 2 h, the mixture was evaporated and purified by column chromatography on silica gel to give the titled product as a solid (25 mg) (MS: $[M+1]^+$ 557).

Step 4: 2-(((7,8-Dichloro-4-(1H-imidazol-1-yl)quinolin-2-yl)amino)methyl)morpholine-4-sulfonamide. A solution of tert-butyl ((2-(((7,8-dichloro-4-(1H-imidazol-1-yl)quinolin-2-yl)amino)methyl)morpholino)sulfonyl)carbamate (11 mg, 0.02 mmol) in 50% TFA in DCM (1 mL) was stirred at rt for 1 h. After evaporation, the crude was purified directly by column chromatography on silica gel to give the titled product as a solid (3 mg) (MS: $[M+1]^+$ 457.0).

The following compounds are prepared essentially by the same method described above to prepare I-398 and I-219.

| I-# | Starting Material | Structure | MS [M + 1]+ |
|---|---|---|---|
| I-399 | 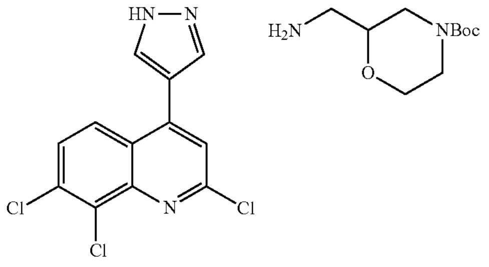 | 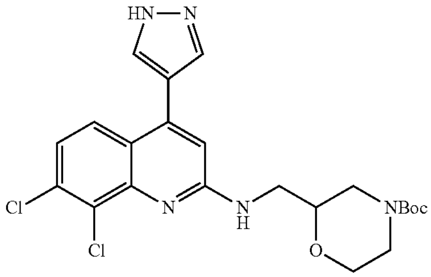 [SMILES: CC(C)(C)OC(=O)N1CCOC(CNc2cc(-c3cn[nH]c3)c3ccc(Cl)c(Cl)c3n2)C1] | 478.2 |
| I-220 | 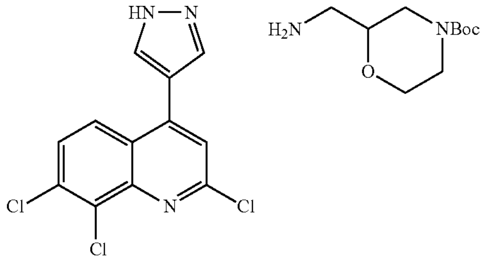 | 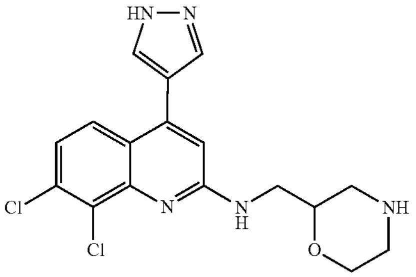 [SMILES: Clc1ccc2c(-c3cn[nH]c3)cc(NCC3CNCCO3)nc2c1Cl] | 378.1 |
| I-217 | 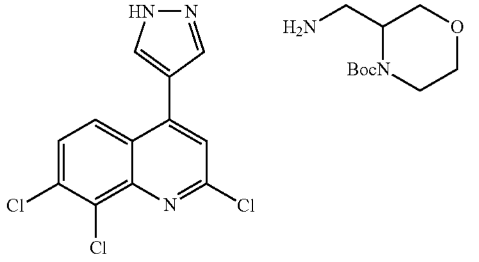 | 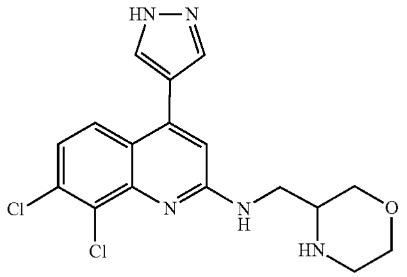 [SMILES: Clc1ccc2c(-c3cn[nH]c3)cc(NCC3COCCN3)nc2c1Cl] | 378.1 |

Example 66: Synthesis of 7-chloro-4-(1H-imidazol-1-yl)-8-methylquinoline (I-221)

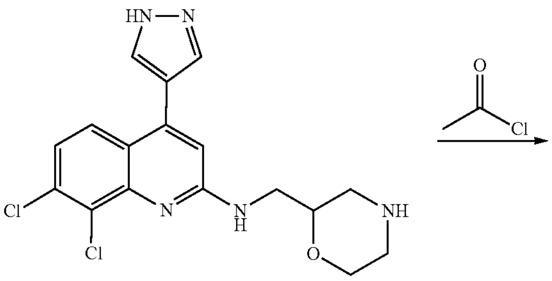

-continued

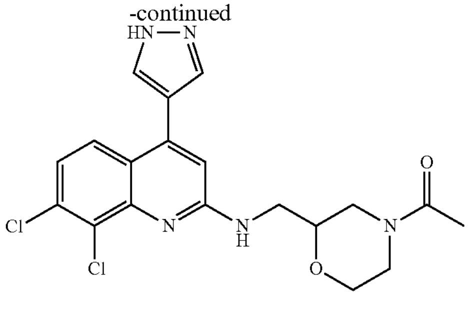

I-221

To a solution of 7,8-dichloro-N-(morpholin-2-ylmethyl)-4-(1H-pyrazol-4-yl)quinolin-2-amine (20 mg, 0.053 mmol) in THF (1 mL) was added triethylamine (0.074 mL, 0.53 mmol) and acetyl chloride (0.0057 mL, 0.08 mmol) at 0° C. After 1 h at rt, the reaction was quenched by MeOH (0.1 mL). After evaporation, the crude was purified directly by column chromatography on silica gel to give 1-(2-(((7,8-dichloro-4-(1H-pyrazol-4-yl)quinolin-2-yl)amino)methyl)morpholino)ethan-1-one as a solid (7 mg) (MS: $[M+1]^+$ 420.0).

The following compounds are prepared essentially by the same method described above to prepare I-221.

| I-# | Starting Material | Structure | MS [M + 1]+ |
|---|---|---|---|
| I-400 | 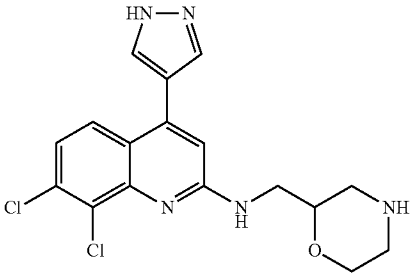 [SMILES: Clc1ccc2c(-c3cn[nH]c3)cc(NCC3CNCCO3)nc2c1Cl] | 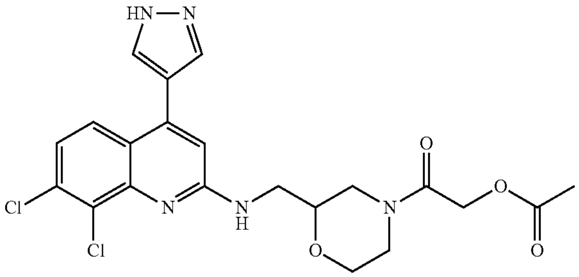 [SMILES: CC(=O)OCC(=O)N1CCOC(CNc2cc(-c3cn[nH]c3)c3ccc(Cl)c(Cl)c3n2)C1] | 478.1 |
| I-222 | 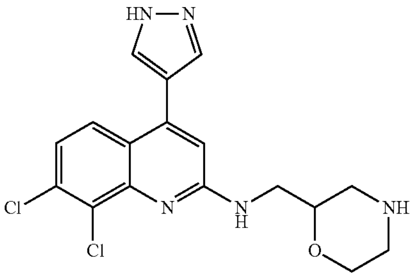 [SMILES: Clc1ccc2c(-c3cn[nH]c3)cc(NCC3CNCCO3)nc2c1Cl] | 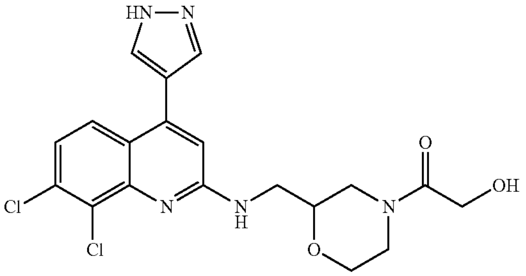 [SMILES: O=C(CO)N1CCOC(CNc2cc(-c3cn[nH]c3)c3ccc(Cl)c(Cl)c3n2)C1] | 436.1 |

Example 67: Synthesis of 7-bromo-4-(1H-imidazol-1-yl)-2-phenylquinoline (I-424)

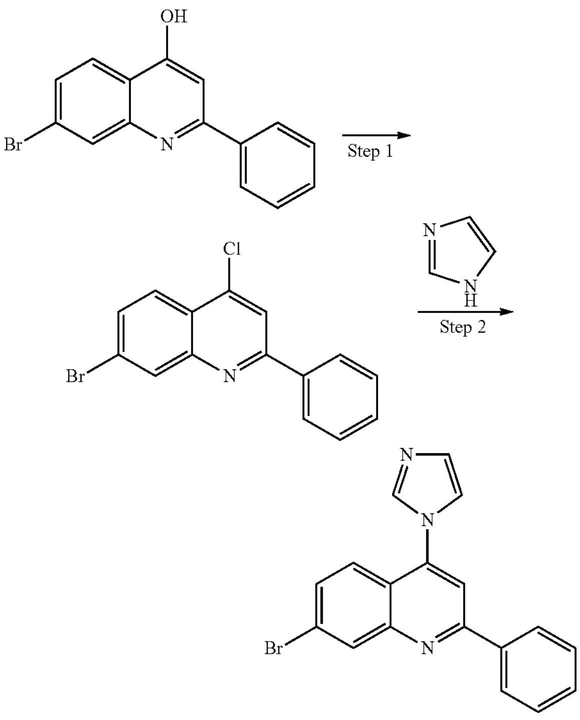

I-424

Step 1: 7-Bromo-2-phenylquinolin-4-ol (250 mg, 0.83 mmol) was placed in a flask with phosphorus oxychloride (8 mL) and heated to 100° C. for 4 h. After removal of the volatiles under reduced pressure, the residue was dried in vacuo. The crude 7-bromo-4-chloro-2-phenylquinoline was taken onward without further purification.

Step 2: 7-Bromo-4-chloro-2-phenylquinoline (50 mg, 0.16 mmol), imidazole (27 mg, 0.39 mmol), potassium t-butoxide (26 mg, 0.23 mmol), Bis(triphenylphosphine) palladium(II) dichloride (6 mg, 0.008 mmol) and DMA (5 mL) were placed in a vial under $N_2$. The mixture was heated at 110° C. for 2 h. After cooling down to room temperature, ice was added and then the aqueous was extracted with EtOAc (2×10 mL) and washed by water (5 mL×2) and brine (5 mL×2). The organic phase was concentrated and purified by column chromatography on silica gel to give 7-bromo-4-(1H-imidazol-1-yl)-2-phenylquinoline as a solid (37 mg) (MS: $[M+1]^+$ 350).

Example 68: Synthesis of 1-(1-(7-chloro-4-(1H-imidazol-1-yl)quinolin-2-yl)piperidin-3-yl)urea (I-104)

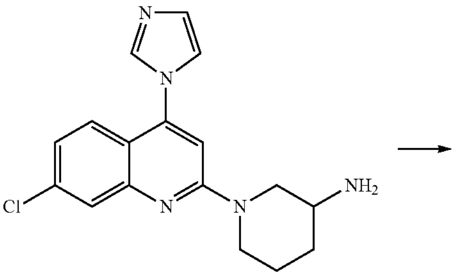

-continued

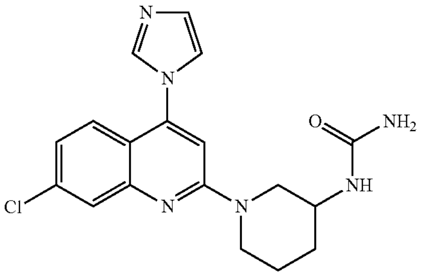

I-204

To a solution of 1-(7-chloro-4-(1H-imidazol-1-yl)quinolin-2-yl)piperidin-3-amine (di TFA salt) (I-108, 23 mg, 0.041 mmol) in THF (3 mL) and triethylamine (0.03 mL, 0.212 mmol) was added (trimethylsilyl) isocyanate (8 mg, 0.071 mmol). The solution was stirred at rt for 3 h. Methanol (1 mL) was added and then the volatiles were removed by rotary evaporation. Water (3 mL) was added to the residue and the resulting solids were filtered and dried to afford 1-(1-(7-chloro-4-(1H-imidazol-1-yl)quinolin-2-yl)piperidin-3-yl)urea (12 mg) (MS: $[M+1]^+$ 371).

Example 69: Synthesis of 2-((7,8-dichloro-4-(1H-imidazol-1-yl)quinolin-2-yl)amino)-3-phenylpropane-1-sulfonic acid (I-162)

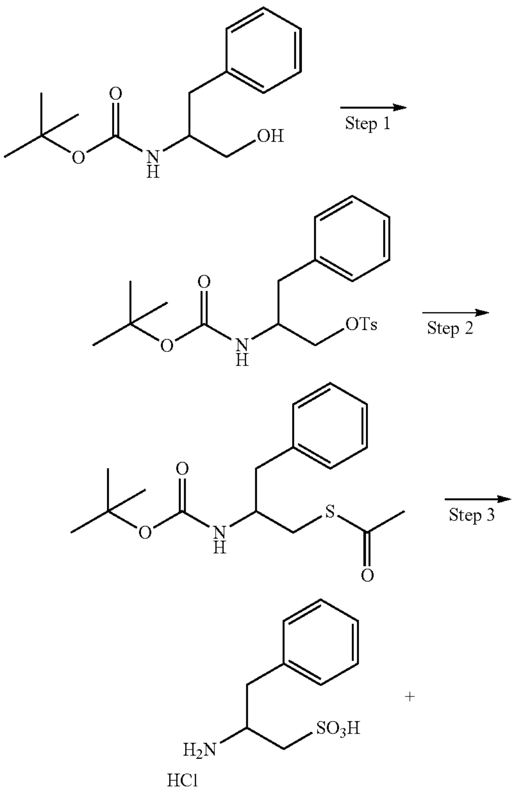

-continued

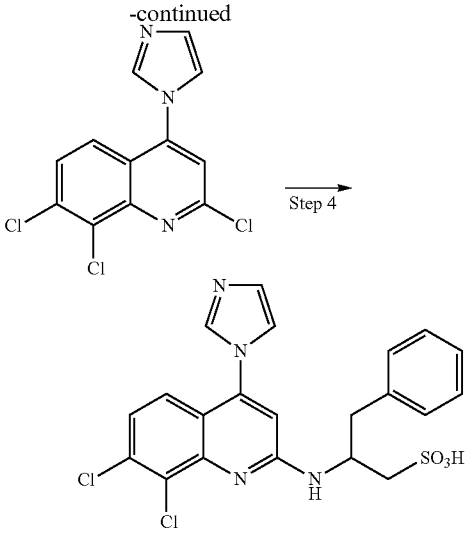

I-162

Step 1: 2-((tert-Butoxycarbonyl)amino)-3-phenylpropyl 4-methylbenzenesulfonate. A solution of tert-butyl (1-hydroxy-3-phenylpropan-2-yl)carbamate (1.25 g, 5.0 mmol) in pyridine (2 mL) was cooled to −10° C. Tosyl chloride (0.95 g, 5.0 mmol) in pyridine (2 mL) was added dropwise. The reaction was stirred at 0° C. for 1 h then warmed to rt and stirred for 16 h. The reaction was poured over ice, then extracted with (4:1) hexanes/Ethyl acetate (2×10 mL). The combined organics were dried ($Na_2SO_4$) and concentrated. The crude 2-((tert-butoxycarbonyl)amino)-3-phenylpropyl 4-methylbenzenesulfonate (MS: $[M+1\text{-Boc}]^+$306) was taken onward directly.

Step 2: S-(2-((tert-Butoxycarbonyl)amino)-3-phenylpropyl) ethanethioate. 2-((tert-Butoxycarbonyl)amino)-3-phenylpropyl 4-methylbenzenesulfonate (1.6 g, 3.95 mmol) was placed in a flask with DMF (10 mL). Potassium thioacetate (677 mg, 5.93 mmol) in DMF (5 mL) was added to the flask then allowed to stir at rt for 16 h. Water (25 mL) was added and the organics were extracted into (4:1) hexanes/EtOAc (2×20 mL). The combined organics were dried ($Na_2SO_4$) and concentrated to afford S-(2-((tert-butoxycarbonyl)amino)-3-phenylpropyl) ethanethioate (MS: $[M+1\text{-Boc}]^+$ 210).

Step 3: 2-Amino-3-phenylpropane-1-sulfonic acid hydrochloride. S-(2-((tert-Butoxycarbonyl)amino)-3-phenylpropyl) ethanethioate (309 mg, 1.0 mmol) was dissolved in formic acid (1.0 mL) and added dropwise at 0° C. to a solution of hydrogen peroxide (1 mL, 30% aq) in formic acid. The reaction was stirred at rt for 16 h. The volatiles were concentrated off to afford 2-amino-3-phenylpropane-1-sulfonic acid hydrochloride (MS: $[M+1]^+$ 216).

Step 4: 2-((7,8-Dichloro-4-(1H-imidazol-1-yl)quinolin-2-yl)amino)-3-phenylpropane-1-sulfonic acid. 2-amino-3-phenylpropane-1-sulfonic acid hydrochloride (62 mg, 0.25 mmol) was placed in a vial with 2,7,8-trichloro-4-(1H-imidazol-1-yl)quinoline (30 mg, 0.1 mmol) in DMSO (0.2 mL) and N,N-diisopropylethylamine (0.1 mL). The solution is stirred at 95° C. for 16 h. After cooling down to room temperature, water (5 mL) was added and the organics were extracted into 10% methanol in dichloromethane (2×5 mL). The combined organics were dried ($Na_2SO_4$) and concentrated. The resulting residue was purified by silica chromatography using 0-25% methanol/dichloromethane to afford 2-((7,8-dichloro-4-(1H-imidazol-1-yl)quinolin-2-yl)amino)-3-phenylpropane-1-sulfonic acid (MS: $[M+1]^+$ 477).

The following compounds are prepared essentially by the same method described above to prepare I-162:

| I-# | Starting Material | Structure | MS [M + 1]+ |
|---|---|---|---|
| I-163 | 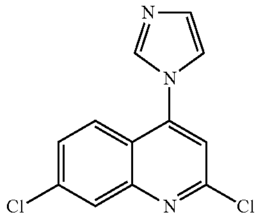 [SMILES: Clc1ccc2c(-n3ccnc3)cc(Cl)nc2c1] 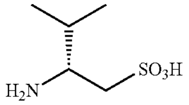 | 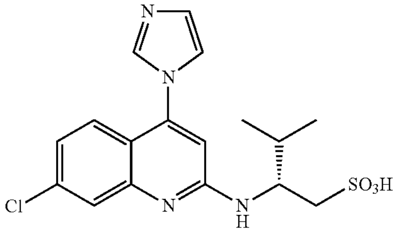 [SMILES: CC(C)[C@H](CS(=O)(=O)O)Nc1cc(-n2ccnc2)c2ccc(Cl)cc2n1] | 395 |

Example 70: Synthesis of 2-((7,8-dichloro-4-(1H-imidazol-1-yl)quinolin-2-yl)amino)-3-phenylpropane-1-sulfonamide (I-208)

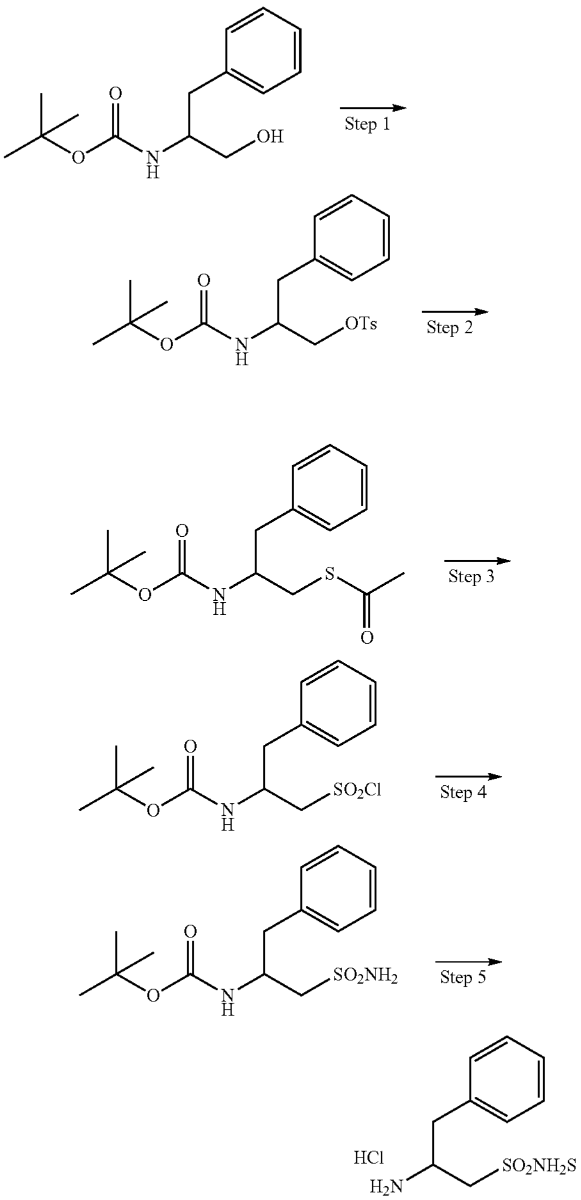

-continued

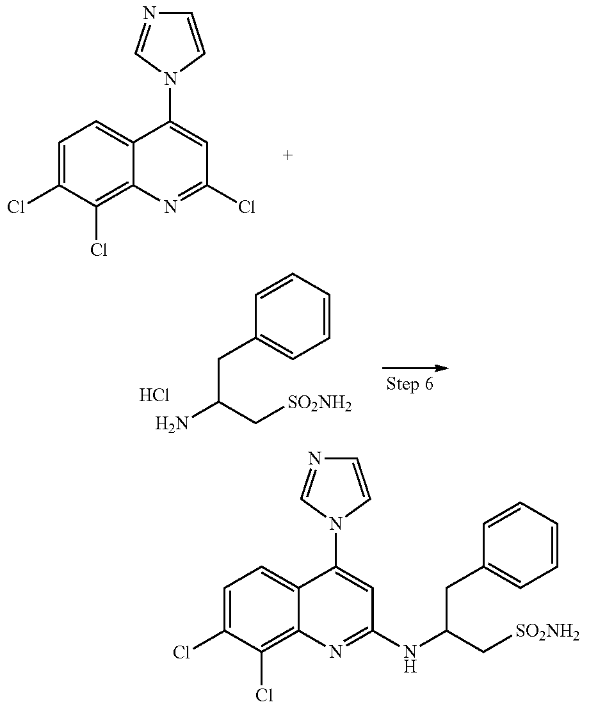

Step 1: 2-((tert-Butoxycarbonyl)amino)-3-phenylpropyl 4-methylbenzenesulfonate. A solution of tert-butyl (1-hydroxy-3-phenylpropan-2-yl)carbamate (1.25 g, 5.0 mmol) in pyridine (2 mL) was cooled to −10° C. Tosyl chloride (0.95 g, 5.0 mmol) in pyridine (2 mL) was added dropwise. The reaction was stirred at 0° C. for 1 h then warmed to rt and stirred for 16 h. The reaction was poured over ice, then extracted with (4:1) hexanes/Ethyl acetate (2×10 mL). The combined organics were dried ($Na_2SO_4$) and concentrated. The crude 2-((tert-butoxycarbonyl)amino)-3-phenylpropyl 4-methylbenzenesulfonate (MS: $[M+1\text{-Boc}]^+$306) was taken onward directly.

Step 2: S-(2-((tert-Butoxycarbonyl)amino)-3-phenylpropyl) ethanethioate. 2-((tert-butoxycarbonyl)amino)-3-phenylpropyl 4-methylbenzenesulfonate (1.6 g, 3.95 mmol) was placed in a flask with DMF (10 mL). Potassium thioacetate (677 mg, 5.93 mmol) in DMF (5 mL) was added to the flask then allowed to stir at rt for 16 h. Water (25 mL) was added and the organics were extracted into (4:1) hexanes/EtOAc (2×20 mL). The combined organics were dried ($Na_2SO_4$)

and concentrated to afford S-(2-((tert-butoxycarbonyl) amino)-3-phenylpropyl) ethanethioate (MS: $[M+1-Boc]^+$ 210).

Step 3: tert-Butyl (1-(chlorosulfonyl)-3-phenylpropan-2-yl)carbamate. S-(2-((tert-Butoxycarbonyl)amino)-3-phenylpropyl) ethanethioate (300 mg, 0.97 mmol) was placed in a vial with acetonitrile (3 mL) and water (52 μL) then cooled to 0° C. tert-butyl hypochlorite (0.33 mL, 2.9 mmol) was added and the reaction allowed to stir at 0° C. for 20 mins. The volatiles were removed by rotary evaporation and the crude tert-butyl (1-(chlorosulfonyl)-3-phenylpropan-2-yl) carbamate taken onward without further purification.

Step 4: tert-Butyl (1-phenyl-3-sulfamoylpropan-2-yl)carbamate. Tert-butyl (1-(chlorosulfonyl)-3-phenylpropan-2-yl)carbamate was placed in a vial with acetonitrile (5 mL) and cooled to 0° C. Ammonium hydroxide (2 mL) was added and the reaction was stirred at 0° C. for 10 minutes then warmed to rt and stirred for 1 h. Dichloromethane (25 mL) was added followed by water (10 mL) and the mixture stirred vigorously for 5 mins. The organics were separated, dried ($Na_2SO_4$) and concentrated to afford tert-butyl (1-phenyl-3-sulfamoylpropan-2-yl)carbamate (MS: $[M+1-Boc]^+$ 215).

Step 5: 2-amino-3-phenylpropane-1-sulfonamide hydrochloride. tert-butyl (1-phenyl-3-sulfamoylpropan-2-yl)carbamate (100 mg, 0.32 mmol) was placed in a vial with dichloromethane (2 mL). Hydrochloric acid (4.0M in dioxane) (0.5 mL) was added and the reaction allowed to stir at rt for 1 h. Acetonitrile was added and the resulting solids were filtered off and vacuum dried to afford 2-amino-3-phenylpropane-1-sulfonamide hydrochloride (MS: $[M+1]^+$ 215).

Step 6: 2-((7,8-dichloro-4-(1H-imidazol-1-yl)quinolin-2-yl)amino)-3-phenylpropane-1-sulfonamide. 2-amino-3-phenylpropane-1-sulfonamide hydrochloride (55 mg, 0.23 mmol) was placed in a vial with 2,7,8-trichloro-4-(1H-imidazol-1-yl)quinoline (30 mg, 0.1 mmol) in DMSO (0.2 mL) and N,N-diisopropylethylamine (0.1 mL). The solution is stirred at 95° C. for 16 h. After cooling down to room temperature, water (5 mL) was added and the organics were extracted into 10% methanol in dichloromethane (2×5 mL). The combined organics are dried ($Na_2SO_4$) and concentrated. The resulting residue was purified by Combiflash using 0-10% Methanol/Dichloromethane to afford 2-((7,8-dichloro-4-(1H-imidazol-1-yl)quinolin-2-yl)amino)-3-phenylpropane-1-sulfonamide (MS: $[M+1]^+$ 476)

The following compounds are prepared essentially by the same method described above to prepare I-208:

Example 71: Synthesis of 2-(benzyl(7,8-dichloro-4-(1H-imidazol-1-yl)quinolin-2-yl)amino)ethane-1-sulfonic acid (I-164)

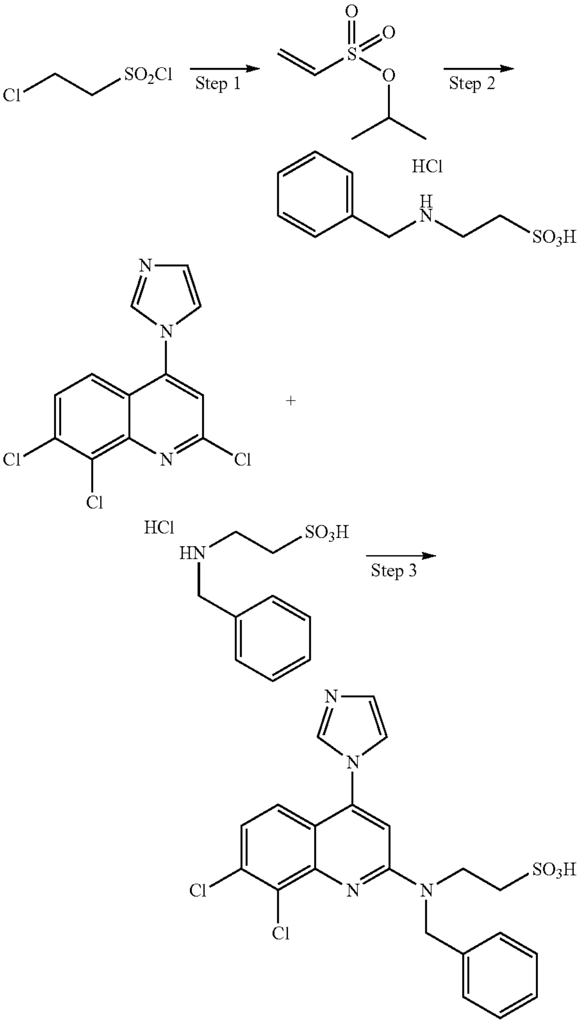

I-164

Step 1: Isopropyl ethenesulfonate. 2-Chloroethane-1-sulfonyl chloride (0.65 mL, 6.1 mmol) was placed in a flask with dichloromethane (3.0 mL) and isopropanol (0.47 mL,

| I-# | Starting Material | Structure | MS [M + 1]+ |
|---|---|---|---|
| I-209 | 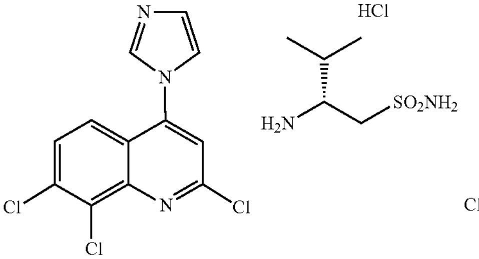 HCl | 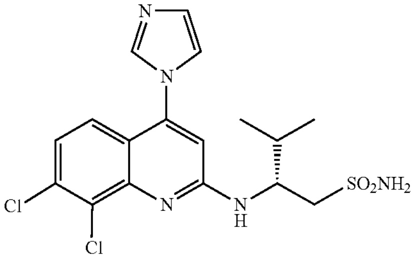 [SMILES: CC(C)[C@H](CS(N)(=O)=O)Nc1cc(-n2ccnc2)c2ccc(Cl)c(Cl)c2n1] | 428.0 |

6.1 mmol) and cooled to −10° C. A solution of pyridine (0.98 mL, 6.1 mmol) in dichloromethane (1.4 mL) was added dropwise and the reaction was allowed to stir at −10° C. for 2 h and warmed to rt over 30 mins. The mixture was quenched by the addition of 1M HCl (20 mL). The aqueous layer was extracted with ethyl acetate (2×10 mL). The combined extracts were dried ($Na_2SO_4$) and concentrated to afford isopropyl ethenesulfonate as an oil and was taken onward without further purification.

Step 2: 2-(Benzylamino)ethane-1-sulfonic acid hydrochloride. A solution of isopropyl ethenesulfonate (440 mg, 0.2 mmol) in methanol (1.5 mL) was added to a solution of benzyl amine (0.31 g, 2.9 mmol) in methanol (1.0 mL) at 0° C. The reaction was stirred at 0° C. for 1.5 h then warmed to rt. The solution was acidified by the addition of HCl (1.0M in MeOH) then heated at 90° C. for 16 h. The resulting precipitate was filtered off and dried to afford 2-(benzylamino)ethane-1-sulfonic acid hydrochloride (MS: $[M+1]^+$ 216).

Step 3: 2-(benzyl(7,8-dichloro-4-(1H-imidazol-1-yl)quinolin-2-yl)amino)ethane-1-sulfonic acid. 2-(Benzylamino) ethane-1-sulfonic acid hydrochloride (50 mg, 0.2 mmol) was placed in a vial with 2,7,8-trichloro-4-(1H-imidazol-1-yl) quinoline (30 mg, 0.1 mmol) in DMSO (0.2 mL) and N,N-diisopropylethylamine (0.1 mL). The solution is stirred at 95° C. for 16 h. After cooling down to room temperature, water (5 mL) was added and the organics were extracted into 10% methanol in dichloromethane (2×5 mL). The combined organics are dried ($Na_2SO_4$) and concentrated. The resulting residue was purified by Combiflash using 0-10% methanol/dichloromethane to afford 2-(benzyl(7,8-dichloro-4-(1H-imidazol-1-yl)quinolin-2-yl)amino)ethane-1-sulfonic acid (33 mg) (MS: $[M+1]^+$ 477).

The following compounds are prepared essentially by the same method described above to prepare I-164:

-continued

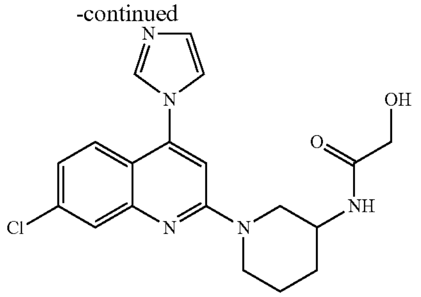

I-106

To a solution of 2-((1-(7-chloro-4-(1H-imidazol-1-yl)quinolin-2-yl)piperidin-3-yl)amino)-2-oxoethyl acetate (I-395) (17 mg, 0.04 mmol) in THF (2 mL) and water (0.5 mL) was added lithium hydroxide monohydrate (5 mg, 0.12 mmol). The solution was stirred at rt for 16 h. The volatiles were removed, and the residue was neutralized with 1M HCl (aq) to pH ~7. The organics were extracted into ethyl acetate (2×5 mL). The combined organics were dried and concentrated to afford N-(1-(7-chloro-4-(1H-imidazol-1-yl)quinolin-2-yl)piperidin-3-yl)-2-hydroxyacetamide (9 mg) (MS: $[M+1]^+$ 386).

| I-# | Starting Material | Structure | MS [M + 1]+ |
|---|---|---|---|
| I-165 | 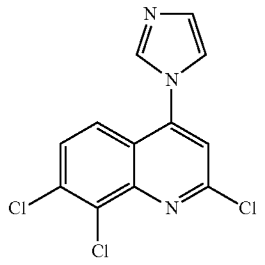 [SMILES: Clc1cc(-n2ccnc2)c2ccc(Cl)c(Cl)c2n1] HCl 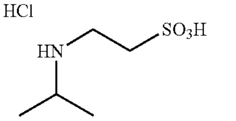 | 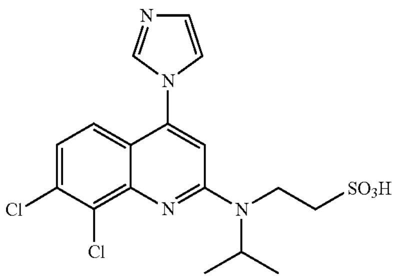 [SMILES: CC(C)N(CCS(=O)(=O)O)c1cc(-n2ccnc2)c2ccc(Cl)c(Cl)c2n1] | 429 |

Example 72: Synthesis of N-(1-(7-chloro-4-(1H-imidazol-1-yl)quinolin-2-yl)piperidin-3-yl)-2-hydroxyacetamide (I-106)

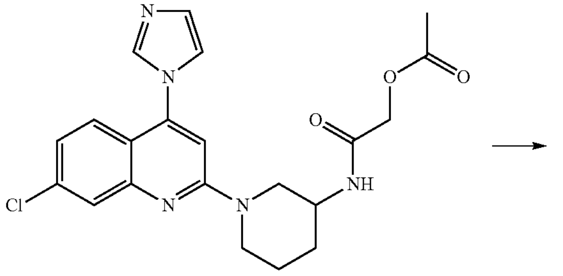

Example 73: Synthesis of (E)-5-((7,8-dichloro-4-(1H-imidazol-1-yl)quinolin-2-yl)methylene)thiazolidine-2,4-dione (I-276)

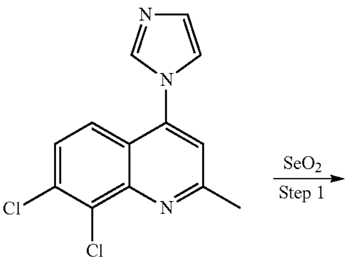

-continued

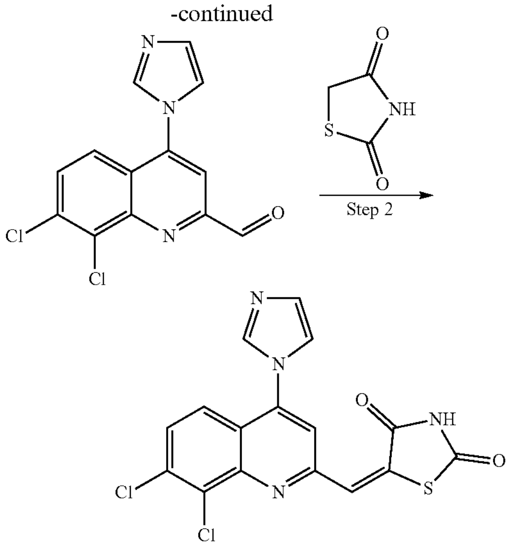

I-276

Step 1: 7,8-Dichloro-4-(1H-imidazol-1-yl)quinoline-2-carbaldehyde. To a solution of 7,8-dichloro-4-(1H-imidazol-1-yl)-2-methylquinoline (104 mg) in dioxane (5 mL) was added selenium dioxide (82 mg). After the reaction mixture was stirred at 85° C. over 2 hours, a filtration through a Celite pad and evaporation under reduced pressure afforded the desired 7,8-dichloro-4-(1H-imidazol-1-yl)quinoline-2-carbaldehyde (90 mg) as a brown solid.

Step 2: (E)-5-((7,8-Dichloro-4-(1H-imidazol-1-yl)quinolin-2-yl)methylene)thiazolidine-2,4-dione. The aldehyde (20 mg) was suspended in HOAc (1 mL) and treated with thiazolidine-2,4-dione (65 mg) and beta-analine (33 mg) at 100° C. over 4 hours. After removal of HOAc under reduced pressure, the residue was diluted with water (1 mL) and saturated $NaHCO_3$ solution (1 mL). The solid was isolated by centrifuge and rinsed with water and 50% acetonitrile/water. Drying in vacuo afforded the desired product (24 mg), (E)-5-((7,8-dichloro-4-(1H-imidazol-1-yl)quinolin-2-yl)methylene)thiazolidine-2,4-dione, as a brown color solid (MS: $[M+1]^+$ 391).

Example 74: Synthesis of 3-(7,8-dichloro-4-(1H-pyrazol-4-yl)quinolin-2-yl)acrylic acid (I-423)

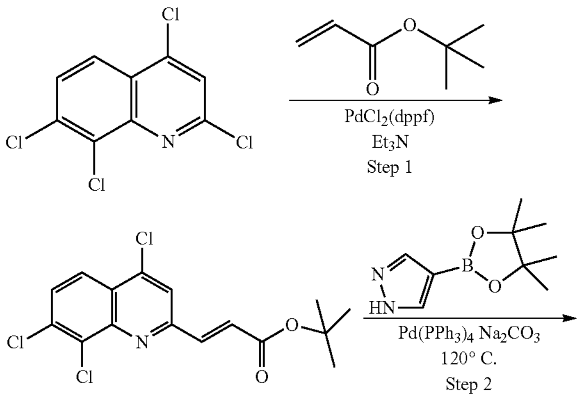

-continued

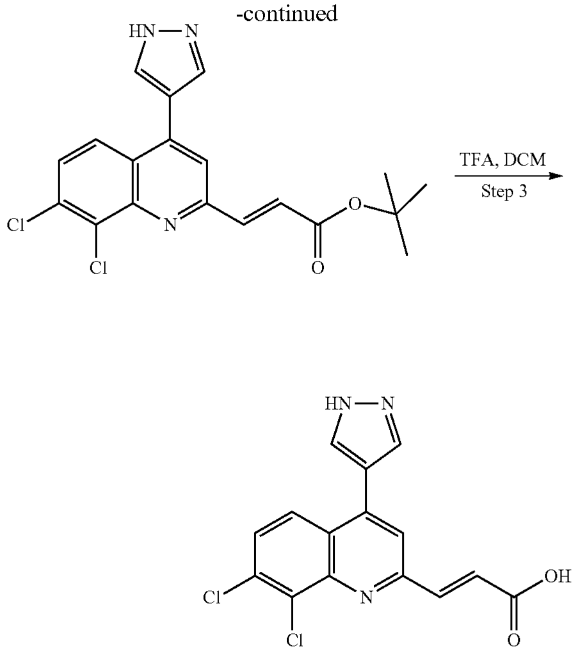

I-423

Step 1: tert-Butyl 3-(4,7,8-trichloroquinolin-2-yl)acrylate. To a solution of 2,4,7,8-tetrachloroquinoline (1.3 g) in dry DMF (1 mL) were added tert-butyl acrylate (3.4 g), TEA (1.96 g) and $PdCl_2(PPh_3)_4$ (0.34 g). The resultant mixture was stirred at 110° C. overnight and diluted with water. The aqueous layer was extracted with EtOAc (80 mL), and the isolated organic layer was rinsed with sat $NH_4Cl$ and dried over anhydrous $Na_2SO_4$. Silica gel column chromatography (eluting with a gradient of petroleum ether and EtOAc) afforded the desired product (1.4 g) (MS: $[M+1]^+$ 358).

Step 2: tert-Butyl 3-(7,8-dichloro-4-(1H-pyrazol-4-yl)quinolin-2-yl)acrylate. To a solution of tert-butyl 3-(4,7,8-trichloroquinolin-2-yl)acrylate (358 mg) in dioxane (5 mL) and water (2 mL) were added 4-(4,4,5,5-tetramethyl-1,3,2-dioxaborolan-2-yl)-1H-pyrazole (580 mg), $Na_2CO_3$ (650 mg) and $Pd(PPh_3)_4$ (115 mg). The resultant mixture was purged with $N_2$ via 3 cycles of vacuum and purging) and stirred at 120° C. over 4 hours under $N_2$. After dilution with water (20 mL), the aqueous layer was extracted with EtOAc (30 mL). The isolated organic layer was washed with brine and dried over anhy. $Na_2SO_4$. A column chromatography gave the desired product (130 mg) (MS: $[M+1]^+$ 390).

Step 3: 3-(7,8-Dichloro-4-(1H-pyrazol-4-yl)quinolin-2-yl)acrylic acid. To a solution of tert-butyl 3-(7,8-dichloro-4-(1H-pyrazol-4-yl)quinolin-2-yl)acrylate (15 mg) in DCM (0.4 mL) was added TFA (0.2 mL). The resultant solution was stirred over 1 hour and concentrated to dryness. The residue was purified by a preparative thin layer chromatography to afford the title compound (1.4 mg) (MS: $[M+1]^+$ 334).

Example 75: Synthesis of 3-(7,8-dichloro-4-(1H-pyrazol-4-yl)quinolin-2-yl)propanoic acid (I-270)

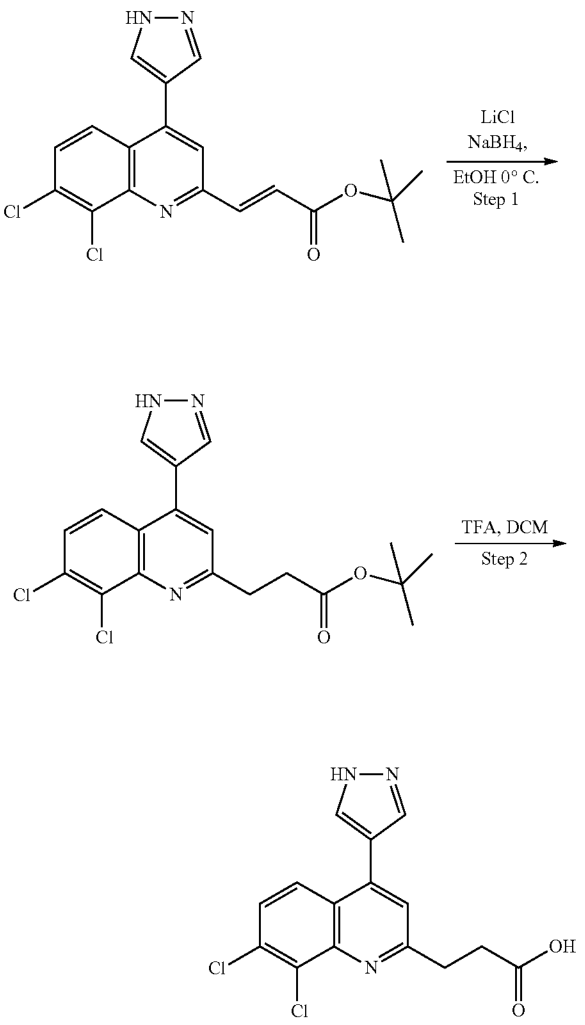

I-270

Step 1: tert-butyl 3-(7,8-dichloro-4-(1H-pyrazol-4-yl)quinolin-2-yl)propanoate. To a solution of tert-butyl 3-(7,8-dichloro-4-(1H-pyrazol-4-yl)quinolin-2-yl)acrylate (60 mg) in EtOH (5 mL) were added LiCl (23 mg) and $NaBH_4$ (9 mg) at 0° C. After stirring at 0° C. over 1 hour, the reaction mixture was quenched with 0.5 N HCl (0.5 mL). The mixture was concentrated to dryness to afford the crude of tert-butyl 3-(7,8-dichloro-4-(1H-pyrazol-4-yl)quinolin-2-yl) propanoate.

Step 2: 3-(7,8-dichloro-4-(1H-pyrazol-4-yl)quinolin-2-yl) propanoic acid. To a solution of tert-butyl 3-(7,8-dichloro-4-(1H-pyrazol-4-yl)quinolin-2-yl)propanoate residue in DCM (2 mL) was added TFA (0.8 mL) and the reaction stirred at rt over 4 hours. The crude product was purified by preparative HPLC to afford the desired 3-(7,8-dichloro-4-(1H-pyrazol-4-yl)quinolin-2-yl)propanoic acid (19 mg). MS: $[M+1]^+$ 336. $^1$H NMR (400 MHz, DMSO-D6): δ 8.193-8.171 (m, 3H), 7.735-7.712 (d, J=8.8 Hz, 1H), 7.626 (s, 1H), 3.216-3.252 (t, J=7.2 Hz, 2H), 2.863-2.899 (t, J=7.2 Hz, 2H) ppm.

Example 76: Synthesis of 3-(7,8-dichloro-4-(1H-pyrazol-4-yl)quinolin-2-yl)propan-1-ol (I-271)

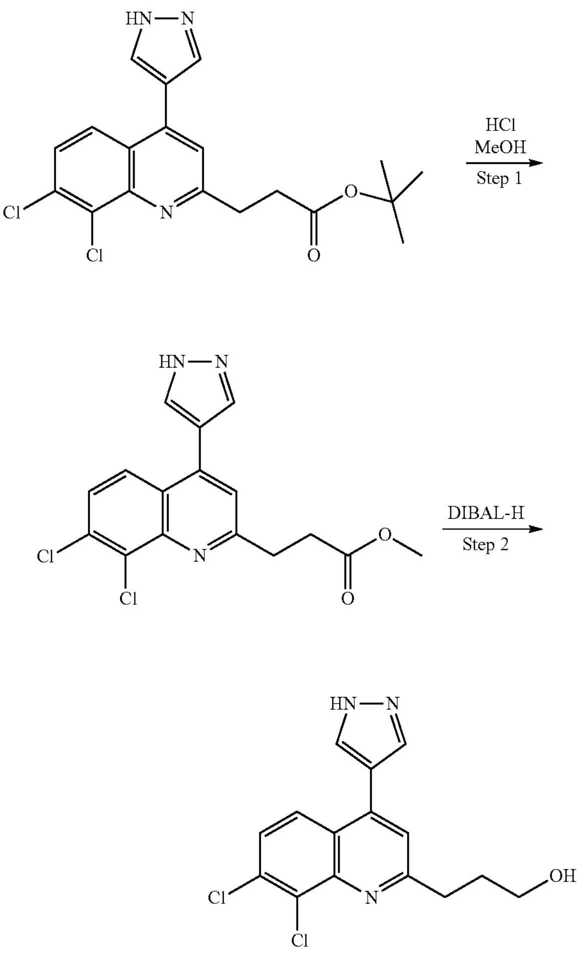

I-271

Step 1: Methyl 3-(7,8-dichloro-4-(1H-pyrazol-4-yl)quinolin-2-yl)propanoate. To a solution of tert-butyl 3-(7,8-dichloro-4-(1H-pyrazol-4-yl)quinolin-2-yl)propanoate (235 mg) in MeOH HCl (5 mL). The resultant solution was stirred at rt overnight. After concentration under reduced pressure, the residue was purified by preparative thin layer chromatography to afford the title compound (150 mg) as a powder (MS: $[M+1]^+$ 322).

Step 2: 3-(7,8-Dichloro-4-(1H-pyrazol-4-yl)quinolin-2-yl)propan-1-ol. To a solution of methyl 3-(7,8-dichloro-4-(1H-pyrazol-4-yl)quinolin-2-yl)propanoate (100 mg) in anhydrous THF (4 mL) was added DIABL-H (1.1 mL, 1M in THF) at −60° C. After stirring over one hour at 60° C., the reaction mixture was slowly warmed up to room temperature, quenched by adding MeOH (1 mL) and diluted with EtOAc (25 mL). The combined organic layers were washed with brine and dried over anhydrous $Na_2SO_4$. Concentration under reduced pressure and purification by preparative HPLC afforded the title compound (6 mg). MS: $[M+1]^+$ 322. $^1$H NMR (400 MHz, DMSO-D6): δ 8.195-8.173 (m, 3H), 7.735-7.712 (d, J=8.8 Hz, 1H), 7.594 (s, 1H), 3.520-3.536 (m, 2H), 2.996-3.034 (t, J=7.6 Hz, 2H), 1.965-2.002 (m, 2H) ppm.

Example 77: Synthesis of 7-chloro-4-(1H-imidazol-1-yl)-8-methylquinoline (I-274)

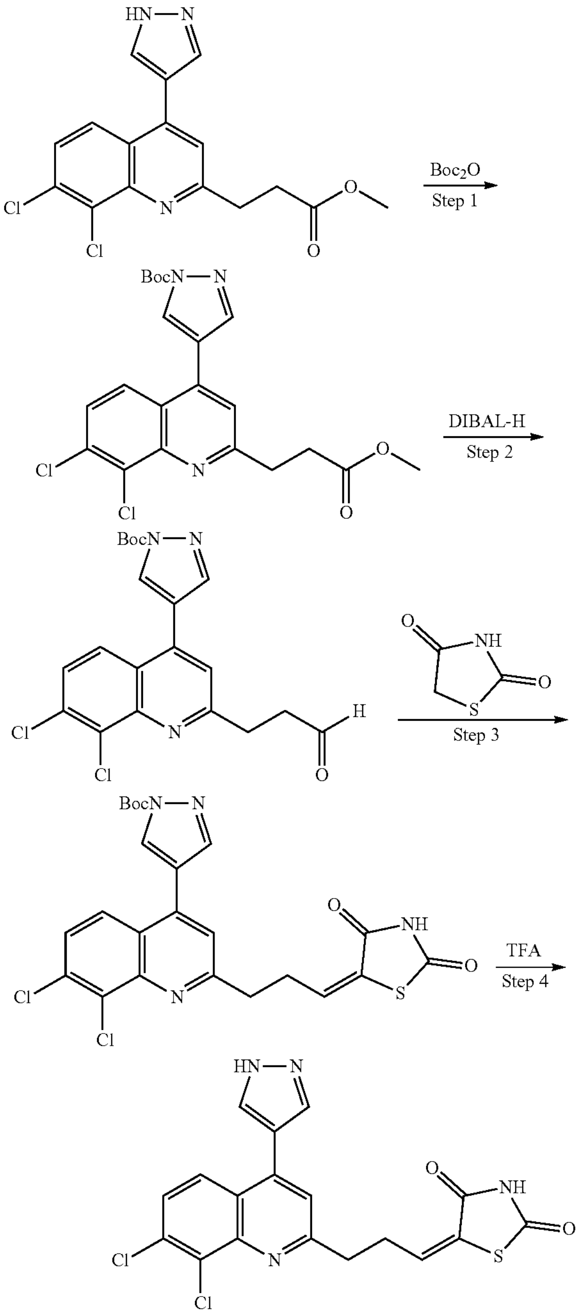

I-274

Step 1: tert-Butyl 4-(7,8-dichloro-2-(3-methoxy-3-oxopropyl)quinolin-4-yl)-1H-pyrazole-1-carboxylate. To a solution of methyl 3-(7,8-dichloro-4-(1H-pyrazol-4-yl)quinolin-2-yl)propanoate (30 mg) in DMF (1 mL) were added DMAP (12 mg), $(BOC)_2O$ (28 mg) and TEA (35 mg) under $N_2$. After stirring over 2 h at room temperature, the reaction mixture was diluted with water (10 mL) and extracted with EtOAc (25 mL). The separated organic layer was washed with saturated $NH_4Cl$ and concentrated to dryness. The residual was purified by preparative thin layer chromatography to afford the title compound (33 mg) as a solid. (MS: $[M+1]^+$ 450)

Step 2: tert-Butyl 4-(7,8-dichloro-2-(3-oxopropyl)quinolin-4-yl)-1H-pyrazole-1-carboxylate. To a solution of tert-butyl 4-(7,8-dichloro-2-(3-methoxy-3-oxopropyl)quinolin-4-yl)-1H-pyrazole-1-carboxylate (190 mg) in DCM (2 mL) was added DIBAL-H (0.56 mL) at −60° C. The reaction mixture was stirred and slowly warmed to room temperature in 2 hours. The reaction was quenched with MeOH (1 mL) and water (100 mL). Extraction with EtOAc, washing with brine and purification by preparative thin layer chromatography afforded the title compound (57 mg) as a solid. (MS: $[M+1]^+$ 420)

Step 3 and Step 4: (E)-5-(3-(7,8-Dichloro-4-(1H-pyrazol-4-yl)quinolin-2-yl)propylidene)thiazolidine-2,4-dione. To a solution of tert-butyl 4-(7,8-dichloro-2-(3-oxopropyl)quinolin-4-yl)-1H-pyrazole-1-carboxylate (30 mg) in EtOH was added thiazolidine-2,4-dione (18 mg) and piperidine (8 mg). The reaction mixture was stirred at 85° C. for 1 hour. After concentration under reduced pressure, the residue was diluted EtOAc (10 mL) and washed with water (10 mL). After removal of organic solvents, the crude intermediate was treated with TFA (0.3 mL) in DCM (0.9 mL) over 2 hour. After concentrated under reduced pressure, the crude product was purified by preparative HPLC to afford the title compound (7.3 mg) as a powder. MS: $[M+1]^+$ 419.1. $^1$H NMR (400 MHz, DMSO-D6): δ 8.186-8.209 (d, J=9.2 Hz, 1H), 8.168 (s, 1H), 7.733-7.756 (d, J=9.2 Hz, 1H), 7.636 (s, 1H), 7.073-7.111 (t, J=7.6 Hz, 1H), 3.3 (m, 2H), 2.768-2.822 (dd, J=14.4 and 7.2 Hz, 2H) ppm.

Example 78: Synthesis of 5-(3-(7,8-dichloro-4-(1H-pyrazol-4-yl)quinolin-2-yl)propyl)thiazolidine-2,4-dione (I-272)

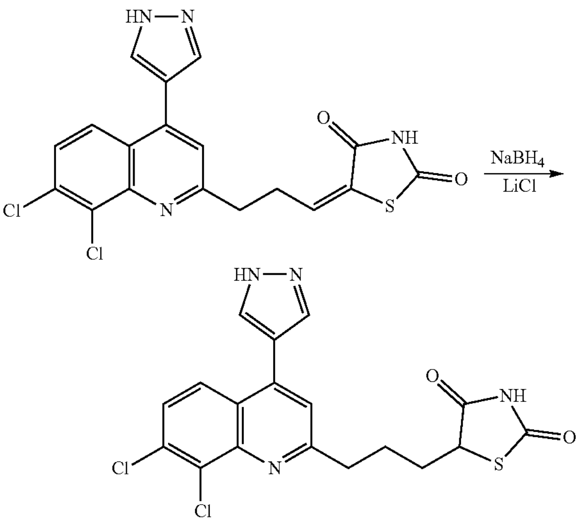

I-272

Crude (E)-5-(3-(7,8-dichloro-4-(1H-pyrazol-4-yl)quinolin-2-yl)propylidene)thiazolidine-2,4-dione (40 mg) in DMF (1 mL) was treated with $NaBH_4$ (7 mg) and LiCl (5 mg) at 0° C. for 3 hours. The product was purified by preparative HPLC to afford the title product (4.5 mg). MS: $[M+1]^+$ 421.0. $^1$H NMR (400 MHz, $CD_3OD$): δ 8.202-8.224 (d, J=9.2 Hz, 1H), 8.143 (s, 1H), 7.733-7.710 (d, J=9.2 Hz, 1H), 7.643-7.650 (d, J=2.8 Hz, 1H), 4.532-7.552 (d, J=8 Hz, 1H), 3.154-3.171 (m, 2H), 2.259-2.291 (m, 2H) and 2.014-2.062 (m, 2H) ppm.

Example 79: Synthesis of 3-(7,8-dichloro-4-(1H-pyrazol-4-yl)quinolin-2-yl)cyclohex-3-ene-1-carboxylic acid (I-273)

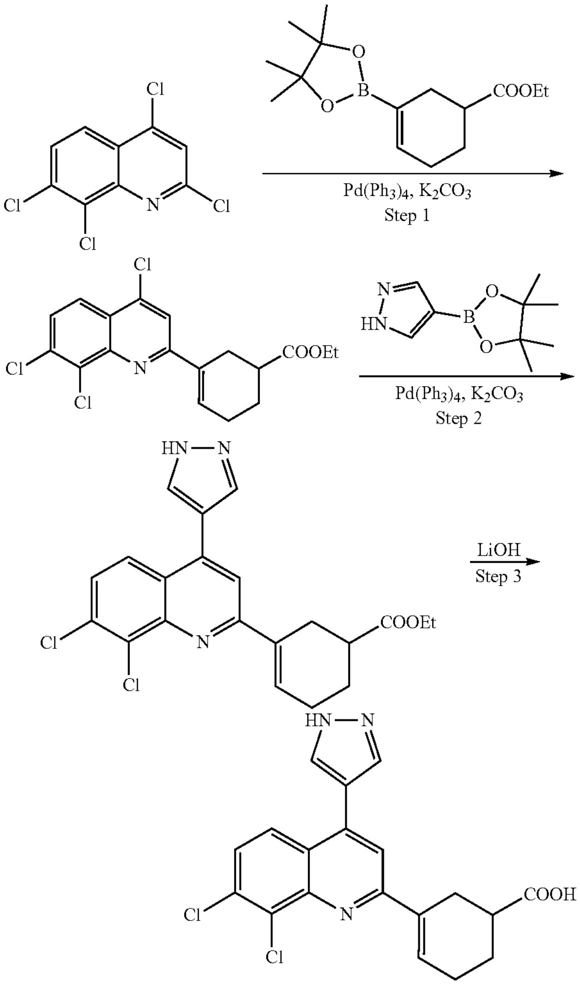

I-273

Step 1: Ethyl 3-(4,7,8-trichloroquinolin-2-yl)cyclohex-3-ene-1-carboxylate. Ethyl 3-(4,4,5,5-tetramethyl-1,3,2-dioxaborolan-2-yl)cyclohex-3-ene-1-carboxylate was synthesized according to WO2020/112706. To a mixture of 2,4,7,8-tetrachloroquinoline, ethyl 3-(4,4,5,5-tetramethyl-1,3,2-dioxaborolan-2-yl)cyclohex-3-ene-1-carboxylate(50 mg, 0.19 mmol), $Na_2CO_3$ (53 mg, 0.38 mmol), $Pd(Ph_3P)_4$ (23 mg, 0.02 mmol) in dioxane/$H_2O$ (5/1, 5 mL) was purged with $N_2$ via 3 cycles of vacuum/purging. Then the reaction mixture was stirred at 100° C. overnight. After cooling to rt, the reaction mixture was taken up with EtOAc, washed with brine, and concentrated under reduced pressure. The crude was purified by prep-TLC with pet. ether/DCM (1/1) to afford the desired product of ethyl 3-(4,7,8-trichloroquinolin-2-yl)cyclohex-3-ene-1-carboxylate (36 mg) as light brown semi-solid. MS ($ES^+$): $[M+1]^+$, m/z 384.1, 386.1

Step 2: Ethyl 3-(7,8-dichloro-4-(1H-pyrazol-4-yl)quinolin-2-yl)cyclohex-3-ene-1-carboxylate. To a mixture of ethyl 3-(4,7,8-trichloroquinolin-2-yl)cyclohex-3-ene-1-carboxylate, 4-(4,4,5,5-tetramethyl-1,3,2-dioxaborolan-2-yl)-1H-pyrazole (36 mg, 0.093 mmol), $Na_2CO_3$ (38.6 mg, 0.28 mmol), $Pd(Ph_3P)_4$ (10.7 mg, 0.009 mmol) dioxane/$H_2O$ (2/1, 15 mL) was purged with $N_2$ via 3 cycles of vacuum/purging. Then the reaction was stirred at 100° C. overnight. After cooling to rt, it was taken up with EtOAc, washed with brine, concentrated. The crude was purified by prep-TLC with pet. ether/DCM (1/1) to afford the desired product of ethyl 3-(7,8-dichloro-4-(1H-pyrazol-4-yl)quinolin-2-yl)cyclohex-3-ene-1-carboxylate (5.1 mg) as an off-white solid. MS: ($ES^+$): $[M+1]^+$ m/z 416.1, 418.1

Step 3: 3-(7,8-Dichloro-4-(1H-pyrazol-4-yl)quinolin-2-yl)cyclohex-3-ene-1-carboxylic acid. To a mixture of ethyl 3-(7,8-dichloro-4-(1H-pyrazol-4-yl)quinolin-2-yl)cyclohex-3-ene-1-carboxylate (10 mg, 0.024 mmol) in $CH_3OH$/$H_2O$/THF (1/1/1, 3 mL) was LiOH (6 mg). The reaction mixture was stirred at rt overnight. After quenched with aq. HCl, it was taken up with DCM/iPrOH, washed with brine, and concentrated. The crude was purified by prep-HPLC to afford the desired product of 3-(7,8-dichloro-4-(1H-pyrazol-4-yl)quinolin-2-yl)cyclohex-3-ene-1-carboxylic acid (3.4 mg) as an off-white solid (MS: ($ES^+$): m/z 388.1 $[M+1]^+$). $^1H$ NMR (400 MHz, $CD_3OD$, ppm): δ 8.38 (s, 1H), 8.00 (d, J=9.2 Hz, 1H), 7.70 (s, 1H), 7.56 (d, J=9.2 Hz, 1H), 5.89 (s, 1H), 2.90 (s, 1H), 2.71-2.63 (m, 2H), 2.42 (s, 2H), 2.01-1.94 (s, 2H).

Example 80: Synthesis of (3-(7,8-dichloro-4-(1H-pyrazol-4-yl)quinolin-2-yl)propyl)glycine (I-336)

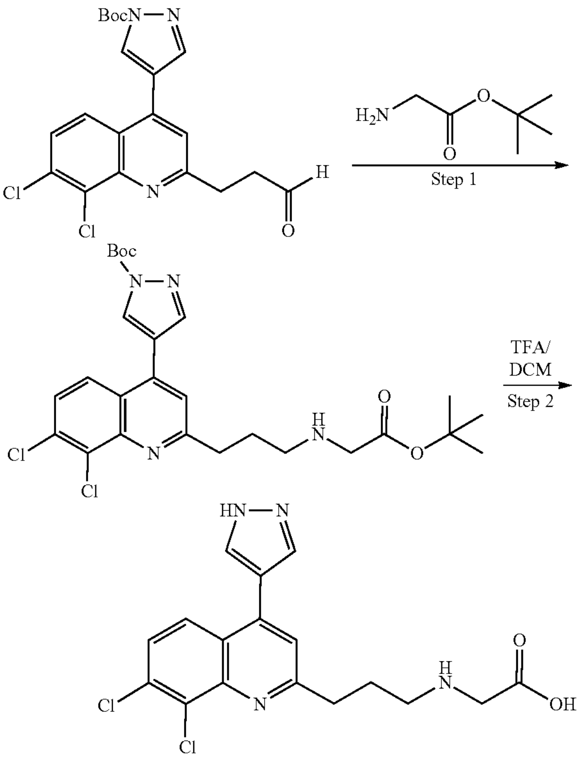

I-336

Step 1: tert-Butyl 4-(2-(3-((2-(tert-butoxy)-2-oxoethyl)amino)propyl)-7,8-dichloroquinolin-4-yl)-1H-pyrazole-1-carboxylate. To a solution of tert-butyl 4-(7,8-dichloro-2-(3- oxopropyl)quinolin-4-yl)-1H-pyrazole-1-carboxylate (100 mg) and tert-butyl glycinate (62 mg) in DCM (0.5 mL) and EtOH (2.5 mL) were added $NaBH_3CN$(100 mg) and acetic acid (1 drop). After stirring overnight, quenching with water, extraction with DCM, and concentration under reduced pressure, the residue was purified by a preparative thin layer chromatography (eluting with 15% MeOH in DCM) to afford the title compound (58 mg). MS: $[M+1]^+$ 479.

Step 2: (3-(7,8-Dichloro-4-(1H-pyrazol-4-yl)quinolin-2-yl)propyl)glycine. To a solution of tert-butyl 4-(2-(3-((2-(tert-butoxy)-2-oxoethyl)amino)propyl)-7,8-dichloroquinolin-4-yl)-1H-pyrazole-1-carboxylate (15 mg) in DCM (3 mL) was added TFA (0.5 mL). The resultant solution was stirred over 6 hours at room temperature. After evaporation under reduced pressure, the residue was purified by preparative HPLC to afford the title compound (6.4 mg) (MS: $[M+1]^+$ 379.1). $^1$H NMR (400 MHz, $CD_3OD$): δ 8.179-8.202 (d, J=9.2 Hz, 1H), 8.140 (s, 1H), 7.690-7.713 (d, J=9.2 Hz, 1H), 7.596 (s, 1H), 4.019 (S, 2H), 3.324-3.365 (m, 4H), 2.338-2.391 (m, 2H) ppm Example 81: Synthesis of N-(3-(7,8-dichloro-4-(1H-pyrazol-4-yl)quinolin-2-yl)propyl)-N-(methylsulfonyl) glycine (I-337)

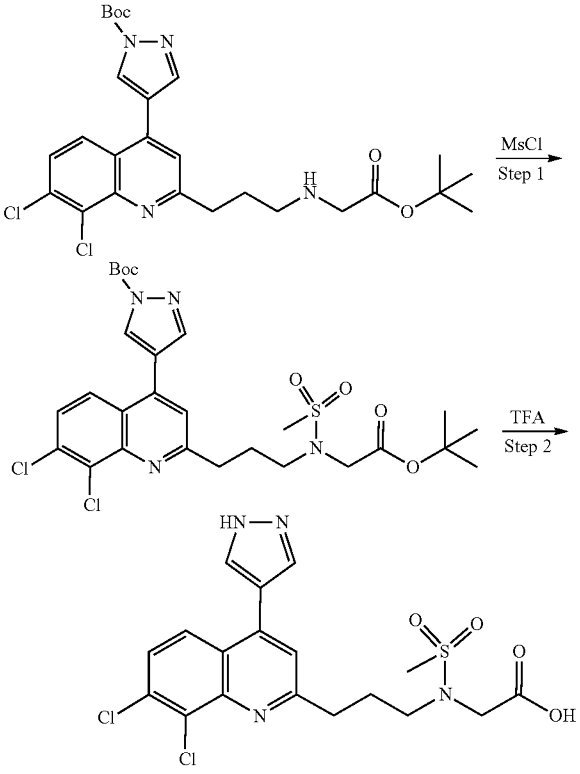

I-337

Step 1: tert-Butyl 4-(2-(3-(N-(2-(tert-butoxy)-2-oxoethyl) methylsulfonamido)propyl)-7,8-dichloroquinolin-4-yl)-1H-pyrazole-1-carboxylate. A solution of tert-butyl 4-(2-(3-((2-(tert-butoxy)-2-oxoethyl)amino)propyl)-7,8-dichloroquinolin-4-yl)-1H-pyrazole-1-carboxylate (15 mg) in DCM (0.5 mL) were added MsCl (6.4 mg) and TEA (14.8 mg). After stirring at room temperature over 1 hour, aqueous work up with DCM, washing with brine, condensation under reduced pressure, and purification by preparative thin layer chromatography afforded the title compound (8 mg). MS: $[M+1]^+$ 613.

Step 2: N-(3-(7,8-Dichloro-4-(1H-pyrazol-4-yl)quinolin-2-yl)propyl)-N-(methylsulfonyl) glycine. To a solution of N-(3-(7,8-dichloro-4-(1H-pyrazol-4-yl)quinolin-2-yl)propyl)-N-(methylsulfonyl) glycine (8 mg) in DCM (5 mL) was added TFA (1 mL). The reaction mixture was stirred over 5 hours at room temperature. Evaporation under reduced pressure and purification by preparative HPLC afforded the title compound (3 mg) as a powder (MS: $[M+1]^+$ 457.1). $^1$H NMR (400 MHz, DMSO-D6): δ 8.192-8.215 (d, J=9.2 Hz, 1H), 8.140 (s, 1H), 7.697-7.720 (d, J=9.2 Hz, 1H), 7.664 (s, 1H), 4.149 (S, 2H), 3.468-3.503 (t, J=7.2 Hz, 2H), 3.160-3.196 (t, J=7.2 Hz, 2H), 3.011 (S, 3H), 2.202-2.237 (m, 2H) ppm.

Example 82: Synthesis of (2S,4S)-4-(carboxymethoxy)-1-(7,8-dichloro-4-(1H-imidazol-1-yl) quinolin-2-yl)pyrrolidine-2-carboxylic acid (I-569)

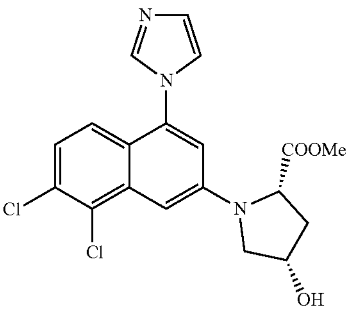

+

I-459

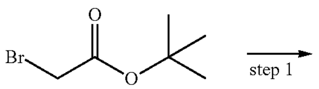

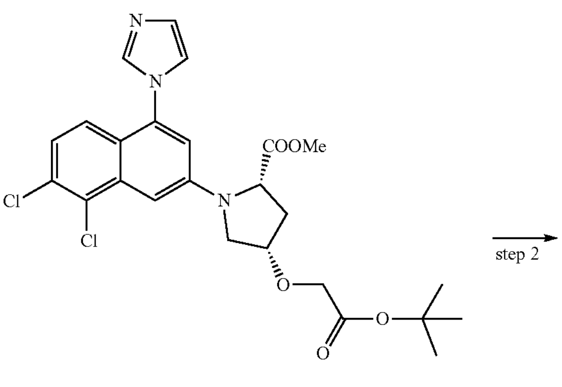

-continued

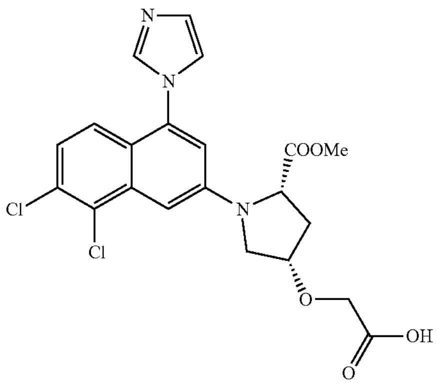

I-569

Step 1: To a mixture of NaH (6 mg, 0.15 mmol), tert-butyl 2-bromoacetate (80 uL, 0.4 mmol) and TBAI (5 mg, 0.01 mmol) and THF (1 mL) was added a solution of methyl (2S,4S)-1-(7,8-dichloro-4-(1H-imidazol-1-yl)naphthalen-2-yl)-4-hydroxypyrrolidine-2-carboxylate (41 mg, 0.1 mmol) in THF (1 mL) at 0° C. The resulting mixture was stirred 2 h at room temperature and quenched by $NH_4Cl$ (aq, sat., 1 mL). The crude was diluted by EtOAc and the organic phase was washed with water, brine and dried over anhy. $Na_2SO_4$. A column chromatography eluting with a gradient of hexanes and EtOAc afforded the desired product (25 mg) as white solids (MS: $[M+1]^+$ 520.1).

Step 2: methyl (2S,4S)-4-(2-(tert-butoxy)-2-oxoethoxy)-1-(7,8-dichloro-4-(1H-imidazol-1-yl)naphthalen-2-yl)pyrrolidine-2-carboxylate (25 mg, 0.05 mmol) was placed in a vial with THF (1.2 mL), methanol (0.4 mL), and water (0.4 mL). Lithium hydroxide monohydrate (8 mg, 0.18 mmol) was added and the reaction was allowed to stir at r.t. for 16 h. The volatiles were concentrated off and the resulting residue neutralized by the addition of 1 N hydrochloric acid. The resulting solution was lyophilized to afford the titled compound (MS: $[M+1]^+$ 450.1).

Synthesis of (2S,4S)-4-(((carboxymethyl)carbamoyl)oxy)-1-(7,8-dichloro-4-(1H-imidazol-1-yl)naphthalen-2-yl)pyrrolidine-2-carboxylic acid (I-570)

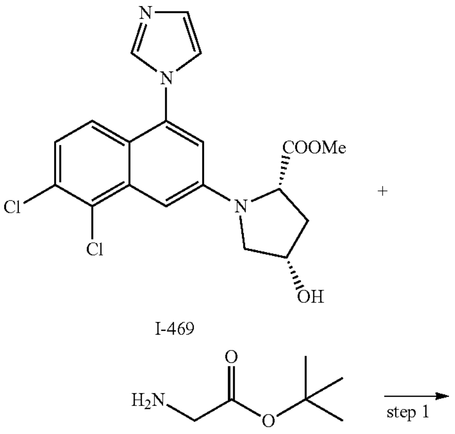

I-469

-continued

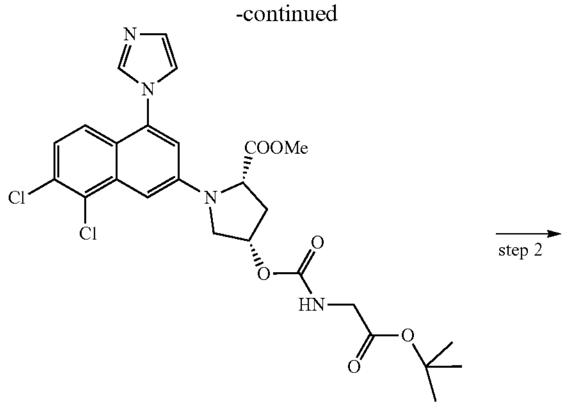

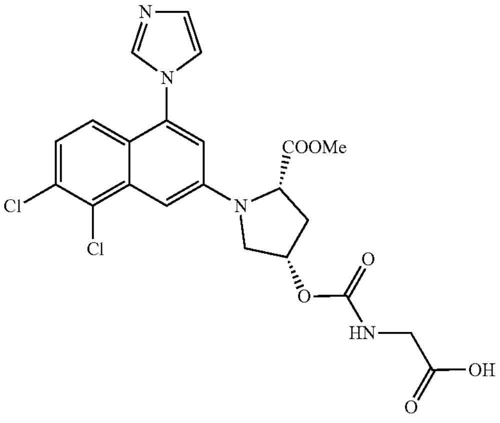

I-570

Step 1: To a solution of methyl (2S,4S)-1-(7,8-dichloro-4-(1H-imidazol-1-yl)naphthalen-2-yl)-4-hydroxypyrrolidine-2-carboxylate (40 mg, 0.1 mmol) in THF (1 mL) was added CDI (32 mg, 0.2 mmol). After 1 h, a solution of tert-butyl glycinate (25 mg, 0.15 mmol) and DIPEA (52 μL, 0.3 mmol) in THF (1 mL) was added. The mixture was stirred at 60° C. overnight. After cooling down to r.t., the solvent was evaporated. The crude was dissolved in EtOAc (5 mL) and washed with water, brine and dried over anhy. $Na_2SO_4$. A column chromatography eluting with a gradient of hexanes and EtOAc afforded the desired product (40 mg) as white solids (MS: $[M+1]^+$ 563.1).

Step 2: methyl (2S,5S)-4-(4-(((2-(tert-butoxy)-2-oxoethyl)carbamoyl)oxy)-1-(7,8-dichloro-4-(1H-imidazol-1-yl) naphthalen-2-yl)pyrrolidine-2-carboxylate (40 mg, 0.07 mmol) was placed in a vial with THF (1.2 mL), methanol (0.4 mL), and water (0.4 mL). Lithium hydroxide monohydrate (8 mg, 0.18 mmol) was added, and the reaction was allowed to stir at r.t. for 16 h. The volatiles were concentrated off and the resulting residue neutralized by the addition of 1 N hydrochloric acid. The resulting solution was lyophilized to afford the titled compound (MS: $[M+1]^+$ 493.1).

The following compounds were prepared essentially by the same method described above to prepare I-570.

| I-# | Starting Material | | Structure | MS [M + 1]+ |
|---|---|---|---|---|
| I-571 | 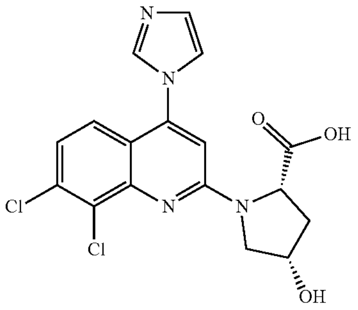 [SMILES: O=C(O)[C@@H]1C[C@H](O)CN1c1cc(-n2ccnc2)c2ccc(Cl)c(Cl)c2n1] | 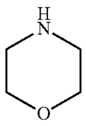 | 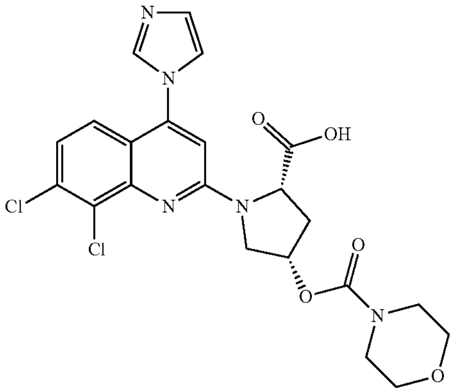 [SMILES: O=C(O)[C@@H]1C[C@H](OC(=O)N2CCOCC2)CN1c1cc(-n2ccnc2)c2ccc(Cl)c(Cl)c2n1] | 506 |

Example 83: Synthesis of methyl (S)-2-(1-(7,8-dichloro-4-(1H-imidazol-1-yl)naphthalen-2-yl)pyrrolidin-2-yl)acetate (I-572)

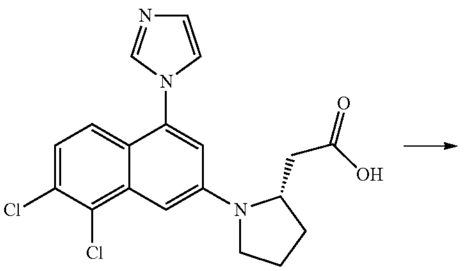

-continued

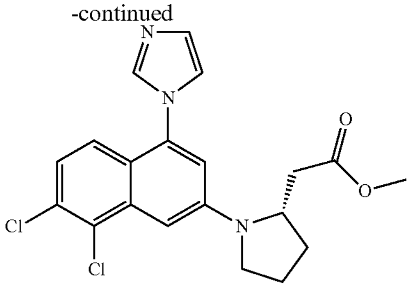

At 0° C., oxalyl chloride (60 uL, 0.5 mmol) or thionyl chloride was added dropwise to MeOH (1 mL). After 30 min, a solution of (S)-2-(1-(7,8-dichloro-4-(1H-imidazol-1-yl)naphthalen-2-yl)pyrrolidin-2-yl)acetic acid (40 mg, 0.1 mmol) in MeOH (0.1 mL) was added. The solution was stirred at r.t. overnight. After evaporation, the crude was dissolved in EtOAc (5 mL) and washed with saturated $NaHCO_3$ (aq.), water, brine and dried over anhy. $Na_2SO_4$. A column chromatography eluting with a gradient of hexanes and EtOAc afforded the desired product (40 mg) as white solids (MS: $[M+1]^+$ 404.1).

The following compounds were prepared essentially by the same method described above to prepare I-572.

| I-# | Starting Material | | Structure | MS [M + 1]+ |
|---|---|---|---|---|
| I-573 | 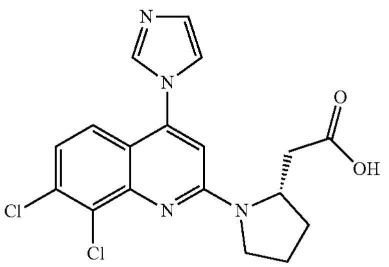 [SMILES: O=C(O)C[C@@H]1CCCN1c1cc(-n2ccnc2)c2ccc(Cl)c(Cl)c2n1] | 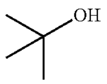 | 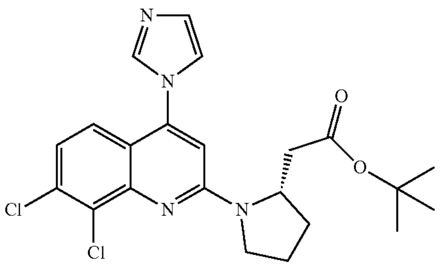 [SMILES: CC(C)(C)OC(=O)C[C@@H]1CCCN1c1cc(-n2ccnc2)c2ccc(Cl)c(Cl)c2n1] | 447 |

-continued
| I-# | Starting Material | | Structure | MS [M + 1]+ |
|---|---|---|---|---|
| I-574 | 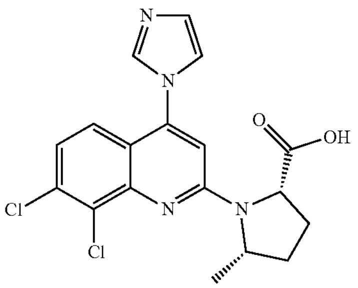 [SMILES: C[C@H]1CC[C@@H](C(=O)O)N1c1cc(-n2ccnc2)c2ccc(Cl)c(Cl)c2n1] | MeOH | 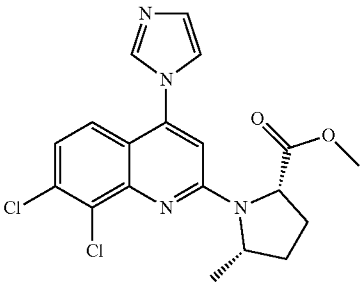 [SMILES: COC(=O)[C@@H]1CC[C@H](C)N1c1cc(-n2ccnc2)c2ccc(Cl)c(Cl)c2n1] | 405 |
| I-575 | 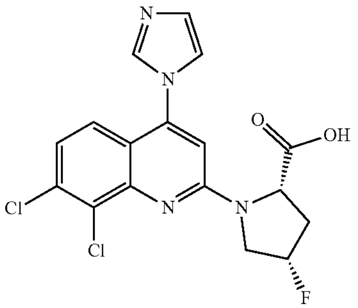 [SMILES: O=C(O)[C@@H]1C[C@H](F)CN1c1cc(-n2ccnc2)c2ccc(Cl)c(Cl)c2n1] | MeOH | 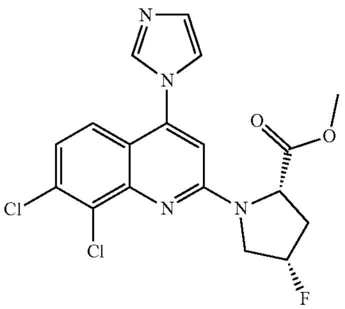 [SMILES: COC(=O)[C@@H]1C[C@H](F)CN1c1cc(-n2ccnc2)c2ccc(Cl)c(Cl)c2n1] | 409 |
| I-576 | 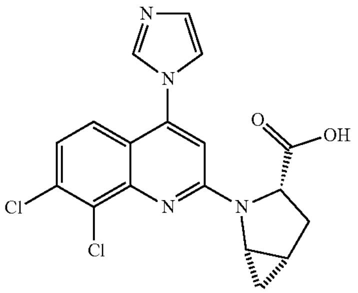 [SMILES: O=C(O)[C@@H]1C[C@@H]2C[C@@H]2N1c1cc(-n2ccnc2)c2ccc(Cl)c(Cl)c2n1] | MeOH | 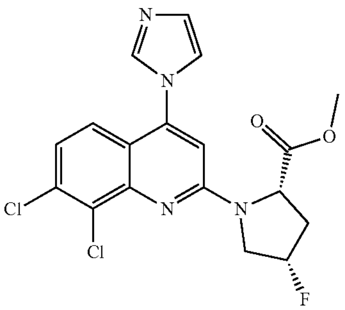 [SMILES: COC(=O)[C@@H]1C[C@H](F)CN1c1cc(-n2ccnc2)c2ccc(Cl)c(Cl)c2n1] | 403 |
| I-577 | 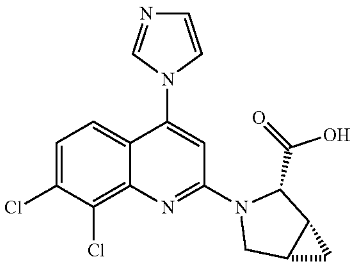 [SMILES: O=C(O)[C@@H]1[C@@H]2C[C@@H]2CN1c1cc(-n2ccnc2)c2ccc(Cl)c(Cl)c2n1] | MeOH | 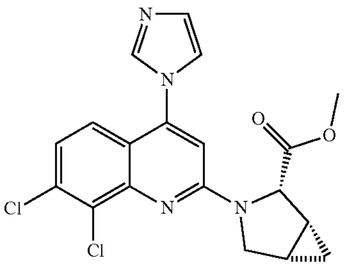 [SMILES: COC(=O)[C@@H]1[C@@H]2C[C@@H]2CN1c1cc(-n2ccnc2)c2ccc(Cl)c(Cl)c2n1] | 403 |
| I-578 | 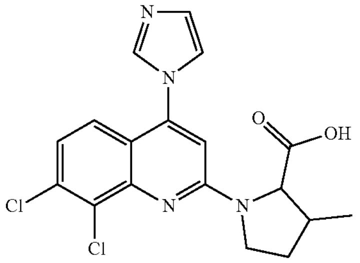 [SMILES: CC1CCN(c2cc(-n3ccnc3)c3ccc(Cl)c(Cl)c3n2)C1C(=O)O] | MeOH | 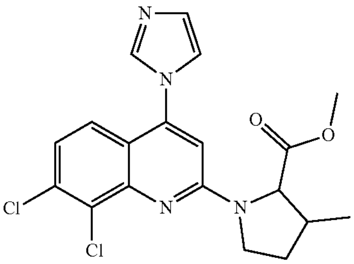 [SMILES: COC(=O)C1C(C)CCN1c1cc(-n2ccnc2)c2ccc(Cl)c(Cl)c2n1] | 405 |

-continued
| I-# | Starting Material | | Structure | MS [M + 1]+ |
|---|---|---|---|---|
| I-579 | 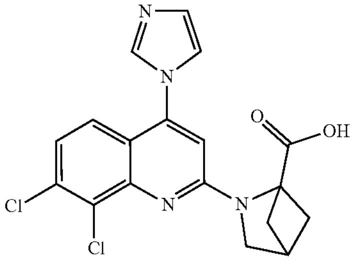 [SMILES: O=C(O)C12CC(CN1c1cc(-n3ccnc3)c3ccc(Cl)c(Cl)c3n1)C2] | MeOH | 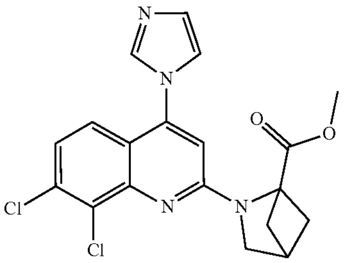 [SMILES: COC(=O)C12CC(CN1c1cc(-n3ccnc3)c3ccc(Cl)c(Cl)c3n1)C2] | 403 |
| I-580 | 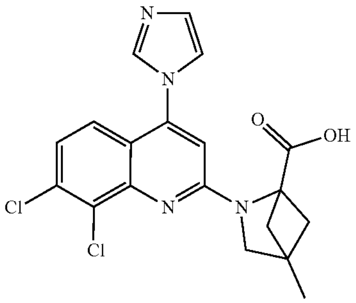 [SMILES: CC12CN(c3cc(-n4ccnc4)c4ccc(Cl)c(Cl)c4n3)C(C(=O)O)(C1)C2] | MeOH | 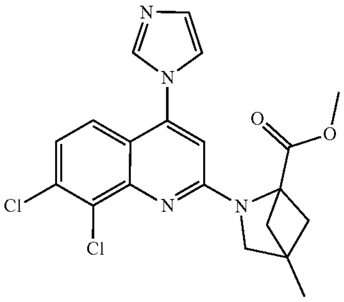 [SMILES: COC(=O)C12CC(C)(CN1c1cc(-n3ccnc3)c3ccc(Cl)c(Cl)c3n1)C2] | 417 |
| I-581 | 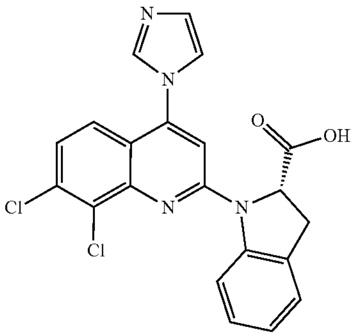 [SMILES: O=C(O)[C@@H]1Cc2ccccc2N1c1cc(-n2ccnc2)c2ccc(Cl)c(Cl)c2n1] | MeOH | 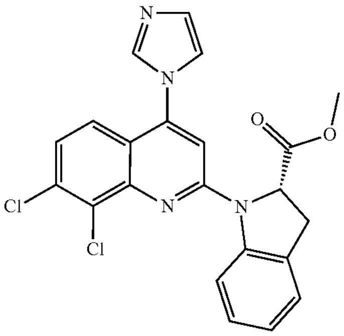 [SMILES: COC(=O)[C@@H]1Cc2ccccc2N1c1cc(-n2ccnc2)c2ccc(Cl)c(Cl)c2n1] | 439 |
| I-582 | 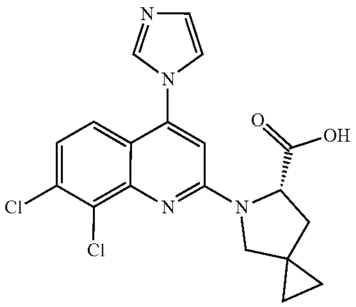 [SMILES: O=C(O)[C@@H]1CC2(CC2)CN1c1cc(-n2ccnc2)c2ccc(Cl)c(Cl)c2n1] | MeOH | 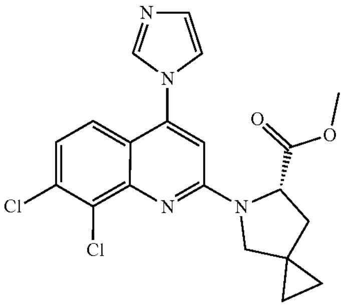 [SMILES: COC(=O)[C@@H]1CC2(CC2)CN1c1cc(-n2ccnc2)c2ccc(Cl)c(Cl)c2n1] | 417 |
| I-583 | 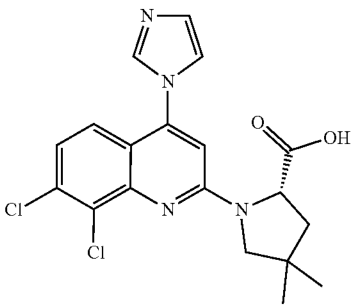 [SMILES: CC1(C)C[C@@H](C(=O)O)N(c2cc(-n3ccnc3)c3ccc(Cl)c(Cl)c3n2)C1] | MeOH | 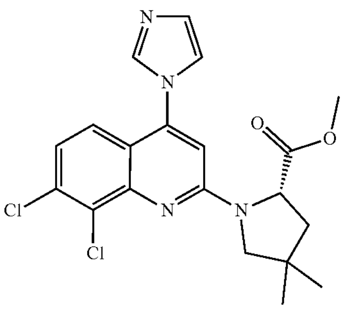 [SMILES: COC(=O)[C@@H]1CC(C)(C)CN1c1cc(-n2ccnc2)c2ccc(Cl)c(Cl)c2n1] | 419 |

-continued
| I-# | Starting Material | | Structure | MS [M + 1]+ |
|---|---|---|---|---|
| I-584 | 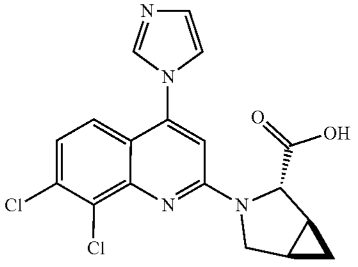 | MeOH | 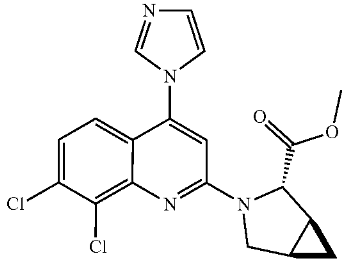 | 403 |
| I-585 | 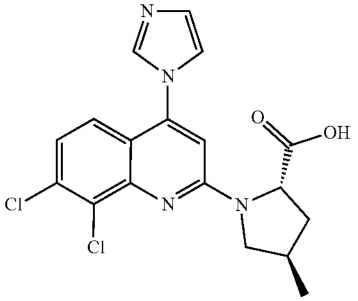 [SMILES: C[C@@H]1C[C@@H](C(=O)O)N(c2cc(-n3ccnc3)c3ccc(Cl)c(Cl)c3n2)C1] | MeOH | 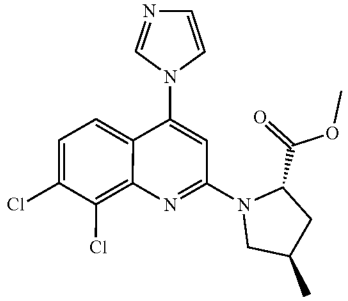 [SMILES: COC(=O)[C@@H]1C[C@@H](C)CN1c1cc(-n2ccnc2)c2ccc(Cl)c(Cl)c2n1] | 405 |
| I-586 | 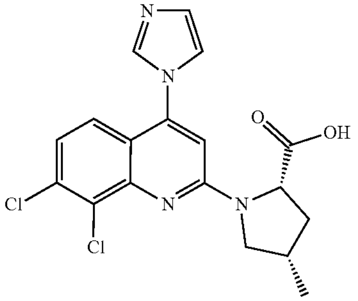 [SMILES: C[C@H]1C[C@@H](C(=O)O)N(c2cc(-n3ccnc3)c3ccc(Cl)c(Cl)c3n2)C1] | MeOH | 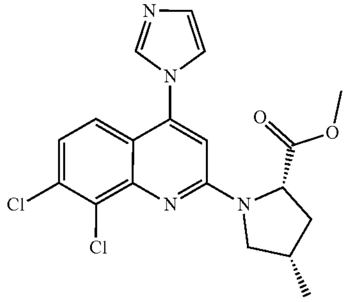 [SMILES: COC(=O)[C@@H]1C[C@H](C)CN1c1cc(-n2ccnc2)c2ccc(Cl)c(Cl)c2n1] | 405 |
| I-587 | 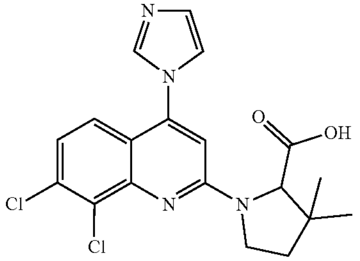 [SMILES: CC1(C)CCN(c2cc(-n3ccnc3)c3ccc(Cl)c(Cl)c3n2)C1C(=O)O] | MeOH | 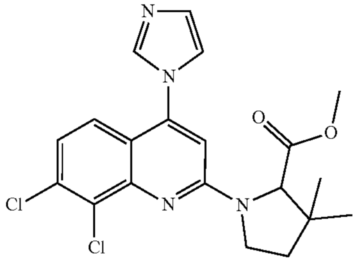 [SMILES: COC(=O)C1N(c2cc(-n3ccnc3)c3ccc(Cl)c(Cl)c3n2)CCC1(C)C] | 419 |
| I-588 | 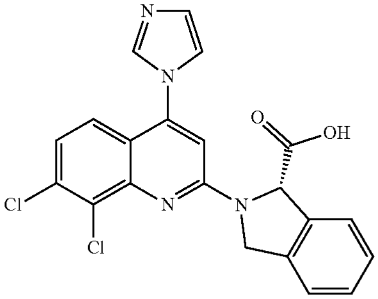 [SMILES: O=C(O)[C@@H]1c2ccccc2CN1c1cc(-n2ccnc2)c2ccc(Cl)c(Cl)c2n1] | MeOH | 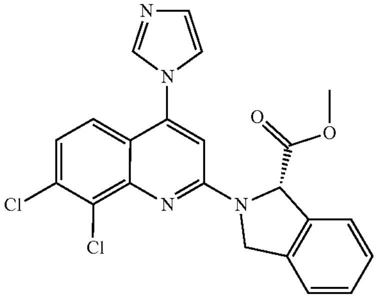 [SMILES: COC(=O)[C@@H]1c2ccccc2CN1c1cc(-n2ccnc2)c2ccc(Cl)c(Cl)c2n1] | 439 |

-continued
| I-# | Starting Material | | Structure | MS [M + 1]+ |
|---|---|---|---|---|
| I-589 | 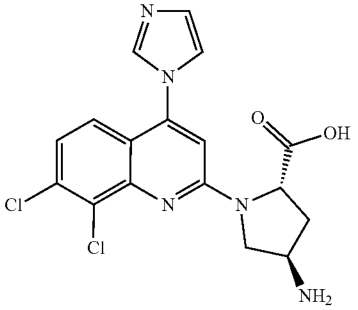 [SMILES: N[C@@H]1C[C@@H](C(=O)O)N(c2cc(-n3ccnc3)c3ccc(Cl)c(Cl)c3n2)C1] | MeOH | 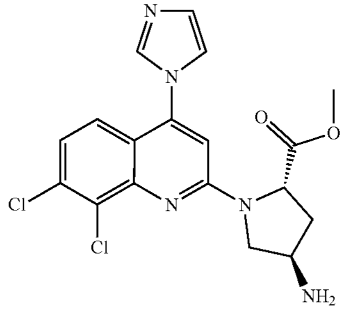 [SMILES: COC(=O)[C@@H]1C[C@@H](N)CN1c1cc(-n2ccnc2)c2ccc(Cl)c(Cl)c2n1] | 406 |
| I-590 | 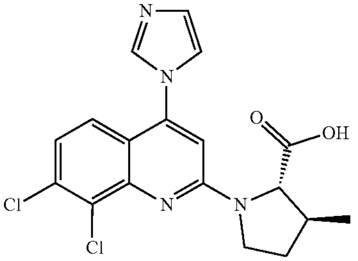 [SMILES: C[C@H]1CCN(c2cc(-n3ccnc3)c3ccc(Cl)c(Cl)c3n2)[C@@H]1C(=O)O] | MeOH | 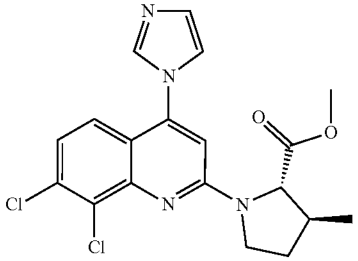 [SMILES: COC(=O)[C@@H]1[C@@H](C)CCN1c1cc(-n2ccnc2)c2ccc(Cl)c(Cl)c2n1] | 405 |
| I-591 | 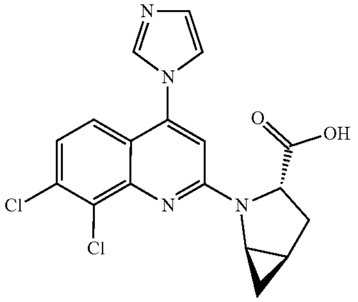 [SMILES: O=C(O)[C@@H]1C[C@H]2C[C@H]2N1c1cc(-n2ccnc2)c2ccc(Cl)c(Cl)c2n1] | MeOH | 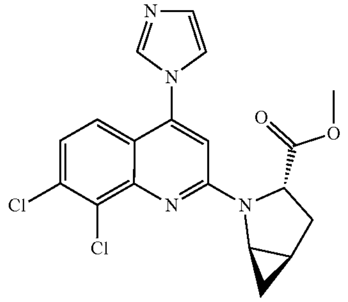 [SMILES: COC(=O)[C@@H]1C[C@H]2C[C@H]2N1c1cc(-n2ccnc2)c2ccc(Cl)c(Cl)c2n1] | 403 |
| I-592 | 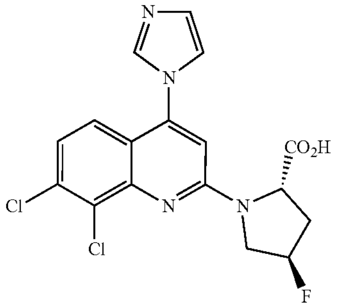 [SMILES: O=C(O)[C@@H]1C[C@@H](F)CN1c1cc(-n2ccnc2)c2ccc(Cl)c(Cl)c2n1] | MeOH | 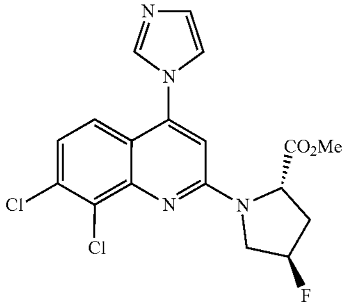 [SMILES: COC(=O)[C@@H]1C[C@@H](F)CN1c1cc(-n2ccnc2)c2ccc(Cl)c(Cl)c2n1] | 409 |
| I-593 | 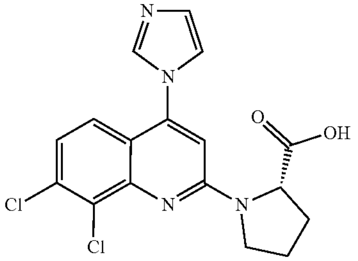 [SMILES: O=C(O)[C@@H]1CCCN1c1cc(-n2ccnc2)c2ccc(Cl)c(Cl)c2n1] | MeOH | 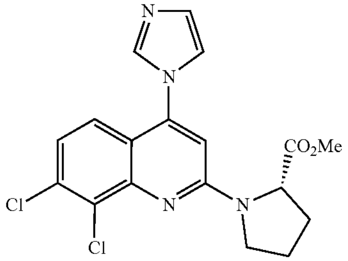 [SMILES: COC(=O)[C@@H]1CCCN1c1cc(-n2ccnc2)c2ccc(Cl)c(Cl)c2n1] | 391 |

-continued
| I-# | Starting Material | | Structure | MS [M + 1]+ |
|---|---|---|---|---|
| I-594 | 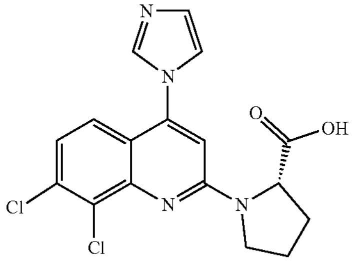 [SMILES: O=C(O)[C@@H]1CCCN1c1cc(-n2ccnc2)c2ccc(Cl)c(Cl)c2n1] | $CH_3CH_2OH$ | 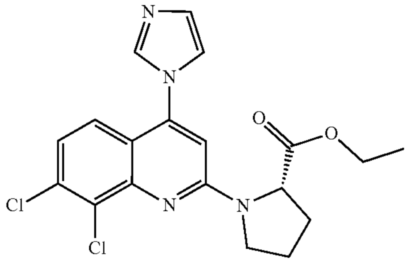 [SMILES: CCOC(=O)[C@@H]1CCCN1c1cc(-n2ccnc2)c2ccc(Cl)c(Cl)c2n1] | 405 |
| I-595 | 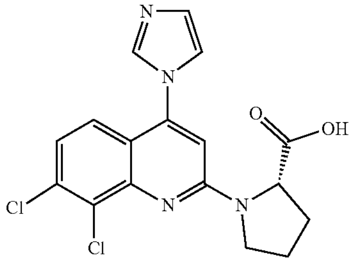 [SMILES: O=C(O)[C@@H]1CCCN1c1cc(-n2ccnc2)c2ccc(Cl)c(Cl)c2n1] | 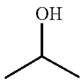 | 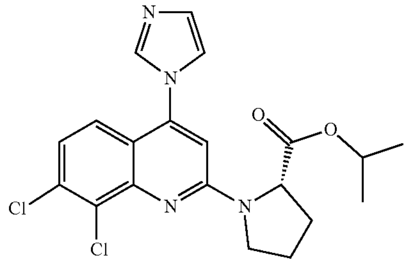 [SMILES: CC(C)OC(=O)[C@@H]1CCCN1c1cc(-n2ccnc2)c2ccc(Cl)c(Cl)c2n1] | 419 |
| I-596 | 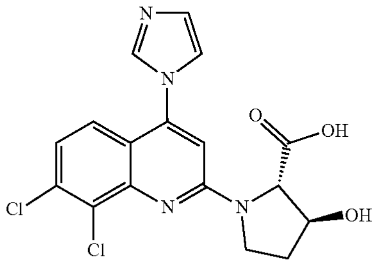 [SMILES: O=C(O)[C@@H]1[C@@H](O)CCN1c1cc(-n2ccnc2)c2ccc(Cl)c(Cl)c2n1] | $CH_3OH$ | 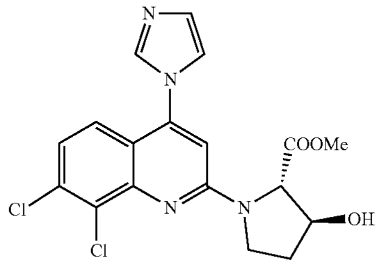 [SMILES: COC(=O)[C@@H]1[C@@H](O)CCN1c1cc(-n2ccnc2)c2ccc(Cl)c(Cl)c2n1] | 407 |
| I-597 | 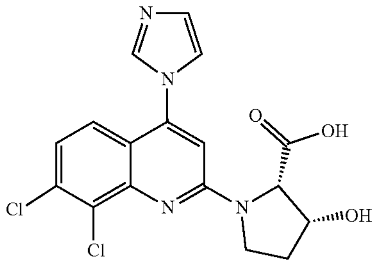 [SMILES: O=C(O)[C@@H]1[C@H](O)CCN1c1cc(-n2ccnc2)c2ccc(Cl)c(Cl)c2n1] | $CH_3OH$ | 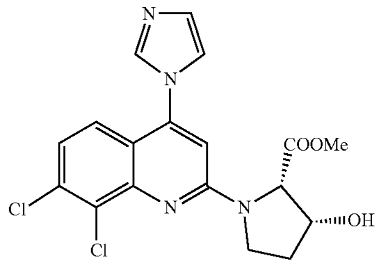 [SMILES: COC(=O)[C@@H]1[C@H](O)CCN1c1cc(-n2ccnc2)c2ccc(Cl)c(Cl)c2n1] | 407 |
| I-598 | 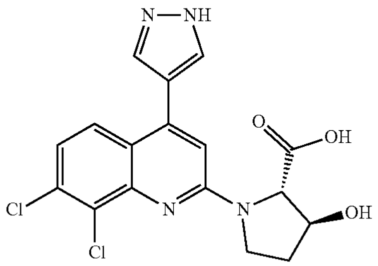 [SMILES: O=C(O)[C@@H]1[C@@H](O)CCN1c1cc(-c2cn[nH]c2)c2ccc(Cl)c(Cl)c2n1] | $CH_3OH$ | 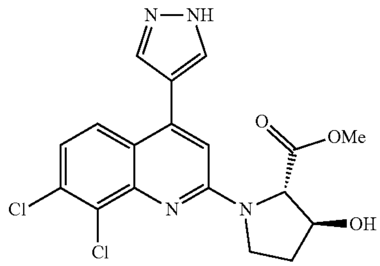 [SMILES: COC(=O)[C@@H]1[C@@H](O)CCN1c1cc(-c2cn[nH]c2)c2ccc(Cl)c(Cl)c2n1] | 407 |

-continued
| I-# | Starting Material | | Structure | MS [M + 1]+ |
|---|---|---|---|---|
| I-599 | 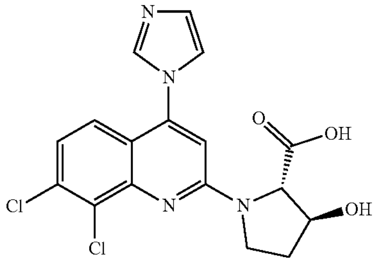 [SMILES: O=C(O)[C@@H]1[C@@H](O)CCN1c1cc(-n2ccnc2)c2ccc(Cl)c(Cl)c2n1] | $CH_3CH_2OH$ | 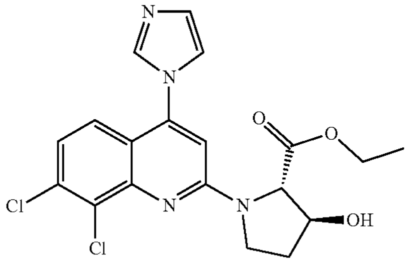 [SMILES: CCOC(=O)[C@@H]1[C@@H](O)CCN1c1cc(-n2ccnc2)c2ccc(Cl)c(Cl)c2n1] | 421 |
| I-600 | 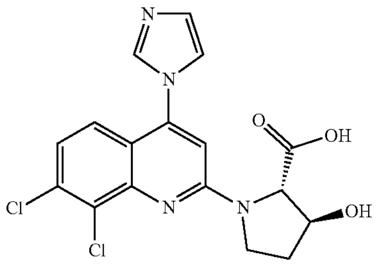 [SMILES: O=C(O)[C@@H]1[C@@H](O)CCN1c1cc(-n2ccnc2)c2ccc(Cl)c(Cl)c2n1] | 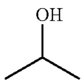 | 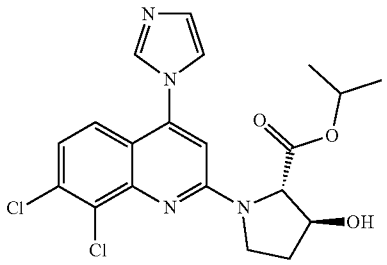 [SMILES: CC(C)OC(=O)[C@@H]1[C@@H](O)CCN1c1cc(-n2ccnc2)c2ccc(Cl)c(Cl)c2n1] | 435 |
| I-601 | 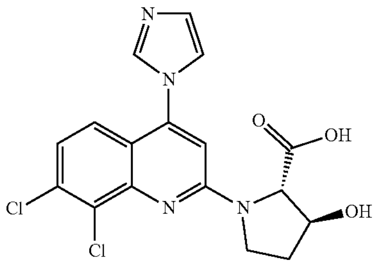 [SMILES: O=C(O)[C@@H]1[C@@H](O)CCN1c1cc(-n2ccnc2)c2ccc(Cl)c(Cl)c2n1] | 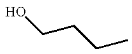 | 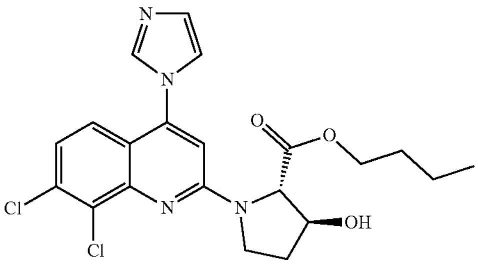 [SMILES: CCCCOC(=O)[C@@H]1[C@@H](O)CCN1c1cc(-n2ccnc2)c2ccc(Cl)c(Cl)c2n1] | 449 |
| I-602 | 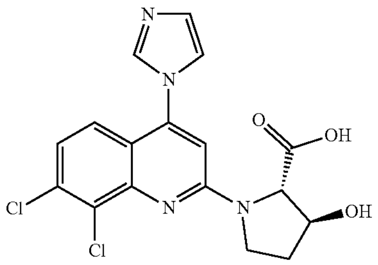 [SMILES: O=C(O)[C@@H]1[C@@H](O)CCN1c1cc(-n2ccnc2)c2ccc(Cl)c(Cl)c2n1] | 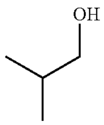 | 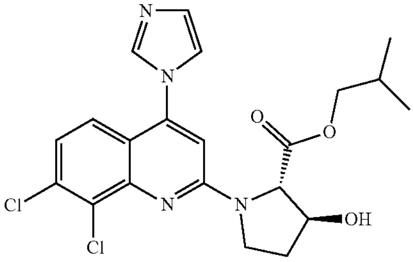 [SMILES: CC(C)COC(=O)[C@@H]1[C@@H](O)CCN1c1cc(-n2ccnc2)c2ccc(Cl)c(Cl)c2n1] | 449 |
| I-662 | 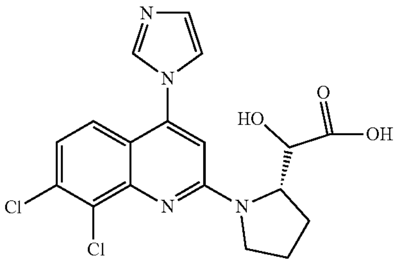 [SMILES: O=C(O)C(O)[C@@H]1CCCN1c1cc(-n2ccnc2)c2ccc(Cl)c(Cl)c2n1] | MeOH | 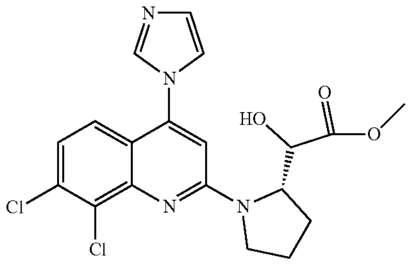 [SMILES: COC(=O)C(O)[C@@H]1CCCN1c1cc(-n2ccnc2)c2ccc(Cl)c(Cl)c2n1] | 421 |

-continued

| I-# | Starting Material | Structure | MS [M + 1]+ |
|---|---|---|---|
| I-663 | 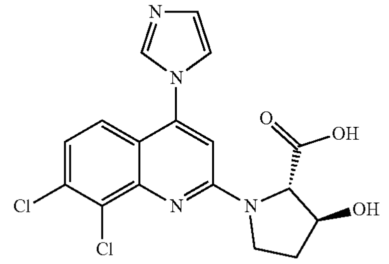 [SMILES: O=C(O)[C@@H]1[C@@H](O)CCN1c1cc(-n2ccnc2)c2ccc(Cl)c(Cl)c2n1] 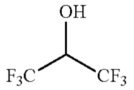 | 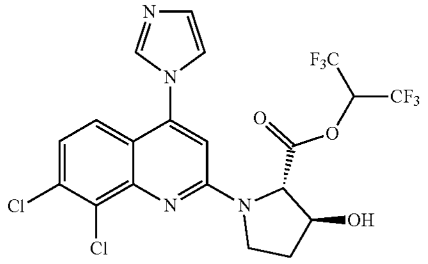 [SMILES: O=C(OC(C(F)(F)F)C(F)(F)F)[C@@H]1[C@@H](O)CCN1c1cc(-n2ccnc2)c2ccc(Cl)c(Cl)c2n1] 1 | 543 |

Example 84: Synthesis of methyl (S)-2-(1-(7,8-dichloro-4-(1H-imidazol-1-yl)naphthalen-2-yl)azetidin-2-yl)acetate (I-604)

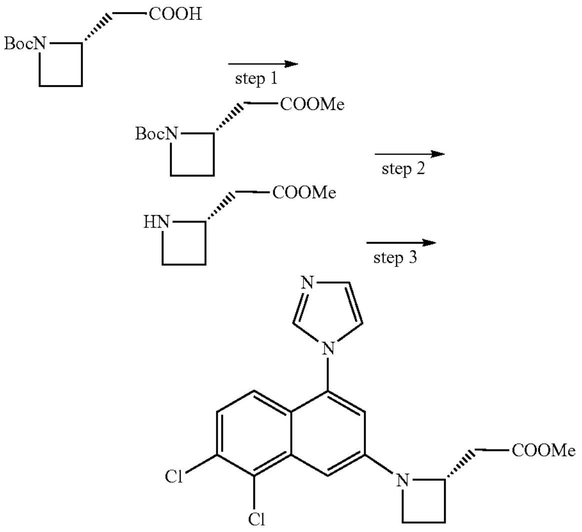

I-604

Step 1: At 0° C., oxalyl chloride (0.1 mL) was added dropwise to MeOH (1 mL). After 30 min, a solution of (S)-2-(1-(tert-butoxycarbonyl)azetidin-2-yl)acetic acid (43 mg, 0.2 mmol) in MeOH (0.1 mL) was added. The solution was stirred at r.t. overnight. After evaporation, the crude was dissolved in EtOAc (5 mL) and washed with saturated $NaHCO_3$ (aq.), water, brine and dried over anhy. $Na_2SO_4$. The crude was used in the next step without further purification. (MS: $[M+1]^+$ 230.1).

Step 2: A solution of tert-butyl (S)-2-(2-methoxy-2-oxoethyl)azetidine-1-carboxylate (50 mg crude, 0.2 mmol) in 50% TFA/DCM was stirred at r.t. for 30 min. After evaporation, the crude was dissolved in DCM (2 mL). The solvent was removed by evaporation. The process was repeated twice. The crude was used in the next step without further purification. (MS: $[M+1]^+$ 130.1).

Step 3: I-604 was prepared essentially by the same method as I-353. (MS: $[M+1]^+$ 390.1).

Example 85: Synthesis of (S)-5-(1-(7,8-dichloro-4-(1H-imidazol-1-yl)quinolin-2-yl)pyrrolidin-2-yl)-1,2,4-oxadiazol-3(2H)-one (I-605)

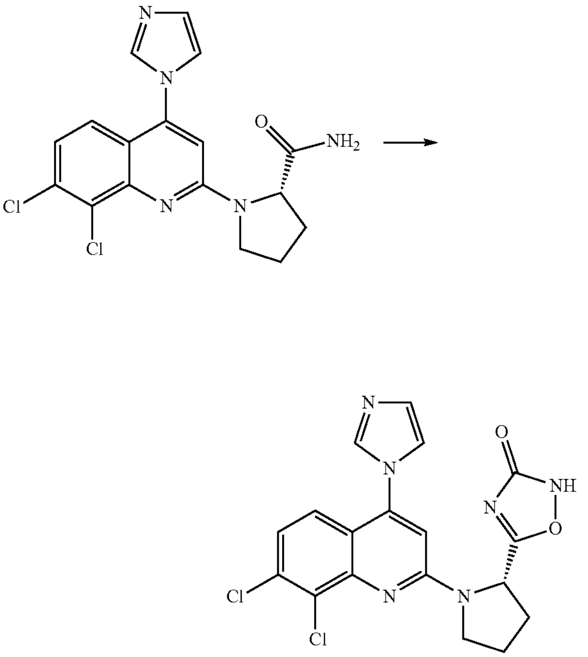

To a mixture of (S)-1-(7,8-dichloro-4-(1H-imidazol-1-yl)quinolin-2-yl)pyrrolidine-2-carboxamide (100 mg, 0.27 mmol) and DCE (2 mL) was added $(COCl)_2$(35 uL, 0.4 mmol) at r.t. The mixture was stirred at 70° C. overnight and then $TMSN_3$ (1 mL) was added. The solution was stirred at 80° C. for 2 days. After cooling down to r.t., the crude was purified directly by a column chromatography on silica gel to give the titled product as a solid (MS: $[M+1]^+$ 417.1).

Example 86: Synthesis of (2S,4R)-1-(7,8-dichloro-4-(1H-imidazol-1-yl)quinolin-2-yl)-4-((morpholine-4-carbonyl)oxy)pyrrolidine-2-carboxylic acid (I-606)

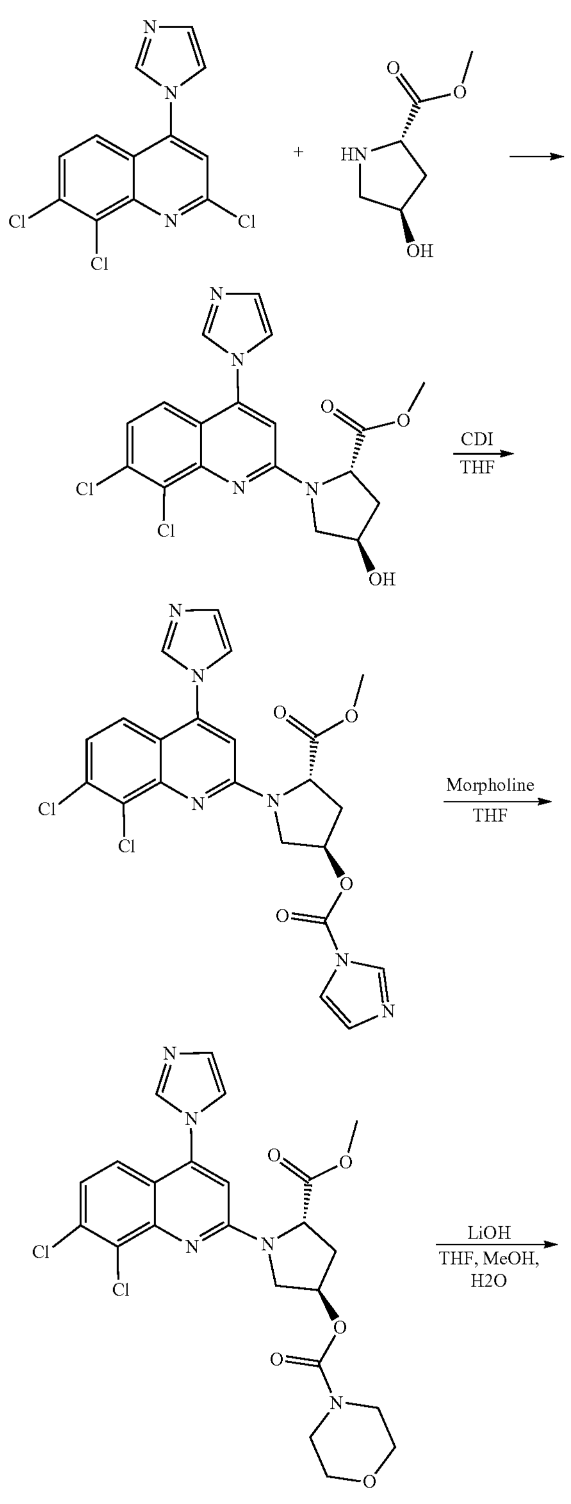

-continued

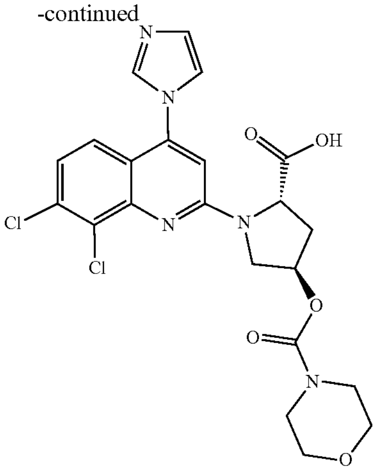

I-606

Step 1: methyl (2S,4R)-1-(7,8-dichloro-4-(1H-imidazol-1-yl)quinolin-2-yl)-4-hydroxypyrrolidine-2-carboxylate. To a vial were added 2,7,8-trichloro-4-(1H-imidazol-1-yl)quinoline (90 mg, 0.302 mmol), methyl (2S,4R)-4-hydroxypyrrolidine-2-carboxylate (146 mg, 0.603 mmol), DMSO (0.20 mL), and N,N-diisopropylethylamine (0.10 mL). The resulting reaction mixture was stirred at 90° C. for 16 h and cooled to room temperature, followed by adding $H_2O$ (20 mL). The cloudy mixture was centrifuged and the residue was extracted with 10% MeOH/DCM (2×10 mL). The organic phase was washed with $H_2O$ (10 mL), brine (10 mL), dried over $Na_2SO_4$, and concentrated. The crude residue was purified by silica chromatography to afford (104 mg) (MS: $[M+1]^+$ 407).

Step 2: (3R,5S)-1-(7,8-dichloro-4-(1H-imidazol-1-yl)quinolin-2-yl)-5-(methoxycarbonyl)pyrrolidin-3-yl 1H-imidazole-1-carboxylate. To a vial were added methyl (2S,4R)-1-(7,8-dichloro-4-(1H-imidazol-1-yl)quinolin-2-yl)-4-hydroxypyrrolidine-2-carboxylate (100 mg, 0.246 mmol), THF (5 mL) and carbonyldiimidazole (CDI) (80 mg, 0.493 mmol). The resulting mixture was stirred at room temperature for 4 hrs. All volatile solvents were then removed under reduced pressure and the residue was dried at high vacuum to afford the titled product. The crude was used in next step.

Step 3: (3R,5S)-1-(7,8-dichloro-4-(1H-imidazol-1-yl)quinolin-2-yl)-5-(methoxycarbonyl)pyrrolidin-3-yl morpholine-4-carboxylate. To a vial were added (3R,5S)-1-(7,8-dichloro-4-(1H-imidazol-1-yl)quinolin-2-yl)-5-(methoxycarbonyl)pyrrolidin-3-yl 1H-imidazole-1-carboxylate (125 mg, 0.250 mmol), THF (2 mL), and morpholine (44 mg, 0.505 mmol). The resulting reaction mixture was stirred at rt for 3h. The volatiles were concentrated off. The reaction mixture was diluted by ethyl acetate (15 mL). The organic phase was washed by $H_2O$ (3×5 mL), brine (5 mL), and dried over $Na_2SO_4$. After concentration, the crude was purified by silica gel chromatography to afford the titled product as an off-white solid (60 mg) (MS: $[M+1]^+$ 520).

Step 4: (2S,4R)-1-(7,8-dichloro-4-(1H-imidazol-1-yl)quinolin-2-yl)-4-((morpholine-4-carbonyl)oxy)pyrrolidine-2-carboxylic acid. To a vial were added (3R,5S)-1-(7,8-dichloro-4-(1H-imidazol-1-yl)quinolin-2-yl)-5-(methoxycarbonyl)pyrrolidin-3-yl morpholine-4-carboxylate (50 mg, 0.096 mmol), THF (0.8 mL), methanol (0.2 mL), water (0.2 mL) and morpholine. Lithium hydroxide monohydrate (12 mg, 0.288 mmol) was added and the resulting reaction mixture was stirred at rt for 16 h. The volatiles were concentrated off. The reaction mixture was diluted by water (2 mL) then acidified with 1M HCl to afford the titled product as an off-white solid (38 mg) (MS: $[M+1]^+$ 506).

The following compound was synthesized in a similar manner as I-606:

| I-# | Starting Material | Structure | MS [M + 1]+ |
|---|---|---|---|
| I-607 | 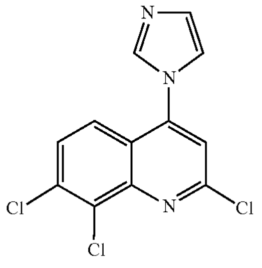 [SMILES: Clc1cc(-n2ccnc2)c2ccc(Cl)c(Cl)c2n1] 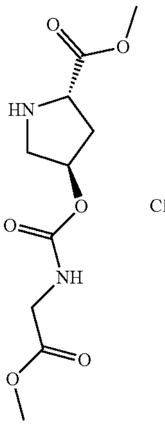 | 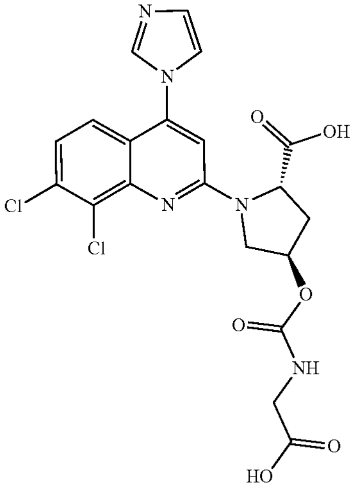 [SMILES: O=C(O)CNC(=O)O[C@@H]1C[C@@H](C(=O)O)N(c2cc(-n3ccnc3)c3ccc(Cl)c(Cl)c3n2)C1] | 494 |

Example 87: Synthesis of 2-((7,8-dichloro-4-(1H-imidazol-1-yl)quinolin-2-yl)(methyl)amino)-N-(2-hydroxyethyl)ethane-1-sulfonamide (I-624)

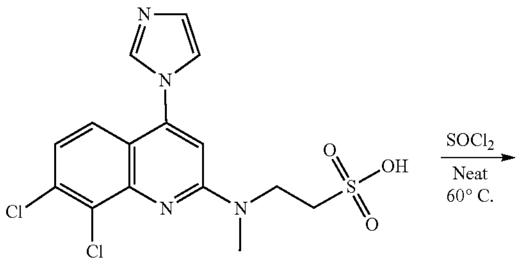

I-159

-continued

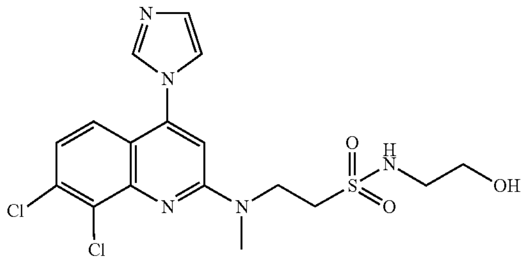

I-624

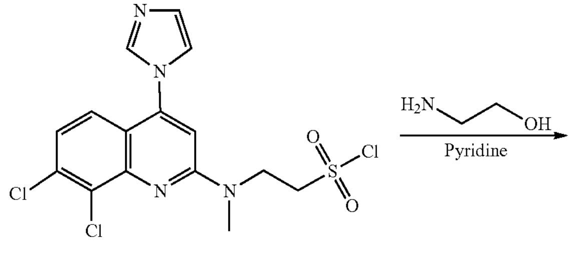

Step 1: I-159 was heated in the excess of thionyl chloride at 60° C. over 4 hours. The resultant solution was concentrated under vacuum to afford 2-((7,8-dichloro-4-(1H-imidazol-1-yl)quinolin-2-yl)(methyl)amino)ethane-1-sulfonyl chloride, which was used in the following step without further purification.

Step 2: 2-((7,8-dichloro-4-(1H-imidazol-1-yl)quinolin-2-yl) (methyl)amino)ethane-1-sulfonyl chloride was mixed with 2-aminoethan-1-ol in pyridine. Aqueous work-up and purification by prep-HPLC afforded the titled compound (I-624). MS $[M+1]^+$ 444.

Following the preparation of I-624 described above, the following compounds were prepared.

| I-# | Starting Materials | | Structure | MS $[M + 1]^+$ |
|---|---|---|---|---|
| I-625 | 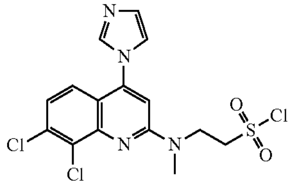 [SMILES: CN(CCS(=O)(=O)Cl)c1cc(-n2ccnc2)c2ccc(Cl)c(Cl)c2n1] | 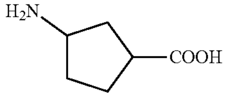 | 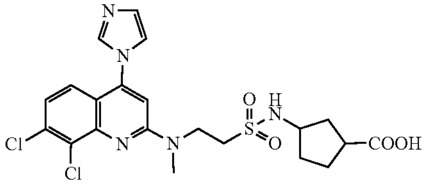 [SMILES: CN(CCS(=O)(=O)NC1CCC(C(=O)O)C1)c1cc(-n2ccnc2)c2ccc(Cl)c(Cl)c2n1] | 512 |
| I-626 | 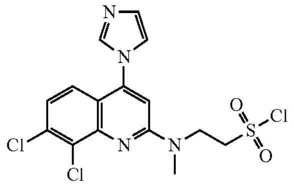 [SMILES: CN(CCS(=O)(=O)Cl)c1cc(-n2ccnc2)c2ccc(Cl)c(Cl)c2n1] | 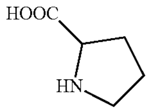 | 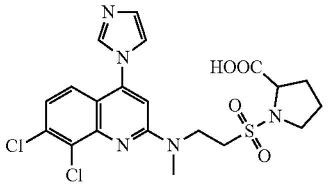 [SMILES: CN(CCS(=O)(=O)N1CCCC1C(=O)O)c1cc(-n2ccnc2)c2ccc(Cl)c(Cl)c2n1] | 498 |
| I-627 | 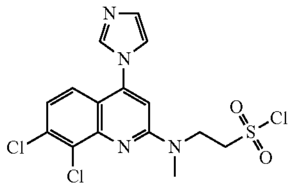 [SMILES: CN(CCS(=O)(=O)Cl)c1cc(-n2ccnc2)c2ccc(Cl)c(Cl)c2n1] | 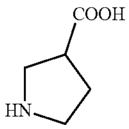 | 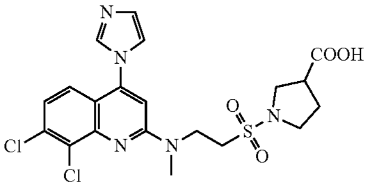 [SMILES: CN(CCS(=O)(=O)N1CCC(C(=O)O)C1)c1cc(-n2ccnc2)c2ccc(Cl)c(Cl)c2n1] | 498 |
| I-628 | 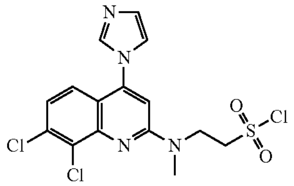 [SMILES: CN(CCS(=O)(=O)Cl)c1cc(-n2ccnc2)c2ccc(Cl)c(Cl)c2n1] | 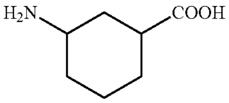 | 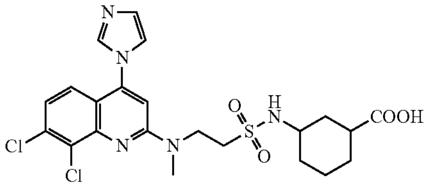 [SMILES: CN(CCS(=O)(=O)NC1CCCC(C(=O)O)C1)c1cc(-n2ccnc2)c2ccc(Cl)c(Cl)c2n1] | 526 |
| I-629 | 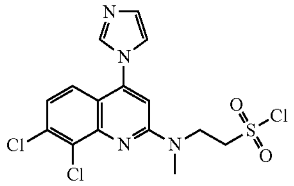 [SMILES: CN(CCS(=O)(=O)Cl)c1cc(-n2ccnc2)c2ccc(Cl)c(Cl)c2n1] | 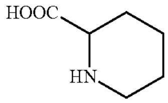 | 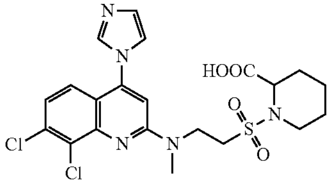 [SMILES: CN(CCS(=O)(=O)N1CCCCC1C(=O)O)c1cc(-n2ccnc2)c2ccc(Cl)c(Cl)c2n1] | 512 |
| I-630 | 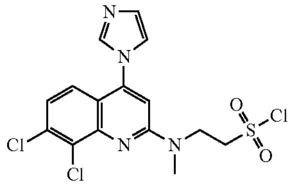 [SMILES: CN(CCS(=O)(=O)Cl)c1cc(-n2ccnc2)c2ccc(Cl)c(Cl)c2n1] | 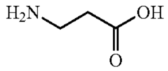 | 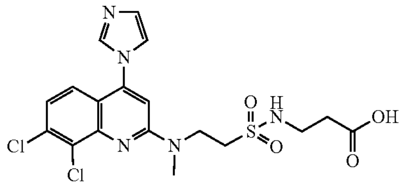 [SMILES: CN(CCS(=O)(=O)NCCC(=O)O)c1cc(-n2ccnc2)c2ccc(Cl)c(Cl)c2n1] | 472 |
| I-631 | 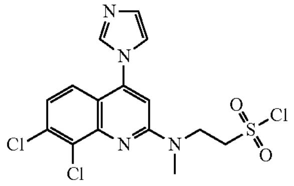 [SMILES: CN(CCS(=O)(=O)Cl)c1cc(-n2ccnc2)c2ccc(Cl)c(Cl)c2n1] | 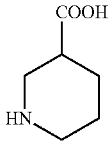 | 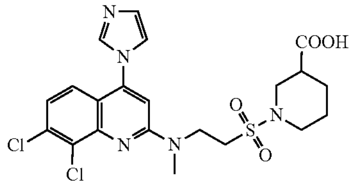 [SMILES: CN(CCS(=O)(=O)N1CCCC(C(=O)O)C1)c1cc(-n2ccnc2)c2ccc(Cl)c(Cl)c2n1] | 512 |
| I-632 | 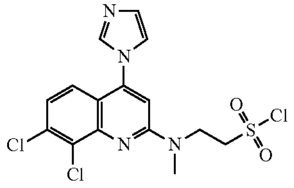 [SMILES: CN(CCS(=O)(=O)Cl)c1cc(-n2ccnc2)c2ccc(Cl)c(Cl)c2n1] | 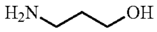 | 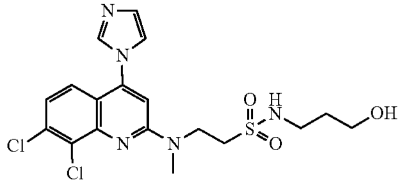 [SMILES: CN(CCS(=O)(=O)NCCCO)c1cc(-n2ccnc2)c2ccc(Cl)c(Cl)c2n1] | 458 |

-continued

| I-# | Starting Materials | | Structure | MS [M + 1]$^+$ |
|---|---|---|---|---|
| I-633 | 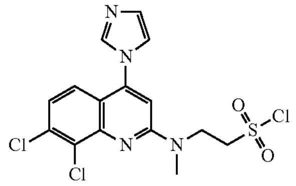 [SMILES: CN(CCS(=O)(=O)Cl)c1cc(-n2ccnc2)c2ccc(Cl)c(Cl)c2n1] | 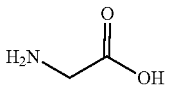 | 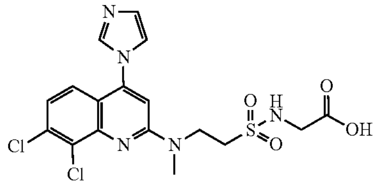 [SMILES: CN(CCS(=O)(=O)NCC(=O)O)c1cc(-n2ccnc2)c2ccc(Cl)c(Cl)c2n1] | 458 |

Example 88: Synthesis of 3-(N-(2-((7,8-dichloro-4-(1H-imidazol-1-yl)quinolin-2-yl)(methyl)amino)ethyl)methylsulfonamido) propanoic acid (I-634)

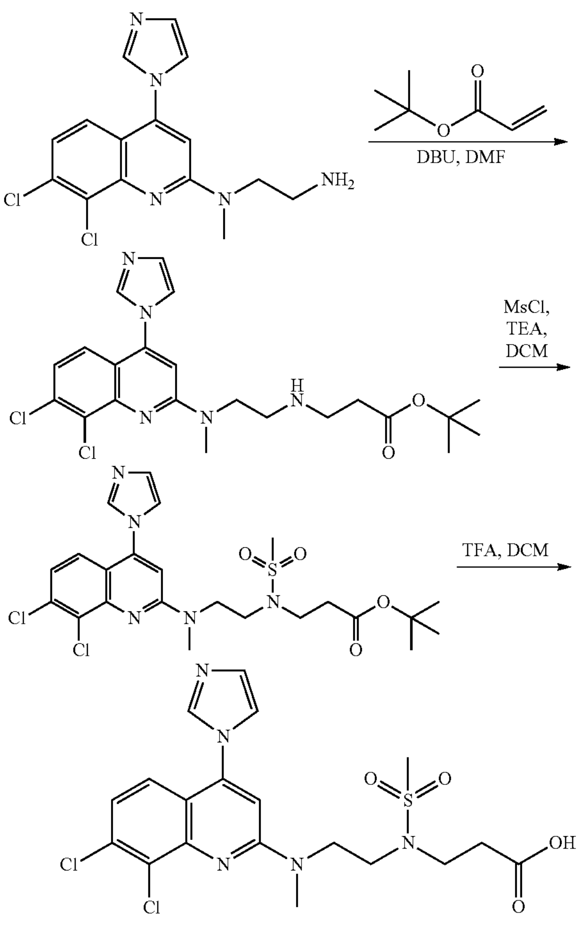

I-634

A mixture of N-1-(7,8-dichloro-4-(1H-imidazol-1-yl)quinolin-2-yl)-N1-methylethane-1,2-diamine (100 mg, 0.3 mmol), tert-butyl acrylate (41.9 mg, 0.33 mmol) and DBU (135 mg, 0.9 mmol) in DMF was stirred at 40° C. until completion by LCMS. After cooling to 0° C., MsCl (103 mg, 0.9 mmol) was added and the mixture was stirred for another 3 h, monitored by TLC. The mixture was then quenched with aq·$NaHCO_3$, taken up with DCM, washed with brine, dried, concentrated, and purified by prep-TLC to afford tert-butyl 3-(N-(2-((7,8-dichloro-4-(1H-imidazol-1-yl)quinolin-2-yl)(methyl)amino)ethyl)methylsulfonamido)propanoate which was dissolved in DCM/TFA (1/1, 2 mL) and stirred for 2 h, monitored by TLC. The solvent was then removed under vacuum and the residue was purified by prep-HPLC to the titled product (I-634) as a light yellow solid. NMR (400 MHz, $CD_3OH$, ppm): δ 9.22 (s, 1H), 7.98 (s, 1H), 7.79 (s, 1H), 7.41-7.33 (m, 3H), 4.05 (s, 2H), 3.59-3.58 (m, 4H), 3.31 (s, 3H), 2.92 (s, 3H), 2.65 (s, 2H). LCMS: ($ES^+$): m/z 486.1 $[M+1]^+$.

Example 89: Synthesis of N-(2-((7,8-dichloro-4-(1H-imidazol-1-yl)quinolin-2-yl)(methyl)amino)ethyl)-N-(methylsulfonyl)glycine (I-635)

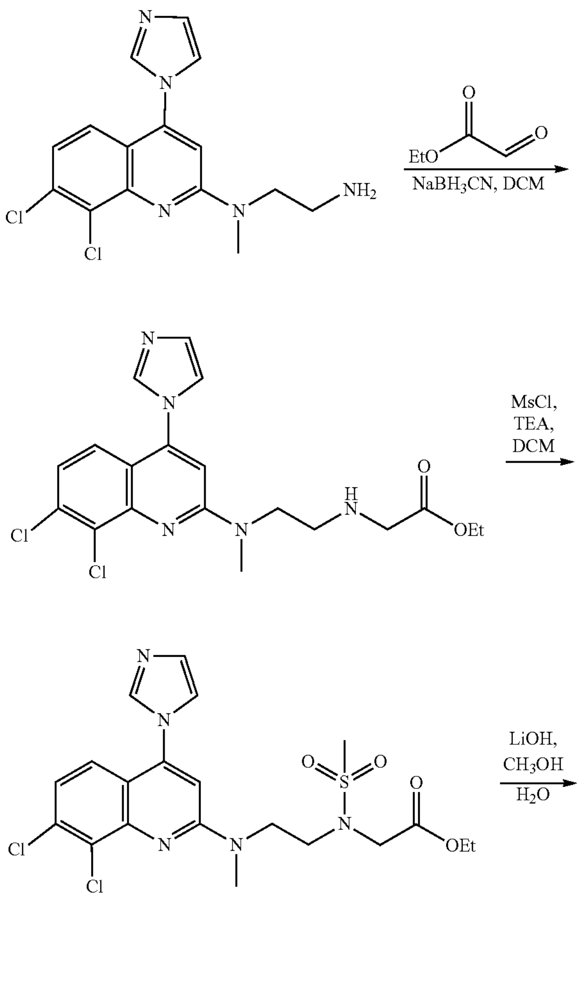

-continued

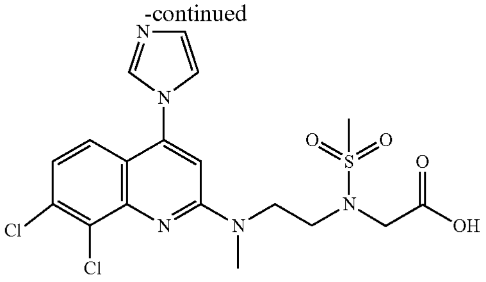

I-635

To a mixture of N-1-(7,8-dichloro-4-(1H-imidazol-1-yl)quinolin-2-yl)-N1-methylethane-1,2-diamine (100 mg, 0.3 mmol) and ethyl 2-oxoacetate (74 mg, 50% in toluene, 0.36 mmol) in DCM/DCM/$CH_3OH$ (2/1, 3 mL) and cat. AcOH (2 drops) was added $NaBH_3CN$ (38 mg, 0.6 mmol) at rt. and stirred for 10 h until completion by LCMS. The mixture was then quenched with aq. $NaHCO_3$, taken up with DCM, washed with brine, dried, and concentrated to afford crude desired product of ethyl 2-oxoacetate, which was used into next step without further purification. The residue was dissolved into DCM/TEA (5/1, 5 mL), then MsCl (150 μL) was added into the mixture at rt, and stirred for another 2 h, monitored by TLC. The mixture was then quenched with aq. $NH_4Cl$, taken up with DCM, washed with brine, dried, and concentrated. The residue was purified by prep-TLC to afford ethyl N-(2-((7,8-dichloro-4-(1H-imidazol-1-yl)quinolin-2-yl)(methyl)amino)ethyl)-N-(methylsulfonyl)glycinate which was dissolved in $CH_3OH/H_2O$ (2/1, 3 mL), added LiOH, and stirred for 1 h, monitored by TLC. The reaction was then quenched with TFA, concentrated, and purified by prep-TLC ($DCM/CH_3OH$=8/1) to afford the titled product (I-635) as a light yellow solid. $^1H$ NMR (400 MHz, $CD_3OD$, ppm): δ 8.09 (s, 1H), 7.56 (s, 1H), 7.36-7.20 (m, 4H), 4.02-3.97 (m, 4H), 3.65 (br, 2H), 3.31 (s, 3H), 3.02 (s, 3H). LCMS: ($ES^+$): m/z 473.1 $[M+1]^+$.

Example 90: Synthesis of 3-((N-(2-((7,8-dichloro-4-(1H-imidazol-1-yl)quinolin-2-yl)(methyl)amino)ethyl)methylsulfonamido) methyl)benzoic acid (I-636)

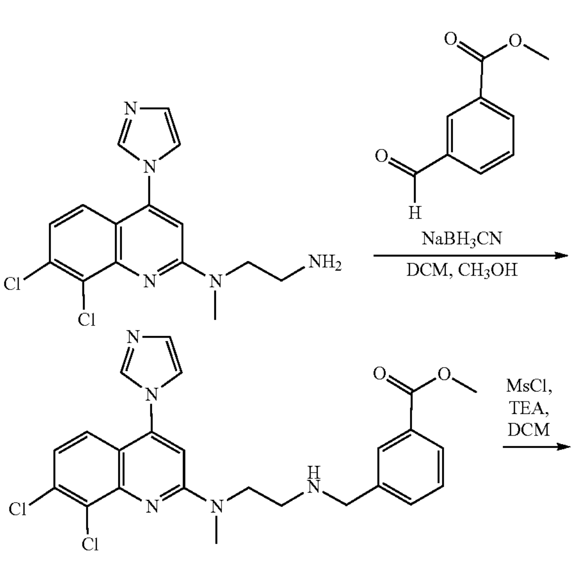

-continued

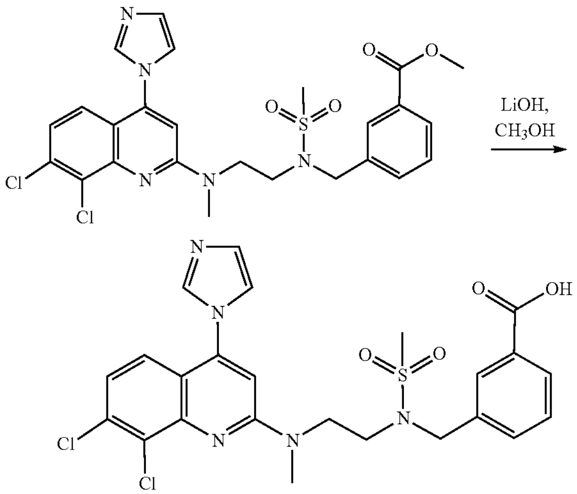

I-636

I-636 was prepared according to the same method to prepare I-635. $^1H$ NMR (400 MHz, $CD_3OD$, ppm): δ 9.20 (s, 1H), 8.00 (s, 1H), 7.81 (s, 1H), 7.64 (s, 1H), 757-7.47 (m, 2H), 7.34 (d, J=8.8 Hz, 1H), 7.25 (d, J=8.8 Hz, 1H), 4.33 (s, 2H), 3.84-3.72 (m, 4H), 3.06 (m, 3H), 3.02 (s, 3H). LCMS: ($ES^+$): m/z 548.1 $[M+1]^+$.

Example 91: Synthesis of methyl (2S,3S)-3-acetoxy-1-(7,8-dichloro-4-(1H-imidazol-1-yl)quinolin-2-yl)pyrrolidine-2-carboxylate (I-642) and (2S,3S)-3-acetoxy-1-(7,8-dichloro-4-(1H-imidazol-1-yl)quinolin-2-yl)pyrrolidine-2-carboxylic acid (I-643)

I-642 and I-643 were prepared according to the follow synthetic scheme:

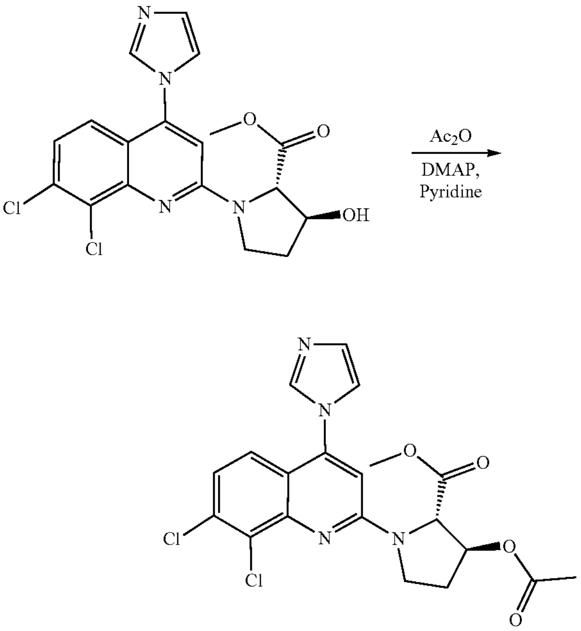

| I-# | Starting Material | Structure | MS [M + 1]+ |
|---|---|---|---|
| I-642 | 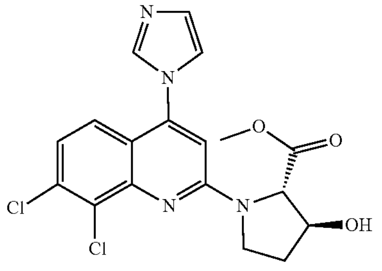 [SMILES: COC(=O)[C@@H]1[C@@H](O)CCN1c1cc(-n2ccnc2)c2ccc(Cl)c(Cl)c2n1] 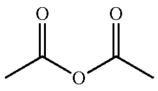 | 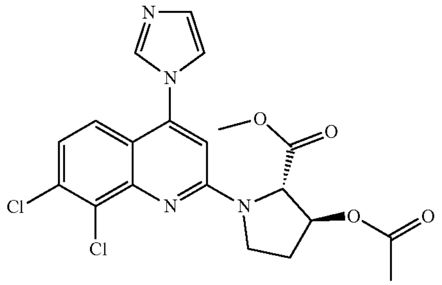 [SMILES: COC(=O)[C@@H]1[C@@H](OC(C)=O)CCN1c1cc(-n2ccnc2)c2ccc(Cl)c(Cl)c2n1] | 449 |
| I-643 | 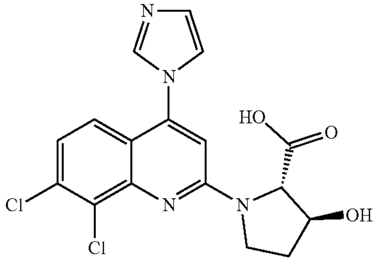 [SMILES: O=C(O)[C@@H]1[C@@H](O)CCN1c1cc(-n2ccnc2)c2ccc(Cl)c(Cl)c2n1] 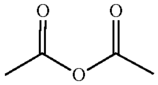 | 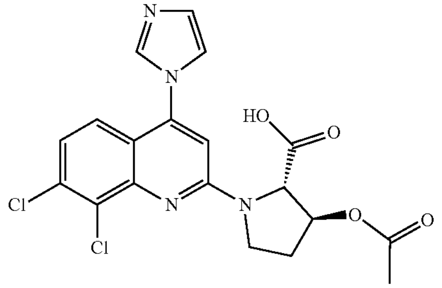 [SMILES: CC(=O)O[C@H]1CCN(c2cc(-n3ccnc3)c3ccc(Cl)c(Cl)c3n2)[C@@H]1C(=O)O] | 435 |

Example 92: Synthesis of tert-butyl (2S,3S)-1-(7,8-dichloro-4-(1H-imidazol-1-yl)quinolin-2-yl)-3-hydroxypyrrolidine-2-carboxylate (I-645)

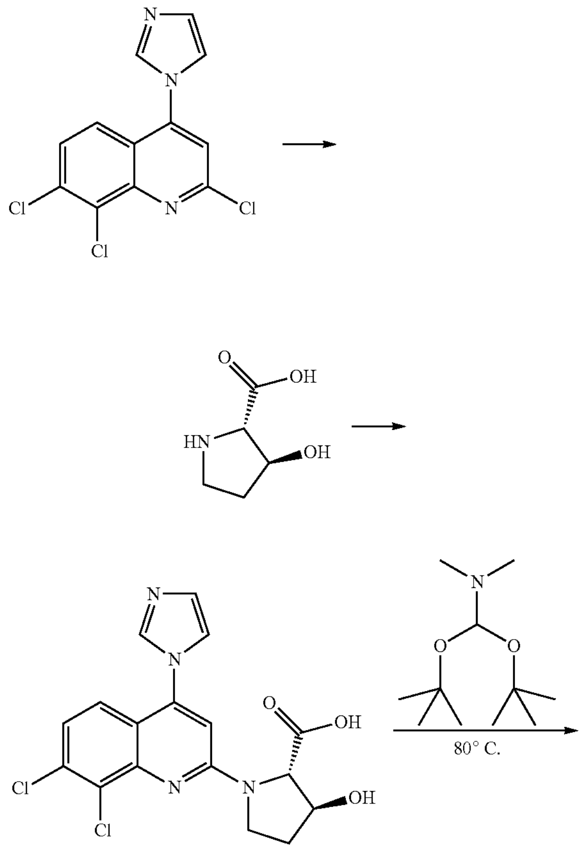

-continued

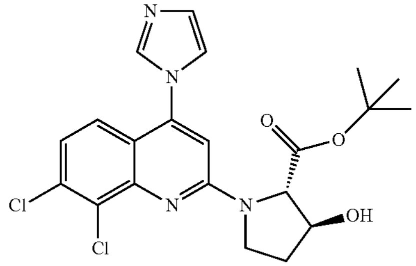

I-645

Step 1: (2S,3S)-1-(7,8-dichloro-4-(1H-imidazol-1-yl)quinolin-2-yl)-3-hydroxypyrrolidine-2-carboxylic acid was prepared similar to the preparation of I-123, step 1.

Step 2: The mixture of (2S,3S)-1-(7,8-dichloro-4-(1H-imidazol-1-yl)quinolin-2-yl)-3-hydroxypyrrolidine-2-carboxylic acid (380 mg, 0.083 mmol) and 1,1-di-tert-butoxy-N,N-dimethylmethanamine (200 mg, 0.983 mmol) was stirred at 80° C. overnight. The crude was purified by silica gel chromatography to afford I-645 (MS: $[M+1]^+$ 449)

Example 93: Synthesis of methyl (2S,3S)-1-(7,8-dichloro-4-(1H-imidazol-1-yl)quinolin-2-yl)-3-methoxypyrrolidine-2-carboxylate (I-646)

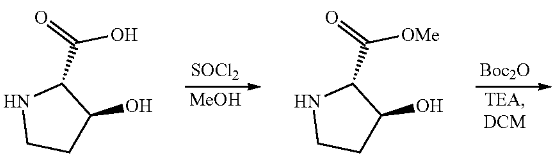

-continued

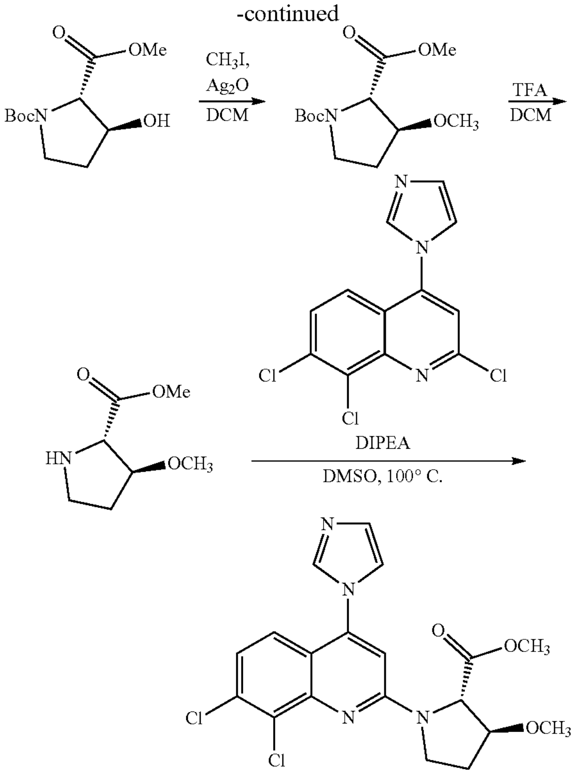

I-646

Step 1: (2S,3S)-methyl 3-hydroxypyrrolidine-2-carboxylate HCl salt was prepared similar to the preparation of I-593.

Step 2: To a solution of (2S,3S)-3-hydroxypyrrolidine-2-carboxylic acid HCl salt (268 mg, 1.47 mmol) in DCN (6 mL) was added $Boc_2O$ (385 mg, 1.76 mmol) and TEA (0.612 mL, 4.39 mmol). The resulting reaction solution was stirred overnight. The mixture was diluted with DCM (20 mL), washed with $H_2O$ (2×10 mL), brine (10 mL), and dried over $Na_2SO_4$. After concentration, the crude (2S,3S)-1-tert-butyl 2-methyl 3-hydroxypyrrolidine-1,2-dicarboxylate was used in next step.

Step 3: To a solution of (2S,3S)-1-tert-butyl 2-methyl 3-hydroxypyrrolidine-1,2-dicarboxylate (0.5 mmol) and iodomethane (0.093 mL, 1.5 mmol) in DCM (1.5 mL) was added 700 mg of $Ag_2O$ (700 mg, 3.02 mmol). After being stirred overnight, the mixture was filtered through a pad of Celite and purified by silica gel chromatography to afford (2S,3S)-1-tert-butyl 2-methyl 3-methoxypyrrolidine-1,2-dicarboxylate as an oil.

Step 4: To a solution of (2S,3S)-1-tert-butyl 2-methyl 3-methoxypyrrolidine-1,2-dicarboxylate (56.5 mg, 0.218 mmol) in DCM (0.5 mL) was added TFA (0.25 mL). After being stirred for 4 hours, the mixture was concentrated to remove all volatiles. The residue (2S,3S)-methyl 3-methoxypyrrolidine-2-carboxylate was used in next step.

Step 5: (2S,3S)-methyl 1-(7,8-dichloro-4-(1H-imidazol-1-yl)quinolin-2-yl)-3-methoxypyrrolidine-2-carboxylate was prepare by a procedure similar to that of I-123, step 1. (MS: $[M+1]^+$ 421).

The following compounds were prepared essentially by the same method to prepare I-646.

| I-# | Starting Material | Structure | MS $[M + 1]^+$ |
|---|---|---|---|
| I-647 | 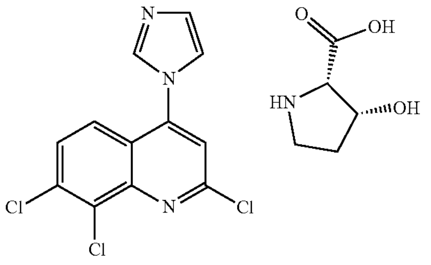 | 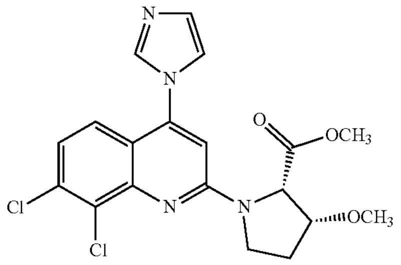 [SMILES: COC(=O)[C@@H]1[C@H](OC)CCN1c1cc(-n2ccnc2)c2ccc(Cl)c(Cl)c2n1] | 421 |
| I-648 | 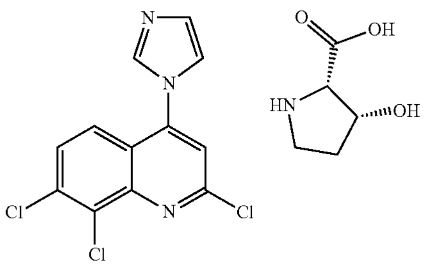 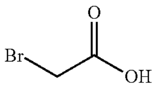 | 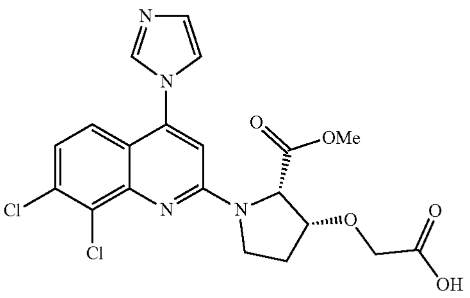 [SMILES: COC(=O)[C@@H]1[C@H](OCC(=O)O)CCN1c1cc(-n2ccnc2)c2ccc(Cl)c(Cl)c2n1] | 465 |

Example 94: Synthesis of methyl (2R,3S)-1-(7,8-dichloro-4-(1H-imidazol-1-yl)quinolin-2-yl)-3-fluoropyrrolidine-2-carboxylate (I-649)

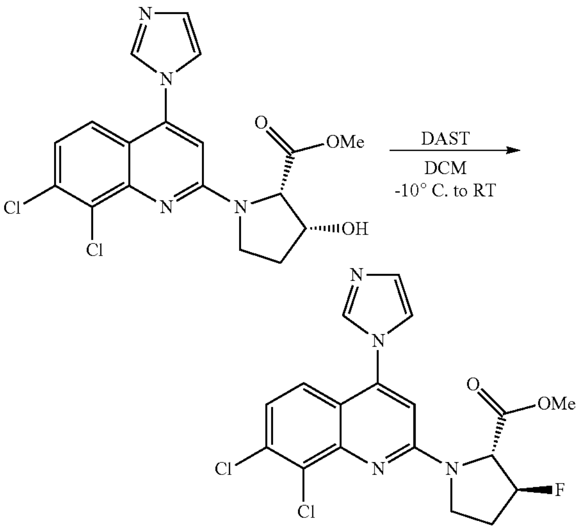

I-649

To a mixture of methyl (2S,3R)-1-(7,8-dichloro-4-(1H-imidazol-1-yl)quinolin-2-yl)-3-hydroxypyrrolidine-2-carboxylate (40.7 mg, 0.1 mmol) in DCM (0.5 mL) was added a solution of DAST (0.040 mL, 0.30 mmol) in DCM (0.2 mL) at −10° C. The mixture was stirred at −10° C. for 2 hours. After aqueous work-up, the crude was purified by PTLC to afford the titled product as a white solid (MS: $[M+1]^+$ 409).

The following compounds were prepared essentially by the same method to prepare I-649.

| I-# | Starting Material | | Structure | MS $[M + 1]^+$ |
|---|---|---|---|---|
| I-650 | 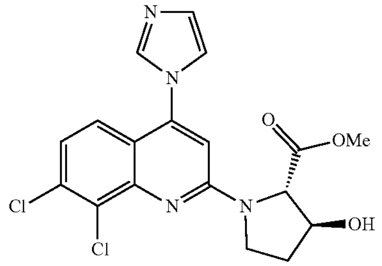 [SMILES: COC(=O)[C@@H]1[C@@H](O)CCN1c1cc(-n2ccnc2)c2ccc(Cl)c(Cl)c2n1] | DAST | 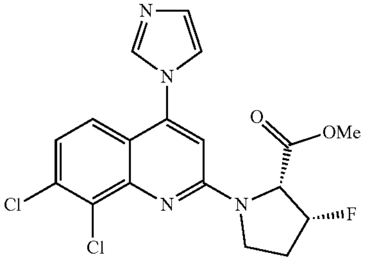 [SMILES: COC(=O)[C@@H]1[C@H](F)CCN1c1cc(-n2ccnc2)c2ccc(Cl)c(Cl)c2n1] | 409 |
| I-651 | 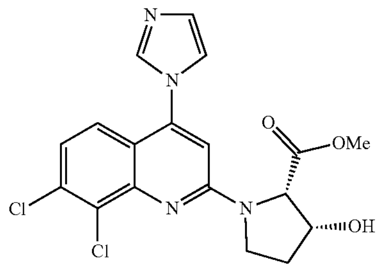 [SMILES: COC(=O)[C@@H]1[C@H](O)CCN1c1cc(-n2ccnc2)c2ccc(Cl)c(Cl)c2n1] | DAST | 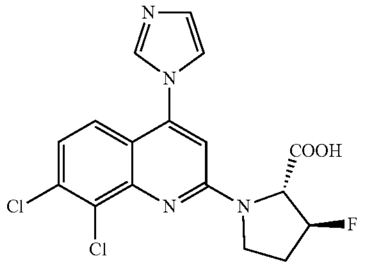 [SMILES: O=C(O)[C@@H]1[C@@H](F)CCN1c1cc(-n2ccnc2)c2ccc(Cl)c(Cl)c2n1] | 395 |

Example 95: Synthesis of methyl 1-(7,8-dichloro-4-(1H-imidazol-1-yl)quinolin-2-yl)-4,5-dihydro-1H-pyrrole-2-carboxylate (I-652)

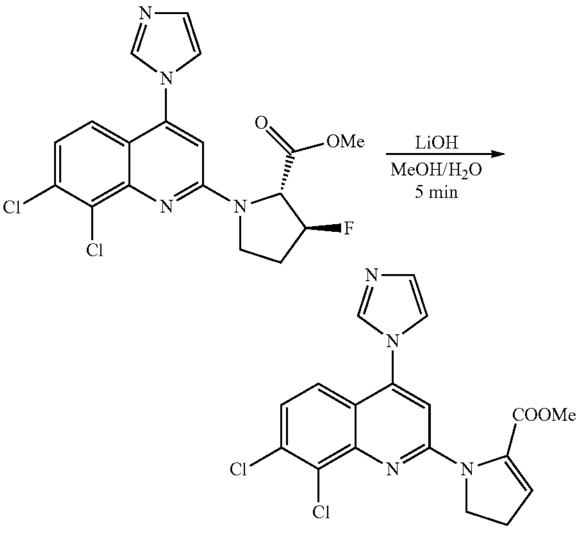

I-652

To the solution of methyl (2R,3S)-1-(7,8-dichloro-4-(1H-imidazol-1-yl)quinolin-2-yl)-3-fluoropyrrolidine-2-carboxylate (10 mg, 0.0244 mmol) in methanol (0.5 mL) was added a solution of LiOH—$H_2O$ (1.57 mg, 0.0366 mmol) in $H_2O$ (0.10 mL) with stirring. After 5 min, the reaction was quenched with HOAc (0.00209 mL, 0.0366 mmol) in $H_2O$ (0.10 mL). The resulting mixture was purified by HPLC to afford the titled product as a white solid. (MS: $[M+1]^+$ 389).

Example 96: Synthesis of methyl (2S,3R)-1-(7,8-dichloro-4-(1H-imidazol-1-yl)quinolin-2-yl)-3-(((2-methoxy-2-oxoethyl)carbamoyl)oxy)pyrrolidine-2-carboxylate (I-653)

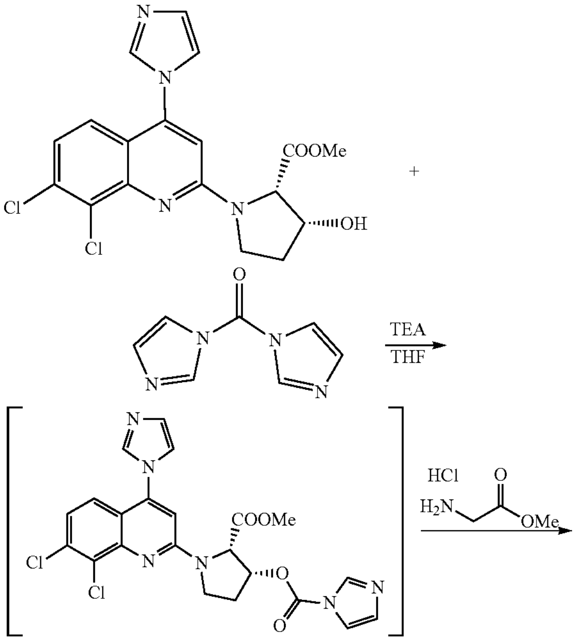

-continued

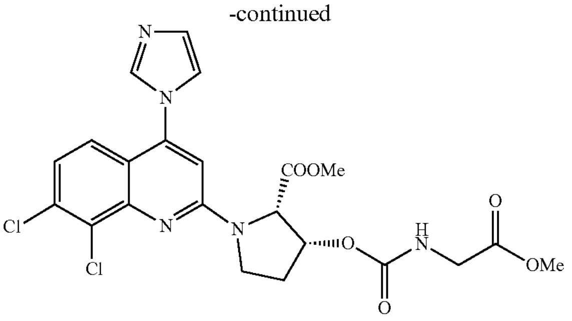

I-653

To a solution of methyl (2S,3R)-1-(7,8-dichloro-4-(1H-imidazol-1-yl)quinolin-2-yl)-3-hydroxypyrrolidine-2-carboxylate (30 mg, 0.0737 mmol) in THF (0.5 mL) was added TEA (0.051 mL, 0.369 mmol) and CDI (40 mg, 0.247 mmol). The resulting mixture was stirred for 2 hours. Methyl glycinate HCl salt (18.5 mg, 0.147 mmol) was then added. After 2 hours of stirring, the mixture was diluted with DCM (20 mL), washed with $H_2O$ (2×10 mL), brine (10 mL), and dried over $Na_2SO_4$. The crude was purified by silica gel chromatography to afford the title product as a white solid. (MS: $[M+1]^+$ 522).

Example 97: Synthesis of (S)-1-((S)-1-(7,8-dichloro-4-(1H-imidazol-1-yl)quinolin-2-yl)pyrrolidin-2-yl)-2,2,2-trifluoroethan-1-ol (I-654) and (R)-1-((S)-1-(7,8-dichloro-4-(1H-imidazol-1-yl)quinolin-2-yl)pyrrolidin-2-yl)-2,2,2-trifluoroethan-1-ol (I-655)

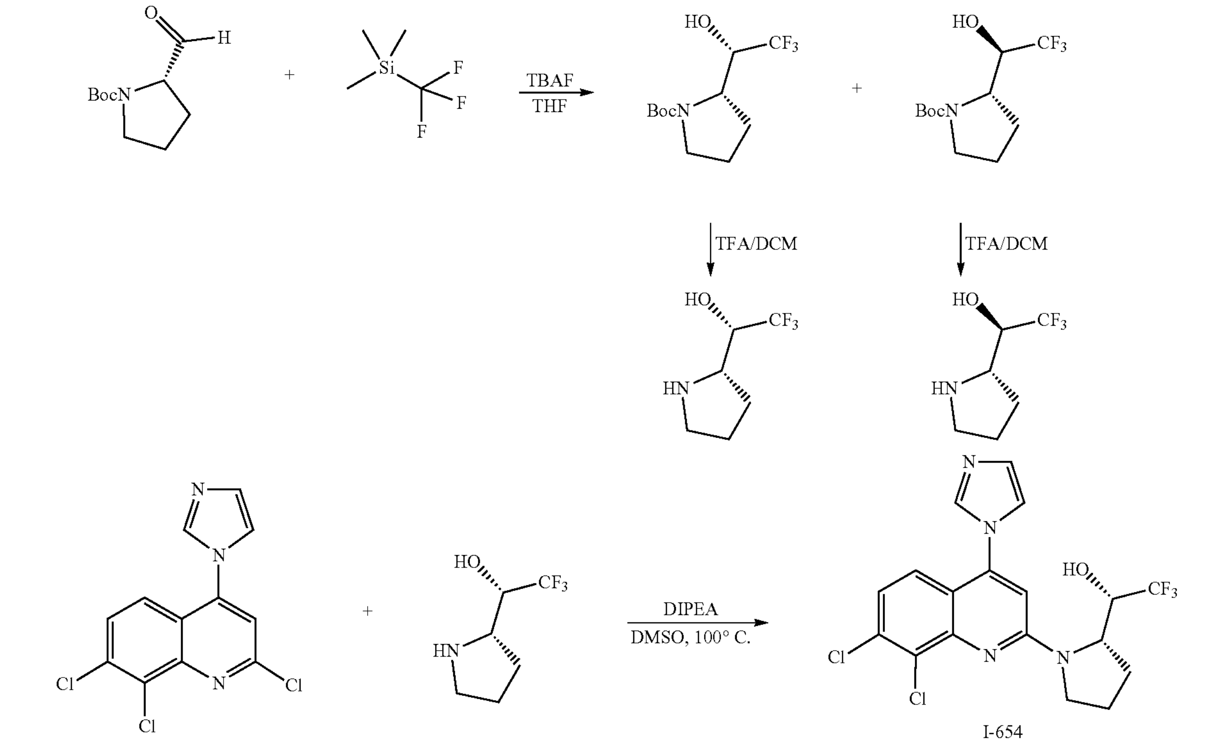

I-654

-continued

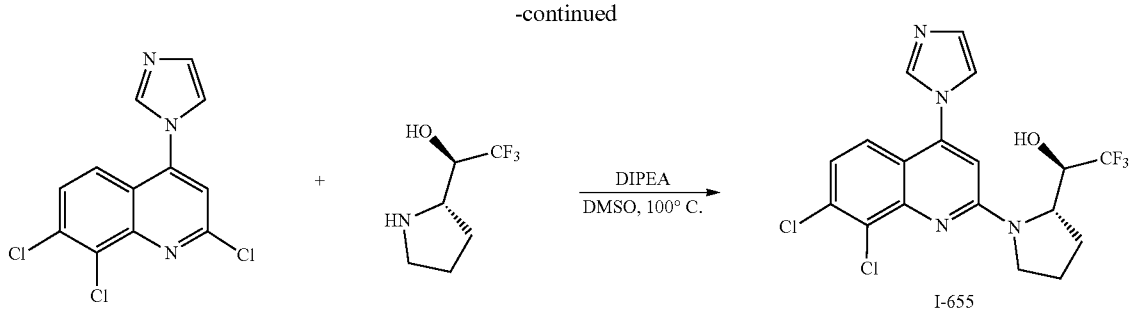

I-655

Step 1: To a flask were added tert-butyl (S)-2-formylpyrrolidine-1-carboxylate (1.992 g, 10 mmol) and THF (25 mL). The solution was cooled in ice bath for 20 min. After the slow addition of a solution of trimethyl(trifluoromethyl) silane in THF (2.0 M, 7.5 mL, 15 mmol) at 0° C., a solution of TBAF in THF (1.0 M, 0.5 mL, 0.5 mmol) was added dropwise. The resultant mixture was stirred at the same temperature for 2 hours. More TBAF solution in THF (1.0 M, 2.0 mL, 2.0 mmol) was added and the mixture was stirred at room temperature for another 2 hours. After being quenched by saturated $NH_4Cl$ and concentrated, the resultant mixture was diluted with DCM (150 mL), washed with $H_2O$, brine, dried over $Na_2SO_4$ and then concentrated. The crude product was purified by silica gel chromatography to afford tert-butyl (S)-2-((S)-2,2,2-trifluoro-1-hydroxyethyl) pyrrolidine-1-carboxylate and tert-butyl (S)-2-((R)-2,2,2-trifluoro-1-hydroxyethyl)pyrrolidine-1-carboxylate.

Step 2: To a vial were added tert-butyl (S)-2-((S)-2,2,2-trifluoro-1-hydroxyethyl)pyrrolidine-1-carboxylate (50 mg, 0.186 mmol), DCM (0.5 mL) and TFA (0.25 mL). The resulting solution was stirred for 2 hours. After removing all volatiles under vacuo, the crude (S)-2,2,2-trifluoro-14(S)-pyrrolidin-2-yl)ethan-1-ol was used directly in next step. The same procedure was used to prepare the (R, S)-isomer.

Step 3: Both of (S)-1-((S)-1-(7,8-dichloro-4-(1H-imidazol-1-yl)quinolin-2-yl)pyrrolidin-2-yl)-2,2,2-trifluoroethan-1-ol I-654 (MS: $[M+1]^+$ 431) and (R)-1-(S)-1-(7,8-dichloro-4-(1H-imidazol-1-yl)quinolin-2-yl)pyrrolidin-2-yl)-2,2,2-trifluoroethan-1-ol I-655 (MS: $[M+1]^+$ 431) were prepared following the synthetic procedure to prepare I-123, step 1.

Example 98: Synthesis of (S)-2-(1-(7,8-dichloro-4-(1H-imidazol-1-yl)quinolin-2-yl)pyrrolidin-2-yl)-1,1,1,3,3,3-hexafluoropropan-2-ol (I-656)

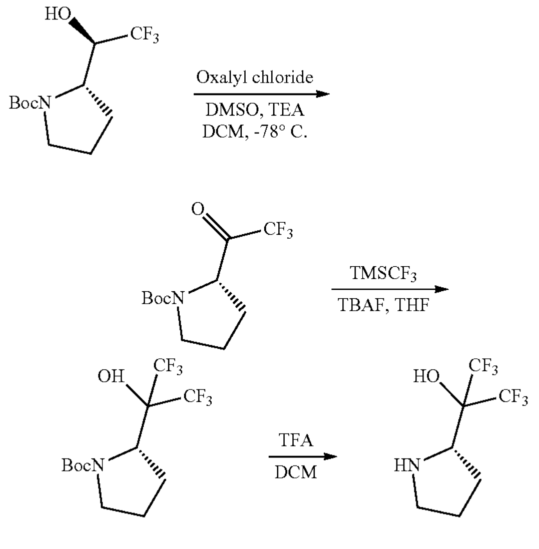

-continued

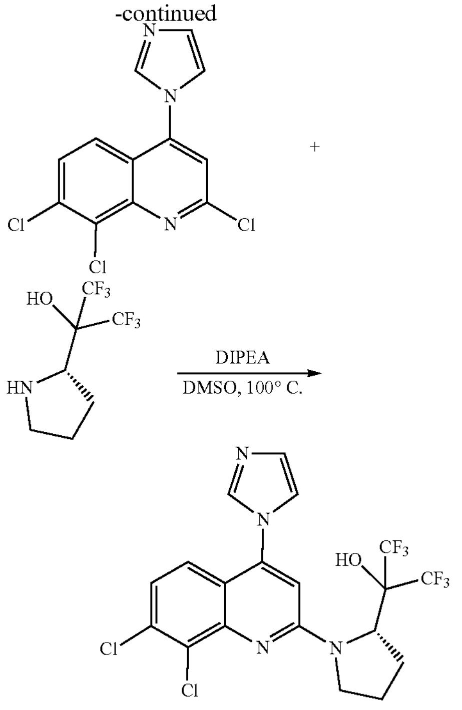

I-656

Step 1: To a vial were added DCM (3 mL) and oxalyl chloride (0.220 mL, 2.6 mmol) followed being cooled in dry ice/acetone bath. A solution of DMSO (0.383 mL, 5.4 mmol) in DCM (2.5 mL) was added dropwise. The mixture was stirred at −78° C. for 30 min. Then a solution of tert-butyl (S)-2-((R)-2,2,2-trifluoro-1-hydroxyethyl)pyrrolidine-1-carboxylate (582 mg, 2.16 mmol) in DCM (2.5 mL) was added dropwise at same temperature. After 30 min, TEA (1.5 mL, 10.8 mmol) was added dropwise and the mixture was stirred at −78° C. for 30 min. The resulting mixture was stirred at room temperature for 1 hour, then quenched by adding $H_2O$ (10 mL). The aqueous phase was extracted by DCM (2x15 mL).

The combined organic phase was concentrated, purified by silica gel chromatography to afforded tert-butyl (S)-2-(2,2,2-trifluoroacetyl)pyrrolidine-1-carboxylate.

Step 2: tert-butyl (S)-2-(1,1,1,3,3,3-hexafluoro-2-hydroxypropan-2-yl)pyrrolidine-1-carboxylate was prepared similar to the procedure to prepare I-654, step 1.

Step 3: (S)-1,1,1,3,3,3-hexafluoro-2-(pyrrolidin-2-yl)propan-2-ol was prepared similar to the procedure to prepare I-654, step 2.

Step 4: (S)-2-(1-(7,8-dichloro-4-(1H-imidazol-1-yl)quinolin-2-yl)pyrrolidin-2-yl)-1,1,1,3,3,3-hexafluoropropan-2-ol was prepared similar to the procedure to prepare I-123, step 1. (MS: $[M+1]^+$ 499)

Example 99: Synthesis of methyl (2S,3S)-1-(7,8-dichloro-4-(1H-imidazol-1-yl)quinolin-2-yl)-3-hydroxypyrrolidine-2-carboxylate (I-657)

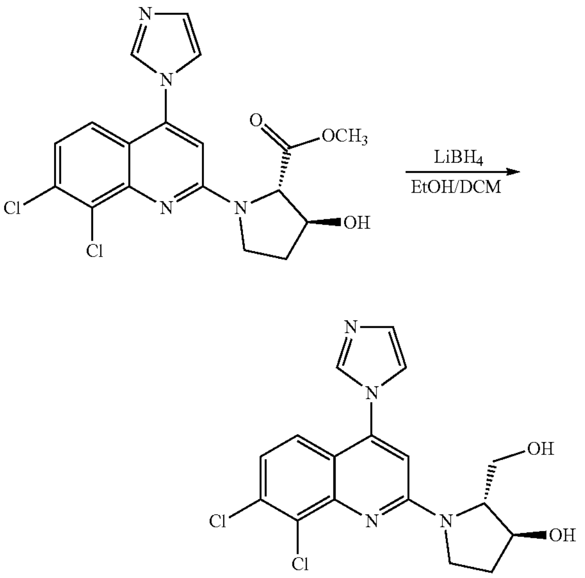

To a vial were added methyl (2S,3S)-1-(7,8-dichloro-4-(1H-imidazol-1-yl)quinolin-2-yl)-3-hydroxypyrrolidine-2-carboxylate (20 mg, 0.0491 mmol) THF(0.5 mL) and ethanol (1.0 mL). At 0° C., $LiBH_4$ (9.5 mg, 0.436 mmol) was added and the resulting mixture was stirred overnight. The mixture was diluted with DCM (20 mL), washed with saturated $NH_4Cl$ (5 mL), $H_2O$ (5 mL), brine (5 mL), and dried over $Na_2SO_4$. The crude was purified by silica gel chromatography to afford the titled compound as white solid (MS: $[M+1]^+$ 379).

Example 100: Synthesis of ((5)-1-(7,8-dichloro-4-(1H-imidazol-1-yl)quinolin-2-yl)pyrrolidin-2-yl) methyl hydrogen phosphonate (I-658)

I-658 was prepared essentially by the same method to prepare I-111.

Example 101: Synthesis of (R)-2-((S)-1-(7,8-dichloro-4-(1H-imidazol-1-yl)quinolin-2-yl)pyrrolidin-2-yl)-2-hydroxyacetic acid. hexafluoropropan-2-ol (I-661)

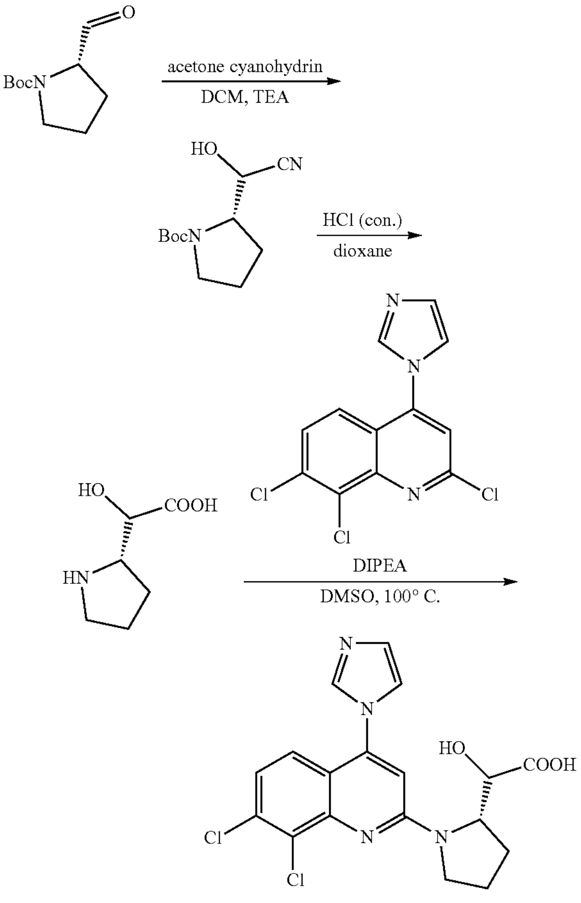

I-661

Step 1: To a vial were added DCM (10 mL), TEA (1 mmol, 0.1 mL) and tert-butyl (S)-2-formylpyrrolidine-1-carboxylate (1 g, 5 mmol) and the mixture was stirred at r.t overnight. After evaporation, the crude tert-butyl (S)-2((R)-cyano(hydroxy)methyl)pyrrolidine-1-carboxylate was used in the next step without further purification. (MS: $[M+1]^+$ 227.1).

| I-# | Starting Material | Structure | MS $[M + 1]^+$ |
|---|---|---|---|
| I-658 | 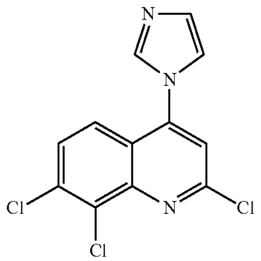 [SMILES: Clc1cc(-n2ccnc2)c2ccc(Cl)c(Cl)c2n1] 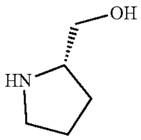 | 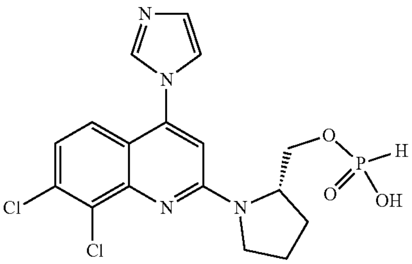 [SMILES: O=[PH](O)OC[C@@H]1CCCN1c1cc(-n2ccnc2)c2ccc(Cl)c(Cl)c2n1] | 427 |

Step 2: A mixture of tert-butyl (S)-2-((R)-cyano(hydroxy) methyl)pyrrolidine-1-carboxylate (230 mg, 1 mmol), HCl (con., 1 mL) and 1,4-dioxane (1 mL) was refluxed for 2 h. After evaporation, the crude (R)-2-hydroxy-2-((S)-pyrrolidin-2-yl)acetic acid was used in the next step without further purification. (MS: $[M+1]^+$ 146.1).

Step 3: (R)-2-((S)-1-(7,8-dichloro-4-(1H-imidazol-1-yl) quinolin-2-yl)pyrrolidin-2-yl)-2-hydroxyacetic acid (I-661) was prepared similar to step 1 for the preparation of I-123. (MS: $[M+1]^+$407.1).

Example 102: Synthesis of methyl (S)-3-((1-(7,8-dichloro-4-(1H-imidazol-1-yl)quinolin-2-yl)pyrrolidin-2-yl)methoxy)propanoate (I-665) and (S)-3-((1-(7,8-dichloro-4-(1H-imidazol-1-yl)quinolin-2-yl) pyrrolidin-2-yl)methoxy)propanoic acid (I-664)

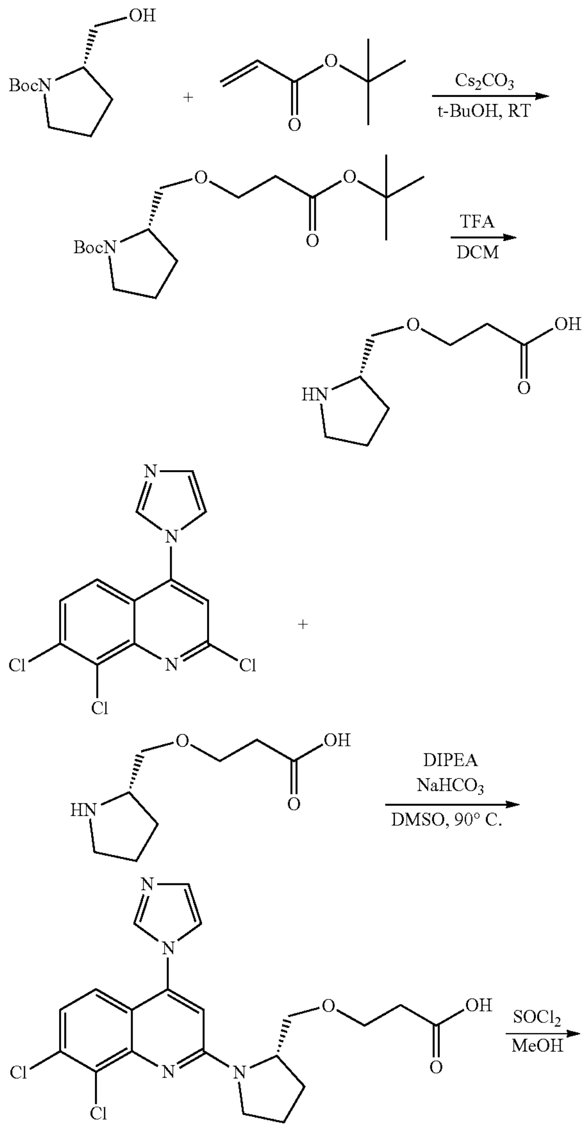

I-664

-continued

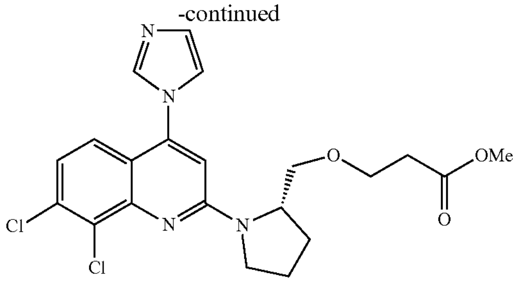

I-665

Step 1: tert-Butyl (S)-2-((3-(tert-butoxy)-3-oxopropoxy) methyl)pyrrolidine-1-carboxylate. To a vial were added tert-butyl (S)-2-(hydroxymethyl)pyrrolidine-1-carboxylate (805 mg, 4.1 mmol, 1.0 eq.), $Cs_2CO_3$ (1.3 g, 4.1 mmol, 1.0 eq.), t-BuOH (5 mL) and tert-butyl acrylate (1.8 mL, 20 mmol, 5 eq.). The resulting reaction mixture was stirred over night. Then the mixture was diluted by ethyl acetate (50 mL), washed by $H_2O$ (3×15 mL), brine (15 mL) and dried over $Na_2SO_4$. After concentration, the crude was purified by a silica gel chromatography to afford the title product (1.22 g).

Step 2: (S)-3-(Pyrrolidin-2-ylmethoxy)propanoic acid. The mixture of tert-butyl (S)-2-((3-(tert-butoxy)-3-oxopropoxy)methyl)pyrrolidine-1-carboxylate (400 mg, 1.21 mmol), TFA (2 mL) and DCM (2 mL) was stirred overnight at room temperature. The mixture was concentrated to remove all volatiles. The crude was used in the next step.

Step 3: (S)-3-((1-(7,8-Dichloro-4-(1H-imidazol-1-yl)quinolin-2-yl)pyrrolidin-2-yl)methoxy)propanoic acid (I-664). To a vial were added 2,7,8-trichloro-4-(1H-imidazol-1-yl) quinoline (227 mg, 0.759 mmol, 1.0 eq.), the crude product in step 2 (0.911 mmol), DMSO (4.0 mL), DIPEA (0.66 mL, 3.8 mmol, 5.0 eq.) and $NaHCO_3$. The reaction mixture was stirred at 90° C. overnight. Then the mixture was diluted by ethyl acetate (30 mL) and acidified by HOAc (1 M, 5 mL), washed by $H_2O$ (3×10 mL), brine (10 mL) and dried over $Na_2SO_4$. After concentration, the crude was used in the next step. The acid product was purified by silica gel chromatography. MS: $[M+1]^+$ 435.

Step 4: Methyl (S)-3-((1-(7,8-dichloro-4-(1H-imidazol-1-yl)quinolin-2-yl)pyrrolidin-2-yl)methoxy)propanoate (I-665). To a vial were added the crude product in step 3 (0.345 mmol) and anhydrous methanol (2.0 mL). The reaction solution was cooled to 0° C. and was treated with $SOCl_2$ (0.100 mL, 1.38 mmol, 4.0 eq.) at 0° C. After being stirred at room temperature for 2 hours, the reaction mixture was diluted by ethyl acetate (30 mL), washed by $NaHCO_3/H_2O$ (5%, 10 mL), $H_2O$ (3×10 mL), brine (10 mL) and dried over $Na_2SO_4$. After concentration, the crude was purified by a silica gel column to afford the title product (135 mg). MS: $[M+1]^+$ 449.

The following compounds are prepared essentially by the same methods as described above for I-664 and 665.

| Example | Starting Material | Structure | MS [M + 1]+ |
| --- | --- | --- | --- |
| I-670 | 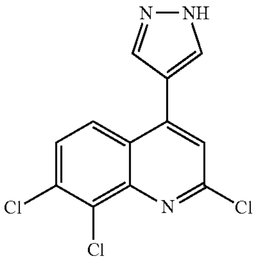 [SMILES: Clc1cc(-c2cn[nH]c2)c2ccc(Cl)c(Cl)c2n1] 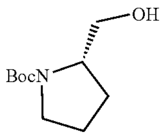 | 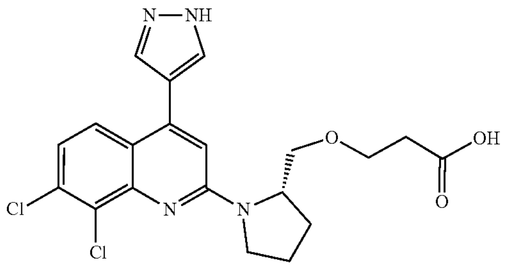 [SMILES: O=C(O)CCOC[C@@H]1CCCN1c1cc(-c2cn[nH]c2)c2ccc(Cl)c(Cl)c2n1] | 435 |
| I-671 | 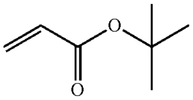 | 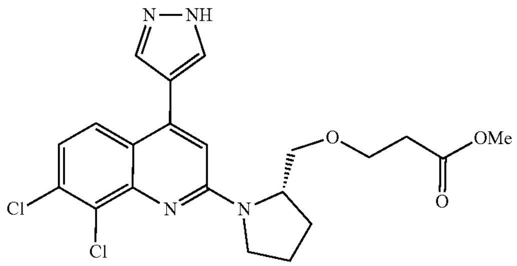 [SMILES: COC(=O)CCOC[C@@H]1CCCN1c1cc(-c2cn[nH]c2)c2ccc(Cl)c(Cl)c2n1] | 449 |
| I-674 | 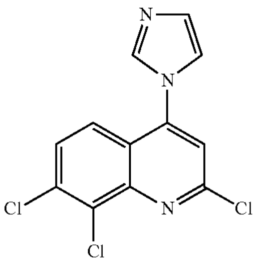 [SMILES: Clc1cc(-n2ccnc2)c2ccc(Cl)c(Cl)c2n1] 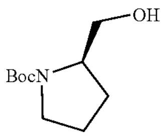 [SMILES: CC(C)(C)OC(=O)N1CCC[C@@H]1CO] 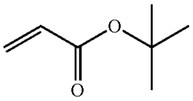 | 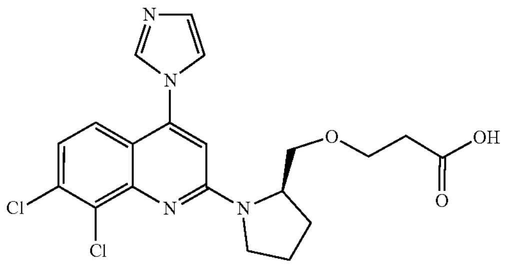 [SMILES: O=C(O)CCOC[C@H]1CCCN1c1cc(-n2ccnc2)c2ccc(Cl)c(Cl)c2n1] | 435 |
| I-688 | 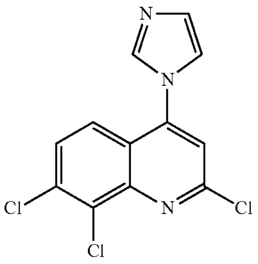 [SMILES: Clc1cc(-n2ccnc2)c2ccc(Cl)c(Cl)c2n1] 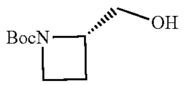 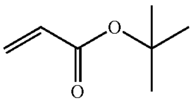 | 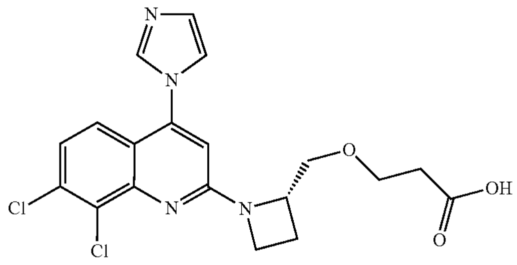 [SMILES: O=C(O)CCOC[C@@H]1CCN1c1cc(-n2ccnc2)c2ccc(Cl)c(Cl)c2n1] | 421 |
| I-696 | 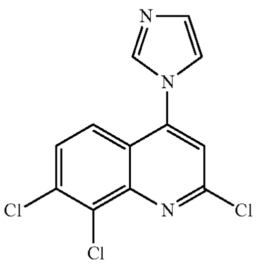 [SMILES: Clc1cc(-n2ccnc2)c2ccc(Cl)c(Cl)c2n1] 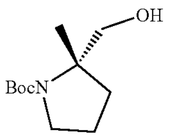 | 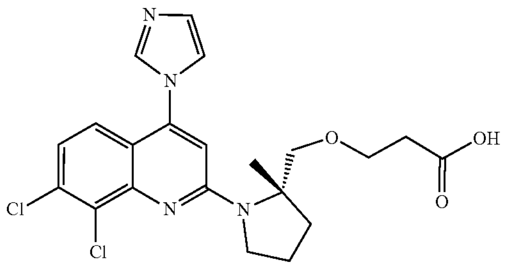 [SMILES: C[C@@]1(COCCC(=O)O)CCCN1c1cc(-n2ccnc2)c2ccc(Cl)c(Cl)c2n1] | 449 |

-continued
| Example | Starting Material | | Structure | MS [M + 1]$^+$ |
|---|---|---|---|---|
| | | 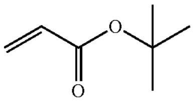 | | |
| I-698 | 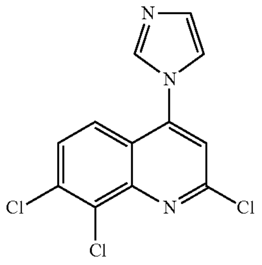 [SMILES: Clc1cc(-n2ccnc2)c2ccc(Cl)c(Cl)c2n1] | 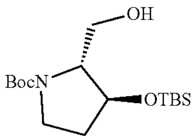 [SMILES: CC(C)(C)OC(=O)N1CC[C@H](O[Si](C)(C)C(C)(C)C)[C@H]1CO] | 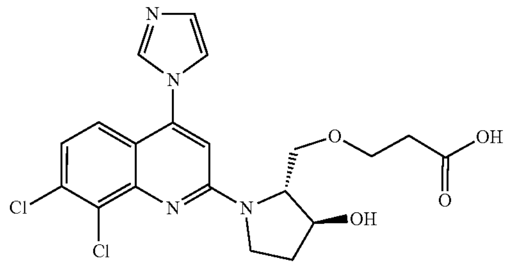 [SMILES: O=C(O)CCOC[C@@H]1[C@@H](O)CCN1c1cc(-n2ccnc2)c2ccc(Cl)c(Cl)c2n1] | 451 |
| I-701 | | 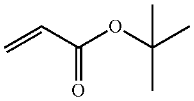 | 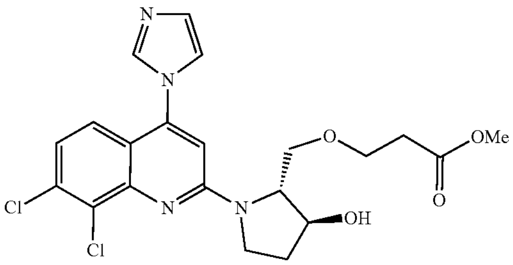 [SMILES: COC(=O)CCOC[C@@H]1[C@@H](O)CCN1c1cc(-n2ccnc2)c2ccc(Cl)c(Cl)c2n1] | 465 |
| I-699 | 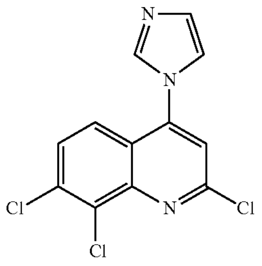 [SMILES: Clc1cc(-n2ccnc2)c2ccc(Cl)c(Cl)c2n1] | 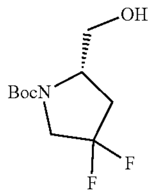 [SMILES: CC(C)(C)OC(=O)N1CC(F)(F)C[C@H]1CO] | 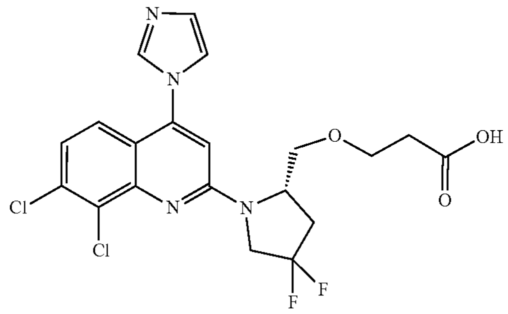 [SMILES: O=C(O)CCOC[C@@H]1CC(F)(F)CN1c1cc(-n2ccnc2)c2ccc(Cl)c(Cl)c2n1] | 471 |
| | | 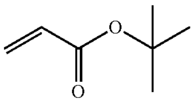 | | |
| I-705 | 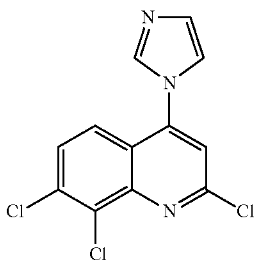 [SMILES: Clc1cc(-n2ccnc2)c2ccc(Cl)c(Cl)c2n1] | 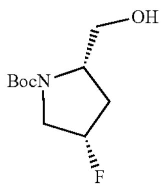 | 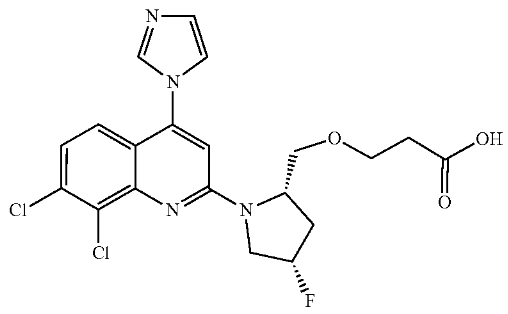 [SMILES: O=C(O)CCOC[C@@H]1C[C@H](F)CN1c1cc(-n2ccnc2)c2ccc(Cl)c(Cl)c2n1] | 453 |
| | | 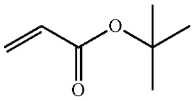 | | |

-continued
| Example | Starting Material | Structure | MS [M + 1]+ |
|---|---|---|---|
| I-708 | 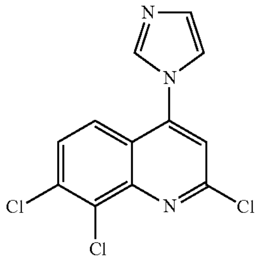 [SMILES: Clc1cc(-n2ccnc2)c2ccc(Cl)c(Cl)c2n1] 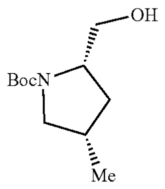 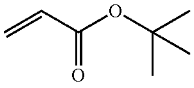 | 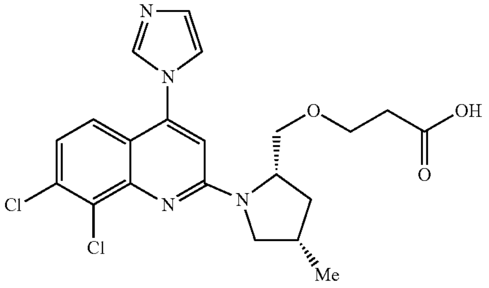 [SMILES: C[C@H]1C[C@@H](COCCC(=O)O)N(c2cc(-n3ccnc3)c3ccc(Cl)c(Cl)c3n2)C1] | 449 |
| I-709 | 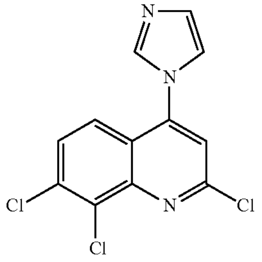 [SMILES: Clc1cc(-n2ccnc2)c2ccc(Cl)c(Cl)c2n1] 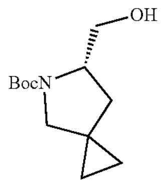 [SMILES: CC(C)(C)OC(=O)N1CC2(CC2)C[C@H]1CO] 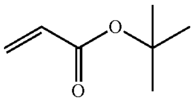 | 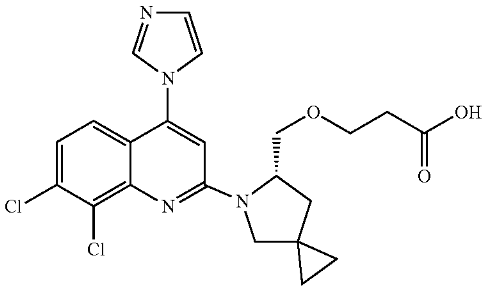 [SMILES: O=C(O)CCOC[C@@H]1CC2(CC2)CN1c1cc(-n2ccnc2)c2ccc(Cl)c(Cl)c2n1] | 461 |
| I-719 | 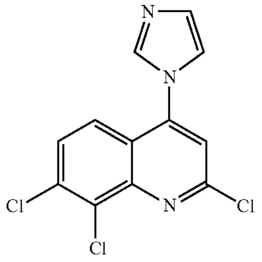 [SMILES: Clc1cc(-n2ccnc2)c2ccc(Cl)c(Cl)c2n1] 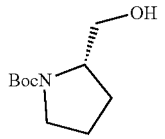 | 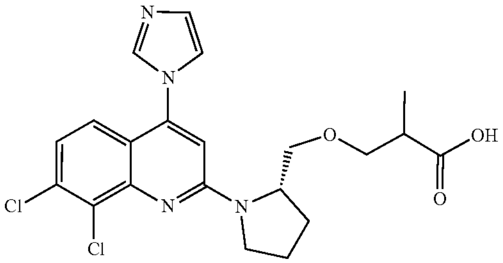 [SMILES: CC(COC[C@@H]1CCCN1c1cc(-n2ccnc2)c2ccc(Cl)c(Cl)c2n1)C(=O)O] | 449 |
| I-720 | 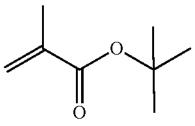 | 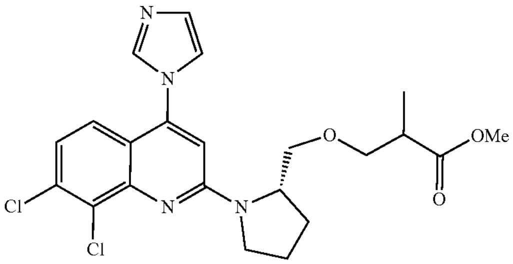 [SMILES: COC(=O)C(C)COC[C@@H]1CCCN1c1cc(-n2ccnc2)c2ccc(Cl)c(Cl)c2n1] | 463 |

-continued
| Example | Starting Material | Structure | MS [M + 1]$^+$ |
|---|---|---|---|
| I-717 | 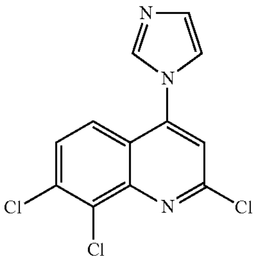 [SMILES: Clc1cc(-n2ccnc2)c2ccc(Cl)c(Cl)c2n1] 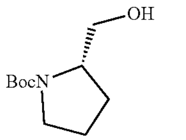 [SMILES: CC(C)(C)OC(=O)N1CCC[C@H]1CO] | 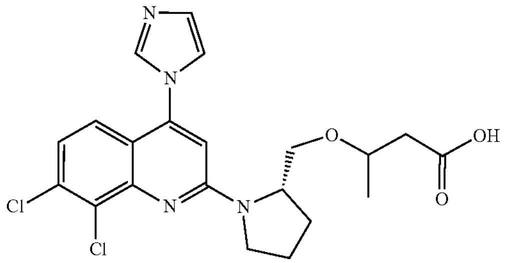 [SMILES: CC(CC(=O)O)OC[C@@H]1CCCN1c1cc(-n2ccnc2)c2ccc(Cl)c(Cl)c2n1] | 449 |
| I-718 | 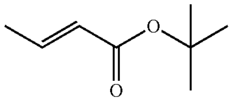 | 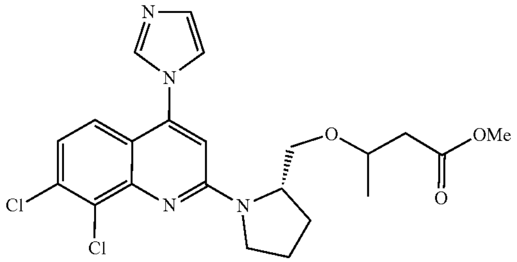 [SMILES: COC(=O)CC(C)OC[C@@H]1CCCN1c1cc(-n2ccnc2)c2ccc(Cl)c(Cl)c2n1] | 463 |
| I-741 | 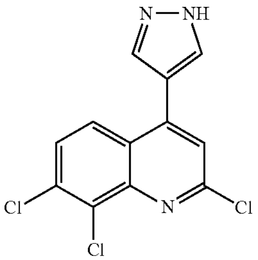 [SMILES: Clc1cc(-c2cn[nH]c2)c2ccc(Cl)c(Cl)c2n1] 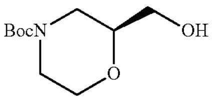 [SMILES: CC(C)(C)OC(=O)N1CCO[C@H](CO)C1] 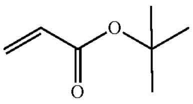 | 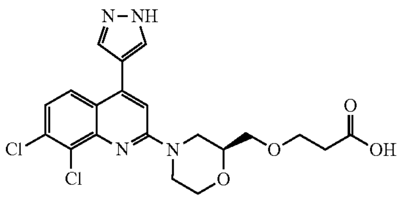 [SMILES: O=C(O)CCOC[C@@H]1CN(c2cc(-c3cn[nH]c3)c3ccc(Cl)c(Cl)c3n2)CCO1] | 451 |
| I-747 | 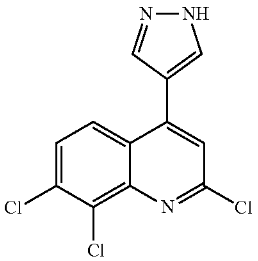 [SMILES: Clc1cc(-c2cn[nH]c2)c2ccc(Cl)c(Cl)c2n1] 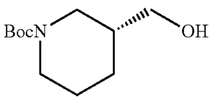 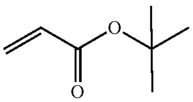 | 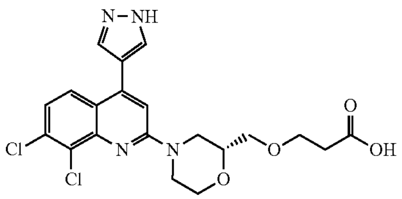 [SMILES: O=C(O)CCOC[C@H]1CN(c2cc(-c3cn[nH]c3)c3ccc(Cl)c(Cl)c3n2)CCO1] | 449 |
| I-745 | 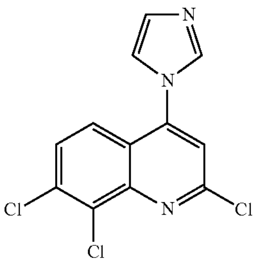 [SMILES: Clc1cc(-n2ccnc2)c2ccc(Cl)c(Cl)c2n1] 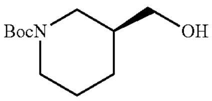 [SMILES: CC(C)(C)OC(=O)N1CCC[C@H](CO)C1] | 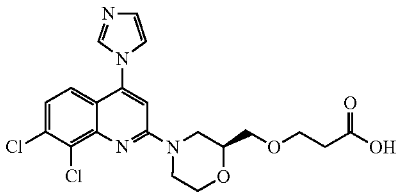 [SMILES: O=C(O)CCOC[C@@H]1CN(c2cc(-n3ccnc3)c3ccc(Cl)c(Cl)c3n2)CCO1] | 449 |

-continued
| Example | Starting Material | | Structure | MS [M + 1]⁺ |
|---|---|---|---|---|
| | | 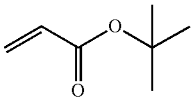 | | |
| I-750 | 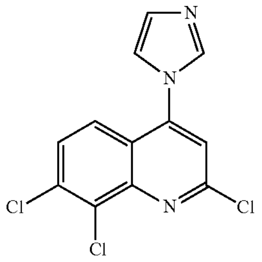 [SMILES: Clc1cc(-n2ccnc2)c2ccc(Cl)c(Cl)c2n1] | 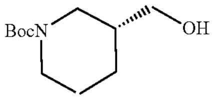 [SMILES: CC[C@@H](CO)CN(CC)C(=O)OC(C)(C)C] | 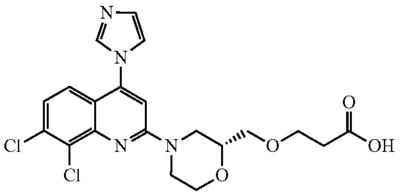 [SMILES: O=C(O)CCOC[C@H]1CN(c2cc(-n3ccnc3)c3ccc(Cl)c(Cl)c3n2)CCO1] | 449 |
| | | 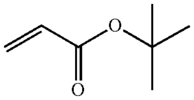 | | |
| I-752 | 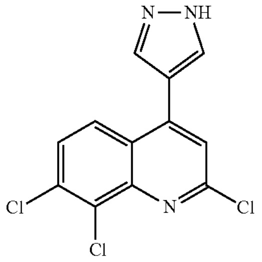 [SMILES: Clc1cc(-c2cn[nH]c2)c2ccc(Cl)c(Cl)c2n1] | 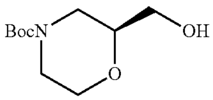 [SMILES: CC(C)(C)OC(=O)N1CCO[C@H](CO)C1] | 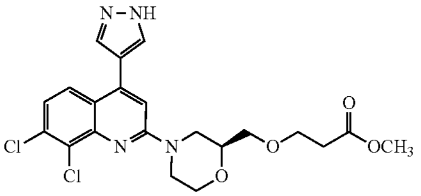 [SMILES: COC(=O)CCOC[C@@H]1CN(c2cc(-c3cn[nH]c3)c3ccc(Cl)c(Cl)c3n2)CCO1] | 465 |
| | | 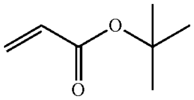 | | |
| I-748 | 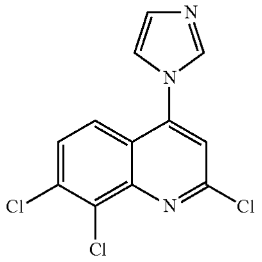 [SMILES: Clc1cc(-n2ccnc2)c2ccc(Cl)c(Cl)c2n1] | 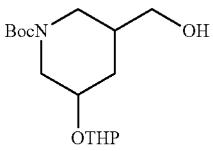 | 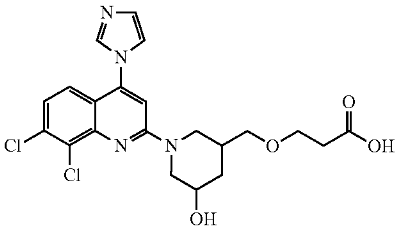 [SMILES: O=C(O)CCOCC1CC(O)CN(c2cc(-n3ccnc3)c3ccc(Cl)c(Cl)c3n2)C1] | 465 |
| | | 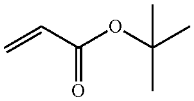 | | |
| I-749 | 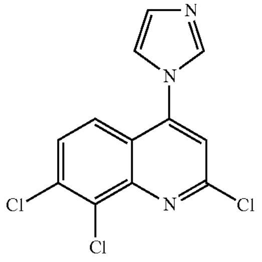 [SMILES: Clc1cc(-n2ccnc2)c2ccc(Cl)c(Cl)c2n1] | 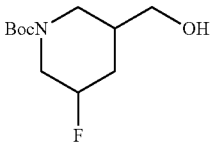 | 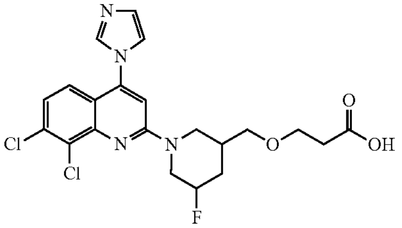 [SMILES: O=C(O)CCOCC1CC(F)CN(c2cc(-n3ccnc3)c3ccc(Cl)c(Cl)c3n2)C1] | 467 |

-continued
| Example | Starting Material | Structure | MS $[M + 1]^+$ |
|---|---|---|---|
| | 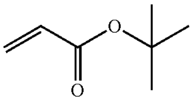 | | |
| I-721 | 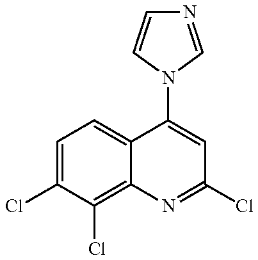 [SMILES: Clc1cc(-n2ccnc2)c2ccc(Cl)c(Cl)c2n1] 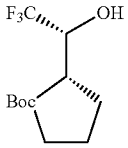 | 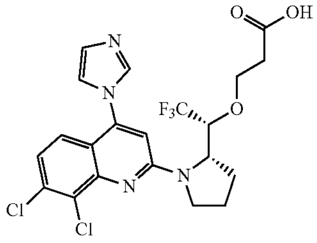 [SMILES: O=C(O)CCO[C@H]([C@@H]1CCCN1c1cc(-n2ccnc2)c2ccc(Cl)c(Cl)c2n1)C(F)(F)F] | 503 |
| | 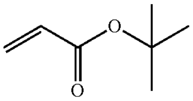 | | |
| I-722 | 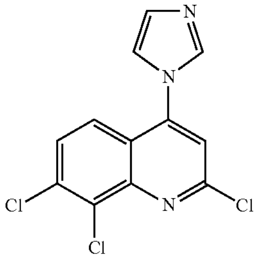 [SMILES: Clc1cc(-n2ccnc2)c2ccc(Cl)c(Cl)c2n1] 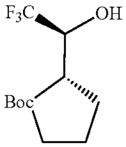 | 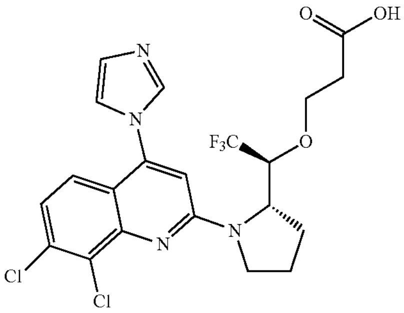 [SMILES: O=C(O)CCO[C@@H]([C@@H]1CCCN1c1cc(-n2ccnc2)c2ccc(Cl)c(Cl)c2n1)C(F)(F)F] | 503 |
| | 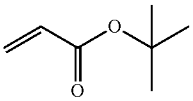 | | |
| I-711 | 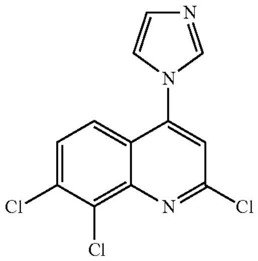 [SMILES: Clc1cc(-n2ccnc2)c2ccc(Cl)c(Cl)c2n1] 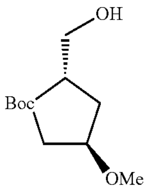 | 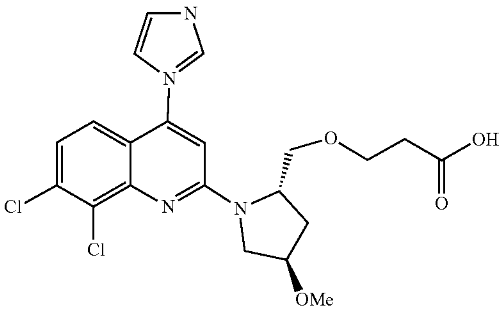 | 465 |
| | 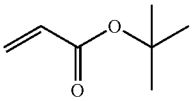 | | |

-continued
| Example | Starting Material | Structure | MS [M + 1]+ |
|---|---|---|---|
| I-704 | 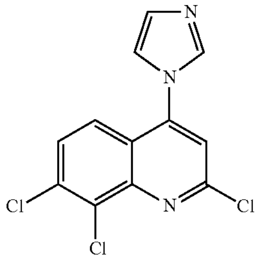 [SMILES: Clc1cc(-n2ccnc2)c2ccc(Cl)c(Cl)c2n1] 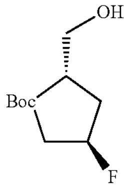 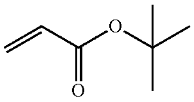 | 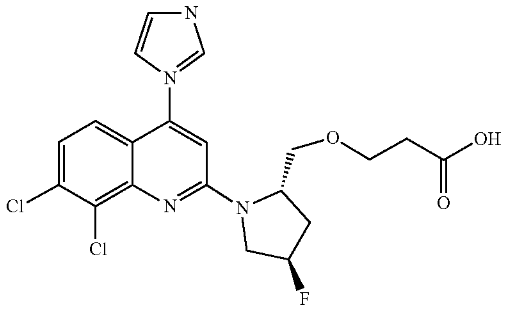 | 453 |
| I-702 | 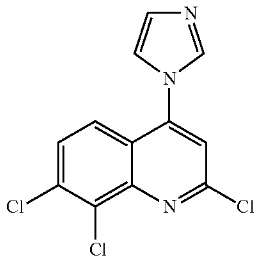 [SMILES: Clc1cc(-n2ccnc2)c2ccc(Cl)c(Cl)c2n1] 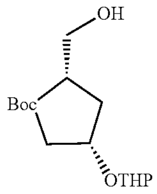 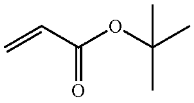 | 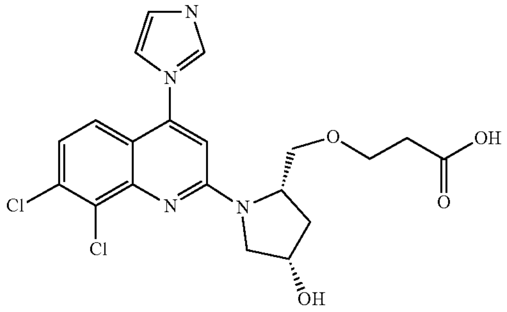 | 451 |
| I-703 | 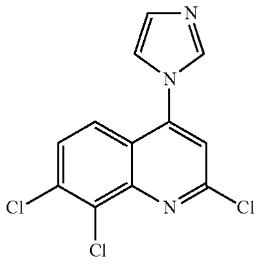 [SMILES: Clc1cc(-n2ccnc2)c2ccc(Cl)c(Cl)c2n1] 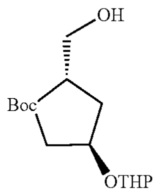 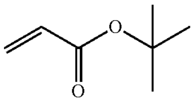 | 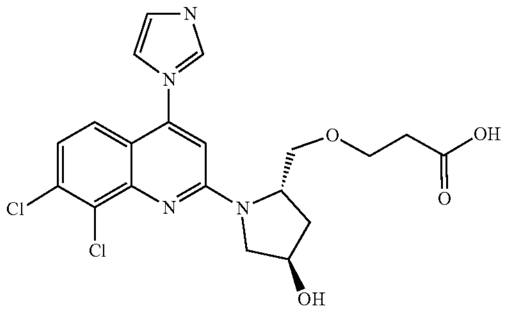 | 451 |

-continued
| Example | Starting Material | Structure | MS [M + 1]+ |
|---|---|---|---|
| I-695 | 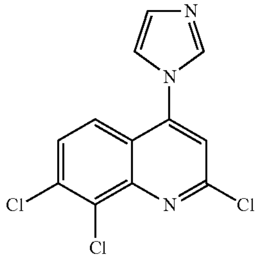 [SMILES: Clc1cc(-n2ccnc2)c2ccc(Cl)c(Cl)c2n1] 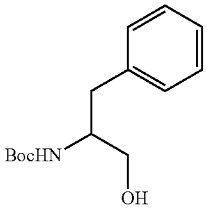 [SMILES: CC(C)(C)OC(=O)NC(CO)Cc1ccccc1] 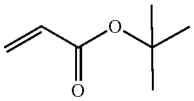 | 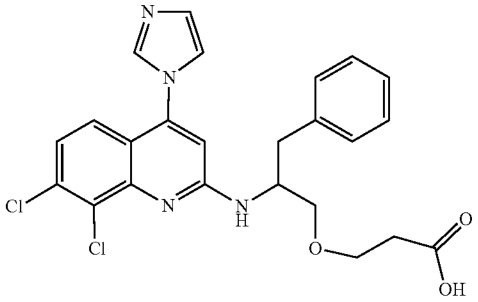 [SMILES: O=C(O)CCOCC(Cc1ccccc1)Nc1cc(-n2ccnc2)c2ccc(Cl)c(Cl)c2n1] | 485 |
| I-672 | 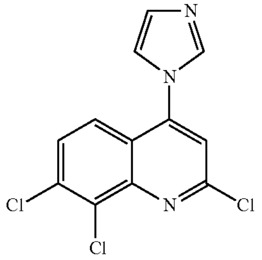 [SMILES: Clc1cc(-n2ccnc2)c2ccc(Cl)c(Cl)c2n1] 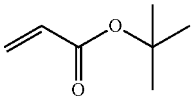 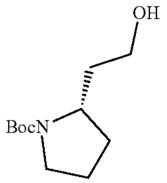 | 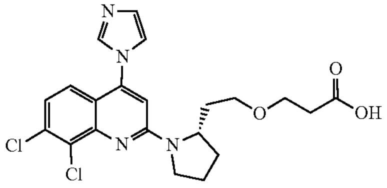 [SMILES: O=C(O)CCOCC[C@@H]1CCCN1c1cc(-n2ccnc2)c2ccc(Cl)c(Cl)c2n1] | 449 |
| I-673 | 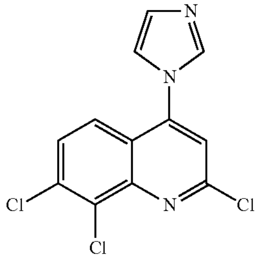 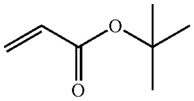 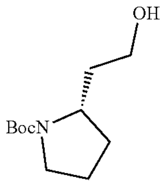 [SMILES: CC(C)(C)OC(=O)N1CCC[C@H]1CCO] | 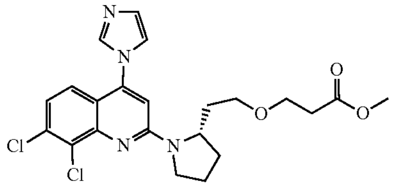 [SMILES: COC(=O)CCOCC[C@@H]1CCCN1c1cc(-n2ccnc2)c2ccc(Cl)c(Cl)c2n1] | 463 |

-continued
| Example | Starting Material | Structure | MS [M + 1]+ |
|---|---|---|---|
| I-677 | 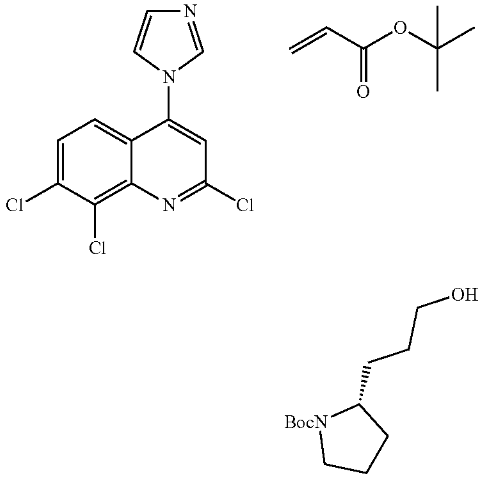 | 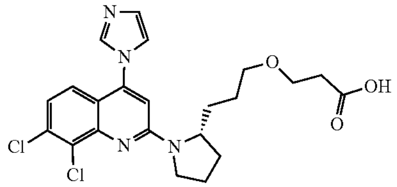 [SMILES: O=C(O)CCOCCC[C@@H]1CCCN1c1cc(-n2ccnc2)c2ccc(Cl)c(Cl)c2n1] | 463 |
| I-713 | 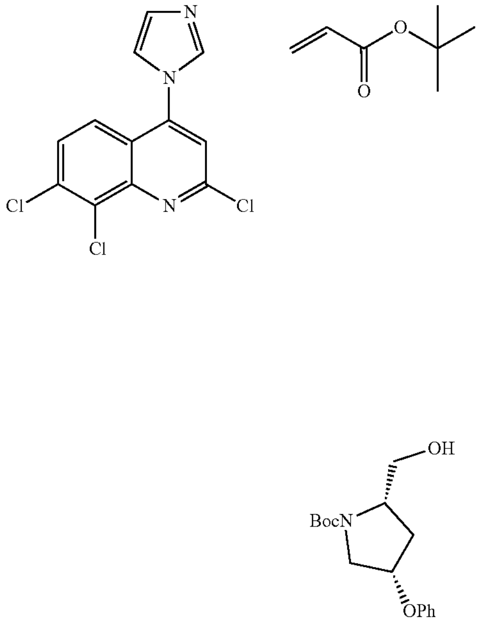 | 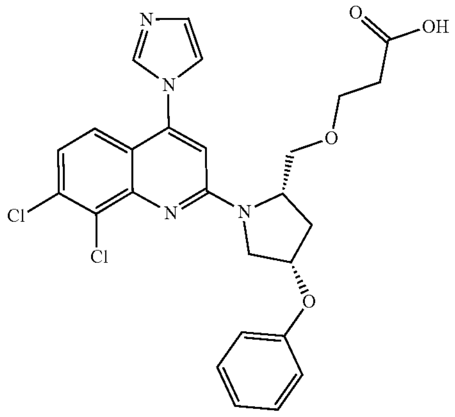 [SMILES: O=C(O)CCOC[C@@H]1C[C@H](Oc2ccccc2)CN1c1cc(-n2ccnc2)c2ccc(Cl)c(Cl)c2n1] | 527 |
| I-712 | 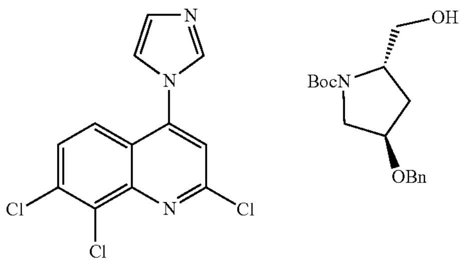 | 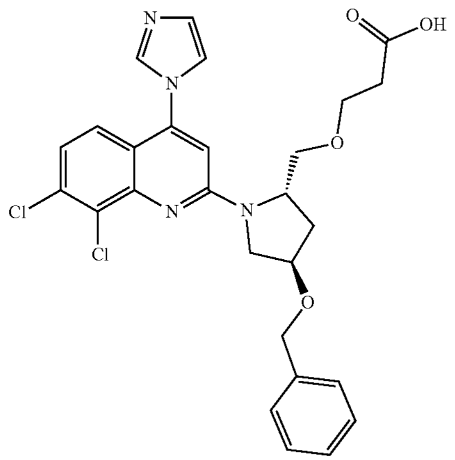 [SMILES: O=C(O)CCOC[C@@H]1C[C@@H](OCc2ccccc2)CN1c1cc(-n2ccnc2)c2ccc(Cl)c(Cl)c2n1] | 541 |

-continued
| Example | Starting Material | Structure | MS [M + 1]+ |
| --- | --- | --- | --- |
| | 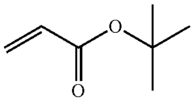 | | |
| I-767 | 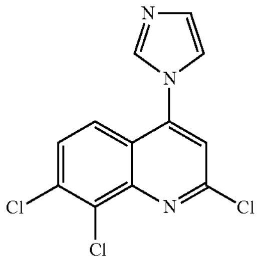 [SMILES: Clc1cc(-n2ccnc2)c2ccc(Cl)c(Cl)c2n1] 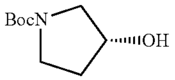 | 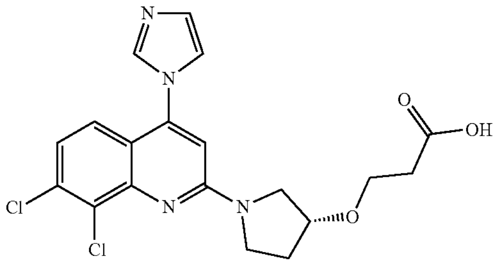 [SMILES: O=C(O)CCO[C@@H]1CCN(c2cc(-n3ccnc3)c3ccc(Cl)c(Cl)c3n2)C1] | 421 |
| I-769 | 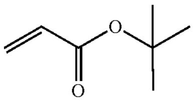 | 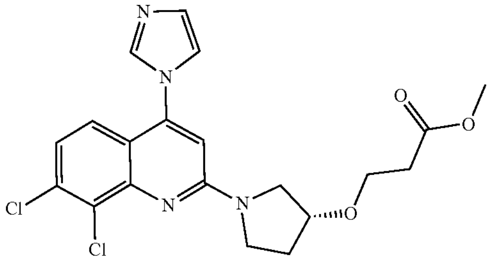 [SMILES: COC(=O)CCO[C@@H]1CCN(c2cc(-n3ccnc3)c3ccc(Cl)c(Cl)c3n2)C1] | 435 |
| I-771 | 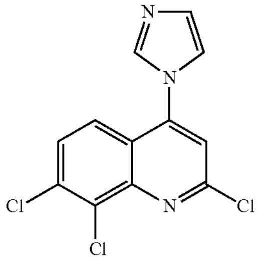 [SMILES: Clc1cc(-n2ccnc2)c2ccc(Cl)c(Cl)c2n1] 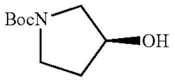 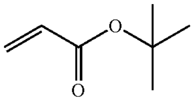 | 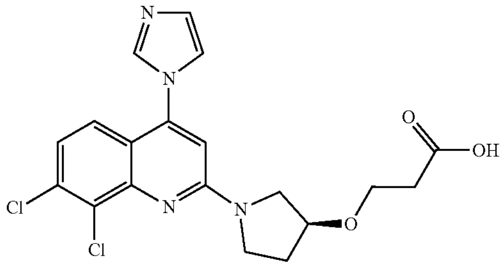 [SMILES: O=C(O)CCO[C@H]1CCN(c2cc(-n3ccnc3)c3ccc(Cl)c(Cl)c3n2)C1] | 421 |
| I-707 | 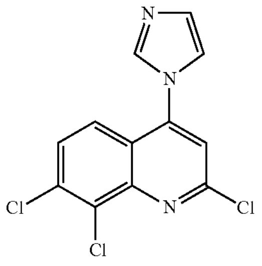 [SMILES: Clc1cc(-n2ccnc2)c2ccc(Cl)c(Cl)c2n1] 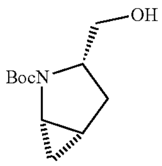 [SMILES: CC(C)(C)OC(=O)N1[C@H](CO)C[C@@H]2C[C@@H]21] 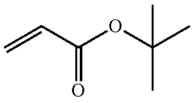 | 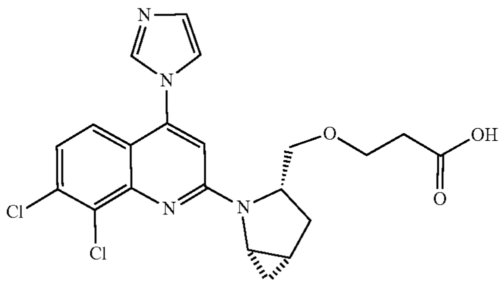 [SMILES: O=C(O)CCOC[C@@H]1C[C@@H]2C[C@@H]2N1c1cc(-n2ccnc2)c2ccc(Cl)c(Cl)c2n1] | 447 |

-continued
| Example | Starting Material | Structure | MS [M + 1]⁺ |
|---|---|---|---|
| I-710 | 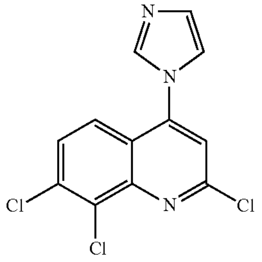 [SMILES: Clc1cc(-n2ccnc2)c2ccc(Cl)c(Cl)c2n1] 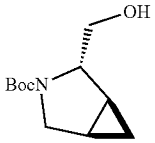 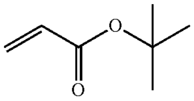 | 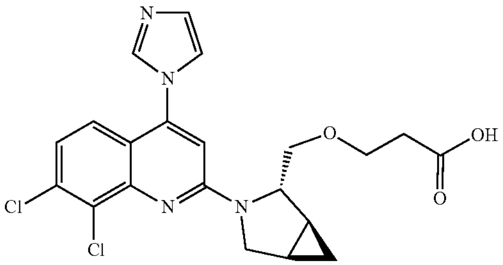 | 447 |
| I-689 | 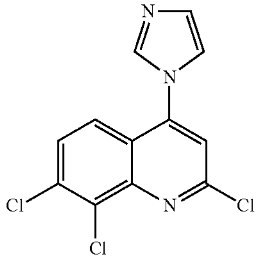 [SMILES: Clc1cc(-n2ccnc2)c2ccc(Cl)c(Cl)c2n1] 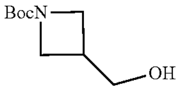 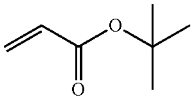 | 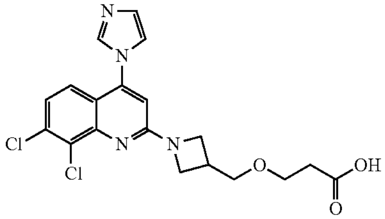 [SMILES: O=C(O)CCOCC1CN(c2cc(-n3ccnc3)c3ccc(Cl)c(Cl)c3n2)C1] | 421 |
| I-772 | 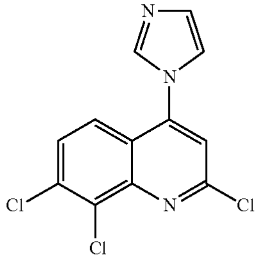 [SMILES: Clc1cc(-n2ccnc2)c2ccc(Cl)c(Cl)c2n1] 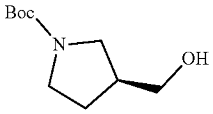 [SMILES: CC(C)(C)OC(=O)N1CC[C@H](CO)C1] 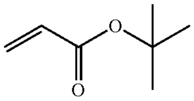 | 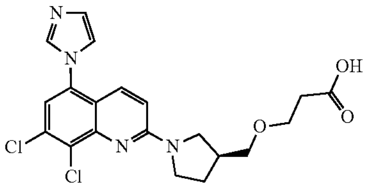 [SMILES: O=C(O)CCOC[C@H]1CCN(c2ccc3c(-n4ccnc4)cc(Cl)c(Cl)c3n2)C1] | 435 |
| I-773 | 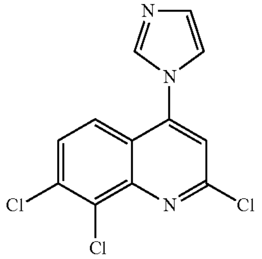 [SMILES: Clc1cc(-n2ccnc2)c2ccc(Cl)c(Cl)c2n1] 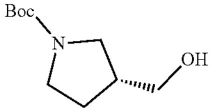 [SMILES: CC(C)(C)OC(=O)N1CC[C@@H](CO)C1] 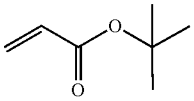 | 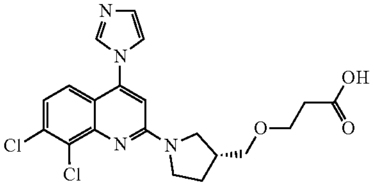 [SMILES: O=C(O)CCOC[C@@H]1CCN(c2cc(-n3ccnc3)c3ccc(Cl)c(Cl)c3n2)C1] | 435 |

-continued
| Example | Starting Material | Structure | MS [M + 1]+ |
|---|---|---|---|
| I-789 | 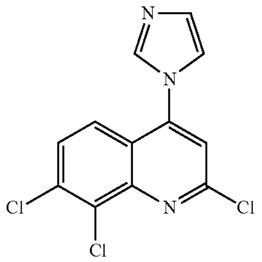 [SMILES: Clc1cc(-n2ccnc2)c2ccc(Cl)c(Cl)c2n1] 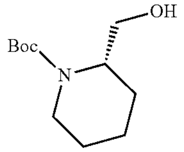 [SMILES: CC(C)(C)OC(=O)N1CCCC[C@H]1CO] 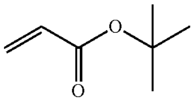 | 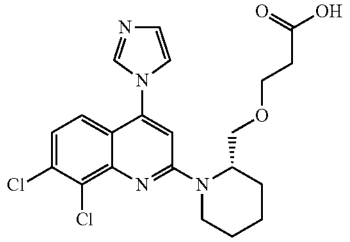 [SMILES: O=C(O)CCOC[C@@H]1CCCCN1c1cc(-n2ccnc2)c2ccc(Cl)c(Cl)c2n1] | 449 |
| I-693 | 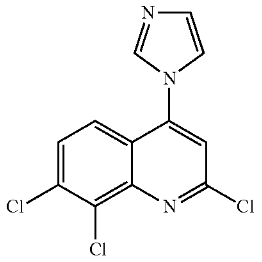 [SMILES: Clc1cc(-n2ccnc2)c2ccc(Cl)c(Cl)c2n1] 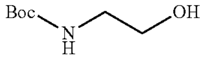 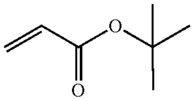 | 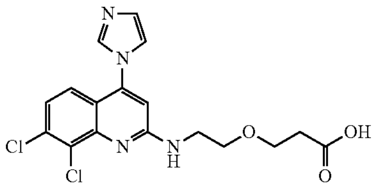 | 395 |
| I-692 | 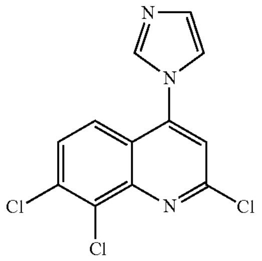 [SMILES: Clc1cc(-n2ccnc2)c2ccc(Cl)c(Cl)c2n1] 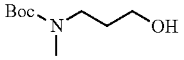 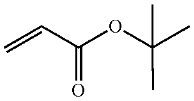 | 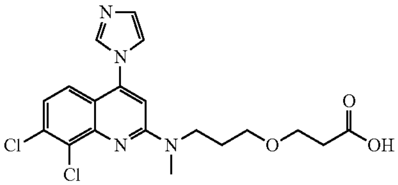 [SMILES: CN(CCCOCCC(=O)O)c1cc(-n2ccnc2)c2ccc(Cl)c(Cl)c2n1] | 423 |
| I-694 | 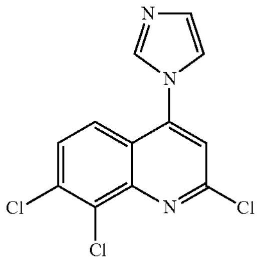 [SMILES: Clc1cc(-n2ccnc2)c2ccc(Cl)c(Cl)c2n1] 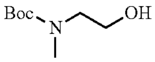 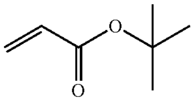 | 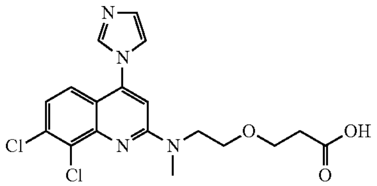 [SMILES: CN(CCOCCC(=O)O)c1cc(-n2ccnc2)c2ccc(Cl)c(Cl)c2n1] | 409 |

-continued
| Example | Starting Material | Structure | MS $[M + 1]^+$ |
| --- | --- | --- | --- |
| I-790 | 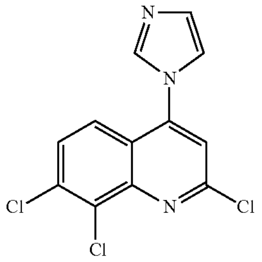 [SMILES: Clc1cc(-n2ccnc2)c2ccc(Cl)c(Cl)c2n1] 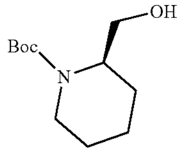 [SMILES: CC(C)(C)OC(=O)N1CCCC[C@@H]1CO] 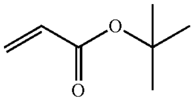 | 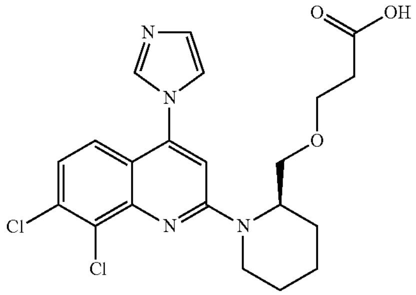 [SMILES: O=C(O)CCOC[C@H]1CCCCN1c1cc(-n2ccnc2)c2ccc(Cl)c(Cl)c2n1] | 449 |
| I-792 | 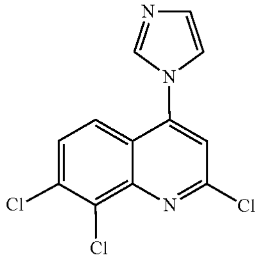 [SMILES: Clc1cc(-n2ccnc2)c2ccc(Cl)c(Cl)c2n1] 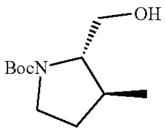 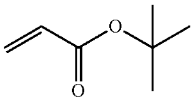 | 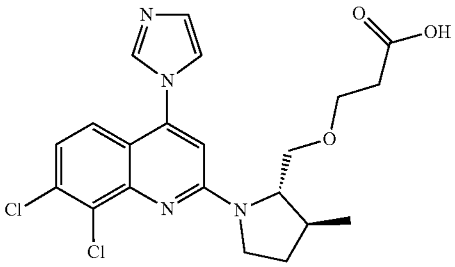 [SMILES: C[C@H]1CCN(c2cc(-n3ccnc3)c3ccc(Cl)c(Cl)c3n2)[C@@H]1COCCC(=O)O] | 449 |
| I-804 | 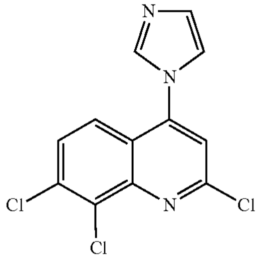 [SMILES: Clc1cc(-n2ccnc2)c2ccc(Cl)c(Cl)c2n1] 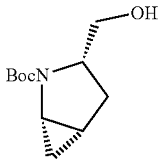 [SMILES: CC(C)(C)OC(=O)N1[C@H](CO)C[C@@H]2C[C@@H]21] 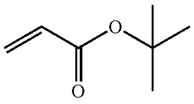 | 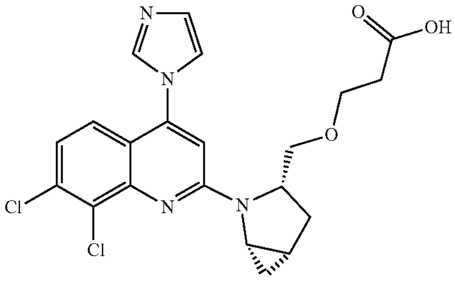 [SMILES: O=C(O)CCOC[C@@H]1C[C@@H]2C[C@@H]2N1c1cc(-n2ccnc2)c2ccc(Cl)c(Cl)c2n1] | 447 |
| I-808 | 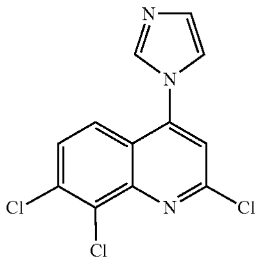 [SMILES: Clc1cc(-n2ccnc2)c2ccc(Cl)c(Cl)c2n1] 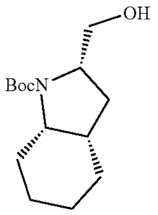 [SMILES: CC(C)(C)OC(=O)N1[C@H](CO)C[C@@H]2CCCC[C@@H]21] | 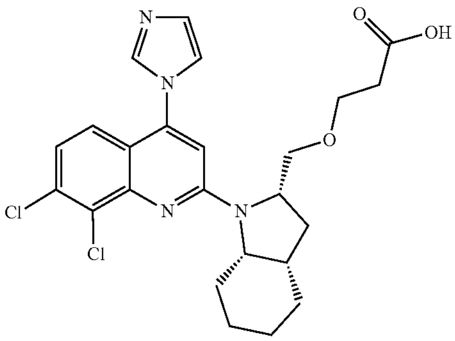 [SMILES: O=C(O)CCOC[C@@H]1C[C@@H]2CCCC[C@@H]2N1c1cc(-n2ccnc2)c2ccc(Cl)c(Cl)c2n1] | 489 |

-continued
| Example | Starting Material | Structure | MS [M + 1]$^+$ |
|---|---|---|---|
| | 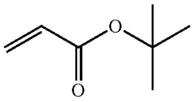 | | |
| I-809 | 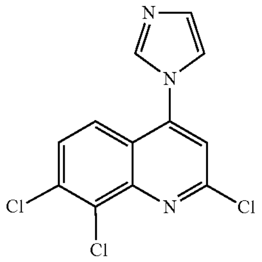 [SMILES: Clc1cc(-n2ccnc2)c2ccc(Cl)c(Cl)c2n1] 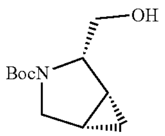 | 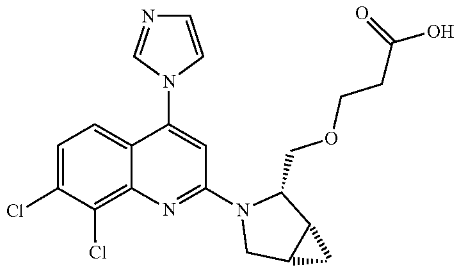 | 447 |
| | 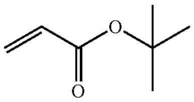 | | |
| I-806 | 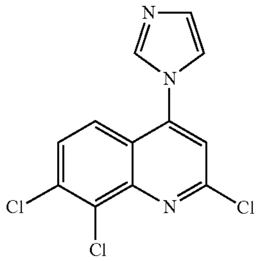 [SMILES: Clc1cc(-n2ccnc2)c2ccc(Cl)c(Cl)c2n1] 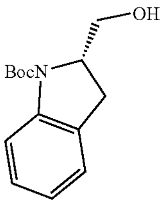 [SMILES: CC(C)(C)OC(=O)N1c2ccccc2C[C@H]1CO] | 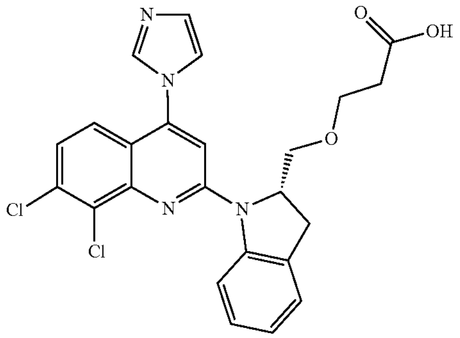 [SMILES: O=C(O)CCOC[C@@H]1Cc2ccccc2N1c1cc(-n2ccnc2)c2ccc(Cl)c(Cl)c2n1] | 483 |
| | 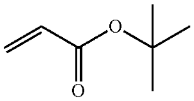 | | |
| I-810 | 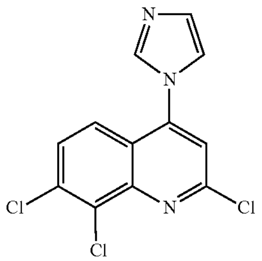 [SMILES: Clc1cc(-n2ccnc2)c2ccc(Cl)c(Cl)c2n1] 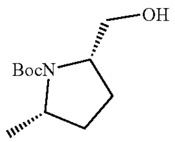 | 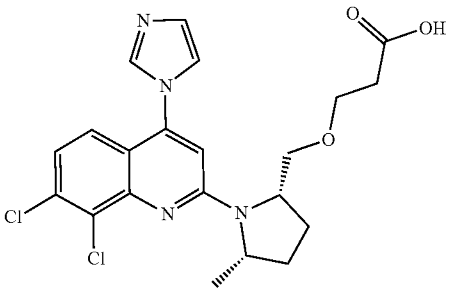 [SMILES: C[C@H]1CC[C@@H](COCCC(=O)O)N1c1cc(-n2ccnc2)c2ccc(Cl)c(Cl)c2n1] | 449 |
| | 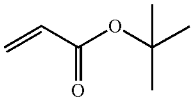 | | |

-continued
| Example | Starting Material | Structure | MS [M + 1]+ |
|---|---|---|---|
| I-832 | 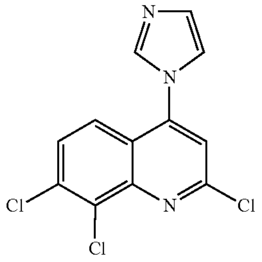 [SMILES: Clc1cc(-n2ccnc2)c2ccc(Cl)c(Cl)c2n1] 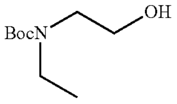 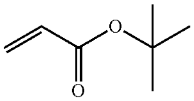 | 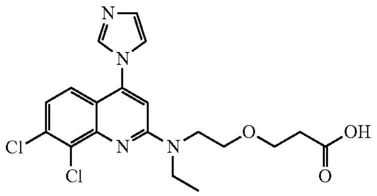 [SMILES: CCN(CCOCCC(=O)O)c1cc(-n2ccnc2)c2ccc(Cl)c(Cl)c2n1] | 423 |
| I-833 | 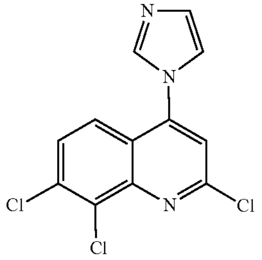 [SMILES: Clc1cc(-n2ccnc2)c2ccc(Cl)c(Cl)c2n1] 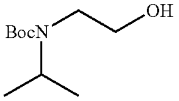 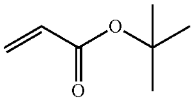 | 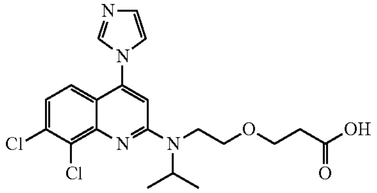 | 437 |
| I-834 | 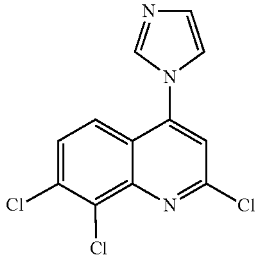 [SMILES: Clc1cc(-n2ccnc2)c2ccc(Cl)c(Cl)c2n1] 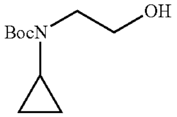 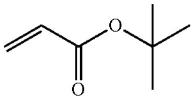 | 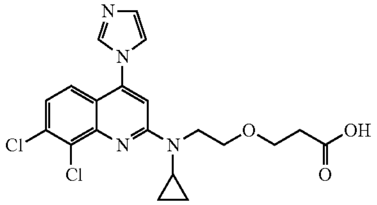 [SMILES: O=C(O)CCOCCN(c1cc(-n2ccnc2)c2ccc(Cl)c(Cl)c2n1)C1CC1] | 435 |
| I-805 | 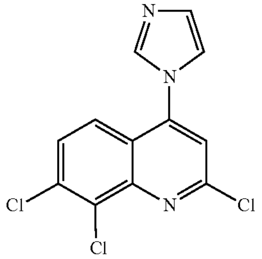 [SMILES: Clc1cc(-n2ccnc2)c2ccc(Cl)c(Cl)c2n1] 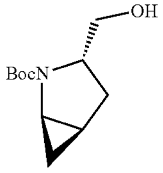 [SMILES: CC(C)(C)OC(=O)N1[C@H](CO)C[C@H]2C[C@H]21] 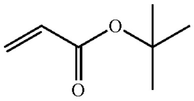 | 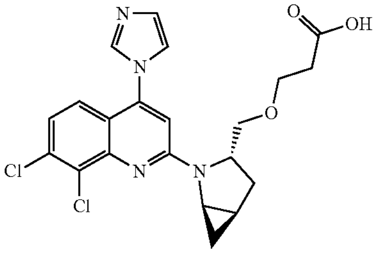 [SMILES: O=C(O)CCOC[C@@H]1C[C@H]2C[C@H]2N1c1cc(-n2ccnc2)c2ccc(Cl)c(Cl)c2n1] | 447 |

-continued
| Example | Starting Material | Structure | MS [M + 1]$^+$ |
|---|---|---|---|
| I-836 | 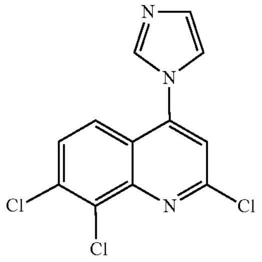 [SMILES: Clc1cc(-n2ccnc2)c2ccc(Cl)c(Cl)c2n1] 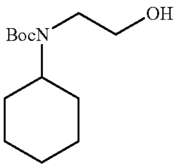 [SMILES: CC(C)(C)OC(=O)N(CCO)C1CCCCC1] 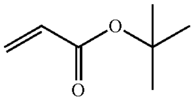 | 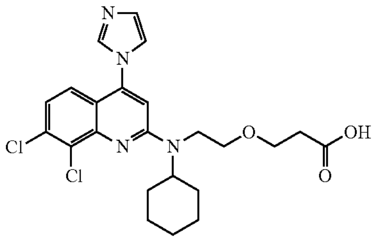 [SMILES: O=C(O)CCOCCN(c1cc(-n2ccnc2)c2ccc(Cl)c(Cl)c2n1)C1CCCCC1] | 477 |
| I-837 | 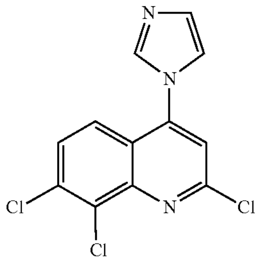 [SMILES: Clc1cc(-n2ccnc2)c2ccc(Cl)c(Cl)c2n1] 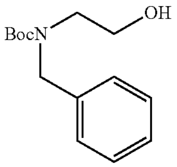 [SMILES: CC(C)(C)OC(=O)N(CCO)Cc1ccccc1] 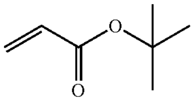 | 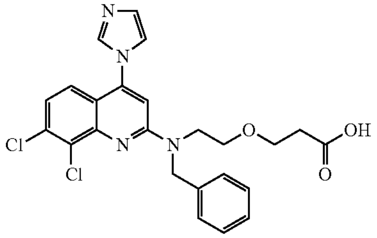 [SMILES: O=C(O)CCOCCN(Cc1ccccc1)c1cc(-n2ccnc2)c2ccc(Cl)c(Cl)c2n1] | 485 |
| I-838 | 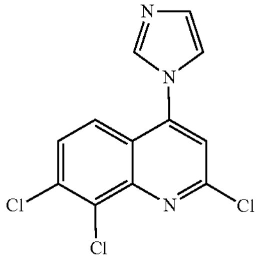 [SMILES: Clc1cc(-n2ccnc2)c2ccc(Cl)c(Cl)c2n1] 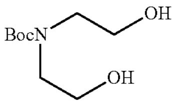 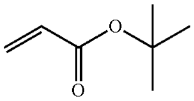 | 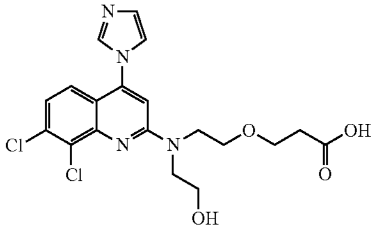 [SMILES: O=C(O)CCOCCN(CCO)c1cc(-n2ccnc2)c2ccc(Cl)c(Cl)c2n1] | 439 |
| I-839 | 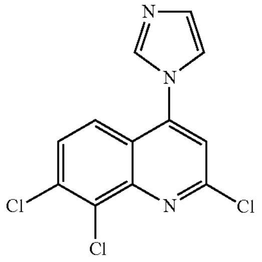 [SMILES: Clc1cc(-n2ccnc2)c2ccc(Cl)c(Cl)c2n1] 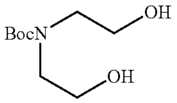 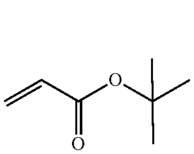 | 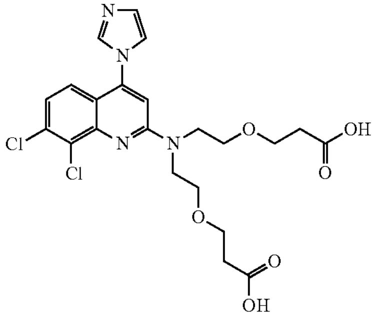 [SMILES: O=C(O)CCOCCN(CCOCCC(=O)O)c1cc(-n2ccnc2)c2ccc(Cl)c(Cl)c2n1] | 511 |

-continued
| Example | Starting Material | Structure | MS [M + 1]+ |
|---|---|---|---|
| I-873 | 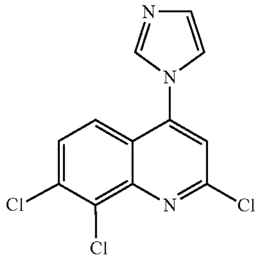 [SMILES: Clc1cc(-n2ccnc2)c2ccc(Cl)c(Cl)c2n1] 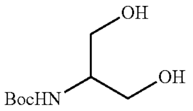 [SMILES: CC(C)(C)OC(=O)NC(CO)CO] 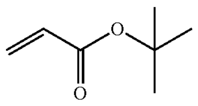 | 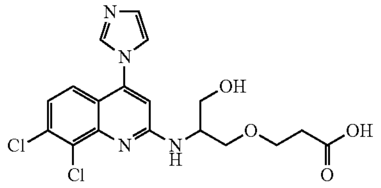 [SMILES: O=C(O)CCOCC(CO)Nc1cc(-n2ccnc2)c2ccc(Cl)c(Cl)c2n1] | 425 |
| I-874 | 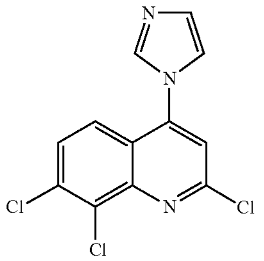 [SMILES: Clc1cc(-n2ccnc2)c2ccc(Cl)c(Cl)c2n1] 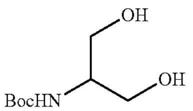 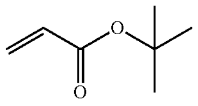 | 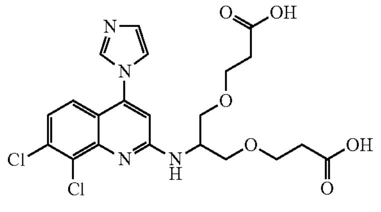 [SMILES: O=C(O)CCOCC(COCCC(=O)O)Nc1cc(-n2ccnc2)c2ccc(Cl)c(Cl)c2n1] | 497 |
| I-816 | 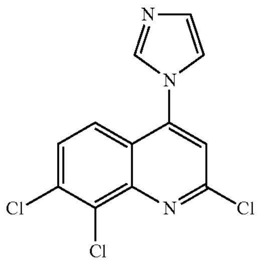 [SMILES: Clc1cc(-n2ccnc2)c2ccc(Cl)c(Cl)c2n1] 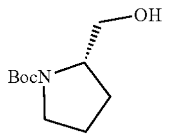 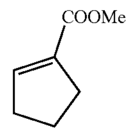 | 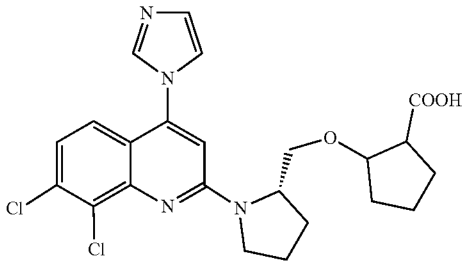 [SMILES: O=C(O)C1CCCC1OC[C@@H]1CCCN1c1cc(-n2ccnc2)c2ccc(Cl)c(Cl)c2n1] | 475 |
| I-796 | 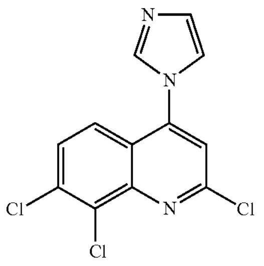 [SMILES: Clc1cc(-n2ccnc2)c2ccc(Cl)c(Cl)c2n1] 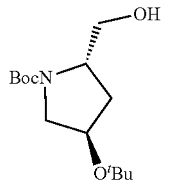 | 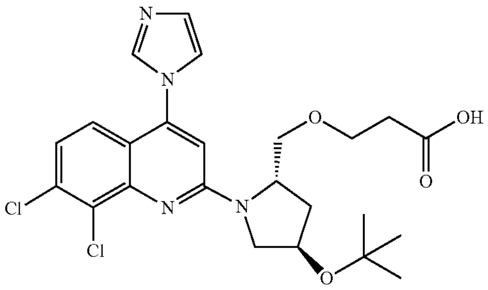 [SMILES: CC(C)(C)O[C@@H]1C[C@@H](COCCC(=O)O)N(c2cc(-n3ccnc3)c3ccc(Cl)c(Cl)c3n2)C1] | 507 |

-continued
| Example | Starting Material | Structure | MS [M + 1]+ |
|---|---|---|---|
| | 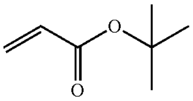 | | |
| I-815 | 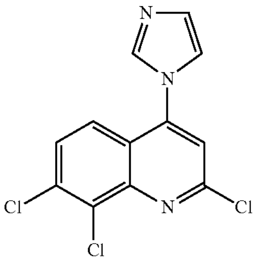 [SMILES: Clc1cc(-n2ccnc2)c2ccc(Cl)c(Cl)c2n1] 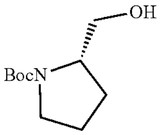 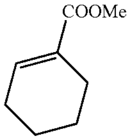 | 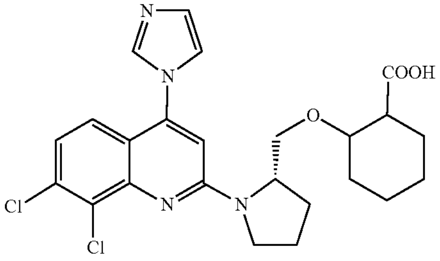 [SMILES: O=C(O)C1CCCCC1OC[C@@H]1CCCN1c1cc(-n2ccnc2)c2ccc(Cl)c(Cl)c2n1] | 489 |
| I-818 | 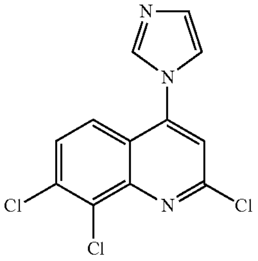 [SMILES: Clc1cc(-n2ccnc2)c2ccc(Cl)c(Cl)c2n1] 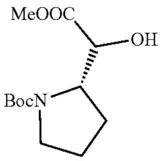 [SMILES: COC(=O)C(O)[C@@H]1CCCN1C(=O)OC(C)(C)C] 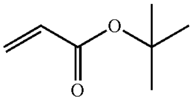 | 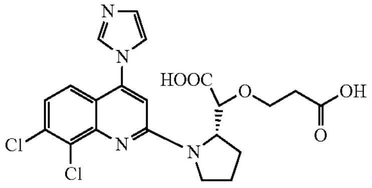 [SMILES: O=C(O)CCOC(C(=O)O)[C@@H]1CCCN1c1cc(-n2ccnc2)c2ccc(Cl)c(Cl)c2n1] | 479 |
| I-858 | 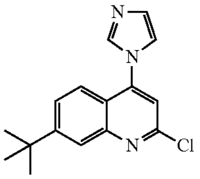 [SMILES: CC(C)(C)c1ccc2c(-n3ccnc3)cc(Cl)nc2c1] 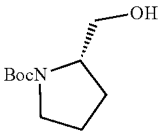 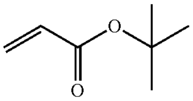 | 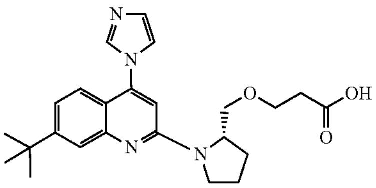 [SMILES: CC(C)(C)c1ccc2c(-n3ccnc3)cc(N3CCC[C@H]3COCCC(=O)O)nc2c1] | 423 |
| I-859 | 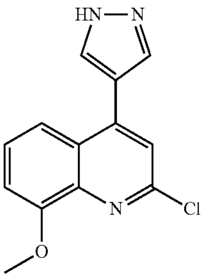 [SMILES: COc1cccc2c(-c3cn[nH]c3)cc(Cl)nc12] 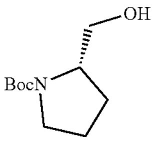 [SMILES: CC(C)(C)OC(=O)N1CCC[C@H]1CO] | 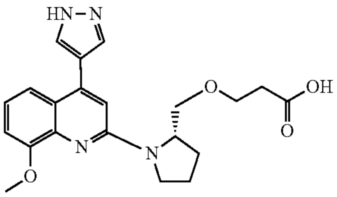 [SMILES: COc1cccc2c(-c3cn[nH]c3)cc(N3CCC[C@H]3COCCC(=O)O)nc12] | 397 |

-continued
| Example | Starting Material | Structure | MS [M + 1]+ |
|---|---|---|---|
| | 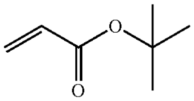 | | |
| I-860 | 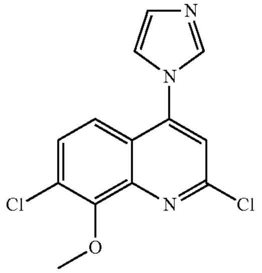 [SMILES: COc1c(Cl)ccc2c(-n3ccnc3)cc(Cl)nc12] 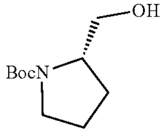 | 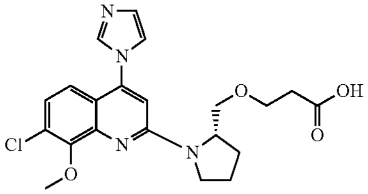 [SMILES: COc1c(Cl)ccc2c(-n3ccnc3)cc(N3CCC[C@H]3COCCC(=O)O)nc12] | 431 |
| | 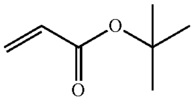 | | |
| I-861 | 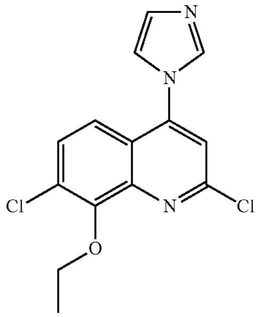 [SMILES: CCOc1c(Cl)ccc2c(-n3ccnc3)cc(Cl)nc12] 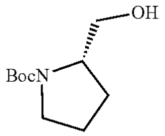 [SMILES: CC(C)(C)OC(=O)N1CCC[C@H]1CO] | 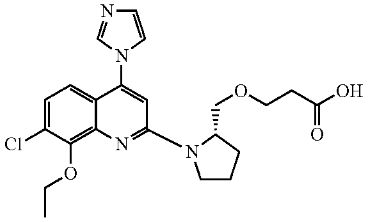 [SMILES: CCOc1c(Cl)ccc2c(-n3ccnc3)cc(N3CCC[C@H]3COCCC(=O)O)nc12] | 445 |
| | 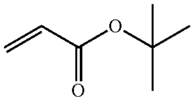 | | |
| I-862 | 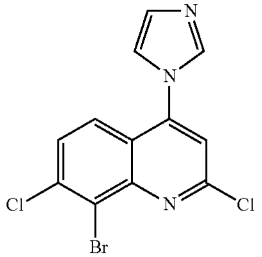 [SMILES: Clc1cc(-n2ccnc2)c2ccc(Cl)c(Br)c2n1] 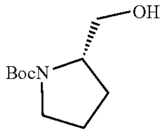 | 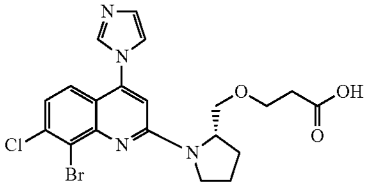 [SMILES: O=C(O)CCOC[C@@H]1CCCN1c1cc(-n2ccnc2)c2ccc(Cl)c(Br)c2n1] | 479 |
| | 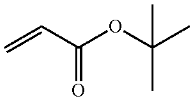 | | |
| I-856 | 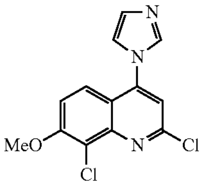 [SMILES: COc1ccc2c(-n3ccnc3)cc(Cl)nc2c1Cl] 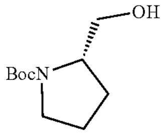 | 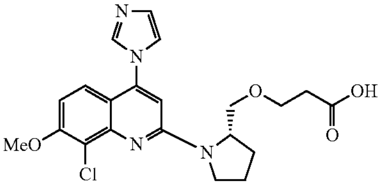 [SMILES: COc1ccc2c(-n3ccnc3)cc(N3CCC[C@H]3COCCC(=O)O)nc2c1Cl] | 431 |

-continued
| Example | Starting Material | Structure | MS [M + 1]$^{+}$ |
| --- | --- | --- | --- |
| | 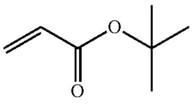 | | |
| I-857 | 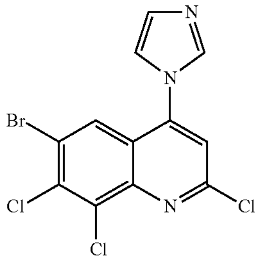 [SMILES: Clc1cc(-n2ccnc2)c2cc(Br)c(Cl)c(Cl)c2n1] 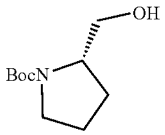 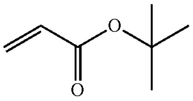 | 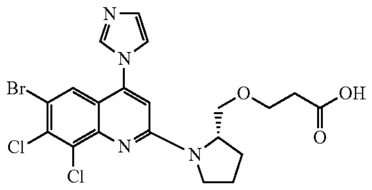 [SMILES: O=C(O)CCOC[C@@H]1CCCN1c1cc(-n2ccnc2)c2cc(Br)c(Cl)c(Cl)c2n1] | 513 |
| I-875 | 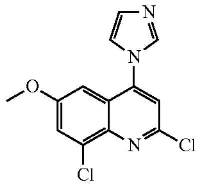 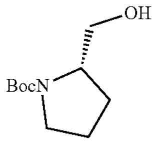 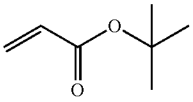 | 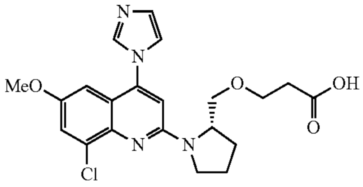 [SMILES: COc1cc(Cl)c2nc(N3CCC[C@H]3COCCC(=O)O)cc(-n3ccnc3)c2c1] | 431 |
| I-876 | 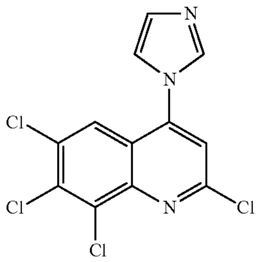 [SMILES: Clc1cc(-n2ccnc2)c2cc(Cl)c(Cl)c(Cl)c2n1] 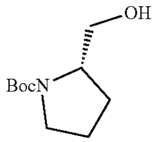 [SMILES: CC(C)(C)OC(=O)N1CCC[C@H]1CO] 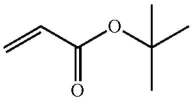 | 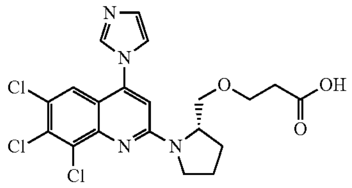 [SMILES: O=C(O)CCOC[C@@H]1CCCN1c1cc(-n2ccnc2)c2cc(Cl)c(Cl)c(Cl)c2n1] | 469 |
| I-793 | 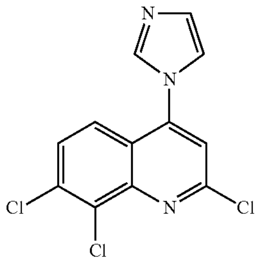 [SMILES: Clc1cc(-n2ccnc2)c2ccc(Cl)c(Cl)c2n1] 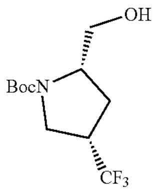 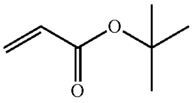 | 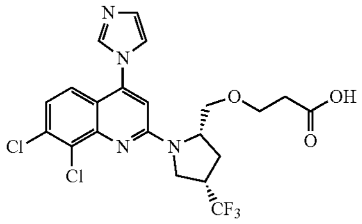 [SMILES: O=C(O)CCOC[C@@H]1C[C@H](C(F)(F)F)CN1c1cc(-n2ccnc2)c2ccc(Cl)c(Cl)c2n1] | 503 |

-continued
| Example | Starting Material | Structure | MS [M + 1]$^+$ |
| --- | --- | --- | --- |
| I-794 | 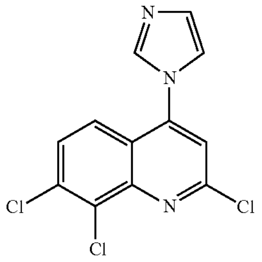 [SMILES: Clc1cc(-n2ccnc2)c2ccc(Cl)c(Cl)c2n1] 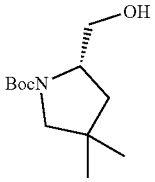 [SMILES: CC1(C)C[C@@H](CO)N(C(=O)OC(C)(C)C)C1] 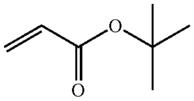 | 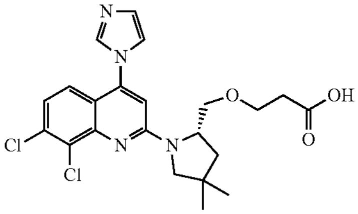 [SMILES: CC1(C)C[C@@H](COCCC(=O)O)N(c2cc(-n3ccnc3)c3ccc(Cl)c(Cl)c3n2)C1] | 463 |
| I-795 | 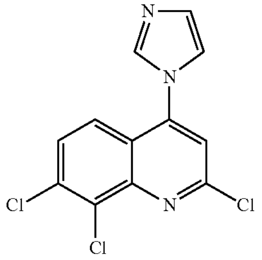 [SMILES: Clc1cc(-n2ccnc2)c2ccc(Cl)c(Cl)c2n1] 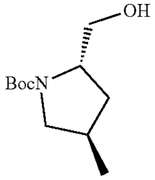 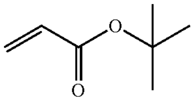 | 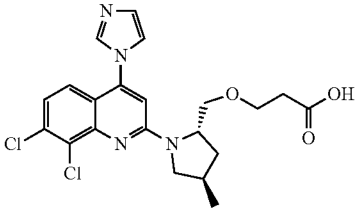 [SMILES: C[C@@H]1C[C@@H](COCCC(=O)O)N(c2cc(-n3ccnc3)c3ccc(Cl)c(Cl)c3n2)C1] | 449 |
| I-827 | 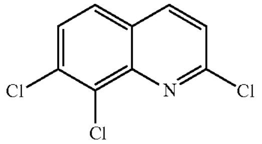 [SMILES: Clc1ccc2ccc(Cl)c(Cl)c2n1] 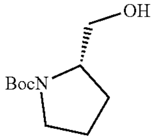 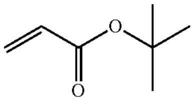 | 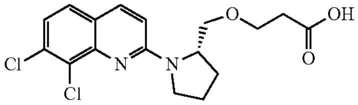 [SMILES: O=C(O)CCOC[C@@H]1CCCN1c1ccc2ccc(Cl)c(Cl)c2n1] | 369 |
| I-800 | 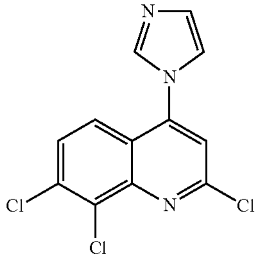 [SMILES: Clc1cc(-n2ccnc2)c2ccc(Cl)c(Cl)c2n1] 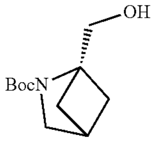 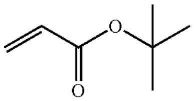 | 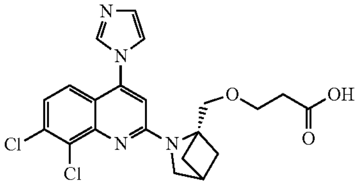 | 447 |

-continued
| Example | Starting Material | Structure | MS [M + 1]+ |
|---|---|---|---|
| I-801 | 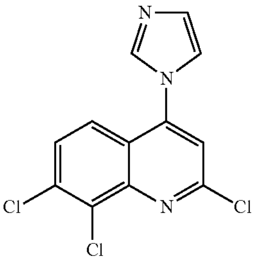 [SMILES: Clc1cc(-n2ccnc2)c2ccc(Cl)c(Cl)c2n1] 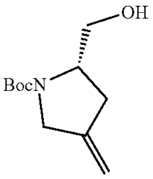 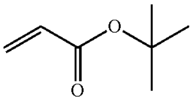 | 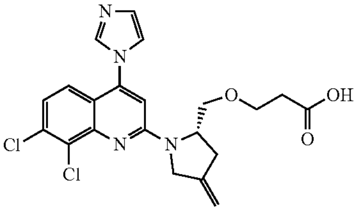 [SMILES: C=C1C[C@@H](COCCC(=O)O)N(c2cc(-n3ccnc3)c3ccc(Cl)c(Cl)c3n2)C1] | 447 |
| I-802 | 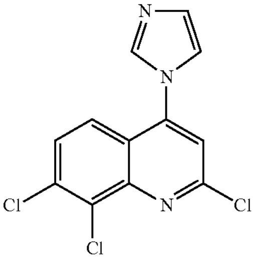 [SMILES: Clc1cc(-n2ccnc2)c2ccc(Cl)c(Cl)c2n1] 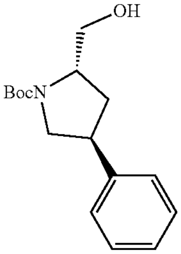 [SMILES: CC(C)(C)OC(=O)N1C[C@H](c2ccccc2)C[C@H]1CO] 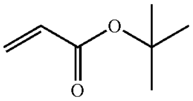 | 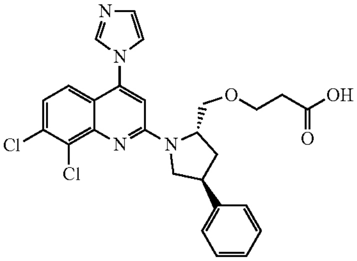 [SMILES: O=C(O)CCOC[C@@H]1C[C@@H](c2ccccc2)CN1c1cc(-n2ccnc2)c2ccc(Cl)c(Cl)c2n1] | 511 |
| I-803 | 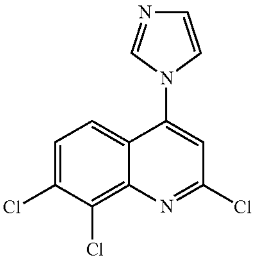 [SMILES: Clc1cc(-n2ccnc2)c2ccc(Cl)c(Cl)c2n1] 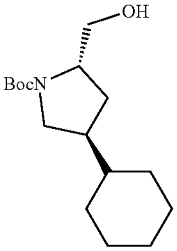 [SMILES: CC(C)(C)OC(=O)N1C[C@H](C2CCCCC2)C[C@H]1CO] 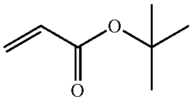 | 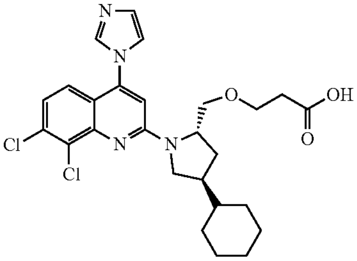 [SMILES: O=C(O)CCOC[C@@H]1C[C@@H](C2CCCCC2)CN1c1cc(-n2ccnc2)c2ccc(Cl)c(Cl)c2n1] | 517 |
| I-797 | 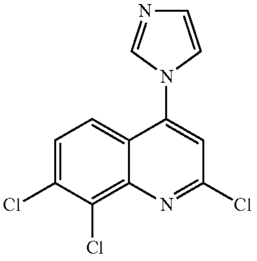 [SMILES: Clc1cc(-n2ccnc2)c2ccc(Cl)c(Cl)c2n1] 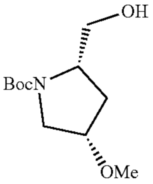 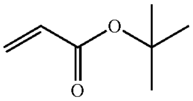 | 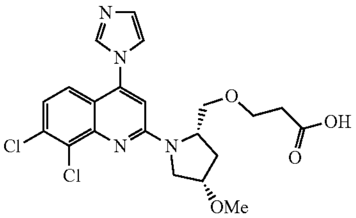 [SMILES: CO[C@H]1C[C@@H](COCCC(=O)O)N(c2cc(-n3ccnc3)c3ccc(Cl)c(Cl)c3n2)C1] | 465 |

-continued
| Example | Starting Material | Structure | MS [M + 1]+ |
|---|---|---|---|
| I-798 | 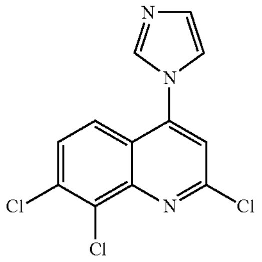 [SMILES: Clc1cc(-n2ccnc2)c2ccc(Cl)c(Cl)c2n1] 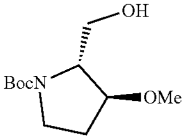 [SMILES: CO[C@H]1CCN(C(=O)OC(C)(C)C)[C@@H]1CO] 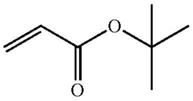 | 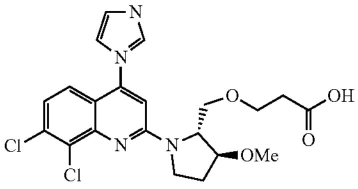 | 465 |
| I-853 | 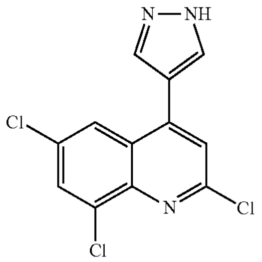 [SMILES: Clc1cc(Cl)c2nc(Cl)cc(-c3cn[nH]c3)c2c1] 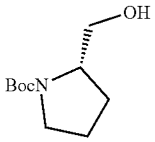 [SMILES: CC(C)(C)OC(=O)N1CCC[C@H]1CO] 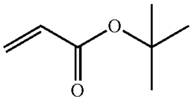 | 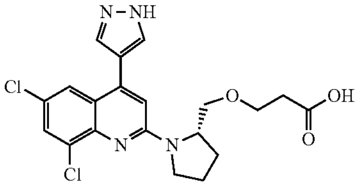 [SMILES: O=C(O)CCOC[C@@H]1CCCN1c1cc(-c2cn[nH]c2)c2cc(Cl)cc(Cl)c2n1] | 435 |
| I-855 | 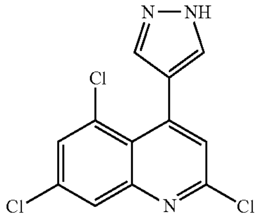 [SMILES: Clc1cc(Cl)c2c(-c3cn[nH]c3)cc(Cl)nc2c1] 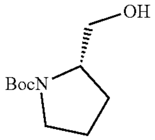 [SMILES: CC(C)(C)OC(=O)N1CCC[C@H]1CO] 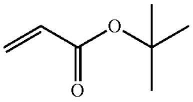 | 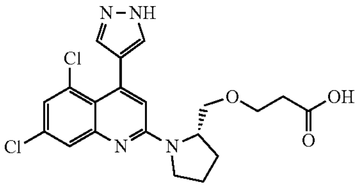 [SMILES: O=C(O)CCOC[C@@H]1CCCN1c1cc(-c2cn[nH]c2)c2c(Cl)cc(Cl)cc2n1] | 435 |
| I-867 | 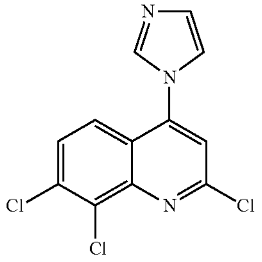 [SMILES: Clc1cc(-n2ccnc2)c2ccc(Cl)c(Cl)c2n1] 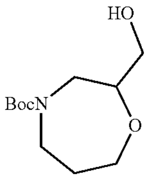 [SMILES: CC(C)(C)OC(=O)N1CCCOC(CO)C1] 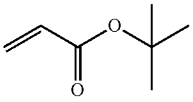 | 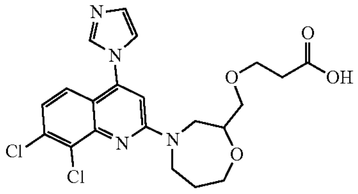 [SMILES: O=C(O)CCOCC1CN(c2cc(-n3ccnc3)c3ccc(Cl)c(Cl)c3n2)CCCO1] | 465 |

-continued
| Example | Starting Material | Structure | MS [M + 1]+ |
| --- | --- | --- | --- |
| I-799 | 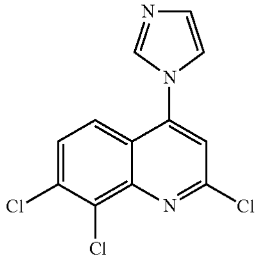 [SMILES: Clc1cc(-n2ccnc2)c2ccc(Cl)c(Cl)c2n1] 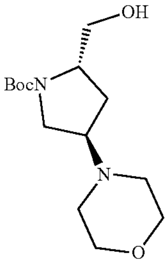 [SMILES: CC(C)(C)OC(=O)N1C[C@H](N2CCOCC2)C[C@H]1CO] 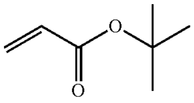 | 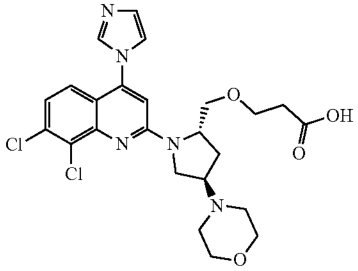 [SMILES: O=C(O)CCOC[C@@H]1C[C@@H](N2CCOCC2)CN1c1cc(-n2ccnc2)c2ccc(Cl)c(Cl)c2n1] | 520 |
| I-865 | 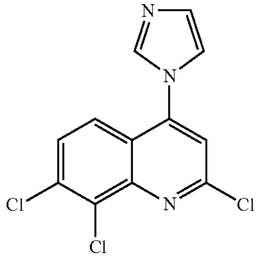 [SMILES: Clc1cc(-n2ccnc2)c2ccc(Cl)c(Cl)c2n1] 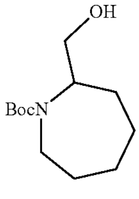 [SMILES: CC(C)(C)OC(=O)N1CCCCCC1CO] 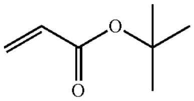 | 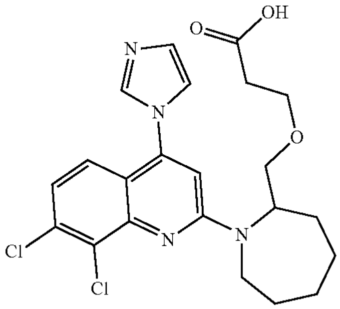 [SMILES: O=C(O)CCOCC1CCCCCN1c1cc(-n2ccnc2)c2ccc(Cl)c(Cl)c2n1] | 463 |
| I-807 | 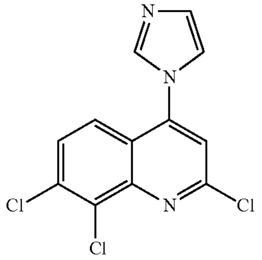 [SMILES: Clc1cc(-n2ccnc2)c2ccc(Cl)c(Cl)c2n1] 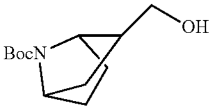 [SMILES: CC(C)(C)OC(=O)N1C2CCC1C(CO)C2] 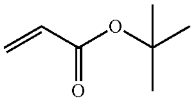 | 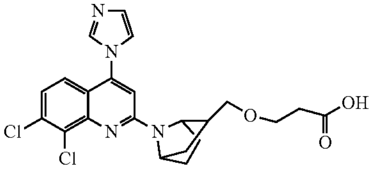 [SMILES: O=C(O)CCOCC1CC2CCC1N2c1cc(-n2ccnc2)c2ccc(Cl)c(Cl)c2n1] | 461 |
| I-864 | 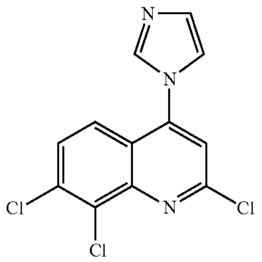 [SMILES: Clc1cc(-n2ccnc2)c2ccc(Cl)c(Cl)c2n1] 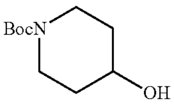 | 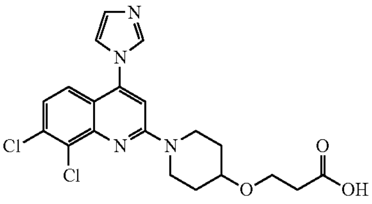 [SMILES: O=C(O)CCOC1CCN(c2cc(-n3ccnc3)c3ccc(Cl)c(Cl)c3n2)CC1] | 435 |

-continued
| Example | Starting Material | | Structure | MS [M + 1]+ |
|---|---|---|---|---|
| | | 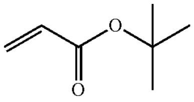 | | |
| I-866 | 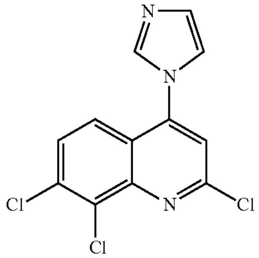 [SMILES: Clc1cc(-n2ccnc2)c2ccc(Cl)c(Cl)c2n1] | 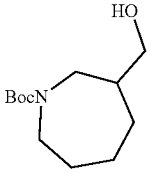 | 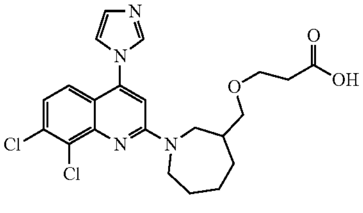 [SMILES: O=C(O)CCOCC1CCCCN(c2cc(-n3ccnc3)c3ccc(Cl)c(Cl)c3n2)C1] | 463 |
| | | 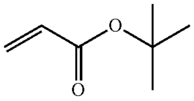 | | |
| I-868 | 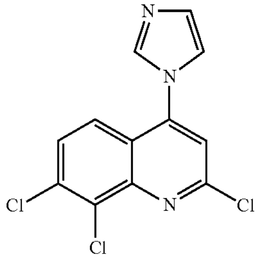 [SMILES: Clc1cc(-n2ccnc2)c2ccc(Cl)c(Cl)c2n1] | 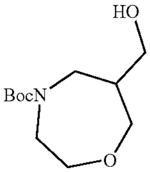 | 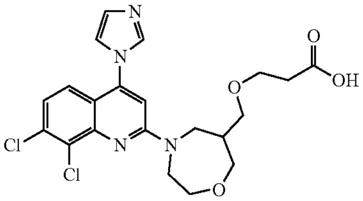 [SMILES: O=C(O)CCOCC1COCCN(c2cc(-n3ccnc3)c3ccc(Cl)c(Cl)c3n2)C1] | 465 |
| | | 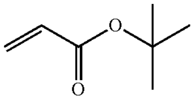 | | |
| I-811 | 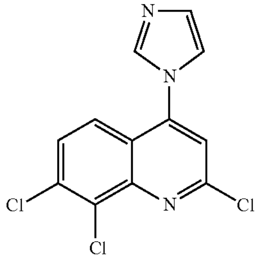 [SMILES: Clc1cc(-n2ccnc2)c2ccc(Cl)c(Cl)c2n1] | 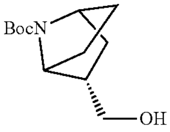 | 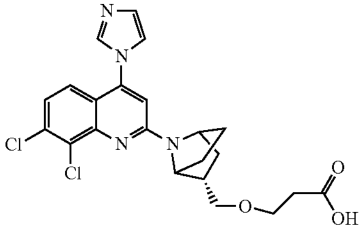 [SMILES: O=C(O)CCOC[C@H]1CC2CCC1N2c1cc(-n2ccnc2)c2ccc(Cl)c(Cl)c2n1] | 461 |
| | | 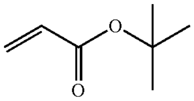 | | |
| I-829 | 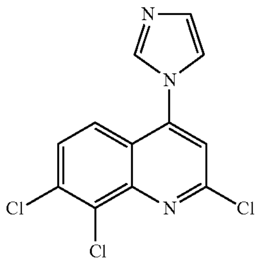 [SMILES: Clc1cc(-n2ccnc2)c2ccc(Cl)c(Cl)c2n1] | 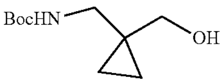 | 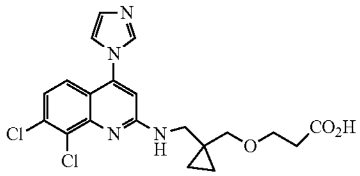 [SMILES: O=C(O)CCOCC1(CNc2cc(-n3ccnc3)c3ccc(Cl)c(Cl)c3n2)CC1] | 435 |

-continued
| Example | Starting Material | Structure | MS $[M + 1]^+$ |
|---|---|---|---|
| | 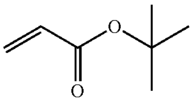 | | |
| I-869 | 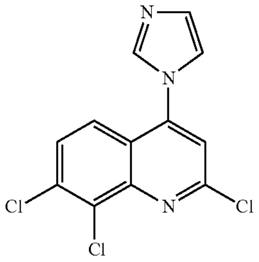 [SMILES: Clc1cc(-n2ccnc2)c2ccc(Cl)c(Cl)c2n1] 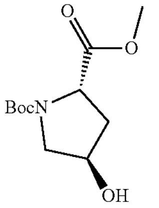 [SMILES: COC(=O)[C@@H]1C[C@@H](O)CN1C(=O)OC(C)(C)C] 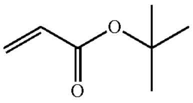 | 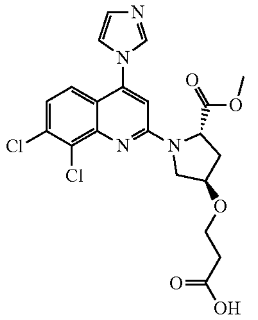 [SMILES: COC(=O)[C@@H]1C[C@@H](OCCC(=O)O)CN1c1cc(-n2ccnc2)c2ccc(Cl)c(Cl)c2n1] | 479 |
| I-870 | 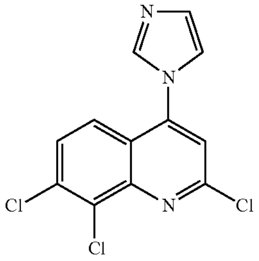 [SMILES: Clc1cc(-n2ccnc2)c2ccc(Cl)c(Cl)c2n1] 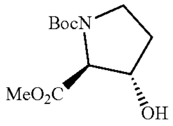 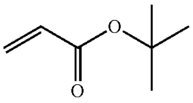 | 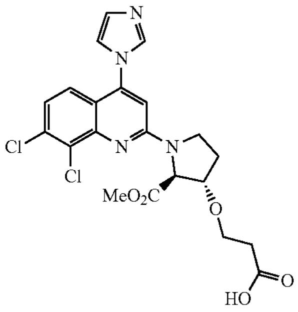 [SMILES: COC(=O)[C@@H]1[C@@H](OCCC(=O)O)CCN1c1cc(-n2ccnc2)c2ccc(Cl)c(Cl)c2n1] | 479 |
| I-871 | 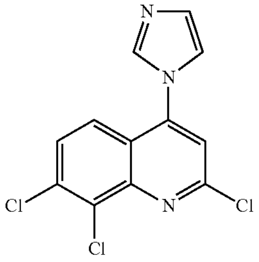 [SMILES: Clc1cc(-n2ccnc2)c2ccc(Cl)c(Cl)c2n1] 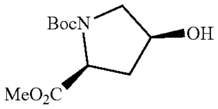 [SMILES: COC(=O)[C@@H]1C[C@H](O)CN1C(=O)OC(C)(C)C] 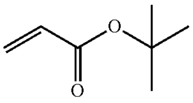 | 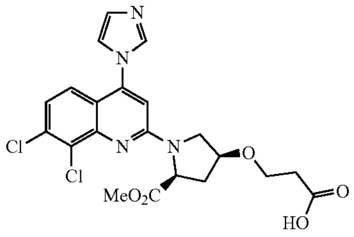 [SMILES: COC(=O)[C@@H]1C[C@H](OCCC(=O)O)CN1c1cc(-n2ccnc2)c2ccc(Cl)c(Cl)c2n1] | 479 |

-continued

| Example | Starting Material | Structure | MS [M + 1]+ |
| --- | --- | --- | --- |
| I-814 | 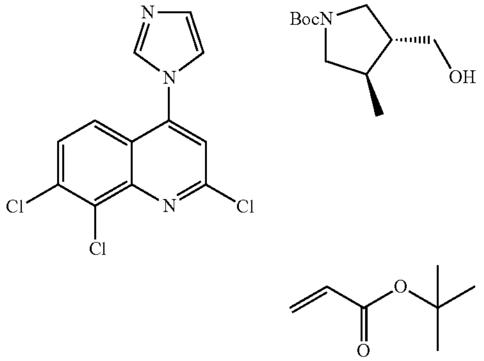 | 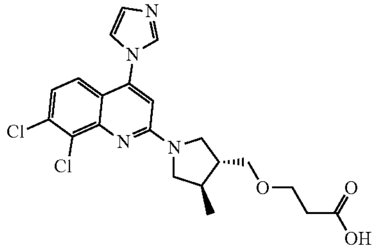 [SMILES: C[C@H]1CN(c2cc(-n3ccnc3)c3ccc(Cl)c(Cl)c3n2)C[C@@H]1COCCC(=O)O] | 449 |

Example 103: Synthesis of methyl (S)-2-((1-(7,8-dichloro-4-(1H-imidazol-1-yl)quinolin-2-yl)pyrrolidin-2-yl)methoxy)acetate (I-667) and (S)-2-((1-(7,8-dichloro-4-(1H-imidazol-1-yl)quinolin-2-yl)pyrrolidin-2-yl)methoxy)acetic acid (I-666)

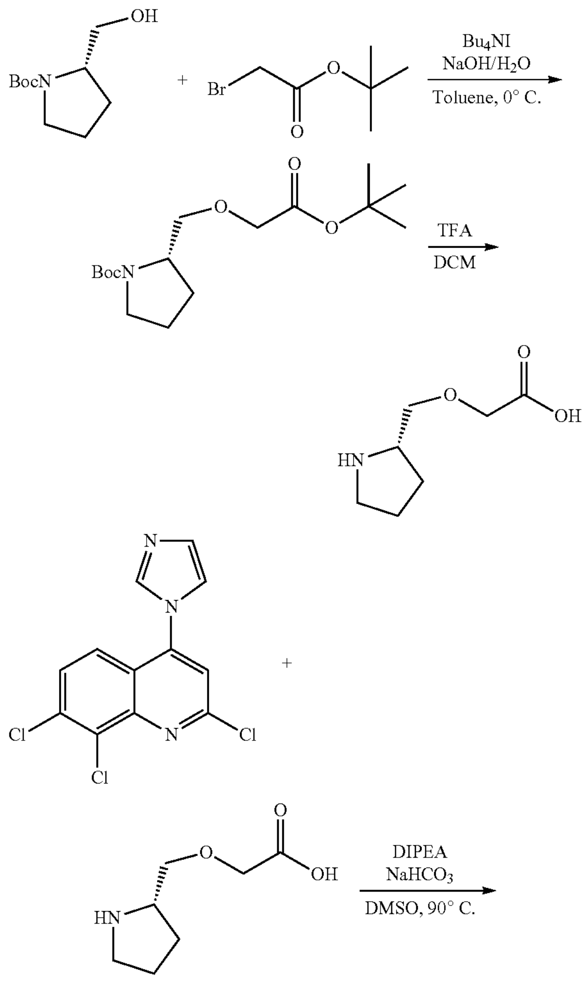

-continued

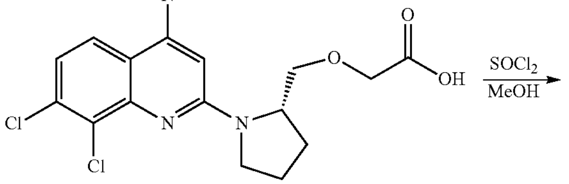

I-666

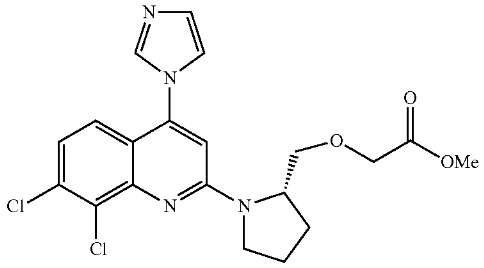

I-667

Step 1: tert-Butyl (S)-2-((2-(tert-butoxy)-2-oxoethoxy)methyl)pyrrolidine-1-carboxylate. To a flask were added tert-butyl (S)-2-(hydroxymethyl)pyrrolidine-1-carboxylate (1.0 g, 4.98 mmol, 1.0 eq.), $Bu_4NI$ (920 mg, 2.49 mmol, 0.50 eq.), toluene (20 mL) and tert-butyl 2-bromoacetate (1.94 g, 9.95 mmol, 2.0 eq.). The reaction mixture was cooled in an ice bath. A solution of $NaOH/H_2O$ (30%, 12 mL) was added slowly at 0° C. The resulting reaction mixture was stirred at 0° C. for 3 hours. Then the mixture was diluted by ethyl acetate (50 mL), washed by $H_2O$ (3×15 mL), brine (15 mL), and dried over $Na_2SO_4$. After concentration, the crude was purified by silica gel chromatography to afford the title product (1.14 g).

Step 2: (S)-2-(Pyrrolidin-2-ylmethoxy)acetic acid. The mixture of tert-butyl (S)-2-((2-(tert-butoxy)-2-oxoethoxy)methyl)pyrrolidine-1-carboxylate (300 mg, 0.951 mmol), TFA (1.5 mL) and DCM (1.5 mL) was stirred overnight at room temperature. The mixture was concentrated to remove all volatiles. The crude was used in the next step.

Step 3: (S)-2-((1-(7,8-Dichloro-4-(1H-imidazol-1-yl)quinolin-2-yl)pyrrolidin-2-yl)methoxy)acetic acid (I-666). The procedure was the same as that in the synthesis of I-665. MS: $[M+1]^+$ 421.

Step 4: Methyl (S)-2-((1-(7,8-dichloro-4-(1H-imidazol-1-yl)quinolin-2-yl)pyrrolidin-2-yl)methoxy)acetate. The procedure was the same as that in the synthesis of I-665. MS: $[M+1]^+$ 435.

The following compounds are prepared essentially by the same methods described above for I-666.

| Example | Starting Material | Structure | MS $[M+1]^+$ |
| --- | --- | --- | --- |
| I-697 | 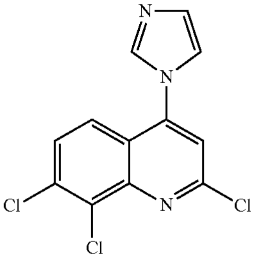 [SMILES: Clc1cc(-n2ccnc2)c2ccc(Cl)c(Cl)c2n1] 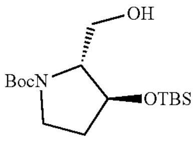 [SMILES: CC(C)(C)OC(=O)N1CC[C@H](O[Si](C)(C)C(C)(C)C)[C@H]1CO] | 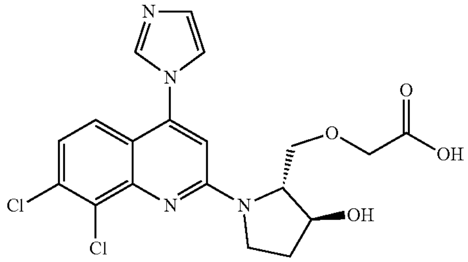 [SMILES: O=C(O)COC[C@@H]1[C@@H](O)CCN1c1cc(-n2ccnc2)c2ccc(Cl)c(Cl)c2n1] | 437 |
| I-706 | 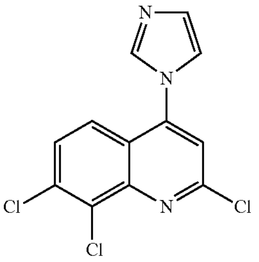 [SMILES: Clc1cc(-n2ccnc2)c2ccc(Cl)c(Cl)c2n1] 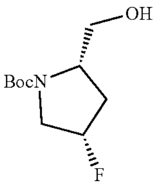 | 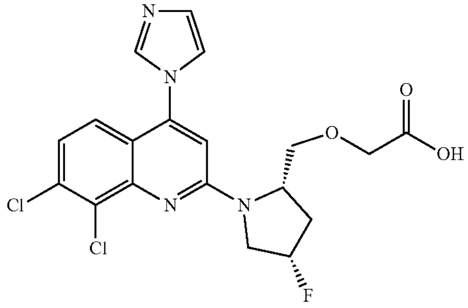 [SMILES: O=C(O)COC[C@@H]1C[C@H](F)CN1c1cc(-n2ccnc2)c2ccc(Cl)c(Cl)c2n1] | 439 |
| I-740 | 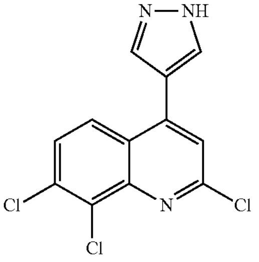 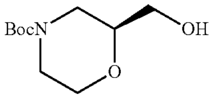 | 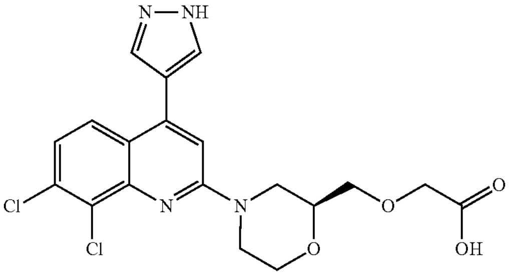 | 437 |
| I-743 | 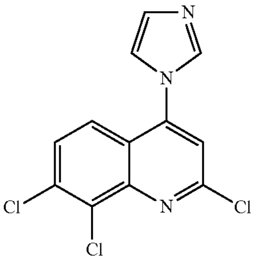 [SMILES: Clc1cc(-n2ccnc2)c2ccc(Cl)c(Cl)c2n1] 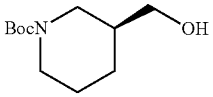 | 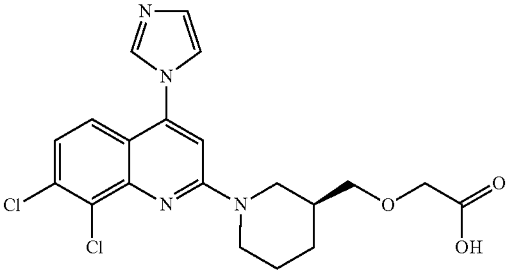 | 435 |

-continued
| Example | Starting Material | Structure | MS [M + 1]+ |
|---|---|---|---|
| I-744 | 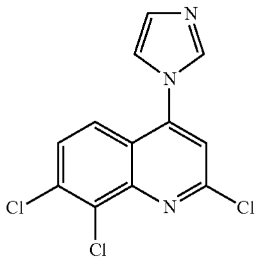 [SMILES: Clc1cc(-n2ccnc2)c2ccc(Cl)c(Cl)c2n1] 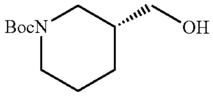 | 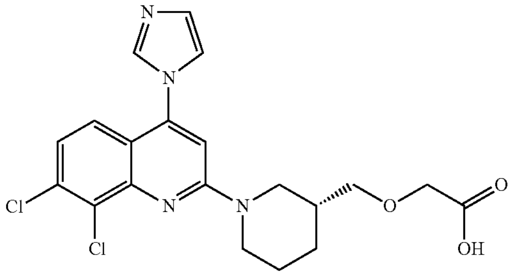 [SMILES: O=C(O)COC[C@@H]1CCCN(c2cc(-n3ccnc3)c3ccc(Cl)c(Cl)c3n2)C1] | 435 |
| I-751 | 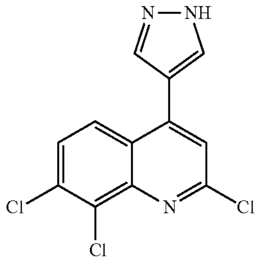 [SMILES: Clc1cc(-c2cn[nH]c2)c2ccc(Cl)c(Cl)c2n1] 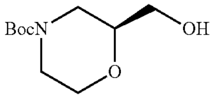 | 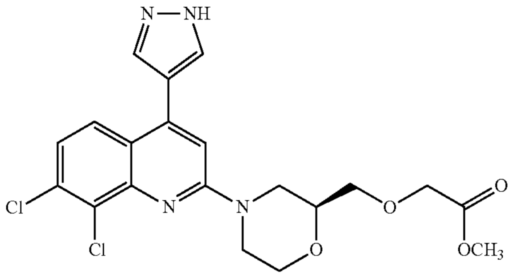 [SMILES: COC(=O)COC[C@@H]1CN(c2cc(-c3cn[nH]c3)c3ccc(Cl)c(Cl)c3n2)CCO1] | 451 |
| I-746 | 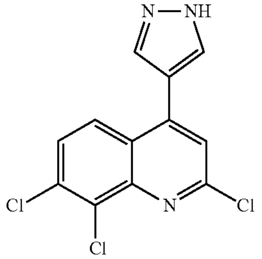 [SMILES: Clc1cc(-c2cn[nH]c2)c2ccc(Cl)c(Cl)c2n1] 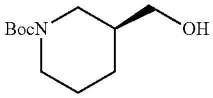 [SMILES: CC(C)(C)OC(=O)N1CCC[C@H](CO)C1] | 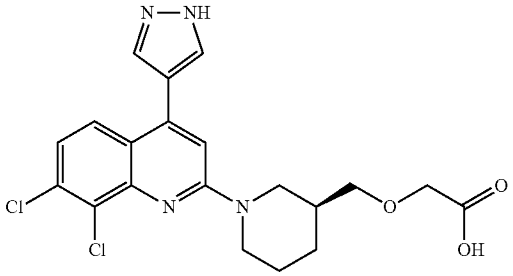 [SMILES: O=C(O)COC[C@H]1CCCN(c2cc(-c3cn[nH]c3)c3ccc(Cl)c(Cl)c3n2)C1] | 435 |
| I-742 | 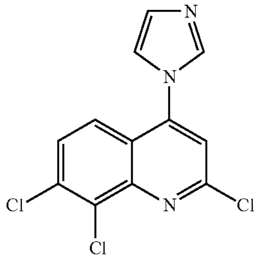 [SMILES: Clc1cc(-n2ccnc2)c2ccc(Cl)c(Cl)c2n1] 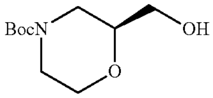 [SMILES: CC(C)(C)OC(=O)N1CCO[C@H](CO)C1] | 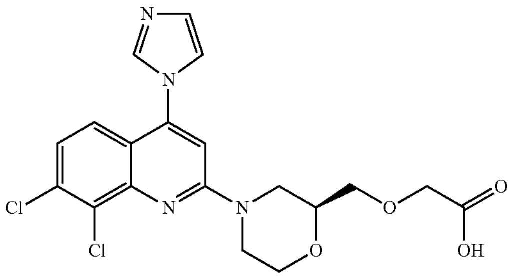 [SMILES: O=C(O)COC[C@@H]1CN(c2cc(-n3ccnc3)c3ccc(Cl)c(Cl)c3n2)CCO1] | 437 |
| I-669 | 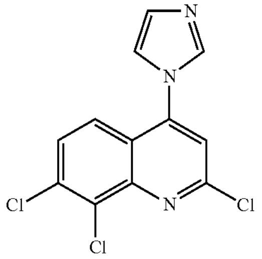 [SMILES: Clc1cc(-n2ccnc2)c2ccc(Cl)c(Cl)c2n1] 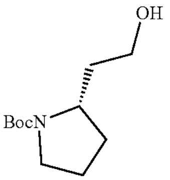 [SMILES: CC(C)(C)OC(=O)N1CCC[C@H]1CCO] | 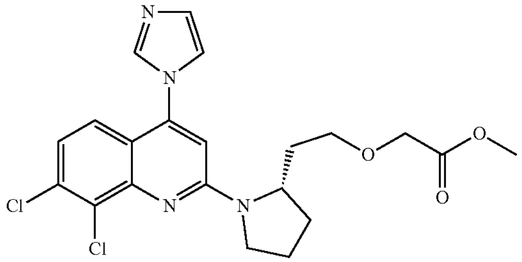 [SMILES: COC(=O)COCC[C@@H]1CCCN1c1cc(-n2ccnc2)c2ccc(Cl)c(Cl)c2n1] | 449 |

-continued
| Example | Starting Material | Structure | MS [M + 1]+ |
|---|---|---|---|
| I-668 | 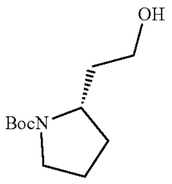 [SMILES: CC(C)(C)OC(=O)N1CCC[C@H]1CCO] | 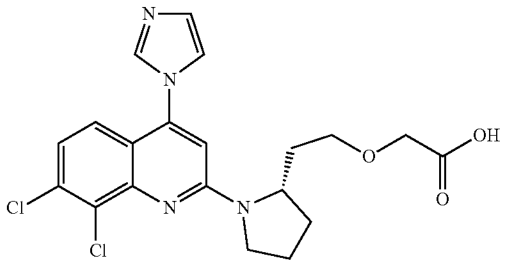 [SMILES: O=C(O)COCC[C@@H]1CCCN1c1cc(-n2ccnc2)c2ccc(Cl)c(Cl)c2n1] | 435 |
| I-766 | 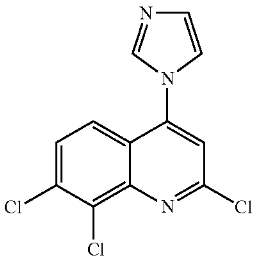 [SMILES: Clc1cc(-n2ccnc2)c2ccc(Cl)c(Cl)c2n1] 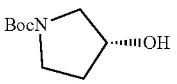 | 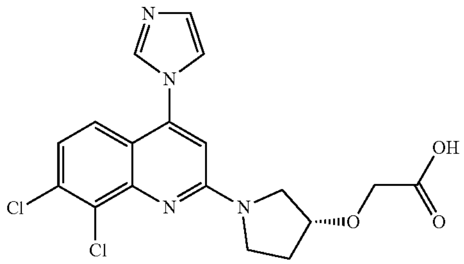 [SMILES: O=C(O)CO[C@@H]1CCN(c2cc(-n3ccnc3)c3ccc(Cl)c(Cl)c3n2)C1] | 407 |
| I-768 | | 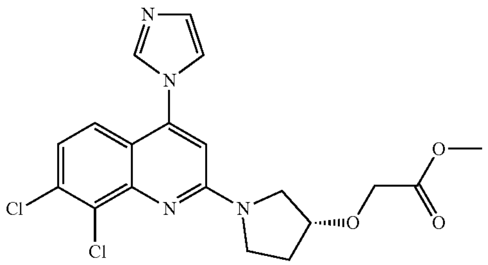 [SMILES: COC(=O)CO[C@@H]1CCN(c2cc(-n3ccnc3)c3ccc(Cl)c(Cl)c3n2)C1] | 421 |
| I-770 | 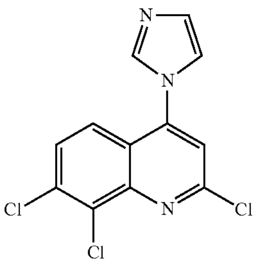 [SMILES: Clc1cc(-n2ccnc2)c2ccc(Cl)c(Cl)c2n1] 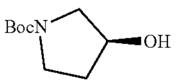 | 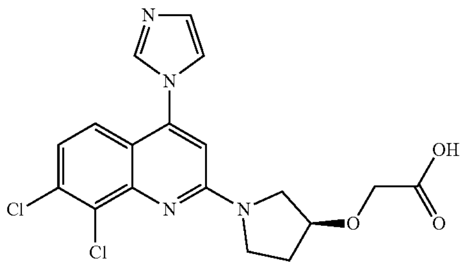 [SMILES: O=C(O)CO[C@H]1CCN(c2cc(-n3ccnc3)c3ccc(Cl)c(Cl)c3n2)C1] | 407 |
| I-820 | 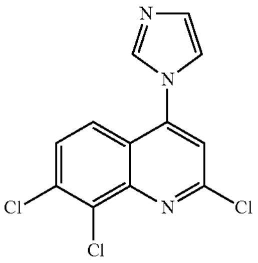 [SMILES: Clc1cc(-n2ccnc2)c2ccc(Cl)c(Cl)c2n1] 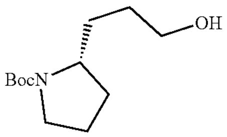 [SMILES: CC(C)(C)OC(=O)N1CCC[C@H]1CCCO] | 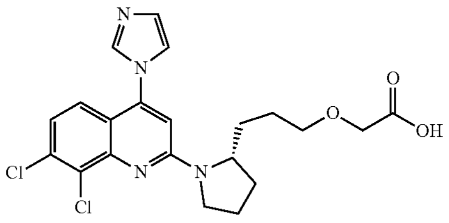 [SMILES: O=C(O)COCCC[C@@H]1CCCN1c1cc(-n2ccnc2)c2ccc(Cl)c(Cl)c2n1] | 449 |

Example 104: Synthesis of 3-(((S)-1-(7,8-dichloro-4-(1H-imidazol-1-yl)quinolin-2-yl)pyrrolidin-2-yl)methoxy)-2-fluoropropanoic acid (I-716) and methyl 3-4(5)-1-(7,8-dichloro-4-(1H-imidazol-1-yl)quinolin-2-yl)pyrrolidin-2-yl)methoxy)-2-fluoropropanoate (I-700)

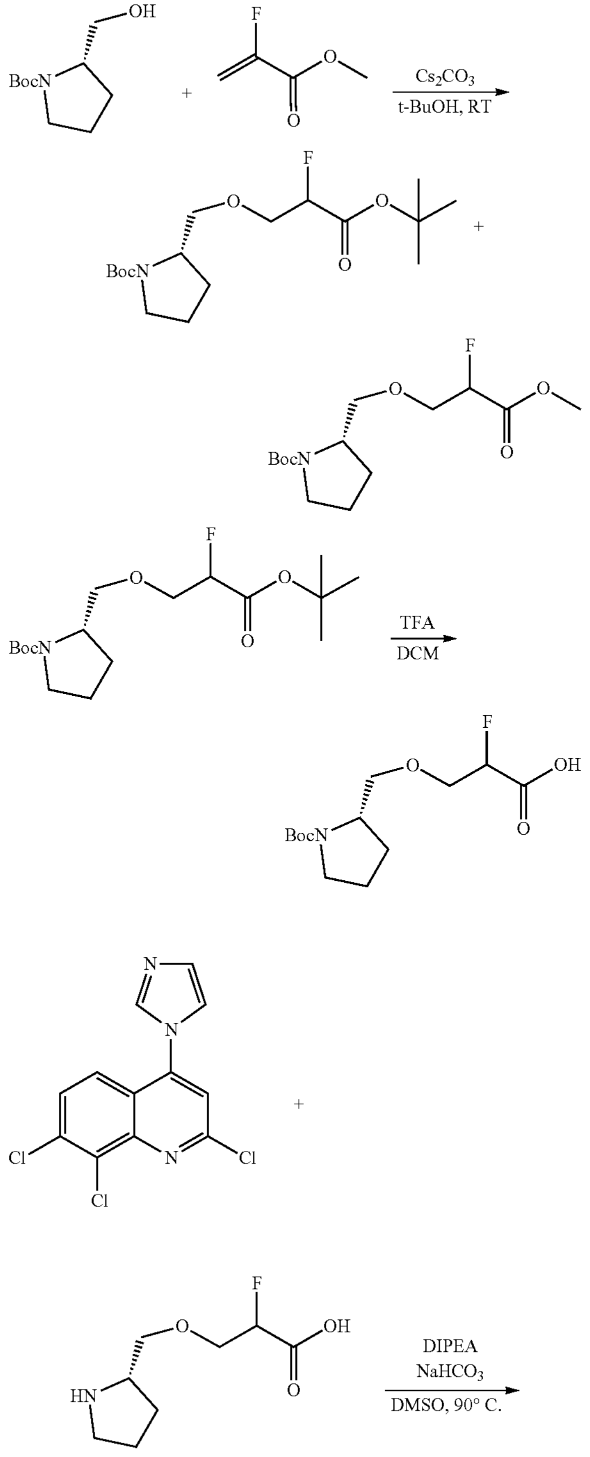

-continued

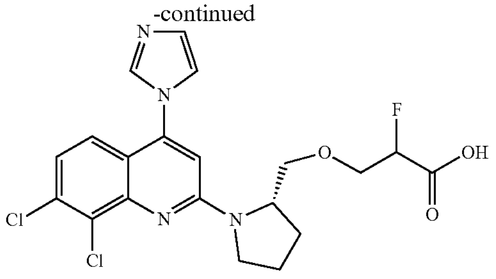

I-716

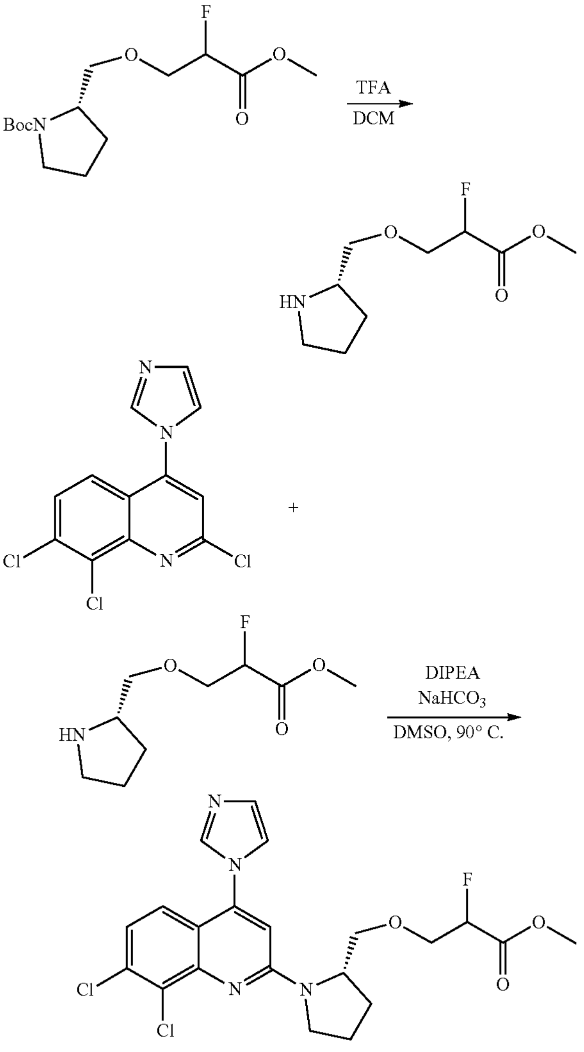

I-700

Step 1: tert-Butyl (2S)-2-((3-(tert-butoxy)-2-fluoro-3-oxopropoxy)methyl)pyrrolidine-1-carboxylate and tert-butyl (2S)-2-((2-fluoro-3-methoxy-3-oxopropoxy)methyl)pyrrolidine-1-carboxylate. The procedure was the same as that in the synthesis of I-665. The two title compounds were obtained.

Step 2: 2-Fluoro-3-(((S)-pyrrolidin-2-yl)methoxy)propanoic acid. The procedure was the same as that in the synthesis of I-665.

Step 3: 3-(((S)-1-(7,8-Dichloro-4-(1H-imidazol-1-yl)quinolin-2-yl)pyrrolidin-2-yl)methoxy)-2-fluoropropanoic acid. The procedure was the same as that in the synthesis of I-665. (MS: $[M+1]^+$ 453)

Step 4: Methyl 2-fluoro-3-4(S)-pyrrolidin-2-yl)methoxy) propanoate. The procedure was the same as that in the synthesis of I-665.

Step 5: Methyl 3-4(S)-1-(7,8-dichloro-4-(1H-imidazol-1-yl)quinolin-2-yl)pyrrolidin-2-yl)methoxy)-2-fluoropropanoate. The procedure was the same as that in the synthesis of I-665. MS: $[M+1]^+$ 467.

Example 105: Synthesis of (2S,5S)-1-(7,8-dichloro-4-(1H-imidazol-1-yl)quinolin-2-yl)-5-(2-hydroxyethyl)pyrrolidine-2-carboxylic acid (I-783)

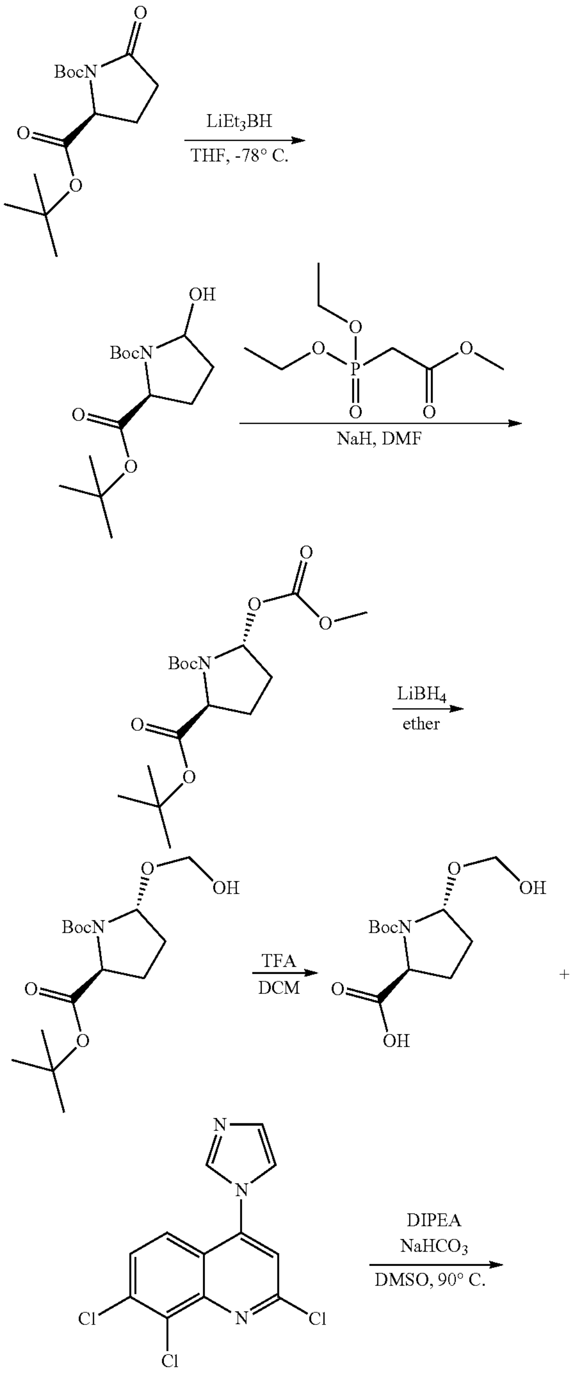

-continued

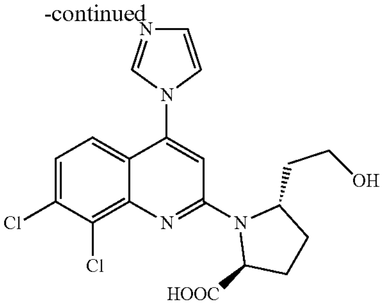

I-783

Step 1: di-tert-Butyl (2S)-5-hydroxypyrrolidine-1,2-dicarboxylate. To a vial were added di-tert-butyl (S)-5-oxopyrrolidine-1,2-dicarboxylate (1.14 g, 4.0 mmol, 1.0 eq.) and anhydrous THF (20 mL). The solution was cooled in a dry ice/acetone bath for 20 min. Then a solution of $LiEt_3BH$ (1 M, 4.8 mL, 4.8 mmol) was added at −78° C. dropwise. After addition, the resulting reaction mixture was stirred at −78° C. for 30 min. A saturated $NaHCO_3$ in $H_2O$ (6 mL) was added to quench the reaction and the reaction mixture was warmed to 0° C. slowly followed by addition of $H_2O_2/H_2O$ (30%, 0.050 mL). After being stirred at room temperature for 20 min, the reaction mixture was concentrated, diluted by $H_2O$ (20 mL), extracted by DCM (3×20 mL), and dried over $Na_2SO_4$. After concentration, the crude was used in the next step.

Step 2: di-tert-Butyl (2S,5S)-5-(2-methoxy-2-oxoethyl) pyrrolidine-1,2-dicarboxylate. To a stirred suspension of sodium hydride (60%, 100 mg, 2.5 mmol, 1.2 eq.) in anhydrous DMF (5 mL) was added methyl 2-(diethoxyphosphoryl)acetate (529 mg, 2.5 mmol, 1.2 eq.). The mixture was stirred at room temperature for 1 hour and then a solution of the crude in step 1 (602 mg, 2.09 mmol) in DMF (5 mL) was added. The reaction was stirred overnight at room temperature, quenched with saturated aqueous $NH_4Cl$ solution, extracted with ethyl acetate (3×25 mL), and dried over $Na_2SO_4$. After concentration, the residue was purified by silica gel chromatography to afford the title product (150 mg).

Step 3: di-tert-Butyl (2S,5S)-5-(2-hydroxyethyl)pyrrolidine-1,2-dicarboxylate. To a vial were added di-tert-butyl (2S,5S)-5-(2-methoxy-2-oxoethyl)pyrrolidine-1,2-dicarboxylate (150 mg, 0.437 mmol, 1.0 eq.) and diethyl ether (2.5 mL). Then $LiBH_4$ (19 mg, 0.874 mmol, 2 eq.) was added and the resulting reaction mixture was stirred overnight at room temperature. After addition of $HOAc/H_2O$ (1 M, 2 mL) and $H_2O$ (10 mL), the reaction mixture was extracted with ethyl acetate (2×20 mL) and dried over $Na_2SO_4$. After concentration, the residue was purified by silica gel chromatography to afford the title product (103 mg).

Step 4: (2S,5S)-5-(2-Hydroxyethyl)pyrrolidine-2-carboxylic acid. The procedure was the same as that in the synthesis of I-665.

Step 5: (2S,5S)-1-(7,8-Dichloro-4-(1H-imidazol-1-yl) quinolin-2-yl)-5-(2-hydroxyethyl)pyrrolidine-2-carboxylic acid. The procedure was the same as that in the synthesis described above for I-665. MS: $[M+1]^+$ 421.

Example 106: Synthesis of (2S,5S)-5-(2-(2-carboxyethoxy)ethyl)-1-(7,8-dichloro-4-(1H-imidazol-1-yl)quinolin-2-yl)pyrrolidine-2-carboxylic acid (I-714)

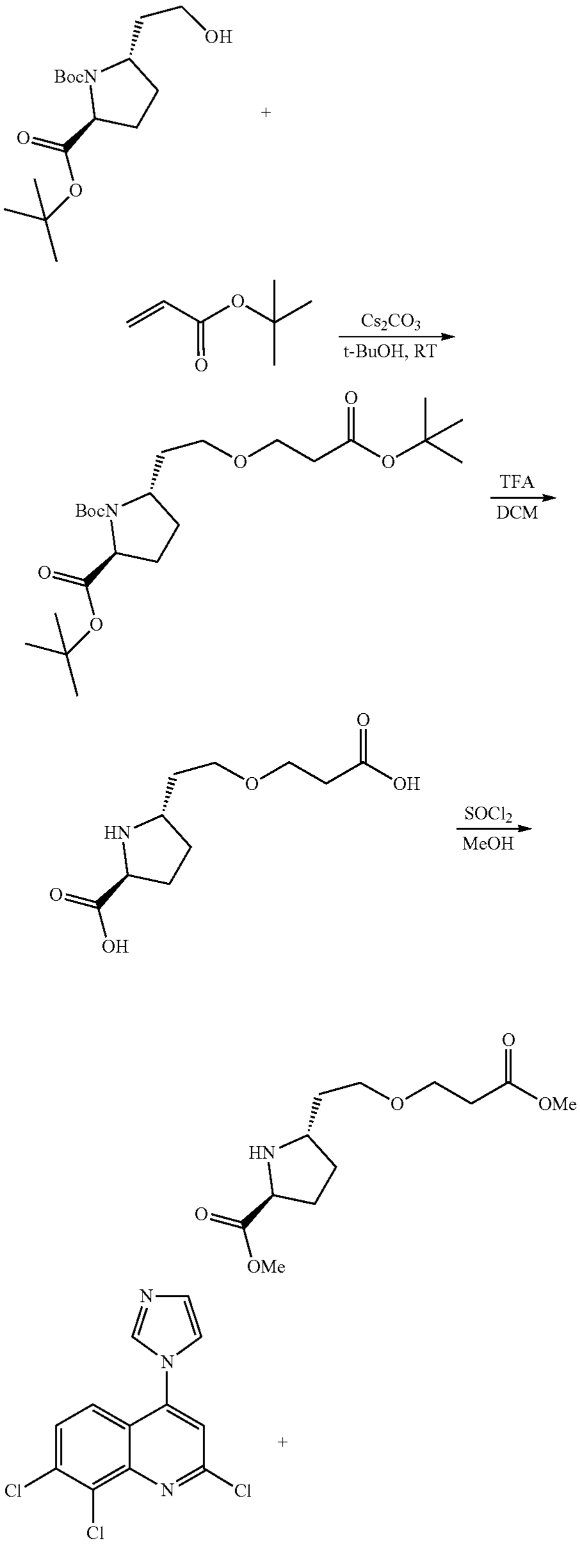

-continued

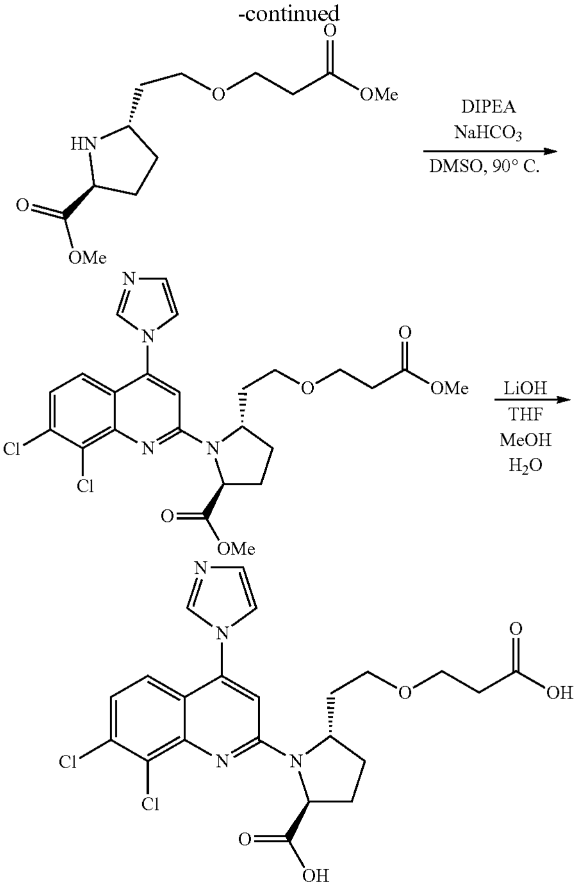

I-714

Step 1: di-tert-Butyl (2S,5S)-5-(2-(3-(tert-butoxy)-3-oxopropoxy)ethyl)pyrrolidine-1,2-dicarboxylate. The procedure was the same as that in the synthesis described above for I-665.

Step 2: (2S,5S)-5-(2-(2-Carboxyethoxy)ethyl)pyrrolidine-2-carboxylic acid. The procedure was the same as that in the synthesis of I-665.

Step 3: Methyl (2S,5S)-5-(2-(3-methoxy-3-oxopropoxy)ethyl)pyrrolidine-2-carboxylate. The procedure was the same as that in the synthesis described above for I-665.

Step 4: Methyl (2S,5S)-1-(7,8-dichloro-4-(1H-imidazol-1-yl)quinolin-2-yl)-5-(2-(3-methoxy-3-oxopropoxy)ethyl)pyrrolidine-2-carboxylate. The procedure was the same as that in the synthesis described above for I-665.

Step 5: (2S,5S)-5-(2-(2-Carboxyethoxy)ethyl)-1-(7,8-dichloro-4-(1H-imidazol-1-yl)quinolin-2-yl)pyrrolidine-2-carboxylic acid (I-714). To a vial were added methyl (2S,5S)-1-(7,8-dichloro-4-(1H-imidazol-1-yl)quinolin-2-yl)-5-(2-(3-methoxy-3-oxopropoxy)ethyl)pyrrolidine-2-carboxylate (3.7 mg, 0.0071 mmol, 1.0 eq.), THF (0.5 mL), MeOH (0.3 mL), and a solution of $LiOH \cdot H_2O$ (1.5 mg, 0.0355 mmol, 5.0 eq.)/$H_2O$ (0.1 mL). The resulting solution was stirred at 40° C. for 6 h and acidized by aqueous HOAc (1 M, 0.040 mL). After concentration, the title product was obtained. MS: $[M+1]^+$ 493.

Example 107: Synthesis of (2S,5S)-5-(2-(carboxymethoxy)ethyl)-1-(7,8-dichloro-4-(1H-imidazol-1-yl)quinolin-2-yl)pyrrolidine-2-carboxylic acid (I-715)

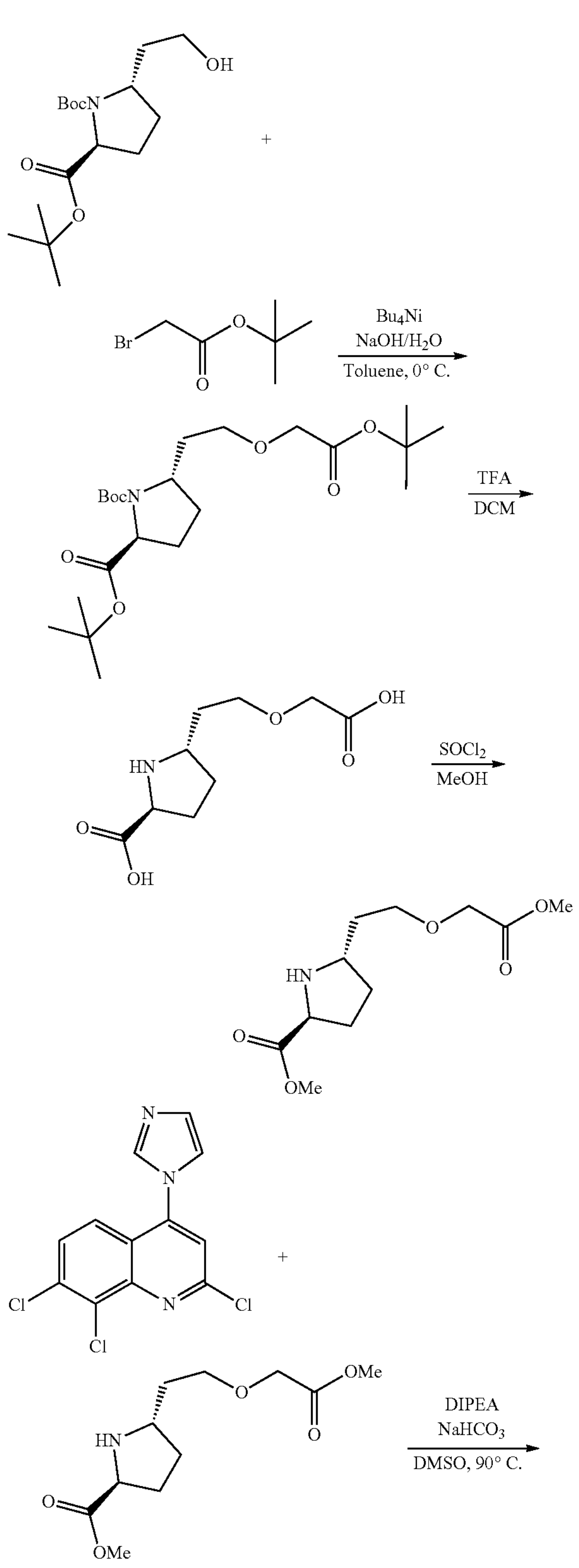

-continued

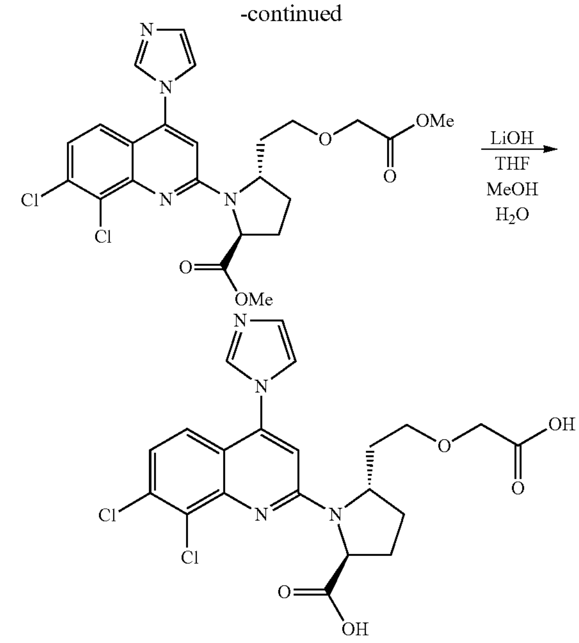

I-715

Step 1: di-tert-Butyl (2S,5S)-5-(2-(2-(tert-butoxy)-2-oxoethoxy)ethyl)pyrrolidine-1,2-dicarboxylate. The procedure was the same as that in the synthesis described above for I-667.

Step 2: (2S,5S)-5-(2-(Carboxymethoxy)ethyl)pyrrolidine-2-carboxylic acid. The procedure was the same as that in the synthesis described above for I-665.

Step 3: Methyl (2S,5S)-5-(2-(2-methoxy-2-oxoethoxy)ethyl)pyrrolidine-2-carboxylate. The procedure was the same as that in the synthesis described above for I-665.

Step 4: Methyl (2S,5S)-1-(7,8-dichloro-4-(1H-imidazol-1-yl)quinolin-2-yl)-5-(2-(2-methoxy-2-oxoethoxy)ethyl)pyrrolidine-2-carboxylate. The procedure was the same as that in the synthesis described above for I-665.

Step 5: (2S,5S)-5-(2-(Carboxymethoxy)ethyl)-1-(7,8-dichloro-4-(1H-imidazol-1-yl)quinolin-2-yl)pyrrolidine-2-carboxylic acid. The procedure was the same as that in the synthesis described above for I-714. MS: $[M+1]^+$ 479.

Example 108: Synthesis of (S)-1-(7,8-dichloro-4-(1H-imidazol-1-yl)quinolin-2-yl)pyrrolidin-3-amine (I-765)

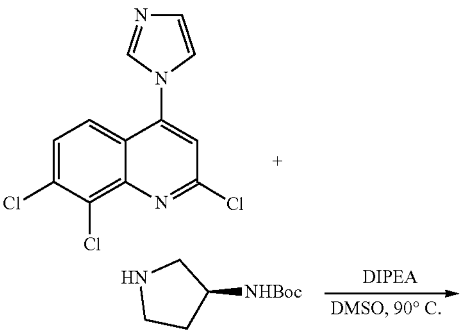

-continued

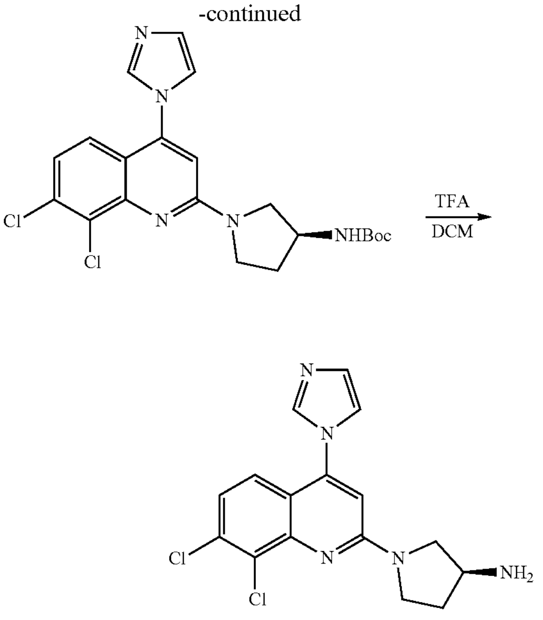

I-765

Step 1: tert-Butyl (S)-(1-(7,8-dichloro-4-(1H-imidazol-1-yl)quinolin-2-yl)pyrrolidin-3-yl)carbamate. The procedure was the same as that in the synthesis of I-665.

Step 2: (S)-1-(7,8-dichloro-4-(1H-imidazol-1-yl)quinolin-2-yl)pyrrolidin-3-amine. The procedure was the same as that in the synthesis described above for I-665. MS: $[M+1]^+$ 348.

Example 109: Synthesis of (S)—N-(1-(7,8-dichloro-4-(1H-imidazol-1-yl)quinolin-2-yl)pyrrolidin-3-yl)acetamide (I-764)

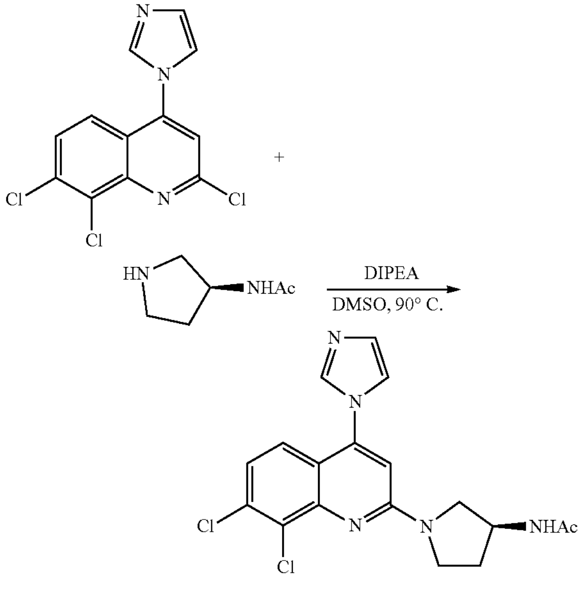

I-764

The procedure used to prepare I-764 was the same as that described above to prepare I-665. MS: $[M+1]^+$ 390.

Example 110: Synthesis of (S)-2-((1-(7,8-dichloro-4-(1H-imidazol-1-yl)quinolin-2-yl)pyrrolidin-2-yl)methoxy)acetamide (I-760)

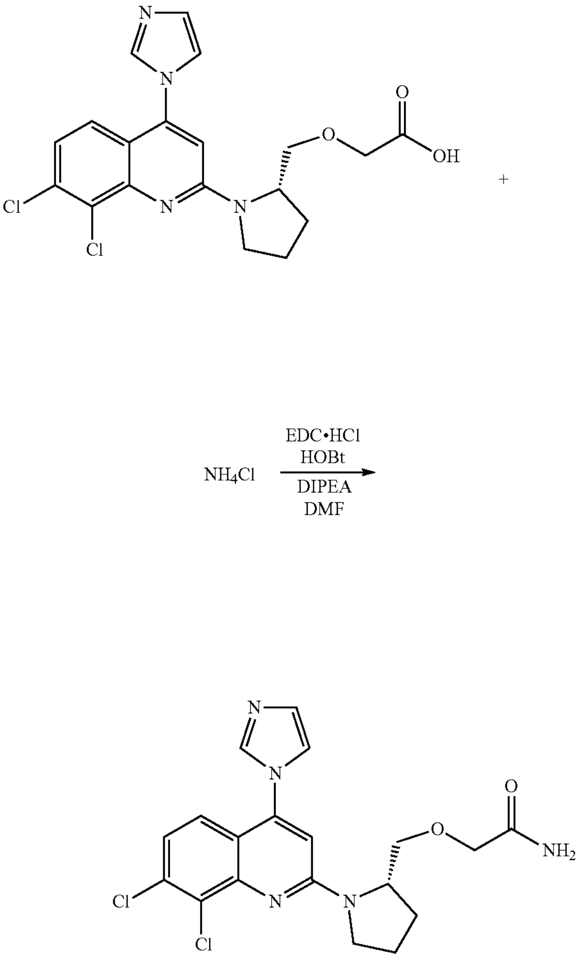

I-760

To a vial were added (S)-2-((1-(7,8-dichloro-4-(1H-imidazol-1-yl)quinolin-2-yl)pyrrolidin-2-yl)methoxy)acetic acid (30 mg, 0.0712 mmol, 1.0 eq.), $NH_4Cl$ (19 mg, 0.356 mmol, 5.0 eq.), EDC·HCl (27 mg, 0.142 mmol, 2.0 eq.), HOBt (9.6 mg, 0.0712 mmol, 1.0 eq), DMF (0.5 mL). With stirring, DIPEA (0.062 mL, 0.356 mmol, 5.0 eq.) was added and the reaction mixture was stirred overnight at room temperature. The reaction mixture was diluted with ethyl acetate (20 mL), washed with $H_2O$ (3×10 mL), brine (10 mL), dried over $Na_2SO_4$. After concentration, the residue was purified by silica gel chromatography to afford the title product. MS: $[M+1]^+$ 420.

The following compounds are prepared essentially by the same methods as described above for I-760.

| Example | Starting Material | | Structure | MS $[M+1]^+$ |
|---|---|---|---|---|
| I-761 | 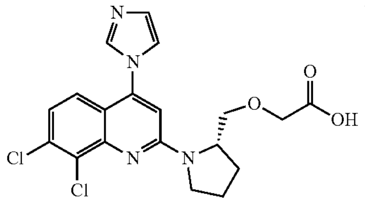 [SMILES: O=C(O)COC[C@@H]1CCCN1c1cc(-n2ccnc2)c2ccc(Cl)c(Cl)c2n1] | $NH_2OH{\cdot}HCl$ | 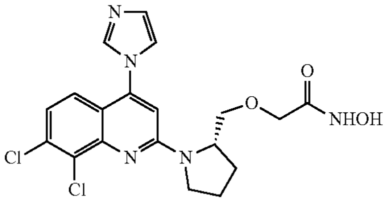 | 436 |
| I-762 | 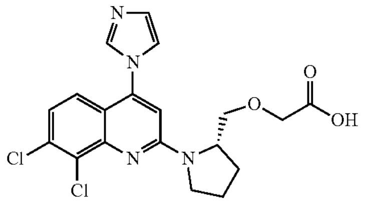 [SMILES: O=C(O)COC[C@@H]1CCCN1c1cc(-n2ccnc2)c2ccc(Cl)c(Cl)c2n1] | $NH_2CN$ | 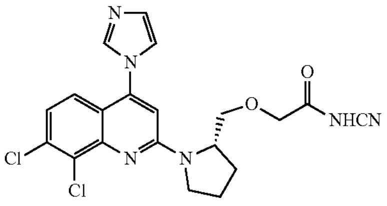 | 445 |

Example 111: Synthesis of (S)-(2-((1-(7,8-dichloro-4-(1H-imidazol-1-yl)quinolin-2-yl)pyrrolidin-2-yl)methoxy)ethyl)phosphonic acid (I-763)

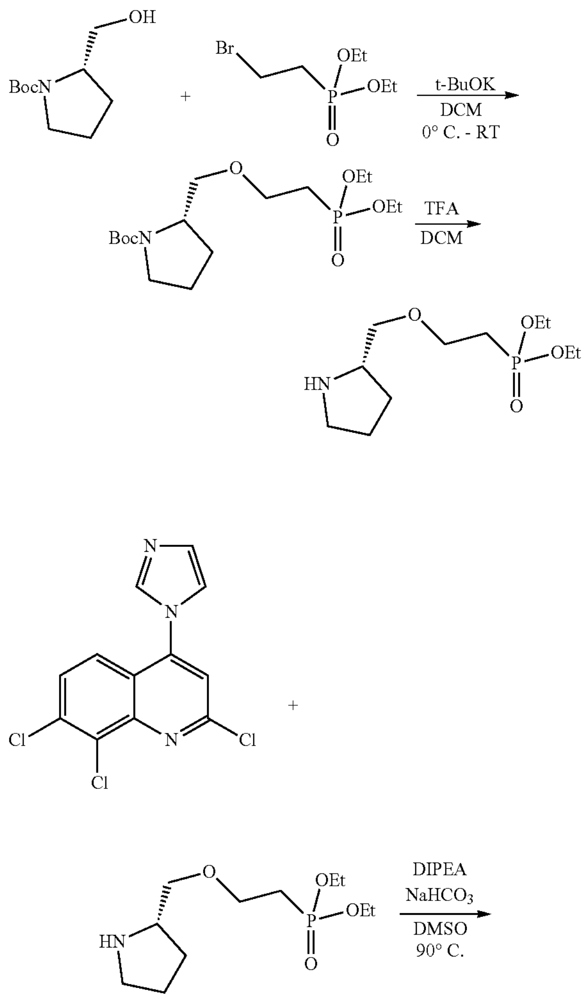

-continued

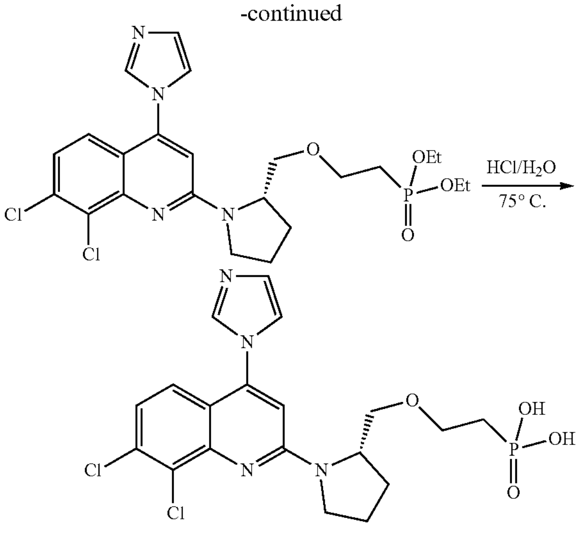

I-763

Step 1: tert-Butyl (S)-2-((2-(diethoxyphosphoryl)ethoxy)methyl)pyrrolidine-1-carboxylate. To a vial were added t-BuOK (247 mg, 2.2 mmol, 2.2 eq.) and anhydrous DCM (2.0 mL). The mixture was cooled in an ice bath for 20 min, followed by addition of tert-butyl (S)-2-(hydroxymethyl)pyrrolidine-1-carboxylate (201 mg, 1.0 mmol, 1.0 eq.). After the mixture was stirred at 0° C. for 30 min, diethyl (2-bromoethyl)phosphonate (294 mg, 1.2 mmol, 1.2 eq.) was added and the resultant reaction mixture was stirred at room temperature overnight. After being quenched by addition of ice (5 g), the mixture was diluted with ethyl acetate (30 mL), washed with $H_2O$ (2×10 mL), brine (10 mL), and dried over $Na_2SO_4$. After concentration, the residue was purified by silica gel chromatography to afford the title product (155 mg).

Step 2: Diethyl (S)-(2-(pyrrolidin-2-ylmethoxy)ethyl)phosphonate. The procedure was the same as that in the synthesis described above for I-665.

Step 3: Diethyl (S)-(2-((1-(7,8-dichloro-4-(1H-imidazol-1-yl)quinolin-2-yl)pyrrolidin-2-yl)methoxy)ethyl)phosphonate. The procedure was the same as that in the synthesis described above for I-665.

Step 4: (S)-(2-((1-(7,8-Dichloro-4-(1H-imidazol-1-yl)quinolin-2-yl)pyrrolidin-2-yl)methoxy)ethyl)phosphonic acid. The mixture of diethyl (S)-(2-((1-(7,8-dichloro-4-(1H-imidazol-1-yl)quinolin-2-yl)pyrrolidin-2-yl)methoxy)ethyl)phosphonate (9.5 mg, 0.018 mmol) and a solution of HCl/$H_2O$ (37%, 1.0 mL) was stirred at 75° C. over two days. The mixture was concentrated to give the title product. (MS: $[M+1]^+$ 471)

Example 112: Synthesis of 3-((2S,3S)-1-(7,8-dichloro-4-(1H-imidazol-1-yl)quinolin-2-yl)-3-hydroxypyrrolidine-2-carboxamido)propanoic acid (I-784) and methyl 3-((2S,3S)-1-(7,8-dichloro-4-(1H-imidazol-1-yl)quinolin-2-yl)-3-hydroxypyrrolidine-2-carboxamido)propanoate (I-791)

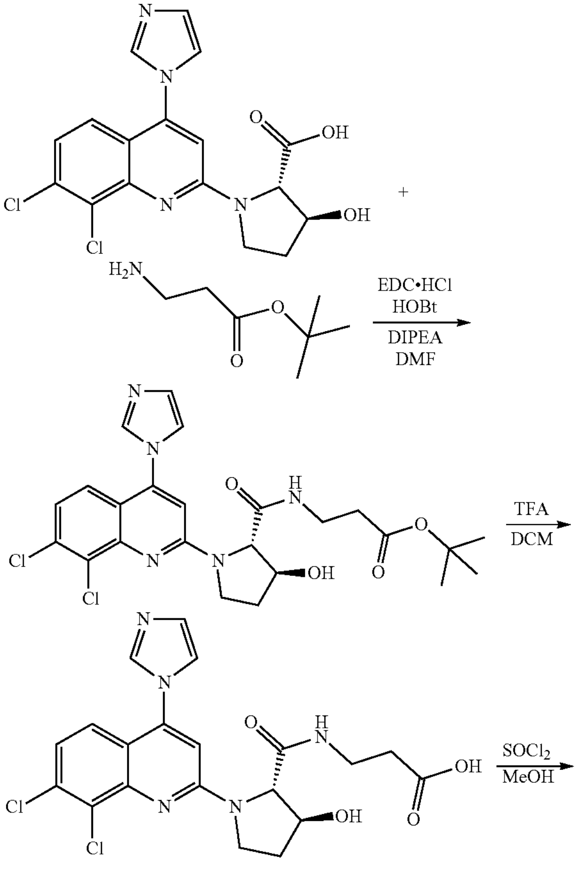

I-784

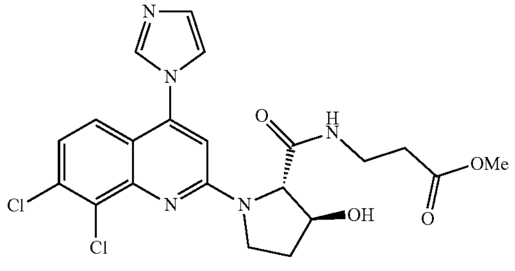

I-791

Step 1: tert-Butyl 3-((2S,3S)-1-(7,8-dichloro-4-(1H-imidazol-1-yl)quinolin-2-yl)-3-hydroxypyrrolidine-2-carboxamido)propanoate. The procedure was the same as that in the synthesis described above for I-760.

Step 2: 3-((2S,3S)-1-(7,8-Dichloro-4-(1H-imidazol-1-yl)quinolin-2-yl)-3-hydroxypyrrolidine-2-carboxamido)propanoic acid. The procedure was the same as that in the synthesis described above for I-665. MS: $[M+1]^+$ 464.

Step 3: Methyl 3-((2S,3S)-1-(7,8-dichloro-4-(1H-imidazol-1-yl)quinolin-2-yl)-3-hydroxypyrrolidine-2-carboxamido)propanoate. The procedure was the same as that in the synthesis described above for I-665. MS: $[M+1]^+$ 478.

Example 113: Synthesis of 2-((2R,3S)-1-(7,8-dichloro-4-(1H-imidazol-1-yl)quinolin-2-yl)-3-hydroxypyrrolidin-2-yl)acetic acid (I-785) and methyl 2-((2R,3S)-1-(7,8-dichloro-4-(1H-imidazol-1-yl)quinolin-2-yl)-3-hydroxypyrrolidin-2-yl)acetate (I-786)

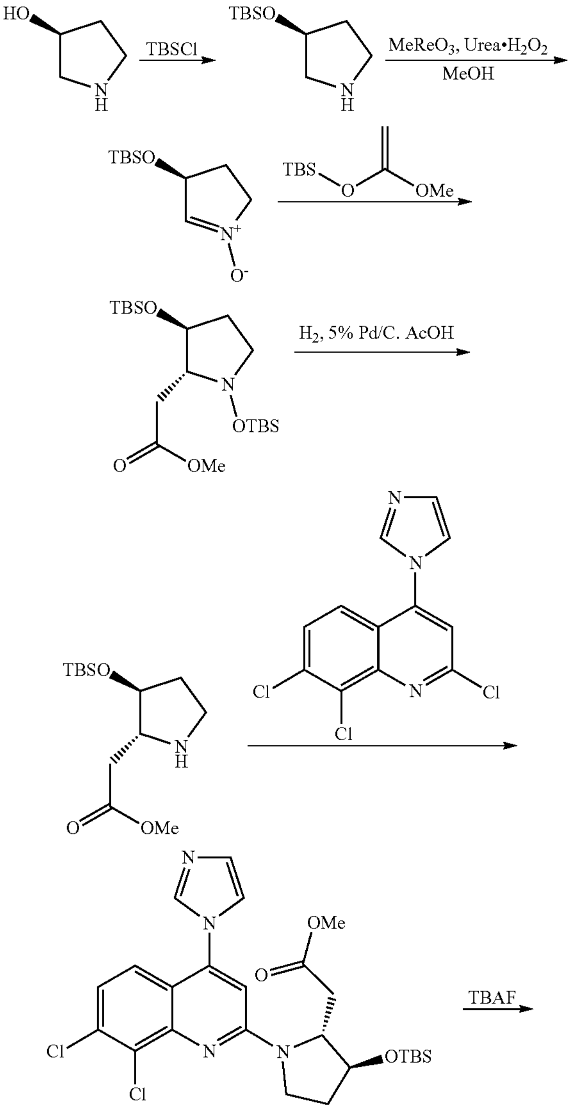

-continued

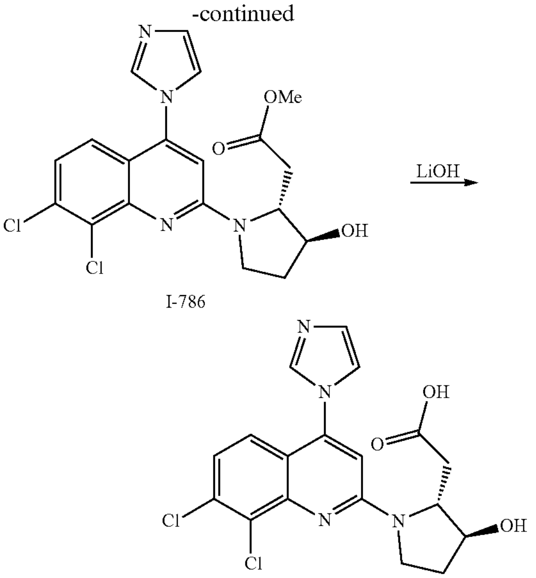

I-786

I-785

Step 1: (S)-4-((tert-Butyldimethylsilyl)oxy)-3,4-dihydro-2H-pyrrole 1-oxide. (S)-Pyrrolidin-3-ol (1.5 g, 17.2 mmol) was treated with TBSCl (3.37 g, 22.3 mol) and imidazole (3.51 g) in DCM (25 mL) overnight. After dilution with DCM (50 mL), the organic layer was washed with water (15 mL), saturated $NaHCO_3$ (15 mL) and brine. The isolated organic layer was dried over anhydrous $Na_2SO_4$. Concentration under reduced pressure afforded the desired crude (S)-3-((tert-butyldimethylsilyl)oxy)pyrrolidine (4.3 g), which was used in the following step without further purification. To an ice-water chilled solution of (S)-3-((tert-butyldimethylsilyl)oxy)pyrrolidine (3.5 g) in MeOH (40 mL) was added urea hydrogen peroxide (4.94 g). Then a solution of $CH_3ReO_3$ (21.8 mg) in MeOH (3 mL) was stepwise added to the above reaction mixture over 3 hours. After being stirred at room temperature over 4 h, the reaction mixture was quenched with $Na_2S_2O_3$ (4 g, 27 mmol) cautiously. After aqueous work up with EtOAc (80 mL), the reaction mixture was purified by silica gel column chromatography to afford two products, the less polar fraction is the title product (0.72 g), eluting with a gradient between DCM and EtOAc. MASS: m/z: $[M+1]^+$ : 216.

Step 2: Methyl 2-((2R,3S)-1,3-bis((tert-butyldimethylsilyl)oxy)pyrrolidin-2-yl)acetate. To a solution of (S)-4-((tert-butyldimethylsilyl)oxy)-3,4-dihydro-2H-pyrrole 1-oxide (0.72 g) in DCM were added 4 Å sieves (1.1 g) and $ZnI_2$ (0.26 g). After the suspended solution was chilled with a bath of dry ice-acetone under $N_2$, tert-butyl((1-methoxyvinyl)oxy)dimethylsilane (640 mg) was added stepwise via a syringe. The reaction mixture was stirred overnight as the temperature slowly rose back to room temperature. After aqueous work-up with DCM and concentration under reduced pressure, the resultant mixture was purified by silica gel column chromatography, eluting with 5% EtOAc in Hexane, to afford the title product (245 mg) as colorless solids. MASS: m/z: $[M+1]^+$ : 404.

Step 3: Methyl 2-((2R,3S)-3-((tert-butyldimethylsilyl)oxy)pyrrolidin-2-yl)acetate. A solution of methyl 2-((2R,3S)-1,3-bis((tert-butyldimethylsilyl)oxy)pyrrolidin-2-yl)acetate (109 mg) with 5% Pd/C in AcOH (3.5 mL) was degassed (vacuum/purge) three times with hydrogen and stirred under hydrogen overnight. After filtration, rinsing with EtOAc, and concentration under reduced pressure, the resultant mixture was dissolved in EtOAc (15 mL). The organic layer was washed with sat. $NaHCO_3$, brine, and dried over anhydrous $Na_2SO_4$. Concentration under reduced pressure afforded the title product (I-786-4, 76.8 mg). MASS: m/z: $[M+1]^+$ : 274.

Step 4: 2-((2R,3S)-1-(7,8-Dichloro-4-(1H-imidazol-1-yl)quinolin-2-yl)-3-hydroxypyrrolidin-2-yl)acetate (I-786). To a solution of methyl 2-((2R,35)-3-((tert-butyldimethylsilyl)oxy)pyrrolidin-2-yl)acetate (76.8 mg) and DIPEA (0.12 mL) in DMSO (0.4 mL) was added 2,7,8-trichloro-4-(1H-imidazol-1-yl)quinoline (50 mg). The resultant mixture was stirred at 90° C. over 3 h and diluted with EtOAc (15 mL). The organic solution was treated with 1 M TBAF in THF (0.4 mL) over 30 min. The organic solution was washed with water and brine, then dried over anhydrous $Na_2SO_4$. Concentration under reduced pressure and purification by silica gel column chromatography afforded the title product (I-786, 18 mg) as light tan solids. MASS: m/z: $[M+1]^+$ : 421.

Step 5: 2-((2R,3S)-1-(7,8-Dichloro-4-(1H-imidazol-1-yl)quinolin-2-yl)-3-hydroxypyrrolidin-2-yl)acetic acid (I-785). To a solution of I-786 (44.8 mg) in MeOH (0.8 mL), THF (0.6 mL) and water (0.2 mL) was added $LiOH \cdot H_2O$ (18 mg). The solution was stirred at room temperature over 3 h. After removal of the organic solvents under reduced pressure, the resultant slurry was mixed with AcOH (0.025 mL) and water (1.5 mL) to afford a suspended solution. The solid was isolated via a centrifuge and rinsed with water (0.5 mL×2). The wet cake was lyophilized to afford the title product (30 mg) as tan solids. MASS: m/z: $[M+1]^+$ : 407.

Example 114: Synthesis of ethyl (2-((2R,3S)-1-(7,8-dichloro-4-(1H-imidazol-1-yl)quinolin-2-yl)-3-hydroxypyrrolidin-2-yl)acetyl)glycinate (I-787) and (2-((2R,3S)-1-(7,8-dichloro-4-(1H-imidazol-1-yl)quinolin-2-yl)-3-hydroxypyrrolidin-2-yl)acetyl)glycine (I-788)

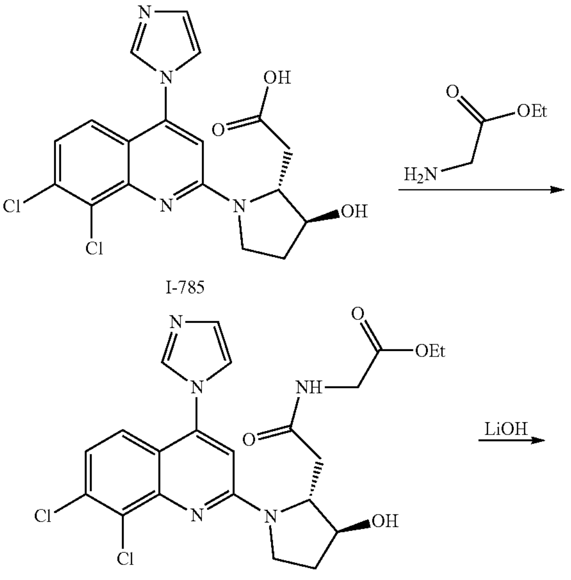

I-785

I-787

-continued

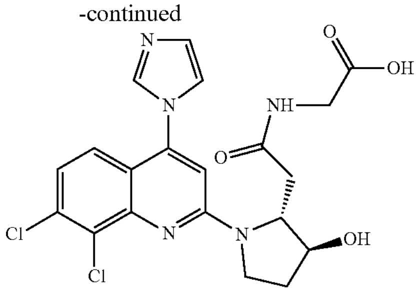

I-788

Step 1: Ethyl (2-((2R,3S)-1-(7,8-dichloro-4-(1H-imidazol-1-yl)quinolin-2-yl)-3-hydroxypyrrolidin-2-yl)acetyl) glycinate (I-787). To a solution of 2-((2R,3S)-1-(7,8-dichloro-4-(1H-imidazol-1-yl)quinolin-2-yl)-3-hydroxypyrrolidin-2-yl)acetic acid (I-785, 20 mg) in DMF (0.7 mL) were added EDC HCl (19 mg), HOBt (13 mg) and TEA (20 mg). The resultant solution was stirred at room temperature over 24 h. After the dilution with EtOAc (15 mL), the organic layer was washed with sat. $NaHCO_3$, brine and dried over anhydrous $Na_2SO_4$. Concentration under reduced pressure and silica gel column chromatography, eluting with a gradient between hexane and EtOAc, afforded the title product (16 mg). MASS: m/z: $[M+1]^+$ : 492.

Step 2: (2-((2R,3S)-1-(7,8-Dichloro-4-(1H-imidazol-1-yl)quinolin-2-yl)-3-hydroxypyrrolidin-2-yl)acetyl)glycine (I-788). To a solution of I-787 (8 mg) in MeOH (0.6 mL) and water (0.2 mL) was added LiOH·$H_2O$ (8 mg). The resultant solution was stirred at room temperature over 2h. After removal of MeOH and acidification of aqueous part with 1M HOAc (0.08 mL), the formed solids were isolated via a centrifuge and lyophilized to afford the titled product (6 mg) as tan solids. MASS: m/z: $[M+1]^+$ : 464.

Example 115: Synthesis of (3aR,6aR)-4-(7,8-dichloro-4-(1H-imidazol-1-yl)quinolin-2-yl)hexahydro-2H-furo[3,2-b]pyrrol-2-one (I-774) and 2-((2R,3R)-1-(7,8-dichloro-4-(1H-imidazol-1-yl)quinolin-2-yl)-3-hydroxypyrrolidin-2-yl)acetic acid (I-781)

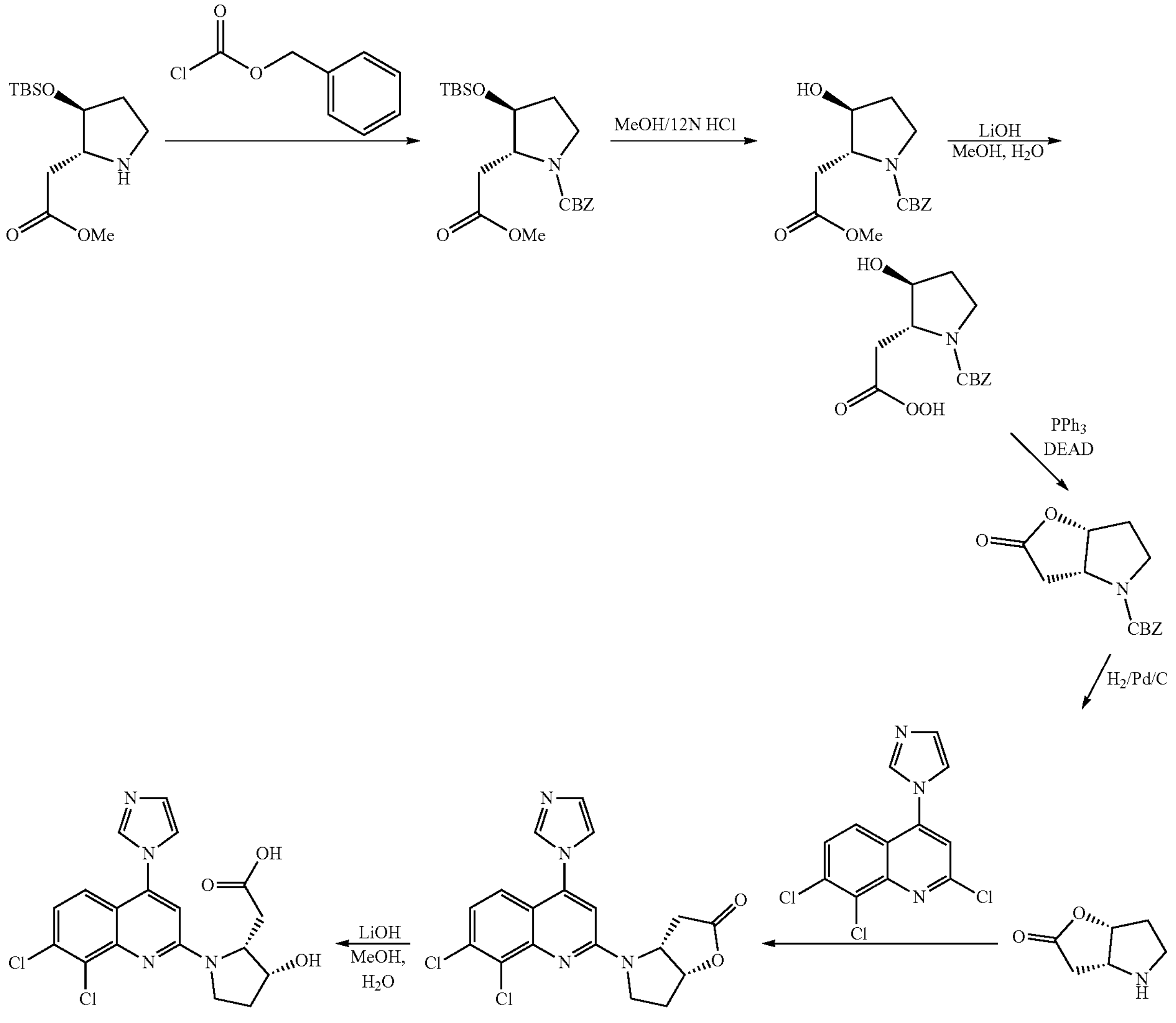

I-781

I-774

Step 1: Benzyl (2R,3S)-3-((tert-butyldimethylsilyl)oxy)-2-(2-methoxy-2-oxoethyl)pyrrolidine-1-carboxylate. To a solution of methyl 2-((2R,3S)-3-((tert-butyldimethylsilyl)oxy)pyrrolidin-2-yl)acetate (280 mg) in EtOAc (8 mL) and water (3 mL) were added benzyl carbonochloridate (CBZ-Cl, 0.2 mL) and $K_2CO_3$ (200 mg). The reaction mixture was stirred at room temperature over 4 h. After the reaction mixture was diluted with EtOAc (25 mL), the organic layer was washed with water and brine, then dried over anhydrous $Na_2SO_4$. Removal of the organic solvents afforded the title product (300 mg) as oil. MASS: m/z: $[M+1]^+$ : 408.

Step 2: Benzyl (2R,3S)-3-hydroxy-2-(2-methoxy-2-oxoethyl)pyrrolidine-1-carboxylate. To a solution of benzyl (2R,3S)-3-((tert-butyldimethylsilyl)oxy)-2-(2-methoxy-2-oxoethyl)pyrrolidine-1-carboxylate (300 mg) in MeOH (5 mL) were added water (0.2 mL) and conc. HCl (0.2 mL). After the resultant solution was stirred overnight, it was diluted with EtOAc (40 mL). The organic layer was washed with water and brine, then dried over anhydrous $Na_2SO_4$. Removal of the organic solvent and purification by a silica gel column afforded the title product (143 mg) as oil. MASS: m/z: $[M+1]^+$ 294.

Step 3: 2-((2R,3S)-1-((Benzyloxy)carbonyl)-3-hydroxypyrrolidin-2-yl)acetic acid. To a solution of benzyl (2R,3S)-3-hydroxy-2-(2-methoxy-2-oxoethyl)pyrrolidine-1-carboxylate (143 mg) in MeOH (5 mL) and water (2 mL) was added $LiOH \cdot H_2O$ (62 mg). After the resultant solution was stirred over 3 h, 12 M HCl (0.014 mL) was added to adjust the pH to 2. After the reaction mixture was extracted with EtOAc (15 mL×3), the combined organic layers were washed with brine and dried over anhydrous $Na_2SO_4$. Removal of the organic solvents afforded the title product (98 mg) as colorless solids. MASS: m/z: $[M+1]^+$ 280.

Step 4: Benzyl (3aR,6aR)-2-oxohexahydro-4H-furo[3,2-b]pyrrole-4-carboxylate. To a solution of 2-((2R,3S)-1-((benzyloxy)carbonyl)-3-hydroxypyrrolidin-2-yl)acetic acid (97 mg) in THF (8 mL) were added $PPh_3$ (137 mg) and DEAD (0.24 mL, 40 wt % in toluene). After being stirred over 4 h, the reaction mixture was diluted with EtOAc. The organic layer was washed with water and brine, then dried over anhydrous $Na_2SO_4$. After removal of the organic solvents, the residuals were purified by a silica gel column, eluting with EtOAc/Hex, to afford the title product (75 mg).

Step 5: (3aR,6aR)-Hexahydro-2H-furo[3,2-b]pyrrol-2-one. To a solution of benzyl (3aR,6aR)-2-oxohexahydro-4H-furo[3,2-b]pyrrole-4-carboxylate (75 mg) in MeOH (4 mL) were added AcOH (0.1 mL) and 5% Pd/C (20 mg). The resultant suspension was degassed (vacuum-purge) with hydrogen three times and stirred under hydrogen overnight. Filtration and concentration afforded the title product. MASS: m/z: $[M+1]^+$ 128.

Step 6: (3aR,6aR)-4-(7,8-dichloro-4-(1H-imidazol-1-yl)quinolin-2-yl)hexahydro-2H-furo[3,2-b]pyrrol-2-one (I-774) and 2-((2R,3R)-1-(7,8-dichloro-4-(1H-imidazol-1-yl)quinolin-2-yl)-3-hydroxypyrrolidin-2-yl)acetic acid (I-781). Following the last two steps of the preparation procedures for I-786 and I-785, both title compounds were prepared. I-774, MASS: m/z: $[M+1]^+$ 389. I-781, MASS: m/z: $[M+1]^+$ 407.

Example 116: Synthesis of 1-(7,8-dichloro-4-(1H-imidazol-1-yl)quinolin-2-yl)hexahydro-6H-furo[3,4-b]pyrrol-6-one (I-775) and 1-(7,8-dichloro-4-(1H-imidazol-1-yl)quinolin-2-yl)-3-(hydroxymethyl)pyrrolidine-2-carboxylic acid (I-782)

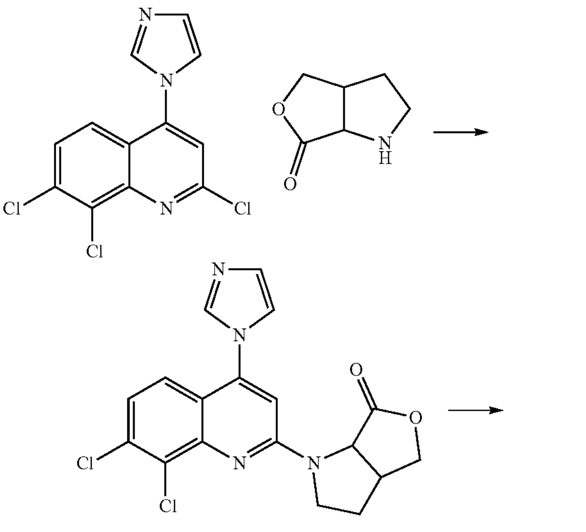

I-775

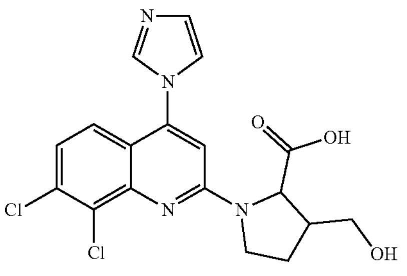

I-782

Following the last two steps of the preparation procedures of I-786 and I-785, I-775 was prepared from hexahydro-6H-furo[3,4-b]pyrrol-6-one and following hydrolysis afforded I-782. I-775, MASS: m/z: $[M+1]^+$ 389. I-782, MASS: m/z: $[M+1]^+$ 407.

Example 117: Synthesis of (S)-1-((1-(7,8-dichloro-4-(1H-imidazol-1-yl)quinolin-2-yl)pyrrolidin-2-yl)methyl)-1H-pyrazole-5-carboxylic acid (I-727)

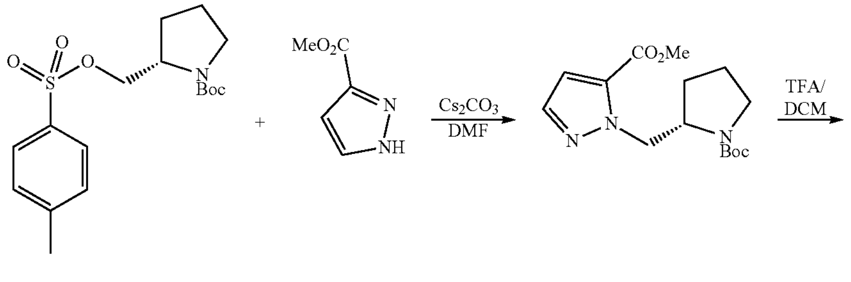

-continued

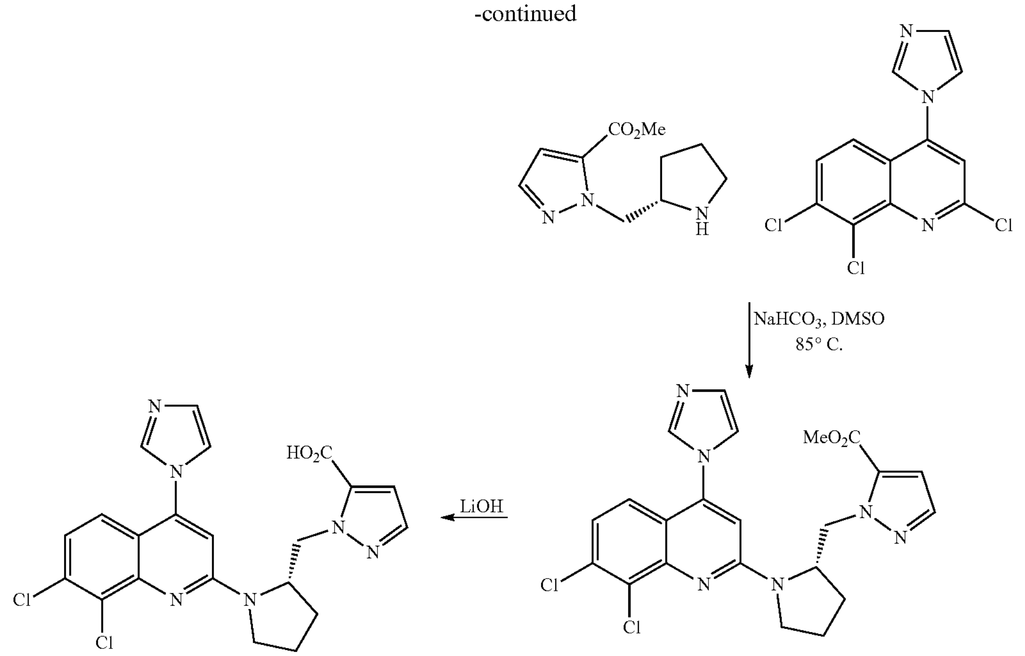

I-727

Step 1: Methyl (S)-1-((1-(tert-butoxycarbonyl)pyrrolidin-2-yl)methyl)-1H-pyrazole-5-carboxylate. To a solution tert-butyl (S)-2-((tosyloxy)methyl)pyrrolidine-1-carboxylate (274 mg) in DMF (1.5 mL) were added methyl 1H-pyrazole-3-carboxylate (145.8 mg) and $Cs_2CO_3$ (377 mg). After the resultant mixture was stirred overnight, it was diluted with EtOAC. The organic layer was washed with water and brine, dried over anhydrous $Na_2SO_4$. Removal of solvents under reduced pressure and a silica gel column purification, eluting with a gradient between hexane and EtOAc/DCM (1:3), afforded the title product.

Step 2: (S)-1-((1-(7,8-dichloro-4-(1H-imidazol-1-yl)quinolin-2-yl)pyrrolidin-2-yl)methyl)-1H-pyrazole-5-carboxylic acid (I-727). The title product was prepared by the deprotection of methyl (S)-1-((1-(tert-butoxycarbonyl)pyrrolidin-2-yl)methyl)-1H-pyrazole-5-carboxylate with TFA/DCM, coupling with 2,7,8-trichloro-4-(1H-imidazol-1-yl)quinoline, and hydrolysis with LiOH which were identical to the last three steps described above to prepare I-664. MASS: m/z: $[M+1]^+$ 457.

The following compounds are prepared essentially by the same methods described above for I-727.

| Example | Starting Material | Structure | MS $[M + 1]^+$ |
|---|---|---|---|
| I-728 | 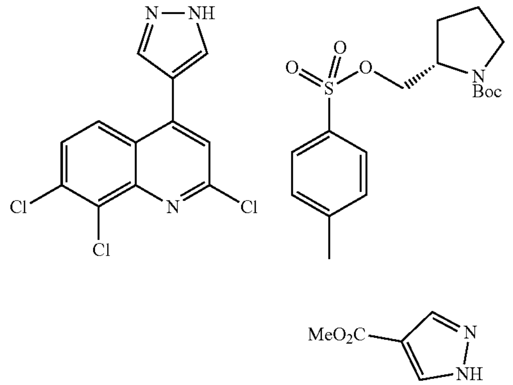 | 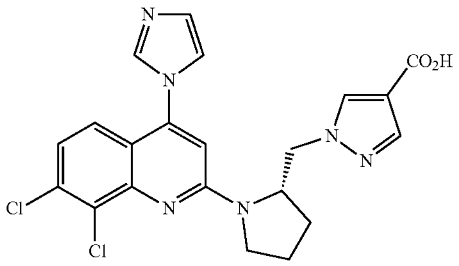 [SMILES: O=C(O)c1cnn(C[C@@H]2CCCN2c2cc(-n3ccnc3)c3ccc(Cl)c(Cl)c3n2)c1] | 457 |

-continued
| Example | Starting Material | Structure | MS [M + 1]+ |
|---|---|---|---|
| I-732 | 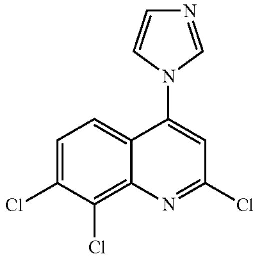 [SMILES: Clc1cc(-n2ccnc2)c2ccc(Cl)c(Cl)c2n1] 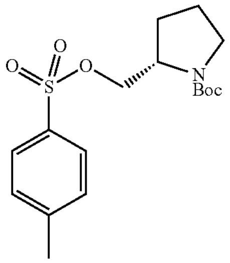 [SMILES: Cc1ccc(S(=O)(=O)OC[C@@H]2CCCN2C(=O)OC(C)(C)C)cc1] 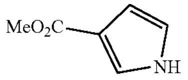 | 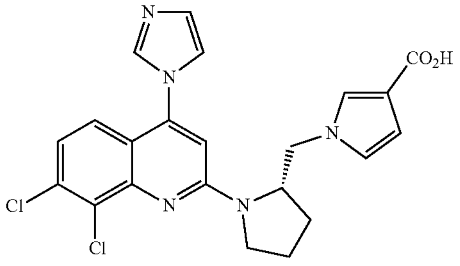 [SMILES: O=C(O)c1ccn(C[C@@H]2CCCN2c2cc(-n3ccnc3)c3ccc(Cl)c(Cl)c3n2)c1] | 456 |
| I-731 | 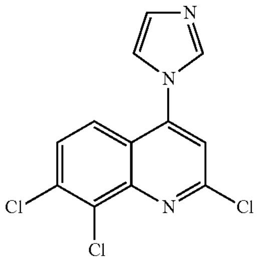 [SMILES: Clc1cc(-n2ccnc2)c2ccc(Cl)c(Cl)c2n1] 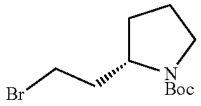 [SMILES: CC(C)(C)OC(=O)N1CCC[C@H]1CCBr] | 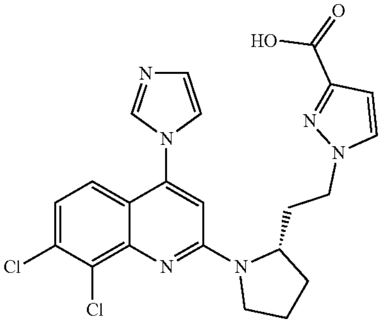 [SMILES: O=C(O)c1ccn(CC[C@@H]2CCCN2c2cc(-n3ccnc3)c3ccc(Cl)c(Cl)c3n2)n1] | 471 |
| I-729 | 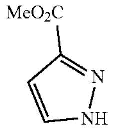 | 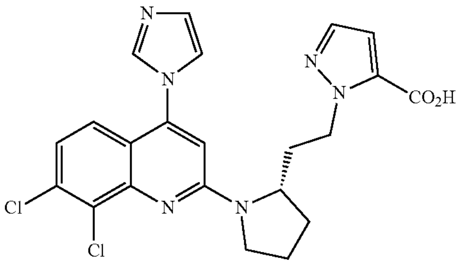 [SMILES: O=C(O)c1ccnn1CC[C@@H]1CCCN1c1cc(-n2ccnc2)c2ccc(Cl)c(Cl)c2n1] | 471 |
| I-730 | 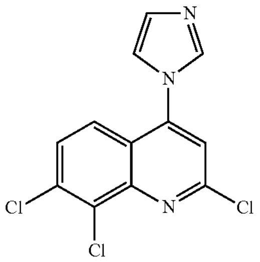 [SMILES: Clc1cc(-n2ccnc2)c2ccc(Cl)c(Cl)c2n1] 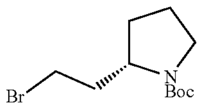 [SMILES: CC(C)(C)OC(=O)N1CCC[C@H]1CCBr] 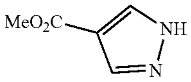 | 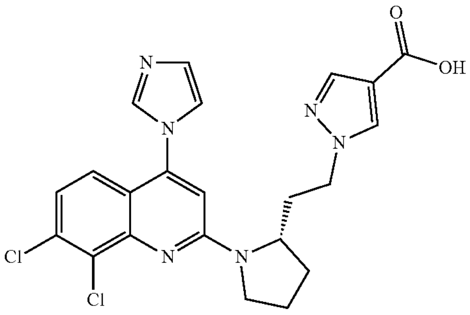 [SMILES: O=C(O)c1cnn(CC[C@@H]2CCCN2c2cc(-n3ccnc3)c3ccc(Cl)c(Cl)c3n2)c1] | 471 |

Example 118: Synthesis of 2-((R)-2-((S)-1-(7,8-dichloro-4-(1H-imidazol-1-yl)quinolin-2-yl)pyrrolidin-2-yl)-2-hydroxyethoxy)acetic acid (I-726)

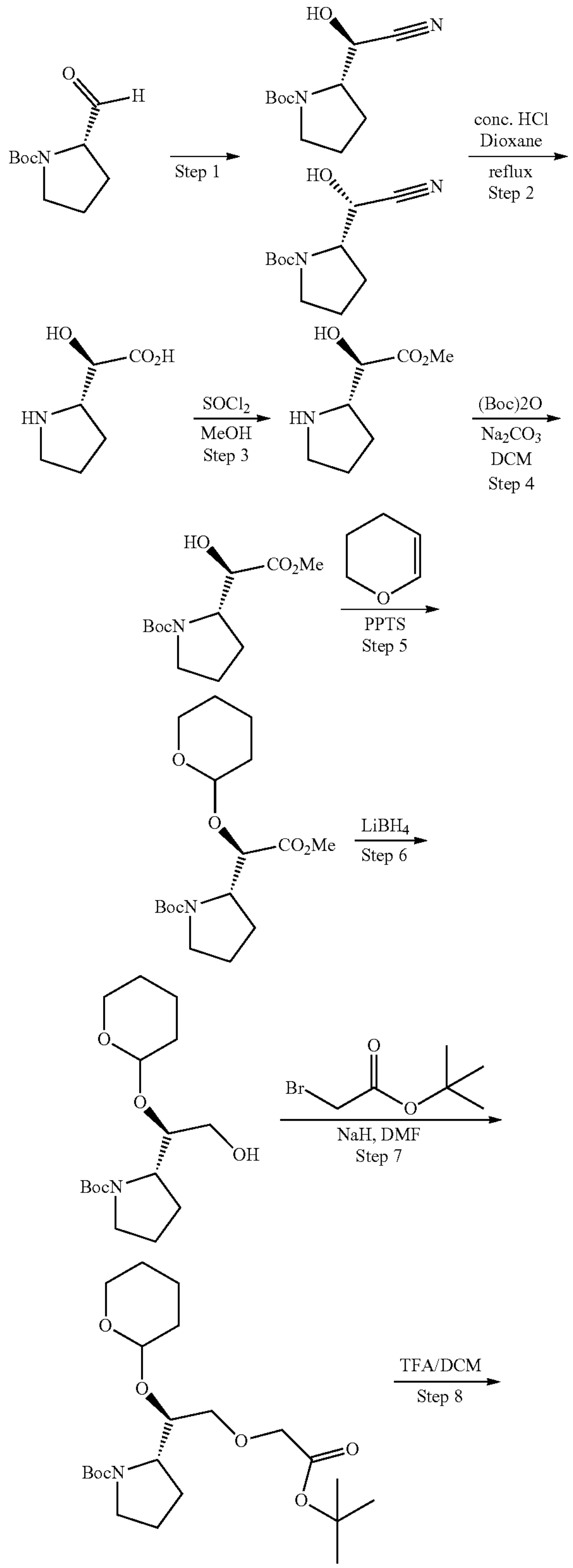

-continued

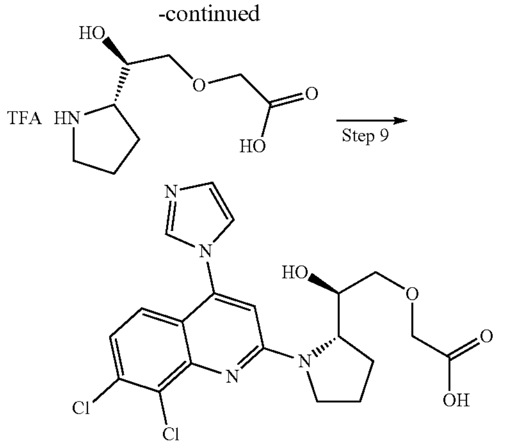

I-726

Step 1: tert-Butyl (S)-2((R)-cyano(hydroxy)methyl)pyrrolidine-1-carboxylate and tert-butyl (S)-2-((S)-cyano(hydroxy)methyl)pyrrolidine-1-carboxylate. To a solution of tert-butyl (S)-2-formylpyrrolidine-1-carboxylate (1.92 g) in DCM (20 mL) was added TEA (2 mL) and acetone cyanohydrin (0.98 g). The resultant solution was stirred at room temperature over 40 h. After removal of DCM under reduced pressure, the residue was diluted with EtOAc (30 mL). The organic layer was washed with diluted HCl (0.5 N) and brine, then dried over anhydrous $Na_2SO_4$. The reaction mixture was purified with a silica gel column, eluting with a gradient of hexane and Hex/EtOAc/DCM (3/1/6), to afford tert-butyl (S)-2-((R)-cyano(hydroxy)methyl)pyrrolidine-1-carboxylate (1.4 g) as oil and tert-butyl (S)-2((S)-cyano (hydroxy)methyl)pyrrolidine-1-carboxylate (0.98 g) as solids.

Step 2-4: tert-Butyl (S)-2-((R)-1-hydroxy-2-methoxy-2-oxoethyl)pyrrolidine-1-carboxylate. To a solution of tert-butyl (S)-2-((R)-cyano(hydroxy)methyl)pyrrolidine-1-carboxylate (0.68 g) in dioxane (8 mL) was added conc. HCl (8 mL). The resultant solution was heated at reflux over 4 h. The solution was concentrated under reduced pressure to dryness. The residuals were dissolved in MeOH (10 mL) and treated with $SOCl_2$ (0.1 mL) overnight. After removal of MeOH under reduced pressure, the residuals were suspended in DCM (10 mL) and water (4 mL) in the presence of $(Boc)_2O$ (1.29 g) and $Na_2CO_3$ (954 mg) overnight. After adding DCM (15 mL), the combined DCM layers were isolated and washed with brine, then dried over anhydrous $Na_2SO_4$. A silica gel column purification afforded the title compound (0.64 g) as oil. MASS: m/z: $[M+Na]^+$282.

Step 5-6: tert-Butyl (2S)-2-((1R)-2-hydroxy-1-((tetrahydro-2H-pyran-2-yl)oxy)ethyl)pyrrolidine-1-carboxylate. To a solution of tert-butyl (S)-2-((R)-1-hydroxy-2-methoxy-2-oxoethyl)pyrrolidine-1-carboxylate (440 mg) in DCM (6 mL) were added 3,4-dihydro-2H-pyran (336 mg) and PPTS (100 mg). The solution was stirred over 6h. After the removal of the solvents under reduced pressure, the residuals were suspended in THF (6 mL) and treated with $LiBH_4$ (96 mg). After the resultant suspension was stirred overnight, it was slowly quenched by adding water. After the aqueous work-up with EtOAc (25 mL), the isolated organic layer was washed with brine and dried over anhydrous $Na_2SO_4$. A silica gel column purification afforded the title product (224 mg). MASS: m/z: $[M+Na]^+$338.

Step 7: tert-Butyl (2S)-2-((1R)-2-(2-(tert-butoxy)-2-oxoethoxy)-1-((tetrahydro-2H-pyran-2-yl)oxy)ethyl)pyrrolidine-1-carboxylate. To an ice-chilled solution of tert-butyl (2S)-2-((1R)-2-hydroxy-1-((tetrahydro-2H-pyran-2-yl)oxy) ethyl)pyrrolidine-1-carboxylate (101 mg) in DMF (3 mL) was slowly added NaH (40 mg, 60% wt suspension in mineral oil). After the resultant solution was stirred over 20 min at 0° C., tert-butyl 2-bromoacetate (187 mg) was added. The reaction mixture was stirred at room temperature overnight and then quenched with water (0.5 mL). Aqueous workup with EtOAc and a silica gel column purification gave the title product (86 mg) as oil. MASS: m/z: $[M+Na]^+$ 452.

Step 8-9: 2-((R)-2-((S)-1-(7,8-Dichloro-4-(1H-imidazol-1-yl)quinolin-2-yl)pyrrolidin-2-yl)-2-hydroxyethoxy)acetic acid (I-726). After tert-butyl (2S)-2-((1R)-2-(2-(tert-butoxy)-2-oxoethoxy)-1-((tetrahydro-2H-pyran-2-yl)oxy) ethyl)pyrrolidine-1-carboxylate(86 mg) in DCM (0.2 mL) was treated with TFA (0.2 mL) overnight, the organic solvents were removed under reduced pressure. Additional co-evaporation with toluene/ACN helped the removal of excess of TFA. The residuals in DMSO (0.4 mL) were mixed with 2,7,8-trichloro-4-(1H-imidazol-1-yl)quinoline (48 mg) and $Na_2CO_3$ (32 mg). The resultant suspension was heated at 90° C. for 5 h. The reaction mixture was treated with AcOH (0.03 mL) and suspended in water. Aqueous work-up with EtOAc and a silica gel column purification with a gradient eluting between EtOAc and DCM/MeOH/AcOH (9/1/0.1) afforded the desired product (14.2 mg) as tan solids. MASS: m/z: $[M+1]^+$ : 451.

Example 119: Synthesis of 2-((S)-2-((S)-1-(7,8-dichloro-4-(1H-imidazol-1-yl)quinolin-2-yl)pyrrolidin-2-yl)-2-hydroxyethoxy)acetic acid (I-725)

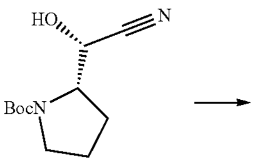

I-725-1

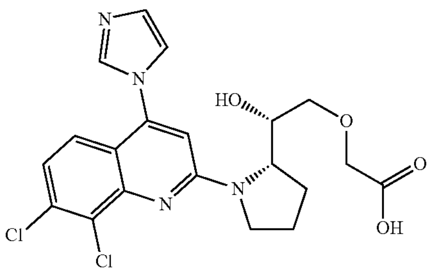

I-725

Following the same methods described above to prepare I-726, I-725 was prepared from tert-butyl (S)-2-((S)-cyano (hydroxy)methyl)pyrrolidine-1-carboxylate. I-725: MASS: m/z: $[M+1]^+$ : 451.

Example 120: Synthesis of 3-((R)-2-((S)-1-(7,8-dichloro-4-(1H-imidazol-1-yl)quinolin-2-yl)pyrrolidin-2-yl)-2-hydroxyethoxy)propanoic acid (I-724)

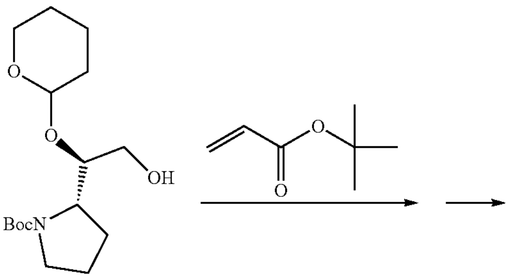

I-726-6

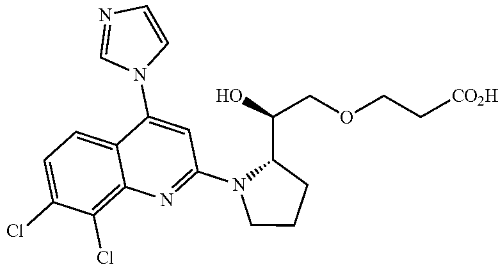

I-724

Following the same methods described above to prepare I-664, I-724 was prepared from tert-butyl (2S)-2-((1R)-2-hydroxy-1-((tetrahydro-2H-pyran-2-yl)oxy)ethyl)pyrrolidine-1-carboxylate. I-724: MASS: m/z: $[M+1]^+$ : 465.

Example 121: Synthesis of (S)-6-((1-(7,8-dichloro-4-(1H-imidazol-1-yl)quinolin-2-yl)pyrrolidin-2-yl) methoxy)hexanoic acid (I-675)

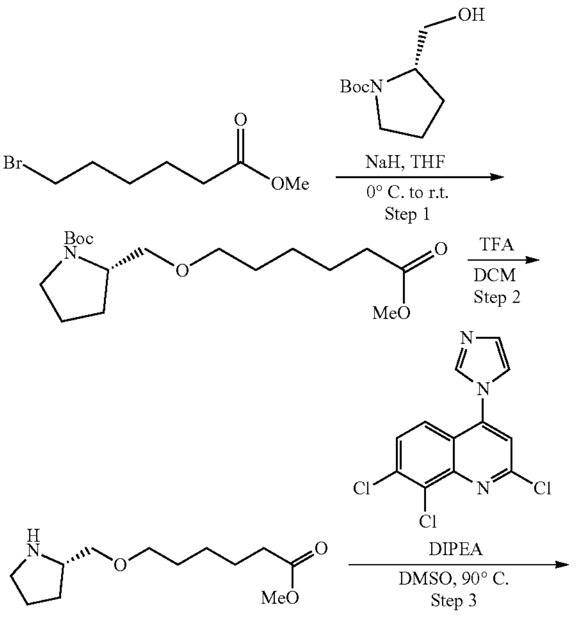

-continued

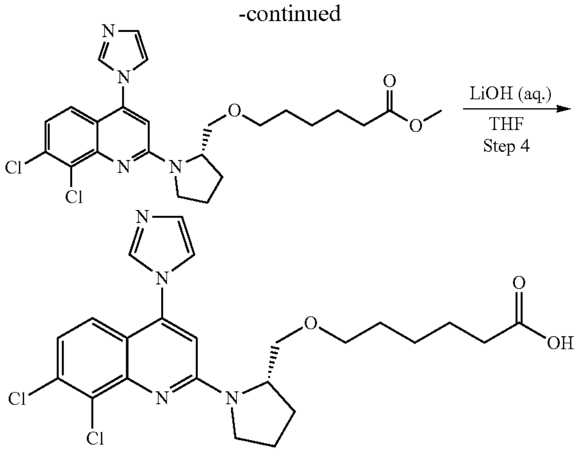

I-675

Step 1: tert-Butyl (S)-2-((3-(tert-butoxy)-3-oxopropoxy) methyl)pyrrolidine-1-carboxylate. At 0° C., NaH (80 mg, 60% in mineral oil, 2.0 mmol) was added to a solution of tert-butyl (S)-2-(hydroxymethyl)pyrrolidine-1-carboxylate (201 mg, 1 mmol) in THF (5 mL). After stirring for 30 min at r.t., a solution of methyl 6-bromohexanoate (0.6 mL) in THF (1 mL) was added at 0° C. The mixture was stirred for 2 h at r.t. before quenching by $H_2O$ (1 mL) at 0° C. The organic phase was concentrated and purified by silica gel column to afford the title product (75 mg) as colorless oil. MS: $[M+1]^+$ 330.

Step 2: Methyl (S)-6-(pyrrolidin-2-ylmethoxy)hexanoate. To a solution of tert-butyl (S)-2-((3-(tert-butoxy)-3-oxopropoxy)methyl)pyrrolidine-1-carboxylate (75 mg, 0.23 mmol) in DCM (0.8 mL) was added TFA (0.8 mL) at 0° C. After stirring 1 h at r.t., the reaction mixture was concentrated to colorless oil (75 mg) under reduced pressure. The crude was used for the next step without further purification. MS: $[M+1]^+$ : 230.

Step 3: Methyl (S)-6-((1-(7,8-dichloro-4-(1H-imidazol-1-yl)quinolin-2-yl)pyrrolidin-2-yl)methoxy)hexanoate. To a solution of methyl (S)-6-(pyrrolidin-2-ylmethoxy)hexanoate (75 mg, crude from last step, about 0.2 mmol) and 2,7,8-trichloro-4-(1H-imidazol-1-yl)quinoline (100 mg, 0.33 mmol) in DMSO (1 mL) was added DIPEA (0.1 mL). The mixture was stirred at 80° C. overnight. After cooling to r.t., $H_2O$ (10 mL) was added. The mixture was acidified to pH.=1 by 1 N HCl and the precipitate was collected by filtration. Purification by silica gel column afforded the title product (100 mg) as colorless oil. MS: $[M+1]^+$ 491.

Step 4: (S)-6-((1-(7,8-Dichloro-4-(1H-imidazol-1-yl)quinolin-2-yl)pyrrolidin-2-yl)methoxy)hexanoic acid. To a solution of methyl (S)-6-((1-(7,8-dichloro-4-(1H-imidazol-1-yl)quinolin-2-yl)pyrrolidin-2-yl)methoxy)hexanoate (100 mg, 0.2 mmol) in THF (2 mL) was added LiOH (aq., 1 M. 0.4 mL) at 0° C. The mixture was stirred at 50° C. overnight. After cooling to r.t., $H_2O$ (3 mL) and 1 N HCl (0.35 mL) was added. The precipitate was collected by filtration to afford the title product (80 mg) as white solid. MS: $[M+1]^+$ 477.

The following compounds are prepared essentially by the same method described above to prepare I-675.

| Example | Starting Material | Structure | MS $[M + 1]^+$ |
|---|---|---|---|
| I-676 | 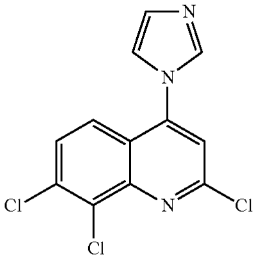 [SMILES: Clc1cc(-n2ccnc2)c2ccc(Cl)c(Cl)c2n1] 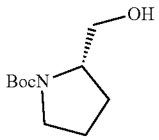 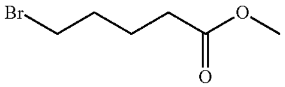 | 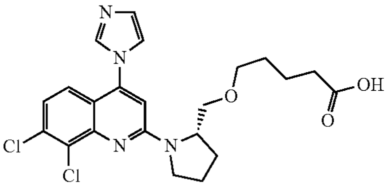 [SMILES: O=C(O)CCCCOC[C@@H]1CCCN1c1cc(-n2ccnc2)c2ccc(Cl)c(Cl)c2n1] | 463 |
| I-723 | 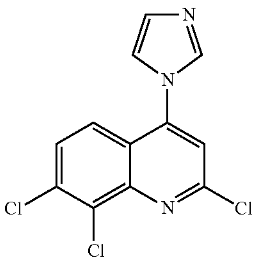 [SMILES: Clc1cc(-n2ccnc2)c2ccc(Cl)c(Cl)c2n1] 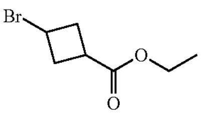 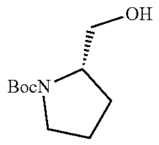 | 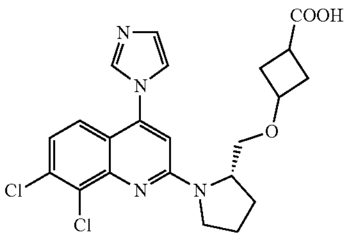 [SMILES: O=C(O)C1CC(OC[C@@H]2CCCN2c2cc(-n3ccnc3)c3ccc(Cl)c(Cl)c3n2)C1] | 461 |

Example 122: Synthesis of tert-Butyl (S)-2-(2-hydroxyethyl)pyrrolidine-1-carboxylate

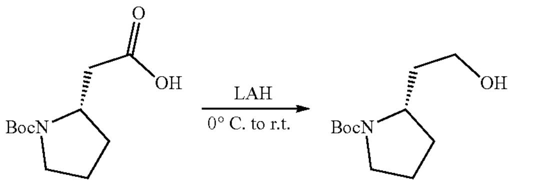 [SMILES: CC(C)(C)OC(=O)N1CCC[C@H]1CC(=O)O ; CC(C)(C)OC(=O)N1CCC[C@H]1CCO]

At 0° C., LAH (1.2 eq.) was added to a solution of (5)-2-(1-(tert-butoxycarbonyl)pyrrolidin-2-yl)acetic acid (4 g, 17 mmol) in THF (75 mL). The mixture was stirred at r.t. for 1 h. The reaction was quenched by $H_2O$ (3 mL), 15% NaOH (3 mL) and $H_2O$ (9 mL) respectively at 0° C. After filtration, the filtrate was purified by silica gel column to afford the title product (2.3 g) as colorless oil. MS: $[M+1]^+$ 216.

Example 123: Synthesis of tert-Butyl (S)-2-(3-hydroxypropyl)pyrrolidine-1-carboxylate

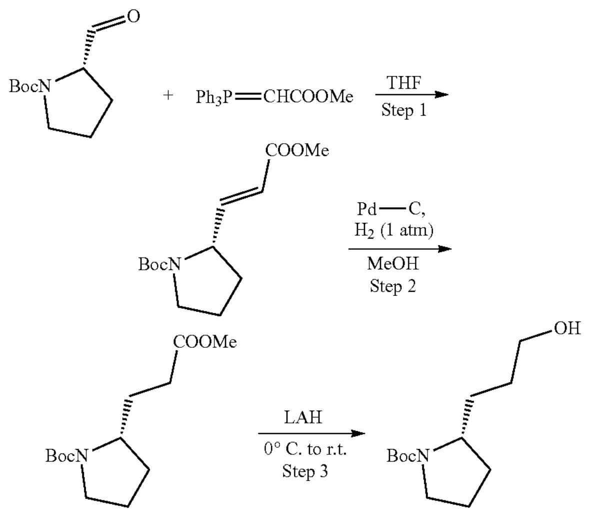

Step 1: tert-Butyl (S,E)-2-(3-methoxy-3-oxoprop-1-en-1-yl)pyrrolidine-1-carboxylate. To a solution of tert-butyl (S)-2-(hydroxymethyl)pyrrolidine-1-carboxylate (398 mg, 2 mmol) in THF (8 mL) was added $Ph_3P$=CHCOOMe (700 mg, 2.2 mmol). The mixture was stirred at 50° C. overnight. After cooling to r.t., the mixture was concentrated by vacuum and purified by silica gel chromatography to afford the title product (430 mg) as colorless oil. MS: $[M+1]^+$ 256.

Step 2: tert-Butyl (S)-2-(3-methoxy-3-oxopropyl)pyrrolidine-1-carboxylate. To a solution of tert-butyl (S,E)-2-(3-methoxy-3-oxoprop-1-en-1-yl)pyrrolidine-1-carboxylate (800 mg, 3.1 mmol) in MeOH (10 mL) was added Pd/C (10%, 40 mg). The mixture was stirred under $H_2$ (1 atm) over night. After filtration, the filtrate was concentrated and afford the title product (800 mg) as colorless oil which was used directly without purification. MS: $[M+1]^+$ 258.

Step 3: tert-Butyl (S)-2-(3-hydroxypropyl)pyrrolidine-1-carboxylate. The procedure was essentially the same as described above for the preparation of tert-butyl (S)-2-(2-hydroxyethyl)pyrrolidine-1-carboxylate. MS: $[M+1]^+$ 230.

Example 124: Synthesis of tert-Butyl (R)-2-(4-methoxy-4-oxobutyl)pyrrolidine-1-carboxylate

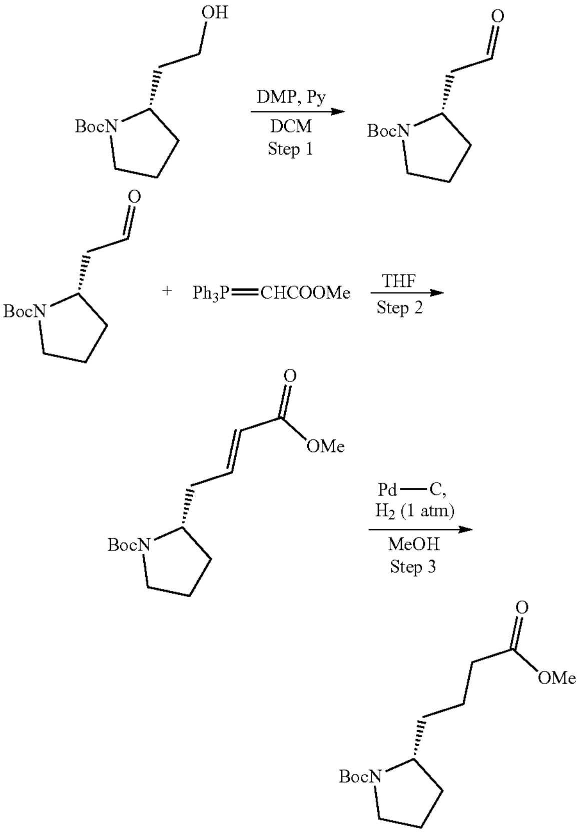

Step 1: tert-Butyl (S)-2-(2-oxoethyl)pyrrolidine-1-carboxylate. To a solution of tert-butyl (S)-2-(2-hydroxyethyl) pyrrolidine-1-carboxylate (340 mg, 1.5 mmol) in DCM (6 mL) and pyridine (1 mL) was added DMP (800 mg) at 0° C. The mixture was stirred at r.t. for 2 h and quenched by $Na_2S_2O_3$/$NaHCO_3$ (sat., 10 mL). The organic phase was concentrated by vacuum and purified by silica gel chromatography to afford the title product (280 mg) as colorless oil. MS: $[M+1]^+$ 214.

Step 2 and step 3 were essentially the same procedure as described above to prepare tert-butyl (S)-2-(3-hydroxypropyl)pyrrolidine-1-carboxylate preparation (Step 1 and Step 2).

Example 125: Synthesis of tert-Butyl (R)-2-(5-methoxy-5-oxopentyl)pyrrolidine-1-carboxylate

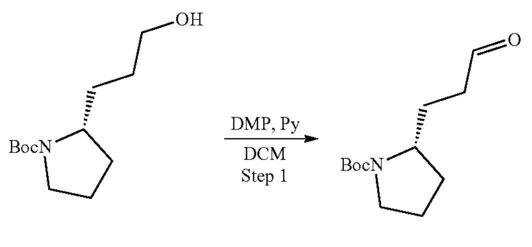

-continued

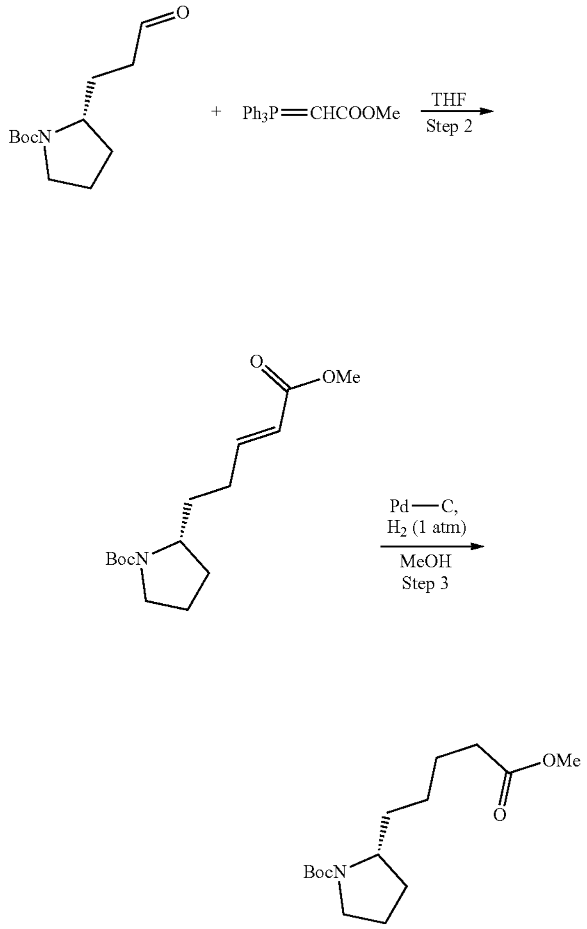

tert-butyl (R)-2-(5-methoxy-5-oxopentyl)pyrrolidine-1-carboxylate was prepared essentially by the same method described above to prepare tert-butyl (R)-2-(4-methoxy-4-oxobutyl)pyrrolidine-1-carboxylate.

Example 126: Synthesis of Ethyl (2S,3S,4R)-3-hydroxy-4-methylpyrrolidine-2-carboxylate and ethyl (2S,3S,4R)-4-hydroxy-3-methylpyrrolidine-2-carboxylate

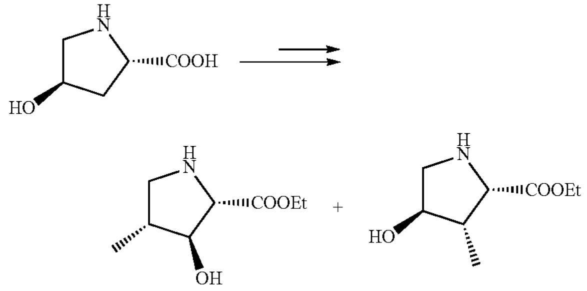

The two intermediates were prepared according the method described in WO 2011/091407, the content of which in herein incorporated by reference.

Example 127: Synthesis of methyl (S)-3-(((1-(7,8-dichloro-4-(1H-imidazol-1-yl)quinolin-2-yl)pyrrolidin-2-yl)methyl)amino)propanoate (I-753) and dimethyl 3,3'-(((1-(7,8-dichloro-4-(1H-imidazol-1-yl)quinolin-2-yl)pyrrolidin-2-yl)methyl)azanediyl)(S)-dipropionate (I-757)

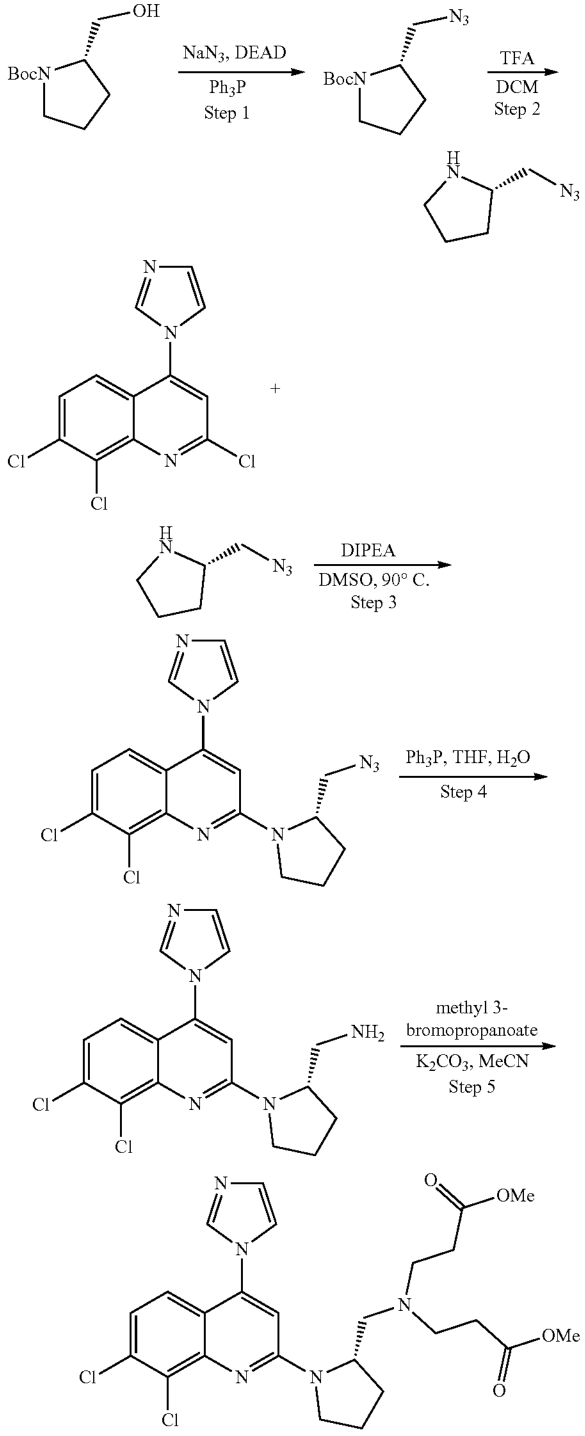

I-757

-continued

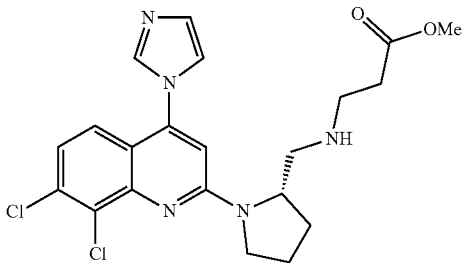

I-753

-continued

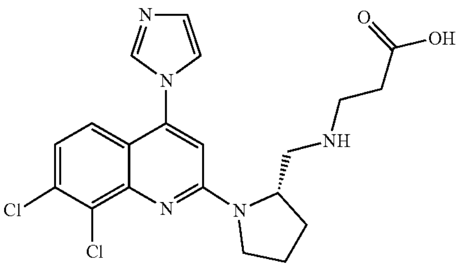

I-756

Step 1: tert-Butyl (S)-2-(azidomethyl)pyrrolidine-1-carboxylate. To a solution of tert-butyl (S)-2-(hydroxymethyl) pyrrolidine-1-carboxylate (400 mg, 2 mmol), $Ph_3P$ (800 mg, 3 mmol) and $NaN_3$ (200 mg, 3 mmol) in THF (10 mL) was added DEAD (0.47 mL, 3 mmol). The reaction was stirred over night at r.t. After evaporation, the crude was purified by silica gel chromatography to afford the title product (280 mg) as colorless oil. MS: $[M+1]^+$ 227.

Step 2 and step 3 were essentially the same as the procedure described above to prepare I-675 (Step 2 and Step 3).

Step 4: (S)-(1-(7,8-Dichloro-4-(1H-imidazol-1-yl)quinolin-2-yl)pyrrolidin-2-yl)methanamine. To a solution of (S)-2-(2-(azidomethyl)pyrrolidin-1-yl)-7,8-dichloro-4-(1H-imidazol-1-yl)quinoline (190 mg, 0.5 mmol) in THF (3 mL) and $H_2O$ (1 mL) was added $Ph_3P$ (262 mg, 1 mmol). The mixture was stirred over night at r.t. After evaporation, the crude was purified by silica gel chromatography to afford the title product (160 mg) as white solid. MS: $[M+1]^+$ 362.

Step 5: Methyl (S)-3-(((1-(7,8-dichloro-4-(1H-imidazol-1-yl)quinolin-2-yl)pyrrolidin-2-yl)methyl)amino)propanoate (I-753) and dimethyl 3,3'-(((1-(7,8-dichloro-4-(1H-imidazol-1-yl)quinolin-2-yl)pyrrolidin-2-yl)methyl)azanediyl) (S)-dipropionate (I-757). To a solution of (S)-(1-(7,8-dichloro-4-(1H-imidazol-1-yl)quinolin-2-yl)pyrrolidin-2-yl)methanamine (160 mg) and methyl 3-bromopropanolate (50 mg, 0.44 mmol) was added $K_2CO_3$ (60 mg). The mixture was stirred at 50° C. overnight. After filtration, the crude was purified by silica gel chromatography to afford the titled compounds I-753 (45 mg, MS: $[M+1]^+$ 448) and I-757 (2.5 mg, MS: $[M+1]^+$ 534) as white solid.

Example 128: Synthesis of (5)-3-(((1-(7,8-dichloro-4-(1H-imidazol-1-yl)quinolin-2-yl)pyrrolidin-2-yl) methyl)amino)propanoic acid (I-756)

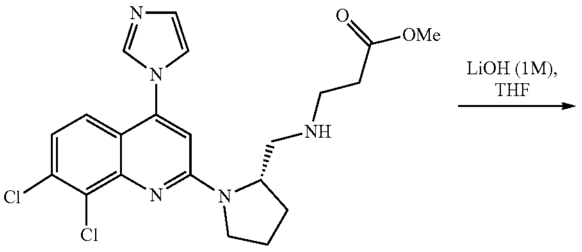

The procedure was essentially the same as the preparation described above for I-675 (Step 4). MS: $[M+1]^+$ 434.

Example 129: Synthesis of methyl (S)-3-(((1-(7,8-dichloro-4-(1H-imidazol-1-yl)quinolin-2-yl)pyrrolidin-2-yl)methyl)(methyl)amino)propanoate (I-755) and (S)-3-(((1-(7,8-dichloro-4-(1H-imidazol-1-yl)quinolin-2-yl)pyrrolidin-2-yl)methyl)(methyl)amino) propanoic acid (I-754)

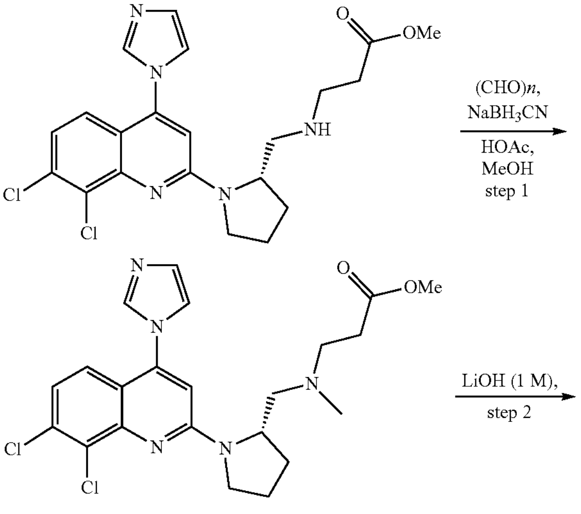

I-755

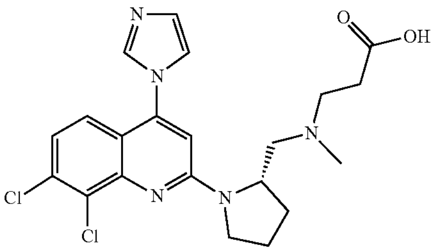

I-754

Step 1: Methyl (S)-3-(((1-(7,8-dichloro-4-(1H-imidazol-1-yl)quinolin-2-yl)pyrrolidin-2-yl)methyl)(methyl)amino) propanoate (I-755). To a solution of methyl (S)-3-(((1-(7,8-dichloro-4-(1H-imidazol-1-yl)quinolin-2-yl)pyrrolidin-2-yl)methyl)amino)propanoate (19 mg, 0.05 mmol), paraformaldehyde (6 mg, 0.2 mmol), HOAc (0.025 mL) in MeOH (1 mL) was added $NaBH_3CN$ (13 mg, 0.2 mmol). The mixture was stirred at r.t. over night. After evaporation, the crude was purified by silica gel chromatography to afford the title product (15 mg). MS: $[M+1]^+$ 462.

Step 2: (S)-3-(((1-(7,8-Dichloro-4-(1H-imidazol-1-yl)quinolin-2-yl)pyrrolidin-2-yl)methyl)(methyl)amino)propanoic acid (I-754). The procedure was essentially the same that described above for the preparation of I-675 (Step 4). MS: $[M+1]^+$ 448.

The following compounds are prepared essentially by the same method described above to prepare I-123.

| Example | Starting Material | Structure | MS $[M + 1]^+$ |
|---|---|---|---|
| I-776 | 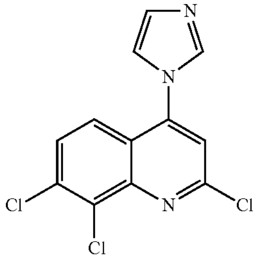 [SMILES: Clc1cc(-n2ccnc2)c2ccc(Cl)c(Cl)c2n1] 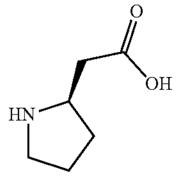 | 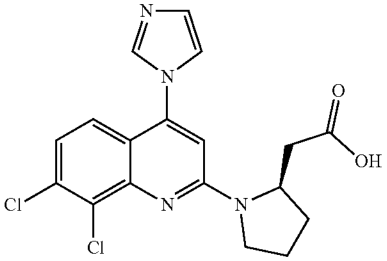 [SMILES: O=C(O)C[C@H]1CCCN1c1cc(-n2ccnc2)c2ccc(Cl)c(Cl)c2n1] | 391 |
| I-687 | 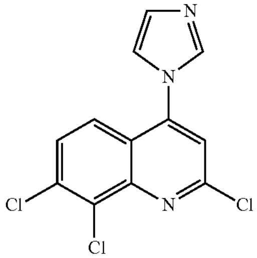 [SMILES: Clc1cc(-n2ccnc2)c2ccc(Cl)c(Cl)c2n1] 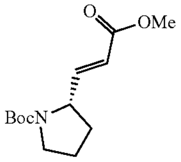 [SMILES: COC(=O)/C=C/[C@@H]1CCCN1C(=O)OC(C)(C)C] | 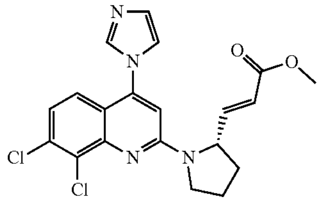 [SMILES: COC(=O)/C=C/[C@@H]1CCCN1c1cc(-n2ccnc2)c2ccc(Cl)c(Cl)c2n1] | 417 |
| I-680 | 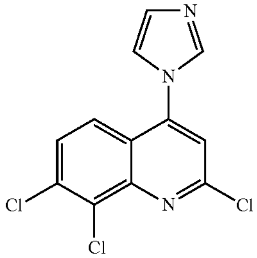 [SMILES: Clc1cc(-n2ccnc2)c2ccc(Cl)c(Cl)c2n1] 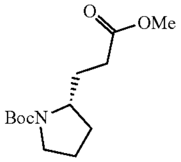 [SMILES: COC(=O)CC[C@@H]1CCCN1C(=O)OC(C)(C)C] | 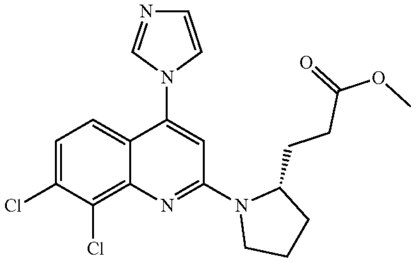 [SMILES: COC(=O)CC[C@@H]1CCCN1c1cc(-n2ccnc2)c2ccc(Cl)c(Cl)c2n1] | 419 |
| I-679 | 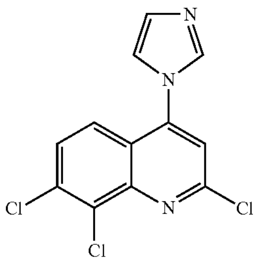 [SMILES: Clc1cc(-n2ccnc2)c2ccc(Cl)c(Cl)c2n1] 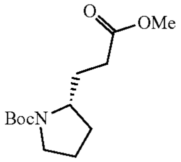 [SMILES: COC(=O)CC[C@@H]1CCCN1C(=O)OC(C)(C)C] | 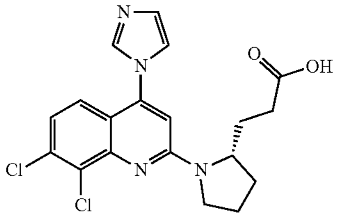 [SMILES: O=C(O)CC[C@@H]1CCCN1c1cc(-n2ccnc2)c2ccc(Cl)c(Cl)c2n1] | 405 |
| I-682 | 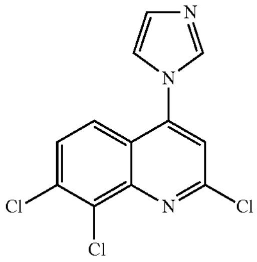 [SMILES: Clc1cc(-n2ccnc2)c2ccc(Cl)c(Cl)c2n1] 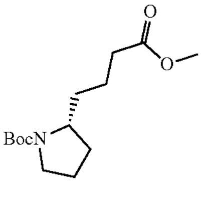 [SMILES: COC(=O)CCC[C@@H]1CCCN1C(=O)OC(C)(C)C] | 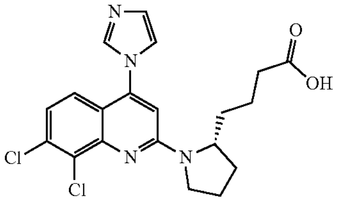 | 419 |

-continued
| Example | Starting Material | Structure | MS [M + 1]$^+$ |
|---|---|---|---|
| I-685 | 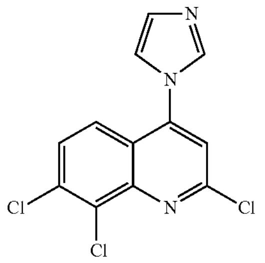 [SMILES: Clc1cc(-n2ccnc2)c2ccc(Cl)c(Cl)c2n1] 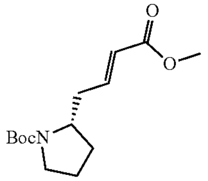 [SMILES: COC(=O)/C=C/C[C@@H]1CCCN1C(=O)OC(C)(C)C] | 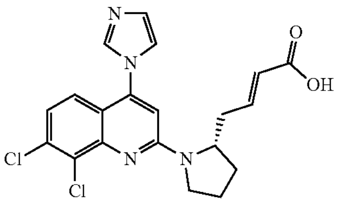 | 417 |
| I-686 | 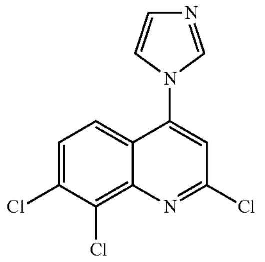 [SMILES: Clc1cc(-n2ccnc2)c2ccc(Cl)c(Cl)c2n1] 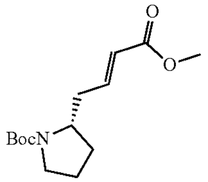 [SMILES: COC(=O)/C=C/C[C@@H]1CCCN1C(=O)OC(C)(C)C] | 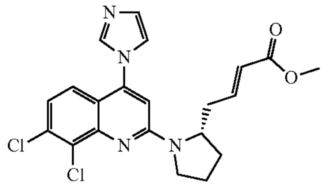 [SMILES: COC(=O)/C=C/C[C@@H]1CCCN1c1cc(-n2ccnc2)c2ccc(Cl)c(Cl)c2n1] | 431 |
| I-681 | 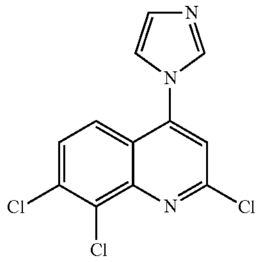 [SMILES: Clc1cc(-n2ccnc2)c2ccc(Cl)c(Cl)c2n1] 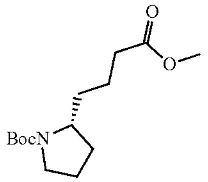 [SMILES: COC(=O)CCC[C@@H]1CCCN1C(=O)OC(C)(C)C] | 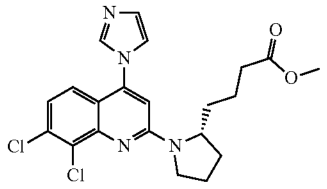 [SMILES: COC(=O)CCC[C@@H]1CCCN1c1cc(-n2ccnc2)c2ccc(Cl)c(Cl)c2n1] | 433 |
| I-683 | 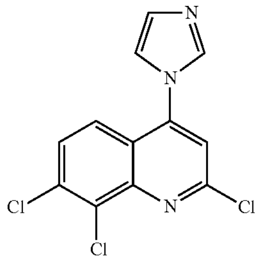 [SMILES: Clc1cc(-n2ccnc2)c2ccc(Cl)c(Cl)c2n1] 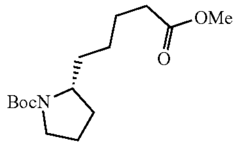 [SMILES: COC(=O)CCCC[C@@H]1CCCN1C(=O)OC(C)(C)C] | 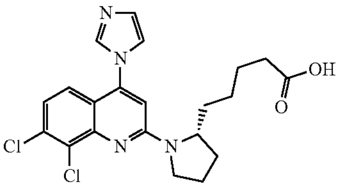 [SMILES: O=C(O)CCCC[C@@H]1CCCN1c1cc(-n2ccnc2)c2ccc(Cl)c(Cl)c2n1] | 433 |
| I-684 | 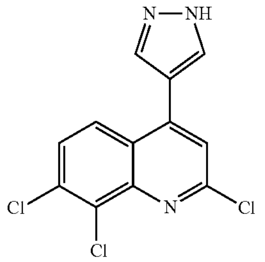 [SMILES: Clc1cc(-c2cn[nH]c2)c2ccc(Cl)c(Cl)c2n1] 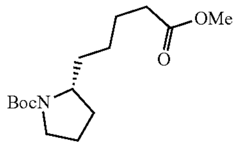 [SMILES: COC(=O)CCCC[C@@H]1CCCN1C(=O)OC(C)(C)C] | 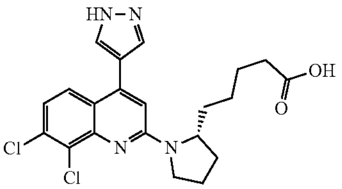 [SMILES: O=C(O)CCCC[C@@H]1CCCN1c1cc(-c2cn[nH]c2)c2ccc(Cl)c(Cl)c2n1] | 433 |

-continued
| Example | Starting Material | | Structure | MS [M + 1]+ |
|---|---|---|---|---|
| I-678 | 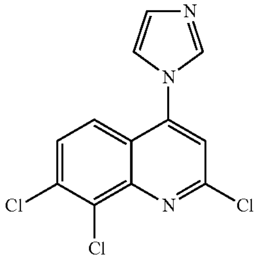 [SMILES: Clc1cc(-n2ccnc2)c2ccc(Cl)c(Cl)c2n1] | 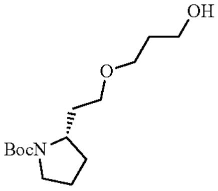 | 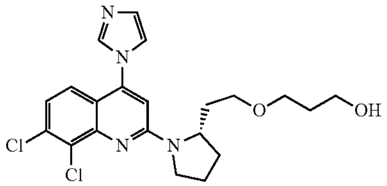 [SMILES: OCCCOCC[C@@H]1CCCN1c1cc(-n2ccnc2)c2ccc(Cl)c(Cl)c2n1] | 435 |
| I-779 | 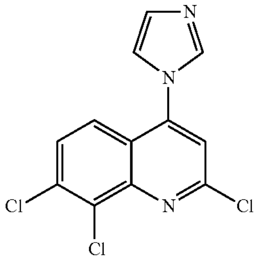 [SMILES: Clc1cc(-n2ccnc2)c2ccc(Cl)c(Cl)c2n1] | 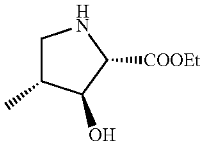 | 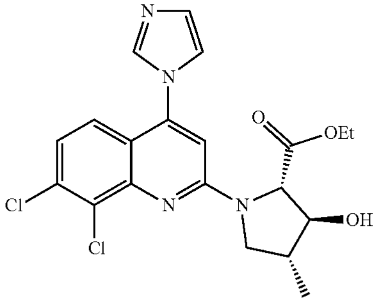 [SMILES: CCOC(=O)[C@@H]1[C@@H](O)[C@H](C)CN1c1cc(-n2ccnc2)c2ccc(Cl)c(Cl)c2n1] | 435 |
| I-780 | 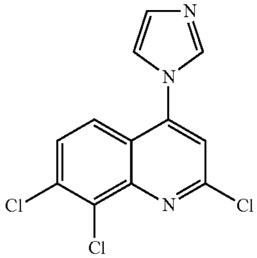 [SMILES: Clc1cc(-n2ccnc2)c2ccc(Cl)c(Cl)c2n1] | 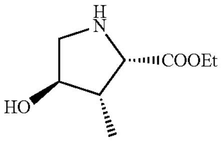 | 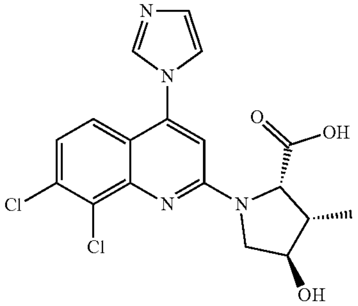 [SMILES: C[C@H]1[C@@H](C(=O)O)N(c2cc(-n3ccnc3)c3ccc(Cl)c(Cl)c3n2)C[C@@H]1O] | 407 |
| I-778 | 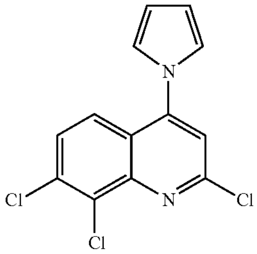 [SMILES: Clc1cc(-n2cccc2)c2ccc(Cl)c(Cl)c2n1] | 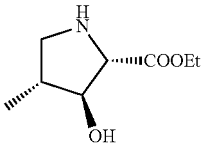 | 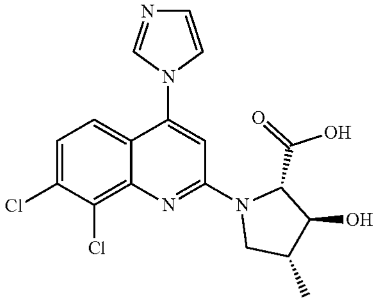 [SMILES: C[C@@H]1CN(c2cc(-n3ccnc3)c3ccc(Cl)c(Cl)c3n2)[C@H](C(=O)O)[C@H]1O] | 407 |
| I-690 | 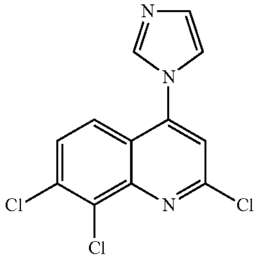 [SMILES: Clc1cc(-n2ccnc2)c2ccc(Cl)c(Cl)c2n1] | 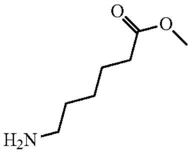 | 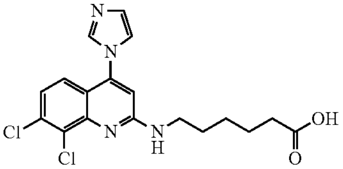 | 393 |

-continued
| Example | Starting Material | Structure | MS [M + 1]+ |
|---|---|---|---|
| I-739 | 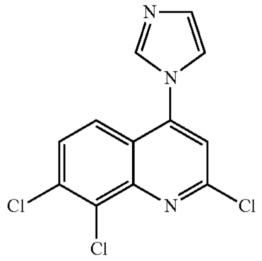 [SMILES: Clc1cc(-n2ccnc2)c2ccc(Cl)c(Cl)c2n1] 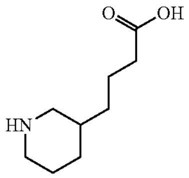 [SMILES: O=C(O)CCCC1CCCNC1] | 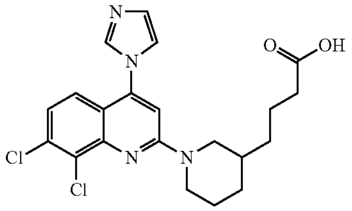 [SMILES: O=C(O)CCCC1CCCN(c2cc(-n3ccnc3)c3ccc(Cl)c(Cl)c3n2)C1] | 433 |
| I-691 | 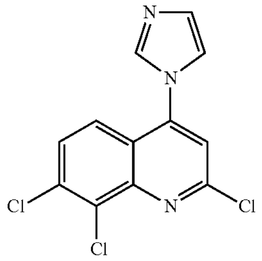 [SMILES: Clc1cc(-n2ccnc2)c2ccc(Cl)c(Cl)c2n1] 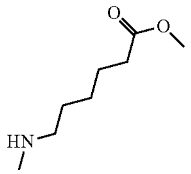 | 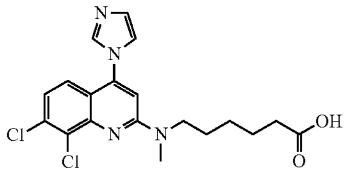 [SMILES: CN(CCCCCC(=O)O)c1cc(-n2ccnc2)c2ccc(Cl)c(Cl)c2n1] | 407 |
| I-758 | 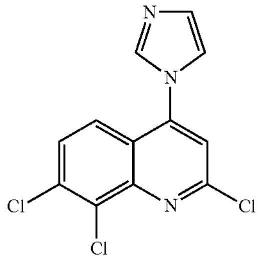 [SMILES: Clc1cc(-n2ccnc2)c2ccc(Cl)c(Cl)c2n1] 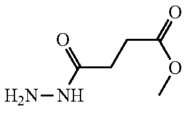 | 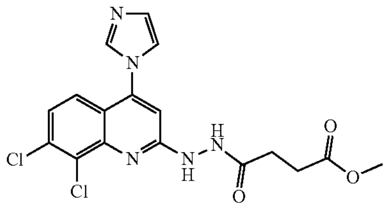 [SMILES: COC(=O)CCC(=O)NNc1cc(-n2ccnc2)c2ccc(Cl)c(Cl)c2n1] | 408 |
| I-759 | | 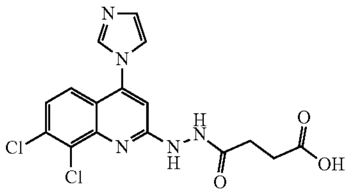 [SMILES: O=C(O)CCC(=O)NNc1cc(-n2ccnc2)c2ccc(Cl)c(Cl)c2n1] | 394 |
Example 130: Synthesis of (S)-3-((1-(7,8-dichloro-4-(1H-imidazol-1-yl)quinolin-2-yl)pyrrolidin-2-yl)methoxy)benzoic acid (I-735)
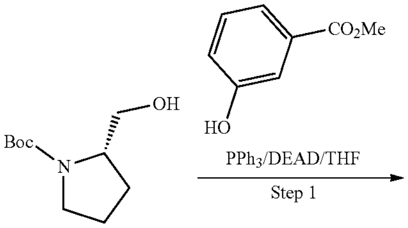
-continued
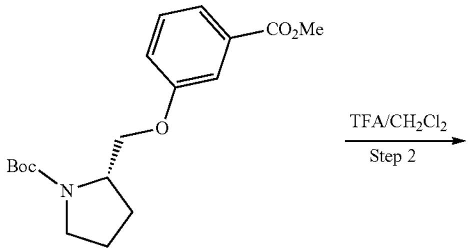

-continued

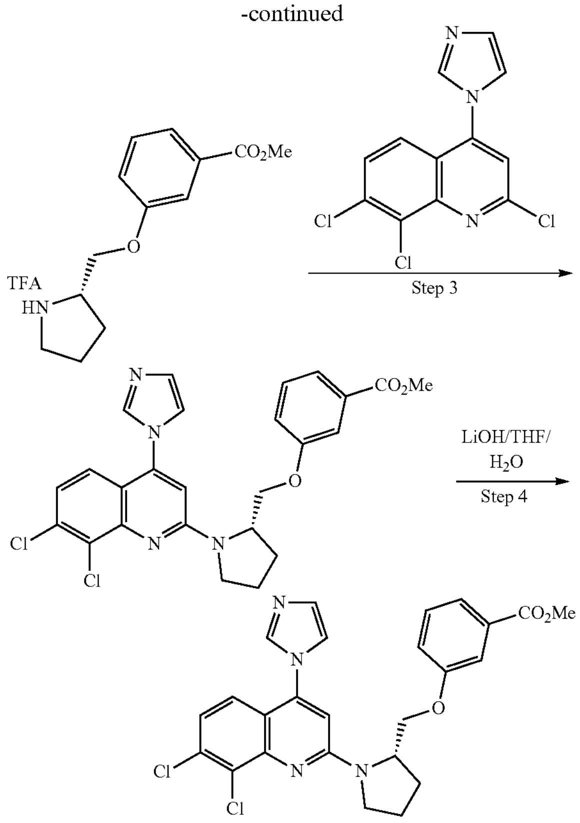

I-735

Step 1: tert-Butyl (S)-2-((3-(methoxycarbonyl)phenoxy)methyl)pyrrolidine-1-carboxylate. To a stirred mixture of Boc-prolinol (300 mg, 1.49 mmol), methyl-3-hydroxybenzoate (240 mg, 1.45 mmol) and triphenylphosphine (391 mg, 1.49 mmol) in THF (10 mL) was added dropwise diethyl azodicarboxylate (261 mg, 0.65 mL, 1.49 mmol (40% in toluene)). The resulting mixture was heated at 75° C. for 3 h. After cooling, the mixture was concentrated in vacuo. The residue was dissolved in EtOAc and washed successively with 1N NaOH, water and then brine. The organics were dried ($Na_2SO_4$) then concentrated. The residue was purified by silica gel chromatography using 0-40% ethyl acetate/hexanes as eluent to afford the title compound. MS: $[M+1]^+$ 280.1 (−t-Bu).

Step 2: Methyl (S)-3-(pyrrolidin-2-ylmethoxy)benzoate. To a flask containing tert-butyl (S)-2-((3-(methoxycarbonyl)phenoxy)methyl)pyrrolidine-1-carboxylate (200 mg, 0.546 mmol) was added dichloromethane (5 mL). Trifluoroacetic acid (1 mL) was added and the reaction allowed to stir at rt for 16 h. The volatiles were removed to afford the title compound which was taken onward without further purification. MS: $[M+1]^+$ 236.1.

Step 3: Methyl (S)-3-((1-(7,8-dichloro-4-(1H-imidazol-1-yl)quinolin-2-yl)pyrrolidin-2-yl)methoxy)benzoate. To a vial containing methyl (S)-3-(pyrrolidin-2-ylmethoxy)benzoate (70 mg, 0.3 mmol) was added DMSO (0.15 mL) and DIPEA (0.10 mL). Next 2,7,8-trichloro-4-(1H-imidazol-1-yl)quinoline (30 mg, 0.1 mmol) was added and the mixture heated to 90° C. for 16 h. The reaction was cooled to rt, then water was added and the organics extracted into 10% $MeOH/CH_2Cl_2$. The combined organic layers were dried ($Na_2SO_4$) then concentrated. The residue was purified by silica gel chromatography using 0-5% $MeOH/CH_2Cl_2$ with 0.5% HOAc as eluent to afford the title compound. MS: $[M+1]^+$ 497.1.

Step 4: (S)-3-((1-(7,8-Dichloro-4-(1H-imidazol-1-yl)quinolin-2-yl)pyrrolidin-2-yl)methoxy)benzoic acid. To a vial containing methyl (S)-3-((1-(7,8-dichloro-4-(1H-imidazol-1-yl)quinolin-2-yl)pyrrolidin-2-yl)methoxy)benzoate (20 mg, 0.040 mmol) THF (2 mL) and water (0.5 mL) was added lithium hydroxide monohydrate (5 mg, 0.12 mmol) and the reaction allowed to stir at rt for 16 h. The volatiles were removed and the residue taken up in water then acidified with 1M HCl until pH~7. The resulting solids were filtered off and vac-dried to afford the title compound. MS: $[M+1]^+$ 483.1.

The following compounds were prepared essentially by the same methods described above to prepare I-735:

| Example | Starting Material | Structure | MS $[M + 1]^+$ |
|---|---|---|---|
| I-733 | 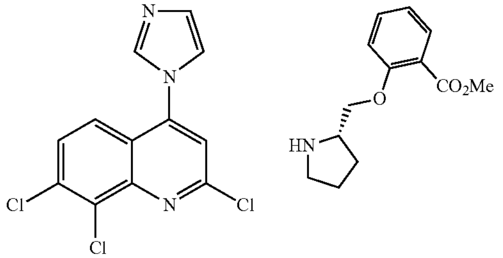 | 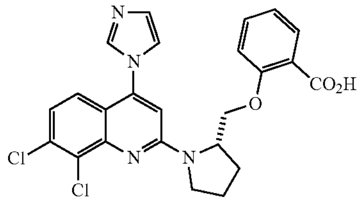 [SMILES: O=C(O)c1ccccc1OC[C@@H]1CCCN1c1cc(-n2ccnc2)c2ccc(Cl)c(Cl)c2n1] | 483.1 |
| I-737 | 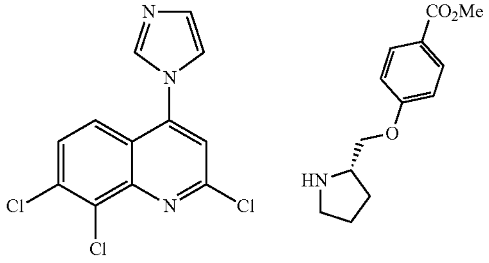 | 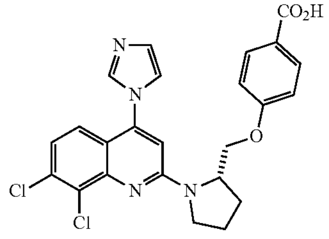 [SMILES: O=C(O)c1ccc(OC[C@@H]2CCCN2c2cc(-n3ccnc3)c3ccc(Cl)c(Cl)c3n2)cc1] | 483.1 |

-continued
| Example | Starting Material | | Structure | MS $[M+1]^+$ |
|---|---|---|---|---|
| I-736 | 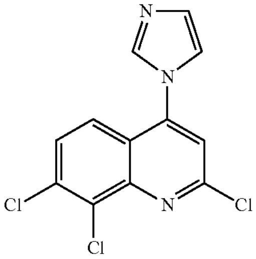 [SMILES: Clc1cc(-n2ccnc2)c2ccc(Cl)c(Cl)c2n1] | 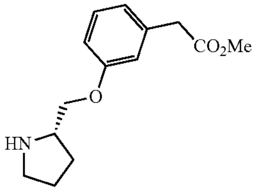 [SMILES: COC(=O)Cc1cccc(OC[C@@H]2CCCN2)c1] | 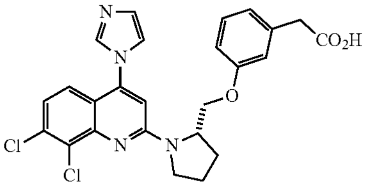 [SMILES: O=C(O)Cc1cccc(OC[C@@H]2CCCN2c2cc(-n3ccnc3)c3ccc(Cl)c(Cl)c3n2)c1] | 497.1 |
| I-738 | 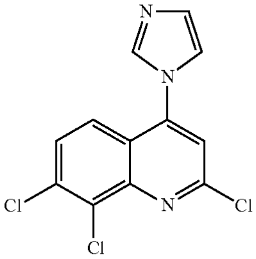 [SMILES: Clc1cc(-n2ccnc2)c2ccc(Cl)c(Cl)c2n1] | 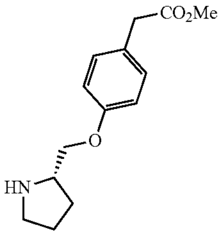 [SMILES: COC(=O)Cc1ccc(OC[C@@H]2CCCN2)cc1] | 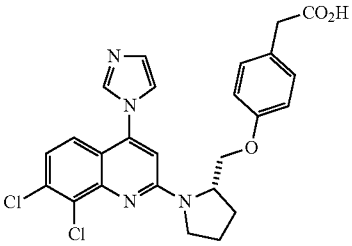 [SMILES: O=C(O)Cc1ccc(OC[C@@H]2CCCN2c2cc(-n3ccnc3)c3ccc(Cl)c(Cl)c3n2)cc1] | 497.1 |
| I-734 | 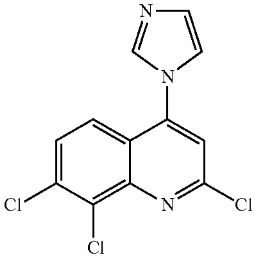 [SMILES: Clc1cc(-n2ccnc2)c2ccc(Cl)c(Cl)c2n1] | 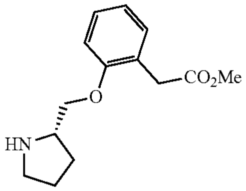 [SMILES: COC(=O)Cc1ccccc1OC[C@@H]1CCCN1] | 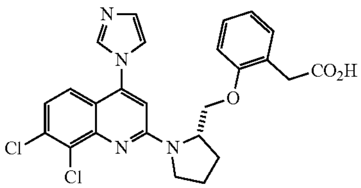 [SMILES: O=C(O)Cc1ccccc1OC[C@@H]1CCCN1c1cc(-n2ccnc2)c2ccc(Cl)c(Cl)c2n1] | 497.1 |
| I-842 | 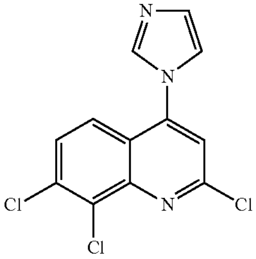 [SMILES: Clc1cc(-n2ccnc2)c2ccc(Cl)c(Cl)c2n1] | 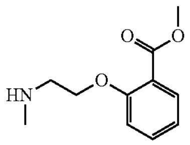 | 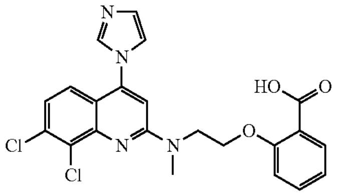 [SMILES: CN(CCOc1ccccc1C(=O)O)c1cc(-n2ccnc2)c2ccc(Cl)c(Cl)c2n1] | 457 |
| I-843 | 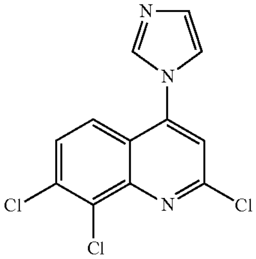 [SMILES: Clc1cc(-n2ccnc2)c2ccc(Cl)c(Cl)c2n1] | 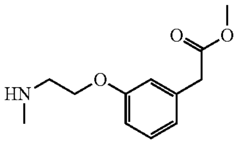 [SMILES: CNCCOc1cccc(CC(=O)OC)c1] | 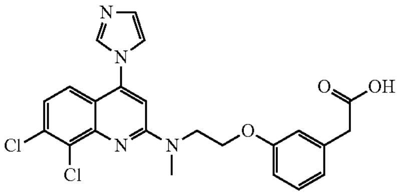 [SMILES: CN(CCOc1cccc(CC(=O)O)c1)c1cc(-n2ccnc2)c2ccc(Cl)c(Cl)c2n1] | 471 |

-continued

| Example | Starting Material | | Structure | MS [M + 1]$^+$ |
|---|---|---|---|---|
| I-846 | 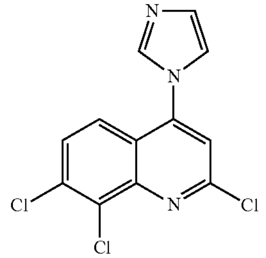 [SMILES: Clc1cc(-n2ccnc2)c2ccc(Cl)c(Cl)c2n1] | 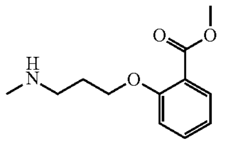 | 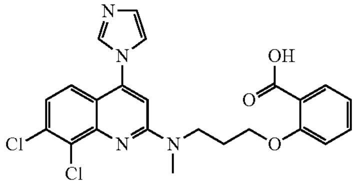 [SMILES: CN(CCCOc1ccccc1C(=O)O)c1cc(-n2ccnc2)c2ccc(Cl)c(Cl)c2n1] | 471 |

Example 131: Synthesis of methyl (S)-2-(2-(pyrrolidin-2-ylmethoxy)phenyl)acetate

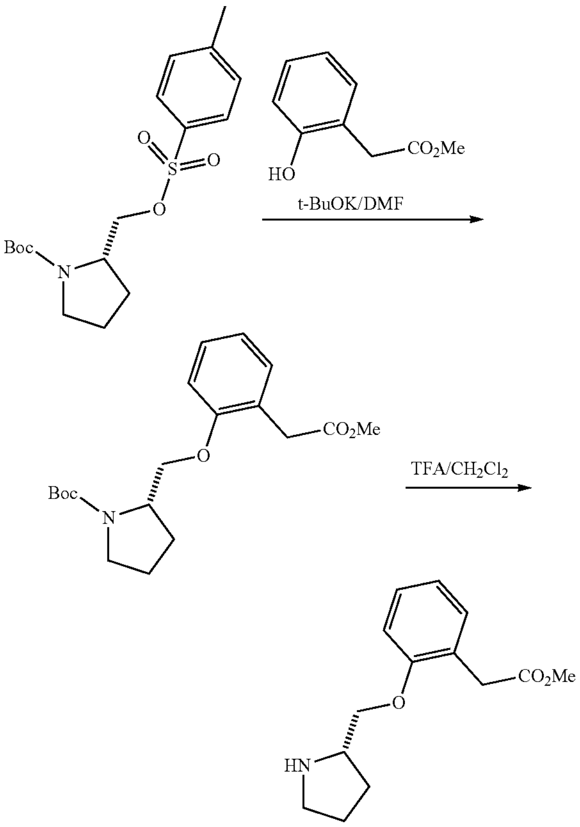

Step 1: tert-Butyl (S)-2-((2-(2-methoxy-2-oxoethyl)phenoxy)methyl)pyrrolidine-1-carboxylate. To a flask containing tert-butyl (S)-2-((tosyloxy)methyl)pyrrolidine-1-carboxylate (355 mg, 1.00 mmol), methyl 2-(2-hydroxyphenyl) acetate (166 mg, 1.00 mmol) and DMF (10 mL) was added potassium tert-butoxide (112 mg, 1.00 mmol) and the reaction was heated at 55° C. for 16 h. The reaction was cooled to rt, quenched by the slow addition of water then diluted with ethyl acetate. The organic layer was separated and washed further with 5% NaOH, water, and brine then dried ($Na_2SO_4$) and concentrated. The resulting residue purified by silica gel chromatography using 0-35% EtOAc/hexanes as eluent to afford to title compound. (MS: [M+1]$^+$ 250.1 (–Boc).

Step 2: Methyl (S)-2-(2-(pyrrolidin-2-ylmethoxy)phenyl) acetate. To a vial containing tert-butyl (S)-2-((2-(2-methoxy-2-oxoethyl)phenoxy)methyl)pyrrolidine-1-carboxylate (25 mg, 0.061 mmol) was added dichloromethane (2 mL) and trifluoroacetic acid (0.5 mL). The reaction allowed to stir at rt for 16 h. The volatiles were removed to afford the title compound used to prepare I-735. MS: [M+1]$^+$ 250.1.

Example 132: Synthesis of 3-(2-((7,8-dichloro-4-(1H-imidazol-1-yl)quinolin-2-yl)amino)ethoxy)benzoic acid (I-885)

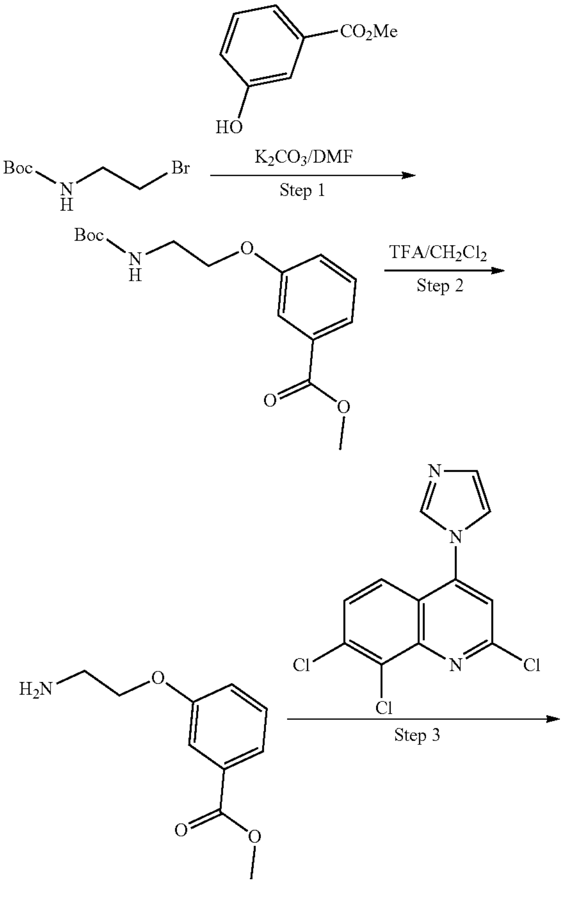

-continued

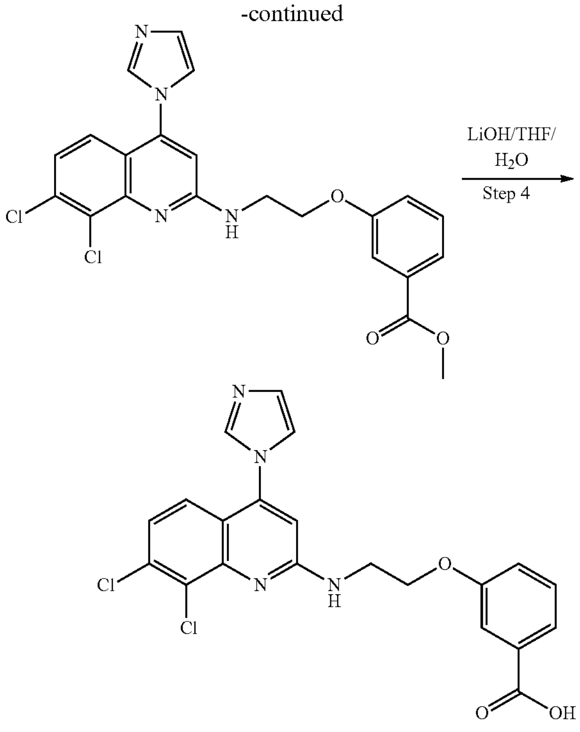

I-885

Step 1: Methyl 3-(2-((tert-butoxycarbonyl)amino)ethoxy)benzoate: To a flask containing methyl 3-hydroxybenzoate (152 mg, 1.0 mmol) and DMF (5 mL) was added potassium carbonate (152 mg, 1.1 mol). The contents were stirred at rt for 10 min then tert-butyl (2-bromoethyl)carbamate (246 mg, 1.1 mmol) was added. The reaction was heated to 65° C. for 16h. Upon cooling, water (10 mL) was added and the organics were extracted into ethyl acetate (2×10 mL), dried ($Na_2SO_4$) and concentrated. The residue was purified by silica gel chromatography to afford 175 mg of the titled compound.

Step 2: Methyl 3-(2-aminoethoxy)benzoate TFA salt: To a flask containing methyl 3-(2-((tert-butoxycarbonyl)amino)ethoxy)benzoate (120 mg, 0.4 mmol) and dichloromethane (5 mL) was added trifluoroacetic acid (1 mL). The reaction was allowed to stir at rt for 16h. The volatiles were concentrated off to afford crude titled compound which was taken on directly to the next step.

Step 3: Methyl 3-(2-((7,8-dichloro-4-(1H-imidazol-1-yl)quinolin-2-yl)amino)ethoxy)benzoate: To a vial containing 2,7,8-trichloro-4-(1H-imidazol-1-yl)quinoline (30 mg, 0.1 mmol) and DMSO was added methyl 3-(2-aminoethoxy)benzoate TFA salt (0.4 mmol) and DIPEA. The reaction was heated to 90° C. for 16 h then cooled to rt. Water (5 mL) was added and the organics extracted into ethyl acetate (2×5 mL), dried ($Na_2SO_4$) and concentrated. The residue was purified by silica gel chromatography to afford 27 mg of the titled compound.

Step 4: 3-(2-((7,8-dichloro-4-(1H-imidazol-1-yl)quinolin-2-yl)amino)ethoxy)benzoic acid: To a vial containing methyl 3-(2-((7,8-dichloro-4-(1H-imidazol-1-yl)quinolin-2-yl)amino)ethoxy)benzoate (20 mg, 0.44 mmol) in $THF/H_2O$ (4 mL/1 mL) was added lithium hydroxide monohydrate (7 mg, 0.175 mmol) and the reaction allowed to stir at rt for 16 h. The volatiles were removed and then residue acidified with 1M HCl. The resulting solids were filtered and dried to afford the titled compound.

The following compounds are prepared essentially by the same method described above to prepare I-885.

| Example | Starting Material | Structure | MS $[M + 1]^+$ |
|---|---|---|---|
| I-886 | 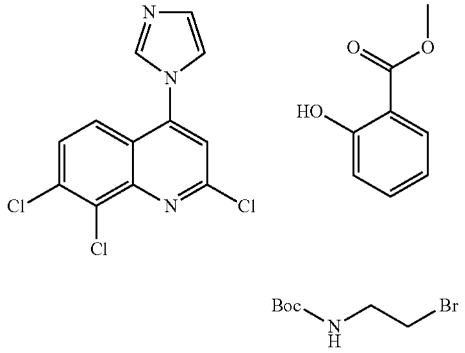 | 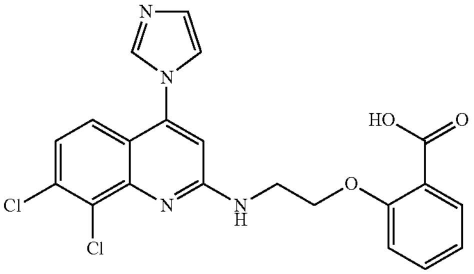 [SMILES: O=C(O)c1ccccc1OCCNc1cc(-n2ccnc2)c2ccc(Cl)c(Cl)c2n1] | 443 |
| I-889 | 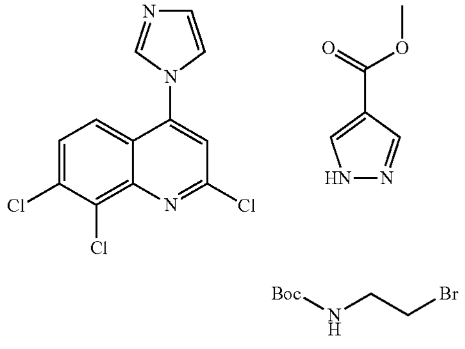 | 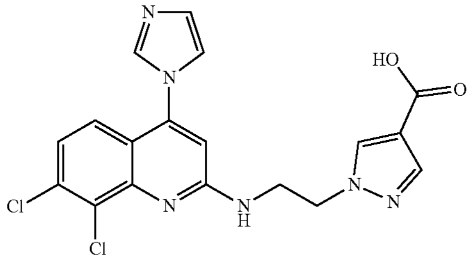 [SMILES: O=C(O)c1cnn(CCNc2cc(-n3ccnc3)c3ccc(Cl)c(Cl)c3n2)c1] | 417 |

Example 133: Synthesis of 4-((S)-1-(7,8-dichloro-4-(1H-imidazol-1-yl)quinolin-2-yl)pyrrolidin-2-yl)-2-hydroxybutanoic acid (I-817)

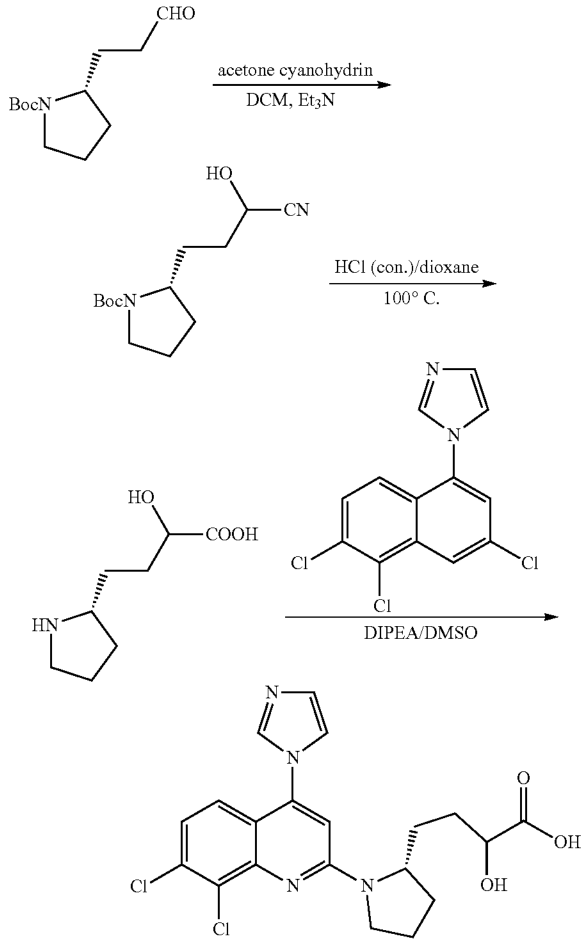

I-817

Step 1: tert-butyl (2S)-2-(3-cyano-3-hydroxypropyl)pyrrolidine-1-carboxylate. To a solution of tert-butyl (S)-2-(3-oxopropyl)pyrrolidine-1-carboxylate (114 mg, 0.5 mmol) in DCM (1 mL) was added $Et_3N$ (0.1 mL) and acetone cyanohydrin (0.1 mL, 1.2 mmol). The mixture was stirred at r.t. over night. The solution was concentrated by vacuum and purified by silica gel column to afford the title product (120 mg) as colorless oil. MS: $[M+1]^+$ 255.

Step 2: 2-hydroxy-4-((S)-pyrrolidin-2-yl)butanoic acid. To a solution of tert-butyl (2S)-2-(3-cyano-3-hydroxypropyl)pyrrolidine-1-carboxylate (60 mg, 0.23 mmol) in dioxane (0.8 mL) was added HCl (con., 0.8 mL). The mixture was stirred at 100° C. overnight. After cooling to r.t., dioxane was removed by evaporation. The residue was washed by EtOAc (0.5 mL×2). The aqueous phase was collected and evaporated to give a crude product which was used directly in the next step without purification. MS: $[M+1]^+$ 174.

Step 3: 4-((S)-1-(7,8-dichloro-4-(1H-imidazol-1-yl)quinolin-2-yl)pyrrolidin-2-yl)-2-hydroxybutanoic acid (I-817). The title compound was prepared essentially by the same methods as for I-664. MS: $[M+1]^+$ 435.

Synthesis of (S)-4-(1-(7,8-dichloro-4-(1H-imidazol-1-yl)quinolin-2-yl)pyrrolidin-2-yl)but-2-ynoic acid (I-819)

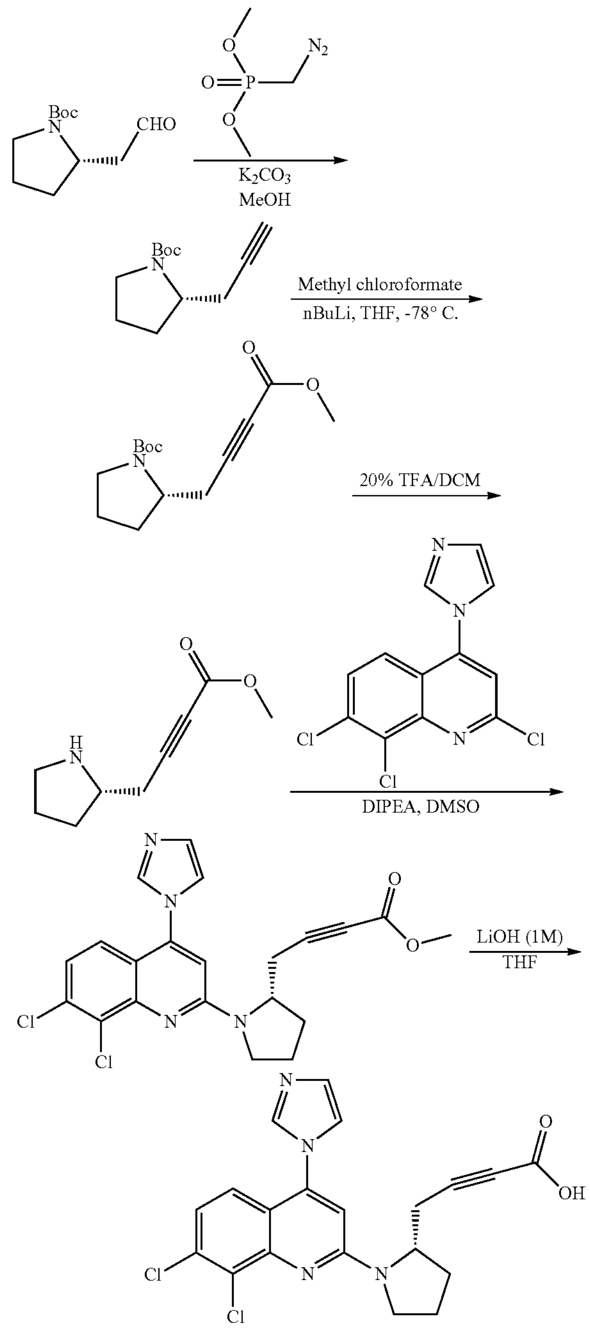

I-819

Step 1: tert-butyl (S)-2-(prop-2-yn-1-yl)pyrrolidine-1-carboxylate. To a solution of tert-butyl (S)-2-(2-oxoethyl) pyrrolidine-1-carboxylate (457 mg, 2.15 mmol) in MeOH (4.5 mL) was added $K_2CO_3$ (594 mg, 4.3 mmol) and diazole (480 mg, 3.22 mmol). The mixture was stirred at r.t. over night. The mixture was concentrated by vacuum and purified by silica gel column to afford the title product (330 mg) as colorless oil. MS: $[M+1]^+$ 210.

Step 2: tert-butyl (S)-2-(4-methoxy-4-oxobut-2-yn-1-yl) pyrrolidine-1-carboxylate. To a solution of tert-butyl (S)-2-(prop-2-yn-1-yl)pyrrolidine-1-carboxylate (330 mg, 1.58 mmol) in THF (3.5 mL) was added n-BuLi (1.1 mL, 1.6 M in hexane) at −78° C. After 30 min, a solution of methyl chloroformate (0.15 mL) in THF (1 mL) was added drop-wise. The mixture was warmed to r.t. and stirred over night. The reaction was then quenched by $NH_4Cl$ (sat., 0.5 mL). The mixture was concentrated by vacuum and purified by silica gel column to afford the title product (200 mg) as colorless oil. MS: $[M+1]^+$ 268.

(S)-4-(1-(7,8-dichloro-4-(1H-imidazol-1-yl)quinolin-2-yl)pyrrolidin-2-yl)but-2-ynoic acid (I-819) is prepared essentially by the same methods as for I-664 from tert-butyl (S)-2-(4-methoxy-4-oxobut-2-yn-1-yl)pyrrolidine-1-carboxylate. MS: $[M+1]^+$ 415.

Example 134: Synthesis of (S)-3-((1-(7-chloro-4-(1H-imidazol-1-yl)-8-phenylquinolin-2-yl)pyrrolidin-2-yl)methoxy)propanoic acid (I-863)

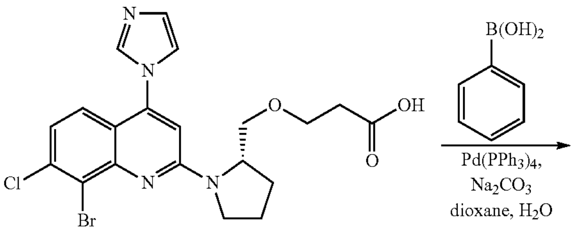

I-862

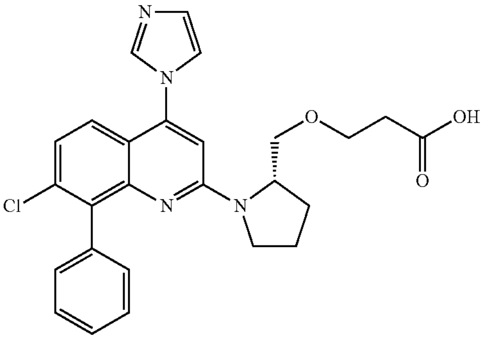

I-863

A mixture of (S)-3-((1-(8-bromo-7-chloro-4-(1H-imidazol-1-yl)quinolin-2-yl)pyrrolidin-2-yl)methoxy)propanoic acid (14 mg, 0.03 mmol), $Na_2CO_3$ (10 mg, 0.14 mmol), dioxane (1 mL) and $H_2O$ (0.5 mL) was purged by $N_2$ for 10 min. Tetrakis (1 mg, 0.001 mmol) was added. The mixture was stirred at 80° C. for 3 h. The mixture was concentrated by vacuum and purified by silica gel column to afford I-863 (6 mg) as white solid. MS: $[M+1]^+$ 477.

Example 135: Synthesis of 3-(((S)-1-(7,8-dichloro-4-((R)-3-hydroxypyrrolidin-1-yl)quinolin-2-yl)pyrrolidin-2-yl)methoxy)propanoic acid (I-821)

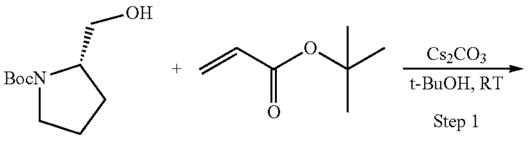

-continued

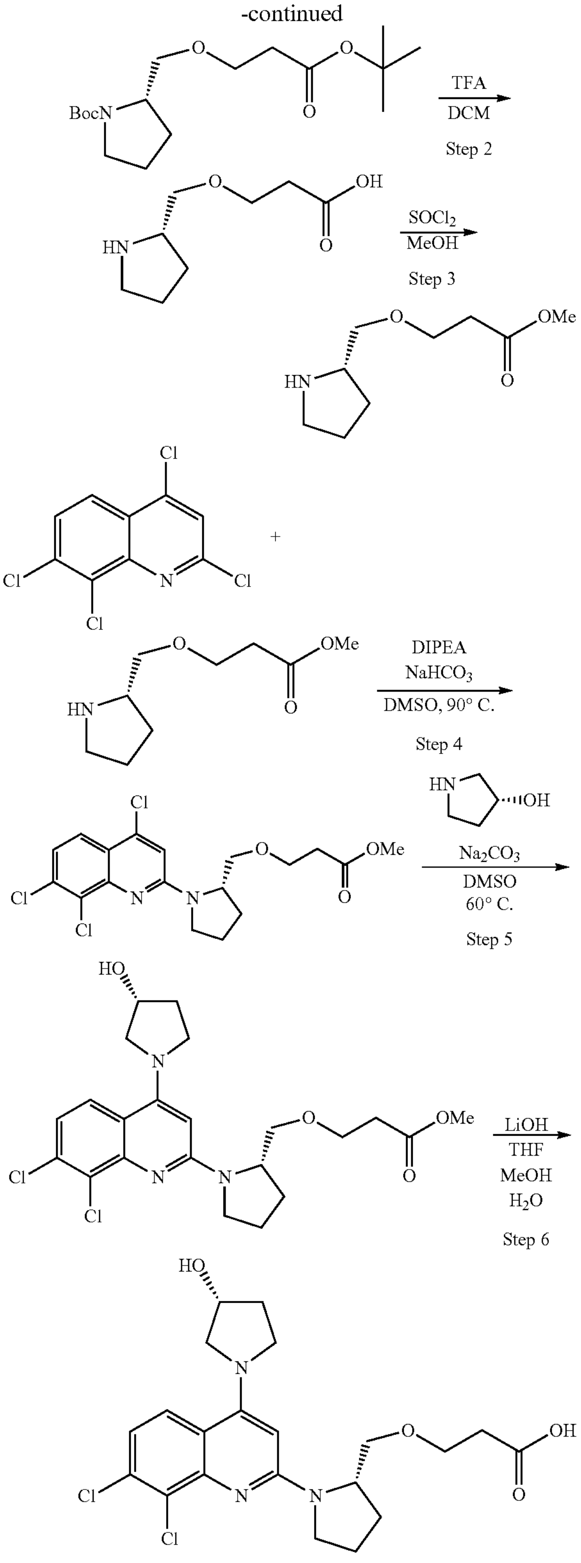

I-821

Step 1: tert-butyl (S)-2-((3-(tert-butoxy)-3-oxopropoxy) methyl)pyrrolidine-1-carboxylate. The procedure was the same as that in the synthesis of I-665.

Step 2: (S)-3-(pyrrolidin-2-ylmethoxy)propanoic acid. The procedure was the same as that in the synthesis of I-665.

Step 3: methyl (S)-3-(pyrrolidin-2-ylmethoxy)propanoate. The procedure was the same as that in the synthesis of I-665.

Step 4: methyl (S)-3-((1-(4,7,8-trichloroquinolin-2-yl) pyrrolidin-2-yl)methoxy)propanoate. The procedure was the same as that in the synthesis of I-665.

Step 5: methyl 3-(((S)-1-(7,8-dichloro-4-((R)-3-hydroxypyrrolidin-1-yl)quinolin-2-yl)pyrrolidin-2-yl)methoxy)propanoate. To a vial were added methyl (S)-3-((1-(4,7,8-trichloroquinolin-2-yl)pyrrolidin-2-yl)methoxy)propanoate (21 mg, 0.050 mmol), (R)-pyrrolidin-3-ol (22 mg, 0.25 mmol), $Na_2CO_3$ (5.3 mg, 0.050 mmol) and DMSO (0.5 ml). The reaction mixture was stirred at 60° C. over-night. After simple work-up, the crude was purified by silica gel chromatography to afford the title product (9.2 mg). (MS: $[M+1]^+$ 454)

Step 6: 3-(((S)-1-(7,8-dichloro-4-((R)-3-hydroxypyrrolidin-1-yl)quinolin-2-yl)pyrrolidin-2-yl)methoxy)propanoic acid. The procedure was the same as that in the synthesis of I-665. (MS: $[M+1]^+$454)

Example 136: Synthesis of (S)-3-((1-(7,8-dichloro-4-(4-methyl-1H-imidazol-1-yl)quinolin-2-yl)pyrrolidin-2-yl)methoxy)propanoic acid (I-825)

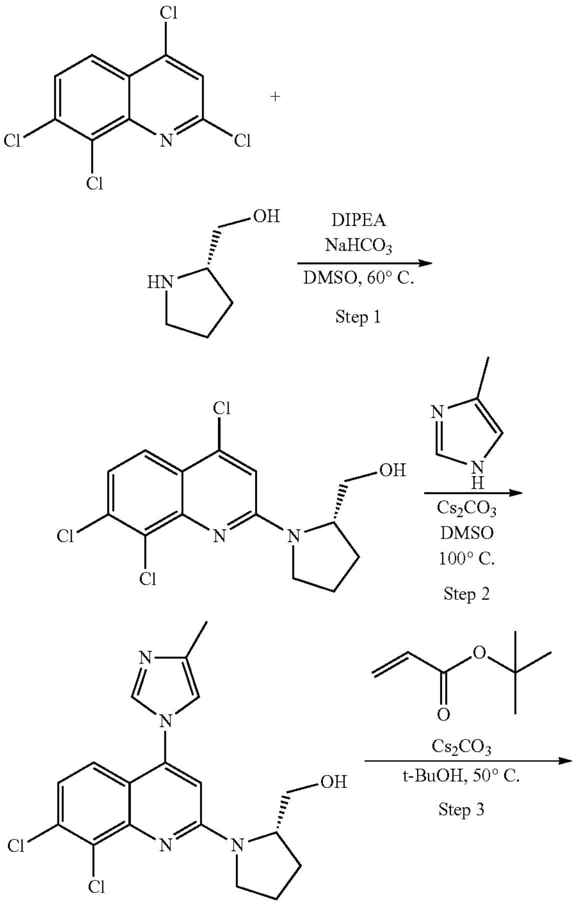

-continued

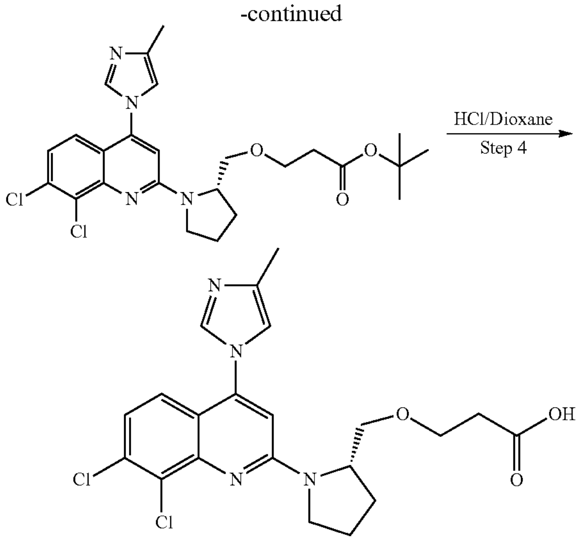

I-825

Step 1: (S)-(1-(4,7,8-trichloroquinolin-2-yl)pyrrolidin-2-yl)methanol. The procedure was the same as that in the synthesis of I-287.

Step 2: (S)-(1-(7,8-dichloro-4-(4-methyl-1H-imidazol-1-yl)quinolin-2-yl)pyrrolidin-2-yl)methanol. The procedure was the same as that in the synthesis of I-821.

Step 3: tert-butyl (S)-3-((1-(7,8-dichloro-4-(4-methyl-1H-imidazol-1-yl)quinolin-2-yl)pyrrolidin-2-yl)methoxy) propanoate. The procedure was the same as that in the synthesis of I-665.

Step 4: (S)-3-((1-(7,8-dichloro-4-(4-methyl-1H-imidazol-1-yl)quinolin-2-yl)pyrrolidin-2-yl)methoxy)propanoic acid (I-825). To a vial were added tert-butyl (S)-3-((1-(7,8-dichloro-4-(4-methyl-1H-imidazol-1-yl)quinolin-2-yl)pyrrolidin-2-yl)methoxy)propanoate (13 mg, 0.0257 mmol) and HCl in 1,4-dioxane (4 N, 0.3 ml). The mixture was stirred at room temperature for 3 hours. All volatiles were removed under reduced pressure. After lyophilization, the title compound was obtained as HCl salt (11 mg). (MS: $[M+1]^+$ 449)

Example 137: Synthesis of (±)3-(((2S,3R)-1-(7,8-dichloro-4-(1H-imidazol-1-yl)quinolin-2-yl)-2-(methoxycarbonyl)pyrrolidin-3-yl)methoxy)propanoic acid (I-813)

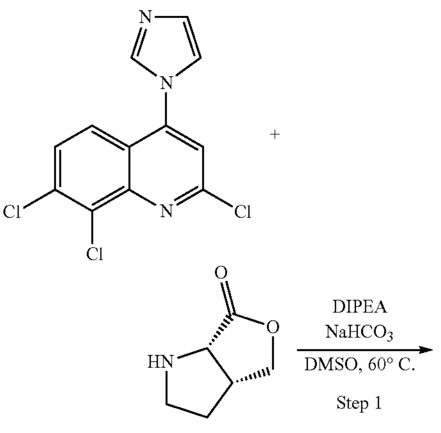

(Racemic)

-continued

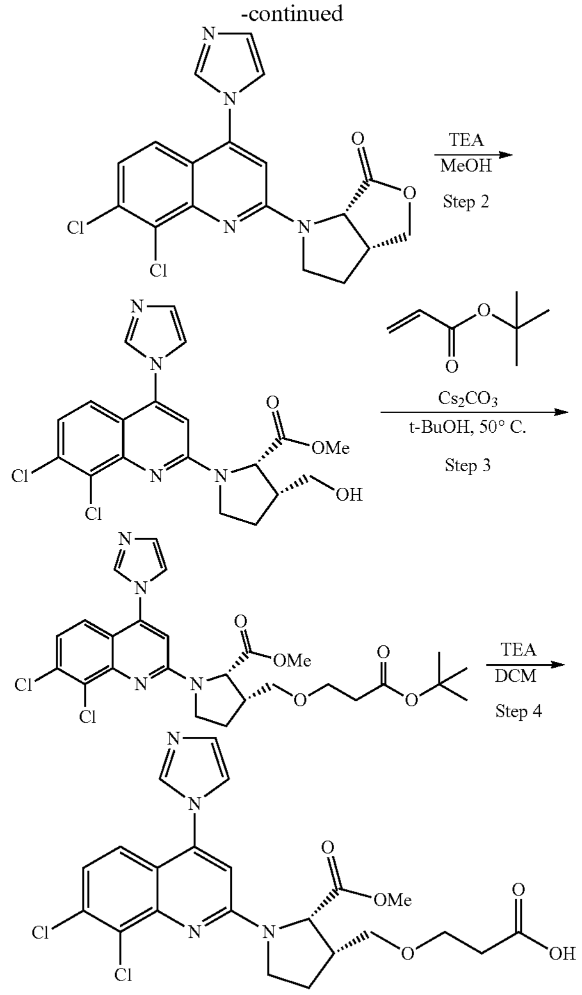

I-813

(Racemic)

Step 1: (±)(3aR,6aS)-1-(7,8-dichloro-4-(1H-imidazol-1-yl)quinolin-2-yl)hexahydro-6H-furo[3,4-b]pyrrol-6-one. The procedure was the same as that in the synthesis of I-665.

Step 2: (±)methyl (2S,3R)-1-(7,8-dichloro-4-(1H-imidazol-1-yl)quinolin-2-yl)-3-(hydroxymethyl)pyrrolidine-2-carboxylate. The crude product in step 1 was treated with TEA (20 μl, 0.143 mmol) and methanol (0.5 ml) for 18 hours. After removing all volatiles, the crude was used in next step.

Step 3: (±)methyl (2S,3R)-3-((3-(tert-butoxy)-3-oxopropoxy)methyl)-1-(7,8-dichloro-4-(1H-imidazol-1-yl)quinolin-2-yl)pyrrolidine-2-carboxylate. The procedure was the same as that in the synthesis of I-665.

Step 4: (±)3-(((2S,3R)-1-(7,8-dichloro-4-(1H-imidazol-1-yl)quinolin-2-yl)-2-(methoxycarbonyl)pyrrolidin-3-yl)methoxy)propanoic acid. The procedure was the same as that in the synthesis of I-665. The title compound was obtained as TFA salt (17 mg). (MS: $[M+1]^+$ 493)

Example 138: Synthesis of (S)-3-((1-(4-(6-aminopyridin-3-yl)-7,8-dichloroquinolin-2-yl)pyrrolidin-2-yl)methoxy)propanoic acid (I-822)

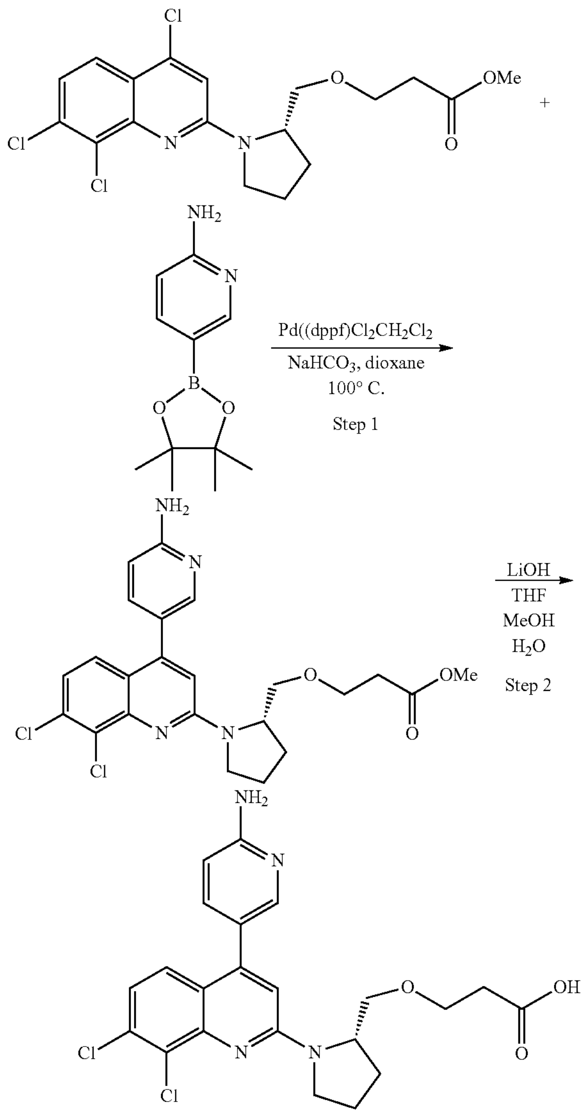

I-822

Step 1: methyl (S)-3-((1-(4-(6-aminopyridin-3-yl)-7,8-dichloroquinolin-2-yl)pyrrolidin-2-yl)methoxy)propanoate. To a flask were added methyl (S)-3-((1-(4,7,8-trichloroquinolin-2-yl)pyrrolidin-2-yl)methoxy)propanoate (104 mg, 0.25 mmol), 1,4-dioxane (8.0 ml), 5-(4,4,5,5-tetramethyl-1,3,2-dioxaborolan-2-yl)pyridin-2-amine (110 mg, 0.50 mmol), $NaHCO_3$ (62 mg, 0.75 mmol), $Pd(dppf)Cl_2$—$CH_2Cl_2$(41 mg, 0.050 mmol) and $H_2O$ (1.0 ml). After degassed with $N_2$ for 4 times, the reaction mixture was stirred at 100° C. for 6 hours. The reaction mixture was diluted with ethyl acetate, washed with $H_2O$, brine and dried over $Na_2SO_4$. After concentration the crude was purified by silica gel column to afford the title product (90 mg).

Step 2: (S)-3-((1-(4-(6-aminopyridin-3-yl)-7,8-dichloroquinolin-2-yl)pyrrolidin-2-yl)methoxy)propanoic acid. The procedure was the same as that in the synthesis of I-636. The title compound was obtained as free acid. (MS: $[M+1]^+$ 461)

The following compounds are prepared essentially by the same methods as for I-822.

| Example | Starting Material | | Structure | MS [M + 1]$^+$ |
|---|---|---|---|---|
| I-823 | 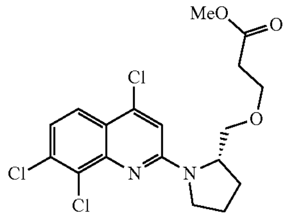 [SMILES: COC(=O)CCOC[C@@H]1CCCN1c1cc(Cl)c2ccc(Cl)c(Cl)c2n1] | 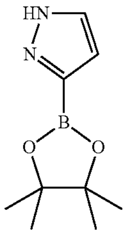 | 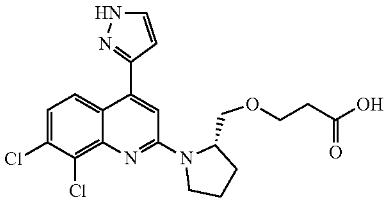 [SMILES: O=C(O)CCOC[C@@H]1CCCN1c1cc(-c2cc[nH]n2)c2ccc(Cl)c(Cl)c2n1] | 435 |
| I-824 | 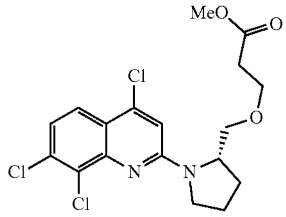 [SMILES: COC(=O)CCOC[C@@H]1CCCN1c1cc(Cl)c2ccc(Cl)c(Cl)c2n1] | 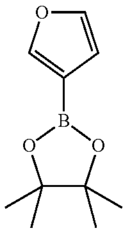 | 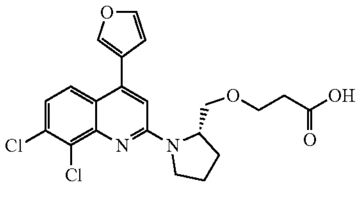 [SMILES: O=C(O)CCOC[C@@H]1CCCN1c1cc(-c2ccoc2)c2ccc(Cl)c(Cl)c2n1] | 435 |
| I-826 | 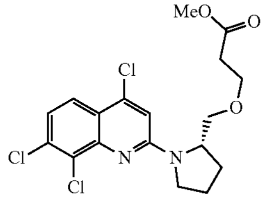 [SMILES: COC(=O)CCOC[C@@H]1CCCN1c1cc(Cl)c2ccc(Cl)c(Cl)c2n1] | 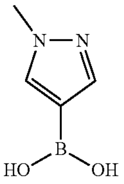 | 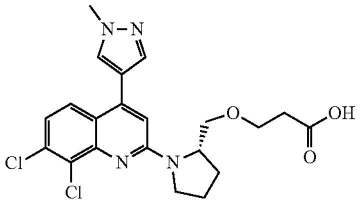 [SMILES: Cn1cc(-c2cc(N3CCC[C@H]3COCCC(=O)O)nc3c(Cl)c(Cl)ccc23)cn1] | 449 |

Example 139: Synthesis of 3-(2-((7,8-dichloro-4-(1H-imidazol-1-yl)quinolin-2-yl)oxy)ethoxy)propanoic acid (I-828)

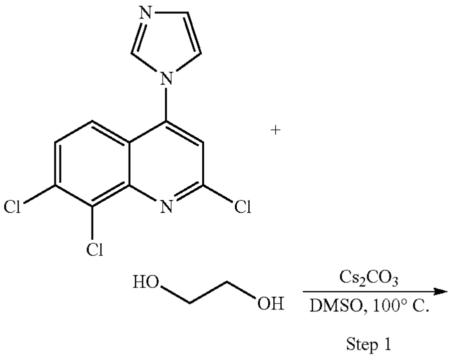

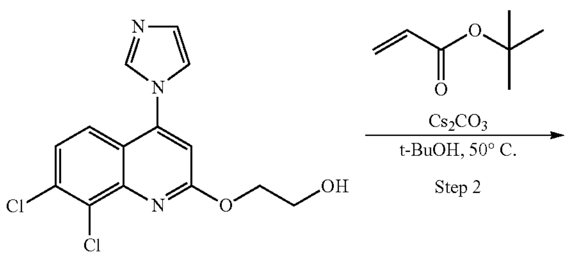

-continued

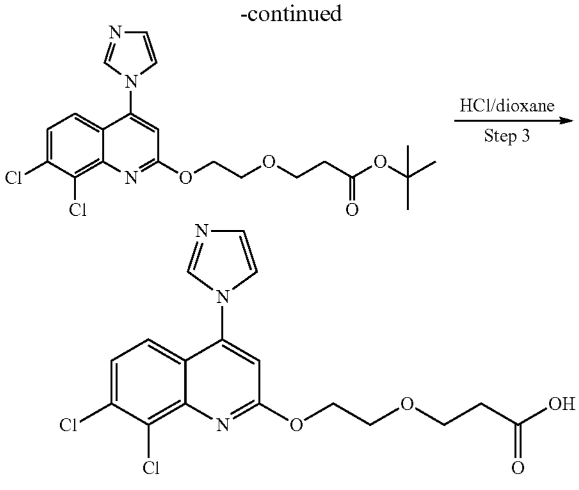

I-828

Step 1: 2-((7,8-dichloro-4-(1H-imidazol-1-yl)quinolin-2-yl)oxy)ethan-1-ol. The procedure was the same as that in the synthesis of I-277.

Step 2: tert-butyl 3-(2-((7,8-dichloro-4-(1H-imidazol-1-yl)quinolin-2-yl)oxy)ethoxy)propanoate. The procedure was the same as that in the synthesis of I-665.

Step 3: 3-(2-((7,8-dichloro-4-(1H-imidazol-1-yl)quinolin-2-yl)oxy)ethoxy)propanoic acid. The procedure was the same as that in the synthesis of I-825. The title compound was obtained as HCl salt. (MS: [M+1]$^+$ 396)

Example 140: Synthesis of 3-((3-(7,8-dichloro-4-(1H-imidazol-1-yl)quinolin-2-yl)benzyl)oxy)propanoic acid (I-840)

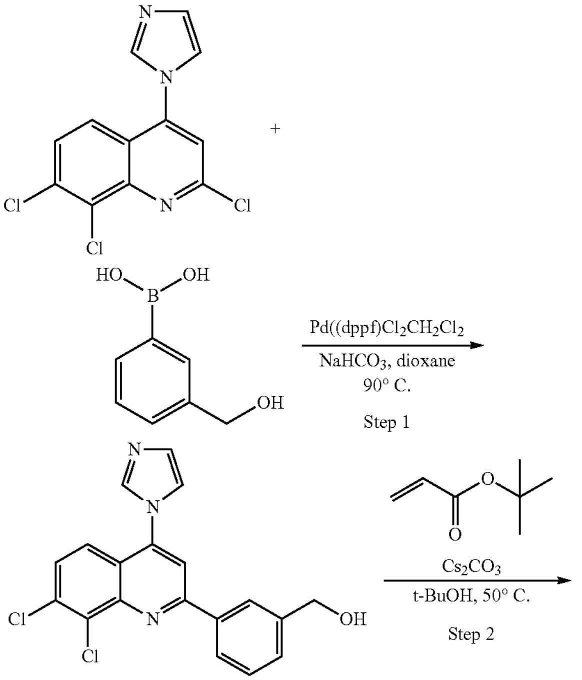

-continued

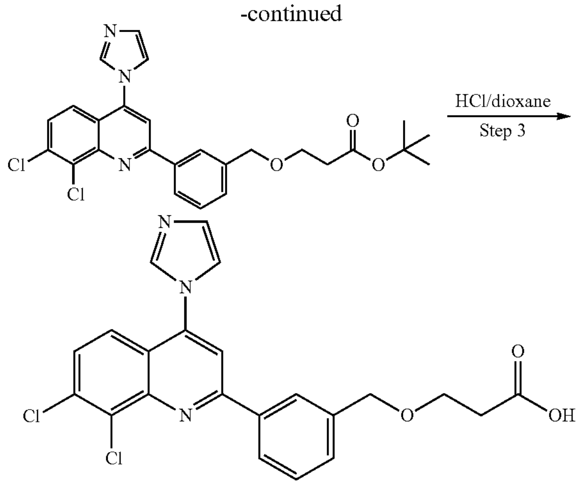

I-840

Step 1: (3-(7,8-dichloro-4-(1H-imidazol-1-yl)quinolin-2-yl)phenyl)methanol. The procedure was the same as that in the synthesis of I-822.

Step 2: tert-butyl 3-((3-(7,8-dichloro-4-(1H-imidazol-1-yl)quinolin-2-yl)benzyl)oxy)propanoate. The procedure was the same as that in the synthesis of I-665.

Step 3: 3-((3-(7,8-dichloro-4-(1H-imidazol-1-yl)quinolin-2-yl)benzyl)oxy)propanoic acid. The procedure was the same as that in the synthesis of I-825. The title compound was obtained as HCl salt. (MS: $[M+1]^+$ 442)

The following compounds are prepared essentially by the same methods as for I-840.

| Example | Starting Material | Structure | MS $[M + 1]^+$ |
| --- | --- | --- | --- |
| I-841 | 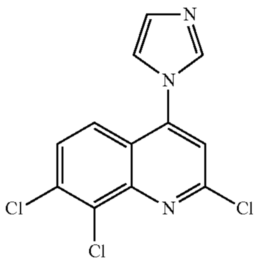 [SMILES: Clc1cc(-n2ccnc2)c2ccc(Cl)c(Cl)c2n1] 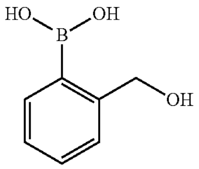 [SMILES: OCc1ccccc1B(O)O] | 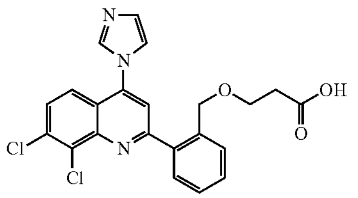 [SMILES: O=C(O)CCOCc1ccccc1-c1cc(-n2ccnc2)c2ccc(Cl)c(Cl)c2n1] | 442 |
| I-877 | 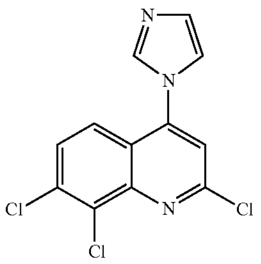 [SMILES: Clc1cc(-n2ccnc2)c2ccc(Cl)c(Cl)c2n1] 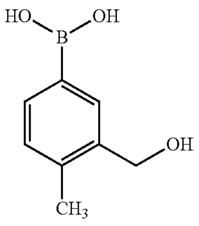 | 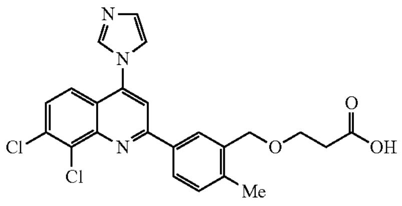 [SMILES: Cc1ccc(-c2cc(-n3ccnc3)c3ccc(Cl)c(Cl)c3n2)cc1COCCC(=O)O] | 456 |

-continued
| Example | Starting Material | | Structure | MS [M + 1]$^+$ |
|---|---|---|---|---|
| I-878 | 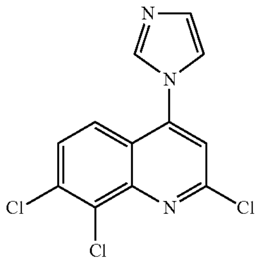 [SMILES: Clc1cc(-n2ccnc2)c2ccc(Cl)c(Cl)c2n1] | 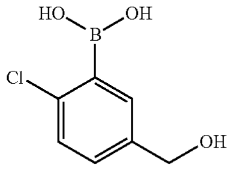 [SMILES: OCc1ccc(Cl)c(B(O)O)c1] | 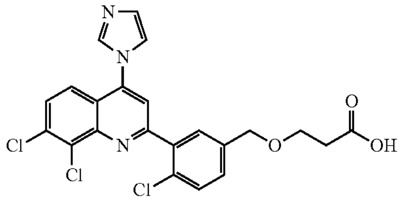 [SMILES: O=C(O)CCOCc1ccc(Cl)c(-c2cc(-n3ccnc3)c3ccc(Cl)c(Cl)c3n2)c1] | 476 |
| I-879 | 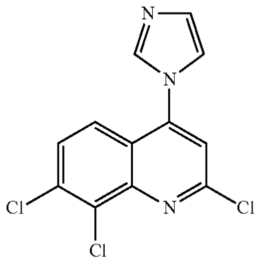 [SMILES: Clc1cc(-n2ccnc2)c2ccc(Cl)c(Cl)c2n1] | 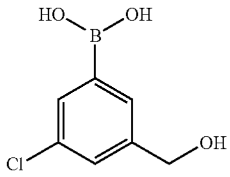 [SMILES: OCc1cc(Cl)cc(B(O)O)c1] | 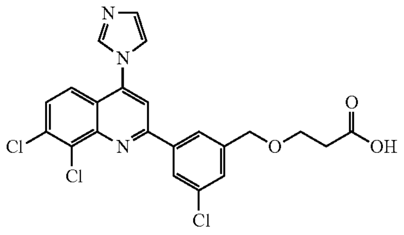 [SMILES: O=C(O)CCOCc1cc(Cl)cc(-c2cc(-n3ccnc3)c3ccc(Cl)c(Cl)c3n2)c1] | 476 |
| I-880 | 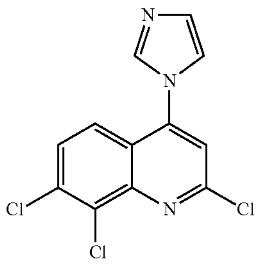 [SMILES: Clc1cc(-n2ccnc2)c2ccc(Cl)c(Cl)c2n1] | 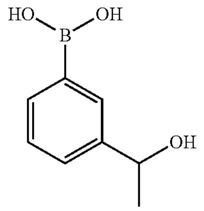 | 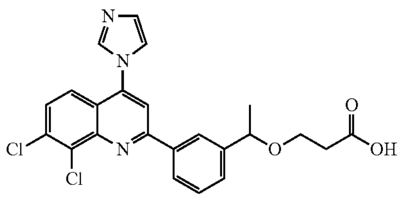 [SMILES: CC(OCCC(=O)O)c1cccc(-c2cc(-n3ccnc3)c3ccc(Cl)c(Cl)c3n2)c1] | 456 |
| I-884 | 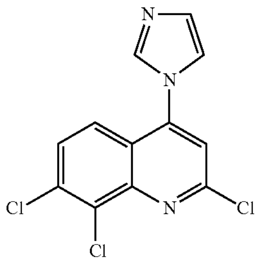 [SMILES: Clc1cc(-n2ccnc2)c2ccc(Cl)c(Cl)c2n1] | 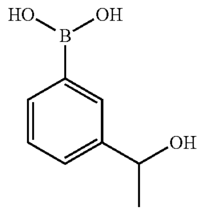 | 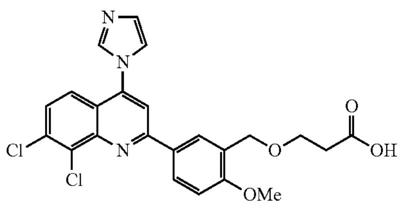 [SMILES: COc1ccc(-c2cc(-n3ccnc3)c3ccc(Cl)c(Cl)c3n2)cc1COCCC(=O)O] | 472 |
Example 141: Synthesis of 5-chloro-2-(3-((7,8-dichloro-4-(1H-imidazol-1-yl)quinolin-2-yl)(isopropyl)amino) propoxy) benzoic acid (I-848)
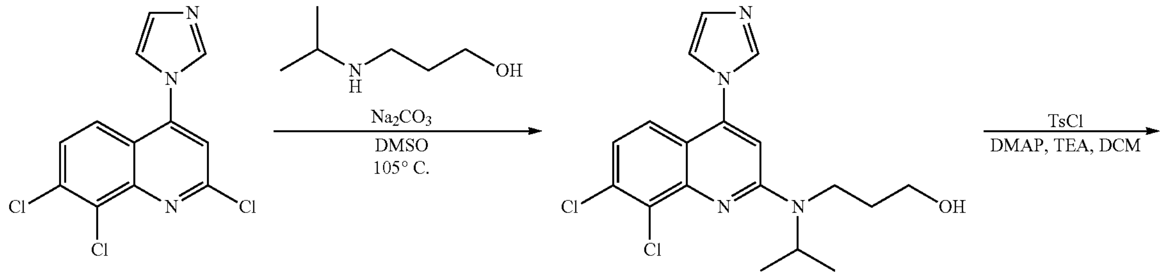

-continued

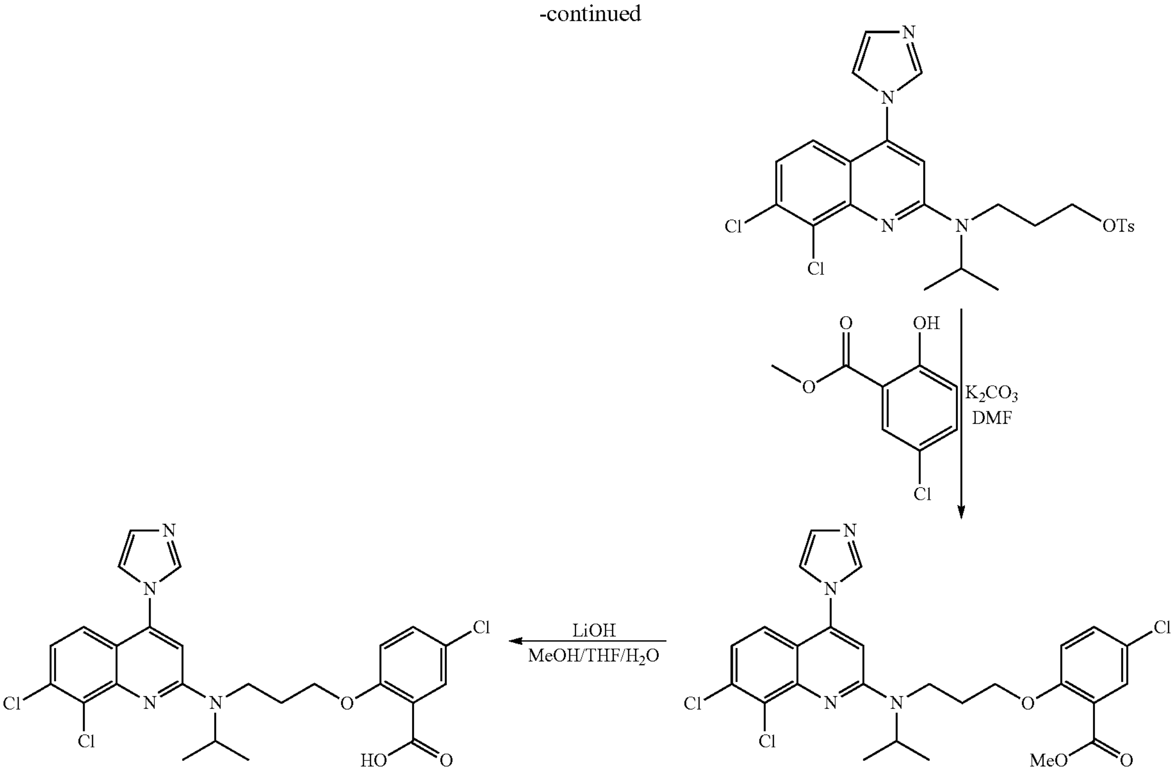

I-848

Step 1: 3-((7,8-dichloro-4-(1H-imidazol-1-yl)quinolin-2-yl)(isopropyl)amino)propan-1-ol. To a mixture of 2,7,8-trichloro-4-(1H-imidazol-1-yl)quinoline (1.074 g), 3-(isopropylamino)propan-1-ol (0.53 g) and $Na_2CO_3$ (0.96 g) was added DMSO (3.4 mL). The resultant suspended solution was heated at 105° C. overnight. After cooling down to room temperature, the reaction mixture was diluted with water (5 mL) and extracted with EtOAc (20 mL). The isolated organic layer was washed with brine and dried over anhydrous $Na_2SO_4$. After concentration under reduced pressure, the residues were purified by silica gel column chromatography, eluting with a gradient of hexane and EtOAc (5% MeOH), to afford the title compound (654 mg) as light brown solid. MS: $[M+1]^+$ 379.

Step 2: 3-((7,8-dichloro-4-(1H-imidazol-1-yl)quinolin-2-yl(isopropyl)amino)propyl 4-methylbenzenesulfonate. To a suspension of 3-((7,8-dichloro-4-(1H-imidazol-1-yl) quinolin-2-yl) (isopropyl)amino)propan-1-ol (654 mg), DMAP (45 mg) and TsCl (228 mg) in DCM (10 mL) was added TEA (0.3 mL). After the reaction mixture was stirred over 3 hours, it was diluted with DCM (20 mL). The resultant organic solution was washed with water (10 mL) and brine (10 mL) and dried over anhydrous $Na_2SO_4$. Concentration under reduced pressure afforded the crude title compound (610 mg), which was used in the next step without further purification. MS: $[M+1]^+$ 533.

Step 3: methyl 5-chloro-2-(3-((7,8-dichloro-4-(1H-imidazol-1-yl)quinolin-2-yl)(isopropyl)amino)propoxy)benzoate. To a solution of 3-((7,8-dichloro-4-(1H-imidazol-1-yl)quinolin-2-yl(isopropyl)amino)propyl 4-methylbenzenesulfonate (32 mg) and methyl 5-chloro-2-hydroxybenzoate (13.5 mg) in anhydrous DMF (0.5 mL) was added anhydrous $K_2CO_3$ (10 mg). After the reaction mixture was stirred over 3 h at 55° C., it was diluted with water (4 mL) and EtOAc (15 mL). The organic layer was isolated, washed with brine (10 mL) and dried over anhydrous $Na_2SO_4$. Concentration under reduced pressure and purification by silica gel column chromatography, eluting with a gradient of hexane and EtOAc (5% MeOH), afforded the title compound (24 mg). MS: $[M+1]^+$ 547.

Step 4: 5-chloro-2-(3-((7,8-dichloro-4-(1H-imidazol-1-yl) quinolin-2-yl) (isopropyl)amino) propoxy) benzoic acid (I-848). To a suspension of methyl 5-chloro-2-(3-((7,8-dichloro-4-(1H-imidazol-1-yl)quinolin-2-yl)(isopropyl) amino)propoxy)benzoate (24 mg) in MeOH (0.4 mL) and water (0.1 mL) was added $LiOH \cdot H_2O$ (10.2 mg). After stirring over 1 h, THF (0.2 mL) was added. A clear solution was afforded after the reaction mixture was stirred overnight. The reaction progress was monitored by LC/MS. After concentration under reduced pressure removed the volatiles, the residues were suspended in water (0.2 mL) and treated with HOAc (0.015 mL). After sonicating over 5 min, the solid was collected by centrifuge and lyophilized to afford the title compound (13 mg). MS: $[M+1]^+$ 533.

The following compounds were prepared essentially by the same methods as described above for I-848.

| Example | Starting Material | | Structure | MS [M + 1]+ |
|---|---|---|---|---|
| I-849 | 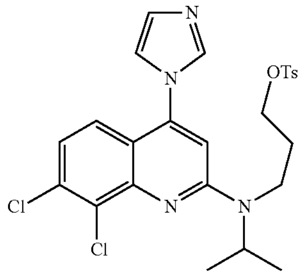 [SMILES: Cc1ccc(S(=O)(=O)OCCCN(c2cc(-n3ccnc3)c3ccc(Cl)c(Cl)c3n2)C(C)C)cc1] | 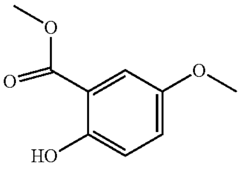 | 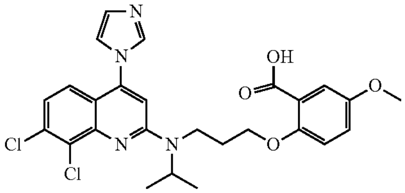 [SMILES: COc1ccc(OCCCN(c2cc(-n3ccnc3)c3ccc(Cl)c(Cl)c3n2)C(C)C)c(C(=O)O)c1] | 529 |
| I-850 | 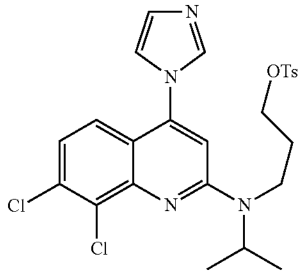 [SMILES: Cc1ccc(S(=O)(=O)OCCCN(c2cc(-n3ccnc3)c3ccc(Cl)c(Cl)c3n2)C(C)C)cc1] | 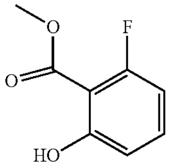 | 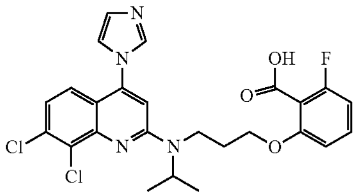 [SMILES: CC(C)N(CCCOc1cccc(F)c1C(=O)O)c1cc(-n2ccnc2)c2ccc(Cl)c(Cl)c2n1] | 517 |
| I-851 | 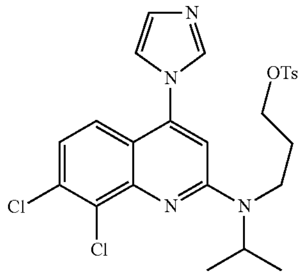 [SMILES: Cc1ccc(S(=O)(=O)OCCCN(c2cc(-n3ccnc3)c3ccc(Cl)c(Cl)c3n2)C(C)C)cc1] | 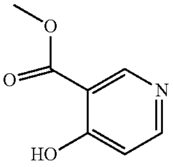 | 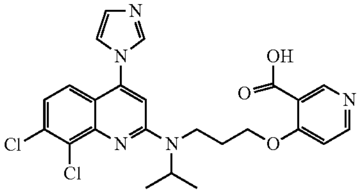 [SMILES: CC(C)N(CCCOc1ccncc1C(=O)O)c1cc(-n2ccnc2)c2ccc(Cl)c(Cl)c2n1] | 500 |
| I-852 | 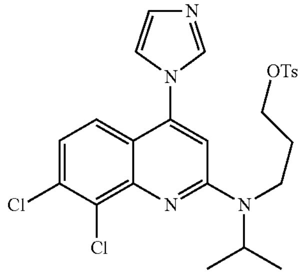 [SMILES: Cc1ccc(S(=O)(=O)OCCCN(c2cc(-n3ccnc3)c3ccc(Cl)c(Cl)c3n2)C(C)C)cc1] | 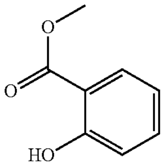 | 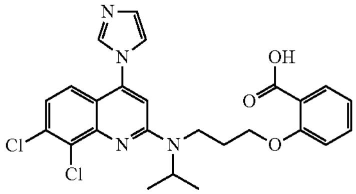 [SMILES: CC(C)N(CCCOc1ccccc1C(=O)O)c1cc(-n2ccnc2)c2ccc(Cl)c(Cl)c2n1] | 499 |
| I-847 | 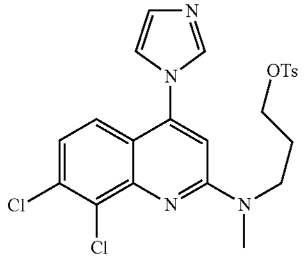 [SMILES: Cc1ccc(S(=O)(=O)OCCCN(C)c2cc(-n3ccnc3)c3ccc(Cl)c(Cl)c3n2)cc1] | 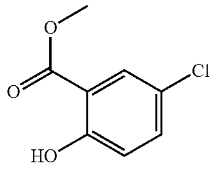 | 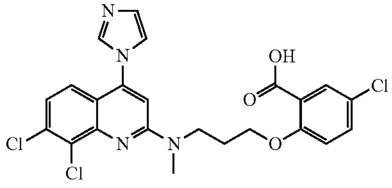 [SMILES: CN(CCCOc1ccc(Cl)cc1C(=O)O)c1cc(-n2ccnc2)c2ccc(Cl)c(Cl)c2n1] | 505 |

Example 142: Synthesis of (S)-3-((1-(7,8-dichloro-4-(1H-imidazol-1-yl)quinolin-2-yl)-5-oxopyrrolidin-2-yl)methoxy)propanoic acid (I-812)

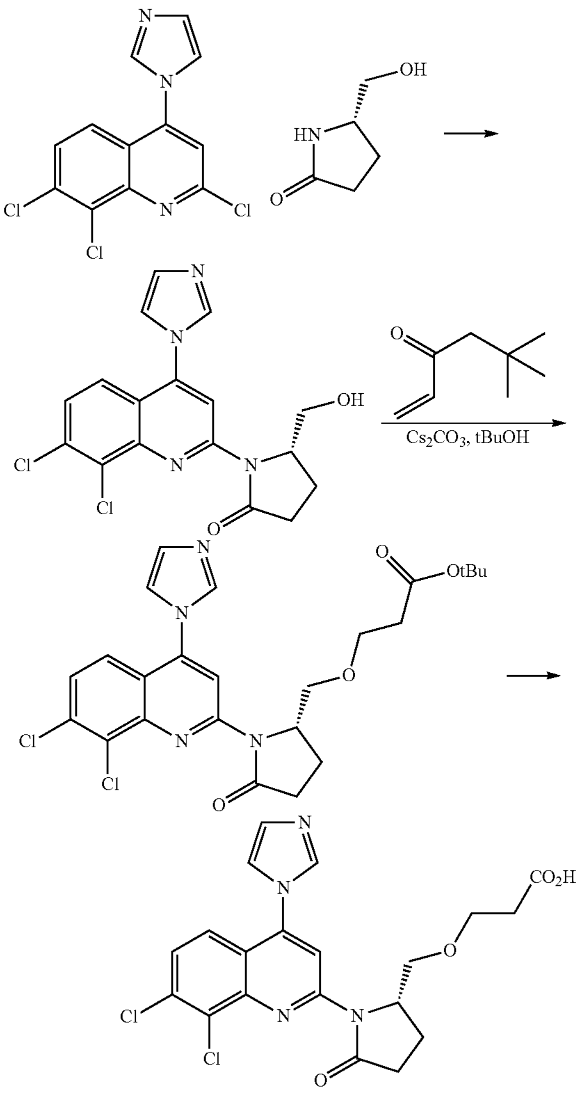

I-812

Step 1: (S)-1-(7,8-dichloro-4-(1H-imidazol-1-yl)quinolin-2-yl)-5-(hydroxymethyl)pyrrolidin-2-one. To a mixture of 2,7,8-trichloro-4-(1H-imidazol-1-yl)quinoline (200 mg), bis(dibenzylideneacetone)palladium(0) (20 mg), Rac-BINAP (14 mg), (S)-5-(hydroxymethyl)pyrrolidin-2-one (92 mg) and $Cs_2CO_3$ (441 mg) were added anhydrous dioxane (6 mL) under $N_2$. The resultant mixtures were degassed three cycles via vacuum and purging with $N_2$. The resultant mixture was heated and stirred at 100° C. overnight under $N_2$. After the aqueous work-up with EtOAc, the isolated organic layer was dried over anhydrous. $Na_2SO_4$. After concentration under reduced pressure, the residues were purified by silica gel column chromatography, eluting with a gradient of hexane and EtOAc (5% MeOH), to afford the title compound (28 mg). MS: $[M+1]^+$ 377.

Step 2: tert-butyl (S)-3-((1-(7,8-dichloro-4-(1H-imidazol-1-yl)quinolin-2-yl)-5-oxopyrrolidin-2-yl)methoxy)propanoate. Following the same preparation procedure as described in step 3 of I-825, the title compound was prepared. MS: $[M+1]^+$ 505.

Step 3: (S)-3-((1-(7,8-dichloro-4-(1H-imidazol-1-yl)quinolin-2-yl)-5-oxopyrrolidin-2-yl)methoxy)propanoic acid (I-812). Following the same preparation procedure as described in step 4 of I-825, the title compound was prepared. MS: $[M+1]^+$ 449.

Example 143: Synthesis of methyl 2-(3-(((7,8-dichloro-4-(1H-imidazol-1-yl)quinolin-2-yl)amino)methyl)-5-fluorophenyl)acetate (I-890) and 2-(3-(((7,8-dichloro-4-(1H-imidazol-1-yl)quinolin-2-yl)amino)methyl)-5-fluorophenyl)acetic acid (I-891)

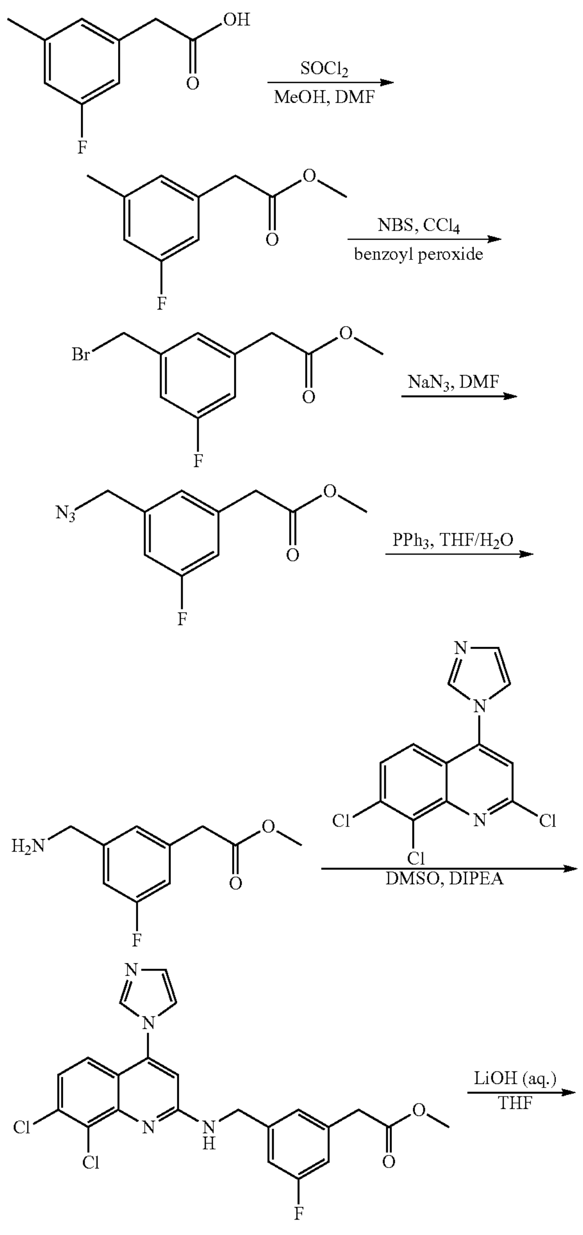

I-890

-continued

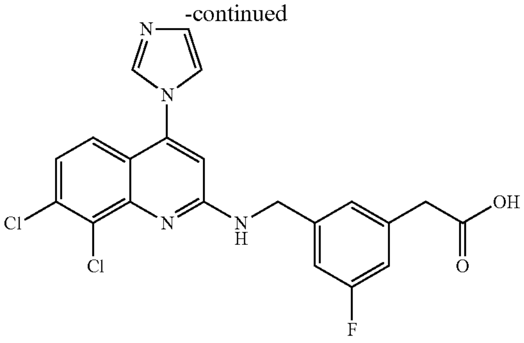

I-891

Step 1: methyl 2-(3-fluoro-5-methylphenyl)acetate. To a solution of 2-(3-fluoro-5-methylphenyl)acetic acid (336 mg, 2 mmol) in MeOH (4 mL) and DMF (0.01 mL) was added $SOCl_2$ (0.22 mL, 3 mmol) dropwise at 0° C. The solution was warmed to r.t. and stirred for 2 h. After evaporation, the reaction was quenched by $NaHCO_3$ (sat., 2 mL) and extracted by EtOAc (5 mL×2). The organic phase was collected and evaporated to give crude product which was used directly for next step without purification.

Step 2: methyl 2-(3-(bromomethyl)-5-fluorophenyl)acetate. To a solution of crude from step 1 in $CCl_4$ (5 mL) was added NBS (392 mg, 2.2 mmol) and benzoyl peroxide (10 mg). The mixture was stirred at 75° C. overnight. After cooling down to r.t., the solution was concentrated and purified by silica gel column to afford the title product (150 mg) as colorless oil.

Step 3: methyl 2-(3-(azidomethyl)-5-fluorophenyl)acetate. To a solution of methyl 2-(3-(bromomethyl)-5-fluorophenyl)acetate (50 mg, 0.19 mmol) in DMF (1 mL) was added $NaN_3$ (19 mg, 0.29 mmol). The mixture was stirred at 75° C. overnight. After cooling down to r.t., the mixture was diluted by $H_2O$ (2 mL) and extracted by EtOAc (3 mL×2). The organic phase was collected and evaporated to give a crude product which was used directly for next step without purification.

Step 4: methyl 2-(3-(aminomethyl)-5-fluorophenyl)acetate. The Staudinger reaction is performed essentially the same as for I-757.

Step 5: methyl 2-(3-(((7,8-dichloro-4-(1H-imidazol-1-yl)quinolin-2-yl)amino)methyl)-5-fluorophenyl)acetate (I-890). I-890 is prepared essentially by the same methods as for I-664. MS: $[M-1]^-$ 457.

Step 6: 2-(3-(((7,8-dichloro-4-(1H-imidazol-1-yl)quinolin-2-yl)amino)methyl)-5-fluorophenyl)acetic acid (I-891). I-891 is prepared essentially by the same methods as for I-714. MS: $[M-1]^-$ 443.

Example 144: Biology

Expression and Purification of Recombinant cGAS Protein: cDNA encoding full-length or amino acids 147-520 of human cGAS was inserted into a modified pET28a vector containing an in-frame His6-SUMO tag. The *E. coli* strain BL21/pLys harboring the plasmid was induced with 0.5 mM IPTG at 18° C. overnight. His6-SUMO tag was removed by a SUMO protease digestion following purification of the His6-SUMO-cGAS as described previously (Sun et al, 2013, *Science* 339, 786).

In vitro inhibition assay of cGAS activity: A 60 μL mixture containing 20 mM Tris-Cl, pH 7.5, 5 mM $MgCl_2$, 0.2 mg/mL BSA, 0.01 mg/mL Herring testis DNA, 6.6 μM ATP, 0.1 mM GTP, 1.5 μg/mL of recombinant human cGAS (aa147-522) and serial dilutions of a test compound in DMSO was added to a 96-well plate and incubated at 37° C. for 20 minutes. At the end of reaction, 40 μL of KinaseGlo Max (Promega) was added and chemiluminescence was measured with a luminometer. Inhibitory effect of a compound is evaluated by plotting percentage of ATP consumption against logarithm of compound concentrations. $IC_{50}$ value was calculated using GraphPad Prism 8 (GraphPad Software, Inc.).

The results of the cGAS inhibition assay for compounds of the disclosure are presented in Table 2 and Table 3. The letter codes for cGAS $IC_{50}$ include: A (<2 μM); B (2-30 μM); C (>30 μM).

TABLE 2 cGAS Inhibition Results

| I-# | $IC_{50}$ |
|---|---|
| I-1 | B |
| I-2 | B |
| I-3 | C |
| I-4 | B |
| I-5 | B |
| I-6 | A |
| I-7 | B |
| I-8 | B |
| I-9 | C |
| I-10 | B |
| I-11 | B |
| I-12 | C |
| I-13 | C |
| I-14 | C |
| I-15 | A |
| I-16 | C |
| I-17 | B |
| I-18 | B |
| I-19 | A |
| I-20 | A |
| I-21 | A |
| I-22 | A |
| I-23 | A |
| I-24 | A |
| I-25 | C |
| I-26 | A |
| I-27 | C |
| I-28 | A |
| I-29 | A |
| I-30 | B |
| I-31 | C |
| I-32 | A |
| I-33 | B |
| I-34 | C |
| I-35 | B |
| I-36 | C |
| I-37 | C |
| I-38 | C |
| I-39 | A |
| I-40 | C |
| I-41 | A |
| I-42 | A |
| I-43 | A |
| I-44 | C |
| I-45 | B |
| I-46 | A |
| I-47 | A |
| I-48 | A |
| I-49 | C |
| I-50 | A |
| I-51 | C |
| I-52 | C |
| I-53 | B |
| I-54 | B |
| I-55 | A |
| I-56 | B |
| I-57 | B |

TABLE 2-continued cGAS Inhibition Results

| I-# | $IC_{50}$ |
|---|---|
| I-58 | C |
| I-59 | C |
| I-60 | C |
| I-61 | C |
| I-62 | C |
| I-63 | C |
| I-64 | C |
| I-65 | C |
| I-66 | C |
| I-67 | B |
| I-68 | C |
| I-69 | C |
| I-70 | C |
| I-71 | C |
| I-72 | C |
| I-73 | C |
| I-74 | C |
| I-75 | C |
| I-76 | B |
| I-77 | C |
| I-78 | C |
| I-79 | A |
| I-80 | A |
| I-81 | A |
| I-82 | A |
| I-83 | B |
| I-84 | B |
| I-85 | A |
| I-86 | A |
| I-87 | B |
| I-88 | B |
| I-89 | B |
| I-90 | C |
| I-91 | A |
| I-92 | A |
| I-93 | A |
| I-94 | A |
| I-95 | B |
| I-96 | A |
| I-97 | B |
| I-98 | B |
| I-99 | B |
| I-100 | A |
| I-101 | A |
| I-102 | B |
| I-103 | B |
| I-104 | B |
| I-105 | B |
| I-106 | B |
| I-107 | C |
| I-108 | C |
| I-109 | C |
| I-110 | A |
| I-111 | A |
| I-112 | A |
| I-113 | A |
| I-114 | B |
| I-115 | A |
| I-116 | A |
| I-117 | B |
| I-118 | A |
| I-119 | B |
| I-120 | A |
| I-121 | B |
| I-122 | B |
| I-123 | B |
| I-124 | A |
| I-125 | A |
| I-126 | B |
| I-127 | B |
| I-128 | B |
| I-130 | B |
| I-131 | B |
| I-132 | B |
| I-133 | A |
| I-134 | B |

TABLE 2-continued cGAS Inhibition Results

| I-# | $IC_{50}$ |
|---|---|
| I-135 | C |
| I-136 | B |
| I-137 | B |
| I-138 | A |
| I-139 | A |
| I-140 | B |
| I-141 | A |
| I-142 | A |
| I-143 | A |
| I-144 | A |
| I-145 | A |
| I-147 | A |
| I-148 | A |
| I-149 | A |
| I-150 | A |
| I-151 | A |
| I-152 | B |
| I-153 | B |
| I-154 | A |
| I-155 | B |
| I-156 | A |
| I-157 | B |
| I-158 | A |
| I-159 | A |
| I-160 | A |
| I-161 | C |
| I-162 | C |
| I-163 | C |
| I-164 | B |
| I-165 | A |
| I-166 | B |
| I-167 | A |
| I-168 | A |
| I-169 | A |
| I-170 | A |
| I-171 | C |
| I-172 | B |
| I-173 | B |
| I-174 | A |
| I-175 | A |
| I-176 | B |
| I-177 | B |
| I-178 | B |
| I-179 | B |
| I-180 | B |
| I-181 | C |
| I-182 | B |
| I-183 | A |
| I-184 | A |
| I-185 | B |
| I-186 | A |
| I-187 | B |
| I-188 | B |
| I-189 | B |
| I-190 | A |
| I-191 | A |
| I-192 | A |
| I-193 | B |
| I-194 | A |
| I-195 | A |
| I-196 | A |
| I-197 | A |
| I-198 | A |
| I-199 | B |
| I-200 | A |
| I-201 | A |
| I-202 | A |
| I-203 | A |
| I-204 | A |
| I-205 | A |
| I-206 | B |
| I-207 | A |
| I-208 | B |
| I-209 | C |
| I-210 | B |
| I-211 | B |

TABLE 2-continued cGAS Inhibition Results

| I-# | $IC_{50}$ |
|---|---|
| I-212 | B |
| I-213 | B |
| I-214 | B |
| I-215 | B |
| I-216 | B |
| I-217 | C |
| I-218 | A |
| I-219 | A |
| I-220 | B |
| I-221 | A |
| I-222 | A |
| I-223 | A |
| I-224 | A |
| I-225 | A |
| I-226 | B |
| I-227 | C |
| I-228 | C |
| I-229 | C |
| I-230 | B |
| I-231 | B |
| I-232 | B |
| I-234 | A |
| I-235 | A |
| I-236 | B |
| I-237 | B |
| I-238 | A |
| I-239 | A |
| I-240 | A |
| I-241 | A |
| I-242 | A |
| I-243 | A |
| I-244 | A |
| I-245 | A |
| I-246 | B |
| I-247 | B |
| I-248 | A |
| I-249 | A |
| I-250 | A |
| I-251 | C |
| I-252 | B |
| I-253 | A |
| I-254 | A |
| I-255 | A |
| I-256 | A |
| I-257 | A |
| I-258 | A |
| I-259 | C |
| I-260 | A |
| I-261 | C |
| I-262 | A |
| I-263 | C |
| I-264 | A |
| I-265 | C |
| I-266 | C |
| I-267 | C |
| I-268 | C |
| I-269 | C |
| I-270 | A |
| I-271 | B |
| I-272 | B |
| I-273 | B |
| I-274 | B |
| I-275 | C |
| I-276 | A |
| I-277 | B |
| I-278 | B |
| I-279 | C |
| I-280 | C |
| I-281 | B |
| I-282 | B |
| I-283 | C |
| I-284 | C |
| I-285 | A |
| I-286 | A |
| I-287 | A |
| I-288 | A |

TABLE 2-continued cGAS Inhibition Results

| I-# | $IC_{50}$ |
|---|---|
| I-289 | B |
| I-290 | B |
| I-291 | B |
| I-292 | B |
| I-293 | B |
| I-294 | C |
| I-295 | C |
| I-296 | C |
| I-297 | C |
| I-298 | C |
| I-299 | C |
| I-300 | C |
| I-301 | C |
| I-302 | C |
| I-303 | C |
| I-304 | C |
| I-305 | C |
| I-306 | C |
| I-307 | C |
| I-308 | C |
| I-309 | C |
| I-310 | C |
| I-311 | C |
| I-312 | C |
| I-313 | C |
| I-314 | C |
| I-315 | C |
| I-316 | C |
| I-317 | C |
| I-318 | C |
| I-319 | C |
| I-320 | A |
| I-321 | A |
| I-322 | A |
| I-323 | A |
| I-324 | A |
| I-325 | A |
| I-326 | A |
| I-327 | A |
| I-328 | A |
| I-329 | A |
| I-330 | A |
| I-331 | B |
| I-332 | A |
| I-333 | C |
| I-334 | C |
| I-335 | A |
| I-336 | B |
| I-337 | A |
| I-338 | A |
| I-339 | A |
| I-340 | A |
| I-341 | A |
| I-342 | A |
| I-343 | B |
| I-344 | A |
| I-345 | A |
| I-346 | A |
| I-347 | A |
| I-348 | C |
| I-349 | A |
| I-350 | A |
| I-351 | A |
| I-352 | B |
| I-353 | C |
| I-354 | C |
| I-355 | B |
| I-356 | C |
| I-357 | B |
| I-358 | B |
| I-359 | B |
| I-360 | A |
| I-361 | B |
| I-362 | C |
| I-363 | B |
| I-364 | B |

TABLE 2-continued cGAS Inhibition Results

| I-# | $IC_{50}$ |
|---|---|
| I-365 | C |
| I-366 | B |
| I-367 | C |
| I-368 | B |
| I-369 | A |
| I-370 | A |
| I-371 | A |
| I-372 | A |
| I-373 | A |
| I-374 | A |
| I-375 | B |
| I-376 | C |
| I-377 | C |
| I-378 | A |
| I-379 | B |
| I-380 | B |
| I-381 | C |
| I-382 | B |
| I-383 | C |
| I-384 | B |
| I-385 | B |
| I-386 | A |
| I-387 | A |
| I-388 | B |
| I-389 | A |
| I-390 | B |
| I-391 | A |
| I-392 | B |
| I-393 | C |
| I-394 | C |
| I-395 | B |
| I-396 | A |
| I-397 | A |
| I-398 | B |
| I-399 | B |
| I-400 | B |
| I-401 | C |
| I-402 | B |
| I-403 | C |
| I-404 | C |
| I-405 | B |
| I-406 | B |
| I-407 | C |
| I-408 | C |
| I-409 | C |
| I-410 | C |
| I-411 | C |
| I-412 | B |
| I-413 | C |
| I-414 | C |
| I-415 | C |
| I-416 | C |
| I-417 | C |
| I-418 | C |
| I-419 | C |
| I-420 | C |
| I-421 | B |
| I-422 | C |
| I-423 | A |
| I-424 | B |
| I-425 | C |
| I-426 | C |
| I-427 | A |
| I-428 | A |
| I-429 | A |
| I-430 | A |
| I-431 | A |
| I-432 | B |
| I-433 | A |
| I-434 | B |
| I-435 | A |
| I-436 | B |
| I-437 | A |
| I-438 | B |
| I-439 | B |
| I-443 | A |

TABLE 2-continued cGAS Inhibition Results

| I-# | $IC_{50}$ |
|---|---|
| I-444 | A |
| I-445 | B |
| I-446 | B |
| I-447 | C |
| I-448 | A |
| I-449 | A |
| I-450 | B |
| I-451 | B |
| I-452 | B |
| I-453 | C |
| I-454 | A |

TABLE 3 cGAS Inhibition Results

| I-# | $IC_{50}$ |
|---|---|
| I-455 | A |
| I-456 | C |
| I-457 | B |
| I-458 | B |
| I-459 | B |
| I-460 | B |
| I-461 | A |
| I-462 | B |
| I-463 | B |
| I-464 | A |
| I-465 | A |
| I-466 | A |
| I-467 | B |
| I-468 | B |
| I-469 | A |
| I-470 | A |
| I-471 | B |
| I-472 | B |
| I-473 | A |
| I-474 | B |
| I-475 | B |
| I-476 | B |
| I-477 | A |
| I-478 | A |
| I-479 | A |
| I-480 | A |
| I-481 | A |
| I-482 | A |
| I-483 | B |
| I-484 | B |
| I-485 | A |
| I-486 | A |
| I-487 | A |
| I-488 | A |
| I-489 | A |
| I-490 | A |
| I-491 | A |
| I-492 | B |
| I-493 | A |
| I-494 | A |
| I-495 | A |
| I-496 | B |
| I-497 | B |
| I-498 | B |
| I-499 | A |
| I-500 | B |
| I-501 | A |
| I-502 | B |
| I-503 | A |
| I-504 | A |
| I-505 | B |
| I-506 | B |
| I-507 | A |
| I-508 | A |
| I-509 | A |

TABLE 3-continued cGAS Inhibition Results

| I-# | $IC_{50}$ |
|---|---|
| I-510 | A |
| I-511 | A |
| I-512 | A |
| I-513 | A |
| I-514 | A |
| I-515 | A |
| I-516 | A |
| I-517 | A |
| I-518 | A |
| I-519 | A |
| I-520 | A |
| I-521 | A |
| I-522 | B |
| I-524 | A |
| I-525 | A |
| I-526 | A |
| I-527 | A |
| I-528 | C |
| I-529 | A |
| I-530 | A |
| I-531 | A |
| I-532 | B |
| I-533 | A |
| I-534 | B |
| I-535 | B |
| I-536 | A |
| I-537 | B |
| I-538 | A |
| I-539 | A |
| I-540 | A |
| I-541 | A |
| I-542 | B |
| I-543 | B |
| I-544 | B |
| I-545 | A |
| I-546 | B |
| I-547 | B |
| I-548 | A |
| I-549 | A |
| I-550 | B |
| I-551 | C |
| I-552 | A |
| I-553 | A |
| I-554 | B |
| I-555 | A |
| I-556 | A |
| I-557 | A |
| I-558 | A |
| I-559 | A |
| I-560 | A |
| I-561 | A |
| I-562 | A |
| I-563 | A |
| I-564 | A |
| I-565 | A |
| I-566 | A |
| I-567 | A |
| I-568 | B |
| I-569 | A |
| I-570 | B |
| I-571 | A |
| I-572 | A |
| I-573 | B |
| I-574 | B |
| I-575 | B |
| I-576 | A |
| I-577 | B |
| I-578 | B |
| I-579 | C |
| I-580 | C |
| I-581 | B |
| I-582 | A |
| I-583 | B |
| I-584 | B |
| I-585 | B |
| I-586 | B |

TABLE 3-continued cGAS Inhibition Results

| I-# | $IC_{50}$ |
|---|---|
| I-587 | B |
| I-588 | A |
| I-589 | B |
| I-590 | B |
| I-591 | B |
| I-592 | B |
| I-593 | B |
| I-594 | B |
| I-595 | B |
| I-596 | B |
| I-597 | B |
| I-598 | B |
| I-599 | B |
| I-600 | B |
| I-601 | B |
| I-602 | B |
| I-603 | A |
| I-604 | B |
| I-605 | C |
| I-606 | B |
| I-607 | A |
| I-608 | B |
| I-609 | C |
| I-610 | A |
| I-611 | C |
| I-612 | B |
| I-613 | A |
| I-614 | B |
| I-615 | B |
| I-616 | A |
| I-617 | A |
| I-618 | A |
| I-619 | B |
| I-620 | B |
| I-621 | B |
| I-622 | A |
| I-623 | B |
| I-624 | A |
| I-625 | A |
| I-626 | A |
| I-627 | A |
| I-628 | A |
| I-629 | A |
| I-630 | A |
| I-631 | A |
| I-632 | A |
| I-633 | A |
| I-634 | A |
| I-635 | A |
| I-636 | A |
| I-637 | A |
| I-638 | B |
| I-639 | A |
| I-640 | A |
| I-641 | A |
| I-642 | B |
| I-643 | A |
| I-644 | B |
| I-645 | B |
| I-646 | B |
| I-647 | B |
| I-648 | B |
| I-649 | B |
| I-650 | B |
| I-651 | A |
| I-652 | B |
| I-653 | A |
| I-654 | A |
| I-655 | A |
| I-656 | C |
| I-657 | A |
| I-658 | A |
| I-659 | A |
| I-660 | B |
| I-661 | A |
| I-662 | B |

TABLE 3-continued

| cGAS Inhibition Results | |
|---|---|
| I-# | $IC_{50}$ |
| I-663 | A |
| I-664 | A |
| I-665 | A |
| I-666 | A |
| I-667 | A |
| I-668 | A |
| I-669 | B |
| I-670 | A |
| I-671 | A |
| I-672 | A |
| I-673 | B |
| I-674 | A |
| I-675 | A |
| I-676 | A |
| I-677 | A |
| I-678 | A |
| I-679 | A |
| I-680 | B |
| I-681 | B |
| I-682 | A |
| I-683 | A |
| I-684 | A |
| I-685 | A |
| I-686 | B |
| I-687 | B |
| I-688 | A |
| I-689 | A |
| I-690 | A |
| I-691 | A |
| I-692 | A |
| I-693 | A |
| I-694 | A |
| I-695 | B |
| I-696 | A |
| I-697 | A |
| I-698 | A |
| I-699 | A |
| I-700 | A |
| I-701 | A |
| I-702 | A |
| I-703 | A |
| I-704 | A |
| I-705 | A |
| I-706 | A |
| I-707 | A |
| I-708 | A |
| I-709 | A |
| I-710 | A |
| I-711 | A |
| I-712 | A |
| I-713 | A |
| I-714 | A |
| I-715 | A |
| I-716 | A |
| I-717 | A |
| I-718 | B |
| I-719 | A |
| I-720 | B |
| I-721 | B |
| I-722 | A |
| I-723 | A |
| I-724 | A |
| I-725 | A |
| I-726 | A |
| I-727 | A |
| I-728 | A |
| I-729 | A |
| I-730 | A |
| I-731 | A |
| I-732 | A |
| I-733 | A |
| I-734 | A |
| I-735 | A |
| I-736 | A |
| I-737 | A |
| I-738 | A |
| I-739 | A |
| I-740 | A |
| I-741 | A |
| I-742 | A |
| I-743 | A |
| I-744 | A |
| I-745 | A |
| I-746 | A |
| I-747 | A |
| I-748 | A |
| I-749 | A |
| I-750 | A |
| I-751 | A |
| I-752 | A |
| I-753 | C |
| I-754 | B |
| I-755 | C |
| I-756 | B |
| I-757 | B |
| I-758 | B |
| I-759 | A |
| I-760 | A |
| I-761 | A |
| I-762 | A |
| I-763 | A |
| I-764 | A |
| I-765 | B |
| I-766 | A |
| I-767 | B |
| I-768 | B |
| I-769 | B |
| I-770 | A |
| I-771 | B |
| I-772 | B |
| I-773 | A |
| I-774 | A |
| I-775 | A |
| I-776 | A |
| I-778 | B |
| I-779 | B |
| I-780 | B |
| I-781 | A |
| I-782 | A |
| I-783 | A |
| I-784 | A |
| I-785 | A |
| I-786 | A |
| I-787 | A |
| I-788 | A |
| I-789 | A |
| I-790 | B |
| I-791 | B |
| I-792 | A |
| I-793 | A |
| I-794 | A |
| I-795 | A |
| I-796 | A |
| I-797 | A |
| I-798 | A |
| I-799 | A |
| I-800 | A |
| I-801 | A |
| I-802 | A |
| I-803 | A |
| I-804 | A |
| I-805 | A |
| I-806 | A |
| I-807 | A |
| I-808 | A |
| I-809 | A |
| I-810 | A |
| I-811 | A |
| I-812 | A |
| I-813 | A |
| I-814 | A |
| I-815 | A |

TABLE 3-continued

| cGAS Inhibition Results | |
|---|---|
| I-# | $IC_{50}$ |
| I-816 | A |
| I-817 | A |
| I-818 | B |
| I-819 | A |
| I-820 | A |
| I-821 | C |
| I-822 | C |
| I-823 | C |
| I-824 | C |
| I-825 | C |
| I-826 | C |
| I-827 | C |
| I-828 | B |
| I-829 | A |
| I-830 | A |
| I-831 | A |
| I-832 | A |
| I-833 | A |
| I-834 | A |
| I-835 | A |
| I-836 | A |
| I-837 | A |
| I-838 | A |
| I-839 | A |
| I-840 | A |
| I-841 | A |
| I-842 | A |
| I-843 | A |
| I-844 | A |
| I-845 | A |
| I-846 | A |
| I-847 | B |
| I-848 | B |
| I-849 | B |
| I-850 | B |
| I-851 | B |
| I-852 | B |
| I-853 | A |
| I-854 | A |
| I-855 | B |
| I-856 | A |
| I-857 | A |
| I-858 | C |
| I-859 | B |
| I-860 | A |
| I-861 | C |
| I-862 | A |
| I-863 | C |
| I-864 | A |
| I-865 | A |
| I-866 | A |
| I-867 | A |
| I-868 | A |
| I-869 | B |
| I-870 | B |
| I-871 | B |
| I-872 | B |
| I-873 | A |
| I-874 | A |
| I-875 | A |
| I-876 | A |
| I-877 | A |
| I-878 | A |
| I-879 | A |
| I-880 | A |
| I-881 | A |
| I-882 | A |
| I-883 | A |
| I-884 | A |
| I-885 | A |
| I-886 | A |
| I-887 | A |
| I-888 | A |
| I-889 | A |
| I-890 | B |
| I-891 | A |

Cellular assay to measure cGAS activity: Reporter THP1 cell line harboring a gene encoding Gaussia Luciferase under the control of 5 tandem repeats of interferon-stimulated response elements (ISRE) fused to an ISG54 minimal promoter was used to test inhibition of cGAS activity by synthetic compounds in human cells. These cells were plated on 96-well plates at $0.3\times10^6$/well and incubated with serial dilutions of compounds or DMSO for 5 min, followed by transfection of 2 μg/mL of ISD (Interferon Stimulatory DNA, a 45 bp DNA oligo) or mock transfected using lipofectamine 2000 (Life Technology) method, according to manufacturer's instructions. 16 hours later, 15 μL of the media from each well was transferred to a new plate, 50 μL of solution containing 50 mM Hepes-NaOH, pH 6.5, 50 mM NaCl, 10 mM EDTA, 1 μM of coelenterazine was added to each well and luminescence was measured immediately. Fold increase in luminescence compared to mock transfection was plotted against concentrations of each compound, and $IC_{50}$ is calculated using Graphpad. To evaluate the specificity of a compound, the same procedure was performed except that cells were transfected with 2 μg/mL poly(I:C) or infected with Sendai Virus (SeV) at 50 Unit/mL, which are known to activate the RIG-I-MAVS pathway. A specific inhibitory compound should inhibit interferon induction by DNA but have minimal effect on poly(I:C) or Sendai virus induced interferon reporter gene expression.

The results of the cellular assay for compounds of the disclosure are presented in Table 4. The letter codes for cGAS $IC_{50}$ include: A (<2 μM); B (2-10 μM); C (>10 μM).

TABLE 4

| Cellular Assay Results | |
|---|---|
| I-# | $IC_{50}$ |
| I-15 | C |
| I-24 | B |
| I-39 | B |
| I-86 | B |
| I-92 | C |
| I-116 | B |
| I-139 | B |
| I-149 | C |
| I-200 | A |
| I-322 | C |
| I-428 | B |
| I-429 | C |
| I-435 | B |
| I-443 | B |
| I-448 | C |
| I-461 | C |
| I-467 | B |
| I-469 | A |
| I-470 | B |
| I-471 | B |
| I-473 | A |
| I-477 | B |
| I-478 | B |
| I-487 | B |
| I-507 | B |
| I-516 | C |
| I-532 | B |
| I-539 | B |
| I-556 | A |
| I-575 | B |

TABLE 4-continued

| Cellular Assay Results | |
|---|---|
| I-# | $IC_{50}$ |
| I-576 | A |
| I-577 | B |
| I-578 | B |
| I-582 | A |
| I-583 | A |
| I-584 | B |
| I-585 | A |
| I-586 | A |
| I-591 | B |
| I-592 | B |
| I-593 | B |
| I-594 | B |
| I-595 | B |
| I-596 | A |
| I-597 | C |
| I-598 | A |
| I-599 | A |
| I-600 | A |
| I-601 | A |
| I-642 | A |
| I-645 | A |
| I-649 | B |
| I-650 | B |
| I-663 | A |
| I-664 | A |
| I-665 | A |
| I-666 | A |
| I-667 | A |
| I-668 | A |
| I-669 | A |
| I-670 | A |
| I-671 | A |
| I-672 | A |
| I-673 | A |
| I-674 | B |
| I-676 | A |
| I-677 | A |
| I-678 | B |
| I-679 | B |
| I-680 | B |
| I-681 | A |
| I-682 | A |
| I-683 | A |
| I-684 | A |
| I-685 | A |
| I-686 | A |
| I-687 | C |
| I-688 | A |
| I-689 | C |
| I-690 | A |
| I-691 | A |
| I-692 | A |
| I-693 | C |
| I-694 | A |
| I-695 | B |
| I-696 | A |
| I-698 | C |
| I-699 | A |
| I-700 | B |
| I-701 | B |
| I-702 | B |
| I-703 | C |
| I-704 | A |
| I-705 | A |
| I-706 | A |
| I-707 | A |
| I-708 | A |
| I-709 | A |
| I-710 | B |
| I-711 | A |
| I-712 | A |
| I-713 | A |
| I-714 | B |
| I-715 | C |
| I-716 | C |
| I-717 | A |

TABLE 4-continued

| Cellular Assay Results | |
|---|---|
| I-# | $IC_{50}$ |
| I-718 | A |
| I-719 | A |
| I-720 | A |
| I-722 | B |
| I-723 | B |
| I-724 | B |
| I-725 | C |
| I-726 | C |
| I-728 | B |
| I-730 | B |
| I-732 | A |
| I-733 | A |
| I-734 | A |
| I-735 | B |
| I-736 | A |
| I-739 | A |
| I-740 | C |
| I-741 | B |
| I-742 | C |
| I-743 | A |
| I-744 | A |
| I-745 | A |
| I-747 | A |
| I-748 | C |
| I-749 | A |
| I-750 | A |
| I-751 | B |
| I-752 | C |
| I-753 | C |

| I-# | $IC_{50}$ |
|---|---|
| I-755 | C |
| I-756 | C |
| I-758 | C |
| I-759 | C |
| I-760 | C |
| I-761 | C |
| I-762 | C |
| I-764 | C |
| I-765 | B |
| I-773 | A |
| I-774 | B |
| I-775 | B |
| I-776 | C |
| I-778 | C |
| I-779 | C |
| I-780 | C |
| I-781 | C |
| I-782 | C |
| I-784 | C |
| I-785 | C |
| I-786 | B |
| I-787 | B |
| I-788 | C |
| I-789 | A |
| I-791 | C |
| I-792 | A |
| I-793 | A |
| I-794 | A |
| I-795 | A |
| I-796 | A |
| I-797 | A |
| I-798 | A |
| I-799 | C |
| I-800 | A |
| I-801 | A |
| I-802 | A |
| I-803 | A |
| I-804 | A |
| I-805 | A |
| I-806 | B |

-continued

| I-# | $IC_{50}$ |
|---|---|
| I-807 | A |
| I-808 | A |
| I-809 | A |
| I-810 | A |
| I-811 | A |
| I-813 | C |
| I-814 | A |
| I-815 | B |
| I-816 | A |
| I-817 | C |
| I-820 | A |
| I-828 | C |
| I-829 | B |
| I-830 | A |
| I-831 | B |
| I-832 | A |
| I-833 | A |
| I-834 | A |
| I-835 | B |
| I-836 | A |
| I-837 | A |
| I-838 | C |
| I-839 | C |
| I-840 | A |
| I-841 | C |
| I-842 | B |
| I-843 | B |
| I-844 | A |
| I-845 | A |
| I-846 | A |
| I-853 | A |
| I-854 | C |
| I-855 | C |
| I-856 | B |
| I-857 | A |
| I-860 | C |
| I-862 | A |
| I-864 | C |
| I-865 | A |
| I-866 | B |
| I-867 | A |
| I-868 | B |
| I-872 | A |
| I-875 | A |
| I-876 | A |
| I-877 | A |
| I-878 | A |
| I-879 | A |
| I-880 | B |
| I-882 | C |
| I-883 | B |
| I-884 | A |
| I-885 | B |
| I-886 | A |
| I-887 | B |
| I-888 | B |
| I-889 | C |
| I-890 | A |
| I-891 | A |

All publications, patents, patent applications and other documents cited in this application, including U.S. Provisional Appl. Nos. 63/074,446, 63/124,713, and 63/196,146, are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the claimed invention(s).

What is claimed is:

1. A compound, wherein the compound is of Formula I-a-4:

I-a-4

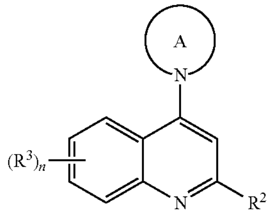

or a pharmaceutically acceptable salt thereof, wherein:

Ring A is an optionally substituted heteroaryl ring, having 0 to 3 heteroatoms (in addition to the nitrogen already depicted in Ring A) independently selected from nitrogen, oxygen, phosphorus, and sulfur;

$R^2$ is —$NRR^5$, —$NR^aR^5$,

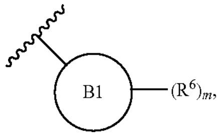

or

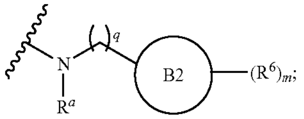

each $R^3$ is independently halogen, —OMe, —OEt, —$NR_2$, —SR, or $R^C$;

Ring B1 is a 4- to 10-membered saturated or partially unsaturated monocyclic or bicyclic carbocyclic or heterocyclic ring having 1 to 3 heteroatoms independently selected from nitrogen, oxygen, and sulfur; or a benzotriazolyl, benzo[d]oxazol-2(3H)-one, benzo[d][1,3]dioxole, thienyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, or indolizinyl ring;

Ring B2 is phenyl; a 4- to 7-membered saturated or partially unsaturated carbocyclic or heterocyclic ring having 1 to 3 heteroatoms independently selected from nitrogen, oxygen, and sulfur; or a 5- to 6-membered heteroaryl ring having 1 to 4 heteroatoms independently selected from nitrogen, oxygen, and sulfur;

each R is independently hydrogen or an optionally substituted group selected from $C_{1-6}$ aliphatic; benzyl; phenyl; a 4- to 7-membered saturated or partially unsaturated carbocyclic or heterocyclic ring having 1 to 3 heteroatoms independently selected from nitrogen, oxygen, and sulfur; and a 5- to 6-membered heteroaryl ring having 1 to 4 heteroatoms independently selected from nitrogen, oxygen, and sulfur, $R^5$ is —$(CR_2)_{0-4}OR$, —$(CR_2)_{0-5}CO_2R$, —$(CR_2)_{0-5}CONR_2$, —$(CR_2)_{0-4}C(O)NR(CR_2)CO_2R$, —$(CR_2)_{0-4}C(O)NR(CR_2)_{0-4}CONR_2$, —$(CR_2)_{0-4}NRC(O)R$, —$(CR_2)_{0-4}SO_3R$, —$(CR_2)_{0-4}SO_2NR_2$, —$(CR_2)_{0-4}OSO_2NR_2$, —$(CR_2)_{0-4}NRSO_2R$, —$(CR_2)_{0-4}NRSO_2OR$, —$(CR_2)_{0-4}OP(OR)_2$, —$(CR_2)_{0-4}OP(O)(OR)_2$, —$(CR_2)_{0-4}P(O)(OR)_2$, —$(CR_2)_{0-4}OP(O)(H)OR$, or $R^B$;

each $R^6$ is independently halogen, —CN, =$CH_2$, =O, —C(O)NHOH, —C(O)N($CH_3$)OH, —C(O)N($CH_3$)$OCH_3$, —C(O)$NHSO_2CHF_2$, —$OCONHCH_2CO_2Me$, —$OCONHCH_2CO_2H$, —$NHCOCH_2CH_2CO_2H$, —$NHCOCH_2CH_2CO_2CH_3$, —COR, —$(CR_2)_{0-4}CO_2R$, —$(CR_2)_{0-4}CONR_2$, —OR, —$(CR_2)_{1-4}OR$, $NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-4}SO_3R$, —$(CR_2)_{0-4}SO_2NR_2$, —$(CR_2)_{0-4}OSO_2NR_2$, —$(CR_2)_{0-4}NRSO_2R$, —$(CR_2)_{0-4}NRSO_2OR$, —$(CR_2)_{0-4}OP(OR)_2$, —$(CR_2)_{0-4}OP(O)(OR)_2$, —$(CR_2)_{0-4}P(O)(OR)_2$, —$(CR_2)_{0-4}OP(O)(H)OR$, —$B(OR)_2$,

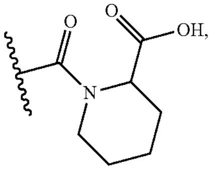
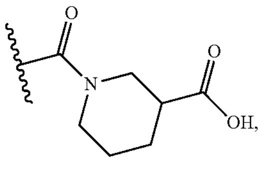
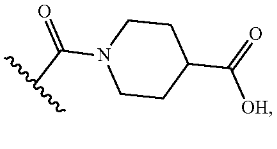
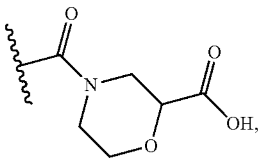
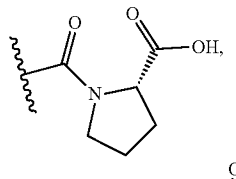
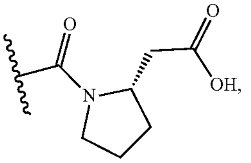
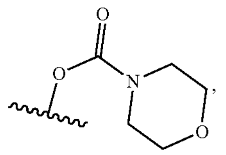

or $R^B$;

$R^B$ and $R^C$, independently, are an optionally substituted group selected from $C_{1-6}$ aliphatic; phenyl; a 4- to 10-membered saturated or partially unsaturated monocyclic or bicyclic carbocyclic or heterocyclic ring having 1 to 3 heteroatoms independently selected from nitrogen, oxygen, and sulfur; and a 5- to 6-membered heteroaryl ring having 1 to 4 heteroatoms independently selected from nitrogen, oxygen, and sulfur;

each $R^a$ is independently H or $C_{1-6}$alkyl;

each m is 0, 1, 2, 3, or 4;

n is 1, 2, 3, or 4; and q is 0, 1, or 2.

2. A compound, wherein the compound is of Formula I-b-3:

I-b-3

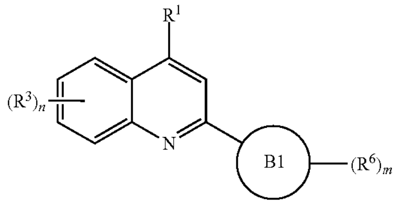

or a pharmaceutically acceptable salt thereof, wherein:

Ring B1 is a 4- to 10-membered saturated or partially unsaturated monocyclic or bicyclic carbocyclic or heterocyclic ring having 1 to 3 heteroatoms independently selected from nitrogen, oxygen, phosphorus, and sulfur; or a benzotriazolyl, benzo[d]oxazol-2(3H)-one, benzo[d][1,3]dioxole, thienyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, or indolizinyl ring;

$R^1$ is

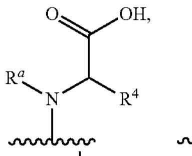
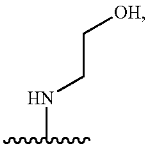
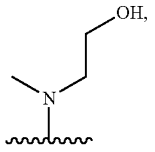
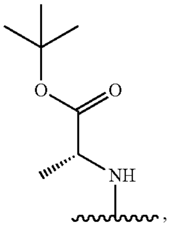
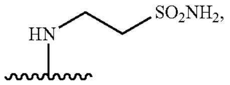

or an optionally substituted 5- to 6-membered heteroaryl ring having 1 to 4 heteroatoms independently selected from nitrogen, oxygen, and sulfur;

each $R^3$ is independently halogen, —OMe, —OEt, —$NR_2$, or —SR;

each R is independently hydrogen or an optionally substituted group selected from $C_{1-6}$ aliphatic; benzyl; phenyl; a 4- to 7-membered saturated or partially unsaturated carbocyclic or heterocyclic ring having 1 to 3 heteroatoms independently selected from nitrogen, oxygen, and sulfur; and a 5- to 6-membered heteroaryl ring having 1 to 4 heteroatoms independently selected from nitrogen, oxygen, and sulfur, $R^4$ is hydrogen or an optionally substituted $C_{1-6}$ aliphatic;

each $R^6$ is independently halogen, —CN, =$CH_2$, =O, —C(O)NHOH, —C(O)N($CH_3$)OH, —C(O)N($CH_3$)$OCH_3$, —C(O)$NHSO_2CHF_2$, —$OCONHCH_2CO_2Me$, —$OCONHCH_2CO_2H$, —$NHCOCH_2CH_2CO_2H$, —$NHCOCH_2CH_2CO_2CH_3$, —COR, —$(CR_2)_{0-4}CO_2R$, —$(CR_2)_{0-4}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-4}SO_3R$, —$(CR_2)_{0-4}SO_2NR_2$, —$(CR_2)_{0-4}OSO_2NR_2$, —$(CR_2)_{0-4}NRSO_2R$, —$(CR_2)_{0-4}NRSO_2OR$, —$(CR_2)_{0-4}OP(OR)_2$, —$(CR_2)_{0-4}OP(O)(OR)_2$, —$(CR_2)_{0-4}P(O)(OR)_2$, —$(CR_2)_{0-4}OP(O)(H)OR$, —$B(OR)_2$,

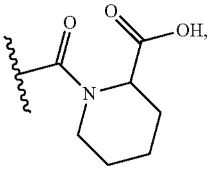
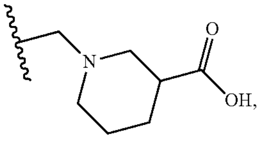
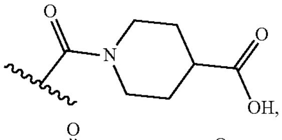
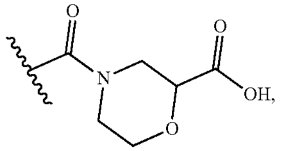
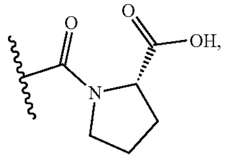
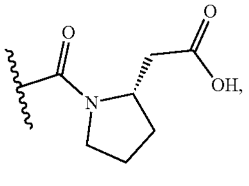
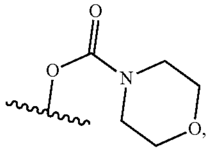

or $R^B$;

$R^B$ is an optionally substituted group selected from $C_{1-6}$ aliphatic; phenyl; a 4- to 10-membered saturated or partially unsaturated monocyclic or bicyclic carbocyclic or heterocyclic ring having 1 to 3 heteroatoms independently selected from nitrogen, oxygen, and sulfur; and a 5- to 6-membered heteroaryl ring having 1 to 4 heteroatoms independently selected from nitrogen, oxygen, and sulfur;

each $R^a$ is independently H or $C_{1-6}$alkyl;

each m is 0, 1, 2, 3, or 4; and n is 1, 2, 3, or 4.

3. The compound of claim 1, wherein Ring A is an optionally substituted imidazole.

4. The compound of claim 2, wherein $R^1$ is an optionally substituted imidazole.

5. The compound of claim 1, wherein Ring A is an optionally substituted pyrazole.

6. The compound of claim 2, wherein $R^1$ is an optionally substituted pyrazole.

7. The compound of claim 1, wherein $R^2$ is

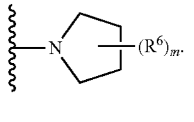

8. The compound of claim 1, wherein Ring B1 is

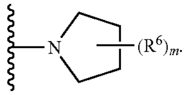

9. The compound of claim 1, wherein at least one occurrence of $R^3$ is halogen.

10. The compound of claim 9, wherein at least one occurrence of $R^3$ is chloro.

11. The compound of claim 9, wherein n is 2 and both $R^3$ are chloro.

12. The compound of claim 9, wherein n is 2 and $R^3$ is chloro at the 7- and 8-positions with respect to the quinoline ring.

13. The compound of claim 2, wherein at least one occurrence of $R^3$ is halogen.

14. The compound of claim 13, wherein at least one occurrence of $R^3$ is chloro.

15. The compound of claim 13, wherein n is 2 and both $R^3$ are chloro.

16. The compound of claim 13, wherein n is 2 and $R^3$ is chloro at the 7- and 8-positions with respect to the quinoline ring.

17. The compound of claim 7, wherein $R^6$ is independently halogen, $=CH_2$, $=O$, —$C_{1-4}$alkyl, —$C_{1-4}$haloalkyl, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}CONH_2$, —$(CH_2)_{0-4}CONHC_{1-4}$alkyl, —$(CH_2)_{0-4}CON(C_{1-4}alkyl)_2$, —$(CH_2)_{0-4}$CO(N-proline), —$(CH_2)_{0-4}$CO(N-pyrrolidine-3-carboxylic acid), —$(CH_2)_{0-4}C(O)NR^a(CH_2)_{1-4}CO_2H$, —$(CH_2)_{0-4}C(O)NR^a$—$CH(C_{1-4}alkyl)$-$CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}alkyl)_2$, —OH, —$(CH_2)_{1-4}OH$, —$(CH_2)_{0-4}OC_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}OC(O)C_{1-4}$alkyl, —$NH_2$, —$(CH_2)_{1-4}NH_2$, —$(CH_2)_{0-4}NHC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}N(C_{1-4}alkyl)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{0-4}CO_2H$, —$(CH_2)_{0-4}OP(OH)_2$, —$(CH_2)_{0-4}OP(OH)(OC_{1-4}alkyl)$, or —$(CR_2)_{0-4}OP(O)(H)OH$, wherein $R^a$, independently for each occurrence, is H or $C_{1-6}$alkyl.

18. The compound of claim 8, wherein $R^6$ is independently halogen, $=CH_2$, $=O$, —$C_{1-4}$alkyl, —$C_{1-4}$haloalkyl, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}CONH_2$, —$(CH_2)_{0-4}CONHC_{1-4}$alkyl, —$(CH_2)_{0-4}CON(C_{1-4}alkyl)_2$, —$(CH_2)_{0-4}$CO(N-proline), —$(CH_2)_{0-4}$CO(N-pyrrolidine-3-carboxylic acid), —$(CH_2)_{0-4}C(O)NR^a(CH_2)_{1-4}CO_2H$, —$(CH_2)_{0-4}C(O)NR^a$—$CH(C_{1-4}alkyl)$-$CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}alkyl)_2$, —OH, —$(CH_2)_{1-4}OH$, —$(CH_2)_{0-4}OC_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}OC(O)C_{1-4}$alkyl, —$NH_2$, —$(CH_2)_{1-4}NH_2$, —$(CH_2)_{0-4}NHC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}N(C_{1-4}alkyl)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, —$(CH_2)_{0-4}OP(OH)(OC_{1-4}alkyl)$, or —$(CR_2)_{0-4}OP(O)(H)OH$, wherein $R^a$, independently for each occurrence, is H or $C_{1-6}$alkyl.

19. The compound of claim 1, wherein m is at least 1, and at least one $R^6$ includes a terminal $—CO_2H$ or $—CO_2C_{1-4}$alkyl group.

20. The compound of claim 2, wherein m is at least 1, and at least one $R^6$ includes a terminal $—CO_2H$ or $—CO_2C_{1-4}$alkyl group.

21. The compound of claim 1, wherein:

Ring A is an optionally substituted 4- to 7-membered heteroaryl ring having 0 to 3 heteroatoms (in addition to the nitrogen already depicted in Ring A) independently selected from nitrogen, oxygen, phosphorus, and sulfur;

$R^2$ is

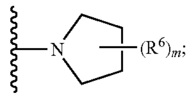

at least one occurrence of $R^3$ is halogen; and m is at least 1, and at least one $R^6$ includes a terminal $—CO_2H$ or $—CO_2C_{1-4}$alkyl group.

22. The compound of claim 21, wherein Ring A is an optionally substituted imidazole.

23. The compound of claim 21, wherein Ring A is an optionally substituted pyrazole.

24. The compound of claim 2, wherein:

$R^1$ is an optionally substituted 5- to 6-membered heteroaryl ring having 1 to 4 heteroatoms independently selected from nitrogen, oxygen, and sulfur;

Ring B1 is

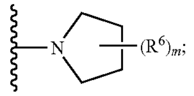

at least one occurrence of $R^3$ is halogen; and m is at least 1, and at least one $R^6$ includes a terminal $—CO_2H$ or $—CO_2C_{1-4}$alkyl group.

25. The compound of claim 24, wherein $R^1$ is an optionally substituted imidazole.

26. The compound of claim 24, wherein $R^1$ is an optionally substituted pyrazole.

27. The compound of claim 1, wherein the compound is selected from:

I-32

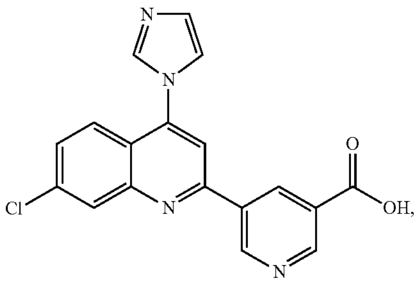

-continued

I-33

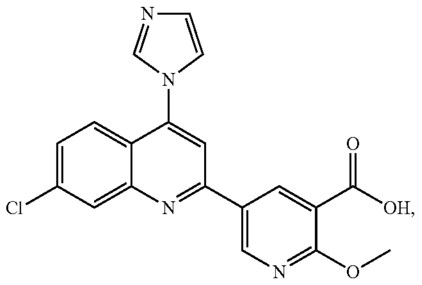

I-34

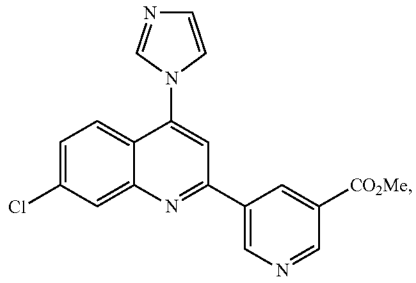

I-35

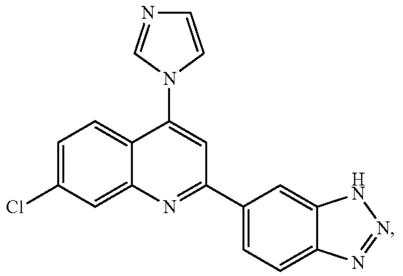

I-36

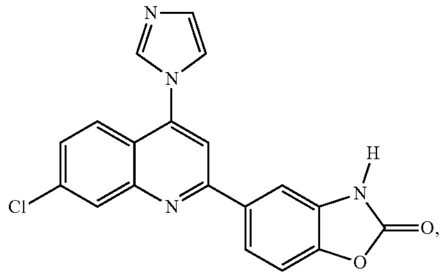

I-37

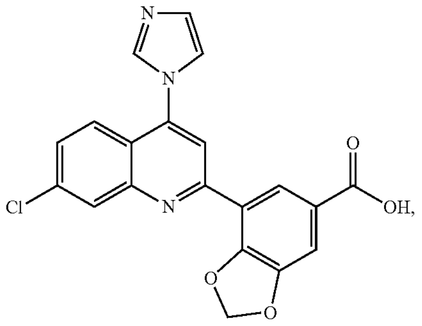

-continued
I-38
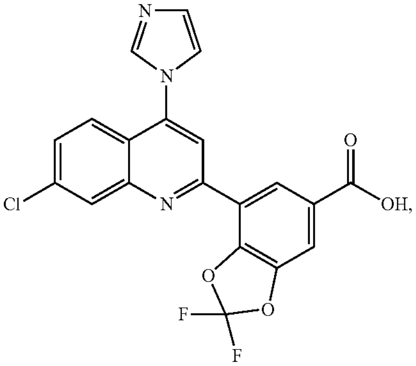
I-55
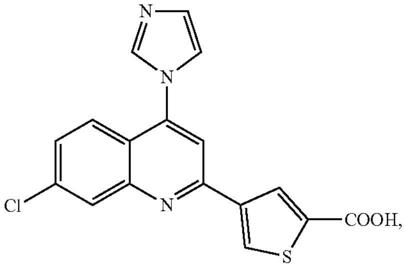
I-56
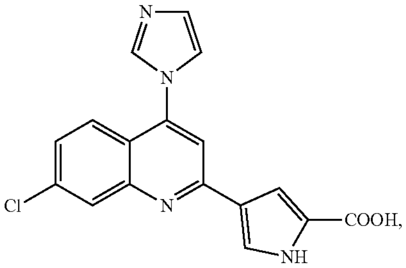
I-57
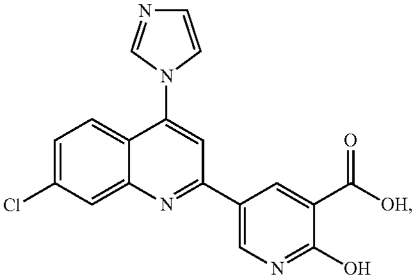
I-58
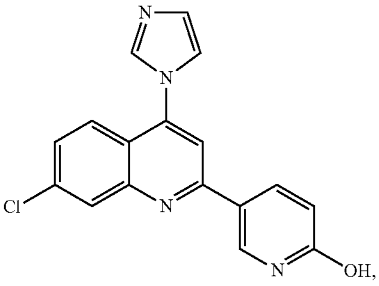
-continued
I-59
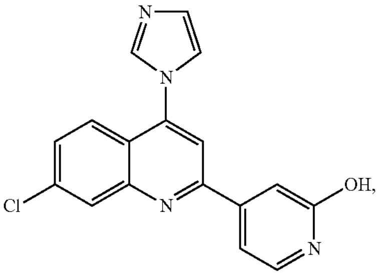
I-76
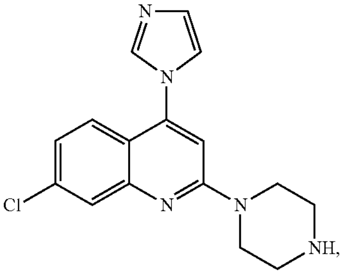
I-77
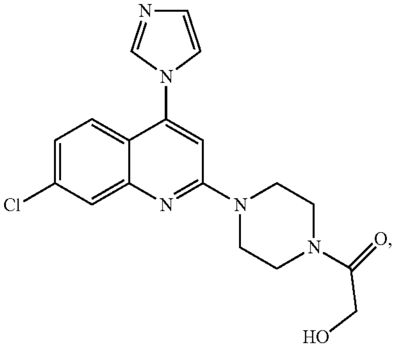
I-78
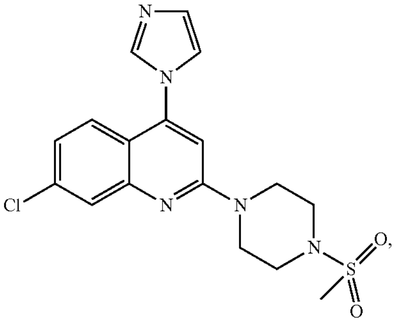
I-79
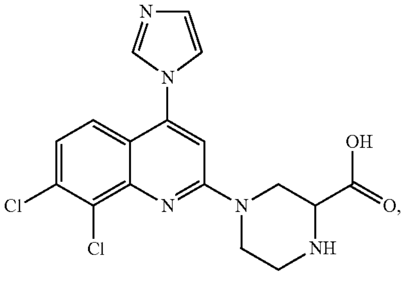

-continued
I-80
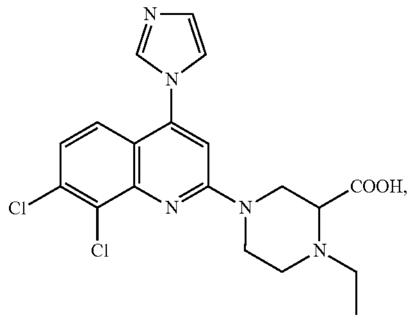
I-81
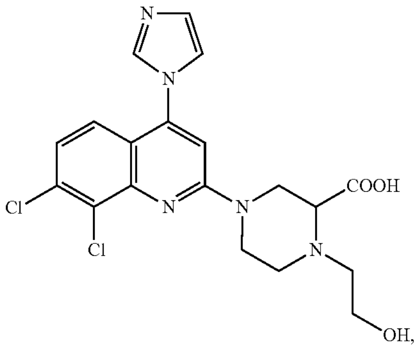
I-82
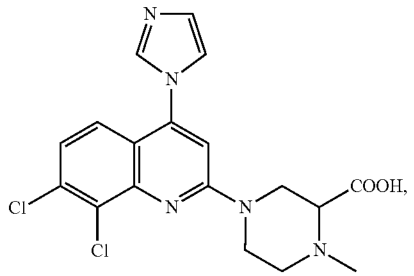
I-83
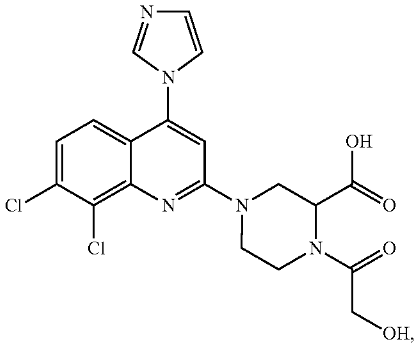
I-84
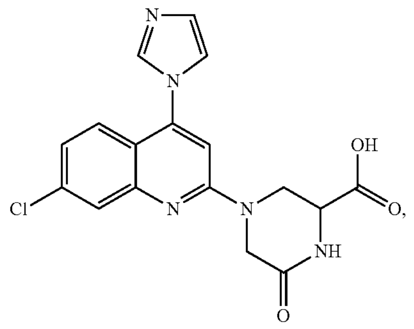
-continued
I-85
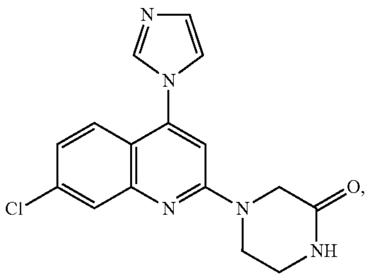
I-86
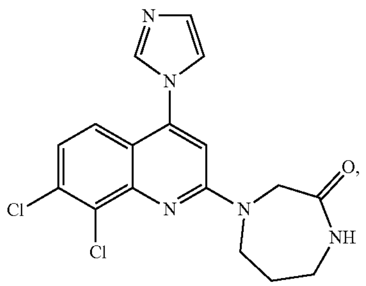
I-87
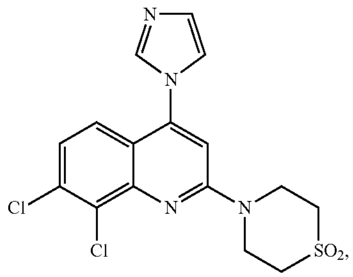
I-88
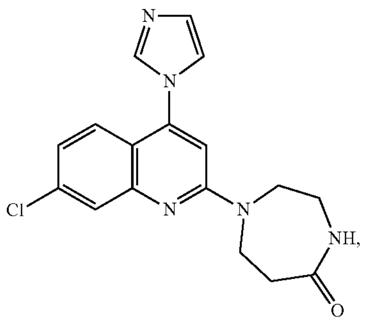
I-89
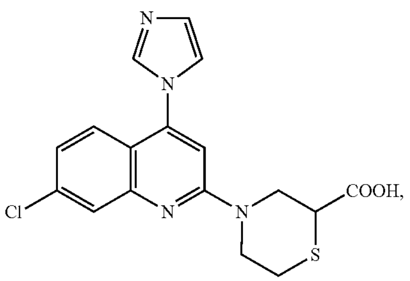

-continued
I-90
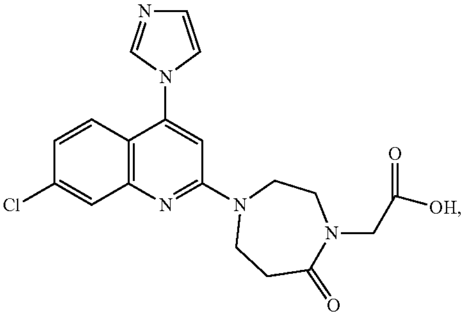
I-91
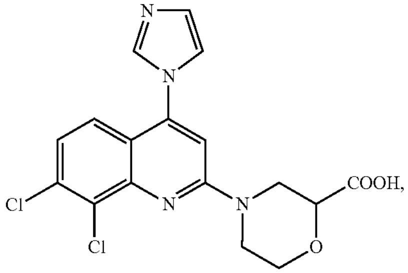
I-92
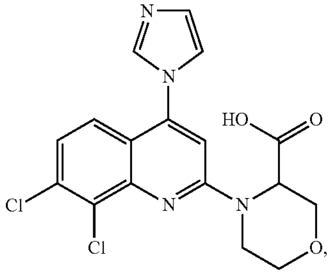
I-94
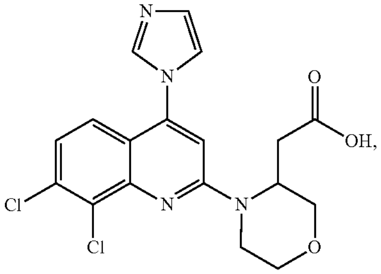
I-95
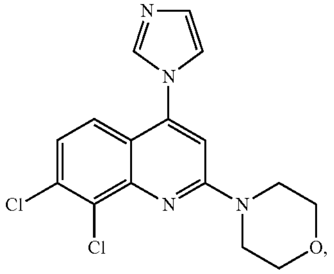
-continued
I-96
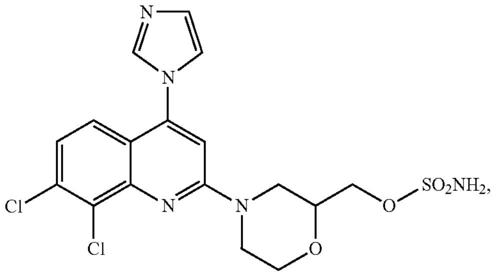
I-97
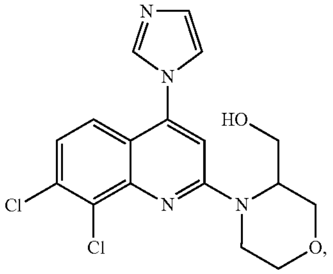
I-98
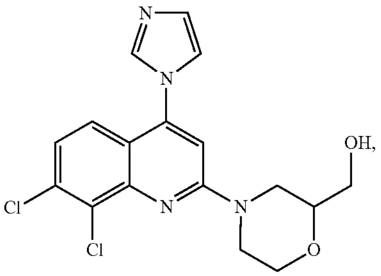
I-99
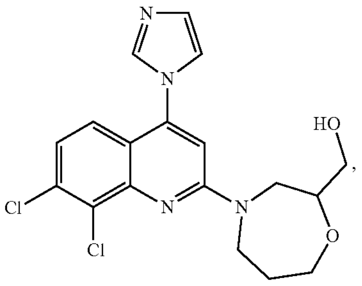
I-100
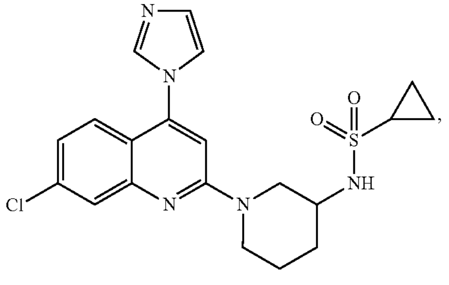

I-101
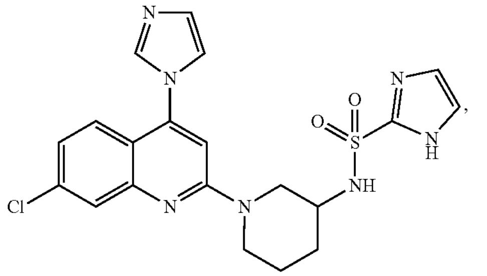
I-102
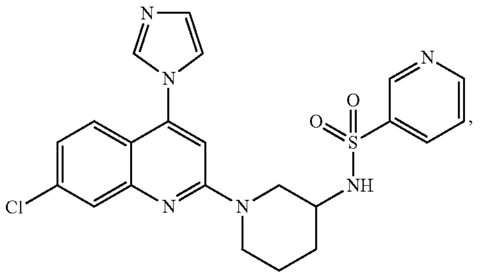
I-103
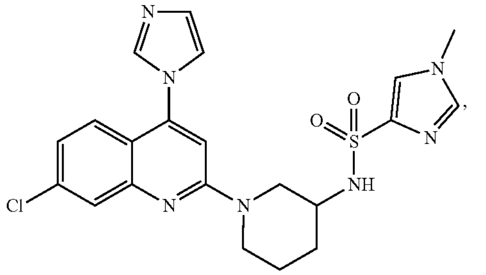
I-104
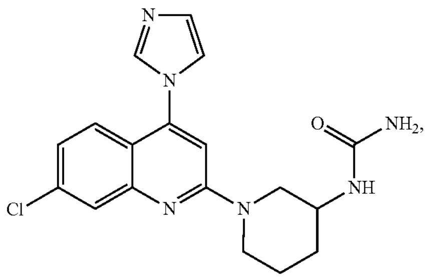
I-105
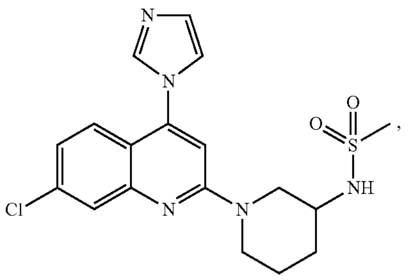
I-106
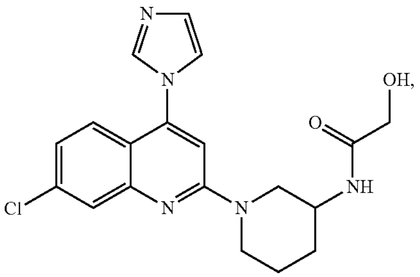
I-107
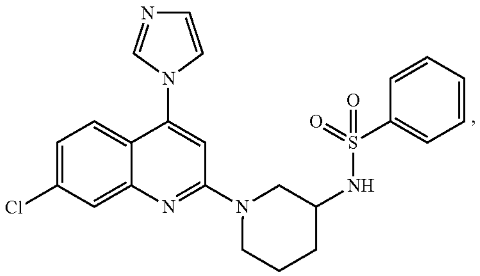
I-108
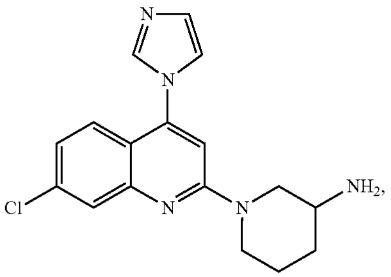
I-109
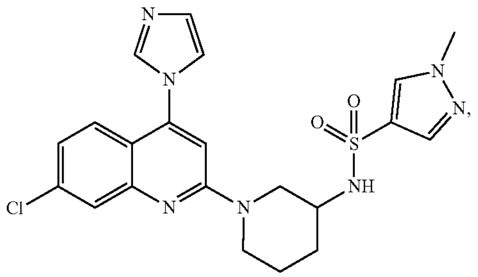
I-110
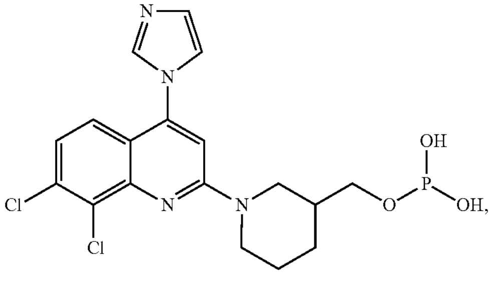

-continued
I-111
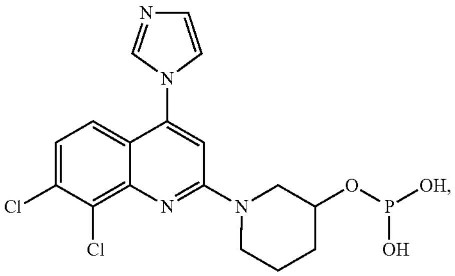
I-112
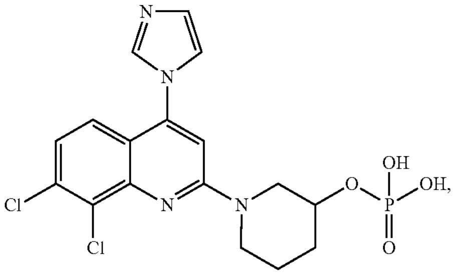
I-113
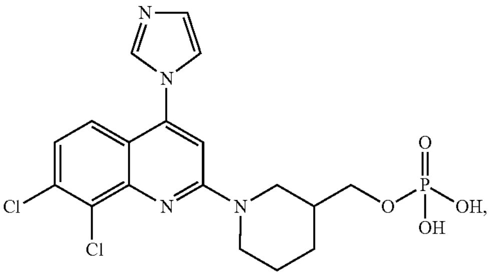
I-114
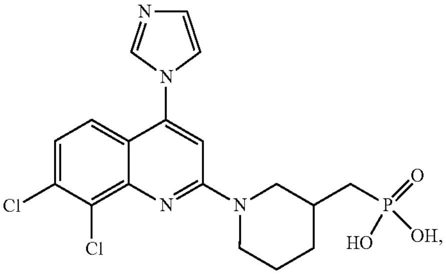
I-115
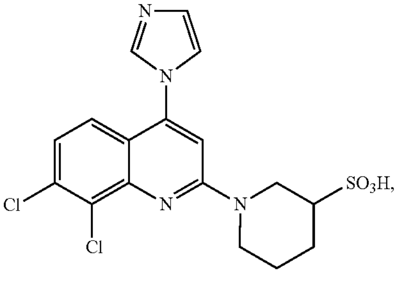
-continued
I-116
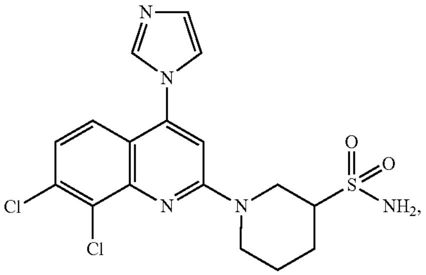
I-117
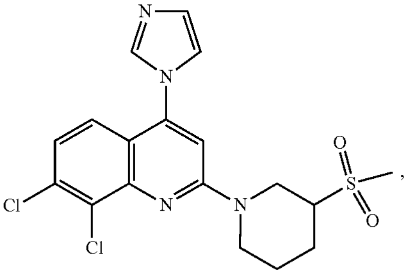
I-118
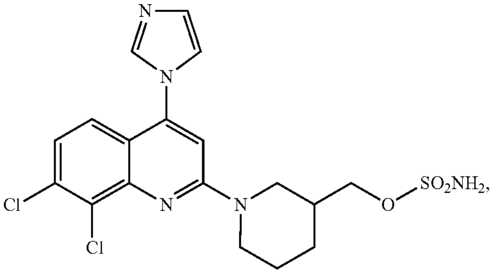
I-119
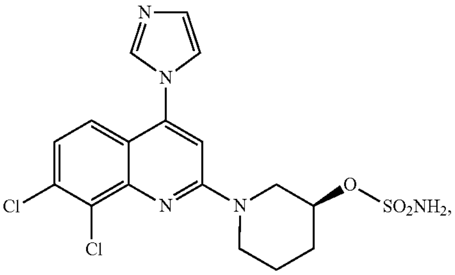
I-120
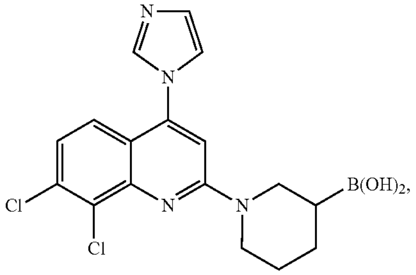

-continued

I-121

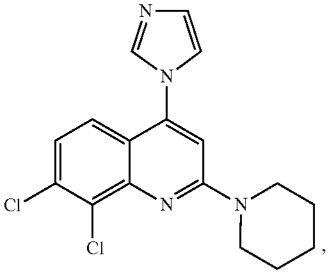

I-122

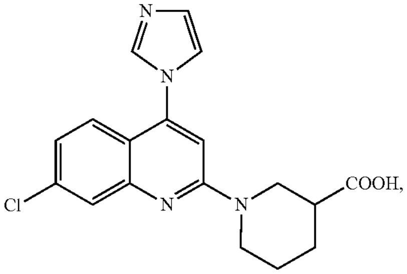

I-123

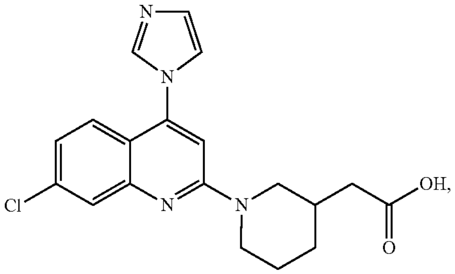

I-124

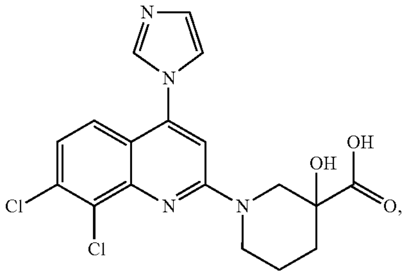

I-125

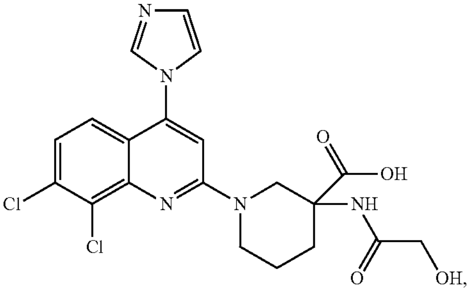

and

-continued

I-126

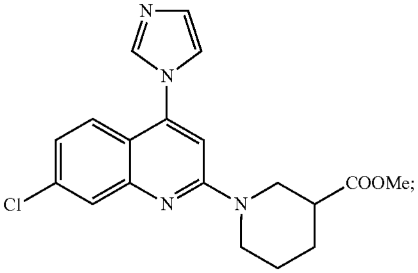

or is a pharmaceutically acceptable salt thereof.

28. The compound of claim 1, wherein the compound is:

I-556

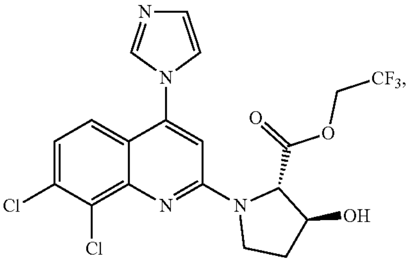

or is a pharmaceutically acceptable salt thereof.

29. The compound of claim 1, wherein the compound is:

I-664

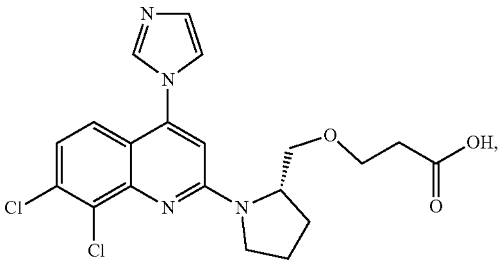

or is a pharmaceutically acceptable salt thereof.

30. The compound of claim 1, wherein the compound is:

I-713

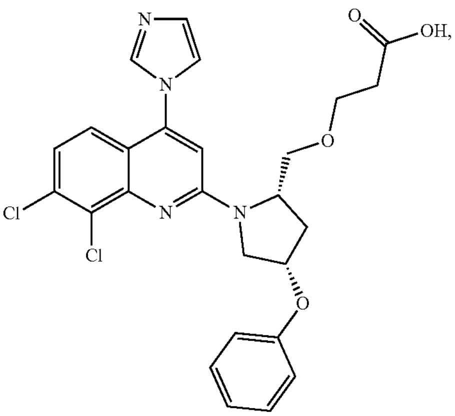

or is a pharmaceutically acceptable salt thereof.

31. The compound of claim 2, wherein the compound is selected from:
I-93
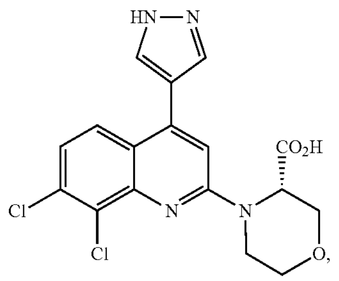
I-128
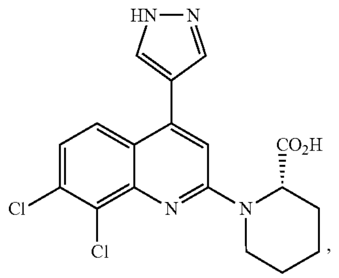
I-138
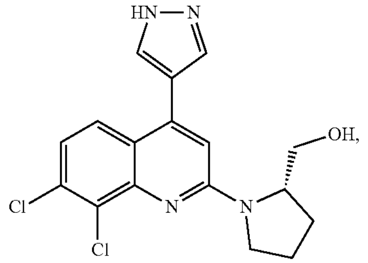
I-273
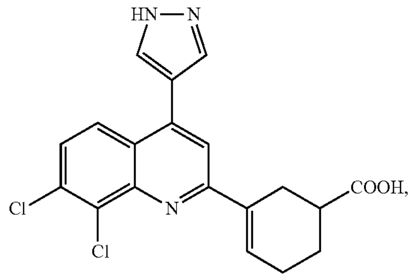
I-285
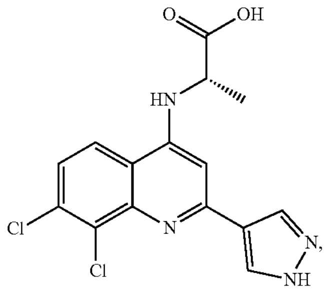
-continued
I-286
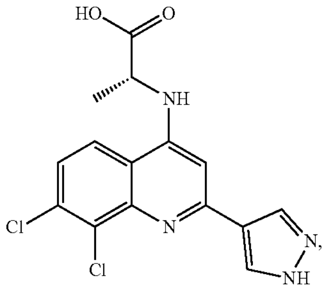
I-287
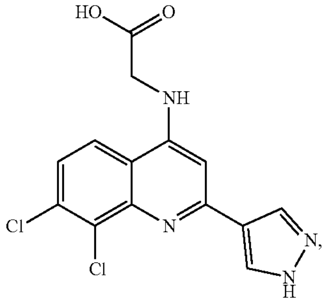
I-288
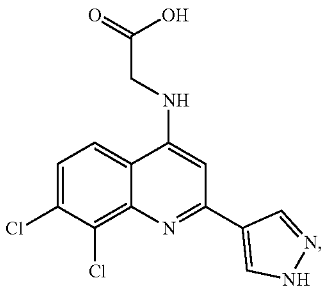
I-289
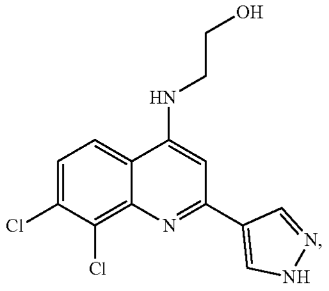
I-290
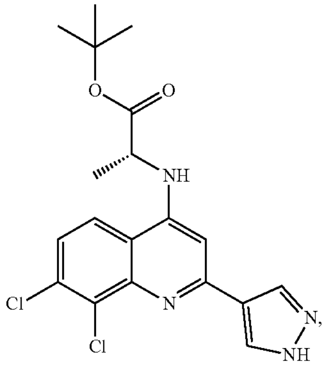

-continued
I-297
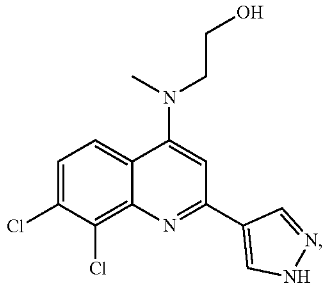
I-300
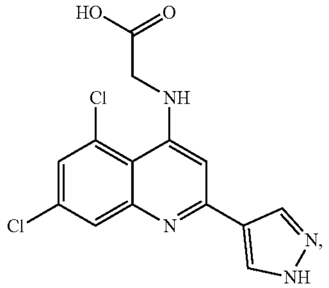
I-325
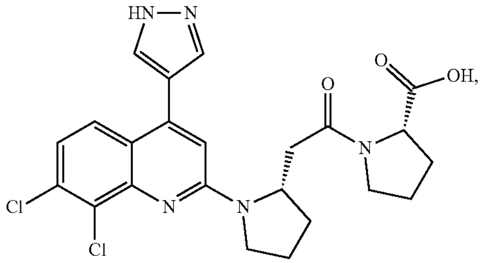
I-326
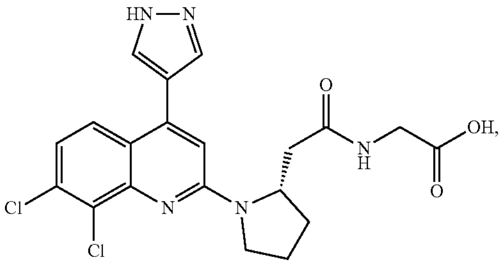
I-327
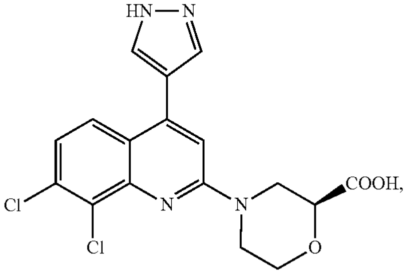
-continued
I-328
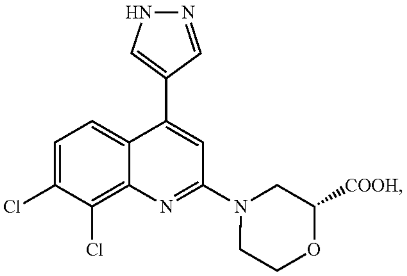
I-329
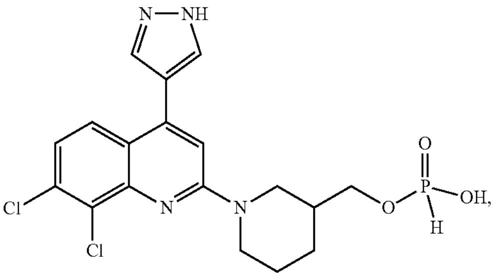
I-330
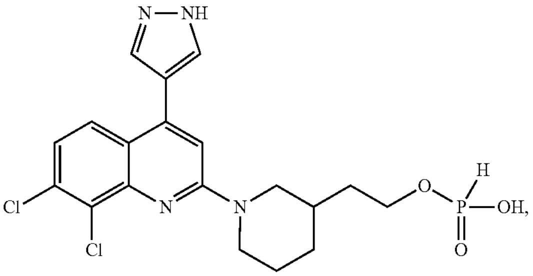
I-341
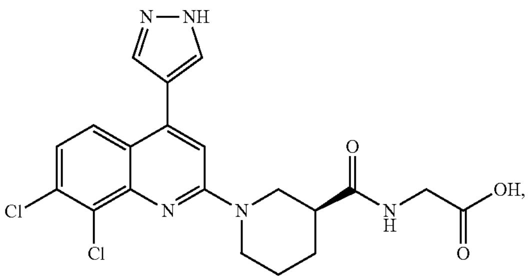
I-342
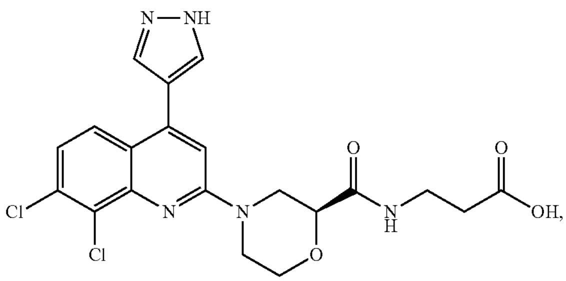

-continued
I-343
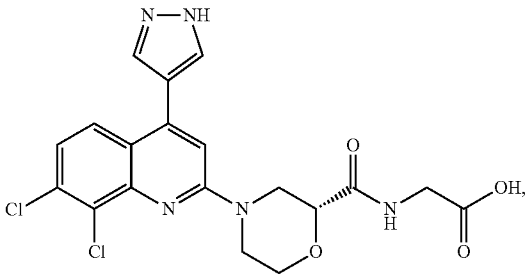
I-344
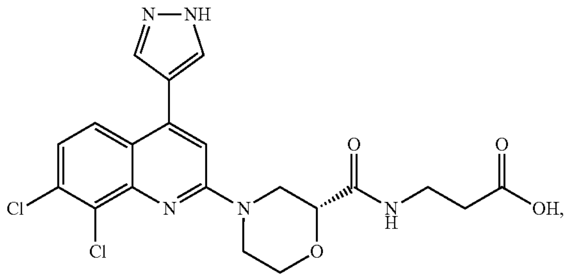
I-352
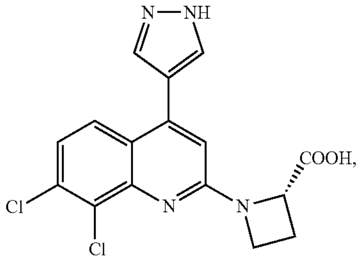
I-359
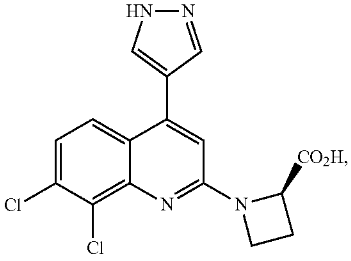
I-360
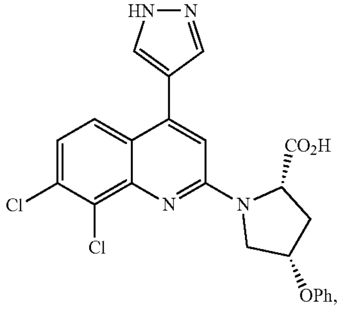
-continued
I-361
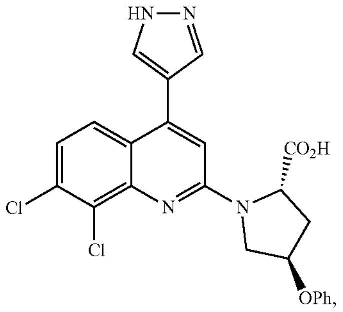
I-369
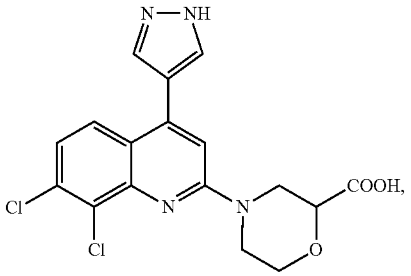
I-370
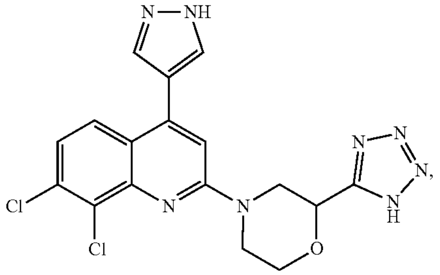
I-371
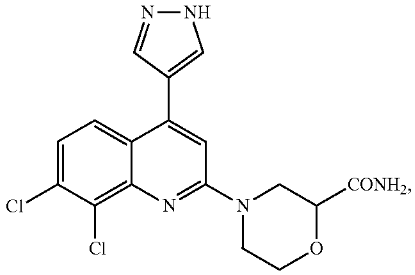
I-372
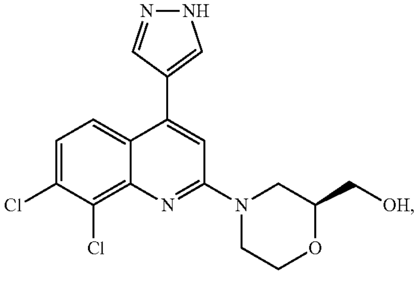

-continued
I-373
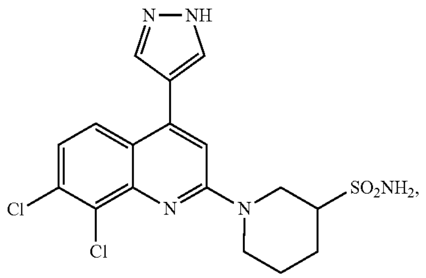
I-375
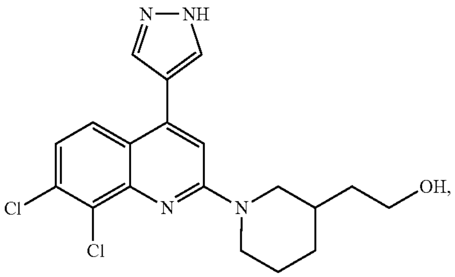
I-396
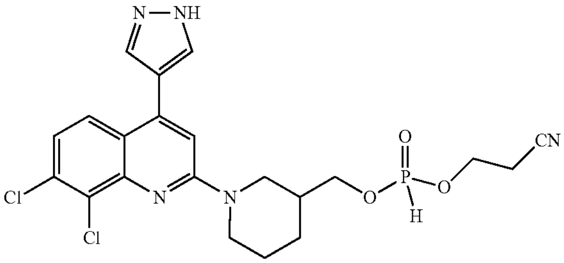
I-401
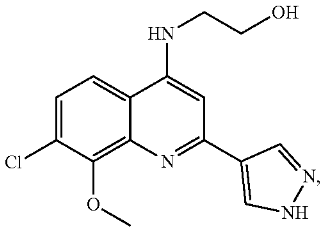
I-425
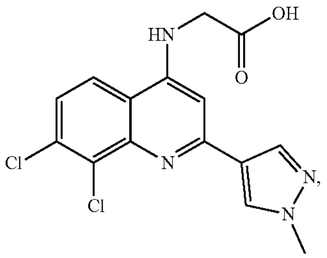
I-426
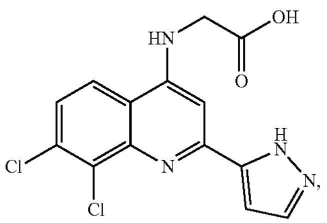
-continued
I-430
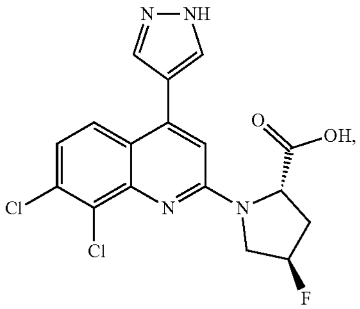
I-431
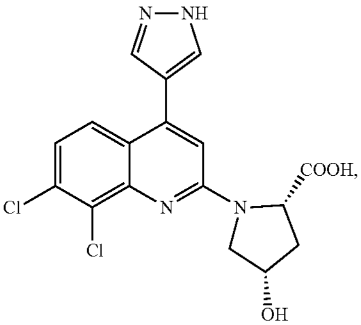
I-432
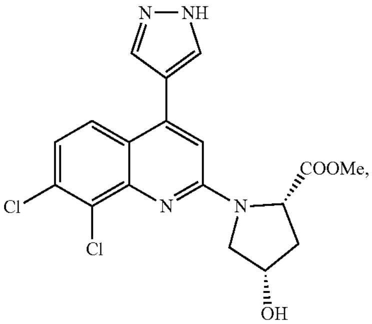
I-433
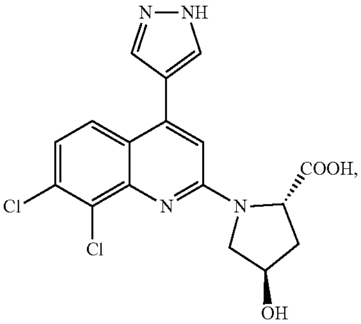
I-434
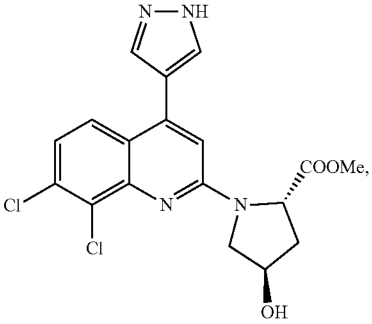

-continued
I-435
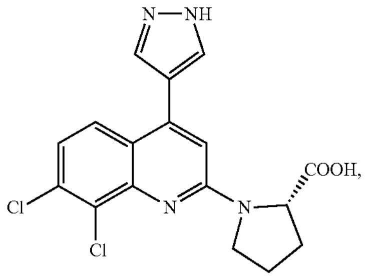
I-437
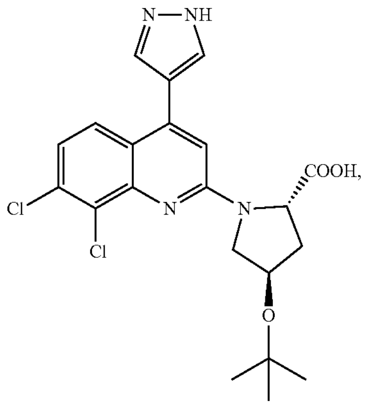
I-438
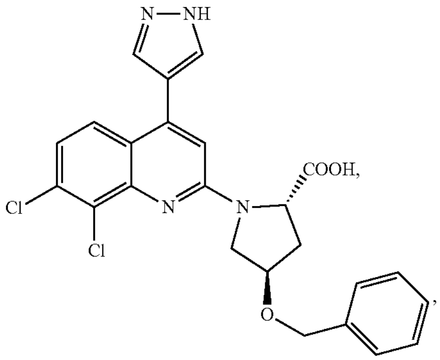
I-439
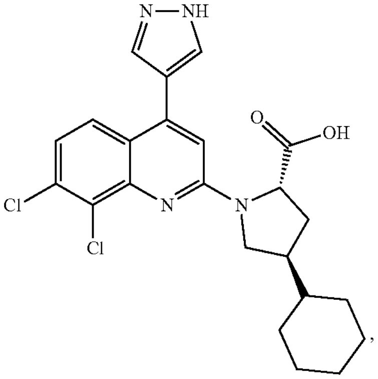
-continued
I-444
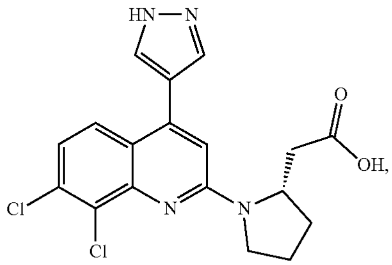
I-454
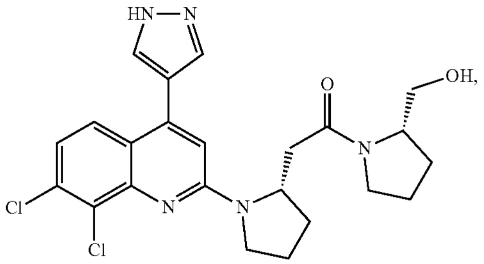
I-598
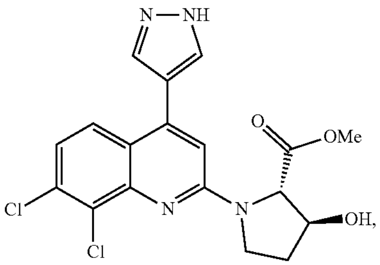
I-670
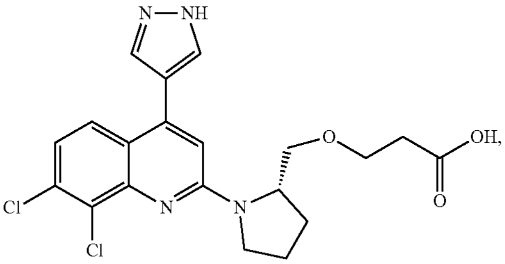
I-671
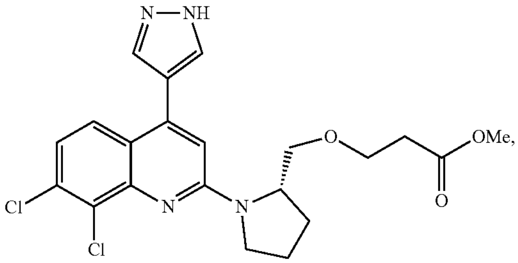

-continued
I-684
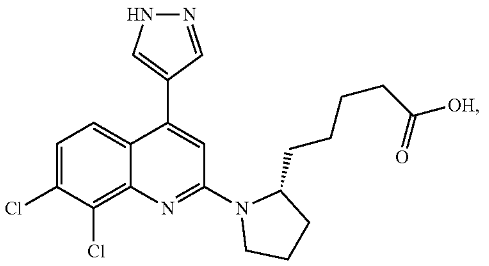
I-740
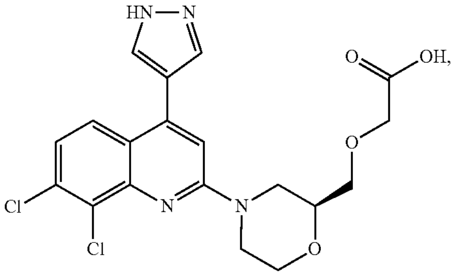
I-741
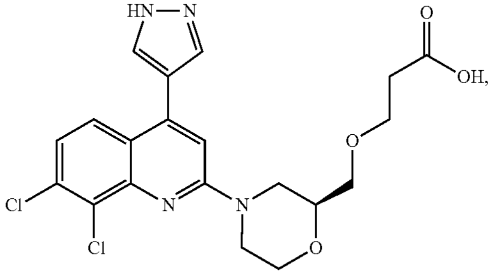
I-746
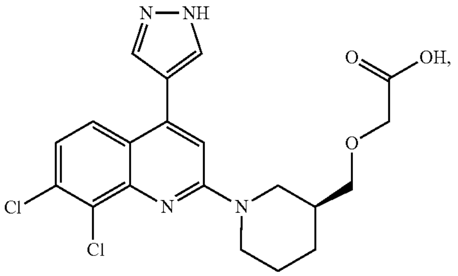
I-747
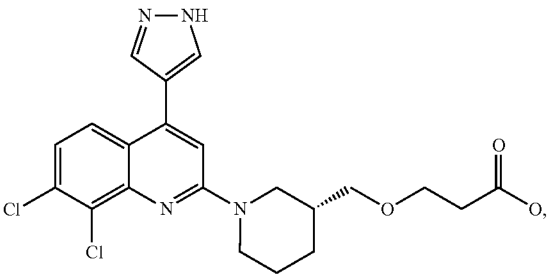
-continued
I-751
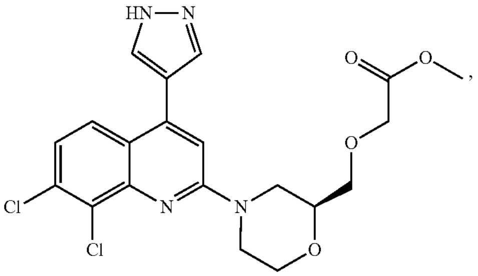
I-752
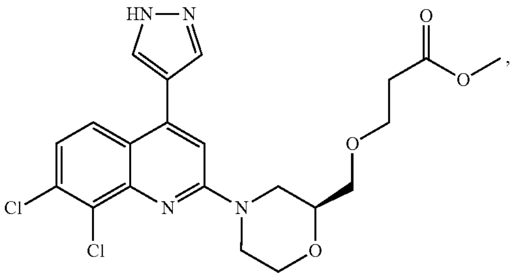
I-822
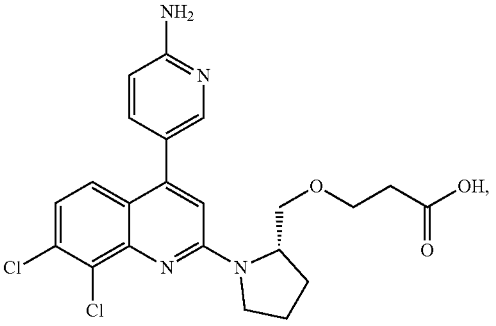
I-823
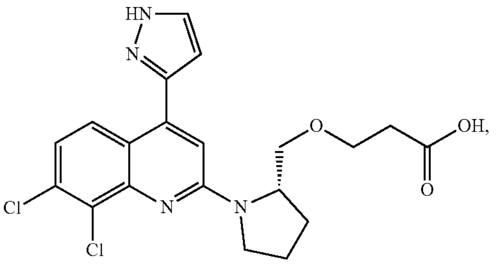
I-824
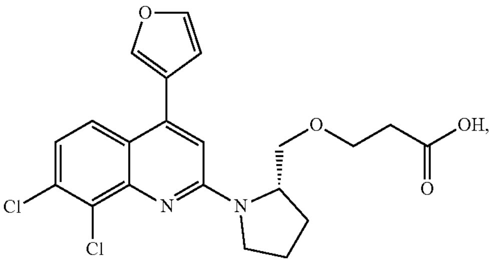

-continued

I-826

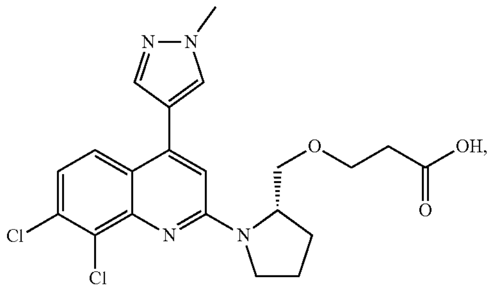

I-853

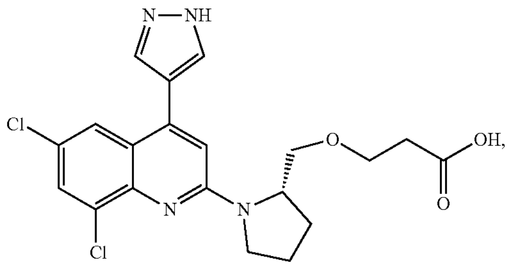

I-855

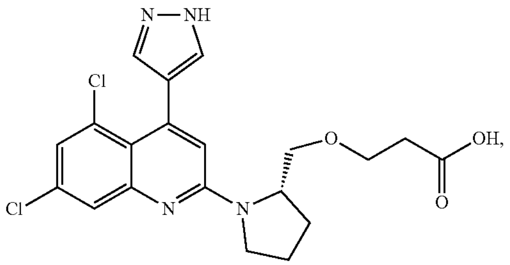

and

I-859

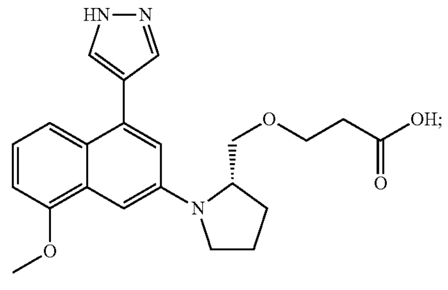

or is a pharmaceutically acceptable salt thereof.

32. A pharmaceutical composition comprising a compound of claim 1 and a pharmaceutically acceptable excipient.

33. A pharmaceutical composition comprising a compound of claim 2 and a pharmaceutically acceptable excipient.

34. A method of antagonizing cyclic GMP-AMP synthase (cGAS) in a patient in need thereof, comprising administering to the patient an effective amount of a compound of claim 1.

35. A method of antagonizing cyclic GMP-AMP synthase (cGAS) in a patient in need thereof, comprising administering to the patient an effective amount of a compound of claim 2.

36. The compound of claim 1, wherein the compound is selected from:

I-127

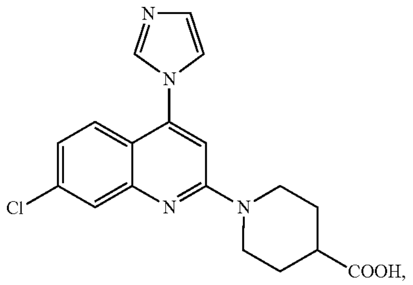

I-130

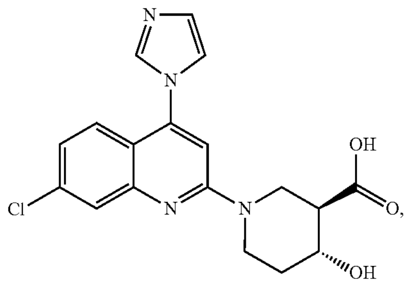

I-131

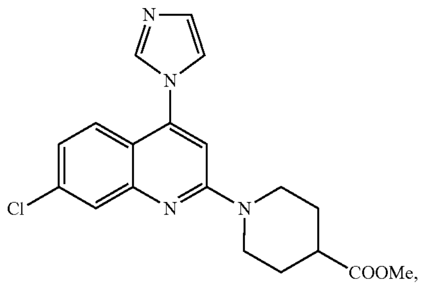

I-132

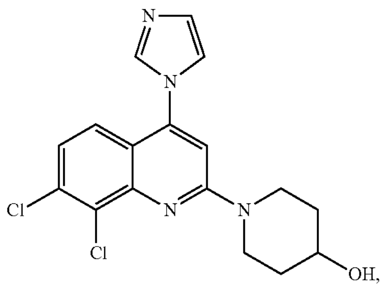

I-133

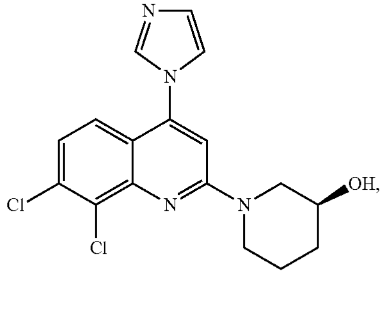

-continued
I-134
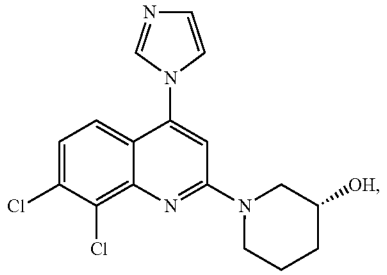
I-135
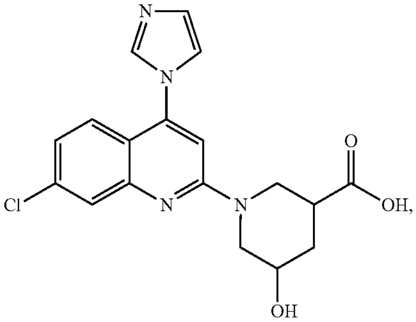
I-136
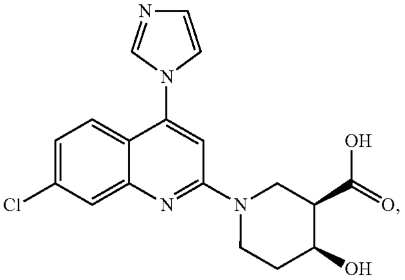
I-137
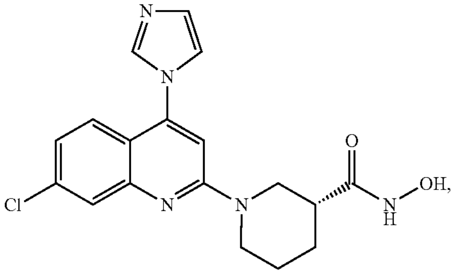
I-139
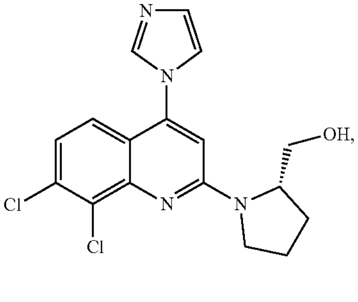
-continued
I-140
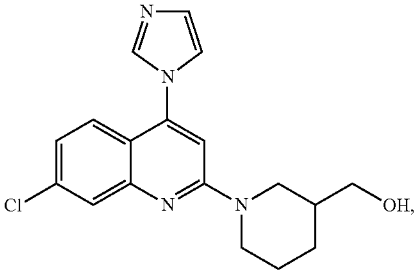
I-141
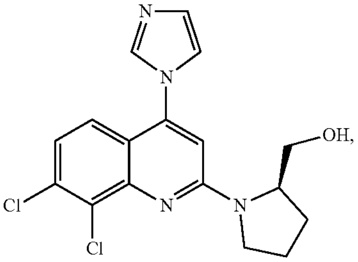
I-142
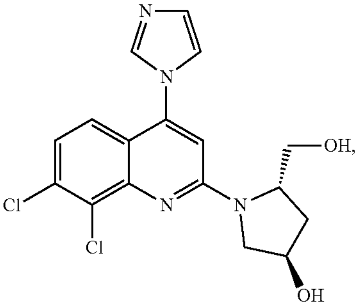
I-143
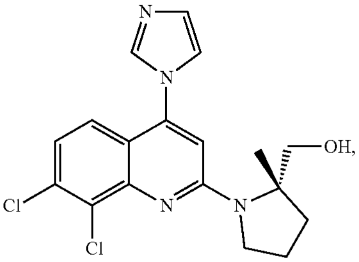
I-144
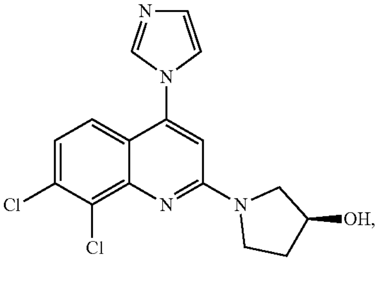

-continued
I-145
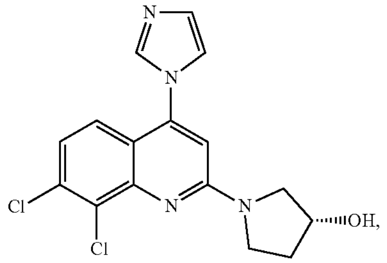
I-147
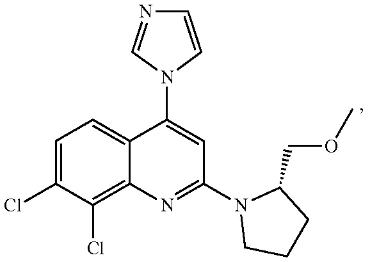
I-148
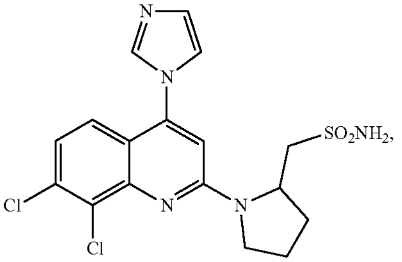
I-149
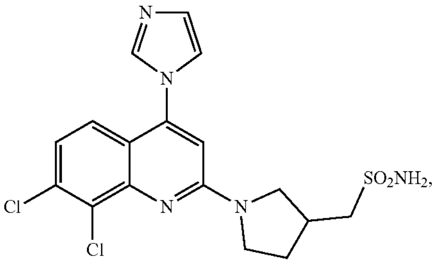
I-150
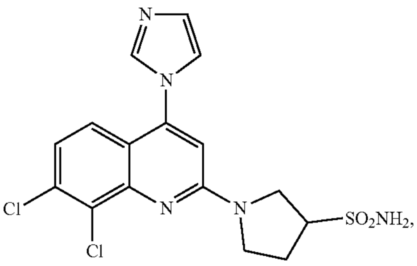
I-151
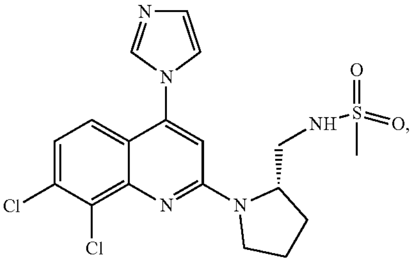
-continued
I-152
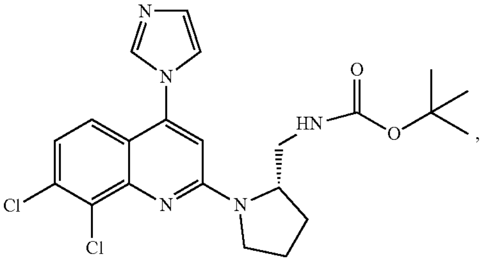
I-153
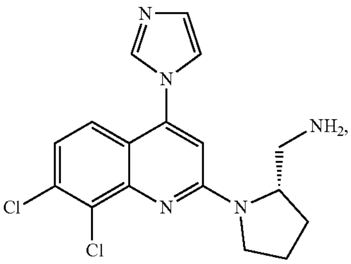
I-154
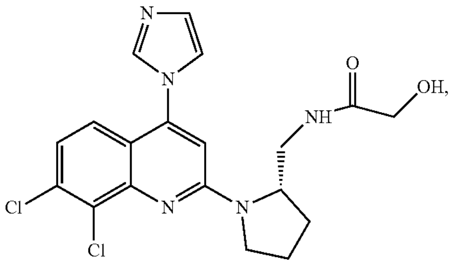
I-155
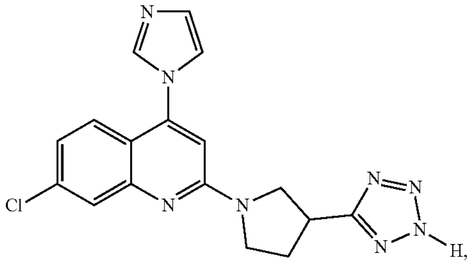
I-156
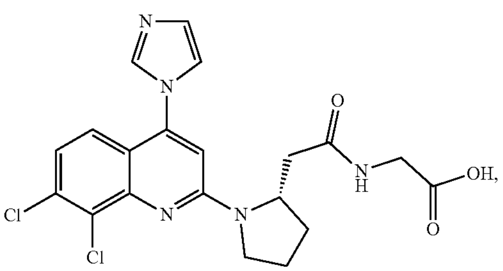

-continued
I-157
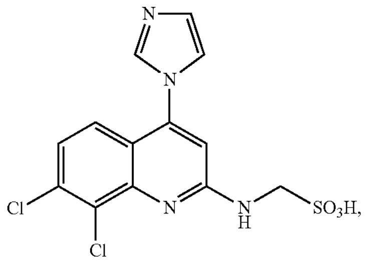
I-158
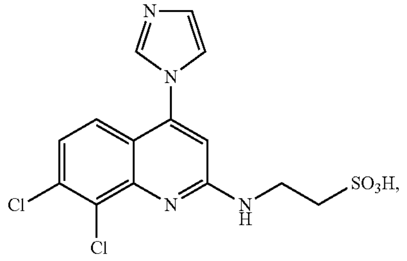
I-159
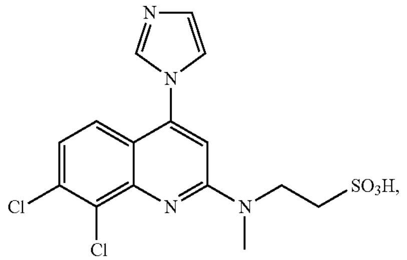
I-160
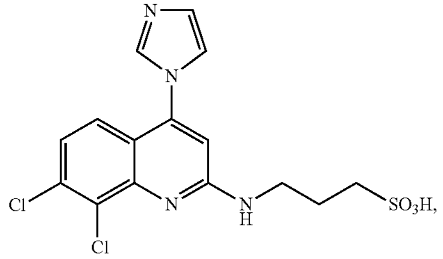
I-162
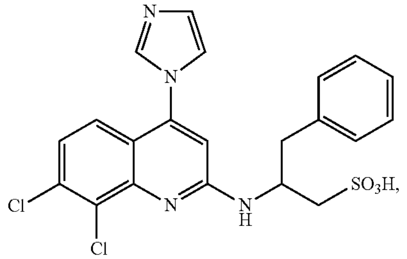
I-163
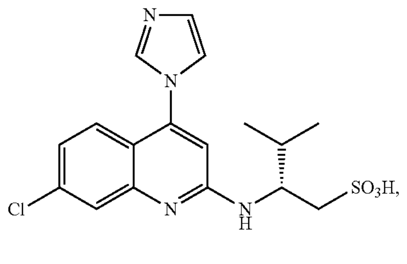
-continued
I-164
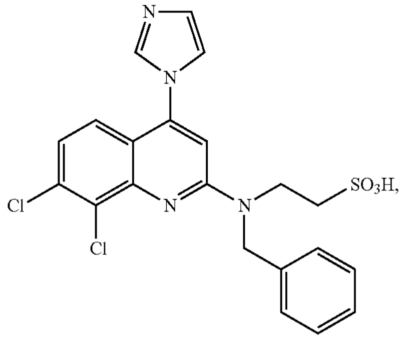
I-165
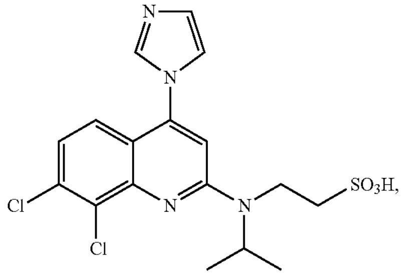
I-166
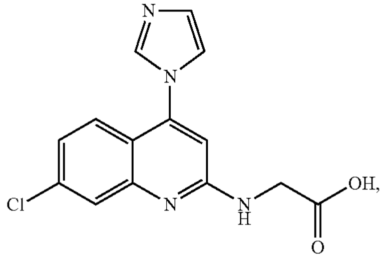
I-167
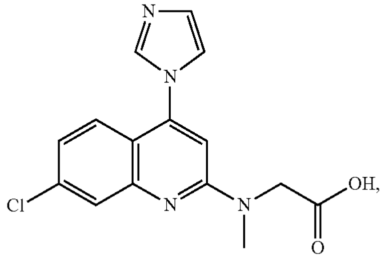
I-168
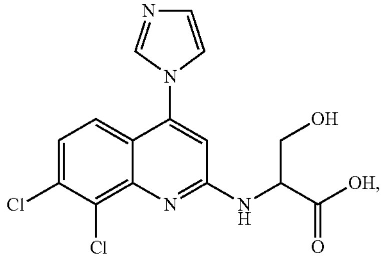

-continued
I-169
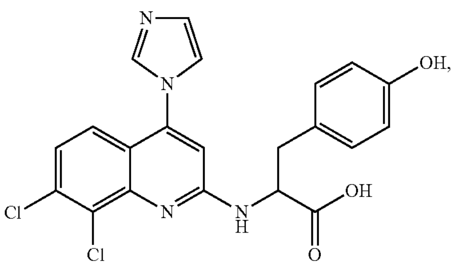
I-170
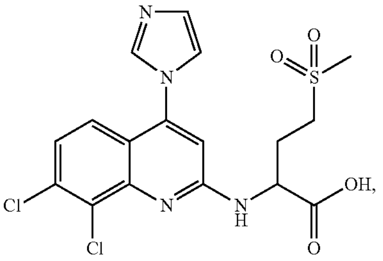
I-172
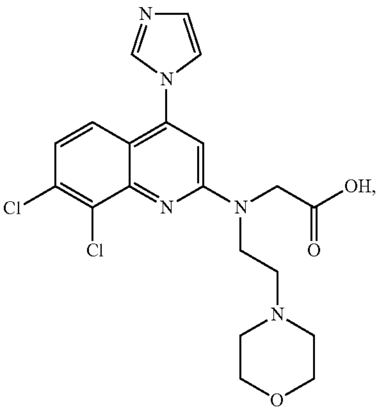
I-173
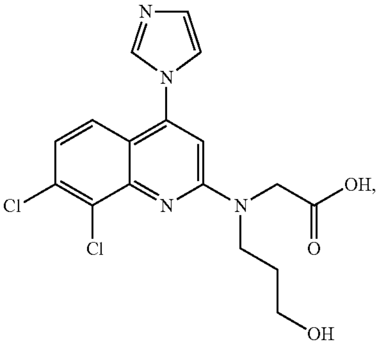
I-174
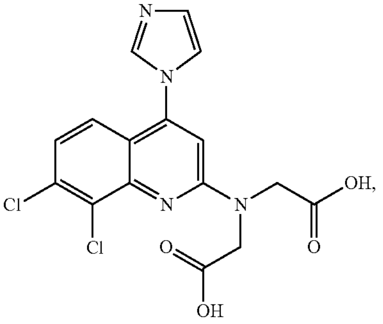
-continued
I-175
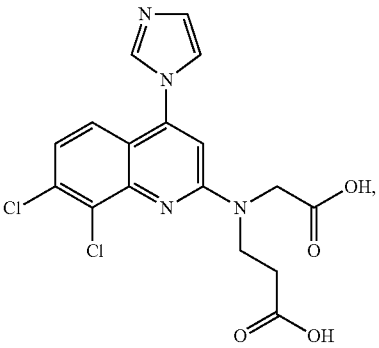
I-176
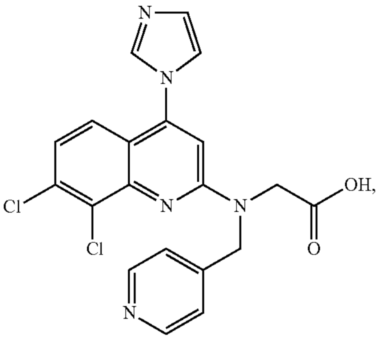
I-178
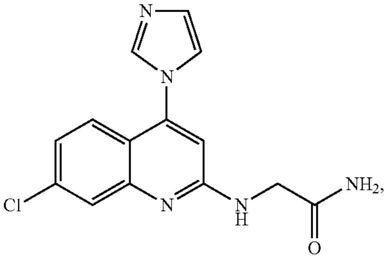
I-179
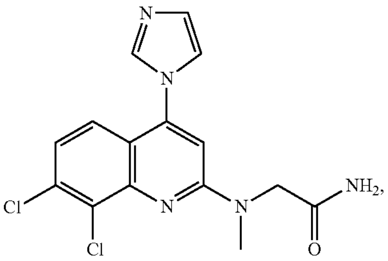
I-182
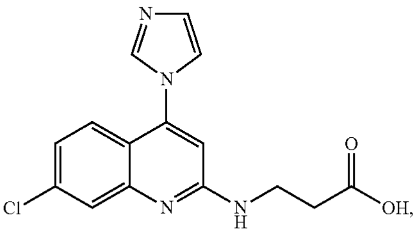

-continued
I-183
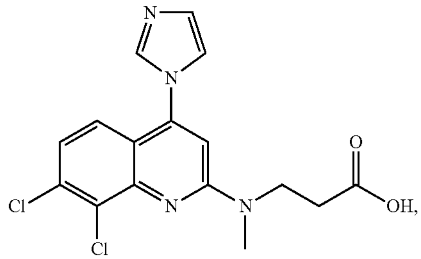
,
I-185
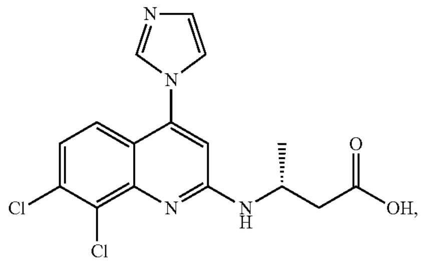
,
I-186
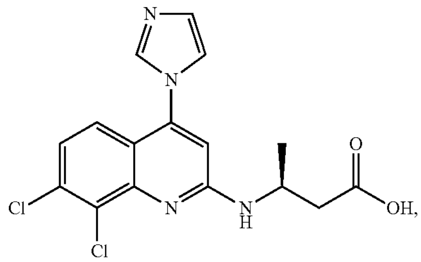
,
I-187
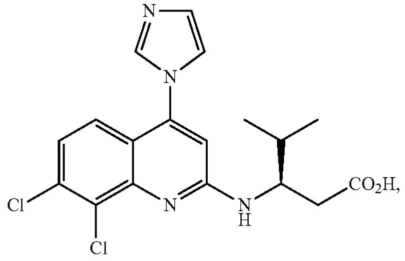
,
I-188
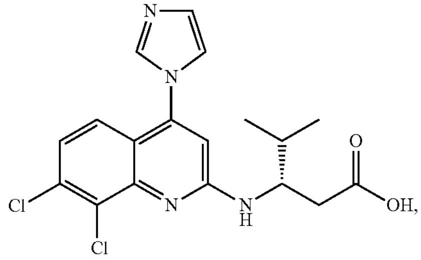
,
I-189
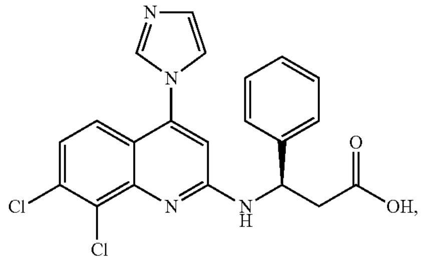
,
-continued
I-200
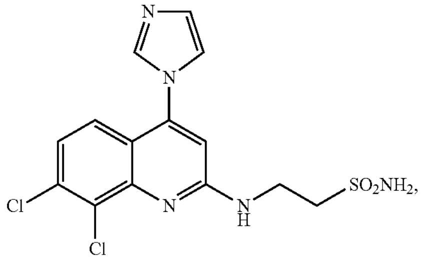
,
I-201
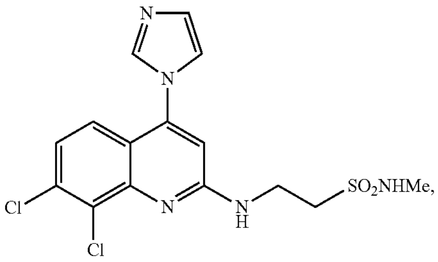
,
I-202
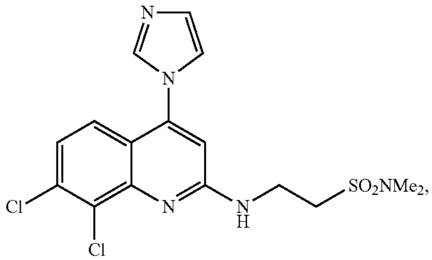
,
I-204
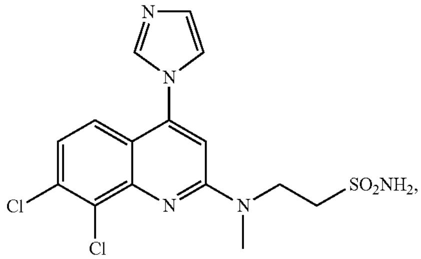
,
I-205
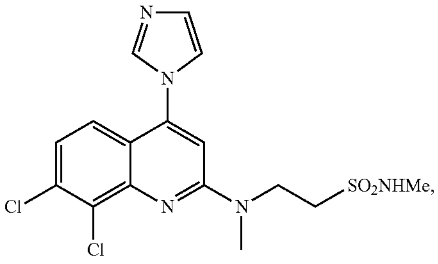
,
I-206
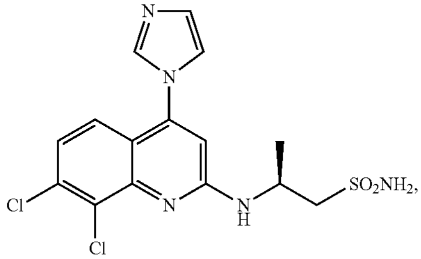
, -continued
I-207
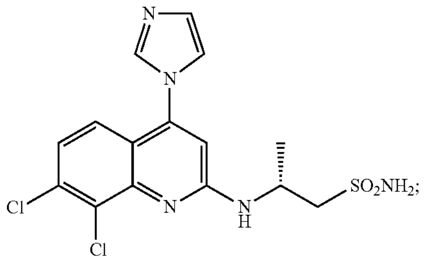
I-208
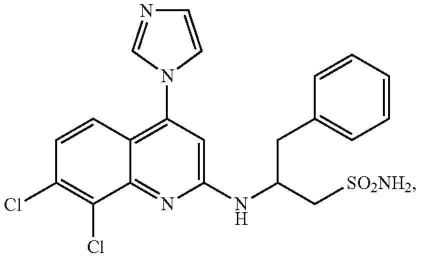
and
I-209
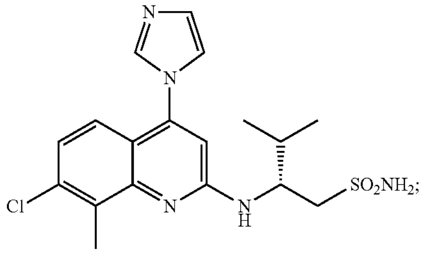
or is a pharmaceutically acceptable salt thereof.
37. The compound of claim 1, wherein the compound is selected from:
I-210
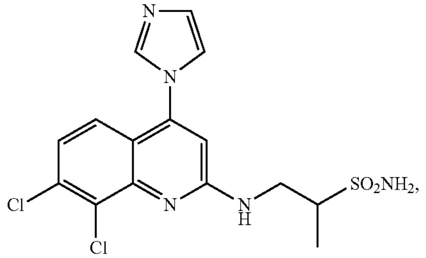
I-215
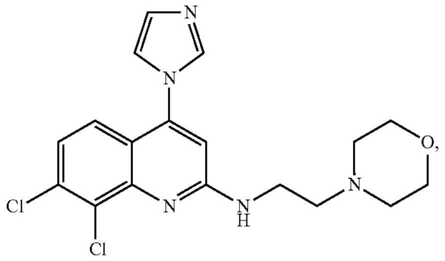
-continued
I-219
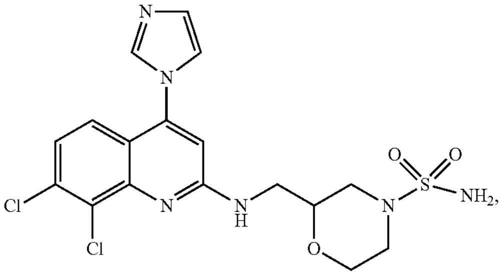
I-223
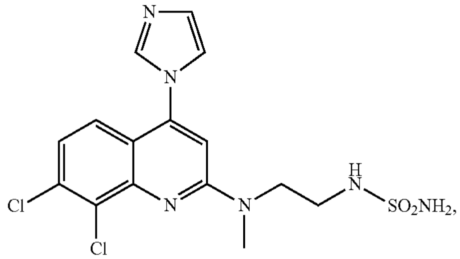
I-224
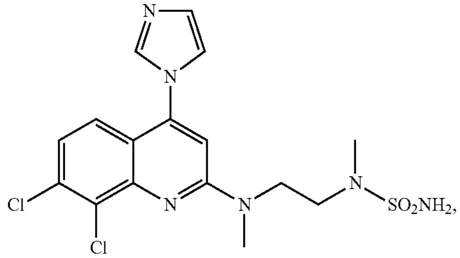
I-225
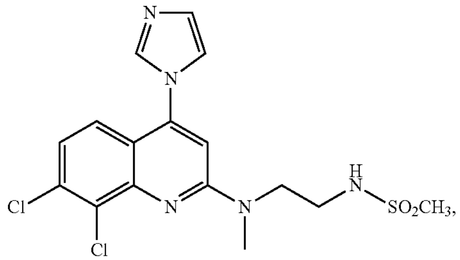
I-226
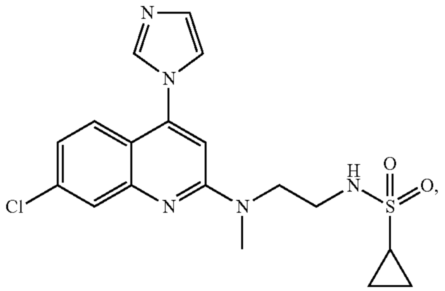

-continued
I-227
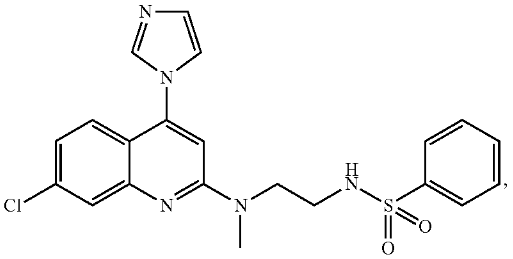
I-228
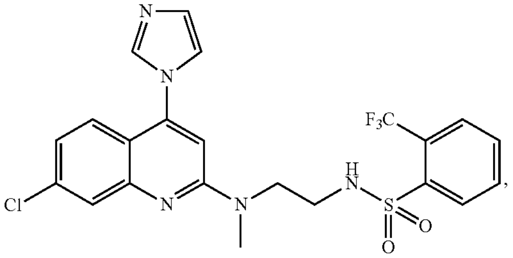
I-229
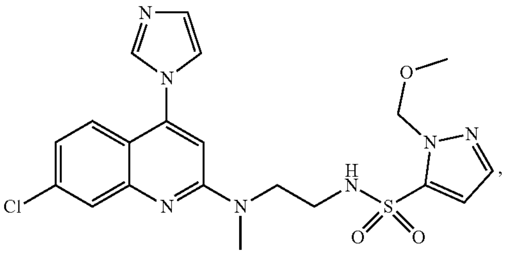
I-230
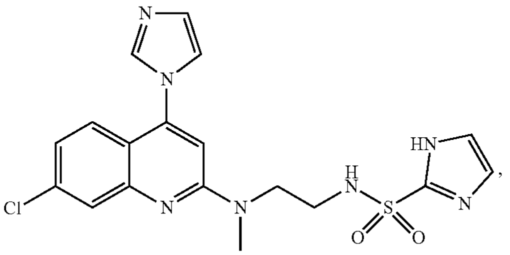
I-231
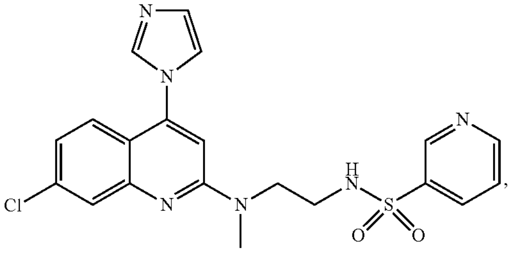
-continued
I-232
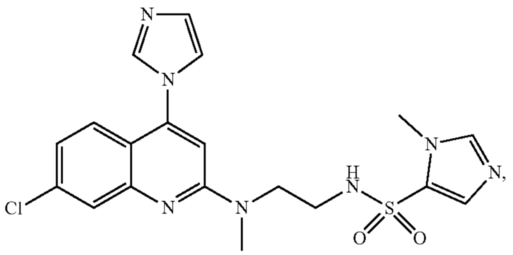
I-234
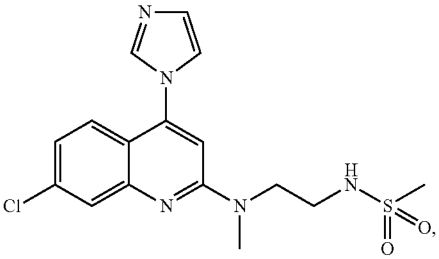
I-236
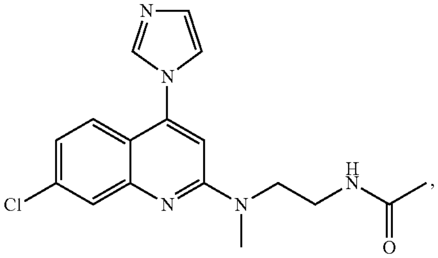
I-237
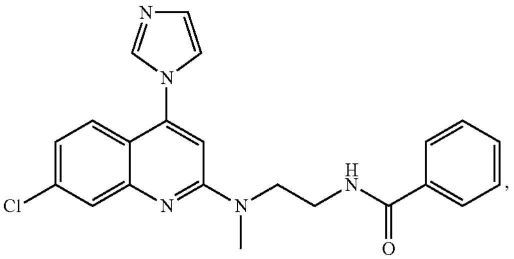
I-238
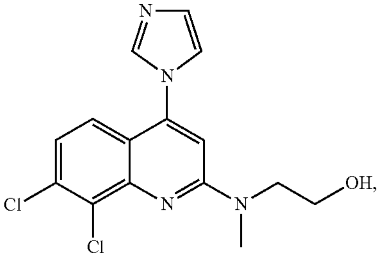
I-239
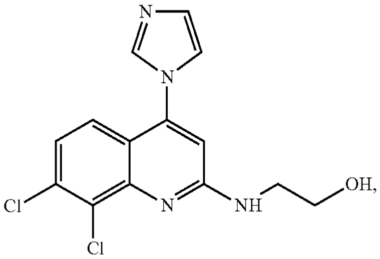

-continued
I-241
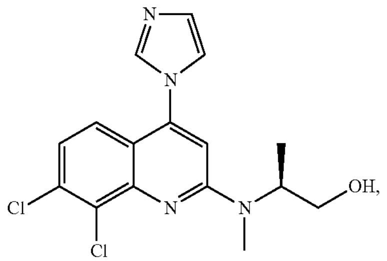
I-242
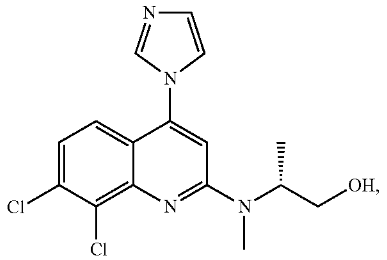
I-243
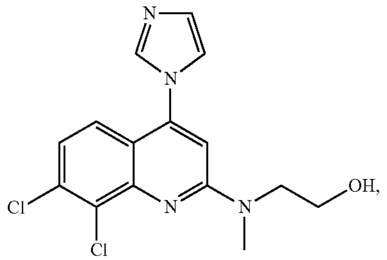
I-244
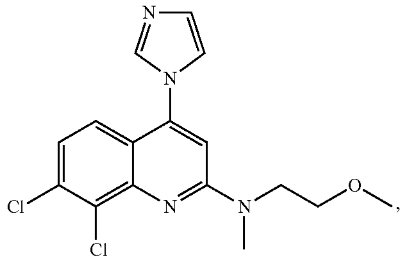
I-245
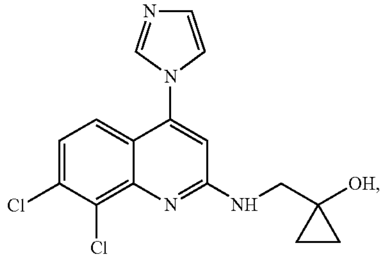
I-246
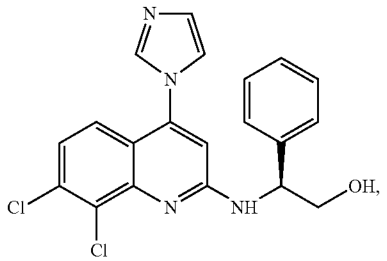
-continued
I-247
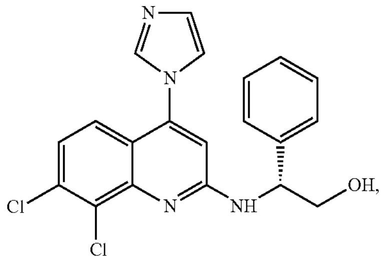
I-249
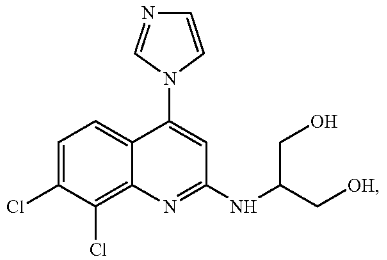
I-250
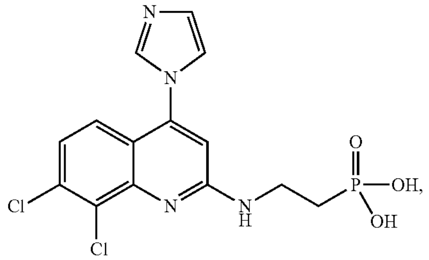
I-255
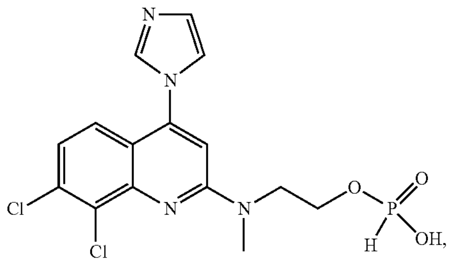
I-259
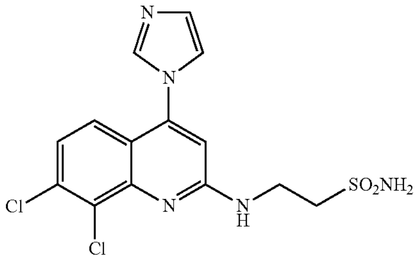
I-291
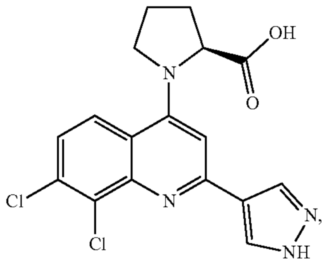

-continued
I-321
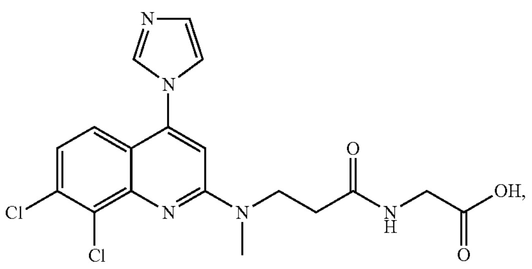
I-322
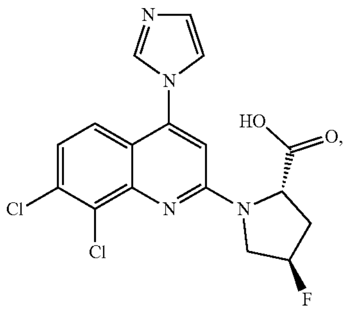
I-323
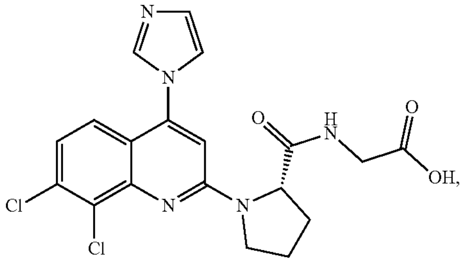
I-324
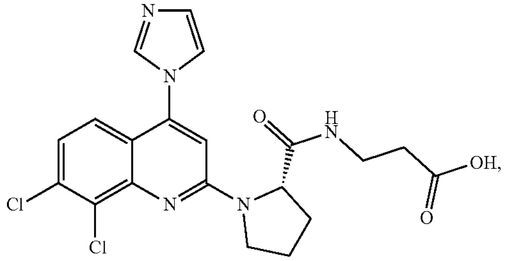
I-331
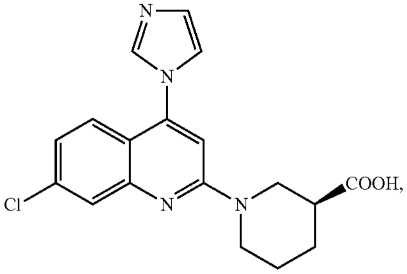
-continued
I-332
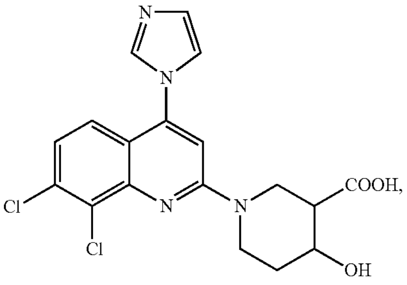
I-333
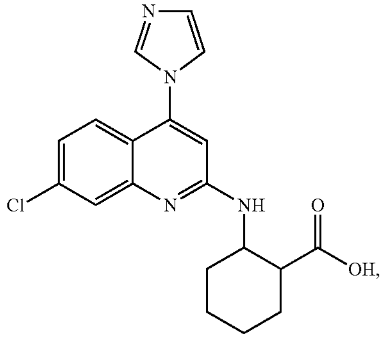
I-334
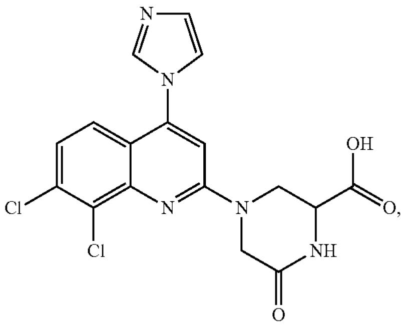
I-335
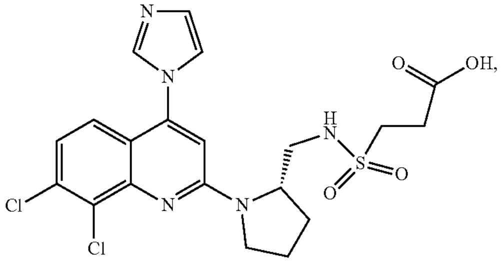
I-338
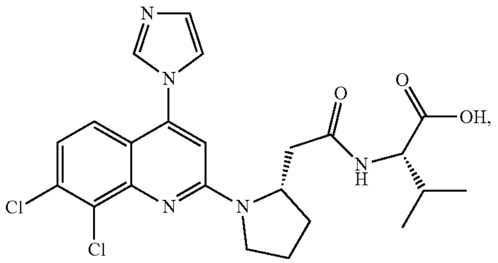

-continued
I-339
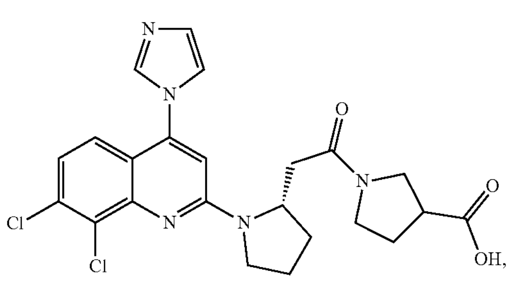
I-340
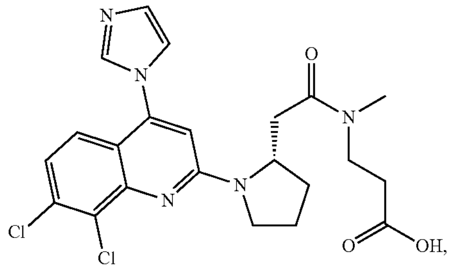
I-345
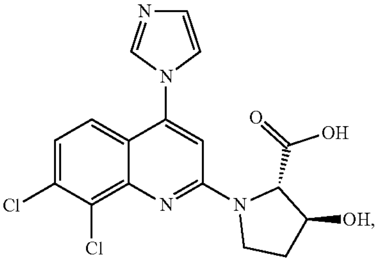
I-346
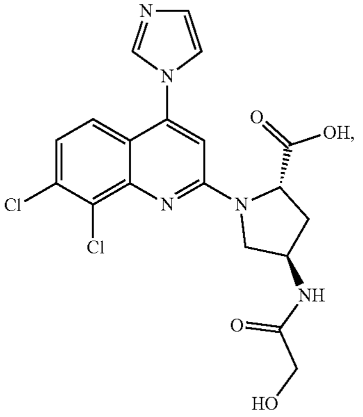
I-347
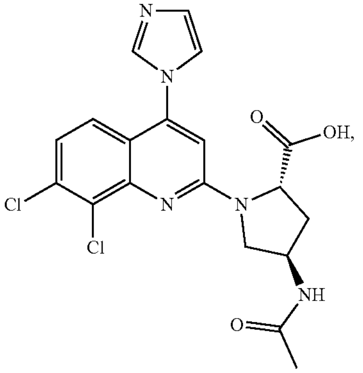
-continued
I-348
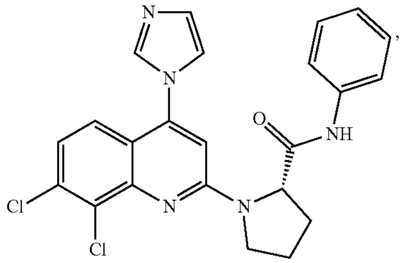
I-349
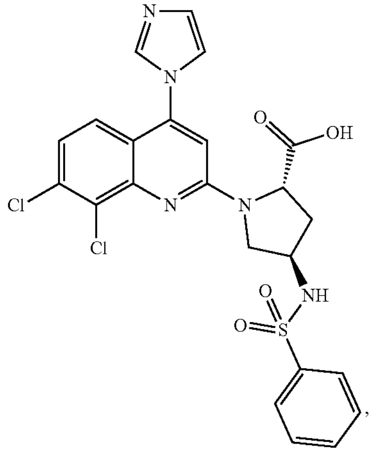
I-350
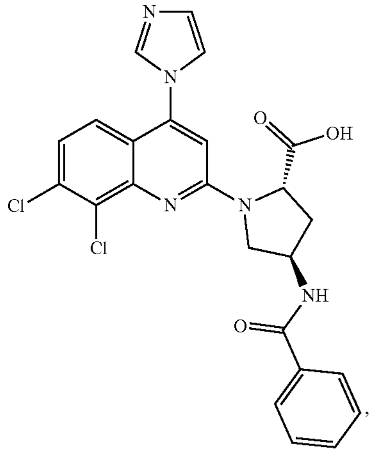
I-351
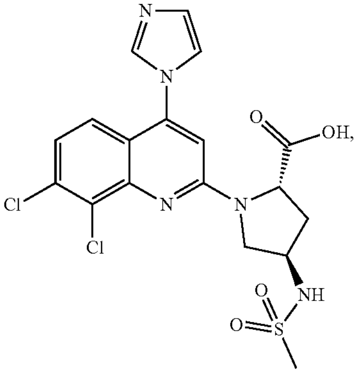

-continued
I-353
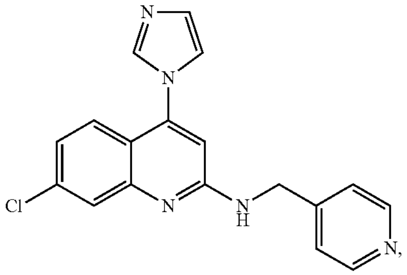
I-354
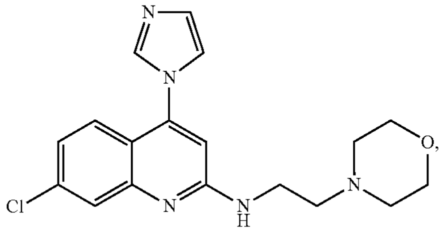
I-355
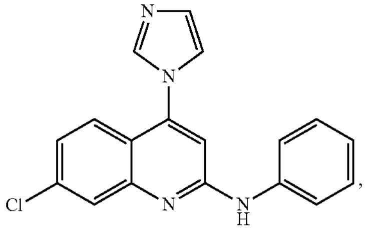
I-356
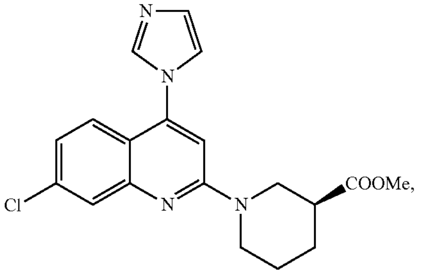
I-357
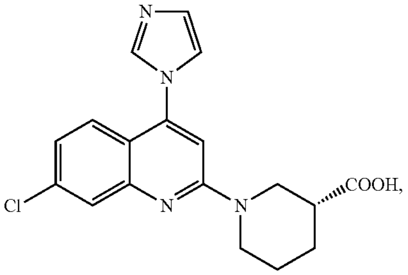
I-362
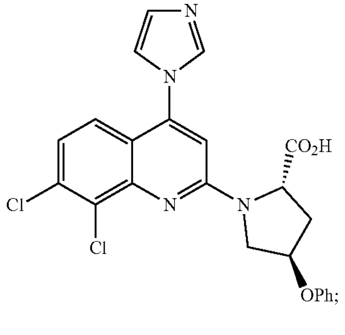
-continued
I-363
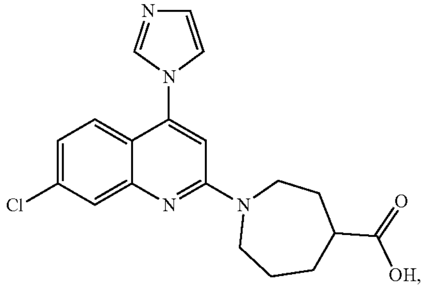
I-364
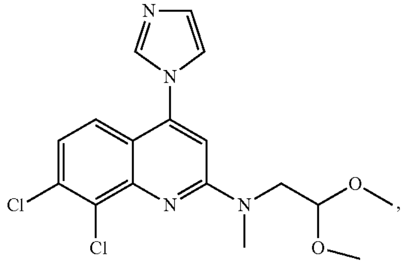
I-365
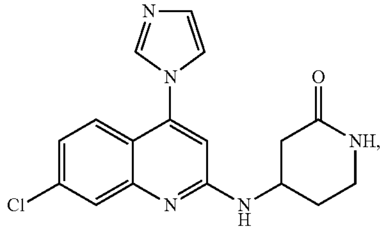
and
I-366
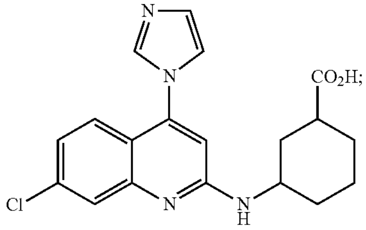
or is a pharmaceutically acceptable salt thereof.
38. The compound of claim 1, wherein the compound is selected from:
I-367
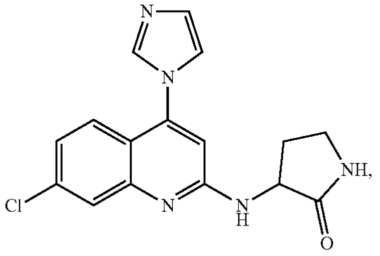

I-368
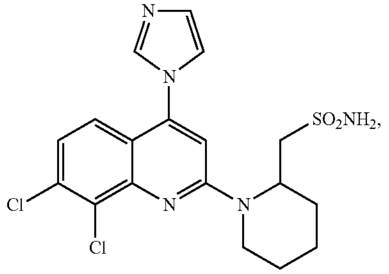
I-374
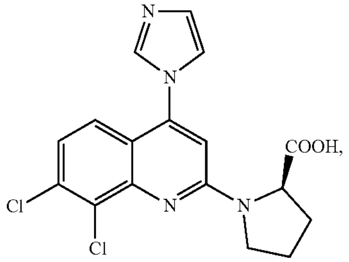
I-376
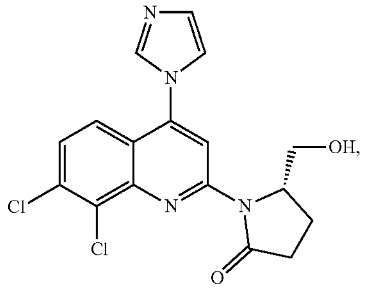
I-378
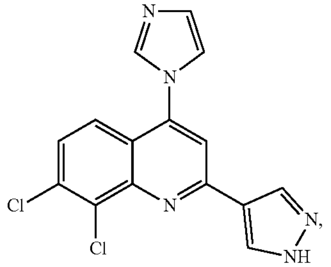
I-380
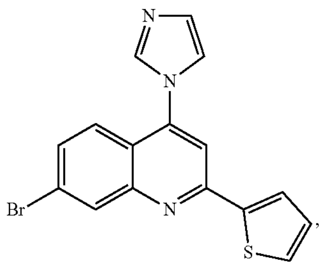
I-383
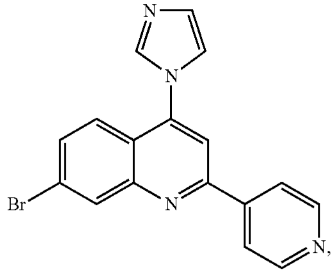
I-384
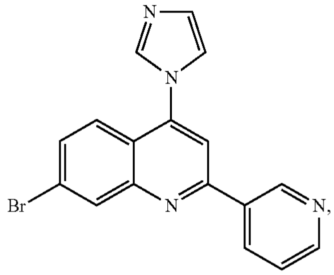
I-386
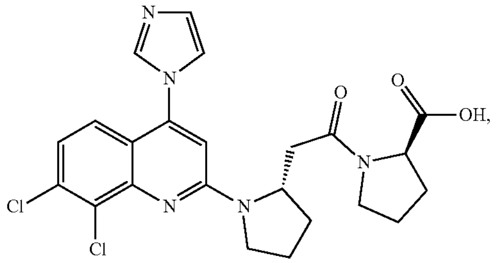
I-387
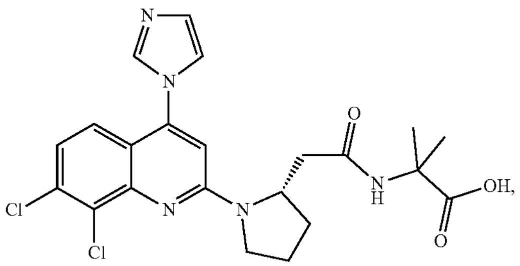
I-388
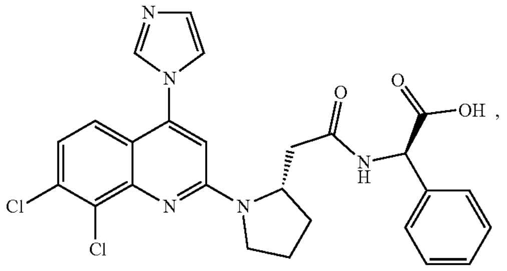

-continued
I-390
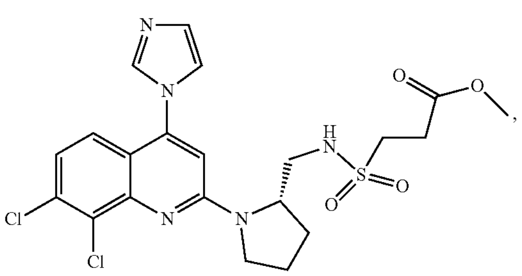
,
I-391
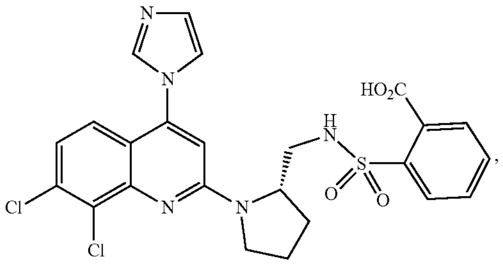
,
I-392
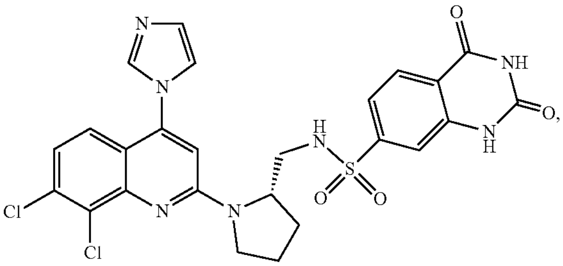
,
I-393
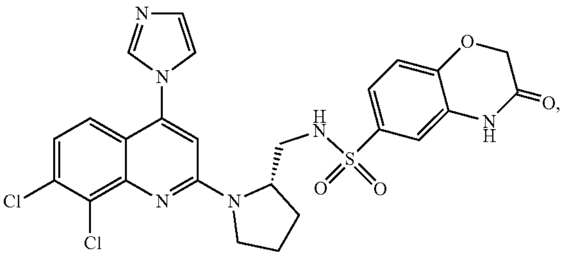
,
I-394
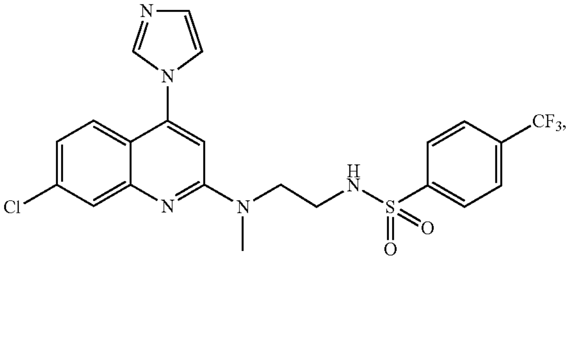
,
-continued
I-395
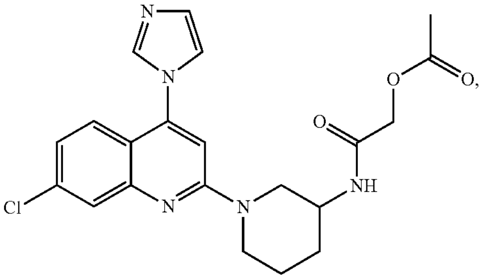
,
I-398
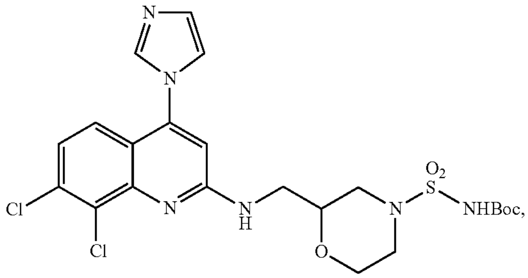
,
I-428
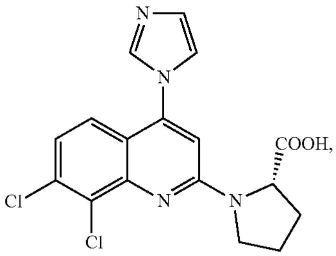
,
I-429
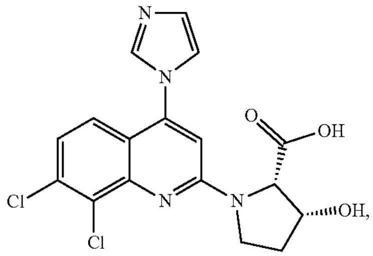
,
I-436
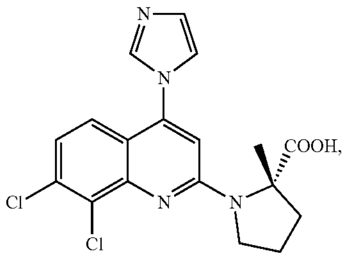
,
I-443
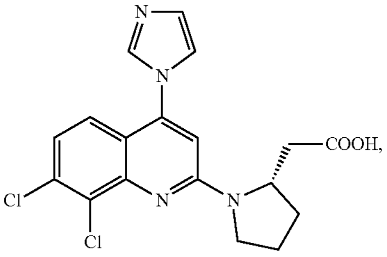
, -continued
I-445
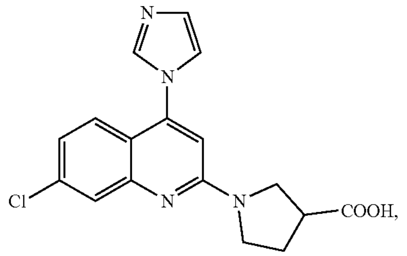
I-446
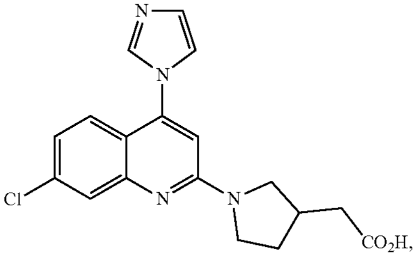
I-447
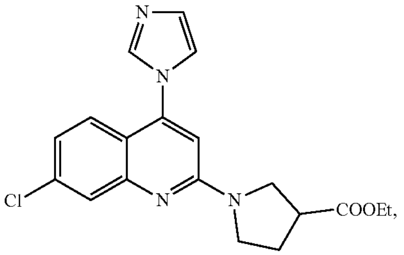
I-448
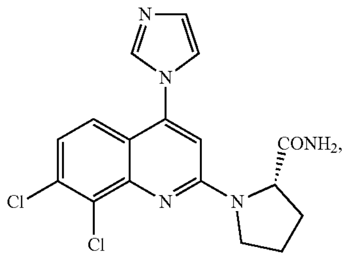
I-449
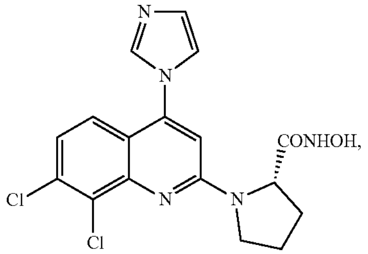
I-450
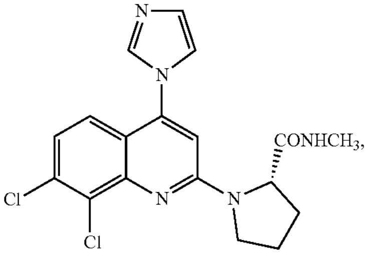
-continued
I-451
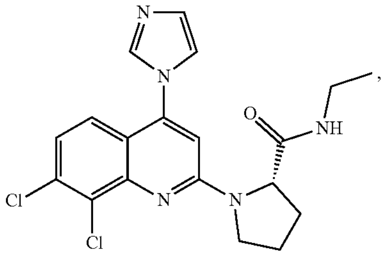
I-452
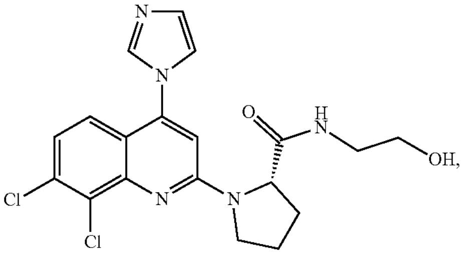
I-453
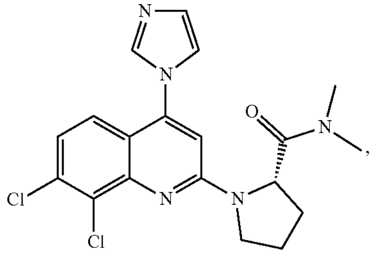
I-455
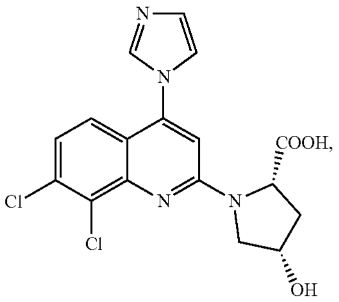
I-456
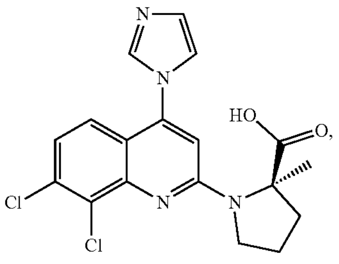
I-457
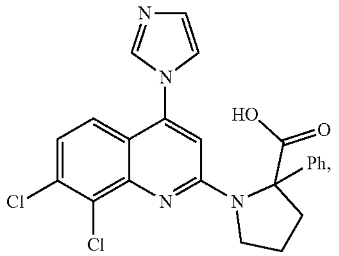

-continued
I-458
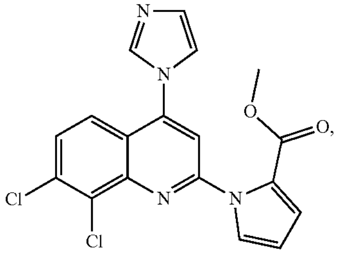
I-459
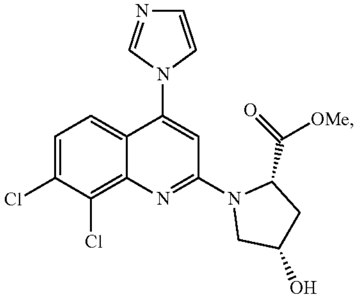
I-460
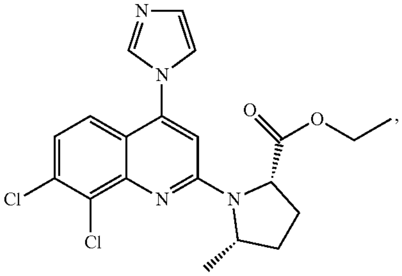
I-461
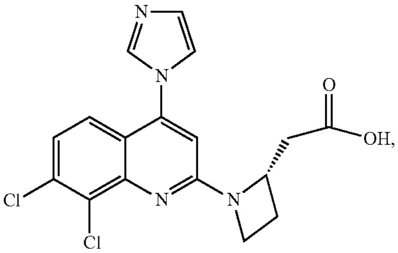
I-462
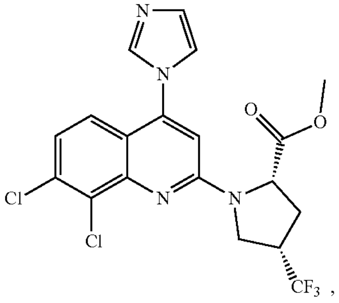
-continued
I-463
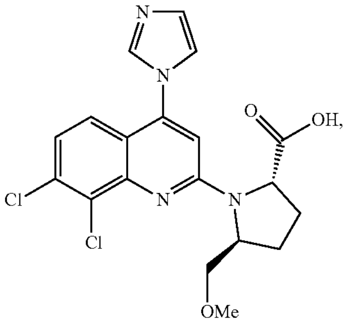
I-464
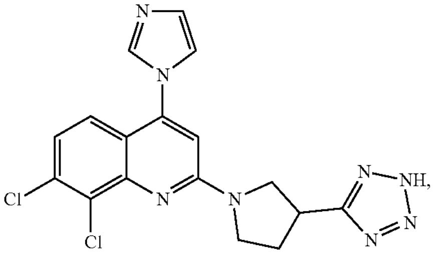
I-465
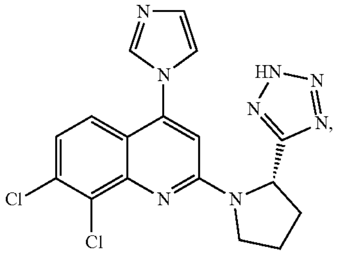
I-466
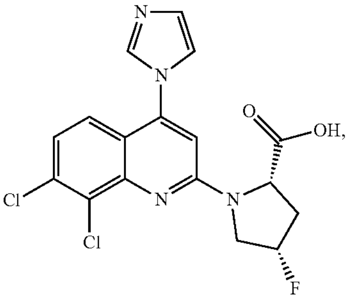
I-467
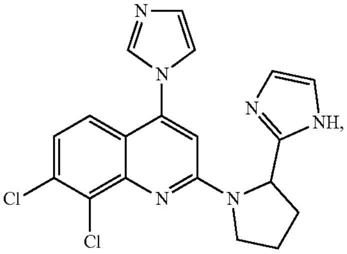

-continued
I-468
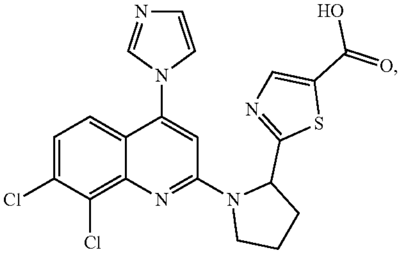
I-469
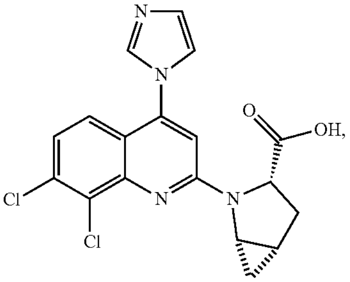
I-470
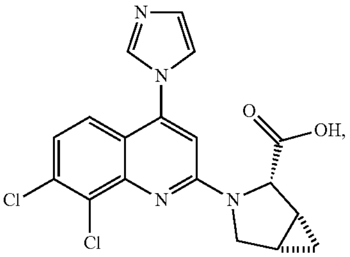
I-471
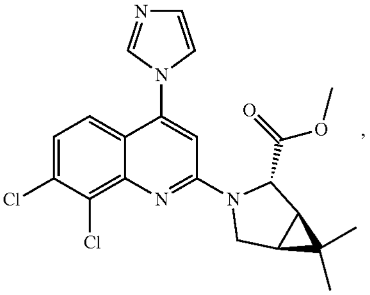
I-472
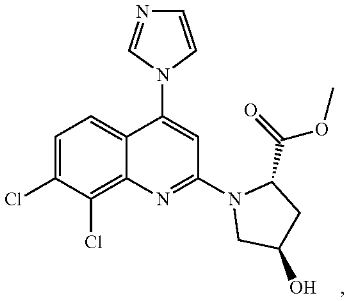
-continued
I-473
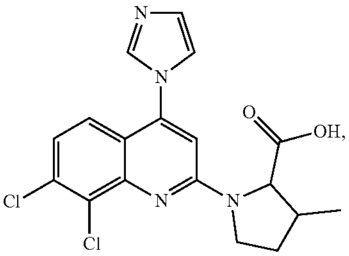
I-474
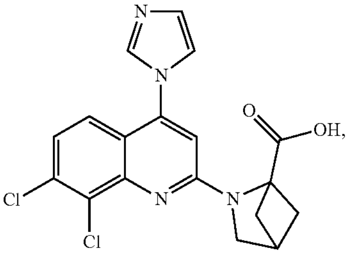
I-475
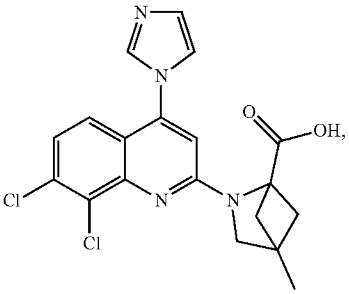
I-476
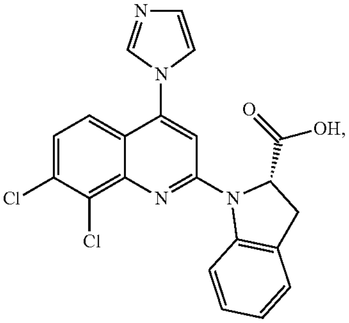
I-477
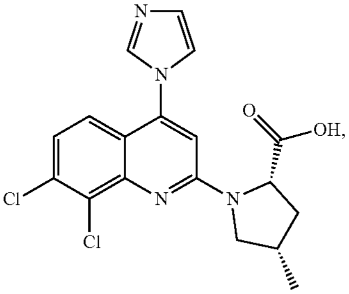

-continued
I-478
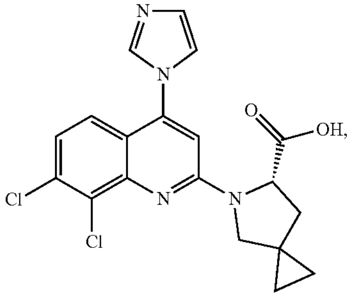
I-479
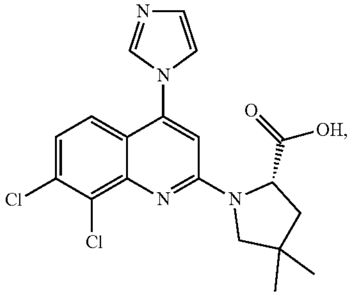
I-480
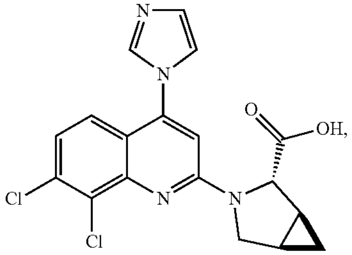
I-481
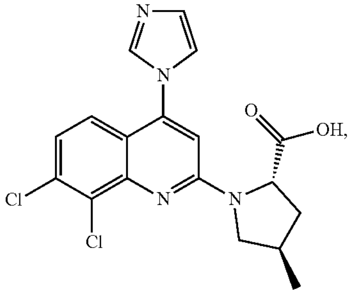
I-482
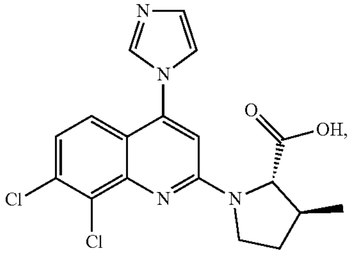
-continued
I-483
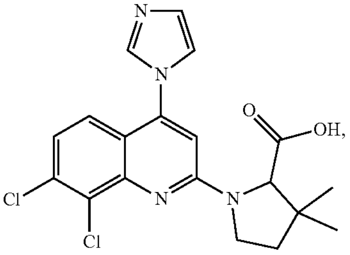
I-484
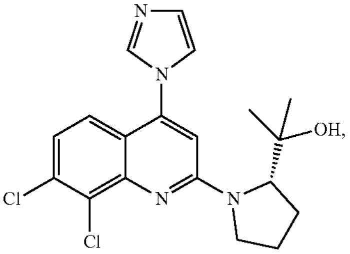
and
I-485
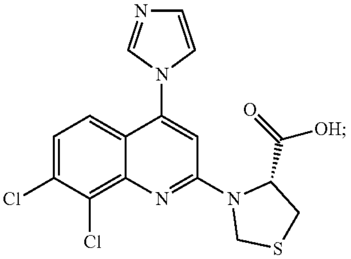
or is a pharmaceutically acceptable salt thereof.
39. The compound of claim 1, wherein the compound is selected from:
I-486
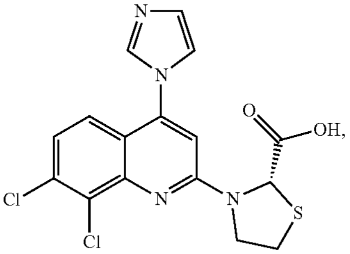
I-487
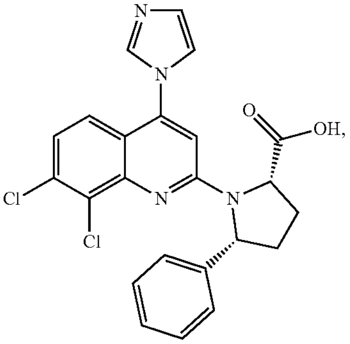

-continued
I-488
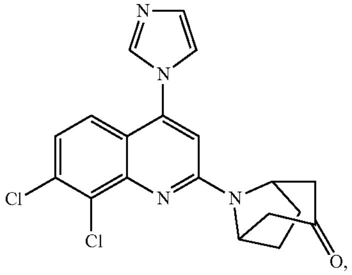
I-489
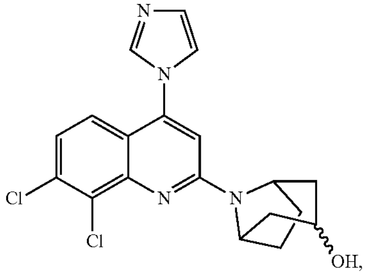
I-490
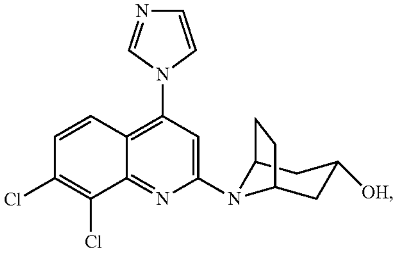
I-491
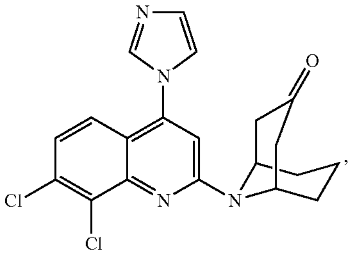
I-491
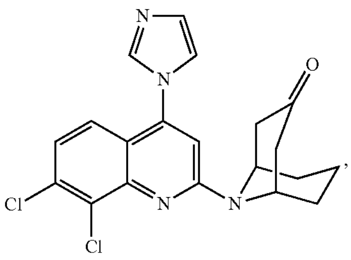
I-492
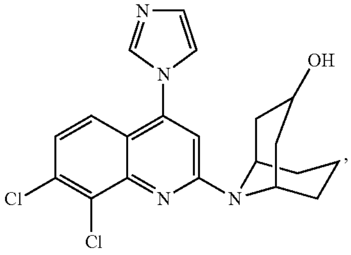
-continued
I-493
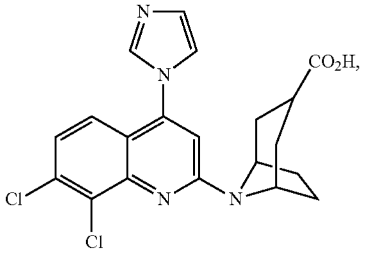
I-494
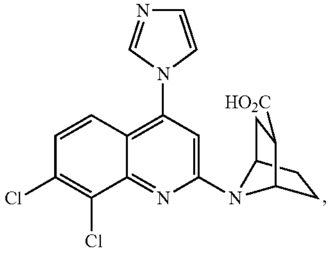
I-495
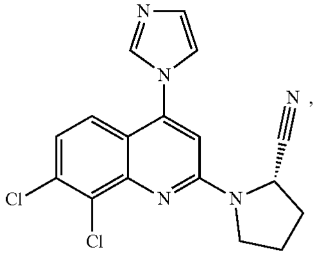
I-496
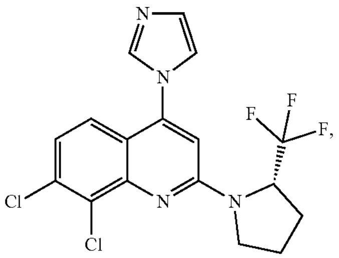
I-497
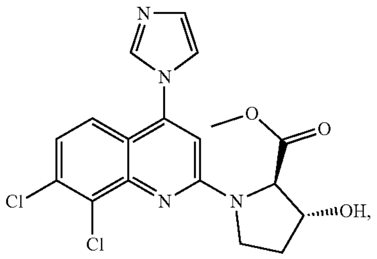
I-498
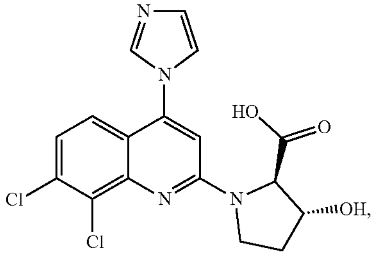

-continued
I-499
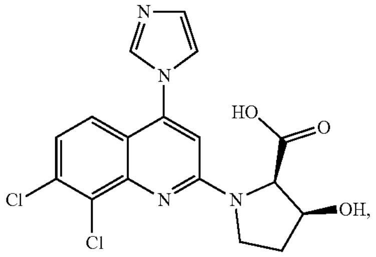
I-500
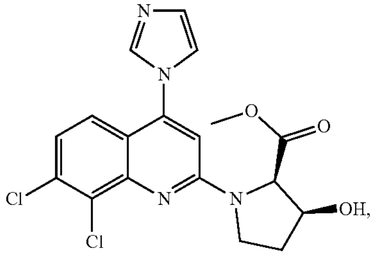
I-501
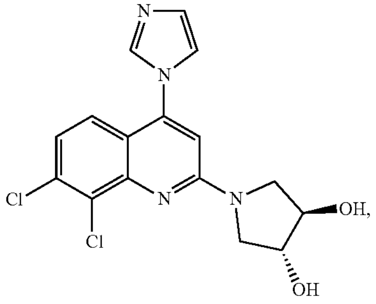
I-502
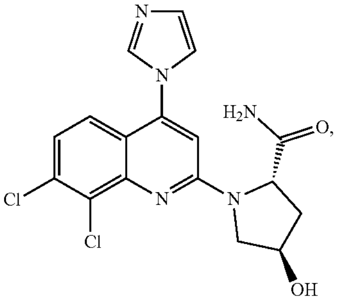
I-503
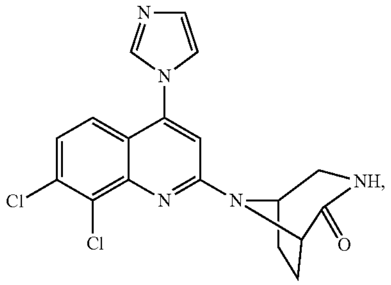
-continued
I-504
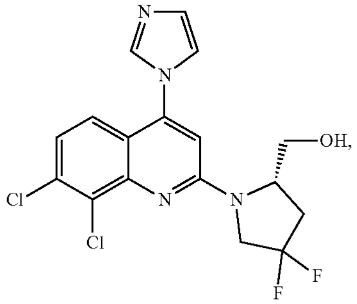
I-505
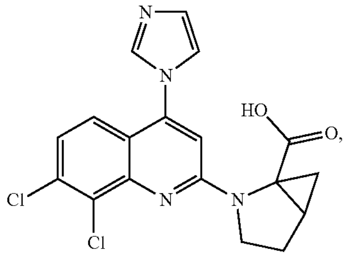
I-506
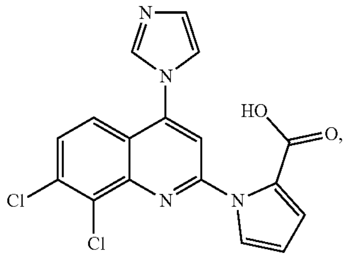
I-507
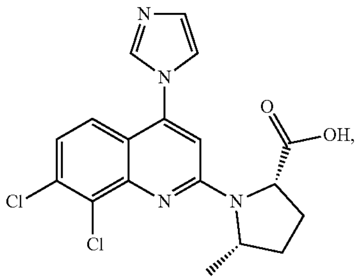
I-508
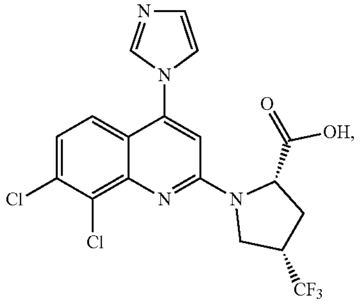

-continued
I-509
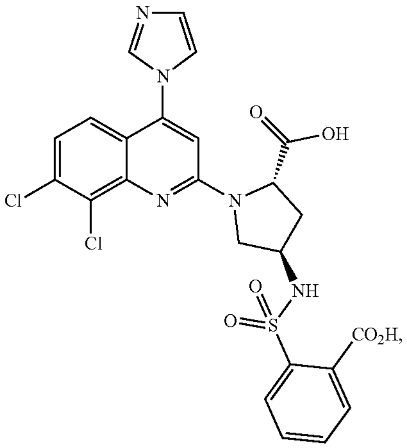
I-510
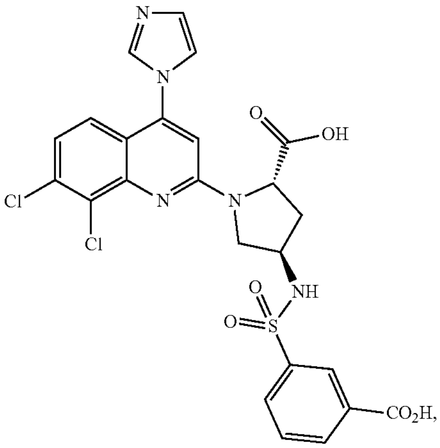
I-511
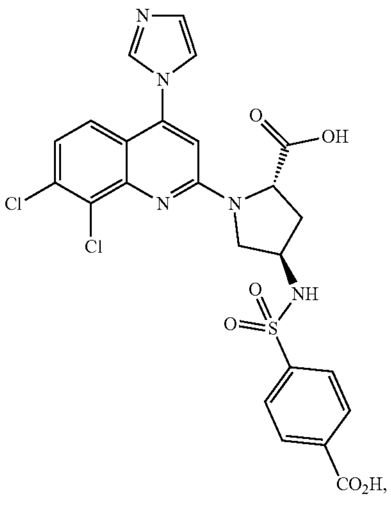
-continued
I-512
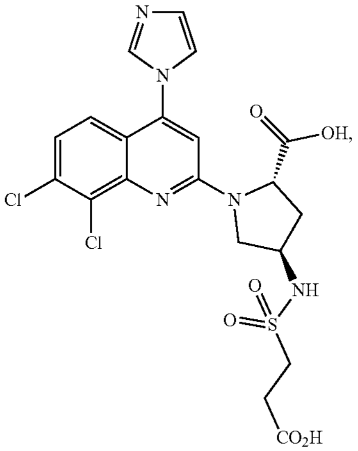
I-513
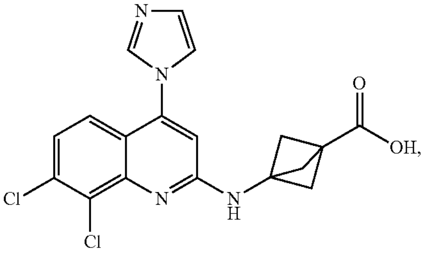
I-514
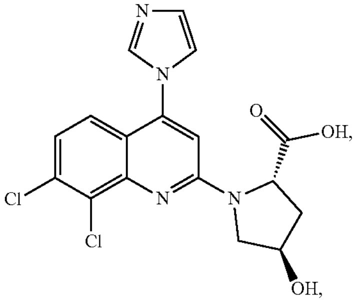
I-515
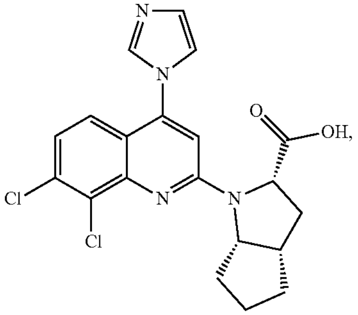
I-516
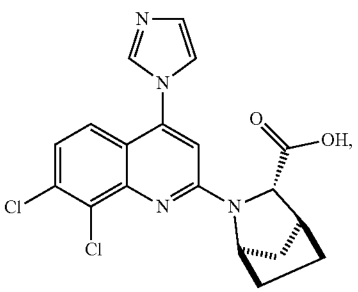

-continued
I-517
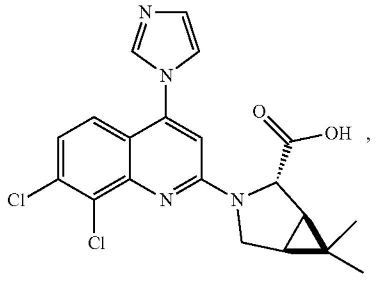
,
I-518
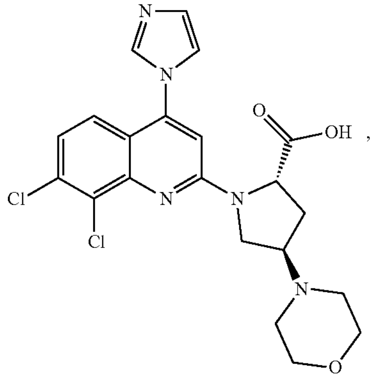
,
I-519
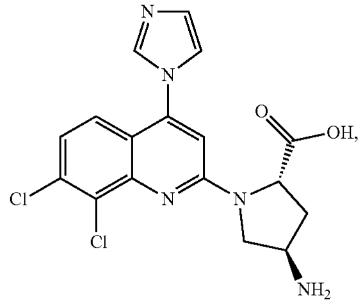
,
I-520
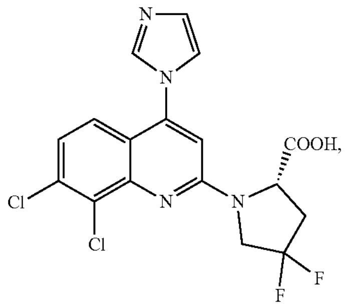
,
I-521
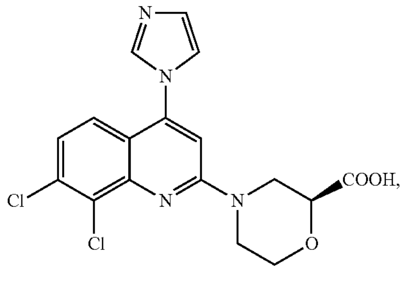
,
-continued
I-522
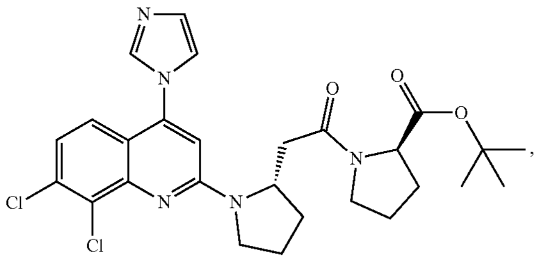
,
I-524
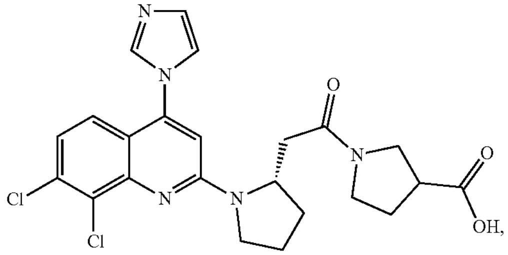
,
I-525
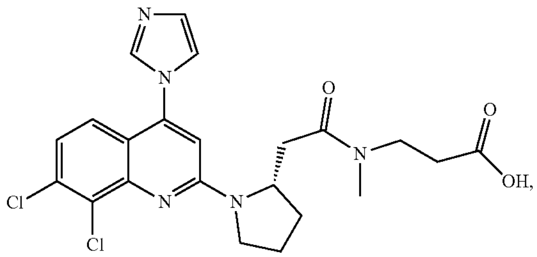
,
I-526
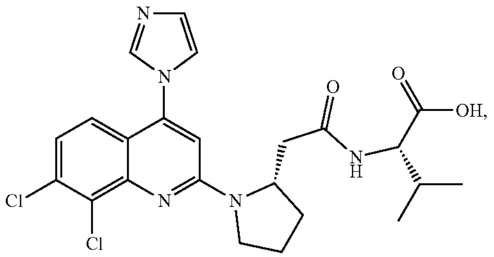
,
I-527
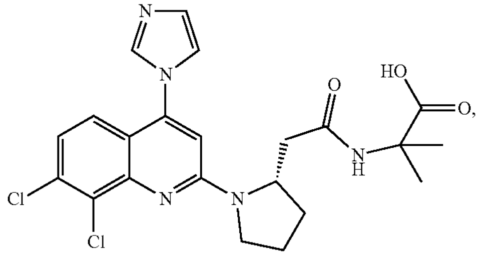
,
I-528
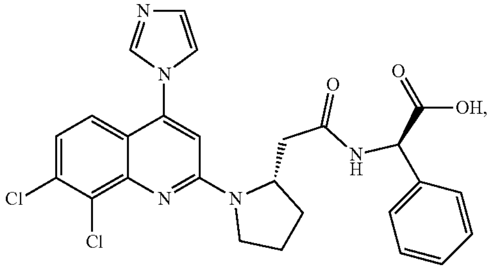
, -continued
I-529
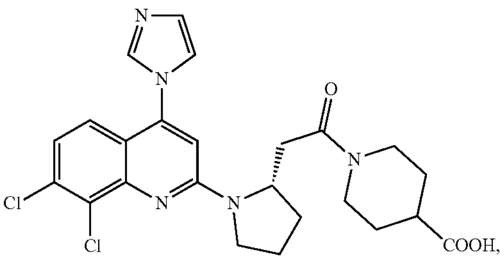
I-530
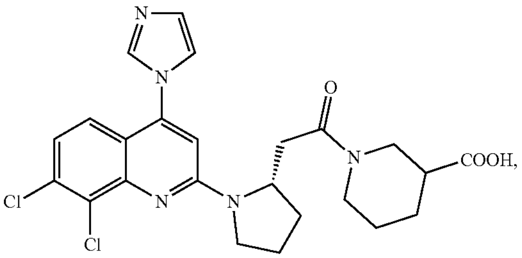
I-531
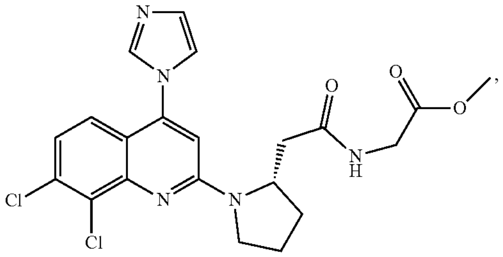
I-532
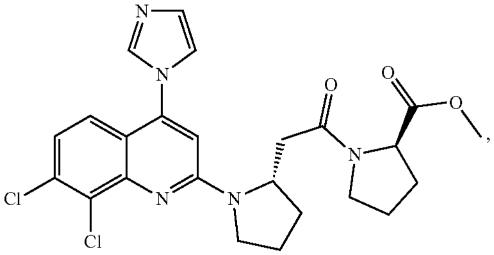
I-533
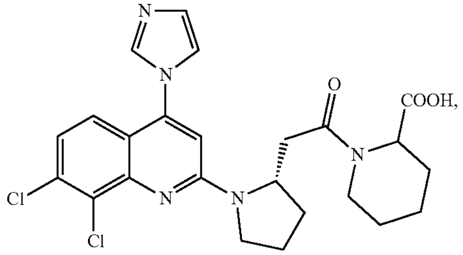
I-534
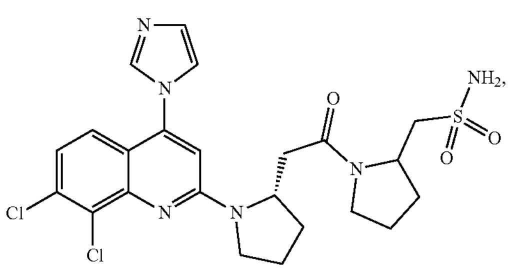
-continued
I-535
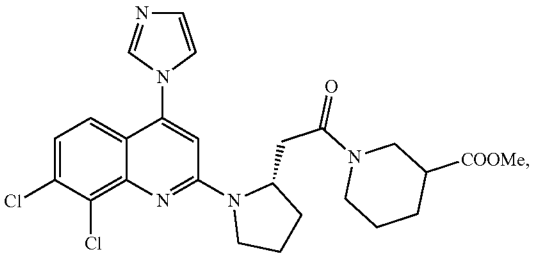
I-536
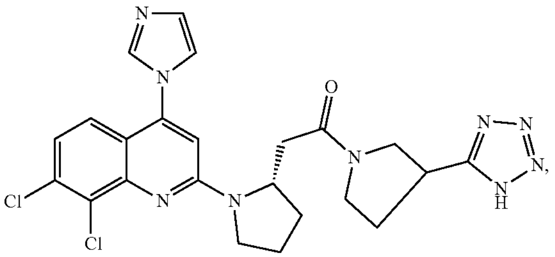
I-537
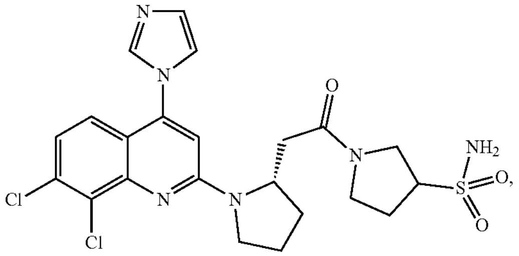
I-538
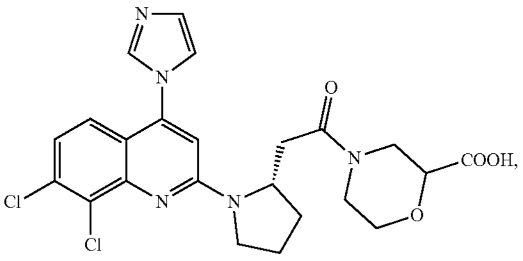
I-539
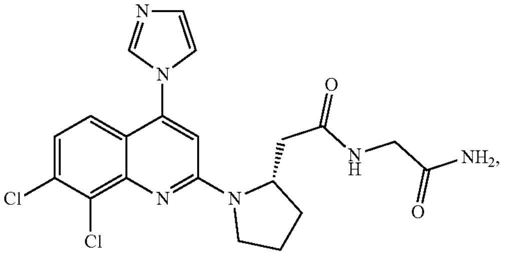

-continued
I-540
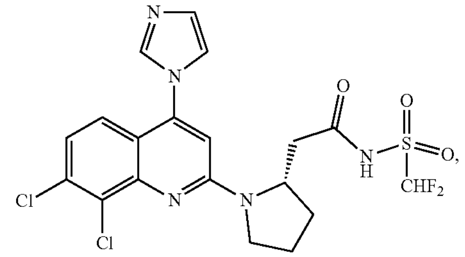
I-541
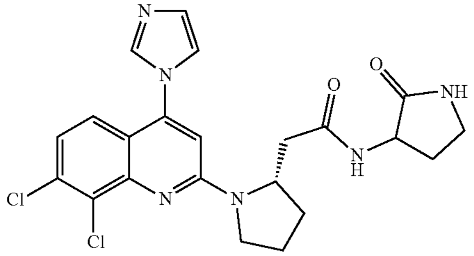
I-542
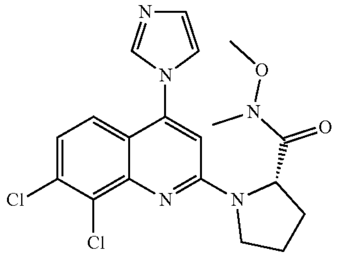
I-543
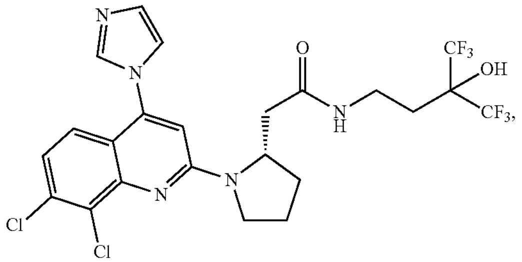
I-544
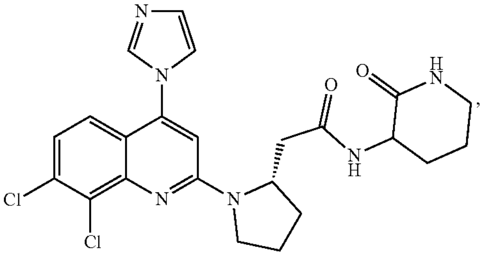
I-545
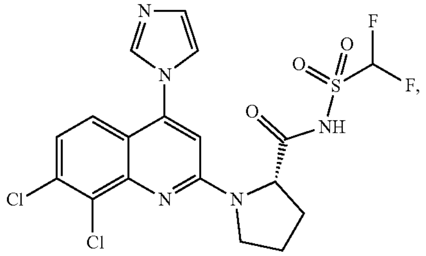
-continued
I-546
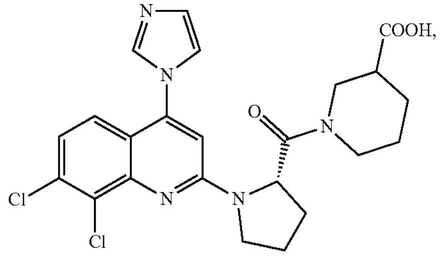
I-547
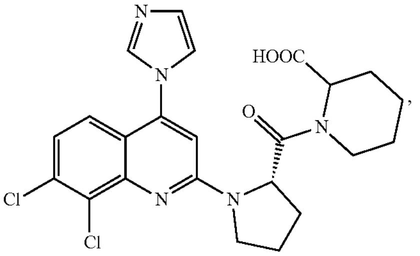
and
I-548
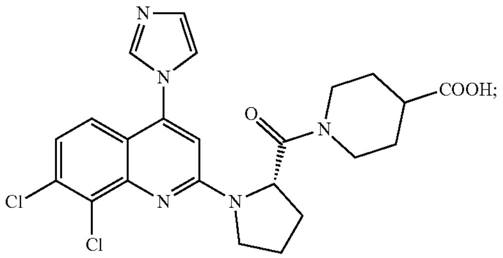
or is a pharmaceutically acceptable salt thereof.
40. The compound of claim 1, wherein the compound is selected from:
I-549
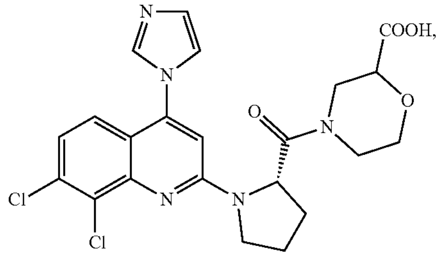
I-550
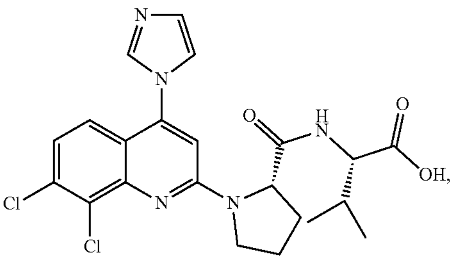

-continued
I-551
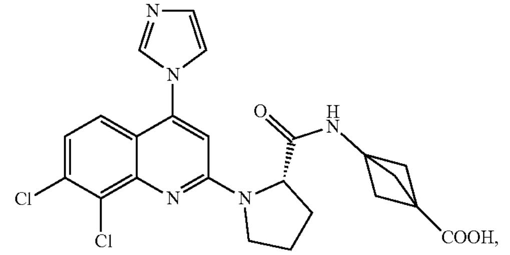
I-552
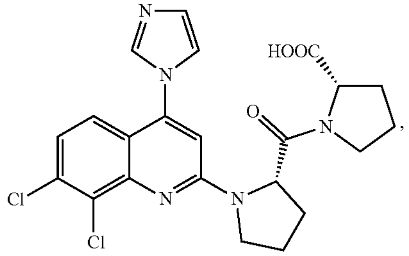
I-553
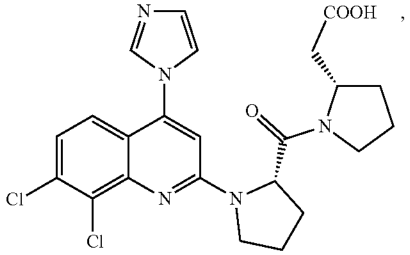
I-554
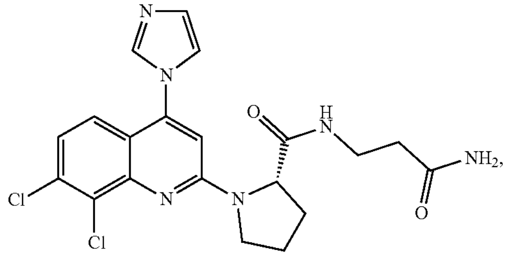
I-555
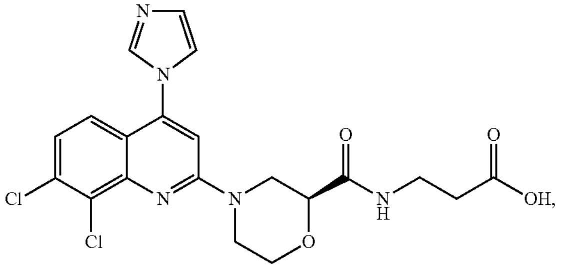
I-556
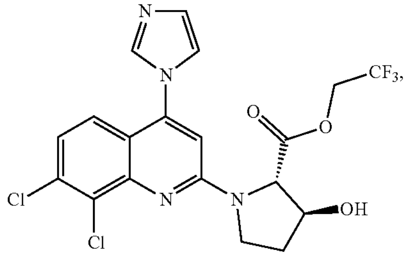
-continued
I-557
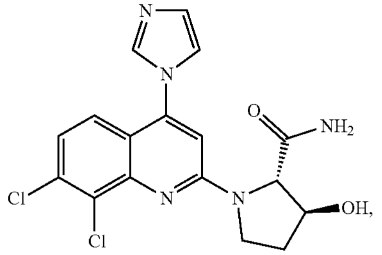
I-558
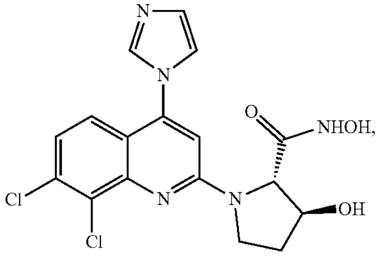
I-559
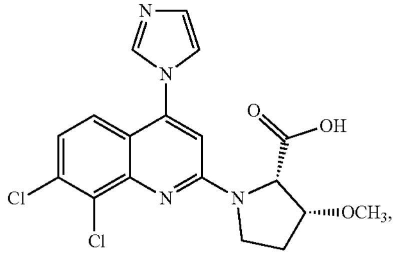
I-560
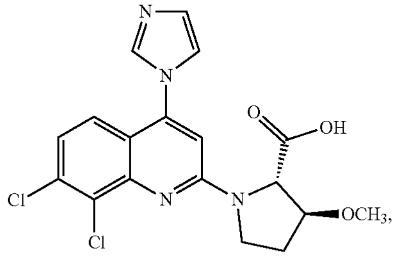
I-561
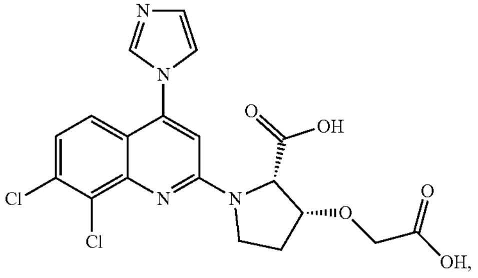
I-562
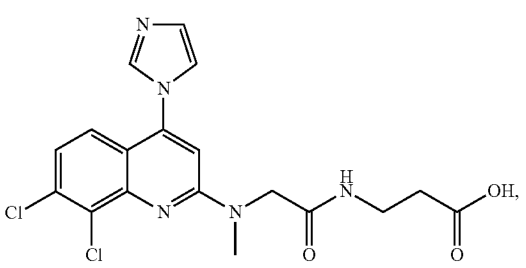

-continued
I-563
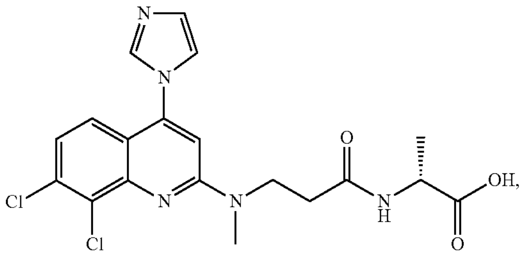
I-564
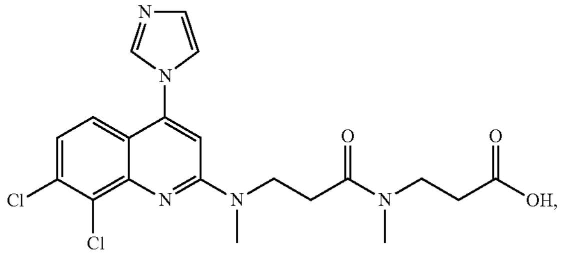
I-565
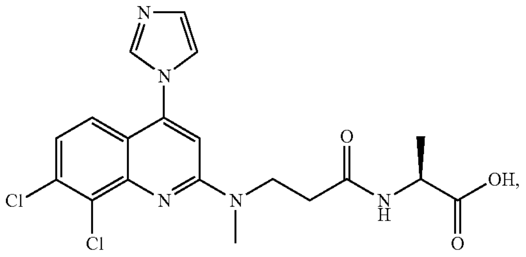
I-566
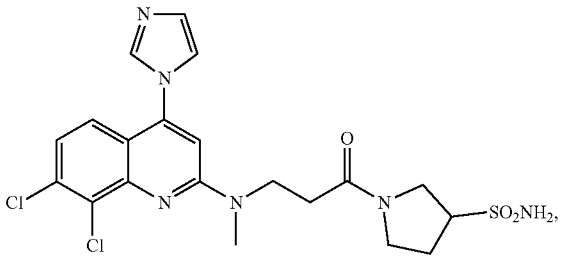
I-567
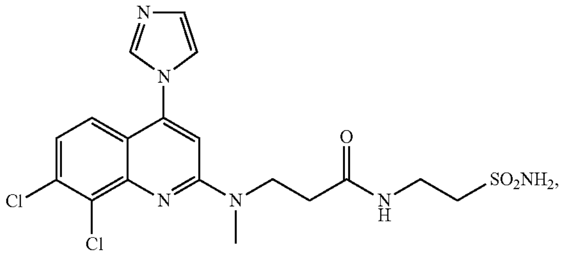
-continued
I-568
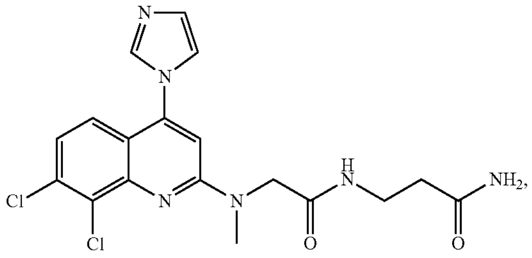
I-569
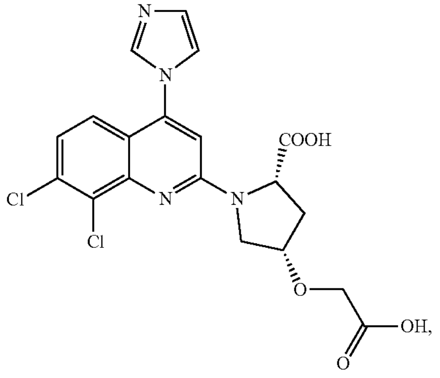
I-570
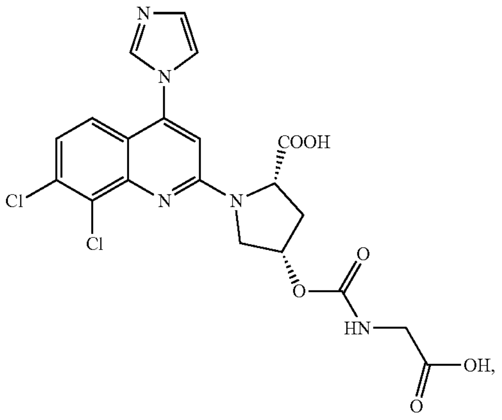
I-571
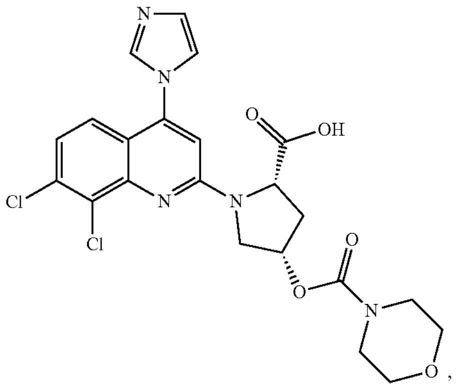

-continued
I-572
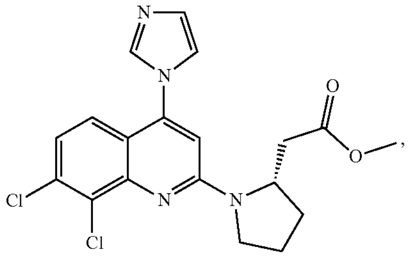
I-573
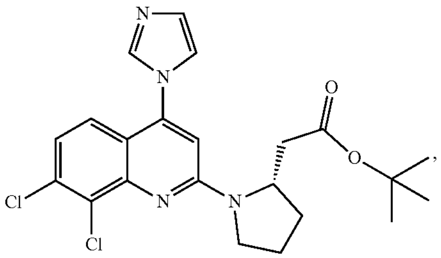
I-574
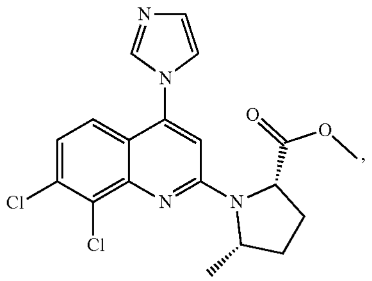
I-575
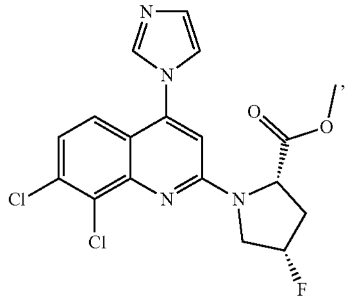
I-576
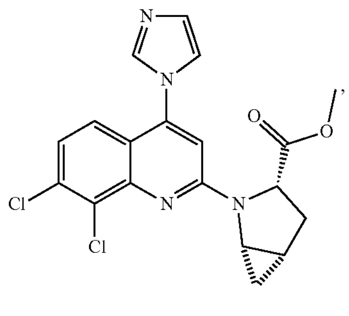
-continued
I-577
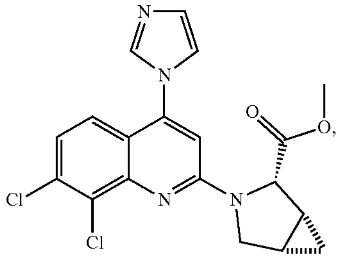
I-578
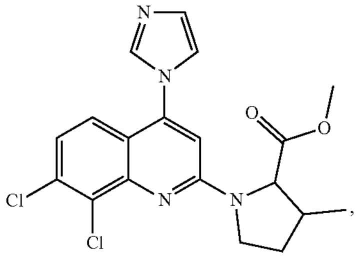
I-579
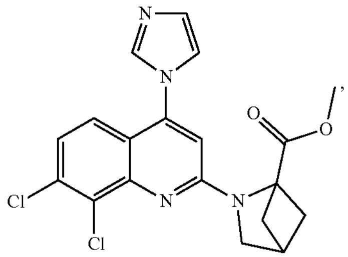
I-580
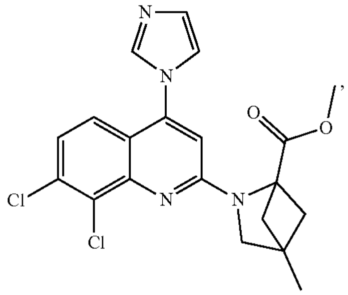
I-581
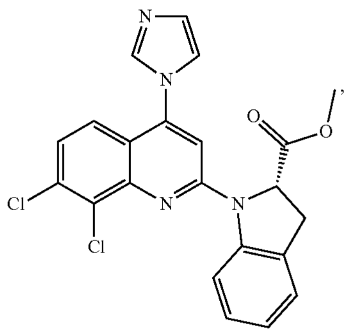

-continued
I-582
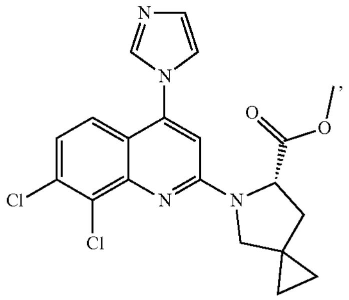
I-583
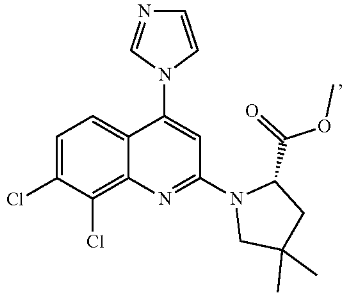
I-584
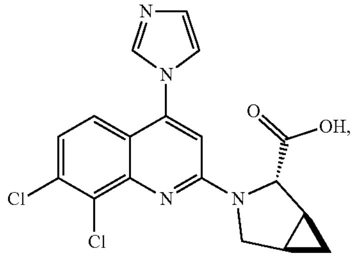
I-585
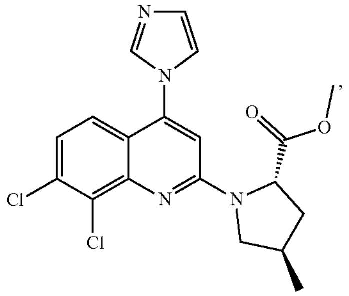
I-586
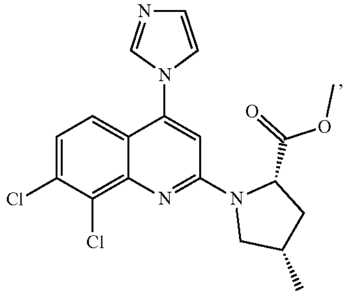
-continued
I-587
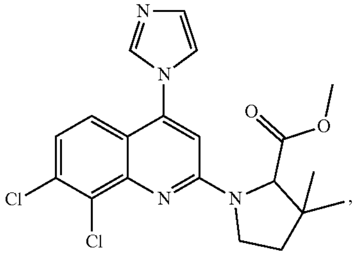
I-588
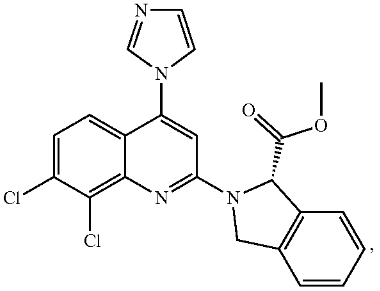
I-589
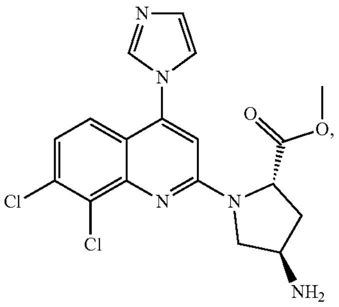
I-590
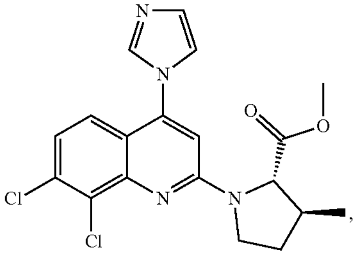
I-591
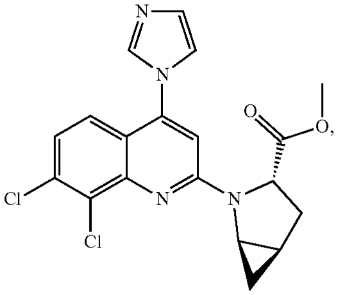

-continued
I-592
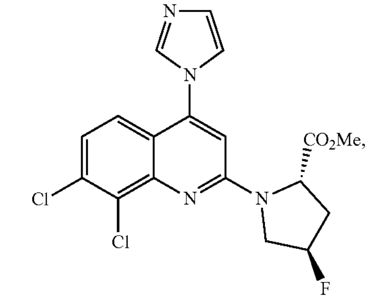
I-593
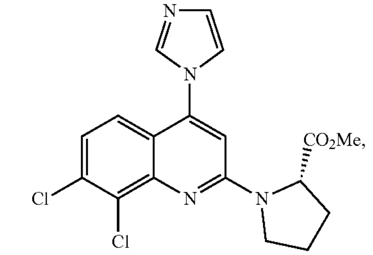
I-594
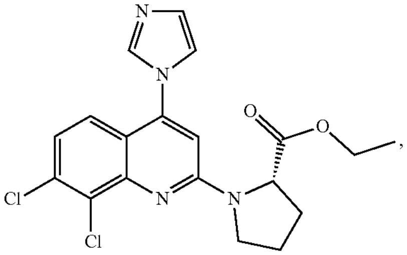
I-595
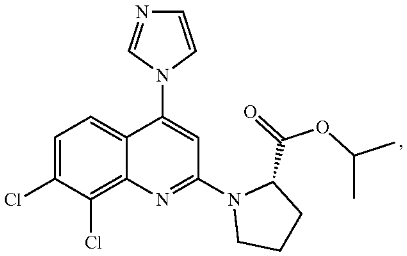
I-596
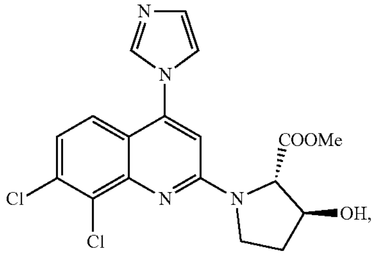
I-597
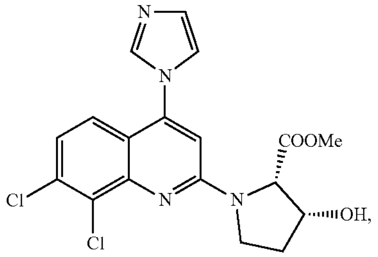
-continued
I-599
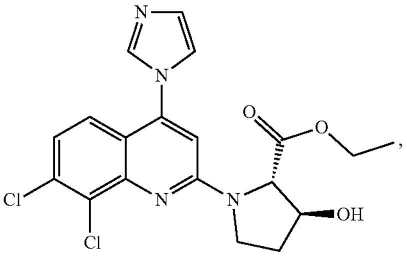
I-600
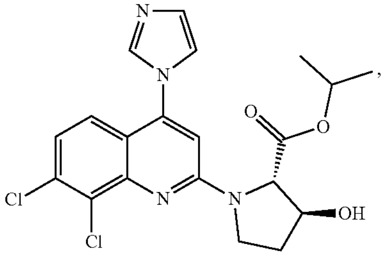
I-601
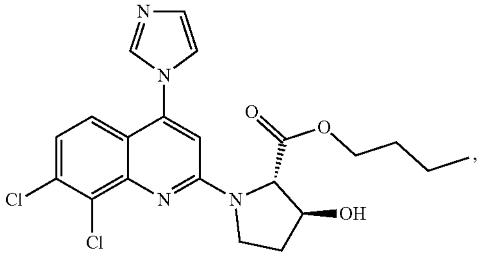
I-602
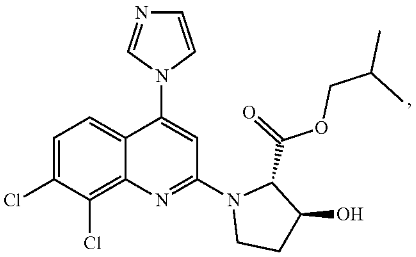
I-603
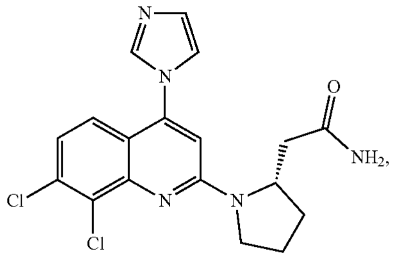
I-604
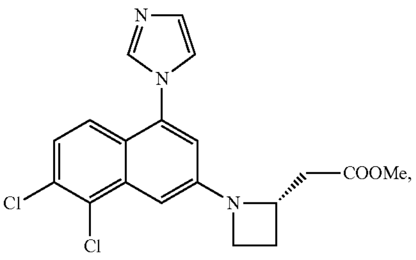

-continued
I-605
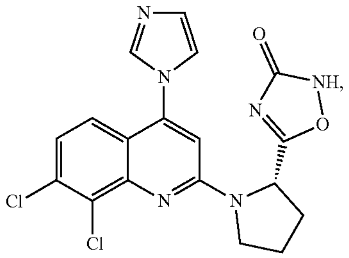
I-606
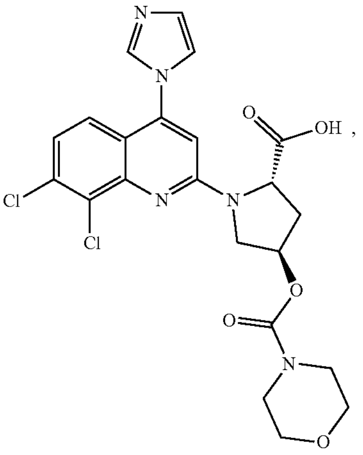
I-607
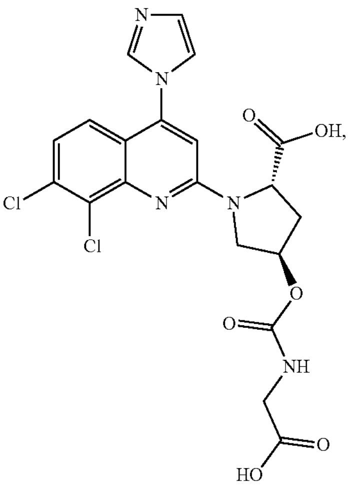
I-608
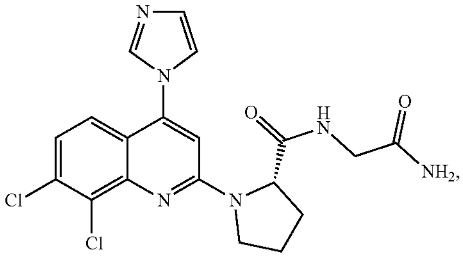
-continued
I-609
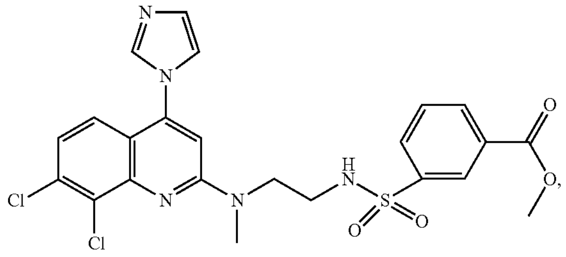
I-610
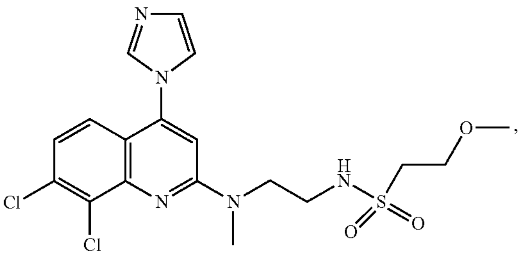
I-611
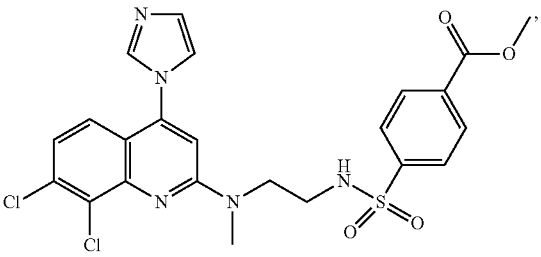
and
I-612
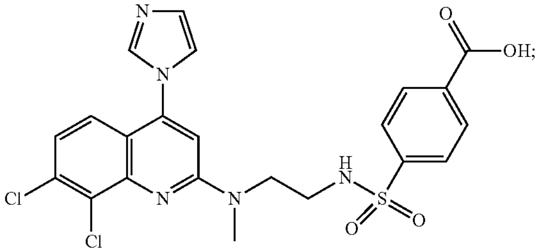
or is a pharmaceutically acceptable salt thereof.
41. The compound of claim 1, wherein the compound is selected from:
I-613
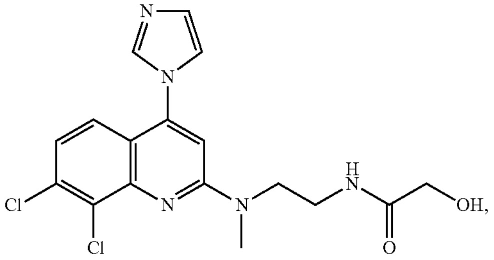

-continued
I-614
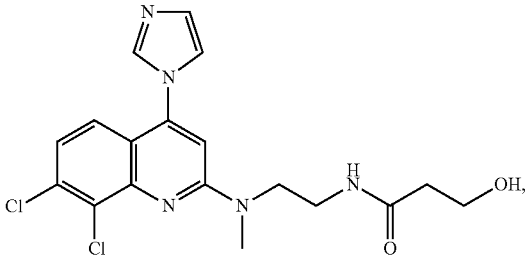
I-615
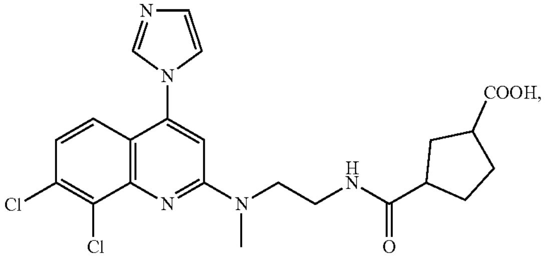
I-616
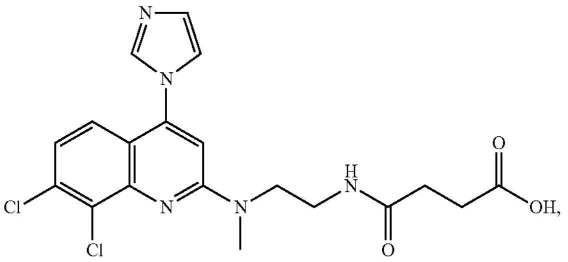
I-617
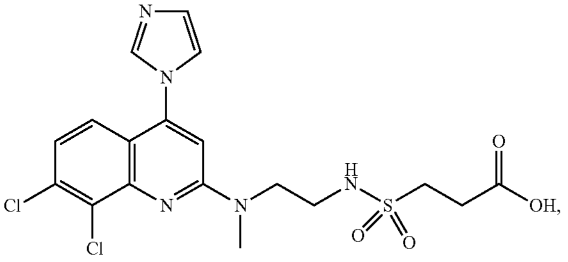
I-618
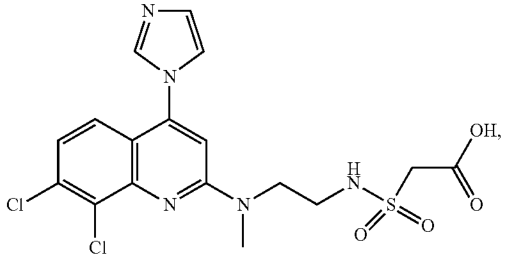
-continued
I-619
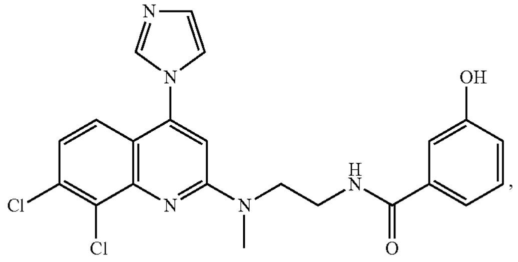
I-620
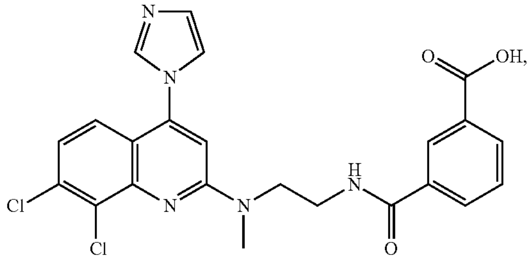
I-621
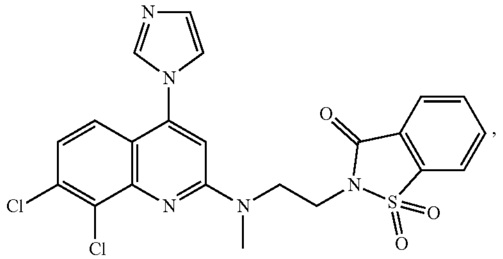
I-622
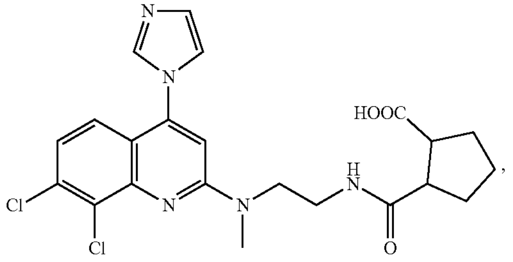
I-623
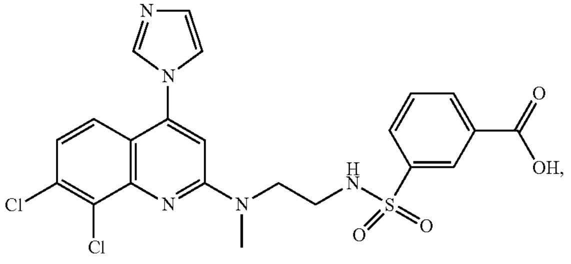

-continued
I-624
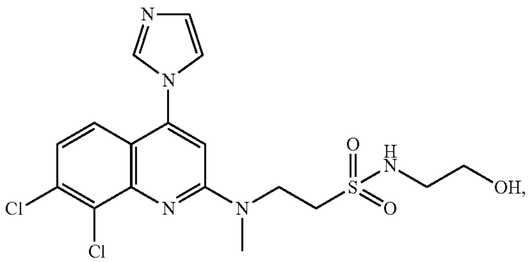
I-625
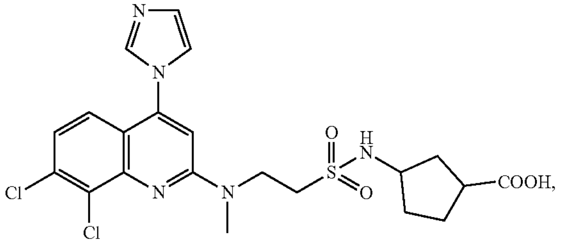
I-626
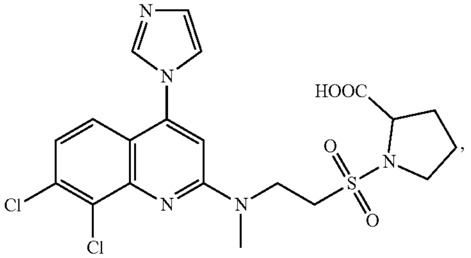
I-627
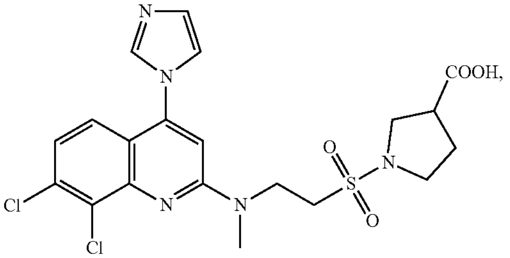
I-628
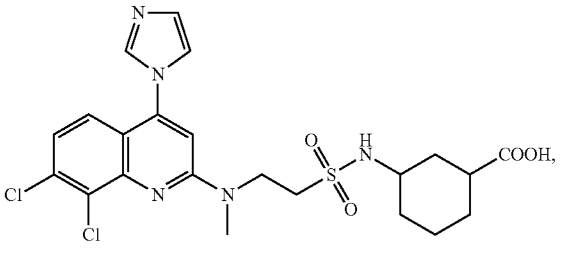
-continued
I-629
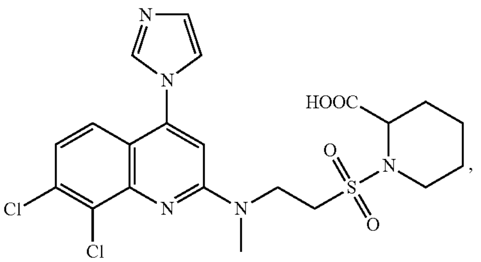
I-630
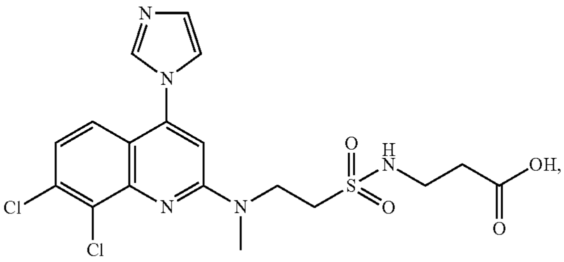
I-631
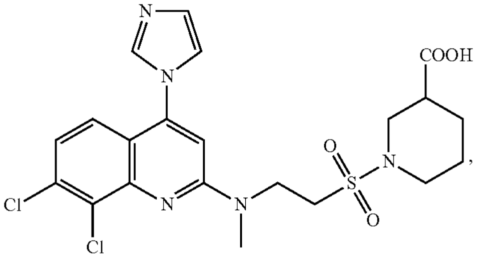
I-632
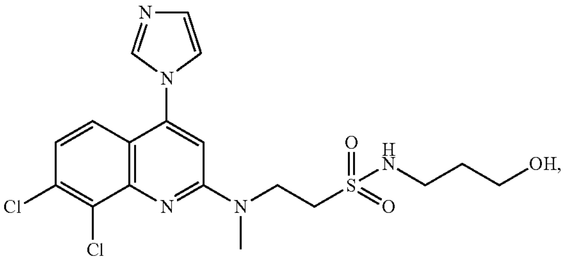
I-633
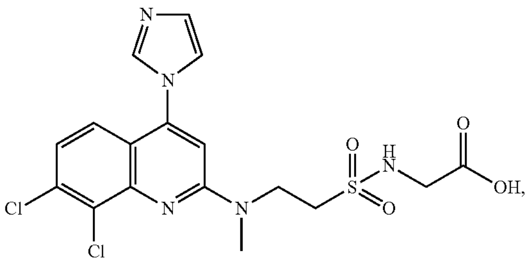

-continued
I-634
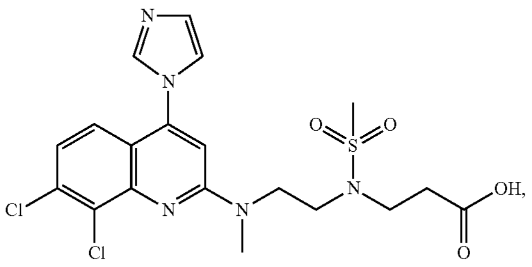
I-635
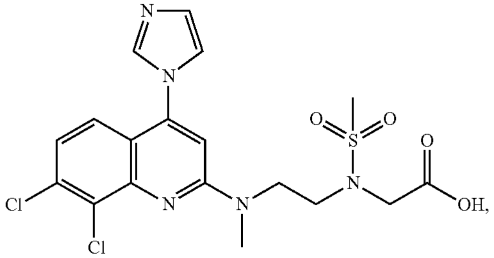
I-636
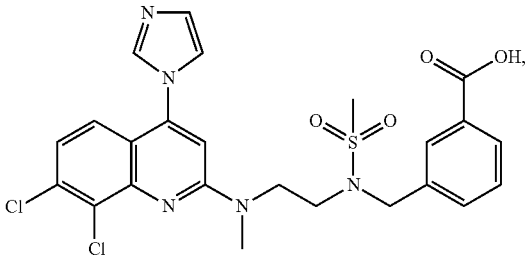
I-637
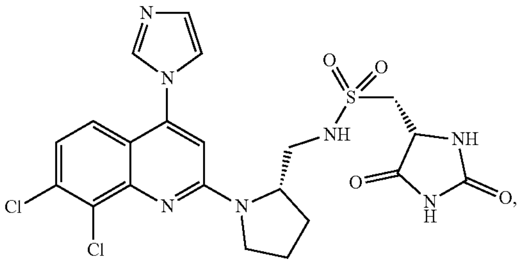
I-638
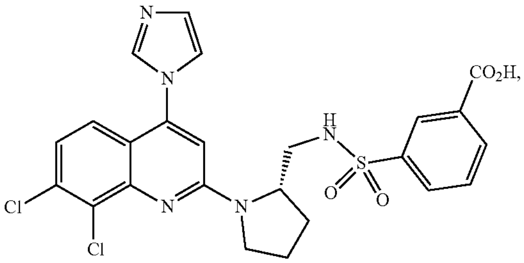
-continued
I-639
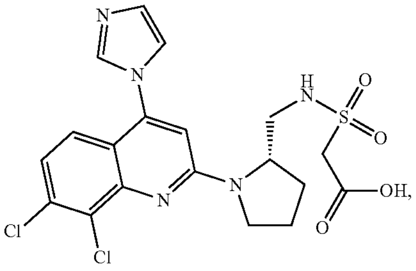
I-640
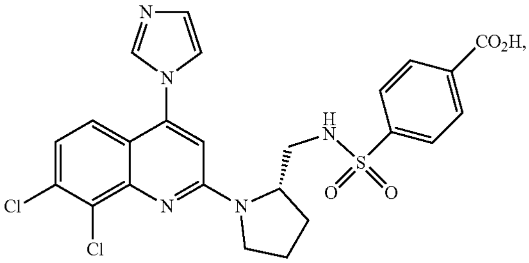
I-641
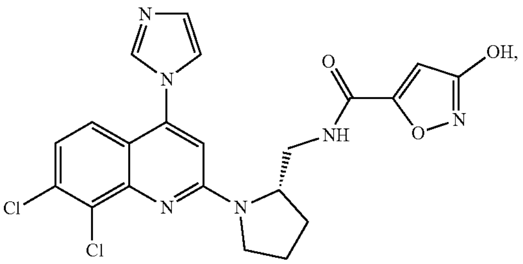
I-642
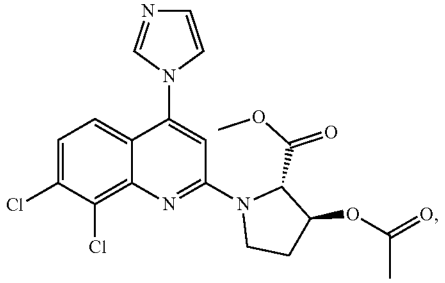
I-643
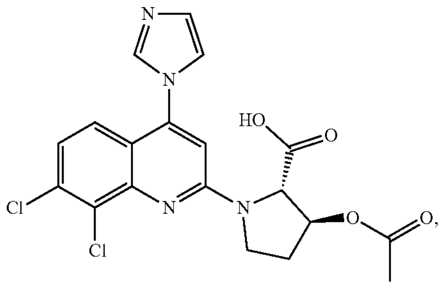

-continued
I-644
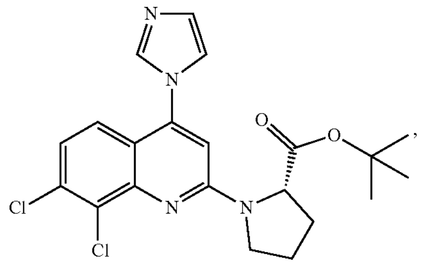
I-645
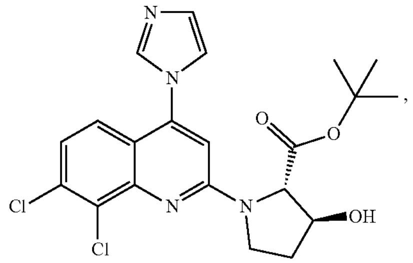
I-646
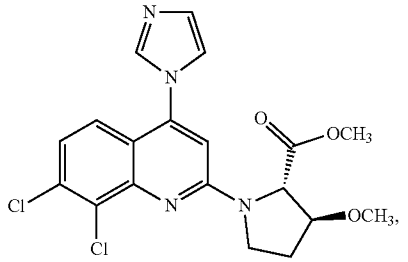
I-647
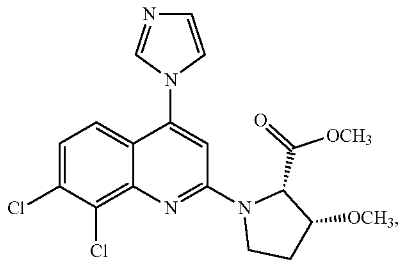
I-648
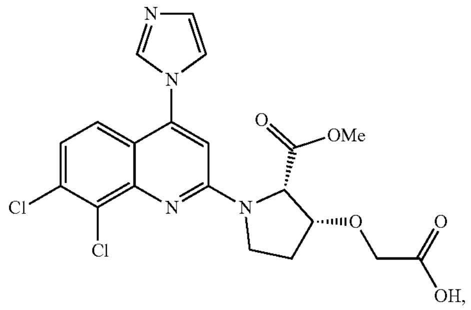
-continued
I-649
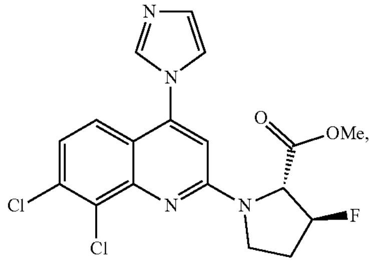
I-650
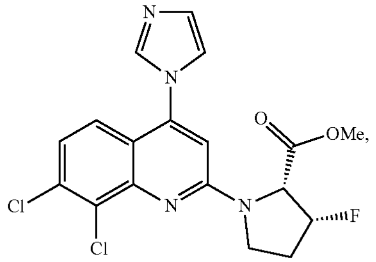
I-651
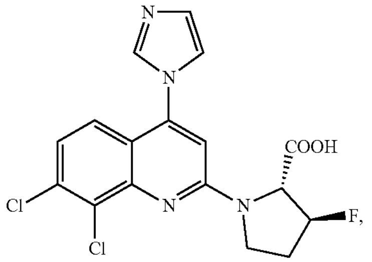
I-652
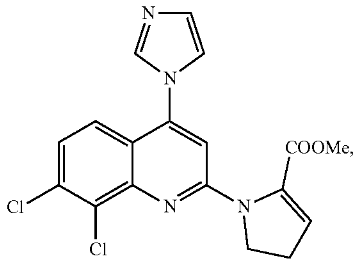
I-653
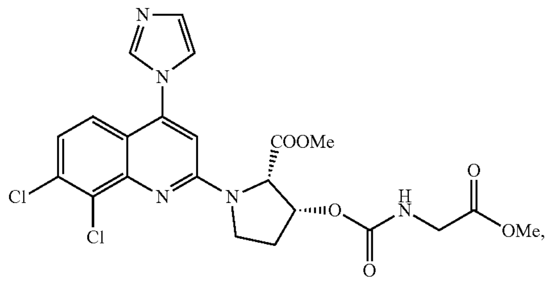
I-654
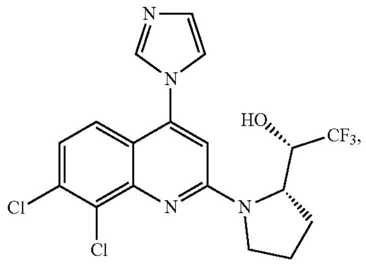

-continued
I-655
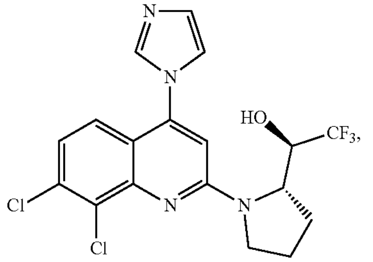
I-656
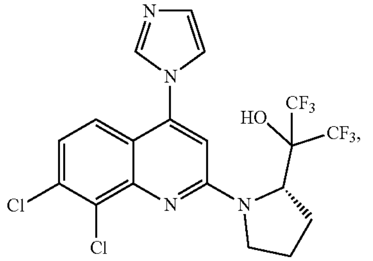
I-657
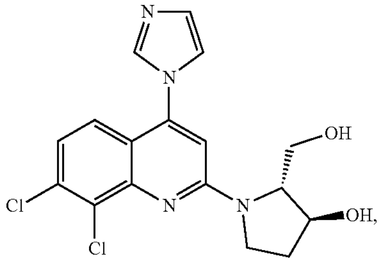
I-658
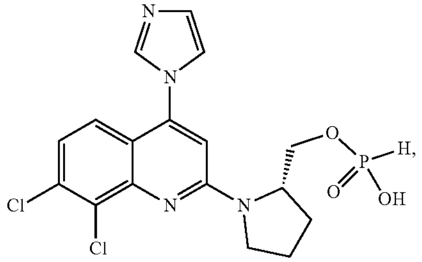
I-659
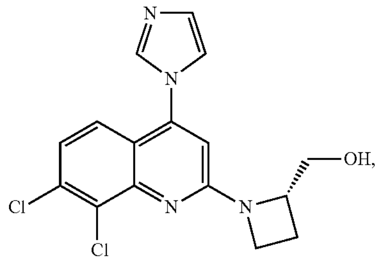
I-660
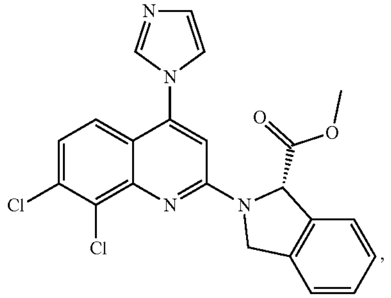
-continued
I-661
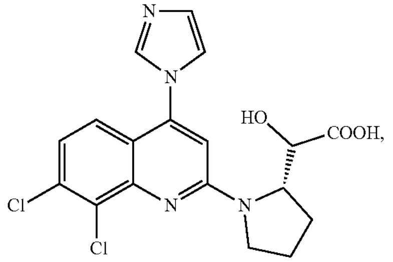
I-662
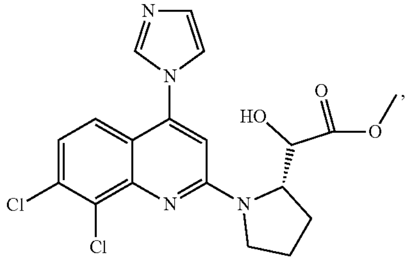
I-663
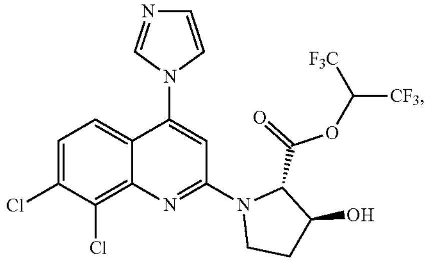
I-664
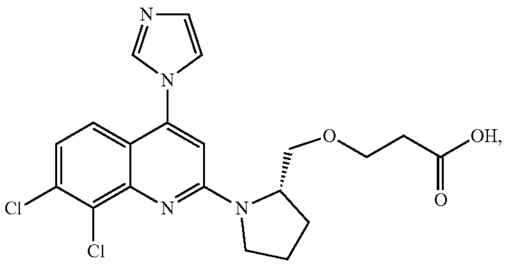
I-665
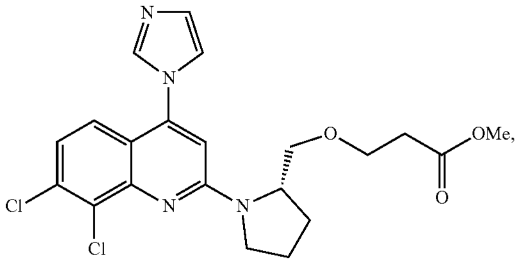
I-666
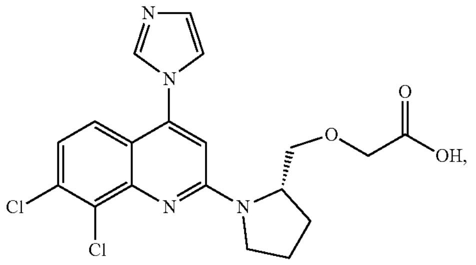

I-667
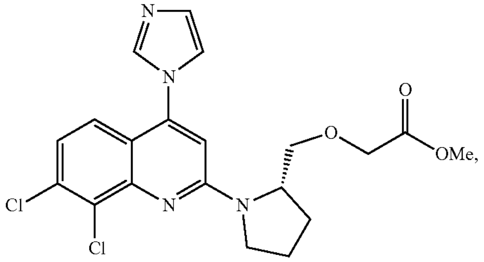
I-668
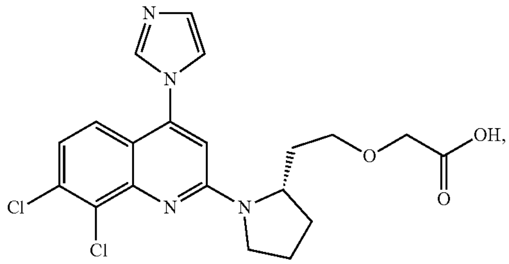
I-669
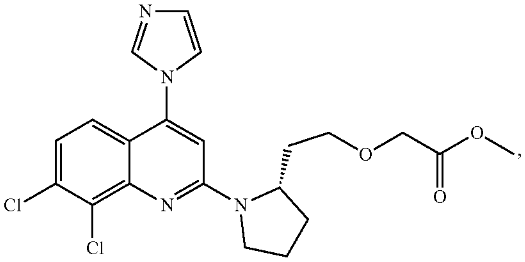
I-672
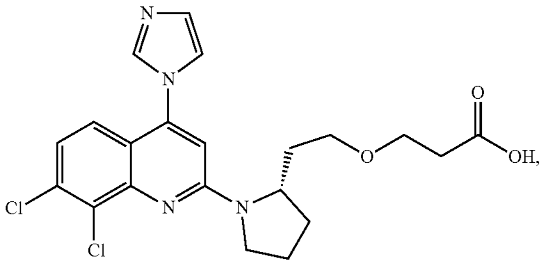
I-673
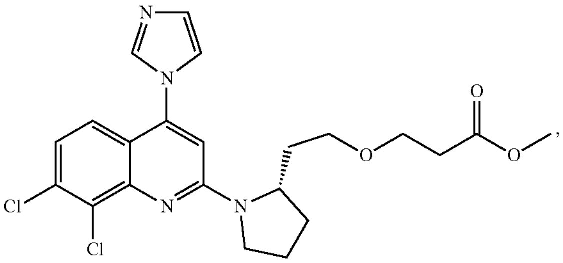
I-674
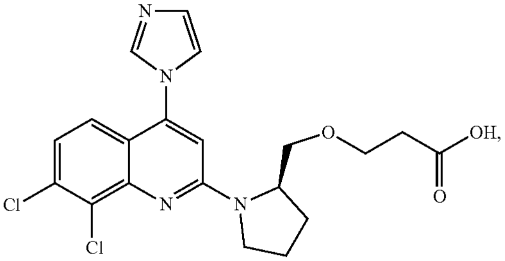
I-675
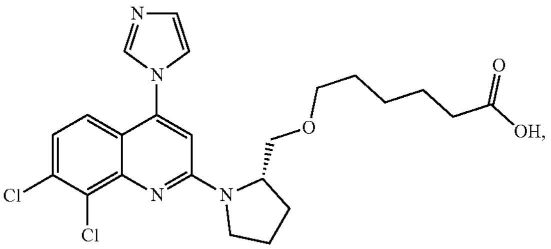
I-676
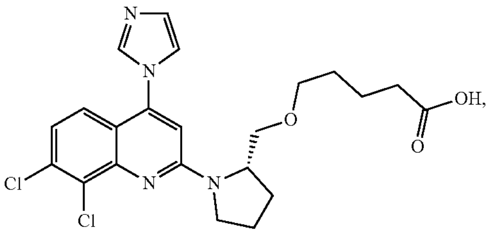
and
I-677
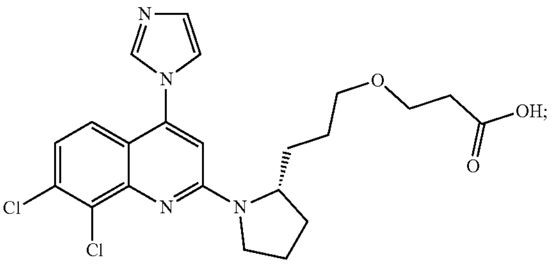
or is a pharmaceutically acceptable salt thereof.
42. The compound of claim 1, wherein the compound is selected from:
I-678
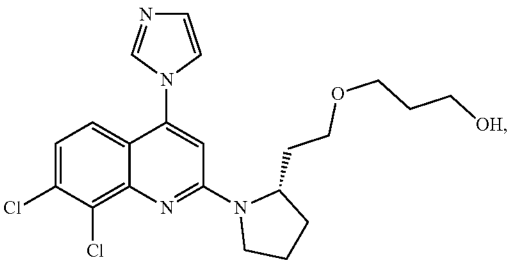

-continued
I-679
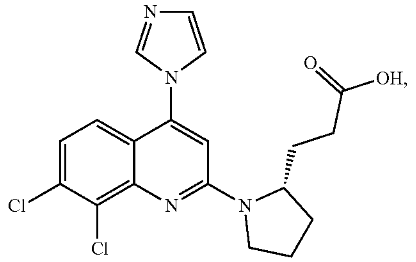
I-680
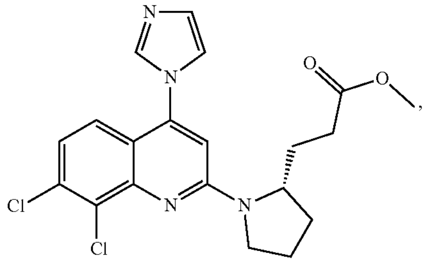
I-681
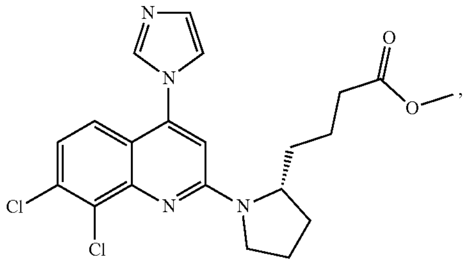
I-682
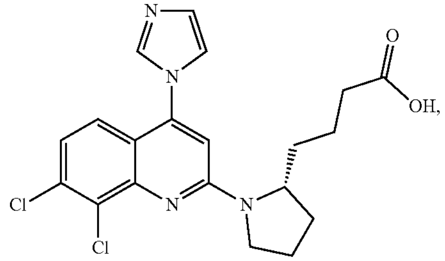
I-683
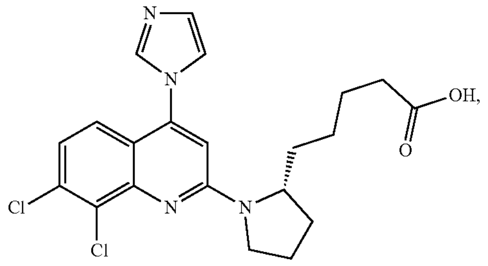
I-685
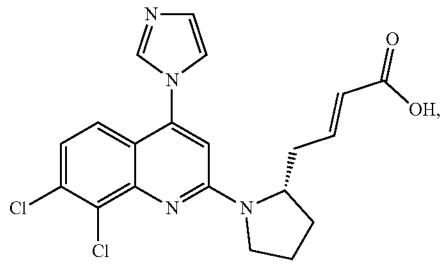
-continued
I-686
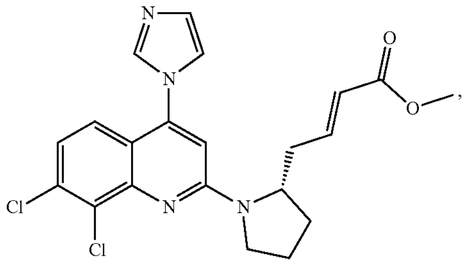
I-687
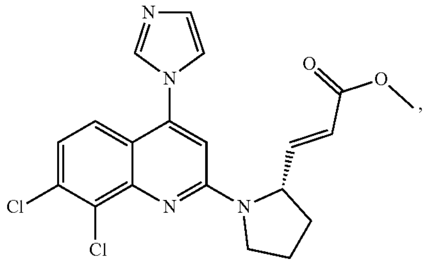
I-688
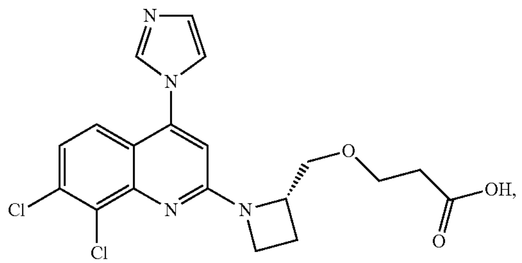
I-689
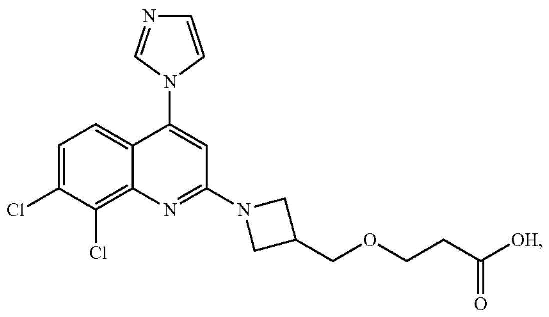
I-690
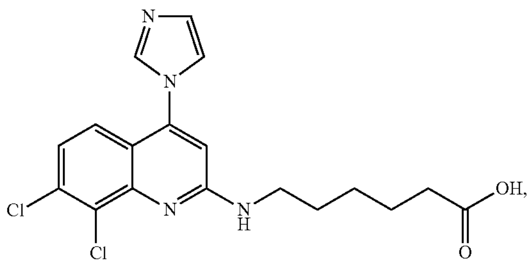

-continued
I-691
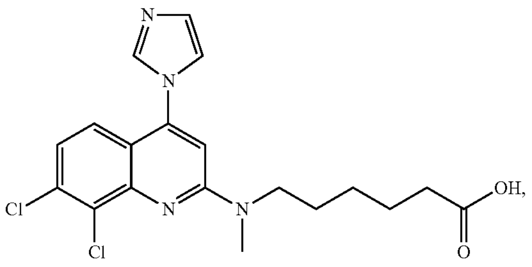
I-692
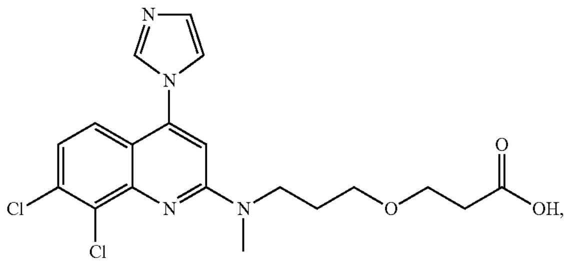
I-693
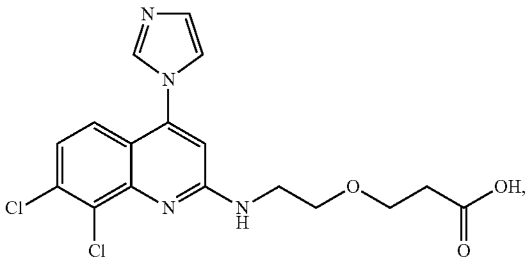
I-694
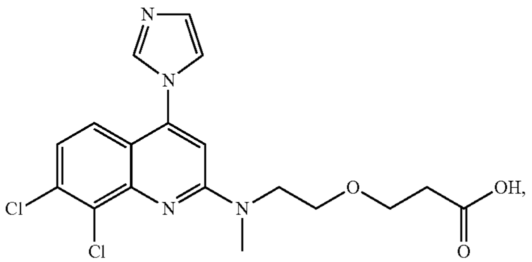
I-695
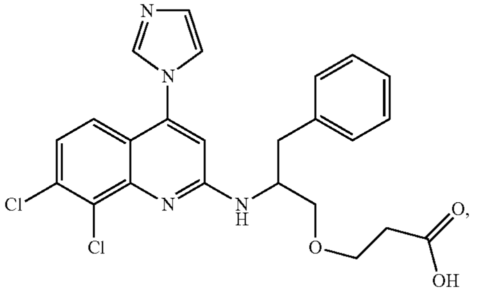
-continued
I-696
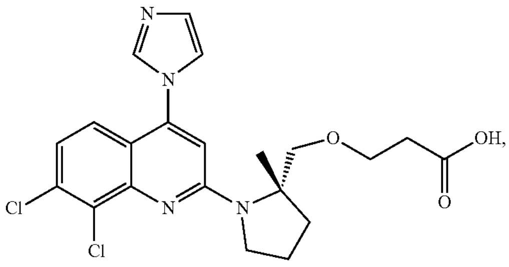
I-697
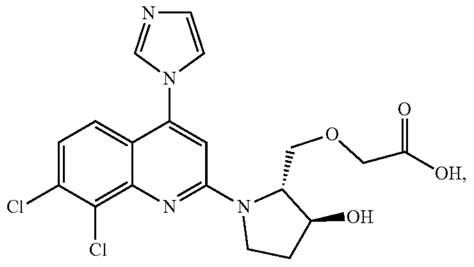
I-698
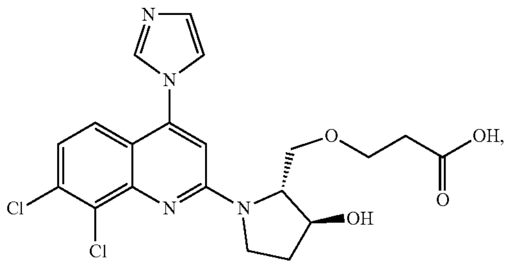
I-699
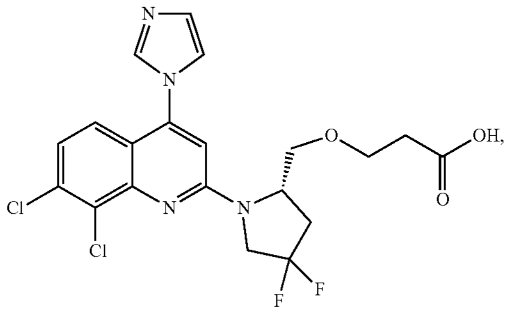
I-700
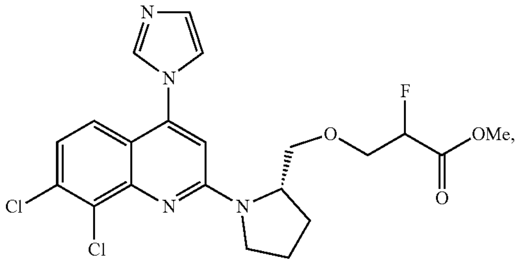

-continued
I-701
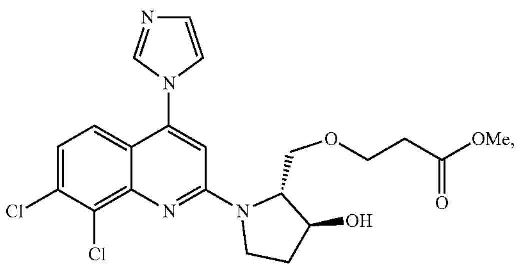
I-702
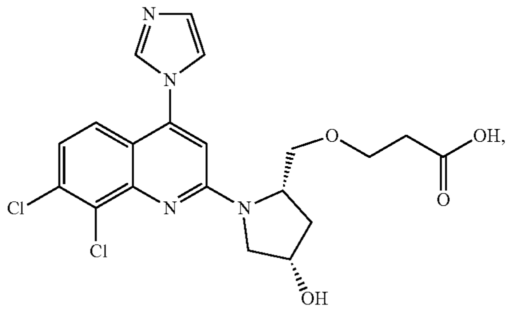
I-703
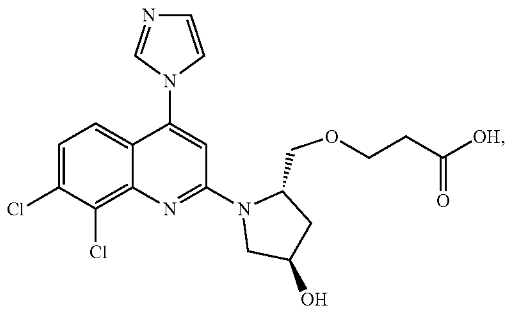
I-704
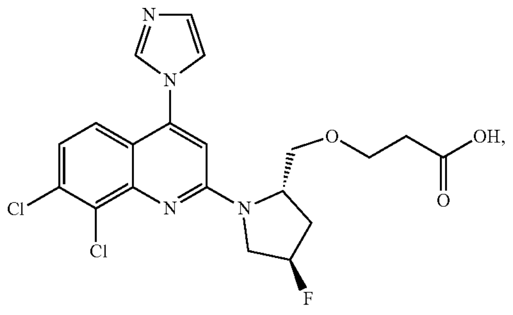
I-705
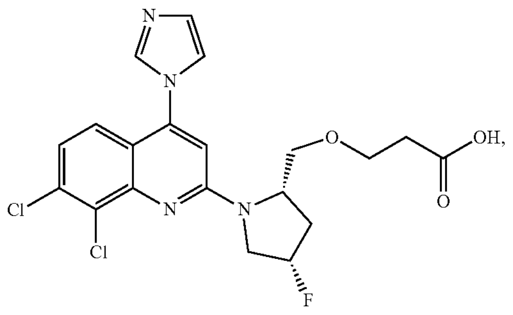
-continued
I-706
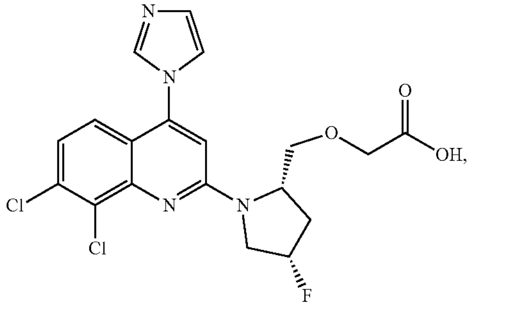
I-707
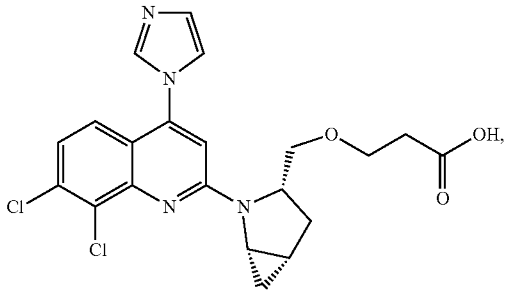
I-708
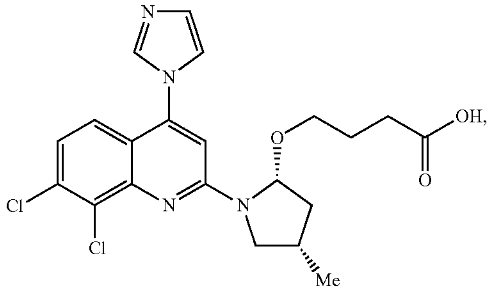
I-709
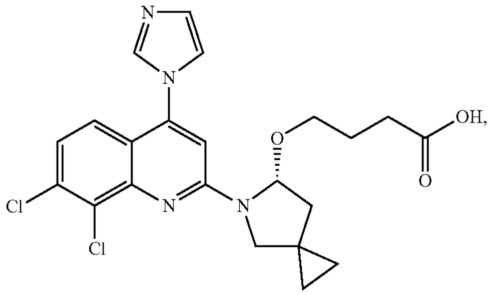
I-710
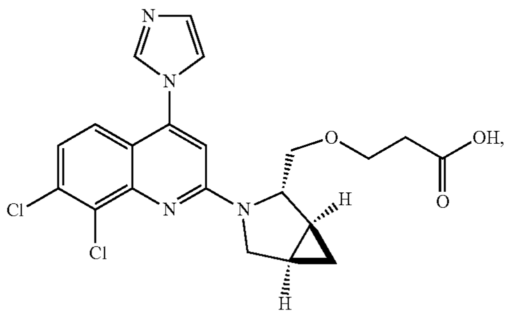

-continued
I-711
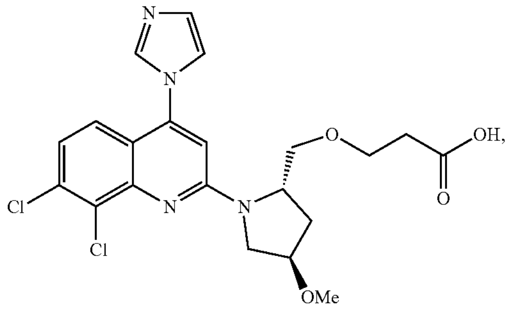
I-712
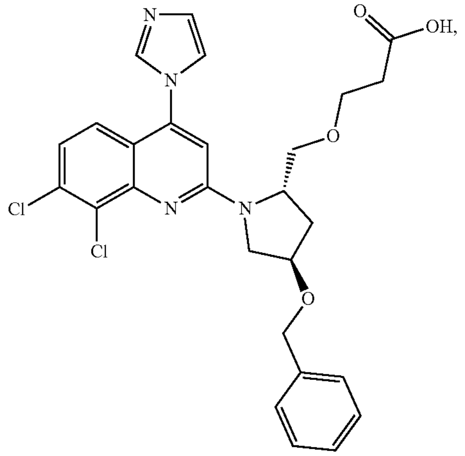
I-713
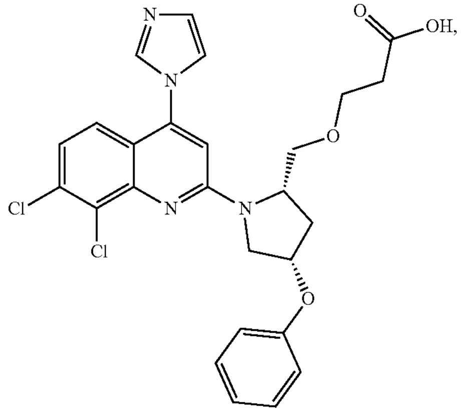
I-714
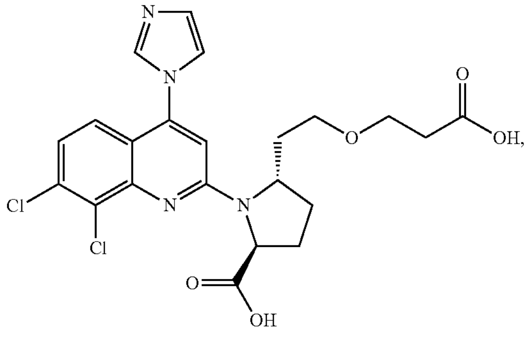
-continued
I-715
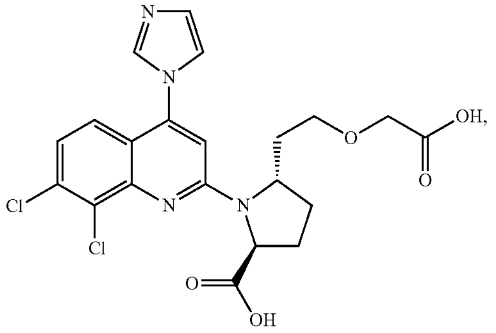
I-716
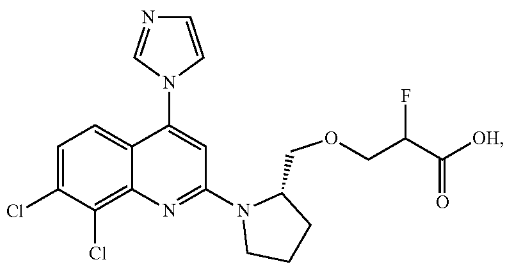
I-717
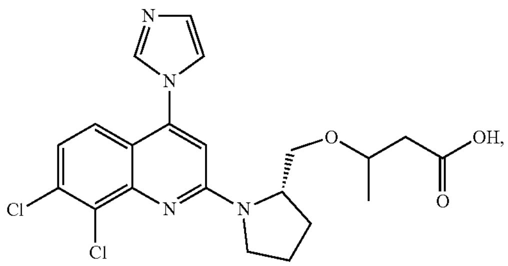
I-718
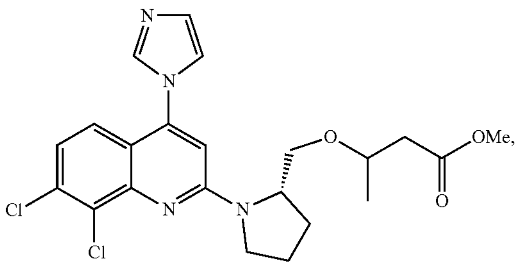
I-719
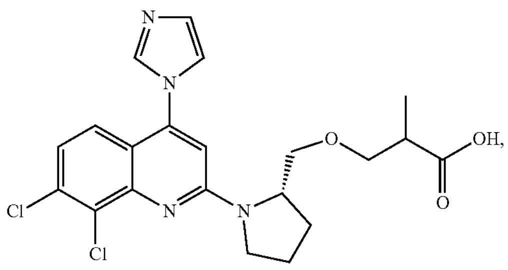

I-720
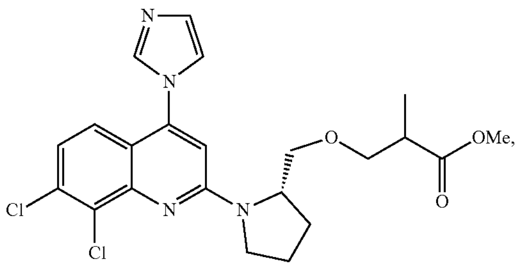
I-721
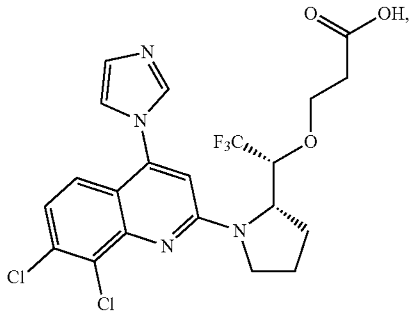
I-722
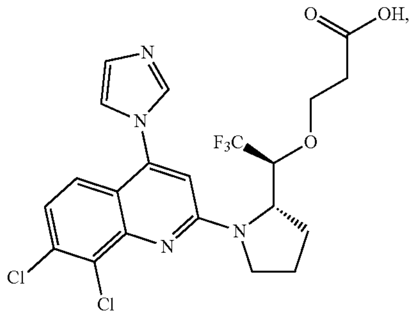
I-723
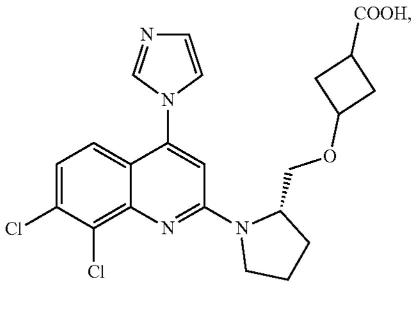
I-724
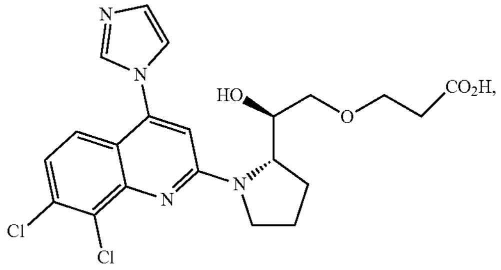
I-725
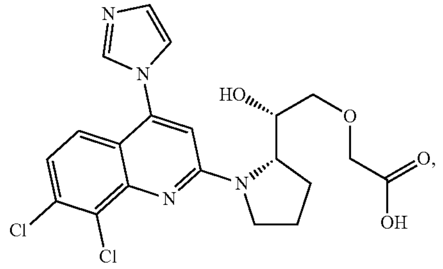
I-726
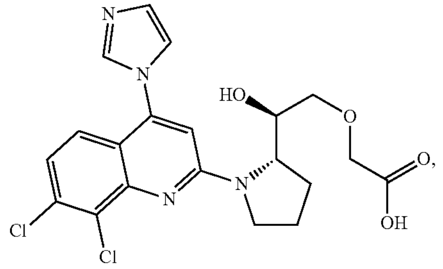
I-727
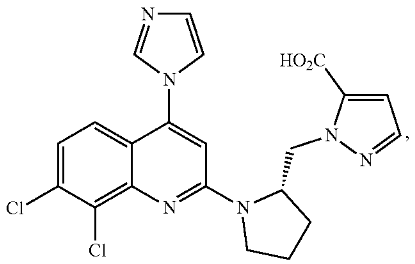
I-728
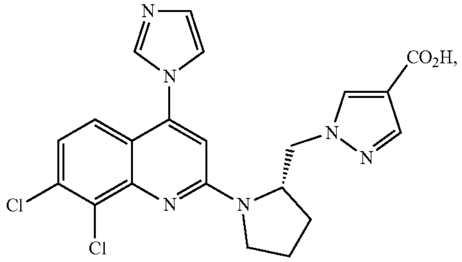
I-729
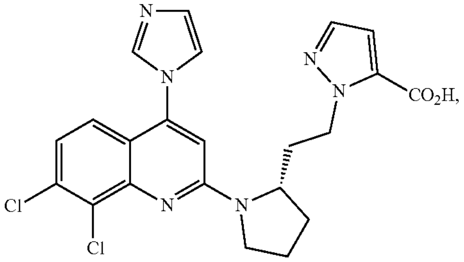

-continued
I-730
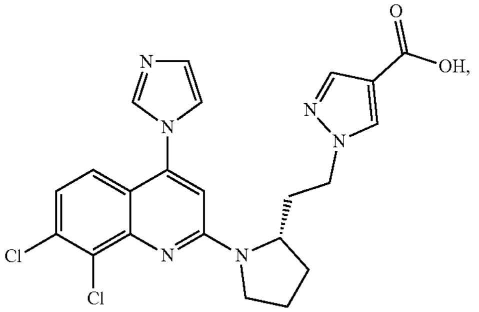
I-731
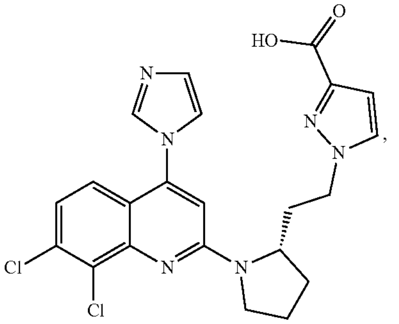
I-732
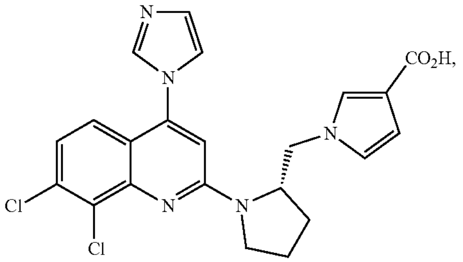
I-733
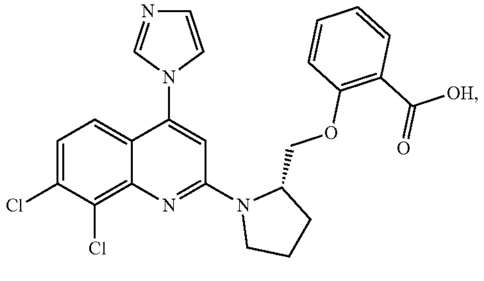
I-734
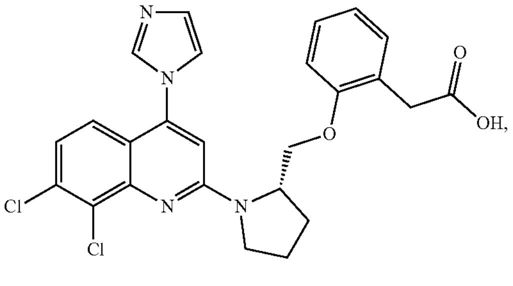
-continued
I-735
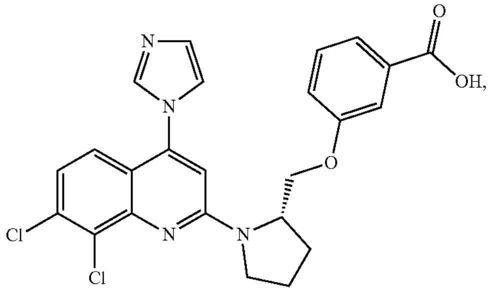
I-736
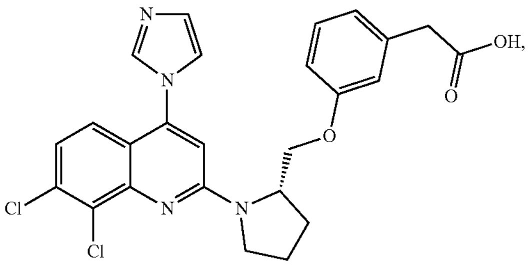
I-737
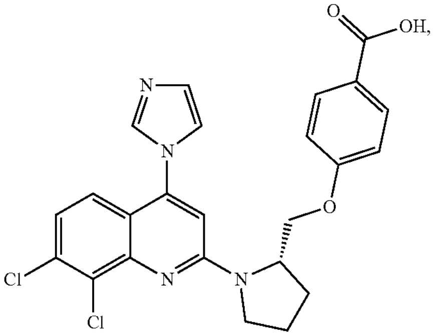
I-738
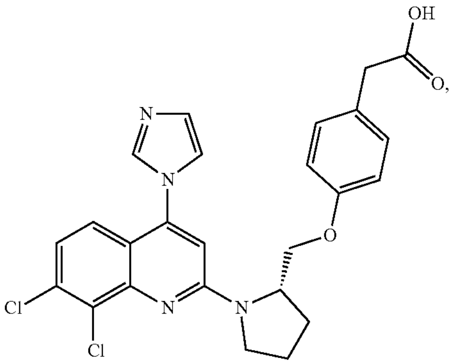
I-739
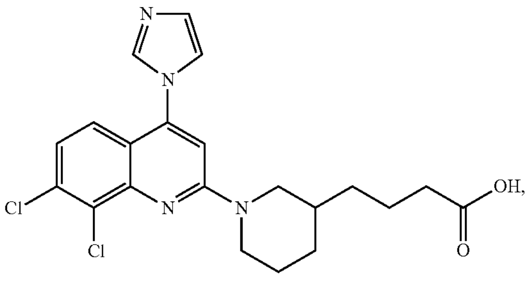

-continued
I-742
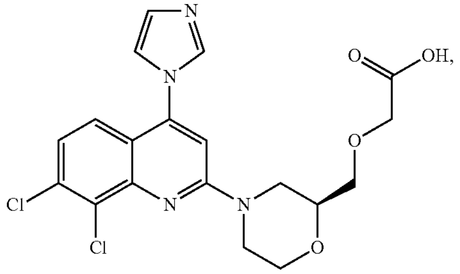
and
I-743
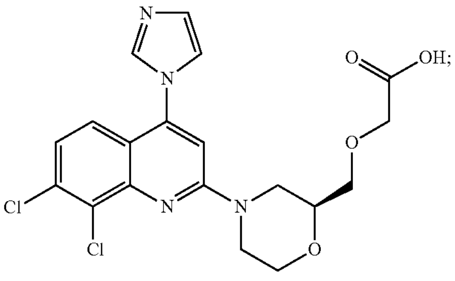
or is a pharmaceutically acceptable salt thereof.
43. The compound of claim 1, wherein the compound is selected from:
I-744
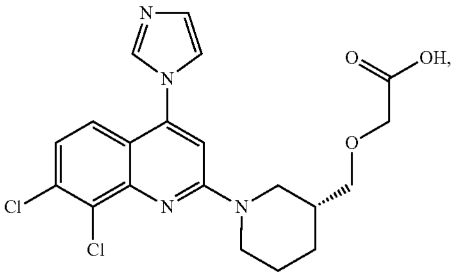
I-745
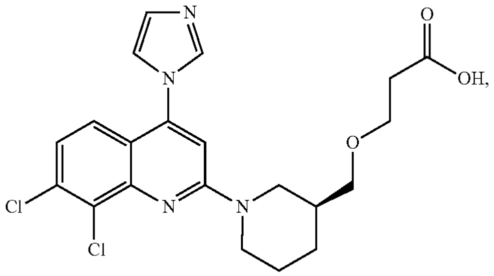
I-748
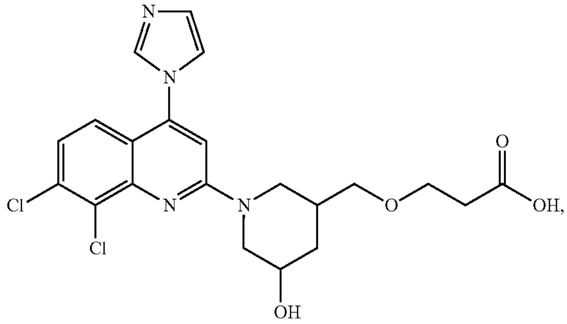
-continued
I-749
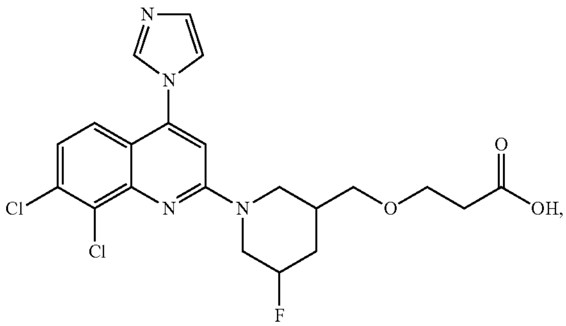
I-750
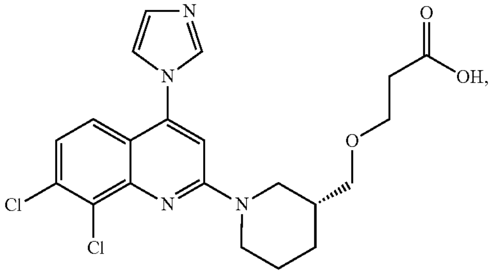
I-753
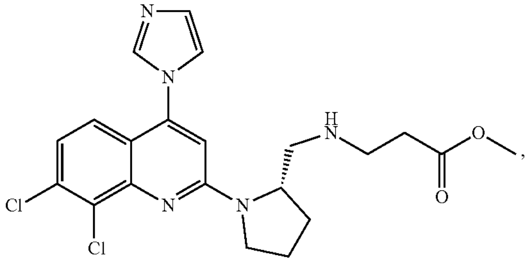
I-754
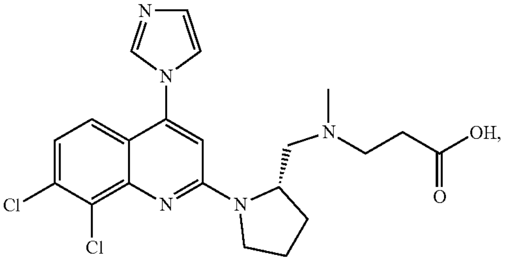
I-755
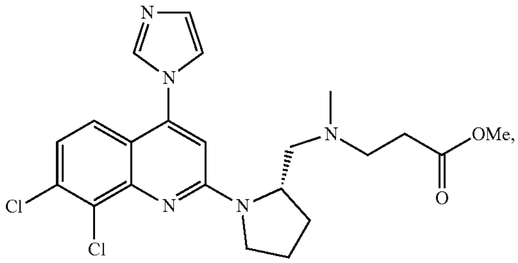

-continued
I-756
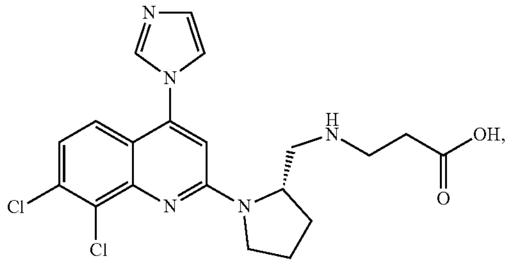
I-757
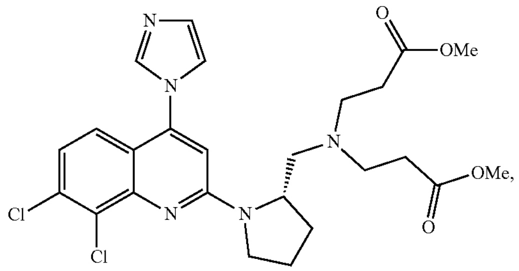
I-758
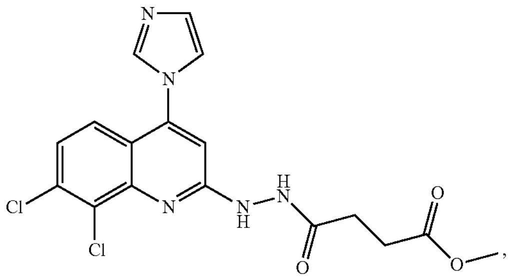
I-759
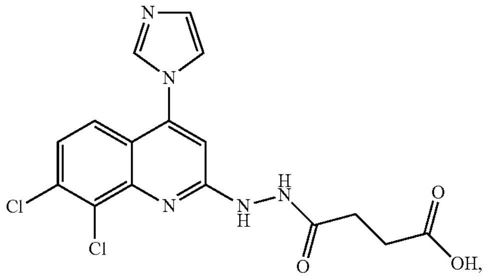
I-760
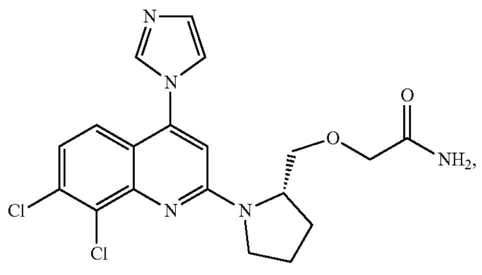
-continued
I-761
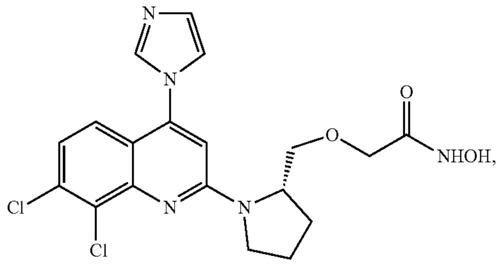
I-762
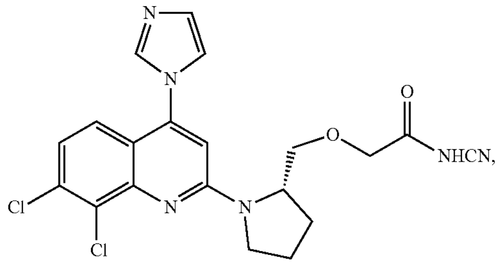
I-763
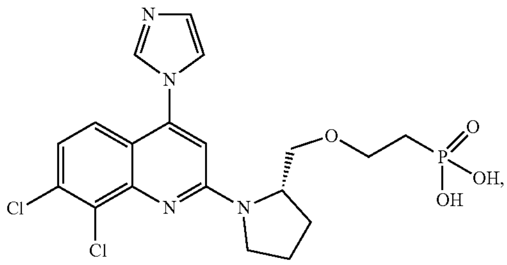
I-764
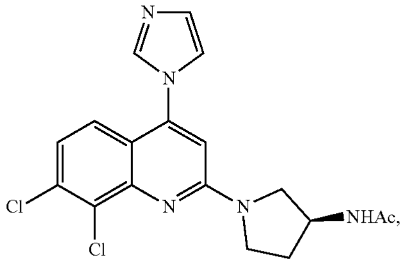
I-765
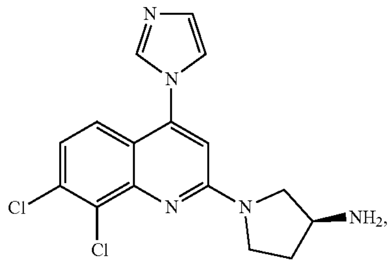

-continued
I-766
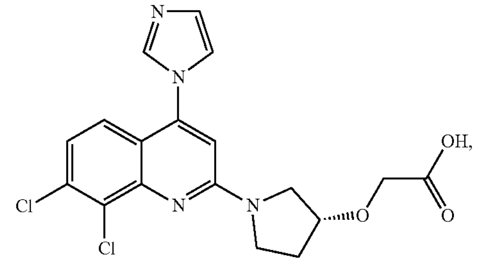
I-767
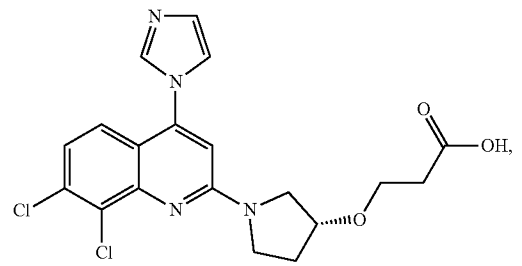
I-768
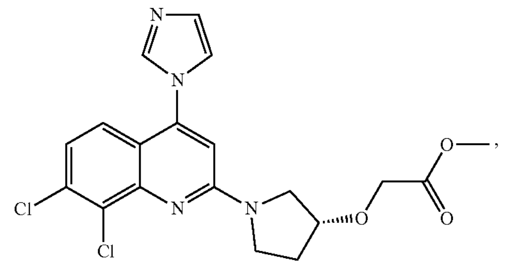
I-769
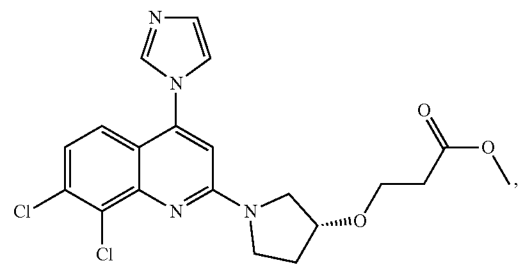
I-770
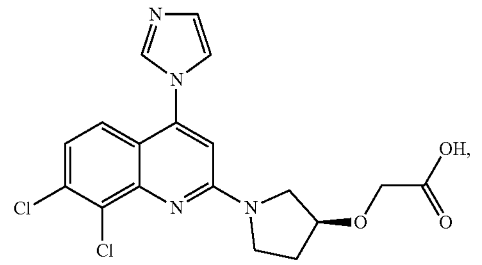
-continued
I-771
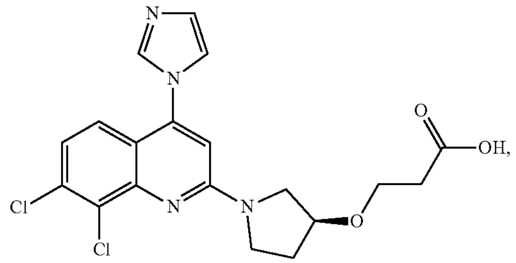
I-772
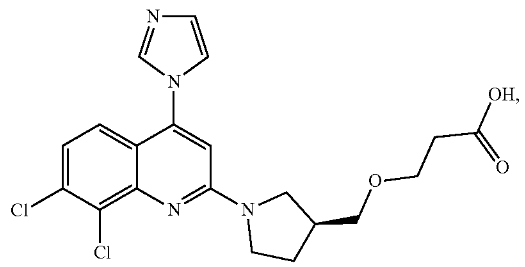
I-773
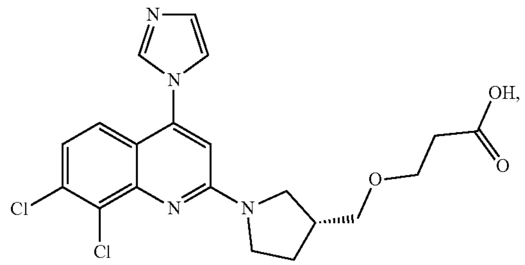
I-774
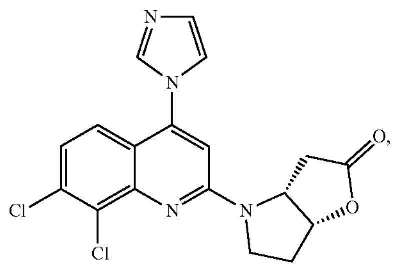
I-775
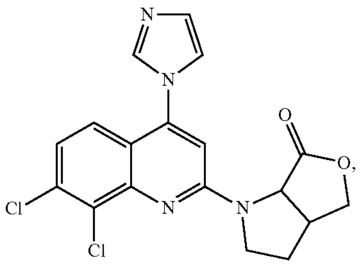

-continued
I-776
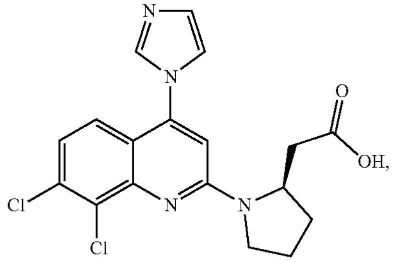
I-778
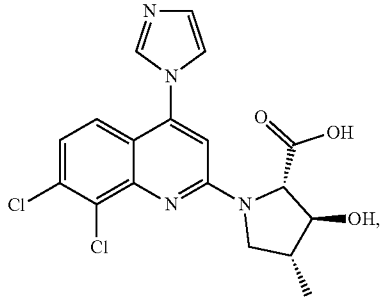
I-779
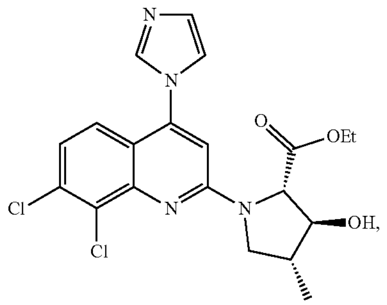
I-780
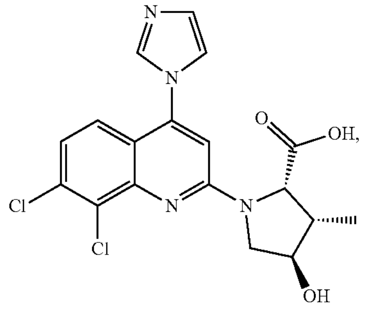
I-781
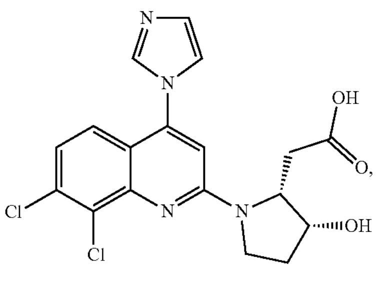
-continued
I-782
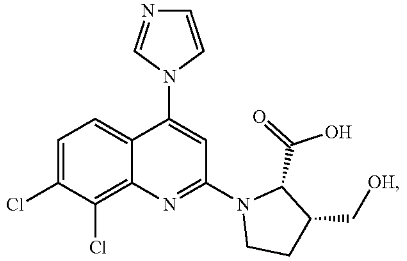
(+/-)
I-783
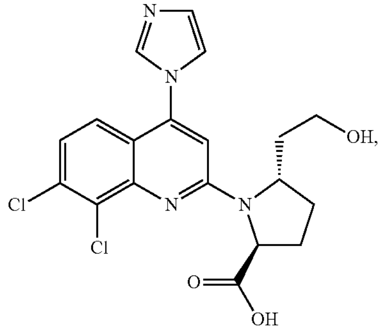
I-784
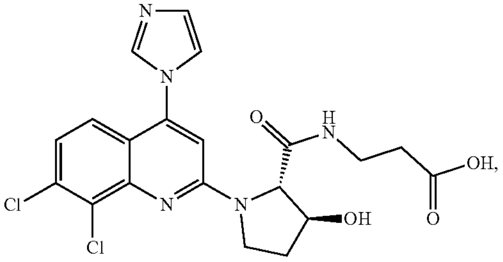
I-785
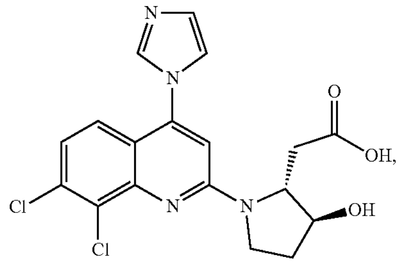
I-786
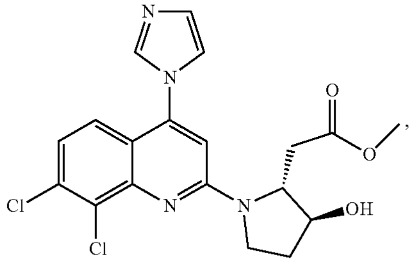

-continued
I-787
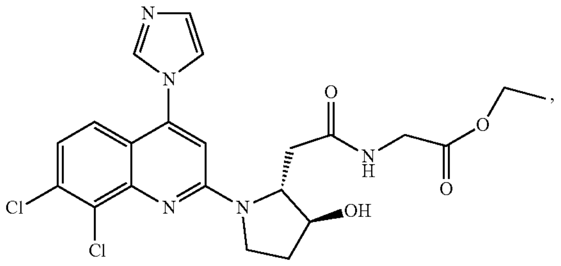
I-788
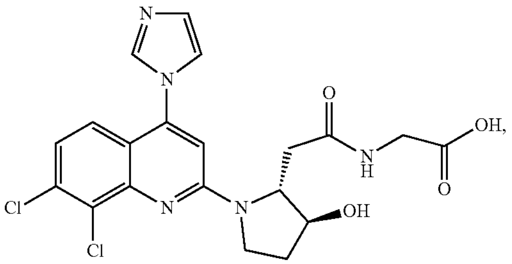
I-789
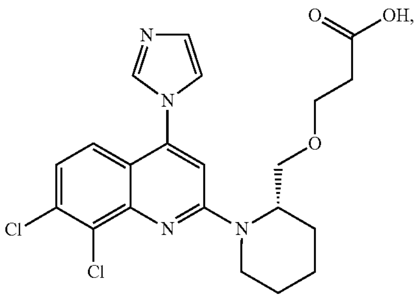
I-790
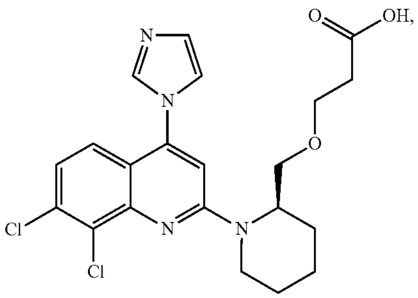
I-791
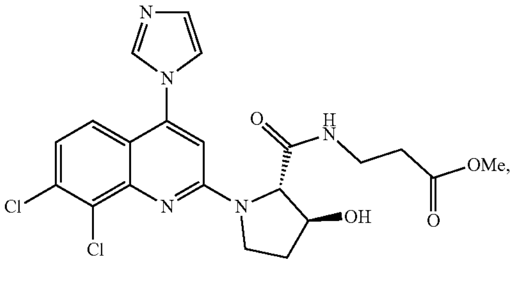
-continued
I-792
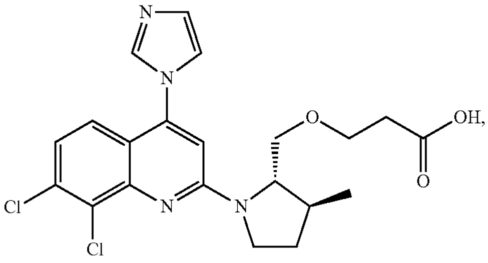
I-793
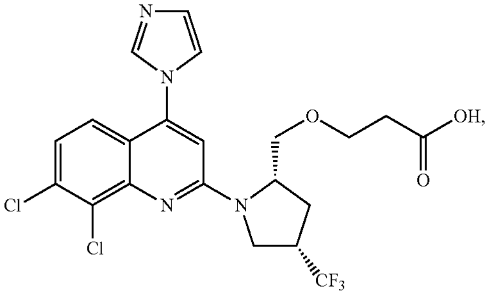
I-794
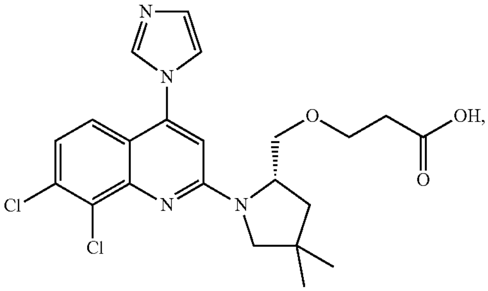
I-795
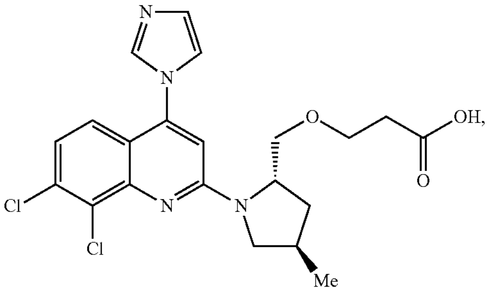
I-796
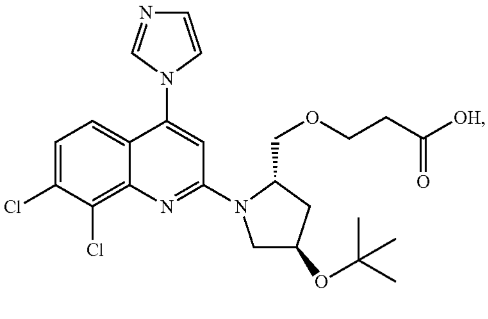

I-797
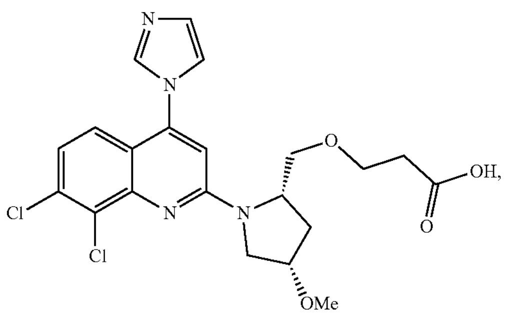
I-798
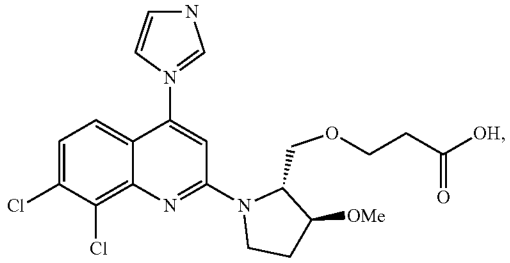
I-799
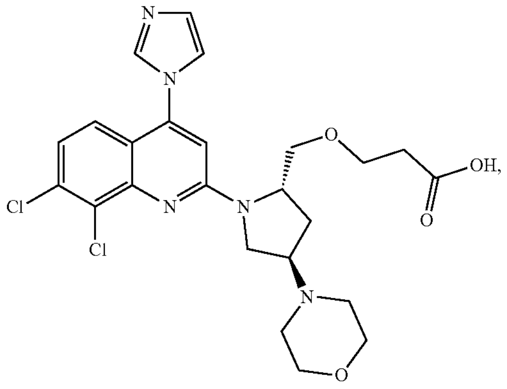
I-800
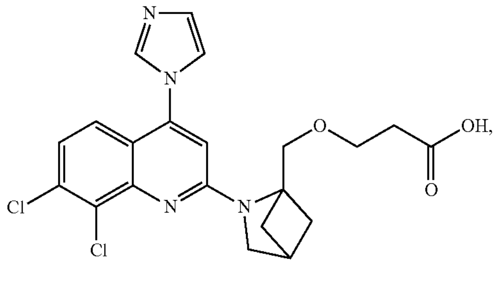
I-801
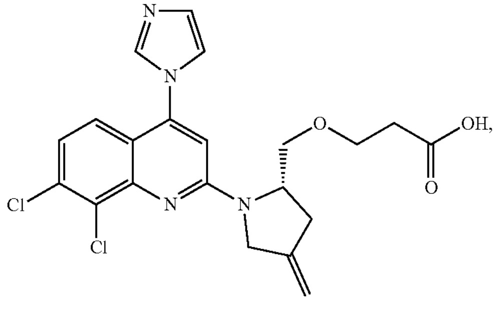
I-802
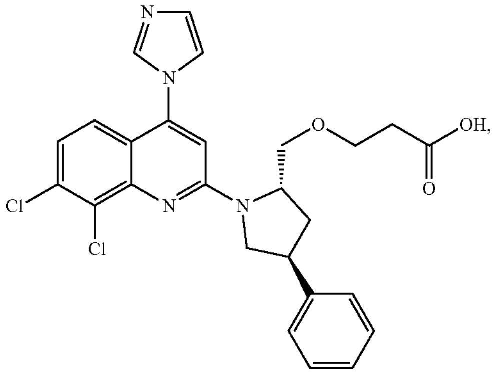
I-803
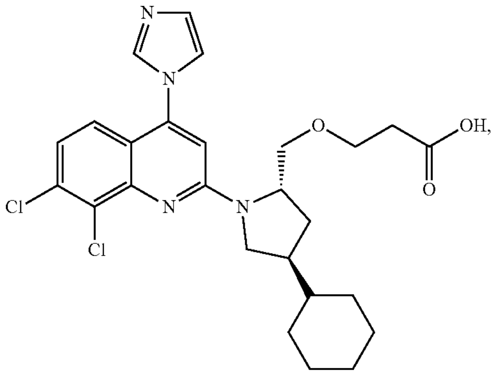
I-804
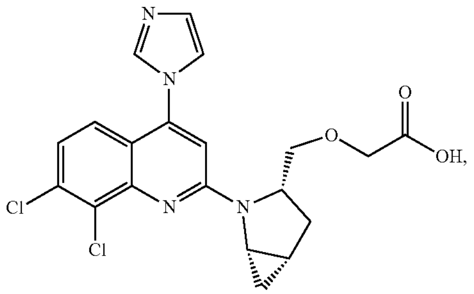
I-805
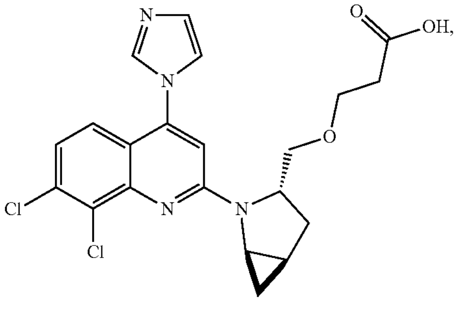

-continued
I-806
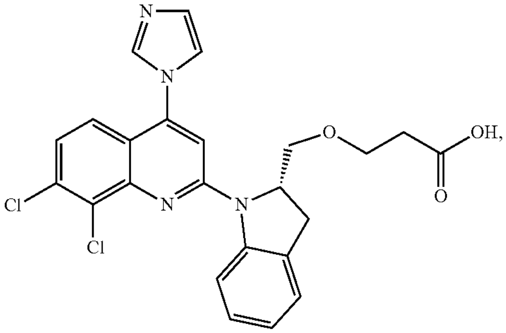
I-807
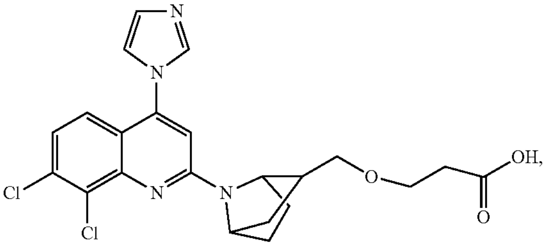
I-808
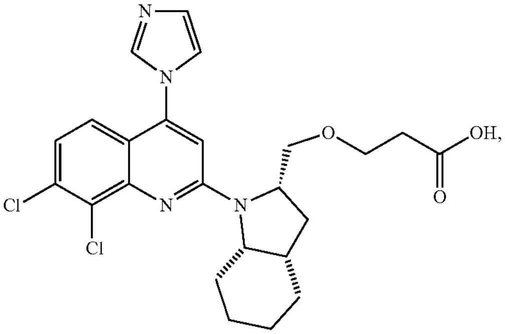
I-809
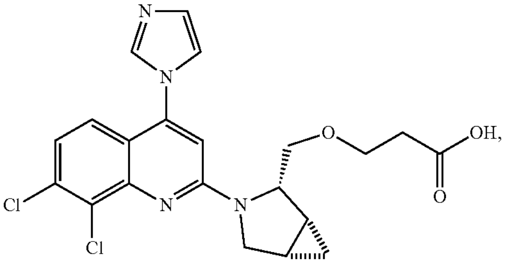
I-810
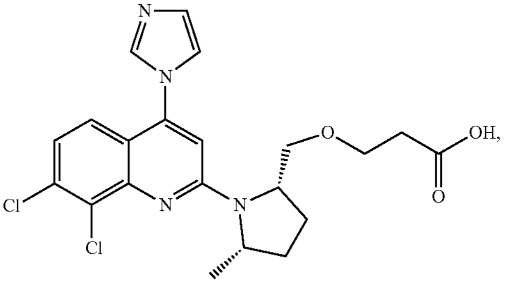
and
-continued
I-811
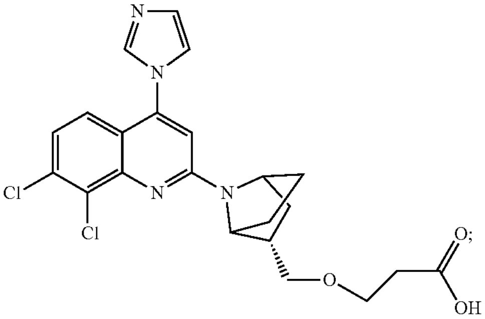
or is a pharmaceutically acceptable salt thereof.
44. The compound of claim 1, wherein the compound is selected from:
I-812
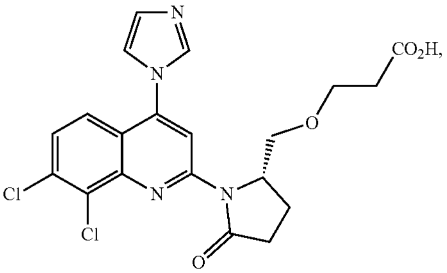
I-813
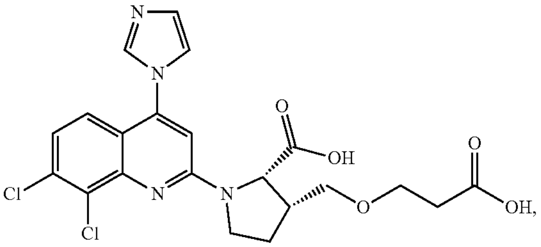
I-814
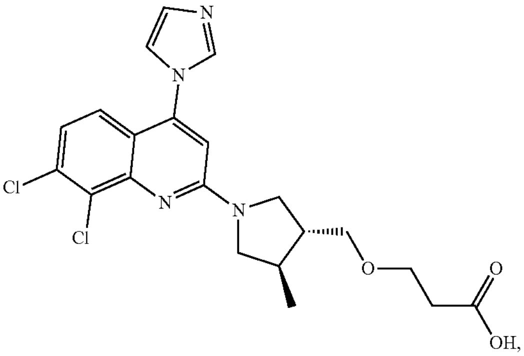

-continued
I-815
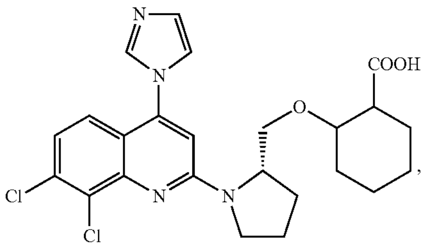
I-816
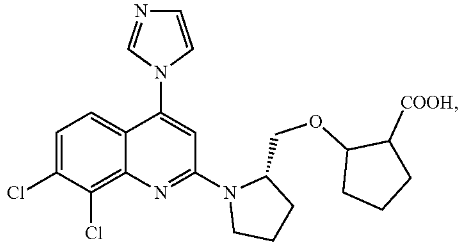
I-817
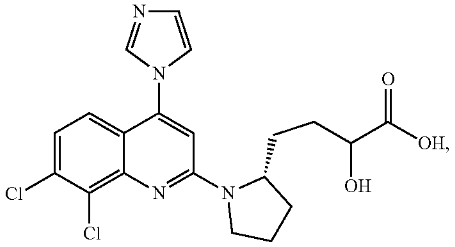
I-818
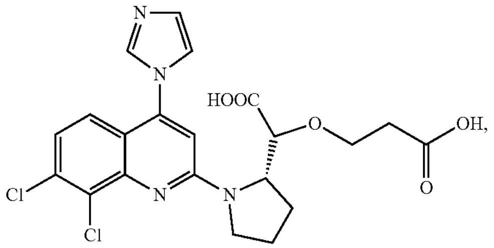
I-819
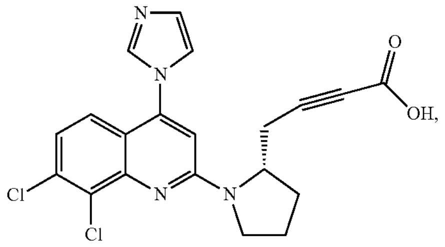
I-820
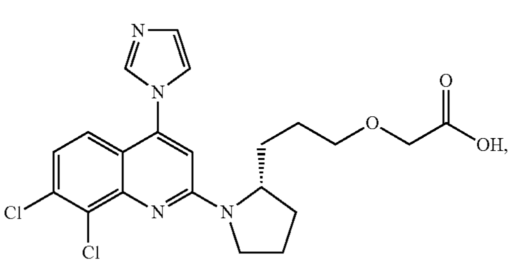
-continued
I-825
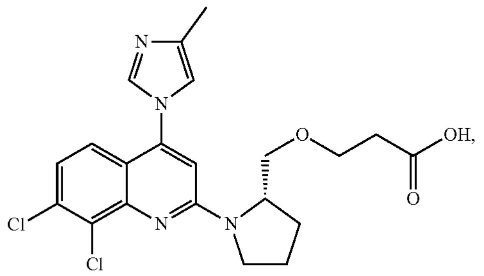
I-829
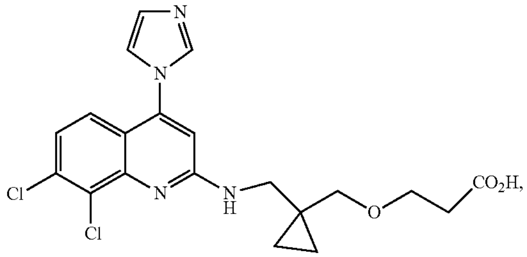
I-831
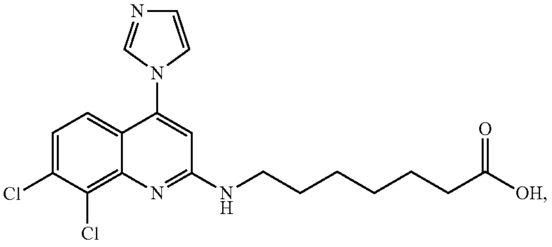
I-832
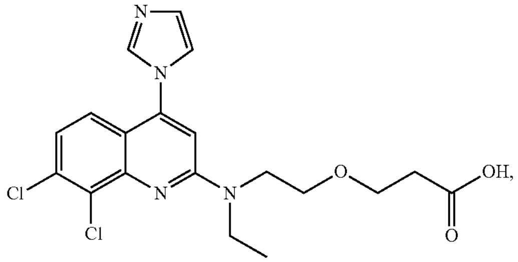
I-833
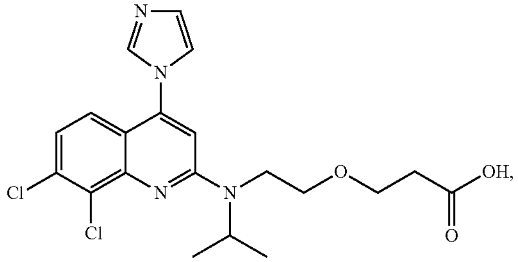

-continued
I-834
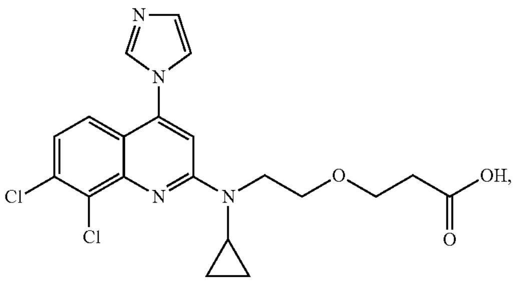
I-835
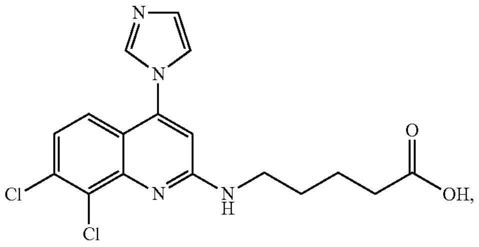
I-836
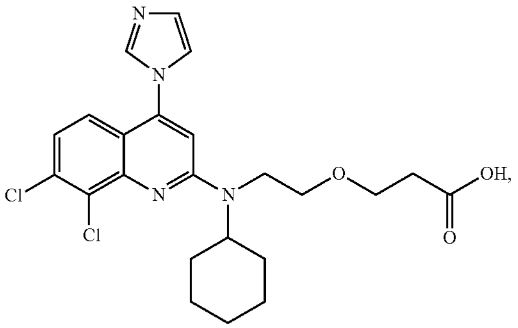
I-837
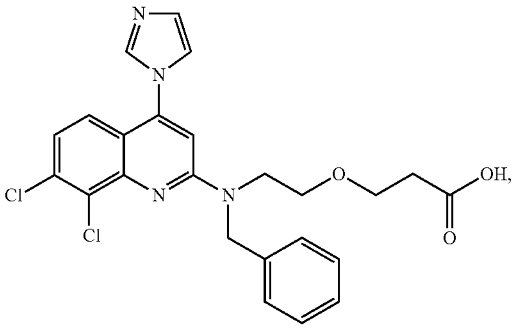
I-838
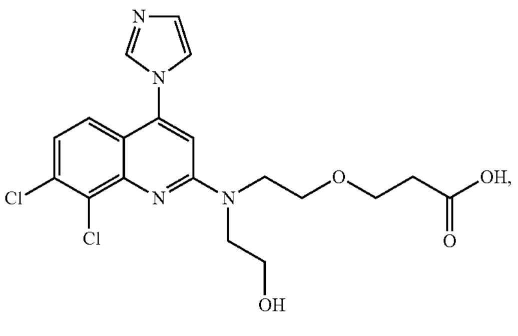
-continued
I-839
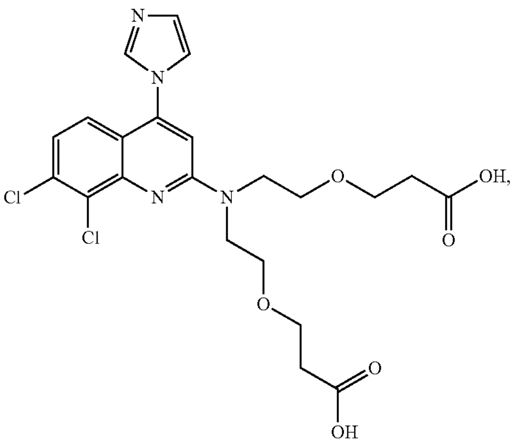
I-842
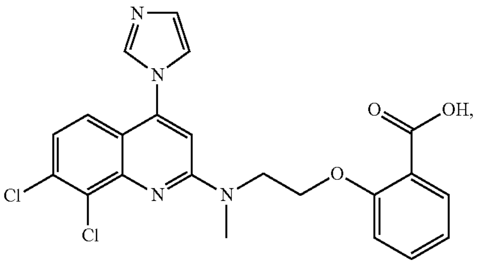
I-843
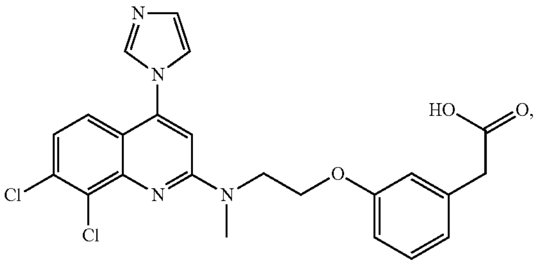
I-844
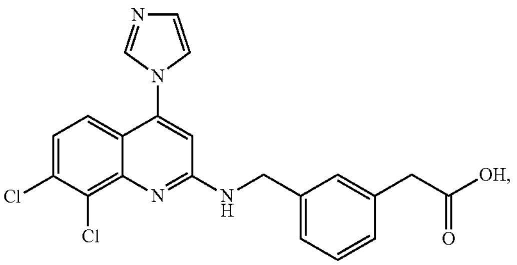
I-845
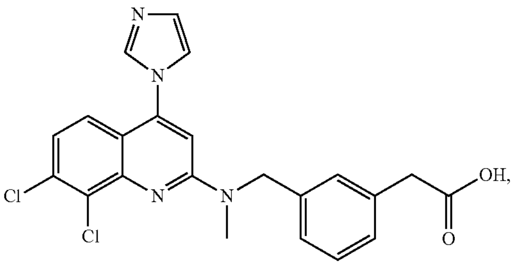

-continued
I-846
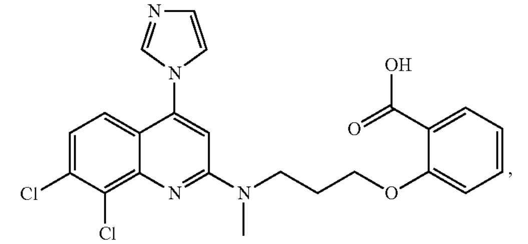
I-847
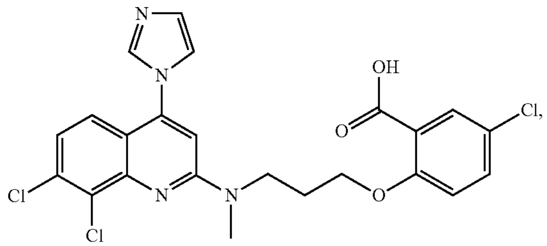
I-848
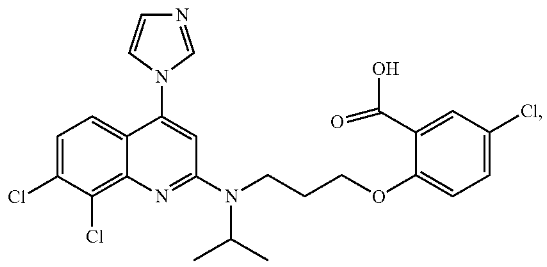
I-849
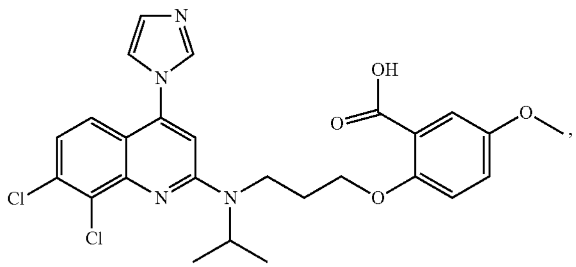
I-850
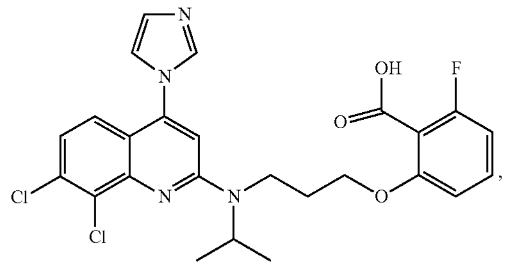
I-851
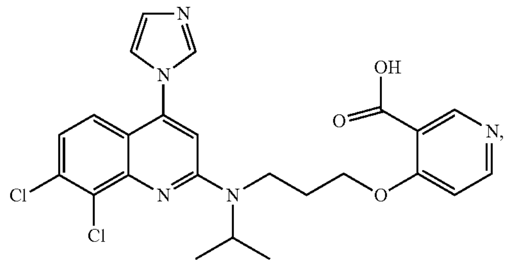
-continued
I-852
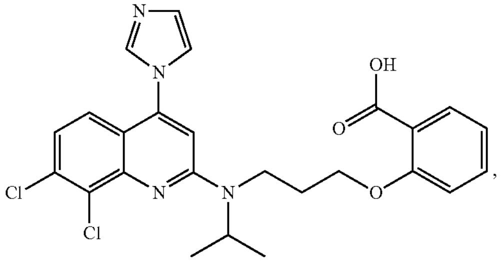
I-856
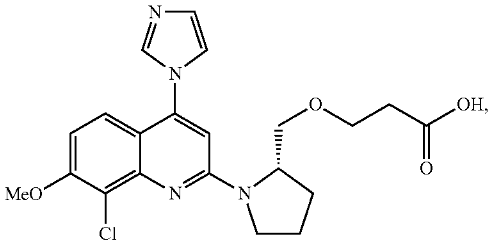
I-857
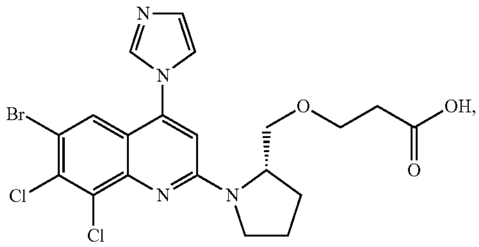
I-858
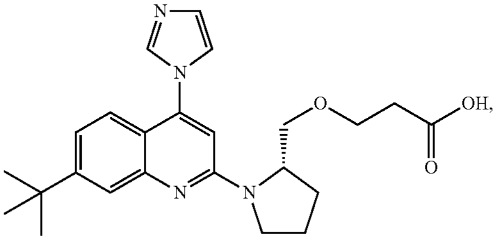
I-860
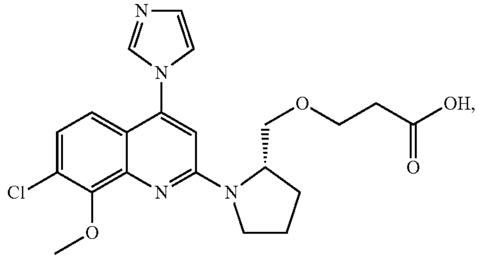
I-861
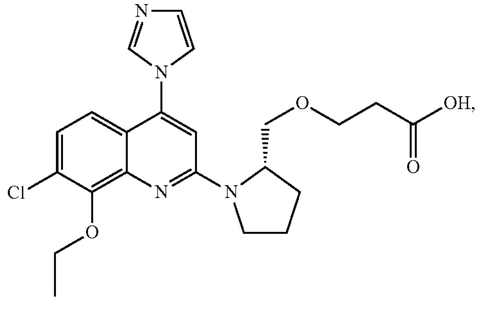

-continued
I-862
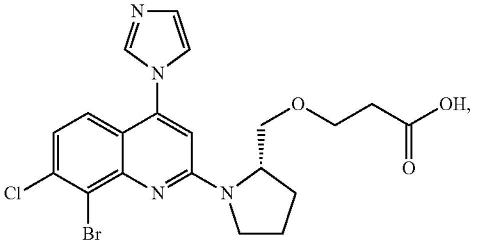
I-863
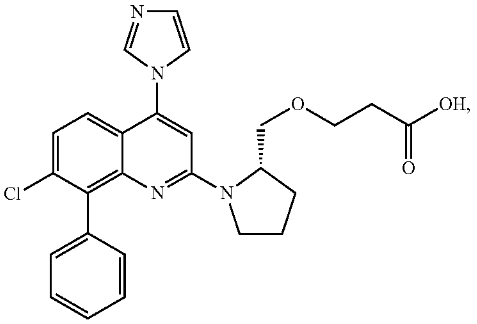
I-864
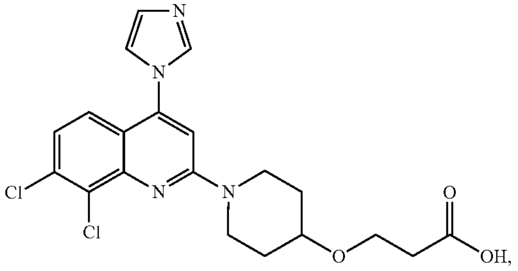
I-865
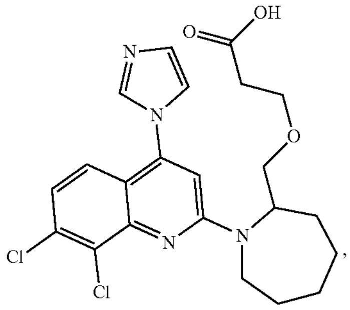
I-866
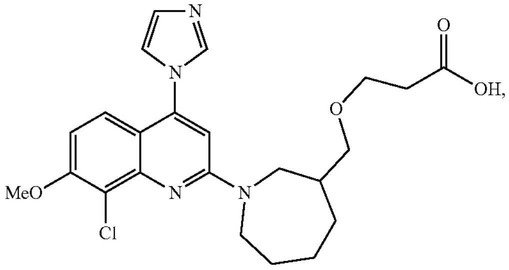
-continued
I-867
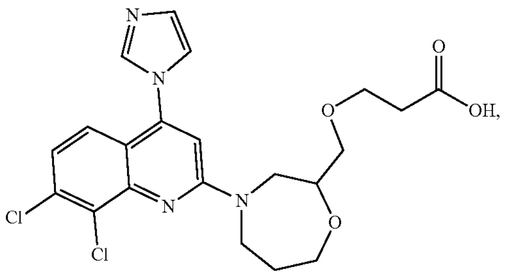
I-868
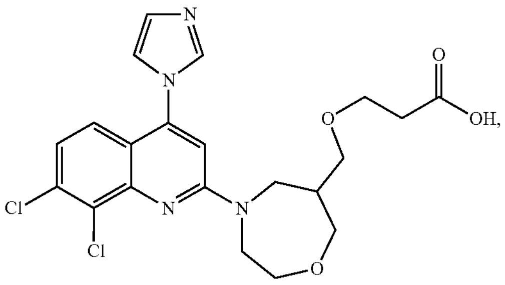
I-869
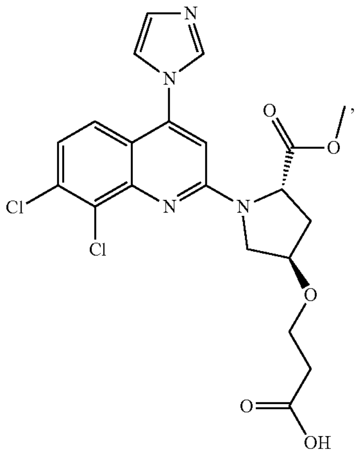
I-870
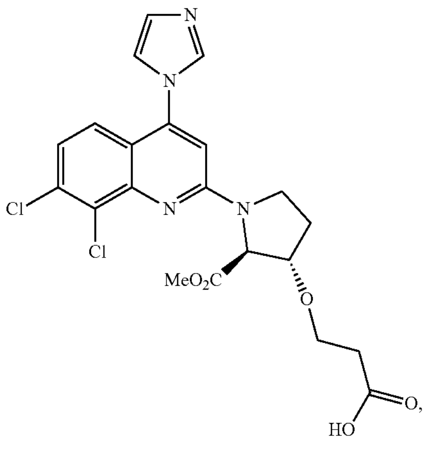

-continued
I-871
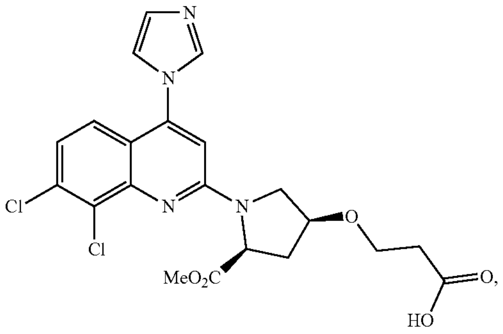
I-872
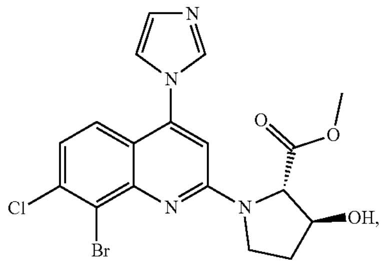
I-873
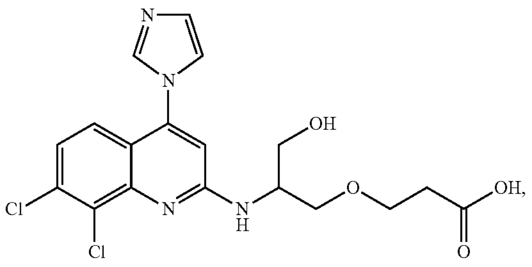
I-874
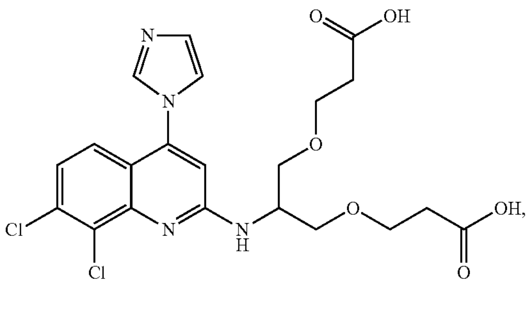
I-875
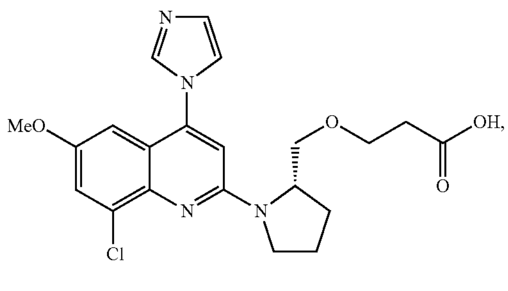
-continued
I-876
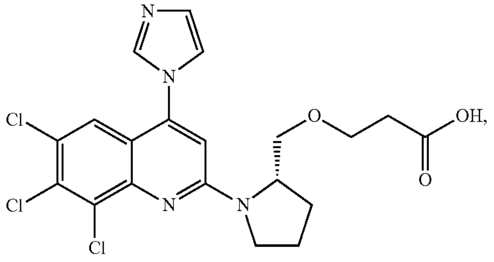
I-881
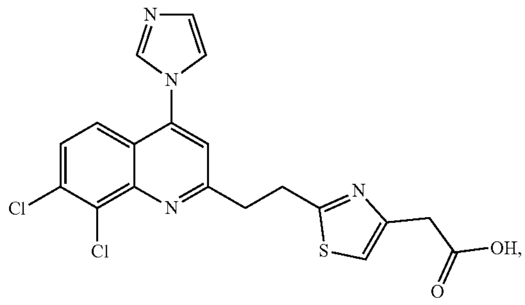
I-882
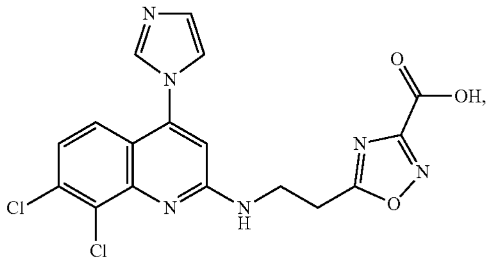
I-883
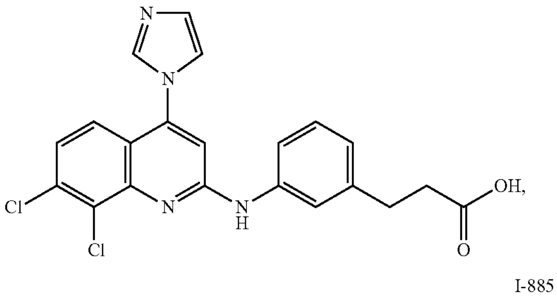
I-885
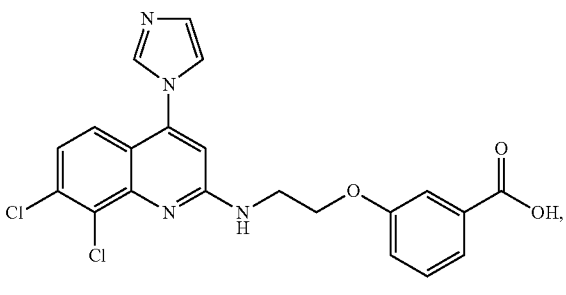

-continued

I-886

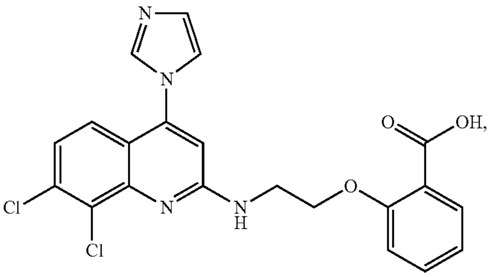

I-887

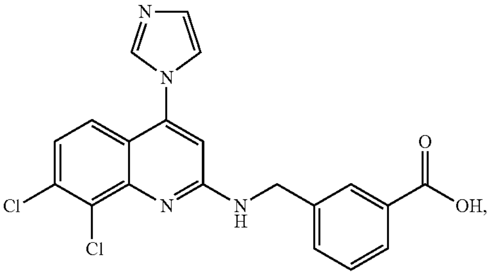

I-888

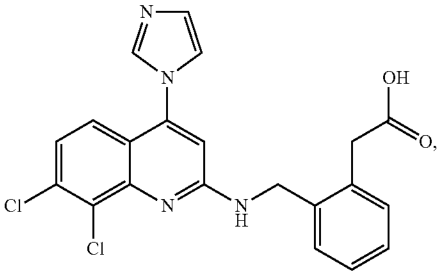

I-889

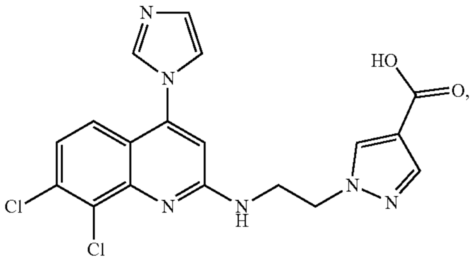

I-890

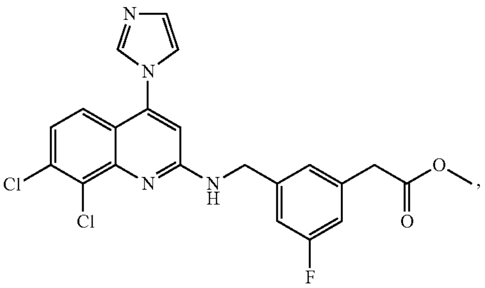

and

-continued

I-891

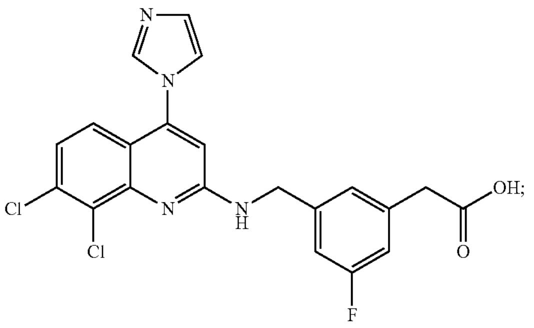

or is a pharmaceutically acceptable salt thereof.

45. The compound of claim 21, wherein:

at least one occurrence of $R^3$ is chloro;

m is 1 or 2; and at least one $R^6$ is $—(CH_2)_{0-4}O(CH_2)_{1-5}CO_2H$, $—(CH_2)_{0-4}O(CH_2)_{1-5}CO_2C_{1-4}$alkyl, $—(CH_2)_{0-4}CO_2H$, or $—(CH_2)_{0-4}CO_2C_{1-4}$alkyl.

46. The compound of claim 45, wherein at least one $R^6$ is $—CO_2CH_2CF_3$.

47. The compound of claim 45, wherein at least one $R^6$ is

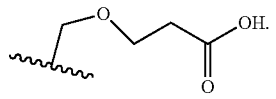 [SMILES: *COCCC(=O)O]

48. The compound of claim 24, wherein:

at least one occurrence of $R^3$ is chloro;

m is 1 or 2; and at least one $R^6$ is $—(CH_2)_{0-4}O(CH_2)_{1-5}CO_2H$, $—(CH_2)_{0-4}O(CH_2)_{1-5}CO_2C_{1-4}$alkyl, $—(CH_2)_{0-4}CO_2H$, or $—(CH_2)_{0-4}CO_2C_{1-4}$alkyl.

49. The compound of claim 48, wherein at least one $R^6$ is $—CO_2CH_2CF_3$.

50. The compound of claim 48, wherein at least one $R^6$ is

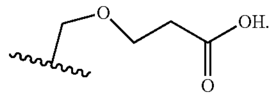 [SMILES: *COCCC(=O)O]

51. A compound, wherein the compound is of Formula I-a-4:

I-a-4

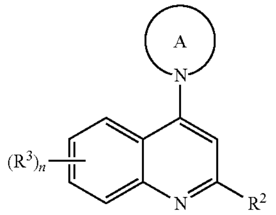

or a pharmaceutically acceptable salt thereof, wherein:

Ring A is a substituted 4- to 7-membered saturated or partially unsaturated heterocyclic ring;

$R^2$ is —$NRR^5$, —$NR^aR^5$,

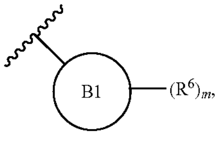

or

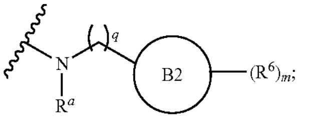

each $R^3$ is independently halogen, —OMe, —OEt, —$NR_2$, —SR, or $R^C$;

Ring B1 is a 4- to 10-membered saturated or partially unsaturated monocyclic or bicyclic carboxylic or heterocyclic ring having 1 to 3 heteroatoms independently selected from nitrogen, oxygen, and sulfur; or a benzotriazolyl, benzo[d]oxazol-2(3H)-one, benzo[d][1,3]dioxole, thienyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, or indolizinyl ring;

Ring B2 is phenyl; a 4- to 7-membered saturated or partially unsaturated carbocyclic or heterocyclic ring having 1 to 3 heteroatoms independently selected from nitrogen, oxygen, and sulfur; or a 5- to 6-membered heteroaryl ring having 1 to 4 heteroatoms independently selected from nitrogen, oxygen, and sulfur;

each R is independently hydrogen or an optionally substituted group selected from $C_{1-6}$ aliphatic; benzyl; phenyl; a 4- to 7-membered saturated or partially unsaturated carbocyclic or heterocyclic ring having 1 to 3 heteroatoms independently selected from nitrogen, oxygen, and sulfur; and a 5- to 6-membered heteroaryl ring having 1 to 4 heteroatoms independently selected from nitrogen, oxygen, and sulfur, $R^5$ is —$(CR_2)_{0-4}OR$, —$(CR_2)_{0-5}CO_2R$, —$(CR_2)_{0-5}CONR_2$, —$(CR_2)_{0-4}C(O)NR(CR_2)CO_2R$, —$(CR_2)_{0-4}C(O)NR(CR_2)_{0-4}CONR_2$, —$(CR_2)_{0-4}NRC(O)R$, —$(CR_2)_{0-4}SO_3R$, —$(CR_2)_{0-4}SO_2NR_2$, —$(CR_2)_{0-4}OSO_2NR_2$, —$(CR_2)_{0-4}NRSO_2R$, —$(CR_2)_{0-4}NRSO_2OR$, —$(CR_2)_{0-4}OP(OR)_2$, —$(CR_2)_{0-4}OP(O)(OR)_2$, —$(CR_2)_{0-4}P(O)(OR)_2$, —$(CR_2)_{0-4}OP(O)(H)OR$, or $R^B$;

each $R^6$ is independently halogen, —CN, =$CH_2$, =O, —C(O)NHOH, —$C(O)N(CH_3)OH$, —$C(O)N(CH_3)OCH_3$, —$C(O)NHSO_2CHF_2$, —$OCONHCH_2CO_2Me$, —$OCONHCH_2CO_2H$, —$NHCOCH_2CH_2CO_2H$, —$NHCOCH_2CH_2CO_2CH_3$, —COR, —$(CR_2)_{0-4}CO_2R$, —$(CR_2)_{0-4}CONR_2$, —OR, —$(CR_2)_{1-4}OR$, $NR_2$, —$(CR_2)_{1-4}NR_2$, —NRC(O)OR, —NRC(O)R, —$NRC(O)NR_2$, —SR, —$SO_2R$, —S(O)R, —$(CR_2)_{0-4}SO_3R$, —$(CR_2)_{0-4}SO_2NR_2$, —$(CR_2)_{0-4}OSO_2NR_2$, —$(CR_2)_{0-4}NRSO_2R$, —$(CR_2)_{0-4}NRSO_2OR$, —$(CR_2)_{0-4}OP(OR)_2$, —$(CR_2)_{0-4}OP(O)(OR)_2$, —$(CR_2)_{0-4}P(O)(OR)_2$, —$(CR_2)_{0-4}OP(O)(H)OR$, —$B(OR)_2$,

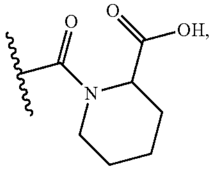
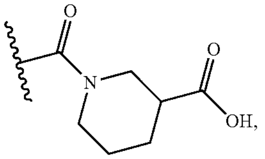
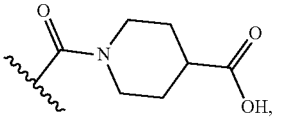
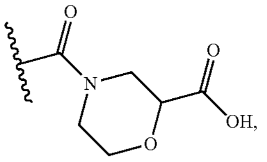
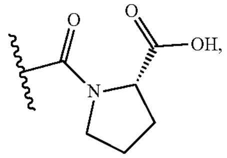
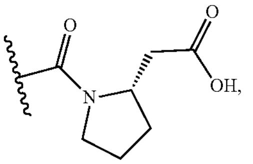
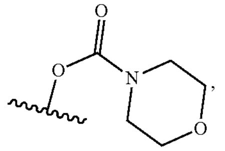

or $R^B$;

$R^B$ is an optionally substituted group selected from $C_{1-6}$ aliphatic; phenyl; a 4- to 10-membered saturated or partially unsaturated monocyclic or bicyclic carboxylic or heterocyclic ring having 1 to 3 heteroatoms independently selected from nitrogen, oxygen, and sulfur; and a 5- to 6-membered heteroaryl ring having 1 to 4 heteroatoms independently selected from nitrogen, oxygen, and sulfur;

$R_C$ is an optionally substituted group selected from phenyl; a 4- to 10-membered saturated or partially unsaturated monocyclic or bicyclic carbocyclic or heterocyclic ring having 1 to 3 heteroatoms independently selected from nitrogen, oxygen, and sulfur; and a 5- to 6-membered heteroaryl ring having 1 to 4 heteroatoms independently selected from nitrogen, oxygen, and sulfur, each $R^a$ is independently H or $C_{1-6}$alkyl;

each m is 0, 1, 2, 3, or 4;

n is 1, 2, 3, or 4; and q is 0, 1, or 2.

52. The compound of claim 51, wherein the compound is selected from:

I-291

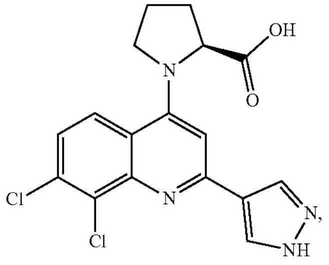

-continued
I-292
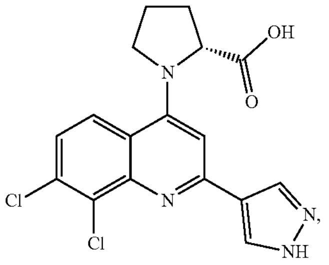
I-298
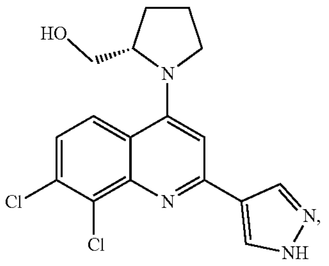
-continued
I-299
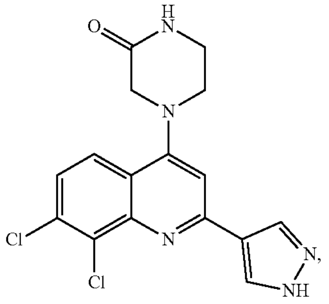
and
I-821
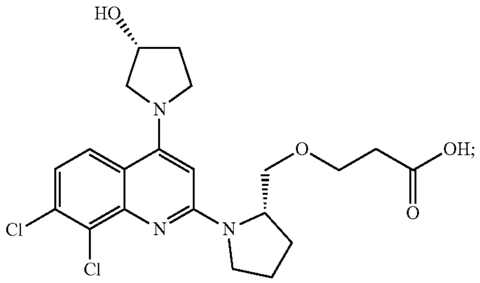
or is a pharmaceutically acceptable salt thereof.
* * * * *